US012083101B2

(12) United States Patent
Bordas et al.

(10) Patent No.: US 12,083,101 B2
(45) Date of Patent: Sep. 10, 2024

(54) BIARYL DERIVATIVES AS YAP/TAZ-TEAD PROTEIN-PROTEIN INTERACTION INHIBITORS

(71) Applicant: Novartis AG, Basel (CH)

(72) Inventors: Vincent Bordas, Village-Neuf (FR); Cara Brocklehurst, Leymen (FR); Patrick Chene, Mulhouse (FR); Pascal Furet, Thann (FR); Vito Guagnano, Lecce (IT); Patricia Imbach-Weese, Bielefeld (DE); Joerg Kallen, Basel (CH); Mickael Le Douget, Muespach (FR); Edwige Liliane Jeanne Lorthiois, Niffer (FR); Joseph McKenna, Nottingham (GB); Bahaa Salem, Basel (CH); Tobias Schmelzle, Riehen (CH); Holger Sellner, Buchs (CH); Nicolas Soldermann, Village-Neuf (FR); Markus Voegtle, Lörrach (CH); Markus Wartmann, Riehen (CH)

(73) Assignee: Novartis AG, Basel (CH)

( * ) Notice: Subject to any disclaimer, the term of this patent is extended or adjusted under 35 U.S.C. 154(b) by 578 days.

(21) Appl. No.: 17/201,268

(22) Filed: Mar. 15, 2021

(65) Prior Publication Data
US 2021/0299100 A1 Sep. 30, 2021

(30) Foreign Application Priority Data
Mar. 16, 2020 (EP) .................... 20163465

(51) Int. Cl.
A61K 31/4155 (2006.01)
A61K 31/343 (2006.01)
A61K 31/351 (2006.01)
A61K 31/357 (2006.01)
A61K 31/4025 (2006.01)
A61K 31/403 (2006.01)
A61K 31/404 (2006.01)
A61K 31/41 (2006.01)
A61K 31/426 (2006.01)
A61K 31/443 (2006.01)
A61K 31/4439 (2006.01)
(Continued)

(52) U.S. Cl.
CPC ........ A61K 31/4155 (2013.01); A61K 31/343 (2013.01); A61K 31/351 (2013.01); A61K 31/357 (2013.01); A61K 31/4025 (2013.01); A61K 31/403 (2013.01); A61K 31/41 (2013.01); A61K 31/426 (2013.01); A61K 31/443 (2013.01); A61K 31/4439 (2013.01); A61K 31/4525 (2013.01); A61K 31/506 (2013.01); A61P 35/00 (2018.01); C07D 307/81 (2013.01); C07D 405/04 (2013.01); C07D 405/12 (2013.01); C07D 405/14 (2013.01); C07D 407/04 (2013.01); C07D 407/12 (2013.01); C07D 417/04 (2013.01)

(58) Field of Classification Search
CPC .............. A61K 31/4155; A61K 31/343; A61K 31/351; A61K 31/357; A61K 31/4025; A61K 31/403; A61K 31/41; A61K 31/426; A61K 31/443; A61K 31/4439; A61K 31/4525; A61K 31/506; A61K 31/404; C07D 307/81; C07D 405/04; C07D 405/12; C07D 405/14; C07D 407/04; C07D 407/12; C07D 417/04; C07D 401/14; C07D 403/04; C07D 405/10; C07D 413/04; C07D 491/04; A61P 35/00

See application file for complete search history.

(56) References Cited

U.S. PATENT DOCUMENTS

2010/0234357 A1* 9/2010 Tsukamoto ............... A61P 9/12
514/233.5
2012/0130147 A1 5/2012 Finsinger et al.

FOREIGN PATENT DOCUMENTS

EP 3156404 A1 4/2017
WO 9728149 A1 8/1997
(Continued)

OTHER PUBLICATIONS

Zanconato, F., M. Cordenonsi and S. Piccolo, "YAP/TAZ at the roots of cancer", Cancer Cell (2016), 29(6), pp. 783-803. (Year: 2016).*

(Continued)

Primary Examiner — Amanda L. Aguirre
Assistant Examiner — Sagar Patel
(74) Attorney, Agent, or Firm — Jessica Chao

(57) ABSTRACT

The present invention provides a compound of formula (I) or a pharmaceutically acceptable salt thereof;

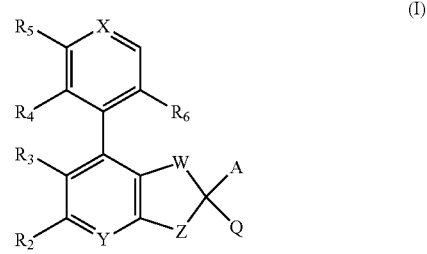

(I)

a method for manufacturing said compound, and its therapeutic uses. The present invention further provides a combination of pharmacologically active agents and a pharmaceutical composition comprising said compound.

33 Claims, No Drawings

(51) Int. Cl.
*A61K 31/4525* (2006.01)
*A61K 31/506* (2006.01)
*A61P 35/00* (2006.01)
*C07D 307/81* (2006.01)
*C07D 401/14* (2006.01)
*C07D 403/04* (2006.01)
*C07D 405/04* (2006.01)
*C07D 405/10* (2006.01)
*C07D 405/12* (2006.01)
*C07D 405/14* (2006.01)
*C07D 407/04* (2006.01)
*C07D 407/12* (2006.01)
*C07D 413/04* (2006.01)
*C07D 417/04* (2006.01)
*C07D 491/04* (2006.01)

(56) References Cited

FOREIGN PATENT DOCUMENTS

| WO | 2004020409 | A1 | 3/2004 |
| WO | 2017035366 | A1 | 3/2017 |
| WO | 2019201283 | A1 | 10/2019 |
| WO | 2019232216 | A1 | 12/2019 |
| WO | 2020006115 | A1 | 1/2020 |
| WO | 2020047035 | A1 | 3/2020 |
| WO | 2020051099 | A1 | 3/2020 |

OTHER PUBLICATIONS

World Health Organization, "Cancer in Children,"(Sep. 28, 2018); archived at Wayback Machine. Retrieved on Oct. 1, 2023 from https://web.archive.org/web/20181008184522/https://www.who.int/news-room/fact-sheets/detail/cancer-in-children. (Year: 2018).*
CAS Registry No. 22248-06-2, Entered 1969.
CAS Registry No. 92796-50-4, Entered 1963.
International Search Report and Written Opinion issued in connection with PCT/IB2021/052136, mailed Apr. 8, 2021 (14 pages).
Rotberg, et al., Derivatives of 2-(3'-coumarinyl)-1, 3-indandione, Chem Heterocycl Compd., 1969, 13-17, 5(1).
Choi, et al., 5-Chloro-2-(4-fluorophenyl)-3-phenylsulfinyl- 1-benzofuran, Acta Crystallographica Section E, 2011, E67, 0498.
PubChem CID 20760195, May 12, 2007.

* cited by examiner

BIARYL DERIVATIVES AS YAP/TAZ-TEAD PROTEIN-PROTEIN INTERACTION INHIBITORS

CROSS-REFERENCE TO RELATED APPLICATIONS

This application claims priority from International Application No. PCT/CN2021/075550, filed on Feb. 5, 2021, and European Application No. 20163465.6, filed on Mar. 16, 2020, each of which is incorporated herein by reference in its entirety.

FIELD OF THE INVENTION

The invention provides biaryl derivative compounds, the use thereof for inhibiting YAP/TAZ-TEAD protein-protein interaction (PPI) and methods of treating disease using said compounds.

BACKGROUND OF THE INVENTION

Normal tissue growth, as well as tissue repair and remodeling, require specific control and regulated balance of transcriptional activity. Transcriptional output is coordinated through a number of key signaling modules, one of which is the Hippo pathway. Genetic studies in *Drosophila* and mammals have defined a conserved core signaling cassette, composed of MST1/2 and LATS1/2 kinases which inhibit the transcriptional co-activators YAP and TAZ (official gene name: WWTR1).

An activated Hippo pathway translates to YAP and TAZ being phosphorylated and sequestered/degraded in the cytoplasm. Upon inactivation of the Hippo pathway, YAP and TAZ translocate to the nucleus and associate with transcription factors, namely members of the TEAD family (TEAD1-4). The YAP/TAZ-TEAD complexes in turn promote transcription of downstream genes involved in cellular proliferation, death and differentiation. While YAP and TAZ can also interact with a number of other factors, TEADs are commonly accepted to be the key mediators of the growth-promoting and tumorigenic potential of YAP and TAZ (pathway reviewed in Yu et al., 2015; Holden and Cunningham, 2018).

Accordingly, a hyperactivation of YAP and/or TAZ (and subsequent hyperactivity of the YAP/TAZ-TEAD transcriptional complex) is commonly observed in several human cancers. This is evidenced by the levels and nuclear localization of YAP/TAZ being elevated in many tumors, including breast, lung (e.g., non-small cell lung cancer; NSCLC), ovarian, colorectal, pancreas, prostate, gastric, esophagus, liver and bone (sarcoma) (Steinhardt et al., 2008; Harvey et al., 2013; Moroishi et al., 2015; extensively reviewed in Zanconato et al., 2016 and references therein).

While genetic alterations of the core Hippo pathway components have thus far been detected with limited frequency in primary samples, the most prominent cancer malignancy associated with inactivating mutations in NF2 or LATS1/2 and associated YAP/TEAD hyperactivity is malignant pleural mesothelioma (MPM) (reviewed in Sekido, 2018). Similarly, a number of human tumors are characterized by amplification of YAP at the 11q22.1 locus (e.g., hepatocellular carcinomas, medulloblastomas, esophageal squamous cell carcinomas), TAZ (WWTR1) at the 3q25.1 locus (e.g., rhabdomyosarcomas, triple negative breast cancer) or gene fusions involving YAP or TAZ (epithelioid hemangioendotheliomas, ependymal tumors) (reviewed in Yu et al., 2015 and references therein). As is the case for MPM, such tumors are also anticipated to depend on their elevated YAP/TAZ-TEAD activity.

Disruption of the YAP/TAZ-TEAD protein-protein interaction (PPI) as the most distal effector node of the Hippo pathway is anticipated to abolish the oncogenic potential of this complex. The compounds of this invention are designed and optimized to bind to TEADs and selectively disrupt their interaction with YAP and TAZ, which is believed to result in drugs useful in the treatment of above-mentioned cancers. In particular, such cancers may be characterized by (but not restricted to) some of the described aberrations.

Notably, tumor cells with activated YAP/TAZ-TEAD display resistance to chemotherapeutic drugs, possibly related to YAP/TAZ conferring cancer stem cell-like characteristics. Moreover, YAP/TAZ-TEAD activation also confers resistance to molecularly targeted therapies, such as BRAF, MEK or EGFR inhibitors, as reported from the outcome of various genetic and pharmacological screens (Kapoor et al., 2014; Shao et al., 2014; Lin et al., 2015). This in turn suggests that inhibiting YAP/TAZ-TEAD activity—either in parallel or sequentially to other cancer treatments—may provide a beneficial therapeutic impact by reducing growth of tumors resistant to other treatments. The inhibition of YAP/TAZ-TEAD activity upon PPI disruption with above mentioned LMW compounds may also blunt the tumor's escape from immune surveillance. This is, for instance, evidenced by reported data on YAP promoting the expression of chemokine CXCL5 which results in the recruitment of myeloid cells that suppress T-cells (Wang et al., 2016). YAP in Tregs (regulatory T-cells) has also been demonstrated to support FOXP3 expression via activin signaling and Treg function. Accordingly, YAP deficiency results in dysfunctional Tregs which are no longer able to suppress antitumor immunity. Selective inhibition of YAP/TEAD activity may therefore contribute to bolster antitumor immunity by preventing Treg function (Ni et al., 2018). Recent literature also suggests that YAP upregulates PD-L1 expression and by this mechanism directly mediates evasion of cytotoxic T-cell immune responses, for instance in BRAF inhibitor-resistant melanoma cells (Kim et al., 2018).

See for example:
Yu, F.-X., Zhao, B. and Guan, K.-L. (2015). Hippo pathway in organ size control, tissue homeostasis, and cancer. Cell, 163, 811-828.
Holden, J. K. and Cunningham, C. N. (2018). Targeting the Hippo pathway and cancer through the TEAD family of transcription factors. Cancers (Basel), 10, E81.
Steinhardt, A. A., Gayyed, M. F., Klein, A. P., Dong, J., Maitra, A., Pan, D., Montgomery, E. A., Anders, R. A. (2008). Expression of Yes-associated protein in common solid tumors. Hum. Pathol., 39, 1582-1589.
Harvey, K. F., Zhang, X., and Thomas, D. M. (2013). The Hippo pathway and human cancer. Nat. Rev. Cancer, 13, 246-257.
Moroishi, T., Hansen, C. G., and Guan, K.-L. (2015). Nat. Rev. Cancer, 15, 73-79.
Zanconato, F., Cordenonsi, M., and Piccolo, S. (2016). YAP/TAZ at the roots of cancer. Cancer Cell, 29, 783-803.
Sekido, Y. (2018). Cancers (Basel), 10, E90.
Kapoor, A., Yao, W., Ying, H., Hua, S., Liewen, A., Wang, Q., Zhong, Y., Wu, C. J., Sadanandam, A., Hu, B. et al. (2014). Yap1 activation enables bypass of oncogenic Kras addiction in pancreatic cancer. Cell, 158, 185-197.
Shao, D. D., Xue, W., Krall, E. B., Bhutkar, A., Piccioni, F., Wang, X., Schinzel, A. C., Sood, S., Rosenbluh, J., Kim, J. W., et al. (2014). KRAS and YAP1 converge to regulate EMT and tumor survival. Cell, 158, 171-184.

Lin, L., Sabnis, A. J., Chan, E., Olivas, V., Cade, L., Pazarentzos, E., Asthana, S., Neel, D., Yan, J. J., Lu, X. et al. (2015). The Hippo effector YAP promotes resistance to RAF- and MEK-targeted cancer therapies. Nat. Genet., 47, 250-256.

Wang, G., Lu, X., Dey, P., Deng, P., Wu, C. C., Jiang, S., Fang, Z., Zhao, K., Konaprathi, R., Hua, S., et al. (2016). Cancer Discov., 6, 80-95.

Ni, X., Tao, J., Barbi, J., Chen, Q., Park B. V., Li, Z., Zhang, N., Lebid, A., Ramaswamy, A., Wei, P., et al. (2018). YAP is essential for Treg-mediated suppression of antitumor immunity. Cancer Discov., 8, 1026-1043.

Kim, M. H., Kim, C. G., Kim, S. K., Shin, S. J., Choe, E. A., Park, S. H., Shin, E. C., and Kim, J. (2018). Cancer Immunol Res., 6, 255-266.

SUMMARY OF THE INVENTION

There is a continuing need to develop new YAP/TAZ-TEAD protein-protein interaction (PPI) inhibitors that are good drug candidates. Such candidates would find applications inter alia in the treatment of cancer, particularly in the treatment of mesothelioma (including malignant pleural mesothelioma), pancreatic cancer, sarcoma and non-small cell lung cancer (e.g. NF2-mutant NSCLC).

The invention provides compounds, pharmaceutically acceptable salts thereof, pharmaceutical compositions thereof and combinations thereof, which compounds are YAP/TAZ-TEAD protein-protein interaction inhibitors. The invention further provides methods of treating, preventing, or ameliorating cancers comprising administering to a subject in need thereof an effective amount of a YAP/TAZ-TEAD PPI inhibitor. For treatment purposes, the YAP/TAZ-TEAD PPI compounds of the invention may be used in combination with cancer immunotherapy drugs, such as immune checkpoint inhibitors (e.g., anti-PD-1 antibodies).

Various embodiments of the invention are described herein.

Within certain aspects, provided herein is a compound of formula (I) or a pharmaceutically acceptable salt thereof:

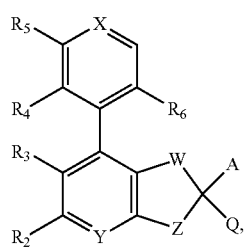

(I)

wherein A, Q, W, X, Y, Z, $R_2$, $R_3$, $R_4$, $R_5$ and $R_6$ are as defined herein.

In another embodiment, the invention provides a pharmaceutical composition comprising a compound according to the definition of formula (I), or a pharmaceutically acceptable salt thereof, or subformulae (Ia), (Ia*), (Ia-1), (Ib), (Ic), (Id), as defined herein, thereof and one or more pharmaceutically acceptable carriers.

In another embodiment, the invention provides a pharmaceutical composition comprising a therapeutically effective amount of a compound according to the definition of formula (I), or a pharmaceutically acceptable salt thereof, or subformulae (Ia), (Ia*), (Ia-1), (Ib), (Ic), (Id) thereof and optionally one or more pharmaceutically acceptable carriers.

In another embodiment, the invention provides a combination, in particular a pharmaceutical combination, comprising a compound according to the definition of formula (I), or a pharmaceutically acceptable salt thereof, or subformulae (Ia), (Ia*), (Ia-1), (Ib), (Ic), (Id) thereof and one or more therapeutically active agents.

In a further embodiment, the invention relates to a method of inhibiting YAP/TAZ-TEAD protein protein interaction activity in a subject, wherein the method comprises administering to the subject a therapeutically effective amount of a compound of formula (I) or subformulae thereof (Ia), (Ia*), (Ia-1), (Ib), (Ic), (Id) as defined herein, or a pharmaceutically acceptable salt thereof.

In yet another embodiment, the invention relates to a method of treating a disorder or disease in a subject in need thereof, wherein the disorder or disease is a cancer or tumor which is selected from mesothelioma (including pleural mesothelioma, malignant pleural mesothelioma, peritoneal mesothelioma, pericardial mesothelioma and mesothelioma of the *Tunica vaginalis*), carcinoma (including cervical squamous cell carcinoma, endometrial carcinoma, esophageal squamous cell carcinoma, esophageal adenocarcinoma, urothelial carcinoma of the bladder and squamous cell carcinoma of the skin), poroma (benign poroma), porocarcinoma (including malignant porocarcinoma), supratentorial ependymoma (including childhood supratentorial ependymoma), epithelioid hemangioendothelioma (EHE), ependymal tumor, a solid tumor, breast cancer (including triple negative breast cancer), lung cancer (including non-small cell lung cancer), ovarian cancer, colorectal cancer (including colorectal carcinoma), melanoma, pancreatic cancer (including pancreatic adenocarcinoma), prostate cancer, gastric cancer, esophageal cancer, liver cancer (including hepatocellular carcinoma, cholangiocarcinoma and hepatoblastoma), neuroblastoma, Schwannoma, kidney cancer, sarcoma (including rhabdomyosarcoma, embryonic rhabdomyosarcoma (ERMS), osteosarcoma, undifferentiated pleomorphic sarcomas (UPS), Kaposi's sarcoma, soft-tissue sarcoma and rare soft-tissue sarcoma), bone cancer, brain cancer, medulloblastoma, glioma, meningioma, and head and neck cancer (including head and neck squamous cell carcinoma), (more particularly breast cancer, lung cancer, ovarian cancer, colorectal cancer, malignant pleural mesothelioma, pancreatic cancer, prostate cancer, gastric cancer, esophageal cancer, liver cancer and bone cancer), and wherein the method comprises administering to the subject a therapeutically effective amount of a compound of formula (I) as defined herein or subformulae thereof (Ia), (Ia*), (Ia-1), (Ib), (Ic), (Id), or a pharmaceutically acceptable salt thereof.

In a further embodiment, the invention relates to a method of inhibiting the formation of a YAP/TAZ-TEAD complex in a subject, wherein the method comprises administering to the subject a therapeutically effective amount of a compound of formula (I) or subformulae thereof (Ia), (Ia*), (Ia-1), (Ib), (Ic), (Id) as defined herein, or a pharmaceutically acceptable salt thereof.

In a further embodiment, the invention relates to a method of inhibiting formation of a YAP/TAZ-TEAD complex in a subject, wherein the method comprises administering to the subject a compound of formula (I) or subformulae thereof (Ia), (Ia*), (Ia-1), (Ib), (Ic), (Id) as defined herein, or a pharmaceutically acceptable salt thereof.

DETAILED DESCRIPTION OF THE INVENTION

The invention provides, in a first aspect, a compound of formula (I) or a pharmaceutically acceptable salt thereof,

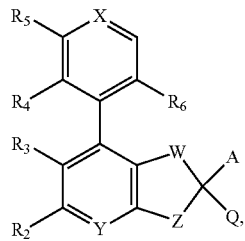
(I)

wherein
W is selected from O; and CH—$R_w$;
X is selected from CH; and N;
Y is selected from CH; and N;
Z is selected from $CH_2$; O; and NH;
wherein when Y is N, W is CH—$R_w$, and Z is O;
A is selected from
- (i) phenyl, which phenyl is optionally substituted with halo; or halo$C_1$-$C_3$alkoxy;
- (ii) a 5- or 6-membered aromatic heterocyclic ring comprising at least one heteroatom selected from N, O, and S, preferably from N and S, which aromatic heterocyclic ring is optionally substituted with hydroxy; $C_1$-$C_3$alkoxy; or oxo; and
- (iii) a halobenzodioxole moiety of formula:

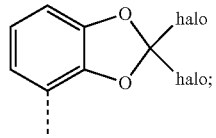

$R_w$ is selected from (i) hydrogen; (ii) hydroxy; (iii) $C_1$-$C_3$alkoxy; (iv) hydroxy$C_1$-$C_3$alkyl; (v) $C_1$-$C_3$alkyl; and (vi) $C_1$-$C_3$alkoxy-$C_1$-$C_3$alkyl;
Q is selected from
- (i) —$C(R^7)_2$—$N(R^8)$—$R_1$;
- (ii) 9- or 10-membered partially saturated heteroaryl comprising at least one N heteroatom; and
- (iii) 4-, 5- or 6-membered saturated heterocyclic ring comprising at least one heteroatom or heteroatom group selected from N, O, S, —S(=O) and —S(=O)$_2$, with the proviso that at least one N heteroatom is present, wherein the heterocyclic ring is unsubstituted or substituted with one or more substituents independently selected from hydroxy, $C_1$-$C_3$alkyl, $C_1$-$C_3$alkoxy, halo and $C_1$-$C_3$alkylene forming a bridge between two ring atoms of the saturated heterocyclic ring, thus forming a bridged bicyclic structure;

$R_1$ is selected from (i) hydrogen; (ii) $C_1$-$C_6$alkyl (wherein the alkyl is in one embodiment optionally deuterated, e.g. perdeuterated; and (iii) $(CH_2)_{0-2}R_{1a}$;

$R_{1a}$ is selected from
- (i) hydroxy$C_1$-$C_4$alkyl;
- (ii) $C_1$-$C_3$alkoxy;
- (iii) a 5- or 6-membered saturated heterocyclic ring comprising at least one heteroatom selected from N and O, which saturated heterocyclic ring is optionally substituted once or more than once independently with $C_1$-$C_3$alkyl; $(CH_2)_{0-1}C(O)di(C_1$-$C_3$alkyl)amino; $SO_2C_1$-$C_3$alkyl; $C(O)C_1$-$C_3$alkyl; or oxo;
- (iv) $C_3$-$C_6$cycloalkyl optionally substituted once or more than once independently with hydroxy; hydroxy$C_1$-$C_4$alkyl; $C_1$-$C_6$alkoxy (preferably $C_1$-$C_4$alkoxy); $C(O)OC_1$-$C_3$alkyl; $CO_2H$; $SO_2C_1$-$C_3$alkyl; halo$C_1$-$C_3$alkyl; $NHR^{1b}$; $(CH_2)_{0-1}C(O)NR^{1c}R^{1d}$(preferably $C(O)NR^{1c}R^{1d}$); $C_1$-$C_6$alkyl; halo$C_1$-$C_3$alkoxy-$C_1$-$C_3$alkyl; halo; a 5- or 6-membered aromatic heterocyclic ring comprising at least one heteroatom selected from N, O, and S; or with two $R^{1e}$ groups,
  wherein the two $R^{1e}$ attached at the same carbon atom form together with the carbon atom to which they are attached a 5-membered saturated heterocyclic ring comprising at least one heteroatom selected from N (which is preferred) and O, or a $C_3$-$C_6$cycloalkyl, which saturated heterocyclic ring or cycloalkyl are optionally substituted with hydroxy or oxo;

$R^{1b}$ is selected from (i) $C(O)C_1$-$C_3$alkyl; and (ii) $SO_2C_1$-$C_3$alkyl;

$R^{1c}$ and $R^{1d}$ are each independently selected from (i) hydrogen; (ii) $C_1$-$C_3$alkyl; and (iii) hydroxy$C_1$-$C_4$alkyl, preferably from (i) hydrogen and (ii) $C_1$-$C_3$alkyl;

$R_2$ is selected from (i) hydrogen; and (ii) halo;

$R_3$ is selected from (i) halo; (ii) halo$C_1$-$C_3$alkyl, especially from halo and mono-, di- or preferably trihalomethyl; and (iii) cyano;

$R_4$ is selected from (i) hydrogen; (ii) halo; and (iii) $C_1$-$C_3$alkyl, especially from hydrogen, halo and methyl;

$R_5$ is selected from
- (i) hydrogen;
- (ii) $C_1$-$C_6$alkoxy optionally substituted with $C_3$-$C_6$cycloalkyl; $CO_2H$; $SO_2C_1$-$C_3$alkyl; a 5- or 6-membered aromatic heterocyclic ring comprising at least one heteroatom selected from N, O, and S, preferably at least one N heteroatom; or a 5- or 6-membered saturated heterocyclic ring comprising at least one heteroatom selected from N and O, which ring is optionally substituted with $C(O)C_1$-$C_3$alkyl;
- (iii) halo;
- (iv) hydroxy$C_1$-$C_6$alkoxy (where the alkoxy part is in one embodiment optionally deuterated, e.g. perdeuterated);
- (v) halo$C_1$-$C_6$alkoxy optionally substituted with hydroxy;
- (vi) S-halo$C_1$-$C_3$alkyl optionally substituted with hydroxy;
- (vii) $C_1$-$C_3$alkoxy$C_1$-$C_3$alkoxy;
- (viii) $NR^{5a}R^{5b}$;
- (ix) $C_1$-$C_3$alkyl;
- (x) a 5- or 6-membered aromatic heterocyclic ring comprising at least one heteroatom selected from N, O, and S, preferably at least one N heteroatom; and
- (xi) hydroxy $R^{5a}$ and $R^{5b}$ are each independently selected from (i) hydrogen; and (ii) $C_1$-$C_3$alkyl;

or $R^{5a}$ and $R^{5b}$ together with the nitrogen atom to which they are attached form a 5- or 6-membered saturated heterocyclic ring, which saturated heterocyclic ring optionally in addition carries a hydroxy group;

$R_6$ is selected from (i) hydrogen; (ii) cyano; (iii) C(O)NHR$^{6a}$; (iv) NHR$^{6b}$; and (v) $C_1$-$C_3$alkoxy substituted with $NH_2$ or hydroxy;

$R^{6a}$ is selected from (i) hydrogen; (ii) $C_1$-$C_3$alkyl; (iii) $C_3$-$C_6$cycloalkyl; (iv) a 5- or 6-membered aromatic heterocyclic ring comprising at least one heteroatom selected from N, O, and S, preferably at least one N heteroatom, which aromatic heterocyclic ring is optionally substituted with $C_1$-$C_3$alkyl;

$R^{6b}$ is $C_1$-$C_3$alkyl substituted with $NH_2$ or hydroxy;

$R^7$ is each independently selected from hydrogen and $C_1$-$C_3$alkyl; and $R^8$ is hydrogen or $C_1$-$C_3$-alkyl, especially hydrogen or methyl.

When $R_2$ is halo, $R_2$ is preferably fluoro. When $R_3$ is halo, $R_3$ is preferably chloro. When $R_4$ is halo, $R_4$ is preferably fluoro. In a preferred embodiment, $R_3$ is chloro and $R_4$ is fluoro. In a more preferred embodiment, $R_2$ is hydrogen or fluoro, $R_3$ is chloro and $R_4$ is fluoro.

In one embodiment of the first aspect of the invention, there is provided a compound of formula (I), wherein Y is CH.

In a further embodiment of the first aspect of the invention, there is provided a compound of formula (I), wherein Y is CH and W is CH—$R_w$.

In a further embodiment of the first aspect of the invention, there is provided a compound of formula (I), wherein Y is CH, W is CH—$R_w$ and Z is O.

The invention provides, in a second aspect, a compound of formula (I) as shown above or a pharmaceutically acceptable salt thereof, wherein W is CH—$R_w$;
X is selected from CH and N;
Y is CH;
Z is selected from O and NH;
A is selected from (i) phenyl, which phenyl is optionally substituted with halo; or halo$C_1$-$C_3$alkoxy;
(ii) a 5- or 6-membered aromatic heterocyclic ring comprising at least one heteroatom selected from N, O, and S, preferably from N and S, which aromatic heterocyclic ring is optionally substituted with hydroxy; $C_1$-$C_3$alkoxy; or oxo; and
(iii) a halobenzodioxole moiety of formula

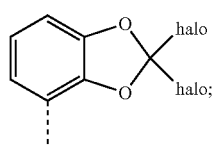

$R_w$ is selected from (i) hydrogen; (ii) hydroxy; (iii) $C_1$-$C_3$alkoxy; (iv) hydroxy-$C_1$-$C_3$alkyl; (v) $C_1$-$C_3$alkyl; and (vi) $C_1$-$C_3$alkoxy-$C_1$-$C_3$alkyl;

Q is selected from (i) —C($R^7$)$_2$—N($R^8$)—$R^1$; (ii) 9- or 10-membered partially saturated heteroaryl comprising at least one N heteroatom, preferably wherein the N is present in the α-positon to the atom binding Q to the rest of the molecule; and (iii) 4-, 5- or 6-membered saturated heterocyclic ring comprising at least one heteroatom selected from N, O and S, with the proviso that at least one N heteroatom is present, preferably wherein the N is present in the α-positon to the atom binding Q to the rest of the molecule, and wherein the heterocyclic ring is unsubstituted or substituted with one or more substituents independently selected from hydroxy, $C_1$-$C_3$alkyl, $C_1$-$C_3$alkoxy, halo and methylene (—$CH_2$—) forming a bridge between two ring atoms of the saturated heterocyclic ring, thus forming a bridged bicyclic structure;

$R_1$ is selected from hydrogen; $C_1$-$C_6$alkyl; and $(CH_2)_{0-2}R_{1a}$ wherein $R_{1a}$ is selected from (i) $C_1$-$C_3$alkoxy; (ii) $C_3$-$C_6$cycloalkyl optionally substituted once or more than once independently with hydroxy; hydroxy$C_1$-$C_4$alkyl; $C_1$-$C_4$alkoxy; C(O)O$C_1$-$C_3$alkyl; $CO_2H$; C(O)NR$^{1c}$R$^{1d}$; $C_1$-$C_6$alkyl; halo; halo$C_1$-$C_3$alkoxy-$C_1$-$C_3$alkyl; $SO_2C_1$-$C_3$alkyl; halo$C_1$-$C_3$alkyl; NHR$^{1b}$; C(O)NR$^{1c}$R$^{1d}$; a 5- or 6-membered aromatic heterocyclic ring comprising at least one heteroatom selected from N, O, and S; or with two $R^{1e}$ groups; wherein the two $R^{1e}$ groups are attached at the same carbon atom and form together with the carbon atom to which they are attached a 5-membered saturated heterocyclic ring comprising at least one heteroatom selected from N (preferred) and O, or a $C_3$-$C_6$cycloalkyl, which saturated heterocyclic ring or cycloalkyl are optionally substituted with hydroxy or oxo; and (iii) a 5- or 6-membered saturated heterocyclic ring comprising at least one heteroatom selected from N and O, which saturated heterocyclic ring is optionally substituted once or more than once independently with $C_1$-$C_3$alkyl; $(CH_2)_{0-1}C(O)di(C_1$-$C_3$alkyl)amino; $SO_2C_1$-$C_3$alkyl; C(O)$C_1$-$C_3$alkyl; or oxo; $R^{1b}$ is selected from C(O)$C_1$-$C_3$alkyl; and $SO_2C_1$-$C_3$alkyl;

$R^{1c}$ and $R^{1d}$ are each independently selected from (i) hydrogen; (ii) $C_1$-$C_3$alkyl; and (iii) hydroxy$C_1$-$C_4$alkyl, $R_2$ is hydrogen or preferably halo, $R_3$ is halo; halo$C_1$-$C_3$alkyl, especially mono-, di- or especially tri-halomethyl; or cyano, $R_4$ is selected from hydrogen; halo; and $C_1$-$C_3$alkyl (which latter is especially methyl), $R_5$ is selected from (i) hydrogen; (ii) halo-$C_1$-$C_6$alkoxy optionally substituted with hydroxy; (iii) S-halo$C_1$-$C_3$alkyl optionally substituted with hydroxy; (iv) $C_1$-$C_3$alkoxy$C_1$-$C_3$alkoxy; (v) $C_1$-$C_6$alkoxy optionally substituted with $SO_2C_1$-$C_3$alkyl, $C_3$-$C_6$cycloalkyl, $CO_2H$ or a 5- or 6-membered saturated heterocyclic ring comprising at least one heteroatom selected from N and O, which ring is optionally substituted with C(O)$C_1$-$C_3$alkyl; (vi) $C_1$-$C_3$alkyl; (vii) hydroxy$C_1$-$C_6$alkoxy; (viii) a 5- or 6-membered aromatic heterocyclic ring comprising at least one heteroatom selected from N, O, and S, preferably at least one N heteroatom; and (ix) hydroxy, $R_6$ is cyano; C(O)NHR$^{6a}$; NHR$^{6b}$; or $C_1$-$C_3$alkoxy substituted with $NH_2$ or hydroxy, $R^{6a}$ is selected from (i) hydrogen; (ii) $C_1$-$C_3$alkyl; (iii) $C_3$-$C_6$cycloalkyl; and (iv) a 5- or 6-membered aromatic heterocyclic ring comprising at least one heteroatom selected from N, O, and S, preferably at least one N heteroatom, which aromatic heterocyclic ring is optionally substituted with $C_1$-$C_3$alkyl;

$R^{6b}$ is $C_1$-$C_3$alkyl substituted with $NH_2$ or hydroxy;

$R^7$ is each independently selected from hydrogen or $C_1$-$C_3$alkyl; and $R^8$ is hydrogen or $C_1$-$C_3$-alkyl, especially hydrogen or methyl.

A third aspect of the invention relates to a compound of the formula (I) as given above, or a pharmaceutically acceptable salt thereof,
wherein
W is CH—$R_w$;
X is selected from CH; and N;
Y is CH;
Z is selected from O and NH;
A is phenyl, which phenyl is optionally substituted with halo; or halo$C_1$-$C_3$alkoxy;
$R_w$ is selected from (i) hydrogen; (ii) $C_1$-$C_3$alkoxy; (iii) hydroxy-$C_1$-$C_3$alkyl; (iv) $C_1$-$C_3$alkyl; and (v) $C_1$-$C_3$alkoxy-$C_1$-$C_3$alkyl;
Q is selected from (i) —C($R^7$)$_2$—NH—$R_1$; and (ii) 4-, 5- or 6-membered saturated heterocyclic ring comprising one or two heteroatoms independently selected from N, O and S, with the proviso that at least one N heteroatom is present, preferably wherein the N is present in the α-positon to the atom binding Q to the rest of the molecule, and wherein the heterocyclic ring is unsubstituted or substituted with one or more substituents independently selected from hydroxy, $C_1$-$C_3$alkyl and halo;
$R_1$ is selected from (i) $C_1$-$C_6$alkyl; and (ii) $R_{1a}$; wherein $R_{1a}$ is selected from $C_3$-$C_6$cycloalkyl optionally substituted once or more than once independently with hydroxy; $C_1$-$C_6$alkyl; or halo;
$R_2$ is hydrogen or preferably halo;
$R_3$ is halo;
$R_4$ is selected from (i) hydrogen; and (ii) halo;
$R_5$ is selected from halo-$C_1$-$C_6$alkoxy, hydroxy, $C_1$-$C_6$alkoxy; and hydroxy$C_1$-$C_6$alkoxy;
$R_6$ is C(O)NH$R^{6a}$;
$R^{6a}$ is selected from (i) hydrogen; and (ii) $C_1$-$C_3$alkyl; and
$R^7$ is each independently selected from hydrogen or $C_1$-$C_3$alkyl.

For the second and third aspect of the invention, especially the following embodiments are preferred:
When $R_2$ is halo, $R_2$ is preferably fluoro. When $R_3$ is halo, $R_3$ is preferably chloro. When $R_4$ is halo, $R_4$ is preferably fluoro. In a preferred embodiment, $R_3$ is chloro and $R_4$ is fluoro. In a more preferred embodiment, $R_2$ is hydrogen or fluoro, $R_3$ is chloro and $R_4$ is fluoro.

In one embodiment of the second or third aspect of the invention, there is provided a compound of formula (I), wherein Y is CH.

In a further embodiment of the second or third aspect of the invention, there is provided a compound of formula (I), wherein Y is CH and W is CH—$R_w$.

In a further embodiment of the second or third aspect of the invention, there is provided a compound of formula (I), wherein Y is CH, W is CH—$R_w$ and Z is O.

The invention provides, in a fourth aspect, a compound of formula (I) or a pharmaceutically acceptable salt thereof, wherein
W is CH—$R_w$;
X is selected from CH; and N;
Y is CH;
Z is selected from O; and NH;
A is phenyl, which phenyl is optionally substituted with halo; or (ii) halo$C_1$-$C_3$alkoxy, especially unsubstituted phenyl;
$R_w$ is selected from (i) hydrogen; (ii) $C_1$-$C_3$alkyl; and (iii) hydroxy-$C_1$-$C_3$alkyl;
Q is selected from (i) —C($R^7$)$_2$—NH—$R_1$; and (ii) 4-, 5- or 6-membered saturated heterocyclic ring comprising one or two heteroatoms independently selected from N and O, with the proviso that at least one N heteroatom is present and is in the α-positon to the carbon atom binding Q to the rest of the molecule, wherein the heterocyclic ring is unsubstituted or substituted with one or more substituents independently selected from hydroxy, $C_1$-$C_3$alkyl and halo;
$R_1$ is selected from (i) $C_1$-$C_6$alkyl; and (ii) $R_{1a}$; wherein $R_{1a}$ is $C_3$-$C_6$cycloalkyl optionally substituted once or more than once independently with hydroxy; $C_1$-$C_6$alkyl; or halo;
$R_2$ is halo, especially fluoro;
$R_3$ is halo, especially chloro;
$R_4$ is halo, especially fluoro;
$R_5$ is selected from $C_1$-$C_6$alkoxy; and hydroxy$C_1$-$C_6$alkoxy;
$R_6$ is C(O)NH$R^{6a}$;
$R^{6a}$ is selected from (i) hydrogen; and (ii) $C_1$-$C_3$alkyl; and
each $R^7$ is hydrogen.

Unless specified otherwise, the terms "compounds of the present invention" or "compounds of the invention" or "compounds of the formula (I)" refer to compounds of formula (I), (Ia), (Ia*), (Ia-1), (Ib), (Ic), (Id) and salts (both preferably pharmaceutically acceptable) thereof, as well as all stereoisomers (including diastereoisomers and enantiomers), atropisomers, rotamers, tautomers, and isotopically labeled compounds (including deuterium substitutions), as well as inherently formed moieties.

In particular, the compounds of formula (Ic) and (Id) are stereospecific atropisomers. The compounds of formula (I), (Ia), (Ia*), (Ia-1), (Ib) include all stereoisomers, including diastereoisomers, atropisomers, enantiomers, mixtures thereof and racemic mixtures. The presence of diastereoisomers can be identified by a person of skill in the art with tools such as NMR. Separation of diastereoisomers can be carried out by a person of skill in the art using chromatographic methods, with tools such as HPLC (High Performance Liquid Chromatography), Thin Layer Chromatography, SFC (Supercritical Fluid Chromatography), GC (Gas Chromatography), or recrystallization techniques. Separation of enantiomers can be carried out by a person of skill in the art with tools such as chiral HPLC, chiral SFC, chiral GC.

Compounds of the present invention, in particular, ortho-substituted biaryl compounds may exhibit conformational, rotational isomerism, herein referred to as atropisomerism (Eliel, E. and Wilen, S. (1994) *Stereochemistry of Organic Compounds*, John Wiley & Sons, Inc., pp. 1142-55). In some instances, depending upon the substituents $R_4$ and $R_6$, such biaryl compounds of the present invention exhibit atropisomerism.

Thus, the compounds of formula (I), and subformulae (Ia), (Ia*), (Ia-1), (Ib), (Ic), (Id) and their isomeric mixtures (including diastereomeric mixtures, enantiomeric mixtures and racemic mixtures), also form part of the invention.

Definitions

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The terms "$C_1$-$C_3$alkyl" and "$C_1$-$C_4$alkyl" are to be construed accordingly. Examples of $C_1$-$C_6$alkyl include, but are not limited to, methyl, ethyl, n-propyl, 1-methylethyl (iso-propyl), n-butyl, n-pentyl, 1,1-dimethylethyl (t-butyl) and hexyl.

In general, unless otherwise indicated herein or otherwise clearly contradicted by context, for substituents comprising two or more subgroups, the last named group is the radical attachment point, for example, "alkylaryl" means a monovalent radical of the formula alkyl-aryl-, while "arylalkyl" means a monovalent radical of the formula arylalkyl-.

As used herein, the term "hydroxy$C_1$-$C_4$alkyl" refers to a radical of formula —$R_a$—OH, wherein $R_a$ is $C_1$-$C_4$alkyl as defined above. Examples of hydroxy$C_1$-$C_4$alkyl include, but are not limited to, hydroxy-methyl, 2-hydroxy-ethyl, 2-hydroxy-propyl and 3-hydroxy-propyl.

As used herein, the term "hydroxy$C_1$-$C_3$alkyl" refers to a radical of formula —$R_a$—OH, wherein $R_a$ is $C_1$-$C_3$alkyl as defined above. Examples of hydroxy$C_1$-$C_3$alkyl include, but are not limited to, hydroxy-methyl, 2-hydroxy-ethyl, 2-hydroxy-propyl and 3-hydroxy-propyl.

As used herein, the term "$C_3$-$C_6$cycloalkyl" refers to a saturated monocyclic hydrocarbon group of 3-6 carbon atoms. Examples of $C_3$-$C_6$cycloalkyl include cyclopropyl, cyclobutyl, cyclopentyl and cyclohexyl.

As used herein, the term "$C_1$-$C_6$alkoxy" refers to a radical of the formula —ORa where $R_a$ is a $C_1$-$C_6$alkyl radical as generally defined above. The terms "$C_1$-$C_3$alkoxy" and "$C_1$-$C_4$alkoxy" are to be construed accordingly. Examples of $C_1$-$C_6$alkoxy include, but are not limited to, methoxy, ethoxy, propoxy, isopropoxy, butoxy, isobutoxy, pentoxy, and hexoxy.

As used herein, the term "$C_1$-$C_3$-alkoxy-$C_1$-$C_3$alkyl" refers to a $C_1$-$C_3$-alkyl radical as defined above, wherein one of the hydrogen atoms of the $C_1$-$C_3$-alkyl radical is replaced by $C_1$-$C_3$-alkoxy.

"Halogen" or "halo" refers to fluoro, chloro, bromo or iodo. Preferably, halo is fluoro, chloro or bromo. More preferably, halo is fluoro or chloro.

The term "oxo" refers to the radical =O.
The term "sulfonyl" refers to the radical —S(=O)$_2$—.
The term "amino" refers to the radical —NH$_2$.
The term "NHR$^{1b}$" refers to the radical —N(H)R$^{1b}$. Similarly, a term such as "NR$^{5a}$R$^{5b}$" refers to the radical —N(R$^{5a}$)R$^{5b}$.

As used herein, the term "halogen$C_1$-$C_3$alkyl" or "halo$C_1$-$C_3$alkyl" refers to a $C_1$-$C_3$alkyl radical, as defined above, substituted with one or more halo radicals, as defined above. Examples of halogen$C_1$-$C_3$alkyl include, but are not limited to, trifluoromethyl, difluoromethyl, fluoromethyl, trichloromethyl, 1,1-difluoroethyl, 2,2-difluoroethyl, 2,2,2-trifluoroethyl, 2-fluoropropyl, 3,3-difluoropropyl and 1-fluoromethyl-2-fluoroethyl.

As used herein, the term "halo$C_1$-$C_6$alkoxy" refers to $C_1$-$C_6$alkoxy as defined above, wherein at least one of the hydrogen atoms of the $C_1$-$C_6$alkoxy radical is substituted with a halo radical, as defined above. The term "halo$C_1$-$C_3$alkoxy" is to be construed accordingly. Examples of halo$C_1$-$C_6$alkoxy include, but are not limited to, trifluoromethoxy, difluoromethoxy, trifluoroethoxy, 2-fluoropropoxy, 3,3-difluoropropoxy.

As used herein, the term "hydroxy$C_1$-$C_6$alkoxy" refers to a $C_1$-$C_6$alkoxy radical as defined above, wherein at least one of the hydrogen atoms of the $C_1$-$C_6$alkoxy radical is replaced by OH. The term "hydroxy$C_1$-$C_3$alkoxy is to be construed accordingly. Examples of hydroxy$C_1$-$C_6$alkoxy include, but are not limited to, hydroxymethoxy, hydroxyethoxy, 2-hydroxypropoxy.

As used herein, the term "$C_1$-$C_3$alkoxy$C_1$-$C_3$alkoxy" refers to a $C_1$-$C_3$alkoxy radical as defined above, wherein one of the hydrogen atoms of the $C_1$-$C_3$alkoxy radical is replaced by —O—$C_1$-$C_3$alkyl. An example of $C_1$-$C_3$alkoxy$C_1$-$C_3$alkoxy includes, but is not limited to, 2-methoxyethoxy.

As used herein, the term "halo$C_1$-$C_3$alkoxy-$C_1$-$C_3$alkyl" refers to a $C_1$-$C_3$alkyl radical as defined above, wherein one of the hydrogen atoms of the $C_1$-$C_3$alkyl radical is replaced by halo$C_1$-$C_3$alkoxy as defined above. Examples of halo$C_1$-$C_3$alkoxy-$C_1$-$C_3$alkyl include, but are not limited to (difluoromethoxy)methyl (i.e. CHF$_2$—O—CH$_2$—).

As used herein, the term "C(O)NR$^{1c}$R$^{1d}$" refers to a radical of the formula —$R_{a1}$-N($R_{a2}$)$_2$ where $R_{a1}$ is a carbonyl radical and each $R_{a2}$ is a R$^{1c}$ or a R$^{1d}$ radical, each of which may be the same or different, as defined herein.

As used herein, the term "C(O)di($C_1$-$C_3$alkyl)amino" refers to a radical of the formula —$R_{a1}$—N($R_{a2}$)$_2$ where $R_{a1}$ is a carbonyl radical and each $R_{a2}$ is a $C_1$-$C_3$alkyl as defined herein, and each may be the same or different.

As used herein, the term "C(O)$C_1$-$C_3$alkyl" refers to a radical of the formula —$R_{a1}$—$C_1$-$C_3$alkyl where $R_{a1}$ is a carbonyl radical and $C_1$-$C_3$alkyl is as defined above.

As used herein, the term "C(O)NHR$^{6a}$" refers to a radical of the formula —$R_{a1}$—N(H)—R$^{6a}$ where $R_{a1}$ is a carbonyl radical and R$^{6a}$ is as defined herein.

As used herein, the term "S-halo$C_1$-$C_3$alkyl" refers to a radical of the formula —S-halo$C_1$-$C_3$alkyl where halo$C_1$-$C_3$alkyl is as defined above.

As used herein, the term "C(O)O$C_1$-$C_3$alkyl" refers to a radical of the formula —$R_{a1}$—O—$C_1$-$C_3$alkyl where $R_{a1}$ is a carbonyl radical and $C_1$-$C_3$alkyl is as defined above.

As used herein, the term "SO$_2$$C_1$-$C_3$alkyl" refers to a radical of the formula —S(=O)$_2$—$R_{a2}$ where $R_{a2}$ is a $C_1$-$C_3$alkyl as defined above.

The term "$C_1$-$C_3$alkylene" as used herein refers to a straight or branched hydrocarbon chain bivalent radical consisting solely of carbon and hydrogen atoms, containing no unsaturation, and having from one to three carbon atoms. In embodiments whereby the 4-, 5- or 6-membered saturated heterocyclic ring of Q (or $Q_1$) is substituted with a $C_1$-$C_3$alkylene forming a bridge between two ring atoms of the saturated heterocyclic ring, thus forming a bridged bicyclic structure, the $C_1$-$C_3$alkylene is preferably propylene (—CH$_2$—CH$_2$—CH$_2$—), ethylene (—CH$_2$—CH$_2$—) or methylene (—CH$_2$—).

The term "(CH$_2$)$_{0-2}$R$_{1a}$" refers to a radical of the formula —(CH$_2$)$_{0-2}$R$_{1a}$, i.e., the radical R$_{1a}$ is attached to the rest of the molecule via a bond, a methylene linker or an ethylene linker.

The term "(CH$_2$)$_{0-1}$C(O)di($C_1$-$C_3$alkyl)amino" refers to a radical of the formula —(CH$_2$)$_{0-1}$-$R_{a3}$ and $R_{a3}$ is a C(O)di($C_1$-$C_3$alkyl)amino radical as defined above.

The term (CH$_2$)$_{0-1}$C(O)NR$^{1c}$R$^{1d}$ refers to a radical of the formula —(CH$_2$)$_{0-1}$C(O)NR$^{1c}$R$^{1d}$.

As used herein, the term "5- or 6-membered saturated heterocyclic ring comprising at least one heteroatom selected from N and O" refers to a monocyclic ring and includes, but is not limited to, piperazinyl, piperidyl, pyrrolidinyl, tetrahydrofuryl, tetrahydropyranyl, dioxanyl and morpholinyl. Preferably this term includes piperidyl, pyrrolidinyl, tetrahydrofuryl, tetrahydropyranyl and morpholinyl. The terms "5-membered saturated heterocyclic ring comprising at least one heteroatom selected from N and O" and "6-membered saturated heterocyclic ring comprising at least one heteroatom selected from N and O" are to be construed accordingly.

As used herein, the term "4-, 5- or 6-membered saturated heterocyclic ring comprising at least one heteroatom or heteroatom group selected from N, O, S, —S(=O) and —S(=O)₂," refers to a monocyclic ring and includes, but is not limited to, azetidinyl, pyrrolidinyl, piperidinyl, piperazinyl, morpholinyl, thiomorpholinyl, S-oxo-thiomorpholinyl or S,S-dioxothiomorpholinyl. For the avoidance of doubt, in certain embodiments whereby the N is present in the α-positon to the atom binding Q to the rest of the molecule, this may be represented by the following formula

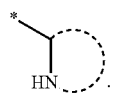

As used herein, the term "5- or 6-membered aromatic heterocyclic ring comprising at least one heteroatom selected from N, O, or S, preferably from N or S" refers to a monocyclic aromatic ring. Examples of this term include but are not limited to oxazolyl, isozaolyl, pyrimidinyl, pyridazinyl, tetrazolyl, pyrazinyl, triazolyl, imidazolyl, pyrazolyl, pyridinyl and thiazolyl.

As used herein, the term "5- or 6-membered aromatic heterocyclic ring comprising at least one heteroatom selected from N, O, and S" refers to an aromatic monocyclic ring and includes, but is not limited to, pyrimidinyl, pyridazinyl, tetrazolyl, pyrazinyl, triazolyl, imidazolyl, pyrazolyl, pyridinyl, oxazolyl, and thiazolyl. The point of attachment to the imidazolyl ring is preferably to the nitrogen atom of the imidazolyl ring.

As used herein, the term "5- or 6-membered aromatic heterocyclic ring comprising at least one heteroatom selected from N and S" refers to a monocyclic aromatic ring and includes, but is not limited to, pyrimidinyl, pyridazinyl, tetrazolyl, pyrazinyl, triazolyl, imidazolyl, pyrazolyl, pyridinyl and thiazolyl.

As used herein, the term "6-membered aromatic heterocyclic ring comprising at least one N heteroatom" refers to a monocyclic aromatic ring and includes, but is not limited to, pyrimidinyl, pyridazinyl, pyrazinyl and pyridinyl.

As used herein, the term "5-membered aromatic heterocyclic ring comprising at least one N heteroatom" (where N may also be NH) refers to a monocyclic aromatic ring and includes, but is not limited to, tetrazolyl, triazolyl, imidazolyl, pyrazolyl.

As used herein, the term "5- or 6-membered aromatic heterocyclic ring comprising at least one N heteroatom" refers to a monocyclic aromatic ring and includes, but is not limited to, pyrimidinyl, pyridazinyl, tetrazolyl, pyrazinyl, triazolyl, imidazolyl, pyrazolyl and pyridinyl.

As used herein, the aromatic heterocyclic ring in the substituent defined as "5- or 6-membered aromatic heterocyclic ring comprising at least one heteroatom selected from N, O, or S, preferably from N or S" may be optionally substituted with hydroxy; $C_1$-$C_3$alkoxy; or oxo.

It will be understood that substitution of said aromatic heterocycle with oxo is meant to include 5- or 6-membered rings in which an aromatic tautomer exists, as for example in the 1H-pyridin-2-one system (see for example Example 92).

As used herein, the term "5- or 6-membered saturated heterocyclic ring" in relation to the embodiments where $R^{5a}$ and $R^{5b}$ together with the N atom (where N may also be NH) to which they are attached form said ring, includes as examples, but is not limited to, an azetidinyl ring, a pyrrolidine ring, or a piperidine ring.

As used herein, the term "9- or 10-membered partially saturated heteroaryl comprising at least one N heteroatom" refers to a partially saturated aromatic bicyclic heterocyclic ring system whereby a 5- or 6-membered heterocyclic ring containing one N heteroatom, is fused with a benzene ring or a heteroaromatic ring. In certain embodiments whereby the N is present in the α-positon to the atom binding Q to the rest of the molecule, this may be represented by the following formula

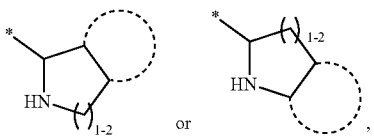

whereby the dashed ring represents the benzo or heteroaryl ring. Representative examples are indolinyl, isoindolinyl, tetrahydroquinolinyl, tetrahydroisoquinolinyl, and the like. Preferably, it is

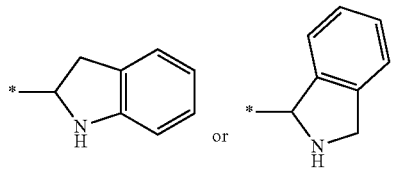

As used herein, the term "optionally substituted" includes unsubstituted or substituted.

As used herein, the term "more than once" includes 2, 3, 4, 5, or 6 times. Preferably, it includes 2 or 3 times.

As used herein, the term "more than one" includes 2, 3, 4, 5, or 6. Preferably, it includes 2 or 3.

As used herein, the term "at least one heteroatom" includes 1, 2, 3, 4 or 5, preferably 1, 2, 3 or 4, more preferably 1 or 2 heteroatoms.

The use of any and all examples, or exemplary language (e.g. "such as" or "preferably") provided herein is intended merely to better illuminate the invention and does not pose a limitation on the scope of the invention otherwise claimed.

As used herein, the term nitrogen protecting group (PG) in a compound of formula (IV) and subformulae thereof refers to a group that should protect the functional groups concerned against unwanted secondary reactions, such as acylations, etherifications, esterifications, oxidations, solvolysis and similar reactions. It may be removed under deprotection conditions. Depending on the protecting group employed, the skilled person would know how to remove the protecting group to obtain the free amine $NH_2$ group by reference to known procedures. These include reference to organic chemistry textbooks and literature procedures such as J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; in "The Peptides"; Volume 3 (editors: E. Gross and J. Meienhofer), Academic Press, London and New York 1981, and in "Methoden der organischen Chemie" (Methods of Organic Chemistry), Houben Weyl, 4th edition, Volume 15/I, Georg Thieme Verlag, Stuttgart 1974 and later editions thereof.

Preferred nitrogen protecting groups generally comprise: $C_1$-$C_6$alkyl (e.g. tert-butyl), preferably $C_1$-$C_4$alkyl, more preferably $C_1$-$C_2$alkyl, most preferably $C_1$alkyl which is mono-, di- or trisubstituted with trialkylsilyl-$C_1$-$C_7$alkoxy (eg. trimethylsilyethoxy), aryl, preferably phenyl, or a heterocyclic group (e.g., benzyl, cumyl, benzhydryl, pyrrolidinyl, trityl, pyrrolidinylmethyl, 1-methyl-1,1-dimethylbenzyl, (phenyl)methylbenzene) wherein the aryl ring or the heterocyclic group is unsubstituted or substituted with one or more, e.g. two or three, residues, e.g. selected from the group consisting of $C_1$-$C_7$alkyl, hydroxy, $C_1$-$C_7$alkoxy (e.g. para-methoxy benzyl (PMB)), $C_2$-$C_a$-alkanoyl-oxy, halogen, nitro, cyano, and $CF_3$, aryl-$C_1$-$C_2$-alkoxycarbonyl (preferably phenyl-$C_1$-$C_2$-alkoxycarbonyl (eg. benzyloxycarbonyl (Cbz), benzyloxymethyl (BOM), pivaloyloxymethyl (POM)), $C_1$-$C_{10}$-alkenyloxycarbonyl, $C_1$-$C_6$alkylcarbonyl (eg. acetyl or pivaloyl), $C_6$-$C_{10}$-arylcarbonyl; $C_1$-$C_6$-alkoxycarbonyl (eg. tertbutoxycarbonyl (Boc), methylcarbonyl, trichloroethoxycarbonyl (Troc), pivaloyl (Piv), allyloxycarbonyl), $C_6$-$C_{10}$-aryl$C_1$-$C_6$-alkoxycarbonyl (e.g. 9-fluorenylmethyloxycarbonyl (Fmoc)), allyl or cinnamyl, sulfonyl or sulfenyl, succinimidyl group, silyl groups (e.g. triarylsilyl, trialkylsilyl, triethylsilyl (TES), trimethylsilylethoxymethyl (SEM), trimethylsilyl (TMS), triisopropylsilyl or tertbutyldimethylsilyl).

According to the disclosure, the preferred protecting group (PG) can be selected from the group comprising tert-butyloxycarbonyl (Boc), benzyloxycarbonyl (Cbz), para-methoxy benzyl (PMB), methyloxycarbonyl and benzyl. The protecting group (PG) is preferably tert-butyloxycarbonyl (Boc).

The term "phenyl" refers to a radical of the formula —$C_6H_5$.

The term "halobenzodioxole" refers to a 1,3-benzodioxole radical of the formula

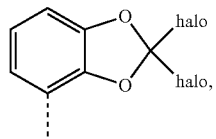

wherein halo is as defined above. Preferably, both halo groups are fluoro.

The term "stereoisomer" or "stereoisomers" refer to compounds, which have identical chemical constitution, but differ with regard to the arrangement of the atoms or groups in space.

The term "diastereoisomer" or "diastereomer" refers to stereoisomers not related as mirror images. Diastereoisomers are characterized by differences in physical properties, and by some differences in chemical behaviour. Mixtures of diastereomers may separate under analytical procedures such as chromatography or crystallisation.

The term "enantiomer" refers to one of a pair of molecular entities which are mirror images of each other and non-superimposable.

The term "enantiomeric mixture" refers to an enantiomerically enriched mixture, a composition that comprises a greater proportion or percentage of one of the enantiomers of the compounds of the invention, in relation to the other enantiomer, or a racemate.

The term "diastereomeric mixture" refers to a diastereomerically enriched mixture or a mixture of diastereoisomers of equal proportion.

The term "diastereomerically enriched" refers to a composition that comprises a greater proportion or percentage of one of the diastereomers of the compounds of the invention, in relation to the other diastereoisomer(s).

The term "atropisomer" refers to a stereoisomer resulting from restricted rotation about single bonds where the rotation barrier is high enough to permit isolation of the isomeric species.

Typically, rotation about the single bond in the molecule is prevented, or greatly slowed, as a result of steric interactions with other parts of the molecule and the substituents at both ends of the single bond are asymmetrical, resulting in a stereogenic unit termed a "chiral axis".

As used herein, the term "YAP" refers to yes-associated protein, also known as YAP1 or YAP65.

Whenever YAP is mentioned herein it can also refer to the YAP/TAZ complex.

As used herein, the term "YAP/TAZ-TEAD" refers to the complex of YAP/TAZ with TEAD transcription factor.

As used herein, the term "NF2/LATS1/LATS2" refers to "NF2", "LATS1", or "LATS2" or any combinations thereof.

As used herein, the term "pharmaceutically acceptable carrier" includes any one or more selected from all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by YAP/TAZ-TEAD protein-protein interaction (PPI), or (ii) associated with YAP/TAZ-TEAD PPI activity, or (iii) characterized by activity of YAP/TAZ-TEAD PPI, or (2) reduce or inhibit the activity of YAP/TAZ-TEAD PPI; or (3) reduce or inhibit the expression of YAP/TAZ-TEAD. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of YAP/TAZ-TEAD PPI.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

Where compound names have a * designated beside the stereochemical configuration, e.g. in the name; N1-(2-((2S*, 4S*)-2-(Aminomethyl)-5-chloro-2-phenyl-2,3-dihydrobenzofuran-4-yl)-3-fluorophenyl)ethane-1,2-diamine (example 2a), this refers to a racemic mixture of both enantiomers, i.e. N1-(2-((2S,4S)-2-(Aminomethyl)-5-chloro-2-phenyl-2,3-dihydrobenzofuran-4-yl)-3-fluorophenyl)ethane-1,2-diamine and N1-(2-((2R,4R)-2-(Aminomethyl)-5-chloro-2-phenyl-2,3-dihydrobenzofuran-4-yl)-3-fluorophenyl)ethane-1,2-diamine, respectively. The name; N1-(2-((2S*, 4R*)-2-(Aminomethyl)-5-chloro-2-phenyl-2,3-dihydrobenzofuran-4-yl)-3-fluorophenyl)ethane-1,2-diamine (example 2b) is to be construed accordingly.

Where compound structures are drawn with undefined absolute stereochemistry, for example, as in example 2a (no wedged bonds) this means a racemic mixture of a single diastereoisomer with the indicated relative stereochemistry.

For the avoidance of doubt, where compounds are drawn with a wedged bond, for instance Example 2a-1, this means a single diastereomer with the absolute stereochemistry as indicated in the chemical structure. Thus the compound of Example 2a-1 with the structure as shown below,

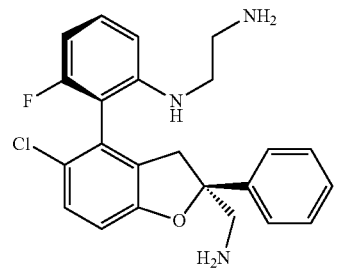

Example 2a-1 is the compound N1-(2-((2S,4S)-2-(Aminomethyl)-5-chloro-2-phenyl-2,3-dihydrobenzofuran-4-yl)-3-fluorophenyl)ethane-1,2-diamine.

Compounds of the invention may also be named using the Cahn-Ingold-Prelog (CIP) helicity rule, with stereodescriptors (P) or (M) *Nomenclature of Organic Chemistry: IUPAC Recommendations and Preferred Names* 2013 (the IUPAC "Blue Book"), Cambridge, UK: Royal Soc. of Chem., 2014, https://doi.org/10.1039/9781849733069, Chapter P-9, "Specification of Configuration and Conformation", https://doi.org/10.1039/9781849733069-01156).

The stereodescriptors "cis" and "trans" can be used to describe the relative configuration of the substituents on the cycloalkyl ring of compounds exemplified herein which bear a disubstituted 1,4-cyclohexyl or a 1,3-cyclobutyl moiety. The stereodescriptors "cis" or "trans" describe the relative arrangement of the substituents of highest CIP priority on each of the two substituted positions of the cycloalkyl ring. For instance, in the case of Example 114a, the stereodescriptor "trans" means that the hydroxyl and the amine group on the cyclohexyl ring are located on opposite sides of the plane of the cyclohexyl ring; whereas in the case of Example 114b the stereodescriptor "cis" means that the hydroxyl and the amine group are located on the same side of the plane of the cyclohexyl ring.

Example 114a: 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide

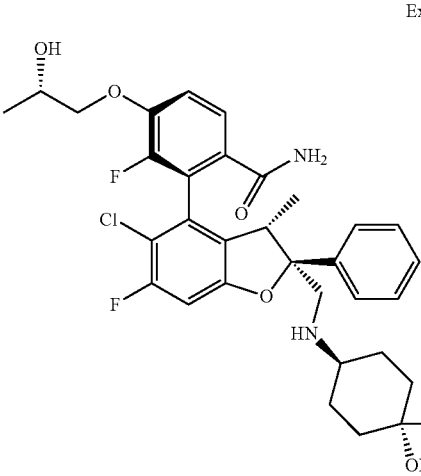

Example 114a

Example 114b: 2-((2S,3S,4S)-5-chloro-6-fluoro-2-((((cis)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide Example 114b

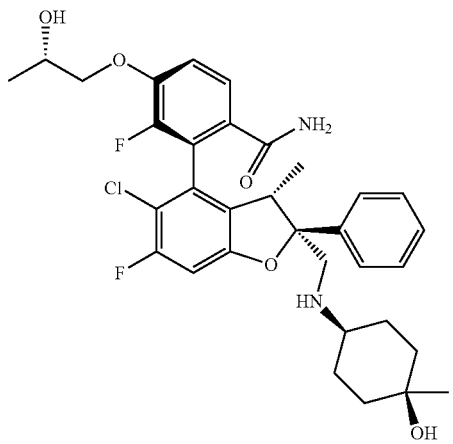

Alternatively, the following names of the compounds of Example 114a and Example 114b may be used:

Example 114a: (2P)-2-[(2S,3S)-5-Chloro-6-fluoro-2-({[(1r,4S)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]benzamide Example 114b: (2P)-2-[(2S,3S)-5-Chloro-6-fluoro-2-({[(1s,4R)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]benzamide Where the stereocentre at the 2-position on the dihydrobenzofuran ring of compounds of the present invention is drawn as depicted below (that is, with wedged bonds)

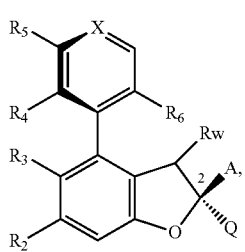

this can also be represented as

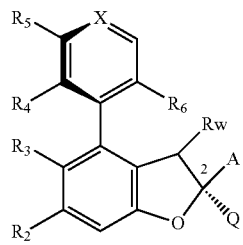

or as

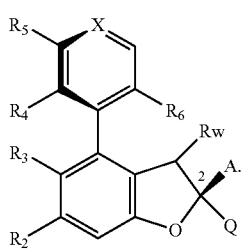

It will thus be understood that, where applicable, the stereochemistry at that position of the compounds of the present invention may be drawn either with a plain bond to the "A" or "Q" substituent or with a wedged bond to the "A" substituent or "Q" substituent.

In an embodiment of the first, second, third or fourth aspect of the invention, there is provided a compound of formula (Ia) or a pharmaceutically acceptable salt thereof

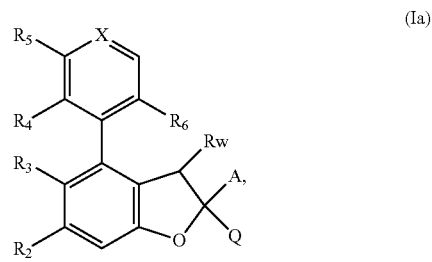

(Ia)

wherein the substituents are defined as above in the first, second, third or fourth embodiment of the invention.

In a preferred embodiment, A is a phenyl ring.

In a further embodiment of the first, second, third or fourth aspect of the invention, there is provided a compound of formula (Ia*) or a pharmaceutically acceptable salt thereof

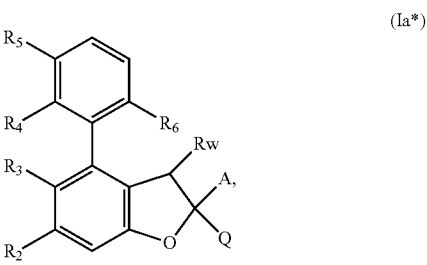

(Ia*)

wherein the substituents are defined as above in the first, second, third or fourth embodiment of the invention.

When $R_2$ is halo, $R_2$ is preferably fluoro. When $R_3$ is halo, $R_3$ is preferably chloro. When $R_4$ is halo, $R_4$ is preferably fluoro. In a preferred embodiment, $R_3$ is chloro and $R_4$ is fluoro. In a more preferred embodiment, $R_2$ is fluoro, $R_3$ is chloro and $R_4$ is fluoro.

In a preferred embodiment, A is a phenyl ring.

In another embodiment of the first, second, third or fourth aspect of the invention, there is provided a compound of formula (Ia-1) or a pharmaceutically acceptable salt thereof

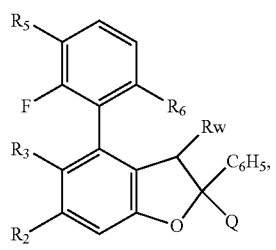

(Ia-1)

wherein the substituents are defined as above in the first, second, third or fourth embodiment of the invention.

In another embodiment of the first, second, third or fourth aspect of the invention, there is provided a compound of formula (Ia-1) or a pharmaceutically acceptable salt thereof

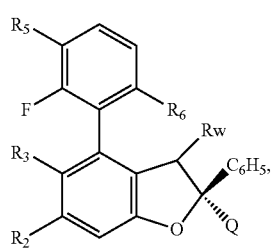

(Ia-1)

wherein the substituents are defined as above in the first, second, third or fourth embodiment of the invention.

When $R_2$ is halo, $R_2$ is preferably fluoro. When $R_3$ is halo, $R_3$ is preferably chloro. In a preferred embodiment, $R_3$ is chloro. In a more preferred embodiment, $R_2$ is fluoro and $R_3$ is chloro.

In another embodiment of the first, second, third or fourth aspect of the invention, there is provided a compound of formula (Ib) or a pharmaceutically acceptable salt thereof

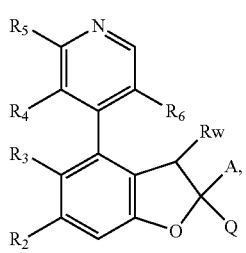

(Ib)

wherein the substituents are defined as above in the first, second, third or fourth embodiment of the invention.

In a preferred embodiment, A is a phenyl ring.

In a further embodiment of the first, second, third or fourth aspect of the invention there is provided a compound of formula (Ic) or a pharmaceutically acceptable salt thereof

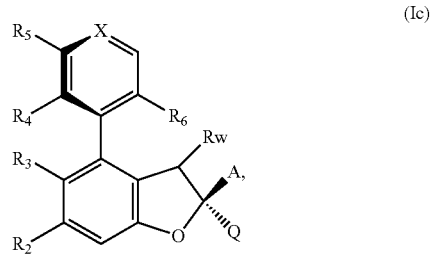

(Ic)

wherein the substituents are defined as above in the first, second, third or fourth embodiment of the invention and preferably $R_3$ and $R_4$ have a meaning other than hydrogen, as disclosed for the respective invention aspect.

In a preferred embodiment, A is a phenyl ring.

In another embodiment, A is a phenyl ring and X is CH.

In another embodiment, A is a phenyl ring and X is N.

In a further embodiment of the first, second, third or fourth aspect of the invention there is provided a compound of formula (Id) or a pharmaceutically acceptable salt thereof

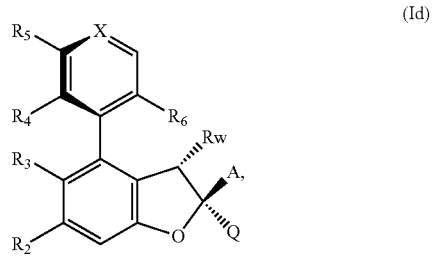

(Id)

wherein the substituents are defined as above in the first, second, third or fourth embodiment of the invention and preferably $R_3$ and $R_4$ have a meaning other than hydrogen, as disclosed for the respective invention aspect.

In a preferred embodiment, A is a phenyl ring.

In another embodiment, A is a phenyl ring and X is CH.

In another embodiment, A is a phenyl ring and X is N.

Various enumerated embodiments of the invention are described herein. It will be recognized that features specified in each embodiment may be combined with single, more than one or all other specified features to provide further embodiments of the present invention.

Embodiment 1. A compound of formula (I), or a pharmaceutically acceptable salt thereof,

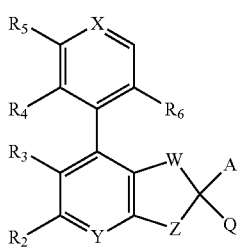

(I)

wherein
W is selected from O; and CH—$R_w$;
X is selected from CH; and N;
Y is selected from CH; and N;
Z is selected from $CH_2$; O; and NH;
wherein when Y is N, W is CH—$R_w$, and Z is O;
A is selected from
(i) phenyl, which phenyl is optionally substituted with halo; or halo$C_1$-$C_3$alkoxy;
(ii) a 5- or 6-membered aromatic heterocyclic ring comprising at least one heteroatom selected from N, O, and S, preferably from N and S, which aromatic heterocyclic ring is optionally substituted with hydroxy; $C_1$-$C_3$alkoxy; or oxo; and
(iii) a halobenzodioxole moiety of formula

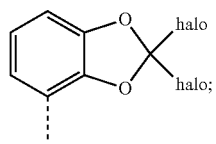

$R_w$ is selected from (i) hydrogen; (ii) hydroxy; (iii) $C_1$-$C_3$alkoxy; (iv) hydroxy-$C_1$-$C_3$alkyl; (v) $C_1$-$C_3$alkyl; and (vi) $C_1$-$C_3$alkoxy-$C_1$-$C_3$alkyl;
Q is selected from (i) —$C(R^7)_2$—$N(R^8)$—$R_1$; (ii) 9- or 10-membered partially saturated heteroaryl comprising at least one N heteroatom; and (iii) 4-, 5- or 6-membered saturated heterocyclic ring comprising at least one heteroatom or heteroatom group selected from N, O, S, —S(=O) and —S(=O)$_2$, with the proviso that at least one N heteroatom is present, wherein the heterocyclic ring is unsubstituted or substituted with one or more substituents independently selected from hydroxy, $C_1$-$C_3$alkyl, $C_1$-$C_3$alkoxy, halo and $C_1$-$C_3$alkylene forming a bridge between two ring atoms of the saturated heterocyclic ring, thus forming a bridged bicyclic structure;
$R_1$ is selected from (i) hydrogen; (ii) $C_1$-$C_6$alkyl (wherein the alkyl is in one embodiment optionally deuterated, e.g. perdeuterated); and (iii) $(CH_2)_{0-2}R_{1a}$;
$R_{1a}$ is selected from (i) hydroxy$C_1$-$C_4$alkyl; (ii) $C_1$-$C_3$alkoxy; (iii) a 5- or 6-membered saturated heterocyclic ring comprising at least one heteroatom selected from N and O, which saturated heterocyclic ring is optionally substituted once or more than once independently with $C_1$-$C_3$alkyl; $(CH_2)_{0-1}C(O)di(C_1$-$C_3$alkyl)amino; $SO_2C_1$-$C_3$alkyl; $C(O)C_1$-$C_3$alkyl; or oxo; (iv) $C_3$-$C_6$cycloalkyl optionally substituted once or more than once independently with hydroxy; hydroxy$C_1$-$C_4$alkyl; $C_1$-$C_6$alkoxy, preferably $C_1$-$C_4$alkoxy; $C(O)OC_1$-$C_3$alkyl; $CO_2H$; $SO_2C_1$-$C_3$alkyl; halo$C_1$-$C_3$alkyl; $NHR^{1b}$; $(CH_2)_{0-1}C(O)$ $NR^{1c}R^{1d}$, preferably $C(O)NR^{1c}R^{1d}$; $C_1$-$C_6$alkyl; halo$C_1$-$C_3$alkoxy-$C_1$-$C_3$alkyl; halo; a 5- or 6-membered aromatic heterocyclic ring comprising at least one heteroatom selected from N, O, and S; or with two $R^{1e}$ groups,
wherein the two $R^{1e}$ attached at the same carbon atom form together with the carbon atom to which they are attached a 5-membered saturated heterocyclic ring comprising at least one heteroatom selected from N (which is preferred) and O, or a $C_3$-$C_6$cycloalkyl, which saturated heterocyclic ring or cycloalkyl are optionally substituted with hydroxy or oxo;
$R^{1b}$ is selected from (i) $C(O)C_1$-$C_3$alkyl; and (ii) $SO_2C_1$-$C_3$alkyl;
$R^{1c}$ and $R^{1d}$ are each independently selected from (i) hydrogen; (ii) $C_1$-$C_3$alkyl; and (iii) hydroxy$C_1$-$C_4$alkyl, preferably from (i) hydrogen and (ii) $C_1$-$C_3$alkyl;
$R_2$ is selected from (i) hydrogen; and (ii) halo;
$R_3$ is selected from (i) halo; (ii) halo$C_1$-$C_3$alkyl, especially from halo and mono-, di- or preferably trihalomethyl; and (iii) cyano;
$R_4$ is selected from (i) hydrogen; (ii) halo; and (iii) $C_1$-$C_3$alkyl, especially from hydrogen, halo and methyl;
$R_5$ is selected from (i) hydrogen; (ii) $C_1$-$C_6$alkoxy optionally substituted with $C_3$-$C_6$cycloalkyl; $CO_2H$; $SO_2C_1$-$C_3$alkyl; a 5- or 6-membered aromatic heterocyclic ring comprising at least one heteroatom selected from N, O, and S, preferably at least one N heteroatom; or a 5- or 6-membered saturated heterocyclic ring comprising at least one heteroatom selected from N and O, which ring is optionally substituted with $C(O)C_1$-$C_3$alkyl;
(iii) halo; (iv) hydroxy$C_1$-$C_6$alkoxy (where the alkoxy part is in one embodiment optionally deuterated, e.g. perdeuterated); (v) halo$C_1$-$C_6$alkoxy optionally substituted with hydroxy; (vi) S-halo$C_1$-$C_3$alkyl optionally substituted with hydroxy; (vii) $C_1$-$C_3$alkoxy$C_1$-$C_3$alkoxy; (viii) $NR^{5a}R^{5b}$; (ix) $C_1$-$C_3$alkyl; (x) a 5- or 6-membered aromatic heterocyclic ring comprising at least one heteroatom selected from N, O, and S, preferably at least one N heteroatom; and (xi) hydroxy
$R^{5a}$ and $R^{5b}$ are each independently selected from (i) hydrogen; and (ii) $C_1$-$C_3$alkyl; or
$R^{5a}$ and $R^{5b}$ together with the nitrogen atom to which they are attached form a 5- or 6-membered saturated heterocyclic ring, which saturated heterocyclic ring optionally in addition carries a hydroxy group;
$R_6$ is selected from (i) hydrogen; (ii) cyano; (iii) $C(O)$ $NHR^{6a}$; (iv) $NHR^{6b}$; and (v) $C_1$-$C_3$alkoxy substituted with $NH_2$ or hydroxy;
$R^{6a}$ is selected from (i) hydrogen; (ii) $C_1$-$C_3$alkyl; (iii) $C_3$-$C_6$cycloalkyl; (iv) a 5- or 6-membered aromatic heterocyclic ring comprising at least one heteroatom selected from N, O, and S, preferably at least one N heteroatom, which aromatic heterocyclic ring is optionally substituted with $C_1$-$C_3$alkyl;
$R^{6b}$ is $C_1$-$C_3$alkyl substituted with $NH_2$ or hydroxy;
$R^7$ is each independently selected from hydrogen and $C_1$-$C_3$alkyl; and
$R^8$ is hydrogen or $C_1$-$C_3$-alkyl, especially hydrogen or methyl.

Embodiment 2. A compound of formula (I) according to embodiment 1, or a pharmaceutically acceptable salt thereof,
W is CH—$R_w$;
X is selected from CH; and N;
Y is CH;
Z is selected from O, and NH;

A is selected from
(i) phenyl, which phenyl is optionally substituted with halo; or haloC$_1$-C$_3$alkoxy;
(ii) a 5- or 6-membered aromatic heterocyclic ring comprising at least one heteroatom selected from N, O, and S, preferably from N and S, which aromatic heterocyclic ring is optionally substituted with hydroxy; C$_1$-C$_3$alkoxy; or oxo; and
(iii) a halobenzodioxole moiety of formula

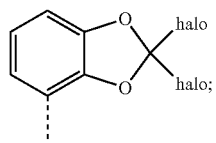

R$_w$ is selected from (i) hydrogen; (ii) hydroxy; (iii) C$_1$-C$_3$alkoxy; (iv) hydroxy-C$_1$-C$_3$alkyl; (v) C$_1$-C$_3$alkyl; and (vi) C$_1$-C$_3$alkoxy-C$_1$-C$_3$alkyl; Q is selected from (i) —C(R$^7$)$_2$—N(R$^8$)—R$^1$; (ii) 9- or 10-membered partially saturated heteroaryl comprising at least one N heteroatom, preferably wherein the N is present in the α-positon to the atom binding Q to the rest of the molecule; and (iii) 4-, 5- or 6-membered saturated heterocyclic ring comprising at least one heteroatom selected from N, O and S, with the proviso that at least one N heteroatom is present, preferably wherein the N is present in the α-positon to the atom binding Q to the rest of the molecule, and wherein the heterocyclic ring is unsubstituted or substituted with one or more substituents independently selected from hydroxy, C$_1$-C$_3$alkyl, C$_1$-C$_3$alkoxy and halo;
R$_1$ is selected from hydrogen; C$_1$-C$_6$alkyl; and (CH$_2$)$_{0-2}$R$_{1a}$ wherein
R$_{1a}$ is selected from (i) C$_1$-C$_3$alkoxy; (ii) C$_3$-C$_6$cycloalkyl optionally substituted once or more than once independently with hydroxy; hydroxyC$_1$-C$_4$alkyl; C$_1$-C$_4$alkoxy; C(O)OC$_1$-C$_3$alkyl; CO$_2$H; C(O)NR$^{1c}$R$^{1d}$; C$_1$-C$_6$alkyl; halo; haloC$_1$-C$_3$alkoxy-C$_1$-C$_3$alkyl; SO$_2$C$_1$-C$_3$alkyl; haloC$_1$-C$_3$alkyl; NHR$^{1b}$; C(O)NR$^{1c}$R$^{1d}$; a 5- or 6-membered aromatic heterocyclic ring comprising at least one heteroatom selected from N, O, and S; or with two R$^{1e}$; (iii) a 5- or 6-membered saturated heterocyclic ring comprising at least one heteroatom selected from N and O, which saturated heterocyclic ring is optionally substituted once or more than once independently with C$_1$-C$_3$alkyl; (CH$_2$)$_{0-1}$C(O)di(C$_1$-C$_3$alkyl)amino; SO$_2$C$_1$-C$_3$alkyl; C(O)C$_1$-C$_3$alkyl; or oxo;
R$^{1b}$ is selected from C(O)C$_1$-C$_3$alkyl; and SO$_2$C$_1$-C$_3$alkyl;
R$_{1c}$ and R$^{1d}$ are each independently selected from (i) hydrogen; (ii) C$_1$-C$_3$alkyl; and (iii) hydroxyC$_1$-C$_4$alkyl, wherein two R$_{1e}$ attached at the same carbon atom form together with the carbon atom to which they are attached a 5-membered saturated heterocyclic ring comprising at least one heteroatom selected from N (preferred) and O, or a C$_3$-C$_6$cycloalkyl, which saturated heterocyclic ring or cycloalkyl are optionally substituted with hydroxy or oxo;
R$_2$ is hydrogen or preferably halo,
R$_3$ is halo; haloC$_1$-C$_3$alkyl, especially mono-, di- or preferably tri-halomethyl; or cyano,
R$_4$ is selected from hydrogen; halo; and C$_1$-C$_3$alkyl (especially methyl), R$_5$ is selected from (i) hydrogen; (ii) halo-C$_1$-C$_6$alkoxy optionally substituted with hydroxy; (iii) S-haloC$_1$-C$_3$alkyl optionally substituted with hydroxy; (iv) C$_1$-C$_3$alkoxyC$_1$-C$_3$alkoxy; (v) C$_1$-C$_6$alkoxy optionally substituted with SO$_2$C$_1$-C$_3$alkyl, C$_3$-C$_6$cycloalkyl, CO$_2$H or a 5- or 6-membered saturated heterocyclic ring comprising at least one heteroatom selected from N and O, which ring is optionally substituted with C(O)C$_1$-C$_3$alkyl; (vi) C$_1$-C$_3$alkyl; (vii) hydroxyC$_1$-C$_6$alkoxy; (viii) a 5- or 6-membered aromatic heterocyclic ring comprising at least one heteroatom selected from N, O, and S, preferably at least one N heteroatom; and (ix) hydroxy,
R$_6$ is cyano; C(O)NHR$^{6a}$; NHR$^{6b}$; or C$_1$-C$_3$alkoxy substituted with NH$_2$ or hydroxy,
R$^{6a}$ is selected from (i) hydrogen; (ii) C$_1$-C$_3$alkyl; (iii) C$_3$-C$_6$cycloalkyl; and (iv) a 5- or 6-membered aromatic heterocyclic ring comprising at least one heteroatom selected from N, O, and S, preferably at least one N heteroatom, which aromatic heterocyclic ring is optionally substituted with C$_1$-C$_3$alkyl;
R$^{6b}$ is C$_1$-C$_3$alkyl substituted with NH$_2$ or hydroxy;
R$^7$ is each independently selected from hydrogen or C$_1$-C$_3$alkyl; and
R$^8$ is hydrogen or C$_1$-C$_3$-alkyl, especially methyl.
Embodiment 3. A compound according to embodiment 1, or a pharmaceutically acceptable salt thereof,
wherein
W is CH—R$_w$;
X is selected from CH; and N;
Y is CH;
Z is selected from O and NH;
A is phenyl, which phenyl is optionally substituted with halo; or haloC$_1$-C$_3$alkoxy;
R$_w$ is selected from (i) hydrogen; (ii) C$_1$-C$_3$alkoxy; (iii) hydroxy-C$_1$-C$_3$alkyl; (iv) C$_1$-C$_3$alkyl; and (v) C$_1$-C$_3$alkoxy-C$_1$-C$_3$alkyl;
Q is selected from (i) —C(R$^7$)$_2$—NH—R$_1$; and (ii) 4-, 5- or 6-membered saturated heterocyclic ring comprising one or two heteroatoms independently selected from N, O and S, with the proviso that at least one N heteroatom is present, preferably wherein the N is present in the α-positon to the atom binding Q to the rest of the molecule, and wherein the heterocyclic ring is unsubstituted or substituted with one or more substituents independently selected from hydroxy, C$_1$-C$_3$alkyl and halo;
R$_1$ is selected from (i) C$_1$-C$_6$alkyl; (ii) R$_{1a}$; wherein
R$_{1a}$ is selected from C$_3$-C$_6$cycloalkyl optionally substituted once or more than once independently with hydroxy; C$_1$-C$_6$alkyl; or halo;
R$_2$ is hydrogen or preferably halo;
R$_3$ is halo;
R$_4$ is selected from (i) hydrogen; and (ii) halo;
R$_5$ is selected from hydroxy, C$_1$-C$_6$alkoxy; and hydroxyC$_1$-C$_6$alkoxy;
R$_6$ is C(O)NHR$^{6a}$;
R$^{6a}$ is selected from (i) hydrogen; and (ii) C$_1$-C$_3$alkyl; and
R$^7$ is each independently selected from hydrogen or C$_1$-C$_3$alkyl.
Embodiment 4. A compound of the formula I according to any of embodiments 1 to 3,
wherein
W is CH—R$_w$;
X is selected from CH; and N;
Y is CH;

Z is selected from O and NH;

A is phenyl, which phenyl is optionally substituted with halo; or haloC$_1$-C$_3$alkoxy, especially unsubstituted phenyl;

R$_w$ is selected from (i) hydrogen; and (ii) C$_1$-C$_3$alkyl, or is hydroxy-C$_1$-C$_3$alkyl;

Q is selected from (i) —C(R$^7$)$_2$—NH—R$_1$; and (ii) 4-, 5- or 6-membered saturated heterocyclic ring comprising one or two heteroatoms independently selected from N and O, with the proviso that at least one N heteroatom is present and is in the α-positon to the carbon atom binding Q to the rest of the molecule, wherein the heterocyclic ring is unsubstituted or substituted with one or more substituents independently selected from hydroxy, C$_1$-C$_3$alkyl and halo;

R$_1$ is selected from (i) C$_1$-C$_6$alkyl; (ii) R$_{1a}$; wherein

R$_{1a}$ is selected from C$_3$-C$_6$cycloalkyl optionally substituted once or more than once independently with hydroxy; C$_1$-C$_6$alkyl; or halo;

R$_2$ is halo, especially fluoro;

R$_3$ is halo, especially chloro;

R$_4$ is halo, especially fluoro;

R$_5$ is selected from C$_1$-C$_6$alkoxy; and hydroxyC$_1$-C$_6$alkoxy; R$_6$ is C(O)NHR$^{6a}$;

R$^{6a}$ is selected from (i) hydrogen; and (ii) C$_1$-C$_3$alkyl;

and each R$^7$ is hydrogen.

Embodiment 5. A compound according to embodiment 1, 2, 3 or 4 of formula (Ia), or a pharmaceutically acceptable salt thereof,

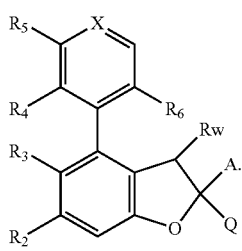
(Ia)

Embodiment 6. A compound according to embodiment 1, 2, 3, 4 or 5 of formula (Ia-1), or a pharmaceutically acceptable salt thereof,

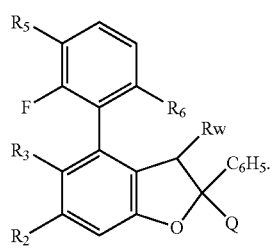
(Ia-1)

Embodiment 7. A compound according to embodiment 1, 2, 3, 4 or 5 of formula (Ib), or a pharmaceutically acceptable salt thereof,

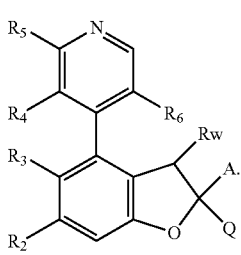
(Ib)

Embodiment 8. A compound according to embodiment 1, 2, 3, 4 or 5 of formula (Ic), or a pharmaceutically acceptable salt thereof

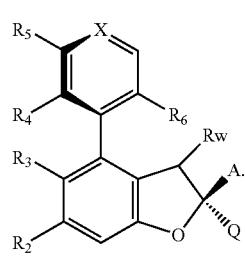
(Ic)

Embodiment 9. A compound according to embodiment 1, 2, 3, 4 or 5 of formula (Id), or a pharmaceutically acceptable salt thereof,

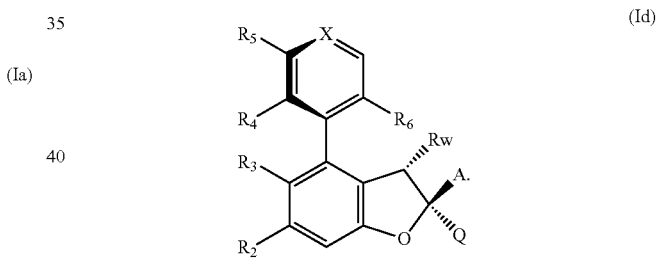
(Id)

Embodiment 10. A compound according to embodiment 1, 2, 3 or 4 or a pharmaceutically acceptable salt thereof, wherein Y is CH.

Embodiment 11. A compound according to embodiment 1, 2, 3 or 4 or a pharmaceutically acceptable salt thereof, wherein Y is CH and W is CH—R$_w$.

Embodiment 12. A compound according to embodiment 1, 2, 3 or 4, or a pharmaceutically acceptable salt thereof, wherein Y is CH, W is CH—R$_w$ and Z is O.

Embodiment 13. A compound according to any of embodiments 1 to 5, 7 to 12, or a pharmaceutically acceptable salt thereof, wherein A is a phenyl ring, which phenyl ring is unsubstituted.

Embodiment 14. A compound according to any of embodiments 1 to 13, or a pharmaceutically acceptable salt thereof, wherein R$_3$ is chloro.

Embodiment 15. A compound according to any of embodiments 1 to 5, 7 to 14, or a pharmaceutically acceptable salt thereof, wherein R$_4$ is fluoro.

Embodiment 16. A compound according to any of embodiments 1 to 15, or a pharmaceutically acceptable salt thereof, wherein R$_2$ is fluoro.

Embodiment 17. A compound according to any of embodiments 1 to 5, 8 to 16, or a pharmaceutically acceptable salt thereof, wherein X is CH.

Embodiment 18. A compound according to any of embodiments 1 to 5, 8 to 16, or a pharmaceutically acceptable salt thereof, wherein X is N.

Embodiment 19. A compound according to any of embodiments 1 to 18, or a pharmaceutically acceptable salt thereof, wherein $R_5$ is selected from (i) $C_1$-$C_6$alkoxy optionally substituted with $C_3$-$C_6$cycloalkyl; $CO_2H$; $SO_2C_1$-$C_3$alkyl; a 5- or 6-membered aromatic heterocyclic ring comprising at least one heteroatom selected from N, O, and S; or a 5- or 6-membered saturated heterocyclic ring comprising at least one heteroatom selected from N and O, which ring is optionally substituted with $C(O)C_1$-$C_3$alkyl; (ii) hydroxy$C_1$-$C_6$alkoxy; (iii) halo$C_1$-$C_6$alkoxy optionally substituted with hydroxy; (iv) $C_1$-$C_3$alkoxy$C_1$-$C_3$alkoxy.

Embodiment 20. A compound according to embodiment 19, or a pharmaceutically acceptable salt thereof, wherein $R_5$ is selected from (i) $C_1$-$C_6$alkoxy optionally substituted with $C_3$-$C_6$cycloalkyl; $CO_2H$; $SO_2C_1$-$C_3$alkyl; a 6-membered aromatic heterocyclic ring comprising at least one N heteroatom; or a 5- or 6-membered saturated heterocyclic ring comprising at least one heteroatom selected from N and O, which ring is optionally substituted with $C(O)C_1$-$C_3$alkyl; (ii) hydroxy$C_1$-$C_6$alkoxy; (iii) halo$C_1$-$C_6$alkoxy optionally substituted with hydroxy; (iv) $C_1$-$C_3$alkoxy$C_1$-$C_3$alkoxy.

Embodiment 21. A compound according to any one of embodiments 1 to 20, or a pharmaceutically acceptable salt thereof, wherein $R_5$ is selected from (i) $C_1$-$C_6$alkoxy; (ii) hydroxy$C_1$-$C_6$alkoxy; (iii) halo$C_1$-$C_6$alkoxy optionally substituted with hydroxy; (iv) $C_1$-$C_3$alkoxy$C_1$-$C_3$alkoxy.

Embodiment 22. A compound according to any of embodiments 1 to 21, or a pharmaceutically acceptable salt thereof, wherein $R_5$ is hydroxy$C_1$-$C_6$alkoxy or $C_1$-$C_6$-alkoxy, preferably wherein $R_5$ is hydroxy$C_1$-$C_6$alkoxy.

Embodiment 23. A compound according to any of embodiments 1 to 22, or a pharmaceutically acceptable salt thereof, wherein $R_6$ is selected from (i) cyano; (ii) $C(O)NHR^{6a}$, preferably $R_6$ is $C(O)NHR^{6a}$.

Embodiment 24. A compound according to embodiment 23, or a pharmaceutically acceptable salt thereof, wherein $R^{6a}$ is selected from (i) hydrogen; (ii) $C_1$-$C_3$alkyl; (iii) $C_3$-$C_6$cycloalkyl; (iv) a 5- or 6-membered aromatic heterocyclic ring comprising at least one N heteroatom, which aromatic heterocyclic ring is optionally substituted with $C_1$-$C_3$alkyl.

Embodiment 25. A compound according to any one of embodiments 1 to 24, or a pharmaceutically acceptable salt thereof, wherein $R^{6a}$ is hydrogen or $C_1$-$C_3$alkyl.

Embodiment 26. A compound according to any of embodiments 1 to 25, or a pharmaceutically acceptable salt thereof, wherein $R^{6a}$ is $C_1$-$C_3$alkyl.

Embodiment 27. A compound according to any of embodiments 1 to 26, or a pharmaceutically acceptable salt thereof, wherein $R^{6a}$ is methyl.

Embodiment 28. A compound according to any of embodiments 1 to 27, or a pharmaceutically acceptable salt thereof, wherein Q is (i) —$C(R^7)_2$—$N(R_8)$—$R_1$, preferably Q is —$C(R^7)_2$—NH—$R_1$; (ii) 9- or 10-membered partially saturated heteroaryl comprising at least one N heteroatom; and (iii) 4-, 5- or 6-membered saturated heterocyclic ring comprising at least one heteroatom selected from N, O and S, with the proviso that at least one N heteroatom is present, wherein the heterocyclic ring is unsubstituted or substituted with one or more substituents independently selected from hydroxy, $C_1$-$C_3$alkyl, $C_1$-$C_3$alkoxy, halo and $C_1$-$C_3$alkylene forming a bridge between two ring atoms of the saturated heterocyclic ring, thus forming a bridged bicyclic structure.

Embodiment 29. A compound according to any of embodiments 1 to 28, or a pharmaceutically acceptable salt thereof, wherein Q is —$C(R^7)_2$—$N(R_8)$—$R_1$, preferably Q is —$C(R^7)_2$—NH—$R_1$, or is selected from the group consisting of:

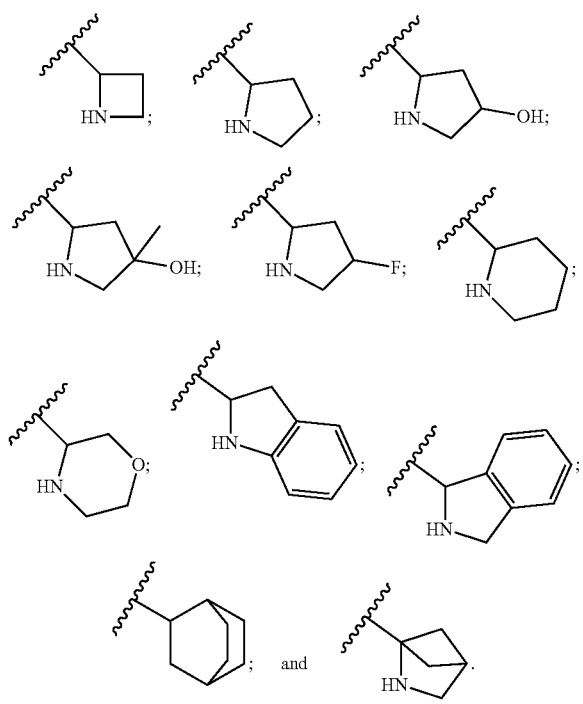

Embodiment 30. A compound according to any of embodiments 1 to 29, or a pharmaceutically acceptable salt thereof, wherein Q is —$C(R^7)_2$—$N(R_8)$—$R_1$, preferably Q is —$C(R^7)_2$—NH—$R_1$, or is selected from the group consisting of:

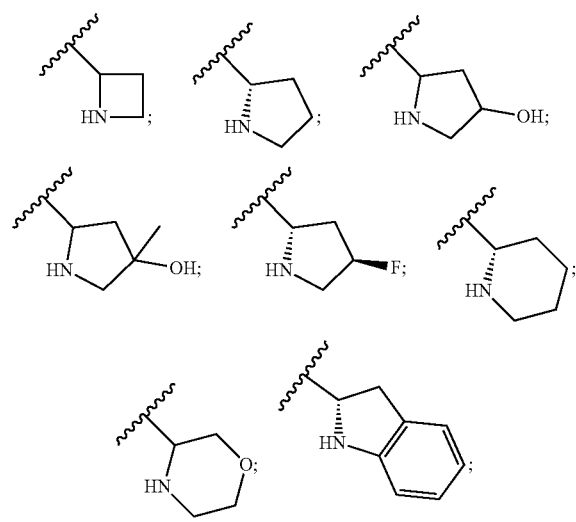

-continued

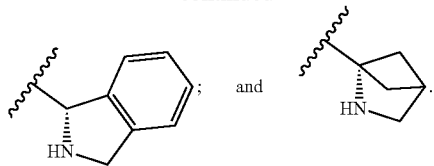

Embodiment 31. A compound according to any of embodiments 1 to 30, or a pharmaceutically acceptable salt thereof, wherein Q is —C($R^7$)$_2$—N($R_8$)—$R_1$, preferably Q is —C($R^7$)$_2$—NH—$R_1$, or is selected from the group consisting of:

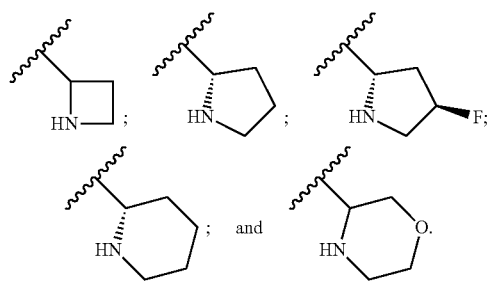

Embodiment 32. A compound according to any of embodiments 1 to 31, or a pharmaceutically acceptable salt thereof, wherein Q is

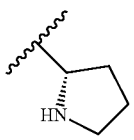

Embodiment 33. A compound according to any of embodiments 1 to 31 or a pharmaceutically acceptable salt thereof, wherein $R_1$ is selected from (i) hydrogen; (ii) $C_1$-$C_6$alkyl; (iii) (CH$_2$)$_{0-2}$$R_{1a}$;
wherein
$R_{1a}$ is selected from (i) hydroxy$C_1$-$C_4$alkyl; (ii) $C_1$-$C_3$alkoxy; (iii) a 5- or 6-membered saturated heterocyclic ring comprising at least one heteroatom selected from N and O, which saturated heterocyclic ring is optionally substituted once or more than once independently with $C_1$-$C_3$alkyl; (CH$_2$)C(O)di($C_1$-$C_3$alkyl)amino; SO$_2$$C_1$-$C_3$alkyl; C(O)$C_1$-$C_3$alkyl; or oxo;
(iv) $C_3$-$C_6$cycloalkyl optionally substituted once or more than once independently with hydroxy; hydroxy$C_1$-$C_4$alkyl; $C_1$-$C_6$alkoxy, preferably $C_1$-$C_4$alkoxy; C(O)OC$_1$-$C_3$alkyl; CO$_2$H; SO$_2$$C_1$-$C_3$alkyl; halo$C_1$-$C_3$alkyl; NHR$^{1b}$; C(O)NR$^{1c}$R$^{1d}$; $C_1$-$C_6$alkyl; halo$C_1$-$C_3$alkoxy-$C_1$-$C_3$alkyl; halo; a 5-membered aromatic heterocyclic ring comprising at least one N heteroatom; or two R$^{1e}$,
wherein the two R$^{1e}$ groups are attached at the same carbon atom and form together with the carbon atom to which they are attached a 5-membered saturated heterocyclic ring comprising at least one N heteroatom, or a $C_3$-$C_6$cycloalkyl, which saturated heterocyclic ring or cycloalkyl are optionally substituted with hydroxy or oxo.

Embodiment 34. A compound according to embodiment 33, or a pharmaceutically acceptable salt thereof, wherein $R_1$ is selected from (i) $C_1$-$C_6$alkyl; (ii) (CH$_2$)$_{0-2}$$R_{1a}$;
wherein
$R_{1a}$ is selected from (i) hydroxy$C_1$-$C_4$alkyl; (ii) $C_3$-$C_6$cycloalkyl, preferably cyclohexyl, optionally substituted once or more than once independently with hydroxy; hydroxy$C_1$-$C_4$alkyl; $C_1$-$C_6$alkoxy, preferably $C_1$-$C_4$alkoxy; C(O)OC$_1$-$C_3$alkyl; CO$_2$H; SO$_2$$C_1$-$C_3$alkyl; halo$C_1$-$C_3$alkyl; NHR$^{1b}$; C(O)NR$^{1c}$R$^{1d}$; $C_1$-$C_6$alkyl; halo$C_1$-$C_3$alkoxy-$C_1$-$C_3$alkyl; halo; a 5-membered aromatic heterocyclic ring comprising at least one N heteroatom; or R$^{1e}$,
wherein the two R$^{1e}$ groups are attached at the same carbon atom and form together with the carbon atom to which they are attached a 5-membered saturated heterocyclic ring comprising at least one N heteroatom, which saturated heterocyclic ring is substituted with oxo, or a $C_3$-$C_6$cycloalkyl, which cycloalkyl are substituted with hydroxy.

Embodiment 35. A compound according to any one of embodiments 1 to 31, 33 or 34, or a pharmaceutically acceptable salt thereof, wherein $R_1$ is selected from (i) $C_1$-$C_6$alkyl; (ii) (CH$_2$)$_0$$R_{1a}$; wherein
$R_{1a}$ is $C_3$-$C_6$cycloalkyl, preferably cyclohexyl, optionally substituted once or more than once independently with hydroxy; hydroxy$C_1$-$C_4$alkyl; $C_1$-$C_6$alkoxy, preferably $C_1$-$C_4$alkoxy; C(O)OC$_1$-$C_3$alkyl; CO$_2$H; SO$_2$$C_1$-$C_3$alkyl; halo$C_1$-$C_3$alkyl; NHR$^{1b}$; C(O)NR$^{1c}$R$^{1d}$; $C_1$-$C_6$alkyl; halo$C_1$-$C_3$alkoxy-$C_1$-$C_3$alkyl; or halo.

Embodiment 36. A compound according to any of embodiments 1 to 31, 33 to 35, or a pharmaceutically acceptable salt thereof, wherein $R_1$ is selected from (i) $C_1$-$C_6$alkyl; (ii) (CH$_2$)$_0$$R_{1a}$; wherein
$R_{1a}$ is $C_3$-$C_6$cycloalkyl, preferably cyclohexyl, optionally substituted once or more than once independently with hydroxy; hydroxy$C_1$-$C_4$alkyl; $C_1$-$C_6$alkoxy, preferably $C_1$-$C_4$alkoxy; C(O)OC$_1$-$C_3$alkyl; halo$C_1$-$C_3$alkyl; $C_1$-$C_6$alkyl; or halo.

Embodiment 37. A compound according to any of embodiments 1 to 31, 33 to 36, or a pharmaceutically acceptable salt thereof, wherein $R_1$ is (CH$_2$)$_0$$R_{1a}$, wherein $R_{1a}$ is cyclohexyl, substituted once or more than once independently with hydroxy; hydroxy$C_1$-$C_4$alkyl; $C_1$-$C_6$alkoxy, preferably $C_1$-$C_4$alkoxy; C(O)OC$_1$-$C_3$alkyl; halo$C_1$-$C_3$alkyl; $C_1$-$C_6$alkyl; or halo.

Embodiment 38. A compound according to any of embodiments 1 to 31, 33 to 37, or a pharmaceutically acceptable salt thereof, wherein $R_1$ is (CH$_2$)$_0$$R_{1a}$, wherein $R_{1a}$ is cyclohexyl, substituted twice independently with hydroxy; hydroxy$C_1$-$C_4$alkyl; $C_1$-$C_4$alkoxy; halo$C_1$-$C_3$alkyl; $C_1$-$C_6$alkyl; or halo.

Embodiment 39. A compound according to any of embodiments 1 to 31, 33 to 38, or a pharmaceutically acceptable salt thereof, wherein $R_1$ is (CH$_2$)$_0$$R_{1a}$, wherein $R_{1a}$ is cyclohexyl, substituted twice independently with hydroxy and $C_1$-$C_6$alkyl.

Embodiment 40. A compound according to any of embodiments 1 to 31, 33 to 39, or a pharmaceutically acceptable salt thereof, wherein $R_1$ is

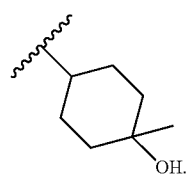 [SMILES: *C1CCC(C)(O)CC1]

Embodiment 41. A compound according to any of embodiments 1 to 31, 33 to 40, or a pharmaceutically acceptable salt thereof, wherein $R_1$ is

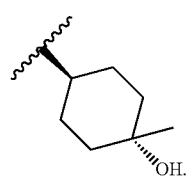 [SMILES: *[C@H]1CC[C@](C)(O)CC1]

Embodiment 42. A compound according to any of embodiments 1 to 31, 33 to 41, or a pharmaceutically acceptable salt thereof, wherein $R^7$ is each independently selected from hydrogen and $C_1$-$C_3$alkyl.

Embodiment 43. A compound according to any of embodiments 1 to 31, 33 to 42, or a pharmaceutically acceptable salt thereof, wherein both $R^7$ groups are hydrogen.

Embodiment 44. A compound according to any of embodiments 1 to 31, 33 to 42, or a pharmaceutically acceptable salt thereof, wherein one $R^7$ is hydrogen and the other is $C_1$-$C_3$alkyl.

Embodiment 45. A compound according to any of embodiments 1 to 31, 33 to 42, 44, or a pharmaceutically acceptable salt thereof, wherein one $R^7$ is hydrogen and the other is methyl.

Embodiment 46. A compound according to any of embodiments 1 to 31, 33 to 43, or a pharmaceutically acceptable salt thereof, wherein Q is —$CH_2$—NH—$R_1$, wherein $R_1$ is as defined in any of embodiments 33 to 41.

Embodiment 47. A compound according to any of embodiments 1 to 31, 33 to 43, 46, or a pharmaceutically acceptable salt thereof, wherein Q is

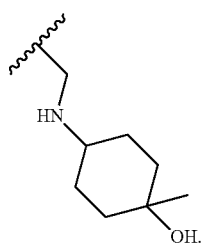 [SMILES: *CNC1CCC(C)(O)CC1]

Embodiment 48. A compound according to any of embodiments 1 to 31, 33 to 43, 46, 47, or a pharmaceutically acceptable salt thereof, wherein Q is

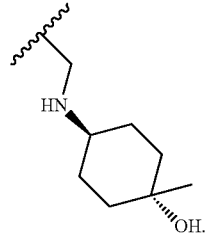 [SMILES: *CN[C@H]1CC[C@](C)(O)CC1]

Embodiment 49. A compound according to any of embodiments 1 to 31, 33 to 36, 42, 43, 46, or a pharmaceutically acceptable salt thereof, wherein Q is —$CH_2$—NH—$C_1$-$C_6$alkyl.

Embodiment 50. A compound according to any of embodiments 1 to 31, 33 to 36, 42, 43, 46, 49, or a pharmaceutically acceptable salt thereof, wherein Q is —$CH_2$—NH—$CH_3$.

Embodiment 51. A compound according to embodiment 1, or a pharmaceutically acceptable salt thereof, where said compound is selected from the compounds of the Examples or from the compounds listed in claim 8.

Embodiment 52. A compound according to embodiment 1, or a pharmaceutically acceptable salt thereof, where said compound is selected from:

N1-(2-((2S*,4S*)-2-(Aminomethyl)-5-chloro-2-phenyl-2,3-dihydrobenzofuran-4-yl)-3-fluoro-phenyl)ethane-1,2-diamine;

N1-(2-((2S,4S)-2-(Aminomethyl)-5-chloro-2-phenyl-2,3-dihydrobenzofuran-4-yl)-3-fluorophenyl)ethane-1,2-diamine;

2-((2S*,4S*)-2-(Aminomethyl)-5-chloro-2-phenyl-2,3-dihydrobenzofuran-4-yl)-3-fluorobenzamide;

2-((2S,4S)-2-(aminomethyl)-5-chloro-2-phenyl-2,3-dihydrobenzofuran-4-yl)-3-fluorobenzamide;

2-((2S,4S)-2-(aminomethyl)-5-chloro-2-phenyl-2,3-dihydrobenzofuran-4-yl)-3-fluoro-4-methoxybenzamide;

2-((2S,4S)-2-(aminomethyl)-5-chloro-2-phenyl-2,3-dihydrobenzofuran-4-yl)-4-chloro-3-fluorobenzamide;

2-((2S,4S)-2-(aminomethyl)-5-chloro-2-phenyl-2,3-dihydrobenzofuran-4-yl)-3,4-difluorobenzamide;

2-((2S,4S)-2-(aminomethyl)-5-chloro-2-phenyl-2,3-dihydrobenzofuran-4-yl)-3-fluoro-4-(2-hydroxyethoxy)benzamide;

2-((2S,4S)-2-(aminomethyl)-5-chloro-2-phenyl-2,3-dihydrobenzofuran-4-yl)-4-(difluoromethoxy)-3-fluorobenzamide;

2-((2S,4S)-2-(aminomethyl)-5-chloro-2-phenyl-2,3-dihydrobenzofuran-4-yl)-3-fluoro-4-(2-methoxyethoxy)benzamide;

2-((2S,4S)-2-(aminomethyl)-5-chloro-2-phenyl-2,3-dihydrobenzofuran-4-yl)-3-fluoro-4-((S)-2-hydroxypropoxy)benzamide;

2-((2S,4S)-2-(aminomethyl)-5-chloro-2-phenyl-2,3-dihydrobenzofuran-4-yl)-3-fluoro-4-((R)-2-hydroxypropoxy)benzamide;

2-((2S,4S)-2-(aminomethyl)-5-chloro-2-phenyl-2,3-dihydrobenzofuran-4-yl)-3-fluoro-4-((R)-2-fluoropropoxy)benzamide;

2-(3-((2S,4S)-2-(aminomethyl)-5-chloro-2-phenyl-2,3-dihydrobenzofuran-4-yl)-4-carbamoyl-2-fluorophenoxy)acetic acid trifluoroacetate salt;

4-(((R)-4-acetylmorpholin-2-yl)methoxy)-2-((2S,4S)-2-(aminomethyl)-5-chloro-2-phenyl-2,3-dihydrobenzofuran-4-yl)-3-fluorobenzamide;

4-((2S,4S)-2-(Aminomethyl)-5-chloro-2-phenyl-2,3-dihydrobenzofuran-4-yl)-5-fluoro-6-methoxynicotinamide;

4-((2S,4S)-2-(Aminomethyl)-5-chloro-2-phenyl-2,3-dihydrobenzofuran-4-yl)-6-(difluoromethoxy)-5-fluoronicotinamide;

2-((2S,4S)-5-Chloro-2-((methylamino)methyl)-2-phenyl-2,3-dihydrobenzofuran-4-yl)-3-fluoro-4-methoxybenzamide;

2-((2S,4S)-2-(Aminomethyl)-5-chloro-2-phenyl-2,3-dihydrobenzofuran-4-yl)-3-fluoro-4-methoxy-N-methylbenzamide;

2-((2S,4S)-2-(aminomethyl)-5-chloro-2-phenyl-2,3-dihydrobenzofuran-4-yl)-N-cyclopropyl-3-fluoro-4-methoxybenzamide;

2-((2S,4S)-2-(aminomethyl)-5-chloro-2-phenyl-2,3-dihydrobenzofuran-4-yl)-3,4-difluoro-N-(1-methyl-1H-pyrazol-5-yl)benzamide;

2-((2S,4S)-2-(aminomethyl)-5-chloro-2-phenyl-2,3-dihydrobenzofuran-4-yl)-3-fluoro-4-methoxy-N-(pyridin-3-yl)benzamide;

2-((2S,4S)-5-Chloro-2-(((trans-4-hydroxycyclohexyl)amino)methyl)-2-phenyl-2,3-dihydrobenzofuran-4-yl)-3-fluoro-4-methoxybenzamide;

2-((2S,4S)-5-chloro-2-(((cis-4-hydroxycyclohexyl)amino)methyl)-2-phenyl-2,3-dihydrobenzofuran-4-yl)-3-fluoro-4-methoxybenzamide;

(trans)-4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylic acid;

(cis)-4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylic acid;

2-((2R,4S)-2-(Aminomethyl)-5-chloro-2-(thiazol-4-yl)-2,3-dihydrobenzofuran-4-yl)-3-fluoro-4-methoxybenzamide;

2-((2S,4S)-2-(Aminomethyl)-5-chloro-2-(2-fluorophenyl)-2,3-dihydrobenzofuran-4-yl)-3-fluoro-4-methoxybenzamide;

2-((2S,4S)-2-(aminomethyl)-5-chloro-6-fluoro-2-phenyl-2,3-dihydrobenzofuran-4-yl)-3-fluoro-4-methoxybenzamide;

2-((2S,4S)-2-(aminomethyl)-5-chloro-6-fluoro-2-phenyl-2,3-dihydrobenzofuran-4-yl)-4-(cyclopropylmethoxy)-3-fluorobenzamide;

2-((2S,4S)-2-(aminomethyl)-5-chloro-6-fluoro-2-phenyl-2,3-dihydrobenzofuran-4-yl)-4-(difluoromethoxy)-3-fluorobenzamide;

2-((2S,4S)-2-(aminomethyl)-5-chloro-6-fluoro-2-phenyl-2,3-dihydrobenzofuran-4-yl)-4-(1,1-difluoro-2-hydroxyethoxy)-3-fluorobenzamide;

2-((2S,4S)-2-(aminomethyl)-5-chloro-6-fluoro-2-phenyl-2,3-dihydrobenzofuran-4-yl)-3-fluoro-4-(2-methoxyethoxy)benzamide;

2-((2S,4S)-2-(aminomethyl)-5-chloro-6-fluoro-2-phenyl-2,3-dihydrobenzofuran-4-yl)-3-fluoro-4-(2-hydroxyethoxy)benzamide;

4-((2S,4S)-2-(aminomethyl)-5-chloro-6-fluoro-2-phenyl-2,3-dihydrobenzofuran-4-yl)-5-fluoro-6-methoxynicotinamide;

4-((2S,4S)-2-(Aminomethyl)-5-chloro-6-fluoro-2-phenyl-2,3-dihydrobenzofuran-4-yl)-5-fluoro-6-(2-hydroxyethoxy)nicotinamide;

2-((2S,4S)-2-(Aminomethyl)-5-chloro-6-fluoro-2-phenyl-2,3-dihydrobenzofuran-4-yl)-3-fluoro-4-(2-hydroxyethoxy)-N-methylbenzamide;

4-((2S,4S)-2-(Aminomethyl)-5-chloro-6-fluoro-2-phenyl-2,3-dihydrobenzofuran-4-yl)-5-fluoro-6-(2-hydroxyethoxy)-N-methylnicotinamide;

2-((2S,4S)-5-Chloro-6-fluoro-2-((methylamino)methyl)-2-phenyl-2,3-dihydrobenzofuran-4-yl)-3-fluoro-4-methoxybenzamide;

4-((2S,4S)-5-Chloro-6-fluoro-2-((methylamino)methyl)-2-phenyl-2,3-dihydrobenzofuran-4-yl)-5-fluoro-6-(2-methoxyethoxy)nicotinamide;

2-((2S,4S)-5-Chloro-6-fluoro-2-((methylamino)methyl)-2-phenyl-2,3-dihydrobenzofuran-4-yl)-3-fluoro-4-(2-hydroxyethoxy)benzamide;

4-((2S,4S)-5-Chloro-6-fluoro-2-((methylamino)methyl)-2-phenyl-2,3-dihydrobenzofuran-4-yl)-5-fluoro-6-(2-hydroxyethoxy)nicotinamide;

2-((2S,4S)-5-Chloro-6-fluoro-2-((methylamino)methyl)-2-phenyl-2,3-dihydrobenzofuran-4-yl)-3-fluoro-4-(2-hydroxyethoxy)-N-methylbenzamide;

2-((2S,4S)-5-chloro-6-fluoro-2-((methylamino)methyl)-2-phenyl-2,3-dihydrobenzofuran-4-yl)-3-fluoro-4-((S)-2-hydroxypropoxy)-N-methylbenzamide;

4-((2S,4S)-5-chloro-6-fluoro-2-((methylamino)methyl)-2-phenyl-2,3-dihydrobenzofuran-4-yl)-5-fluoro-6-(2-hydroxyethoxy)-N-methylnicotinamide;

2-((2S,4S)-5-chloro-6-fluoro-2-(((((trans)-4-(methylsulfonyl)cyclohexyl)amino)methyl)-2-phenyl-2,3-dihydrobenzofuran-4-yl)-4-(difluoromethoxy)-3-fluorobenzamide;

2-((2S,4S)-5-chloro-6-fluoro-2-(((4-(fluoromethyl)-4-hydroxycyclohexyl)amino)methyl)-2-phenyl-2,3-dihydrobenzofuran-4-yl)-4-(difluoromethoxy)-3-fluorobenzamide;

2-((2S,4S)-2-(((4-acetamidocyclohexyl)amino)methyl)-5-chloro-6-fluoro-2-phenyl-2,3-dihydrobenzofuran-4-yl)-4-(difluoromethoxy)-3-fluorobenzamide;

2-((2S,4S)-5-chloro-6-fluoro-2-(((4-(methylsulfonamido)cyclohexyl)amino)methyl)-2-phenyl-2,3-dihydrobenzofuran-4-yl)-4-(difluoromethoxy)-3-fluorobenzamide;

2-((2S,4S)-5-chloro-2-(((4-(dimethylcarbamoyl)cyclohexyl)amino)methyl)-6-fluoro-2-phenyl-2,3-dihydrobenzofuran-4-yl)-4-(difluoromethoxy)-3-fluorobenzamide;

2-((2S,4S)-5-chloro-6-fluoro-2-(((2-oxo-1-azaspiro[4.5]decan-8-yl)amino)methyl)-2-phenyl-2,3-dihydrobenzofuran-4-yl)-4-(difluoromethoxy)-3-fluorobenzamide;

2-((2S,4S)-5-chloro-2-(((1-(2-(dimethylamino)-2-oxoethyl)piperidin-4-yl)amino)methyl)-6-fluoro-2-phenyl-2,3-dihydrobenzofuran-4-yl)-4-(difluoromethoxy)-3-fluorobenzamide;

2-((2S,4S)-5-chloro-6-fluoro-2-(((4-(hydroxymethyl)cyclohexyl)amino)methyl)-2-phenyl-2,3-dihydrobenzofuran-4-yl)-4-(difluoromethoxy)-3-fluorobenzamide;

2-((2S,4S)-5-chloro-6-fluoro-2-(((3-(2-hydroxypropan-2-yl)cyclobutyl)amino)methyl)-2-phenyl-2,3-dihydrobenzofuran-4-yl)-4-(difluoromethoxy)-3-fluorobenzamide;

2-((2S,4S)-5-chloro-6-fluoro-2-((((trans)-3-(hydroxymethyl)cyclobutyl)amino)methyl)-2-phenyl-2,3-dihydrobenzofuran-4-yl)-3-fluoro-4-(2-hydroxyethoxy)benzamide;

2-((2S,4S)-5-chloro-6-fluoro-2-((((cis)-3-(hydroxymethyl)cyclobutyl)amino)methyl)-2-phenyl-2,3-dihydrobenzofuran-4-yl)-3-fluoro-4-(2-hydroxyethoxy)benzamide;

2-((2S,4S)-5-chloro-2-(((((2R,4r,6S)-2,6-dimethyltetrahydro-2H-pyran-4-yl)amino)methyl)-6-fluoro-2-phenyl-2,3-dihydrobenzofuran-4-yl)-3-fluoro-4-(2-hydroxyethoxy)benzamide;

4-((2S,4S)-5-chloro-6-fluoro-2-((((trans)-4-hydroxy-4-methylcyclohexyl)amino)methyl)-2-phenyl-2,3-dihydrobenzofuran-4-yl)-5-fluoro-6-methoxynicotinamide;

4-((2S,4S)-5-chloro-6-fluoro-2-((((cis)-4-hydroxy-4-methylcyclohexyl)amino)methyl)-2-phenyl-2,3-dihydrobenzofuran-4-yl)-5-fluoro-6-methoxynicotinamide;

2-((2S,4S)-5-chloro-6-fluoro-2-((((cis)-4-hydroxy-4-methylcyclohexyl)amino)methyl)-2-phenyl-2,3-dihydrobenzofuran-4-yl)-3-fluoro-4-(((R)-tetrahydrofuran-2-yl)methoxy)benzamide;

2-((2S,4S)-5-chloro-6-fluoro-2-((((trans)-4-hydroxy-4-methylcyclohexyl)amino)methyl)-2-phenyl-2,3-dihydrobenzofuran-4-yl)-3-fluoro-4-(((R)-tetrahydrofuran-2-yl)methoxy)benzamide;

2-((2S,4S)-5-chloro-6-fluoro-2-((((trans)-4-hydroxy-4-methylcyclohexyl)amino)methyl)-2-phenyl-2,3-dihydrobenzofuran-4-yl)-4-ethyl-3-fluorobenzamide;

2-((2S,4S)-5-chloro-6-fluoro-2-((((cis)-4-hydroxy-4-methylcyclohexyl)amino)methyl)-2-phenyl-2,3-dihydrobenzofuran-4-yl)-4-ethyl-3-fluorobenzamide;

2-((2S,4S)-5-chloro-6-fluoro-2-((((trans)-4-hydroxy-4-methylcyclohexyl)amino)methyl)-2-phenyl-2,3-dihydrobenzofuran-4-yl)-3-fluoro-4-(1H-imidazol-1-yl)benzamide;

2-((2S,4S)-5-chloro-6-fluoro-2-((((cis)-4-hydroxy-4-methylcyclohexyl)amino)methyl)-2-phenyl-2,3-dihydrobenzofuran-4-yl)-3-fluoro-4-(1H-imidazol-1-yl)benzamide;

2-((2S,4S)-2-(((1-acetylpiperidin-4-yl)amino)methyl)-5-chloro-6-fluoro-2-phenyl-2,3-dihydrobenzofuran-4-yl)-4-(difluoromethoxy)-3-fluorobenzamide;

2-((2S,4S)-5-chloro-6-fluoro-2-((((trans)-4-hydroxy-4-methylcyclohexyl)amino)methyl)-2-phenyl-2,3-dihydrobenzofuran-4-yl)-3-fluoro-4-(pyrimidin-2-ylmethoxy)benzamide;

2-((2S,4S)-5-chloro-6-fluoro-2-((((cis)-4-hydroxy-4-methylcyclohexyl)amino)methyl)-2-phenyl-2,3-dihydrobenzofuran-4-yl)-3-fluoro-4-(pyrimidin-2-ylmethoxy)benzamide;

2-((2S,4S)-5-chloro-6-fluoro-2-((((trans)-4-hydroxycyclohexyl)amino)methyl)-2-phenyl-2,3-dihydrobenzofuran-4-yl)-4-(difluoromethoxy)-3-fluorobenzamide;

2-((2S,4S)-2-((tert-butylamino)methyl)-5-chloro-6-fluoro-2-phenyl-2,3-dihydrobenzofuran-4-yl)-4-(difluoromethoxy)-3-fluorobenzamide;

2-((2S,4S)-2-((((trans)-4-(1H-tetrazol-1-yl)cyclohexyl)amino)methyl)-5-chloro-6-fluoro-2-phenyl-2,3-dihydrobenzofuran-4-yl)-4-(difluoromethoxy)-3-fluorobenzamide;

2-((2S,4S)-5-chloro-2-(((trans-3-((difluoromethoxy)methyl)cyclobutyl)amino)methyl)-6-fluoro-2-phenyl-2,3-dihydrobenzofuran-4-yl)-4-(difluoromethoxy)-3-fluorobenzamide;

2-((2S,4S)-5-Chloro-6-fluoro-2-(((6-hydroxyspiro[3.3]heptan-2-yl)amino)methyl)-2-phenyl-2,3-dihydrobenzofuran-4-yl)-4-(difluoromethoxy)-3-fluorobenzamide;

2-((2S,3S,4S)-2-(Aminomethyl)-5-chloro-3-hydroxy-2-phenyl-2,3-dihydrobenzofuran-4-yl)-3-fluoro-4-methoxybenzamide;

2-((2S,3S,4S)-2-(aminomethyl)-5-chloro-3-hydroxy-2-phenyl-2,3-dihydrobenzofuran-4-yl)-3-fluoro-4-(2-methoxyethoxy)benzamide;

2-((2R,3S,4S)-2-(Aminomethyl)-5-chloro-3-hydroxy-2-(pyridin-2-yl)-2,3-dihydrobenzofuran-4-yl)-3-fluoro-4-methoxybenzamide;

2-((2S,3S,4S)-2-(Aminomethyl)-5-chloro-3-hydroxy-2-(2-(trifluoromethoxy)phenyl)-2,3-dihydrobenzofuran-4-yl)-3-fluoro-4-methoxybenzamide;

2-((2S,3S,4S)-5-chloro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide;

2-((2S,3S,4S)-5-Chloro-3-hydroxy-2-((((cis)-4-hydroxycyclohexyl)amino)methyl)-2-phenyl-2,3-dihydrobenzofuran-4-yl)-4-(difluoromethoxy)-3-fluorobenzamide;

2-((2R,3S,4S)-5-Chloro-3-hydroxy-2-((((trans)-4-hydroxycyclohexyl)amino)methyl)-2-(pyridin-2-yl)-2,3-dihydrobenzofuran-4-yl)-3-fluoro-4-methoxybenzamide;

2-((2R,3S,4S)-5-chloro-3-hydroxy-2-((((cis)-4-hydroxycyclohexyl)amino)methyl)-2-(pyridin-2-yl)-2,3-dihydrobenzofuran-4-yl)-3-fluoro-4-methoxybenzamide;

2-((2S,3S,4S)-5-chloro-2-((cyclobutylamino)methyl)-3-hydroxy-2-phenyl-2,3-dihydrobenzofuran-4-yl)-4-(difluoromethoxy)-3-fluorobenzamide;

2-((2S,3S,4S)-2-(Aminomethyl)-5-chloro-6-fluoro-3-hydroxy-2-phenyl-2,3-dihydrobenzofuran-4-yl)-3-fluoro-4-methoxybenzamide;

2-((2S,3S,4S)-2-(Aminomethyl)-5-chloro-6-fluoro-3-hydroxy-2-phenyl-2,3-dihydrobenzofuran-4-yl)-3-fluoro-4-(2-hydroxyethoxy)benzamide;

2-((2S,3S,4S)-5-Chloro-2-((cyclobutylamino)methyl)-6-fluoro-3-hydroxy-2-phenyl-2,3-dihydrobenzofuran-4-yl)-3-fluoro-4-(2-hydroxyethoxy)benzamide;

2-((2S,3S,4S)-5-Chloro-6-fluoro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide;

2-((2S,3S,4S)-5-chloro-6-fluoro-3-hydroxy-2-((((cis)-4-hydroxycyclohexyl)amino)methyl)-2-phenyl-2,3-dihydrobenzofuran-4-yl)-4-(difluoromethoxy)-3-fluorobenzamide;

2-((2S,3S,4S)-2-(Aminomethyl)-5-chloro-6-fluoro-3-methoxy-2-phenyl-2,3-dihydrobenzofuran-4-yl)-3-fluoro-4-(2-hydroxyethoxy)benzamide;

2-((2S,3S,4S)-5-Chloro-6-fluoro-2-((((trans)-4-hydroxycyclohexyl)amino)methyl)-3-methoxy-2-phenyl-2,3-dihydrobenzofuran-4-yl)-4-(difluoromethoxy)-3-fluorobenzamide;

2-((2S,3S,4S)-5-chloro-6-fluoro-2-((((cis)-4-hydroxycyclohexyl)amino)methyl)-3-methoxy-2-phenyl-2,3-dihydrobenzofuran-4-yl)-4-(difluoromethoxy)-3-fluorobenzamide;

2-((2S,3S,4S)-2-(aminomethyl)-5-chloro-3-methyl-2-phenyl-2,3-dihydrobenzofuran-4-yl)-4-(difluoromethoxy)-3-fluorobenzamide;

2-((2S,3S,4S)-5-chloro-2-((((cis)-4-hydroxy-4-methylcyclohexyl)amino)methyl)-3-methyl-2-phenyl-2,3-dihydrobenzofuran-4-yl)-4-(difluoromethoxy)-3-fluorobenzamide;

2-((2S,3S,4S)-5-chloro-2-((((trans)-4-hydroxy-4-methylcyclohexyl)amino)methyl)-3-methyl-2-phenyl-2,3-dihydrobenzofuran-4-yl)-4-(difluoromethoxy)-3-fluorobenzamide;

2-((2S,3S,4S)-2-(Aminomethyl)-5-chloro-6-fluoro-3-methyl-2-phenyl-2,3-dihydrobenzofuran-4-yl)-4-(difluoromethoxy)-3-fluorobenzamide;

2-((2S,3S,4S)-2-(aminomethyl)-5-chloro-6-fluoro-3-methyl-2-phenyl-2,3-dihydrobenzofuran-4-yl)-3-fluoro-4-(2-methoxyethoxy)benzamide;

2-((2S,3S,4S)-2-(aminomethyl)-5-chloro-6-fluoro-3-methyl-2-phenyl-2,3-dihydrobenzofuran-4-yl)-3-fluoro-4-(2-hydroxyethoxy)benzamide;

4-((2S,3S,4S)-2-(aminomethyl)-5-chloro-6-fluoro-3-methyl-2-phenyl-2,3-dihydrobenzofuran-4-yl)-5-fluoro-6-(2-methoxyethoxy)nicotinamide;

2-((2R,3S,4S)-2-(aminomethyl)-5-chloro-6-fluoro-3-methyl-2-(pyridin-2-yl)-2,3-dihydrobenzofuran-4-yl)-3-fluoro-4-methoxybenzamide;

2-((2S,3S,4S)-5-Chloro-6-fluoro-3-methyl-2-((methylamino)methyl)-2-phenyl-2,3-dihydrobenzofuran-4-yl)-3-fluoro-4-(2-hydroxyethoxy)benzamide;

2-((2R,3S,4S)-5-chloro-6-fluoro-3-methyl-2-((methylamino)methyl)-2-(pyridin-2-yl)-2,3-dihydrobenzofuran-4-yl)-3-fluoro-4-(2-methoxyethoxy)benzamide;

2-((2R,3S,4S)-5-chloro-6-fluoro-3-methyl-2-((methylamino)methyl)-2-(pyridin-2-yl)-2,3-dihydrobenzofuran-4-yl)-3-fluoro-4-(2-hydroxyethoxy)benzamide;

2-((2S,3S,4S)-5-Chloro-6-fluoro-3-methyl-2-((methylamino)methyl)-2-phenyl-2,3-dihydrobenzofuran-4-yl)-3-fluoro-4-(2-hydroxyethoxy)-N-methylbenzamide;

2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide;

2-((2S,3S,4S)-5-chloro-6-fluoro-2-((((cis)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide;

2-((2S,3S,4S)-5-chloro-6-fluoro-2-(((trans-4-hydroxycyclohexyl)amino)methyl)-3-methyl-2-phenyl-2,3-dihydrobenzofuran-4-yl)-4-(difluoromethoxy)-3-fluorobenzamide;

2-((2S,3S,4S)-5-chloro-6-fluoro-2-((((cis)-4-hydroxycyclohexyl)amino)methyl)-3-methyl-2-phenyl-2,3-dihydrobenzofuran-4-yl)-4-(difluoromethoxy)-3-fluorobenzamide;

2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-methoxyethoxy)benzamide;

2-((2S,3S,4S)-5-chloro-6-fluoro-2-((((cis)-4-hydroxy-4-methylcyclohexyl)amino)methyl)-3-methyl-2-phenyl-2,3-dihydrobenzofuran-4-yl)-3-fluoro-4-(2-methoxyethoxy)benzamide;

2-((2S,3S,4S)-5-chloro-6-fluoro-2-(((trans-4-hydroxy-4-methylcyclohexyl)amino)methyl)-3-methyl-2-phenyl-2,3-dihydrobenzofuran-4-yl)-3-fluoro-4-(2-hydroxyethoxy)benzamide;

2-((2S,3S,4S)-5-chloro-6-fluoro-2-(((cis-4-hydroxy-4-methylcyclohexyl)amino)methyl)-3-methyl-2-phenyl-2,3-dihydrobenzofuran-4-yl)-3-fluoro-4-(2-hydroxyethoxy)benzamide;

2-((2S,3S,4S)-5-chloro-2-((cyclobutylamino)methyl)-6-fluoro-3-methyl-2-phenyl-2,3-dihydrobenzofuran-4-yl)-3-fluoro-4-(2-hydroxyethoxy)benzamide;

4-((2S,3S,4S)-5-Chloro-6-fluoro-2-((((trans-4-hydroxy-4-methylcyclohexyl)amino)methyl)-3-methyl-2-phenyl-2,3-dihydrobenzofuran-4-yl)-5-fluoro-6-(2-hydroxyethoxy)nicotinamide;

2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzonitrile;

2-((2S,3S,4S)-5-Chloro-6-fluoro-2-(((trans-4-hydroxy-4-methylcyclohexyl)amino)methyl)-3-methyl-2-phenyl-2,3-dihydrobenzofuran-4-yl)-3-fluoro-4-(2-hydroxyethoxy)-N-methylbenzamide;

2-((2S,3S,4S)-5-Chloro-6-fluoro-3-methyl-2-((methylamino)methyl)-2-phenyl-2,3-dihydrobenzofuran-4-yl)-3-fluoro-4-((S)-2-hydroxypropoxy)-N-methylbenzamide;

2-((2S,3S,4S)-2-(Aminomethyl)-5-chloro-6-fluoro-3-methyl-2-phenyl-2,3-dihydrobenzofuran-4-yl)-3-fluoro-4-((S)-2-hydroxypropoxy)benzamide;

2-(2-((2S,3S,4S)-2-(Aminomethyl)-5-chloro-6-fluoro-3-methyl-2-phenyl-2,3-dihydrobenzofuran-4-yl)-3,4-difluorophenoxy)ethan-1-ol;

2-((2R,3S,4S)-5-Chloro-6-fluoro-2-(6-hydroxypyridin-2-yl)-3-methyl-2-((methylamino)methyl)-2,3-dihydrobenzofuran-4-yl)-3-fluoro-4-methoxybenzamide;

2-((2R,3S,4S)-5-Chloro-6-fluoro-2-((((trans)-4-hydroxy-4-methylcyclohexyl)amino)methyl)-3-methyl-2-(pyridin-2-yl)-2,3-dihydrobenzofuran-4-yl)-3-fluoro-4-(2-methoxyethoxy)benzamide;

2-((2S,3S,4S)-5-Chloro-6-fluoro-2-((((trans)-4-hydroxy-4-methylcyclohexyl)amino)methyl)-3-methyl-2-(pyridin-3-yl)-2,3-dihydrobenzofuran-4-yl)-3-fluoro-4-methoxybenzamide;

2-((2S,4S)-5-Chloro-2-((cyclohexylamino)methyl)-2-phenyl-2,3-dihydrobenzofuran-4-yl)-4-(difluoromethoxy)-3-fluorobenzamide;

2-((2S,3S,4S)-5-Chloro-6-fluoro-3-hydroxy-2-((((cis)-4-methoxycyclohexyl)amino)methyl)-2-phenyl-2,3-dihydrobenzofuran-4-yl)-4-(difluoromethoxy)-3-fluorobenzamide;

2-((2S,3S,4S)-5-chloro-6-fluoro-3-hydroxy-2-((((trans)-4-methoxycyclohexyl)amino)methyl)-2-phenyl-2,3-dihydrobenzofuran-4-yl)-4-(difluoromethoxy)-3-fluorobenzamide;

Methyl (cis)-4-((((2S,4S)-4-(6-carbamoyl-2,3-difluorophenyl)-5-chloro-2-phenyl-2,3-dihydrobenzofuran-2-yl)methyl)amino)cyclohexane-1-carboxylate;

Methyl (trans)-4-((((2S,4S)-4-(6-carbamoyl-2,3-difluorophenyl)-5-chloro-2-phenyl-2,3-dihydrobenzofuran-2-yl)methyl)amino)cyclohexane-1-carboxylate;

2-((2S,4S)-2-((((Trans)-4-carbamoylcyclohexyl)amino)methyl)-5-chloro-2-phenyl-2,3-dihydrobenzofuran-4-yl)-3-fluorobenzamide;

2-((2S,4S)-2-((((cis)-4-carbamoylcyclohexyl)amino)methyl)-5-chloro-2-phenyl-2,3-dihydrobenzofuran-4-yl)-3-fluorobenzamide;

2-((2S,4S)-5-Chloro-2-((((trans)-4-(methylcarbamoyl)cyclohexyl)amino)methyl)-2-phenyl-2,3-dihydrobenzofuran-4-yl)-3-fluorobenzamide;

2-((2S,4S)-5-chloro-2-((((cis)-4-(methylcarbamoyl)cyclohexyl)amino)methyl)-2-phenyl-2,3-dihydrobenzofuran-4-yl)-3-fluorobenzamide;

2-((2S,4S)-5-Chloro-2-((((cis)-3-(difluoromethyl)cyclobutyl)amino)methyl)-6-fluoro-2-phenyl-2,3-dihydrobenzofuran-4-yl)-3-fluoro-4-(2-hydroxyethoxy)benzamide;

2-((2S,4S)-5-chloro-2-((((trans)-3-(difluoromethyl)cyclobutyl)amino)methyl)-6-fluoro-2-phenyl-2,3-dihydrobenzofuran-4-yl)-3-fluoro-4-(2-hydroxyethoxy)benzamide;

2-((2S,4S)-2-(Aminomethyl)-5-chloro-6-fluoro-2-phenyl-2,3-dihydrobenzofuran-4-yl)-3-fluoro-4-(2-hydroxyethoxy-1,1,2,2-d4)-N-methylbenzamide;

2-((2S,3S,4S)-5-Chloro-6-fluoro-3-methyl-2-((methylamino)methyl)-2-phenyl-2,3-dihydrobenzofuran-4-yl)-3-fluoro-4-methoxybenzamide;

4-((2S,4S)-5-Chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide;

2-((2S,4S)-5-Chloro-6-fluoro-2-(((methyl-d3)amino)methyl)-2-phenyl-2,3-dihydrobenzofuran-4-yl)-4-(difluoromethoxy)-3-fluorobenzamide; and 2-((2S,4S)-5-Chloro-6-fluoro-2-(((methyl-d3)amino)methyl)-2-phenyl-2,3-dihydrobenzofuran-4-yl)-3-fluoro-4-(2-hydroxyethoxy-1,1,2,2-d4)benzamide.

Embodiment 53. A compound according to embodiment 1, or a pharmaceutically acceptable salt thereof, said compound selected from the group consisting of 2-((2S,3S,4S)-5-Chloro-6-fluoro-3-methyl-2-((methylamino)methyl)-2-phenyl-2,3-dihydrobenzofuran-4-yl)-3-fluoro-4-methoxybenzamide;
4-((2S,3S,4S)-5-Chloro-6-fluoro-3-methyl-2-((methylamino)methyl)-2-phenyl-2,3-dihydrobenzofuran-4-yl)-5-fluoro-6-(2-hydroxyethoxy)-N-methylnicotinamide;
2-((2S,3R,4S)-5-Chloro-6-fluoro-3-(methoxymethyl)-2-((methylamino)methyl)-2-phenyl-2,3-dihydrobenzofuran-4-yl)-3-fluoro-4-methoxybenzamide;
2-((2S,3R,4S)-5-Chloro-6-fluoro-3-(hydroxymethyl)-2-((methylamino)methyl)-2-phenyl-2,3-dihydrobenzofuran-4-yl)-3-fluoro-4-methoxybenzamide;
2-((2S,3S,4S)-5-Chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-hydroxy-2-methylpropoxy)benzamide;
2-((2S,4S)-2-(Azetidin-2-yl)-5-chloro-6-fluoro-2-phenyl-2,3-dihydrobenzofuran-4-yl)-3-fluoro-4-(2-hydroxyethoxy)-N-methylbenzamide;
2-((2S,3S,4S)-2-(Azetidin-2-yl)-5-chloro-6-fluoro-3-methyl-2-phenyl-2,3-dihydrobenzofuran-4-yl)-3-fluoro-4-((S)-2-hydroxypropoxy)-N-methylbenzamide;
2-((2S,3S,4S)-2-(Azetidin-2-yl)-5-chloro-6-fluoro-3-methyl-2-phenyl-2,3-dihydrobenzofuran-4-yl)-3-fluoro-4-((S)-2-hydroxypropoxy)-N-methylbenzamide;
(2-((2S,4S)-5-Chloro-6-fluoro-2-phenyl-2-((S)-pyrrolidin-2-yl)-2,3-dihydrobenzofuran-4-yl)-3-fluoro-4-(2-hydroxyethoxy)benzamide;
2-((2S,4S)-5-Chloro-6-fluoro-2-phenyl-2-((S)-pyrrolidin-2-yl)-2,3-dihydrobenzofuran-4-yl)-3-fluoro-4-((S)-2-hydroxypropoxy)benzamide;
2-((2S,4S)-5-Chloro-6-fluoro-2-phenyl-2-((S)-pyrrolidin-2-yl)-2,3-dihydrobenzofuran-4-yl)-3-fluoro-4-(2-hydroxyethoxy)-N-methylbenzamide;
2-((2S,4S)-5-Chloro-6-fluoro-2-phenyl-2-((S)-pyrrolidin-2-yl)-2,3-dihydrobenzofuran-4-yl)-3-fluoro-4-((S)-2-hydroxypropoxy)-N-methylbenzamide;
4-((2S,4S)-5-Chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide;
2-((4-((2S,4S)-5-Chloro-6-fluoro-2-phenyl-2-((S)-pyrrolidin-2-yl)-2,3-dihydrobenzofuran-4-yl)-3-fluoro-5-(methylcarbamoyl)pyridin-2-yl)oxy)acetic acid;
4-((2S,4S)-5-chloro-6-fluoro-2-phenyl-2-((S)-pyrrolidin-2-yl)-2,3-dihydrobenzofuran-4-yl)-5-fluoro-6-hydroxy-N-methylnicotinamide;
2-((2S,4S)-5-Chloro-6-fluoro-2-(4-hydroxypyrrolidin-2-yl)-2-phenyl-2,3-dihydrobenzofuran-4-yl)-4-(difluoromethoxy)-3-fluorobenzamide;
2-((2S,4S)-5-Chloro-6-fluoro-2-(4-hydroxy-4-methylpyrrolidin-2-yl)-2-phenyl-2,3-dihydrobenzofuran-4-yl)-3-fluoro-4-((S)-2-hydroxypropoxy)benzamide;
(2S,4R)-2-((S)-5-chloro-6-fluoro-2,4-diphenyl-2,3-dihydrobenzofuran-2-yl)-4-fluoropyrrolidine;
2-((2S,4S)-5-Chloro-6-fluoro-2-phenyl-2-((S)-piperidin-2-yl)-2,3-dihydrobenzofuran-4-yl)-3-fluoro-4-(2-hydroxyethoxy)-N-methylbenzamide; (3-((S)-5-Chloro-6-fluoro-2,4-diphenyl-2,3-dihydrobenzofuran-2-yl)morpholine;
2-((2S,4S)-5-Chloro-6-fluoro-2-(morpholin-3-yl)-2-phenyl-2,3-dihydrobenzofuran-4-yl)-3-fluoro-4-methoxybenzamide;
2-((2S,3S,4S)-5-chloro-6-fluoro-3-hydroxy-2-phenyl-2-(pyrrolidin-2-yl)-2,3-dihydrobenzofuran-4-yl)-3-fluoro-4-methoxybenzamide;
2-((2S,3S,4S)-5-chloro-6-fluoro-3-methoxy-2-phenyl-2-(pyrrolidin-2-yl)-2,3-dihydrobenzofuran-4-yl)-3-fluoro-4-methoxybenzamide;
2-((2S,3S,4S)-5-chloro-6-fluoro-3-methoxy-2-phenyl-2-(pyrrolidin-2-yl)-2,3-dihydrobenzofuran-4-yl)-3-fluoro-4-(2-hydroxyethoxy)benzamide;
2-((2S,3S,4S)-5-chloro-6-fluoro-3-methyl-2-phenyl-2-(pyrrolidin-2-yl)-2,3-dihydrobenzofuran-4-yl)-3-fluoro-4-((S)-2-hydroxypropoxy)benzamide;
2-((2S,4S)-2-(1-aminoethyl)-5-chloro-2-phenyl-2,3-dihydrobenzofuran-4-yl)-3-fluoro-4-methoxybenzamide;
2-((2S,3S,4S)-2-(1-aminoethyl)-5-chloro-6-fluoro-3-methyl-2-phenyl-2,3-dihydrobenzofuran-4-yl)-3-fluoro-4-(2-methoxyethoxy)benzamide;
2-((2S,4S)-5-chloro-6-fluoro-2-phenyl-2-((S)-pyrrolidin-2-yl)indolin-4-yl)-3-fluoro-4-(2-hydroxyethoxy)benzamide;
2-((2S,4S)-5-Chloro-6-fluoro-2-phenyl-2-((S)-pyrrolidin-2-yl)indolin-4-yl)-3-fluoro-4-methoxybenzamide;
2-((2S,4S)-5-Chloro-6-fluoro-2-phenyl-2-((S)-pyrrolidin-2-yl)indolin-4-yl)-3-fluoro-4-((S)-2-hydroxypropoxy)-N-methylbenzamide;
4-((2S,4S)-5-Chloro-6-fluoro-2-phenyl-2-((S)-pyrrolidin-2-yl)indolin-4-yl)-5-fluoro-6-(2-hydroxyethoxy)-N-methylnicotinamide;
2-((2S,4S)-5-Chloro-6-fluoro-2-phenyl-2-((S)-pyrrolidin-2-yl)-2,3-dihydrobenzofuran-4-yl)-3-fluoro-4-methoxybenzamide;
2-((2S,4S)-5-Chloro-6-fluoro-2-phenyl-2-((S)-pyrrolidin-2-yl)-2,3-dihydrobenzofuran-4-yl)-3-fluoro-4-methoxy-N-methylbenzamide; and
2-((2S,3S,4S)-2-(Aminomethyl)-5-chloro-6-fluoro-3-methyl-2-phenyl-2,3-dihydrobenzofuran-4-yl)-3-fluoro-4-methoxybenzamide.

Embodiment 54. A compound according to embodiment 1 or a pharmaceutically acceptable salt thereof, which is selected from 2-((2S,3S,4S)-5-chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide;
2-((2S,3S,4S)-5-Chloro-6-fluoro-3-methyl-2-((methylamino)methyl)-2-phenyl-2,3-dihydrobenzofuran-4-yl)-3-fluoro-4-((S)-2-hydroxypropoxy)-N-methylbenzamide;
2-((2S,3S,4S)-5-Chloro-6-fluoro-3-methyl-2-((methylamino)methyl)-2-phenyl-2,3-dihydrobenzofuran-4-yl)-3-fluoro-4-methoxybenzamide;
4-((2S,3S,4S)-5-Chloro-6-fluoro-3-methyl-2-((methylamino)methyl)-2-phenyl-2,3-dihydrobenzofuran-4-yl)-5-fluoro-6-(2-hydroxyethoxy)-N-methylnicotinamide;
4-((2S,4S)-5-Chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide; and
2-((2S,4S)-5-Chloro-6-fluoro-2-phenyl-2-((S)-pyrrolidin-2-yl)indolin-4-yl)-3-fluoro-4-(2-hydroxyethoxy)benzamide.

Embodiment 55. A pharmaceutical composition comprising a compound or a pharmaceutically acceptable salt thereof according to any of embodiments 1 to 54.

Embodiment 56. A combination comprising a compound or a pharmaceutically acceptable salt thereof according to any of embodiments 1 to 54 and one or more therapeutically active agents.

Embodiment 57. A combination according to embodiment 56, wherein the one or more therapeutically active agents is selected from an anti-cancer agent.

Embodiment 58. A compound according to any one of embodiments 1 to 54, or a pharmaceutically acceptable salt thereof, in simultaneous or sequential combination with an anti-cancer therapeutic.

Embodiment 59. A compound or a pharmaceutically acceptable salt thereof according to any of embodiments 1 to 54 for use as a medicament.

Embodiment 60. A compound or a pharmaceutically acceptable salt thereof according to any of embodiments 1 to 54 for use in inhibiting YAP/TAZ-TEAD protein-protein interaction activity in a subject.

Embodiment 61. A compound or a pharmaceutically acceptable salt thereof according to any of embodiments 1 to 54 for use in treating a disorder or disease, which is treated by inhibition of YAP/TAZ-TEAD protein-protein interaction in a subject, preferably wherein the disorder or disease is cancer.

Embodiment 62. A compound or a pharmaceutically acceptable salt thereof according to any of embodiments 1 to 54 for use in treating a disorder or disease which is a cancer or a tumor. Embodiment 63. A compound or a pharmaceutically acceptable salt thereof for use according to embodiment 62, wherein the cancer or tumor is a cancer or a tumor harboring (i)one or more YAP/TAZ fusions; (ii) one or more NF2/LATS1/LATS2 truncating mutations or deletions; or (iii) one or more functional YAP/TAZ fusions.

Embodiment 64. A compound or a pharmaceutically acceptable salt thereof for use according to embodiment 62 or 63, wherein the cancer or tumor is selected from mesothelioma (including pleural mesothelioma, malignant pleural mesothelioma, peritoneal mesothelioma, pericardial mesothelioma and mesothelioma of the *Tunica vaginalis*), carcinoma (including cervical squamous cell carcinoma, endometrial carcinoma, esophageal squamous cell carcinoma, esophageal adenocarcinoma, urothelial carcinoma of the bladder and squamous cell carcinoma of the skin), poroma (benign poroma), porocarcinoma (including malignant porocarcinoma), supratentorial ependymoma (including childhood supratentorial ependymoma), epithelioid hemangioendothelioma (EHE), ependymal tumor, a solid tumor, breast cancer (including triple negative breast cancer), lung cancer (including non-small cell lung cancer), ovarian cancer, colorectal cancer (including colorectal carcinoma), melanoma, pancreatic cancer (including pancreatic adenocarcinoma), prostate cancer, gastric cancer, esophageal cancer, liver cancer (including hepatocellular carcinoma, cholangiocarcinoma and hepatoblastoma), neuroblastoma, Schwannoma, kidney cancer, sarcoma (including rhabdomyosarcoma, embryonic rhabdomyosarcoma (ERMS), osteosarcoma, undifferentiated pleomorphic sarcomas (UPS), Kaposi's sarcoma, soft-tissue sarcoma and rare soft-tissue sarcoma), bone cancer, brain cancer, medulloblastoma, glioma, meningioma, and head and neck cancer (including head and neck squamous cell carcinoma).

Embodiment 65. A compound or a pharmaceutically acceptable salt thereof for use according to any of embodiments 61 to 64, wherein the disease or cancer is selected from breast cancer, lung cancer (including non small cell lung cancer), ovarian cancer, colorectal cancer, malignant pleural mesothelioma, pancreatic cancer, prostate cancer, gastric cancer, esophageal cancer, liver cancer, sarcoma and bone cancer, preferably wherein the cancer is malignant pleural mesothelioma or epithelioid hemangioendothelioma (EHE).

Embodiment 66. A method of inhibiting YAP/TAZ-TEAD protein-protein interaction activity in a subject, wherein the method comprises administering to a subject a therapeutically effective amount of a compound or a pharmaceutically acceptable salt thereof, according to any one of embodiments 1 to 54.

Embodiment 67. A method of modulating YAP/TAZ-TEAD protein-protein interaction activity in a subject in need thereof, the method comprising administering to the subject a therapeutically effective amount of a compound or a pharmaceutically acceptable salt thereof, according to any one of embodiments 1 to 54.

Embodiment 68. A method of inhibiting, reducing, or eliminating YAP/TAZ-TEAD protein-protein interaction, the method comprising administering to the subject a compound of any one of embodiments 1 to 54, or a pharmaceutically acceptable salt thereof.

Embodiment 69. A method of treating a disease or disorder that is affected by the modulation of YAP/TAZ-TEAD protein-protein interaction activity comprising administering to the patient in need thereof a compound of any one of embodiments 1 to 54, or a pharmaceutically acceptable salt thereof.

Embodiment 70. A method of treating a disease or disorder that is affected by the inhibiting, reducing, or eliminating of YAP/TAZ-TEAD protein-protein interaction, in a subject in need thereof, the method comprising administering to the subject a therapeutically effective amount of a compound of any one of embodiments 1 to 54, or a pharmaceutically acceptable salt thereof.

Embodiment 71. The method of Embodiment 69 or 70, wherein the disease or disorder is cancer or a tumor.

Embodiment 72. A method of treating a cancer or a tumor in a subject in need thereof, wherein the method comprises administering to the subject a therapeutically effective amount of a compound or a pharmaceutically acceptable salt thereof, according to any one of embodiments 1 to 54.

Embodiment 73. The method according to any one of embodiments 71 or 72, wherein the cancer or tumor is selected from mesothelioma (including pleural mesothelioma, malignant pleural mesothelioma, peritoneal mesothelioma, pericardial mesothelioma and mesothelioma of the *Tunica vaginalis*), carcinoma (including cervical squamous cell carcinoma, endometrial carcinoma, esophageal squamous cell carcinoma, esophageal adenocarcinoma, urothelial carcinoma of the bladder and squamous cell carcinoma of the skin), poroma (benign poroma), porocarcinoma (including malignant porocarcinoma), supratentorial ependymoma (including childhood supratentorial ependymoma), epithelioid hemangioendothelioma (EHE), ependymal tumor, a solid tumor, breast cancer (including triple negative breast cancer), lung cancer (including non-small cell lung cancer), ovarian cancer, colorectal cancer (including colorectal carcinoma), melanoma, pancreatic cancer (including pancreatic adenocarcinoma), prostate cancer, gastric cancer, esophageal cancer, liver cancer (including hepatocellular carcinoma, cholangiocarcinoma and hepatoblastoma), neuroblastoma, Schwannoma, kidney cancer, sarcoma (including rhabdomyosarcoma, embryonic rhabdomyosarcoma (ERMS), osteosarcoma, undifferentiated pleomorphic sarcomas (UPS), Kaposi's sarcoma, soft-tissue sarcoma and rare soft-tissue sarcoma), bone cancer, brain cancer, medulloblastoma, glioma, meningioma, and head and neck cancer (including head and neck squamous cell carcinoma).

Embodiment 74. The method according to any one of embodiments 71 to 73, wherein the cancer is breast cancer, lung cancer (including non small cell lung cancer), ovarian cancer, colorectal cancer, malignant pleural mesothelioma, pancreatic cancer, prostate cancer, gastric cancer, esophageal cancer, liver cancer, sarcoma and bone cancer, preferably wherein the cancer is malignant pleural mesothelioma or epithelioid hemangioendothelioma (EHE).

Embodiment 75. The use of a compound or a pharmaceutically acceptable salt thereof according to any of embodiments 1 to 54 for the preparation of a medicament, preferably for the treatment of a disease, or a cancer or a tumor as described herein (e.g. as defined in any of embodiments 73 or 74).

In the compounds according to any of enumerated embodiments 1 to 50, A is preferably an unsubstituted phenyl ring.

Pharmaceutically Acceptable Salts

Depending on the choice of the starting materials and procedures, the compounds can be present in the form of one of the possible isomers or as mixtures thereof, for example as pure optical isomers, or as isomer mixtures, such as racemates and diastereomeric mixtures, depending on the number of asymmetric centres. The present invention is meant to include all such possible isomers, including racemic mixtures, enantiomerically enriched mixtures, diastereomeric mixtures and optically pure forms. Optically active (R)- and (S)-isomers may be prepared using chiral synthons or chiral reagents, or resolved using conventional techniques. If the compound contains a disubstituted or trisubstituted cycloalkyl, the cycloalkyl substituent(s) may have a cis- or trans-configuration. The present invention includes cis and trans configurations of substituted cycloalkyl groups as well as mixtures thereof. All tautomeric forms are also intended to be included. In particular, where a heteroaryl ring containing N as a ring atom is 2-pyridone, for example, tautomers where the carbonyl is depicted as a hydroxy (e.g., 2-hydroxypyridine) are included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, trifluoroacetic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Isotopically Labelled Compounds

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{17}$O, $^{18}$O, $^{18}$F, $^{35}$S, $^{36}$Cl, $^{123}$I, $^{124}$I, $^{125}$I, respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The invention also relates to the compounds of any of the embodiments mentioned wherein one or more hydrogen atoms in one or more substituents are replaced with deuterium, e.g. all hydrogens in one or more alkyl substituents are replaced with deuterium (the respective moiety/moieties are then perdeuterated).

Pharmaceutically acceptable solvates in accordance with the invention include those wherein the solvent of crystallization may be isotopically substituted, e.g. $D_2O$, $d_6$-acetone, $d_6$-DMSO.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric centre in the compounds of the present invention can be present in a racemic mixture or in a mixture of enantiomers or in enantiomerically enriched form. In certain embodiments, for example, as a mixture of enantiomers, each asymmetric centre is present in at least 10% enantiomeric excess, at least 20% enantiomeric excess, at least 30% enantiomeric excess, at least 40% enantiomeric excess, at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. In certain embodiments, for example, in enantiomerically enriched form, each asymmetric centre is present in at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess.

Accordingly, as used herein a compound of the present invention can be in the form of one of the possible isomers, enantiomers, atropisomers, diastereoisomers, tautomers or mixtures thereof, for example, as substantially pure, diastereoisomers, optical isomers (enantiomers), racemates or mixtures thereof.

Any resulting mixtures of isomers can be separated on the basis of the physicochemical differences of the constituents, into the pure or substantially pure optical isomers, diastereoisomers, racemates, for example, by chromatography and/or fractional crystallization.

Any resulting racemates of final products or intermediates can be resolved into the optical enantiomers by known methods, e.g., by separation of the diastereomeric salts thereof, obtained with an optically active acid or base, and liberating the optically active acidic or basic compound.

In particular, a basic moiety may thus be employed to resolve the compounds of the present invention into their optical enantiomers, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The presence of solvates can be identified by a person of skill in the art with tools such as NMR. The compounds of the present invention, including salts, hydrates and solvates thereof, may inherently or by design form polymorphs.

Methods of Making

Typically, the compounds of formula (I) can be prepared according to the Schemes provided infra. The schemes provided infra are intended to represent single diastereomers/enantiomers as well as their isomeric mixtures. Separation of diastereomers/enantiomers may be performed according to techniques described herein. If not defined otherwise, in the general schemes described below, $R_2$, $R_3$, $R_4$, $R_5$, $R_7$, $R_w$, A, Q, W, X, Y and Z are as defined herein. In particular, $R_2$, $R_3$, $R_4$, $R_5$, $R_7$, $R_w$, A, Q, W, X, Y and Z are as defined in any of enumerated embodiments 1 to 50. The amine protecting group is also referred to herein as nitrogen protecting group or PG.

Scheme 1: General Synthesis of Compounds of formula (I)

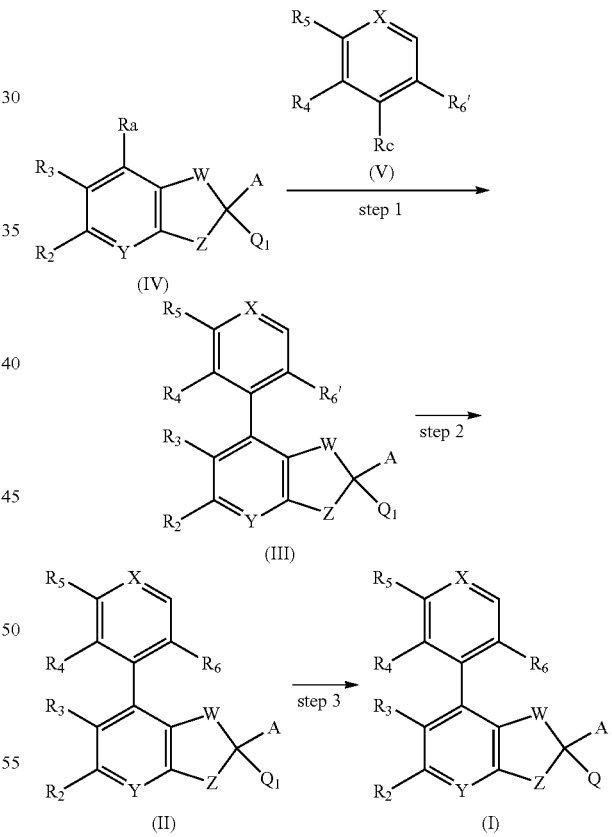

Step 1: The compound of formula (IV) is cross-coupled with a compound of formula (V) using a suitable catalyst, such as a Pd catalyst and a base. $R_a$ can be a boronic acid or a boronate ester while $R_c$ is a halide, such as a bromide or iodide. Alternatively, $R_a$ can be a halide such as a bromide or iodide while $R_c$ is a boronic acid or a boronate ester. Compounds of formula (III) generally consist of a mixture of diastereoisomers in the case $R_4$ and/or $R_6'$ are non-hydrogen.

$R_6'$ may be any functional group capable of being converted into $R_6$, wherein $R_6$ is as defined herein. In particular, $R_6$ is defined according to any one of enumerated embodiments 1 to 49.

Step 2: Following the cross-coupling (step 1) functional groups $R_6'$ can be converted to functional groups $R_6$.

Step 3: A compound of formula (I) can be obtained by transformation of group $Q_1$ into Q, for example, when $Q_1$ contains a nitrogen-protected amine, under deprotection conditions.

Synthesis of compounds of formula (I) are described in further detail, provided infra.

Scheme 2: General Synthesis of Compounds of Formula (I)

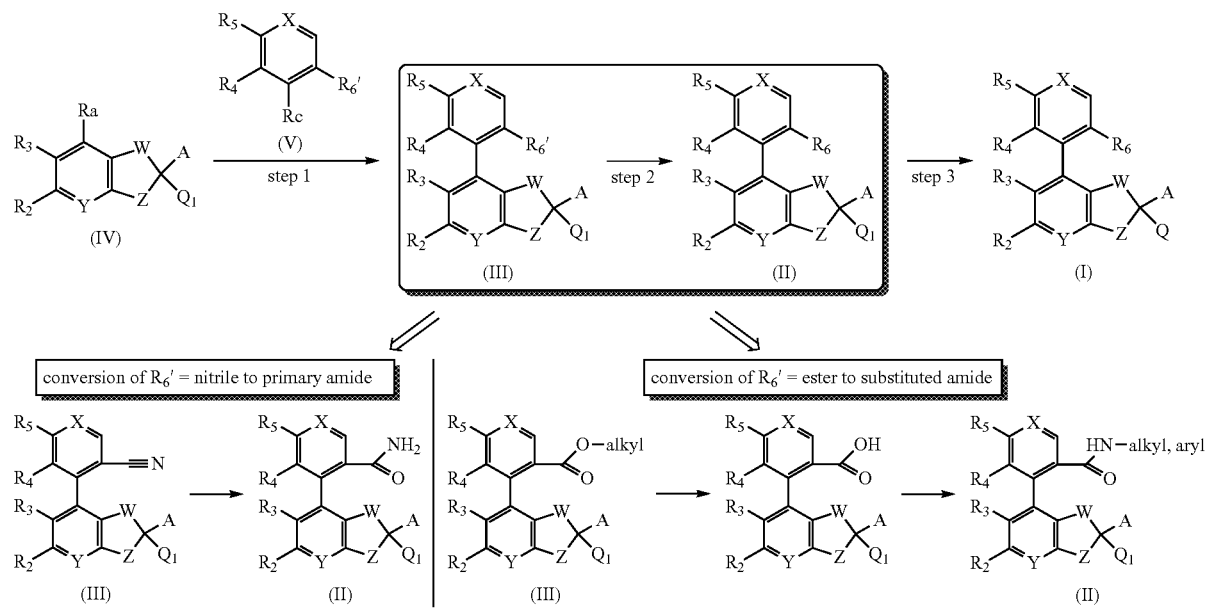

Step 1: The compound of formula (IV) is cross-couple with an aryl halide of formula (V) using suitable Pd catalyst such as N-XantPhos-Pd-G3 and a base such as potassium phosphate. Compounds of formula (III) general consist of a mixture of diastereoisomers in the case $R_4$ and/or $R^{6t}$ are non-hydrogen.

Step 2: Following the cross-coupling (step 1) Functional group $R_6'$ can be converted to functional groups $R_6$ (e.g. $R_6'$=nitrile can be converted into $R_6$=amide group using the catalyst hydrido(dimethylphosphinous acid-kP)[hydrogen bis(dimethylphosphinito-kP)]platinum(II) in EtOH and water; or $R_6'$=ester can be converted into $R_6$=substituted amides) to afford compounds of formula (II).

Step 3: When $Q_1$ contains a nitrogen-protected amine, the amine protecting group of compounds of formula (II) is cleaved to afford compounds of formula (I) with a free amine. E.g. a Boc group can be cleaved under acidic conditions, benzyl groups can be removed by hydrogenation in the presence of a metal such as palladium.

In case $Q=C(R^7)_2$—$NH_2$ The $NH_2$ group of compounds of formula (I) can then be functionalised further according to procedures described herein and schemes provided infra as well as according to methods generally known to those skilled in the art.

Scheme 3: Compounds of Formula (I) with an
Alkyl Group Attached to the Amine Group

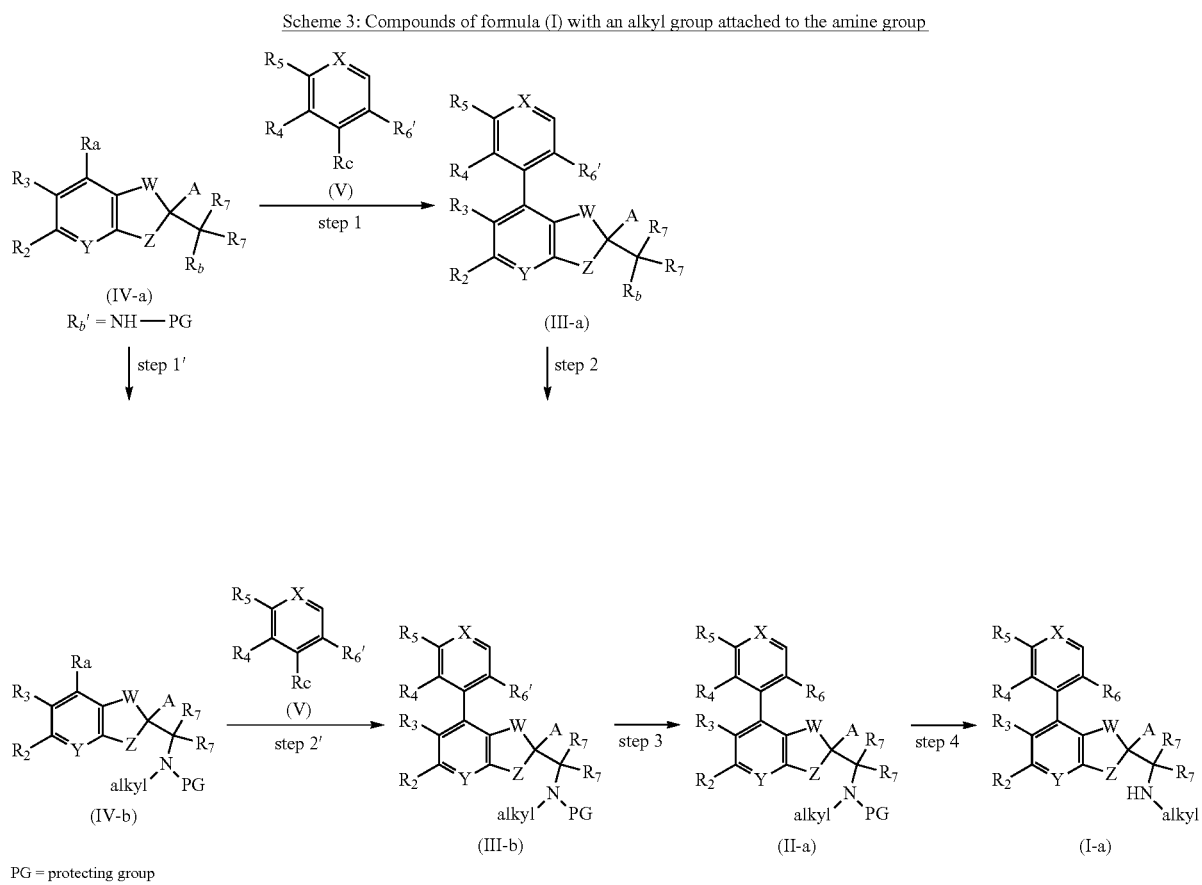

Step 1 and Step 2: A compound of formula (IV-a) is cross-coupled with a compound of formula (V) to afford a compound of formula (III-a) using similar conditions as outlined in Scheme 2, step 1. The compound of formula (IIa) is then alkylated to give a compound of formula (III-b).

Step 1' and Step 2': A compound of formula (IV-a) is alkylated to afford a compound of formula (IV-b) which is converted into a compound of formula (III-b) by cross coupling with a compound of formula (V) using similar conditions as outlined in Scheme 2, step 1.

Typical reaction conditions for the alkylation involve a base such as sodium hydride and an alkyl halide such as methyl iodide.

Step 3 and Step 4: a compound of formula (III-b) can be converted into a compound of formula (II-a) by interconversion of a functional group such as $R_6'$ into a functional group $R_6$ (step 3, refer to Scheme 2 and specific examples outlined therein) followed by cleavage of the protecting group (step 4) as outlined in Scheme 2, step 3.

Scheme 4: Compounds of Formula (I) Wherein $R_1$=Unsubstituted or Substituted Cycloalkyl

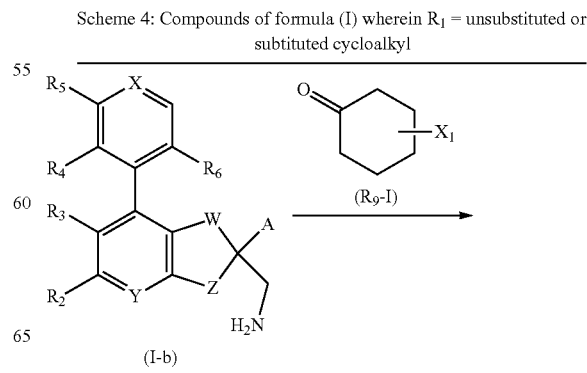

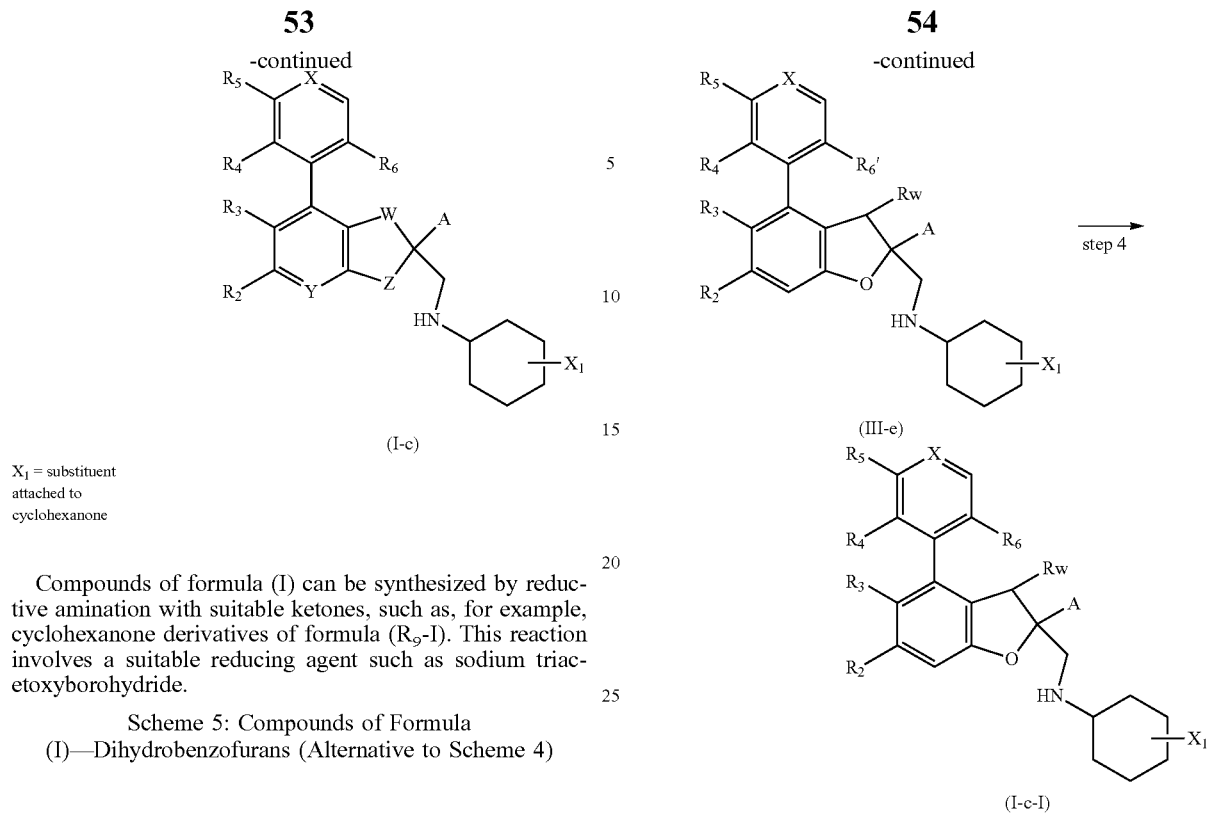

(I-c)

$X_1$ = substituent attached to cyclohexanone

Compounds of formula (I) can be synthesized by reductive amination with suitable ketones, such as, for example, cyclohexanone derivatives of formula ($R_9$-I). This reaction involves a suitable reducing agent such as sodium triacetoxyborohydride.

Scheme 5: Compounds of Formula (I)—Dihydrobenzofurans (Alternative to Scheme 4)

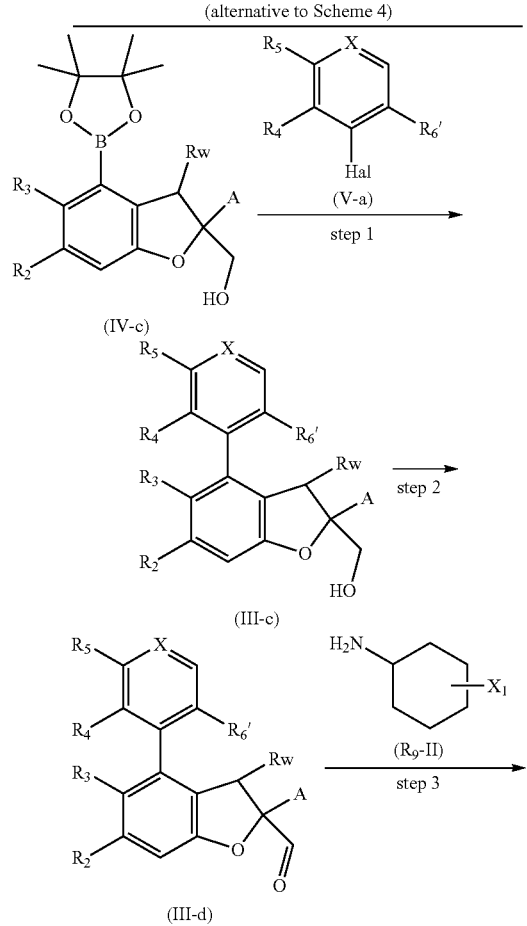

$X_1$ = substituent attached to cyclohexylamine

Step 1: Compounds of formula (III-c) can be synthesized by cross-coupling of boronate of formula (IV-c) with an aromatic halide of formula (V-a) using similar reaction conditions as outlined in Scheme 2, step 1.

Step 2: Oxidation of an alcohol of formula (III-c) affords the aldehyde of formula (III-d). Typical reaction conditions are oxalyl chloride/DMSO/triethylamine in dichloromethane (Swern oxidation conditions).

Step 3: Compounds of formula (III-e) can be obtained by reductive amination of an aldehyde of formula (III-d) with an amine such as, for example, a cyclohexylamine of formula ($R_9$-II) using similar reaction conditions as outlined in Scheme 4.

Step 4: Conversion of functional groups $R_6'$ into functional groups $R_6$ as outlined in Scheme 2, step 2 affords a compound of formula (I-c-I).

Scheme 6: Compounds of Formula (I)—Dihydrobenzofurans (Alternative to Schemes 4 and 5)

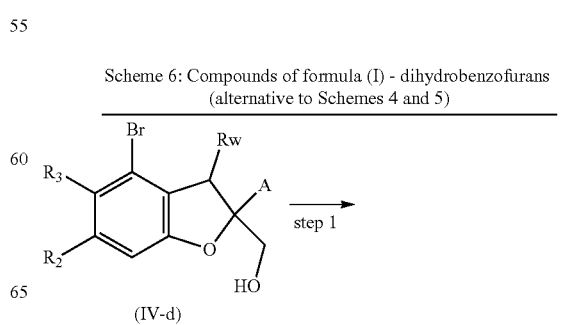

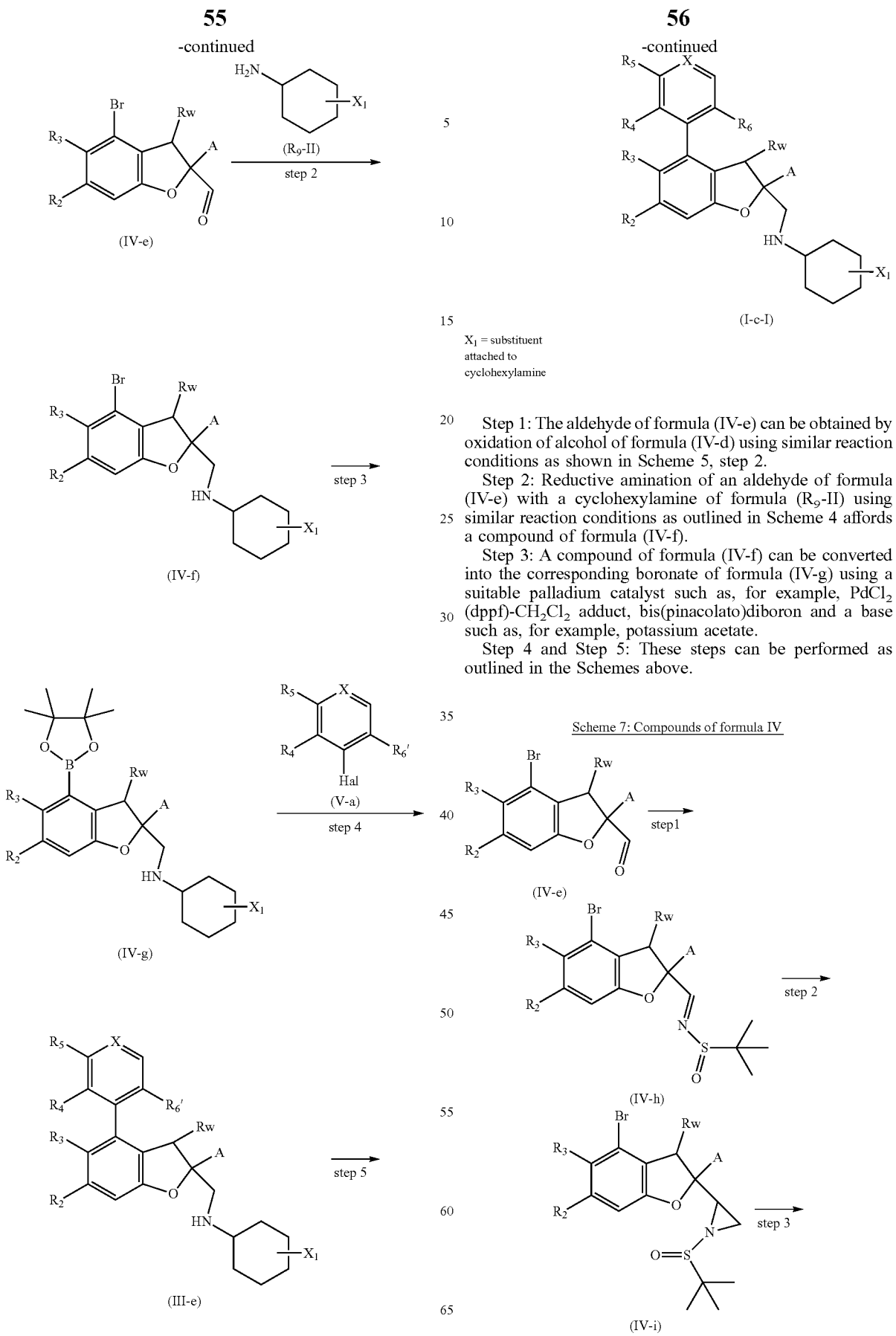

$X_1$ = substituent attached to cyclohexylamine

Step 1: The aldehyde of formula (IV-e) can be obtained by oxidation of alcohol of formula (IV-d) using similar reaction conditions as shown in Scheme 5, step 2.

Step 2: Reductive amination of an aldehyde of formula (IV-e) with a cyclohexylamine of formula ($R_9$-II) using similar reaction conditions as outlined in Scheme 4 affords a compound of formula (IV-f).

Step 3: A compound of formula (IV-f) can be converted into the corresponding boronate of formula (IV-g) using a suitable palladium catalyst such as, for example, $PdCl_2$(dppf)-$CH_2Cl_2$ adduct, bis(pinacolato)diboron and a base such as, for example, potassium acetate.

Step 4 and Step 5: These steps can be performed as outlined in the Schemes above.

Scheme 7: Compounds of formula IV

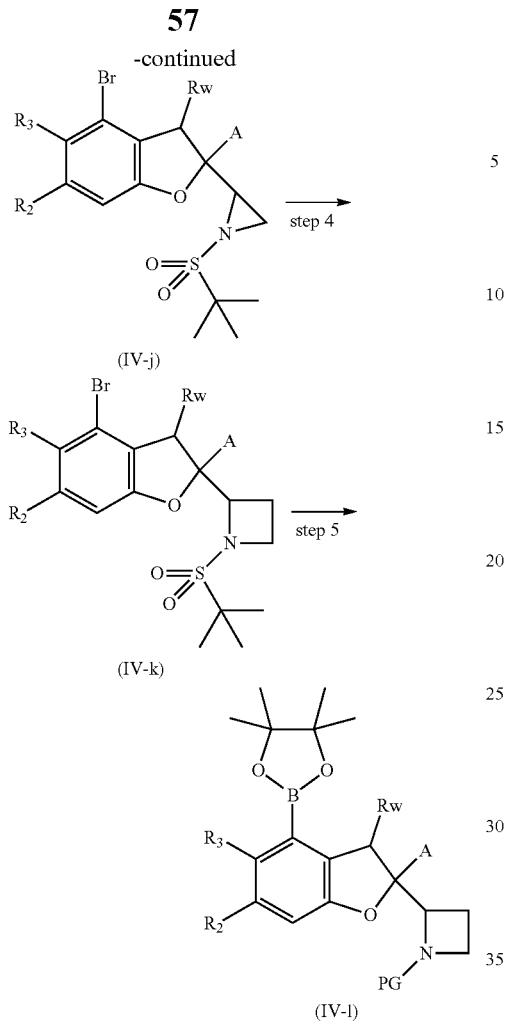

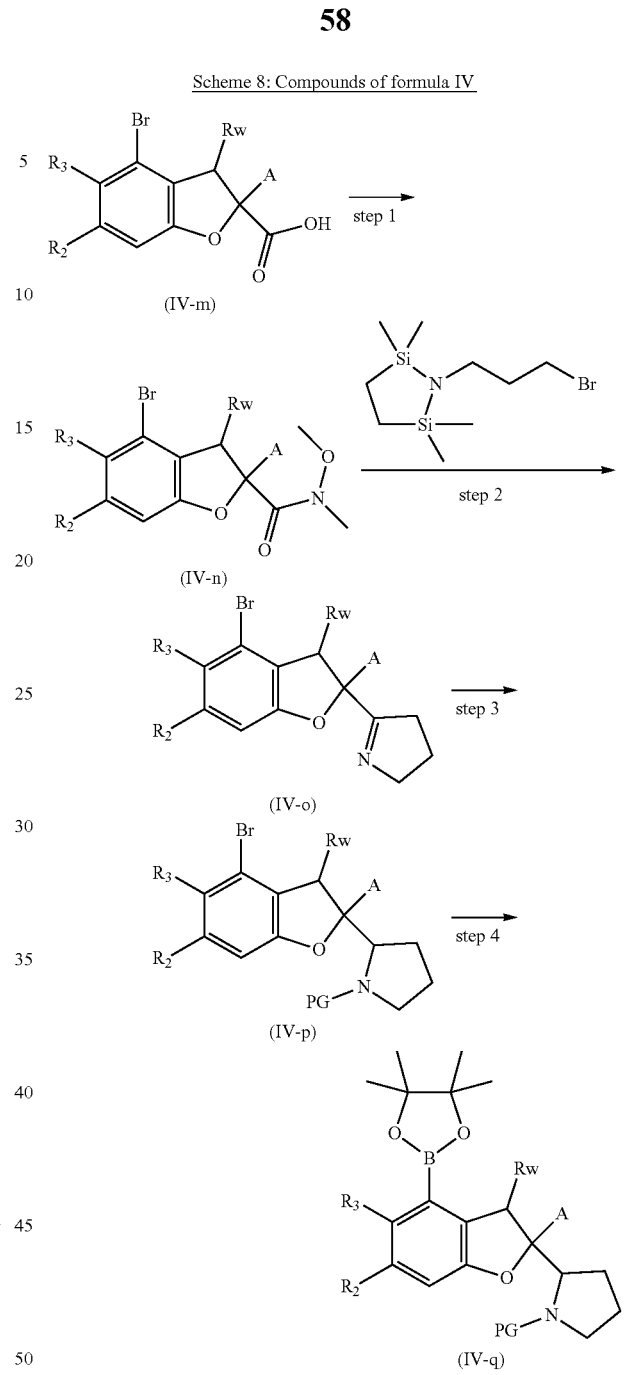

Scheme 8: Compounds of formula IV

PG = protecting group

Step 1: The sulfinamide of formula (IV-h) can be obtained by reaction of aldehyde of formula (IV-e) with 2-methylpropane-2-sulfinamide.

Step 2: The aziridine of formula (IV-i) can be formed by reaction of sulfinamide of formula (IV-h) with trimethylsulfoxonium iodide and sodium hydride (Corey Chaykovsky reaction).

Step 3: The oxidation of a compound of formula (IV-i) to the corresponding sulfonamide of formula (IV-j) can be achieved using an oxidating reagent such as, for example, m-CPBA.

Step 4: A compound of formula (IV-k) can be obtained by reaction of a compound of formula (IV-j) with trimethylsulfoxonium iodide and sodium hydride (Corey Chaykovsky reaction).

Step 5: A boronate of formula (IV-l) can be synthesized from a compound of formula (IV-k) by cleavage of the sulfone group (e.g. by using trifluoromethanesulfonic acid) followed by reprotection of the amine (e.g. with a Boc group) and conversion of the bromine into the corresponding boronate as outlined in Scheme 6, step 3.

Step 1: A Weinreb amide of formula (IV-n) can be obtained by reacting an acid of formula (IV-m) with N,O-dimethylhydroxylamine using standard peptide coupling.

Step 2: A dihydro-2H-pyrrole of formula (IV-o) can be synthesized by Grignard addition of the corresponding Mg species of 1-(3-bromopropyl)-2,2,5,5-tetramethyl-1,2,5-azadisilolidine to the Weinreb amide of formula (IV-n) followed by intramolecular imine formation.

Step 3: The dihydro-2H-pyrrole of formula (IV-o) can be reduced using, for example, sodium borohydride, followed by protection of the pyrrolidine nitrogen with a suitable protecting group such as, for example, a Boc group to afford a compound of formula (IV-p).

Step 4: A compound of formula (IV-q) can be obtained from a compound of formula (IV-p) using similar reaction conditions as shown in Scheme 6, step 3.

Scheme 9: Compounds of formula IV

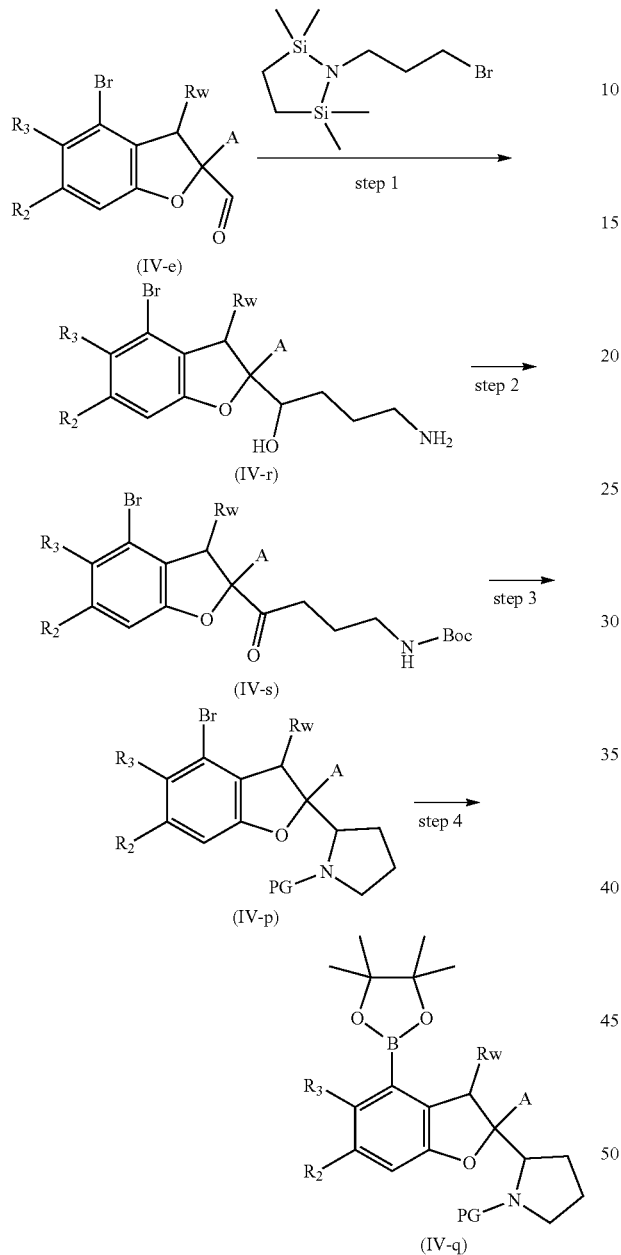

Step 1: An aminoalcohol of formula (IV-r) can be synthesized by Grignard addition of the corresponding Mg species of 1-(3-bromopropyl)-2,2,5,5-tetramethyl-1,2,5-aza-disilolidine to an aldehyde of formula (IV-e).

Step 2: A ketone of formula (IV-s) can be synthesized from a compound of formula (IV-r) by Boc-protection followed by oxidation of the alcohol using, for example, Swern oxidation conditions (oxalyl chloride/DMSO/TEA).

Step 3 and Step 4: A compound of formula (IV-p) can be obtained from a compound of formula (IV-s) by removal of the Boc group followed by cyclization using conditions as outlined in Scheme 8, steps 2 and 3 and reprotection of the pyrrolidine with, for example, a Boc group. A boronate of formula (IV-q) can be synthesized as outlined in Scheme 6, step 3.

Scheme 10: Compounds of Formula IV

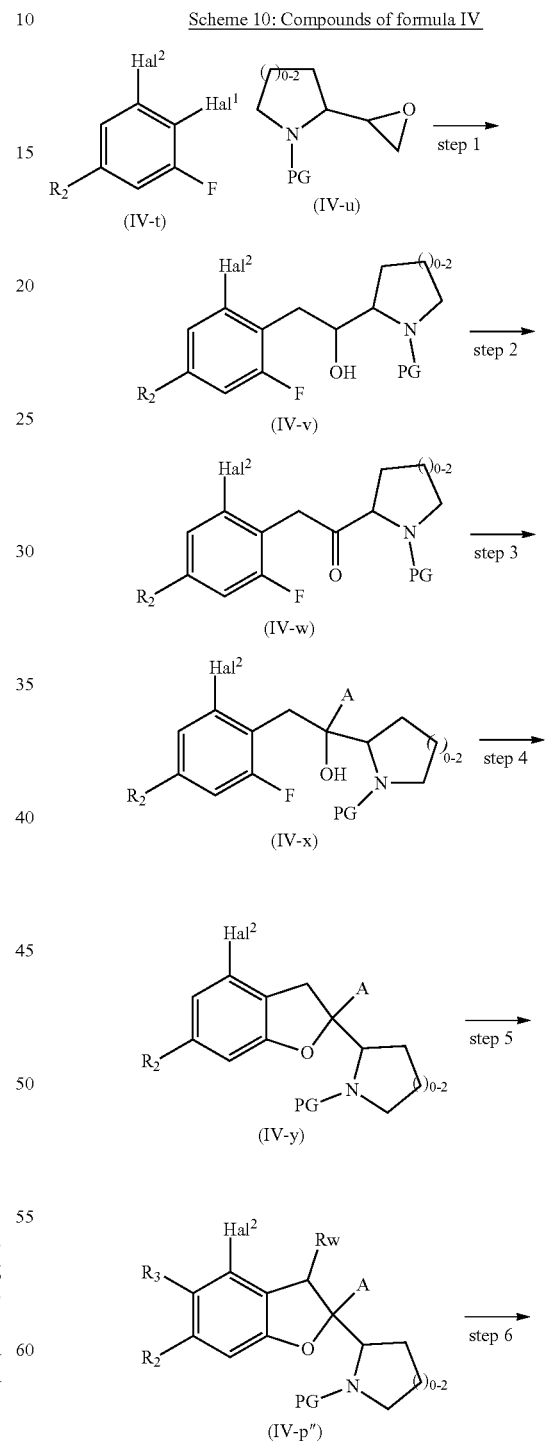

PG = protecting group, e.g. Boc

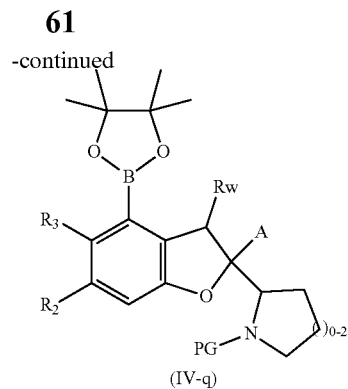
(IV-q)

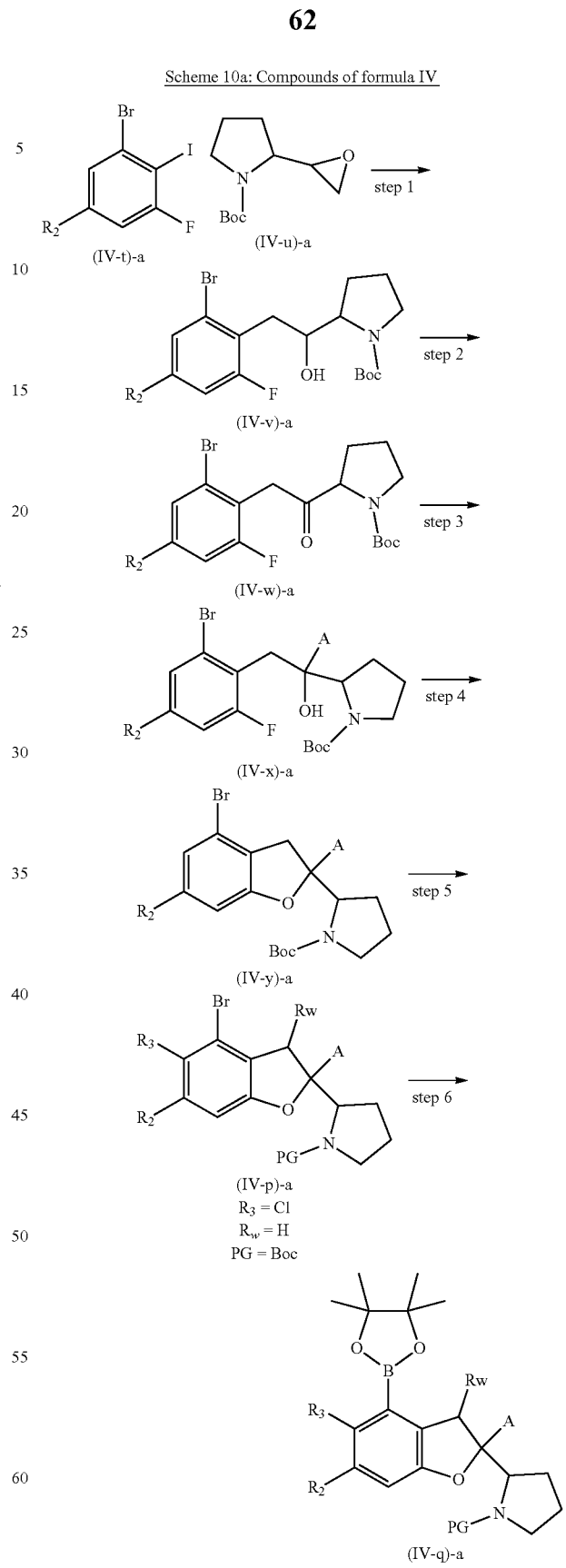

Scheme 10a: Compounds of formula IV

Step 1: Synthesis of alcohol (IV-v) can be achieved by an epoxide ring opening of a compound of formula (IV-u), with a suitable organometallic species generated by treatment of (IV-t) with a reagent such as an organolithium or an organomagnesium reagent (optionally in the presence of a transition metal salt such as CuI to form an organocuprate reagent), an organozinc, an organocuprate or an organocerium reagent. For example, the reagent may be an alkyl lithium (t-BuLi), a Grignard reagent, a dialkylzinc reagent, a dialkylcuprate or a trialkyl cerium reagent. The suitable organometallic species can also be converted into another suitable organometallic species by transmetallation with magnesium halides, zinc halides, copper halides, or cerium halides. Preferably the reagent is a Grignard reagent, e.g. iPrMgCl. $Hal^1$ and $Hal^2$ may each be I, Cl or Br, provided that the halide of $Hal^1$ is less electronegative (and hence more reactive towards the organometallic reagent) than the halide of $Hal^2$. For example, if $Hal^1$ is I, then $Hal^2$ must be Cl or Br. If $Hal^2$ is Cl, then $Hal^1$ must be Br or I. Preferably, $Hal^1$ is I and $Hal^2$ is Br.

Step 2: Oxidation of an alcohol of formula (IV-v) to a ketone of formula (IV-w) can be achieved by a suitable oxidation method for secondary alcohols, for example, using Dess-Martin periodinane.

Step 3: A compound of formula (IV-x) can be obtained by the addition of a suitable organometallic species generated by treatment of a compound of formula A-X (where X=Cl, Br, I) with an alkyl lithium, a Grignard reagent, or a trialkyl cerium reagent. For example, a compound of formula (IV-x) can be obtained by Grignard addition of a Grignard reagent of formula AMgX (where X=Cl, Br, I), e.g. AMgBr, wherein A is as described herein, to a ketone of formula (IV-w). For example, the Grignard reagent may be PhMgBr.

Step 4: A dihydrobenzofuran of formula (IV-y) can be obtained by intramolecular cyclization of (IV-x) using a suitable base, such as KOtBu.

Step 5: Chlorination of (IV-y) using N-chlorosuccinimide affords a compound of formula (IV-p″).

Step 6: A compound of formula (IV-q) can be obtained from a compound of formula (IV-p″) using similar reaction conditions as shown in Scheme 6, step 3.

Preferably, compounds of formula (IV) are prepared according to Scheme 10a.

Step 1: Epoxide opening of a compound of formula (IV-u)-a with a magnesium species generated by treatment of iodide (IV-t)-a with iPrMgCl in the presence of CuI affords an alcohol of formula (IV-v)-a.

Step 2: Oxidation of an alcohol of formula (IV-v)-a to a ketone of formula (IV-w)-a can be achieved by, for example, using Dess-Martin periodinane.

Step 3: A compound of formula (IV-x)-a can be obtained by Grignard addition of a Grignard reagent of formula AMgBr, wherein A is as described herein, to a ketone of formula (IV-w)-a. For example, the Grignard reagent may be PhMgBr.

Step 4: A dihydrobenzofuran of formula (IV-y)-a can be obtained from an alcohol of formula (IV-x)-a by intramolecular cyclization using a suitable base, such as KOtBu.

Step 5: Chlorination of (IV-y)-a using N-chlorosuccinimide affords a compound of formula (IV-p)-a.

Step 5: A compound of formula (IV-q)-a can be obtained from a compound of formula (IV-p)-a using similar reaction conditions as shown in Scheme 6, step 3.

Scheme 11: Compounds of formula IV

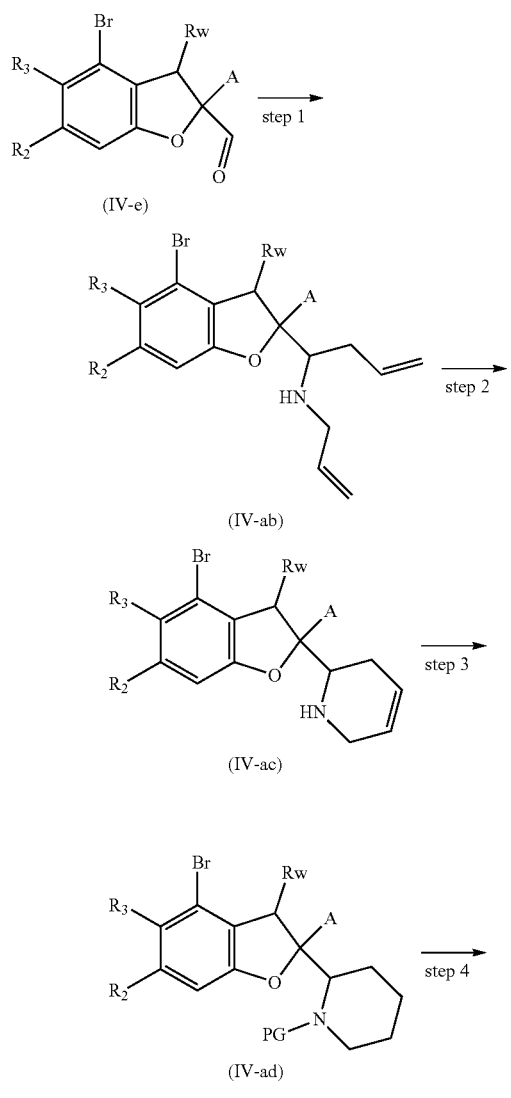

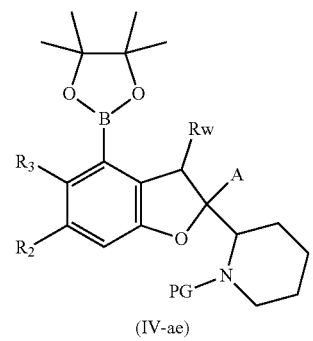

(IV-ae)

Step 1: A compound of formula (IV-ab) can be obtained from an aldehyde of formula (IV-e) by reaction with allylamine followed by Grignard addition of allylmagnesium bromide.

Step 2: Ring closing metathesis of a bis-allyl compound of formula (IV-ab) can be achieved by, for example, using a $2^{nd}$ generation Grubb's catalyst to afford a tetrahydropyridine compound of formula (IV-ac).

Step 3 and Step 4: Hydrogenation of the tetrahydropyridine and protection of the piperidine nitrogen with a suitable group (PG), such as Boc, gave a compound of formula (IV-ad) which can be converted to a boronate of formula (IV-ae) using the conditions described in Scheme 6, step 3.

Scheme 12: Compounds of Formula IV

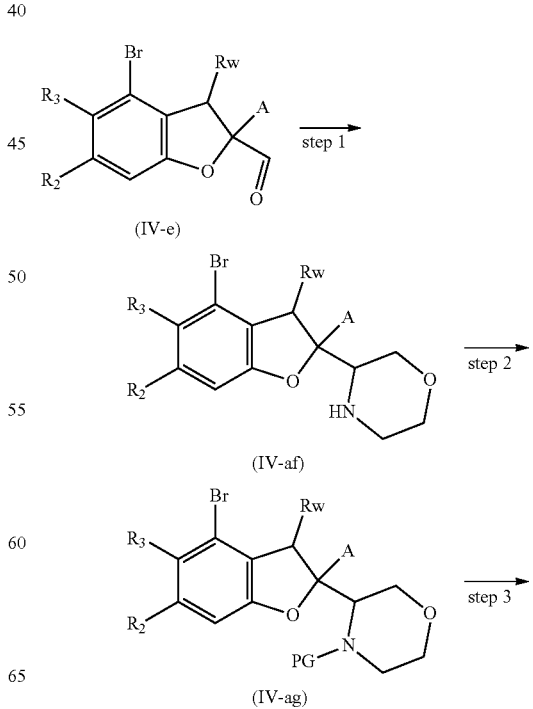

-continued

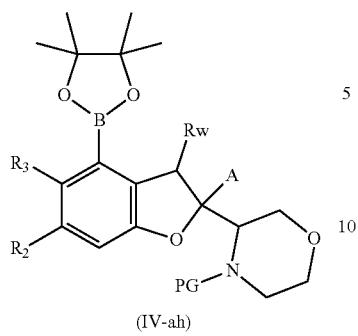

(IV-ah)

-continued

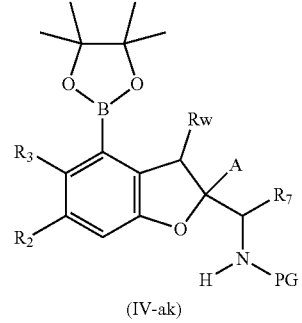

(IV-ak)

Step 1: A compound of formula (IV-af) can be obtained from an aldehyde of formula (IV-e) by reaction with SnAP M reagent=2-[(tributylstannyl)methoxy]-ethanamine.

Step 2 and Step 3: Protection of the morpholine nitrogen with a suitable group such as, for example, Boc gives a compound of formula (IV-ag) which can be converted to a boronate of formula (IV-ah) using the conditions described in Scheme 6, step 3.

Step 1: A compound of formula (IV-ai) can be obtained from a sulfinamide of formula (IV-h) by reaction with a Grignard reagent.

Step 2 and Step 3: Cleavage of the sulfinamide followed by reprotection with a suitable protecting group such as, for example, Boc gives a compound of formula (IV-aj) which can be converted to a boronate of formula (IV-ak) using the conditions described in Scheme 6, step 3.

In an embodiment, there is provided a compound of formula (IV) or a salt thereof Scheme 13: Compounds of Formula IV

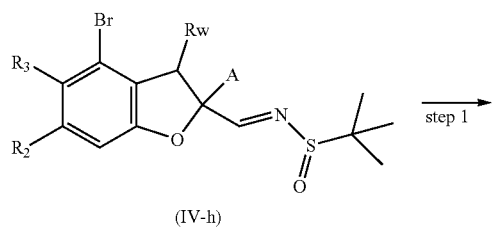

(IV-h)

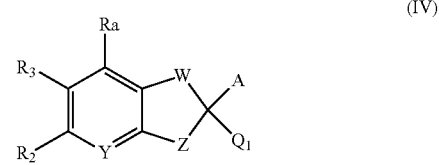

(IV)

wherein $R_a$ is selected from (i) halide such as bromo or iodide (preferably bromo); and (ii) $B(R'_a)_2$ wherein each $R'_a$ is hydroxy or two $R'_a$ groups together with the boron to which they are attached form a pinacol boronate moiety of formula

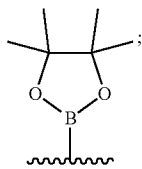

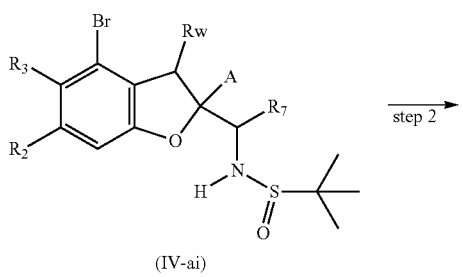

(IV-ai)

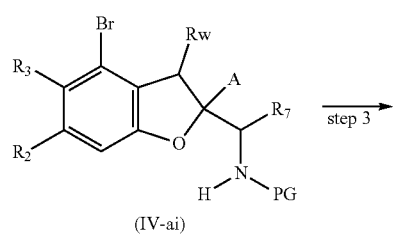

(IV-ai)

$Q_1$ is selected from (i) —C($R^7$)$_2$— $R_b$; and (ii) 9- or 10-membered partially saturated heteroaryl comprising at least one N heteroatom; and (iii) 4-, 5- or 6-membered saturated heterocyclic ring comprising at least one heteroatom or heteroatom group selected from N, O, S, —S(=O) and —S(=O)$_2$, with the proviso that at least one N heteroatom is present, which N heteroatom is optionally substituted with a protecting group, wherein the heterocyclic ring is unsubstituted or substituted with one or more substituents independently selected from hydroxy, $C_1$-$C_3$alkyl, $C_1$-$C_3$alkoxy, halo and $C_1$-$C_3$alkylene forming a bridge between two ring atoms of the saturated heterocyclic ring, thus forming a bridged bicyclic structure;

$R_b$ is selected from (i) hydroxy; (ii) N($R^8$)—$R_b'$; (iii) azido, $R_b'$ is selected from (i) a nitrogen protecting group; (ii) $C_3$-$C_6$cycloalkyl optionally substituted once or more than once independently with hydroxy; hydroxy$C_1$-$C_4$alkyl; $C_1$-$C_6$alkoxy, preferably $C_1$-$C_4$alkoxy; C(O)OC$_1$-$C_3$alkyl; CO$_2$H; SO$_2$C$_1$-$C_3$alkyl; haloC$_1$-$C_3$alkyl; NHR$^{1b}$; (CH$_2$)$_{0-1}$C(O)NR$^{1c}$R$^{1d}$; $C_1$-$C_6$alkyl; haloC$_1$-$C_3$alkoxy-$C_1$-$C_3$alkyl; halo; a 5- or 6-membered aromatic heterocyclic ring comprising at least one heteroatom selected from N, O, and S; or 2 R$^{1e}$ groups, wherein the two R$^{1e}$ groups are attached at the same carbon atom and form together with the carbon atom to which they are attached a 5-membered saturated heterocyclic ring comprising at least one heteroatom selected from N and O, or a $C_3$-$C_6$cycloalkyl, which saturated heterocyclic ring or cycloalkyl are optionally substituted with hydroxy or oxo;

R$^{1b}$ is selected from (i) C(O)C$_1$-$C_3$alkyl; and (ii) SO$_2$C$_1$-$C_3$alkyl;

R$^{1c}$ and R$^{1d}$ are each independently selected from (i) hydrogen; (ii) $C_1$-$C_3$alkyl; and (iii) hydroxy$C_1$-$C_4$alkyl;

$R_2$, $R_3$, $R^7$, $R^8$, A, W, Y and Z are as defined in any of enumerated embodiments 1 to 50.

In an embodiment, there is provided a compound of the formula (IV-I) or a salt thereof,

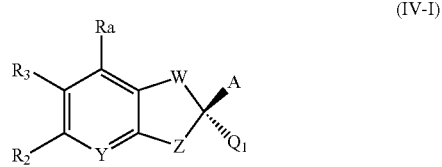

(IV-I)

wherein $R_a$ is selected from (i) bromo; (ii) B(R'$_a$)$_2$ wherein each R'$_a$ is hydroxy or two R'$_a$ groups together with the boron to which they are attached form a pinacol boronate moiety of formula

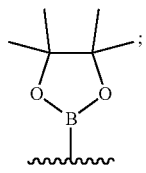

$Q_1$ is selected from (i) —C(R$^7$)$_2$—R$_b$; (ii) 9- or 10-membered partially saturated heteroaryl comprising at least one N heteroatom; and (iii) 4-, 5- or 6-membered saturated heterocyclic ring comprising at least one heteroatom or heteroatom group selected from N, O, S, —S(═O) and —S(═O)$_2$, with the proviso that at least one N heteroatom is present, which N heteroatom is optionally substituted with a protecting group, wherein the heterocyclic ring is unsubstituted or substituted with one or more substituents independently selected from hydroxy, $C_1$-$C_3$alkyl, $C_1$-$C_3$alkoxy, halo and $C_1$-$C_3$alkylene forming a bridge between two ring atoms of the saturated heterocyclic ring, thus forming a bridged bicyclic structure;

$R_b$ is selected from (i) hydroxy; (ii) N(R$^8$)—R$_b$'; (iii) azido, $R_b'$ is selected from (i) a nitrogen protecting group; (ii) $C_3$-$C_6$cycloalkyl optionally substituted once or more than once independently with hydroxy; hydroxy$C_1$-$C_4$alkyl; $C_1$-$C_6$alkoxy, preferably $C_1$-$C_4$alkoxy; C(O)OC$_1$-$C_3$alkyl; CO$_2$H; SO$_2$C$_1$-$C_3$alkyl; haloC$_1$-$C_3$alkyl; NHR$^{1b}$; (CH$_2$)$_{0-1}$C(O)NR$^{1c}$R$^{1d}$; $C_1$-$C_6$alkyl; haloC$_1$-$C_3$alkoxy-$C_1$-$C_3$alkyl; halo; a 5- or 6-membered aromatic heterocyclic ring comprising at least one heteroatom selected from N, O, and S; or 2 R$^{1e}$ groups, wherein the two R$^{1e}$ groups are attached at the same carbon atom and form together with the carbon atom to which they are attached a 5-membered saturated heterocyclic ring comprising at least one heteroatom selected from N and O, or a $C_3$-$C_6$cycloalkyl, which saturated heterocyclic ring or cycloalkyl are optionally substituted with hydroxy or oxo;

R$^{1b}$ is selected from (i) C(O)C$_1$-$C_3$alkyl; and (ii) SO$_2$C$_1$-$C_3$alkyl;

R$^{1c}$ and R$^{1d}$ are each independently selected from (i) hydrogen; (ii) $C_1$-$C_3$alkyl; and (iii) hydroxy$C_1$-$C_4$alkyl;

$R_2$, $R_3$, $R^7$, $R^8$, A, W, Y and Z are as defined in any of enumerated embodiments 1 to 50.

In an embodiment, there is provided a compound of formula (IV-II) or salt thereof

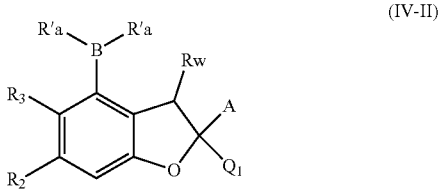

(IV-II)

wherein each R'$_a$ is hydroxy or two R'$_a$ groups together with the boron to which they are attached form a pinacol boronate moiety of formula

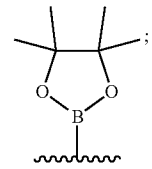

$Q_1$ is selected from (i) —C(R$^7$)$_2$—R$_b$; (ii) 9- or 10-membered partially saturated heteroaryl comprising at least one N heteroatom; and (iii) 4-, 5- or 6-membered saturated heterocyclic ring comprising at least one heteroatom or heteroatom group selected from N, O, S, —S(═O) and —S(═O)$_2$, with the proviso that at least one N heteroatom is present, which N heteroatom is optionally substituted with a protecting group, wherein the heterocyclic ring is unsubstituted or substituted with one or more substituents independently selected from hydroxy, $C_1$-$C_3$alkyl, $C_1$-$C_3$alkoxy, halo and $C_1$-$C_3$alkylene forming a bridge between two ring atoms of the saturated heterocyclic ring, thus forming a bridged bicyclic structure;

$R_b$ is selected from (i) hydroxy; (ii) N(R$^8$)—R$_b$'; (iii) azido, $R_b'$ is selected from (i) a nitrogen protecting group; (ii) $C_3$-$C_6$cycloalkyl optionally substituted once or more than once independently with hydroxy; hydroxy$C_1$-$C_4$alkyl; $C_1$-$C_6$alkoxy, preferably $C_1$-$C_4$alkoxy; C(O)OC$_1$-$C_3$alkyl; CO$_2$H; SO$_2$C$_1$-$C_3$alkyl; haloC$_1$-$C_3$alkyl;

NHR$^{1b}$; (CH$_2$)$_{0-1}$C(O)NR$^{1c}$R$^{1d}$; C$_1$-C$_6$alkyl; haloC$_1$-C$_3$alkoxy-C$_1$-C$_3$alkyl; halo; a 5- or 6-membered aromatic heterocyclic ring comprising at least one heteroatom selected from N, O, and S; or 2 R$^{1e}$ groups,
wherein the two R$^{1e}$ groups are attached at the same carbon atom and form together with the carbon atom to which they are attached a 5-membered saturated heterocyclic ring comprising at least one heteroatom selected from N and O, or a C$_3$-C$_6$cycloalkyl, which saturated heterocyclic ring or cycloalkyl are optionally substituted with hydroxy or oxo;

R$^{1b}$ is selected from (i) C(O)C$_1$-C$_3$alkyl; and (ii) SO$_2$C$_1$-C$_3$alkyl;

R$^{1c}$ and R$^{1d}$ are each independently selected from (i) hydrogen; (ii) C$_1$-C$_3$alkyl; and (iii) hydroxyC$_1$-C$_4$alkyl;

R$_2$, R$_3$, R$^1$, R$^8$, A, W, Y and Z are as defined in any of enumerated embodiments 1 to 49.

In an embodiment, there is provided a compound of formula (IV-III) or salt thereof

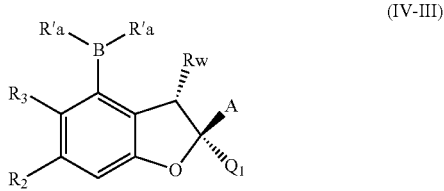

(IV-III)

wherein
each R'$_a$ is hydroxy or two R'$_a$ groups together with the boron to which they are attached form a pinacol boronate moiety of formula

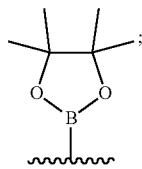

;

Q$_1$ is selected from (i) —C(R$^7$)$_2$—R$_b$; (ii) 9- or 10-membered partially saturated heteroaryl comprising at least one N heteroatom; and (iii) 4-, 5- or 6-membered saturated heterocyclic ring comprising at least one heteroatom or heteroatom group selected from N, O, S, —S(=O) and —S(=O)$_2$, with the proviso that at least one N heteroatom is present, which N heteroatom is optionally substituted with a protecting group, wherein the heterocyclic ring is unsubstituted or substituted with one or more substituents independently selected from hydroxy, C$_1$-C$_3$alkyl, C$_1$-C$_3$alkoxy, halo and C$_1$-C$_3$alkylene forming a bridge between two ring atoms of the saturated heterocyclic ring, thus forming a bridged bicyclic structure;

R$_b$ is selected from (i) hydroxy; (ii) N(R$^8$)—R$_b$'; (iii) azido,

R$_b$' is selected from (i) a nitrogen protecting group; (ii) C$_3$-C$_6$cycloalkyl optionally substituted once or more than once independently with hydroxy; hydroxyC$_1$-C$_4$alkyl; C$_1$-C$_6$alkoxy, preferably C$_1$-C$_4$alkoxy; C(O)OC$_1$-C$_3$alkyl; CO$_2$H; SO$_2$C$_1$-C$_3$alkyl; haloC$_1$-C$_3$alkyl; NHR$^{1b}$; (CH$_2$)oi-C(O)NR$^{1c}$R$^{1d}$; C$_1$-C$_6$alkyl; haloC$_1$-C$_3$alkoxy-C$_1$-C$_3$alkyl; halo; a 5- or 6-membered aromatic heterocyclic ring comprising at least one heteroatom selected from N, O, and S; or 2 R$^{1e}$ groups,
wherein the two R$^{1e}$ groups are attached at the same carbon atom and form together with the carbon atom to which they are attached a 5-membered saturated heterocyclic ring comprising at least one heteroatom selected from N and O, or a C$_3$-C$_6$cycloalkyl, which saturated heterocyclic ring or cycloalkyl are optionally substituted with hydroxy or oxo;

R$^{1b}$ is selected from (i) C(O)C$_1$-C$_3$alkyl; and (ii) SO$_2$C$_1$-C$_3$alkyl;

R$^{1c}$ and R$^{1d}$ are each independently selected from (i) hydrogen; (ii) C$_1$-C$_3$alkyl; and (iii) hydroxyC$_1$-C$_4$alkyl;

R$_2$, R$_3$, R$^7$, R$^8$, A, W, Y and Z are as defined in any of enumerated embodiments 1 to 50.

In an additional embodiment, there is provided a compound or salt thereof selected from the group consisting of:

tert-butyl (S)-((5-chloro-2-phenyl-4-(4,4,5,5-tetramethyl-1,3,2-dioxaborolan-2-yl)-2,3-dihydrobenzofuran-2-yl)methyl)carbamate;

tert-butyl ((5-chloro-2-phenyl-4-(4,4,5,5-tetramethyl-1,3,2-dioxaborolan-2-yl)-2,3-dihydrobenzofuran-2-yl)methyl)carbamate;

tert-butyl ((5-chloro-4-(4,4,5,5-tetramethyl-1,3,2-dioxaborolan-2-yl)-2-(thiazol-4-yl)-2,3-dihydrobenzofuran-2-yl)methyl)carbamate;

tert-butyl-((5-chloro-2-(2,2-difluorobenzo[d][1,3]dioxol-4-yl)-4-(4,4,5,5-tetramethyl-1,3,2-dioxaborolan-2-yl)-2,3-dihydrobenzofuran-2-yl)methyl)carbamate;

tert-butyl (S)-((5-chloro-2-(2-fluorophenyl)-4-(4,4,5,5-tetramethyl-1,3,2-dioxaborolan-2-yl)-2,3-dihydrobenzofuran-2-yl)methyl)carbamate;

tert-butyl (((2S,3S)-5-chloro-3-hydroxy-2-phenyl-4-(4,4,5,5-tetramethyl-1,3,2-dioxaborolan-2-yl)-2,3-dihydrobenzofuran-2-yl)methyl)carbamate;

tert-butyl (((2R*,3S*)-5-chloro-3-hydroxy-2-(pyridin-2-yl)-4-(4,4,5,5-tetramethyl-1,3,2-dioxaborolan-2-yl)-2,3-dihydrobenzofuran-2-yl)methyl)carbamate;

tert-butyl (((2S*,3S*)-5-chloro-3-hydroxy-4-(4,4,5,5-tetramethyl-1,3,2-dioxaborolan-2-yl)-2-(2-(trifluoromethoxy)phenyl)-2,3-dihydrobenzofuran-2-yl)methyl)carbamate;

tert-butyl (((2R*,3S*)-5-chloro-3-hydroxy-2-(6-methoxypyridin-2-yl)-4-(4,4,5,5-tetramethyl-1,3,2-dioxaborolan-2-yl)-2,3-dihydrobenzofuran-2-yl)methyl)carbamate;

((2S*,3S*)-2-(((tert-butoxycarbonyl)amino)methyl)-5-chloro-3-hydroxy-2-(2-methoxypyridin-3-yl)-2,3-dihydrobenzofuran-4-yl)boronic acid;

tert-butyl (((2S,3S)-5-chloro-3-methyl-2-phenyl-4-(4,4,5,5-tetramethyl-1,3,2-dioxaborolan-2-yl)-2,3-dihydrobenzofuran-2-yl)methyl)carbamate;

tert-butyl (S)-((5-chloro-6-fluoro-2-phenyl-4-(4,4,5,5-tetramethyl-1,3,2-dioxaborolan-2-yl)-2,3-dihydrobenzofuran-2-yl)methyl)carbamate;

(S)-(5-chloro-6-fluoro-2-phenyl-4-(4,4,5,5-tetramethyl-1,3,2-dioxaborolan-2-yl)-2,3-dihydrobenzofuran-2-yl)methanol;

tert-butyl (((2S,3S)-5-chloro-6-fluoro-3-hydroxy-2-phenyl-4-(4,4,5,5-tetramethyl-1,3,2-dioxaborolan-2-yl)-2,3-dihydrobenzofuran-2-yl)methyl)carbamate;

tert-butyl (((2S,3S)-5-chloro-6-fluoro-3-methoxy-2-phenyl-4-(4,4,5,5-tetramethyl-1,3,2-dioxaborolan-2-yl)-2,3-dihydrobenzofuran-2-yl)methyl)carbamate;

tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)carbamate;

((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methanol;
tert-butyl (((2R,3S)-5-chloro-6-fluoro-3-methyl-2-(pyridin-2-yl)-4-(4,4,5,5-tetramethyl-1,3,2-dioxaborolan-2-yl)-2,3-dihydrobenzofuran-2-yl)methyl)carbamate;
((2S,3S)-2-(6-(benzyloxy)pyridin-2-yl)-5-chloro-6-fluoro-3-methyl-4-(4,4,5,5-tetramethyl-1,3,2-dioxaborolan-2-yl)-2,3-dihydrobenzofuran-2-yl)methanol;
(trans)-4-((((2R,3S)-5-chloro-6-fluoro-3-methyl-2-(pyridin-2-yl)-4-(4,4,5,5-tetramethyl-1,3,2-dioxaborolan-2-yl)-2,3-dihydrobenzofuran-2-yl)methyl)amino)-1-methylcyclohexan-1-ol;
(trans)-4-((((2S,3S)-5-chloro-6-fluoro-3-methyl-2-(pyridin-3-yl)-4-(4,4,5,5-tetramethyl-1,3,2-dioxaborolan-2-yl)-2,3-dihydrobenzofuran-2-yl)methyl)amino)-1-methylcyclohexan-1-ol;
tert-butyl (S)-((2-phenyl-4-(4,4,5,5-tetramethyl-1,3,2-dioxaborolan-2-yl)-5-(trifluoromethyl)-2,3-dihydrobenzofuran-2-yl)methyl)carbamate;
(S)-2-(hydroxymethyl)-2-phenyl-4-(4,4,5,5-tetramethyl-1,3,2-dioxaborolan-2-yl)-2,3-dihydrobenzofuran-5-carbonitrile;
(S)-4-bromo-2-((((trans)-4-hydroxycyclohexyl)amino)methyl)-2-phenyl-2,3-dihydrobenzofuran-5-carbonitrile;
tert-butyl (S)-((4-bromo-5-chloro-2-phenyl-2,3-dihydrofuro[2,3-b]pyridin-2-yl)methyl)carbamate tert-butyl ((6-chloro-2-phenyl-7-(4,4,5,5-tetramethyl-1,3,2-dioxaborolan-2-yl)-2,3-dihydrobenzofuran-2-yl)methyl)carbamate;
tert-butyl ((4-bromo-5-chloro-2-phenylbenzo[d][1,3]dioxol-2-yl)methyl)carbamate (S)-2-(azidomethyl)-4-bromo-5-chloro-6-fluoro-2-phenylindoline;
tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)(methyl)carbamate;
tert-butyl (((2S,3R)-5-chloro-6-fluoro-3-(methoxymethyl)-2-phenyl-4-(4,4,5,5-tetramethyl-1,3,2-dioxaborolan-2-yl)-2,3-dihydrobenzofuran-2-yl)methyl)(methyl)carbamate;
tert-butyl (((2S,3R)-3-((benzyloxy)methyl)-5-chloro-6-fluoro-2-phenyl-4-(4,4,5,5-tetramethyl-1,3,2-dioxaborolan-2-yl)-2,3-dihydrobenzofuran-2-yl)methyl)(methyl)carbamate;
tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)azetidine-1-carboxylate;
tert-butyl 2-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)azetidine-1-carboxylate;
tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate;
(S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine;
tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)-4-hydroxypyrrolidine-1-carboxylate;
tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)-4-hydroxy-4-methylpyrrolidine-1-carboxylate;
tert-butyl (2S,4R)-2-((S)-4-bromo-5-chloro-6-fluoro-2-phenyl-2,3-dihydrobenzofuran-2-yl)-4-fluoropyrrolidine-1-carboxylate;
tert-butyl 2-((2S,3S)-5-chloro-6-fluoro-3-hydroxy-2-phenyl-4-(4,4,5,5-tetramethyl-1,3,2-dioxaborolan-2-yl)-2,3-dihydrobenzofuran-2-yl)pyrrolidine-1-carboxylate;
tert-butyl 2-((2S,3S)-5-chloro-6-fluoro-3-methoxy-2-phenyl-4-(4,4,5,5-tetramethyl-1,3,2-dioxaborolan-2-yl)-2,3-dihydrobenzofuran-2-yl)pyrrolidine-1-carboxylate;
tert-butyl 2-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)pyrrolidine-1-carboxylate;
tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)piperidine-1-carboxylate;
tert-butyl 3-((S)-5-chloro-6-fluoro-2-phenyl-4-(4,4,5,5-tetramethyl-1,3,2-dioxaborolan-2-yl)-2,3-dihydrobenzofuran-2-yl)morpholine-4-carboxylate;
tert-butyl (1-((S)-5-chloro-2-phenyl-4-(4,4,5,5-tetramethyl-1,3,2-dioxaborolan-2-yl)-2,3-dihydrobenzofuran-2-yl)ethyl)carbamate;
tert-butyl (1-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)ethyl)carbamate; and
tert-butyl (S)-2-((S)-1-(tert-butoxycarbonyl)pyrrolidin-2-yl)-5-chloro-6-fluoro-2-phenyl-4-(4,4,5,5-tetramethyl-1,3,2-dioxaborolan-2-yl)indoline-1-carboxylate.

In a further aspect, the invention relates to a process for the preparation of a compound of formula (I), in free form or in pharmaceutically acceptable salt form, comprising the step of:
a) coupling a compound of formula (IV), (IV-1), (IV-II) or (IV-III) as defined herein with a suitable cross-coupling partner, such as a suitable aryl halide or aryl boronic acid or ester, in the presence of a suitable catalyst, such as a Pd catalyst, to give a compound of general formula (III) as defined in Schemes 1 and 2 or of subformulae thereof as defined in any of Schemes 3, 5 and 6.

Hence, the invention relates to a process for the preparation of a compound of formula (I), (Ia), (Ic) or (Id), or a pharmaceutically acceptable salt thereof, comprising the step of;
a) coupling a compound of formula (IV) as defined herein with a compound of formula (V)

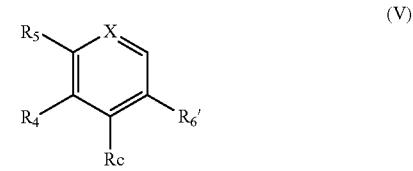

(V)

in the presence of a suitable catalyst, such as a Pd catalyst, to give a compound of general formula (III)

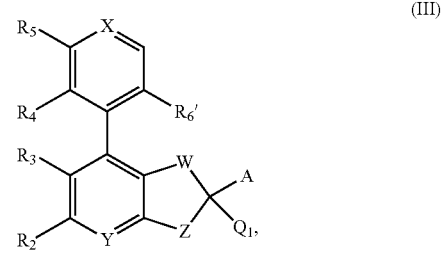

(III)

wherein
A, W, X, Y, Z, $R_2$, $R_3$, $R_4$, $R_5$ are as defined herein;
wherein when $R_a$ is a halide such as a bromide or iodide, $R_w$ is $B(R'_a)_2$ wherein each $R'_a$ is hydroxy or two $R'_a$ groups together with the boron to which they are attached form a pinacol boronate moiety of formula

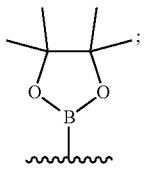

wherein when $R_a$ is $B(R'_a)_2$ wherein each $R'_a$ is hydroxy or two $R'_a$ groups together with the boron to which they are attached form a pinacol boronate moiety of formula

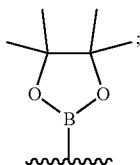

$R_c$ is a halide such as a bromide or iodide;
$Q_1$ is as defined herein and;
$R_6'$ is a functional group capable of being transformed into $R_6$, such as —CN or $C(O)OC_1$-$C_6$alkyl, wherein $R_6$ is as defined herein.

In a further aspect, the invention relates to a process for the preparation of a compound of formula (I), in free form or in pharmaceutically acceptable salt form, comprising the steps of:
a) coupling a compound of formula (IV) as defined herein with a compound of formula (V) as defined herein, in the presence of a suitable catalyst to give a compound of formula (III) as defined herein;
b) converting the compound of formula (III) as defined herein obtained in step a) under suitable hydrolysis conditions to give a compound of formula (II) as defined herein;
c) deprotecting the compound of formula (II) as defined herein obtained in step b) to give a compound of formula (I) as defined herein;
d) optionally further functionalising the amine group of the compound of formula (I);
e) recovering the so obtainable compound of formula (I) in free form or in pharmaceutically acceptable salt form.

In a further aspect, the invention provides a process for the preparation of a compound of formula (IV-v), or a salt thereof, comprising the steps of (i) treating a compound of formula (IV-t) with an organometallic reagent and (ii) reacting the resulting mixture with an epoxide of formula

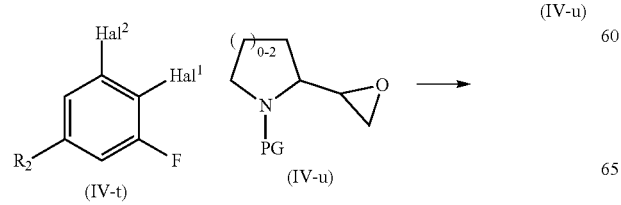

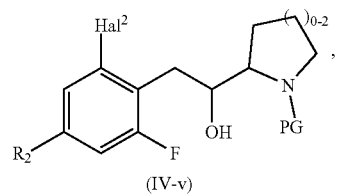

wherein $R_2$ is as defined herein; PG is a nitrogen protecting group;
when $Hal^1$ is I, $Hal^2$ is Cl or Br and when $Hal^2$ is Cl, $Hal^1$ is Br or I.

In a further aspect, the invention provides a process for the preparation of a compound of formula (IV-q) from a compound of formula (IV-v) and a compound of formula (IV-u) according to the synthetic scheme below:

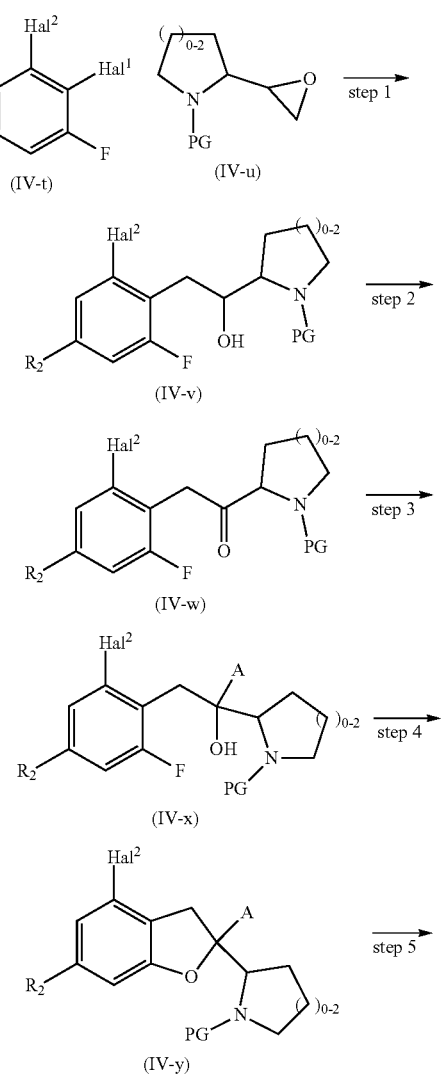

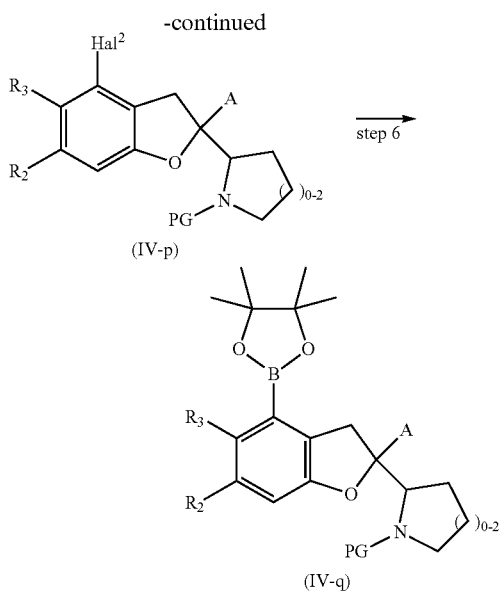

wherein $R_2$, PG, $Hal^1$ and $Hal^2$ are as defined herein and $R_3$ is chloro.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

Pharmaceutical Compositions

Compounds of formula (V), (IV), (III) and (II) as defined herein are useful in the preparation of compounds of the invention, e.g., compounds of Formula (I). Thus, in an aspect, the invention relates to a compound of formula (V), (IV), (III) or (II) or salts thereof. In another aspect, the invention relates to the use of a compound of formula (V), (IV), (III) or (II) or salts thereof in the manufacture of a compound of formula (I).

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of;
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol;
c) binders, e.g., magnesium aluminum silicate, starch paste, gelatin, tragacanth, methylcellulose, sodium carboxymethylcellulose and/or polyvinylpyrrolidone;
d) disintegrants, e.g., starches, agar, alginic acid or its sodium salt, or effervescent mixtures; and
e) absorbents, colorants, flavors and sweeteners.

In an embodiment, the pharmaceutical compositions are capsules comprising the active ingredient only.

Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emul-sifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a pro-longed period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant. The compounds of formula (I) in free form or in pharmaceutically acceptable salt form, exhibit valuable pharmacological properties, e.g. YAP/TAZ-TEAD modulating properties; e.g. YAP/TAZ-TEAD inhibiting properties, e.g. as indicated in the in vitro tests as provided in the examples, and are therefore indicated for therapy or for use as research chemicals, e.g. as tool compounds.

Diseases and Disorders and Methods of Use

Particularly interesting compounds of the invention have good potency in the biological assays described herein. In another aspect, they should have a favourable safety profile. In another aspect, they should possess favourable pharmacokinetic properties. Furthermore, the ideal drug candidate will be in a form that is stable, non-hygroscopic and easily formulated.

Having regard to their activity as YAP/TAZ-TEAD PPI inhibitors, compounds of the formula (I) in free or pharmaceutically acceptable salt form, are useful in the treatment of conditions which are mediated by YAP or TAZ amplifications, and/or dysregulated Hippo pathway and/or elevated YAP/TEAD or TAZ/TEAD activity, such as cancer, and/or that are responsive (meaning especially in a therapeutically beneficial way) to inhibition of YAP/TAZ-TEAD interaction, most especially a disease or disorder as mentioned herein below.

Compounds of the invention may be useful in the treatment of cancer or a tumor. In particular, the compounds of the invention may be useful in the treatment of a cancer or tumor which is selected from mesothelioma (including pleural mesothelioma, malignant pleural mesothelioma, peritoneal mesothelioma, pericardial mesothelioma and mesothelioma of the *Tunica vaginalis*), carcinoma (including cervical squamous cell carcinoma, endometrial carcinoma, esophageal squamous cell carcinoma, esophageal adenocarcinoma, urothelial carcinoma of the bladder and squamous cell carcinoma of the skin), poroma (benign poroma), porocarcinoma (including malignant porocarcinoma), supratentorial ependymoma (including childhood supratentorial ependymoma), epithelioid hemangioendothelioma (EHE), ependymal tumor, a solid tumor, breast cancer (including triple negative breast cancer), lung cancer (including non-small cell lung cancer), ovarian cancer, colorectal cancer (including colorectal carcinoma), melanoma, pancreatic cancer (including pancreatic adenocarcinoma), prostate cancer, gastric cancer, esophageal cancer, liver cancer (including hepatocellular carcinoma, cholangiocarcinoma and hepatoblastoma), neuroblastoma, Schwannoma, kidney cancer, sarcoma (including rhabdomyosarcoma, embryonic rhabdomyosarcoma (ERMS), osteosarcoma, undifferentiated pleomorphic sarcomas (UPS), Kaposi's sarcoma, soft-tissue sarcoma and rare soft-tissue sarcoma), bone cancer, brain cancer, medulloblastoma, glioma, meningioma, and head and neck cancer (including head and neck squamous cell carcinoma).

The compounds of the invention may also be useful in the treatment of solid malignancies characterized by overexpression of YAP.

The compounds of the invention may also be useful in the treatment of solid malignancies characterized by dysregulated YAP/TAZ-TEAD interaction.

The compounds of the invention may also be useful in the treatment of solid malignancies characterized by YAP amplification.

The compounds of the invention may also be useful in the treatment of a tumor or cancer cancer or tumor is a cancer or a tumor harboring (i) one or more YAP/TAZ fusions; (ii) one or more NF2/LATS1/LATS2 truncating mutations or deletions; and/or (iii) one or more functional YAP/TAZ fusions.

The compounds of the invention may also be useful in the treatment of NF2-mutant cancer, particularly NF2-mutant NSCLC.

Any positive expression in YAP as described above can be assessed by methods known to the skilled person such as e.g. immunohistochemistry, qRT-PCR, RNASeq or similar methods.

Thus, as a further embodiment, the present invention provides the use of a compound of formula (I) or a pharmaceutically acceptable salt thereof, in therapy. In a preferred embodiment, the therapy is selected from a disease which may be treated by inhibition of YAP/TAZ-TEAD interaction. In a more preferred embodiment, the disease is selected from the afore-mentioned list, suitably malignant pleural mesothelioma.

Thus, as a further embodiment, the present invention provides a compound of formula (I) or a pharmaceutically acceptable salt thereof for use in therapy. In a preferred embodiment, the therapy is for a disease which may be treated by inhibition of YAP/TAZ-TEAD interaction. In a more preferred embodiment, the disease is selected from the afore-mentioned list, suitably malignant pleural mesothelioma.

In another embodiment, the invention provides a method of treating a disease which is treated by inhibition of YAP/TAZ-TEAD interaction in a subject in need thereof, comprising administration of a therapeutically effective amount of a compound of formula (I) or a pharmaceutically acceptable salt thereof to the subject. In a preferred embodiment, the disease is selected from the afore-mentioned list, suitably malignant pleural mesothelioma.

Thus, as a further embodiment, the present invention provides the use of a compound of formula (I), or subformulae thereof, or a pharmaceutically acceptable salt thereof, for the manufacture of a medicament. In a preferred embodiment, the medicament is for treatment of a disease which may be treated by inhibition of YAP/TAZ-TEAD interaction. In a more preferred embodiment, the disease is selected from the afore-mentioned list, suitably malignant pleural mesothelioma.

In one embodiment of the present invention, there is provided 2-((2S,4S)-5-Chloro-2-(((trans-4-hydroxycyclohexyl)amino)methyl)-2-phenyl-2,3-dihydrobenzofuran-4- yl)-3-fluoro-4-methoxybenzamide or a pharmaceutically acceptable salt thereof for use in the treatment of malignant pleural mesothelioma. In another embodiment of the present invention, there is provided 2-((2S,4S)-5-Chloro-2-(((trans-4-hydroxycyclohexyl)amino)methyl)-2-phenyl-2,3-dihydrobenzofuran-4-yl)-3-fluoro-4-methoxybenzamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,4S)-5-chloro-6-fluoro-2-(((trans-4-hydroxycyclohexyl)amino)methyl)-2-phenyl-2,3-dihydrobenzofuran-4-yl)-4-(difluoromethoxy)-3-fluorobenzamide or a pharmaceutically acceptable salt thereof for use in the treatment of malignant pleural mesothelioma. In another embodiment of the present invention, there is 2-((2S,4S)-5-chloro-6-fluoro-2-(((trans-4-hydroxycyclohexyl)amino)methyl)-2-phenyl-2,3-dihydrobenzofuran-4-yl)-4-(difluoromethoxy)-3-fluorobenzamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-hydroxyethoxy)benzamide or a pharmaceutically acceptable salt thereof for use in the treatment of malignant pleural mesothelioma. In another embodiment of the present invention, there is provided 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-hydroxyethoxy)benzamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,4S)-5-Chloro-6-fluoro-2-((methylamino)methyl)-2-phenyl-2,3-dihydrobenzofuran-4-yl)-3-fluoro-4-(2-hydroxyethoxy)-N-methylbenzamide or a pharmaceutically acceptable salt thereof for use in the treatment of malignant pleural mesothelioma. In another embodiment of the present invention, there is provided 2-((2S,4S)-5-Chloro-6-fluoro-2-((methylamino)methyl)-2-phenyl-2,3-dihydrobenzofuran-4-yl)-3-fluoro-4-(2-hydroxyethoxy)-N-methylbenzamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide or a pharmaceutically acceptable salt thereof for use in the treatment of malignant pleural mesothelioma. In another embodiment of the present invention, there is provided 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzonitrile or a pharmaceutically acceptable salt thereof for use in the treatment of malignant pleural mesothelioma. In another embodiment of the present invention, there is provided 2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzonitrile or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-hydroxyethoxy)-N-methylbenzamide or a pharmaceutically acceptable salt thereof for use in the treatment of malignant pleural mesothelioma. In another embodiment of the present invention, there is provided 2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-hydroxyethoxy)-N-methylbenzamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,3S,4S)-5-Chloro-6-fluoro-3-methyl-2-((methylamino)methyl)-2-phenyl-2,3-dihydrobenzofuran-4-yl)-3-fluoro-4-((S)-2-hydroxypropoxy)-N-methylbenzamide or a pharmaceutically acceptable salt thereof for use in the treatment of malignant pleural mesothelioma. In another embodiment of the present invention, there is provided 2-((2S,3S,4S)-5-Chloro-6-fluoro-3-methyl-2-((methylamino)methyl)-2-phenyl-2,3-dihydrobenzofuran-4-yl)-3-fluoro-4-((S)-2-hydroxypropoxy)-N-methylbenzamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,3S,4S)-5-Chloro-6-fluoro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide or a pharmaceutically acceptable salt thereof for use in the treatment of malignant pleural mesothelioma. In another embodiment of the present invention, there is provided 2-((2S,3S,4S)-5-Chloro-6-fluoro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,3S,4S)-5-Chloro-6-fluoro-3-methyl-2-((methylamino)methyl)-2-phenyl-2,3-dihydrobenzofuran-4-yl)-3-fluoro-4-methoxybenzamide or a pharmaceutically acceptable salt thereof for use in the treatment of malignant pleural mesothelioma. In another embodiment of the present invention, there is provided 2-((2S,3S,4S)-5-Chloro-6-fluoro-3-methyl-2-((methylamino)methyl)-2-phenyl-2,3-dihydrobenzofuran-4-yl)-3-fluoro-4-methoxybenzamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 4-((2S,3S,4S)-5-Chloro-6-fluoro-3-methyl-2-((methylamino)methyl)-2-phenyl-2,3-dihydrobenzofuran-4-yl)-5-fluoro-6-(2-hydroxyethoxy)-N-methylnicotinamide or a pharmaceutically acceptable salt thereof for use in the treatment of malignant pleural mesothelioma. In another embodiment of the present invention, there is provided 4-((2S,3S,4S)-5-Chloro-6-fluoro-3-methyl-2-((methylamino)methyl)-2-phenyl-2,3-dihydrobenzofuran-4-yl)-5-fluoro-6-(2-hydroxyethoxy)-N-methylnicotinamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 4-((2S,4S)-5-Chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide or a pharmaceutically acceptable salt thereof for use in the treatment of malignant pleural mesothelioma. In another embodiment of the present invention, there is provided 4-((2S,4S)-5-Chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

In one embodiment of the present invention, there is provided 2-((2S,4S)-5-Chloro-6-fluoro-2-phenyl-2-((S)-pyrrolidin-2-yl)indolin-4-yl)-3-fluoro-4-(2-hydroxyethoxy)benzamide. or a pharmaceutically acceptable salt thereof for use in the treatment of malignant pleural mesothelioma. In another embodiment of the present invention, there is provided 2-((2S,4S)-5-Chloro-6-fluoro-2-phenyl-2-((S)-pyrrolidin-2-yl)indolin-4-yl)-3-fluoro-4-(2-hydroxyethoxy)benzamide. or a pharmaceutically acceptable salt thereof for use in the treatment of solid malignancies characterized by YAP or TAZ overexpression and/or YAP or TAZ amplification and/or TEAD amplification and/or YAP/TAZ-TEAD (hyper)activation.

Dosage

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

The activity of a compound according to the present invention can be assessed by the in vitro methods described in the Examples.

Combination Therapy

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention. Thus, in one embodiment, the invention provides a combination comprising a therapeutically effective amount of a compound of formula (I) or a pharmaceutically acceptable salt thereof and one or more therapeutically active agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by YAP overexpression and/or YAP amplification and/or YAP/TAZ-TEAD interaction. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In certain instances, compounds of the present invention may be combined with other therapeutic agents, such as other anti-cancer agents, anti-allergic agents, anti-nausea agents (or anti-emetics), pain relievers, cytoprotective agents, and combinations thereof.

Anti-cancer agents of particular interest for combinations with the compounds of the present invention include B-RAF inhibitors; Mitogen-activated protein kinase (MEK) inhibitors; Epidermal growth factor receptor (EGFR) inhibitors; inhibitors of an immune checkpoint molecule (e.g. one or more inhibitors of PD-1, PD-L1).

Compounds of the present invention may be used together or separately in combination with another treatment of cancer, particularly malignant pleural mesothelioma, such as surgery, chemotherapy (with among others cisplatin, carboplatin, alimta (pemetrexed), gemcitabine and doxorubicin) and radiation. For instance, combination therapy with one or more of agents selected from pemetrexed, cisplatin, bevacizumab, nivoluab, gemcitabine, vinorelbine, nivolumab and ipilimumab may be particularly useful, specially for the treatment of pleural mesothelioma (particularly malignant pleural mesothelioma).

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, antihistamines, and bronchodilators.

Some patients may experience nausea during and after administration of the compound of the present invention and/or other anti-cancer agent(s); therefore, anti-emetics are used in preventing nausea (upper stomach) and vomiting.

Medication to alleviate the pain experienced during the treatment period is often prescribed to make the patient more comfortable.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by YAP overexpression and/or YAP amplification and/or YAP/TAZ-TEAD interaction, wherein the medicament is prepared for administration with another therapeutic agent. The invention also provides the use of another therapeutic agent for treating a disease or condition mediated by YAP overexpression and/or YAP amplification and/or YAP/TAZ-TEAD interaction, wherein the medicament is administered with a compound of formula (I).

The invention also provides a compound of formula (I) for use in a method of treating a disease or condition mediated by YAP overexpression and/or YAP amplification and/or YAP/TAZ-TEAD interaction, wherein the compound of formula (I) is prepared for administration with another therapeutic agent. The invention also provides another therapeutic agent for use in a method of treating a disease or condition mediated by YAP overexpression and/or YAP amplification and/or YAP/TAZ-TEAD interaction, wherein the other therapeutic agent is prepared for administration with a compound of formula (I). The invention also provides a compound of formula (I) for use in a method of treating a disease or condition mediated by YAP overexpression and/or YAP amplification and/or YAP/TAZ-TEAD interaction, wherein the compound of formula (I) is administered with another therapeutic agent. The invention also provides another therapeutic agent for use in a method of treating a disease or condition mediated by YAP overexpression and/or YAP amplification and/or YAP/TAZ-TEAD interaction, wherein the other therapeutic agent is administered with a compound of formula (I).

The invention also provides the use of a compound of formula (I) for treating a disease or condition mediated by YAP overexpression and/or YAP amplification and/or YAP/TAZ-TEAD interaction, wherein the patient has previously (e.g. within 24 hours) been treated with another therapeutic agent. The invention also provides the use of another therapeutic agent for treating a disease or condition mediated by YAP overexpression and/or YAP amplification and/or YAP/TAZ-TEAD interaction, wherein the patient has previously (e.g. within 24 hours) been treated with a compound of formula (I).

In one embodiment, the other therapeutic agent is selected from an anti-cancer agent.

Preparation of Compounds

The following examples are intended to illustrate the invention and are not to be construed as being limitations thereof. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., spectroscopic characteristics, e.g., MS, IR, NMR. Stereochemistry has been assigned by single crystal X-ray structural analysis for several intermediates and Examples, as indicated below, and by cocrystal structures of several Examples bound to the YAP binding domain of TEAD3 or TEAD4. All other stereochemical assignments are by analogy, and are based upon the relative affinities determined for the YAP binding domain of TEAD, e.g., the $IC_{50}$ determined in the YAP-TEAD TR-FRET assay for the diasteroisomer X was found to be significantly higher than for the diastereoisomer Y. Abbreviations used are those conventional in the art.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

| Abbreviations: | |
| --- | --- |
| Abbreviation | Describtion |
| ACN | acetonitrile |
| aq. | aqueous |
| Ar | Argon |
| BPR | Back pressure |
| brine | Saturated aqueous sodium chloride |
| calcd | calculated |
| CH2CL2 | $CH_2Cl_2$ |
| conc | concentrated |
| DAST | (Diethylamino)sulfur trifluoride |
| dba | Dibenzylideneacetone |
| DBU | 1,8-Diazabicxclo[5.4.0]undec-7-ene |

-continued

| Abbreviation | Description |
|---|---|
| DCE | 1,2-Dichloroethane |
| DCM | Dichloromethane |
| DEA | Diethylamine |
| DEAD | Diethyl azodicarboxylate |
| DIAD | Diisopropyl azodicarboxylate |
| DIPEA | N,N-Diisopropylethylamine, N-Ethyl-N-isopropylpropan-2-amine |
| DMA | N,N-Dimethylacetamide |
| DMAP | 4-Dimethylaminopyridine |
| DMF | N,N-Dimethylformamide |
| DMSO | Dimethylsulfoxide |
| DMSO-$d_6$ or DMSO-d6 | Hexadeuterodimethyl sulfoxide |
| dppf | 1,1'-bis(diphenylphosphino) ferrocene |
| DSC | Differential scanning calorimetry |
| ee | Enantiomeric excess |
| ESI-MS | Electrospray ionization mass spectroscopy |
| EtOAc | Ethyl acetate |
| EtOH | Ethanol |
| $Et_2O$ | Diethylether |
| h | hour |
| HPLC | High-performance liquid chromatography |
| HV | High vacuum |
| IPA | 2-Propanol |
| L/mL/μL | litre/millilitre/microlitre |
| LDA | Lithium diisopropylamide |
| LC-MS | liquid chromatography and mass spectroscopy |
| LHMDS | Lithium hexamethyldisilazide |
| M | molar |
| mCPBA | meta-chloroperoxybenzoic acid |
| MeOH | methanol |
| min | minutes |
| mp | melting point |
| MW, mw | microwave |
| m/z | mass to charge ratio |
| NaOtBu | Sodium tert-butoxide |
| NBS | N-Bromosuccinimide |
| n-BuLi | n-Butyllithium |
| $NEt_3$, $Et_3N$ | Triethylamine |
| NMP | N-methylpyrrolidinone |
| NMR | Nuclear magnetic resonance |
| 1H-NMR, $^1$H-NMR | 1H-Nuclear Magnetic Resonance |
| org. | organic |
| PE | Petrol ether |
| p-TsOH | para-toulene sulfonic acid |
| RM or rm | Reaction mixture |
| RP | reversed phase |
| RT | Room temperature |
| sat | saturated |
| TBAF | Tetrabutylammonium fluoride |
| TBME | 2-Methoxy-2-methylpropane |
| TEA | Triethylamine |
| TFA | Trifluoroacetic acid |
| THF | Tetrahydrofuran |
| $t_R$ | Retention time (if not indicated, in minutes) |
| UPLC | Ultra-performance liquid chromatography |

General Conditions:

Mass spectra were acquired on LC-MS systems using electrospray ionization methods with a range of instruments of the following configurations: Waters Acquity UPLC with Waters SQ detector, [M+H]$^+$ refers to the protonated molecular ion of the chemical species.

NMR spectra were run with Bruker Ultrashield™400 (400 MHz) and Bruker Ultrashield™600 (600 MHz) spectrometers, both with and without trimethylsilane as an internal standard. Chemical shifts (d-values) are reported in ppm downfield from tetramethylsilane, spectra splitting pattern are designated as singlet (s), doublet (d), triplet (t), quartet (q), multiplet, unresolved or more overlapping signals (in), broad signal (br). Solvents are given in parentheses.

Instrumentation

Microwave: All microwave reactions were conducted in a Biotage Initiator, irradiating at 0-400 W from a magnetron at 2.45 GHz with Robot Eight/Robot Sixty processing capacity, unless otherwise stated.

UPLC-MS Methods: Using Waters Acquity UPLC with Waters SQ detector.

Method UPLC-MS 1: UPLC-MS instrument: Waters Acquity UPLC with Waters SQ detector; column: Acquity UPLC HSS T3, 1.8 μm, 2.1×50 mm, column temperature: 60° C.; eluent: A: water +0.05% formic acid+3.75 mM ammonium acetate (pH 3.8), B: acetonitrile+0.04% formic acid; flow rate: 1.0 mL/min; gradient: 5 to 98% B in 1.40 min, 98% B for 0.40 min.

Method UPLC-MS 2: UPLC-MS instrument: Waters Acquity UPLC with Waters SQ detector; column: Acquity UPLC HSS T3, 1.8 μm, 2.1×100 mm, column temperature: 60° C.; eluent: A: water+0.05% formic acid+3.75 mM ammonium acetate (pH 3.8), B: acetonitrile+0.04% formic acid; flow rate: 0.8 mL/min; gradient: 5 to 98% B in 9.40 min, 98% B for 0.40 min.

Method UPLC-MS 3: UPLC-MS instrument: Waters Acquity UPLC with Waters SQ detector; column: Acquity UPLC BEH C18, 1.7 μm, 2.1×50 mm, column temperature: 80° C.; eluent: A: water+4.76% isopropanol+0.05% formic acid+3.75 mM ammonium acetate, B: isopropanol+0.05% formic acid; flow rate: 0.6 mL/min; gradient: 1 to 98% B in 1.70 min, 98% B for 0.10 min.

Method UPLC-MS 4: UPLC-MS instrument: Waters Acquity UPLC with Waters SQ detector; column: CORTECS C18+, 2.7 μm, 2.1×50 mm, column temperature: 80° C.; eluent: A: water+4.76% isopropanol+0.05% formic acid+3.75 mM ammonium acetate, B: isopropanol+0.05% formic acid; flow rate: 1.0 mL/min; gradient: 1 to 50% B in 1.40 min, 50 to 98% B in 0.30 min.

Method UPLC-MS 5: UPLC-MS instrument: Waters Acquity UPLC with Waters Q-TOF detector; column: Waters BEH C18, 1.7 μm, 2.1×100 mm, column temperature: 40° C.; eluent: A: water+0.1% formic acid, B: acetonitrile+0.1% formic acid; flow rate: 0.5 mL/min; gradient: 5% B for 0.5 min, 5 to 95% B in 5.5 min, 95% B for 2.0 min, 95 to 5% B in 0.1 min, 5% B for 1.9 min.

Intermediates

Intermediates for Suzuki Cross-Coupling Reactions with Boronate Building Blocks:

Synthesis of tert-butyl (2-((2-bromo-3-fluorophenyl)amino)ethyl)carbamate (N-I)

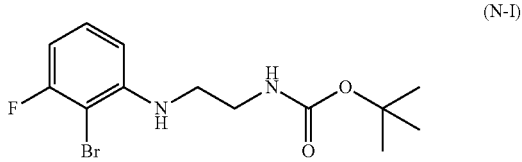 [SMILES: CC(C)(C)OC(=O)NCCNc1cccc(F)c1Br]

(N-I)

At RT sodium triacetoxyborohydride (12.68 g, 59.8 mmol) was added to a stirred solution of 2-bromo-3-fluoroaniline (3.79 g, 20 mmol) and tert-butyl (2-oxoethyl) carbamate (3.65 g, 23 mmol) in DCM (30 mL) and stirring at RT was continued for 1 day. DCM was added followed by a sat solution of NaHCO$_3$. The organic phase was separated and the aqueous phase was extracted with DCM. The combined organic extracts were washed with brine, dried over anhydrous Na₂SO₄ and concentrated. The crude product was purified by flash chromatography (silica, heptane/EtOAc, gradient: 0% to 30% EtOAc) to afford the title compound (2.30 g). UPLC-MS 1: m/z 333.1 [M+H]⁺. $t_R$=1.19 min. ¹H NMR (400 MHz, DMSO-d6) δ 7.23-7.10 (m, 1H), 7.00 (t, J=5.7 Hz, 1H), 6.60-6.42 (m, 2H), 5.56 (d, J=5.6 Hz, 1H), 3.15 (dt, J=16.8, 6.0 Hz, 4H), 1.37 (s, 9H).

Synthesis of 2-(2-bromo-3,4-difluorophenoxy)ethan-1-ol (N-II)

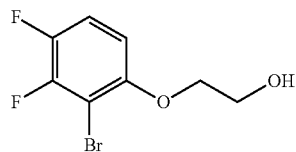

(N-II)

Step 1: (2-(2-Bromo-3,4-difluorophenoxy)ethoxy)(tert-butyl)dimethylsilane (N-II-a)

K₂CO₃ (2.26 g, 16.3 mmol) and KI (0.135 g, 0.81 mmol) were added to a solution of 2-bromo-3,4-difluorophenol (CAS 1376335-05-5) (1.7 g, 8.13 mmol) and (2-bromoethoxy)(tert-butyl)dimethylsilane (CAS 86864-60-0) (1.946 g, 8.13 mmol) in DMF (27 mL). The reaction mixture was heated at 80° C. for 3.5 h. More K₂CO₃ (2.25 g, 16.3 mmol) and KI (0.135 g, 0.81 mmol) were added and stirring at 80° C. was continued for 1 h. The reaction mixture was quenched with water and extracted with EtOAc. The aqueous layer was extracted again with EtOAc, then the combined organic layers were dried (phase separator cartridge) and concentrated. The residue was purified by flash chromatography (silica, cyclohexane/EtOAc, gradient: 0% to 10% EtOAc) to afford the title compound (1.00 g) as a colorless oil. UPLC-MS 1: m/z 384.1/386.3 [M+NH₄]⁺. $t_R$=1.57 min.

Step 4: 2-(2-Bromo-3,4-difluorophenoxy)ethanol (N-II)

TBAF trihydrate (515 mg, 1.63 mmol) was added to a solution of 2-(2-bromo-3,4-difluorophenoxy)ethoxy)(tert-butyl)dimethylsilane (N-II-a) (500 mg, 1.361 mmol) in THF (14 mL), and the reaction mixture was stirred at RT for 1.5 h. The reaction mixture was concentrated and the residue was purified by flash chromatography (silica, cyclohexane/EtOAc, gradient: 0% to 100% EtOAc) to afford the title compound (344 mg) as a colorless liquid. ¹H NMR (400 MHz, DMSO-d₆) δ 7.43-7.36 (m, 1H), 7.20-7.15 (m, 1H), 4.85 (t, J=5.4 Hz, 1H), 4.13 (td, J=4.9, 1.0 Hz, 2H), 3.72 (q, J=5.4 Hz, 2H).

Synthesis of tert-butyl (2-(3-fluoro-2-(4,4,5,5-tetramethyl-1,3,2-dioxaborolan-2-yl)phenoxy)ethyl)carbamate (N-III)

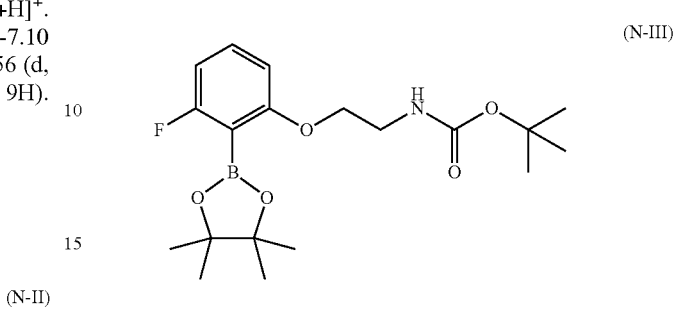

(N-III)

Step 1: Tert-butyl (2-(2-bromo-3-fluorophenoxy)ethyl)carbamate (N-III-a)

Tert-butyl (2-bromoethyl)carbamate (2.29 g, 10.2 mmol) was added to a solution of 2-bromo-3-fluorophenol (1.5 g, 7.9 mmol) and K₂CO₃ (1.63 g, 11.8 mmol) in DMF (10 mL) at RT and the reaction mixture was stirred at RT for 18 h. Water was added and the mixture was extracted with EtOAc. The organic layers were combined and washed with brine, dried over anhydrous Na₂SO₄ and concentrated. The residue was purified by flash chromatography (silica, hexane/EtOAc, gradient 0% to 50% EtOAc) to afford the title compound (2.6 g) as a colorless foam. UPLC-MS 1: m/z 334.0/336.0 [M+H]⁺, $t_R$=1.18 min.

Step 2: Tert-butyl (2-(3-fluoro-2-(4,4,5,5-tetramethyl-1,3,2-dioxaborolan-2-yl)phenoxy)ethyl)carbamate (N-III)

PdCl₂(dppf)·CH₂Cl₂ adduct (0.39 g, 0.48 mmol) was added to a stirred suspension of tert-butyl (2-(2-bromo-3-fluorophenoxy)ethyl)carbamate (N-III-a) (1.6 g, 4.8 mmol), bis(pinacolato) diboron (2.43 g, 9.6 mmol) and KOAc (1.41 g, 14.4 mmol) in dioxane (10 mL) at 100° C. and the reaction mixture was stirred at 100° C. for 5 h. After filtration through a pad of Celite and concentration under reduced pressure the residue was purified by flash chromatography (silica, hexane/EtOAc, gradient 0% to 40% EtOAc) to afford the title compound (927 mg) as a yellow oil. UPLC-MS 1: m/z 382.2 [M+H]⁺, $t_R$=1.32 min Synthesis of 2-bromo-3-fluoro-4-methoxybenzonitrile (N-IV)

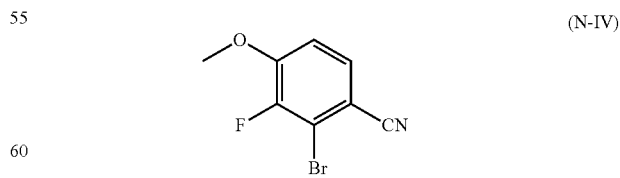

(N-IV)

To a stirred solution of 2-bromo-3,4-difluorobenzonitrile (4 g, 18.35 mmol) in MeOH (50 mL) under Ar was added sodium methoxide (6.29 mL, 27.5 mmol, 25% in MeOH). Then, the reaction mixture was stirred for 16 h at RT. The reaction mixture was quenched with a sat solution of NaHCO₃ and extracted with EtOAc. The organic layers were combined and washed with a sat solution of NaHCO₃, dried over Na₂SO₄ and concentrated. The residue was purified by normal phase chromatography (silica, hexane/EtOAc; gradient: 0% to 80% EtOAc) to give the title compound (4.17 g). ¹H NMR (400 MHz, DMSO-d₆) δ (ppm) 7.87-7.67 (m, 1H), 7.44-7.20 (m, 1H), 3.95 (s, 3H).

Synthesis of
2-bromo-4-(difluoromethoxy)-3-fluorobenzonitrile
(N-V)

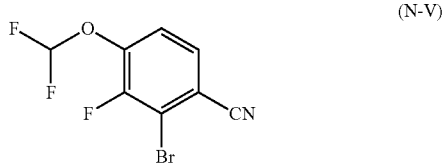 [SMILES: N#Cc1ccc(OC(F)F)c(F)c1Br]

Step 1: 2-Bromo-3-fluoro-4-hydroxybenzonitrile
(N-V-a)

Under Ar NaH (3.48 g, 138 mmol, 95%) was added to a stirred solution of 2-bromo-3,4-difluorobenzonitrile (10 g, 45.9 mmol) and 2-hydroxyethyl methyl sulfone (6.26 g, 50.5 mmol) in DMF (100 mL) at 0° C. and stirring at RT was continued for another 2 h. The reaction mixture was quenched with 0.1 N HCl and extracted with EtOAc. The organic layers were combined and washed with 0.1 N HCl, dried over anhydrous Na₂SO₄ and concentrated. The residue was purified by flash chromatography (silica, hexane/EtOAc gradient: 0% to 80% EtOAc) to afford the desired product (8.97 g). UPLC-MS 1: m/z 215.9 [M+H]⁺, t_R=0.80 min.

Step 2:
2-Bromo-4-(difluoromethoxy)-3-fluorobenzonitrile
(N-V)

At 0° C. a solution of KOH (46.6 g, 831 mmol) in H₂O (150 mL) followed by diethyl (bromodifluoromethyl)phosphonate (14.75 mL, 83 mmol) were added to a stirred solution of 2-bromo-3-fluoro-4-hydroxybenzonitrile (N-V-a) (8.97 g, 41.5 mmol) in ACN (150 mL). Stirring at RT was continued for 2 h. The reaction mixture was quenched with a sat solution of NaHCO₃ and extracted with EtOAc. The organic layers were combined and washed with a sat solution of NaHCO₃, dried over anhydrous Na₂SO₄ and concentrated. The residue was purified by flash chromatography (silica, hexane/EtOAc; gradient: 0% to 40% EtOAc) to give the title compound (10.45 g). ¹H NMR (400 MHz, DMSO-d₆) δ (ppm) 7.94-7.87 (m, 1H), 7.62-7.57 (m, 1H), 7.57-7.20 (m, 1H).

Synthesis of 2-bromo-3-fluoro-4-(2-((tetrahydro-2H-pyran-2-yl)oxy)ethoxy)benzonitrile (N-VI)

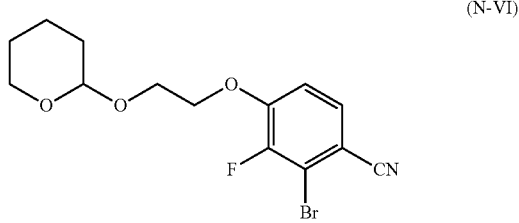 [SMILES: N#Cc1ccc(OCCOC2CCCCO2)c(F)c1Br]

At 0° C. NaH (0.477 g, 11.9 mmol, 60% in mineral oil) was added portionwise to a stirred solution of 2-(tetrahydro-2H-pyran-2-yloxy)ethanol (1.34 g, 9.17 mmol) in DMF (40 mL) under Ar. After 5 min, 2-bromo-3,4-difluorobenzonitrile (2 g, 9.17 mmol) was added and the reaction mixture was stirred at 0° C. for 1.5 h. The reaction mixture was quenched with a sat solution of NH₄Cl, then extracted with EtOAc. The organic layers were combined and washed with a sat solution of NH₄Cl, dried over Na₂SO₄ and concentrated. The residue was purified by flash chromatography (silica, hexane/EtOAc 2:1) to afford the title compound (1.93 g). ¹H NMR (400 MHz, DMSO-d₆) δ (ppm): 7.87-7.74 (m, 1H), 7.53-7.29 (m, 1H), 4.73-4.57 (m, 1H), 4.47-4.28 (m, 2H), 4.04-3.90 (m, 1H), 3.87-3.63 (m, 2H), 3.55-3.35 (m, 1H), 1.88-1.24 (m, 6H).

Synthesis of 2-bromo-3-fluoro-4-(2-hydroxyethoxy)benzonitrile (N-VII)

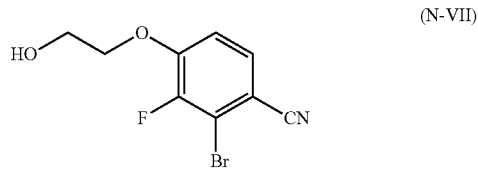 [SMILES: N#Cc1ccc(OCCO)c(F)c1Br]

A solution of 2-bromo-3-fluoro-4-(2-((tetrahydro-2H-pyran-2-yl)oxy)ethoxy)benzonitrile (N-VI) (2.47 g, 7.2 mmol) and p-TsOH (0.55 g, 2.9 mmol) in EtOH (35 mL) was stirred at RT for 24 h. A sat solution of NaHCO₃ was added and the mixture was extracted with EtOAc. The combined organic extracts were dried over anhydrous Na₂SO₄ and concentrated to afford the title compound (1.48 g) as a colorless powder. UPLC-MS 1 m/z 304.0 [M+formate]⁻.

Synthesis of (R)-2-bromo-3-fluoro-4-(2-fluoropropoxy)benzonitrile (N-VIII)

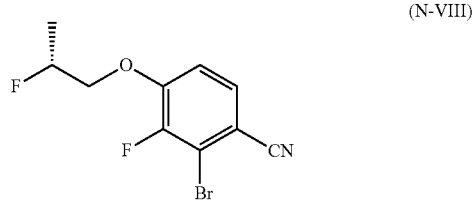

The title compound was synthesized in analogy to 2-bromo-3-fluoro-4-(2-((tetrahydro-2H-pyran-2-yl)oxy)ethoxy)benzonitrile (N-VI) from 2-bromo-3,4-difluorobenzonitrile and (R)-2-fluoropropan-1-ol. ¹H NMR (400 MHz, DMSO-d₆) δ (ppm): 7.80 (dd, J=8.6, 2.0 Hz, 1H), 7.40 (t, J=8.2 Hz, 1H), 5.14-4.95 (m, 1H), 4.43-4.23 (m, 2H), 1.36 (dd, J=23.8, 6.6 Hz, 3H).

Synthesis of 2-bromo-3-fluoro-4-(2-methoxyethoxy)benzonitrile (N-IX)

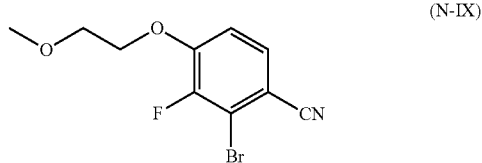

(N-IX)

Under an Ar atmosphere sodium (79 mg, 3.44 mmol) was added to a stirred solution of 2-methoxyethanol (10 mL). After 1 h at RT, 2-bromo-3,4-difluorobenzonitrile (500 mg, 2.294 mmol) was added and stirring was continued for 1 h. The reaction mixture was quenched with a sat solution of NaHCO$_3$ and extracted with DCM. The organic layers were combined and washed with a sat solution of NaHCO$_3$, dried over anhydrous Na$_2$SO$_4$ and concentrated. The residue was purified by flash chromatography (silica, hexane/EtOAc; gradient 0% to 85% EtOAc) to yield the desired product (593 mg). $^1$H NMR (400 MHz, DMSO-d$_6$) δ (ppm) 7.84-7.70 (m, 1H), 7.39 (t, J=8.4 Hz, 1H), 4.35-4.25 (m, 2H), 3.74-3.61 (m, 2H), 3.29 (s, 3H).

Synthesis of 2-bromo-4-(cyclopropylmethoxy)-3-fluorobenzonitrile (N-X)

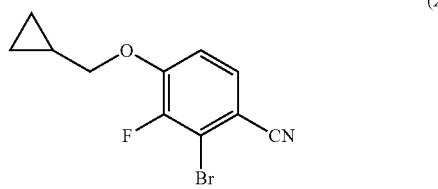

(X)

Under Ar, NaH (0.413 g, 10.3 mmol, 60% in mineral oil) was added to a stirred solution of cyclopropyl carbinol (0.744 g, 10.32 mmol) in THF (15 mL) at RT. The suspension was stirred at RT for 1 h, then 2-bromo-3,4-difluorobenzonitrile (1.5 g, 6.88 mmol) was added. The resulting thick suspension was diluted in THF (10 mL) and further stirred for 1.5 h at RT. A sat solution of NaHCO$_3$ was added and the reaction mixture was extracted with EtOAc. The combined organic layers were washed with brine, dried over anhydrous Na$_2$SO$_4$ and concentrated. The crude product was purified by flash chromatography (silica, hexane/EtOAc 9:1) to afford the title compound (1.6 g). $^1$H NMR (600 MHz, DMSO-d$_6$) δ (ppm) 7.77 (d, J=8.7 Hz, 1H), 7.34 (t, J=8.3 Hz, 1H), 4.03 (d, J=7.2 Hz, 2H), 1.29-1.21 (m, 1H), 0.63-0.56 (m, 2H), 0.38-0.31 (m, 2H).

Synthesis of 4-chloro-5-fluoro-6-(2-methoxyethoxy)nicotinonitrile (N-XI)

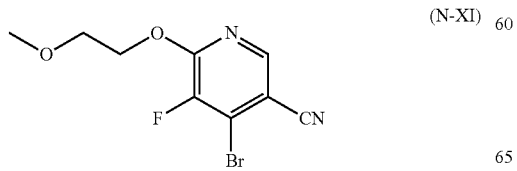

(N-XI)

Step 1: 4-Chloro-5,6-difluoronicotinamide (N-XI-a)

At RT DMF (2 mL) was added to a solution of 4-chloro-5,6-difluoronicotinic acid (3.00 g, 15.55 mmol) in SOCl2 (20 mL) and stirred at 80° C. was continued for 16 h. The reaction mixture was concentrated and the resulting residue was suspended in DCM (50 mL). NH$_4$Cl (0.914 g, 17.10 mmol) and NEt$_3$ (10.8 mL, 77.73 mmol) were added at 0° C. and the reaction mixture was allowed to stir at this temperature for another 3 h. A sat solution of NaHCO$_3$ and NaCl were added and the mixture was extracted with DCM. The combined organic layers were dried over anhydrous Na$_2$SO$_4$ and concentrated. The residue was purified by flash chromatography (silica, hexane/EtOAc; gradient 0% to 60% EtOAc) to afford the title compound (1.70 g) as a colorless powder. UPLC-MS m/z 192.8 [M+H]$^+$.

Step 2: 4-Chloro-5-fluoro-6-(2-methoxyethoxy)nicotinamide (N-XI-b)

At 0° C. NaH (0.21 g, 5.2 mmol, 60% in mineral oil) was added portion wise to a stirred solution of 2-methoxyethanol (0.41 mL, 5.2 mmol) in THF (30 mL). After 5 min, 4-chloro-5,6-difluoronicotinamide (N-XI-a) (1.00 g, 5.2 mmol) was added and the reaction mixture was stirred at 0° C. for 10 min. Water was added and the mixture was extracted with EtOAc. The combined organic layers were dried over anhydrous Na$_2$SO$_4$ and concentrated. The crude product was purified by flash chromatography (silica, hexane/EtOAc; gradient 0% to 65% EtOAc) to afford the title compound (0.80 g) as a colorless powder. UPLC-MS m/z 248.9 [M+H]$^+$.

Step 3: 4-Chloro-5-fluoro-6-(2-methoxyethoxy)nicotinonitrile (N-XI)

CuCl (0.016 g, 0.16 mmol) followed by 2,2,2-trifluoro-N-methyl-N-(trimethylsilyl)acetamide (3.851 g, 19.4 mmol) were added to a stirred solution of 4-chloro-5-fluoro-6-(2-methoxyethoxy)nicotinamide (N-XI-b) (1.60 g, 6.5 mmol) in toluene (20 mL) and the resulting reaction mixture was stirred at 100° C. for 24 h. The reaction mixture was diluted with water and extracted with EtOAc. The combined organic phases were dried over anhydrous Na$_2$SO$_4$ and concentrated. The residue was purified by flash chromatography (silica, hexane/EtOAc; gradient 0% to 15% EtOAc) to afford the title compound (1.20 g) as a colorless powder. $^1$H NMR (400 MHz, DMSO-d$_6$) δ (ppm) 8.63 (d, J=08 Hz, 1H), 4.60-4.57 (m, 2H), 3.72-3.70 (m, 2H), 3.30 (s, 3H). UPLC-MS m/z 230.9 [M+H]$^+$.

Synthesis of 5-fluoro-4-iodo-6-(2-((tetrahydro-2H-pyran-2-yl)oxy)ethoxy)nicotinonitrile (N-XII)

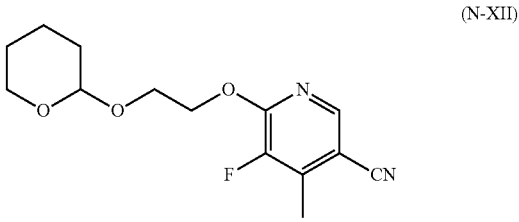 [SMILES: Cc1c(C#N)cnc(OCCOC2CCCCO2)c1F]

(N-XII)

Step 1: 5-Bromo-3-fluoro-2-(2-((tetrahydro-2H-pyran-2-yl)oxy)ethoxy)pyridine (N-XII-a)

At 0° C. NaH (0.21 g, 5.2 mmol, 60% in mineral oil) was added portion wise to a stirred solution of 2-((tetrahydro-2H-pyran-2-yl)oxy)ethan-1-ol (1.2 mL, 7.8 mmol) in THF (20 mL). After 5 min 5-bromo-2,3-difluoropyridine (1.00 g, 5.2 mmol) was added and the reaction mixture was stirred at 0° C. for 45 min. NH$_4$Cl solution (50 mL) was added and the mixture was stirred for 5 min before it was extracted with EtOAc. The combined organic layers were washed with brine, dried over anhydrous Na$_2$SO$_4$ and concentrated. The residue was purified by flash chromatography (silica, hexane/EtOAc; gradient 0% to 10% EtOAc) to afford the title compound (1.00 g) as a colorless powder. UPLC-MS m/z 322.2 [M+H]$^+$.

Step 2: 5-Fluoro-6-(2-((tetrahydro-2H-pyran-2-yl)oxy)ethoxy)nicotinonitrile (N-XII-b)

A mixture of 5-bromo-3-fluoro-2-(2-((tetrahydro-2H-pyran-2-yl)oxy)ethoxy)pyridine (N-XII-a) (0.50 g, 1.6 mmol), zinc cyanide (0.36 g, 3.1 mmol) and tetrakis(triphenylphosphine)palladium (0) (0.180 g, 0.16 mmol) in DMF (8 mL) was heated at 100° C. under MW irradiation for 1 h. The reaction mixture was diluted with water and extracted with EtOAc. The organic layer was washed with brine, dried over anhydrous Na$_2$SO$_4$ and concentrated. The crude product was purified by flash chromatography (silica, hexane/EtOAc; gradient 0% to 14% EtOAc) to afford the title compound (0.35 g) as a colorless oil. $^1$H NMR (400 MHz, DMSO-d$_6$) δ (ppm) 8.53 (d, J=2.0 Hz, 1H), 8.31 (dd, J=10.8, 2.0 Hz, 1H), 4.66-4.64 (m, 1H), 4.63-4.53 (m, 2H), 3.98-3.93 (m, 1H), 3.79-3.72 (m, 2H), 3.45-3.40 (m, 1H), 1.69-1.57 (m, 2H), 1.49-1.44 (m, 4H).

Step 3: 5-Fluoro-4-iodo-6-(2-((tetrahydro-2H-pyran-2-yl)oxy)ethoxy)nicotinonitrile (N-XII)

At −78° C. LDA (4.0 mL, 7.90 mmol) was added dropwise to a stirred solution of 5-fluoro-6-(2-((tetrahydro-2H-pyran-2-yl)oxy)ethoxy)nicotinonitrile (N-XII-b) (0.70 g, 2.6 mmol) in THF (20 mL). After 10 min at −78° C. I$_2$ (0.67 g, 5.3 mmol) was added and the reaction mixture was allowed to warm to RT and stirred for another 16 h. Ice water was added and the mixture was stirred for 5 min before it was extracted with EtOAc, dried over anhydrous Na$_2$SO$_4$ and concentrated. The residue was purified by flash chromatography (silica, hexane/EtOAc; gradient 0% to 14% EtOAc) to afford the title compound (0.70 g) as a colorless oil. $^1$H NMR (400 MHz, DMSO-d$_6$) δ (ppm) 8.44 (s, 1H), 4.65-4.63 (m, 1H), 4.63-4.52 (m, 2H), 3.97-3.92 (m, 1H), 3.78-3.72 (m, 2H), 3.45-3.41 (m, 1H), 1.69-1.51 (m, 2H), 1.46-1.44 (m, 4H).

Synthesis of 2-bromo-3-fluoro-4-((2S)-2-((tetrahydro-2H-pyran-2-yl)oxy)propoxy)benzonitrile (N-XIII)

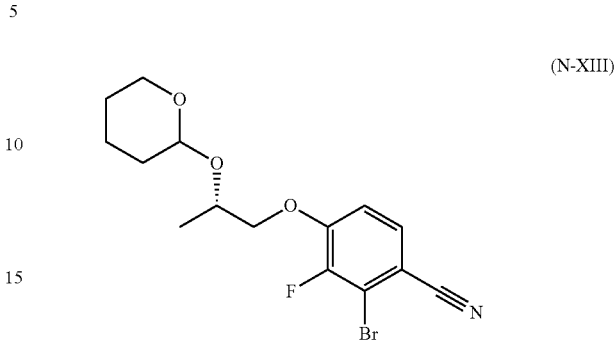

(N-XIII)

Step 1: (2S)-ethyl 2-((tetrahydro-2H-pyran-2-yl)oxy)propanoate (N-XIII-a)

Under Ar 3,4-dihydro-2H-pyran (13.16 mL, 144 mmol) and pyridinium toluene-4-sulfonate (1.064 g, 4.23 mmol) were added to a stirred solution of (−)-ethyl L-lactate (9.67 mL, 85 mmol) in DCM (100 mL) at 0° C. Stirring at RT was continued for 16 h. The reaction mixture was quenched with water, then extracted with DCM. The organic layers were combined and washed with water, dried over anhydrous Na$_2$SO$_4$ and concentrated. The residue was purified by flash chromatography (silica, hexane/EtOAc, gradient: 0% to 30% EtOAc) to afford the title compound (16.3 g). $^1$H NMR (400 MHz, DMSO-d$_6$) δ (ppm) 4.71-4.65 (m, 1H), 4.64-4.55 (m, 1H), 4.15-4.00 (m, 4H), 3.83-3.64 (m, 2H), 3.49-3.30 (m, 2H), 1.76-1.54 (m, 5H), 1.52-1.34 (m, 9H), 1.32-1.28 (m, 3H), 1.27-1.21 (m, 3H), 1.20-1.14 (m, 6H)

Step 2: (2S)-2-((Tetrahydro-2H-pyran-2-yl)oxy)propan-1-ol (N-XIII-b)

At 0° C. lithium aluminium hydride (23.03 mL, 81 mmol, 18% in toluene) was added dropwise over 6 min to a solution of (2S)-ethyl 2-((tetrahydro-2H-pyran-2-yl)oxy)propanoate (N-XIII-a) (16.3 g, 81 mmol) in Et$_2$O (800 mL). The resulting reaction mixture was stirred at 0° C. for 1.5 h before it was carefully quenched with a sat solution of NH$_4$Cl. The precipitate was filtered off and the mother liquor was extracted with Et$_2$O. The organic layers were combined and washed with brine, dried over anhydrous Na$_2$SO$_4$ and concentrated to afford the titled compound (10.12 g). $^1$H NMR (400 MHz, DMSO-d$_6$) δ (ppm) 4.75-4.69 (m, 1H), 4.68-4.62 (m, 1H), 3.89-3.74 (m, 2H), 3.73-3.62 (m, 2H), 3.49-3.19 (m, 6H), 1.80-1.54 (m, 4H), 1.52-1.36 (m, 8H), 1.10-0.99 (m, 6H).

Step 3: 2-Bromo-3-fluoro-4-((2S)-2-((tetrahydro-2H-pyran-2-yl)oxy)propoxy)benzonitrile (N-XIII)

At 0° C. NaH (2.03 g, 50.7 mmol, 60% in mineral oil) was added portionwise over 4 min to a stirred solution of (2S)-2-((tetrahydro-2H-pyran-2-yl)oxy)propan-1-ol (N-XIII-b) (7.50 g, 46.8 mmol) in DMF (140 mL). Then, 2-bromo-3,4-difluorobenzonitrile (8.50 g, 39.0 mmol) was added and the reaction mixture was stirred at 0° C. for 2 h. The reaction mixture was quenched with a sat solution of NH$_4$Cl and extracted with EtOAc. The organic layers were combined and washed with brine, dried over anhydrous Na₂SO₄ and concentrated. The resulting crude product was purified by flash chromatography (silica, hexane/EtOAc 2:1) to give the title product (14.68 g). UPLC-MS 1: m/z 375.2 [M+NH₄]⁺, $t_R$=1.22 min.

Synthesis of (S)-2-bromo-3-fluoro-4-(2-hydroxypropoxy)benzonitrile (N-XIV)

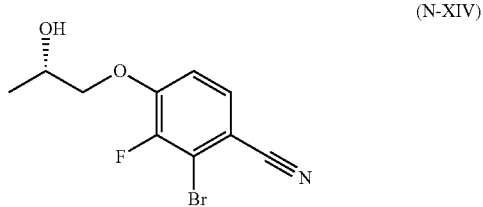

(N-XIV)

p-TsOH (158 mg, 0.83 mmol) was added to to a solution of 2-bromo-3-fluoro-4-((2S)-2-((tetrahydro-2H-pyran-2-yl)oxy)propoxy)benzonitrile (N-XIII) (746 mg, 2.08 mmol) in EtOH (10 mL) and the resulting reaction mixture was stirred at RT for 16 h. For workup a sat solution of NaHCO₃ was added followed by extraction with EtOAc. The combined organic extracts were washed with a sat solution of NaHCO₃ and dried over anhydrous Na₂SO₄. Concentration afforded the crude product which was purified by flash chromatography (silica, hexane/EtOAc, gradient: 0% to 100% EtOAc) to give the title compound (528 mg) as a colorless powder. UPLC-MS 1: m/z 317.9 [M+formate]⁻, $t_R$=0.84 min.

Synthesis of (R)-2-bromo-3-fluoro-4-(2-hydroxypropoxy)benzonitrile (N-XV)

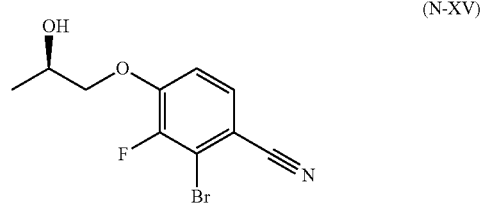

(N-XV)

The title compound was synthesized in analogy to (S)-2-bromo-3-fluoro-4-(2-hydroxypropoxy)benzonitrile (N-XIV) from 2-bromo-3,4-difluorobenzonitrile and (+)-ethyl-D-lactate. UPLC-MS 1: m/z 318.1 [M+formate]⁻, $t_R$=0.87 min.

Synthesis of ethyl 2-(3-bromo-4-cyano-2-fluorophenoxy)acetate (N-XVI)

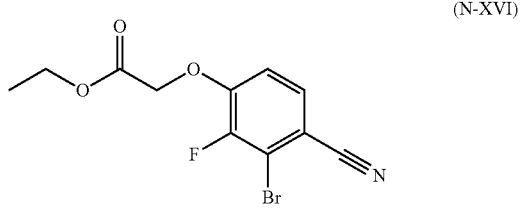 [SMILES: CCOC(=O)COc1ccc(C#N)c(Br)c1F]

(N-XVI)

A solution of ethyl-2-hydroxyacetate (25 mg, 2.1 mmo and KOtBu (170 mg, 1.5 mmol) in THF (5 mL) was slowly added to a solution of 2-bromo-3,4-difluorobenzonitrile (300 mg, 1-4 mmol) in THF (5 mL) cooled to 0° C. The reaction mixture was allowed to warm to RT and stirred for another 40 min. The reaction mixture was concentrated under reduced pressure and the residue was treated with a sat solution of NH₄Cl followed by extraction with EtOAc. The combined organic layers were dried over anhydrous Na₂SO₄ and concentrated. Purification of the crude product by flash chromatography (silica, cyclohexane/EtOAc, gradient: 0% to 20% EtOAc) furnished the title compound (280 mg) as a colorless powder. ¹H NMR (400 MHz, DMSO-d₆) δ (ppm) 7.78 (dd, J=9.0, 2.0 Hz, 1H), 7.35 (t, J=8.2 Hz, 1H), 5.06 (s, 2H), 4.17 (q, J=7.0 Hz, 2H), 1.20 (t, J=7.0 Hz, 3H).

Synthesis of (R)-4-((4-acetylmorpholin-2-yl)methoxy)-2-bromo-3-fluorobenzonitrile (N-XVII)

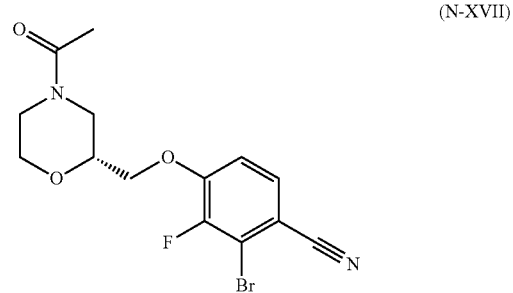 [SMILES: CC(=O)N1CCO[C@@H](COc2ccc(C#N)c(Br)c2F)C1]

(N-XVII)

The title compound was synthesized in analogy to ethyl 2-(3-bromo-4-cyano-2-fluorophenoxy)acetate (N-XVI) from 2-bromo-3,4-difluorobenzonitrile and (R)-morpholin-2-ylmethanol (CAS 1664380-75-9). UPLC-MS 1: m/z 357.1/359.1 [M+H]⁺, $t_R$=0.84 min Synthesis of (R)-2-bromo-3-fluoro-4-((tetrahydrofuran-2-yl)methoxy)benzonitrile (N-XVIII)

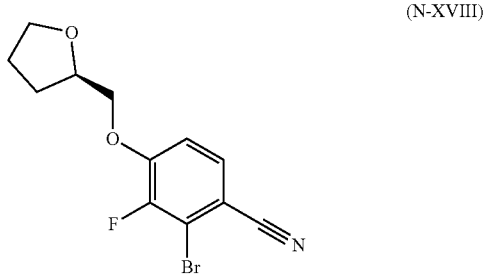 [SMILES: N#Cc1ccc(OC[C@H]2CCCO2)c(F)c1Br]

(N-XVIII)

A solution containing (R)-(tetrahydrofuran-2-yl)methanol (211 mg, 2.06 mmol) and KOtBu (170 mg, 1.51 mmol) in THF (2.5 mL) was added dropwise to a stirred solution of 2-bromo-3,4-difluorobenzonitrile (300 mg, 1.37 mmol) in THF (7.5 mL) at 0° C. The reaction mixture was stirred at 0° C. for 40 min. The reaction mixture was then partitioned between EtOAc and a 10% citric acid solution. The organic layer was dried over anhydrous Na₂SO₄ and concentrated. The crude product was purified by flash chromatography (silica, EtOAc/cyclohexane, gradient: 0% to 33% EtOAc) to Synthesis of 2-bromo-4-ethyl-3-fluorobenzonitrile (N-XIX)

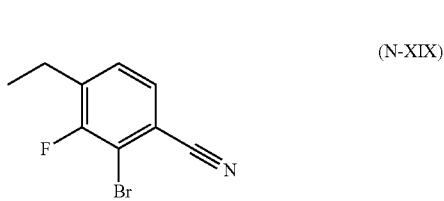

Step 1: 3-Fluoro-4-vinylbenzonitrile (N-XIX-a)

To a stirred solution of 4-bromo-3-fluorobenzonitrile (1.00 g, 32.26 mmol) in dioxane/water (20 mL, 3:1) were added vinylboronic anhydride pyridine complex (600 mg, 2.50 mmol), Pd(tBu$_3$P)$_2$ (128 mg, 0.25 mmol) and K$_2$CO$_3$ (1.04 g, 7.50 mmol) under Ar. The reaction mixture was stirred at 100° C. for 1 h and then cooled to RT. The reaction mixture was partitioned between a sat solution of NaHCO$_3$ and EtOAc. The organic layer was washed with a sat solution of NaHCO$_3$, dried over anhydrous Na$_2$SO$_4$ and concentrated. The crude product was purified by flash chromatography (silica, cyclohexane/EtOAc, gradient: 0% to 8% EtOAc) to afford the desired product (616 mg). $^1$H NMR (400 MHz, DMSO-d$_6$) δ (ppm) 7.93-7.75 (m, 2H), 7.67 (dd, J=8.1, 1.7 Hz, 1H), 6.85 (dd, J=17.8, 11.3 Hz, 1H), 6.10 (d, J=17.8 Hz, 1H), 5.61 (d, J=11.3 Hz, 1H).

Step 2: 4-Ethyl-3-fluorobenzonitrile (N-XIX-b)

A solution of 3-fluoro-4-vinylbenzonitrile (N-XIX-a) (200 mg, 1.40 mmol) in THF (10 mL) was treated with Pd/C 10%(145 mg) and hydrogenated at 0.1 bar overpressure in a shaked flask at RT for 10 min. The reaction mixture was filtered and concentrated. The crude product was purified by flash chromatography (silica, cyclohexane/EtOAc, gradient: 0% to 10% EtOAc) to afford the title compound (169 mg). $^1$H NMR (400 MHz, DMSO-d$_6$) δ (ppm) 7.75 (dd, J=10.0, 1.7 Hz, 1H), 7.62 (dd, J=7.8, 1.6 Hz, 1H), 7.51 (t, J=7.8 Hz, 1H), 2.67 (q, J=7.5 Hz, 2H), 1.16 (t, J=7.5 Hz, 2H).

Step 3: 2-Bromo-4-ethyl-3-fluorobenzonitrile (N-XIX)

At −78° C. LDA (0.608 mL, 1.217 mmol, 2 M in THF/heptane/ethylbenzene) was added to a stirred solution of 4-ethyl-3-fluorobenzonitrile (N-XIX-b) (165 mg, 1.10 mmol) in THF (10 mL) under Ar. The reaction mixture was stirred for 1 h at −78° C. before 1,2-dibromotetrachloroethane (720 mg, 2.21 mmol) was added. Stirring at −78° C. was continued for 1 h. The reaction mixture was then quenched with a saturated solution of NaHCO$_3$ and extracted with EtOAc. The combined organic layers were washed with a sat solution of NaHCO$_3$, dried over anhydrous Na$_2$SO$_4$ and concentrated. The crude product was purified by flash chromatography (silica, cyclohexane/EtOAc, gradient: 0% to 7% EtOAc) to afford the title compound (206 mg). $^1$H NMR (400 MHz, DMSO-d$_6$) δ (ppm) 7.73 (dd, J=7.9, 1.2 Hz, 1H), 7.57-7.48 (m, 1H), 2.72 (qd, J=7.5, 1.5 Hz, 2H), 1.17 (t, J=7.5 Hz, 3H).

Synthesis of 2-bromo-3-fluoro-4-(1H-imidazol-1-yl)benzonitrile (N-XX)

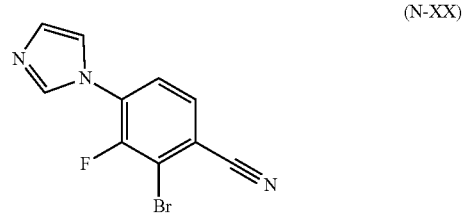 [SMILES: N#Cc1ccc(-n2ccnc2)c(F)c1Br]

A solution of imidazole (94 mg, 1.37 mmol) in THF (2 mL) was treated with solid NaH (34 mg, 1.38 mmol, 95%) and the resulting suspension was stirred at RT for 30 min. Then, a solution of 2-bromo-3,4-difluorobenzonitrile (200 mg, 0.92 mmol) in THF (4 mL) was slowly added and the reaction mixture was stirred at RT for 2 h. The reaction mixture was then quenched with a sat solution of NaHCO$_3$ and extracted with EtOAc. The organic layer was dried over anhydrous MgSO$_4$ and concentrated. The crude product was purified by flash chromatography (silica, DCM/MeOH, gradient: 0% to 3% MeOH) to afford the title compound (121 mg) as a colorless powder. UPLC-MS 1: m/z 266.0/268.0 [M+H]$^+$; $t_R$=0.71 min.

Synthesis of 2-bromo-3-fluoro-4-(pyrimidin-2-yl-methoxy)benzonitrile (N-XXI)

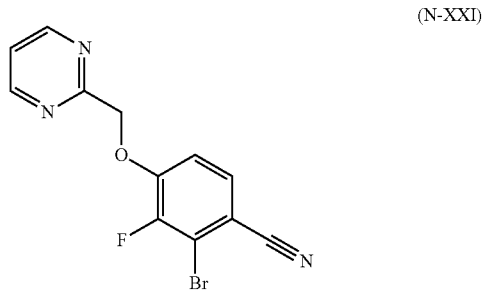 [SMILES: N#Cc1ccc(OCc2ncccn2)c(F)c1Br]

A solution of pyrimidin-2-ylmethanol (227 mg, 2.06 mmol) in THF (2.5 mL) was treated with solid KOtBu (170 mg, 1.51 mmol) and the resulting suspension was stirred at RT for 30 min. Then, this mixture was added to a solution of 2-bromo-3,4-difluorobenzonitrile (300 mg, 1.38 mmol) in THF (7.5 mL) cooled to 0° C. The reaction mixture was stirred at RT for 2 h before it was quenched with a citric acid solution. The solid formed was collected by filtration to afford the title compound (350 mg). UPLC-MS 1: m/z 308.0 [M+H]$^+$; $t_R$=0.87 min.

Synthesis of 2-bromo-4-(1,1-difluoro-2-hydroxy-ethoxy)-3-fluorobenzonitrile (N-XXII)

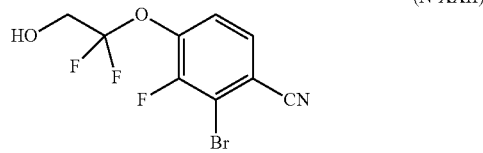

Reaction Scheme N-XXII

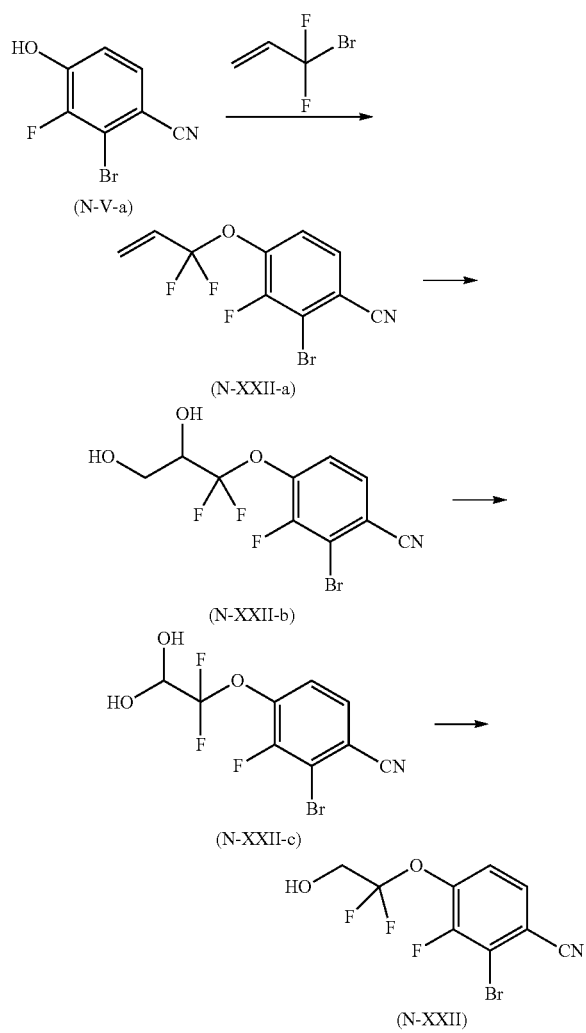

Step 1: 2-Bromo-4-((1,1-difluoroallyl)oxy)-3-fluorobenzonitrile (N-XXII-a)

To a stirred solution of 2-bromo-3-fluoro-4-hydroxybenzonitrile (N-V-a) (1.4 g, 6.42 mmol) in THF (50 mL) were added NaH (0.257 g, 6.42 mmol, 60%), Pd(OAc)$_2$ (14 mg, 0.06 mmol), triphenylphosphine (67 mg, 0.26 mmol) and 3-bromo-3,3-difluoroprop-1-ene (1.0 g, 6.4 mmol). The reaction mixture was stirred a RT overnight. A sat solution of NaHCO$_3$ was added and the reaction mixture was extracted with EtOAc. The combined organic layers were washed with brine, dried over anhydrous Na$_2$SO$_4$ and concentrated. The crude product was purified by flash chromatography (silica, cyclohexane/EtOAc, gradient: 0% to 10% EtOAc) to afford the title compound (1.3 g). $^1$H NMR (600 MHz, DMSO-d6) δ 7.92 (d, J=8.6 Hz, 1H), 7.67 (t, J=8.1 Hz, 1H), 6.33 (dq, J=17.7, 8.2 Hz, 1H), 6.01 (d, J=17.2 Hz, 1H), 5.85 (d, J=10.9 Hz, 1H).

Step 2: 2-Bromo-4-(1,1-difluoro-2,3-dihydroxypropoxy)-3-fluorobenzonitrile (N-XXII-b)

To a suspension of 2-bromo-4-((1,1-difluoroallyl)oxy)-3-fluorobenzonitrile (N-XXII-a) (0.7 g, 2.40 mmol) in dioxane (16 mL) and water (5 mL) were added osmium tetroxide (0.3 mL, 0.048 mmol, 4% in water) and N-methylmorpholine-N-oxide (0.3 g, 2.64 mmol) at RT. The reaction mixture was stirred at RT for 3 days. A sat solution of NaHCO$_3$ was added and the reaction mixture was extracted with EtOAc. The combined organic layers were washed with brine, dried over anhydrous Na$_2$SO$_4$ and concentrated. The crude product was purified by flash chromatography (silica, cyclohexane/EtOAc, gradient: 20 to 90% EtOAc) to afford the title compound (590 mg). $^1$H NMR (600 MHz, DMSO-d6) δ 7.90 (dd, J=8.7, 1.7 Hz, 1H), 7.63 (t, J=7.9 Hz, 1H), 6.20 (d, J=6.5 Hz, 1H), 4.98 (t, J=5.9 Hz, 1H), 3.98 (ddt, J=13.6, 10.1, 5.0 Hz, 1H), 3.72 (dt, J=11.7, 3.9 Hz, 1H), 3.52 (ddd, J=11.5, 7.3, 3.8 Hz, 1H).

Step 3: 2-Bromo-4-(1,1-difluoro-2,2-dihydroxyethoxy)-3-fluorobenzonitrile (N-XXII-c)

At RT sodium periodate (2.95 g, 13.8 mmol) was added to a suspension of 2-bromo-4-(1,1-difluoro-2,3-dihydroxypropoxy)-3-fluorobenzonitrile (N-XXII-b) (0.45 g, 1.38 mmol) in dioxane (16 mL) and water (5 mL). The reaction mixture was stirred at RT for 2 days. A sat solution of NaHCO$_3$ was added and the reaction mixture was extracted with EtOAc. The combined organic layers were washed with brine, dried over anhydrous Na$_2$SO$_4$ and concentrated to afford the title compound used directly in the next step without purification. UPLC-MS 1: t$_R$=0.75 min.

Step 4: 2-Bromo-4-(1,1-difluoro-2-hydroxyethoxy)-3-fluorobenzonitrile (N-XXII)

At RT NaBH$_4$ (546 mg, 14.4 mmol) was added to a solution of 2-bromo-4-(1,1-difluoro-2,2-dihydroxyethoxy)-3-fluorobenzonitrile (N-XXII-c) (450 mg, 1.44 mmol) in THF (14.4 mL). The reaction mixture was stirred at RT for 1 h. A sat solution of NaHCO$_3$ was added and the reaction mixture was extracted with EtOAc. The combined organic extracts were washed with brine, dried over anhydrous Na$_2$SO$_4$ and concentrated. The residue was purified by flash chromatography (silica, cyclohexane/EtOAc, gradient: 20 to 80% EtOAc) to afford the title compound (130 mg). $^1$H NMR (600 MHz, DMSO-d6) δ 7.90 (dd, J=8.6, 1.7 Hz, 1H), 7.74-7.48 (m, 1H), 6.06 (t, J=6.7 Hz, 1H), 3.94 (td, J=10.4, 6.7 Hz, 2H).

Synthesis of 2-bromo-4-((1,1-difluoro-2-((tetrahydro-2H-pyran-2-yl)oxy)ethyl)thio)benzonitrile (N-XXIII)

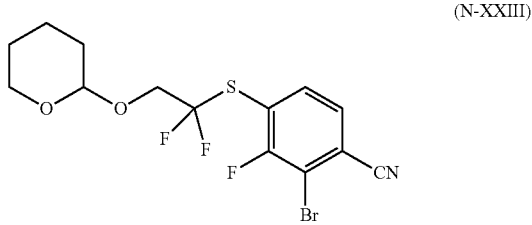 [SMILES: N#Cc1ccc(SC(F)(F)COC2CCCCO2)c(F)c1Br]
(N-XXIII)

Step 1: 2-Bromo-4-mercaptobenzonitrile (N-XXIII-a)

A solution of 2-bromo-3,4-difluorobenzonitrile (5.0 g, 25.0 mmol) in DMF (25 mL) was treated with $Na_2S$ (2.14 g, 27.5 mmol) and stirred at RT for 1 h. The reaction mixture was cooled to 0° C., quenched with 1 N NaOH and extracted with DCM. The aqueous layer was acidified with 6 N HCl and back-extracted with DCM. The combined organic layers were washed with brine, dried over anhydrous $Na_2SO_4$ and concentrated. The resulting crude product was dissolved in 10% HCl (100 mL), cooled to 0° C. and Zinc dust (10 g) was added. The reaction mixture was stirred for 1 h, then diluted with EtOAc (250 mL) and stirred for an additional 30 min. The separated organic layer was washed with water and brine, dried over anhydrous $Na_2SO_4$ and concentrated to give the title compound (2.5 g) which was used in the next step without further purification. UPLC-MS m/z 214.1 $[M+H]^+$.

Step 2: 2-Bromo-4-((1,1-difluoro-2-hydroxyethyl)thio)benzonitrile (N-XXIII-b)

To a stirred solution of 2-bromo-4-mercaptobenzonitrile (N-XXIII-a) (0.2 g, 0.94 mmol) in DMSO (5 mL) at 0° C. was added portionwise NaH (0.040 g, 0935 mmol, 60% in mineral oil). The suspension was stirred for 30 min before 2-bromo-2,2-difluoroacetate (0.208 g, 1.03 mmol) was added. The reaction mixture was stirred at RT for 16 h, then quenched with water and extracted with EtOAc. The combined organic layers were dried over anhydrous $Na_2SO_4$ and concentrated. The crude material (0.17 g) was then dissolved in MeOH (11 mL). Sodium borohydride (0.038 g, 1.012 mmol) was added portionwise at RT. The reaction mixture was stirred at RT for 30 min, then quenched with water and extracted with EtOAc. The combined organic layers were dried over anhydrous $Na_2SO_4$ and concentrated to give the title compound (0.16 g) which was used in the next step without further purification.

Step 3: 2-Bromo-4-((1,1-difluoro-2-((tetrahydro-2H-pyran-2-yl)oxy)ethyl)thio)benzonitrile (N-XXIII)

To a solution of crude 2-bromo-4-((1,1-difluoro-2-hydroxyethyl)thio)benzonitrile (N-XXIII-b) (0.16 g, 0.55 mmol) in DCM (10 mL) were successively added at 0° C. 3,4-dihydro-2H-pyran (0.092 g, 1.09 mmol) and pyridinium p-toluenesulfonate (0.007 g, 0.027 mmol). The reaction mixture was stirred at RT for 2 h, then quenched with water and extracted with DCM. The combined organic layers were dried over anhydrous $Na_2SO_4$ and concentrated. The crude product was purified by flash chromatography (silica, hexane/EtOAc 85:15) to afford the title compound (0.13 g). $^1$H NMR (400 MHz, DMSO-$d_6$) δ (ppm) 8.10 (br. s, 1H), 8.03 (d, J=8.3 Hz, 1H), 7.80 (dd, J=1.7 Hz, J=8.3 Hz, 1H), 4.75 (br s, 1H), 3.75-3.69 (m, 1H), 3.55-3.43 (m, 1H), 1.73-1.62 (m, 3H), 1.55-1.45 (m, 5H).

Synthesis of 2-bromo-3-fluoro-4-((methylsulfonyl)methoxy)benzonitrile (N-XXIV)

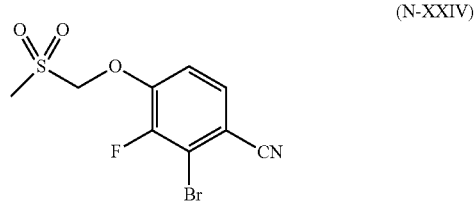 [SMILES: CS(=O)(=O)COc1ccc(C#N)c(Br)c1F]
(N-XXIV)

Under Ar, NaH (46 mg, 1.83 mmol, 95%) was added to a stirred solution of 2-bromo-3-fluoro-4-hydroxybenzonitrile (N-V-a) (283 mg, 1.31 mmol) in DMF (2.2 mL). The suspension was stirred at RT for 30 min, then (chloromethyl)(methyl)sulfane (132 µl, 1.572 mmol) was added and the reaction mixture was stirred at RT overnight. Water was added and the reaction mixture was extracted with EtOAc. The combined organic layers were dried over anhydrous $Na_2SO_4$ and concentrated. The crude product was dissolved in DCM (2.2 mL). At 0° C. mCPBA was added (734 mg, 3.28 mmol, 77%). The reaction mixture was stirred at RT for 1 h. To complete the reaction, more mCPBA was added (734 mg, 3.28 mmol, 77%) and the reaction mixture was stirred at RT for 1 h. Water was added and the pH was adjusted to 6-7 with 1 N NaOH. The reaction mixture was extracted with DCM, the combined organic layers were dried (phase separator cartridge) and concentrated. The crude product was purified by flash chromatography (silica, hexane/EtOAc, gradient: 0% to 40% EtOAc) to afford the title compound (240 mg). $^1$H NMR (400 MHz, DMSO-$d_6$) δ 7.86 (d, J=8.7 Hz, 1H), 7.65 (t, J=8.4 Hz, 1H), 5.59 (s, 2H), 3.09 (s, 3H). UPLC-MS 1: m/z 352.1/354.1 [M+formate]$^-$, $t_R$=0.79 min.

Synthesis of 2-bromo-4-(3,3-difluoropropoxy)-3-fluorobenzonitrile (N-XXV)

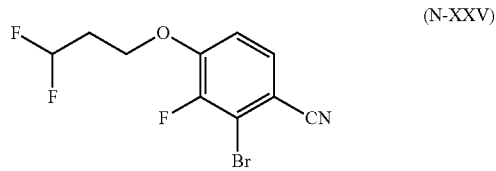 [SMILES: N#Cc1ccc(OCCC(F)F)c(F)c1Br]
(N-XXV)

Step 1: 2-Bromo-4-(3,3-diethoxypropoxy)-3-fluorobenzonitrile (N-XXV-a)

At 0° C. a solution of KOtBu (260 mg, 2.32 mmol) in THF was added dropwise to a solution of 2-bromo-3,4-difluorobenzonitrile (460 mg, 2.110 mmol) and 3,3-diethoxypropan-1-ol (0.85 mL, 5.4 mmol) in THF (3 mL). The reaction mixture was stirred at RT for 30 min, then diluted with EtOAc. The organic phase was successively washed with a sat solution of NH₄Cl, water and brine. The organic layer was dried over anhydrous MgSO₄ and concentrated to afford the title compound used as crude material in the next step without purification. UPLC-MS 1: m/z 390.2/392.2 [M+formate]⁻, $t_R$=1.21 min.

Step 2: 2-Bromo-3-fluoro-4-(3-oxopropoxy)benzonitrile (N-XXV-b)

The crude material N-XXV-a (700 mg) from the previous step was treated with a mixture of HCl (5 mL, 4 N in dioxane) and water (5 mL). The reaction mixture was stirred at RT for 6 h. DCM was added and the organic layer was washed with 1 N HCl and brine, dried over anhydrous MgSO₄ and concentrated to afford the title compound used as crude material in the next step without purification. UPLC-MS 1: $t_R$=0.87/0.90 min.

Step 3: 2-Bromo-4-(3,3-difluoropropoxy)-3-fluorobenzonitrile (N-XXV)

To a solution of crude 2-bromo-3-fluoro-4-(3-oxopropoxy)benzonitrile (N-XXV-b) from the previous step (500 mg, 1.84 mmol) in DCM (4 mL) was added dropwise at 0° C. diethylaminosulfur trifluoride (0.36 mL, 2.8 mmol). The reaction mixture was stirred at RT for 2 h. DCM and water were added, the organic layer was separated and the aqueous layer was extracted with DCM. The combined organic phases were dried over anhydrous MgSO₄ and concentrated. The residue was purified by flash chromatography (silica, heptane/EtOAc, gradient: 10% to 70% EtOAc) to afford the title compound (50 mg). ¹H NMR (600 MHz, DMSO-d₆) δ 7.82 (d, J=8.8 Hz, 1H), 7.44 (t, J=8.3 Hz, 1H), 6.24 (tt, J=56.3, 4.5 Hz, 1H), 4.35 (t, J=6.1 Hz, 2H), 2.44-2.33 (m, 2H).

Synthesis of methyl 2-bromo-3-fluoro-4-methoxybenzoate (N-XXVI)

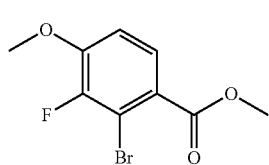

(N-XXVI)

At RT DBU (0.50 mL, 3.3 mmol) was added to a solution of methyl 2-bromo-3,4-difluorobenzoate (550 mg, 2.2 mmol) in MeOH (10 mL) and the reaction mixture was stirred at 50° C. for 22 h. A sat solution of NaHCO₃ was added and the mixture was extracted with EtOAc. The combined organic layers were dried over anhydrous MgSO₄ and concentrated. The crude product was purified by flash chromatography (silica, cyclohexane/EtOAc; gradient: 0% to 20% EtOAc) to afford the title compound (390 mg) as a colorless powder. UPLC-MS 1: m/z 263.1 [M+H]⁺, $t_R$=1.00 min.

Synthesis of methyl 2-bromo-3-fluoro-4-(2-((tetrahydro-2H-pyran-2-yl)oxy)ethoxy)benzoate (N-XXVII)

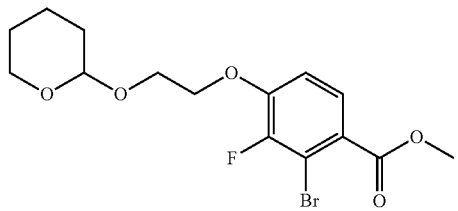

(N-XXVII)

Step 1: Methyl 2-bromo-3-fluoro-4-hydroxybenzoate (N-XXVII-a)

At 0° C. a solution of 2-(methylsulfonyl)ethanol (59.7 g, 482.1 mmol) in DMF (100 mL) was added dropwise to a stirred suspension of NaH (35.2 g, 876 mmol, 60% in mineral oil) in DMF (800 mL). After 15 min, a solution of methyl 2-bromo-3,4-difluorobenzoate (110 g, 438.2 mmol) in DMF (100 mL) was added dropwise and the reaction mixture was stirred at 0° C. for 20 min. The reaction mixture was quenched with a sat solution of NH₄Cl and extracted with EtOAc. The organic layers were combined and washed with water and brine, dried over anhydrous Na₂SO₄ and concentrated to afford the title compound. ¹H NMR (400 MHz, DMSO-d₆) δ (ppm) 11.17 (s, 1H), 2.00 (dd, J=8.68, 1.80 Hz, 1H), 7.03 (t, J=8.60 Hz, 1H), 3.82 (s, 3H).

Step 2: Methyl 2-bromo-3-fluoro-4-(2-((tetrahydro-2H-pyran-2-yl)oxy)ethoxy)benzoate (N-XXVII)

At 0° C. triphenylphosphine (63.4 g, 241.9 mmol) followed by a solution of DIAD (48.8 g, 241.9 mol) in THF (100 mL) was added dropwise to a stirred solution of methyl 2-bromo-3-fluoro-4-hydroxybenzoate (N-XXVII-a) (50 g, 201.6 mmol) and 2-((tetrahydro-2H-pyran-2-yl)oxy)ethanol (32.4 g, 221.7 mmol) in THF (500 mL). After addition, the reaction mixture was stirred at RT for 2 h. The reaction mixture was quenched with water and extracted with EtOAc. The organic layers were combined and washed with a sat solution of NaHCO₃ and brine, dried over Na₂SO₄ and concentrated. The resulting residue was triturated in PE/EtOAc (95:5), the mother liquor was concentrated and the crude product was purified by flash chromatography (silica, PE/EtOAc 9:1) to afford the title compound. ¹H NMR (400 MHz, DMSO-d₆) δ (ppm) 7.69 (q, J=1.4 Hz, 1H), 7.33 (t, J=8.5 Hz, 1H), 4.66 (d, J=3.3 Hz, 1H), 4.33 (d, J=2.2 Hz, 2H), 3.97-3.92 (m, 1H), 3.83 (s, 3H), 3.77-3.72 (m, 2H), 3.43 (q, J=6.2 Hz, 1H), 1.68-1.58 (m, 2H), 1.46 (t, J=9.0 Hz, 4H).

Synthesis of methyl 2-bromo-3-fluoro-4-((2S)-2-((tetrahydro-2H-pyran-2-yl)oxy)propoxy)benzoate (N-XXVIII)

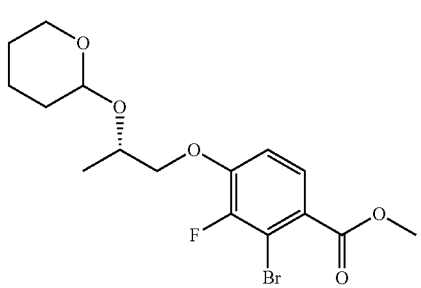

(N-XXVIII)

At 0° C. NaH (0.704 g, 17.6 mmol, 60% in mineral oil) was added portionwise to a stirred solution of (2S)-2-((tetrahydro-2H-pyran-2-yl)oxy)propan-1-ol (N-XIII-b) (2.60 g, 16.25 mmol) in DMF (50 mL). Then, methyl 2-bromo-3,4-difluorobenzoate (3.4 g, 13.5 mmol) was added and the reaction mixture was stirred for 2 h at 0° C. The reaction mixture was quenched with a sat solution of NH₄Cl and extracted with EtOAc. The organic phases were washed with brine, dried over anhydrous Na₂SO₄ and concentrated. The residue was purified by flash chromatography (silica, hexane/EtOAc 2:1) to afford the title compound (3.27 g) as a beige oil. UPLC-MS 1: m/z 408.2/410.2 [M+NH₄]⁺, $t_R$=1.24 min.

Synthesis of methyl 4-chloro-5-fluoro-6-methoxynicotinate (N-XXIX)

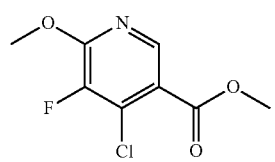

(N-XXIX)

Conc H₂SO₄ (0.551 mL, 10.33 mmol) was added to a stirred solution of 4-chloro-5,6-difluoronicotinic acid (200 mg, 1.033 mmol) in MeOH (10 mL) and the reaction mixture was stirred at 80° C. for 2 h. The reaction mixture was quenched by the addition of a sat solution of NaHCO₃ and extracted with DCM. The organic layers were combined and washed with a sat solution of NaHCO₃, dried over anhydrous Na₂SO₄ and concentrated. The crude product was purified by flash chromatography (silica, hexane/EtOAc; gradient: 0% to 10% EtOAc) to afford the title compound (143 mg) as a colorless powder. UPLC-MS 1: m/z 220.0 [M+H]⁺, $t_R$=1.02 min.

Synthesis of methyl 4-chloro-6-(difluoromethoxy)-5-fluoronicotinate (N-XXX)

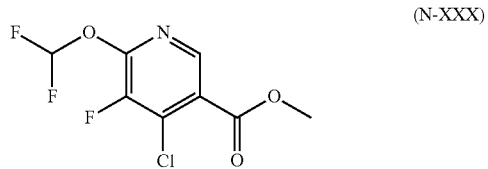 [SMILES: COC(=O)c1cnc(OC(F)F)c(F)c1Cl]

(N-XXX)

Step 1: Methyl 4-chloro-5,6-difluoronicotinate (N-XXX-a)

At RT TMS-diazomethane (11.37 mL, 22.7 mmol, 2M in Et₂O) was slowly added to a solution of 4-chloro-5,6-difluoronicotinic acid (4.00 g, 20.7 mmol) in MeOH (69 mL). Over the next 24 h more TMS-diazomethane (in total: 34.2 mL, 68.3 mmol, 2 M in Et₂O) was added in 4 portions until the starting material had been fully consumed. Water was added and the organic solvents were removed under reduced pressure. The residue was extracted with EtOAc and the combined organic layers were washed with brine, dried over anhydrous Na₂SO₄ and concentrated to afford the title compound (3.92 g) as a light yellow oil. UPLC-MS 1: m/z 208.1 [M+H]⁺, $t_R$=0.93 min.

Step 2: Methyl 4-chloro-5-fluoro-6-hydroxynicotinate (N-XXX-b)

At 0° C. NaH (1.36 g, 34 mmol, 60% in mineral oil) was added to a solution of methyl 4-chloro-5,6-difluoronicotinate (N-XXX-a) (2.90 g, 11.3 mmol) and 2-(methylsulfonyl)ethanol (1.55 g, 12.45 mmol) in DMF (49 mL) and stirring at this temperature was continued for 30 min. Water was added and the pH was adjusted to ca 5 using 1 N HCl. The organic solvents were removed under reduced pressure. More water was added and the mixture was filtered. The aqueous phase was extracted with EtOAc, dried over anhydrous Na₂SO₄ and concentrated to afford the title compound (2.50 g) as a colorless powder. UPLC-MS 1: m/z 204.0 [M−H]⁻, $t_R$=0.57 min.

Step 3: 4-Chloro-6-(difluoromethoxy)-5-fluoronicotinic acid (N-XXX-c)

At 0° C. a solution of KOH (1.82 g, 32.3 mmol) in water (6 mL) followed by diethyl (bromodifluoromethyl)phosphonate (0.58 mL, 3.2 mmol) was added to a stirred solution of methyl 4-chloro-5-fluoro-6-hydroxynicotinate (N-XXX-b) (350 mg) in ACN (6 mL). The reaction mixture was stirred at RT for 1.5 h. The pH of the reaction mixture was adjusted to 3 by the addition of 2 N HCl and the organic solvents were removed under reduced pressure. MeOH was added and the solids were removed by filtration. The organic phase was concentrated to yield the title compound (170 mg). UPLC-MS 1: m/z 240.1 [M−H]⁻, $t_R$=0.66 min.

Step 4: Methyl 4-chloro-6-(difluoromethoxy)-5-fluoronicotinate (N-XXX)

Thionyl chloride (0.077 mL, 1.06 mmol) followed by one drop of DMF were added to a solution of 4-chloro-6-

(difluoromethoxy)-5-fluoronicotinic acid (N-XXX-c) (170 mg, 0.70 mmol) in DCM (4.7 mL). The reaction mixture was stirred at RT for 45 min. More thionyl chloride (0.205 mL, 2.8 mmol) was added and stirring was continued for 15 min. Then, MeOH (20 mL) was added and the reaction mixture was stirred at RT overnight. A sat solution of NaHCO₃ was added and the organic solvents were removed under reduced pressure. The residue was extracted with DCM, the combined organic layers were dried over anhydrous Na₂SO₄ and concentrated to afford the title compound (102 mg). UPLC-MS 1: product not ionizable, $t_R$=1.05 min.

Synthesis of methyl 4-chloro-5-fluoro-6-(2-((tetrahydro-2H-pyran-2-yl)oxy)ethoxy)nicotinate (N-XXXI)

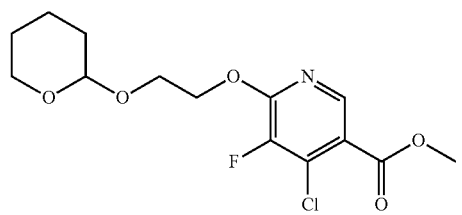

(N-XXXI)

At 0° C. NaH (0.31 g, 7.7 mmol) was added portion wise to a stirred solution of 2-((tetrahydro-2H-pyran-2-yl)oxy)ethan-1-ol (0.78 mL, 7.7 mmol) in THF (10 mL). After 5 min, methyl 4-chloro-5,6-difluoronicotinate (N-XXX-a) (1.60 g, 7.7 mmol) was added and stirring was continued for 1 h at 0° C. The reaction mixture was diluted with water, extracted with EtOAc, dried over anhydrous Na₂SO₄ and concentrated. The residue was purified by flash chromatography (silica, hexane/EtOAc; gradient: 0 to 10% EtOAc) to afford the title compound (1.20 g) as a colorless powder. ¹H NMR (400 MHz, DMSO-d₆) δ (ppm) 8.53 (d, J=1.2 Hz, 1H), 4.66-4.65 (m, 1H), 4.64-4.58 (m, 2H), 3.98-3.94 (m, 1H), 3.87 (s, 3H), 3.80-3.75 (m, 2H), 3.44-3.42 (m, 1H), 1.66-1.61 (m, 2H), 1.49-1.45 (m, 4H).

Alternative Synthesis of methyl 4-chloro-5-fluoro-6-(2-((tetrahydro-2H-pyran-2-yl)oxy)ethoxy)nicotinate (N-XXXI)

Reaction Scheme N-XXXI

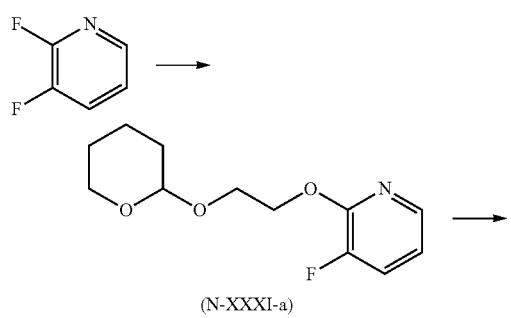

(N-XXXI-a)

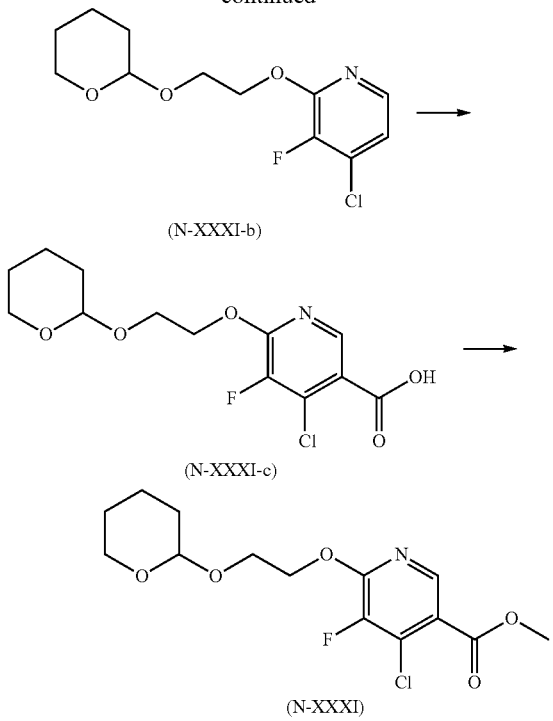

Step 1: 3-Fluoro-2-(2-((tetrahydro-2H-pyran-2-yl)oxy)ethoxy)pyridine (N-XXXi-a)

A reactor was charged with t-BuOK (7.80 kg, 69.51 mol) and THF (20 L), the mixture was cooled to −5-0° C. 2-((Tetrahydro-2H-pyran-2-yl)oxy)ethan-1-ol (6.60 kg, 45.15 mol) was added dropwise over 1 h. and the resulting mixture was stirred for 1 h at −5-0° C. 2,3-Difluoropyridine (4.0 kg, 34.76 mol) was added dropwise. The mixture was stirred for another 30 min, quenched with water (20 L) and extracted with ethyl acetate (2×20 L). The organic phase was washed with brine (20 L), dried over anhydrous Na₂SO₄ and concentrated. The crude product was purified by flash chromatography (silica, heptane/ethyl acetate 10:1) to give the title compound (7.46 kg) as a yellow oil. ¹H NMR (400 MHz, CDCl₃) δ 7.89 (dd, J=5.0, 1.6 Hz, 1H), 7.32 (ddd, J=10.3, 7.8, 1.6 Hz, 1H), 6.84 (ddd, J=8.0, 5.0, 3.2 Hz, 1H), 4.72 (t, J=3.6 Hz, 1H), 4.64-4.53 (m, 2H), 4.16-4.04 (m, 1H), 3.96-3.81 (m, 2H), 3.58-3.46 (m, 1H), 1.91-1.78 (m, 1H), 1.77-1.67 (m, 1H), 1.67-1.47 (m, 4H). UPLC-MS 5: HRMS m/z calcd for C₁₂H₁₇FNO₃ [M+H]⁺ 242.1187, found 242.1182.

Step 2: 4-Chloro-3-fluoro-2-(2-((tetrahydro-2H-pyran-2-yl)oxy)ethoxy)pyridine (N-XXXI-b)

A reactor was charged with compound 3-fluoro-2-(2-((tetrahydro-2H-pyran-2-yl)oxy)ethoxy)pyridine (N-XXXi-a) (3.60 kg, 14.92 mol) and THF (18 L). The solution was cooled to −78° C. n-BuLi (7.79 L, 19.40 mol, 2.5 M in hexanes) was added dropwise and the reaction was stirred for 4 h at −78° C. C₂Cl₆ (4.59 kg, 19.40 mol) was added at −78° C. The mixture was stirred for 30 min, quenched by addition of water (18 L), stirred for another 2 h and extracted with ethyl acetate (2×18 L). The organic phase was washed with brine (18 L), dried over anhydrous Na₂SO₄ and concentrated. The crude product was purified by flash chromatography (silica, heptane/ethyl acetate 10:1) to give the title compound (3.74 kg) as a light-yellow oil. ¹H NMR (400 MHz, CDCl₃) δ 7.79 (dd, J=5.5, 1.0 Hz, 1H), 6.91 (dd, J=5.4, 4.4 Hz, 1H), 4.72 (t, J=3.6 Hz, 1H), 4.58 (dt, J=6.0, 3.7 Hz, 2H), 4.08 (ddd, J=11.5, 5.6, 3.9 Hz, 1H), 3.94-3.80 (m, 2H), 3.52 (ddd, J=10.6, 6.0, 4.2 Hz, 1H), 1.90-1.77 (m, 1H), 1.77-1.67 (m, 1H), 1.66-1.47 (m, 4H). UPLC-MS 5: HRMS m/z calcd for C₁₂H₁₅ClFNNaO₃ [M+Na]⁺ 298.0617, found 298.0657.

Step 3: 4-Chloro-5-fluoro-6-(2-((tetrahydro-2H-pyran-2-yl)oxy)ethoxy)nicotinic acid (N-XXXI-c)

A reactor was charged with diisopropylamine (1.91 kg, 18.88 mol) and THF (20 L). n-BuLi (7.56 L, 18.88 mol, 2.5 M in hexanes) was added dropwise at −78° C. The mixture was stirred for 30 min and 4-chloro-3-fluoro-2-(2-((tetrahydro-2H-pyran-2-yl)oxy)ethoxy)pyridine (N-XXXI-b) (4.00 kg, 14.51 mol) was added dropwise. The reaction was stirred for 3 h and poured into dry ice (12.8 kg). The mixture was stirred for 2 h. Water (16 L) was added and the mixture was extracted with MTBE (20 L). The organic phase was washed with brine (4 L), then the combined aqueous phases were added to a mixture of ethyl acetate (40 L) and citric acid solution (3.77 kg citric acid dissolved in 22 L of water). The mixture was stirred for 30 min and the organic phase was separated. The aqueous phase was extracted with ethyl acetate (40 L). The combined organic phases were washed with brine (16 L), dried over anhydrous Na₂SO₄ and concentrated to give the title compound (3.68 kg) as an off-white solid. ¹H NMR (400 MHz, CDCl₃) δ 8.64 (d, J=1.3 Hz, 1H), 8.02 (brs, 1H), 4.77 (t, J=3.4 Hz, 1H), 4.68 (ddd, J=5.9, 4.0, 1.8 Hz, 2H), 4.11 (ddd, J=11.6, 5.4, 4.0 Hz, 1H), 3.97-3.84 (m, 2H), 3.62-3.53 (m, 1H), 1.90-1.70 (m, 2H), 1.68-1.49 (m, 4H). UPLC-MS 5: HRMS m/z calcd for C₁₃H₁₄ClFNO₅[M−H]⁻ 318.0550, found 318.0482.

Step 4: 4-Chloro-5-fluoro-6-(2-((tetrahydro-2H-pyran-2-yl)oxy)ethoxy)nicotinate (N-XXXI)

To a solution of 4-chloro-5-fluoro-6-(2-((tetrahydro-2H-pyran-2-yl)oxy)ethoxy)nicotinic acid (N-XXXI-c) (4.00 kg, 12.5 mol) in DMF (20 L) were added K₂CO₃ (4.32 kg, 31.3 mol) and MeI (2.67 kg, 18.8 mol). The mixture was stirred overnight at RT. MTBE (40 L) and water (40 L) were added. The mixture was stirred for 10 min and the phases were separated. The organic phase was washed with water (40 L) twice, dried over anhydrous Na₂SO₄ and concentrated. The crude product was purified by slurring with n-heptane (4 L) to give the title compound (3.37 kg) as a colorless solid. ¹H NMR (400 MHz, DMSO-d₆) δ 8.51 (d, J=1.2 Hz, 1H), 4.64 (t, J=2.9, 1H), 4.63-4.52 (m, 2H), 3.99-3.92 (m, 1H), 3.86 (s, 3H), 3.81-3.71 (m, 2H), 3.46-3.38 (m, 1H), 1.75-1.56 (m, 2H), 1.52-1.37 (m, 4H). UPLC-MS 5: HRMS m/z calcd for C₁₄H₁₃ClFNO₅[M+H]⁺ 334.0852, found 334.0823.

Synthesis of methyl 4-chloro-5-fluoro-6-(2-methoxyethoxy)nicotinate (N-XXXII)

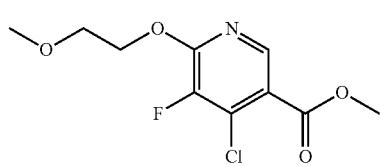

(N-XXXII)

At 0° C. DEAD (2.54 g, 14.598 mmol) was added to a stirred solution of methyl 4-chloro-5-fluoro-6-hydroxynicotinate (N-XXX-b) (2.0 g, 9.7 mmol), 2-methoxyethan-1-ol (815 mg, 1.07 mmol) and triphenylphosphine (3.31 g, 12.7 mmol) in THF (40 mL) and stirring was continued at this temperature for 3 h. The reaction mixture was quenched with a sat solution of NH₄Cl and extracted with EtOAc. The organic layer was washed with water, brine, dried over anhydrous Na₂SO₄ and concentrated. The residue was purified by flash chromatography (silica, hexane/EtOAc; gradient: 10% to 20% EtOAc) to afford the title compound (3.0 g). ¹H NMR (400 MHz, DMSO-d₆) δ (ppm) 8.50 (d, J=1.2 Hz, 1H), 4.56-4.54 (m, 2H), 3.85 (s, 3H), 3.70-3.67 (m, 2H), 3.32 (s, 3H). (UPLC-MS m/z 264.3 [M+H]⁺.

Synthesis of methyl (S)-2-bromo-3-fluoro-4-(2-hydroxypropoxy)benzoate (N-XXXIII)

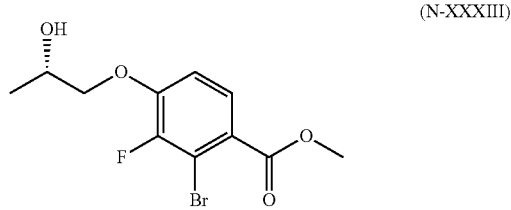 [SMILES: COC(=O)c1ccc(OC[C@H](C)O)c(F)c1Br]

Pyridinium p-toluenesulfonate (10.28 g, 40.9 mmol) was added to a solution of methyl 2-bromo-3-fluoro-4-((2S)-2-((tetrahydro-2H-pyran-2-yl)oxy)propoxy)benzoate (N-XXVIII) (8.0 g, 20.45 mmol) in EtOH (124 mL) and stirring at RT was continued for 16 h. The reaction mixture was quenched by the addition of a sat solution of NaHCO₃ and extracted with EtOAc. The combined organic layers were washed with a sat solution of NaHCO₃ (200 mL), dried over anhydrous Na₂SO₄ and concentrated. The crude product was purified by flash chromatography (silica, cyclohexane/EtOAc; gradient: 5 to 40% EtOAc) to afford the title compound (5.50 g). ¹H NMR (600 MHz, DMSO-d₆) δ 7.69 (d, J=8.7 Hz, 1H), 7.31 (t, J=8.4 Hz, 1H), 4.99 (d, J=3.8 Hz, 1H), 4.07-3.93 (m, 3H), 3.83 (s, 3H), 1.15 (d, J=5-0 Hz, 3H).

Synthesis of methyl 2-bromo-3-fluoro-4-(2-hydroxyethoxy)benzoate (N-XXXIV)

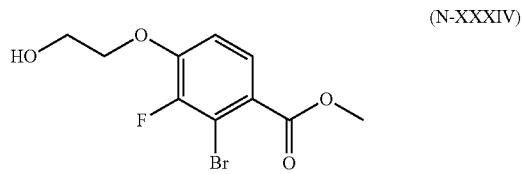 [SMILES: COC(=O)c1ccc(OCCO)c(F)c1Br]

A solution of methyl 2-bromo-3-fluoro-4-(2-((tetrahydro-2H-pyran-2-yl)oxy)ethoxy)benzoate (N-XXVII) (1.00 g, 2.65 mmol) in HCl (6.63 mL, 26.5 mmol, 4 M in dioxane) was stirred at RT for 1 h. The reaction mixture was quenched by the addition of a sat solution of NaHCO₃ (100 mL) and extracted twice with EtOAc. The combined organic layers were washed with a sat solution of NaHCO₃ (100 mL), dried over anhydrous Na₂SO₄ and concentrated. The crude product was purified by flash chromatography (silica, cyclohexane/EtOAc; gradient: 0 to 84% EtOAc) to afford the title compound (694 mg) as a colorless oil. $^1$H NMR (400 MHz, DMSO-$d_6$) δ 7.69 (d, J=8.9 Hz, 1H), 7.32 (t, J=8.5 Hz, 1H), 4.97 (t, J=5.4 Hz, 1H), 4.18 (t, J=4.9 Hz, 2H), 3.84 (s, 3H), 3.75 (q, J=5.1 Hz, 2H).

Synthesis of methyl 4-chloro-5-fluoro-6-(2-hydroxyethoxy)nicotinate (N-XXXV)

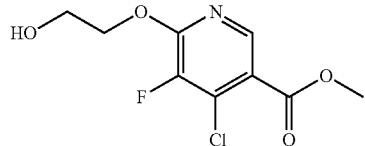
(N-XXXV)

Under Ar pyridinium p-toluenesulfonate (11.52 g, 45.8 mmol) was added to a solution of methyl 4-chloro-5-fluoro-6-(2-((tetrahydro-2H-pyran-2-yl)oxy)ethoxy)nicotinate (N-XXXI) (7.65 g, 22.9 mmol) in EtOH (150 mL) and stirring at RT was continued for 16 h at RT. The reaction mixture was quenched by the addition of a sat solution of NaHCO$_3$ (100 mL) and extracted twice with EtOAc. The combined organic layers were washed with a sat solution of NaHCO$_3$ (200 mL), dried over anhydrous Na$_2$SO$_4$ and concentrated. The crude product was purified by flash chromatography (silica, cyclohexane/EtOAc; gradient: 0 to 76% EtOAc) to afford the title compound (4.91 g) as a colorless powder. $^1$H NMR (400 MHz, DMSO-$d_6$) δ 8.52 (d, J=1.3 Hz, 1H), 4.94 (t, J=5.5 Hz, 1H), 4.51-4.42 (m, 2H), 3.87 (s, 3H), 3.76 (q, J=5.3 Hz, 2H). UPLC-MS 1: m/z 250.3 [M−H]$^-$, $t_R$=0.77 min.

Intermediates for Reductive Amination with Primary Amines:

Synthesis of 4-(fluoromethyl)-4-hydroxycyclohexan-1-one (S-I)

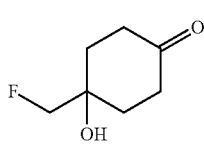
(S-I)

Step 1: 8-(Fluoromethyl)-1,4-dioxaspiro[4.5]decan-8-ol (S-I-a)

To a stirred solution of 1,7,10-trioxadispiro[2.2.4$^6$.0.2$^3$] dodecane (CAS 83365-44-0) (5.00 g, 29.40 mmol) in toluene (200 mL) was added TBAF (294 mL, 294 mmol, 1 M in THF) at RT and the reaction mixture was stirred at 80° C. for 16 h. The reaction mixture was concentrated and redissolved in EtOAc. The organic layer was washed with brine, dried over anhydrous Na$_2$SO$_4$ and concentrated to give the title compound (3.00 g), which was used without further purification in the next step. $^1$H NMR (400 MHz, DMSO-$d_6$) δ (ppm) 4.59 (s, 1H), 4.12 (d, J=48 Hz, 2H), 3.84 (s, 4H), 1.76-1.72 (m, 2H), 1.55-1.46 (m, 6H).

Step 2: 4-(Fluoromethyl)-4-hydroxycyclohexan-1-one (S-I)

At RT p-TsOH (0.815 g, 4.73 mmol) was added to a stirred solution of 8-(fluoromethyl)-1,4-dioxaspiro[4.5]decan-8-ol (S-I-a.) (3.00 g, 15.78 mmol) in acetone/H$_2$O (2:1, 18 mL) and the reaction mixture was stirred at RT for 16 h. The reaction mixture was concentrated and redissolved in EtOAc. The organic layer was washed with a sat solution of NaHCO$_3$, dried over anhydrous Na$_2$SO$_4$ and concentrated. The residue was purified by flash chromatography (silica, hexane/EtOAc 1:1) to give the title compound (1.30 g). $^1$H NMR (400 MHz, DMSO-$d_6$) δ (ppm) 5.05 (s, 1H), 4.25 (d, J=47.8 Hz, 2H), 2.61-2.49 (m, 2H), 2.12-2.07 (m, 2H), 1.83-1.80 (m, 2H), 1.79-1.72 (m, 2H).

Synthesis of trans-4-(1H-tetrazol-1-yl)cyclohexanamine (S-II)

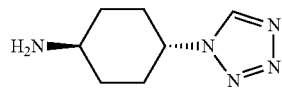
(S-II)

Step 1: Benzyl (trans-4-(1H-tetrazol-1-yl)cyclohexyl)carbamate (S-II-a)

Under a nitrogen atmosphere, a suspension of benzyl (trans-4-aminocyclohexyl)carbamate (1500 mg, 5.27 mmol), triethyl orthoformate (25 mL, 5.27 mmol), Et3N (0.77 mL, 5.53 mmol) and acetic acid (1.96 mL, 34.2 mmol) was stirred for 45 min at 100° C. Sodium azide (1.54 g, 23.7 mmol) was added dropwise at 50° C. and stirring at 100° C. was continued for 20 h. The reaction mixture was quenched by the addition of a sat solution of NaHCO$_3$ and the resulting solid was collected by filtration followed by trituration in Et$_2$O/Pentane (1:1) to afford the title compound (1050 mg). UPLC-MS 1: m/z 302.3 [M+H]$^+$, $t_R$=0.82 min.

Step 2: Trans-4-(1H-tetrazol-1-yl)cyclohexanamine (S-II)

At RT Palladium (0.1 g, 10% on activated carbon) was added to a solution of benzyl (trans-4-(1H-tetrazol-1-yl)cyclohexyl)carbamate (S-II-a) (1 g, 3.32 mmol) in MeOH (5 mL). The flask was evacuated and flushed with hydrogen. The mixture was stirred at RT for 30 min. The solids were removed by filtration and the filter cake was washed with MeOH. The filtrate was concentrated under reduced pressure to afford the desired product (540 mg). UPLC-MS 1: m/z 168.1 [M+H]$^+$, $t_R$=0.18 min.

Synthesis of trans-3-((difluoromethoxy)methyl)cyclobutanamine (S-III)

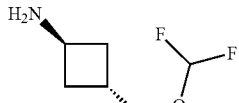
(S-III)

Step 1: Tert-butyl (trans-3-(hydroxymethyl)cyclobutyl)carbamate (S-III-a)

At RT borane-methyl sulfide complex (1.16 mL, 2.323 mmol, 2 M in THF) was added to a stirred solution of trans-3-((tert-butoxycarbonyl)amino)cyclobutanecarboxylic acid (500 mg, 2.32 mmol) in THF (10 mL) and the reaction mixture was stirred overnight under Ar. The reaction mixture was quenched with a sat solution of NH₄Cl, then extracted with TBME. The organic layers were combined and washed with a sat solution of NaHCO₃, dried over anhydrous Na₂SO₄ and concentrated to afford the title compound (460 mg) as a colorless powder. MS: m/z 202.2.

Step 2: Tert-butyl (trans-3-((difluoromethoxy)methyl)cyclobutyl)carbamate (S-III-b)

At RT 2,2-difluoro-2-(fluorosulfonyl)acetic acid (0.077 mL, 0.745 mmol) was added to a suspension of tert-butyl (trans-3-(hydroxymethyl)cyclobutyl)carbamate (S-III-a) (100 mg, 0.497 mmol) and CuI (47.3 mg, 0.248 mmol) in ACN (2.5 mL) and the reaction mixture was stirred for 4 h. The reaction mixture was quenched with a sat solution of NaHCO₃ and extracted with EtOAc. The organic layers were combined and washed with a sat solution of NaHCO₃, dried over anhydrous Na₂SO₄ and concentrated. The crude product was purified by flash chromatography (silica, hexane/EtOAc, gradient 0% to 30% EtOAc) to afford the title compound (38 mg) as a colorless powder. ¹H NMR (400 MHz, Chloroform-d) δ 6.21 (t, J=74.8 Hz, 1H), 4.71 (s, 1H), 4.31-4.10 (m, 1H), 3.87 (d, J=7.0 Hz, 2H), 2.61-2.36 (m, 1H), 2.29-2.14 (m, 2H), 2.10-1.94 (m, 2H), 1.43 (s, 9H).

Step 3: Trans-3-((difluoromethoxy)methyl)cyclobutanamine (S-III)

At RT HCl (2.5 mL, 9.85 mmol, 4M in dioxane) was added to a solution of tert-butyl (trans-3-((difluoromethoxy)methyl)cyclobutyl)carbamate (S-III-b) (165 mg, 0.66 mmol) in 1,4-dioxane (2 mL) and the reaction mixture was stirred for 1 h. The reaction mixture was quenched with a sat solution of NaHCO₃ and extracted with TBME. The organic layers were combined and washed with a sat solution of NaHCO₃, dried over anhydrous Na₂SO₄ and concentrated to afford the title compound (25 mg).

Synthesis of (1R,2R,4S)-4-amino-2-fluorocyclohexanol (S-IV)

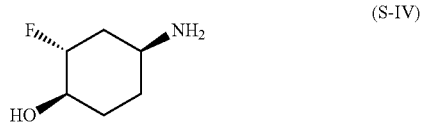
(S-IV)

Step 1: Benzyl (1S,3S,6R)-7-oxabicyclo[4.1.0]heptan-3-ylcarbamate (S-IV-a1) and benzyl (1R,3R,6S)-7-oxabicyclo[4.1.0]heptan-3-ylcarbamate (S-IV-a2) The racemate benzyl (1S*,3S*,6R*)-7-oxabicyclo[4.1.0]heptan-3-ylcarbamate (13.84 g) (Tetrahedron 2005, 61, 1207) was subjected to chiral separation (ChiralpakAY, 50×250 mm I.D., 10 μm. hexane/IPA 80:20, 35° C., flow rate: 30 mL/min) to afford the two enantiomers benzyl (1S,3S,6R)-7-oxabicyclo[4.1.0]heptan-3-ylcarbamate (S-IV-a1) and benzyl (1R,3R,6S)-7-oxabicyclo[4.1.0]heptan-3-ylcarbamate (S-IV-a2) with an enantiomeric excess of >99%, respectively.

Benzyl (1S,3S,6R)-7-oxabicyclo[4.1.0]heptan-3-ylcarbamate (S-IV-a1) (6.03 g): Chiral SFC: (Chiralpak AY-H 150×4.6 mm I.D., 5 μm, Hexane/IPA 7:3, flow rate: 1 mL/min) $t_R$=5.88 min; UPLC-MS 1: m/z 248.1[M+H]⁺, $t_R$=0.90 min.

Benzyl (1R,3R,6S)-7-oxabicyclo[4.1.0]heptan-3-ylcarbamate (S-IV-a2) (6.20 g): Chiral SFC: (Chiralpak AY-H 150×4.6 mm I.D., 5 μm, Hexane/IPA 7:3, flow rate: 1 mL/min) $t_R$=9.08 min; UPLC-MS 1: m/z 248.1[M+H]⁺, $t_R$=0.90 min.

Step 2: Benzyl ((1S,3R,4R)-3-fluoro-4-hydroxycyclohexyl)carbamate (S-IV-b)

At RT triethylamine trihydrofluoride (1.65 mL, 10.1 mmol) was added to benzyl (1S,3S,6R)-7-oxabicyclo[4.1.0]heptan-3-ylcarbamate (S-IV-a1) (500 mg, 2.0 mmol) and the reaction mixture was stirred at 100° C. for 2 h. The reaction mixture was quenched with a sat solution of NaHCO₃, then extracted with DCM. The organic layers were combined and washed with a sat solution of NaHCO₃, dried over anhydrous Na₂SO₄ and concentrated. The crude product was purified by SFC to afford the title compound (364 mg) as a colorless oil. UPLC-MS 1: m/z 268.3 [M+H]⁺, $t_R$=0.82 min.

Step 3: (1R,2R,4S)-4-amino-2-fluorocyclohexanol (S-IV)

At RT Palladium (71.7 mg, 0.07 mmol, 10% on activated carbon) was added to a solution of benzyl ((1S,3R,4R)-3-fluoro-4-hydroxycyclohexyl)carbamate (S-IV-b1) (360 mg, 1.35 mmol) in EtOH (19 mL). The flask was evacuated and flushed with hydrogen. The mixture was stirred at RT for 20 h. The solids were filtered off and the filter cake was washed with EtOH. The filtrate was concentrated under vacuum to afford the desired product (190 mg). ¹H NMR (600 MHz, DMSO-d₆) δ 4.96 (d, J=3.3 Hz, 1H), 4.68-4.48 (m, 1H), 3.53 (br s, 1H), 2.98 (br s, 1H), 1.93-1.52 (m, 6H), 1.48-1.35 (m, 2H).

Synthesis of (1S,2S,4R)-4-amino-2-fluorocyclohexanol (S-V)

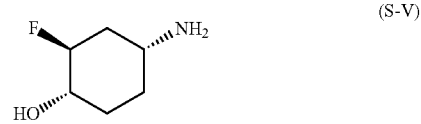
(S-V)

The title compound was prepared in a manner analogous to that of (1R,2R,4S)-4-amino-2-fluorocyclohexanol (S-IV) from benzyl (1R,3R,6S)-7-oxabicyclo[4.1.0]heptan-3-ylcarbamate (S-IV-a2), ¹H NMR (600 MHz, DMSO-d₆) δ 5.09-4.90 (m, 1H), 4.67-4.49 (m, 1H), 3.70-3.48 (m, 1H), 3.35 (s, 1H), 2.98 (br s, 1H), 1.77-1.52 (m, 5H), 1.48-1.30 (m, 2H).

Intermediates for Suzuki Cross-Coupling Reactions:
Synthesis of tert-butyl (S)-((5-chloro-2-phenyl-4-(4,4,5,5-tetramethyl-1,3,2-dioxaborolan-2-yl)-2,3-dihydrobenzofuran-2-yl)methyl)carbamate (C-I)
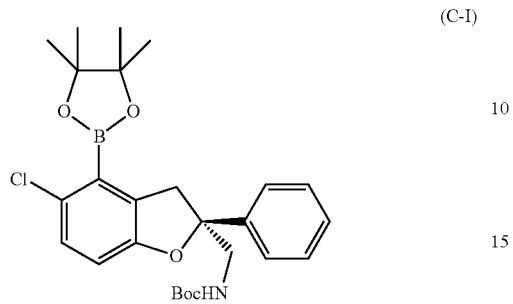
Reaction Scheme C-I
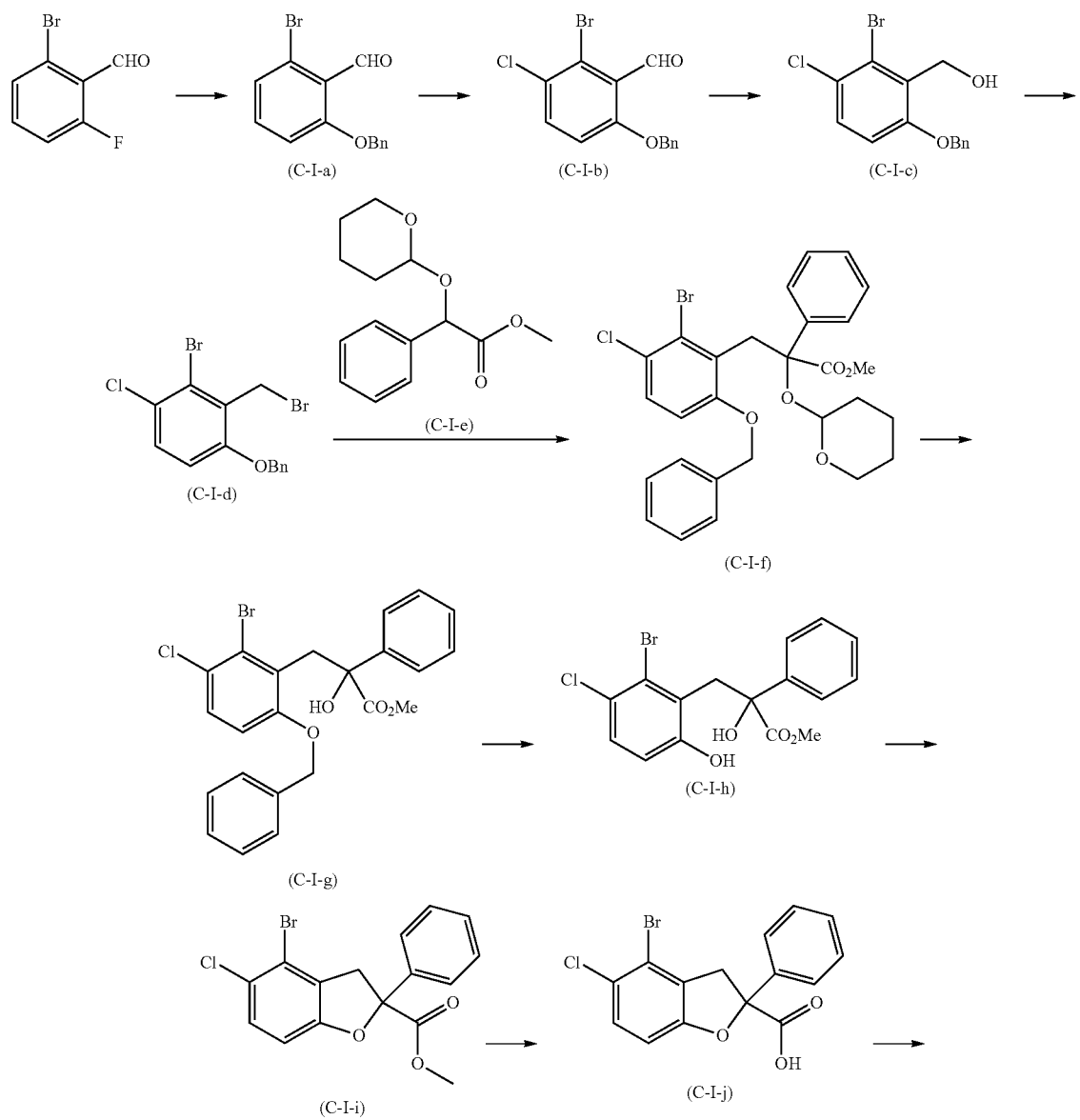

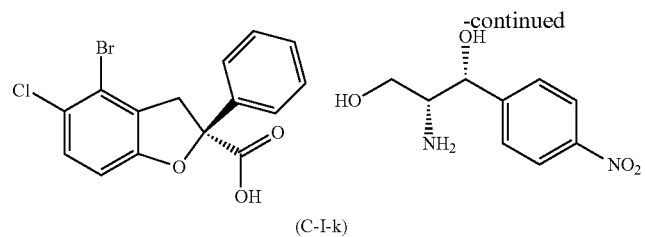
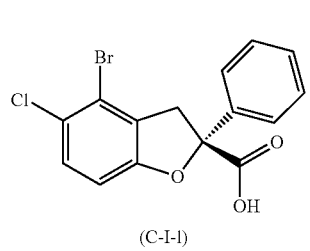
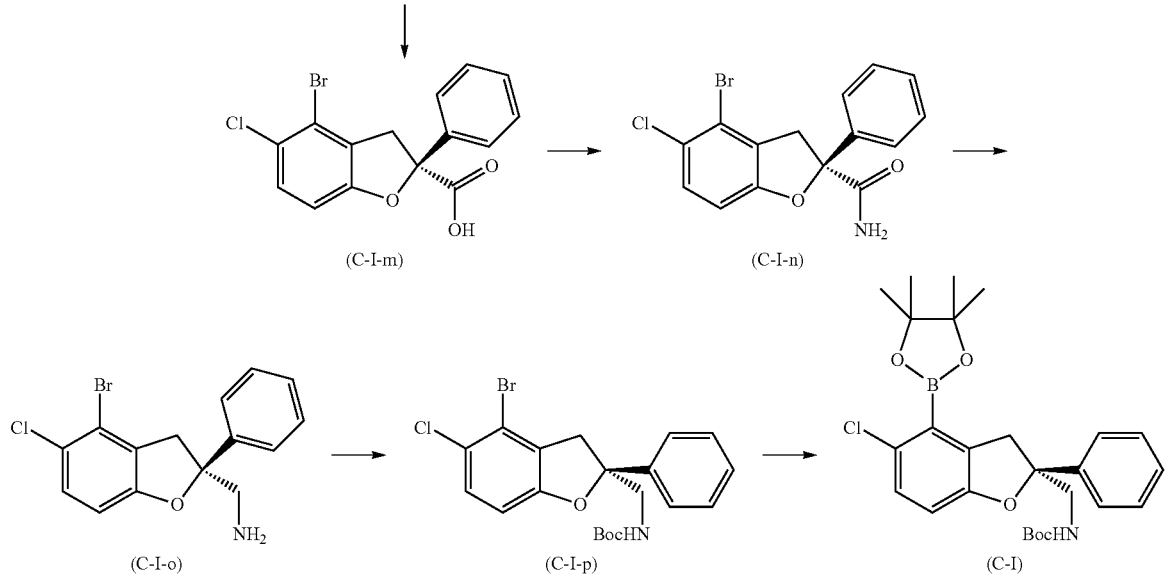

Step 1: 2-(Benzyloxy)-6-bromobenzaldehyde (C-I-a)

In a 20-L 4-necked round-bottom flask, purged and maintained with an inert atmosphere of nitrogen, was placed a solution of 2-bromo-6-fluorobenzaldehyde (CAS 360575-28-6) (1500 g, 7.39 mol) in DMF (11.25 L), benzyl alcohol (1042 g, 9.64 mol), and $Cs_2CO_3$ (4840 g, 14.81 mol).

The resulting solution was stirred overnight at 80° C. The reaction mixture was cooled to RT with a water bath and diluted with water. The solution was extracted with EtOAc and the organic layers were combined. The resulting mixture was washed with brine, dried over anhydrous $Na_2SO_4$ and concentrated under vacuum. The residue was purified by flash chromatography (silica, PE/EtOAc 40:1) to afford the title compound (2150 g) as a colorless powder. $^1$H-NMR (400 MHz, DMSO-$d_6$) δ (ppm) 10.31 (s, 1H), 7.50-7.44 (m, 3H), 7.43-7.35 (m, 2H), 7.35-7.28, (m, 3H), 5.25 (s, 2H). UPLC-MS 1: m/z 291.2/293.1 [M+H]+

Step 2: 6-(Benzyloxy)-2-bromo-3-chlorobenzaldehyde (C-I-b)

In a 20-L 4-necked round-bottom flask, purged and maintained with an inert atmosphere of nitrogen, was placed a solution of 2-(benzyloxy)-6-bromobenzaldehyde (C-I-a) (1004 g, 3.45 mol) in ACN (10 L), p-TsOH (658 g, 3.46 mol), and N-chlorosuccinimide (598 g, 4.5 mol). The resulting solution was stirred overnight at RT. The reaction mixture was then quenched by the addition of water/ice. The solids were collected by filtration. The filter cake was washed with water and PE to give the desired product (1786 g) as a light yellow oil. $^1$H-NMR (400 MHz, DMSO-$d_6$) δ (ppm) 10.24 (s, 1H), 7.80 (d, J=8.8 Hz, 1H), 7.54-7.23 (m, 6H), 5.26 (s, 2H). UPLC-MS 1: m/z 325.0 [M+H]+

Step 3: (6-(benzyloxy)-2-bromo-3-chlorophenyl) methanol (C-I-c)

In a 20-L 4-necked round-bottom flask, purged and maintained with an inert atmosphere of nitrogen, was placed a solution of 6-(benzyloxy)-2-bromo-3-chlorobenzaldehyde (C-I-b) (893 g, 2.74 mol) in THF (8 L). $NaBH_4$ (105 g, 2.78 mol) was added in several batches at 0° C. The resulting solution was stirred at RT for 3 h. This reaction was repeated once. The reaction mixture was then quenched by the addition of acetone. The solution was diluted with water. The resulting solution was extracted with EtOAc and the organic layers were combined. The mixture was washed with brine, dried over anhydrous $Na_2SO_4$ and concentrated under reduced pressure. The residue was purified by flash chromatography (silica, PE/EtOAc 20:1) to afford the title compound (1496 g) as a colorless powder. $^1$H-NMR (400 MHz, DMSO-$d_6$) δ (ppm): 7.50 (dd, 1H), 7.48-7.43 (m, 2H), 7.42-7.35 (m, 2H), 7.35-7.27 (m, 1H), 7.12 (d, 1H), 5.16 (s, 2H), 4.94-4.86 (m, 1H), 4.67 (d, 2H). UPLC-MS 1: m/z 324.7 [M−H]−

Step 4: 1-(Benzyloxy)-3-bromo-2-(bromomethyl)-4-chlorobenzene (C-I-d)

In a 20-L 4-necked round-bottom flask, purged and maintained with an inert atmosphere of nitrogen, was placed a solution of [6-(benzyloxy)-2-bromo-3-chlorophenyl]methanol (C-I-c) (1469 g, 4.48 mol) in DCM (12 L) and tetrabromomethane (2217 g, 6.69 mol). Then, a solution of triphenylphosphine (1770 g, 6.75 mol) in DCM (3 L) was added dropwise with stirring at 0° C. The resulting solution was stirred overnight at RT. The reaction mixture was diluted with EtOAc. The solids were removed by filtration and the filter cake was washed with EtOAc. The filtrate was concentrated under reduced pressure and the crude product was purified by flash chromatography (silica, PE/EtOAc 10:1) to give the desired product (1201 g) as a colorless powder. $^1$H-NMR (400 MHz, DMSO-$d_6$) δ (ppm) 7.59 (d, 1H), 7.51-7.46 (m, 2H), 7.43-7.29 (m, 3H), 7.19 (d, 1H), 5.25 (s, 2H), 4.77 (s, 2H).

Step 5: Methyl 3-(6-(benzyloxy)-2-bromo-3-chlorophenyl)-2-phenyl-2-((tetrahydro-2H-pyran-2-yl)oxy)propanoate (C-I-f)

In a 20-L 4-necked round-bottom flask, purged and maintained with an inert atmosphere of nitrogen, was placed a solution of (C-I-e) (CAS 33973-12-5, obtained from methyl mandelate and dihydropyran according to Du, Wu; Hagmann, William K.; He, Shuwen; Lai, Zhong; Shah, Shrenik K.; Truong, Quang T. PCT Int. Appl. (2010), WO 2010083136 A1) (774 g, 3.09 mol) in THF (9 L). At −78° C., LDA (1934 mL, 2 M in THF) was added dropwise and the resulting reaction mixture was stirred at −70° C. for 1.5 h. At −78° C., a solution of 1-(benzyloxy)-3-bromo-2-(bromomethyl)-4-chlorobenzene (C-I-d) (1201 g, 3.08 mol) in THF (3 L) was added dropwise. The reaction mixture was allowed to warm to RT and stirring was continued for another 3 h. The reaction was then quenched by the addition of an aqueous NH$_4$Cl solution at −10° C. The resulting solution was extracted with EtOAc, the combined organic layers were washed with brine, dried over anhydrous Na$_2$SO$_4$ and concentrated under reduced pressure to afford the title compound (1870 g) as a brown oil. UPLC-MS 1: m/z 557.2/559.2 [M−H]$^-$.

Step 6: Methyl 3-(6-(benzyloxy)-2-bromo-3-chlorophenyl)-2-hydroxy-2-phenyl-propanoate (C-I-g)

In a 20-L 4-necked round-bottom flask, purged and maintained with an inert atmosphere of nitrogen, was placed a solution of methyl 3-(6-(benzyloxy)-2-bromo-3-chlorophenyl)-2-phenyl-2-((tetrahydro-2H-pyran-2-yl)oxy)propanoate (C-I-f) (935 g, 1.67 mol) in ACN (9 L). This was followed by the dropwise addition of hydrogen chloride (6 L, 2 N) at RT. The resulting solution was stirred at RT for 3 h. The solids were collected by filtration and the filter cake was washed with water and PE/EtOAc (8:1) to give the title compound (1100 g) as a light yellow powder. $^1$H-NMR (400 MHz, DMSO-$d_6$) δ (ppm) 7.52-7.18 (m, 11H), 6.95 (d, 1H), 5.60 (s, 1H), 5.07-4.84 (m, 2H), 3.94 (d, 1H), 3.65 (d, 1H), 3.46 (s, 3H). UPLC-MS 1: m/z 475.1 [M+H]$^+$.

Step 7: Methyl 3-(2-bromo-3-chloro-6-hydroxyphenyl)-2-hydroxy-2-phenylpropanoate (C-I-h)

In a 3 L 4-necked round-bottom flask, purged and maintained with an inert atmosphere of nitrogen, was placed a solution of methyl 3-[6-(benzyloxy)-2-bromo-3-chlorophenyl]-2-hydroxy-2-phenylpropanoate (C-I-g) (100 g, 210.2 mmol) in MeOH/THF (5:1) (2 L) and Raney-Ni (30 g). The flask was evacuated and flushed three times with nitrogen, followed by flushing with hydrogen.

The mixture was stirred at RT for 5 h. This reaction was repeated ten times. The solids were filtered off and the filter cake was washed with MeOH. The filtrate was concentrated under vacuum to afford the desired product (930 g) as a yellow oil. $^1$H-NMR (400 MHz, DMSO-$d_6$) δ (ppm) 7.56-7.45 (m, 2H), 7.37-7.19 (m, 4H), 6.77 (d, 1H), 3.84 (d, 1H), 3.67-3.48 (m, 4H). UPLC-MS 1: m/z 383.1/385.1 [M−H]$^-$.

Step 8: Methyl 4-bromo-5-chloro-2-phenyl-2,3-dihydrobenzofuran-2-carboxylate (C-I-i)

In a 20-L 4-necked round-bottom flask, purged and maintained with an inert atmosphere of nitrogen, was placed a solution of methyl 3-(2-bromo-3-chloro-6-hydroxyphenyl)-2-hydroxy-2-phenylpropanoate (C-I-h) (930 g, 2.41 mol) in THF (9 L) and triphenylphosphine (761 g, 2.90 mol). Then, DIAD (587 g, 2.91 mol) was added dropwise at 0° C. Stirring of the reaction solution was continued for 3 h at RT. The solution was diluted with EtOAc and washed with brine. The organic phase was dried over anhydrous Na$_2$SO$_4$ and concentrated. The resulting crude product was purified by flash chromatography (silica, PE/EtOAc, gradient 0% to 5% EtOAc) to give the title compound (582 g) as a colorless powder. $^1$H-NMR (300 MHz, CDCl$_3$) δ (ppm) 7.55-7.58 (m, 2H), 7.40-7.43 (m, 3H), 7.25-7.37 (m, 1H), 6.88-6.91 (m, 1H), 4.18-4.23 (m, 1H), 3.77 (s, 3H), 3.53-3.59 (m, 1H). UPLC-MS 1: m/z 365.1/367.0 [M−H]$^-$.

Step 9: 4-Bromo-5-chloro-2-phenyl-2,3-dihydrobenzofuran-2-carboxylic acid (C-I-j)

At RT NaOH (3.5 L, 2 N) was added to a solution of methyl 4-bromo-5-chloro-2-phenyl-2,3-dihydrobenzofuran-2-carboxylate (C-I-i) (520 g, 1.414 mol) in MeOH/THF (1:1, 6 L). The clear solution was stirred at RT for 15 min. The reaction mixture was concentrated under reduced pressure and the resulting residue was partioned between DCM (4 L) and water (2 L). The aqueous phase was adjusted to pH 2 with 2 N HCl and extracted with EtOAc. The combined organic extracts were dried over anhydrous Na$_2$SO$_4$, filtered and concentrated to afford the title compound (474 g) as a colorless powder. $^1$H-NMR (400 MHz, DMSO-$d_6$) δ (ppm) 7.61-7.49 (m, 2H), 7.49-7.31 (m, 4H), 7.03 (d, 1H), 4.05 (d, 1H), 3.55 (d, 1H). UPLC-MS 1: m/z 351.0/353.0 [M−H]$^-$, $t_R$=1.09 min.

Step 10: (1R,2R)-2-Amino-1-(4-nitrophenyl)propane-1,3-diol (S)-4-bromo-5-chloro-2-phenyl-2,3-dihydrobenzofuran-2-carboxylate (C-I-k) and (R)-4-bromo-5-chloro-2-phenyl-2,3-dihydrobenzofuran carboxylic acid (C-I-l)

4-Bromo-5-chloro-2-phenyl-2,3-dihydrobenzofuran-2-carboxylic acid (C-I-j) (470 g, 1.33 mol) and (1R,2R)-(−)-2-amino-1-(4-nitrophenyl)-1,3-propanediol (Aldrich Nr: A7,070-4) (282 g, 1.33 mol) were suspended in MeOH (5.310 L) and heated to 80° C. After 30 min the clear solution was allowed to slowly cool down to RT. The resulting white suspension was stirred at RT overnight. The solids were collected by filtration, washed with motherliquor (500 mL) and dried in vacuo at 30° C. to afford the salt (1R,2R)-2-amino-1-(4-nitrophenyl)propane-1,3-diol (S)-4-bromo-5-chloro-2-phenyl-2,3-dihydrobenzofuran-2-carboxylate (C-I-k) (340 g) with an enantiomeric excess of >99%. UPLC-MS 1: m/z 351.0/353.0 [M−H]$^-$, $t_R$=1.10 min and 213.1 [M+H]$^+$, $t_R$=0.33 min. Chiral HPLC: (Chiralpak AD-H, heptane/EtOH/MeOH 90/6/4+0.05% TFA, flow rate 1 mL/min) $t_R$=13.00 min. The opposite enantiomer (R)-4-bromo-5-chloro-2-phenyl-2,3-dihydrobenzofuran-2-carboxylic acid (C-I-l) remained in the mother liquor. Chiral HPLC: (Chiralpak AD-H, heptane/EtOH/MeOH 90/6/4+ 0.05% TFA, flow rate: 1 mL/min) $t_R$=10.03 min.

Step 11: (S)-4-Bromo-5-chloro-2-phenyl-2,3-dihydrobenzofuran-2-carboxylic acid (C-I-m)

(1R,2R)-2-Amino-1-(4-nitrophenyl)propane-1,3-diol (S)-4-bromo-5-chloro-2-phenyl-2,3-dihydrobenzofuran-2-carboxylate (C-I-k) (340 g, 601 mmol) was suspended in EtOAc (4.5 L) and then stirred at RT. 2 N HCl (750 mL) and water were added. The layers were separated. The organic layer was washed with brine, dried over anhydrous $Na_2SO_4$, filtered and concentrated to give the title compound (202 g). UPLC-MS 1: m/z 351.1/353.1 [M–H]$^-$, $t_R$=1.10 min. The absolute configuration (S) was determined by an x-ray crystal structure.

Step 12: (S)-4-Bromo-5-chloro-2-phenyl-2,3-dihydrobenzofuran-2-carboxamide (C-I-n)

A solution of (S)-4-bromo-5-chloro-2-phenyl-2,3-dihydrobenzofuran-2-carboxylic acid (C-I-m) (180 g, 499 mmol) in DCM (2 L) was cooled to 0° C. The yellow clear solution was treated with DMF (1 mL). Oxalylchloride (56.2 mL, 655 mmol) was added via dropping funnel over a period of 10 min. The resulting mixture was allowed to warm to RT and stirred for another 4.5 h at RT. At 0° C. this solution was then added to a 25% aqueous ammonia solution via dropping funnel over 45 min. The resulting milky reaction mixture was allowed to warm to RT with stirring. The organic phase was separated and the aqueous layer was extracted with DCM. The combined organic layers were washed with water and dried over anhydrous $Na_2SO_4$, filtered and concentrated to give the title compound (168 g). $^1$H-NMR (400 MHz, DMSO-$d_6$) δ (ppm) 7.81 (s, 1H), 7.63-7.48 (m, 3H), 7.48-7.28 (m, 4H), 6.99 (d, 1H), 4.04 (d, 1H), 3.42 (d, 1H). UPLC-MS 1: m/z 352.0/353.9 [M+H]$^+$, $t_R$=1.15 min.

Step 13: (S)-(4-bromo-5-chloro-2-phenyl-2,3-dihydrobenzofuran-2-yl)methanamine (C-I-o)

(S)-4-bromo-5-chloro-2-phenyl-2,3-dihydrobenzofuran-2-carboxamide (C-I-n) (163 g, 462 mmol) was dissolved in THF (2.6 L) at RT. Borane dimethyl sulfide complex (925 mL, 1849 mmol, 2 M in THF) was added via dropping funnel at RT over 45 min. The reaction mixture was stirred for another 60 min and then heated to gentle reflux for 3 h. The reaction mixture was allowed to cool to RT and stirred overnight. MeOH was added dropwise with cooling over 60 min and stirring at RT was continued for another 45 min. Then, 1 N HCl was added dropwise followed by stirring at RT for another 3.5 h. Finally, 1 N NaOH was added carefully, followed by a sat $NaHCO_3$ solution. The reaction mixture was diluted with DCM and the layers were separated. The aqueous layer was extracted with DCM. The combined organic layers were washed with water and dried over anhydrous $Na_2SO_4$, filtered and concentrated to give the title compound (154 g). $^1$H-NMR (400 MHz, DMSO-$d_6$) δ (ppm) 7.52-7.19 (m, 6H), 6.92 (d, 1H), 3.80 (d, 1H), 3.16 (d, 1H), 2.96 (s, 2H), 1.65 (s, 2H). UPLC-MS 1: m/z 338.0/340.0 [M+H]$^+$, $t_R$=0.83 min.

Step 14: (S)-tert-butyl ((4-bromo-5-chloro-2-phenyl-2,3-dihydrobenzofuran-2-yl)methyl)carbamate (C-I-p)

(S)-(4-Bromo-5-chloro-2-phenyl-2,3-dihydrobenzofuran-2-yl)methanamine (C-I-o) (133 g, 255 mmol) was dissolved in DCM (1.2 L). The solution was cooled to 0° C. and a solution of $Boc_2O$ (58.5 g, 268 mmol) in DCM (200 mL) was added via dropping funnel over 25 min. The reaction mixture was stirred at RT for another 3 h before it was concentrated to ca. 300 mL and diluted with EtOAc. The organic layer was extracted with water and brine, dried over anhydrous $Na_2SO_4$, filtered and concentrated. The crude product was purified by flash chromatography (silica, cyclohexane/EtOAc 9:1) to afford the title compound (113 g) as a colorless solid. $^1$H-NMR (400 MHz, DMSO-$d_6$) δ (ppm) 7.49-7.26 (m, 6H), 7.12 (t, 1H), 6.90 (d, 1H), 3.73 (d, 1H), 3.58-3.31 (m, 2H), 3.23 (d, 1H), 1.27 (s, 9H). UPLC-MS 1: m/z 436.0/438.2 [M–H]$^-$, $t_R$=1.45 min.

Step 15: (S)-tert-butyl ((5-chloro-2-phenyl-4-(4,4,5,5-tetramethyl-1,3,2-dioxaborolan-2-yl)-2,3-dihydrobenzofuran-2-yl)methyl)carbamate (C-I)

(S)-tert-Butyl ((4-bromo-5-chloro-2-phenyl-2,3-dihydrobenzofuran-2-yl)methyl)carbamate (C-I-p) (29 g, 66 mmol), bis(pinacolato)diboron (25 g, 99 mmol) and KOAc (19.5 g, 198 mmol) were dissolved in toluene (116 mL) under Ar. The reaction mixture was heated at 80° C. before $PdCl_2(dppf)*CH_2Cl_2$ (5.4 g, 6.6 mmol) was added and heating at 110° C. was continued overnight.

The reaction mixture was cooled to RT, filtered over Hyflo and concentrated. The crude product was purified flash chromatography (silica, cyclohexane/EtOAc, gradient 0% to 20% EtOAc) to give the title compound (25.1 g). $^1$H-NMR (400 MHz, DMSO-$d_6$) δ (ppm) 7.42-7.31 (m, 4H), 7.29-7.23 (m, 1H), 7.11 (d, J=8.6 Hz, 1H), 7.08-7.01 (m, 1H), 6.90 (d, J=8.2 Hz, 1H), 3.66 (d, J=17.2 Hz, 1H), 3.56-3.47 (m, 1H), 3.38-3.30 (m, 1H), 3.61-3.30 (m, 2H), 3.18 (d, J=16.4 Hz, 1H), 1.30-1.24 (m, 21H). UPLC-MS 1: m/z 486.2 [M+H]$^+$, $t_R$=1.49 min.

Synthesis of tert-butyl ((5-chloro-2-phenyl-4-(4,4,5,5-tetramethyl-1,3,2-dioxaborolan-2-yl)-2,3-dihydrobenzofuran-2-yl)methyl)carbamate (C-II)

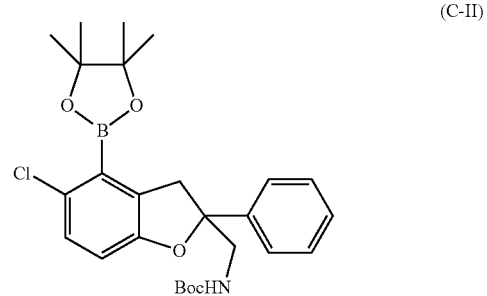 [SMILES: CC(C)(C)OC(=O)NCC1(c2ccccc2)Cc2c(ccc(Cl)c2B2OC(C)(C)C(C)(C)O2)O1]

(C-II)

The racemic title compound was prepared in a manner analogous to that of tert-butyl (S)-((5-chloro-2-phenyl-4-(4,4,5,5-tetramethyl-1,3,2-dioxaborolan-2-yl)-2,3-dihydrobenzofuran-2-yl)methyl)carbamate (C-I) without resolution of the enantiomers. $^1$H-NMR (600 MHz, DMSO-$d_6$) δ (ppm) 7.44-7.37 (m, 4H), 7.33-7.29 (m, 1H), 7.17-7.12 (m, 2H), 6.94 (d, J=8.4 Hz, 1H), 3.70 (d, J=16.5 Hz, 1H), 3.58-3.53 (m, 1H), 3.39-3.35 (m, 1H), 3.22 (d, J=16.9 Hz, 1H), 1.34-1.28 (m, 21H). UPLC-MS 1: m/z 486.2 [M+H]$^+$, $t_R$=1.52 min.

Synthesis of tert-butyl ((5-chloro-4-(4,4,5,5-tetramethyl-1,3,2-dioxaborolan-2-yl)-2-(thiazol-4-yl)-2,3-dihydrobenzofuran-2-yl)methyl)carbamate (C-III)
(C-III)
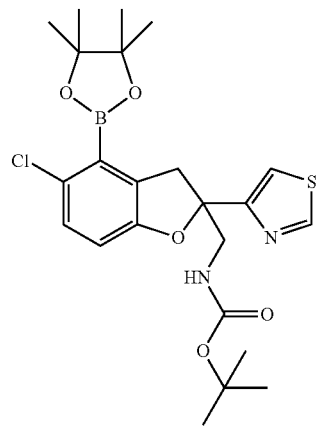
Reaction Scheme C-III
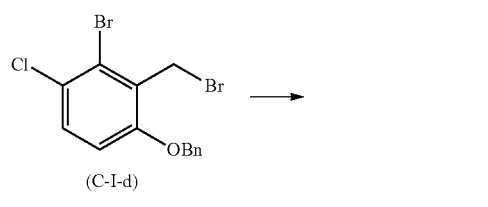
(C-I-d)
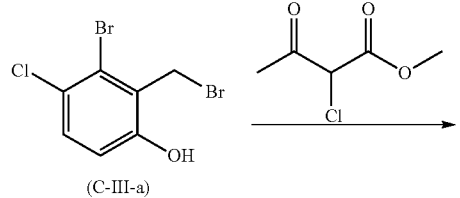
(C-III-a)
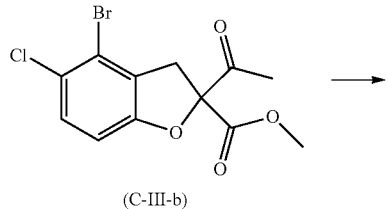
(C-III-b)
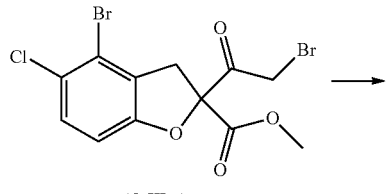
(C-III-c)
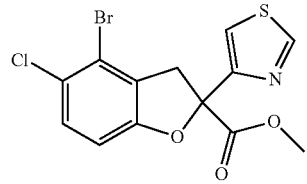
(C-III-d)
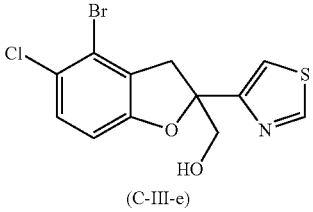
(C-III-e)
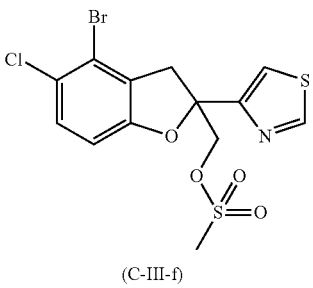
(C-III-f)
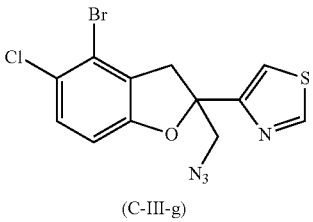
(C-III-g)
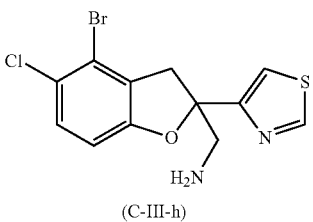
(C-III-h)
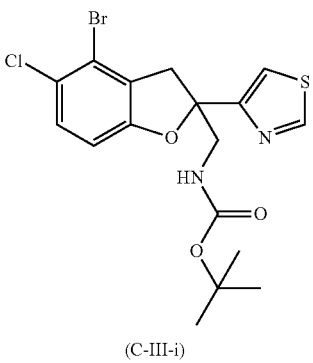
(C-III-i)

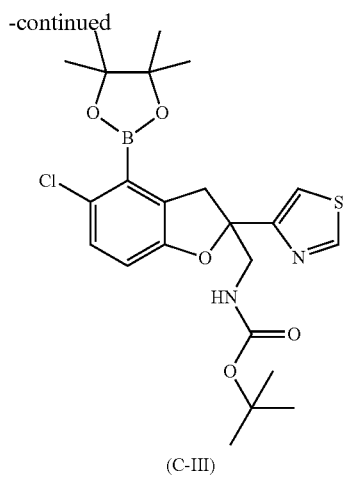

(C-III)

Step 1: 3-Bromo-2-(bromomethyl)-4-chlorophenol (C-III-a)

At −78° C. BBr$_3$ (56.3 mL, 56.3 mmol) was added to a stirred solution of 1-(benzyloxy)-3-bromo-2-(bromomethyl)-4-chlorobenzene (C-I-d) (20 g, 51.2 mmol) in DCM (200 mL) under Ar. The reaction mixture was stirred for 2 h at −78° C. The reaction mixture was quenched with MeOH (20 mL) and concentrated. The crude product was purified by flash chromatography (silica, heptane/EtOAc, gradient: 0% to 30% EtOAc) to afford the title compound (14.64 g) as a brown powder. $^1$H NMR (400 MHz, CDCl$_3$) δ 7.30 (t, J=8.6 Hz, 1H), 6.75 (d, J=8.6 Hz, 1H), 5.45 (s, 1H), 4.77 (s, 2H).

Step 2: Methyl 2-acetyl-4-bromo-5-chloro-2,3-dihydrobenzofuran-2-carboxylate (C-III-b)

At RT 2-chloroacetoacetic acid methyl ester (4.06 mL, 33.3 mmol) and TEA (9.74 mL, 70 mmol) were added to a stirred solution of 3-bromo-2-(bromomethyl)-4-chlorophenol (C-III-a) (10 g, 33.3 mmol) in ACN (100 mL) under Ar. The reaction mixture was stirred at RT for 1 h. The reaction mixture was diluted with a sat solution of NaHCO$_3$ and extracted with EtOAc. The combined organic extracts were washed with brine, dried over anhydrous Na$_2$SO$_4$ and concentrated. The reside was purified by flash chromatography (silica; cyclohexane/EtOAc; gradient 0% to 30% EtOAc) to afford the title compound (8.26 g) as a colorless powder. UPLC-MS 1: $t_R$=1.17 min.

Step 3: Methyl 4-bromo-2-(2-bromoacetyl)-5-chloro-2,3-dihydrobenzofuran-2-carboxylate (C-III-c)

At RT Br$_2$ (1.403 mL, 27.2 mmol) was added to a solution of methyl 2-acetyl-4-bromo-5-chloro-2,3-dihydrobenzofuran-2-carboxylate (C-III-b) (8.26 g, 24.76 mmol) in CHCl$_3$ (75 mL) under Ar. The reaction mixture was stirred for 5 h before it was diluted with a sat solution of NaHCO$_3$ and extracted with EtOAc. The combined organic extracts were washed with brine, dried over anhydrous Na$_2$SO$_4$ and concentrated. The reside was purified by flash chromatography (silica; cyclohexane/EtOAc; gradient 0% to 20% EtOAc) to afford the title compound (9.26 g) as a colorless powder. UPLC-MS 1: $t_R$=1.21.

Step 4: Methyl 4-bromo-5-chloro-2-(thiazol-4-yl)-2,3-dihydrobenzofuran-2-carboxylate (C-III-d)

Under Ar phosphorus pentasulfide (1.846 g, 8.31 mmol) was added to a solution of methyl 4-bromo-2-(2-bromoacetyl)-5-chloro-2,3-dihydrobenzofuran-2-carboxylate (C-III-c) (9.26 g, 22.45 mmol) and formamide (1.790 mL, 44.9 mmol) in dioxane (50 mL). The reaction mixture was stirred for 60 min at 100° C. The reaction mixture was diluted with a sat solution of NaHCO$_3$ and extracted with EtOAc. The combined organic extracts were washed with brine, dried over anhydrous Na$_2$SO$_4$ and concentrated. The reside was purified by flash chromatography (silica; cyclohexane/EtOAc; gradient 0% to 80% EtOAc) to afford the title compound (6.98 g) as a yellow powder. UPLC-MS 1: m/z 375.9 [M+H]$^+$, $t_R$=1.14 min.

Step 5: (4-Bromo-5-chloro-2-(thiazol-4-yl)-2,3-dihydrobenzofuran-2-yl)methanol (C-III-e)

At 0° C. LiBH$_4$ (0.812 g, 37.3 mmol) was added portionwise to a stirred solution of methyl 4-bromo-5-chloro-2-(thiazol-4-yl)-2,3-dihydrobenzofuran-2-carboxylate (C-III-d) (6.98 g, 18.6 mmol) in a mixture of THF (70 mL) and MeOH (3.0 mL, 74.5 mmol) under Ar. The resulting suspension was stirred for 10 min at RT. The reaction mixture was diluted with a sat solution of NH$_4$Cl and extracted with EtOAc. The combined organic extracts were washed with brine, dried over anhydrous Na$_2$SO$_4$ and concentrated. The reside was purified by flash chromatography (silica; cyclohexane/EtOAc; gradient 0% to 85% EtOAc) to afford the title compound (6.08 g) as a colorless powder. UPLC-MS 1: m/z 348.0 [M+H]$^+$, $t_R$=1.01 min.

Step 6: (4-Bromo-5-chloro-2-(thiazol-4-yl)-2,3-dihydrobenzofuran-2-yl)methyl methanesulfonate (C-III-f)

At 0° C. methanesulfonic anhydride (2.412 g, 13.85 mmol) and TEA (4.83 mL, 34.6 mmol) were added portionwise to a stirred solution of (4-bromo-5-chloro-2-(thiazol-4-yl)-2,3-dihydrobenzofuran-2-yl)methanol (C-III-e) (2.40 g, 6.92 mmol) in DCM (50 mL) under Ar. The reaction mixture was stirred for 2 h at RT. The reaction mixture was diluted with brine and extracted with DCM. The combined organic extracts were washed with brine, dried over anhydrous Na$_2$SO$_4$ and concentrated. The reside was purified by flash chromatography (silica; cyclohexane/EtOAc; gradient 0% to 93% EtOAc) to afford the title compound (2.85 g). UPLC-MS 1: m/z 426.0 [M+H]$^+$, $t_R$=1.12 min.

Step 7: 4-(2-(Azidomethyl)-4-bromo-5-chloro-2,3-dihydrobenzofuran-2-yl)thiazole (C-III-g)

Under Ar sodium azide (2.181 g, 33.6 mmol) was added to a stirred solution of (4-bromo-5-chloro-2-(thiazol-4-yl)-2,3-dihydrobenzofuran-2-yl)methyl methanesulfonate (C-III-f) (2.85 g, 6.71 mmol) in DMF (50 mL). The reaction mixture was stirred for 20 h at 130° C. The reaction mixture was diluted with a sat solution of NaHCO$_3$ and extracted with EtOAc. The combined organic extracts were washed with brine, dried over anhydrous Na$_2$SO$_4$ and concentrated. The residue was purified by flash chromatography (silica; cyclohexane/EtOAc; gradient 0% to 30% EtOAc) to afford the title compound (1.90 g) as a colorless powder. UPLC-MS 1: m/z 373.1 [M+H]$^+$, $t_R$=1.28 min.

Step 8: (4-Bromo-5-chloro-2-(thiazol-4-yl)-2,3-di-hydrobenzofuran-2-yl)methanamine (C-III-h)

At 0° C. NaBH$_4$ (1.934 g, 51.1 mmol) was added portionwise to a stirred solution of 4-(2-(azidomethyl)-4-bromo-5-chloro-2,3-dihydrobenzofuran-2-yl)thiazole (C-III-g) (1.9 g, 5.11 mmol) in a mixture of THF (40 mL) and MeOH (4.1 mL, 102 mmol) under Ar. The resulting suspension was stirred for 16 h at 70° C. The reaction mixture was diluted with a sat solution of NaHCO$_3$ and extracted with EtOAc. The combined organic extracts were washed with brine, dried over anhydrous Na$_2$SO$_4$ and concentrated. The reside was purified by flash chromatography (silica; DCM/MeOH; gradient: 0% to 10% MeOH) to afford the title compound (1.30 g) as a colorless oil.
UPLC-MS 1: m/z 347.0 [M+H]$^+$, $t_R$=0.66 min.

Step 9: Tert-butyl ((4-bromo-5-chloro-2-(thiazol-4-yl)-2,3-dihydrobenzofuran-2-yl)methyl)carbamate (C-III-i)

At RT Boc-anhydride (0.961 mL, 4.14 mmol) was added to a stirred solution of (4-bromo-5-chloro-2-(thiazol-4-yl)-2,3-dihydrobenzofuran-2-yl)methanamine (C-III-h) (1.3 g, 3.76 mmol) in DCM (40 mL) and stirring at RT was continued for 2 h. The reaction mixture was diluted with brine and extracted with DCM. The combined organic extracts were washed with brine, dried over anhydrous Na$_2$SO$_4$ and concentrated. The reside was purified by flash chromatography (silica; cyclohexane/EtOAc; gradient 0% to 70% EtOAc) to afford the title compound (1.36 g) as a colorless powder. UPLC-MS 1: m/z 447.1 [M+H]$^+$, $t_R$=1.29 min.

Step 10: Tert-butyl ((5-chloro-4-(4,4,5,5-tetramethyl-1,3,2-dioxaborolan-2-yl)-2-(thiazol-4-yl)-2,3-dihydrobenzofuran-2-yl)methyl)carbamate (C-III)

A deoxygenated suspension of tert-butyl ((4-bromo-5-chloro-2-(thiazol-4-yl)-2,3-dihydrobenzofuran-2-yl)methyl)carbamate (C-III-i) (1.36 g, 3.05 mmol), bis(pinacolato)diboron (1.55 g, 6.1 mmol), KOAc (0.898 g, 9.15 mmol) and PdCl$_2$(dppf)·CH$_2$Cl$_2$ adduct (0.249 g, 0.305 mmol) in DMSO (400 mL) was stirred at 120° C. for 16 h under an Ar atmosphere. The reaction mixture was diluted with a sat solution of NaHCO$_3$ and extracted with EtOAc. The combined organic extracts were washed with brine, dried over anhydrous Na$_2$SO$_4$ and concentrated. The residue was purified by flash chromatography (silica; cyclohexane/EtOAc; gradient 0% to 70% EtOAc) to afford the racemic title compound (1.02 g) as a colorless powder. UPLC-MS 1: m/z 493.3 [M+H]$^+$, $t_R$=1.37 min.

Synthesis of tert-butyl ((5-chloro-2-(2,2-difluorobenzo[d][1,3]dioxol-4-yl)-4-(4,4,5,5-tetramethyl-1,3,2-dioxaborolan-2-yl)-2,3-dihydrobenzofuran-2-yl)methyl)carbamate (C-IV)

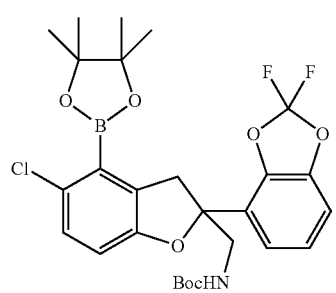

(C-IV)

The racemic title compound was prepared in a manner analogous to that of tert-butyl (S)-((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII) from 2-bromo-3-chloro-6-hydroxybenzaldehyde (C-VI-a) and 2-(2,2-difluorobenzo[d][1,3]dioxol-4-yl)acetonitrile (synthesized as follows: reduction of 2,2-difluorobenzo[d][1,3]dioxole-4-carbaldehyde into corresponding alcohol followed by formation of benzyl chloride and transformation into corresponding nitrile) without resolution of the enantiomers. UPLC-MS 1: m/z 610.4 [M+formate]$^-$, $t_R$=1.56 min.

Synthesis of tert-butyl (S)-((5-chloro-2-(2-fluorophenyl)-4-(4,4,5,5-tetramethyl-1,3,2-dioxaborolan-2-yl)-2,3-dihydrobenzofuran-2-yl)methyl)carbamate (C-V)

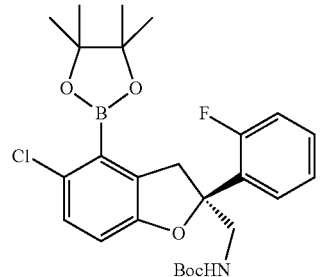

(C-V)

Reaction Scheme C-V

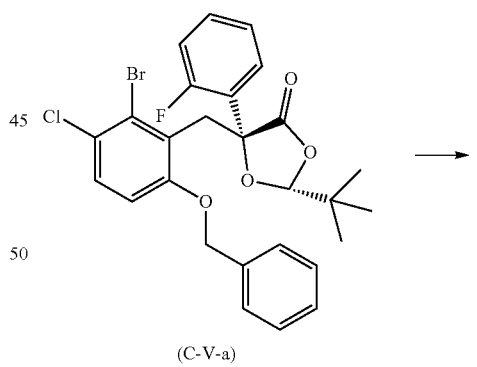

(C-V-a)

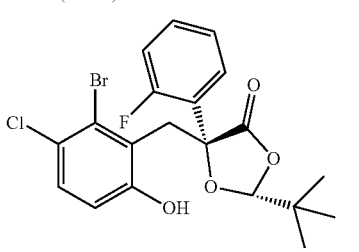

(C-V-b)

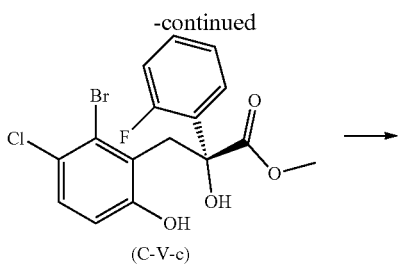

(C-V-c)

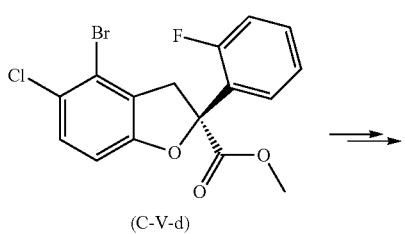

(C-V-d)

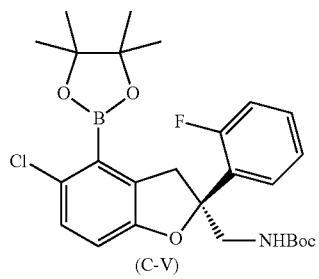

(C-V)

(2R,5R)-5-(6-(Benzyloxy)-2-bromo-3-chlorobenzyl)-2-(tert-butyl)-5-(2-fluorophenyl)-1,3-dioxolan-4-one (C-V-a) was synthesized in analogy to C-XVII-c (synthesis of intermediate C-XVII step 3) from 1-(benzyloxy)-3-bromo-2-(bromomethyl)-4-chlorobenzene (C-I-d) and (2R,5R)-2-(tert-butyl)-5-(2-fluorophenyl)-1,3-dioxolan-4-one using LDA instead of NaH as a base.

Step 1: (2R,5R)-5-(2-Bromo-3-chloro-6-hydroxybenzyl)-2-(tert-butyl)-5-(2-fluorophenyl)-1,3-dioxolan-4-one (C-V-b)

Ra-Ni (2.66 g, 31.1 mmol) was added to a solution of (2R,5R)-5-(6-(benzyloxy)-2-bromo-3-chlorobenzyl)-2-(tert-butyl)-5-(2-fluorophenyl)-1,3-dioxolan-4-one (C-V-a) (15.49 g, 28.3 mmol) in MeOH (225 mL) and THF (45 mL) and stirred under a hydrogen atmosphere for 43 h. The catalyst was filtered off and the filtrate was concentrated. The residue was purified by flash chromatography (silica, hexane/EtOAc 9:1) to afford the title compound (11.47 g). UPLC-MS 1: m/z 455.0/457.0 [M−H]⁻, $t_R$=1.37 min.

Step 2: Methyl (R)-3-(2-bromo-3-chloro-6-hydroxyphenyl)-2-(2-fluorophenyl)-2-hydroxypropanoate (C-V-c)

At 0° C. sodium methoxide (5.70 mL, 24.9 mmol, 25% in MeOH) was added to a solution of (2R,5R)-5-(2-bromo-3-chloro-6-hydroxybenzyl)-2-(tert-butyl)-5-(2-fluorophenyl)-1,3-dioxolan-4-one (C-V-b) (11.4 g, 24.9 mmol) in MeOH (60 mL) and stirring at this temperature was continued for 2 h. A sat solution of NH₄Cl was added and the mixture was extracted with EtOAc. The combined organic extracts were dried over anhydrous Na₂SO₄ and concentrated and the residue was purified by flash chromatography (silica, hexane/EtOAc 2:1) to afford the title compound (9.06 g). UPLC-MS 1: m/z 401.0/402.9 [M−H]⁻, $t_R$=1.14 min.

Step 3: Methyl (S)-4-bromo-5-chloro-2-(2-fluorophenyl)-2,3-dihydrobenzofuran-2-carboxylate (C-V-d)

At 0° C. PPh₃ (7.06 g, 26.9 mmol) followed by DIAD (5.23 mL, 26.9 mmol) were added to a solution of methyl (R)-3-(2-bromo-3-chloro-6-hydroxyphenyl)-2-(2-fluorophenyl)-2-hydroxypropanoate (C-V-c) (9.06 g, 22.4 mmol) in THF (215 mL). The cooling bath was removed and the reaction mixture was stirred at RT for 22 h. The reaction mixture was concentrated and the residue was purified by flash chromatography (silica, hexane/EtOAc 95:5) to afford the title compound (7.76 g). UPLC-MS 1: m/z 383.0/385.0 [M−H]⁻, $t_R$=1.37 min.

(S)-((5-chloro-2-(2-fluorophenyl)-4-(4,4,5,5-tetramethyl-1,3,2-dioxaborolan-2-yl)-2,3-dihydrobenzofuran-2-yl)methyl)carbamate (C-V)

The title compound was synthesized from methyl (S)-4-bromo-5-chloro-2-(2-fluorophenyl)-2,3-dihydrobenzofuran-2-carboxylate (C-V-d) following procedures as described for the synthesis of intermediate C-XXV. The boronate was synthesized in the final step as described for intermediate C-I. ¹H-NMR (600 MHz, DMSO-d₆) δ (ppm) 7.51 (t, J=7.7 Hz, 1H), 7.43-7.33 (m, 1H), 7.27-7.21 (m, 1H), 7.20-7.13 (m, 2H), 7.13-7.08 (m, 1H), 6.94 (d, J=8.4 Hz, 1H), 3.70 (d, J=17.1 Hz, 1H), 3.60 (dd, J=14.3, 6.3 Hz, 1H), 3.39 (dd, J=14.5, 6.5 Hz, 1H), 3.28 (d, J=17.3 Hz, 1H), 1.34-1.19 (m, 12H), 1.15 (s, 9H). UPLC-MS 1: m/z 504.2 [M+H]⁺, $t_R$=1.52 min.

Synthesis of tert-butyl (((2S,3S)-5-chloro-3-hydroxy-2-phenyl-4-(4,4,5,5-tetramethyl-1,3,2-dioxaborolan-2-yl)-2,3-dihydrobenzofuran-2-yl)methyl)carbamate (C-VI)

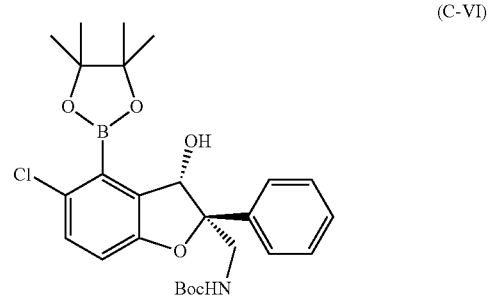 [SMILES: CC(C)(C)OC(=O)NC[C@]1(c2ccccc2)Oc2ccc(Cl)c(B3OC(C)(C)C(C)(C)O3)c2[C@@H]1O]

(C-VI)

Reaction Scheme C-VI

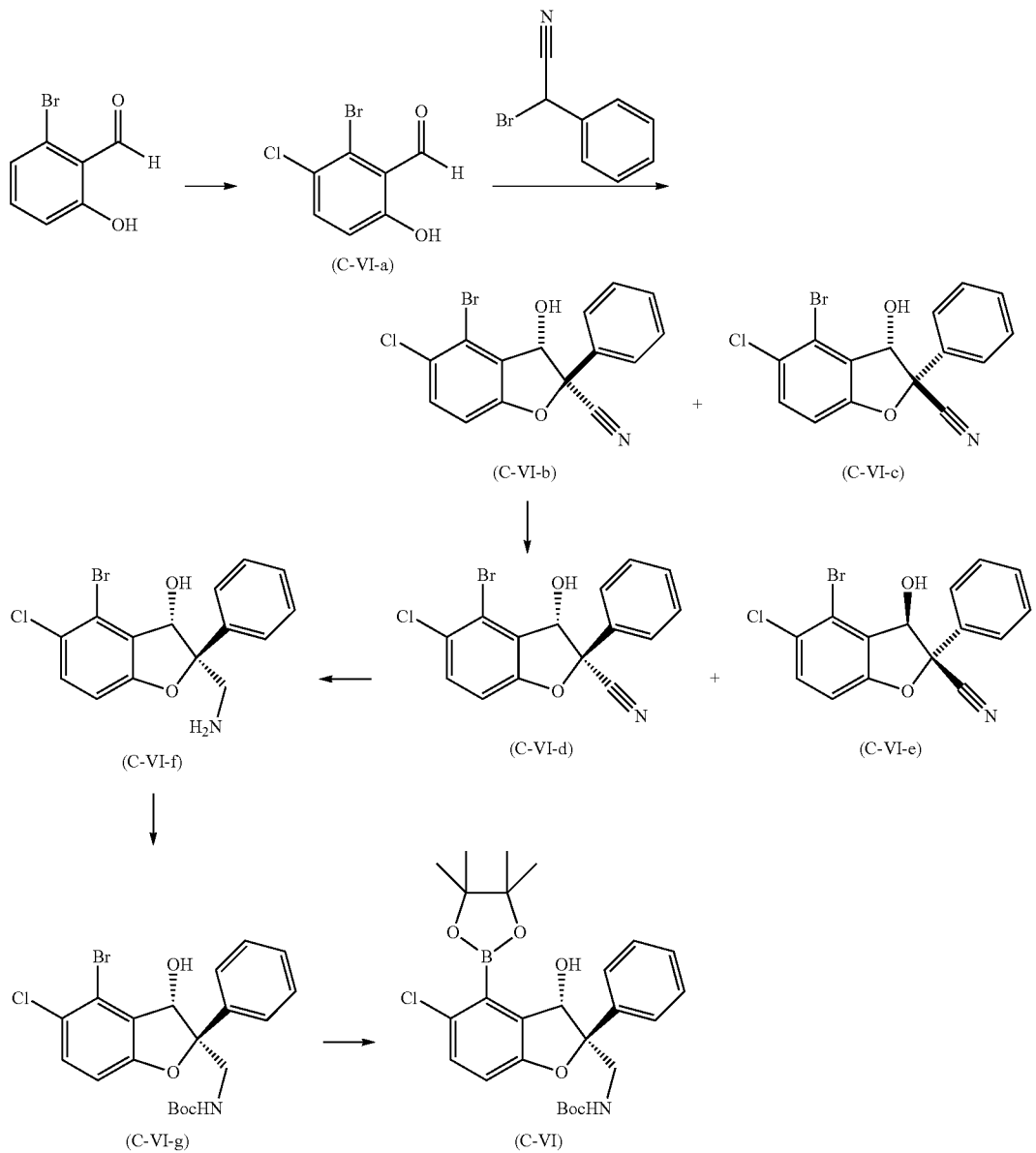

Step 1: 2-Bromo-3-chloro-6-hydroxybenzaldehyde (C-VI-a)

At 0° C. sulfuryl chloride (101.2 g, 0.75 mol) was added to a solution of 2-bromo-6-hydroxybenzaldehyde (CAS 22532-61-2) (100 g, 0.5 mol) in ACN (500 mL) and stirring at 0° C. was continued overnight. The solids were collected by filtration, washed with a sat solution of NaHCO$_3$ and dried under HV to afford the title compound (200 g). UPLC-MS 1: m/z 232.9/234.9 [M−H]$^-$. $t_R$=1.09 min.

Step 2: (2S*,3S*)-4-Bromo-5-chloro-3-hydroxy-2-phenyl-2,3-dihydrobenzofuran-2-carbonitrile (C-VI-b) and (2R*,3S*)-4-bromo-5-chloro-3-hydroxy-2-phenyl-2,3-dihydrobenzofuran-2-carbonitrile (C-VI-c)

At RT DIPEA (8.34 mL, 47.8 mmol) was added to a stirred solution of 2-bromo-3-chloro-6-hydroxybenzaldehyde (C-VI-a) (7.5 g, 31.9 mmol) and 2-bromo-2-phenylacetonitrile (CAS 5798-79-8) (6.24 g, 31.9 mmol) in DCM (159 mL) and the reaction mixture was stirred at RT for 2 days to afford a brown solution. The reaction mixture was diluted with DCM and water, extracted twice with DCM and the combined organic extracts were washed with water and brine, dried (Phase separator cartridge) and concentrated. The cis- and trans-configurated racemic diastereoisomers (2S*,3S*)-4-bromo-5-chloro-3-hydroxy-2-phenyl-2,3-dihydrobenzofuran-2-carbonitrile (C-VI-b) (6.4 g) and (2R*,3S*)-4-bromo-5-chloro-3-hydroxy-2-phenyl-2,3-dihydrobenzofuran-2-carbonitrile (C-VI-c) (1.1 g) were separated by flash chromatography (silica, cyclohexane/EtOAc; gradient 0% to 20% EtOAc).

(2S*,3S*)-4-Bromo-5-chloro-3-hydroxy-2-phenyl-2,3-dihydrobenzofuran-2-carbonitrile (C-VI-b): $^1$H-NMR (400 MHz, DMSO-d$_6$) δ 7.65 (d, J=8.8 Hz, 1H), 7.58-7.40 (m, 6H), 7.24 (d, J=8.9 Hz, 1H), 5.27 (d, J=7.7 Hz, 1H). UPLC-MS 1: m/z 348.0/350.0 [M−H]$^-$. $t_R$=1.14 min.

(2R*,3S*)-4-Bromo-5-chloro-3-hydroxy-2-phenyl-2,3-dihydrobenzofuran-2-carbonitrile (C-VI-c): $^1$H-NMR (400 MHz, DMSO-$d_6$) δ 7.69 (d, J=8.6 Hz, 1H), 7.65-7.44 (m, 5H), 7.29 (d, J=8.6 Hz, 1H), 6.46 (d, J=8.6 Hz, 1H), 5.50 (d, J=8.5 Hz, 1H); UPLC-MS 1: m/z 348.0/350.0 [M–H]$^-$, $t_R$=1.14 min.

Step 3: (2S,3S)-4-Bromo-5-chloro-3-hydroxy-2-phenyl-2,3-dihydrobenzofuran-2-carbonitrile (C-VI-d) and (2R,3R)-4-bromo-5-chloro-3-hydroxy-2-phenyl-2,3-dihydrobenzofuran-2-carbonitrile (C-VI-e)

The racemate (2S*,3S*)-4-bromo-5-chloro-3-hydroxy-2-phenyl-2,3-dihydrobenzofuran-2-carbonitrile (C-VI-b) (21.9 g) was separated by chiral SFC (Sepiatec Prep SFC 100 & Jasco Prep SFC, column: Chiralpak OJ-H 5 μm, 250×30 mm, 40° C., 3 mL/injection, 170 injections, $CO_2$/IPA 9:1, flow rate: 80 mL/min, cycle time: 15 min) to afford (2S,3S)-4-bromo-5-chloro-3-hydroxy-2-phenyl-2,3-dihydrobenzofuran-2-carbonitrile (C-VI-d) (9.35 g) and (2R,3R)-4-bromo-5-chloro-3-hydroxy-2-phenyl-2,3-dihydrobenzofuran-2-carbonitrile (C-VI-e) (9.30 g) with an enantiomeric excess of >98%, respectively.

(2S,3S)-4-Bromo-5-chloro-3-hydroxy-2-phenyl-2,3-dihydrobenzofuran-2-carbonitrile (C-VI-d): Chiral SFC: (Chiralpak OJ-H 5 μm 100×4.6 mm, $CO_2$/IPA 8:2, flow rate: 3 mL/min) $t_R$=2.38 min;
UPLC-MS 1: m/z 394.1/396.1 [M+formate]$^-$, $t_R$=1.14 min.

(2R,3R)-4-Bromo-5-chloro-3-hydroxy-2-phenyl-2,3-dihydrobenzofuran-2-carbonitrile (C-VI-e): Chiral SFC: (Chiralpak OJ-H 5 μm 100×4.6 mm, $CO_2$/IPA 8:2, flow rate: 3 mL/min) $t_R$=1.82 min; UPLC-MS 1: m/z 394.1/396.1 [M+formate]$^-$, $t_R$=1.14 min.

The (2R,3R) absolute configuration of this intermediate was confirmed by an X-ray crystal structure of (2R,3R)-2-(aminomethyl)-5-chloro-2,4-diphenyl-2,3-dihydrobenzofuran-3-ol which was synthesized from (2R,3R)-4-bromo-5-chloro-3-hydroxy-2-phenyl-2,3-dihydrobenzofuran-2-carbonitrile (C-VI-e) by reduction of the nitrile to the amine (using similar reaction conditions as in Step 4 below) followed by Suzuki cross-coupling with phenylboronic acid.

Step 4: (2S,3S)-2-(Aminomethyl)-4-bromo-5-chloro-2-phenyl-2,3-dihydrobenzofuran-3-ol (C-VI-f)

Borane-methyl sulfide complex (14.26 mL, 28.5 mmol, 2M in THF) was added to a stirred solution of (2S,3S)-4-bromo-5-chloro-3-hydroxy-2-phenyl-2,3-dihydrobenzofuran-2-carbonitrile (C-VI-d) (2 g, 5.70 mmol) in THF (38 mL) at RT and the reaction mixture was stirred at 65° C. for 1 h. After cooling to RT, the reaction mixture was quenched by careful addition of MeOH, followed by 1 N HCl. A sat solution of $NaHCO_3$ was added and the mixture was extracted with EtOAc. The combined organic extracts were washed with brine, dried (phase separator cartridge) and concentrated to afford the title compound. UPLC-MS 1: m/z 354.1/356.1 [M+H]$^+$. $t_R$=0.72 min.

Step 5: Tert-butyl (((2S,3S)-4-bromo-5-chloro-3-hydroxy-2-phenyl-2,3-dihydrobenzofuran-2-yl)methyl)carbamate (C-VI-g)

At RT Boc-anhydride (1.067 mL, 4.59 mmol) and TEA (0.582 mL, 4.18 mmol) were added to a stirred solution of (2S,3S)-2-(aminomethyl)-4-bromo-5-chloro-2-phenyl-2,3-dihydrobenzofuran-3-ol (C-VI-f) (2.31 g, 4.18 mmol) in DCM (21 mL). The reaction mixture was stirred at RT for 2 h.

For workup a sat solution of $NaHCO_3$ was added and the mixture was extracted with DCM. The combined organic extracts were washed with water and brine, dried (phase separator cartridge) and concentrated. The crude product was purified by flash chromatography (silica, cyclohexane/EtOAc, gradient: 0% to 30% EtOAc) to afford the desired product (1.57 g). UPLC-MS 1: m/z 498.2/500.2 [M+formate]$^-$. $t_R$=1.28 min.

Step 6: Tert-butyl (((2S,3S)-5-chloro-3-hydroxy-2-phenyl-4-(4,4,5,5-tetramethyl-1,3,2-dioxaborolan-2-yl)-2,3-dihydrobenzofuran-2-yl)methyl)carbamate (C-VI)

At 80° C. $PdCl_2(dppf)·CH_2Cl_2$ adduct (0.252 g, 0.308 mmol) was added to a stirred suspension of tert-butyl (((2S,3S)-4-bromo-5-chloro-3-hydroxy-2-phenyl-2,3-dihydrobenzofuran-2-yl)methyl)carbamate (C-V-g) (1.65 g, 3.1 mmol), bis(pinacolato)diboron (1.02 g, 4.0 mmol) and potassium acetate (0.908 g, 9.3 mmol) in toluene (21 mL) and the reaction mixture was stirred vigorously at 100° C. for 17 h. The reaction mixture was filtered through Celite, and concentrated to afford the crude product which was purified by flash chromatography (silica, eluent cyclohexane/EtOAc, gradient: 0% to 40% EtOAc) to give the desired product (1.03 g). $^1$H-NMR (400 MHz, DMSO-$d_6$) δ (ppm) 7.42-7.36 (m, 2H), 7.33 (t, J=7.5 Hz, 2H), 7.28-7.21 (m, 2H), 7.00 (d, J=8.6 Hz, 1H), 6.25 (t, J=6.1 Hz, 1H), 6.09 (d, J=7.0 Hz, 1H), 5.18 (d, J=6.9 Hz, 1H), 3.80 (dd, J=14.2, 7.3 Hz, 1H), 3.55 (dd, J=14.3, 5.0 Hz, 1H), 1.31-1.20 (m, 21H). UPLC MS 1: m/z 502.3 [M+H]$^+$. $t_R$=1.40 min.

Synthesis of tert-butyl (((2R*,3S*)-5-chloro-3-hydroxy-2-(pyridin-2-yl)-4-(4,4,5,5-tetramethyl-1,3,2-dioxaborolan-2-yl)-2,3-dihydrobenzofuran-2-yl)methyl)carbamate (C-VII)

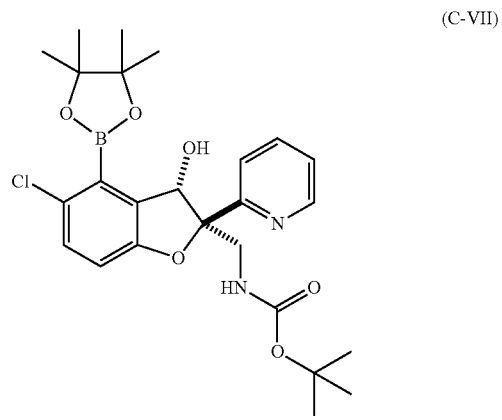 [SMILES: CC(C)(C)OC(=O)NC[C@]1(c2ccccn2)Oc2ccc(Cl)c(B3OC(C)(C)C(C)(C)O3)c2[C@@H]1O]

(C-VII)

The racemic title compound was prepared in a manner analogous to that of tert-butyl (((2S,3S)-5-chloro-3-hydroxy-2-phenyl-4-(4,4,5,5-tetramethyl-1,3,2-dioxaborolan-2-yl)-2,3-dihydrobenzofuran-2-yl)methyl)carbamate (C-VI) from 2-bromo-3-chloro-6-hydroxybenzaldehyde (C-VI-a) and 2-bromo-2-(pyridin-2-yl)acetonitrile (obtained by bromination of 2-pyridyl acetonitrile with NBS) without resolution of the enantiomers. UPLC-MS 1: m/z 503.2 [M+H]$^+$, $t_R$=1.28 min.

Synthesis of tert-butyl (((2S*,3S*)-5-chloro-3-hydroxy-4-(4,4,5,5-tetramethyl-1,3,2-dioxaborolan-2-yl)-2-(2-(trifluoromethoxy)phenyl)-2,3-dihydrobenzofuran-2-yl)methyl)carbamate (C-VIII)

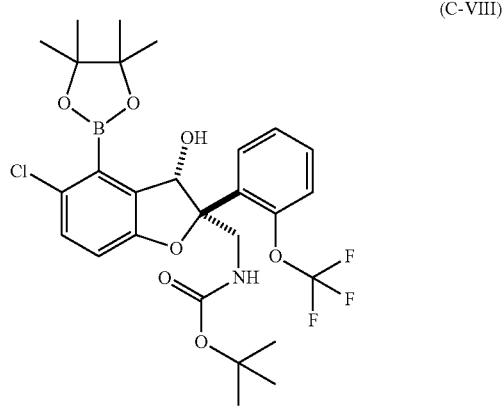 [SMILES: CC(C)(C)OC(=O)NC[C@]1(c2ccccc2OC(F)(F)F)Oc2ccc(Cl)c(B3OC(C)(C)C(C)(C)O3)c2[C@@H]1O]

(C-VIII)

The racemic title compound was prepared analogously to tert-butyl (((2S,3S)-5-chloro-3-hydroxy-2-phenyl-4-(4,4,5,5-tetramethyl-1,3,2-dioxaborolan-2-yl)-2,3-dihydrobenzofuran-2-yl)methyl)carbamate (C-VI) from 2-bromo-3-chloro-6-hydroxybenzaldehyde (C-VI-a) and 2-bromo-2-(2-(trifluoromethoxy)phenyl)acetonitrile (obtained by bromination of 2-trifluoromethoxy)phenylacetonitrile with Br$_2$) without resolution of the enantiomers. UPLC-MS 1: m/z 584.2 [M–H]$^-$, $t_R$=1.49 min.

Synthesis of tert-butyl (((2R*,3S*)-5-chloro-3-hydroxy-2-(6-methoxypyridin-2-yl)-4-(4,4,5,5-tetramethyl-1,3,2-dioxaborolan-2-yl)-2,3-dihydrobenzofuran-2-yl)methyl)carbamate (C-IX)

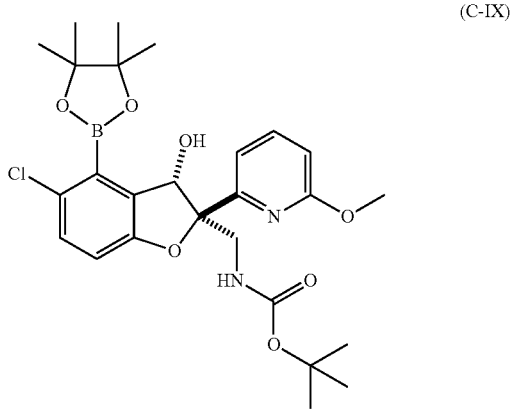 [SMILES: COc1cccc([C@@]2(CNC(=O)OC(C)(C)C)Oc3ccc(Cl)c(B4OC(C)(C)C(C)(C)O4)c3[C@@H]2O)n1]

(C-IX)

The racemic title compound was prepared analogously to tert-butyl (((2S,3S)-5-chloro-3-hydroxy-2-phenyl-4-(4,4,5,5-tetramethyl-1,3,2-dioxaborolan-2-yl)-2,3-dihydrobenzofuran-2-yl)methyl)carbamate (C-VI) from 2-bromo-3-chloro-6-hydroxybenzaldehyde (C-VI-a) and 2-bromo-2-(6-methoxypyridin-2-yl)acetonitrile (obtained by bromination of 2-(6-methoxypyridin-2-yl)acetonitrile with NBS) without resolution of the enantiomers. UPLC-MS 1: m/z 577.3 [M–H]$^-$, $t_R$=1.36 min.

Synthesis of ((2S*,3S*)-2-(((tert-butoxycarbonyl)amino)methyl)-5-chloro-3-hydroxy-2-(2-methoxypyridin-3-yl)-2,3-dihydrobenzofuran-4-yl)boronic acid (C-X)

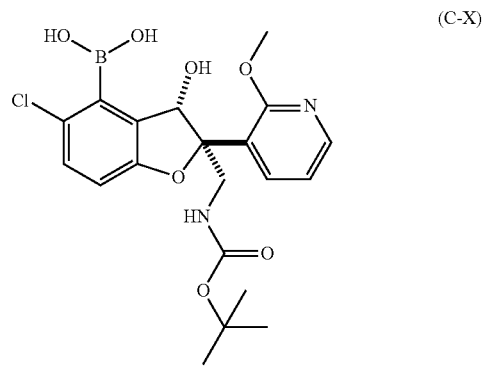 [SMILES: COc1ncccc1[C@@]1(CNC(=O)OC(C)(C)C)Oc2ccc(Cl)c(B(O)O)c2[C@@H]1O]

(C-X)

The racemic title compound was prepared analogously to tert-butyl (((2S,3S)-5-chloro-3-hydroxy-2-phenyl-4-(4,4,5,5-tetramethyl-1,3,2-dioxaborolan-2-yl)-2,3-dihydrobenzofuran-2-yl)methyl)carbamate (C-VI) from 2-bromo-3-chloro-6-hydroxybenzaldehyde (C-VI-a) and 2-bromo-2-(2-methoxypyridin-3-yl)acetonitrile (obtained by bromination of 2-(2-methoxypyridin-3-yl)acetonitrile with NBS) without resolution of the enantiomers. During the final purification the pinacol group largely fell off to afford the corresponding boronic acid containing ca 30% of the pinicol boronate. UPLC-MS 1: m/z 451.2 [M+H]$^+$. $t_R$=0.95 min.

Synthesis of tert-butyl (((2S,3S)-5-chloro-3-methyl-2-phenyl-4-(4,4,5,5-tetramethyl-1,3,2-dioxaborolan-2-yl)-2,3-dihydrobenzofuran-2-yl)methyl)carbamate (C-XI)

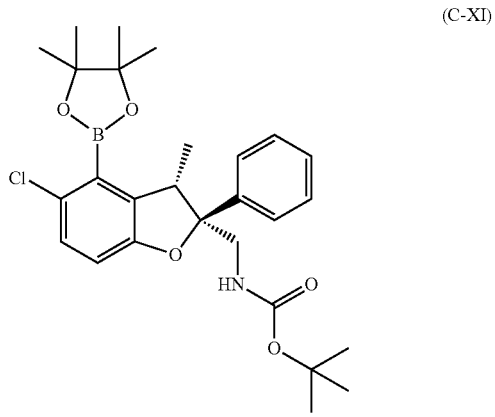 [SMILES: C[C@H]1c2c(ccc(Cl)c2B2OC(C)(C)C(C)(C)O2)O[C@]1(CNC(=O)OC(C)(C)C)c1ccccc1]

(C-XI)

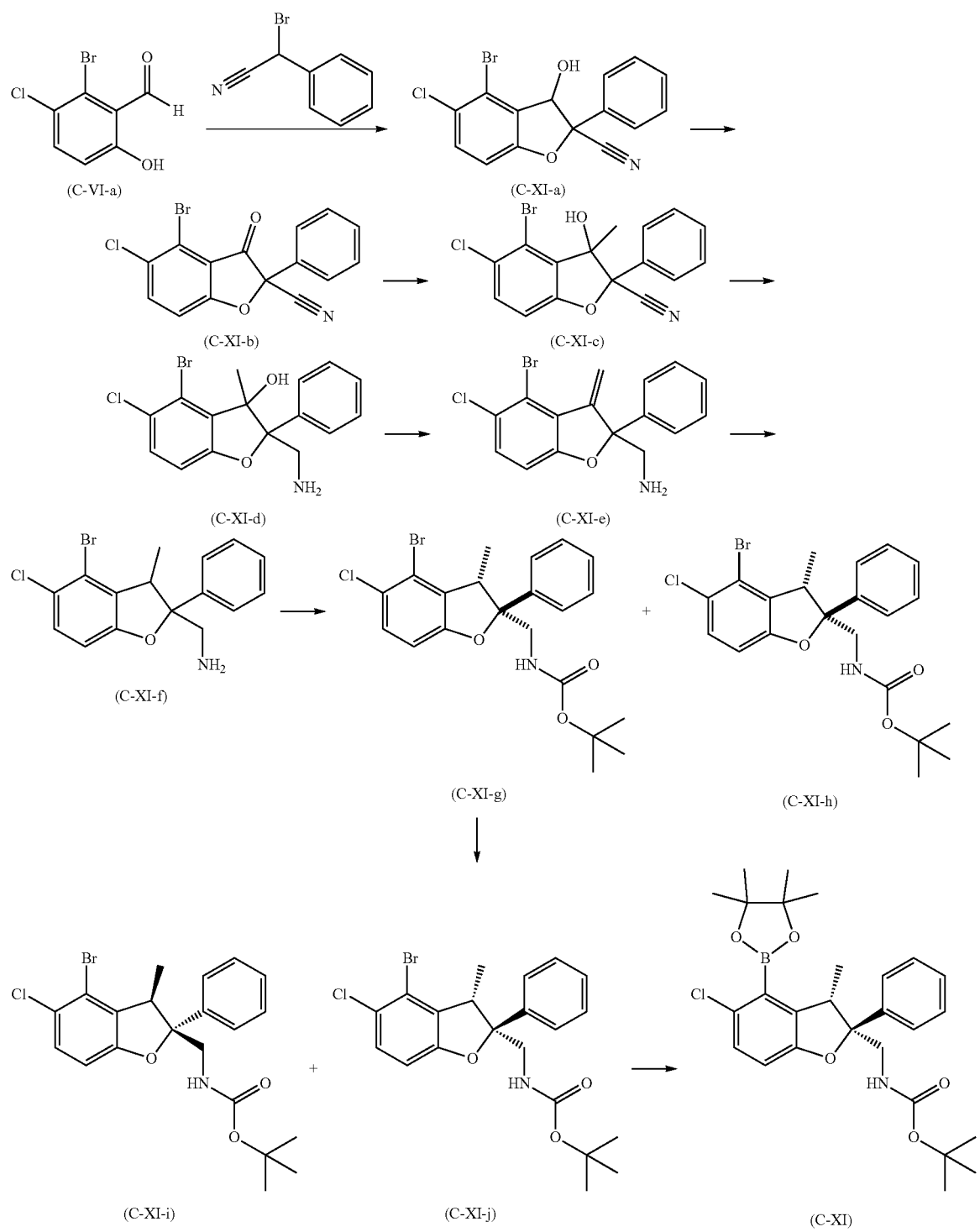

Step 1: 4-Bromo-5-chloro-3-hydroxy-2-phenyl-2,3-dihydrobenzofuran-2-carbonitrile (C-XI-a)

To a stirred solution of 2-bromo-3-chloro-6-hydroxybenzaldehyde (C-VI-a) (10 g, 42.5 mmol) and 2-bromo-2-phenylacetonitrile (9.16 g, 46.7 mmol) in ACN (100 mL) was added DIPEA (11.13 mL, 63.7 mmol) at RT and stirring was continued for 4 h. The reaction mixture was concentrated, diluted in DCM/water and extracted with DCM. The combined organic extracts were washed with water and brine, dried over anhydrous $Na_2SO_4$ and concentrated. The crude product was purified by flash chromatography (silica, hexane/EtOAc; gradient: 0% to 25% EtOAc) to afford the title compound (111.39 g, colorless foam) as a diastereomeric mixture. UPLC-MS 1: mz 348.0/350.0 [M+H]$^+$, $t_R$=1.11 min.

Step 2: 4-Bromo-5-chloro-3-oxo-2-phenyl-2,3-dihydrobenzofuran-2-carbonitrile (C-XI-b)

At 0° C. Dess-Martin periodinane (27.6 g, 65.0 mmol) was added to a stirred solution of 4-bromo-5-chloro-3-hydroxy-2-phenyl-2,3-dihydrobenzofuran-2-carbonitrile (C-XI-a) (11.39 g, 32.5 mmol) in DCM (200 mL) and the reaction mixture was stirred at RT for 18 h. The reaction mixture was diluted in a mixture of DCM, a sat solution of NaHCO$_3$ and a 10% sodium thiosulfate solution and extracted with DCM. The combined organic extracts were washed with brine, dried over anhydrous Na$_2$SO$_4$ and concentrated. The crude product was purified by flash chromatography (silica, heptane/EtOAc; gradient: 20% to 40% EtOAc) to afford the title compound (10.86 g) as a colorless powder. $^1$H NMR (400 MHz, DMSO-d$_6$) δ (ppm): 8.12 (d, J=9.1 Hz, 1H), 7.61 (d, J=9.1 Hz, 1H), 7.55-7.47 (m, 5H).

Step 3: 4-Bromo-5-chloro-3-hydroxy-3-methyl-2-phenyl-2,3-dihydrobenzofuran-2-carbonitrile (C-XI-c)

At −78° C. methylmagnesium bromide (15.58 mL, 46.7 mmol, 3 M in Et$_2$O) was added to a stirred solution of 4-bromo-5-chloro-3-oxo-2-phenyl-2,3-dihydrobenzofuran-2-carbonitrile (C-XI-b) (10.86 g, 31.2 mmol) in THF (250 mL) and the reaction mixture was stirred at this temperature for another 1.5 h. The reaction mixture was quenched at −30° C. with a saturated ammonium chloride solution, diluted in EtOAc and a sat ammonium chloride solution and extracted with EtOAc. The combined organic extracts were washed with water and brine, dried over anhydrous Na$_2$SO$_4$ and concentrated. The residue was purified by flash chromatography (silica, heptane/EtOAc; gradient: 0% to 30% EtOAc) to afford the title product (10.15 g, colorless powder) as a diastereomeric mixture. UPLC-MS 1: m/z 362.0/364.0 [M+H]$^+$, t$_R$=1.21 min and 1.22 min.

Step 4: 2-(Aminomethyl)-4-bromo-5-chloro-3-methyl-2-phenyl-2,3-dihydrobenzofuran-3-ol (C-XI-d)

At RT borane dimethyl sulfide complex (55.7 mL, 111 mmol, 2 M in THF) was added to a stirred solution of 4-bromo-5-chloro-3-hydroxy-3-methyl-2-phenyl-2,3-dihydrobenzofuran-2-carbonitrile (C-XI-c) (10.15 g, 27.8 mmol) in THF (200 mL) and the reaction mixture was stirred at 65° C. for 30 min. The reaction mixture was then quenched by the addition of 40 mL of MeOH at 0° C. and stirring at RT was continued for 16 h. The reaction mixture was concentrated, diluted in DCM and a sat solution of NaHCO$_3$. The organic phase was separated and the aqueous phase was extracted with DCM. The combined organic extracts were dried over anhydrous Na$_2$SO$_4$ and concentrated.

The crude product was purified by flash chromatography (silica, DCM/(7N ammonia in MeOH); gradient: 0% to 6% (7N ammonia in MeOH)) to afford title compound (8.69 g, colorless powder) as a diastereomeric mixture. UPLC-MS 1: m/z 368.1/370.1 [M+H]$^+$, t$_R$=0.62 min and 0.77 min.

Step 5: (4-Bromo-5-chloro-3-methylene-2-phenyl-2,3-dihydrobenzofuran-2-yl)methanamine (C-XI-e)

To a stirred solution of 2-(aminomethyl)-4-bromo-5-chloro-3-methyl-2-phenyl-2,3-dihydrobenzofuran-3-ol (C-XI-d) (5.81 g, 15.76 mmol) in DCM (60 mL) was added TFA (20 mL, 260 mmol) at 0° C. and the reaction mixture was stirred at RT for 5 h. The reaction mixture was diluted in DCM and added dropwise to a stirred mixture of a sat solution of NaHCO$_3$ and DCM at 0° C. The organic phase was separated and the aqueous layer was extracted with DCM. The combined organic extracts were dried over anhydrous Na$_2$SO$_4$ and concentrated to afford the title compound (5.18 g) as a yellow oil. $^1$H NMR (400 MHz, DMSO-d$_6$) δ (ppm): 7.50 (d, J=8.7 Hz, 1H), 7.44-7.41 (m, 2H), 7.36-7.23 (m, 3H), 7.08 (d, J=8.7 Hz, 1H), 6.40 (s, 1H), 5.33 (s, 1H), 3.20 (s, 2H), 1.36 (s, 2H). UPLC-MS 1: m/z 349.9/352.0 [M+H]$^+$, t$_R$=0.83 min.

Step 6: (4-Bromo-5-chloro-3-methyl-2-phenyl-2,3-dihydrobenzofuran-2-yl)methanamine (C-XI-f)

At RT hydrazine hydrate (5.79 mL, 118 mmol) was added to a stirred solution of (4-bromo-5-chloro-3-methylene-2-phenyl-2,3-dihydrobenzofuran-2-yl)methanamine (C-XI-e) (5.18 g, 14.76 mmol) in EtOH (60 mL). The reaction mixture was cooled to 0° C. and O$_2$ was bubbled into the solution for 5 min. The reaction mixture was stirred at reflux under O$_2$ atmosphere for 3 days. The reaction mixture was concentrated, diluted in EtOAc/water and the organic phase was separated. The aqueous phase was extracted with EtOAc. The combined organic extracts were washed with brine, dried over anhydrous Na$_2$SO$_4$ and concentrated. The crude product was purified by flash chromatography (silica, DCM/(7N ammonia in MeOH); gradient: 0% to 5% (7N ammonia in MeOH)) to afford the title compound (3.00 g, yellow oil) as a diastereomeric mixture (ratio 12:1). UPLC-MS 1: m/z 352.0/354.0 [M+H]$^+$, t$_R$=0.85 min and 0.92 min.

Step 7: Tert-butyl (((2S*,3S*)-4-bromo-5-chloro-3-methyl-2-phenyl-2,3-dihydrobenzofuran-2-yl)methyl)carbamate (C-XI-g) and tert-butyl (((2R*,3S*)-4-bromo-5-chloro-3-methyl-2-phenyl-2,3-dihydrobenzofuran-2-yl)methyl)carbamate (C-XI-h)

At RT TEA (2.371 mL, 17.01 mmol) followed by Boc-anhydride (2.37 mL, 10.21 mmol) were added to a stirred solution of (4-bromo-5-chloro-3-methyl-2-phenyl-2,3-dihydrobenzofuran-2-yl)methanamine (C-XI-f) (3 g, 8.51 mmol) in DCM (30 mL) and the reaction mixture was stirred at RT for 30 min. The reaction mixture was diluted in DCM/water and the organic phase was separated. The aqueous phase was extracted with DCM, the combined organic extracts were washed with brine, dried over anhydrous Na$_2$SO$_4$ and concentrated. The crude product was purified by flash chromatography (silica, heptane/EtOAc; gradient: 0% to 10% EtOAc) to afford, after trituration in hexane:

(((2S*,3S*)-4-bromo-5-chloro-3-methyl-2-phenyl-2,3-dihydrobenzofuran-2-yl)methyl)carbamate (C-XI-g) (3.3 g, colorless powder): $^1$H NMR (400 MHz, DMSO-d$_6$) δ (ppm): 7.53-7.13 (m, 6H), 6.98 (d, J=8.5 Hz, 1H), 6.49 (t, J=6.2 Hz, 1H), 3.90-3.71 (m, 1H), 3.67-3.49 (m, 2H), 1.37 (d, J=7.0 Hz, 3H), 1.18 (s, 9H). UPLC-MS 1: m/z 352.0/354.0 [M−Boc]$^+$, t$_R$=1.43 min. The filtrate was repurified by flash chromatography (silica, heptane/EtOAc; gradient: 0% to 18% EtOAc) to afford (((2R*,3S*)-4-bromo-5-chloro-3-methyl-2-phenyl-2,3-dihydrobenzofuran-2-yl)methyl)carbamate (C-XI-h) (230 mg): $^1$H NMR (400 MHz, DMSO-d$_6$) δ (ppm): 7.54-7.23 (m, 6H), 6.89 (d, J=8.5 Hz, 1H), 6.68 (t, J=6.4 Hz, 1H), 3.67 (q, J=7.0 Hz, 1H), 3.53 (dd, J=14.4, 6.2 Hz, 1H), 3.41 (dd, J=14.3, 6.5 Hz, 1H), 1.22 (s, 9H), 0.69 (d, J=7.0 Hz, 3H). UPLC-MS 1: m/z 352.0/354.0 [M−Boc]$^+$, t$_R$=1.46 min.

Step 8: Tert-butyl (((2R,3R)-4-bromo-5-chloro-3-methyl-2-phenyl-2,3-dihydrobenzofuran-2-yl)methyl)carbamate (C-XI-i) and tert-butyl (((2S,3S)-4-bromo-5-chloro-3-methyl-2-phenyl-2,3-dihydrobenzofuran-2-yl)methyl)carbamate (C-XI-j)

The racemate (((2S*,3S*)-4-bromo-5-chloro-3-methyl-2-phenyl-2,3-dihydrobenzofuran-2-yl)methyl)carbamate (C-XI-g) (3.3 g, 7.3 mmol) was subjected to chiral preparative HPLC (Chiralpak IA 5 μm 2.5×25 cm, injection volume: 80×0.5 mL, mobile phase: heptane:EtOH 98:2, flow rate: 15 mL/min, UV: 220 nm)) to afford the enantiomerically pure title compounds with an enantiomeric excess of >99%, respectively:

Tert-butyl (((2R,3R)-4-bromo-5-chloro-3-methyl-2-phenyl-2,3-dihydrobenzofuran-2-yl)methyl) carbamate (C-XI-i) (1.66 g, colorless powder): Chiral analytical HPLC (Agilent 1200 HPLC system, Injection volume: 10 μL, Mobile phase: heptane:EtOH 97:3, Flow rate: 1 mL/min, Column: Chiralpak IA 5 μm 4.6×250 mm, Detection UV: 220 nm) $t_R$=5.75 min. $^1$H NMR (400 MHz, DMSO-$d_6$) δ (ppm): 7.42-7.40 (m, 2H), 7.36 (d, J=7.1 Hz, 1H), 7.28-7.19 (m, 3H), 6.98 (d, J=7.1 Hz, 1H), 6.63-6.38 (m, 1H) 3.85-3.75 (m, 1H), 3.63-3.53 (m, 2H), 1.37 (d, J=7.0 Hz, 3H), 1.17 (s, 9H).

Tert-butyl (((2S,3S)-4-bromo-5-chloro-3-methyl-2-phenyl-2,3-dihydrobenzofuran-2-yl)methyl) carbamate (C-XI-j) (1.62 g, colorless powder): Chiral analytical HPLC (Agilent 1200 HPLC system, Injection volume: 10 μL, Mobile phase: Hep:EtOH 97:3, Flow rate: 1 mL/min, Column: Chiralpak IA 5 μm 4.6×250 mm, Detection UV: 220 nm) $t_R$=7.59 min. $^1$H NMR (400 MHz, DMSO-$d_6$) δ (ppm): 7.42-7.40 (m, 2H), 7.36 (d, J=7.1 Hz, 1H), 7.28-7.16 (m, 3H) 6.98 (d, J=7.1 Hz, 1H), 6.51-6.47 (m, 1H), 3.83-3.78 (m, 1H), 3.62-3.53 (m, 2H), 1.37 (d, J=7.0 Hz, 3H), 1.17 (s, 9H).

Step 9: Tert-butyl (((2S,3S)-5-chloro-3-methyl-2-phenyl-4-(4,4,5,5-tetramethyl-1,3,2-dioxaborolan-2-yl)-2,3-dihydrobenzofuran-2-yl)methyl)carbamate (C-XI)

A suspension of tert-butyl (((2S,3S)-4-bromo-5-chloro-3-methyl-2-phenyl-2,3-dihydrobenzofuran-2-yl)methyl) carbamate (C-XI-j) (1.38 g, 3.05 mmol), bis(pinacolato)diboron (1.16 g, 4.57 mmol), KOtBu (0.479 g, 4.27 mmol) and PdCl$_2$(dppf)-CH$_2$Cl$_2$ adduct (0.249 g, 0.305 mmol) in toluene (15 mL) was stirred at 100° C. for 5 h. The reaction mixture was filtered through a pad of Celite and concentrated. The crude product was purified by flash chromatography (silica, heptane/EtOAc, gradient: 0% to 25% EtOAc) to afford the title compound (1.20 g) as a colorless foam. $^1$H NMR (400 MHz, DMSO-$d_6$) δ: 7.39-7.35 (m, 2H), 7.17-7.28 (m, 3H), 7.12 (d, J=8.5 Hz, 1H), 6.95 (d, J=8.5 Hz, 1H), 6.42-6.39 (m, 1H), 3.77-3.72 (m, 1H), 3.58-3.53 (m, 2H), 1.29-1.26 (m, 15H), 1.15 (s, 9H). UPLC-MS 1: m/z 400.3 [M−Boc+H]$^+$, $t_R$=1.49 min.

Synthesis of tert-butyl (S)-((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII)

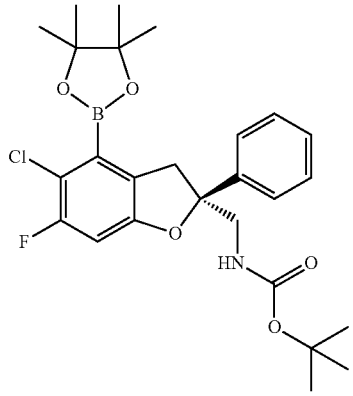

(C-XII)

Reaction Scheme. C-XII

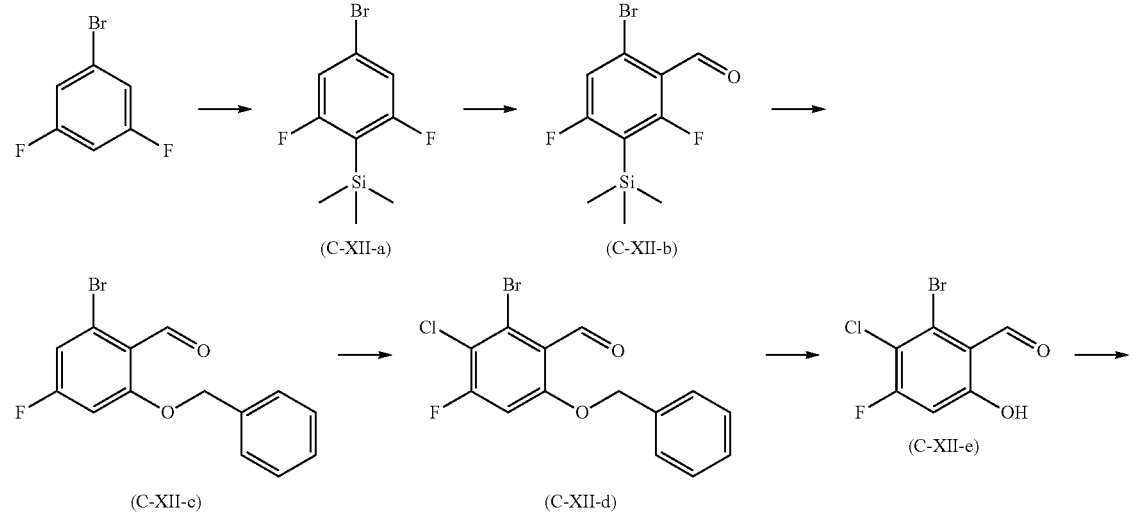

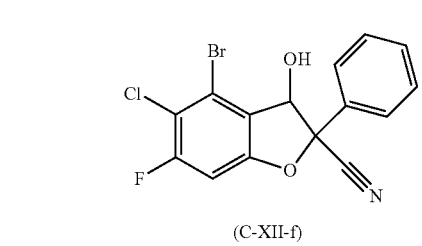

(C-XII-f)

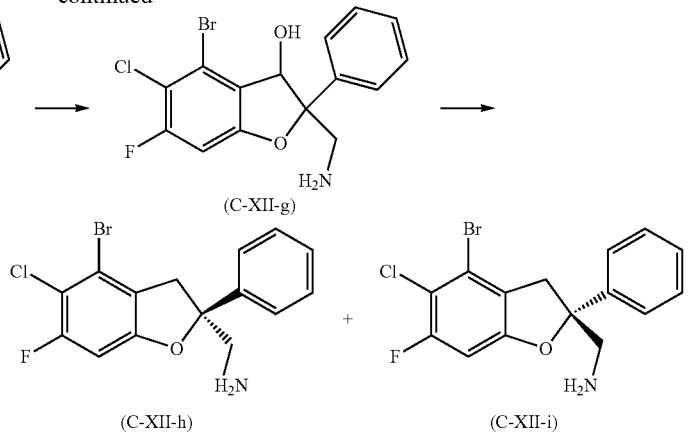

(C-XII-g)

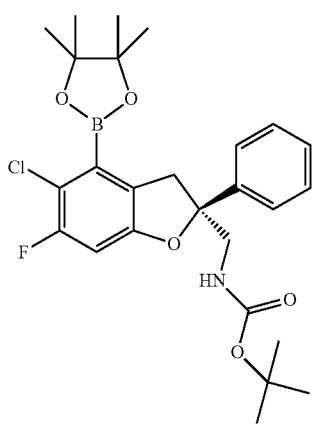

(C-XII-h)     (C-XII-i)

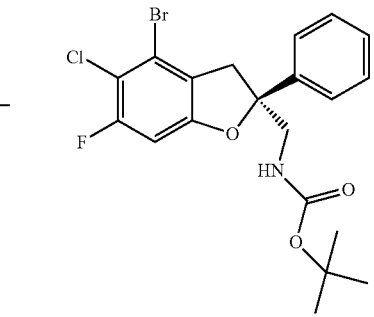

(C-XII)     (C-XiI-j)

Step 1: (4-Bromo-2,6-difluorophenyl)trimethylsilane (C-XII-a)

At −78° C. diisopropylamine (555 mL, 3.9 mol) was added dropwise to a solution of n-butyllithium (1560 mL, 3.9 mol, 2.5 M in hexane) in THF (3000 mL) within 10 min. After 10 min, 1-bromo-3,5-difluorobenzene (500 g, 2.6 mol) was added dropwise to the freshly prepared LDA solution. The reaction mixture was stirred at −78° C. for 2 h before chlorotrimethylsilane (488 mL, 3.9 mol) was added dropwise at −78° C. within 10 min. The resulting solution was stirred at −78° C. for 1 h. After evaporation of the solvents, the resulting crude material was distilled to afford the title compound (470 g) as a colorless oil. UPLC-MS 1: m/z 282.4 [M+NH$_4$]$^+$, $t_R$=1.53 min. $^1$HNMR (300 MHz, CDCl$_3$): δ 7.01 (s, 1H), 6.99 (s, 1H), 0.37 (s, 9H).

Step 2: 6-Bromo-2,4-difluoro-3-(trimethylsilyl)benzaldehyde (C-XII-b)

At −78° C. redistilled diisopropylamine (186 mL, 1.13 mol) was added dropwise to a solution of n-butyllithium in hexane (453 mL, 1.13 mol) in THF (1000 mL) cooled at −78° C. within 10 min and stirring was continued for 1 h. Then, the freshly prepared LDA solution was added dropwise to a solution of (4-bromo-2,6-difluorophenyl)trimethylsilane (C-XII-a) (200 g, 0.754 mol) in THF (1000 mL) cooled to −78° C. The yellow solution was stirred for 1 h at −78° C. before DMF (104 mL, 1.36 mol) was added dropwise within 5 min. The resulting yellow reaction mixture was stirred at −78° C. for 1 h. Then, an acetic acid solution (188 mL) and water (800 mL) were added. The yellow suspension was stirred at RT for an additional 1.5 h. The two phases were separated and the aqueous phase was extracted with EtOAc. The combined organic phases were washed with brine, dried over anhydrous Na$_2$SO$_4$, filtered and concentrated under reduced pressure affording the title product (176 g). UPLC-MS 1: m/z 293.0/295.0 [M+H]$^+$, $t_R$=1.25/1.38 min. $^1$H-NMR (600 MHz, DMSO-d$_6$) b ppm 10.13 (s, 1H), 7.61 (d, J=8.3 Hz, 1H), 0.35 (s, 9H).

Step 3: 2-(Benzyloxy)-6-bromo-4-fluorobenzaldehyde (C-XII-c)

At RT a solution of sodium benzyloxide (1020 mL, 1.02 mol freshly prepared: 23.46 g Na in 1020 mL benzyl alcohol) was added dropwise to a solution of 6-bromo-2,4-difluoro-3-(trimethylsilyl)benzaldehyde (C-XII-b) (300 g, 1.02 mol) in benzyl alcohol (500 mL) within 30 min. The light yellow reaction mixture was stirred at 40° C. for 15 min. The resulting suspension was diluted with EtOAc, then extracted successively with a sat solution of NH$_4$Cl and brine. The separated aqueous phase was back-extracted with EtOAc. The combined organic phases were dried over anhydrous Na$_2$SO$_4$, filtered and concentrated under reduced pressure to give the crude product which was purified by flash chromatography (silica, PE) to give the title compound (90 g) as a light beige solid. UPLC-MS 1: m/z 309.0/311.0 [M+H]$^+$, $t_R$=1.24 min. $^1$H-NMR (600 MHz, DMSO-d$_6$) δ ppm 10.24 (s, 1H), 7.48 (d, J=7.5 Hz, 2H), 7.41 (t, J=7.5 Hz, 2H), 7.37-7.28 (m, 3H), 5.27 (s, 2H).

Step 4: 6-(Benzyloxy)-2-bromo-3-chloro-4-fluorobenzaldehyde (C-XII-d)

To a solution of 2-(benzyloxy)-6-bromo-4-fluorobenzaldehyde (C-XII-c) (240 g, 777 mmol) in ACN (3000 mL) were added N-chlorosuccinimide (134 g, 1010 mmol) and p-TsOH monohydrate (221 g, 1165 mmol) at RT. The light yellow solution was stirred for 24 h at RT. The reaction mixture was diluted with EtOAc and extracted with a sat solution of NaHCO$_3$ and brine. The combined aqueous phases were back-extracted with EtOAc. The combined organic phases were dried over anhydrous Na$_2$SO$_4$, filtered and concentrated under reduced pressure to give the crude product which was suspended in a mixture of MTBE and PE (ratio 1:8). The crystallized material was filtered, washed with PE and dried under HV at 50° C. overnight to give the title product (186 g) as a colorless powder. UPLC-MS 1: m/z 342.8/344.8 [M+H]$^+$, $t_R$=1.31 min. $^1$HNMR (300 MHz, CDCl$_3$): δ 10.37 (s, 1H), 7.43-7.37 (m, 5H), 6.91 (d, J=10.2 Hz, 1H), 5.18 (s, 2H).

Step 5: 2-Bromo-3-chloro-4-fluoro-6-hydroxybenzaldehyde (C-XII-e)

To a suspension of 6-(benzyloxy)-2-bromo-3-chloro-4-fluorobenzaldehyde (C-XII-d) (300 g, 873 mmol) in DCM (3 L), placed under nitrogen and cooled to −78° C., was added a solution of boron tribromide (960 mL, 960 mmol, 1 M in DCM) within 5 min. The resulting brown solution was stirred at −78° C. for 1.5 h. The reaction mixture was slowly quenched with MeOH and the solvents were removed under reduced pressure. The crude material was redissolved in MeOH and concentrated under reduced pressure again. The crude product was purified by flash chromatography (silica, PE/EtOAc, gradient 0% to 10% EtOAc) to give the title compound (180 g) as a beige powder. UPLC-MS 1: m/z 251.0/252.9 [M-1], $t_R$=1.12 min. $^1$H-NMR (600 MHz, DMSO-d$_6$) δ ppm 12.05 (s, 1H), 10.19 (s, 1H), 7.18 (d, J=10.6 Hz, 1H).

Step 6: 4-Bromo-5-chloro-6-fluoro-3-hydroxy-2-phenyl-2,3-dihydrobenzofuran-2-carbonitrile (C-XII-f)

At RT 2-bromo-2-phenylacetonitrile (196 g, 1 mol) followed by DIPEA (238 mL, 1.4 mol) were added to a solution of 2-bromo-3-chloro-4-fluoro-6-hydroxybenzaldehyde (C-XII-e) (230 g, 910 mmol) in DCM (4.5 L) and stirring was continued for 5 h at RT. For workup the reaction mixture was diluted with DCM and washed with water. The aqueous layer was back-extracted with DCM. The combined organic phases were dried over anhydrous Na$_2$SO$_4$, filtered and concentrated under reduced pressure. The crude material was purified by flash chromatography (silica, heptane/EtOAc then DCM) to give the title compound as a diastereomeric mixture (230 g). UPLC-MS 1: m/z 366.0/368.0 [M−H]$^-$, $t_R$=1.20 min (both diastereoisomers coelute).

Step 7: 2-(Aminomethyl)-4-bromo-5-chloro-6-fluoro-2-phenyl-2,3-dihydrobenzofuran-3-ol (C-XII-g)

At RT a solution of borane-methyl sulfide complex (1.6 L, 3.25 mol, 2 M in THF) was added to a solution of 4-bromo-5-chloro-6-fluoro-3-hydroxy-3-methyl-2-phenyl-2,3-dihydrobenzofuran-2-carbonitrile (C-XII-f) (240 g, 0.65 mol) in THF (2.4 L). The reaction mixture was stirred at 65° C. for 2 h. The solution was cooled to RT and MeOH (5 L) was carefully added dropwise within 3 min. After 30 min at RT, 1 N HCl was added and stirring at RT was continued for 18 h. The reaction solution was quenched by the addition of a sat solution of NaHCO$_3$ and extracted with DCM. The combined organic phases were washed with water, dried over anhydrous Na$_2$SO$_4$, filtered and concentrated under reduced pressure to afford the title compound as a diastereomeric mixture (175 g) as a yellow foam. UPLC-MS 1: m/z 372.1/374.1 [M+1]$^+$, $t_R$=0.65 min and 0.78 min.

Step 8: (S)-(4-Bromo-5-chloro-6-fluoro-2-phenyl-2,3-dihydrobenzofuran-2-yl)methanamine (C-XII-h) and (R)-(4-bromo-5-chloro-6-fluoro-2-phenyl-2,3-dihydrobenzofuran-2-yl)methanamine (C-XII-i)

At RT triethylsilane (930 mL, 5.8 mol) followed by boron trifluoride diethyletherate (244 mL, 2 mol) were added to a solution of 2-(aminomethyl)-4-bromo-5-chloro-6-fluoro-2-phenyl-2,3-dihydrobenzofuran-3-ol (C-XII-g) (250 g, 671 mmol) in DCM (3 L) The reaction solution was stirred at RT overnight before it was quenched by the addition of a sat solution of NaHCO$_3$ (sat.) and extracted with DCM. The combined organic phases were washed with brine, dried over anhydrous Na$_2$SO$_4$, filtered and concentrated under reduced pressure. The crude product was purified by flash chromatography (silica, DCM/MeOH/NH$_3$ 100:1:0.5) to give racemic (4-bromo-5-chloro-6-fluoro-2-phenyl-2,3-dihydrobenzofuran-2-yl)methanamine (115 g). UPLC-MS 1: m/z 356.0/358.0 [M+H]$^+$, $t_R$=0.89 min.

The racemate (4-bromo-5-chloro-6-fluoro-2-phenyl-2,3-dihydrobenzofuran-2-yl)methanamine was subjected to chiral SFC (ChiralPak IC, 300×50 mm I.D., 10 μm, CO$_2$/IPA (0.1% ammonia) 7:3, 40° C., flow rate: 200 mL/min, 7 mL/injection, cycle time 7 min) to afford the two enantiomers (S)-(4-bromo-5-chloro-6-fluoro-2-phenyl-2,3-dihydrobenzofuran-2-yl)methanamine (C-XII-h) and (R)-(4-bromo-5-chloro-6-fluoro-2-phenyl-2,3-dihydrobenzofuran-2-yl)methanamine (C-XII-i) with an enantiomeric excess of >98%, respectively.

(S)-(4-bromo-5-chloro-6-fluoro-2-phenyl-2,3-dihydrobenzofuran-2-yl)methanamine (C-XII-h):

Chiral SFC: (Chiralpak IC 150×4.6 mm I.D., 3 μm, CO$_2$/IPA (0.05% DEA) 8:2, flow rate: 2.4 mL/min) $t_R$=5.64 min; UPLC-MS 1: m/z 356.0/358.0 [M+H]$^+$, $t_R$=0.89 min. $^1$H NMR (600 MHz, DMSO-d$_6$) δ 7.46 (d, J=7.6 Hz, 2H), 7.40 (t, J=7.6 Hz, 2H), 7.32 (t, J=7.3 Hz, 1H), 7.16 (d, J=9.6 Hz, 1H), 3.81 (dd, J=16.2, 1.8 Hz, 1H), 3.19 (d, J=16.2 Hz, 1H), 3.01 (s, 2H).

An X-ray crystal structure of (S)-(4-bromo-5-chloro-6-fluoro-2-phenyl-2,3-dihydrobenzofuran-2-yl)methanamine (C-XII-h) as a besylate salt confirmed the absolute configuration (S):

(R)-(4-bromo-5-chloro-6-fluoro-2-phenyl-2,3-dihydrobenzofuran-2-yl)methanamine C-XII-i):

Chiral SFC: (Chiralpak IC 150×4.6 mm I.D., 3 μm, CO$_2$/IPA (0.05% DEA) 8:2, flow rate: 2.4 mL/min) $t_R$=6.55 min; UPLC-MS 1: m/z 356.0/358.0 [M+H]$^+$, $t_R$=0.89 min.

Step 9: Tert-butyl (S)-((4-bromo-5-chloro-6-fluoro-2-phenyl-2,3-dihydrobenzofuran-2-yl)methyl)carbamate (C-XII-j)

Boc$_2$O (46.27 g, 212.00 mmol, 48.71 mL) was added in portions to a solution of (S)-(4-bromo-5-chloro-6-fluoro-2-phenyl-2,3-dihydrobenzofuran-2-yl)methanamine (C-XII-h) (72.00 g, 201.9 mmol) in DCM (1500 mL). The reaction mixture was stirred at RT for 16 h. After removal of the solvents under reduced pressure the crude product was purified by flash chromatography (silica, PE/EtOAc, gradient 0% to 15% EtOAc) to afford the title compound (102 g) as a colorless oil. UPLC-MS 1: m/z 458.1/460.0 [M+H]$^+$, $t_R$=1.48 min. $^1$H NMR (600 MHz, DMSO-d$_6$) δ 7.46 (d, J=7.6 Hz, 2H), 7.41 (t, J=7.7 Hz, 2H), 7.33 (t, J=7.3 Hz, 1H), 7.21 (t, J=6.2 Hz, 1H), 7.12 (d, J=9.5 Hz, 1H), 3.75 (d, J=16.4 Hz, 1H), 3.54 (dd, J=14.5, 6.5 Hz, 1H), 3.38 (dd, J=14.6, 6.1 Hz, 1H), 3.25 (d, J=16.6 Hz, 1H), 1.30 (s, 9H).

Step 10: Tert-butyl (S)-((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII)

At 100° C. PdCl$_2$(dppf)·CH$_2$Cl$_2$ adduct (3.58 g, 4.38 mmol) was added to a stirred solution of tert-butyl (S)-((4-bromo-5-chloro-6-fluoro-2-phenyl-2,3-dihydrobenzofuran-2-yl)methyl)carbamate (C-XII-j) (20 g, 43.8 mmol), bis(pinacolato)diboron (16.68 g, 65.7 mmol) and KOAc (12.89 g, 131 mmol) in dioxane (100 mL) under Ar and stirring at 100° C. was continued for 16 h. The reaction mixture was filtered over Celite and concentrated. The crude product was purified by flash chromatography (silica, hexane/EtOAc; gradient: 0% to 25% EtOAc) to afford the title compound (15.1 g) as a colorless powder. $^1$H NMR (600 MHz, DMSO-d$_6$) δ 7.44-7.38 (m, 4H), 7.34-7.31 (m, 1H), 7.17 (d, J=6.2 Hz, 1H), 7.08 (d, J=9.9 Hz, 1H), 3.70 (d, J=16.5 Hz, 1H), 3.56 (dd, J=14.7, 6.8 Hz, 1H), 3.37 (dd, J=14.5, 5.9 Hz, 1H), 3.22 (d, J=16.9 Hz, 1H), 1.32 (s, 9H), 1.31 (s, 6H), 1.30 (s, 6H). UPLC-MS 1: m/z 521.3/523.3 [M+17]$^+$, $t_R$=1.52 min.

Synthesis of (S)-(5-chloro-6-fluoro-2-phenyl-4-(4,4,5,5-tetramethyl-1,3,2-dioxaborolan-2-yl)-2,3-dihydrobenzofuran-2-yl)methanol (C-XIII)

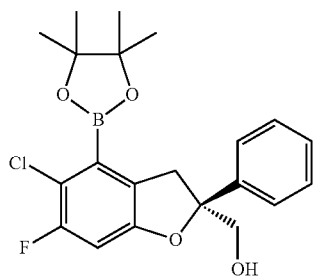

(C-XIII)

Reaction Scheme C-XIII

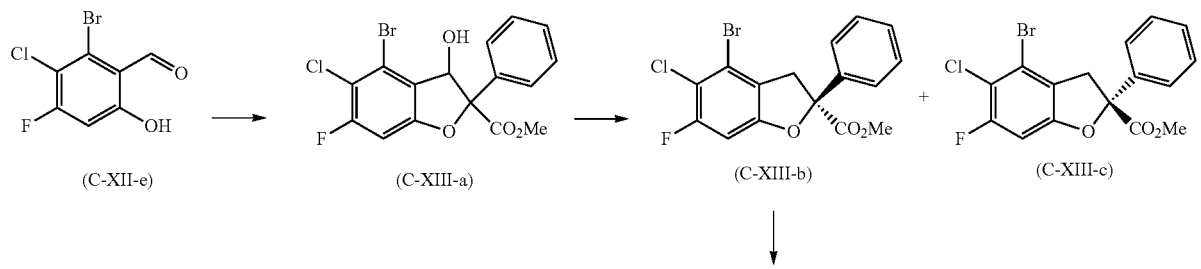

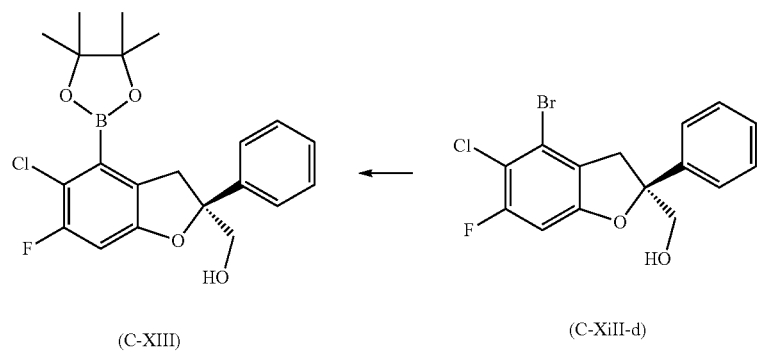

Step 1: Methyl 4-bromo-5-chloro-6-fluoro-3-hydroxy-2-phenyl-2,3-dihydrobenzofuran-2-carboxylate (C-XIII-a)

To a solution of 2-bromo-3-chloro-4-fluoro-6-hydroxybenzaldehyde (C-XII-e) (500 g, 1.97 mol) in ACN (2.3 L) were added methyl 2-bromo-2-phenylacetate (542 g, 2.37 mol) and DIEA (381.2 g, 2.96 mol). The reaction mixture was refluxed for 16 h. After removal of solvents under reduced pressure MTBE was added and the organic phase was washed with brine. The organic phase was dried over anhydrous $Na_2SO_4$ and concentrated under vacuum. The obtained crude material was purified by flash chromatography to give the title compound as a diastereomeric mixture (608 g) as a colorless powder. $^1$H NMR (300 MHz, DMSO-$d_6$) δ ppm: 7.44 (d, 1H, J=6 Hz), 7.43-7.41 (d, 1H, J=4.4 Hz), 7.39-7.36 (m, 4H), 6.90-6.88 (d, 0.5H, J=7.2 Hz), 6.10-6.08 (d, 0.4H, J=8.8 Hz), 5.60-5.58 (d, 0.47H, J=8.4 Hz), 5.42-5.41 (d, 0.52H, J=7.2 Hz), 3.72-3.64 (m, 3H).

Step 2: Methyl (S)-4-bromo-5-chloro-6-fluoro-2-phenyl-2,3-dihydrobenzofuran-2-carboxylate (C-XIII-b) and methyl (R)-4-bromo-5-chloro-6-fluoro-2-phenyl-2,3-dihydrobenzofuran-2-carboxylate (C-XIII-c)

At 0° C. and under a $N_2$ atmosphere $Et_3SiH$ (878 g, 7.55 mol) and $BF_3 \cdot Et_2O$ (643 g, 3.06 mol) were added dropwise to a solution of methyl 4-bromo-5-chloro-6-fluoro-3-hydroxy-2-phenyl-2,3-dihydrobenzofuran-2-carboxylate (C-XIII-a) (607 g, 1.51 mol) in DCM (6 L). The reaction mixture was stirred for 24 h at RT. A sat solution of $NaHCO_3$ was added to adjust the pH to 8-9. The organic layer was separated, washed with brine, dried over anhydrous $Na_2SO_4$, filtered and concentrated under reduced pressure. The obtained crude product was purified by flash chromatography (silica, hexane/EtOAc) to give racemic methyl-4-bromo-5-chloro-6-fluoro-2-phenyl-2,3-dihydrobenzofuran-2-carboxylate (362 g). $^1$H NMR (300 MHz, $CDCl_3$) b ppm: 7.56 (d, 2H, J=6.9 Hz), 7.44-7.37 (m, 3H), 6.84 (d, 1H, J=8.7 Hz), 4.19 (d, 1H, J=15.9 Hz), 3.79 (s, 3H), 3.55 (d, 1H, J=16.2 Hz).

The racemate methyl-4-bromo-5-chloro-6-fluoro-2-phenyl-2,3-dihydrobenzofuran-2-carboxylate was subjected to chiral SFC (ChiralPak AD, 300×50 mm I.D., 10 μm. $CO_2$/IPA 8:2, 38° C., flow rate: 200 mL/min, 5 mL/injection, cycle time 3.7 min) to afford methyl (S)-4-bromo-5-chloro-6-fluoro-2-phenyl-2,3-dihydrobenzofuran-2-carboxylate (C-XIII-b) and methyl (R)-4-bromo-5-chloro-6-fluoro-2-phenyl-2,3-dihydrobenzofuran-2-carboxylate (C-XIII-c) as pure enantiomers with an enantiomeric excess of >98%, respectively.

Methyl (S)-4-bromo-5-chloro-6-fluoro-2-phenyl-2,3-dihydrobenzofuran-2-carboxylate (C-XIII-b): Chiral SFC: (Chiralpak AD 150×4.6 mm I.D., 3 μm, $CO_2$/IPA (0.05% DEA) from 95/5 to 60/40, flow rate: 2.5 mL/min) $t_R$=3.02 min; UPLC-MS 1: no ionization, $t_R$=1.38 min.

Methyl (R)-4-bromo-5-chloro-6-fluoro-2-phenyl-2,3-dihydrobenzofuran-2-carboxylate (C-XIII-c): Chiral SFC: (Chiralpak AD 150×4.6 mm I.D., 3 μm, $CO_2$/IPA (0.05% DEA) from 95/5 to 60/40, flow rate: 2.5 mL/min) $t_R$=2.75 min; UPLC-MS 1: no ionization, $t_R$=1.38 min.

Step 3: (S)-(4-Bromo-5-chloro-6-fluoro-2-phenyl-2,3-dihydrobenzofuran-2-yl)methanol (C-XIII-d)

Under Ar $LiBH_4$ (4.52 g, 207 mmol) was added portionwise to a stirred solution of methyl (S)-4-bromo-5-chloro-6-fluoro-2-phenyl-2,3-dihydrobenzofuran-2-carboxylate (C-XIII-b) (40 g, 104 mmol) in a mixture of THF (400 mL) and MeOH (17 mL) at 0° C. and stirring at RT was continued for 30 min. The reaction mixture was quenched by the addition of a sat solution of $NaHCO_3$ and extracted with EtOAc. The combined organic layers were washed with a sat solution of $NaHCO_3$, dried over anhydrous $Na_2SO_4$ and concentrated under reduced pressure. The crude product was purified by flash chromatography (silica, hexane/EtOAc; gradient 0% to 40% EtOAc) to give the title product (39 g) as a colorless oil. UPLC-MS 1: m/z 401.2/403.2/405.1 [M+formate]$^-$, $t_R$=1.24 min.

Step 4: (S)-(5-Chloro-6-fluoro-2-phenyl-4-(4,4,5,5-tetramethyl-1,3,2-dioxaborolan-2-yl)-2,3-dihydrobenzofuran-2-yl)methanol (C-XIII)

A deoxygenated suspension of (S)-(4-bromo-5-chloro-6-fluoro-2-phenyl-2,3-dihydrobenzofuran-2-yl)methanol (C-XIII-d) (18.50 g, 51.7 mmol), bis(pinacolato)diboron (19.71 g, 78 mmol), KOAc (15.23 g, 155 mmol) and $PdCl_2(dppf) \cdot CH_2Cl_2$ adduct (4.22 g, 5.17 mmol) in dioxane (200 mL) was stirred at 100° C. for 16 h under an Ar atmosphere. The reaction mixture was filtered over Celite and concentrated under reduced pressure. The residue was purified by flash chromatography (silica, hexane/EtOAc; gradient: 0% to 50%) to afford the title product (19.7 g) as a yellow oil. $^1$H NMR (400 MHz, DMSO-$d_6$) δ 7.45-7.40 (m, 2H), 7.40-7.33 (m, 2H), 7.31-7.26 (m, 1H), 7.07 (d, J=9.9 Hz, 1H), 5.34-5.27 (m, 1H), 3.73 (d, J=16.5 Hz, 1H), 3.69-3.64 (m, 2H), 3.18 (d, J=16.4 Hz, 1H), 1.30 (s, 12H). UPLC-MS 1: m/z 449.1 [M+formate]$^-$, $t_R$=1.32 min.

Synthesis of tert-butyl (((2S,3S)-5-chloro-6-fluoro-3-hydroxy-2-phenyl-4-(4,4,5,5-tetramethyl-1,3,2-dioxaborolan-2-yl)-2,3-dihydrobenzofuran-2-yl)methyl)carbamate (C-XIV)

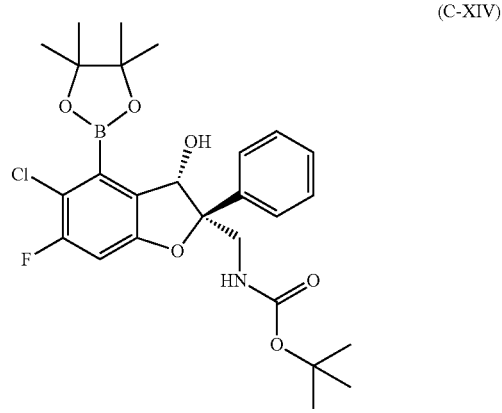 [SMILES: CC(C)(C)OC(=O)NC[C@]1(c2ccccc2)Oc2cc(F)c(Cl)c(B3OC(C)(C)C(C)(C)O3)c2[C@@H]1O]

(C-XIV)

Reaction Scheme C-XIV

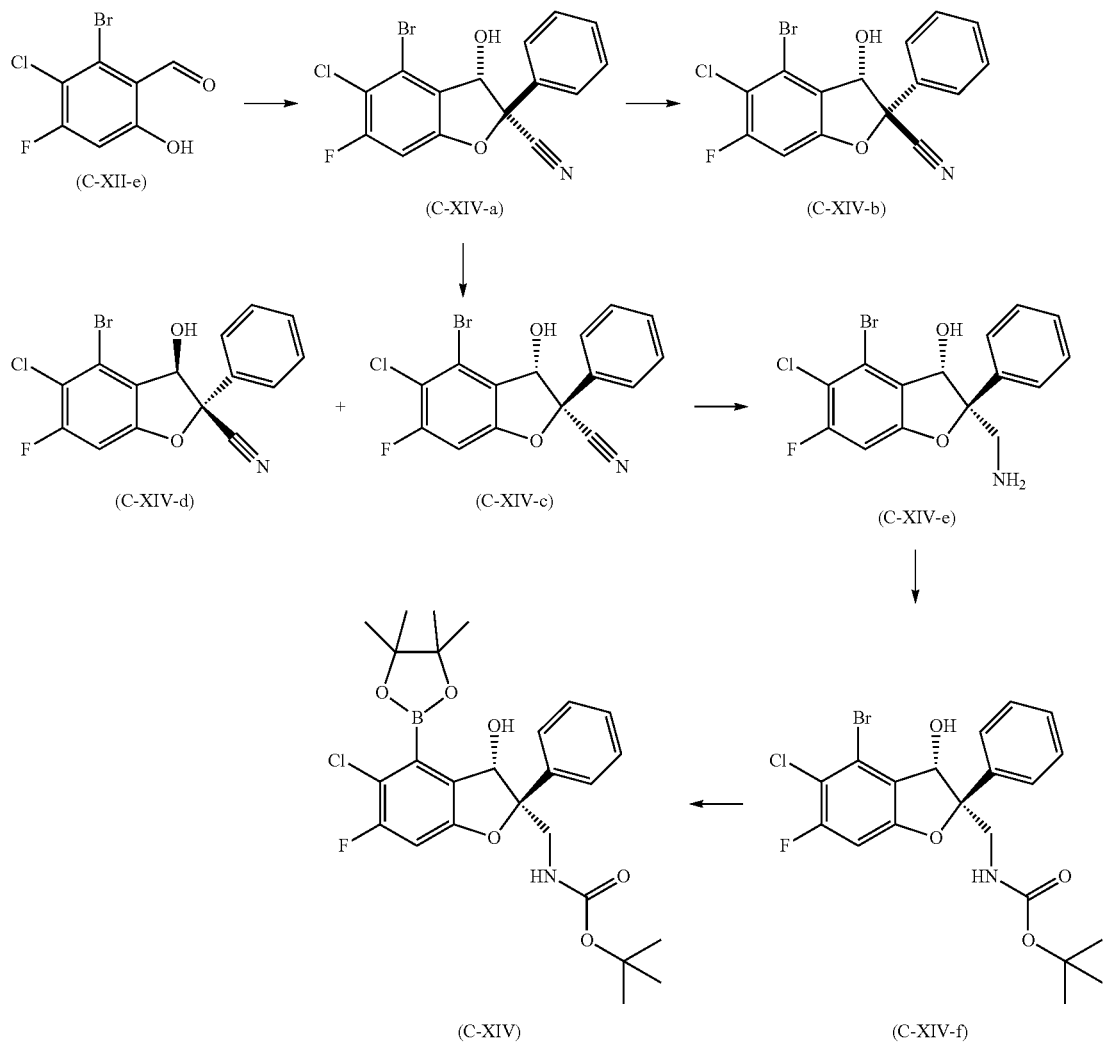

Step 1: (2S*,3S*)-4-Bromo-5-chloro-6-fluoro-3-hydroxy-2-phenyl-2,3-dihydrobenzofuran-2-carbonitrile (C-XIV-a) and (2R*,3S*)-4-bromo-5-chloro-6-fluoro-3-hydroxy-2-phenyl-2,3-dihydrobenzofuran-2-carbonitrile (C-XIV-b)

At RT 2-bromo-2-phenylacetonitrile (648.5 g, 2.845 mol) and DIPEA (734.2 g, 5.69 mol) were added to a solution of 2-bromo-3-chloro-4-fluoro-6-hydroxybenzaldehyde (C-XII-e) (500 g, 1.973 mol) in dichloromethane (6 L). The resulting brown solution was stirred at RT for 21 h. The solution was then diluted with DCM and washed with water. The aqueous layer was back-extracted with DCM. The combined organic phases were washed with water, brine, dried over anhydrous $Na_2SO_4$ and concentrated under reduced pressure to give a diastereomeric cis/trans mixture of 4-bromo-5-chloro-6-fluoro-3-hydroxy-2-phenyl-2,3-dihydrobenzofuran-2-carbonitrile. The cis- and trans-configurated racemic title compounds were separated by two consecutive flash chromatographies (silica, heptane/EtOAc; gradient: 2% to 20% EtOAc):

(2S*,3S*)-4-bromo-5-chloro-6-fluoro-3-hydroxy-2-phenyl-2,3-dihydrobenzofuran-2-carbonitrile (C-XIV-a):

$^1$HNMR (600 MHz, DMSO-$d_6$) δ 7.55-7.48 (m, 7H), 5.27 (d, J=7.7 Hz, 1H). UPLC-MS 1: m/z 412.0/414.0 [M+formate]$^-$, $t_R$=1.17 min.

(2R*,3S*)-4-bromo-5-chloro-6-fluoro-3-hydroxy-2-phenyl-2,3-dihydrobenzofuran-2-carbonitrile (C-XIV-b): $^1$H NMR (600 MHz, DMSO-$d_6$) δ 7.60-7.55 (m, 3H), 7.55-7.47 (m, 3H), 6.50 (d, J=8.6 Hz, 1H), 5.54 (d, J=8.5 Hz, 1H). UPLC-MS 1: m/z 412.0/414.0 [M+formate]$^-$, $t_R$=1.17 min.

Step 2: (2S,3S)-4-Bromo-5-chloro-6-fluoro-3-hydroxy-2-phenyl-2,3-dihydrobenzofuran-2-carbonitrile (C-XIV-c) and (2R,3R)-4-Bromo-5-chloro-6-fluoro-3-hydroxy-2-phenyl-2,3-dihydrobenzofuran-2-carbonitrile (C-XIV-d)

The racemate (2S*,3S*)-4-bromo-5-chloro-6-fluoro-3-hydroxy-2-phenyl-2,3-dihydrobenzofuran-2-carbonitrile (C-XIV-a) (504 g, 1.37 mol) was subjected to chiral SFC (ChiralPak AD, 300×50 mm I.D., 10 μm. $CO_2$/IPA 8:2, 38° C., flow rate: 200 mL/min, 6 mL/injection, cycle time 12 min) to afford (2S,3S)-4-bromo-5-chloro-6-fluoro-3-hydroxy-2-phenyl-2,3-dihydrobenzofuran-2-carbonitrile (C-XVI-c) (228 g) and (2R,3R)-4-bromo-5-chloro-6-fluoro-3-hydroxy-2-phenyl-2,3-dihydrobenzofuran-2-carbonitrile (C-XIV-d) (232 g) as pure enantiomers with an enantiomeric excess of >98%, respectively.

(2S,3S)-4-Bromo-5-chloro-6-fluoro-3-hydroxy-2-phenyl-2,3-dihydrobenzofuran-2-carbonitrile (C-XIV-c): Chiral SFC: (Chiralpak AD 150×4.6 mm I.D., 3 μm, $CO_2$/IPA (0.05% DEA) from 95/5 to 60/40, flow rate: 2.5 mL/min) $t_R$=3.68 min; $^1$H NMR (600 MHz, DMSO-$d_6$) δ 7.59-7.44 (m, 7H), 5.30 (d, J=7.0 Hz, 1H); UPLC-MS 1: m/z 385.1/387.0 $[M+NH_4]^+$, $t_R$=1.20 min.

The absolute configuration (2S,3S) was confirmed by an X-ray crystal structure: (2R,3R)-4-Bromo-5-chloro-6-fluoro-3-hydroxy-2-phenyl-2,3-dihydrobenzofuran-2-carbonitrile (C-XIV-d): Chiral SFC: (Chiralpak AD 150×4.6 mm I.D., 3 μm, $CO_2$/IPA (0.05% DEA) from 95/5 to 60/40, flow rate: 2.5 mL/min) $t_R$=4.18 min; UPLC-MS 1: m/z 385.1/387.2 $[M+NH_4]^+$, $t_R$=1.20 min. The absolute configuration (2R,3R) was confirmed by an X-ray crystal structure:

Step 3: (2S,3S)-2-(Aminomethyl)-4-bromo-5-chloro-6-fluoro-2-phenyl-2,3-dihydrobenzofuran-3-ol (C-XIV-e)

At RT borane-methyl sulfide complex (139 mL, 278 mmol, 2M in THF) was added to a stirred solution of (2S,3S)-4-bromo-5-chloro-6-fluoro-3-hydroxy-2-phenyl-2,3-dihydrobenzofuran-2-carbonitrile (C-XIV-c) (20.5 g, 55.6 mmol) in THF (309 mL) and the yellow solution was stirred at 65° C. for 3.25 h. Under ice bath cooling the reaction mixture was quenched very slowly with MeOH (100 mL) and stirred for 30 min, then 1N HCl (200 mL) was added and stirring was continued overnight. A sat solution of $NaHCO_3$ was added and the reaction mixture was extracted with EtOAc. The combined organic extracts were washed with brine, dried over anhydrous $Na_2SO_4$, filtered and concentrated to afford the title compound (22 g) which was used in the next step without further purification. UPLC-MS 1: m/z 372.0/374.0 $[M+H]^+$, $t_R$=0.74 min.

Step 4: tert-Butyl (((2S,3S)-4-bromo-5-chloro-6-fluoro-3-hydroxy-2-phenyl-2,3-dihydrobenzofuran-2-yl)methyl)carbamate (C-XIV-f)

At RT Boc-anhydride (15.03 mL, 64.7 mmol) was added to a stirred solution of (2S,3S)-2-(aminomethyl)-4-bromo-5-chloro-6-fluoro-2-phenyl-2,3-dihydrobenzofuran-3-ol (C-XIV-e) (21.93 g, 58.9 mmol) in DCM (294 mL). The reaction mixture was stirred at RT for 26 h before a sat solution of $NaHCO_3$ was added for workup. The mixture was extracted with DCM and the combined organic extracts were washed with water and brine and concentrated to afford the title compound (33.2 g). UPLC-MS 1: m/z 516.2/518.2 [M+formate]$^-$, $t_R$=1.30 min.

Step 5: tert-Butyl (((2S,3S)-5-chloro-6-fluoro-3-hydroxy-2-phenyl-4-(4,4,5,5-tetramethyl-1,3,2-dioxaborolan-2-yl)-2,3-dihydrobenzofuran-2-yl)methyl)carbamate (C-XIV)

$PdCl_2(dppf)\cdot CH_2Cl_2$ adduct (2.5 g, 3.01 mmol) was added at 80° C. to a stirred suspension of tert-butyl (((2S,3S)-4-bromo-5-chloro-6-fluoro-3-hydroxy-2-phenyl-2,3-dihydrobenzofuran-2-yl)methyl)carbamate (C-XIV-f) (16.2 g, 30.1 mmol), bis(pinacolato)diboron (11.5 g, 45.2 mmol) and potassium acetate (8.9 g, 90 mmol) in 1,4-dioxane (75 mL). The reaction mixture was stirred at 100° C. for 28 h. After completion of the reaction the mixture was filtered through Celite which was carefully rinsed with toluene. Concentration of the filtrate afforded the crude product which was purified by flash chromatography (silica, cyclohexane/EtOAc; gradient: 0% to 30% EtOAc) to give the title product (8.2 g) as a colorless powder. $^1$H NMR (400 MHz, DMSO-$d_6$) δ 7.42-7.36 (m, 2H), 7.36-7.30 (m, 2H), 7.29-7.22 (m, 1H), 7.13 (d, J=9.4 Hz, 1H), 6.30-6.25 (m, 1H). 6.13 (d, J=6.7 Hz, 1H), 5.16 (d, J=6.5 Hz, 1H), 3.80 (dd, J=14.4, 7.1 Hz, 1H), 3.56 (dd, J=14.6, 5.0 Hz, 1H), 1.31 (s, 6H), 1.27 (s, 6H), 1.22 (s, 9H). UPLC-MS 1: m/z 518.3 [M−H]$^-$, $t_R$=1.43 min.

Synthesis of tert-butyl (((2S,3S)-5-chloro-6-fluoro-3-methoxy-2-phenyl-4-(4,4,5,5-tetramethyl-1,3,2-dioxaborolan-2-yl)-2,3-dihydrobenzofuran-2-yl)methyl)carbamate (C-XV)

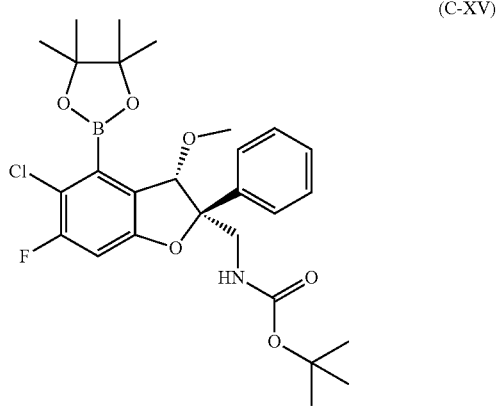 [SMILES: CO[C@H]1c2c(cc(F)c(Cl)c2B2OC(C)(C)C(C)(C)O2)O[C@]1(CNC(=O)OC(C)(C)C)c1ccccc1]

(C-XV)

Reaction Scheme. C-XV

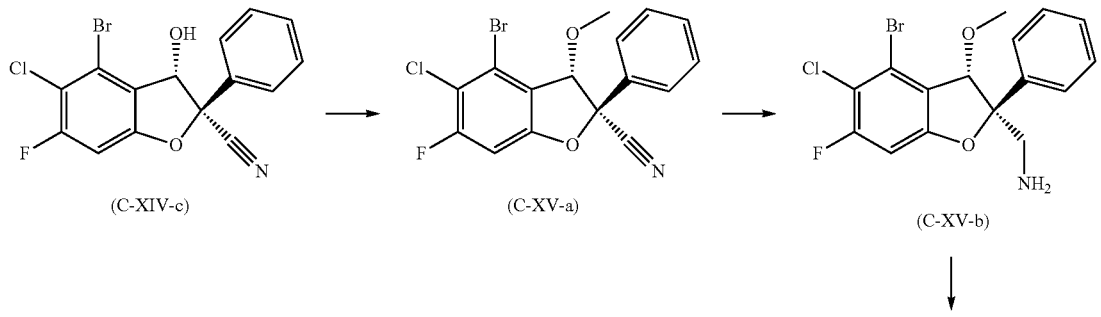

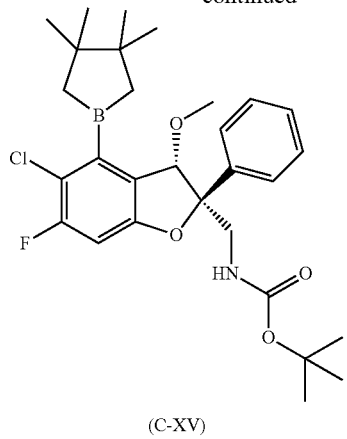

(C-XV)

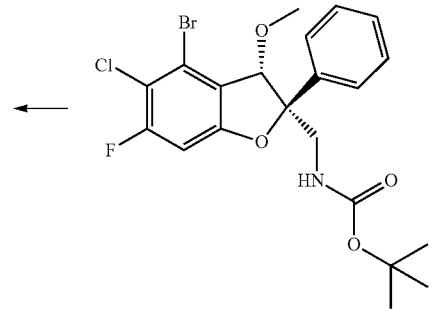

(C-XV-c)

Step 1: (2S,3S)-4-Bromo-5-chloro-6-fluoro-3-methoxy-2-phenyl-2,3-dihydrobenzofuran-2-carbonitrile (C-XV-a)

At 0° C. NaH (0.206 g, 8.14 mmol, 95%) was slowly added to a solution of (2S,3S)-4-bromo-5-chloro-6-fluoro-3-hydroxy-2-phenyl-2,3-dihydrobenzofuran-2-carbonitrile (C-XIV-c) (2.0 g, 5.43 mmol) in THF (20 mL) and DMF (5 mL). After 1 h, methyl iodide (1.02 mL, 16.3 mmol) was slowly added and the reaction mixture was stirred at RT for 15 min. A sat solution of NaHCO$_3$ was added and the mixture was extracted with ethyl acetate. Drying of the combined organic layers over anhydrous MgSO$_4$ and concentration gave the title compound (2.35 g). UPLC-MS 1: product not ionizable, $t_R$=1.34 min

Step 2: ((2S,3S)-4-Bromo-5-chloro-6-fluoro-3-methoxy-2-phenyl-2,3-dihydrobenzofuran-2-yl) methanamine (C-XV-b)

Borane-methyl sulfide complex (14.5 mL, 29.0 mmol, 2 M in THF) was added to a stirred solution of (2S,3S)-4-bromo-5-chloro-6-fluoro-3-methoxy-2-phenyl-2,3-dihydrobenzofuran-2-carbonitrile (C-XV-a) (2.22 g, 5.8 mmol) in THF (40 mL) and the reaction mixture was stirred at 60° C. for 3 h. The reaction mixture was cooled to RT, MeOH and 1 N HCl were carefully added and the mixture was vigorously stirred at RT for 3 h. A sat solution of NaHCO$_3$ was added and the mixture was extracted with EtOAc. The combined extracts were dried (MgSO$_4$) and concentrated to give the crude product which was purified by flash chromatography (silica, DCM/MeOH, gradient: 0% to 10% MeOH) to furnish the title compound (1.27 g) as a colorless foam. UPLC-MS 1: m/z 386.1 [M+H]$^+$, $t_R$=0.0.85 min.

Step 3: Tert-butyl (((2S,3S)-4-bromo-5-chloro-6-fluoro-3-methoxy-2-phenyl-2,3-dihydrobenzofuran-2-yl)methyl)carbamate (C-XV-c)

A solution of ((2S,3S)-4-bromo-5-chloro-6-fluoro-3-methoxy-2-phenyl-2,3-dihydrobenzofuran-2-yl)methanamine (C-XV-b) (615 mg, 1.6 mmol) and Boc-anhydride (0.406 mL, 1.750 mmol) in DCM (18 mL) was stirred at RT for 2 h. A sat solution of NaHCO$_3$ was added and the mixture was extracted with EtOAc. The combined extracts were dried (MgSO$_4$) and concentrated to give the title compound (766 mg, 1.6 mmol) as a colorless powder. UPLC-MS 1: m/z 530.3 [M+formate]$^-$, $t_R$=1.45 min.

Step 4: Tert-butyl (((2S,3S)-5-chloro-6-fluoro-3-methoxy-2-phenyl-4-(4,4,5,5-tetramethyl-1,3,2-dioxaborolan-2-yl)-2,3-dihydrobenzofuran-2-yl)methyl)carbamate (C-XV)

A solution of tert-butyl (((2S,3S)-4-bromo-5-chloro-6-fluoro-3-methoxy-2-phenyl-2,3-dihydrobenzofuran-2-yl)methyl)carbamate (C-XV-c) (1.20 g, 2.5 mmol), bis(pinacolato)diboron (0.88 g, 3.5 mmol), PdCl$_2$(dppf)-CH$_2$Cl$_2$ adduct (0.201 g, 0.25 mmol) and KOtBu (0.415 g, 3.7 mmol) was stirred at 100° C. for 20 min. The reaction mixture was cooled to RT and filtered over Celite. The filter cake was thoroughly washing with toluene. The organic phase was concentrated. The residue was purified by flash chromatography (silica, cyclohexane/EtOAc, gradient: EtOAc 0% to 20%) to afford the title compound (687 mg) as a slightly pink powder. UPLC-MS 1: m/z 578.4 [M+formate]$^-$, $t_R$=1.49 min

Synthesis of tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)carbamate (C-XVI)

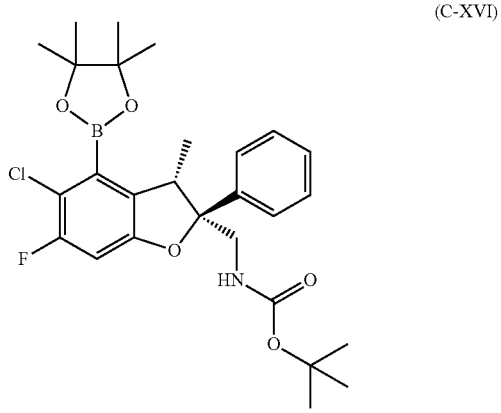 [SMILES: C[C@H]1c2c(cc(F)c(Cl)c2B2OC(C)(C)C(C)(C)O2)O[C@]1(CNC(=O)OC(C)(C)C)c1ccccc1]

(C-XVI)

Reaction Scheme C-XVI

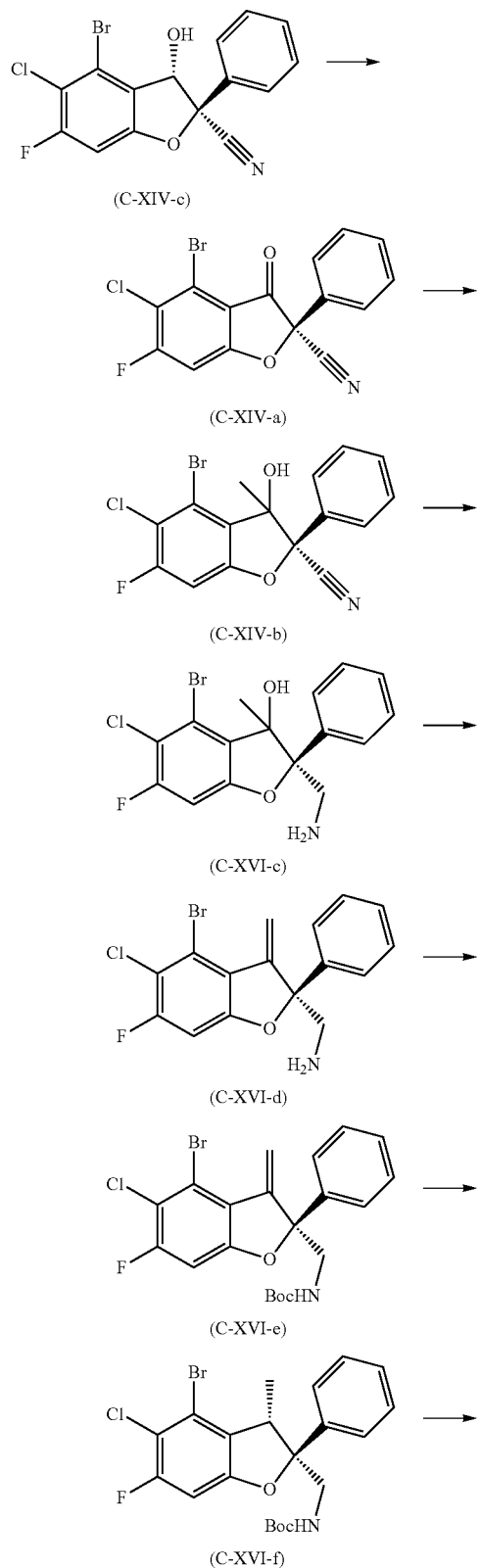

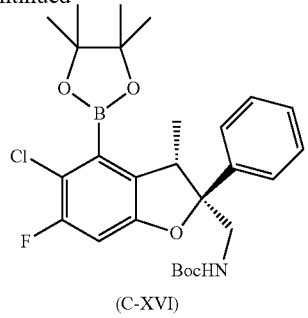

(C-XVI)

Step 1: (S)-4-Bromo-5-chloro-6-fluoro-3-oxo-2-phenyl-2,3-dihydrobenzofuran-2-carbonitrile (1) (C-XVI-a)

To a stirred solution of (2S,3S)-4-bromo-5-chloro-6-fluoro-3-hydroxy-2-phenyl-2,3-dihydrobenzofuran-2-carbonitrile (C-XIV-c) (12 g, 32.6 mmol) in DCM (200 mL) was added Dess-Martin Periodinane (16.57 g, 39.1 mmol) at 0° C. The ice bath was removed and the reaction mixture was stirred at RT for 16 h. The reaction mixture was quenched with 10% sodium thiosulfate solution and a sat solution of NaHCO₃ and extracted with DCM. The organic phase was washed with water and brine, dried and concentrated. The crude product was purified by flash chromatography (silica, eluent: DCM/EtOAc; gradient: 0% to 100% EtOAc) to afford the desired product (11.79 g). UPLC-MS 1: m/z 363.9 [M−H]⁻, $t_R$=1.26 min.

Step 2: (2S)-4-Bromo-5-chloro-6-fluoro-3-hydroxy-3-methyl-2-phenyl-2,3-dihydrobenzofuran-2-carbonitrile (C-XVI-b)

To a stirred solution of (S)-4-bromo-5-chloro-6-fluoro-3-oxo-2-phenyl-2,3-dihydrobenzofuran-2-carbonitrile (C-XVI-a) (24.17 g, 65.9 mmol) in THF (500 mL) was added methylmagnesium bromide (30.8 mL, 92 mmo, 3 M in Et₂O) at −50° C. and the reaction mixture was allowed to warm to −30° C. over 1.5 h. The reaction mixture was quenched at −30° C. with a sat ammonium chloride solution. The mixture was washed with a sat ammonium chloride solution, extracted with EtOAc and the combined organic extracts were washed with water and brine, dried (Na₂SO₄) and concentrated. The crude product was triturated in DCM and filtered to afford the desired product. More product was isolated by concentration of the filtrate and purification of the residue by flash chromatography (silica, heptane/EtOAc; gradient: 0% to 30% EtOAc). Both product portions were combined to afford the title compound (24.53 g) as a mixture of diastereoisomers. UPLC-MS 1: m/z 380.0 [M−H]⁻, $t_R$=1.20 min (diastereoisomers coelute).

Step 3: (2S)-2-(Aminomethyl)-4-bromo-5-chloro-6-fluoro-3-methyl-2-phenyl-2,3-dihydrobenzofuran-3-ol (C-XVI-c)

At RT borane methyl sulfide complex (100 mL, 200 mmol, 2M in THF) was added to a stirred solution of (2S)-4-bromo-5-chloro-6-fluoro-3-hydroxy-3-methyl-2-phenyl-2,3-dihydrobenzofuran-2-carbonitrile (C-XVI-b) (25.5 g, 66.6 mmol) in THF (400 mL) and stirring at 80° C. was continued for 2 h. The reaction mixture was quenched by careful addition of MeOH at 0° C. and stirred overnight at RT. THF and MeOH were evaporated under reduced pressure. EtOAc and a sat solution of NaHCO$_3$ were added, the organic phase was separated and the aqueous phase was extracted with EtOAc. The combined organic extracts were washed with water and brine, dried (Na$_2$SO$_4$) and concentrated. The crude product was triturated in DCM and filtered to afford the desired product. The concentrated filtrate was purified by flash chromatography (silica, DCM/(7N ammonia in MeOH), gradient 0% to 10% (7N ammonia in MeOH)) to afford additional product. Both product portions were combined to yield the title compound (18.7 g) as a mixture of diastereoisomers. UPLC-MS 1: m/z 386.0 [M+H]$^+$, $t_R$=0.0.64 min and 0.78 min.

Step 4: (R)-(4-Bromo-5-chloro-6-fluoro-3-methylene-2-phenyl-2,3-dihydrobenzofuran-2-yl)methanamine (C-XVI-d)

To a stirred solution of (2S)-2-(aminomethyl)-4-bromo-5-chloro-6-fluoro-3-methyl-2-phenyl-2,3-dihydrobenzofuran-3-ol (C-XVI-c) (18.73 g, 48.4 mmol) in DCM (200 mL) was added BF$_3$·OEt$_2$ (12.3 mL, 97 mmol) at 0° C. and stirring at RT was continued for 6 h. The reaction mixture was quenched with a sat solution of NaHCO$_3$ and extracted with DCM. The combined organic extracts were washed with brine, dried (Na$_2$SO$_4$) and concentrated to afford the title compound. UPLC-MS 1: product not ionizable; $t_R$=0.84 min.

Step 5: (R)-tert-Butyl ((4-bromo-5-chloro-6-fluoro-3-methylene-2-phenyl-2,3-dihydrobenzofuran-2-yl)methyl)carbamate (C-XVI-e)

At 0° C. TEA (13.5 mL, 97 mmol) followed by Boc-anhydride (16.9 mL, 72.7 mmol) was added to a stirred solution of (R)-(4-bromo-5-chloro-6-fluoro-3-methylene-2-phenyl-2,3-dihydrobenzofuran-2-yl)methanamine (C-XVI-d) (17.86 g, 48.4 mmol) in DCM (250 mL) and stirring at RT was continued for 2.5 h. The reaction mixture was diluted with DCM and water, the organic phase was separated and the aqueous phase was extracted with DCM. The combined organic extracts were washed with water and brine, dried (Na$_2$SO$_4$) and concentrated. The crude product was purified by flash chromatography (silica, heptane/EtOAc. gradient 0% to 20% EtOAc) to afford the title product (20.17 g) as a colorless foam. UPLC-MS 1: product not ionizable; $t_R$=1.46 min; $^1$H NMR (400 MHz, DMSO-d$_6$) δ 7.53-7.22 (m, 6H), 6.97 (t, J=6.2 Hz, 1H), 6.38 (s, 1H), 5.33 (d, J=1.4 Hz, 1H), 3.79 (t, J=6.1 Hz, 2H), 1.30 (s, 9H).

Step 6: tert-Butyl (((2S,3S)-4-bromo-5-chloro-6-fluoro-3-methyl-2-phenyl-2,3-dihydrobenzofuran-2-yl)methyl)carbamate (C-XVI-f)

TEA (30 mL, 215 mmol) and 3-nitrobenzenesulfonyl hydrazine (18.7 g, 86 mmol) were added to a stirred solution of (R)-tert-butyl ((4-bromo-5-chloro-6-fluoro-3-methylene-2-phenyl-2,3-dihydrobenzofuran-2-yl)methyl)carbamate (C-XVI-e) (20.17 g, 38.7 mmol) in DCE (400 mL) and the reaction mixture was stirred at 60° C. for 18 h. Over the next 72 h more TEA (in total: 78 mL, 559 mmol) and 3-nitrobenzenesulfonyl hydrazine (in total: 48.6 g, 222 mmol) were added in 3 portions until the reaction was complete. Water and brine were added and the organic phase was separated. The aqueous phase was extracted with DCM once again. The combined organic phases were dried over anhydrous Na$_2$SO$_4$ and concentrated. The crude product was purified by two consecutive flash chromatographies (silica, heptane/DCM, gradient: 0% to 100% DCM) and (silica, heptane/EtOAC, gradient 0% to 15% EtOAc) to afford the title product (15.7 g) as a colorless powder. UPLC-MS 1: m/z 370.1/372.1 [M+H−Boc]$^+$, $t_R$=1.46 min; $^1$H NMR (400 MHz, DMSO-d$_6$) δ 7.55-7.11 (m, 6H), 6.56 (t, J=6.2 Hz, 1H), 3.83 (dd, J=14.2, 6.7 Hz, 1H), 3.70-3.52 (m, 2H), 1.39 (d, J=7.0 Hz, 3H), 1.19 (s, 9H). Only one diastereoisomer was isolated and assigned to have the indicated absolute stereochemistry by comparison of its $^1$H NMR spectrum with the $^1$H NMR spectra of structurally related intermediates C-XI-g and C-XI-h.

Step 7: Tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)carbamate (C-XVI)

A suspension of tert-butyl (((2S,3S)-4-bromo-5-chloro-6-fluoro-3-methyl-2-phenyl-2,3-dihydrobenzofuran-2-yl)methyl)carbamate (C-XVI-f) (6.8 g, 14.44 mmol), bis(pinacolato)diboron (5.50 g, 21.7 mmol), KOtBu (2.269 g, 20.22 mmol) and PdCl$_2$(dppf)-CH$_2$Cl$_2$ adduct (1.180 g, 1.444 mmol) in toluene (72 mL) was stirred at 105° C. for 6 h. The reaction mixture was filtered through Celite and concentrated. The crude product was purified by flash chromatography (silica, eluent cyclohexane/EtOAc, gradient EtOAc 0% to 20%) to afford the desired product (4.47 g). $^1$H NMR (400 MHz, DMSO-d$_6$) δ 7.43-7.38 (m, 2H), 7.32-7.27 (m, 2H), 7.25-7.20 (m, 1H), 7.11 (d, J=9.8 Hz, 1H), 6.46-6.41 (m, 1H). 3.76 (dd, J=13.7, 6.1 Hz, 1H), 3.63-3.55 (m, 2H), 1.33-1.30 (m, 15H), 1.21 (s, 9H). UPLC-MS 1: m/z 518.3 [M+H]$^+$, $t_R$=1.49 min.

Synthesis of ((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methanol (C-XVII)

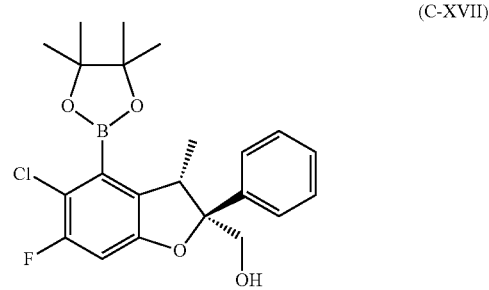 [SMILES: C[C@H]1c2c(cc(F)c(Cl)c2B2OC(C)(C)C(C)(C)O2)O[C@]1(CO)c1ccccc1]

(C-XVII)

Reaction Scheme CXVII

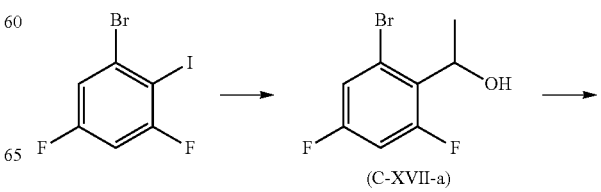

(C-XVII-a)

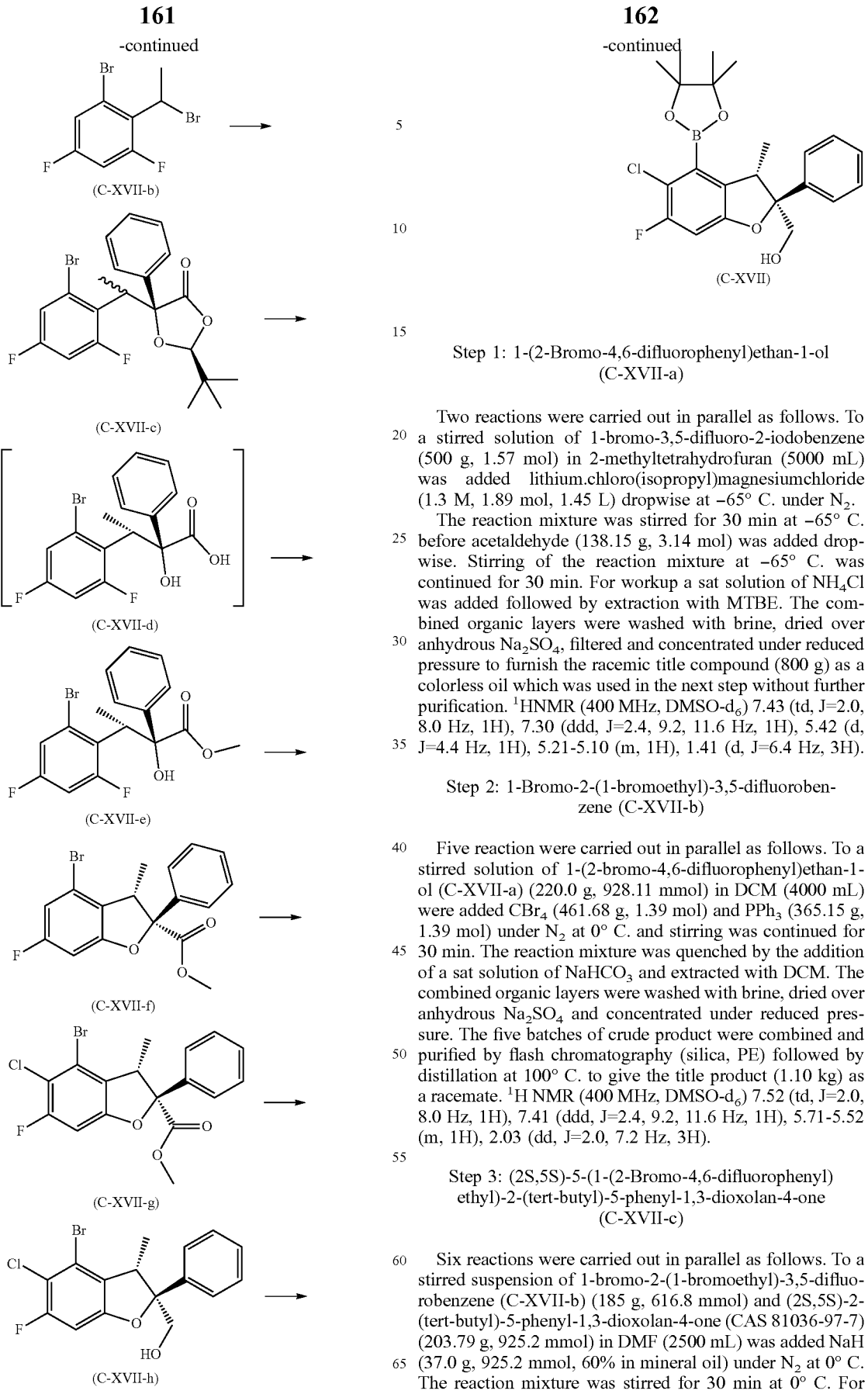

Step 1: 1-(2-Bromo-4,6-difluorophenyl)ethan-1-ol (C-XVII-a)

Two reactions were carried out in parallel as follows. To a stirred solution of 1-bromo-3,5-difluoro-2-iodobenzene (500 g, 1.57 mol) in 2-methyltetrahydrofuran (5000 mL) was added lithium.chloro(isopropyl)magnesiumchloride (1.3 M, 1.89 mol, 1.45 L) dropwise at −65° C. under $N_2$.

The reaction mixture was stirred for 30 min at −65° C. before acetaldehyde (138.15 g, 3.14 mol) was added dropwise. Stirring of the reaction mixture at −65° C. was continued for 30 min. For workup a sat solution of $NH_4Cl$ was added followed by extraction with MTBE. The combined organic layers were washed with brine, dried over anhydrous $Na_2SO_4$, filtered and concentrated under reduced pressure to furnish the racemic title compound (800 g) as a colorless oil which was used in the next step without further purification. $^1$HNMR (400 MHz, DMSO-$d_6$) 7.43 (td, J=2.0, 8.0 Hz, 1H), 7.30 (ddd, J=2.4, 9.2, 11.6 Hz, 1H), 5.42 (d, J=4.4 Hz, 1H), 5.21-5.10 (m, 1H), 1.41 (d, J=6.4 Hz, 3H).

Step 2: 1-Bromo-2-(1-bromoethyl)-3,5-difluorobenzene (C-XVII-b)

Five reaction were carried out in parallel as follows. To a stirred solution of 1-(2-bromo-4,6-difluorophenyl)ethan-1-ol (C-XVII-a) (220.0 g, 928.11 mmol) in DCM (4000 mL) were added $CBr_4$ (461.68 g, 1.39 mol) and $PPh_3$ (365.15 g, 1.39 mol) under $N_2$ at 0° C. and stirring was continued for 30 min. The reaction mixture was quenched by the addition of a sat solution of $NaHCO_3$ and extracted with DCM. The combined organic layers were washed with brine, dried over anhydrous $Na_2SO_4$ and concentrated under reduced pressure. The five batches of crude product were combined and purified by flash chromatography (silica, PE) followed by distillation at 100° C. to give the title product (1.10 kg) as a racemate. $^1$H NMR (400 MHz, DMSO-$d_6$) 7.52 (td, J=2.0, 8.0 Hz, 1H), 7.41 (ddd, J=2.4, 9.2, 11.6 Hz, 1H), 5.71-5.52 (m, 1H), 2.03 (dd, J=2.0, 7.2 Hz, 3H).

Step 3: (2S,5S)-5-(1-(2-Bromo-4,6-difluorophenyl)ethyl)-2-(tert-butyl)-5-phenyl-1,3-dioxolan-4-one (C-XVII-c)

Six reactions were carried out in parallel as follows. To a stirred suspension of 1-bromo-2-(1-bromoethyl)-3,5-difluorobenzene (C-XVII-b) (185 g, 616.8 mmol) and (2S,5S)-2-(tert-butyl)-5-phenyl-1,3-dioxolan-4-one (CAS 81036-97-7) (203.79 g, 925.2 mmol) in DMF (2500 mL) was added NaH (37.0 g, 925.2 mmol, 60% in mineral oil) under $N_2$ at 0° C. The reaction mixture was stirred for 30 min at 0° C. For workup the mixture was quenched by the addition of a sat solution of NaHCO$_3$ and extracted with MTBE. The combined organic layers were washed with brine, dried over anhydrous Na$_2$SO$_4$, filtered and concentrated under reduced pressure. The crude material was purified by flash chromatography (silica, PE/EtOAc, gradient: 0% to 5% EtOAc) to give the title compound (810 g) as a mixture of diastereoisomers as a light yellow oil.

Step 4: Methyl (2S,3S)-3-(2-bromo-4,6-difluorophenyl)-2-hydroxy-2-phenylbutanoate (C-XVII-e)

Four reactions were carried out in parallel as follows. To a stirred solution of (2S,5S)-5-(1-(2-bromo-4,6-difluorophenyl)ethyl)-2-(tert-butyl)-5-phenyl-1,3-dioxolan-4-one (C-XVII-c) (202 g, 459.8 mmol) in MeOH (2800 mL) was added sodium methanolate (331.23 g, 708 mL, 1.84 mol, 30% in MeOH) at RT and stirring at 60° C. was continued for 1 h. The reaction mixture was cooled down to RT, quenched by the addition of a sat solution of NaHCO$_3$ and extracted with DCM. The combined organic layers were washed with brine, dried over anhydrous Na$_2$SO$_4$, filtered and concentrated under reduced pressure to afford the crude product. The four batches of crude product were combined and purified by flash chromatography (silica, PE/EtOAc, gradient: 0% to 5% EtOAc) to give the title product (60 g) as a colorless oil with an enantiomeric excess of 82%: Chiral SFC: Chiralcel OD-3, 150×4.6 mm I.D., 3 μm, CO$_2$/ethanol (0.05% DEA), gradient: from 95/5 to 60/40 in 5.5 min and hold at 60/40 for 3 min, then 95/5 for 1.5 min; column temperature 40° C., flow rate: 2.5 mL/min, $t_R$=1.94 min; UPLC-MS 1: not ionizable, $t_R$=1.24 min (other diastereoisomer methyl (2S,3R)-3-(2-bromo-4,6-difluorophenyl)-2-hydroxy-2-phenylbutanoate: UPLC-MS 1: not ionizable, $t_R$=1.31 min).

In addition, the pH of the combined aqueous layers was adjusted to pH=3-4 with 1 N HCl and back-extracted with EtOAc. The combined organic extracts were dried over anhydrous Na$_2$SO$_4$, filtered and concentrated to give the crude carboxylic acid by-product (2S,3S)-3-(2-bromo-4,6-difluorophenyl)-2-hydroxy-2-phenylbutanoic acid (C-XVII-d) (460 g) as a colorless powder: $^1$H NMR (400 MHz, DMSO-d$_6$) 7.38-7.28 (m, 2H), 7.21-7.03 (m, 5H), 6.04 (s, 1H), 4.43-4.25 (m, 1H), 3.78 (s, 3H), 1.38 (dd, J=1.6, 6.8 Hz, 3H). UPLC-MS 1: not ionizable, $t_R$=1.04 min (other diastereoisomer (2S,3R)-3-(2-bromo-4,6-difluorophenyl)-2-hydroxy-2-phenylbutanoic acid: UPLC-MS 1: not ionizable, $t_R$=1.13 min).

A suspension of (2S,3S)-3-(2-bromo-4,6-difluorophenyl)-2-hydroxy-2-phenylbutanoic acid (C-XVII-d) (460.0 g, 1.24 mol), CH$_3$I (209.4 g, 91.85 mL, 1.48 mol) and K$_2$CO$_3$ (256.9 g, 1.86 mol) in acetone (4600 mL) was stirred at RT for 6 h. The mixture was quenched by the addition of water and extracted with EtOAc. The combined organic layers were washed with brine, dried over anhydrous Na$_2$SO$_4$, filtered and concentrated under reduced pressure. The resulting residue was purified by flash chromatography (silica PE/EtOAc, gradient: 0% to 2% EtOAc) to give an additional amount of the title product (67 g, enantiomeric excess 80%). $^1$H NMR (400 MHz, DMSO-d$_6$) 7.38-7.28 (m, 2H), 7.21-7.03 (m, 5H), 6.04 (s, 1H), 4.43-4.25 (m, 1H), 3.78 (s, 3H), 1.38 (dd, J=6.8, 1.6 Hz, 3H).

Step 5: Methyl (2S,3S)-4-bromo-6-fluoro-3-methyl-2-phenyl-2,3-dihydrobenzofuran-2-carboxylate (C-XVII-f)

At 0° C. NaH (7.65 g, 191.33 mmol, 60% in mineral oil) was added to a stirred solution of methyl (2S,3S)-3-(2-bromo-4,6-difluorophenyl)-2-hydroxy-2-phenylbutanoate (C-XVII-e) (67 g, 173.94 mmol) in DMF (644 mL) under N$_2$. The resulting reaction mixture was stirred at 0° C. for 1 h before it was quenched by the addition of a sat solution of NaHCO$_3$ and extracted with MTBE. The combined organic layers were washed with a sat solution of NaHCO$_3$, dried over anhydrous Na$_2$SO$_4$, filtered and concentrated. The crude product was suspended in n-hexane and stirred for 30 min. The solid was collected by filtration and dried under HV to give the title compound (54 g) as a colorless powder with an enantiomeric excess of 90%. Chiral SFC: ChiralPak-AD-3, 150×4.6 mm I.D., 3 μm, CO$_2$/ethanol (0.05% DEA), gradient: from 95/5 to 60/40 in 5.5 min and hold at 60/40 for 3 min, then 95/5 for 1.5 min; column temperature 40° C., flow rate: 2.5 mL/min, $t_R$=1.71 min. $^1$H NMR (400 MHz, DMSO-d$_6$) 7.62 (d, J=7.2 Hz, 2H), 7.43-7.30 (m, 3H), 7.07 (br d, J=9.2 Hz, 1H), 7.03 (br d, J=9.2 Hz, 1H), 3.92 (q, J=6.8 Hz, 1H), 3.74 (s, 3H), 1.31 (d, J=6.8 Hz, 3H).

Step 6: Methyl (2S,3S)-4-bromo-5-chloro-6-fluoro-3-methyl-2-phenyl-2,3-dihydrobenzofuran-2-carboxylate (C-XVII-g)

To a stirred solution of methyl (2S,3S)-4-bromo-6-fluoro-3-methyl-2-phenyl-2,3-dihydrobenzofuran-2-carboxylate (C-XVII-f) (54 g, 147.87 mmol) in ACN (920 mL) were added N-chlorosuccinimide (19.75 g, 147.87 mmol) and 4-methylbenzenesulfonic acid hydrate (42.2 g, 221.80 mmol) under N$_2$. The resulting reaction mixture was stirred at 60° C. for 12 h before it was quenched by the addition of a sat solution of NaHCO$_3$ and extracted with EtOAc. The same reaction conditions were carried out on a second batch of methyl (2S,3S)-4-bromo-6-fluoro-3-methyl-2-phenyl-2,3-dihydrobenzofuran-2-carboxylate (C-XVII-f) (51 g). The combined organic layers were washed with a sat solution of NaHCO$_3$, dried over anhydrous Na$_2$SO$_4$, filtered and concentrated under reduced pressure. The crude product thus obtained was suspended in n-hexane and stirred for 30 min. The solid was collected by filtration and dried under HV to afford the title product (115 g) as a colorless powder with an enantiomeric excess of 82%. Chiral SFC: Chiralpak AD-3, 150×4.6 mm I.D., 3 μm, CO$_2$/IPA (0.05% DEA), gradient: from 95/5 to 60/40 in 5.5 min and hold at 60/40 for 3 min, then 95/5 for 1.5 min; column temperature 40° C., flow rate: 2.5 mL/min, $t_R$=2.55 min. $^1$H NMR (400 MHz, DMSO-d$_6$) 7.75-7.55 (m, 2H), 7.45-7.26 (m, 4H), 4.01-3.91 (m, 1H), 3.75 (s, 3H), 1.32 (d, J=6.8 Hz, 3H).

Step 7: ((2S,3S)-4-Bromo-5-chloro-6-fluoro-3-methyl-2-phenyl-2,3-dihydrobenzofuran-2-yl)methanol (C-XVII-h)

Three reactions were carried out in parallel as follows. LiBH$_4$ (5.01 g, 230.21 mmol) was added portionwise to a stirred solution of methyl (2S,3S)-4-bromo-6-fluoro-3-methyl-2-phenyl-2,3-dihydrobenzofuran-2-carboxylate (C-XVII-g) (46.0 g, 115.1 mmol) in a mixture of THF (620 mL) and MeOH (14.75 g, 18.63 mL, 460.4 mmol) under N$_2$. The resulting suspension was stirred for 60 min at 10° C. The reaction mixture was quenched by the addition of a sat solution of NaHCO$_3$ and extracted with EtOAc. The combined organic layers were washed with a sat solution of NaHCO$_3$, dried over anhydrous Na$_2$SO$_4$, filtered and concentrated under reduced pressure. The crude product was dissolved in MeOH and purified by chiral SFC (Cellulose-2, 300 mm×50 mm I.D., 10 μm, CO$_2$/EtOH (0.1% ammonia); 7:3, 38° C., flow rate: 200 mL/min, 2.5 mL/injection, cycle time 2.5 min) to afford the title product (110 g) as a light yellow oil with an enantiomeric excess of 99% (Chiral SFC: Lux Cellulose-2, 150 mm×4.6 mm I.D., 3 μm, CO$_2$/EtOH (0.05% DEA), gradient: from 95/5 to 60/40 in 5.5 min and hold at 60/40 for 3 min, then 95/5 for 1.5 min; column temperature 40° C.; flow rate: 2.5 mL/min, $t_R$=4.24 min). $^1$H NMR (400 MHz, DMSO-d$_6$) 7.50-7.41 (m, 2H), 7.32 (t, J=7.2 Hz, 2H), 7.28-7.18 (m, 2H), 5.08 (t, J=5.2 Hz, 1H), 3.95 (dq, J=5.8, 13.6 Hz, 2H), 3.56 (q, J=6.8 Hz, 1H), 1.44 (d, J=6.8 Hz, 3H).

Step 8: ((2S,3S)-5-Chloro-6-fluoro-3-methyl-2-phenyl-4-(4,4,5,5-tetramethyl-1,3,2-dioxaborolan-2-yl)-2,3-dihydrobenzofuran-2-yl)methanol (C-XVII)

At 60° C. PdCl$_2$(dppf)·CH$_2$Cl$_2$ adduct (4.39 g, 5.38 mmol) was added to a stirred suspension of ((2S,3S)-4-bromo-5-chloro-6-fluoro-3-methyl-2-phenyl-2,3-dihydrobenzofuran-2-yl)methanol (C-XVII-h) (20 g, 53.8 mmol), bis(pinacolato)diboron (20.50 g, 81 mmol) and potassium hydroxide (6.04 g, 108 mmol) in toluene (200 mL). The reaction mixture was stirred at 100° C. for 3 h before it was filtered through Celite and concentrated under reduced pressure. The obtained crude material was purified twice by flash chromatography (silica, heptane/EtOAc, gradient: 0% to 30% EtOAc) to give the title product (16.7 g) as a colorless foam. $^1$H NMR (400 MHz, DMSO-d$_6$) δ 7.45-7.40 (m, 2H), 7.33 (t, J=7.5 Hz, 2H), 7.28-7.22 (m, 1H), 7.12 (d, J=9.5 Hz, 1H), 4.98 (t, J=5.1 Hz, 1H), 3.95 (dd, J=11.7, 5.6 Hz, 1H), 3.87 (dd, J=11.7, 5.4 Hz, 1H), 3.55 (q, J=7.0 Hz, 1H), 1.37 (d, J=7.1 Hz, 3H), 1.32 (s, 6H), 1.30 (s, 6H). UPLC-MS 1: m/z 463.3 [M+formate]$^-$, $t_R$=1.30 min.

Alternative Procedure for the Conversion of C-XVII-c into C-XVII-f

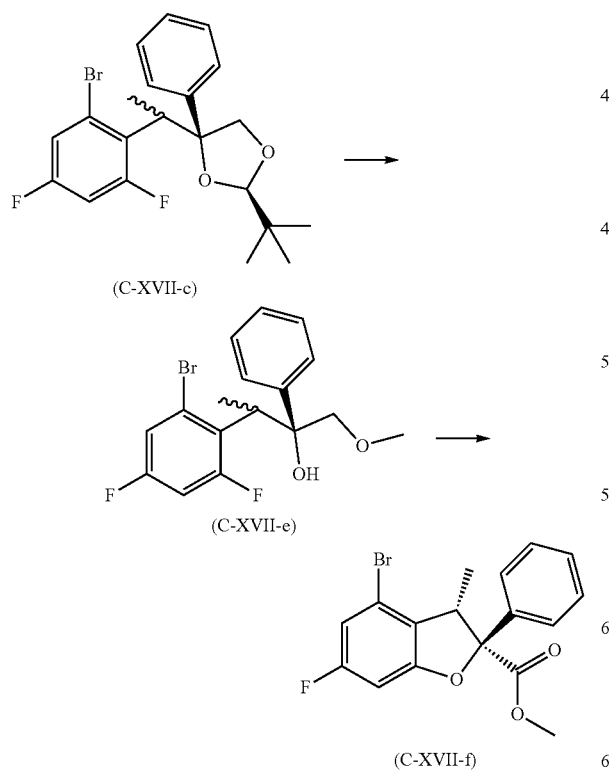

Step 1: Methyl (2S,3S)-3-(2-bromo-4,6-difluorophenyl)-2-hydroxy-2-phenylbutanoate (C-XVII-e)

Two reactions were carried out in parallel as follows. To a stirred solution of (2S,5S)-5-(1-(2-bromo-4,6-difluorophenyl)ethyl)-2-(tert-butyl)-5-phenyl-1,3-dioxolan-4-one (C-XVII-c) (425 g, 967 mmol) in MeOH (4500 mL) was added sodium methanolate (261 g, 1.45 mol, 30% in MeOH) at RT and stirring at 60° C. was continued for 3 h. The reaction mixture was concentrated and the residue was poured into a solution of NH$_4$Cl (200 g) and citric acid (40 g) in water 2.5 L) The organic layer was separated and washed with brine (1 L), dried and filtered. The filtrate was concentrated under reduced pressure to afford the title product (800 g) as a mixture of diastereoisomers and used in the next step without any additional purification.

Step 2: Methyl (2S,3S)-4-bromo-6-fluoro-3-methyl-2-phenyl-2,3-dihydrobenzofuran-2-carboxylate (C-XVII-f)

Three reactions were carried out in parallel as follows. At 15° C. NaH (40.2 g, 1.00 mol, 60% in mineral oil) was added to a stirred solution of methyl (2S,3S)-3-(2-bromo-4,6-difluorophenyl)-2-hydroxy-2-phenylbutanoate (C-XVII-e) (430 g, 1.12 mol) in NMP (2.6 L) under N$_2$. The resulting reaction mixture was stirred at 15° C. for 15 min. The reaction mixture was poured into a sat solution of NH$_4$Cl (5 L) and extracted three times with TBME (2 L). before it was quenched by the addition of a sat solution of NaHCO$_3$ and extracted tree times with MTBE (2 L). The combined organic layers were washed with brine (3 L), dried, filtered and concentrated. The crude product was purified by flash chromatography (silica, PE/EtOAc, gradient: 2% to 20% EtOAc) to afford a yellow solid (360 g) The solid was recrystallized from PE/ethyl acetate (1.8 L, heated to 70° C. with stirring to dissolve all solid and allowed to cool to 10° C., the solid was collected by filtration). The title product (260 g) was isolated as a colorless solid with an enantiomeric excess of >99%. Chiral SFC: ChiralPak AD-3, 150× 4.6 mm I.D., 3 μm, CO$_2$/ethanol (0.05% DEA), gradient: from 95/5 to 60/40 in 5.5 min and hold at 60/40 for 3 min, then 95/5 for 1.5 min; column temperature 40° C., flow rate: 2.5 mL/min, $t_R$=1.72 min. $^1$H NMR (400 MHz, DMSO-d$_6$) 7.62 (d, J=7.2 Hz, 2H), 7.43-7.30 (m, 3H), 7.07 (br d, J=9.2 Hz, 1H), 7.03 (br d, J=9.2 Hz, 1H), 3.92 (q, J=6.8 Hz, 1H), 3.74 (s, 3H), 1.31 (d, J=6.8 Hz, 3H). In addition, a second batch of the title compound (100 g) with a purity of 70% was isolated.

Synthesis of tert-butyl (((2R,3S)-5-chloro-6-fluoro-3-methyl-2-(pyridin-2-yl)-4-(4,4,5,5-tetramethyl-1,3,2-dioxaborolan-2-yl)-2,3-dihydrobenzofuran-2-yl)methyl)carbamate (C-XVIII)

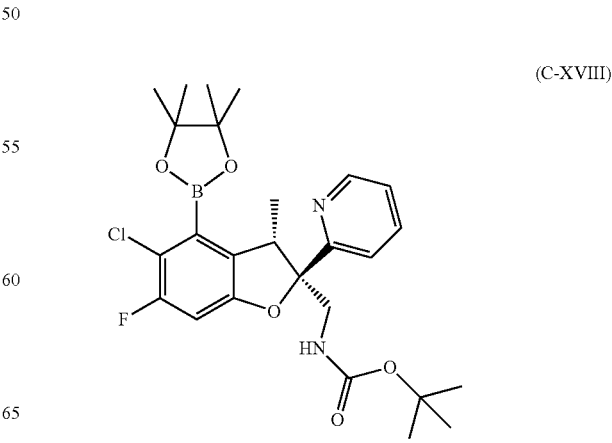

167
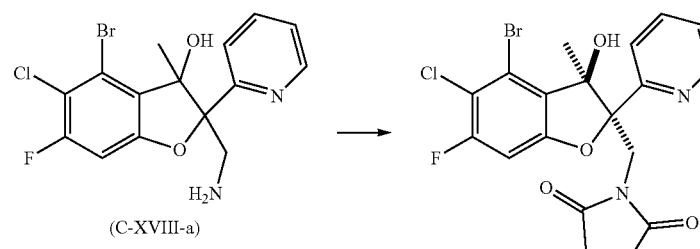
168
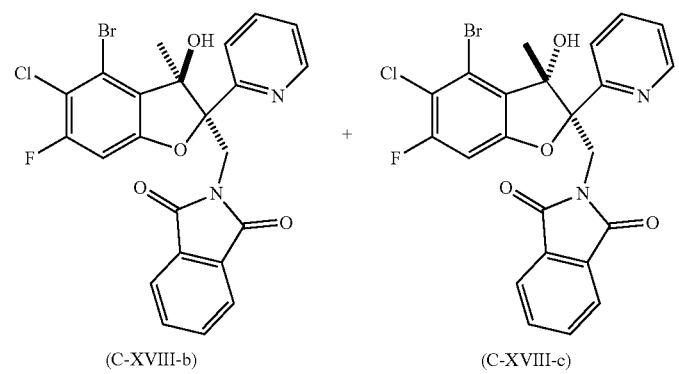
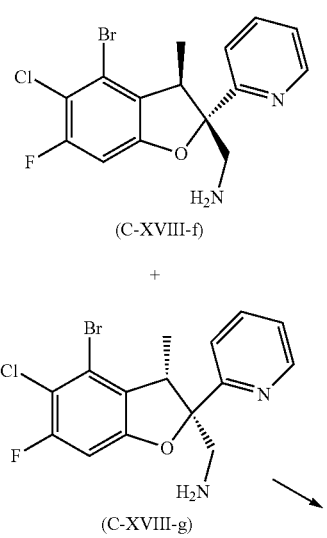
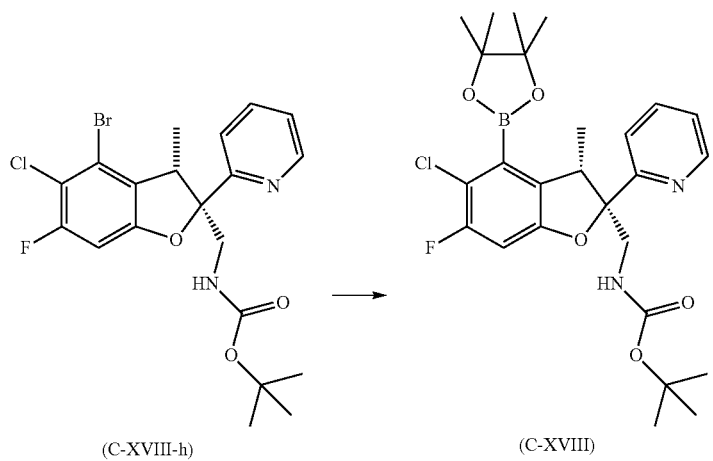

2-(Aminomethyl)-4-bromo-5-chloro-6-fluoro-3-methyl-2-(pyridin-2-yl)-2,3-dihydrobenzofuran-3-ol (C-XVIII-a) as a diastereoisomeric mixture was prepared from 2 bromo-3-chloro-4-fluoro-6-hydroxybenzaldehyde (C-XII-e) and 2-bromo-2-(pyridin-2-yl)acetonitrile according to the procedures outlined in the syntheses of intermediates (C-XIV) and (C-XVI).

Step 1: 2-(((2R*,3R*)-4-Bromo-5-chloro-6-fluoro-3-hydroxy-3-methyl-2-(pyridin-2-yl)-2,3-dihydrobenzofuran-2-yl)methyl)isoindoline-1,3-dione (C-XVIII-b) and 2-(((2R*,3S*)-4-bromo-5-chloro-6-fluoro-3-hydroxy-3-methyl-2-(pyridin-2-yl)-2,3-dihydrobenzofuran-2-yl)methyl)isoindoline-1,3-dione (C-XVIII-c)

To a stirred solution of 2-(aminomethyl)-4-bromo-5-chloro-6-fluoro-3-methyl-2-(pyridin-2-yl)-2,3-dihydrobenzofuran-3-ol (C-XVIII-a) (7.43 g, 17.4 mmol) in toluene (100 ml) was added phthalic anhydride (2.84 g, 19.2 mmol) at RT and the reaction mixture was stirred at 105° C. for 2 h. The reaction mixture was concentrated and a sat solution of NaHCO$_3$ and EtOAc were added. The organic phase was separated and the aqueous phase was extracted with EtOAc. The combined organic extracts were washed with water and brine, dried over anhydrous Na$_2$SO$_4$ and concentrated. The crude product was purified by flash chromatography (silica, DCM/EtOAc, gradient 0% to 60% EtOAc) to afford the title compounds as colorless powders:
2-(((2R*,3R*)-4-Bromo-5-chloro-6-fluoro-3-hydroxy-3-methyl-2-(pyridin-2-yl)-2,3-dihydrobenzofuran-2-yl)methyl)isoindoline-1,3-dione (C-XVIII-b) (1.44 g). UPLC-MS 1: m/z 517.0/519.0 [M+H]$^+$, t$_R$=1.15 min.
2-(((2R*,3R*)-4-Bromo-5-chloro-6-fluoro-3-hydroxy-3-methyl-2-(pyridin-2-yl)-2,3-dihydrobenzofuran-2-yl)methyl)isoindoline-1,3-dione (C-XVIII-c) (5.82 g): UPLC-MS 1: m/z 517.0/519.0 [M+H]$^+$, t$_R$=1.22 min.

Step 2: 2-((4-Bromo-5-chloro-6-fluoro-3-methylene-2-(pyridin-2-yl)-2,3-dihydrobenzofuran-2-yl)methyl)isoindoline-1,3-dione (C-XVIII-d)

A solution of 2-(((2R*,3R*)-4-bromo-5-chloro-6-fluoro-3-hydroxy-3-methyl-2-(pyridin-2-yl)-2,3-dihydrobenzofuran-2-yl)methyl)isoindoline-1,3-dione (C-XVIII-b) (5.47 g, 6.8 mmol) and TFA (25 mL, 324 mmol) in DCM (25 mL) was stirred at RT for 18 h. The reaction mixture was added to a sat solution of NaHCO$_3$ and extracted with DCM. The combined organic extracts were washed with water and brine, dried over anhydrous Na$_2$SO$_4$ and concentrated. The crude product was purified by flash chromatography (silica, DCM/EtOAc, gradient 0% to 30% EtOAc) to afford the title compound (3.15 g) as a colorless powder. UPLC-MS 1: m/z 499.0/501.0 [M+H]$^+$, t$_R$=1.35 min. $^1$H NMR (600 MHz, DMSO-d$_6$) δ 8.75 (dt, J=4.8, 1.4 Hz, 1H), 7.87-7.77 (m, 5H), 7.48-7.41 (m, 2H), 7.33 (d, J=9.2 Hz, 1H), 6.39 (s, 1H), 5.74 (s, 1H), 4.66 (d, J=14.7 Hz, 1H), 4.41 (d, J=14.7 Hz, 1H).
The same reaction was repeated with 2-(((2R*,3S*)-4-bromo-5-chloro-6-fluoro-3-hydroxy-3-methyl-2-(pyridin-2-yl)-2,3-dihydrobenzofuran-2-yl)methyl)isoindoline-1,3-dione (C-XVIII-c) (3.8 g, 7.3 mmol) affording the title compound (2.06 g). The reaction was stopped after 5 d and there was still unreacted starting material left.

Step 3: ((2R*,3S*)-4-Bromo-5-chloro-6-fluoro-3-methyl-2-(pyridin-2-yl)-2,3-dihydrobenzofuran-2-yl)methanamine (C-XVIII-e)

To a stirred solution of 2-((4-bromo-5-chloro-6-fluoro-3-methylene-2-(pyridin-2-yl)-2,3-dihydrobenzofuran-2-yl)methyl)isoindoline-1,3-dione (C-XVIII-d) (5.2 g, 10.1 mmol) in DCE (100 mL) was added TEA (2.81 mL, 20.19 mmol) followed by 3-nitrobenzenesulfonyl hydrazine (4.38 g, 20.2 mmol) at RT and the reaction mixture was stirred at 75° C. for 14 h. More TEA (1.4 mL, 10.1 mmol) and 3-nitrobenzenesulfonyl hydrazine (2.2 g, 10.1 mmol) were added and stirring at 75° C. was continued for 8 h. DCM and water were added. The organic phase was separated and the aqueous phase was extracted with DCM. The combined organic extracts were washed with water and brine, dried over anhydrous Na$_2$SO$_4$ and concentrated. The crude intermediate was dissolved in EtOH (125 mL), hydrazine hydrate (1.22 mL, 25.2 mmol) was added and the reaction mixture was stirred at 75° C. for 2 h. The reaction mixture was concentrated, then taken up in EtOAc and water. The organic layer was separated and the aqueous layer was extracted with EtOAc. The combined organic extracts were washed with brine, dried over anhydrous Na$_2$SO$_4$ and concentrated. The crude product was purified by flash chromatography (silica, DCM/(7N ammonia in MeOH), gradient 0% to 10% (7N ammonia in MeOH)) to afford the title compound (7.43 g) as a colorless powder. UPLC-MS 1: m/z 371.0/373.1 [M+H]$^+$, t$_R$=0.74 min.
$^1$H NMR (400 MHz, DMSO-d$_6$) δ 8.61 (dt, J=4.7, 1.5 Hz, 1H), 7.76 (td, J=7.8, 1.8 Hz, 1H), 7.46 (dt, J=8.1, 1.2 Hz, 1H), 7.33-7.28 (m, 1H), 7.23 (d, J=9.5 Hz, 1H), 3.92 (q, J=7.1 Hz, 1H), 3.27 (d, J=3.0 Hz, 2H), 1.38 (d, J=7.1 Hz, 3H), 1.15 (s, 2H).

Step 4: ((2S,3R)-4-Bromo-5-chloro-6-fluoro-3-methyl-2-(pyridin-2-yl)-2,3-dihydrobenzofuran-2-yl)methanamine (C-XVIII-f) and ((2R,3S)-4-bromo-5-chloro-6-fluoro-3-methyl-2-(pyridin-2-yl)-2,3-dihydrobenzofuran-2-yl)methanamine (C-XVIII-g)

Racemic ((2R*,3S*)-4-bromo-5-chloro-6-fluoro-3-methyl-2-(pyridin-2-yl)-2,3-dihydrobenzofuran-2-yl)methanamine (C-XVIII-e) (4.63 g, 12.46 mmol) was subjected to chiral preparative SFC (ChiralPakAD-H 250×30 mm I.D., 5 μm, CO$_2$/IPA (+1% isopropylamine) 3:1, flow rate: 80 mL/min, column temperature 40° C.) to afford the title compounds as separate enantiomers in an enantiomeric excess of >99%, respectively.
((2S,3R)-4-Bromo-5-chloro-6-fluoro-3-methyl-2-(pyridin-2-yl)-2,3-dihydrobenzofuran-2-yl)methanamine (2.47 g) (C-XVIII-f): chiral SFC (ChiralPakAD-H 250×4.6 mm I.D., 5 μm, CO$_2$/IPA (+1% isopropylamine) 7:3, flow rate: 3 mL/min) t$_R$=3.06 min
((2R,3S)-4-Bromo-5-chloro-6-fluoro-3-methyl-2-(pyridin-2-yl)-2,3-dihydrobenzofuran-2-yl)methanamine (2.32 g) (C-XVIII-g): chiral SFC (ChiralPakAD-H 250×4.6 mm I.D., 5 μm, CO$_2$/IPA (+1% isopropylamine) 7:3, flow rate: 3 mL/min) t$_R$=4.05 min Step 5: Tert-butyl (((2R,3S)-4-bromo-5-chloro-6-fluoro-3-methyl-2-(pyridin-2-yl)-2,3-dihydrobenzofuran-2-yl)methyl)carbamate (C-XVIII-h)

((2R,3S)-4-Bromo-5-chloro-6-fluoro-3-methyl-2-(pyridin-2-yl)-2,3-dihydrobenzofuran-2-yl)methanamine (C-XVII-g) (2.25 g, 6.1 mmol) was converted into the title compound (2.86 g) following similar reaction conditions as for the synthesis of intermediate C-I-p (step 14 of intermediate C-I). UPLC-MS 1: m/z 471.2/473.2 [M+H]$^+$, t$_R$=1.41 min.

Step 6: Tert-butyl (((2R,3S)-5-chloro-6-fluoro-3-methyl-2-(pyridin-2-yl)-4-(4,4,5,5-tetramethyl-1,3,2-dioxaborolan-2-yl)-2,3-dihydrobenzofuran-2-yl)methyl)carbamate (C-XVIII)

Synthesis of ((2S,3S)-2-(6-(benzyloxy)pyridin-2-yl)-5-chloro-6-fluoro-3-methyl-4-(4,4,5,5-tetramethyl-1,3,2-dioxaborolan-2-yl)-2,3-dihydrobenzofuran-2-yl)methanol (C-XIX)

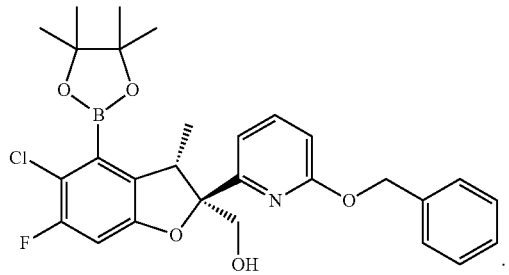

(C-XIX)

Tert-butyl (((2R,3S)-4-bromo-5-chloro-6-fluoro-3-methyl-2-(pyridin-2-yl)-2,3-dihydrobenzofuran-2-yl)methyl)carbamate (C-XVII-h) (2.88 g, 6.1 mmol) was converted into the title compound following similar reaction conditions as for the synthesis of intermediate C-XVI (step 7 of intermediate C-XVI). UPLC-MS 1: m/z 519.4 [M+H]$^+$, $t_R$=1.43 min. $^1$H NMR (400 MHz, DMSO-$d_6$) δ 8.53 (d, J=4.6 Hz, 1H), 7.68 (t, J=7.8 Hz, 1H), 7.41 (d, J=8.0 Hz, 1H), 7.23 (t, J=6.2 Hz, 1H), 7.11 (d, J=9.6 Hz, 1H), 6.61-6.48 (m, 1H), 3.79-3.67 (m, 1H), 3.64-3.52 (m, 1H), 3.39-3.22 (m, 1H), 1.33-1.12 (m, 24H).

Reaction Scheme C-XIX

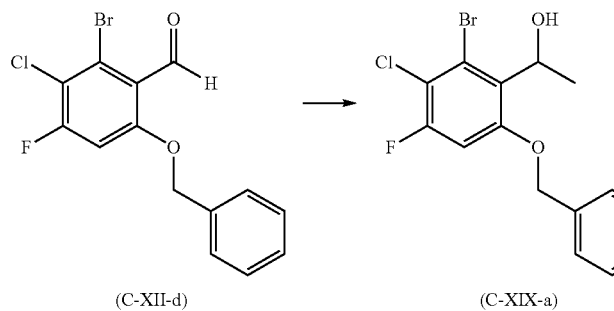

(C-XII-d)   (C-XIX-a)   (C-XIX-b)

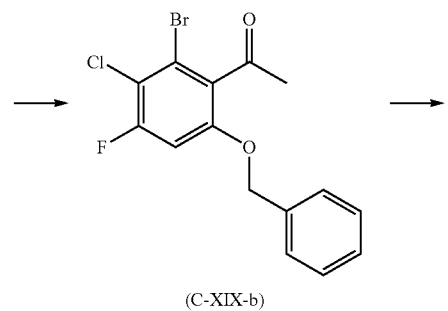

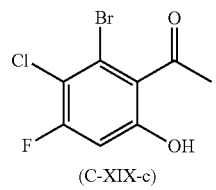

(C-XIX-c)

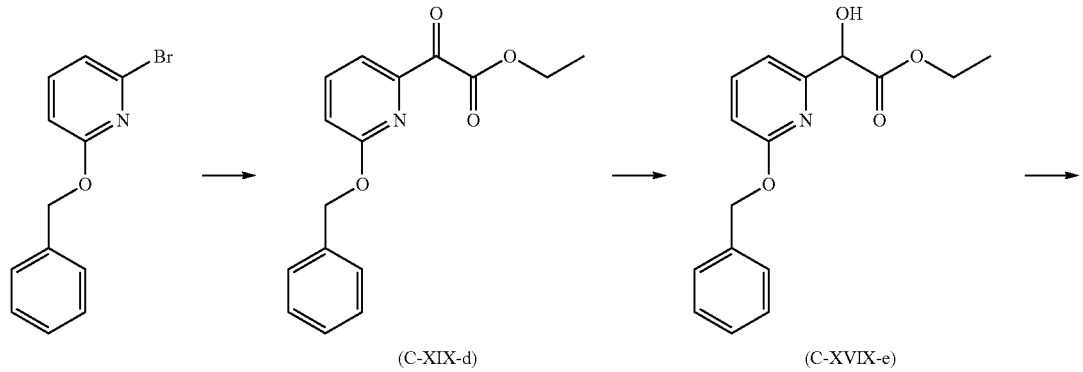

(C-XIX-d)   (C-XVIX-e)

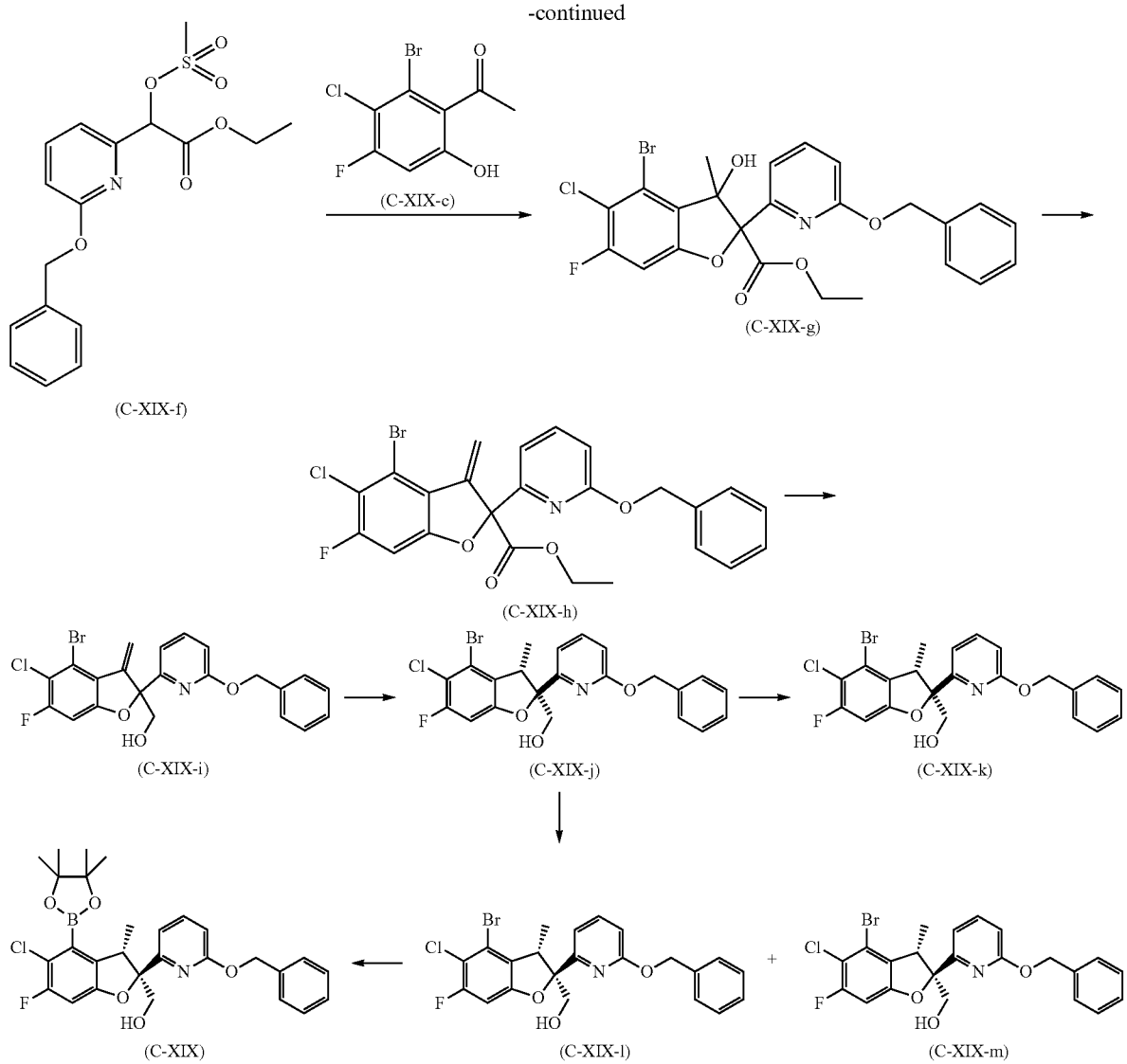

Step 1: 1-(6-(Benzyloxy)-2-bromo-3-chloro-4-fluorophenyl)ethanol (C-XIX-a)

At −30° C. methylmagnesium bromide (67.9 mL, 204 mmol, 3 M in Et$_2$O) was added to a solution of 6-(benzyloxy)-2-bromo-3-chloro-4-fluorobenzaldehyde (C-XII-d) (50.0 g, 146 mmol) in THF (570 mL). The reaction mixture was allowed to warm to 0° C. over 2 h. The reaction mixture was quenched by the addition of a sat solution of NH$_4$Cl and extracted with EtOAc. The combined organic layers were dried over anhydrous Na$_2$SO$_4$ and concentrated to afford the title compound (51.8 g) as a colorless solid. UPLC-MS 1: m/z 357.1 [M−H]$^-$, t$_R$=1.28 min.

Step 2: 1-(6-(Benzyloxy)-2-bromo-3-chloro-4-fluorophenyl)ethanone (C-XIX-b)

At 0° C. Dess-Martin periodinane (69.4 g, 164 mmol) was added to a solution of 1-(6-(benzyloxy)-2-bromo-3-chloro-4-fluorophenyl)ethanol (C-XIXI-a) (51.1 g, 136 mmol) in DCM (640 mL) and the reaction mixture was allowed to warm to RT. Stirring at RT was continued for 12 h before a sat solution of NaHCO$_3$/10% sodium thiosulfate (800 mL) was added. The organic phase was separated and the aqueous phase was extracted with DCM. The combined organic extracts were dried over anhydrous Na$_2$SO$_4$ and concentrated. The residue was triturated in Et$_2$O/heptane 4:1 (300 mL), collected by filtration and dried under HV. The isolated product was dissolved in DCM, extracted again with NaHCO$_3$/10% sodium thiosulfate (800 mL) and triturated in Et$_2$O/heptane 4:1 (250 mL) to afford the title compound (56.0 g) as a colorless solid. UPLC-MS 1: m/z 373.9 [M+NH$_4$]$^+$, t$_R$=1.29 min.

Step 3: 1-(2-Bromo-3-chloro-4-fluoro-6-hydroxyphenyl)ethanone (C-XIX-c)

A mixture of 1-(6-(benzyloxy)-2-bromo-3-chloro-4-fluorophenyl)ethanone (C-XIX-b) (41.0 g, 115 mmol) and PtO$_2$ (6.51 g, 28.7 mmol) in THF (460 mL) in a shaking duck flask was stirred under 0.1 bar H$_2$ pressure for 17 h. The solids were removed by filtration and the filtrate was concentrated under reduced pressure to afford the title compound (32.2 g). UPLC-MS 1: m/z 265.0 [M–H]⁻, $t_R$=0.95 min.

Step 4: Ethyl 2-(6-(benzyloxy)pyridin-2-yl)-2-oxoacetate (C-XIX-d)

At –78° C. n-BuLi (36.3 mL, 91 mmol, 2.5 M in hexane) was added to a stirred solution of 2-benzyloxy-6-bromopyridine (20 g, 76 mmol) in THF (120 mL) and stirring at –78° C. was continued for 30 min. This solution was added dropwise via a cannula to a stirred solution of diethyl oxalate (12.4 mL, 91 mmol) in THF (200 mL) at –78° C. 15 min after the end of the addition the reaction mixture was quenched with a sat solution of NH₄Cl and extracted with EtOAc. The organic extract was washed with water and brine, dried over anhydrous Na₂SO₄ and concentrated. The crude product was purified by flash chromatography (silica, heptane/EtOAc, gradient: 0% to 25% EtOAc) to afford the title compound (16.5 g) as a yellow oil. UPLC-MS 1: m/z 286.1 [M+–H]⁺, $t_R$=1.18 min.

Step 5: Ethyl 2-(6-(benzyloxy)pyridin-2-yl)-2-hydroxyacetate (C-XIX-e)

At RT sodium triacetoxyborohydride (24.52 g, 116 mmol) was added to a stirred solution of ethyl 2-(6-(benzyloxy)pyridin-2-yl)-2-oxoacetate (C-XIX-d) (16.5 g, 57.8 mmol) in EtOH (102 mL), water (34 mL) and AcOH (17 mL) and the reaction mixture was stirred at RT for 1 h. A sat solution of NaHCO₃ was added and the mixture was extracted with EtOAc, the combined organic extracts were washed with water and brine, dried over anhydrous Na₂SO₄ and concentrated. The residue was purified by flash chromatography (silica, heptane/EtOAc, gradient: 0% to 40% EtOAc) to afford the title compound (11.8 g) as a yellow oil. UPLC-MS 1: m/z 288.0 [M+–H]⁺, $t_R$=1.00 min.

Step 6: Ethyl 2-(6-(benzyloxy)pyridin-2-yl)-2-((methylsulfonyl)oxy)acetate (C-XIX-f)

At 0° C. methanesulfonic anhydride (10.72 g, 61.6 mmol) was added to a stirred solution of ethyl 2-(6-(benzyloxy)pyridin-2-yl)-2-hydroxyacetate (C-XIX-e) (13.1 g, 41.0 mmol) and TEA (17.2 mL, 123 mmol) in DCM (120 mL) and the reaction mixture was stirred at 0° C. for 2 h. Water was added and the mixture was extracted with DCM. The combined organic extracts were washed with water and brine, dried over anhydrous Na₂SO₄ and concentrated. The crude product was purified by flash chromatography (silica, heptane/EtOAc, gradient: 0% to 40% EtOAc) to afford the title compound (16.2 g) as a colorless oil. UPLC-MS 1: m/z 366.5 [M+H]⁺, $t_R$=1.12 min.

Step 7: Ethyl 2-(6-(benzyloxy)pyridin-2-yl)-4-bromo-5-chloro-6-fluoro-3-hydroxy-3-methyl-2,3-dihydrobenzofuran-2-carboxylate (C-XIX-g)

At RT ethyl 2-(6-(benzyloxy)pyridin-2-yl)-2-((methylsulfonyl)oxy)acetate (C-XIX-f) (15.88 g, 40.8 mmol) was added to a stirred solution of 1-(2-bromo-3-chloro-4-fluoro-6-hydroxyphenyl)ethanone (C-XIX-c) (9.50 g, 35.5 mmol) and K₂CO₃ (7.36 g, 53.3 mmol) in DMF (100 mL). After stirring at RT for 40 h water was added and the mixture was extracted with EtOAc. The combined organic extracts were washed with brine, dried over anhydrous Na₂SO₄ and concentrated. The crude product was purified by flash chromatography (silica, heptane/EtOAc, gradient: 0% to 100% EtOAc) to afford the title compound (17.29 g) as a mixture of diastereoisomers. UPLC-MS 1: m/z 536.0 [M+–H]⁺, $t_R$=1.37 and 1.39 min.

Step 8: Ethyl 2-(6-(benzyloxy)pyridin-2-yl)-4-bromo-5-chloro-6-fluoro-3-methylene-2,3-dihydrobenzofuran-2-carboxylate (C-XIX-h)

At RT triethylamine (18.6 mL, 134 mmol) followed by methanesulfonic anhydride (9.31 g, 53.5 mmol) were added to a stirred solution of ethyl 2-(6-(benzyloxy)pyridin-2-yl)-4-bromo-5-chloro-6-fluoro-3-hydroxy-3-methyl-2,3-dihydrobenzofuran-2-carboxylate (C-XIX-g) (17.29 g, 26.7 mmol) in DCM (200 mL). After 4 h water was added and the mixture was extracted with DCM. The combined organic extracts were washed with water and brine, dried over anhydrous Na₂SO₄ and concentrated. The residue was purified by flash chromatography (silica, heptane/EtOAc, gradient: 0% to 20% EtOAc) to give the title compound (14.83 g) as a colorless oil. UPLC-MS 1: m/z 518.0 [M+–H]⁺, $t_R$=1.52 min.

Step 9: (2-(6-(Benzyloxy)pyridin-2-yl)-4-bromo-5-chloro-6-fluoro-3-methylene-2,3-dihydrobenzofuran-2-yl)methanol (C-XIX-i)

At 0° C. sodium borohydride (1.46 g, 38.6 mmol) was added to a stirred solution of ethyl 2-(6-(benzyloxy)pyridin-2-yl)-4-bromo-5-chloro-6-fluoro-3-methylene-2,3-dihydrobenzofuran-2-carboxylate (C-XIX-h) (14.83 g, 25.7 mmol) in MeOH (200 mL) and the reaction mixture was allowed to warm to RT. After 1 h, sodium borohydride (1.460 g, 38.6 mmol) was again added. Over the course of 12 h three more portions of sodium borohydride (1.460 g, 38.6 mmol) were added. For workup, acetone was added, the reaction mixture was concentrated and diluted in EtOAc/water. The organic phase was separated and the aqueous layer was extracted with EtOAc. The combined organic extracts were washed with water and brine, dried over anhydrous Na₂SO₄ and concentrated. The residue was purified by flash chromatography (silica, heptane/EtOAc, gradient: 0% to 40% EtOAc) to give the title compound (7.80 g). UPLC-MS 1: m/z 476.1 [M+–H]⁺, $t_R$=1.42 min.

Step 10: ((2S*,3S*)-2-(6-(benzyloxy)pyridin-2-yl)-4-bromo-5-chloro-6-fluoro-3-methyl-2,3-dihydrobenzofuran-2-yl)methanol (C-XIX-j) and ((2S*,3R*)-2-(6-(benzyloxy)pyridin-2-yl)-4-bromo-5-chloro-6-fluoro-3-methyl-2,3-dihydrobenzofuran-2-yl)methanol (C-XIX-k)

At RT 3-nitrobenzenesulfonyl hydrazine (10.8 g, 49.8 mmol) and TEA (17.4 mL, 125 mmol) were added to a stirred solution of (2-(6-(benzyloxy)pyridin-2-yl)-4-bromo-5-chloro-6-fluoro-3-methylene-2,3-dihydrobenzofuran-2-yl)methanol (C-XIX-i) (11.88 g, 24.9 mmol) in DCE (250 mL) and the reaction mixture was stirred at 70° C. for 5 h. More 3-nitrobenzenesulfonyl hydrazine (5.4 g, 24.9 mmol) and TEA (8.7 mL, 62.3 mmol) were added and stirring at 70° C. was continued for 16 h. Water was added, the organic phase was separated and the aqueous phase was extracted with DCM The combined organic extracts were washed with water and brine, dried over anhydrous Na₂SO₄ and concentrated. The two title compounds were isolated by two consecutive flash chromatographies (silica, heptane/EtOAc, gradient: 0% to 30% EtOAc and gradient: 0% to 20% EtOAc):

((2S*,3S*)-2-(6-(benzyloxy)pyridin-2-yl)-4-bromo-5-chloro-6-fluoro-3-methyl-2,3-dihydrobenzofuran-2-yl)methanol (C-XIX-j) (9.11 g, colorless powder): UPLC-MS 1: m/z 478.0 [M+−H]$^+$, $t_R$=1.41 min.

((2S*,3R*)-2-(6-(benzyloxy)pyridin-2-yl)-4-bromo-5-chloro-6-fluoro-3-methyl-2,3-dihydrobenzofuran-2-yl)methanol (C-XIX-k) (1.56 g, colorless powder): UPLC-MS 1: m/z 478.0 [M+−H]$^+$, $t_R$=1.45 min.

Step 11: ((2S,3S)-2-(6-(Benzyloxy)pyridin-2-yl)-4-bromo-5-chloro-6-fluoro-3-methyl-2,3-dihydrobenzofuran-2-yl)methanol (C-XIX-l) and ((2R,3R)-2-(6-(benzyloxy)pyridin-2-yl)-4-bromo-5-chloro-6-fluoro-3-methyl-2,3-dihydrobenzofuran-2-yl) methanol (C-XIX-m)

The racemate ((2S*,3S*)-2-(6-(benzyloxy)pyridin-2-yl)-4-bromo-5-chloro-6-fluoro-3-methyl-2,3-dihydrobenzofuran-2-yl)methanol (C-XIX-j) (8.8 g) was subjected to chiral SFC (ChiralCel OJ, 250×30 mm I.D., 5 μm. CO$_2$/MeOH (0.1% ammonia) 7:3, column temperature 38° C., flow rate: 65 mL/min, cycle time 4 min) to afford the two enantiomers ((2S,3S)-2-(6-(benzyloxy)pyridin-2-yl)-4-bromo-5-chloro-6-fluoro-3-methyl-2,3-dihydrobenzofuran-2-yl)methanol (C-XIX-l) (4.02 g) and ((2R,3R)-2-(6-(benzyloxy)pyridin-2-yl)-4-bromo-5-chloro-6-fluoro-3-methyl-2,3-dihydrobenzofuran-2-yl)methanol (C-XIX-m) (3.91 g) with an enantiomeric excess of >98%, respectively.

((2S,3S)-2-(6-(Benzyloxy)pyridin-2-yl)-4-bromo-5-chloro-6-fluoro-3-methyl-2,3-dihydrobenzofuran-2-yl)methanol (C-XIX-l): Chiral SFC: (ChiralCel OJ 150×4.6 mm I.D., 3 μm, CO$_2$/MeOH (0.05% DEA) 5 to 40%, flow rate: 2.5 mL/min, column temperature 35° C.) $t_R$=5.01 min; UPLC-MS 1: m/z 478.0 [M+H]$^+$, $t_R$=1.40 min.

((2R,3R)-2-(6-(benzyloxy)pyridin-2-yl)-4-bromo-5-chloro-6-fluoro-3-methyl-2,3-dihydrobenzofuran-2-yl)methanol (C-XIX-m): Chiral SFC: (ChiralCel OJ 150×4.6 mm I.D., 3 μm, CO$_2$/MeOH (0.05% DEA) 5 to 40%, flow rate: 2.5 mL/min, column temperature 35° C.) $t_R$=4.61 min; UPLC-MS 1: m/z 478.0 [M+H]$^+$, $t_R$=1.40 min.

Step 12: ((2S,3S)-2-(6-(Benzyloxy)pyridin-2-yl)-5-chloro-6-fluoro-3-methyl-4-(4,4,5,5-tetramethyl-1,3,2-dioxaborolan-2-yl)-2,3-dihydrobenzofuran-2-yl) methanol (C-XIX)

To a stirred solution of ((2S,3S)-2-(6-(benzyloxy)pyridin-2-yl)-4-bromo-5-chloro-6-fluoro-3-methyl-2,3-dihydrobenzofuran-2-yl)methanol (C-XIX-l) (2.00 g, 4.2 mmol), bis(pinacolato)dibron (1.59 g, 6.3 mmol) and KOH (0.47 g, 8.4 mmol) in toluene (40 mL) was added PdCl$_2$(dppf)·CH$_2$Cl$_2$ adduct (0.34 g, 0.42 mmol) at 60° C. and the reaction mixture was stirred at 100° C. for 2 h. The reaction mixture was filtered through Celite and concentrated. The crude product was purified by flash chromatography (silica, heptane/EtOAc, gradient: 0% to 30% EtOAc) to afford the title compound (1.65 g) as a colorless foam. $^1$H NMR (600 MHz, DMSO-d$_6$) δ 7.65 (t, J=7.8 Hz, 1H), 7.46-7.43 (m, 2H), 7.38 (t, J=7.4 Hz, 2H), 7.34-7.31 (m, 1H), 7.11 (d, J=9.7 Hz, 1H), 7.05 (d, J=7.4 Hz, 1H), 6.74 (d, J=8.3 Hz, 1H), 5.35 (dd, J=21.5, 12.3 Hz, 2H), 4.93 (t, J=5.5 Hz, 1H), 3.99-3.92 (m, 2H), 1.31-1.27 (m, 15H). UPLC-MS 1: m/z 526.1 [M+H]$^+$, $t_R$=1.42 min.

Synthesis of (trans)-4-(((((2R,3S)-5-chloro-6-fluoro-3-methyl-2-(pyridin-2-yl)-4-(4,4,5,5-tetramethyl-1,3,2-dioxaborolan-2-yl)-2,3-dihydrobenzofuran-2-yl)methyl)amino)-1-methylcyclohexan-1-ol (C-XX)

(C-XX)

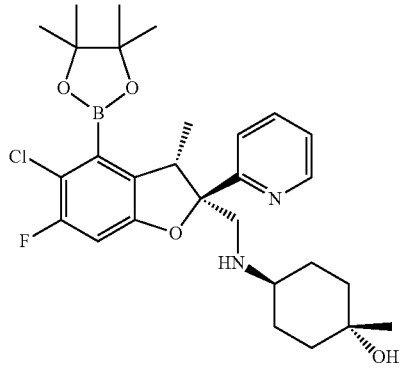

The title compound was synthesized in analogy to ((2S,3S)-2-(6-(benzyloxy)pyridin-2-yl)-5-chloro-6-fluoro-3-methyl-4-(4,4,5,5-tetramethyl-1,3,2-dioxaborolan-2-yl)-2,3-dihydrobenzofuran-2-yl)methanol (C-XIX) from 1-(2-bromo-3-chloro-4-fluoro-6-hydroxyphenyl)ethanone (C-XIX-c) and ethyl 2-bromo-2-(pyridin-2-yl)acetate. The intermediate ((2S,3S)-4-bromo-5-chloro-6-fluoro-3-methyl-2-(pyridin-2-yl)-2,3-dihydrobenzofuran-2-yl)methanol (see below) was oxidized to the corresponding aldehyde ((COCl)$_2$/TEA/DMSO, DCM) followed by reductive amination with trans-4-amino-1-methylcyclohexanol (compare Example 114a alternative synthesis) and formation of the boronate. UPLC-MS 1: m/z 531.3 [M+H]$^+$, $t_R$=0.95 min.

The racemic intermediate ((2S*,3S*)-4-bromo-5-chloro-6-fluoro-3-methyl-2-(pyridin-2-yl)-2,3-dihydrobenzofuran-2-yl)methanol was subjected to chiral SFC (ChiralPak IG, 250×30 mm, 5 μm, CO$_2$/(MeOH+1% IPAm) 85:15, flow rate: 80 mL/min) to afford the separate enantiomers with an enantiomeric excess of >98%, respectively:

((2S,3S)-4-Bromo-5-chloro-6-fluoro-3-methyl-2-(pyridin-2-yl)-2,3-dihydrobenzofuran-2-yl)methanol: chiral SFC (ChiralPak IG, 250×4.6 mm, 5 μm, CO$_2$/(MeOH+1% IPAm) 85:15, flow rate: 3 mL/min): $t_R$=4.20 min.

((2R,3R)-4-Bromo-5-chloro-6-fluoro-3-methyl-2-(pyridin-2-yl)-2,3-dihydrobenzofuran-2-yl)methanol: chiral SFC (ChiralPak IG, 250×4.6 mm, 5 μm, CO$_2$/(MeOH+1% IPAm) 85:15, flow rate: 3 mL/min): $t_R$=5.20 min.

Synthesis of (trans)-4-(((((2S,3S)-5-chloro-6-fluoro-3-methyl-2-(pyridin-3-yl)-4-(4,4,5,5-tetramethyl-1,3,2-dioxaborolan-2-yl)-2,3-dihydrobenzofuran-2-yl)methyl)amino)-1-methylcyclohexan-1-ol (C-XXI)

(C-XXI)

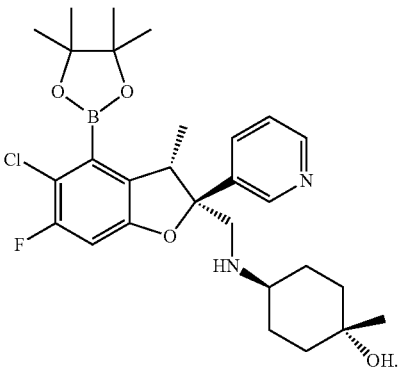

The title compound was synthesized in analogy to ((2S,3S)-2-(6-(benzyloxy)pyridin-2-yl)-5-chloro-6-fluoro-3-methyl-4-(4,4,5,5-tetramethyl-1,3,2-dioxaborolan-2-yl)-2,3-dihydrobenzofuran-2-yl)methanol (C-XIX) from 1-(2-bromo-3-chloro-4-fluoro-6-hydroxyphenyl)ethanone (C-XIX-c) and ethyl 2-bromo-2-(pyridin-3-yl)acetate. The intermediate ((2S,3S)-4-bromo-5-chloro-6-fluoro-3-methyl-2-(pyridin-3-yl)-2,3-dihydrobenzofuran-2-yl)methanol (see below) was oxidized to the corresponding aldehyde ((COCl)$_2$/TEA/DMSO, DCM) followed by reductive amination with trans-4-amino-1-methylcyclohexanol (compare Example 114a alternative synthesis) and formation of the boronate. UPLC-MS 1: m/z 531.4 [M+H]$^+$, $t_R$=0.96 min.

The racemic intermediate ((2S*,3S*)-4-bromo-5-chloro-6-fluoro-3-methyl-2-(pyridin-3-yl)-2,3-dihydrobenzofuran-2-yl)methanol was subjected to chiral HPLC (ChiralPak IG, 250×30 mm, 5 μm, heptane/(EtOH+0.1% DEA) 1:1, flow rate: 20 mL/min) to afford the separate enantiomers with an enantiomeric excess of >98%, respectively:

((2S,3S)-4-Bromo-5-chloro-6-fluoro-3-methyl-2-(pyridin-3-yl)-2,3-dihydrobenzofuran-2-yl)methanol: chiral SFC (ChiralPak IG, 250×4.6 mm, CO$_2$/(MeOH+0.1% NH$_3$) 6:4, flow rate: 3 mL/min): $t_R$=3.71 min.

((2R,3R)-4-Bromo-5-chloro-6-fluoro-3-methyl-2-(pyridin-3-yl)-2,3-dihydrobenzofuran-2-yl)methanol: chiral SFC (ChiralPak IG, 250×4.6 mm, CO$_2$/(MeOH+0.1% NH$_3$) 6:4, flow rate: 3 mL/min): $t_R$=2.81 min.

Synthesis of tert-butyl (S)-((2-phenyl-4-(4,4,5,5-tetramethyl-1,3,2-dioxaborolan-2-yl)-5-(trifluoromethyl)-2,3-dihydrobenzofuran-2-yl)methyl)carbamate (C-XXII)

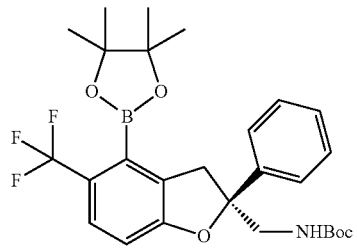

(C-XXII)

Reaction Scheme C-XXII

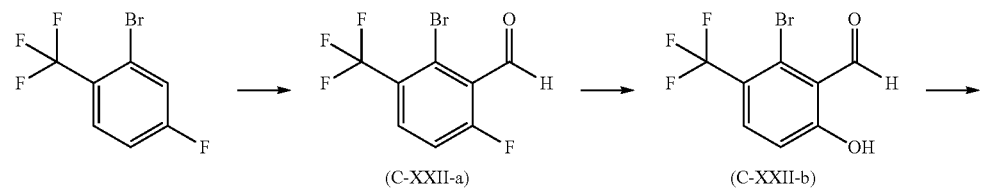

(C-XXII-a)  (C-XXII-b)

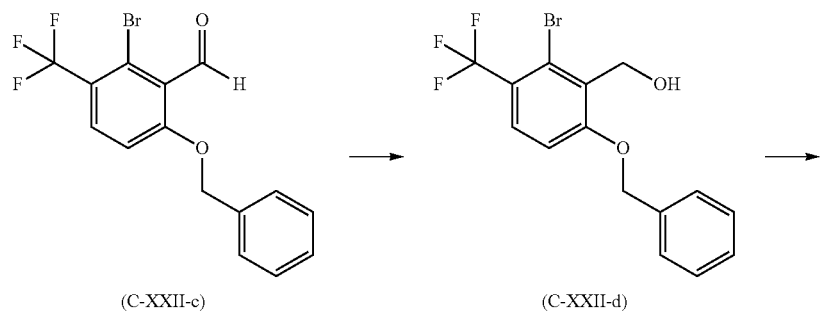

(C-XXII-c)  (C-XXII-d)

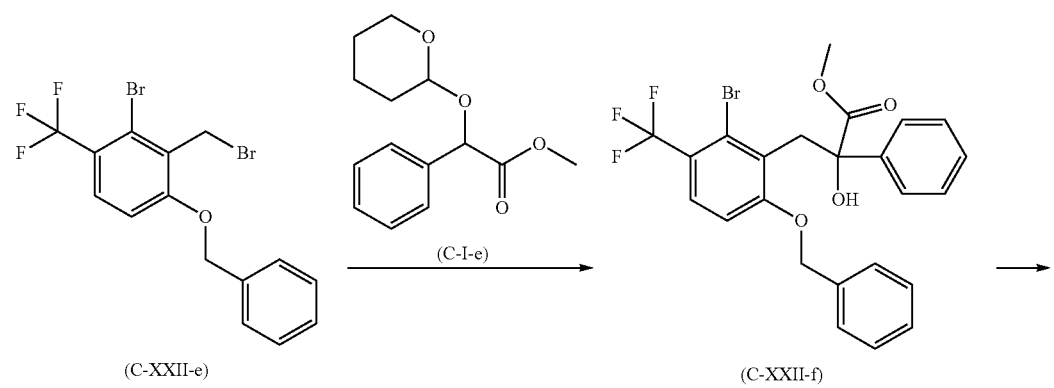

(C-XXII-e)  (C-I-e)  (C-XXII-f)

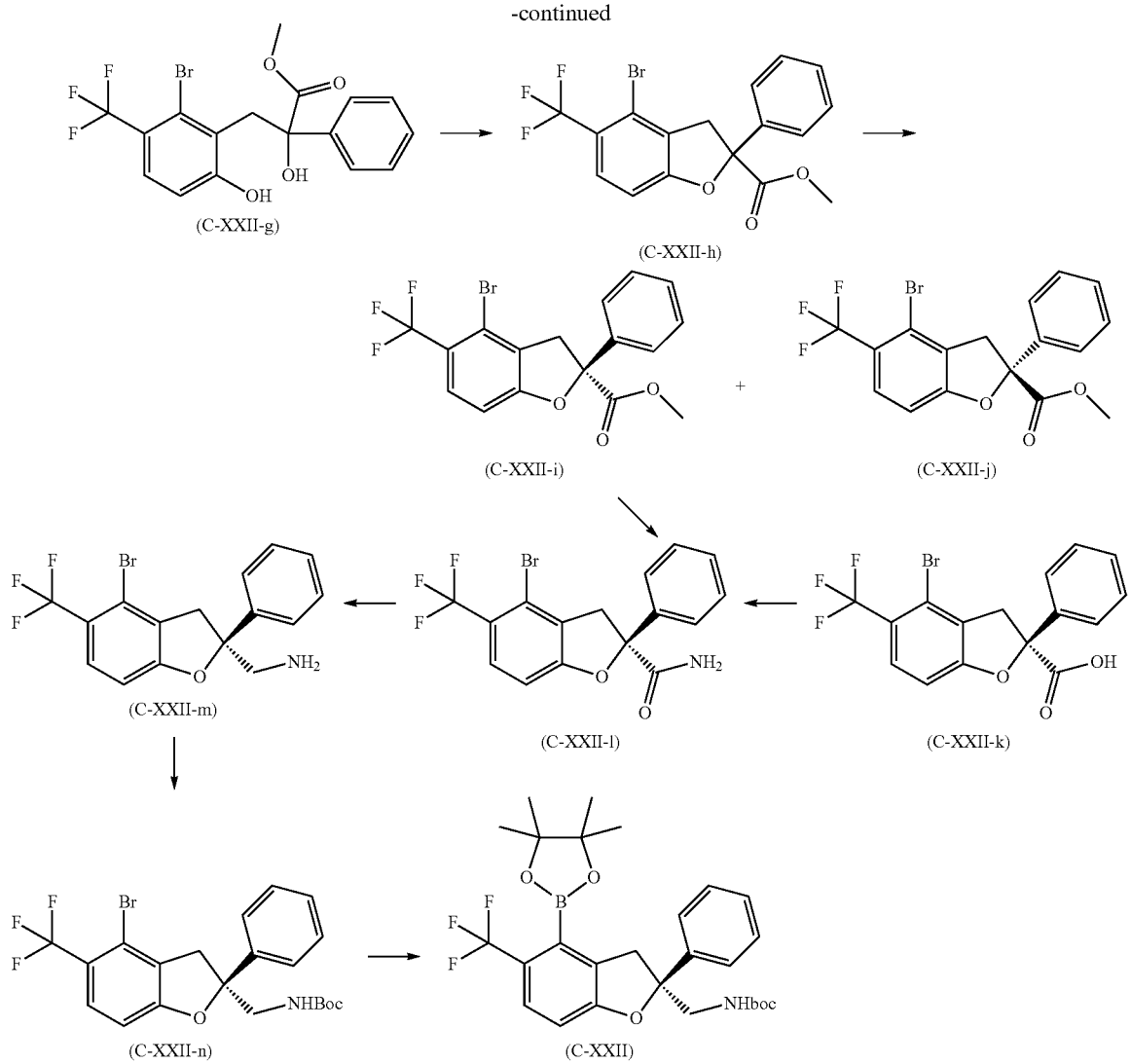

Step 1: 2-Bromo-6-fluoro-3-(trifluoromethyl)benzaldehyde (C-XXII-a)

LDA (53.5 mL, 107 mmol, 2 M in THF/heptane/ethylbenzene) was added to a stirred solution of 2-bromo-4-fluoro-1-(trifluoromethyl)benzene (20 g, 82 mmol) in THF (400 mL) within 1 min and the reaction mixture was stirred at −78° C. for 5 min. A solution of N-methylformanilide (10.67 mL, 86 mmol) in THF (20 mL) was added and the reaction mixture was quenched at −78° C. with a sat ammonium chloride solution. EtOAc was added followed by a sat solution of NH₄Cl. The organic phase was separated and the aqueous phase was extracted with EtOAc. The combined organic extracts were dried over anhydrous Na$_2$SO$_4$ and concentrated. The crude product was triturated in Et$_2$O to afford a white solid (discarded) and the filtrate was absorbed onto silica gel, dried at 40° C. under vacuum and purified by flash chromatography (silica, hexane/EtOAc, gradient: 0% to 10% EtOAc) to afford the desired product (14.3 g). $^1$H NMR (400 MHz, DMSO-d$_6$) δ 10.21 (s, 1H), 8.13 (dd, J=8.9, 5.3 Hz, 1H), 7.61 (t, J=9.4 Hz, 1H).

Step 2: 2-Bromo-6-hydroxy-3-(trifluoromethyl)benzaldehyde (C-XXII-b)

At 0° C. NaH (2.00 g, 50.1 mmol, 60% in mineral oil) was added to a stirred solution of 2-(trimethylsilyl)ethanol (6.67 mL, 46.5 mmol) in DMF (60 mL) and the reaction mixture was stirred at 0° C. for 15 min. A solution of 2-bromo-6-fluoro-3-(trifluoromethyl)benzaldehyde (C-XXII-a) (10 g, 35.8 mmol) in DMF (10 mL) was added and stirring at 0° C. was continued for 30 min. The reaction mixture was quenched with water and extracted with Et$_2$O. The combined organic extracts were dried over anhydrous Na$_2$SO$_4$ and concentrated. The crude product was treated with TBAF (4.68 g, 17.9 mmol) in THF (100 mL) for 4.5 h at RT. Water was added and the pH was adjusted to 5 with 2 N HCl. The aqueous layer was extracted with Et$_2$O, the combined organic extracts were washed with brine, dried over anhydrous Na$_2$SO$_4$ and concentrated. The crude product was purified by flash chromatography (silica, hexane/EtOAc, gradient: 0% to 10% EtOAc) to afford the title compound (7.00 g) as a yellow powder. $^1$H NMR (400 MHz, DMSO-d$_6$) δ 11.97 (s, 1H), 10.29 (s, 1H), 7.86 (d, J=9.0 Hz, 1H), 7.12 (d, J=9.0 Hz, 1H). UPLC-MS 1: m/z 266.9/268.9 [M−H]⁻. t$_R$=1.16 min.

Step 3: 6-(Benzyloxy)-2-bromo-3-(trifluoromethyl) benzaldehyde (C-XXII-c)

A mixture of 2-bromo-6-hydroxy-3-(trifluoromethyl)benzaldehyde (C-XXII-b) (7.00 g, 25.0 mmol), benzyl bromide (3.27 mL, 27.5 mmol) and K$_2$CO$_3$ (5.18 g, 37.5 mmol) in DMF (70 mL) were stirred at RT for 20 h. EtOAc and water were added. The organic phase was separated and the aqueous phase was extracted with EtOAc. The combined organic extracts were washed with water and brine, dried over anhydrous Na$_2$SO$_4$ and concentrated. The crude product was purified by flash chromatography (silica, hexane/EtOAc, gradient: 0% to 20% EtOAc) to afford the title compound (8.49 g) as a colorless powder. ¹H NMR (400 MHz, DMSO-d$_6$) δ 10.26 (s, 1H), 7.96 (d, J=9.0 Hz, 1H), 7.51-7.28 (m, 6H), 5.32 (s, 2H). UPLC-MS 1: m/z 358.9/361.0 [M+H]⁺. t$_R$=1.32 min.

Step 4: (6-(Benzyloxy)-2-bromo-3-(trifluoromethyl) phenyl)methanol (C-XXII-d)

NaBH$_4$ (0.850 g, 22.5 mmol) was added to a stirred suspension of 6-(benzyloxy)-2-bromo-3-(trifluoromethyl) benzaldehyde (C-XXII-c) (8.49 g, 22.5 mmol) in MeOH (100 mL) at 0° C. and stirring at 0° C. was continued for 15 min. The reaction mixture was quenched with acetone and concentrated. DCM and water were added. The organic phase was separated and the aqueous layer was extracted with DCM. The combined organic extracts were washed with water and brine, dried over anhydrous Na$_2$SO$_4$ and concentrated. The crude product was purified by flash chromatography (silica, hexane/EtOAc, gradient: 10% to 30% EtOAc) to afford the title compound (7.5 g) as a colorless powder. UPLC-MS 1: m/z 378.0/380.0 [M+NH$_4$]⁺. t$_R$=1.22 min. ¹H NMR (400 MHz, DMSO-d$_6$) δ 7.72 (d, J=8.8 Hz, 1H), 7.52-7.28 (m, 5H), 7.22 (d, J=8.9 Hz, 1H), 5.24 (s, 2H), 4.96 (t, J=5.3 Hz, 1H), 4.71 (d, J=5.3 Hz, 2H).

Step 5: 1-(Benzyloxy)-3-bromo-2-(bromomethyl)-4-(trifluoromethyl)benzene (C-XXII-e)

CBr$_4$ (9.52 g, 28.7 mmol) was added to a stirred solution of (6-(benzyloxy)-2-bromo-3-(trifluoromethyl)phenyl) methanol (C-XXII-d) (7.515 g, 19.1 mmol) and PPh$_3$ (7.53 g, 28.7 mmol) in DCM (150 mL) at 0° C. and stirring was continued for 4 h. DCM and a 0.5 N NaOH solution were added. The organic phase was separated and the aqueous phase was extracted with DCM. The combined organic extracts were washed with brine, dried over anhydrous Na$_2$SO$_4$ and concentrated. The crude product was purified by flash chromatography (silica, hexane/EtOAc, gradient: 0% to 15% EtOAc) to afford the title compound (7.51 g). ¹H NMR (400 MHz, DMSO-d$_6$) δ 7.79 (d, J=8.9 Hz, 1H), 7.56-7.47 (m, 2H), 7.45-7.25 (m, 4H), 5.34 (s, 2H), 4.79 (s, 2H).

Step 6: Methyl 3-(6-(benzyloxy)-2-bromo-3-(trifluoromethyl)phenyl)-2-hydroxy-2-phenylpropanoate (C-XXII-f)

LDA (15.30 mL, 30.6 mmol, 2 M in THF/heptane/ ethylbenzene) was added within 5 min to a stirred solution of methyl 2-phenyl-2-((tetrahydro-2H-pyran-2-yl)oxy)acetate (C-I-e) (6.58 g, 25.5 mmol) in THF (150 mL) at −78° C. After 30 min a solution of 1-(benzyloxy)-3-bromo-2-(bromomethyl)-4-(trifluoromethyl)benzene (C-XXII-e) (7.51 g, 17.00 mmol) in THF (50 mL) was added within 10 min. After 30 min at −78° C. the cooling bath was removed. The white suspension turned into a clear solution when the temperature reached 0° C. Stirring at 0° C. was continued for 1 h. The reaction mixture was quenched with a sat ammonium chloride solution and extracted with EtOAc. The combined organic extracts were washed with brine, dried over anhydrous Na$_2$SO$_4$ and concentrated. The crude product was dissolved in ACN (50 mL) and treated with 2 N HCl (30 mL) at RT for 15 min. The reaction mixture was poured into a sat solution of NaHCO$_3$ and extracted with EtOAc. The combined organic extracts were washed with brine, dried over anhydrous Na$_2$SO$_4$ and concentrated. The crude product was triturated in Et$_2$O to afford a first portion of the title compound as a colorless powder. The filtrate was purified by flash chromatography (silica, hexane/EtOAc, gradient: 0% to 30% EtOAc) to afford a second portion of the title compound. Both portions were combined (6.94 g). ¹H NMR (400 MHz, DMSO-d$_6$) δ 7.62 (d, J=8.9 Hz, 1H), 7.46-7.40 (m, 2H), 7.36-7.20 (m, 8H), 7.05 (d, J=8.8 Hz, 1H), 5.67 (s, 1H), 5.02 (q, J=12.7 Hz, 2H), 3.97 (d, J=13.6 Hz, 1H), 3.70 (d, J=13.7 Hz, 1H), 3.47 (s, 3H). UPLC-MS 1: m/z 509.0/511.0 [M+H]⁺. t$_R$=1.45 min.

Step 7: Methyl 3-(2-bromo-6-hydroxy-3-(trifluoromethyl)phenyl)-2-hydroxy-2-phenylpropanoate (C-XXII-g)

A mixture of methyl 3-(6-(benzyloxy)-2-bromo-3-(trifluoromethyl)phenyl)-2-hydroxy-2-phenylpropanoate (C-XXII-f) (6.94 g, 13.6 mmol) and Ra-Ni (1.5 g, 17.51 mmol) in MeOH (140 mL) was stirred under atmospheric pressure of H$_2$ at RT for 1 h. The reaction mixture was filtered through a pad of Celite and concentrated. The crude product was subjected to flash chromatography (silica, hexane/EtOAc, gradient: 0% to 30% EtOAc) to afford the title compound (5.7 g). ¹H NMR (400 MHz, DMSO-d$_6$) δ 7.56-7.43 (m, 3H), 7.36-7.19 (m, 3H), 6.86 (d, J=8.6 Hz, 1H), 3.87 (d, J=13.8 Hz, 1H), 3.65-3.54 (m, 4H). UPLC-MS 1: m/z 417.0/419.0 [M−H]⁻. t$_R$=1.22 min.

Step 8: Methyl 4-bromo-2-phenyl-5-(trifluoromethyl)-2,3-dihydrobenzofuran-2-carboxylate (C-XXII-h)

DIAD (2.88 mL, 14.8 mmol) was added to a stirred solution of methyl 3-(2-bromo-6-hydroxy-3-(trifluoromethyl)phenyl)-2-hydroxy-2-phenylpropanoate (C-XXII-g) (5.7 g, 13.5 mmol) and PPh$_3$ (3.88 g, 14.8 mmol) in THF (80 mL) at 0° C. The reaction mixture was stirred at RT for 20 h. For workup the reaction mixture was concentrated and EtOAc and water were added. The organic layer was separated and the aqueous layer was extracted with EtOAc. The combined organic extracts were washed with brine, dried over anhydrous Na$_2$SO$_4$ and concentrated. The crude product was purified by flash chromatography (silica, hexane/ EtOAc, gradient: 0% to 15% EtOAc) to afford the title compound (5.13 g) as a colorless oil. ¹H NMR (400 MHz, DMSO-d$_6$) δ 7.67 (d, J=8.6 Hz, 1H), 7.57-7.51 (m, 2H), 7.46-7.35 (m, 3H), 7.17 (d, J=8.5 Hz, 1H), 4.14 (d, J=16.8 Hz, 1H), 3.68 (s, 4H). UPLC-MS 1: m/z 399.0/401.1 [M−H]⁻. t$_R$=1.39 min.

Step 9: (S)-Methyl 4-bromo-2-phenyl-5-(trifluoromethyl)-2,3-dihydrobenzofuran-2-carboxylate (C-XXII-i) and (R)-methyl 4-bromo-2-phenyl-5-(trifluoromethyl)-2,3-dihydrobenzofuran-2-carboxylate (C-XXII-j)

Racemic methyl 4-bromo-2-phenyl-5-(trifluoromethyl)-2,3-dihydrobenzofuran-2-carboxylate (C-XXII-h) (4.8 g, 11.96 mmol) was separated by chiral preparative HPLC (Chiralcel OJ, 500×100 mm, 20 µm. heptane/IPA 80:20, flow rate: 120 mL/min) to afford the title compounds as pure enantiomers with an enantiomeric access of >99%, respectively:

(S)-Methyl 4-bromo-2-phenyl-5-(trifluoromethyl)-2,3-dihydrobenzofuran-2-carboxylate (C-XXII-i) (2.30 g): chiral HPLC (Chiralcel OJ-H, 250×4.6 mm, 5 µm. heptane/IPA 80:20, flow rate: 1 mL/min) $t_R$=8.20 min. $^1$H NMR (400 MHz, DMSO-$d_6$) δ 7.67 (d, J=8.5 Hz, 1H), 7.59-7.49 (m, 2H), 7.48-7.32 (m, 3H), 7.17 (d, J=8.5 Hz, 1H), 4.14 (d, J=16.8 Hz, 1H), 3.73-3.59 (m, 4H). UPLC-MS 1: m/z 418.0/419.9 [M+NH$_4$]$^+$. $t_R$=1.39 min.

(R)-Methyl 4-bromo-2-phenyl-5-(trifluoromethyl)-2,3-dihydrobenzofuran-2-carboxylate (C-XXII-j) (1.90 g): chiral HPLC (Chiralcel OJ-H, 250×4.6 mm, 5 µm. heptane/IPA 80:20, flow rate: 1 mL/min) $t_R$=17.39 min. $^1$H NMR (400 MHz, DMSO-$d_6$) δ 7.67 (d, J=8.5 Hz, 1H), 7.59-7.50 (m, 2H), 7.48-7.33 (m, 3H), 7.17 (d, J=8.5 Hz, 1H), 4.14 (d, J=16.8 Hz, 1H), 3.73-3.58 (m, 4H). UPLC-MS 1: m/z 418.0/420.0 [M+NH$_4$]$^+$. $t_R$=1.39 min.

Step 10: (S)-4-Bromo-2-phenyl-5-(trifluoromethyl)-2,3-dihydrobenzofuran-2-carboxylic acid (C-XXII-k)

At RT 2 N NaOH (28.7 mL, 57.3 mmol) was added to a stirred solution of (S)-methyl 4-bromo-2-phenyl-5-(trifluoromethyl)-2,3-dihydrobenzofuran-2-carboxylate (C-XXII-i) (2.3 g, 5.7 mmol) in MeOH (30 mL) and THF (30 mL) and the reaction mixture was stirred at RT for 30 min. The organic solvents were removed under reduced pressure, the remaining aqueous layer was acidified to pH 3 with 2 N HCl and extracted with DCM. The combined organic extracts were dried over anhydrous Na$_2$SO$_4$ and concentrated to afford the title product (2.2 g) as a colorless powder. $^1$H NMR (400 MHz, DMSO-$d_6$) δ 7.66 (d, J=8.4 Hz, 1H), 7.61-7.51 (m, 2H), 7.48-7.32 (m, 3H), 7.15 (d, J=8.4 Hz, 1H), 4.09 (d, J=16.7 Hz, 1H), 3.62 (d, J=16.7 Hz, 1H). UPLC-MS 1: m/z 385.1/387.1 [M−H]$^−$. $t_R$=1.08 min.

Step 11: (S)-4-Bromo-2-phenyl-5-(trifluoromethyl)-2,3-dihydrobenzofuran-2-carboxamide (C-XXII-l)

Oxalyl chloride (0.647 mL, 7.39 mmol) followed by 3 drops of DMF were added to a stirred solution of (S)-4-bromo-2-phenyl-5-(trifluoromethyl)-2,3-dihydrobenzofuran-2-carboxylic acid (C-XXII-k) (2.2 g, 5.7 mmol) in DCM (40 mL) at 0° C. The ice bath was removed and stirring at RT was continued for 30 min. The acid chloride solution was slowly added via a dropping funnel to ice cold ammonium hydroxide (40 mL, 308 mmol, 30% in water). The reaction mixture was stirred at 0° C. for 1 h. DCM and water were added and the mixture was filtered through Celite. The filtrate was extracted with DCM and the combined organic extracts were washed with water and brine, dried over anhydrous Na$_2$SO$_4$ and concentrated to afford the title product (1.9 g) as a colorless powder. $^1$H NMR (400 MHz, DMSO-$d_6$) δ 7.88 (s, 1H), 7.69 (d, J=8.5 Hz, 1H), 7.63-7.51 (m, 3H), 7.49-7.31 (m, 3H), 7.11 (d, J=8.5 Hz, 1H), 4.09 (d, J=16.6 Hz, 1H), 3.48 (d, J=16.6 Hz, 1H). UPLC-MS 1: m/z 384.0/386.0 [M−H]$^−$. $t_R$=1.15 min.

Step 12: (S)-(4-Bromo-2-phenyl-5-(trifluoromethyl)-2,3-dihydrobenzofuran-2-yl)methanamine (C-XXII-m)

Borane-methyl sulfide complex (10.02 mL, 20.04 mmol) was added to a stirred solution of (S)-4-bromo-2-phenyl-5-(trifluoromethyl)-2,3-dihydrobenzofuran-2-carboxamide (C-XXII-l) (1.94 g, 5.0 mmol) in THF (40 mL) at RT and the reaction mixture was stirred at reflux for 18 h. After cooling to RT MeOH (10 mL) was added. After 30 min at RT, 1 N HCl (30 mL) was added and the reaction mixture was stirred at RT for 72 h. DCM and a sat solution of NaHCO$_3$ were added, the organic phase was separated and the aqueous phase was extracted with DCM. The combined organic extracts were washed with brine, dried over anhydrous Na$_2$SO$_4$ and concentrated. The crude product was purified by flash chromatography (silica, DCM/MeOH, gradient: 0% to 5% MeOH) to afford the title compound (1.58 g) as a colorless oil. $^1$H NMR (400 MHz, DMSO-$d_6$) δ 7.60 (d, J=8.4 Hz, 1H), 7.52-7.23 (m, 5H), 7.04 (d, J=8.4 Hz, 1H), 3.85 (d, J=16.6 Hz, 1H), 3.22 (d, J=16.5 Hz, 1H), 3.01 (s, 2H), 1.90 (s, 2H). UPLC-MS 1: m/z 372.0/374.0 [M+H]$^+$. $t_R$=0.85 min.

Step 13: Tert-butyl (S)-((4-bromo-2-phenyl-5-(trifluoromethyl)-2,3-dihydrobenzofuran-2-yl)methyl)carbamate (C-XXII-n)

Boc protection of (S)-(4-Bromo-2-phenyl-5-(trifluoromethyl)-2,3-dihydrobenzofuran-2-yl)methanamine (C-XXII-m) was performed as described for intermediate C-I-p (step 14 of synthesis of intermediate C-I). UPLC-MS 1: m/z 372.0/374.0 [M+H−Boc]$^+$. $t_R$=1.43 min.

Step 14: Tert-butyl (S)-((2-phenyl-4-(4,4,5,5-tetramethyl-1,3,2-dioxaborolan-2-yl)-5-(trifluoromethyl)-2,3-dihydrobenzofuran-2-yl)methyl)carbamate (C-XXII)

Tert-butyl (S)-((4-bromo-2-phenyl-5-(trifluoromethyl)-2,3-dihydrobenzofuran-2-yl)methyl)carbamate (C-XXII-n) was converted into the title compound in analogy to step 15 of the synthesis of intermediate C-I. UPLC-MS 1: m/z 420.2 [M+H]$^+$. $t_R$=1.49 min.

Synthesis of (S)-2-(hydroxymethyl)-2-phenyl-4-(4,4,5,5-tetramethyl-1,3,2-dioxaborolan-2-yl)-2,3-dihydrobenzofuran-5-carbonitrile (C-XXIII)

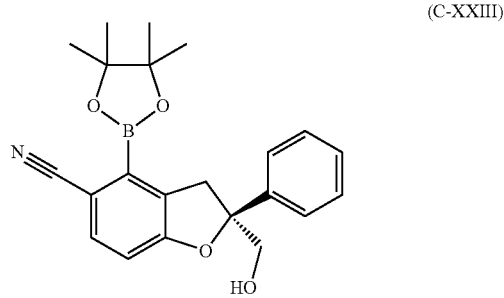 [SMILES: CC1(C)OB(c2c(C#N)ccc3c2C[C@@](CO)(c2ccccc2)O3)OC1(C)C]

(C-XXIII)

Reaction Scheme C-XXIII

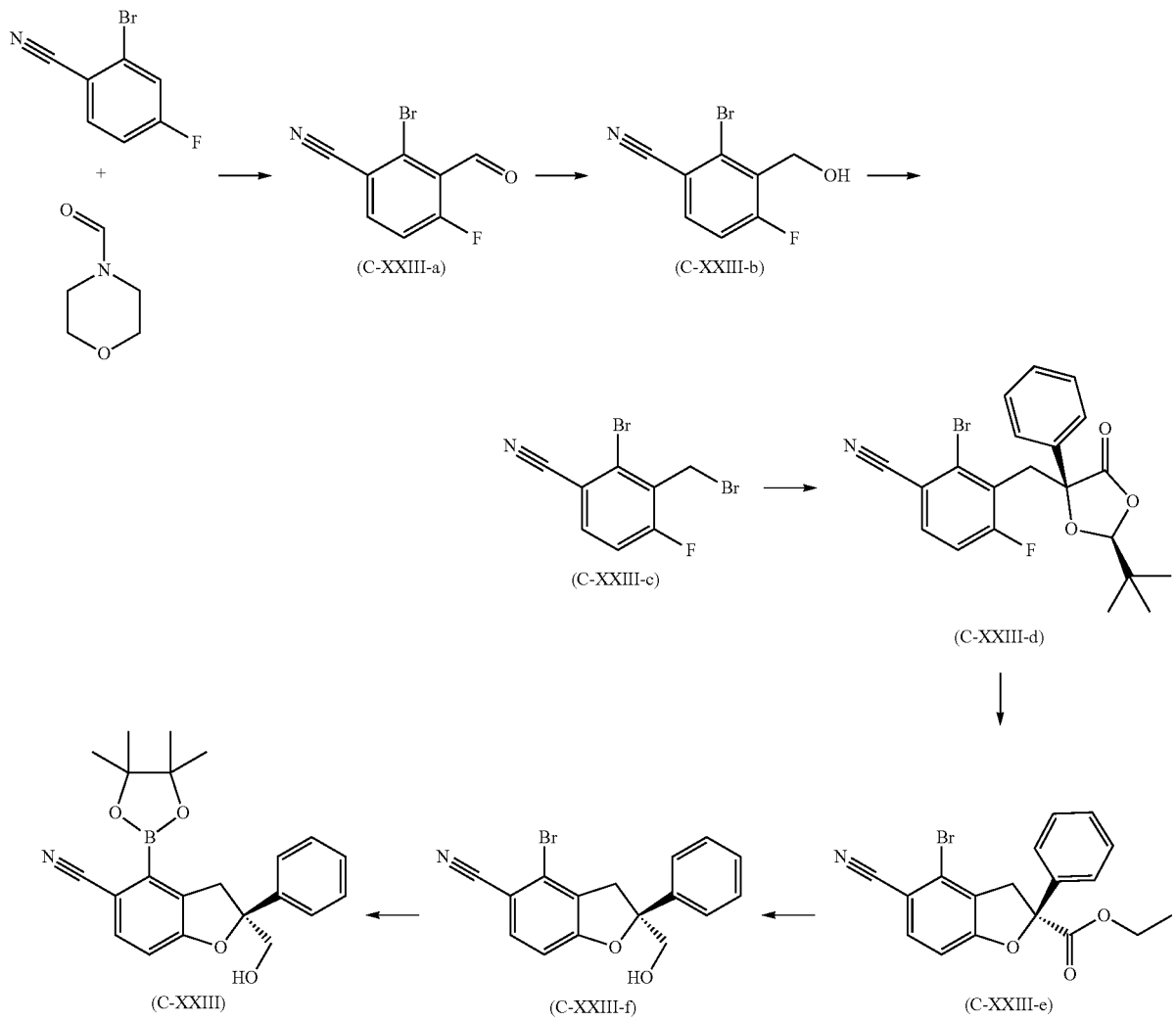

Step 1: 2-Bromo-4-fluoro-3-formylbenzonitrile (C-XXIII-a)

At −78° C. a solution LDA (31.5 mL, 63.0 mmol, 2 N in heptane) was added to a stirred solution of 2-bromo-4-fluorobenzonitrile (10.5 g, 52.5 mmol) in THF (250 mL) under Ar. The reaction mixture was stirred for 30 min at −78° C. before 4-formylmorpholine (6.33 mL, 63.0 mmol) was added. The reaction mixture was quenched with of 0.1M HCl (100 mL) and extracted with EtOAc. The combined organic extracts were washed with a sat solution of NaHCO$_3$, dried over anhydrous Na$_2$SO$_4$ and concentrated. The crude product was purified by flash chromatography (silica, heptane/EtOAc, gradient: 0% to 30% EtOAc) to afford the title compound (9.2 g). UPLC-MS 1: m/z 224.0/226.0 [M−H]$^-$. t$_R$=0.80 min.

Step 2: 2-Bromo-4-fluoro-3-(hydroxymethyl)benzonitrile (C-XXIII-b)

At 0° C. NaBH$_4$ (0.772 g, 20.4 mmol) was added to a stirred solution of 2-bromo-4-fluoro-3-formylbenzonitrile (C-XXIII-a) (9.3 g, 40.8 mmol) in MeOH (80 mL) under Ar and stirring at this temperature was continued for 60 min. The reaction mixture was concentrated and quenched with a sat solution of NH$_4$Cl. The aqueous phase was extracted with EtOAc. The combined organic extracts were washed with a sat solution of NaHCO$_3$, dried over anhydrous Na$_2$SO$_4$ and concentrated. The crude product was purified by flash chromatography (silica, heptane/EtOAc, gradient: 0% to 70% EtOAc) to afford the desired product (8.18 g). $^1$H NMR (400 MHz, DMSO-d$_6$) δ 8.01 (dd, J=8.6, 5.6 Hz, 1H), 7.52 (t, J=8.8 Hz, 1H), 5.42 (t, J=5.6 Hz), 4.63 (dd, J=5.6, 2.5 Hz, 2H).

Step 3: 2-Bromo-3-(bromomethyl)-4-fluorobenzonitrile (C-XXIII-c)

At 0° C. CBr$_4$ (15.27 g, 46.0 mmol) and triphenylphosphine (12.07 g, 46.0 mmol) were added to a stirred solution of 2-bromo-4-fluoro-3-(hydroxymethyl)benzonitrile (C-XXIII-b) (7.06 g, 30.7 mmol) in DCM (100 mL) under Ar. Stirring at 0° C. was continued for 30 min before the reaction mixture was quenched by the addition of a sat solution of NaHCO$_3$ and extracted with EtOAc. The combined organic layers were washed with a sat solution of NaHCO₃, dried over anhydrous Na₂SO₄ and concentrated. The crude product was purified by flash chromatography (silica, hexane/EtOAc; gradient 0% to 20% EtOAc) to give the title product (7.43 g) as a colorless foam. ¹H NMR (400 MHz, DMSO-d₆) δ 10.03 (s, 1H), 7.92 (d, J=8.8 Hz, 1H), 7.30 (d, J=8.8 Hz, 1H), 3.76-3.72 (m, 4H), 3.23-3.19 (m, 4H).

Step 4: 2-Bromo-3-(((2S,4S)-2-(tert-butyl)-5-oxo-4-phenyl-1,3-dioxolan-4-yl)methyl)-4-fluorobenzonitrile (C-XXIII-d)

At −78° C. LDA (18.64 mL, 37.3 mmol, 2 M in THF) was added to a stirred suspension of (2S,5S)-2-(tert-butyl)-5-phenyl-1,3-dioxolan-4-one (CAS 81036-97-7) (8.21 g, 37.3 mmol) in THF (200 mL) under Ar. The reaction mixture was stirred at this temperature for 30 min before a solution of 2-bromo-3-(bromomethyl)-4-fluorobenzonitrile (C-XXIII-c) (8.4 g, 28.7 mmol) in THF (20 mL) was added. The reaction mixture was allowed to warm up to 0° C., quenched by the addition of a sat solution of NaHCO₃ and extracted with EtOAc. The combined organic layers were washed with a sat solution of NaHCO₃, dried over anhydrous Na₂SO₄ and concentrated. The crude product was purified by flash chromatography (silica, hexane/EtOAc; gradient 0% to 15% EtOAc) to give the title product (12.21 g) as a colorless foam. UPLC-MS 1: m/z 449.2/451.2 [M+NH₄]⁺, $t_R$=1.37 min.

Step 5: (S)-Ethyl 4-bromo-5-cyano-2-phenyl-2,3-dihydrobenzofuran-2-carboxylate (C-XXIII-e)

At 0° C. a solution of sodium ethoxide (10.54 mL, 28.2 mmol, 21 wt % in EtOH) was added to a stirred solution of 2-bromo-3-(((2S,4S)-2-(tert-butyl)-5-oxo-4-phenyl-1,3-dioxolan-4-yl)methyl)-4-fluorobenzonitrile (C-XXIII-d) (12.21 g, 28.2 mmol) in EtOH (100 mL) and stirring at 0° C. was continued for 30 min. The reaction mixture was quenched by the addition of a sat solution of NaHCO₃ and extracted with DCM. The combined organic layers were washed with a sat solution of NaHCO₃, dried over anhydrous Na₂SO₄ and concentrated. The crude product was purified by flash chromatography (silica, hexane/EtOAc; gradient 0% to 10% EtOAc) to give the title product (7.81 g) as a colorless oil. UPLC-MS 1: m/z 389.2/391.2 [M+NH₄]⁺, $t_R$=1.24 min.

Step 6: (S)-4-Bromo-2-(hydroxymethyl)-2-phenyl-2,3-dihydrobenzofuran-5-carbonitrile (C-XXIII-f)

At RT MeOH (2.72 mL, 67.3 mmol) and LiBH4 (1.465 g, 67.3 mmol) were added to a stirred solution of (S)-ethyl 4-bromo-5-cyano-2-phenyl-2,3-dihydrobenzofuran-2-carboxylate (C-XXIII-e) (6.26 g, 16.8 mmol) in THF (100 mL). After 16 h the reaction mixture was quenched by the addition of a sat solution of NaHCO₃ and extracted with EtOAc. The combined organic layers were washed with a sat solution of NaHCO₃, dried over anhydrous Na₂SO₄ and concentrated. The crude product was purified by flash chromatography (silica, hexane/EtOAc; gradient 0% to 60% EtOAc) to give the title product (4.20 g) as a colorless oil. UPLC-MS 1: m/z 347.1/349.2 [M+NH₄]⁺, $t_R$=1.04 min.

Step 7: (S)-2-(Hydroxymethyl)-2-phenyl-4-(4,4,5,5-tetramethyl-1,3,2-dioxaborolan-2-yl)-2,3-dihydrobenzofuran-5-carbonitrile (C-XXIII)

(S)-4-Bromo-2-(hydroxymethyl)-2-phenyl-2,3-dihydrobenzofuran-5-carbonitrile (C-XXIII-f) was converted into the title compound in analogy to step 15 of the synthesis of intermediate C-I. UPLC-MS 1: m/z 422.3 [M+formate]⁻. $t_R$=1.18 min.

Synthesis of (S)-4-bromo-2-((((trans)-4-hydroxycyclohexyl)amino)methyl)-2-phenyl-2,3-dihydrobenzofuran-5-carbonitrile (C-XXIV)

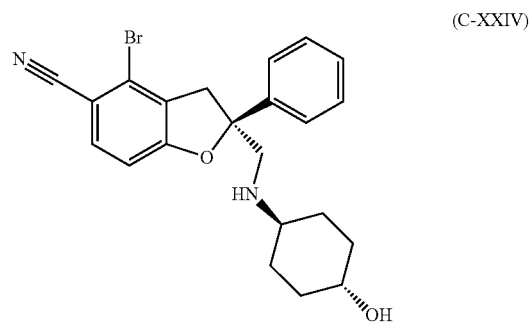 [SMILES: N#Cc1ccc2c(c1Br)C[C@@](CN[C@H]1CC[C@H](O)CC1)(c1ccccc1)O2]

(C-XXIV)

The title compound was prepared from (S)-4-Bromo-2-(hydroxymethyl)-2-phenyl-2,3-dihydrobenzofuran-5-carbonitrile (C-XXIII-f) by oxidation ((COCl)₂/TEA/DMSO, DCM) to the corresponding aldehyde followed by reductive amination with trans-4-aminocyclohexanol using NaBH(OAc)₃. UPLC-MS 1: m/z 427.2/429.2 [M+H]⁺, $t_R$=0.71 min.

Synthesis of tert-butyl (S)-((4-bromo-5-chloro-2-phenyl-2,3-dihydrofuro[2,3-b]pyridin-2-yl)methyl)carbamate (C-XXV)

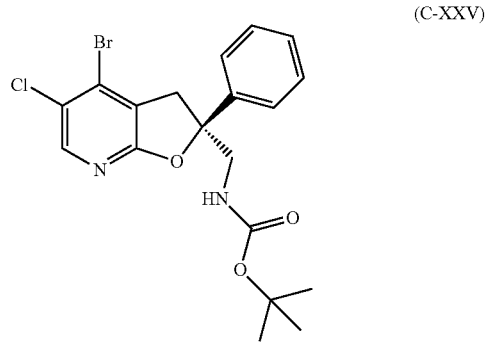 [SMILES: CC(C)(C)OC(=O)NC[C@@]1(c2ccccc2)Cc2c(ncc(Cl)c2Br)O1]

(C-XXV)

Reaction Scheme XXV

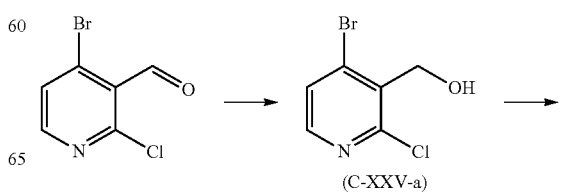

(C-XXV-a)

-continued

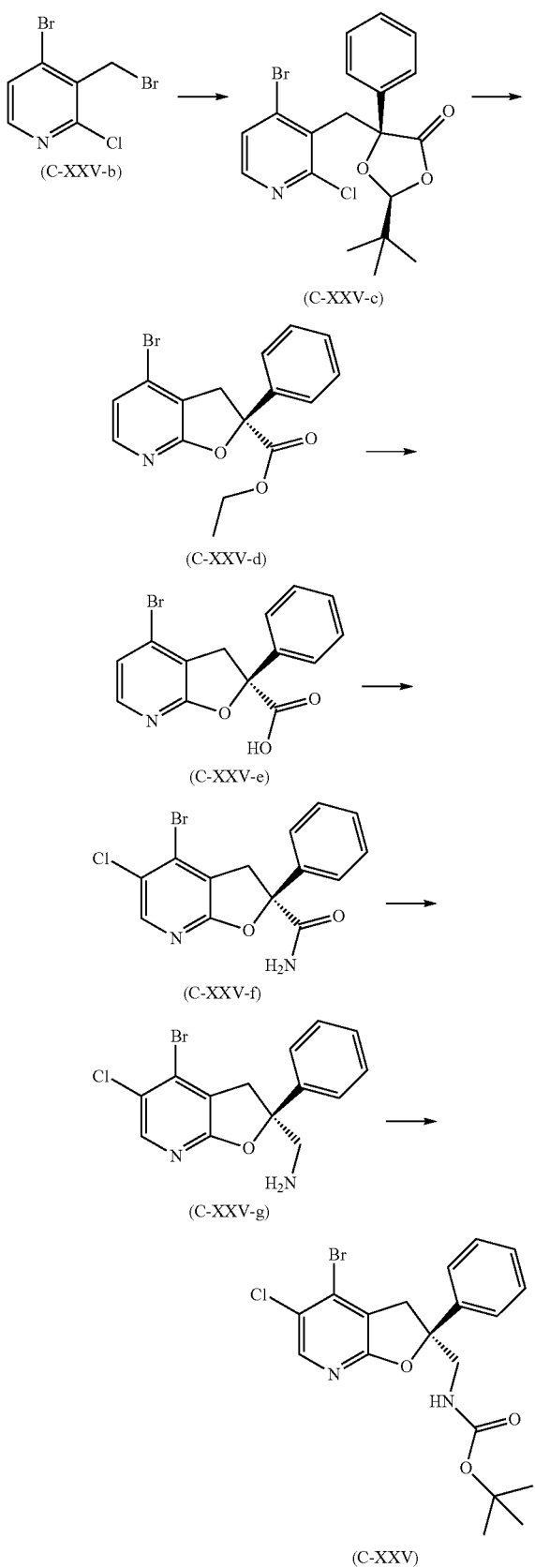

Step 1: (4-Bromo-2-fluoropyridin-3-yl)methanol (C-XXV-a)

4-Bromo-2-chloronicotinaldehyde (5.05 g, 24.8 mmol) was dissolved in THF (50 mL) under an atmosphere of Ar. The reaction mixture was cooled down to 0° C. and NaBH$_4$ (0.936 g, 24.76 mmol) was added. The reaction mixture was warmed to RT and stirred for 5 h. The reaction mixture was quenched with ice cooled water and extracted with EtOAc. The aqueous phase was separated and extracted with EtOAc. The combined organic fractions were washed with brine, dried over anhydrous MgSO$_4$, filtrated and the filtrate was concentrated under reduced pressure to afford the title compound (5.19 g). UPLC-MS 1: $t_R$=0.52 min, mass-ion not observed.

Step 2: 4-Bromo-3-(bromomethyl)-2-fluoropyridine (C-XXV-b)

(4-Bromo-2-fluoropyridin-3-yl)methanol (C-XXV-a) (3.91 g, 15.0 mmol) was dissolved in DCM (40 mL) under an atmosphere of Ar. The reaction mixture was cooled to 0° C.; PPh$_3$ (6.69 g, 25.5 mmol) and CBr$_4$ (8.45 g, 25.5 mmol) were added. The resulting solution was warmed to RT and stirred for 2.5 h. The reaction mixture was concentrated under reduced pressure; the crude residue was purified using flash chromatography (silica, hexane/EtOAc; gradient 0% to 40% EtOAc) to afford the title compound (3.17 g). UPLC-MS 1: $t_R$=1.01 mins, mass-ion not observed.

Step 3: (2S,5S)-5-((4-Bromo-2-fluoropyridin-3-yl)methyl)-2-(tert-butyl)-5-phenyl-1,3-dioxolan-4-one (C-XXV-c)

4-Bromo-3-(bromomethyl)-2-fluoropyridine (C-XXV-b) (2.32 g, 8.63 mmol) and (2S,5S)-2-(tert-butyl)-5-phenyl-1,3-dioxolan-4-one (CAS 81036-97-7) (2.470 g, 11.22 mmol) were dissolved in DMF (50 mL) under an atmosphere of Ar and the reaction mixture was cooled to 0° C. Then NaH (0.518 g, 12.94 mmol, 60% in mineral oil) was added and the reaction mixture was stirred for 2 h at 0° C. The reaction mixture was partitioned between a sat solution of NaHCO$_3$ and EtOAc. The aqueous layer was extracted with EtOAc. The combined organic fractions were washed with brine, dried over anhydrous MgSO$_4$, filtered and concentrated under reduced pressure. The crude residue was purified using flash chromatography (silica, cyclohexane/EtOAc; gradient 0% to 20% EtOAc) to afford the title compound (2.71 g). UPLC-MS 1: 408.3 [M+H]$^+$, $t_R$=1.37 min.

Step 4: Ethyl (S)-4-bromo-2-phenyl-2,3-dihydrofuro[2,3-b]pyridine-2-carboxylate (C-XXV-d)

(2S,5S)-5-((4-bromo-2-fluoropyridin-3-yl)methyl)-2-(tert-butyl)-5-phenyl-1,3-dioxolan-4-one (C-XXV-c) (2.7 g, 6.61 mmol) was dissolved in EtOH (27 mL) under Ar and was cooled down to 0° C. Then was added a solution of sodium ethoxide (0.450 g, 6.61 mmol) in EtOH (27 mL) and the reaction mixture was stirred for 1.5 h at 0° C. The reaction mixture was quenched via the addition of 0.1N HCl and then EtOH was removed in vacuo. The aqueous layer was separated and extracted with EtOAc, then washed with brine. The organic layers were combined, dried over anhydrous Na$_2$SO$_4$, filtered and concentrated under reduced pressure to afford the title compound (2.26 g), which was used for the subsequent hydrolysis without further purification. UPLC-MS 1: 348.2 [M+H]$^+$, $t_R$=1.18 min.

Step 5: (S)-4-Bromo-2-phenyl-2,3-dihydrofuro[2,3-b]pyridine-2-carboxylic acid (C-XXV-e)

Ethyl (S)-4-bromo-2-phenyl-2,3-dihydrofuro[2,3-b]pyridine-2-carboxylate (C-XXV-d) (2.26 g, 6.5 mmol) was dissolved in THF (13.5 mL) and diluted with water (9.0 mL). The solution was cooled to 0° C., then LiOH·H$_2$O (0.207 g, 8.64 mmol) was added. The reaction mixture was allowed to warm up to RT and stirred for 2 h before it was quenched with citric acid (10% in water and ethylacetate). The layers were separated. The aqueous layer was extracted with EtOAc. The combined organic layers were extracted with water and washed with brine. The organic layers were combined, dried over anhydrous Na$_2$SO$_4$, filtered and the filtrate was concentrated under reduced pressure to afford the title compound (2.20 g). UPLC-MS 1: 320.1 [M+H]$^+$, $t_R$=0.80 min.

Step 6: (S)-4-bromo-2-phenyl-2,3-dihydrofuro[2,3-b]pyridine-2-carboxamide (C-XXV-f)

(S)-4-bromo-2-phenyl-2,3-dihydrofuro[2,3-b]pyridine-2-carboxylic acid (C-XXV-e) (2.2 g, 5.6 mmol) was dissolved in DCM (22 mL) and cooled down to 0° C. DMF (7.3 µl, 0.095 mmol) and oxalylchloride (677 µl, 7.89 mmol) were added. The reaction mixture was allowed to warm up to RT and was stirred at RT for 1.5 h. The reaction mixture was cooled down to 0° C. and ammonia solution (16.5 mL, 133 mmol, 32% in water) was added. Stirring at 0° C. was continued for 1.25 h. The reaction mixture was quenched with a sat solution of NaHCO$_3$ and DCM was added. The organic layer was separated and the aqueous layer was extracted with DCM. The combined organic layers were washed with water, brine, dried over anhydrous Na$_2$SO$_4$, filtered and the filtrate was concentrated under reduced pressure to afford the title compound (1.59 g). UPLC-MS 1: 319.1 [M+H]$^+$, $t_R$=0.89 min.

Step 7: (S)-4-Bromo-5-chloro-2-phenyl-2,3-dihydrofuro[2,3-b]pyridine-2-carboxamide (C-XXV-g)

(S)-4-Bromo-2-phenyl-2,3-dihydrofuro[2,3-b]pyridine-2-carboxamide (C-XXV-f) (1.59 g, 4.98 mmol) was dissolved in ACN (33 mL). N-chlorosuccinimide (0.998 g, 7.47 mmol) was added and the reaction mixture was warmed up to 50° C. and stirred for 26 h at 50° C. The reaction mixture was concentrated under reduced pressure. The crude residue was purified using flash chromatography (silica, n-heptane/EtOAc; gradient 0% to 40% EtOAc) to afford the title compound (989 mg). UPLC-MS 1: 353.1 [M+H]$^+$, $t_R$=1.02 min.

Step 8: (S)-(4-Bromo-5-chloro-2-phenyl-2,3-dihydrofuro[2,3-b]pyridin-2-yl)methanamine (C-XXV-h)

(S)-4-Bromo-5-chloro-2-phenyl-2,3-dihydrofuro[2,3-b]pyridine-2-carboxamide (C-XXV-g) (989 mg, 2.8 mmol) was dissolved in THF (4.7 mL). Borane tetrahydrofuran complex solution (15.6 mL, 15.60 mmol, 1 M in THF) was added and the reaction mixture was stirred at RT for 2.5 h. The reaction mixture was quenched with MeOH (1 mL). The mixture was stirred at RT for 20 minutes, then 2 N HCl was added and the solution was stirred for 30 minutes at RT. To the mixture was added a sat solution of NaHCO$_3$ and EtOAc. The organic phase was separated and the aqueous layer was extracted with EtOAc. The combined organic fractions were washed with brine, dried over anhydrous Na$_2$SO$_4$ and concentrated to afford the title compound (727 mg). UPLC-MS 1: 339.0 [M+H]$^+$, $t_R$=0.72 min.

Step 9: Tert-butyl (S)-((4-bromo-5-chloro-2-phenyl-2,3-dihydrofuro[2,3-b]pyridin-2-yl)methyl)carbamate (C-XXV)

Boc anhydride (467 mg, 2.14 mmol) was added to a solution of (S)-(4-bromo-5-chloro-2-phenyl-2,3-dihydrofuro[2,3-b]pyridin-2-yl)methanamine (C-XXV-h) (727 mg, 1.4 mmol) in DCM (17 mL) at 0° C. The reaction mixture was stirred at 0° C. for 2.5 h before it was concentrated. The residue was purified by flash chromatography (silica, cyclohexane/EtOAc; gradient 0% to 50% EtOAc) to afford the title compound (367 mg). UPLC-MS: 383.1 [M+H−tBu]$^+$, $t_R$=1.31 min.

Synthesis of tert-butyl ((6-chloro-2-phenyl-7-(4,4,5,5-tetramethyl-1,3,2-dioxaborolan-2-yl)-2,3-dihydrobenzofuran-2-yl)methyl)carbamate (C-XXVI)

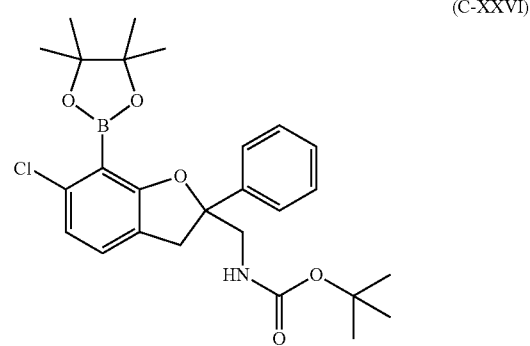 [SMILES: CC(C)(C)OC(=O)NCC1(c2ccccc2)Cc2ccc(Cl)c(B3OC(C)(C)C(C)(C)O3)c2O1]

(C-XXVI)

Reaction Scheme C-XXVI

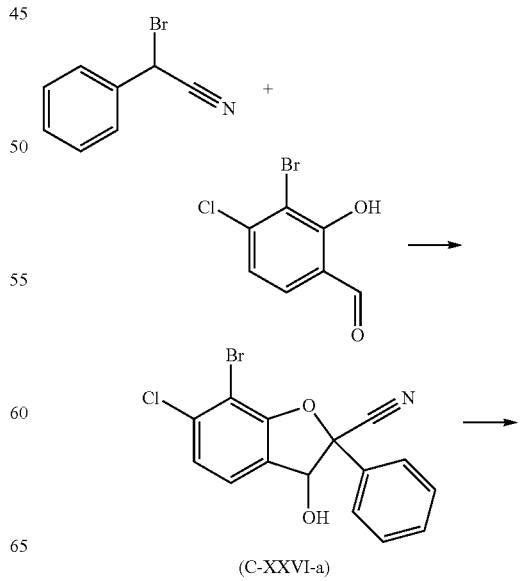

(C-XXVI-a)

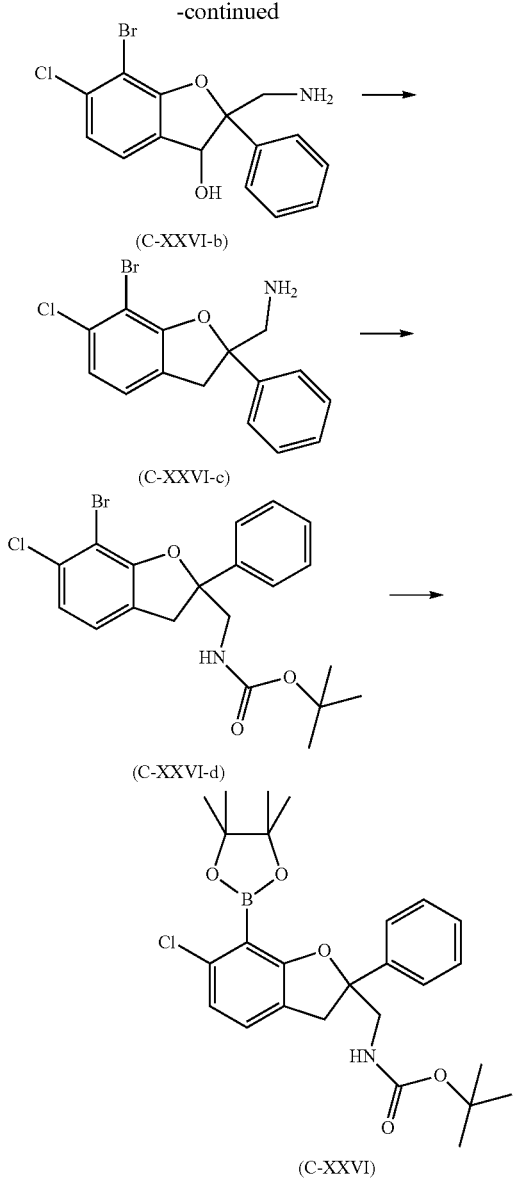

Step 1: 7-Bromo-6-chloro-3-hydroxy-2-phenyl-2,3-dihydrobenzofuran-2-carbonitrile (C-XXVI-a)

At RT DIPEA (3.34 mL, 19.1 mmol) was added to a stirred solution of 3-bromo-4-chloro-2-hydroxybenzaldehyde (3.00 g, 12.74 mmol) and 2-bromo-2-phenylacetonitrile (3.00 g, 15.3 mmol) in DCM (42 mL) and the reaction mixture was stirred at RT for 5 days to afford a brown solution. The reaction mixture was filtered over Hyflo and concentrated. The crude product was purified by flash chromatography (silica, cyclohexane/EtOAc, gradient: 10% to 30% EtOAc) to afford the desired product (2.57 g) as diastereomeric mixture. UPLC-MS 1: m/z 348.1/350.1 [M−H]⁻. $t_R$=1.14 min.

Step 2: 2-(Aminomethyl)-7-bromo-6-chloro-2-phenyl-2,3-dihydrobenzofuran-3-ol (C-XXVI-b)

Borane-methyl sulfide complex (19.40 mL, 38.8 mmol, 2M in THF) was added to a stirred solution of 7-bromo-6-chloro-3-hydroxy-2-phenyl-2,3-dihydrobenzofuran-2-carbonitrile (C-XXVI-a) (2.72 g, 7.76 mmol) in THF (30 mL) at RT and the reaction mixture was stirred at 65° C. for 2 h. After cooling to 0° C., the reaction mixture was quenched by careful addition of 1 N NaOH (30 mL). The reaction mixture was concentrated and redissolved in EtOAc. The organic extracts were washed with brine, dried over anhydrous Na₂SO₄ and concentrated to afford the title compound as a diastereomeric mixture (2.9 g). UPLC-MS 1: m/z 354.1/356.1 [M+H]⁺. $t_R$=0.63 and 0.74 min.

Step 3: (7-Bromo-6-chloro-2-phenyl-2,3-dihydrobenzofuran-2-yl)methanamine (C-XXVI-c)

At RT tripropylsilane (19.25 mL, 92 mmol) followed by boron trifluoride diethyletherate (2.33 mL, 18.40 mmol) and TFA (1.14 mL, 18.40 mmol) were added to a solution of 2-(aminomethyl)-7-bromo-6-chloro-2-phenyl-2,3-dihydrobenzofuran-3-ol (C-XXVI-b) (2.9 g, 6.13 mmol) in DCM (50 mL). The reaction solution was stirred at 50° C. for 4 h before it was quenched by the addition of a sat solution of NaHCO₃ at RT. The aqueous phase was extracted with DCM. The combined organic phases were washed with brine, dried over anhydrous Na₂SO₄, filtered and concentrated to afford the title compound (2.08 g). UPLC-MS 1: m/z 338.1/340.0 [M+H]⁺, $t_R$=0.78 min.

Step 4: Tert-butyl ((7-bromo-6-chloro-2-phenyl-2,3-dihydrobenzofuran-2-yl)methyl)carbamate (C-XXVI-d)

At RT Boc-anhydride (2.00 g, 9.20 mmol) and TEA (1.71 mL, 12.26 mmol) were added to a stirred solution of (7-bromo-6-chloro-2-phenyl-2,3-dihydrobenzofuran-2-yl)methanamine (C-XXVI-c) (2.08 g, 6.13 mmol) in DCM (30 mL). The reaction mixture was stirred at RT for 1 h. The reaction mixture was treated with a sat solution of NaHCO₃. The aqueous phase was extracted with EtOAc. The combined organic extracts were washed with water and brine, dried over anhydrous Na₂SO₄ and concentrated. The crude product was purified by flash chromatography (silica, cyclohexane/EtOAc, gradient: 10% to 60% EtOAc) to afford the title compound (1.30 g). UPLC-MS 1: m/z 438.2/440.0 [M+H]⁺. $t_R$=1.43 min.

Step 5: Tert-butyl ((6-chloro-2-phenyl-7-(4,4,5,5-tetramethyl-1,3,2-dioxaborolan-2-yl)-2,3-dihydrobenzofuran-2-yl)methyl)carbamate (C-XXVI)

At 80° C. PdCl₂(dppf)·CH₂Cl₂ adduct (146 mg, 0.18 mmol) was added under Ar to a stirred suspension of tert-butyl ((7-bromo-6-chloro-2-phenyl-2,3-dihydrobenzofuran-2-yl)methyl)carbamate (C-XXVI-d) (1.29 g, 1.79 mmol), bis(pinacolato)diboron (683 mg, 2.7 mmol) and potassium acetate (528 mg, 5.4 mmol) in toluene (4 mL) and the reaction mixture was vigorously stirred at 110° C. for 16 h. The reaction mixture was cooled to RT, filtered through Celite and concentrated to afford the crude product which was purified by flash chromatography (silica, eluent cyclohexane/EtOAc, gradient: 0% to 20% EtOAc) to give the title compound (480 mg). UPLC MS 1: m/z 486.3 [M+H]⁺. $t_R$=1.49 min.

Synthesis of tert-butyl ((4-bromo-5-chloro-2-phenylbenzo[d][1,3]dioxol-2-yl)methyl)carbamate (C-XXVII)

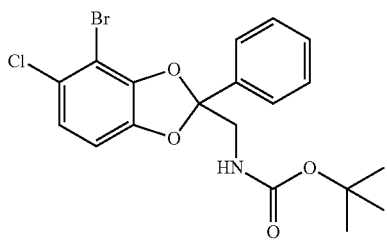
(C-XXVII)

Reaction Scheme XXVII

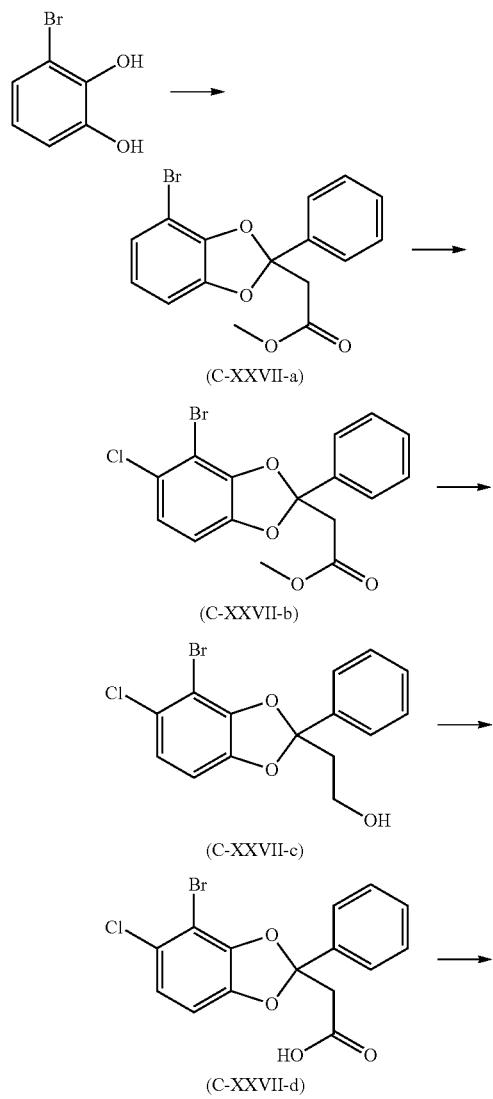

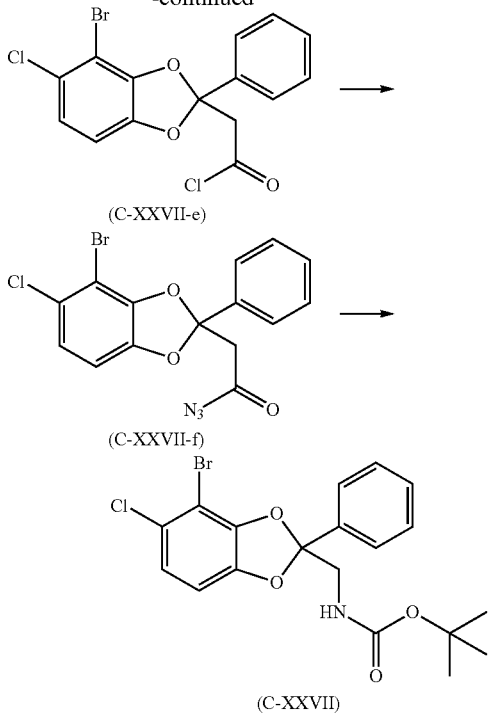

Step 1: Methyl 2-(4-bromo-2-phenyl benzo[d][1,3]dioxol-2-yl)acetate (C-XXVII-a)

To a stirred solution of 3-bromobenzene-1,2-diol (80.47 g, 425.7 mmol) and methyl-3-phenylpropiolate (75 g, 468.3 mmol) in toluene (600 mL) was added triruthenium dodecacarbonyl (13.61 g, 21.3 mmol) under an atmosphere of $N_2$. The reaction mixture was heated to 130° C. and stirred for 5 h. The reaction mixture was concentrated in vacuo. The residue was purified by flash chromatography (silica, petroleum ether/EtOAc; gradient 0% to 30% EtOAc) to afford the title compound (96.0 g). $^1$H NMR (400 MHz, CDCl$_3$) δ 7.65-7.63 (m, 2H), 7.42-7.40 (m, 3H), 6.95 (dd, J=8.3, 1.0 Hz, 1H), 6.81-6.79 (m, 1H), 6.73-6.71 (m, 1H), 3.60 (s, 3H), 3.35 (s, 2H), 3.35 (s, 2H).

Step 2: Methyl 2-(4-bromo-5-chloro-2-phenylbenzo[d][1,3]dioxol-2-yl)acetate (C-XXVII-b)

To a stirred solution of methyl 2-(4-bromo-2-phenylbenzo[d][1,3]dioxol-2-yl)acetate (C-XXVII-a) (85 g, 0.24 mol) in ACN (1.3 L) was added N-chlorosuccinimide (38.99 g, 0.292 mol) and TFA (24.7 mL, 0.32 mol). The solution was heated to 60° C. and stirred for 18 h. The reaction mixture was diluted with TBME (500 mL). The organic fraction was washed twice with a sat solution of NaHCO$_3$ (300 mL). The residue was purified by flash chromatography (silica, PE/EtOAc; gradient 0% to 10% EtOAc) to afford the title product (67.0 g). $^1$H NMR (400 MHz, CDCl$_3$) δ 7.62-7.60 (m, 2H), 7.44-7.41 (m, 3H), 6.94 (d, J=8.4 Hz, 1H), 6.73 (d, J=8.4 Hz, 1H), 3.62 (s, 3H), 3.35 (s, 3H).

Step 3: 2-(4-Bromo-5-chloro-2-phenylbenzo[d][1,3]dioxol-2-yl)ethan-1-ol (C-XXVII-c)

To a stirred solution of methyl 2-(4-bromo-5-chloro-2-phenylbenzo[d][1,3]dioxol-2-yl)acetate (C-XXVII-b) (1.0 g, 2.61 mmol) was added LiBH$_4$ (1.30 mL, 2.61 mmol, 2 M in THF) by dropping funnel under an atmosphere of Ar. at 0° C. The reaction mixture was warmed to RT and stirred for 4 days at RT. The reaction solution was cooled to 4° C. and then quenched via the addition of a solution of 10% aqueous citric acid (500 mL). The mixture was stirred for 5 min, then TBME (600 mL) was added. The aqueous phase was separated and extracted with TBME. The combined organic fractions were washed with brine, dried over anhydrous MgSO$_4$ and then concentrated under reduced pressure to afford a colorless oil. The residue was purified by flash chromatography (silica, heptane/EtOAc; gradient 0-10% EtOAc) to afford the title compound (610 mg). $^1$H NMR (600 MHz, DMSO-d$_6$) δ ppm 7.57-7.51 (m, 2H), 7.49-7.37 (m, 3H), 7.08 (d, J=8.4 Hz, 1H), 6.98 (d, 8.4 Hz), 4.63 (s, 1H), 3.48 (dd, J=7.8, 6.9 Hz, 2H), 2.52 (dd, J=7.8, 6.8 Hz, 2H).

Step 4: 2-(4-Bromo-5-chloro-2-phenylbenzo[d][1,3]dioxol-2-yl)acetic acid (C-XXVII-d)

2-(4-Bromo-5-chloro-2-phenylbenzo[d][1,3)]dioxol-2-yl)ethanol (C-XXVII-c) (5.0 g, 14.1 mmol) was dissolved in DCM (150 mL). Water (75 mL) was added and the reaction mixture was cooled to 0° C. TEMPO (550 mg, 3.52 mmol) was added, followed by the addition of (diacetoxyiodo)benzene (10.20 g, 31.7 mmol). The resulting pale brown emulsion was stirred for 1 h at 0° C. The cooling bath was removed and the mixture was stirred at RT for 4 h. The reaction mixture was diluted with MeOH (3 mL) and stirred for 10 min. The reaction mixture was partitioned between water and DCM. The aqueous phase was extracted with DCM, dried over anhydrous MgSO$_4$ and evaporated to dryness. To the residue was added petroleum benzene (50 mL) and the mixture was stirred at RT for 2 h, then stirred overnight at RT. The suspension was filtered and the resulting solid was dried at 50° C., 0.1 mbar for 1 h to give 1.56 g of the title compound. A second crop was obtained from the mother liquor to give a further 1.44 g of the title compound. UPLC-MS m/z 369.1 [M+H]$^+$.

Step 5: 2-(4-Bromo-5-chloro-2-phenylbenzo[d][1,3]dioxol-2-yl)acetyl chloride (C-XXVII-e)

2-(4-Bromo-5-chloro-2-phenylbenzo[d][1,3]dioxol-2-yl)acetic acid (C-XXVII-d) (1.40 g, 3.8 mmol) was dissolved in DCM (30 mL) and DMF (3 mL). The resulting pale yellow solution was cooled to 0° C. At this temperature was added oxalyl dichloride solution (8.3 mL, 8.3 mmol, 1 M in DCM) over 15 min. The ice-bath was removed and the solution was stirred at RT for 6 h. The reaction mixture was concentrated under reduced pressure to afford the title product as a yellow gum (1.60 g). The acid chloride was used without further purification.

Step 6: 2-(4-Bromo-5-chloro-2-phenylbenzo[d][1,3]dioxol-2-yl)acetyl azide (C-XXVII-f)

The crude 2-(4-bromo-5-chloro-2-phenylbenzo[d][1,3]dioxol-2-yl)acetyl chloride (C-XXVII-e) (1.60 g, 4.1 mmol) was dissolved in acetone (40 mL). The resulting pale yellow solution was cooled to 0° C. and then was added dropwise via dropping funnel to a stirred solution of sodium azide solution (20 mL, 20 mmol, 1 M in water). The cooling bath was removed and the reaction mixture was stirred at RT for 2 h. The reaction solution was concentrated under reduced pressure to afford an orange residue. The residue (slurry) was diluted with EtOAc (100 mL) and water (50 mL). The aqueous phase was separated and extracted with EtOAc. The combined organic phases were washed with water and brine, then dried over anhydrous MgSO$_4$ and concentrated under reduced pressure to give the title compound (590 mg). Used without further purification. UPLC-MS m/z 394.1 [M+H]$^+$.

Step 7: Tert-butyl ((4-bromo-5-chloro-2-phenylbenzo[d][1,3]dioxol-2-yl)methyl)carbamate (C-XXVII)

2-(4-Bromo-5-chloro-2-phenylbenzo[d][1,3]dioxol-2-yl)acetyl azide (C-XXVII-f) (590 mg, 1.5 mmol) was dissolved in t-BuOH (30 mL). The reaction mixture was heated to 100° C. and stirred at this temperature for 2 h. The solution was evaporated to dryness. The residue was purified by flash chromatography (silica, heptane/EtOAc; gradient 0% to 30% EtOAc) to afford the title product (474 mg). $^1$H NMR (400 MHz, DMSO-d$_6$) δ ppm 7.55 (h, J=3.4, 2.9 Hz, 2H), 7.50-7.45 (m, 3H), 7.33 (t, J=6.4 Hz, 1H), 7.09 (d, J=8.4 Hz, 1H), 6.96 (d, J=8.3 Hz, 1H), 3.72 (q, J=8.7, 7.8 Hz, 2H), 1.31 (s, 9H).

Synthesis of (S)-2-(azidomethyl)-4-bromo-5-chloro-6-fluoro-2-phenylindoline (C-XXVIII)

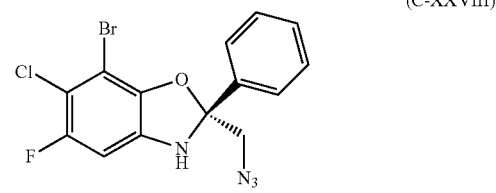

Reaction Scheme C-XXVIII

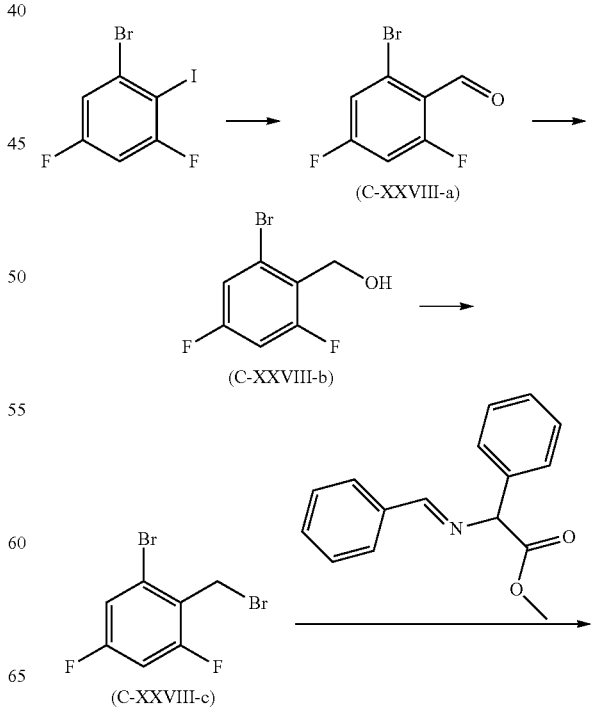

-continued

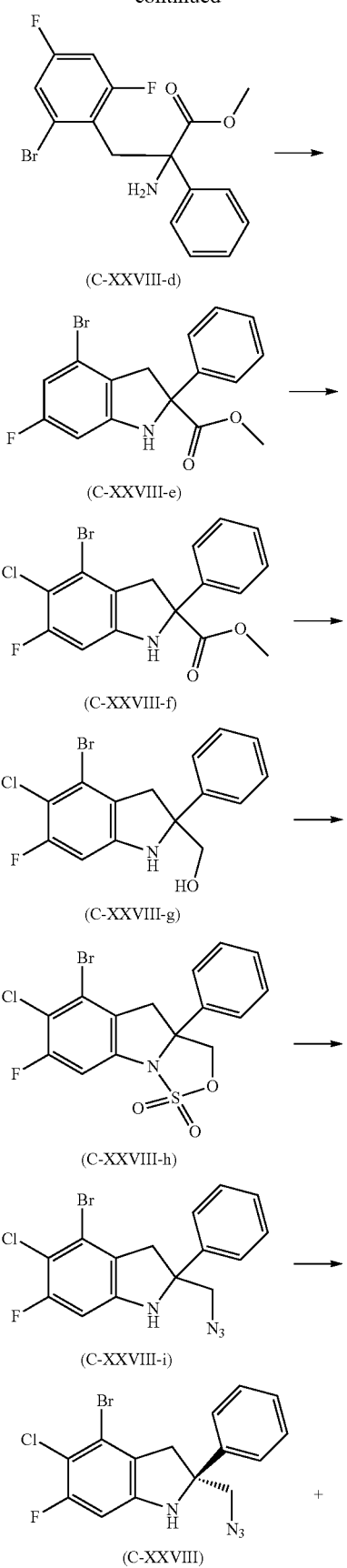

(C-XXVIII-d)

(C-XXVIII-e)

(C-XXVIII-f)

(C-XXVIII-g)

(C-XXVIII-h)

(C-XXVIII-i)

(C-XXVIII)

+

-continued

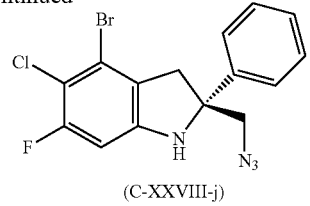

(C-XXVIII-j)

Step 1: 2-Bromo-4,6-difluorobenzaldehyde (C-XXVIII-a)

To a stirred solution of 2-bromo-4,6-difluoroiodobenzene (638 g, 2.0 mol) in Me-THF (5 L) cooled at −10° C. was added dropwise isopropylmegnesium chloride LiCl complex (2000 mL, 2.6 mol, 1.3 M in THF) under Ar. The reaction mixture was stirred for 30 min at −5° C. 4-Formylmorpholine (7.98 mL, 79 mmol) was then added at −500. Stirring at this temperature was continued for 1 h before the reaction mixture was quenched with 2 N HCl (1.5 L). The product was extracted with DCM (3×2 L). The organic layers were combined and washed with brine, dried over anhydrous $Na_2SO_4$ and concentrated. The crude product was purified by flash chromatography (silica, hexane/EtOAc, gradient: 0% to 10% EtOAc) to give the title compound (265 g). UPLC-MS 1: $t_R$=0.94 min.

Step 2: (2-bromo-4,6-difluorophenyl)methanol (C-XXVIII-b)

At 0° C. $NaBH_4$ (36.1 g, 0.95 mol) was added portionwise to a stirred solution of 2-bromo-4,6-difluorobenzaldehyde (C-XXVIII-a) (420 g, 1.90 mol) in MeOH (3.2 L). The reaction mixture was stirred at 0° C. for 1 h, then quenched with a sat $NH_4Cl$ solution (1 L). The product was extracted with EtOAc (3×300 mL), dried over anhydrous $Na_2SO_4$ and concentrated. The crude product was purified by flash chromatography (silica, hexane/EtOAc, gradient: 0% to 50% EtOAc) to give the title compound (311 g). UPLC-MS 1: $t_R$=0.80 min.

Step 3: 1-Bromo-2-(bromomethyl)-3,5-difluorobenzene (C-XXVIII-c)

At 0° C. $PPh_3$ (161 g, 612 mmol) followed by NBS (109 g, 612 mmol) were added to a stirred solution of (2-bromo-4,6-difluorophenyl)methanol (C-XXVIII-b) (105 g, 471 mmol) in DCM (800 mL). The reaction mixture was stirred at 0° C. for 1 h. After concentration the crude material was purified by flash chromatography (silica, hexane 100%) to give the title compound (95 g). UPLC-MS 1: $t_R$=1.22 min. $^1$H NMR (400 MHz, DMSO-$d_6$) δ ppm 7.58 (td, J=8.2, 2.4 Hz, 1H), 7.47-7.41 (m, 1H), 4.65 (s, 2H).

Steps 4: Methyl 2-amino-3-(2-bromo-4,6-difluorophenyl)-2-phenylpropanoate (C-XXVIII-d)

To a stirred solution of methyl (E)-2-(benzylideneamino)-2-phenylacetate CAS [153924-62-0] (55 g, 217 mmol) in THF (500 mL) cooled at −5° C. was added dropwise KOtBu (261 mL, 261 mmol, 1 M in THF) over 30 min. The reaction mixture was stirred at RT for 1 h, then cooled to 0° C. and a solution of 1-bromo-2-(bromomethyl)-3,5-difluorobenzene (C-XXVIII-c) (68 g, 239 mmol) in THF (90 mL) was added. The reaction mixture was stirred for 30 min, then quenched with 1 N HCl. The mixture was stirred for 1 h and extracted with heptane (3×500 mL). The pH of the aqueous layer was adjusted to pH ~8-9 and extracted with EtOAc (3×500 mL). The combined organic layers were washed with brine, dried over anhydrous $Na_2SO_4$ and concentrated to give the racemic title compound (35 g), which was used in the next step without further purification. UPLC-MS 1: m/z 370.2/372.2 $[M+H]^+$, $t_R$=1.07 min.

Step 5: Methyl 4-bromo-6-fluoro-2-phenylindoline-2-carboxylate (C-XXVIII-e)

To a solution of methyl 2-amino-3-(2-bromo-4,6-difluorophenyl)-2-phenylpropanoate (C-XXVIII-d) (75 g, 203 mmol) in THF (1.5 L) cooled at 0° C. was added under Ar a solution of LDA (200 mL, 400 mmol, 2 M in THF). The reaction mixture was stirred for 30 min at 0° C. before it was quenched with a solution of 10% citric acid. The mixture was extracted with TBME (3×1 L). The combined organic layers were washed with brine, dried over anhydrous $Na_2SO_4$ and concentrated to give the title racemic compound (41 g), which was used in the next step without further purification. UPLC-MS 1: m/z 350.2/352.2 $[M+H]^+$, $t_R$=1.31 min.

Step 6: Methyl 4-bromo-5-chloro-6-fluoro-2-phenylindoline-2-carboxylate (C-XXVIII-f)

To a solution of methyl 4-bromo-6-fluoro-2-phenylindoline-2-carboxylate (C-XXVIII-e) (35.0 g, 100 mmol) in THF (350 mL), cooled at 0° C., were successively added N-chloro succinimide (14.6 g, 110 mmol) and p-TsOH monohydrate (20.9 g, 110 mmol). The reaction mixture was stirred at 0° C. for 1 h before it was quenched with a solution of 10% $Na_2S_2O_3$ (100 mL). The product was extracted with TBME (3×500 mL). The combined organic layers were washed with brine, dried over anhydrous $Na_2SO_4$ and concentrated. The crude product was purified by flash chromatography (silica, heptane/EtOAc, gradient: 0% to 5% EtOAc) to give the racemic title product (23 g). UPLC-MS 1: m/z 384.1/386.1 $[M+H]^+$, $t_R$=1.37 min.

Step 7: (4-Bromo-5-chloro-6-fluoro-2-phenylindolin-2-yl)methanol (C-XXVIII-g)

To a solution of methyl 4-bromo-5-chloro-6-fluoro-2-phenylindoline-2-carboxylate (C-XXVIII-f) (10 g, 26 mmol) in THF (200 mL), cooled at 0° C., was added dropwise a solution of $LiBH_4$ (13 mL, 26 mmol, 2M in THF). The reaction mixture was stirred at 0° C. for 1 h, then at RT for 6 h. The mixture was cooled to 0° C. and quenched with a solution of 10% citric acid (500 mL), then extracted with TBME (2×1 L). The combined organic layers were washed with brine (2×500 mL), dried over anhydrous $Na_2SO_4$ and concentrated. The product was crystallized in a mixture of TBME (100 mL) and heptane (200 mL). The suspension was filtered, washed with heptane (50 mL), then dried under HV at 50° C. to give the racemic title compound (8.3 g). UPLC-MS 1: m/z 356.1/358.1 $[M+H]^+$, $t_R$=1.21 min.

Step 8: 5-Bromo-6-chloro-7-fluoro-3a-phenyl-3a,4-dihydro-3H-[1,2,3]oxathiazolo[3,4-a]indole 1,1-dioxide (C-XXVIII-h)

To a solution of imidazole (19 g, 278 mmol) in THF (150 mL) cooled at −78° C. was added a solution of thionyl chloride (5.1 mL, 69.6 mmol) in THF (65 mL) over 20 min (very exothermic reaction, temperature was maintained between −60° C. and −40° C.). The suspension was stirred for 20 min at −78° C. A solution of (4-bromo-5-chloro-6-fluoro-2-phenylindolin-2-yl)methanol (C-XXVIII-g) (8.3 g, 23.2 mmol) in THF (60 mL) was then added over 5 min at −78° C. and the resulting suspension was stirred at 0° C. for 2 h. The mixture was diluted with EtOAc (500 mL), quenched with a solution of 2 N citric acid (400 mL) and washed with brine (2×300 mL). The aqueous layers were back-extracted with EtOAc (500 mL). The combined organic layers were dried over anhydrous $Na_2SO_4$ and concentrated to give the intermediate N-sulfoxide ketimine UPLC-MS 1: m/z 402.1/404.1 $[M+H]^+$, $t_R$=1.34 min.

The obtained crude material was quickly suspended in ACN (150 mL). To the mixture, cooled at 0° C., were successively added Ruthenium (III) chloride (0.270 g, 1.287 mmol) and sodium periodate (7.9 g, 36.8 mmol), followed by dropwise addition of water (105 mL) over 3 min. The reaction mixture was then stirred at 0° C. for 30 min and at RT for 1 h. Water (300 mL) was added and the mixture was extracted with EtOAc (2×600 mL). The organic layers were washed with water (300 mL) and brine (300 mL), then combined, dried over anhydrous $Na_2SO_4$ and concentrated. The crude product was purified by flash chromatography (silica, hexane/EtOAc, 9:1) to give the title compound (3.7 g). UPLC-MS 1: m/z 462.2/464.2 $[M+formate]^-$, $t_R$=1.32 min.

Steps 9 and 10: (S)-2-(azidomethyl)-4-bromo-5-chloro-6-fluoro-2-phenylindoline (C-XXVIII) and (R)-2-(azidomethyl)-4-bromo-5-chloro-6-fluoro-2-phenylindoline (C-XXVIII-j)

Sodium azide (0.6 g, 9.2 mmol) was added at RT to a solution of 5-bromo-6-chloro-7-fluoro-3a-phenyl-3a,4-dihydro-3H-[1,2,3]oxathiazolo[3,4-a]indole 1,1-dioxide (C-XXVIII-h) (3.7 g, 8.8 mmol) in DMF (100 mL). The reaction mixture was stirred at RT for 18 h, then quenched with sulfuric acid (49.5 mL, 4.95 mmol) at RT and stirred for another 1.5 h at RT. Water (500 mL) was added and the mixture was extracted with EtOAc (2×1 L). The organic layers were washed with brine (500 mL), combined, dried over anhydrous $Na_2SO_4$ and concentrated. The crude product was purified by flash chromatography (silica, heptane/EtOAc 95:5) to give the racemic product. Both enantiomers were separated by chiral SFC (Lux Amylose-1, 250×30 mm, 50 μm. $CO_2/(MeOH+0.1\% NH_3)$ 1:1, 40° C., flow rate: 80 mL/min, 3 mL/injection, cycle time 11 min) to afford (S)-2-(azidomethyl)-4-bromo-5-chloro-6-fluoro-2-phenylindoline (C-XXVIII) (1.3 g) and (R)-2-(azidomethyl)-4-bromo-5-chloro-6-fluoro-2-phenylindoline (C-XXVIII-j) (1.3 g) with an enantiomeric excess of 99%, respectively.

(S)-2-(azidomethyl)-4-bromo-5-chloro-6-fluoro-2-phenylindoline (C-XXVIII):

Chiral SFC: Chiralpak AD 100×4.6 mm, 5 μm, $CO_2/(MeOH+0.1\% NH_3)$ 1:1, flow rate 3 mL/min), $t_R$: 2.76 min. UPLC-MS 1: m/z 381.0/383.0 $[M+H]^+$, $t_R$=1.42 min.

Other enantiomer (R)-2-(azidomethyl)-4-bromo-5-chloro-6-fluoro-2-phenylindoline (C-XXVIII-j): Chiral SFC: Chiralpak AD 100×4.6 mm, 5 μm, $CO_2/(MeOH+0.1\% NH_3)$ 1:1, flow rate 3 mL/min), $t_R$: 1.12 min. UPLC-MS 1: m/z 381.0/383.0 $[M+H]^+$, $t_R$=1.42 min.

Synthesis of tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)(methyl)carbamate (C-XXIX)

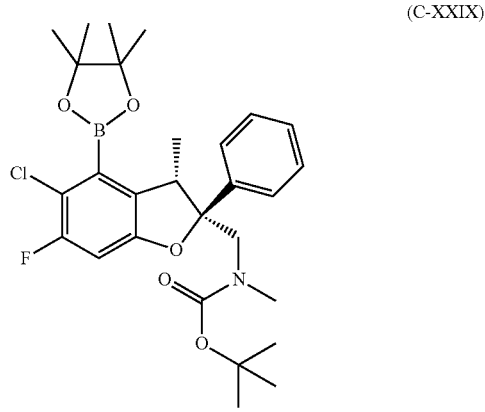 [SMILES: C[C@H]1c2c(cc(F)c(Cl)c2B2OC(C)(C)C(C)(C)O2)O[C@]1(CN(C)C(=O)OC(C)(C)C)c1ccccc1]

Reaction Scheme C-XXIX

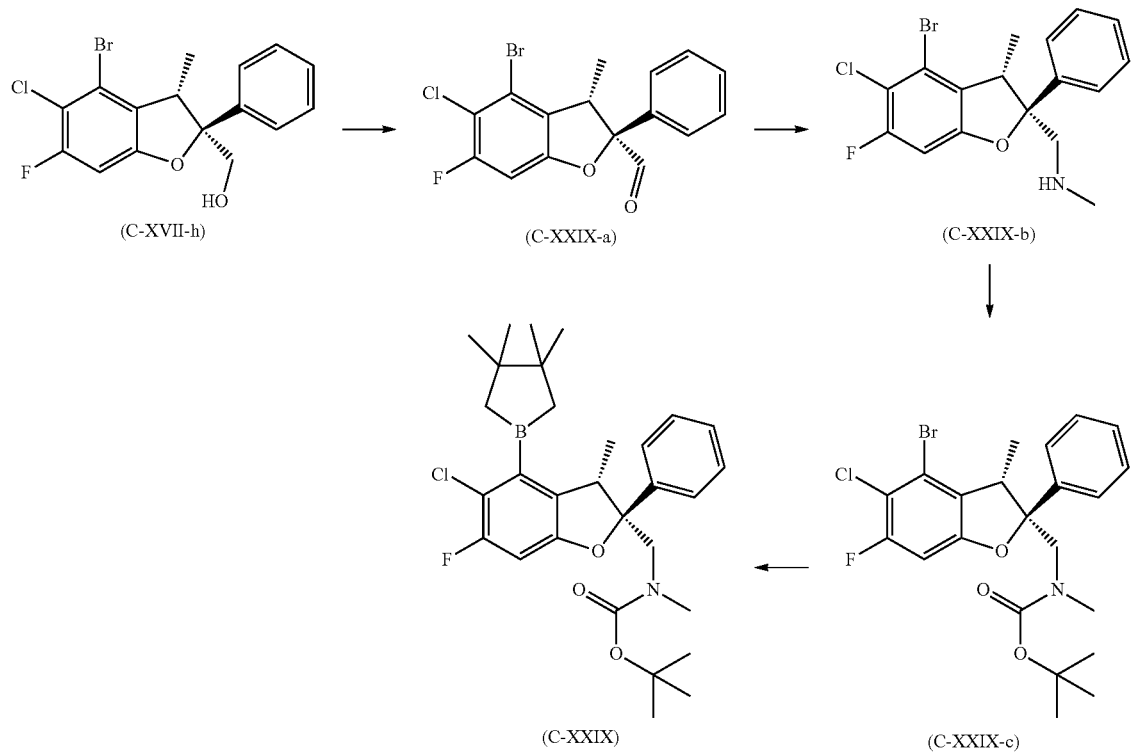

Step 1: (2S,3S)-4-Bromo-5-chloro-6-fluoro-3-methyl-2-phenyl-2,3-dihydrobenzofuran-2-carbaldehyde (C-XXIX-a)

To a stirred solution of oxalyl chloride (3.01 mL, 34.4 mmol) in DCM (60 mL) was added DMSO (4.9 mL, 68.9 mmol) in DCM (10 mL) at −78° C. and the reaction mixture was stirred at −78° C. for 15 min. A solution of ((2S,3S)-4-bromo-5-chloro-6-fluoro-3-methyl-2-phenyl-2,3-dihydrobenzofuran-2-yl)methanol (C-XVII-h) (8 g, 21.5 mmol) in DCM (30 mL) was then added and stirring at −78° C. was continued for 15 min. TEA (15.0 mL, 108 mmol) was added and the reaction mixture was allowed to warm to 0° C. over 30 min. The mixture was diluted in DCM and water, extracted twice with DCM and the combined organic extracts were washed with water and brine, dried over anhydrous $Na_2SO_4$ and concentrated to afford the title compound (8,6 g) as a yellow foam, which was used without purification. UPLC-MS 1: m/z 367.0/368.8 [M−H]⁻, $t_R$=1.39 min.

Step 2: 1-((2S,3S)-4-Bromo-5-chloro-6-fluoro-3-methyl-2-phenyl-2,3-dihydrobenzofuran-2-yl)-N-methylmethanamine (C-XXIX-b)

A solution of (2S,3S)-4-bromo-5-chloro-6-fluoro-3-methyl-2-phenyl-2,3-dihydrobenzofuran-2-carbaldehyde (C-XXIX-a) (8.6 g, 20.9 mmol) and methylamine hydrochloride (14.14 g, 209 mmol) (finely ground and dried for 1 h under HV) in DCM (100 mL) was stirred at RT for 14 h. Sodium triacetoxyborohydride (8.88 g, 41.9 mmol) was added and the reaction mixture was stirred at RT for 4 h before it was diluted with a sat solution of $NaHCO_3$ and extracted with DCM. The combined organic extracts were washed with brine, dried over anhydrous $Na_2SO_4$ and concentrated. The crude product was purified flash chromatography (silica, (7N ammonia in MeOH)/DCM, gradient 0% to 4% (7N ammonia in MeOH)) to give the title compound (5.27 g) as a yellow oil. UPLC-MS 1: m/z 383.7/385.7 [M+H]⁺, $t_R$=0.87 min.

Step 3: Tert-butyl (((2S,3S)-4-bromo-5-chloro-6-fluoro-3-methyl-2-phenyl-2,3-dihydrobenzofuran-2-yl)methyl)(methyl)carbamate (C-XXIX-c)

To a stirred solution of 1-((2S,3S)-4-bromo-5-chloro-6-fluoro-3-methyl-2-phenyl-2,3-dihydrobenzofuran-2-yl)-N-methylmethanamine (C-XXIX-b) (5.27 g, 13.29 mmol) and TEA (3.70 mL, 26.6 mmol) in DCM (50 mL) was added BOC-anhydride (4.01 mL, 17.3 mmol) at RT and stirring was continued for 14 hr. The reaction mixture was diluted in DCM and water, the organic phase was separated and the aqueous phase was extracted with DCM. The combined organic extracts were washed with brine, dried over anhydrous $Na_2SO_4$ and concentrated. The crude product was purified by flash chromatography (silica, EtOAc/Hep, gradient 0% to 30% EtOAc) to give the title compound (6.55 g) as a white foam. UPLC-MS 1: m/z 484.4/486.4 $[M+H]^+$, $t_R$=1.57 min.

Step 4: Tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)(methyl)carbamate (C-XXIX)

To a stirred solution of tert-butyl (((2S,3S)-4-bromo-5-chloro-6-fluoro-3-methyl-2-phenyl-2,3-dihydrobenzofuran-2-yl)methyl)(methyl)carbamate (C-XXIX-c) (6.55 g, 13.1 mmol), bis(pinacolato)diboron (4.99 g, 19.7 mmol) and potassium hydroxide (1.838 g, 32.8 mmol) in toluene (60 mL) was added $PdCl_2(dppf) \cdot CH_2Cl_2$ adduct (1.07 g, 1.31 mmol) at 60° C. and the reaction mixture was stirred at 100° C. for 2 h. The reaction mixture was filtered over Hyflo and concentrated. The crude product was purified flash chromatography (silica, EtOAc/heptane, gradient 0% to 30% EtOAc) to give the title compound (6.1 g). 1H NMR (400 MHz, DMSO-d6) δ 7.53-7.02 (m, 6H), 4.61-3.43 (m, 3H), 2.69 (s, 3H), 1.38-1.10 (m, 24H). UPLC-MS 1: m/z 532.5 $[M+H]^+$, $t_R$=1.58 min.

Synthesis of tert-butyl (((2S,3R)-5-chloro-6-fluoro-3-(methoxymethyl)-2-phenyl-4-(4,4,5,5-tetramethyl-1,3,2-dioxaborolan-2-yl)-2,3-dihydrobenzofuran-2-yl)methyl)(methyl)carbamate (C-XXX)

(C-XXX)

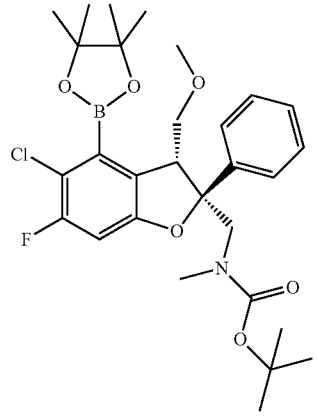

Reaction Scheme C-XXX

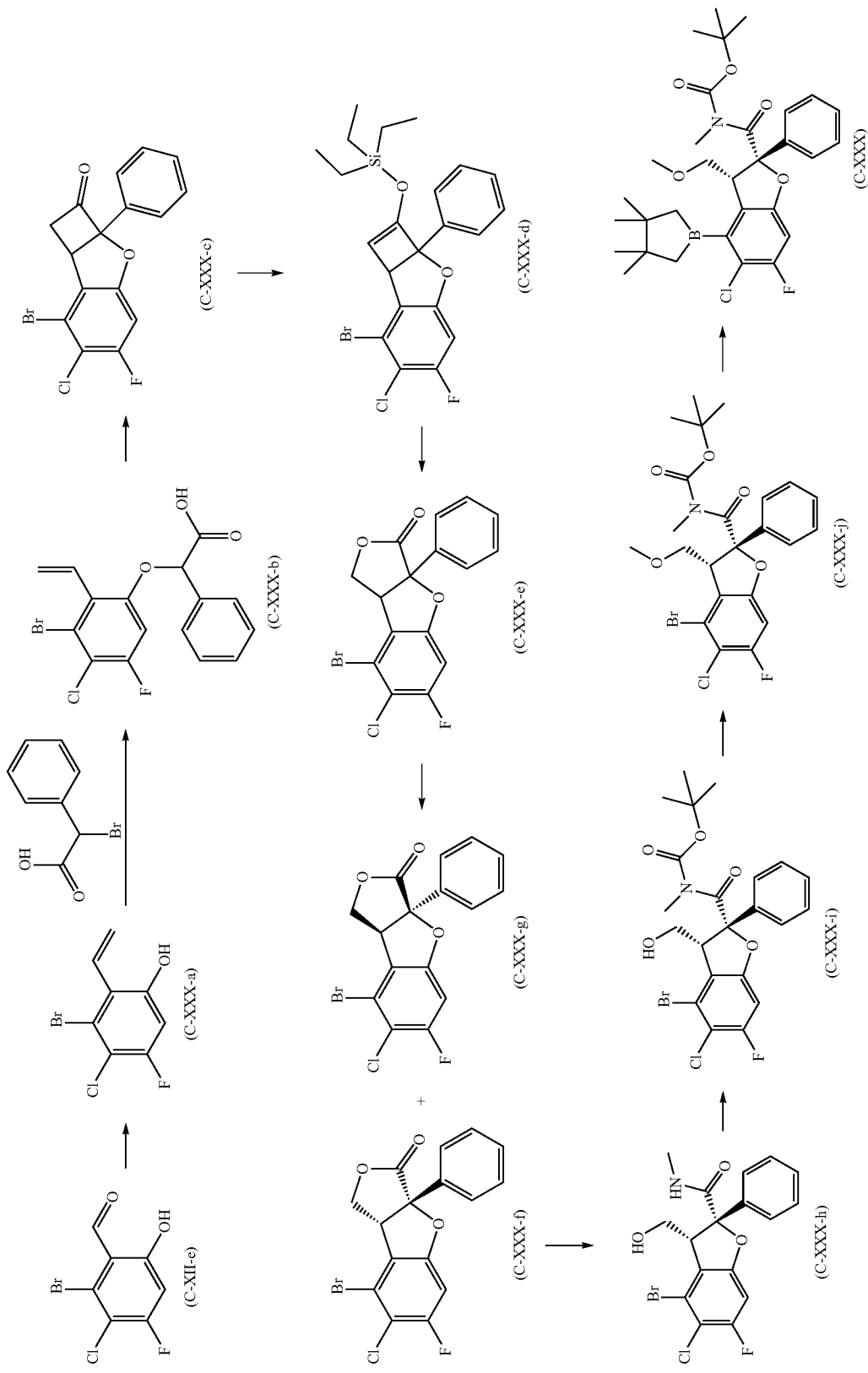

Step 1: 3-Bromo-4-chloro-5-fluoro-2-vinylphenol (C-XXX-a)

To a stirred suspension of methyltriphenylphosphonium bromide (67.7 g, 189 mmol) in THF (800 mL) was added potassium tert-butoxide (21.25 g, 189 mmol) at RT within 15 min and the reaction mixture was stirred at RT for 1 h. The mixture was cooled to −78° C. and a solution of 2-bromo-3-chloro-4-fluoro-6-hydroxybenzaldehyde (C-XII-e) (24 g, 95 mmol) in THF (200 mL) was added drop-wise. The reaction mixture was allowed to slowly warm up to 0° C. over 5 h and quenched with 400 mL of 1N HCl. The crude mixture was diluted in water and extracted with EtOAc. The organic extract was washed with brine, dried over anhydrous $Na_2SO_4$ and concentrated. The crude product was purified by flash chromatography (silica, DCM/heptane, gradient 10% to 40% DCM) to afford the title compound (15.85 g) as a colorless solid. UPLC-MS 1: m/z 249.0/251.0 [M−H]⁻, $t_R$=1.10 min.

Step 2: 2-(3-Bromo-4-chloro-5-fluoro-2-vinylphenoxy)-2-phenylacetic acid (X-XXX-b)

At 0° C. sodium hydride (5.37 g, 134 mmol) was added portion-wise to a stirred solution of 3-bromo-4-chloro-5-fluoro-2-vinylphenol (C-XXX-a) (15.83 g, 61.1 mmol) in THF (400 mL) followed by dropwise addition of a solution of 2-bromo-2-phenylacetic acid (14.44 g, 67.2 mmol) in THF (200 mL). The reaction mixture was stirred at 75° C. for 1 h before it was quenched with 1N HCl. The crude mixture was diluted in water and extracted with EtOAc. The organic extract was dried over anhydrous $Na_2SO_4$ and concentrated to afford the title compound (27 g) as a colorless solid. UPLC-MS 1: m/z 382.9/384.9 [M−H]⁻, $t_R$ 1.21 m.

Step 3: 7-Bromo-6-chloro-5-fluoro-2a-phenyl-2a,7b-dihydrocyclobuta[b]benzofuran-2(1H)-one (C-XXX-c)

To a stirred solution of tosylchloride (22.69 g, 119 mmol) and TEA (41.5 mL, 298 mmol) in toluene (300 mL) was added at 100° C. a solution of 2-(3-bromo-4-chloro-5-fluoro-2-vinylphenoxy)-2-phenylacetic acid (C-XXX-b) (27 g, 59.5 mmol) in toluene (300 mL) and the reaction mixture was stirred at 10000 for 1.5 h. The crude mixture was diluted in water and extracted with EtOAc. The organic extract was washed with brine, dried over anhydrous $Na_2SO_4$ and concentrated. The crude product was purified by flash chromatography (silica, EtOAc/heptane, gradient 0% to 20% EtOAc) to afford, after trituration in heptane, the title compound (18.59 g) as a colorless solid. UPLC-MS 1: m/z 365.2/367.2 [M−H]⁻, $t_R$=1.36 min.

Step 4: ((7-Bromo-6-chloro-5-fluoro-2a-phenyl-2a,7b-dihydrocyclobuta[b]benzofuran-2-yl)oxy)triethylsilane (C-XXX-d)

To a stirred solution of 7-bromo-6-chloro-5-fluoro-2a-phenyl-2a,7b-dihydrocyclobuta[b]benzofuran-2(1H)-one (C-XXX-c) (18.59 g, 47.0 mmol) in DCM (300 mL) was added 2,6-lutidine (54.8 mL, 470 mmol) followed by TfOSiEt₃ (53.2 mL, 235 mmol) at RT and stirring of the reaction mixture was continued for 18 h at RT. A sat solution of $NaHCO_3$. was added and the mixture was extracted with DCM. The combined organic extracts were washed with water and brine, dried over anhydrous $Na_2SO_4$ and concentrated to afford a brown oil. ¹H NMR (400 MHz, CDCl3) δ 7.63-7.51 (m, 2H), 7.49-7.33 (m, 3H), 6.75 (d, J=9.2 Hz, 1H), 5.42 (s, 1H), 3.83 (s, 1H), 1.04-0.86 (m, 9H), 0.74-0.61 (m, 6H). UPLC-MS 1: product non ionisable, $t_R$=1.79 min.

Step 5: 8-Bromo-7-chloro-6-fluoro-3a-phenyl-3a,8b-dihydrofuro[3,4-b]benzofuran-3(1 H)-one (C-XXX-e)

At −78° C. 03 was bubbled through a stirred solution of ((7-bromo-6-chloro-5-fluoro-2a-phenyl-2a,7b-dihydrocyclobuta[b]benzofuran-2-yl)oxy)triethylsilane (C-XXX-d) (38.9 g, 48.4 mmol) in DCM (450 mL) and MeOH (100 mL) until a blue color persisted (45 min). After 10 min at −78° C., $O_2$ was bubbled through the RM for 10 min, then argon for 10 min (RM turned yellow again). Sodium borohydride (18.32 g, 484 mmol) was added portion-wise and the reaction mixture was allowed to reach RT over 1 h. HCl (646 mL, 1.94 mol, 3M in MeOH) was then added drop-wise over a period of 1.5 h. The crude mixture was diluted in brine and extracted with DCM. The organic extract was dried over anhydrous $Na_2SO_4$ and concentrated. The crude product was purified by flash chromatography (silica, DCM/EtOAc, gradient 0% to 30% EtOAc) to afford the title compound (17.09 g) as a colorless solid. 1H NMR (400 MHz, DMSO-d6) δ 7.65-7.58 (m, 2H), 7.56-7.46 (m, 3H), 7.42 (d, J=9.3 Hz, 1H), 5.07 (dd, J=9.8, 7.2 Hz, 1H), 4.84 (dd, J=9.8, 2.1 Hz, 1H), 4.76 (dt, J=7.2, 1.9 Hz, 1H). UPLC-MS 1: m/z 400.1/402.1 [M+$H_2O$]⁺, $t_R$=1.27 min.

Step 6: (3aS,8bR)-8-Bromo-7-chloro-6-fluoro-3a-phenyl-3a,8b-dihydrofuro[3,4-b]benzofuran-3(1 H)-one (C-XXX-f) and (3aR,8bS)-8-bromo-7-chloro-6-fluoro-3a-phenyl-3a,8b-dihydrofuro[3,4-b]benzofuran-3(1H)-one (C-XXX-g)

The racemate 8-bromo-7-chloro-6-fluoro-3a-phenyl-3a,8b-dihydrofuro[3,4-b]benzofuran-3(1 H)-one (C-XXX-e) (22.65 g, 59.0 mmol) dissolved in DCM/MeOH (900 mL) was subjected to chiral SFC (ChiralPak IG, 250×30 mm I.D., 10 μm. CO2/(IPA+0.1% NH4OH) 6:4, 38° C., flow rate: 200 mL/min, 5 mL per injection, cycle time 3.2 min) to afford (3aS,8bR)-8-Bromo-7-chloro-6-fluoro-3a-phenyl-3a,8b-dihydrofuro[3,4-b]benzofuran-3(1 H)-one (C-XXX-f) (9.77 g) and (3aR,8bS)-8-bromo-7-chloro-6-fluoro-3a-phenyl-3a,8b-dihydrofuro[3,4-b]benzofuran-3(1 H)-one (C-XXX-g) (9.04 g) as pure enantiomers with an enantiomeric excess of >99%, respectively.

(3aS,8bR)-8-Bromo-7-chloro-6-fluoro-3a-phenyl-3a,8b-dihydrofuro[3,4-b]benzofuran-3(1 H)-one (C-XXX-f): Chiral SFC: (Chiralpak IG 100×4.6 mm I.D., 3 μm, CO₂/(IPA+0.05% DEA) from 95/5 to 60/40, 35° C., flow rate: 2.5 mL/min) $t_R$=4.03 min. 1 H NMR (400 MHz, DMSO-d6) δ 7.65-7.58 (m, 2H), 7.56-7.45 (m, 3H), 7.42 (d, J=9.3 Hz, 1H), 5.07 (dd, J=9.8, 7.2 Hz, 1H), 4.84 (dd, J=9.9, 2.1 Hz, 1H), 4.80-4.71 (m, 1H). UPLC-MS 1: product non ionisable, $t_R$=1.29 min.

(3aR,8bS)-8-Bromo-7-chloro-6-fluoro-3a-phenyl-3a,8b-dihydrofuro[3,4-b]benzofuran-3(1H)-one (C-XXX-g): Chiral SFC: (Chiralpak IG 100×4.6 mm I.D., 3 μm, CO₂/(IPA+0.05% DEA) from 95/5 to 60/40, 35° C., flow rate: 2.5 mL/min) $t_R$=4.59 min. 1 H NMR (400 MHz, DMSO-d6) δ 7.64-7.58 (m, 2H), 7.55-7.45 (m, 3H), 7.42 (d, J=9.3 Hz, 1H), 5.07 (dd, J=9.8, 7.2 Hz, 1H), 4.84 (dd, J=9.8, 2.1 Hz, 1H), 4.81-4.71 (m, 1H). UPLC-MS 1: product non ionisable, $t_R$=1.29 min.

Step 7: ((2S,3R)-4-Bromo-5-chloro-6-fluoro-2-((methylamino)methyl)-2-phenyl-2,3-dihydrobenzofuran-3-yl)methanol (C-XXX-h)

A solution of (3aS,8bR)-8-bromo-7-chloro-6-fluoro-3a-phenyl-3a,8b-dihydrofuro[3,4-b]benzofuran-3(1H)-one (C-XXX-f) (5 g, 12.4 mmol) in methylamine (100 mL, 200 mmol, 2 N in THF) was stirred at RT for 10 min, then for 10 min at reflux. After cooling to BH$_3$·DMS (31.0 mL, 61.9 mmol, 2 N in THF) was added and the reaction mixture was stirred at reflux for 2 h. More BH$_3$·DMS (5 mL, 10.00 mmol, 2 N in THF) was added and stirred at reflux was continued for 15 min. The reaction mixture was quenched by the addition of MeOH. The crude mixture was concentrated. The crude residue was diluted in DCM and water and extracted with DCM. The combined organic extracts were washed with brine, dried over anhydrous Na$_2$SO$_4$ and concentrated. The crude product was purified by flash chromatography (silica, DCM/(7N ammonia in MeOH), gradient 0% to 13% (7N ammonia in MeOH)) to afford the title compound (5.2 g) as a colorless foam. UPLC-MS 1: m/z 400.4/402.4 [M+H]$^+$, t$_R$=0.81 min.

Step 8: Tert-butyl (((2S,3R)-4-bromo-5-chloro-6-fluoro-3-(hydroxymethyl)-2-phenyl-2,3-dihydrobenzofuran-2-yl)methyl)(methyl)carbamate (C-XXX-i)

To a stirred solution of ((2S,3R)-4-bromo-5-chloro-6-fluoro-2-((methylamino)methyl)-2-phenyl-2,3-dihydrobenzofuran-3-yl)methanol (C-XXX-h) (1.8 g, 4.49 mmol) in DCM (20 mL) was added TEA (1.88 mL, 13.5 mmol) followed by Boc-anhydride (1.25 mL, 5.4 mmol) at RT and the reaction mixture was stirred at RT for 16 h. The crude mixture was diluted in water and extracted with DCM. The combined organic extracts were washed with water and brine, dried over anhydrous Na$_2$SO$_4$ and concentrated. The crude product was purified by flash chromatography (silica, EtOAc/heptane, gradient 0% to 50% EtOAc) to afford the title compound (1.86 g) as a colorless foam. UPLC-MS 1: m/z 500.4/502.4 [M+1]$^+$, t$_R$=1.36 min.

Step 9: Tert-butyl (((2S,3R)-4-bromo-5-chloro-6-fluoro-3-(methoxymethyl)-2-phenyl-2,3-dihydrobenzofuran-2-yl)methyl)(methyl)carbamate (C-XXX-j)

To a stirred solution of tert-butyl (((2S,3R)-4-bromo-5-chloro-6-fluoro-3-(hydroxymethyl)-2-phenyl-2,3-dihydrobenzofuran-2-yl)methyl)(methyl)carbamate (C-XXX-i) (1.85 g, 3.69 mmol) in DMF (20 mL) was added sodium hydride (0.222 g, 5.54 mmol) at 0° C. and the reaction mixture was stirred at 0° C. for 15 min. Iodomethane (0.254 mL, 4.06 mmol) was added and the reaction mixture was stirred at RT for 30 min. The crude mixture was quenched with water, then diluted in EtOAc and water and extracted with EtOAc. The organic extract was washed with water and brine, dried over anhydrous Na$_2$SO$_4$ and concentrated. The crude product was purified by flash chromatography (silica, EtOAc/heptane, gradient 0% to 20% EtOAc) to afford the title compound (1.57 g) as a colorless foam. UPLC-MS 1: m/z 514.5/516.4 [M+1]$^+$, t$_R$=1.56 min.

Step 10: Tert-butyl (((2S,3R)-5-chloro-6-fluoro-3-(methoxymethyl)-2-phenyl-4-(4,4,5,5-tetramethyl-1,3,2-dioxaborolan-2-yl)-2,3-dihydrobenzofuran-2-yl)methyl)(methyl)carbamate (C-XXX)

To a stirred solution of tert-butyl (((2S,3R)-4-bromo-5-chloro-6-fluoro-3-(methoxymethyl)-2-phenyl-2,3-dihydrobenzofuran-2-yl)methyl)(methyl)carbamate (C-XXX-j) (1.44 g, 2.18 mmol), bis(pinacolato)diboron (0.831 g, 3.27 mmol) and potassium hydroxide (0.306 g, 5.45 mmol) in toluene (15 mL) was added PdCl$_2$(dppf)·CH$_2$Cl$_2$ adduct (0.178 g, 0.218 mmol) at 60° C. and the reaction mixture was stirred at 100° C. for 1.5 h. More bis(pinacolato)diboron (0.388 g, 1.527 mmol) and potassium hydroxide (0.184 g, 3.27 mmol) were added and the reaction mixture was stirred at 100° C. for another 30 min. The reaction mixture was filtered over Hyflo and concentrated. The crude product was purified flash chromatography (silica, heptane/EtOAc, gradient 0% to 25% EtOAc) to give the title compound (1.07 g) as a colorless foam. UPLC-MS 1: m/z 562.4 [M+H]$^+$, t$_R$=1.53 min.

Synthesis of tert-butyl (((2S,3R)-3-((benzyloxy)methyl)-5-chloro-6-fluoro-2-phenyl-4-(4,4,5,5-tetramethyl-1,3,2-dioxaborolan-2-yl)-2,3-dihydrobenzofuran-2-yl)methyl)(methyl)carbamate (C-XXXI)

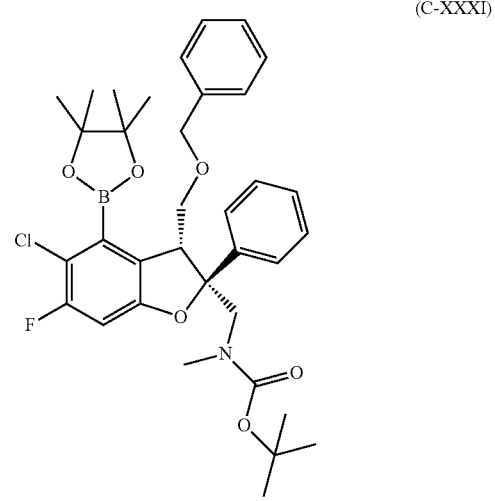 [SMILES: CN(C[C@]1(c2ccccc2)Oc2cc(F)c(Cl)c(B3OC(C)(C)C(C)(C)O3)c2[C@@H]1COCc1ccccc1)C(=O)OC(C)(C)C]

(C-XXXI)

Reaction Scheme C-XXXI

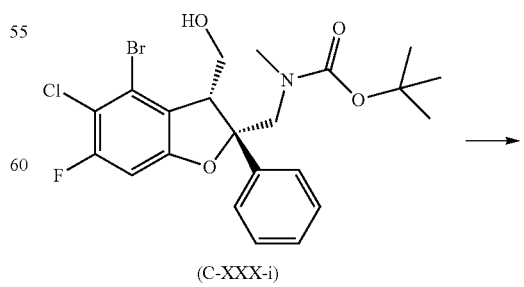

(C-XXX-i)

215

-continued

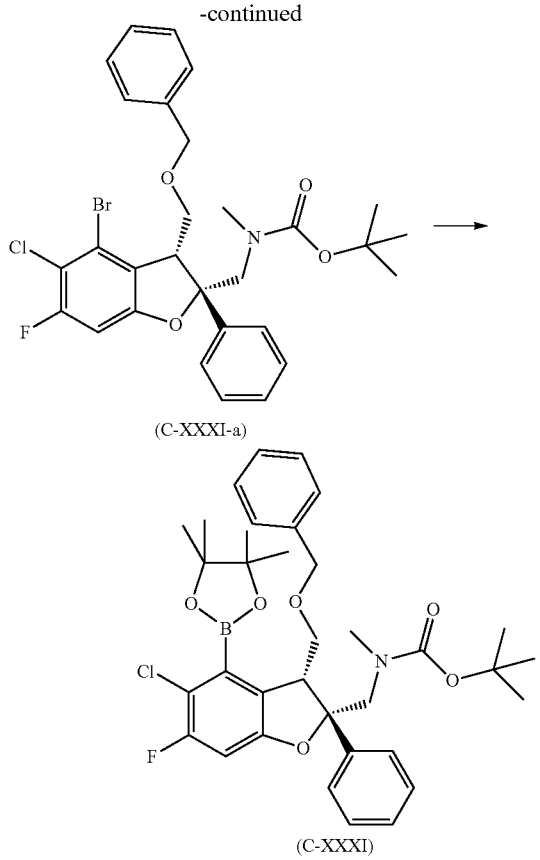

(C-XXXI-a)

(C-XXXI)

Step 1: Tert-butyl (((2S,3R)-3-((benzyloxy)methyl)-4-bromo-5-chloro-6-fluoro-2-phenyl-2,3-dihydrobenzofuran-2-yl)methyl)(methyl)carbamate (C-XXXI-a)

To a stirred solution of tert-butyl (((2S,3R)-4-bromo-5-chloro-6-fluoro-3-(hydroxymethyl)-2-phenyl-2,3-dihydrobenzofuran-2-yl)methyl)(methyl)carbamate (C-XXX-i) (2.00 g, 3.39 mmol) in DMF (25 mL) was added sodium hydride (0.204 g, 5.09 mmol, 60% dispersion in mineral oil) at 0° C. and the reaction mixture was stirred at 0° C. for 15 min. Benzyl bromide (0.444 mL, 3.73 mmol) was added and stirring at 0° C. was continued for 1 h. The reaction mixture was quenched by the addition of water and extracted with EtOAc. The combined organic extracts were washed with brine, dried over anhydrous $Na_2SO_4$ and concentrated. The crude product was purified by flash chromatography (silica, heptane/EtOAc, gradient 0% to 15% EtOAc) to afford the title compound (1.76 g) as a colorless foam. UPLC-MS 1: m/z 490.4/492.5 [M+H−BOC]$^+$, $t_R$=1.65 min.

Step 2: Tert-butyl (((2S,3R)-3-((benzyloxy)methyl)-5-chloro-6-fluoro-2-phenyl-4-(4,4,5,5-tetramethyl-1,3,2-dioxaborolan-2-yl)-2,3-dihydrobenzofuran-2-yl)methyl)(methyl)carbamate (C-XXXI)

To a stirred solution of tert-butyl (((2S,3R)-3-((benzyloxy)methyl)-4-bromo-5-chloro-6-fluoro-2-phenyl-2,3-dihydrobenzofuran-2-yl)methyl)(methyl)carbamate (C-XXXI-a) (1.95 g, 3.30 mmol), bis(pinacolato)diboron (1.257 g, 4.95 mmol) and potassium hydroxide (0.555 g, 9.90 mmol) in toluene (20 mL) was added PdCl$_2$(dppf)

216

·CH$_2$Cl$_2$ adduct (0.269 g, 0.33 mmol) at 60° C. and the reaction mixture was stirred at 100° C. for 1 h. The reaction mixture was filtered over Hyflo and concentrated. The crude product was purified flash chromatography (silica, heptane/EtOAc, gradient 0% to 20% EtOAc) to give the title compound (1.85 g) as a colorless foam. UPLC-MS 1: m/z 638.7 [M+H]$^+$, $t_R$=1.68 min.

Synthesis of tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)azetidine-1-carboxylate (C-XXXII)

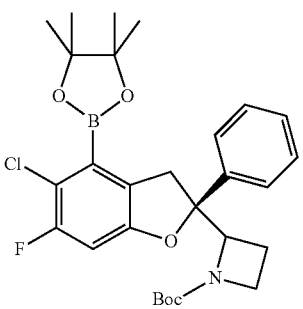

(C-XXXII)

Reaction Scheme C-XXXII

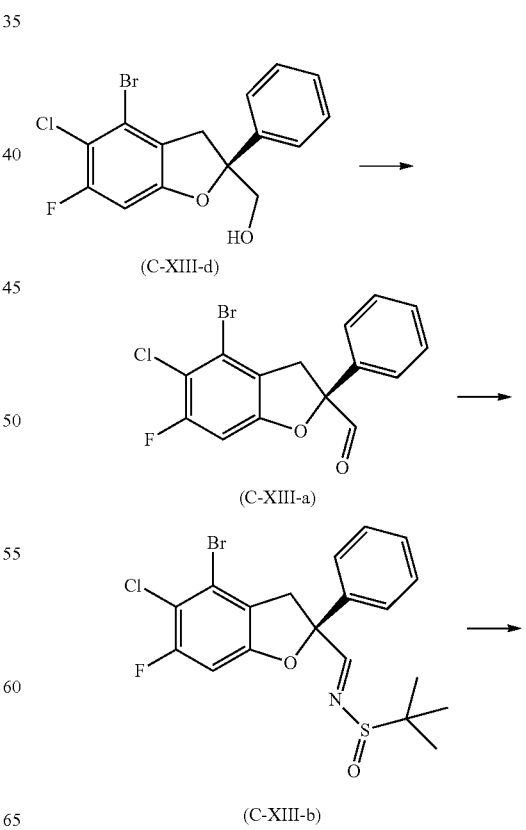

(C-XIII-d)

(C-XIII-a)

(C-XIII-b)

217
-continued

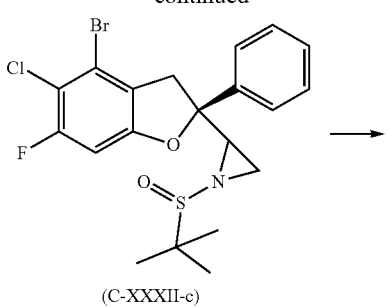

(C-XXXII-c)

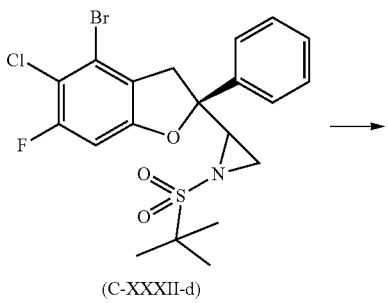

(C-XXXII-d)

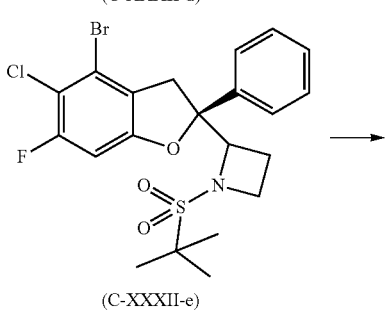

(C-XXXII-e)

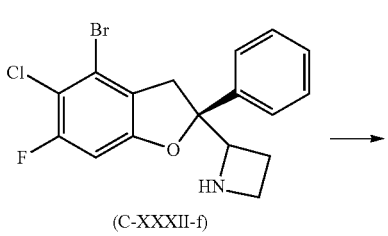

(C-XXXII-f)

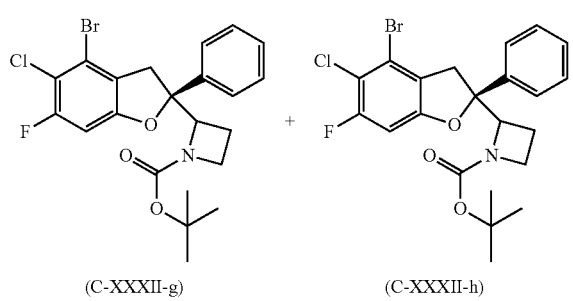

(C-XXXII-g)    (C-XXXII-h)

218
-continued

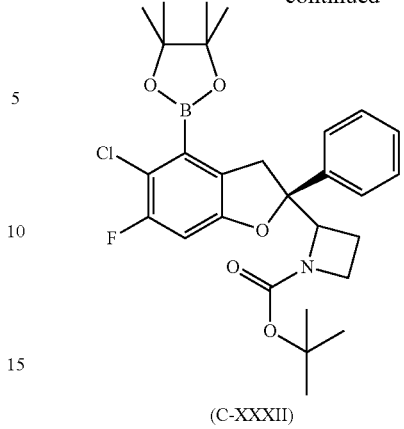

(C-XXXII)

Step 1: (S)-4-Bromo-5-chloro-6-fluoro-2-phenyl-2,3-dihydrobenzofuran-2-carbaldehyde (C-XXXII-a)

At −78° C. DMSO (12.7 mL, 179 mmol) was added to a solution of oxalyl chloride (7.8 mL, 89 mmol) in DCM (150 mL). After 30 min, a solution of (S)-(4-bromo-5-chloro-6-fluoro-2-phenyl-2,3-dihydrobenzofuran-2-yl)methanol (C-XIII-d) (20 g, 55.9 mmol) in DCM (150 mL) followed by TEA (39 mL, 280 mmol) were added at −78° C. The reaction mixture was stirred for 1 h at −78° C., then quenched with brine (250 mL). The mixture was extracted twice with DCM (2×150 mL). The combined organic layers were washed with brine (250 mL), dried over anhydrous $Na_2SO_4$ and concentrated to give the title product (21 g) as a colorless solid, which was used in the next step without further purification. UPLC-MS 1: m/z 399.1/401.2 [M+formate]⁻, $t_R$=1.27 min.

Step 2: ((S)-4-Bromo-5-chloro-6-fluoro-2-phenyl-2,3-dihydrobenzofuran-2-yl)methylene)-2-methylpropane-2-sulfinamide (C-XXXII-b)

At RT, (S)-4-bromo-5-chloro-6-fluoro-2-phenyl-2,3-dihydrobenzofuran-2-carbaldehyde (C-XXXII-a) (5 g, 8.44 mmol, 60%) and 2-methylpropane-2-sulfinamide (1.13 g, 9.28 mmol) were dissolved in DCE (211 mL). Tetraisopropoxytitanium (4.5 mL, 15.2 mmol) was added dropwise and the solution was heated to 60° C. under Ar. After 1 h, more 2-methylpropane-2-sulfinamide (0.41 g, 3.4 mmol) and tetraisopropoxytitanium (1.44 g, 5.6 mmol) were added. The reaction mixture was stirred further for 30 min to complete conversion. At RT, Hyflo and $H_2O$ (15 mL) were added and the reaction mixture was stirred for 10 min. The reaction mixture was filtered over Hyflo and concentrated to give the title compound (6.1 g), which was used in the next step without further purification. UPLC-MS 1: m/z 458.0/460.0 [M+H]⁺. $t_R$=1.47/1.48 min.

Step 3: 2-((S)-4-Bromo-5-chloro-6-fluoro-2-phenyl-2,3-dihydrobenzofuran-2-yl)-1-(tert-butylsulfinyl)aziridine (C-XXXII-c)

At RT, to a solution of trimethylsulfoxonium iodide (5.76 g, 26.2 mmol) in DMSO (81 mL) was added sodium hydride (1.1 g, 26.2 mmol, 60%). The mixture was stirred at RT for 1 h. The solution thus obtained was then added dropwise over 5 min to a solution of ((S)-4-bromo-5-chloro-6-fluoro- 2-phenyl-2,3-dihydrobenzofuran-2-yl)methylene)-2-methylpropane-2-sulfinamide (C-XXXII-b) (5.0 g, 6.54 mmol, 60%) in toluene (40 mL). The reaction mixture was then stirred for 1 h at RT. A saturated solution of NH$_4$Cl was added. The mixture was extracted twice with EtOAc. The combined organic layers were washed with water and brine, dried over anhydrous Na$_2$SO$_4$ and concentrated. The residue was purified by flash chromatography (silica; cyclohexane/EtOAc; gradient 0% to 20% EtOAc) to afford the title compound (2.6 g) as a colorless foam, as mixture of diastereoisomers. UPLC-MS 1: m/z 472.0/474.0 [M+H]$^+$, $t_R$=1.43/1.44/1.45 min.

Step 4: 2-((S)-4-Bromo-5-chloro-6-fluoro-2-phenyl-2,3-dihydrobenzofuran-2-yl)-1-(tert-butylsulfonyl)aziridine (C-XXXII-d)

A solution of 2-((S)-4-bromo-5-chloro-6-fluoro-2-phenyl-2,3-dihydrobenzofuran-2-yl)-1-(tert butylsulfinyl)aziridine (C-XXXII-c) (2.6 g, 5.5 mmol, 50%) in DCM (110 mL) was treated with mCPBA (2.1 g, 8.25 mmol, 70%) and the reaction mixture was stirred at RT for 10 min. A saturated solution of NaHCO$_3$ was added. The mixture was extracted twice with DCM. The combined organic layers were washed with brine, dried over anhydrous Na$_2$SO$_4$ and concentrated. The residue was purified by flash chromatography (silica; cyclohexane/EtOAc; gradient 0% to 20% EtOAc) to afford the title compound (1.7 g) as a colorless foam as mixture of diastereoisomers. UPLC-MS 1, no ionization, $t_R$=1.42/1.45 min.

Step 5: 2-((S)-4-Bromo-5-chloro-6-fluoro-2-phenyl-2,3-dihydrobenzofuran-2-yl)-1-(tert-butylsulfonyl)azetidine (C-XXXII-e)

At RT, to a solution of trimethylsulfoxonium iodide (3.12 g, 14.2 mmol) in DMSO (10 mL) was added sodium hydride (0.6 g, 14.2 mmol, 60%). The mixture was stirred at RT for 1 h. The solution thus obtained was then added dropwise over 5 min to a solution of 2-((S)-4-bromo-5-chloro-6-fluoro-2-phenyl-2,3-dihydrobenzofuran-2-yl)-1-(tert-butylsulfonyl)azetidine (C-XXXII-d) (1.73 g, 3.54 mmol) in DMSO (25 mL). The mixture was extracted twice with EtOAc. The combined organic layers were washed with water and brine, dried over anhydrous Na$_2$SO$_4$ and concentrated to afford the title compound (1.8 g) as mixture of diastereoisomers which was used in the next step without further purification. UPLC-MS 1: m/z 501.9/503.9 [M–H]$^-$, $t_R$=1.44/1.50 min.

Step 6: 2-((S)-4-Bromo-5-chloro-6-fluoro-2-phenyl-2,3-dihydrobenzofuran-2-yl)azetidine (C-XXXII-f)

At 0° C., to a solution of 2-((S)-4-bromo-5-chloro-6-fluoro-2-phenyl-2,3-dihydrobenzofuran-2-yl)-1-(tert-butylsulfonyl)azetidine (C-XXXII-e) (1.8 g, 3.58 mmol) in DCM (72 mL) was added trifluoromethanesulfonic acid (1 mL, 10.7 mmol). The reaction mixture was stirred at 0° C. for 20 min, then at RT for 20 min. 1 M NaOH solution was added. The mixture was extracted twice with DCM. The combined organic layers were washed with water and brine, dried over anhydrous Na$_2$SO$_4$ and concentrated to afford the title compound (1.4 g) as mixture of diastereoisomers which was used in the next step without further purification. UPLC-MS 1: m/z 381.9/383.9 [M+H]$^+$, $t_R$=0.87/0.94 min.

Step 7: Tert-butyl 2-((S)-4-bromo-5-chloro-6-fluoro-2-phenyl-2,3-dihydrobenzofuran-2-yl)azetidine-1-carboxylate (C-XXXII-g and C-XXXII-h)

At RT, to a solution of 2-((S)-4-bromo-5-chloro-6-fluoro-2-phenyl-2,3-dihydrobenzofuran-2-yl)azetidine (C-XXXII-f) (1.4 g, 3.66 mmol) in dioxane (20 mL) was added TEA (1.5 mL, 11 mmol) and Boc-anhydride (0.88 g, 4.02 mmol) and the reaction mixture was stirred at RT for 4 h. Water was added. The mixture was extracted with EtOAc. The combined organic layers were washed with water and brine, dried over anhydrous Na$_2$SO$_4$ and concentrated. The obtained residue was purified by flash chromatography (silica; cyclohexane/EtOAc; gradient 0% to 20% EtOAc) to afford the title compounds as separated diastereoisomers.

Diastereomer 1 (C-XXXII-g): tert-butyl 2-((S)-4-bromo-5-chloro-6-fluoro-2-phenyl-2,3-dihydrobenzofuran-2-yl)azetidine-1-carboxylate (340 mg, yellow resin). UPLC-MS 1: m/z 482.0/484.0 [M+H]$^+$, $t_R$=1.57 min.

Diastereomer 2 (C-XXXII-h): tert-butyl 2-((S)-4-bromo-5-chloro-6-fluoro-2-phenyl-2,3-dihydrobenzofuran-2-yl)azetidine-1-carboxylate (350 mg, yellow resin). UPLC-MS 1: m/z 480.0/481.9 [M–H]$^-$, $t_R$=1.50 min.

Step 8: Tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)azetidine-1-carboxylate (C-XXXII)

A suspension of tert-butyl 2-((S)-4-bromo-5-chloro-6-fluoro-2-phenyl-2,3-dihydrobenzofuran-2-yl)azetidine-1-carboxylate (C-XXXII-g) (340 mg, 0.74 mmol), bis(pinacolato)diboron (268 mg, 1.05 mmol), potassium acetate (207 mg, 2.11 mmol) and PdCl$_2$(dppf)·CH$_2$Cl$_2$ adduct (58 mg, 0.07 mmol) in toluene (1.8 mL) was purged with Ar, then stirred at 100° C. for 16 h under Ar. The reaction mixture was diluted with DCM, filtered over Hyflo and concentrated. The residue was purified by flash chromatography (silica; cyclohexane/EtOAc; gradient 5% to 40% EtOAc) to afford the title compound (220 mg) as a solid foam. UPLC-MS 1: m/z 530.1/532.1 [M+H]$^+$, $t_R$=1.60 min; absolute configuration at C-2 position of azetidine unassigned.

Synthesis of tert-butyl 2-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)azetidine-1-carboxylate (C-XXXIII)

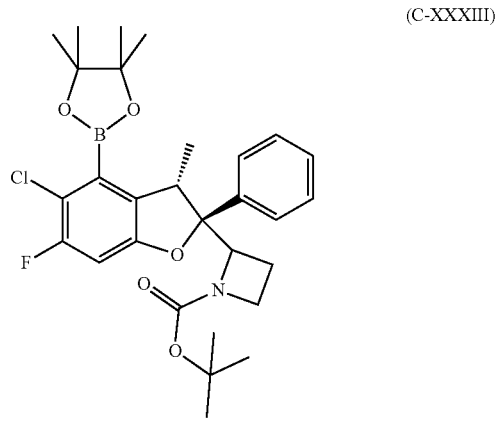 [SMILES: C[C@H]1c2c(cc(F)c(Cl)c2B2OC(C)(C)C(C)(C)O2)O[C@@]1(c1ccccc1)C1CCN1C(=O)OC(C)(C)C]

(C-XXXIII)

Reaction Scheme C-XXXIII:

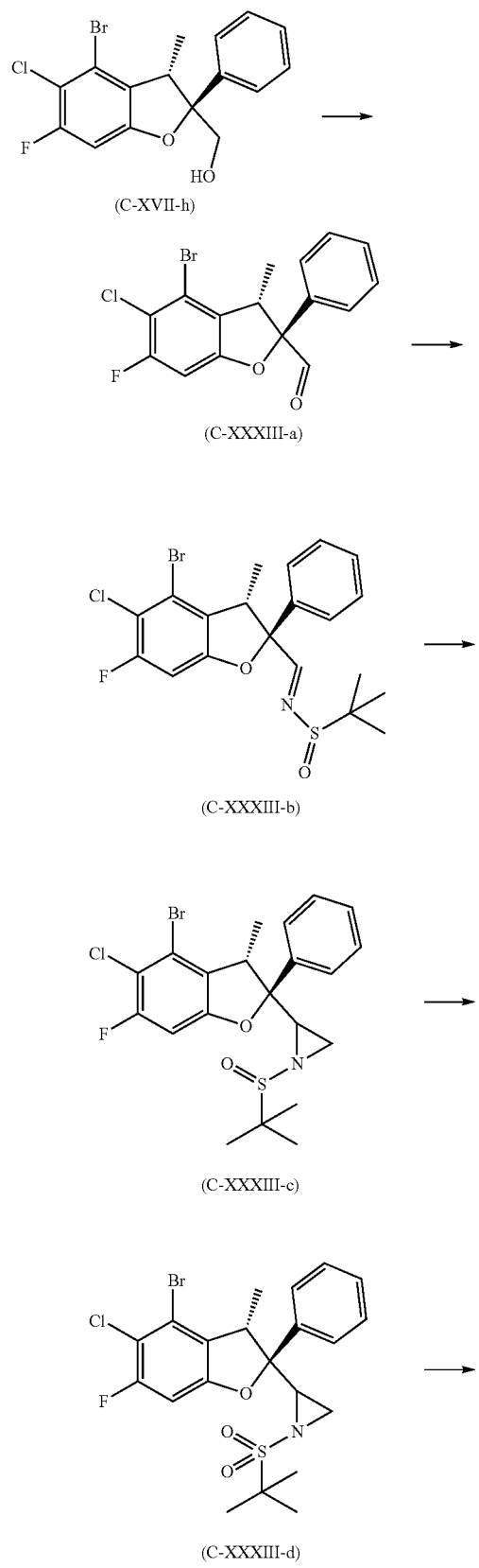

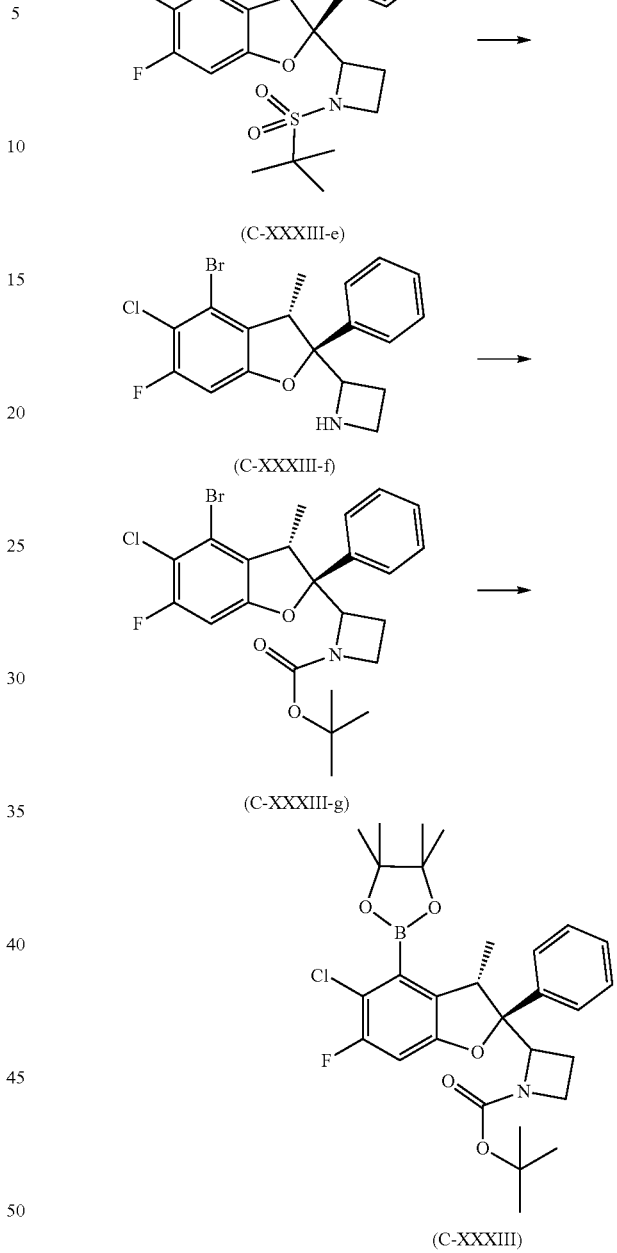

Step 1: (2S,3S)-4-Bromo-5-chloro-6-fluoro-3-methyl-2-phenyl-2,3-dihydrobenzofuran-2-carbaldehyde (C-XXXIII-a)

The title compound (13.2 g, yellow foam) was obtained from ((2S,3S)-4-bromo-5-chloro-6-fluoro-3-methyl-2-phenyl-2,3-dihydrobenzofuran-2-yl)methanol (C-XVII-h) (12 g, 32.3 mmol) using similar reaction conditions as described for compound (CXXXII-a). $^1$H NMR (600 MHz, DMSO-$d_6$) δ (ppm) 9.93 (s, 1H), 7.62 (d, J=7.7 Hz, 2H), 7.52-7.36 (m, 4H), 3.89 (q, J=7.2 Hz, 1H), 1.36 (d, J=6.9 Hz, 3H). UPLC-MS 1: m/z 367.0/366.8 [M+H]$^+$, $t_R$=1.36 min.

Step 2: N-((E)-((2S,3S)-4-Bromo-5-chloro-6-fluoro-3-methyl-2-phenyl-2,3-dihydrobenzofuran-2-yl)methylene)-2-methylpropane-2-sulfinamide (C-XXXIII-b)

At RT, under Ar, to a mixture of (2S,3S)-4-bromo-5-chloro-6-fluoro-3-methyl-2-phenyl-2,3-dihydrobenzofuran-2-carbaldehyde (C-XXXIII-a) (15.5 g, 25.2 mmol, 60%) and 2-methylpropane-2-sulfinamide (3.35 g, 27.7 mmol) dissolved in DCE (500 mL) was added dropwise Ti(OiPr)$_4$ (12.8 g, 45.3 mmol). The reaction mixture was stirred at 60° C. After 1 h, more 2-methylpropane-2-sulfinamide (1.34 g, 11.10 mmol) and Ti(OiPr)$_4$ (5.15 g, 18.10 mmol) were added. The reaction mixture was then stirred for 90 min. At RT, Hyflo and H$_2$O (50 mL) were added and the mixture was stirred for 10 min. The reaction mixture was filtered over Hyflo and concentrated to give the title compound (17.3 g, yellow resin) as a diastereomeric mixture which was used in the next step without further purification. UPLC-MS 1: m/z 472.1/473.9 [M+H]$^+$. $t_R$=1.46/1.49 min.

Step 3: 2-((2S,3S)-4-Bromo-5-chloro-6-fluoro-3-methyl-2-phenyl-2,3-dihydrobenzofuran-2-yl)-1-(tert-butylsulfinyl)aziridine (C-XXXIII-c)

To a solution of trimethylsulfoxonium iodide (21.9 g, 100 mmol, 68%) in DMSO (310 mL) was added sodium hydride (3.98 g, 100 mmol, 60%). The mixture was stirred at RT for 1 h. The solution thus obtained was then added dropwise over 5 min to a solution of N-((E)-((2S,3S)-4-bromo-5-chloro-6-fluoro-3-methyl-2-phenyl-2,3-dihydrobenzofuran-2-yl)methylene)-2-methylpropane-2-sulfinamide (C-XXXIII-b) (17.3 g, 24.90 mmol, 68%) in toluene (155 mL). The reaction mixture was then stirred for 30 min at RT. A saturated solution of NH$_4$Cl was added. The mixture was extracted twice with EtOAc. The combined organic layers were washed with water and brine, dried over anhydrous Na$_2$SO$_4$ and concentrated. The residue was purified by flash chromatography (silica; cyclohexane/EtOAc; gradient 0% to 20% EtOAc) to afford the title compound (10.9 g, colorless foam) as a diastereoisomeric mixture. UPLC-MS 1: m/z 486.0/488.0 [M+H]$^+$, $t_R$=1.46/1.49 min.

Step 4: 2-((2S,3S)-4-Bromo-5-chloro-6-fluoro-3-methyl-2-phenyl-2,3-dihydrobenzofuran-2-yl)-1-(tert-butylsulfonyl)aziridine (C-XXXIII-d)

A solution of 2-((2S,3S)-4-bromo-5-chloro-6-fluoro-3-methyl-2-phenyl-2,3-dihydrobenzofuran-2-yl)-1-(tert-butylsulfinyl)aziridine (C-XXXIII-c) (10.9 g, 17.91 mmol, 80%) in DCM (360 mL) was treated with mCPBA (6.62 g, 26.9 mmol, 70%) and the reaction mixture was stirred at RT for 10 min. A sat solution of NaHCO$_3$ was added. The mixture was extracted twice with EtOAc. The combined organic layers were washed with water and brine, dried over anhydrous Na$_2$SO$_4$ and concentrated. The residue was purified by flash chromatography (silica; cyclohexane/EtOAc; gradient 0% to 20% EtOAc) to afford the title compound (8.7 g) as a colorless foam. UPLC-MS 1, no ionization, $t_R$=1.46 min.

Step 5: 2-((2S,3S)-4-Bromo-5-chloro-6-fluoro-3-methyl-2-phenyl-2,3-dihydrobenzofuran-2-yl)-1-(tert-butylsulfonyl)aziridine (C-XXXIII-e)

To a solution of trimethylsulfoxonium iodide (14.32 g, 65.1 mmol) in DMSO (190 mL) was added sodium hydride (2.60 g, 65.1 mmol, 60%). The mixture was stirred at RT for 1 h. The solution thus obtained was then added dropwise over 5 min to a solution of 2-((2S,3S)-4-bromo-5-chloro-6-fluoro-3-methyl-2-phenyl-2,3-dihydrobenzofuran-2-yl)-1-(tert-butylsulfonyl)aziridine (C-XXXIII-d) (8.7 g, 16.3 mmol) in DMSO (115 mL). The reaction mixture was then stirred at 50° C. for 16 h. A saturated solution of NH$_4$Cl was added. The mixture was extracted twice with EtOAc. The combined organic layers were washed with water and brine, dried over anhydrous Na$_2$SO$_4$ and concentrated to afford the title compound (11.7 g) as a yellow resin which was used in the next step without further purification. UPLC-MS 1: no ionization, $t_R$=1.51 min.

Step 6: 2-((2S,3S)-4-Bromo-5-chloro-6-fluoro-3-methyl-2-phenyl-2,3-dihydrobenzofuran-2-yl)azetidine (C-XXXIII-f)

At 0° C., to a solution of 2-((2S,3S)-4-bromo-5-chloro-6-fluoro-3-methyl-2-phenyl-2,3-dihydrobenzofuran-2-yl)-1-(tert-butylsulfonyl)azetidine (C-XXXIII-e) (11.7 g, 14.9 mmol, 66%) in DCM (300 mL) was added trifluoromethanesulfonic acid (3.96 mL, 44.8 mmol). The reaction mixture was stirred at 0° C. for 30 min, then at RT for 24 h. Trifluoromethanesulfonic acid (3.96 mL, 44.8 mmol) was added and the mixture was stirred for 60 min to complete conversion. 1 M NaOH solution was added. The mixture was extracted twice with DCM. The combined organic layers were washed with water and brine, dried over anhydrous Na$_2$SO$_4$ and concentrated to afford the title compound (7.1 g) as a yellow foam which was used in the next step without further purification. UPLC-MS 1: m/z 396.0/398.0 [M+H]$^+$, $t_R$=0.90 min.

Step 7: Tert-butyl 2-((2S,3S)-4-bromo-5-chloro-6-fluoro-3-methyl-2-phenyl-2,3-dihydrobenzofuran-2-yl)azetidine-1-carboxylate (C-XXXIII-g)

At RT, to a solution of 2-((2S,3S)-4-bromo-5-chloro-6-fluoro-3-methyl-2-phenyl-2,3-dihydrobenzofuran-2-yl)-1-(tert-butylsulfonyl)azetidine (C-XXXIII-f) (7.1 g, 12.0 mmol, 67%) in dioxane (65 mL) were added TEA (5 mL, 36.0 mmol) and Boc-anhydride (2.90 g, 13.2 mmol). The reaction mixture was stirred at RT for 3 h. The mixture was extracted with EtOAc. The organic layer was washed with water and brine, dried over anhydrous Na$_2$SO$_4$ and concentrated. The residue was purified by flash chromatography (silica; cyclohexane/EtOAc; gradient 0% to 20% EtOAc) to afford the title compound (4.36 g) as a yellow foam. UPLC-MS 1: m/z 496.0/497.9 [M+H]$^+$, $t_R$=1.60 min.

Step 8: Tert-butyl 2-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)azetidine-1-carboxylate (C-XXXIII)

A suspension of tert-butyl 2-((2S,3S)-4-bromo-5-chloro-6-fluoro-3-methyl-2-phenyl-2,3-dihydrobenzofuran-2-yl)azetidine-1-carboxylate (C-XXXIII-g) (4.36 g, 8.25 mmol), bis(pinacolato)diboron (3.14 g, 12.37 mmol), potassium acetate (2.4 g, 24.7 mmol) and PdCl$_2$(dppf)·CH$_2$Cl$_2$ adduct (675 mg, 0.825 mmol) in toluene (21 mL) was purged with Ar and then stirred at 100° C. for 16 h under Ar. The reaction mixture was diluted with DCM, filtered over Hyflo and concentrated. The residue was purified by flash chromatography (silica; cyclohexane/EtOAc; gradient 0% to 20% EtOAc) to afford the title compound (1.3 g) as a colorless foam. UPLC-MS 1: m/z 544.3/546.2 [M+H]⁺, $t_R$=1.59 min; absolute configuration at C-2 position of azetidine unassigned.
Synthesis of tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate (C-XXXIV)
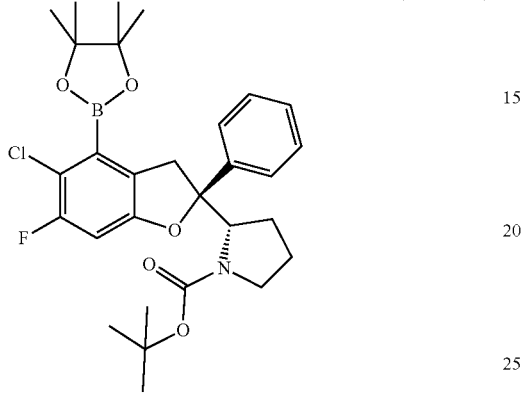
(C-XXXIV)
The title product could be synthesized via the following routes:
Reaction Scheme C-XXXIV-1:
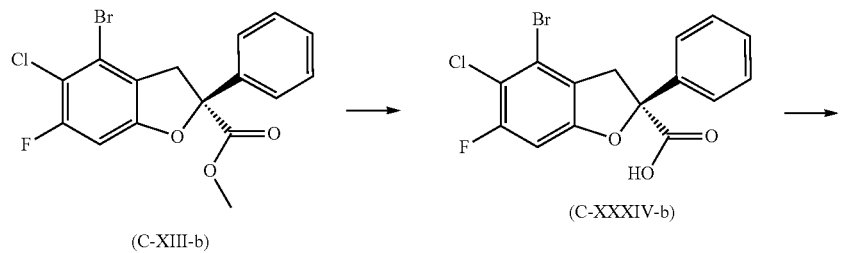
(C-XIII-b)   (C-XXXIV-b)
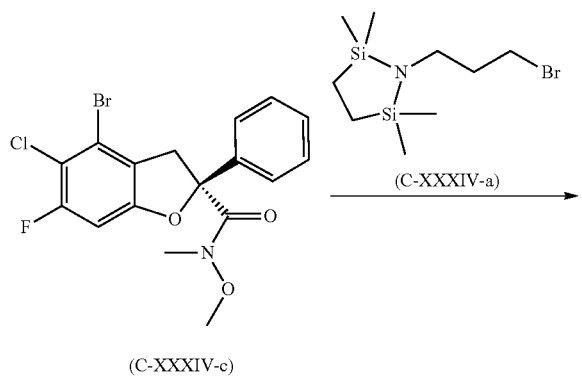
(C-XXXIV-c)

227 228
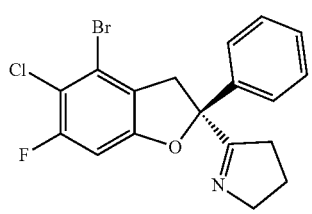
(C-XXXIV-d)
-continued
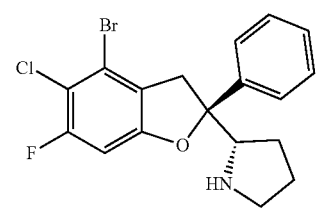
(C-XXXIV-e)
+
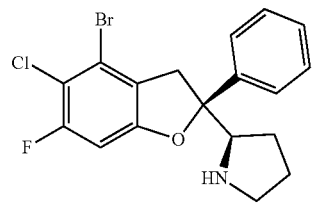
(C-XXXIV-f)
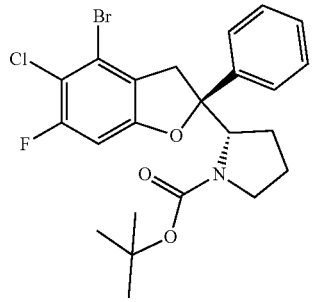
(C-XXXIV-g)
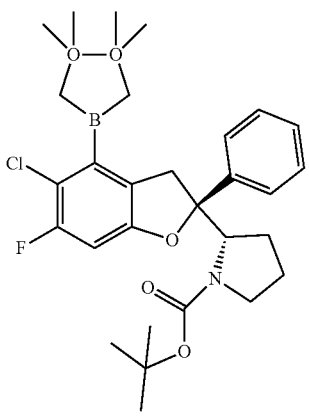
(C-XXXIV)
Alternative synthesis of intermediate C-XXXIV-b:
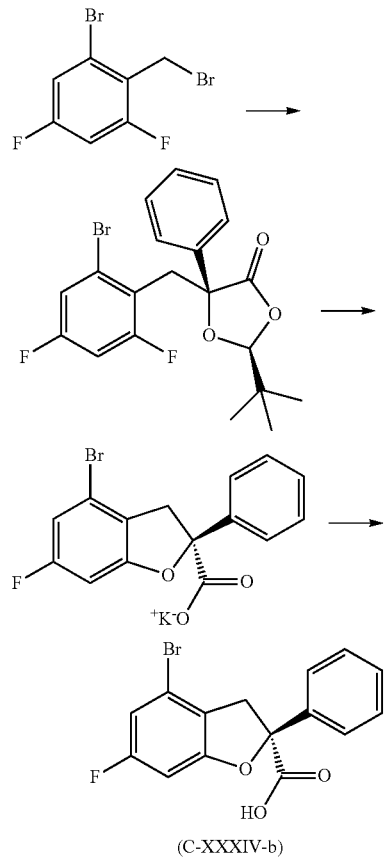
(C-XXXIV-b)

Synthesis of 1-(3-bromopropyl)-2,2,5,5-tetramethyl-1,2,5-azadisilolidine (C-XXXIV-a)

At 0° C. TEA (172 mL, 1233 mmol) was added to a stirred solution of 3-bromopropan-1-amine in DCM (623 mL). After 5 min, a solution of 1,2-bis(chlorodimethylsilyl)ethane (97 g, 452 mmol) in DCM (200 mL) was added dropwise and the reaction mixture was stirred for 2.5 h at RT. The reaction mixture was then filtered and the filtrate concentrated. The crude material, resuspended in pentane (500 mL), was then stirred for 1 h. The mixture was filtered through Celite and concentrated. The crude material was resuspended in pentane (200 mL) and processed in the same way as previously. The product was isolated as a colorless liquid which was filtered and dried under HV for 2 min. The title compound (107 g) was used as such without further purification and was stored for a limited period of time, only. $^1$H NMR (600 MHz, DMSO-d$_6$) δ (ppm) 3.53-3.49 (m, 1H), 2.90 (t, J=6.9 Hz, 2H), 1.90-1.85 (m, 2H), 0.66 (s, 4H), 0.05 (s, 12H).

Step 1: (S)-4-Bromo-5-chloro-6-fluoro-2-phenyl-2,3-dihydrobenzofuran-2-carboxylic acid (C-XXXIV-b)

LiOH·H$_2$O (3.40 g, 42.0 mmol) was added to a solution of (S)-methyl 4-bromo-5-chloro-6-fluoro-2-phenyl-2,3-dihydrobenzofuran-2-carboxylate (C-XIII-a) (15.00 g, 38.9 mmol) in dioxane (70 mL) and water (70 mL). The reaction mixture was stirred at RT for 17 h. 2 N HCl (100 mL) was added and the resulting white suspension was extracted with DCM. The organic layers were washed with brine, dried over anhydrous Na$_2$SO$_4$ and concentrated to give the title compound (17.2 g). $^1$H-NMR (600 MHz, DMSO-d$_6$) δ (ppm) 13.73 (s, 1H), 7.59-7.53 (m, 2H), 7.48-7.36 (m, 3H), 7.29 (d, J=9.4 Hz, 1H), 4.05 (dd, J=16.4, 1.3 Hz, 1H), 358 (dd, J=16.0, 2.0 Hz, 1H). UPLC-MS 1: m/z 369.1/371.9 [M–H]$^-$, t$_R$=1.12 min.

Step 2: (S)-4-Bromo-5-chloro-6-fluoro-N-methoxy-N-methyl-2-phenyl-2,3-dihydrobenzofuran-2-carboxamide (C-XXXIV-c)

At RT, to a solution of (S)-4-bromo-5-chloro-6-fluoro-2-phenyl-2,3-dihydrobenzofuran-2-carboxylic acid (C-XXXIV-b) (12.6 g, 30.5 mmol) in dioxane (500 mL) were successively added DIPEA (21.3 mL, 122 mmol), N,O-dimethylhydroxylamine hydrochloride (3.57 g, 36.6 mmol), DMAP (0.19 g, 1.53 mmol) and HATU (13.92 g, 36.6 mmol). The resulting solution was stirred at RT for 1.5 h. After concentration und reduced pressure the residue was dissolved in EtOAc (500 mL) and washed subsequently with water (200 mL), 1 N HCl (150 mL), 1 N NaOH (150 mL) and brine (200 mL). The organic phase was dried over anhydrous Na$_2$SO$_4$, filtered and concentrated to give the crude product which was purified by flash chromatography (silica; hexane/EtOAc; 9:1) to afford the title compound (10.83 g). UPLC-MS 1: m/z 414.1/416.1 [M+H]$^+$, t$_R$=1.36 min.

Step 3: (S)-5-(4-Bromo-5-chloro-6-fluoro-2-phenyl-2,3-dihydrobenzofuran-2-yl)-3,4-dihydro-2H-pyrrole (C-XXXIV-d)

At RT, 60 mL of a solution of 1-(3-bromopropyl)-2,2,5,5-tetramethyl-1,2,5-azadisilolidine (C-XXXIV-a) (89 g, 316 mmol) in Et$_2$O (300 mL) were added to a suspension of magnesium (8.3 g, 343 mmol) in Et$_2$O (150 mL), followed by iodine (4.58 g, 18.04 mmol). The reaction mixture was then heated under reflux. The rest of the solution of 1-(3-bromopropyl)-2,2,5,5-tetramethyl-1,2,5-azadisilolidine in Et$_2$O (240 mL) was added over 27 min under reflux. The reaction mixture was then stirred under reflux for 1.5 h. The mixture thus obtained was added at RT over 15 min to a solution of (S)-4-bromo-5-chloro-6-fluoro-N-methoxy-N-methyl-2-phenyl-2,3-dihydrobenzofuran-2-carboxamide (C-XXXIV-c) (37.4 g, 90 mmol) in THF (300 mL). The resulting suspension was stirred at RT for 2 h. The reaction mixture was quenched with 2 N citric acid solution (600 mL), neutralized with a sat solution of NaHCO$_3$ (1200 mL) and extracted twice with EtOAc (2×1000 mL). The combined organic layers were washed with brine, dried over anhydrous Na$_2$SO$_4$ and concentrated. The yellow residue was then treated with MeOH (50 mL) and the resulting white suspension was stirred at RT for 16 h. The suspension was filtered, washed with MeOH (20 mL) to obtain the desired product. After concentration of the mother liquor, the crude product was treated similarly. The resulting mother liquor was concentrated and purified by flash chromatography (silica, heptane/EtOAc 95:5). In total the title product (26.43 g) were obtained as a colorless solid. $^1$H NMR (400 MHz, DMSO-d$_6$) δ (ppm) 7.46-7.40 (m, 4H), 7.39-7.33 (m, 1H), 7.27 (d, J=9.5 Hz, 1H), 4.45 (dd, J=16.1, 1.4 Hz, 1H), 3.30 (dd, under d$_6$-DMSO peak), 3.90-3.75 (m, 2H), 2.69-2.56 (m, 1H), 2.38-2.12 (m, 2H), 1.90-1.71 (m, 2H). UPLC-MS 1: m/z 394.2/396.2 [M+H]$^+$, t$_R$=1.49 min.

Step 4: (S)-2-((S)-4-Bromo-5-chloro-6-fluoro-2-phenyl-2,3-dihydrobenzofuran-2-yl)pyrrolidine (C-XXXIV-e) and (R)-2-((S)-4-bromo-5-chloro-6-fluoro-2-phenyl-2,3-dihydrobenzofuran-2-yl)pyrrolidine (C-XXXIV-f)

At 0° C. sodium borohydride (8.1 g, 212 mmol) was added portionwise over 5 min to a solution of (S)-5-(4-bromo-5-chloro-6-fluoro-2-phenyl-2,3-dihydrobenzofuran-2-yl)-3,4-dihydro-2H-pyrrole (C-XXXIV-d) (27.9 g, 70.7 mmol) in THF/MeOH (220 mL, ratio 1:1). The reaction mixture was stirred at RT for 1.5 h, then quenched with a sat solution of NaHCO$_3$ (400 mL) and extracted twice with EtOAc (2×1000 mL). The combined organic layers were washed with a sat solution of NaHCO$_3$ (400 mL) and brine, dried over anhydrous Na$_2$SO$_4$ and concentrated. The residue was purified by flash chromatography (silica, hexane/EtOAc, gradient: 10% to 100% EtOAc) to give the title compound as a diastereomeric mixture (18.7 g) as a colorless oil. UPLC-MS 1: m/z 396.2/398.2 [M+H]$^+$, t$_R$=0.88 min and 0.91 min.

The diastereomeric mixture (18.7 g) was subjected to chiral SFC (ChiralPak IG, 250×30 mm I.D., 10 µm. CO$_2$/IPA (0.1% ammonia) 1:1, 38° C., flow rate: 60 mL/min) to afford the title compounds as separate diastereoisomers with an diastereomeric excess of >99%, respectively: (S)-2-((S)-4-bromo-5-chloro-6-fluoro-2-phenyl-2,3-dihydrobenzofuran-2-yl)pyrrolidine (C-XXXIV-e) (11.69 g): Chiral SFC: (Chiralpak IG 250×4.6 mm I.D., 5 µm, CO$_2$/IPA (0.05% DEA) 6:4, flow rate: 2.5 mL/min) t$_R$=6.92 min. $^1$H NMR (400 MHz, DMSO-d$_6$) δ (ppm) 7.60-7.47 (m, 2H), 7.41-7.34 (m, 2H), 7.33-7.27 (m, 1H), 7.09 (d, J=9.6 Hz, 1H), 3.69 (dd, J=16.1, 1.9 Hz, 1H), 3.62-3.50 (m, 1H), 3.41-3.28 (m, 2H), 2.86-2.74 (m, 1H), 2.72-2.58 (m, 1H), 1.63-1.28 (m, 4H). UPLC-MS 1: m/z 396.2/398.2 [M+H]$^+$, t$_R$=0.85 min. The absolute configuration was confirmed by an X-ray crystal structure of the HCl salt of the title compound.

Other diastereoisomer (R)-2-((S)-4-bromo-5-chloro-6-fluoro-2-phenyl-2,3-dihydrobenzofuran-2-yl)pyrrolidine (C-XXXIV-f) (5.70 g): Chiral SFC: (Chiralpak IG 250×4.6 mm I.D., 5 μm, $CO_2$/IPA (0.05% DEA) 6:4, flow rate: 2.5 mL/min) $t_R$=2.87 min. $^1$H NMR (400 MHz, DMSO-$d_6$) δ (ppm) 7.48-7.34 (m, 4H), 7.32-7.23 (m, 1H), 7.10 (d, J=9.6 Hz, 1H), 3.84 (dd, J=16.0, 1.9 Hz, 1H), 3.71-3.56 (m, 1H), 3.15 (dd, J=16.1, 1.6 Hz, 1H), 2.84-2.73 (m, 1H), 2.64-2.52 (m, 2H), 1.76-1.59 (m, 1H), 1.54-1.31 (m, 3H). UPLC-MS 1: m/z 396.2/398.2 [M+H]$^+$, $t_R$=0.86 min.

Step 5: Tert-butyl (S)-2-((S)-4-bromo-5-chloro-6-fluoro-2-phenyl-2,3-dihydrobenzofuran-2-yl)pyrrolidine-1-carboxylate (C-XXXIV-g)

At RT and under Ar Boc-anhydride (6.71 g, 30.7 mmol) and TEA (7.8 mL, 55.9 mmol) were added to a solution of (S)-2-((S)-4-bromo-5-chloro-6-fluoro-2-phenyl-2,3-dihydrobenzofuran-2-yl)pyrrolidine (C-XXXIV-e) (11.1 g, 27.9 mmol) in THF (100 mL). The reaction mixture was stirred at RT for 15 min, then quenched with a sat solution of NaHCO$_3$ (75 mL). The mixture was extracted twice with EtOAc (2×100 mL). The combined organic layers were washed with a sat solution of NaHCO$_3$ (400 mL) and brine, dried over anhydrous Na$_2$SO$_4$ and concentrated. The residue was purified by flash chromatography (silica, cyclohexane/EtOAc, gradient: 0% to 15% EtOAc) to give the title compound (14.2 g) as a colorless solid. $^1$H NMR (400 MHz, DMSO-$d_6$) δ (ppm) 7.52-7.27 (m, 5H), 7.18 (d, J=9.5 Hz, 1H), 4.42 (dd, J=7.0, 3.3 Hz, 1H), 4.22-3.85 (m, 1H), 3.48-3.31 (m, 1H), 2.92-2.70 (m, 1H), 1.94-1.77 (m, 2H), 1.56-1.21 (m, 10H), 1.10-0.65 (m, 1H). UPLC-MS 1: m/z 440.3/442.3 [M−tBu+H]$^+$, $t_R$=1.63 min.

Step 6: Tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate (C-XXXIV)

A suspension of tert-butyl (S)-2-((S)-4-bromo-5-chloro-6-fluoro-2-phenyl-2,3-dihydrobenzofuran-2-yl)pyrrolidine-1-carboxylate (C-XXXIV-g) (14.2 g, 28.6 mmol), bis(pinacolato)diboron (10.9 g, 42.9 mmol), potassium acetate (8.4 g, 86 mmol) and PdCl$_2$(dppf)·CH$_2$Cl$_2$ adduct (2.3 g, 2.86 mmol) in toluene (100 mL) was purged with Ar, then stirred at 100° C. for 16 h under Ar. The reaction mixture was diluted with DCM at RT, filtered over Celite and concentrated. The residue was purified by flash chromatography (silica; cyclohexane/EtOAc; gradient 0% to 15% EtOAc) to afford the title compound (13.4 g) as a colorless solid. UPLC-MS 1: m/z 588.5 [M+formate]$^-$, $t_R$=1.65 min.

Alternative Synthesis of Intermediate C-XXXIV-b

Step 1: (2S,5S)-5-(2-Bromo-4,6-difluorobenzyl)-2-(tert-butyl)-5-phenyl-1,3-dioxolan-4-one At RT, (2S,5S)-2-(tert-butyl)-5-phenyl-1,3-dioxolan-4-one (CAS 81036-97-7) (28.2 g, 128.2 mmol) was added to a solution of 1-bromo-2-(bromomethyl)-3,5-difluorobenzene (CAS 1807193-40-3) (70.9 mmol) in THF (250 mL). The mixture was cooled to −10.0° C. and a solution of LiHMDS (108.1 g, 116 mmol, 1M in THF) was added slowly over 1.5 h. The reaction mixture was allowed to warm to RT and was stirred for an additional 18 h. 20% NH$_4$Cl solution (220 mL) was added. The mixture was extracted with MTBE (200 mL) and stirred for 1 h. The organic phase was separated and partially concentrated to afford a solution of the title product in MTBE. UPLC-MS 1: $t_R$=1.52 min.

Step 2: Potassium (S)-4-bromo-6-fluoro-2-phenyl-2,3-dihydrobenzofuran-2-carboxylate A solution of (2S,5S)-5-(2-bromo-4,6-difluorobenzyl)-2-(tert-butyl)-5-phenyl-1,3-dioxolan-4-one in MTBE (103.11 mmol) was diluted with THF (400 mL) and cooled at 0±5° C. tBuOK (34.7 g, 309.3 mmol) was added within 30 min, the mixture was allowed to warm to RT and stirred for 18 h. 10% NH$_4$Cl solution (220 mL) was added. The mixture was extracted with isopropyl acetate, then stirred for 1 h. The organic phase was separated and partially concentrated. THF was progressively exchanged by isopropyl acetate by iterative addition of IPAC and partial concentration. The mixture was then cooled to 10° C. and stirred for 1 h. The solid was filtered off and recrystallized with isopropyl acetate to give the title product (34 g) as a colorless solid.
$^1$H NMR (300 MHz, DMSO-$d_6$) δ 7.56 (d, J=7.1 Hz, 2H), 7.49-7.35 (m, 3H), 7.05 (ddd, J=15.8, 9.3, 2.2 Hz, 2H), 3.99 (d, J=18.0 Hz, 1H), 3.51 (d, J=18.0 Hz, 1H). UPLC-MS 1: m/z 335.0/337.0 [M−H]$^-$, $t_R$=1.07 min.

Step 3: (S)-4-Bromo-5-chloro-6-fluoro-2-phenyl-2,3-dihydrobenzofuran-2-carboxylic acid (C-XXXIV-b)

At 0±5° C., p-TsOH (21.3 g, 112 mmol) and N-chlorosuccinimide (11.68 g, 87.5 mmol) were added to a solution of potassium (S)-4-bromo-6-fluoro-2-phenyl-2,3-dihydrobenzofuran-2-carboxylate (30 g, 80.0 mmol) in ACN (255 mL). The reaction mixture was stirred for 1 h at 0° C. Upon completion, water (150 mL) was added. 10% Na$_2$SO$_3$ aqueous solution was added slowly at 0-10° C. TBME (150 mL) was added and the mixture was stirred for 0.5 h. The two phases were separated. To the aqueous phase was added toluene (150 mL) and the mixture was stirred for 0.5 h. The combined organic phases were washed with 2N HCl solution (60 mL) and the obtained mixture was stirred for 1 h. The organic phase was separated and concentrated to afford the title compound with an enantiomeric excess of 91%.

The obtained residue was dissolved in THF (200 mL). The mixture was heated to 60-65° C. and a solution of (R)-(+)-phenylethylamine (6.95 g) in THF (40 mL) was added over 30 min. The mixture was kept stirring for 30 min. and then slowly cooled to RT within 1 h and was stirred for an additional 2 h. The mixture was filtered. The solid was washed with THF (24 mL), and then dried at 50° C. for 5 h under reduced pressure to give the (R)-(+)-phenylethylamine salt of title product (21.1 g) which was suspended in toluene (105 mL) and water (30 mL). Concentrated HCl solution (6.4 g) was slowly added at RT to the mixture. The mixture was then stirred at RT for 0.5 h. The aqueous phase was separated. The organic phase was washed with water (20 mL), and then concentrated under reduced pressure to give a solution of title product as (R)-(+)-phenylethylamine salt with an enantiomeric excess of 99%. This salt (60.0 g, 121.8 mmol) was slowly added into a solution of NaOH (7.5 g) in water (375 mL). The suspension was stirred at RT for 30 min, then extracted twice with DCM (2×250 mL). To the aqueous layer was added DCM (200 mL) and the pH was adjusted to pH=1 with 2 N aq. HCl at 0-5° C. The mixture was stirred for 10 min. The organic layer was separated and the aqueous layer was extracted with DCM (200 mL). The Reaction Scheme C-XXXIV-2:

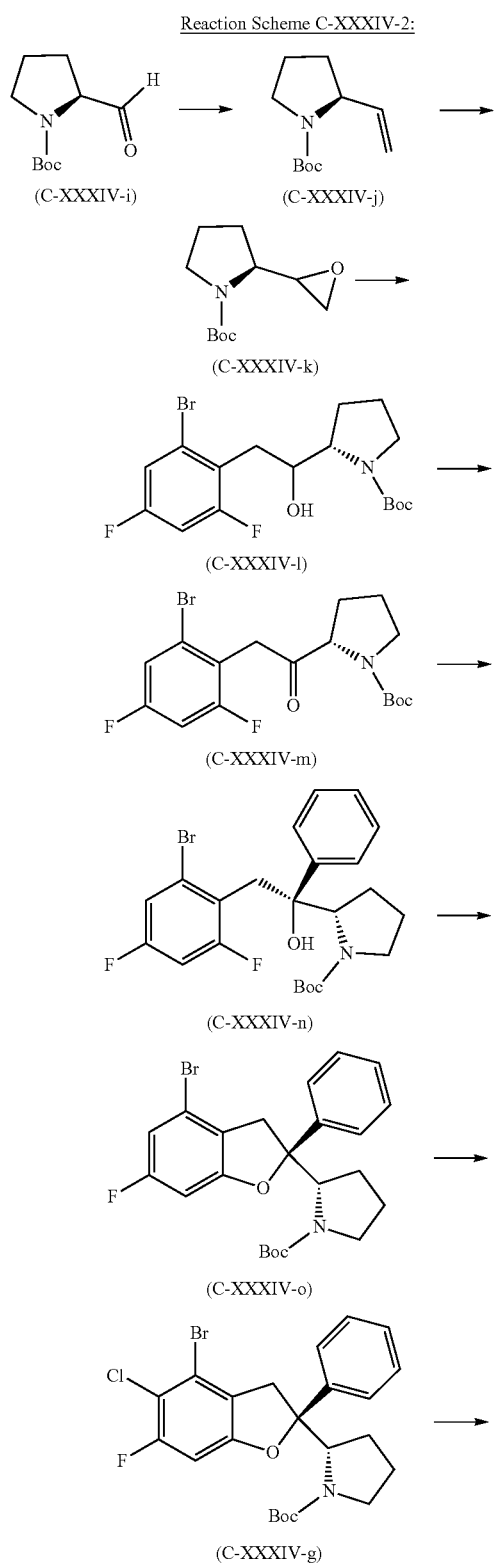

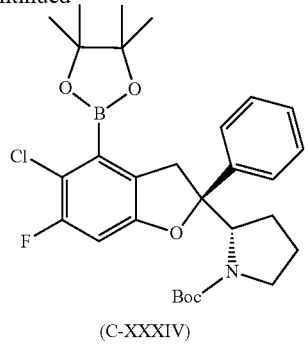

(C-XXXIV)

Step 1: Tert-butyl (S)-2-vinylpyrrolidine-1-carboxylate (C-XXXIV-j)

At RT, under a nitrogen atmosphere, a suspension of Ph$_3$PCH$_3$Br (161.4 g, 451.7 mmol) and KO$^t$Bu (50.7 g, 451.7 mmol) in THF (500 mL) was stirred for 4 h, then cooled to −70° C. A solution of (S)-tert-butyl 2-formylpyrrolidine-1-carboxylate (C-XXXIV-i) (75.0 g, 376 mmol) in THF (150 mL) was added dropwise over 30 min while maintaining the internal temperature below −20° C. The reaction mixture was then stirred for 16 h at RT. Upon completion of the reaction, 20 wt % NH$_4$Cl (200 mL) was added and the organic layer was separated. The water layer was extracted with EtOAC (100 mL). The combined organic layers were washed with brine, dried over anhydrous Na$_2$SO$_4$, filtered and concentrated to give a pale yellow oil. Heptane (400 mL) was added and the resulting suspension was stirred vigorously at 0-5° C. for 1 h and filtered. The filtrate was dried under HV to give the title product (76 g) as a yellow oil which was directly used in the next step without further purification.

Step 2: Tert-butyl (2S)-2-(oxiran-2-yl)pyrrolidine-1-carboxylate (C-XXXIV-k)

At 0° C., under a nitrogen atmosphere, mCPBA (155.4 g, 693.5 mmol, 77% w/w) was added portionwise to tert-butyl (S)-2-vinylpyrrolidine-1-carboxylate (C-XXXIV-j) (76 g, 424 mmol) dissolved in DCM (700 mL), while maintaining the internal temperature below 10° C. The reaction mixture was then stirred for 2 h at RT. Upon completion of the reaction, a solution of Na$_2$S$_2$O$_3$ (48.6 g, 385.3 mmol) in water (300 mL) was added slowly to quench the excess of mCPBA. Saturated aq. Na$_2$CO$_3$ (200 mL) was added to adjust the pH to 7-8. The organic layer was separated and the water layer was extracted with DCM (100 mL). The combined organic layers were washed with 5% NaHCO$_3$ (100 mL), then with brine (100 mL), dried over Na$_2$SO$_4$, filtered and concentrated to a volume of ca. 100 mL. Heptane (600 mL) was added and the resulting suspension was filtered. The filtrate was concentrated and the obtained residue was purified by flash chromatography on silica gel with n-heptane/EtOAc to give the title product (62 g) as a yellow oil.

Step 3: Tert-butyl (2S)-2-(2-(2-bromo-4,6-difluorophenyl)-1-hydroxyethyl)pyrrolidine-1-carboxylate (C-XXXIV-l)

At −70° C., under a nitrogen atmosphere, iPrMgCl (190 mL, 2.0 M in THF, 102.8 mmol) was added dropwise over 30 min to a solution of 1-bromo-3,5-difluoro-2-iodobenzene (120.5 g, 377.9 mmol) in THF (800 mL) while maintaining an internal temperature at −40° C. to −35° C. The reaction mixture was stirred at this temperature for 1 h. Upon completion of the reaction CuI (11.1 g, 58.1 mmol) was added quickly in one portion. A solution of tert-butyl (2S)-2-(oxiran-2-yl)pyrrolidine-1-carboxylate (C-XXXIV-k) (62 g, 290.7 mmol) in THF (100 mL) was added dropwise over 10 min while maintaining the internal temperature at −40° C. to −30° C. The reaction mixture was then gradually warmed to RT and stirred overnight. 20 wt % aq. NH$_4$Cl (700 mL) was added carefully to quench the reaction followed by MTBE (400 mL). The organic layer was separated and the water layer was extracted with MTBE (200 mL). The combined organic layers were washed with 20 wt % brine (300 mL), dried over anhydrous Na$_2$SO$_4$, filtered and concentrated to give the title product (118 g) as a pale yellow oil which was used directly in the next step. $^1$H NMR (400 MHz, CDCl$_3$) δ 7.13 (dt, J=8.1, 2.2 Hz, 1H), 6.80 (td, J=9.1, 2.6 Hz, 1H), 4.63 (s, 1H), 4.04-3.94 (m, 1H), 3.86-3.72 (m, 1H), 3.58-3.44 (m, 1H), 3.41-3.28 (m, 1H), 3.01-2.78 (m, 2H), 2.14-1.81 (m, 4H), 1.47 (s, 9H). UPLC-MS 5: HRMS m/z calcd for C$_{12}$H$_{15}$BrF$_2$NO [M−Boc]$^+$306.0300, found 306.0292.

Step 4: Tert-butyl (S)-2-(2-(2-bromo-4,6-difluorophenyl)acetyl)pyrrolidine-1-carboxylate (C-XXXIV-m)

At RT, under a nitrogen atmosphere, a solution of tert-butyl (2S)-2-(2-(2-bromo-4,6-difluorophenyl)-1-hydroxyethyl)pyrrolidine-1-carboxylate (C-XXXIV-l) (118 g, 290 mmol) in DCM (700 mL) was added dropwise over 30 min at RT to a solution of Dess-Martin periodinane (135.5 g, 319.5 mmol) in DCM (700 mL). The reaction mixture was stirred at RT for 45 min. Upon completion of the reaction a solution of Na$_2$SO$_3$ (58.6 g) in water (300 mL) was added carefully to quench the reaction while maintaining the internal temperature at 0 to 5° C. 15 wt % Na$_2$CO$_3$ (350 mL) was added to adjust the pH to 7-8 while maintaining the internal temperature below 10° C. The organic layer was separated and the water layer was extracted with DCM (500 mL). The combined organic layers were washed with 5 wt % NaHCO$_3$ (300 mL) then with 20 wt % brine (300 mL), dried over anhydrous Na$_2$SO$_4$, filtered and concentrated. The residue was purified by flash chromatography (silica; heptane/MTBE; gradient: 3% to 20% MTBE) to give the title product (75 g). $^1$H NMR (400 MHz, CDCl$_3$) δ 7.21-7.12 (m, 1H), 6.88-6.78 (m, 1H), 4.49 (dd, J=8.5, 4.5 Hz, 0.3H), 4.37 (dd, J=8.8, 5.2 Hz, 0.7H), 4.08-3.86 (m, 2H), 3.67-3.39 (m, 2H), 2.35-2.05 (m, 2H), 2.02-1.86 (m, 2H), 1.48 (s, 2.7H), 1.47 (s, 6.3H). UPLC-MS 5: HRMS m/z calcd for C$_{12}$H$_{13}$BrF$_2$NO [M−Boc]$^+$304.0143, found 303.9271.

Step 5: Tert-butyl (S)-2-((S)-2-(2-bromo-4,6-difluorophenyl)-1-hydroxy-1-phenylethyl)pyrrolidine-1-carboxylate (C-XXXIV-n)

At 0° C., under a nitrogen atmosphere PhMgBr (40 mL, 128.6 mmol, 2.5 M in Et$_2$O) was added dropwise over 30 min to tert-butyl (S)-2-(2-(2-bromo-4,6-difluorophenyl)acetyl)pyrrolidine-1-carboxylate (C-XXXIV-m) (26 g, 64.3 mmol) in a mixture of DCM (260 mL) and heptane (260 mL), while maintaining the internal temperature at −5-0° C. The reaction mixture was stirred at 0° C. for 10 min before it was quenched by adding slowly sat. aq. NH$_4$Cl (150 mL). MTBE (200 mL) was added and the organic layer was separated. The water layer was extracted with MTBE (200 mL). The combined organic layers were washed with 20 wt % brine (300 mL), dried over anhydrous Na$_2$SO$_4$, filtered and concentrated. The residue was purified by flash chromatography (silica; heptane/MTBE; gradient: 2% to 3% MTBE) to afford the title product (14 g), as a light yellow solid.
$^1$H NMR (400 MHz, DMSO-d$_6$) δ 7.48 (s, 2H), 7.31 (dt, J=8.4, 2.1 Hz, 1H), 7.26-7.16 (m, 3H), 7.08-7.00 (m, 1H), 4.42-4.19 (m, 1H), 3.62-3.45 (m, 2H), 3.45-3.34 (m, 2H), 1.93-1.82 (m, 1H), 1.75-1.60 (m, 1H), 1.43 (s, 9H), 1.41-1.21 (m, 2H). UPLC-MS 5: HRMS m/z calcd for C$_{23}$H$_{27}$BrF$_2$NO$_3$ [M+H]$^+$ 482.1137, found 481.9654.

Step 6: Tert-butyl (S)-2-((S)-4-bromo-6-fluoro-2-phenyl-2,3-dihydrobenzofuran-2-yl)pyrrolidine-1-carboxylate (C-XXXIV-o)

At 0° C., under a nitrogen atmosphere, KOtBu (37.3 mL, 37.3 mmol, 1 M in THF) was added dropwise over 15 min to a solution of tert-butyl (S)-2-((S)-2-(2-bromo-4,6-difluorophenyl)-1-hydroxy-1-phenylethyl)pyrrolidine-1-carboxylate (C-XXXIV-n) (15 g, 31.1 mmol) in THF (150 mL), while maintaining the internal temperature at −5-0° C. The reaction mixture was stirred at −5-0° C. for 30 min. Upon completion, the mixture was diluted with MTBE (200 mL) and was quenched by adding 5 wt % aq. NaHCO$_3$ (150 mL) while maintaining the internal temperature at −5-0° C. The mixture was stirred for 15 min at −5-0° C. The organic layer was separated and the aqueous layer was extracted with MTBE (200 mL). The combined organic phases were washed with brine, dried over anhydrous Na$_2$SO$_4$, filtered and concentrated to afford the title product (14.3 g) which was used directly in the next step. $^1$H NMR (400 MHz, DMSO-d$_6$) δ 7.45-7.28 (m, 5H), 6.98 (dd, J=9.1, 2.2 Hz, 1H), 6.90 (dd, J=9.5, 2.2 Hz, 1H), 4.41 (dd, J=6.9, 3.5 Hz, 1H), 4.19-3.78 (m, 1H), 3.44-3.19 (m, 2H), 2.91-2.72 (m, 1H), 1.90-1.83 (m, 2H), 1.57-1.47 (m, 1H), 1.35 (s, 2H), 1.34 (s, 7H), 1.28-1.21 (m, 1H). UPLC-MS 5: HRMS m/z calcd for C$_{16}$H$_{18}$BrFNO [M−Boc]+362.0550, found 361.9654.

Step 7: Tert-butyl (S)-2-((S)-4-bromo-5-chloro-6-fluoro-2-phenyl-2,3-dihydrobenzofuran-2-yl)pyrrolidine-1-carboxylate (C-XXXIV-g)

At 0° C., under a nitrogen atmosphere, p-TsOH (6.9 g, 36.3 mmol) and N-chlorosuccinimide (4.85 g, 36.3 mmol) were added to a solution of tert-butyl (S)-2-((S)-4-bromo-6-fluoro-2-phenyl-2,3-dihydrobenzofuran-2-yl)pyrrolidine-1-carboxylate (C-XXXIV-o) (14 g, 30.3 mmol) in ACN (280 mL) and THF (140 mL), while maintaining the internal temperature at −8-0° C. The reaction mixture was stirred at −8-0° C. for 3 h. The mixture was diluted with MTBE (200 mL) and quenched by adding 6 wt % aq. Na$_2$CO$_3$ (150 mL). The organic layer was separated and the aqueous layer was extracted with MTBE (200 mL). The combined organic phases were washed with 6 wt % aq. Na$_2$CO$_3$, brine, dried over anhydrous Na$_2$SO$_4$, filtered and concentrated. The residue was purified by flash chromatography (silica; heptane/MTBE; 5% MTBE) to afford the title product (14 g), as a light yellow foam.

Step 8: Tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate (C-XXXIV)

A 250 mL three-necked round bottomed flask was charged with tert-butyl (S)-2-((S)-4-bromo-5-chloro-6-fluoro-2-phenyl-2,3-dihydrobenzofuran-2-yl)pyrrolidine-1-carboxylate (C-XXXIV-g) (20.0 g, 40.26 mmol), bis(pinacolato)diboron (13.3 g, 52.34 mmol), KOAc (11.9 g, 120.77 mmol) and toluene (140 mL). The mixture was degassed with nitrogen for 20 min. PdCl$_2$(dppf) (2.4 g, 3.22 mmol) was added under a nitrogen atmosphere in one portion. The mixture was heated to 100° C. and stirred for 16 h. The mixture was then cooled to RT, filtered through Celite and concentrated to dryness. The residue was purified by flash chromatography (silica, heptane/MTBE 5:1) to give the title compound (14.5) as a foam. $^1$H NMR (400 MHz, CDCl$_3$) δ 7.46-7.41 (m, 2H), 7.34-7.27 (m, 3H), 6.70 (d, J=9.3 Hz, 1H), 4.54-4.38 (m, 1H), 4.34-3.98 (m, 1H), 3.45 (d, J=16.7 Hz, 2H), 3.06-2.83 (m, 1H), 2.09-1.78 (m, 2H), 1.58-1.46 (m, 2H), 1.42 (s, 9H), 1.36 (s, 12H). UPLC-MS 5: HRMS m/z calcd for C$_{29}$H$_{37}$BClFNO$_5$ [M+H]$^+$ 544.2432, found 544.2897.

Synthesis of tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)-4-hydroxypyrrolidine-1-carboxylate (C-XXXV)

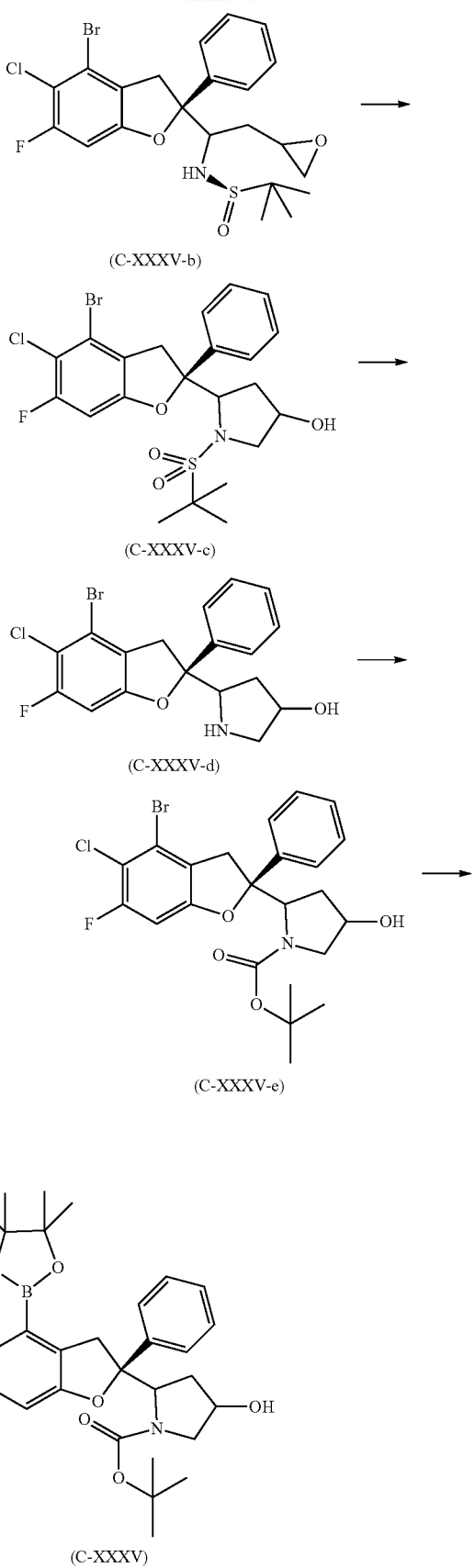

Reaction Scheme C-XXXV:

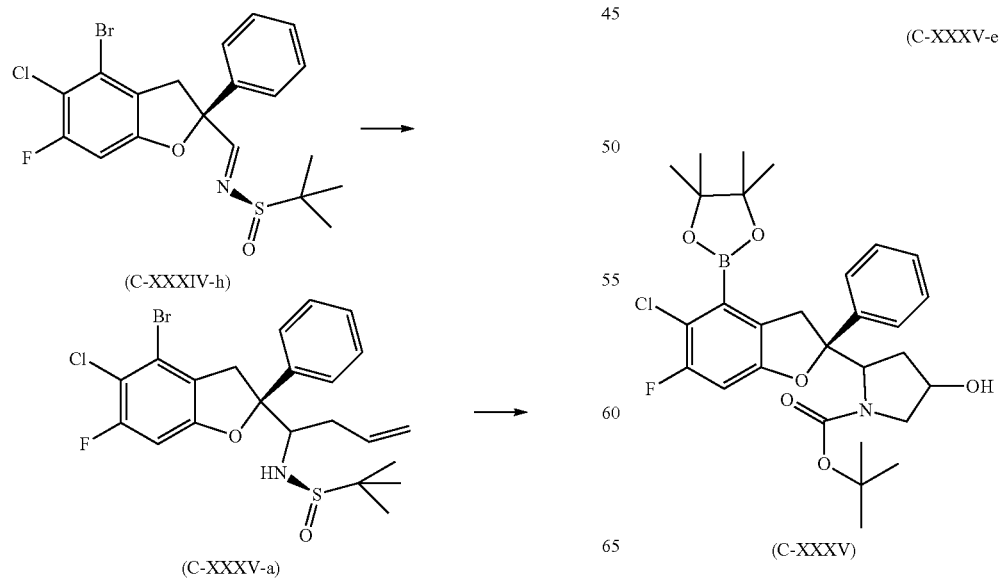

Step 1: (R)—N-(1-((S)-4-Bromo-5-chloro-6-fluoro-2-phenyl-2,3-dihydrobenzofuran-2-yl) but-3-en-1-yl)-2-methylpropane-2-sulfinamide (C-XXXV-a)

At 0° C., allylmagnesium bromide (15 mL, 15 mmol, 1 M in Et$_2$O) was added dropwise to a solution of (R)—N—((E)-((S)-4-bromo-5-chloro-6-fluoro-2-phenyl-2,3-dihydrobenzofuran-2-yl)methylene)-2-methylpropane-2-sulfinamide (C-XXXIV-h, prepared from aldehyde C-XXXII-a and (R)-2-methylpropane-2-sulfinamide using Ti(OEt)$_4$ as Lewis acid) (3.0 g, 3.27 mmol) in DCM (17 mL). The RM was stirred at 0° C. for 1.5 h. A saturated solution of NH$_4$Cl was added. The mixture was stirred for 10 min at RT then neutralized with 2 N HCl solution. The mixture was extracted twice with DCM. The combined organic layers were washed with water and brine, dried over anhydrous Na$_2$SO$_4$ and concentrated. The residue was purified by flash chromatography (silica; cyclohexane/EtOAc; gradient 5% to 30% EtOAc) to afford the title compound (1.0 g) as a colorless foam. UPLC-MS 1: m/z 500.2/502.2 [M+H]$^+$, $t_R$=1.43 min.

Step 2: N-(1-((S)-4-Bromo-5-chloro-6-fluoro-2-phenyl-2,3-dihydrobenzofuran-2-yl)-2-(oxiran-2-yl)ethyl)-2-methylpropane-2-sulfonamide (C-XXXV-b)

At RT, a solution of (R)—N-(1-((S)-4-bromo-5-chloro-6-fluoro-2-phenyl-2,3-dihydrobenzofuran-2-yl)but-3-en-1-yl)-2-methylpropane-2-sulfinamide (C-XXXVa) (1.00 g, 1.92 mmol) in DCM (38 mL) was treated with mCPBA (1.42 g, 5.75 mmol, 70%). The reaction mixture was stirred at RT for 16 h. A sat solution of NaHCO$_3$ was added. The mixture was extracted twice with DCM. The combined organic layers were washed with water and brine, dried over anhydrous Na$_2$SO$_4$ and concentrated. The residue was purified by flash chromatography (silica; DCM/MeOH; gradient 0% to 10% MeOH) to afford the title compound (930 mg) as a colorless solid. UPLC-MS 1, m/z 532.1/534.2 [M+H]$^+$, $t_R$=1.37 min.

Step 3: 5-((S)-4-Bromo-5-chloro-6-fluoro-2-phenyl-2,3-dihydrobenzofuran-2-yl)-1-(tert-butylsulfonyl)pyrrolidin-3-ol (C-XXXV-c)

At RT, to a solution of N-(1-((S)-4-bromo-5-chloro-6-fluoro-2-phenyl-2,3-dihydrobenzofuran-2-yl)-2-(oxiran-2-yl)ethyl)-2-methylpropane-2-sulfonamide (C-XXXV-b) (930 mg, 1.54 mmol, 88%) in DMF (15 mL) was added K$_2$CO$_3$ (637 mg, 4.6 mmol). The mixture was stirred at 100° C. for 24 h. The reaction mixture was allowed to cool to RT, then filtered and concentrated to afford the title compound as a diastereomeric mixture (1.1 g) which was used in the next step without further purification. UPLC-MS 2: m/z 576.1/578.1 [M+formate]$^-$, $t_R$=6.52/6.68/6.76/6.82 min.

Step 4: 5-((S)-4-Bromo-5-chloro-6-fluoro-2-phenyl-2,3-dihydrobenzofuran-2-yl)pyrrolidin-3-ol (C-XXXV-d)

At 0° C., trifluoromethanesulfonic acid (0.40 mL, 4.61 mmol) was added to a solution of 5-((S)-4-bromo-5-chloro-6-fluoro-2-phenyl-2,3-dihydrobenzofuran-2-yl)-1-(tert-butylsulfonyl)pyrrolidin-3-ol (C-XXXV-c) (1.10 g, 1.54 mmol, 90%) in DCM (30 mL). The reaction mixture was stirred at 0° C. for 90 min. 1 M NaOH solution was added. The mixture was extracted with DCM. The combined organic layers were dried over anhydrous Na$_2$SO$_4$ and concentrated to afford the title compound as a diastereomeric mixture (800 mg) which was used in the next step without further purification. UPLC-MS 1: m/z 412.2/414.1 [M+H]$^+$, $t_R$=0.84/0.86 min.

Step 5: Tert-butyl 2-((S)-4-bromo-5-chloro-6-fluoro-2-phenyl-2,3-dihydrobenzofuran-2-yl)-4-hydroxypyrrolidine-1-carboxylate (C-XXXV-e)

At RT, to a solution of 5-((S)-4-bromo-5-chloro-6-fluoro-2-phenyl-2,3-dihydrobenzofuran-2-yl)pyrrolidin-3-ol (C-XXXV-d) (800 mg, 1.54 mmol, 80%) in dioxane (8 mL) were added TEA (0.65 mL, 4.6 mmol) and Boc-anhydride (370 mg, 1.7 mmol). The reaction mixture was stirred at RT for 2 d. Water was added. The mixture was extracted with EtOAc. The organic layer was dried over anhydrous Na$_2$SO$_4$ and concentrated. The residue was purified by flash chromatography (silica; cyclohexane/EtOAc; gradient 0% to 15% EtOAc) to afford the title compound as a diastereomeric mixture (620 mg) as a yellowish foam. UPLC-MS 1: m/z 512.3/514.3 [M+H]$^+$, $t_R$=1.41/1.42/1.46/1.47 min.

Step 6: Tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)-4-hydroxypyrrolidine-1-carboxylate (C-XXXV)

A suspension of tert-butyl 2-((S)-4-bromo-5-chloro-6-fluoro-2-phenyl-2,3-dihydrobenzofuran-2-yl)-4-hydroxypyrrolidine-1-carboxylate (C-XXXV-e) (610 mg, 1.15 mmol), bis(pinacolato)diboron (440 mg, 1.73 mmol), potassium acetate (340 mg, 4.46 mmol) and PdCl$_2$(dppf)·CH$_2$Cl$_2$ adduct (94 mg, 0.115 mmol) in toluene (2 mL) was purged with Ar, then stirred at 110° C. for 16 h under Ar. The reaction mixture was diluted with EtOAc, filtered over Hyflo and concentrated. The residue was purified by flash chromatography (silica; cyclohexane/EtOAc; gradient: 10% to 30% EtOAc) to afford the title compound as a diastereomeric mixture (600 mg) as a solid foam. UPLC-MS 1: m/z 560.4/562.4 [M+H]$^+$, $t_R$=1.46/1.47/1.49/1.51 min.

Synthesis of tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)-4-hydroxy-4-methylpyrrolidine-1-carboxylate (C-XXXVI)

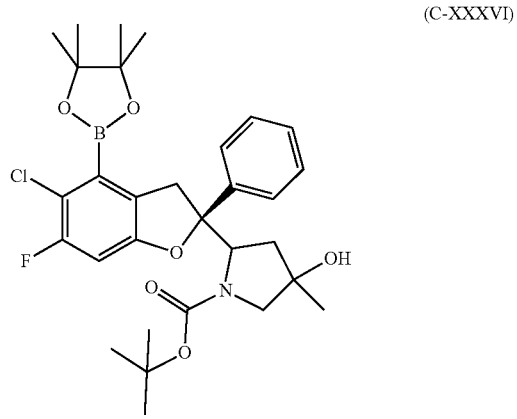 [SMILES: CC1(O)CC([C@@]2(c3ccccc3)Cc3c(cc(F)c(Cl)c3B3OC(C)(C)C(C)(C)O3)O2)N(C(=O)OC(C)(C)C)C1]

(C-XXXVI)

Reaction Scheme C-XXXVI:
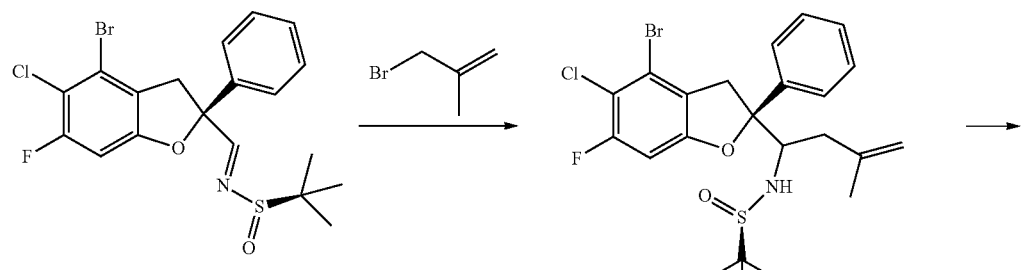
(C-XXXIV-h) → (C-XXXVI-a)
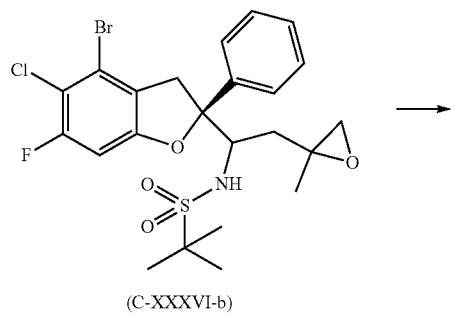
(C-XXXVI-b)
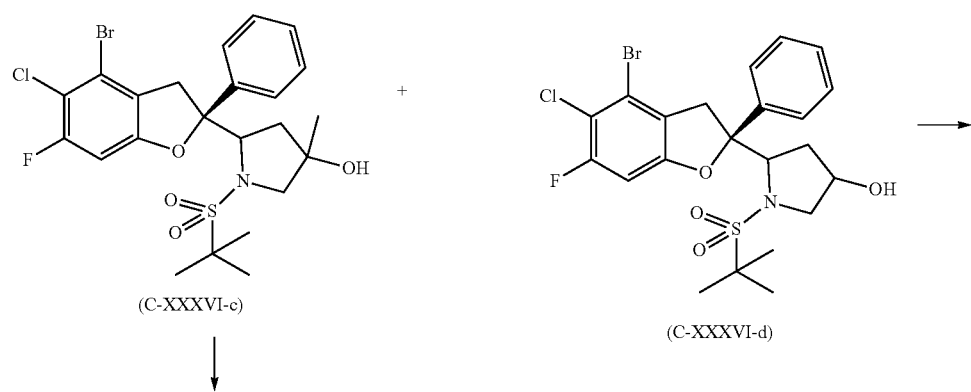
(C-XXXVI-c) + (C-XXXVI-d)
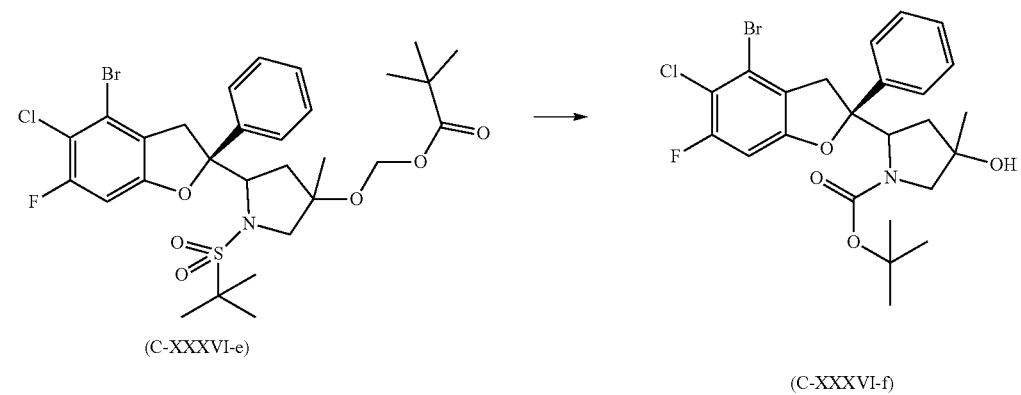
(C-XXXVI-e) → (C-XXXVI-f)

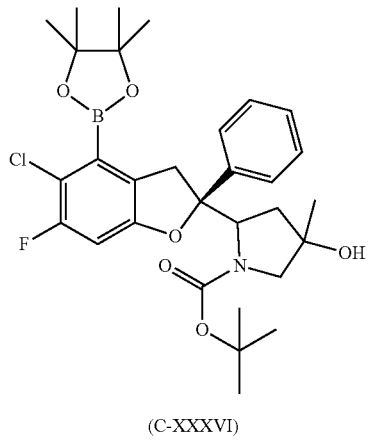

(C-XXXVI)

Step 1: (R)—N-(1-((S)-4-Bromo-5-chloro-6-fluoro-2-phenyl-2,3-dihydrobenzofuran-2-yl)-3-methylbut-3-en-1-yl)-2-methylpropane-2-sulfinamide (C-XXXVI-a)

At RT, a solution of 3-bromo-2-methylprop-1-ene (0.45 g, 3.37 mmol) in Et$_2$O (5 mL) and 2 drops of methyliodide were added to a suspension of magnesium powder (1.23 g, 50 mmol) in Et$_2$O (5 mL). The remaining solution of 3-bromo-2-methylprop-1-ene (4.10 g, 30.3 mmol) in Et$_2$O (20 mL) was then added dropwise while keeping the internal temperature below 35° C. The reaction mixture was stirred at RT for 16 h. The solution thus obtained was added dropwise at RT to a solution of (R)—N-((E)-((S)-4-bromo-5-chloro-6-fluoro-2-phenyl-2,3-dihydrobenzofuran-2-yl)methylene)-2-methylpropane-2-sulfinamide (C-XXXIV-h) (1.7 g, 3.37 mmol) in Et$_2$O (24 mL).

The reaction mixture was stirred at RT for 2 h. A saturated NH$_4$Cl solution was added and the reaction mixture was stirred for 10 min. The mixture was then neutralized with 2 M HCl solution and extracted with EtOAc. The combined organic layers were dried over anhydrous Na$_2$SO$_4$, filtered and concentrated to afford the title compound as a diastereomeric mixture (1.9 g). UPLC-MS 1: m/z 514.2/516.3 [M+H]$^+$, $t_R$=1.46/1.48 min.

Step 2: N-(1-((S)-4-Bromo-5-chloro-6-fluoro-2-phenyl-2,3-dihydrobenzofuran-2-yl)-2-(2-methyloxiran-2-yl)ethyl)-2-methylpropane-2-sulfonamide (C-XXXVI-b)

At RT, a solution of (R)—N-(1-((S)-4-Bromo-5-chloro-6-fluoro-2-phenyl-2,3-dihydrobenzofuran-2-yl)-3-methylbut-3-en-1-yl)-2-methylpropane-2-sulfinamide (C-XXXVI-a) (4.1 g, 6.29 mmol, 79%) in DCM (125 mL) was treated with mCPBA (4.65 g, 18.9 mmol, 70%). The reaction mixture was stirred at RT for 16 h, then quenched with a sat solution of NaHCO$_3$. The organic layer was dried over anhydrous Na$_2$SO$_4$, filtered and concentrated. The residue was purified by flash chromatography (silica; DCM/MeOH; gradient 0% to 10% MeOH) to afford the title compound as a diastereomeric mixture (3.06 g) as a colorless foam. UPLC-MS 2: m/z 544.1/546.1 [M−H]$^-$, $t_R$=7.28/7.33 min.

Step 3: 5-((S)-4-Bromo-5-chloro-6-fluoro-2-phenyl-2,3-dihydrobenzofuran-2-yl)-1-(tert-butylsulfonyl)-3-methylpyrrolidin-3-ol (C-XXXVI-c and C-XXXVI-d)

To a solution of N-(1-((S)-4-bromo-5-chloro-6-fluoro-2-phenyl-2,3-dihydrobenzofuran-2-yl)-2-(2-methyloxiran-2-yl)ethyl)-2-methylpropane-2-sulfonamide (C-XXXVI-b) (3.05 g, 4.80 mmol, 86%) in DMF (45 mL) was added K$_2$CO$_3$ (1.99 g, 14.4 mmol). The mixture was stirred at 100° C. for 24 h, then at RT. The solids were filtered off. After concentration the residue was purified by flash chromatography (silica; cyclohexane/EtOAc; gradient 0% to 30% EtOAc) to afford two separate diastereoisomers.

Diastereomer C-XXXVI-c (420 mg): UPLC-MS 1: m/z 590.2/592.2 [M+formate]$^-$, $t_R$=1.33 min.

Diastereomer C-XXXVI-d: (1.0 g): UPLC-MS 1: m/z 590.2/592.2 [M+formate]$^-$, $t_R$=1.40 min.

Step 4: ((5-((S)-4-Bromo-5-chloro-6-fluoro-2-phenyl-2,3-dihydrobenzofuran-2-yl)-1-(tert-butylsulfonyl)-3-methylpyrrolidin-3-yl)oxy)methyl pivalate (C-XXXVI-e)

At 0° C., NaH (35.3 mg, 0.88 mmol, 60% in mineral oil) was added to a solution of 5-((S)-4-bromo-5-chloro-6-fluoro-2-phenyl-2,3-dihydrobenzofuran-2-yl)-1-(tert-butylsulfonyl)-3-methylpyrrolidin-3-ol (C-XXXVI-c) (420 mg, 0.77 mmol) in THF (10 mL) and the reaction mixture was stirred at 0° C. for 45 min. Chloromethyl pivalate (0.13 mL, 0.85 mmol) was then added and the mixture was stirred at RT for 16 h. More NaH (35.3 mg, 0.88 mmol, 60% in mineral oil) followed by chloromethyl pivalate (130 mg, 0.85 mmol) was added. The mixture was stirred for an additional 24 h before it was quenched with water. The mixture was extracted twice with EtOAc. The combined organic layers were washed with brine, dried over anhydrous Na$_2$SO$_4$ and concentrated to afford the title compound (600 mg) as a colorless foam which was used in the next step without further purification. UPLC-MS 1: m/z 677.3/679.3 [M+OH]$^+$, $t_R$=1.57 min.

Step 5: Tert-butyl 2-((S)-4-bromo-5-chloro-6-fluoro-2-phenyl-2,3-dihydrobenzofuran-2-yl)-4-hydroxy-4-methylpyrrolidine-1-carboxylate (C-XXXVI-f)

At RT, trifluoromethanesulfonic acid (0.20 mL, 2.30 mmol) was added to a solution of ((5-((S)-4-bromo-5- chloro-6-fluoro-2-phenyl-2,3-dihydrobenzofuran-2-yl)-1-(tert-butylsulfonyl)-3-methylpyrrolidin-3-yl)oxy)methyl pivalate (C-XXXVI-e) (508 mg, 0.77 mmol) in DCM (15 mL). The reaction mixture was stirred for 20 min at RT before it was quenched with 1 M NaOH solution. The mixture was extracted twice with EtOAc. The combined organic layers were washed with brine, dried over anhydrous $Na_2SO_4$ and concentrated to afford the intermediate 5-((S)-4-bromo-5-chloro-6-fluoro-2-phenyl-2,3-dihydrobenzofuran-2-yl)-3-methylpyrrolidin-3-ol (800 mg, UPLC-MS 1: m/z 426.1/428.1 $[M+H]^+$, $t_R$=1.00 min) which was re-dissolved in DCM (15 mL). TEA (0.32 mL, 2.3 mmol) and Boc-anhydride (250 mg, 1.2 mmol) were added and the reaction mixture was stirred at RT for 16 h. After removal of the solvent, the residue was purified by flash chromatography (silica; cyclohexane/EtOAc; gradient 0% to 20% EtOAc) to afford the title compound (200 mg) as colorless foam. UPLC-MS 1: m/z 526.2/528.2 $[M+H]^+$, $t_R$=1.42 min.

Step 6: Tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)-4-hydroxy-4-methylpyrrolidine-1-carboxylate (C-XXXVI)

A suspension of tert-butyl 2-((S)-4-bromo-5-chloro-6-fluoro-2-phenyl-2,3-dihydrobenzofuran-2-yl)-4-hydroxy-4-methylpyrrolidine-1-carboxylate (C-XXXVI-f) (200 mg, 0.35 mmol), bis(pinacolato)diboron (134 mg, 0.53 mmol), potassium acetate (105 mg, 1.06 mmol) and $PdCl_2(dppf)$·$CH_2Cl_2$ adduct (29 mg, 0.035 mmol) in toluene (0.9 mL) was purged with Ar, then stirred at 100° C. for 16 h under Ar. The reaction mixture was diluted with toluene, filtered over Hyflo and concentrated. The residue was purified by flash chromatography (silica; cyclohexane/EtOAc; gradient 0% to 20% EtOAc) to afford the title compound (150 mg) as a foam. UPLC-MS 1: m/z 574.4 $[M+H]^+$, $t_R$=1.47 min; absolute configuration at C-2 position and C-4 position of pyrrolidine unassigned.

Synthesis of tert-butyl (2S,4R)-2-((S)-4-bromo-5-chloro-6-fluoro-2-phenyl-2,3-dihydrobenzofuran-2-yl)-4-fluoropyrrolidine-1-carboxylate (C-XXXVII)

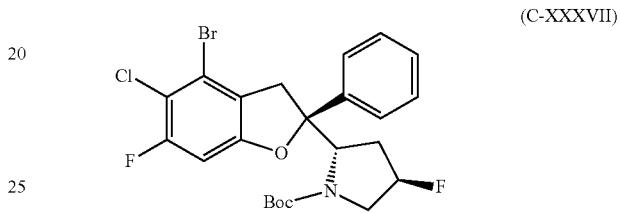

(C-XXXVII)

Reaction Scheme C-XXXVII:

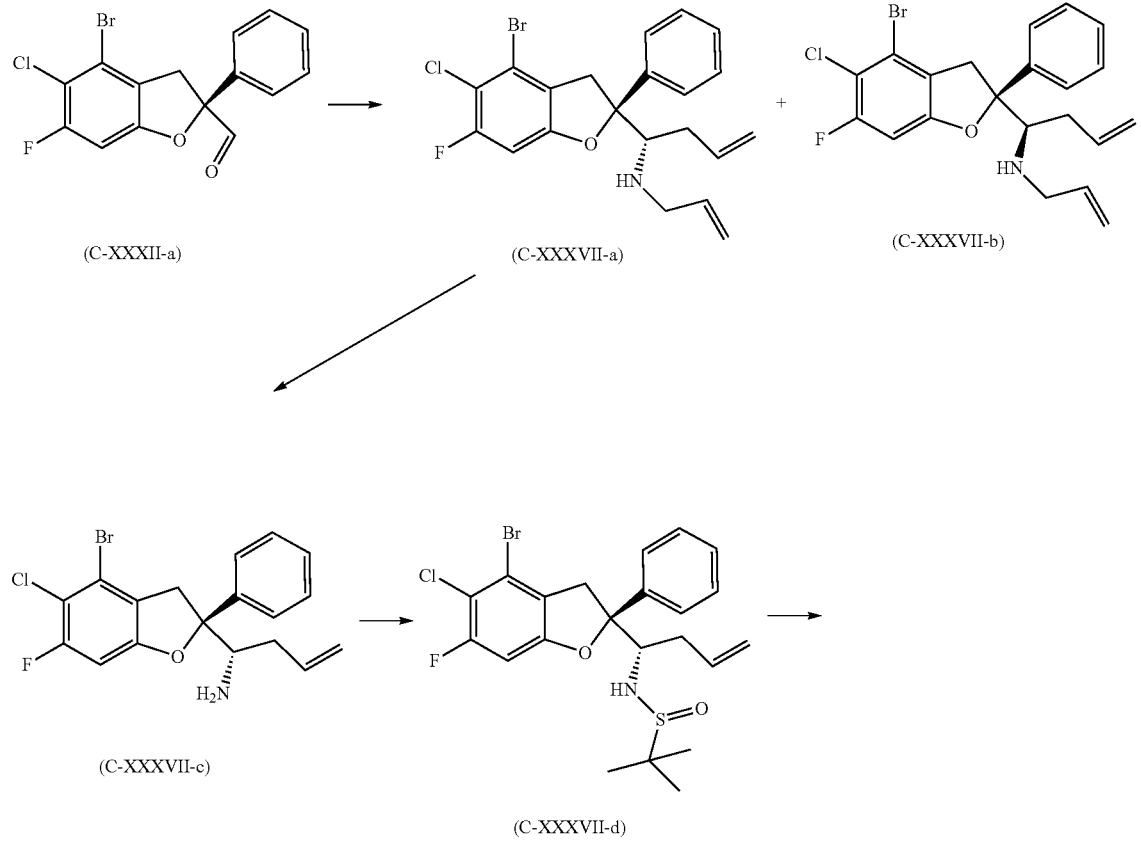

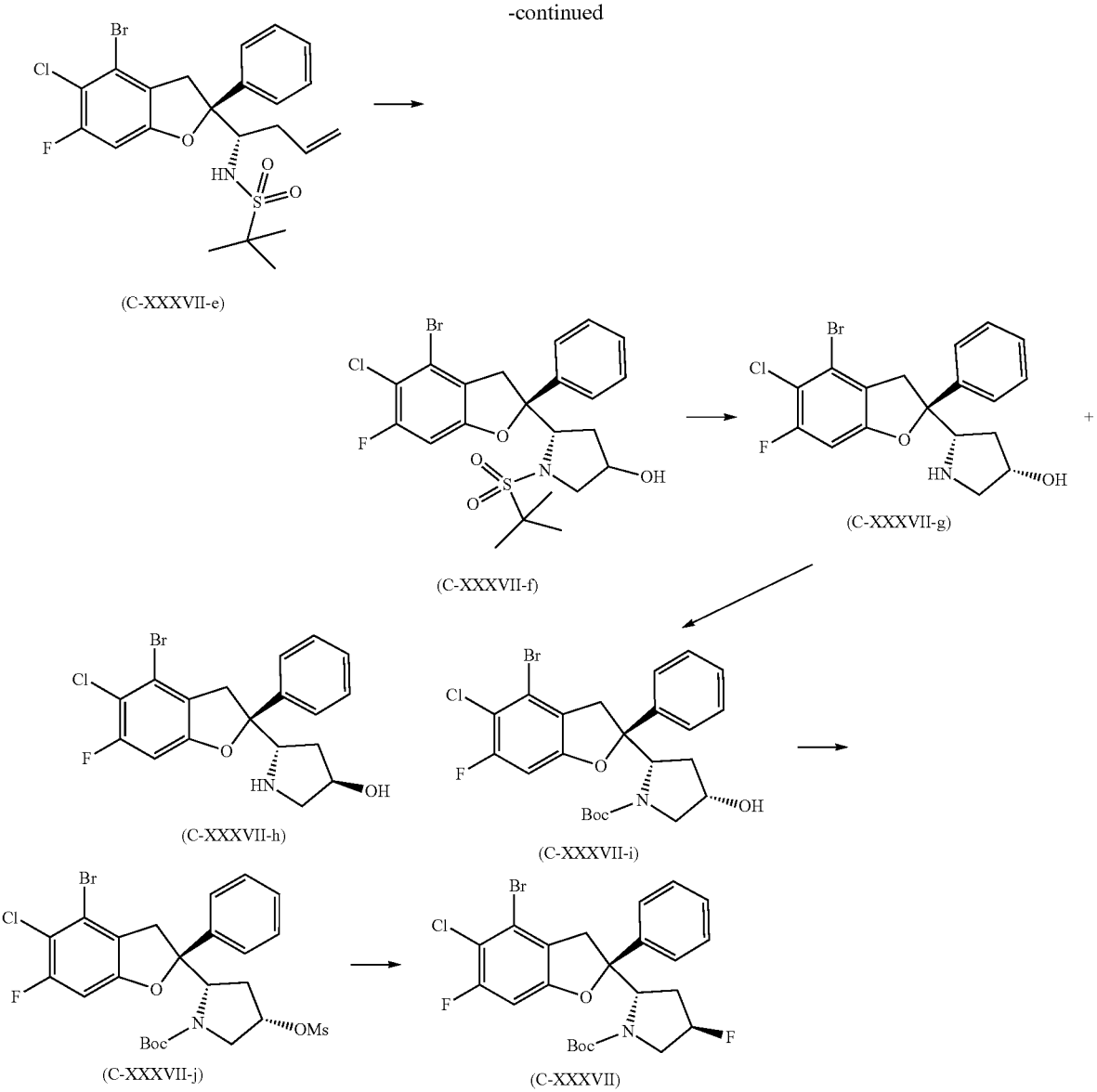

Step 1: (S)—N-Allyl-1-((S)-4-bromo-5-chloro-6-fluoro-2-phenyl-2,3-dihydrobenzofuran-2-yl)but-3-en-1-amine (C-XXXVII-a) and (R)—N-allyl-1-((S)-4-bromo-5-chloro-6-fluoro-2-phenyl-2,3-dihydrobenzofuran-2-yl)but-3-en-1-amine (C-XXXVII-b)

Under Ar, allylamine (13 mL, 173 mmol) and AcOH (2 mL, 34.5 mmol) were added to a stirred solution of ((S)-4-bromo-5-chloro-6-fluoro-2-phenyl-2,3-dihydrobenzofuran-2-carbaldehyde (C-XXXII-a) (12.3 g, 34.5 mmol) in DCM (75 mL). The reaction mixture was stirred for 3 h at RT and concentrated. The crude intermediate was dissolved in THF (75 mL) and a solution of allyl magnesium bromide in Et$_2$O (52 mL, 52 mmol) was added at 0° C. The reaction mixture was stirred for 1 h at RT, then was quenched by the addition of a sat. solution of NH$_4$Cl (200 mL) and extracted twice with EtOAc (2×200 mL). The combined organic layers were washed with a sat solution of NaHCO$_3$ (150 mL), dried over anhydrous Na$_2$SO$_4$ and concentrated. The crude product was subjected to flash chromatography (silica, cyclohexane/EtOAc; gradient 0% to 6% EtOAc) to afford two separate diastereoisomers:

(S)—N-Allyl-1-((S)-4-bromo-5-chloro-6-fluoro-2-phenyl-2,3-dihydrobenzofuran-2-yl)but-3-en-1-amine (C-XXXVII-a) (6.1 g): UPLC-MS 1: m/z 436.4/438.4 [M+H]$^+$, t$_R$=1.51 min.

(R)—N-allyl-1-((S)-4-bromo-5-chloro-6-fluoro-2-phenyl-2,3-dihydrobenzofuran-2-yl)but-3-en-1-amine (C-XXXVII-b) (5.7 g): UPLC-MS 1: m/z 436.1/438.1 [M+H]$^+$, t$_R$=1.54 min.

Step 2: (S)-1-((S)-4-Bromo-5-chloro-6-fluoro-2-phenyl-2,3-dihydrobenzofuran-2-yl)but-3-en-1-amine (C-XXXVII-c)

Under Ar, N,N'-dimethylbarbituric acid (6.54 g, 41.9 mmol) and Pd(PPh$_3$)$_4$ (0.161 g, 0.140 mmol) were added to a stirred solution of (S)—N-allyl-1-((S)-4-bromo-5-chloro-6-fluoro-2-phenyl-2,3-dihydrobenzofuran-2-yl)but-3-en-1- amine (C-XXXVII-a) (6.1 g, 14.0 mmol) in DCM (75 mL). The reaction mixture was stirred at 40° C. for 2 h. A sat solution of NaHCO$_3$ was added and the mixture was extracted with DCM. The combined organic layers were washed with water and brine, dried over anhydrous Na$_2$SO$_4$ and concentrated. The crude product was purified by flash chromatography (silica, cyclohexane/EtOAc, gradient: 0% to 35% EtOAc) to afford the title product (5.7 g). UPLC-MS 1: m/z 396.3/398.3 [M+H]$^+$, t$_R$=0.93 min.

Step 3: N—((S)-1-((S)-4-Bromo-5-chloro-6-fluoro-2-phenyl-2,3-dihydrobenzofuran-2-yl)but-3-en-1-yl)-2-methylpropane-2-sulfinamide (C-XXXVII-d)

Under Ar, TEA (4.02 mL, 28.8 mmol) and tert-butylsulfinyl chloride (2.0 mL, 15.9 mmol) were added to a stirred solution of (S)-1-((S)-4-bromo-5-chloro-6-fluoro-2-phenyl-2,3-dihydrobenzofuran-2-yl)but-3-en-1-amine (C-XXXVII-c) (5.72 g, 14.42 mmol) in DCM (100 mL). The reaction mixture was stirred at 0° C. for 1 h. A sat solution of NaHCO$_3$ (125 mL) was added and the mixture was extracted twice with DCM (2×100 mL). The combined organic extracts were washed with water and brine, dried (phase separator cartridge) and concentrated. The crude product was purified by flash chromatography (silica, cyclohexane/EtOAc, gradient: 0% to 60% EtOAc) to afford the title product (5.5 g) as a diastereomeric mixture. UPLC-MS 1: m/z 500.1/502.1 [M+H]$^+$, t$_R$=1.45 min.

Step 4: N-((1S)-1-((S)-4-Bromo-5-chloro-6-fluoro-2-phenyl-2,3-dihydrobenzofuran-2-yl)-2-(oxiran-2-yl)ethyl)-2-methylpropane-2-sulfonamide (C-XXXVII-e)

At RT, under Ar, mCPBA (8.1 g, 32.7 mmol) was added to a stirred solution of N—((S)-1-((S)-4-Bromo-5-chloro-6-fluoro-2-phenyl-2,3-dihydrobenzofuran-2-yl)but-3-en-1-yl)-2-methylpropane-2-sulfinamide (C-XXXVII-d) (5.46 g, 10.9 mmol) in DCM (100 mL). The reaction mixture was stirred at RT for 20 h. A sat solution of NaHCO$_3$ (50 mL) was added and the mixture was extracted twice with DCM (2×100 mL). The combined organic extracts were washed with water and brine, dried (phase separator cartridge) and concentrated. The crude product was purified by flash chromatography (silica, cyclohexane/EtOAc, gradient: 0% to 50% EtOAc) to afford the title product (5.1 g) as a diastereomeric mixture. UPLC-MS 1: m/z 530.0/532.0 [M−H]$^-$, t$_R$=1.33 min.

Step 5: (5S)-5-((S)-4-Bromo-5-chloro-6-fluoro-2-phenyl-2,3-dihydrobenzofuran-2-yl)-1-(tert-butylsulfonyl)pyrrolidin-3-ol (C-XXXVII-f)

Under Ar, KI (1.57 g, 9.48 mmol) and K$_2$CO$_3$ (3.93 g, 28.4 mmol) were added to a stirred solution of N-((1S)-1-((S)-4-bromo-5-chloro-6-fluoro-2-phenyl-2,3-dihydrobenzofuran-2-yl)-2-(oxiran-2-yl)ethyl)-2-methylpropane-2-sulfonamide (C-XXXVII-e) (5.05 g, 9.48 mmol) in DMF (40 mL). The reaction mixture was stirred at 100° C. for 1 h. A sat solution of NaHCO$_3$ (50 mL) was added and the mixture was extracted twice with EtOAC (2×75 mL). The combined organic extracts were washed with a sat solution of NaHCO$_3$ (75 mL) and brine, dried over anhydrous Na$_2$SO$_4$ and concentrated. The crude product was purified by flash chromatography (silica, cyclohexane/EtOAc, gradient: 0% to 55% EtOAc) to afford the title product (4.9 g) as a diastereomeric mixture. UPLC-MS 1: m/z 551.1.1 [M+NH3]$^+$, t$_R$=1.34 min.

Step 6: (3S,5S)-5-((S)-4-Bromo-5-chloro-6-fluoro-2-phenyl-2,3-dihydrobenzofuran-2-yl)pyrrolidin-3-ol (C-XXXVII-g) and (3R,5S)-5-((S)-4-Bromo-5-chloro-6-fluoro-2-phenyl-2,3-dihydrobenzofuran-2-yl)pyrrolidin-3-ol (C-XXXVII-h)

At 0° C., under Ar, triflic acid (2.5 mL, 28.0 mmol) was added dropwise to a stirred solution of (5S)-5-((S)-4-Bromo-5-chloro-6-fluoro-2-phenyl-2,3-dihydrobenzofuran-2-yl)-1-(tert-butylsulfonyl)pyrrolidin-3-ol (C-XXXVII-f) (5.0 g, 9.35 mmol) in DCM (50 mL). The reaction mixture was stirred at 0° C. for 1 h. A sat solution of NaHCO$_3$ (125 mL) was added and the mixture was extracted twice with DCM (2×100 mL). The combined organic extracts were washed with a sat solution of NaHCO$_3$ (125 mL) and brine, dried over anhydrous Na$_2$SO$_4$ and concentrated. The crude product was subjected to flash chromatography (silica, DCM/MeOH, gradient: 0% to 7% MeOH) to separate the diasteroisomers:

(3S,5S)-5-((S)-4-Bromo-5-chloro-6-fluoro-2-phenyl-2,3-dihydrobenzofuran-2-yl)pyrrolidin-3-ol (C-XXXVII-g) (1.2 g). $^1$H NMR (600 MHz, DMSO-d$_6$) δ 7.52 (d, J=7.5 Hz, 2H), 7.38 (t, J=7.6 Hz, 2H), 7.31 (t, J=7.3 Hz, 1H), 7.07 (d, J=9.5 Hz, 1H), 4.71 (t, J=3.6 Hz, 1H), 4.05 (q, J=5.9 Hz, 1H), 3.80 (d, J=16.1 Hz, 1H), 3.55 (t, J=8.4 Hz, 1H), 3.36 (s, 1H), 2.90 (dd, J=10.2, 6.3 Hz, 1H), 2.45 (dd, J=10.5, 5.9 Hz, 1H), 1.74 (dt, J=13.6, 7.1 Hz, 1H), 1.31 (ddd, J=12.4, 9.5, 6.9 Hz, 1H). UPLC-MS 1: m/z 412.1/414.1 [M+H]$^+$, t$_R$=0.83 min.

(3R,5S)-5-((S)-4-Bromo-5-chloro-6-fluoro-2-phenyl-2,3-dihydrobenzofuran-2-yl)pyrrolidin-3-ol (C-XXXVII-h) (1.6 g)$^1$H NMR (600 MHz, DMSO-d$_6$) δ (ppm) 7.53 (d, J=7.6 Hz, 2H), 7.37 (t, J=7.5 Hz, 2H), 7.30 (t, J=7.3 Hz, 1H), 7.09 (d, J=9.5 Hz, 1H), 4.53 (d, J=3.7 Hz, 1H), 3.99 (s, 1H), 3.79 (t, J=8.0 Hz, 1H), 3.66 (d, J=16.1 Hz, 1H), 2.69 (s, 3H), 1.50 (td, J=11.4, 9.2, 5.2 Hz, 1H), 1.41 (dd, J=13.4, 6.9 Hz, 1H). UPLC-MS 1: m/z 412.1/414.1 [M+H]$^+$, t$_R$=0.84 min.

Step 7: Tert-butyl (2S,4S)-2-((S)-4-bromo-5-chloro-6-fluoro-2-phenyl-2,3-dihydrobenzofuran-2-yl)-4-hydroxypyrrolidine-1-carboxylate (C-XXXVII-i)

At RT, Boc-anhydride (0.75 mL, 3.10 mmol) and TEA (0.8 mL, 5.62 mmol) were added to a stirred solution of (3S,5S)-5-((S)-4-bromo-5-chloro-6-fluoro-2-phenyl-2,3-dihydrobenzofuran-2-yl)pyrrolidin-3-ol (C-XXXVII-g) (1.2 g, 2.81 mmol) in THF (20 mL). The reaction mixture was stirred at RT for 1 h. A sat solution of NaHCO$_3$ (75 mL) was added and the mixture was extracted twice with DCM (2×100 mL). The combined organic extracts were washed with water and brine, dried over anhydrous Na$_2$SO$_4$ and concentrated. The crude product was purified by flash chromatography (silica, cyclohexane/EtOAc, gradient: 0% to 60% EtOAc) to afford the title product (1.42 g). UPLC-MS 1: m/z 556.0/557.9 [M+formate]$^-$, t$_R$=1.38 min.

Step 8: Tert-butyl (2S,4S)-2-((S)-4-bromo-5-chloro-6-fluoro-2-phenyl-2,3-dihydrobenzofuran-2-yl)-4-((methylsulfonyl)oxy)pyrrolidine-1-carboxylate (C-XXXVII-j)

At 0° C., under Ar, methanesulfonic anhydride (68 mg, 0.390 mmol) and TEA (0.14 mL, 0.98 mmol) were added to a stirred solution of tert-butyl (2S,4S)-2-((S)-4-bromo-5- chloro-6-fluoro-2-phenyl-2,3-dihydrobenzofuran-2-yl)-4-hydroxypyrrolidine-1-carboxylate (C-XXXVII-i) (100 mg, 0.195 mmol) in DCM (3 mL). The reaction mixture was stirred at RT for 2 h. A sat solution of $NH_4Cl$ (100 mL) was added and the mixture was extracted twice with DCM (2×75 mL). The combined organic extracts were washed with a sat solution of $NaHCO_3$ (50 mL) and brine, dried over anhydrous $Na_2SO_4$ and concentrated to afford the title product. UPLC-MS 1: m/z 534.0/536.0 [M−tertButyl]$^+$, $t_R$=1.42 min.

Step 9: Tert-butyl (2S,4R)-2-((S)-4-bromo-5-chloro-6-fluoro-2-phenyl-2,3-dihydrobenzofuran-2-yl)-4-fluoropyrrolidine-1-carboxylate (C-XXXVII)

At RT, under Ar, TBAF (15.1 mL, 15.1 mmol, 1 M in THF) was added to a stirred solution of tert-butyl (2S,4S)-2-((S)-4-bromo-5-chloro-6-fluoro-2-phenyl-2,3-dihydrobenzofuran-2-yl)-4-((methylsulfonyl)oxy)pyrrolidine-1-carboxylate (C-XXXVII-j) (890 mg, 1.51 mmol) in THF (10 mL). The reaction mixture was then stirred at 40° C. for 1 h. A sat solution of $NaHCO_3$ (50 mL) was added and the mixture was extracted twice with EtOAc (2×75 mL). The combined organic extracts were washed with a sat solution of $NaHCO_3$ and brine, dried over anhydrous $Na_2SO_4$ and concentrated. The residue was purified by preparative HPLC (Waters Sunfire prep C18, OBD 5 μm. 30×100 mm, A: H2O+0.1% TFA, B: ACN, Gradient: 25 to 100% B in 20 min hold 1 min, Flow 40 mL/min) to afford the title product (109 mg). UPLC-MS 1: m/z 458.0/460.0 [M−tertButyl]$^+$, $t_R$=1.43 min. $^1$H NMR (400 MHz, DMSO-d$_6$) δ (ppm) 7.48-7.43 (m, 2H), 7.42-7.30 (m, 3H), 7.16 (d, J=9.5 Hz, 1H), 5.04 (d, J=54 Hz, 1H), 4.72 (dd, J=8.5, 5.6 Hz, 11H), 3.84 (s br, 2H), 3.44 (d, J=16.7 Hz, 1H), 2.37-2.02 (m, 3H), 1.29 (s, 9H).

Synthesis of tert-butyl 2-((2S,3S)-5-chloro-6-fluoro-3-hydroxy-2-phenyl-4-(4,4,5,5-tetramethyl-1,3,2-dioxaborolan-2-yl)-2,3-dihydrobenzofuran-2-yl)pyrrolidine-1-carboxylate (C-XXXVIII)

(C-XXXVIII)

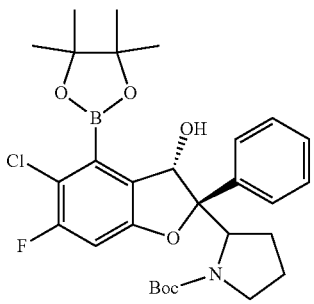

Reaction Scheme C-XXXVIII:

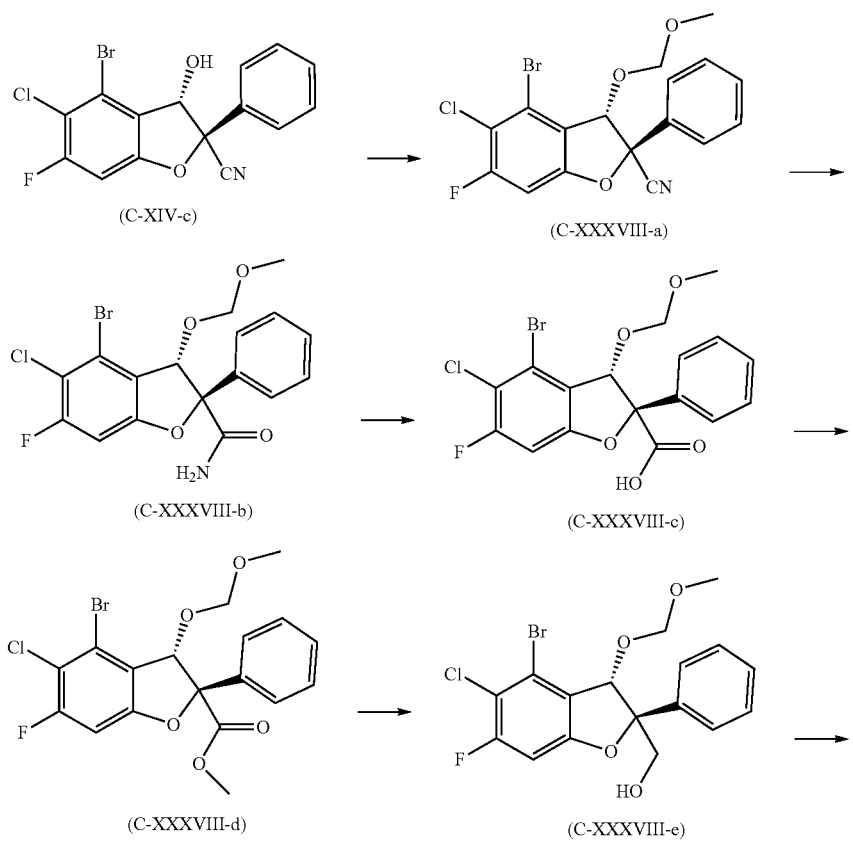

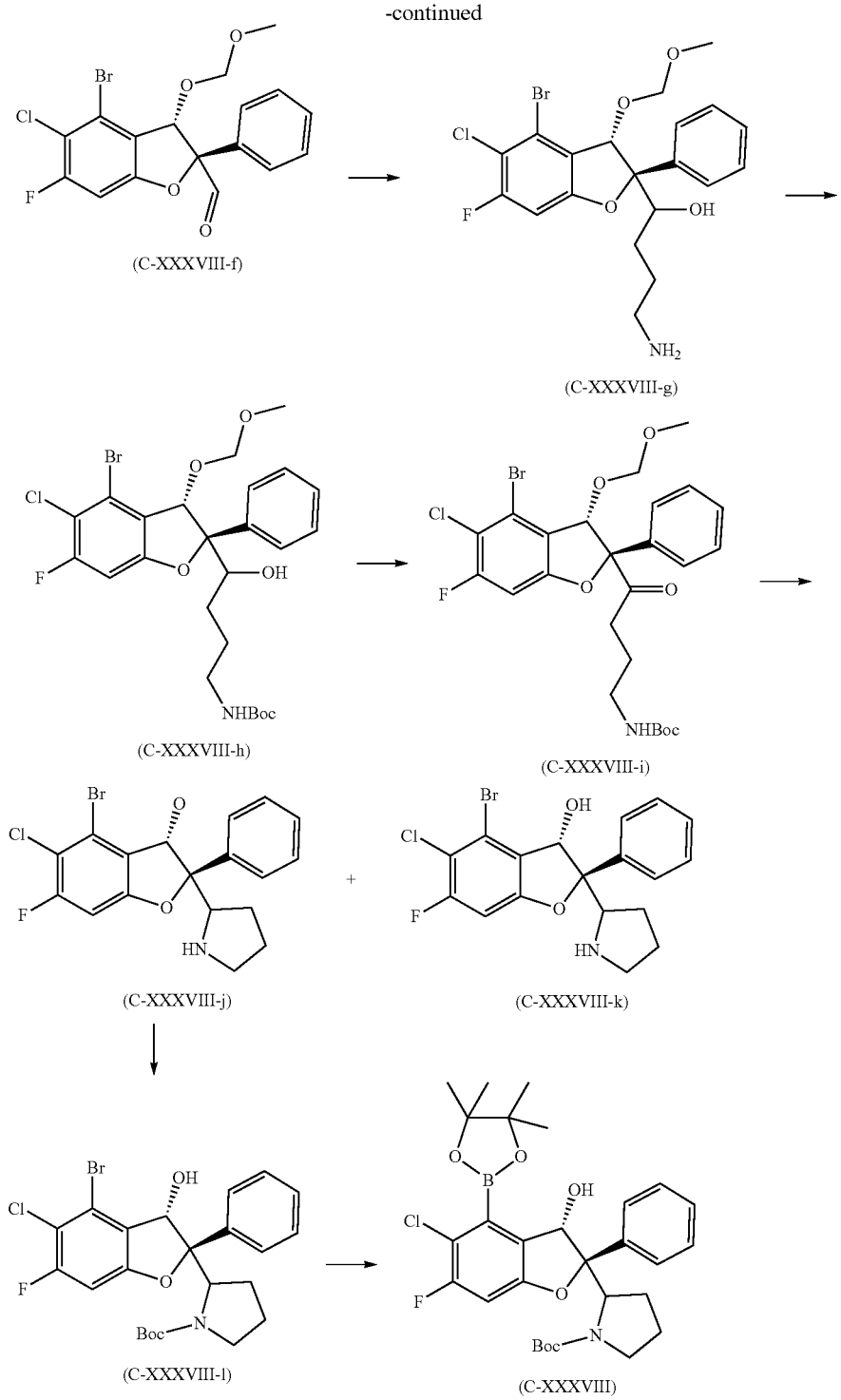

Step 1: (2S,3S)-4-Bromo-5-chloro-6-fluoro-3-(methoxymethoxy)-2-phenyl-2,3-dihydrobenzofuran-2-carbonitrile (C-XXXVIII-a)

At 0° C., Under Ar, NaH (1.65 g, 65.1 mmol, 95%) was added to a stirred solution of (2S,3S)-4-bromo-5-chloro-6-fluoro-3-hydroxy-2-phenyl-2,3-dihydrobenzofuran-2-carbonitrile (C-XIV-c) (20 g, 54.3 mmol) in DMF (200 mL). After 30 min, chloromethyl methyl ether (5.36 mL, 70.5 mmol) was added and the mixture was stirred at RT for another 2 h. A sat solution of NaHCO₃ (100 mL) was added followed by extraction with EtOAc (2×100 mL). The combined organic extracts were washed with a sat solution of NaHCO₃ (50 mL) and dried over Na₂SO₄. Concentration afforded the crude product which was purified by flash chromatography (silica, hexane/EtOAc, gradient: 0% to 15% EtOAc) to give the title compound (10.6 g) as a white solid. UPLC-MS 1: no ionization, $t_R$=1.33 min.

Step 2: (2R,3S)-4-Bromo-5-chloro-6-fluoro-3-(methoxymethoxy)-2-phenyl-2,3-dihydrobenzofuran-2-carboxamide (C-XXXVIII-b)

At RT, LiOH (3.1 g, 128 mmol) was added to a stirred solution of (2S,3S)-4-bromo-5-chloro-6-fluoro-3-(methoxymethoxy)-2-phenyl-2,3-dihydrobenzofuran-2-carbonitrile (C-XXXVIII-a) (10.6 g, 25.7 mmol) in dioxane (75 mL) and water (75 mL). After 2 h at 100° C. the reaction mixture was quenched by the addition of 1 N HCl and extracted twice with DCM (2×100 mL). The combined organic layers were washed with 1 N HCl (100 mL), dried over anhydrous $Na_2SO_4$ and concentrated. The crude product was purified by flash chromatography (silica, hexane/EtOAc, gradient 0% to 85% EtOAc) to give the title product (6.9 g) as a colorless solid. UPLC-MS 1: m/z 428.1/430.1 $[M-H]^-$, $t_R$=1.11 min.

Step 3: (2R,3S)-4-Bromo-5-chloro-6-fluoro-3-(methoxymethoxy)-2-phenyl-2,3-dihydrobenzofuran-2-carboxylic acid (C-XXXVIII-c)

At RT, LiOH·$H_2O$ (1.92 g, 80.0 mmol) was added to a stirred solution of (2R,3S)-4-bromo-5-chloro-6-fluoro-3-(methoxymethoxy)-2-phenyl-2,3-dihydrobenzofuran-2-carboxamide (C-XXXVIII-b) (6.9 g, 16.02 mmol) in dioxane (20 mL) and water (20 mL). After 20 h at 100° C., the reaction mixture was quenched by the addition of 1 N HCl and extracted twice with DCM (2×100 mL). The combined organic layers were washed with 1 N HCl, dried over anhydrous $Na_2SO_4$ and concentrated. The crude product was purified by flash chromatography (silica, hexane/EtOAc, gradient 0% to 100% EtOAc) to give the title product (5.61 g) as a colorless solid. UPLC-MS 1: m/z 448.1/450.1 $[M+NH3]^+$, $t_R$=1.05 min.

Step 4: (2R,3S)-Methyl 4-bromo-5-chloro-6-fluoro-3-(methoxymethoxy)-2-phenyl-2,3-dihydrobenzofuran-2-carboxylate (C-XXXVIII-d)

At 0° C., DMF (0.101 mL, 1.300 mmol) was added to a solution of (2R,3S)-4-bromo-5-chloro-6-fluoro-3-(methoxymethoxy)-2-phenyl-2,3-dihydrobenzofuran-2-carboxylic acid (C-XXXVIII-c) (5.61 g, 13.00 mmol) and oxalyl chloride (1.48 mL, 16.90 mmol) in DCM (50 mL). After 1 h at 0° C., MeOH (26.3 mL, 650 mmol) was added and the reaction mixture was stirred further at RT for 1 h. The mixture was quenched by the addition of a sat solution of $NaHCO_3$, (100 mL), then extracted twice with DCM (2×125 mL). The organic layers were combined and washed with a sat solution of $NaHCO_3$, (125 mL), dried over anhydrous $Na_2SO_4$ and concentrated. The crude product was purified by flash chromatography (silica, hexane/EtOAc, gradient: 0% to 25% EtOAc) to afford the title product (3.39 g). UPLC-MS 1: m/z 462.1/464.1 $[M+NH3]^+$, $t_R$=1.31 min.

Step 5: ((2S,3S)-4-Bromo-5-chloro-6-fluoro-3-(methoxymethoxy)-2-phenyl-2,3-dihydrobenzofuran-2-yl)methanol (C-XXXVIII-e)

At 0° C., under Ar, $LiBH_4$ (0.331 g, 15.21 mmol) was added portionwise to a stirred solution of (2R,3S)-methyl-4-bromo-5-chloro-6-fluoro-3-(methoxymethoxy)-2-phenyl-2,3-dihydrobenzofuran-2-carboxylate (C-XXXVIII-d) (3.39 g, 7.61 mmol) in a mixture of THF (50 mL) and MeOH (1.23 mL, 30.4 mmol). The reaction mixture was stirred for 1 h. The reaction mixture was then quenched by adding a sat solution of $NaHCO_3$ (100 mL) and extracted with EtOAc (2*100 mL). The combined organic layers were washed with a sat solution of $NaHCO_3$ (75 mL), dried over anhydrous $Na_2SO_4$ and concentrated under reduced pressure. The crude product was purified by flash chromatography (silica, hexane/EtOAc; gradient 0% to 75% EtOAc) to give the title product (2.81 g). UPLC-MS 1: m/z 461.1/463.1 $[M+formate]^-$, $t_R$=1.24 min.

Step 6: (2R,3S)-4-Bromo-5-chloro-6-fluoro-3-(methoxymethoxy)-2-phenyl-2,3-dihydrobenzofuran-2-carbaldehyde (C-XXXVIII-f)

At −78° C., DMSO (0.95 mL, 10.76 mmol) was added to a solution of oxalyl chloride (0.95 mL, 10.76 mmol) in DCM (15 mL). After 30 min at −78° C., a solution of ((2S,3S)-4-bromo-5-chloro-6-fluoro-3-(methoxymethoxy)-2-phenyl-2,3-dihydrobenzofuran-2-yl)methanol (C-XXXVIII-e) (2.81 g, 6.73 mmol) in DCM (10 mL) followed by TEA (4.7 mL, 33.6 mmol) were added. The reaction mixture was stirred at −78° C. for 1 h. The reaction mixture was quenched by the addition of brine (75 mL), then extracted twice with DCM (2×75 mL). The combined organic layers were washed with brine (75 mL), dried over anhydrous $Na_2SO_4$ and concentrated to give the title compound (2.85 g) which was used directly in the next step without further purification. UPLC-MS 1: $t_R$=1.25 min.

Step 7: 4-Amino-1-((2S,3S)-4-bromo-5-chloro-6-fluoro-3-(methoxymethoxy)-2-phenyl-2,3-dihydrobenzofuran-2-yl)butan-1-ol (C-XXXVIII-g)

Under Ar, a solution of 1-(3-bromopropyl)-2,2,5,5-tetramethyl-1,2,5-azadisilolidine (C-XXXIV-a) (0.29 g, 1.03 mmol) in $Et_2O$ (2 mL) and a crystal of $I_2$ were added to a stirred suspension of magnesium (0.333 g, 13.71 mmol) in $Et_2O$ (3 mL). The suspension was heated at reflux until the color disappeared and more solution of 1-(3-bromopropyl)-2,2,5,5-tetramethyl-1,2,5-azadisilolidine (C-XXXIV-a) (2.592 g, 9.26 mmol) in $Et_2O$ (15 mL) was added. After 1 h at 40° C., (2R,3S)-4-bromo-5-chloro-6-fluoro-3-(methoxymethoxy)-2-phenyl-2,3-dihydrobenzofuran-2-carbaldehyde (C-XXXVIII-f) (2.85 g, 6.86 mmol) in THF (15 mL) was added at 0° C. and stirring was continued for 1 h. The reaction mixture was quenched with a sat solution of $NH_4Cl$ (100 mL) and extracted twice with EtOAc (2*100 mL). The organic layers were combined and washed with brine, dried over anhydrous $Na_2SO_4$ and concentrated. The resulting crude product was purified by flash chromatography (silica DCM/MeOH, gradient: 0% to 15% MeOH) to give the desired product (1.1 g) as a colorless solid. UPLC-MS 1: m/z 476.2/478.2 $[M+H]^+$, $t_R$=0.92 min.

Step 8: Tert-butyl (4-((2S,3S)-4-bromo-5-chloro-6-fluoro-3-(methoxymethoxy)-2-phenyl-2,3-dihydrobenzofuran-2-yl)-4-hydroxybutyl)carbamate (C-XXXVIII-h)

At RT, Boc-anhydride (0.554 mL, 2.39 mmol) and TEA (0.61 mL, 4.34 mmol) were added to a stirred solution of 4-amino-1-((2S,3S)-4-bromo-5-chloro-6-fluoro-3-(methoxymethoxy)-2-phenyl-2,3-dihydrobenzofuran-2-yl)butan-1-ol (C-XXXVIII-g) (1.03 g, 2.170 mmol) in THF (15 mL). The reaction mixture was stirred at RT for 1 h. A sat solution of $NaHCO_3$ (75 mL) was added and the mixture was extracted twice with EtOAc (2*100 mL). The combined organic extracts were washed with water and brine, dried over anhydrous $Na_2SO_4$ and concentrated. The crude product was purified by flash chromatography (silica, hexane/EtOAc, gradient: 0% to 75% EtOAc) to afford the desired product (1.2 g). UPLC-MS 1: m/z 574.2/576.2 $[M+H]^+$, $t_R$=1.43 min.

Step 9: Tert-butyl ((2R,3S)-4-bromo-5-chloro-6-fluoro-3-(methoxymethoxy)-2-phenyl-2,3-dihydrobenzofuran-2-yl)-4-oxobutyl)carbamate (C-XXXVIII-i)

At −78° C., DMSO (0.47 mL, 6.68 mmol) was added to a solution of oxalyl chloride (0.292 mL, 3.34 mmol) in DCM (15 mL). After 30 min at −78° C., a solution of tert-butyl (4-((2S,3S)-4-bromo-5-chloro-6-fluoro-3-(methoxymethoxy)-2-phenyl-2,3-dihydrobenzofuran-2-yl)-4-hydroxybutyl)carbamate (C-XXXVIII-h) (1.20 g, 2.09 mmol) in DCM (15 mL) as well as TEA (1.46 mL, 10.5 mmol) were added and the reaction mixture was stirred at −78° C. for 1 h. The reaction mixture was quenched by the addition of brine (100 mL), then extracted twice with DCM (2*100 mL). The organic layers were combined and washed with brine (100 mL), dried over anhydrous $Na_2SO_4$ and concentrated. The crude product was purified by flash chromatography (silica, hexane/EtOAc, gradient: 0% to 60% EtOAc) to afford the title product (870 mg) as a colorless solid. UPLC-MS 1: m/z 572.2/574.2 $[M+H]^+$, $t_R$=1.45 min.

Step 10: (2S,3S)-4-Bromo-5-chloro-6-fluoro-2-phenyl-2-(pyrrolidin-2-yl)-2,3-dihydrobenzofuran-3-ol (C-XXXVIII-j and C-XXXVIII-k)

At RT, HCl (3.80 mL, 15.2 mmol, 4 M in dioxane) was added to tert-butyl (4-((2R,3S)-4-bromo-5-chloro-6-fluoro-3-(methoxymethoxy)-2-phenyl-2,3-dihydrobenzofuran-2-yl)-4-oxobutyl)carbamate (C-XXXVIII-i) (870 mg, 1.519 mmol) and the reaction mixture was stirred for 1 h. After removal of solvent, the residue was dissolved in DCM (3 mL) then $NaBH(OAc)_3$ (966 mg, 4.56 mmol) was added and the mixture was stirred at RT for 16 h. A sat solution of $NaHCO_3$ (75 mL) was added and the mixture was extracted twice with EtOAc (2×75 mL). The combined organic extracts were washed with water and brine, dried over anhydrous $Na_2SO_4$ and concentrated. The resulting crude product was purified by flash chromatography (silica DCM/MeOH, gradient: 0% to 10% MeOH) to give the separate diastereoisomers: Diastereomer C-XXXVIII-j (380 mg): $^1$H NMR (400 MHz, DMSO-$d_6$) δ (ppm)$^1$H NMR (400 MHz, DMSO-$d_6$) δ 7.66-7.58 (m, 2H), 7.36-7.23 (m, 5H), 5.15 (s, 1H), 3.93 (dd, J=8.2, 6.6 Hz, 1H), 3.79-3.63 (m, 1H), 2.82-2.72 (m, 1H), 2.58-2.52 (m, 1H), 1.86-1.71 (m, 1H), 1.58-1.38 (m, 2H), 1.18-1.03 (m, 1H). UPLC-MS 1: m/z 414.1/416.1 $[M+H]^+$, $t_R$=0.81 min.

Diastereomer C-XXXVIII-k (213 mg): UPLC-MS 1: m/z 414.1/416.2 $[M+H]^+$, $t_R$=0.79 min.

Step 11: Tert-butyl 2-((2S,3S)-4-bromo-5-chloro-6-fluoro-3-hydroxy-2-phenyl-2,3-dihydrobenzofuran-2-yl)pyrrolidine-1-carboxylate (C-XXXVIII-l)

At RT, Boc-anhydride (0.25 mL, 1.02 mmol) and TEA (0.26 mL, 1.84 mmol) were added to a stirred solution of (2S,3S)-4-bromo-5-chloro-6-fluoro-2-phenyl-2-(pyrrolidin-2-yl)-2,3-dihydrobenzofuran-3-ol (C-XXXVIII-j) (380 mg, 0.921 mmol) in THF (8 mL). The reaction mixture was stirred at RT for 1 h. A sat solution of $NaHCO_3$ (75 mL) was added and the mixture was extracted twice with EtOAc (2*100 mL). The combined organic extracts were washed with water and brine, dried over anhydrous $Na_2SO_4$ and concentrated. The crude product was purified by flash chromatography (silica, hexane/EtOAc, gradient: 0% to 20% EtOAc) to afford the title product (328 mg). UPLC-MS 1: m/z 514.2 $[M+H]^+$, $t_R$=1.59 min.

Step 12: Tert-butyl 2-((2S,3S)-5-chloro-6-fluoro-3-hydroxy-2-phenyl-4-(4,4,5,5-tetramethyl-1,3,2-dioxaborolan-2-yl)-2,3-dihydrobenzofuran-2-yl)pyrrolidine-1-carboxylate (C-XXXVIII)

A deoxygenated suspension of tert-butyl 2-((2S,3S)-4-bromo-5-chloro-6-fluoro-3-hydroxy-2-phenyl-2,3-dihydrobenzofuran-2-yl)pyrrolidine-1-carboxylate (C-XXXVIII-1) (328 mg, 0.64 mmol), bis(pinacolato)diboron (244 mg, 0.959 mmol), KOAc (188 mg, 1.92 mmol) and $PdCl_2(dppf)\cdot CH_2Cl_2$ adduct (52.2 mg, 0.064 mmol) in dioxane (6 mL) was stirred at 100° C. for 16 h under an Ar atmosphere. The reaction mixture was filtered over Celite and concentrated under reduced pressure. The residue was purified by flash chromatography (silica, hexane/EtOAc; gradient: 0 to 100% EtOAc) to afford the title product (399 mg) as a colorless solid. UPLC-MS 1: m/z 604.4 [M+formate]$^-$, $t_R$=1.61 min; absolute configuration at C-2 position of pyrrolidine unassigned.

Synthesis of tert-butyl 2-((2S,3S)-5-chloro-6-fluoro-3-methoxy-2-phenyl-4-(4,4,5,5-tetramethyl-1,3,2-dioxaborolan-2-yl)-2,3-dihydrobenzofuran-2-yl)pyrrolidine-1-carboxylate

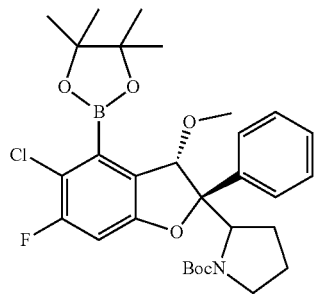

(C-XXXIX)

Reaction Scheme C-XXXIX
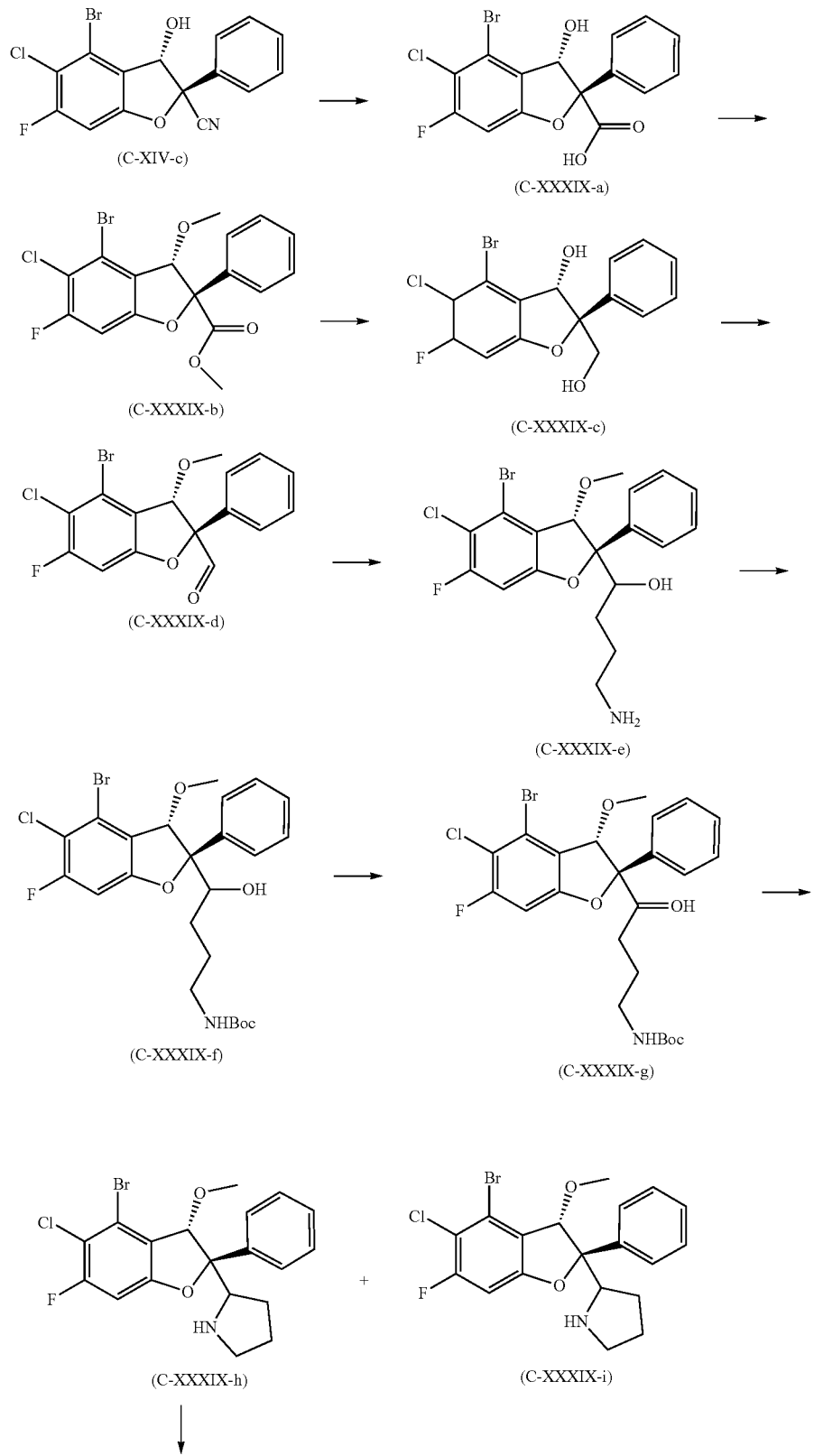

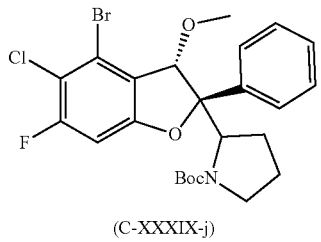

(C-XXXIX-j)

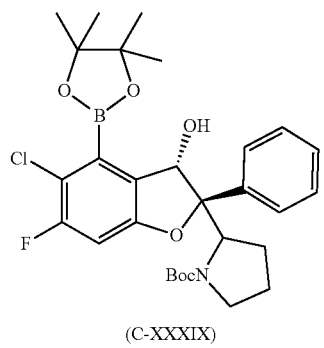

(C-XXXIX)

Step 1: (2R,3S)-4-Bromo-5-chloro-6-fluoro-3-hydroxy-2-phenyl-2,3-dihydrobenzofuran-2-carboxylic acid (C-XXXIX-a)

At RT, LiOH·H$_2$O (6.50 g, 271 mmol) was added to a stirred solution of (2S,3S)-4-bromo-5-chloro-6-fluoro-3-hydroxy-2-phenyl-2,3-dihydrobenzofuran-2-carbonitrile (C-XIV-c) (20 g, 54.3 mmol) in dioxane (100 mL) and water (100 mL). After 2 h at 100° C., the reaction mixture was quenched by the addition of 1 N HCl and extracted with DCM. The combined organic layers were washed with 1 N HCl, dried over anhydrous Na$_2$SO$_4$ and concentrated. The crude product was purified by flash chromatography (silica, DCM/MeOH; gradient 0% to 8% MeOH) to give the title compound (21.5 g) as a colorless solid. LC-MS 1: m/z 386.9 [M+H]$^+$, t$_R$=0.92 min.

Step 2: (2R,3S)-Methyl 4-bromo-5-chloro-6-fluoro-3-methoxy-2-phenyl-2,3-dihydrobenzofuran-2-carboxylate (C-XXXIX-b)

Under Ar NaH (5.99 g, 150 mmol, 60% suspended in mineral oil) was added to a stirred solution of (2R,3S)-4-bromo-5-chloro-6-fluoro-3-hydroxy-2-phenyl-2,3-dihydrobenzofuran-2-carboxylic acid (C-XXXIX-a) (21.5 g, 55.5 mmol) in DMF (200 mL) at 0° C. After 30 min, MeI (7.98 mL, 128 mmol) was added and stirring at RT was continued for another 2 h. For workup a sat solution of NaHCO$_3$ was added followed by extraction with EtOAc. The combined organic extracts were washed with a sat solution of NaHCO$_3$ and dried over anhydrous Na$_2$SO$_4$. Concentration afforded the crude product which was purified by flash chromatography (silica, hexane/EtOAc, gradient: 0% to 10% EtOAc) to give the title compound (10.7 g) as a colorless solid. UPLC-MS 1: m/z 432.0 [M+H]$^+$, t$_R$=1.33 min.

Step 3: ((2S,3S)-4-Bromo-5-chloro-6-fluoro-3-methoxy-2-phenyl-2,3-dihydrobenzofuran-2-yl)methanol (C-XXXIX-c)

Under Ar LiBH$_4$ (1.122 g, 51.5 mmol) was added portionwise to a stirred solution of (2R,3S)-methyl 4-bromo-5-chloro-6-fluoro-3-methoxy-2-phenyl-2,3-dihydrobenzofuran-2-carboxylate (C-XXXIX-b) (10.7 g, 25.7 mmol) in a mixture of THF (200 mL) and MeOH (5 mL) at 0° C. and stirring was continued for 2 h. The reaction mixture was quenched by the addition of a sat solution of NaHCO$_3$ and extracted with EtOAc. The combined organic layers were washed with a sat solution of NaHCO$_3$, dried over anhydrous Na$_2$SO$_4$ and concentrated under reduced pressure. The crude product was purified by flash chromatography (silica, hexane/EtOAc; gradient 0% to 60% EtOAc) to give the title product (7.8 g) as a colorless solid. UPLC-MS 1: no ionization, t$_R$=1.22 min.

Step 4: (2R,3S)-4-Bromo-5-chloro-6-fluoro-3-methoxy-2-phenyl-2,3-dihydrobenzofuran-2-carbaldehyde (C-XXXIX.d)

At −78° C. DMSO (4.57 mL, 64.4 mmol) was added to a solution of oxalyl chloride (2.82 mL, 32.2 mmol) in DCM (50 mL). After 30 min at −78° C., a solution of ((2S,3S)-4-bromo-5-chloro-6-fluoro-3-methoxy-2-phenyl-2,3-dihydrobenzofuran-2-yl)methanol (C-XXXIX-c) (7.8 g, 20.12 mmol) in DCM (50 mL) as well as TEA (14.02 mL, 101 mmol) was added and the reaction mixture was stirred at −78° C. for 1 h. The reaction mixture was quenched by the addition of brine and extracted with DCM. The organic layers were combined and washed with brine, dried over anhydrous Na$_2$SO$_4$ and concentrated to give the title compound (7.9 g) as a brownish powder. UPLC-MS 1: t$_R$=1.26 min.

Step 5: 4-Amino-1-((2S,3S)-4-bromo-5-chloro-6-fluoro-3-methoxy-2-phenyl-2,3-dihydrobenzofuran-2-yl)butan-1-ol (C-XXXIX-e)

Under Ar a solution of 1-(3-bromopropyl)-2,2,5,5-tetramethyl-1,2,5-azadisilolidine (C-XXXIV-a) (0.862 g, 3.07 mmol) in Et$_2$O (6.25 mL) and a crystal of I$_2$ was added to a stirred suspension of magnesium (0.996 g, 41.0 mmol) in Et$_2$O (10 mL). The suspension was heated at reflux until the color disappeared and more solution of 1-(3-bromopropyl)-2,2,5,5-tetramethyl-1,2,5-azadisilolidine (C-XXXIV-a) (7.758 g, 27.63 mmol) in Et$_2$O (56.25 mL) was added. After 1 h at 40° C., (2R,3S)-4-bromo-5-chloro-6-fluoro-3-methoxy-2-phenyl-2,3-dihydrobenzofuran-2-carbaldehyde (C-XXXIX-d) (7.9 g, 20.49 mmol) in THF (50 mL) was added at RT and stirring was continued for 1 h. The reaction mixture was quenched with a sat solution of NH$_4$Cl and extracted with EtOAc. The organic layers were combined and washed with brine, dried over anhydrous Na$_2$SO$_4$ and concentrated. The resulting crude product was purified by flash chromatography (silica DCM/MeOH, gradient: 0% to 10% MeOH) to give the desired product (6.65 g) as a colorless solid. UPLC-MS 1: m/z 446.1 [M+H]$^+$, t$_R$=0.96 min.

Step 6: Tert-butyl (4-((2S,3S)-4-bromo-5-chloro-6-fluoro-3-methoxy-2-phenyl-2,3-dihydrobenzofuran-2-yl)-4-hydroxybutyl)carbamate (C-XXXIX-f)

At RT Boc-anhydride (3.81 mL, 16.42 mmol) and TEA (4.16 mL, 29.9 mmol) were added to a stirred solution of 4-amino-1-((2S,3S)-4-bromo-5-chloro-6-fluoro-3-methoxy-2-phenyl-2,3-dihydrobenzofuran-2-yl)butan-1-ol (C-XXXIX-e) (6.64 g, 14.93 mmol) in THF (100 mL). The reaction mixture was stirred at RT for 1 h. For workup a sat solution of NaHCO$_3$ was added and the mixture was extracted with EtOAc. The combined organic extracts were washed with water and brine, dried over anhydrous Na$_2$SO$_4$ and concentrated. The crude product was purified by flash chromatography (silica, hexane/EtOAc, gradient: 0% to 60% EtOAc) to afford the desired product (6.3 g). UPLC-MS 1: m/z 546.1 [M+H]$^+$, t$_R$=1.40 min.

Step 7: Tert-butyl (4-((2R,3S)-4-bromo-5-chloro-6-fluoro-3-methoxy-2-phenyl-2,3-dihydrobenzofuran-2-yl)-4-oxobutyl)carbamate (C-XXXIX-g)

At −78° C. DMSO (2.63 mL, 37.0 mmol) was added to a solution of oxalyl chloride (1.619 mL, 18.50 mmol) in DCM (50 mL). After 30 min at −78° C., a solution of tert-butyl 4-((2S,3S)-4-bromo-5-chloro-6-fluoro-3-methoxy-2-phenyl-2,3-dihydrobenzofuran-2-yl)-4-hydroxybutyl)carbamate (C-XXXIX-f) (6.3 g, 11.56 mmol) in DCM (50 mL) as well as TEA (8.06 mL, 57.8 mmol) were added and the reaction mixture was stirred at −78° C. for 1 h. The reaction mixture was quenched by the addition of brine, then extracted with DCM. The organic layers were combined and washed with brine, dried over anhydrous Na$_2$SO$_4$ and concentrated. The crude product was purified by flash chromatography (silica, cyclohexane/EtOAc, gradient: 0% to 40% EtOAc) to afford the title product (5.38 g) as a colorless solid. UPLC-MS 1: m/z 544.1 [M+H]$^+$, t$_R$=1.45 min. Step 8: 2-((2S,3S)-4-Bromo-5-chloro-6-fluoro-3-methoxy-2-phenyl-2,3-dihydrobenzofuran-2-yl)pyrrolidine (C-XXXIX-h and C-XXXIX-i)

At RT HCl (24.78 mL, 99 mmol, 4 M in dioxane) was added to tert-butyl (4-((2R,3S)-4-bromo-5-chloro-6-fluoro-3-methoxy-2-phenyl-2,3-dihydrobenzofuran-2-yl)-4-oxobutyl)carbamate (C-XXXIX-g) (5.38 g, 9.91 mmol) and the reaction mixture was stirred for 16 h. The reaction mixture was concentrated and the residue was dissolved in DCM (25 mL) and NaBH(OAc)$_3$ (6.30 g, 29.7 mmol) was added before stirring for 1 h. For workup a sat solution of NaHCO$_3$ was added and the mixture was extracted with EtOAc. The combined organic extracts were washed with water and brine, dried over anhydrous Na$_2$SO$_4$ and concentrated. The resulting crude product was subjected to flash chromatography (silica DCM/MeOH, gradient: 0% to 10% MeOH) to afford the separate diastereoisomers, C-XXXIX-h and C-XXXIX-i: Diastereoisomer C-XXXIX-h (1.48 g). $^1$H NMR (400 MHz, DMSO-d$_6$) δ (ppm) 7.69-7.56 (m, 2H), 7.38-7.23 (m, 4H), 4.84 (s, 1H), 4.10-3.94 (m, 1H), 3.76 (s, 3H), 2.80-2.66 (m, 1H), 2.57-2.54 (m, 1H), 2.31-2.20 (m, 1H), 1.91-1.77 (m, 1H), 1.53-1.32 (m, 2H), 1.11-0.97 (m, 1H). UPLC-MS 1: m/z 426.1 [M+H]$^+$, t$_R$=0.96 min.

Diastereoisomer C-XXXIX-i (928 mg): UPLC-MS 1: m/z 426.4 [M+H]$^+$, t$_R$=1.04 min.

Step 9: Tert-butyl 2-((2S,3S)-4-bromo-5-chloro-6-fluoro-3-methoxy-2-phenyl-2,3-dihydrobenzofuran-2-yl)pyrrolidine-1-carboxylate (C-XXXIX-j)

At RT Boc-anhydride (0.838 mL, 3.61 mmol) and TEA (0.915 mL, 6.56 mmol) were added to a stirred solution of 2-((2S,3S)-4-bromo-5-chloro-6-fluoro-3-methoxy-2-phenyl-2,3-dihydrobenzofuran-2-yl)pyrrolidine (C-XXXIX-h) (1.40 g, 3.28 mmol) in THF (15 mL). The reaction mixture was stirred at RT for 1 h. For workup a sat solution of NaHCO$_3$ was added and the mixture was extracted with EtOAc. The combined organic extracts were washed with water and brine, dried over anhydrous Na$_2$SO$_4$ and concentrated. The crude product was purified by flash chromatography (silica, cyclohexane/EtOAc, gradient: 0% to 10% EtOAc) to afford the desired product (1.69 g) as a colorless solid. UPLC-MS 1: m/z 528.1 [M+H]$^+$, t$_R$=1.64 min.

Step 10: Tert-butyl 2-((2S,3S)-5-chloro-6-fluoro-3-methoxy-2-phenyl-4-(4,4,5,5-tetramethyl-1,3,2-dioxaborolan-2-yl)-2,3-dihydrobenzofuran-2-yl)pyrrolidine-1-carboxylate (C-XXXIX)

A deoxygenated suspension of tert-butyl 2-((2S,3S)-4-bromo-5-chloro-6-fluoro-3-methoxy-2-phenyl-2,3-dihydrobenzofuran-2-yl)pyrrolidine-1-carboxylate (C-XXXIX-j) (1.28 g, 2.430 mmol), bis(pinacolato)diboron (0.925 g, 3.64 mmol), KOAc (0.715 g, 7.29 mmol) and PdCl$_2$(dppf)·CH$_2$Cl$_2$ adduct (0.198 g, 0.243 mmol) in dioxane (15 mL) was stirred at 100° C. for 16 h under a Ar atmosphere. The reaction mixture was filtered over Celite and concentrated under reduced pressure. The residue was purified by flash chromatography (silica, hexane/EtOAc; gradient: 0 to 50%) to afford the title product (403 mg) as a colorless solid. UPLC-MS 1: m/z 574.3 [M+H]$^+$, t$_R$=1.61 min; absolute configuration at C-2 position of pyrrolidine unassigned.

Synthesis of tert-butyl 2-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)pyrrolidine-1-carboxylate (C-XL)

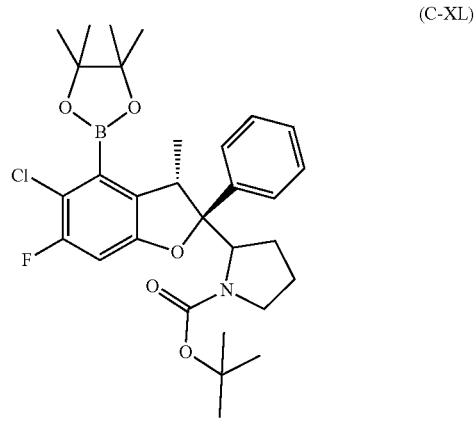 [SMILES: C[C@H]1c2c(cc(F)c(Cl)c2B2OC(C)(C)C(C)(C)O2)O[C@@]1(c1ccccc1)C1CCCN1C(=O)OC(C)(C)C]

(C-XL)

Reaction Scheme C-XL:

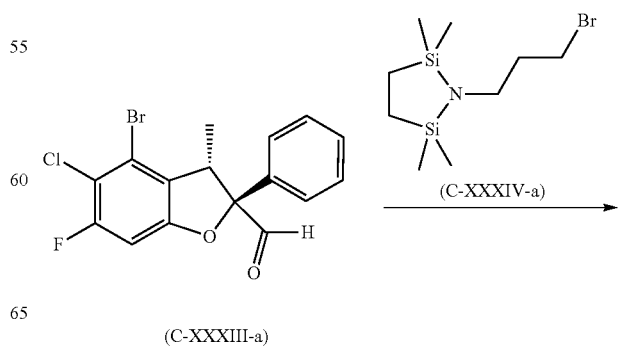

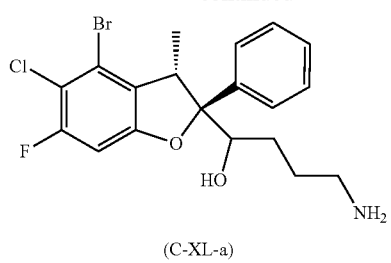

(C-XL-a)

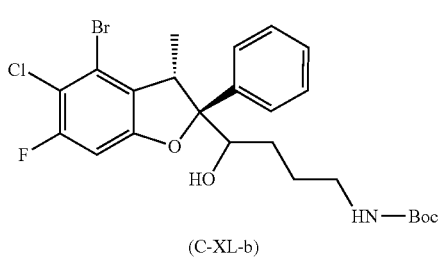

(C-XL-b)

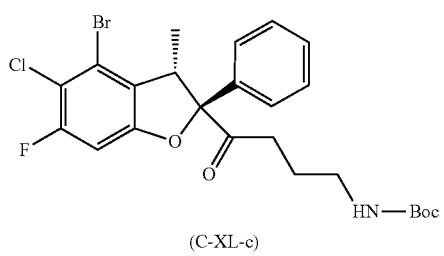

(C-XL-c)

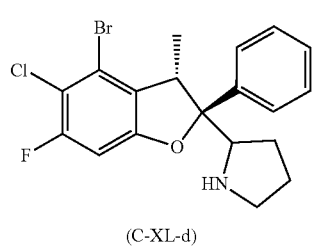

(C-XL-d)

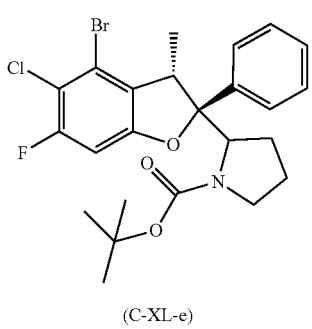

(C-XL-e)

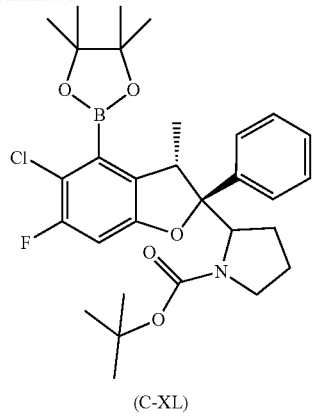 [SMILES: C[C@H]1c2c(cc(F)c(Cl)c2B2OC(C)(C)C(C)(C)O2)O[C@@]1(c1ccccc1)C1CCCN1C(=O)OC(C)(C)C]

(C-XL)

Step 1: 4-Amino-1-((2S,3S)-4-bromo-5-chloro-6-fluoro-3methyl-2-phenyl-2,3-dihydrobenzofuran-2-yl)butan-1-d (C-XL-a)

To magnesium (1.12 g, 46.0 mmol) in Et$_2$O (20 mL) at RT was added 3 mL of a solution of 1-(3-bromopropyl)-2,2,5,5-tetramethyl-1,2,5-azadisilolidine (C-XXXIV-a) (9.28 g, 33.1 mmol) in Et$_2$O (40 mL). Iodine (0.233 g, 0.920 mmol) was added and the reaction mixture was stirred at 45° C. The rest of the 1-(3-bromopropyl)-2,2,5,5-tetramethyl-1,2,5-azadisilolidine solution was added dropwise at reflux. After 1.5 h at reflux, the Grignard solution was allowed to cool to RT and added dropwise at 000 to a stirred solution of (2S,3S)-4-bromo-5-chloro-6-fluoro-3-methyl-2-phenyl-2,3-dihydrobenzofuran-2-carbaldehyde (C-XXXIII-a) (8 g, 18.40 mmol) in THF (40 mL). The reaction mixture was quenched with a sat NH$_4$Cl solution. The mixture was extracted twice with EtOAc. The combined organic extracts were washed with brine, dried over anhydrous Na$_2$SO$_4$ and concentrated. The crude material was purified by flash chromatography (silica, DCM/(7N ammonia in MeOH), gradient 0% to 15% (7N ammonia in MeOH)) to afford the title compound as a diastereomeric mixture (3.2 g) as a colorless foam. UPLC-MS 1: m/z 428.1/430.1 [M+H]$^+$, t$_R$=0.91 min and 0.93 min.

Step 2: Tert-butyl (4-((2S,3S)-4-bromo-5-chloro-6-fluoro-3-methyl-2-phenyl-2,3-dihydrobenzofuran-2-yl)-4-hydroxybutyl)carbamate (C-XL-b)

To a stirred solution of 4-amino-1-((2S,3S)-4-bromo-5-chloro-6-fluoro-3-methyl-2-phenyl-2,3-dihydrobenzofuran-2-yl)butan-1-ol (C-XL-a) (3.23 g, 7.35 mmol) in DCM (30 mL) were successively added TEA (3.07 mL, 22.1 mmol) and Boc-anhydride (2.56 mL, 11.03 mmol) at RT. The reaction mixture were stirred at RT for 15 min. The crude mixture was diluted in DCM and water and was extracted with DCM. The combined organic extracts were washed with water and brine, dried over anhydrous Na$_2$SO$_4$ and concentrated. The crude product was purified by flash chromatography (silica, EtOAc/Heptane, gradient 0% to 60% EtOAc) to afford the title compound as a diastereomeric mixture (3.9 g) as a colorless foam. UPLC-MS 1: m/z 528.0/530.0 [M+H]$^+$, t$_R$=1.30 min and 1.34 min.

Step 3: Tert-butyl (4-((2S,3S)-4-bromo-5-chloro-6-fluoro-3-methyl-2-phenyl-2,3-dihydrobenzofuran-2-yl)-4-oxobutyl)carbamate (C-XL-c)

At −78° C., to a stirred solution of oxalyl chloride (1.05 mL, 11.8 mmol) in DCM (20 mL) was added DMSO (1.675 mL, 23.60 mmol) in DCM (10 mL). The reaction mixture was stirred for 15 min at −78° C. A solution of tert-butyl (4-((2S,3S)-4-bromo-5-chloro-6-fluoro-3-methyl-2-phenyl-2,3-dihydrobenzofuran-2-yl)-4-hydroxybutyl)carbamate (C-XL-b) (3.9 g, 7.37 mmol) in DCM (20 mL) was then added and the mixture was stirred at −78° C. for 15 min. TEA (5.14 mL, 36.9 mmol) was added and the reaction mixture was allowed to warm to RT over 1 h. The crude material was purified by flash chromatography (silica, EtOAc/Heptane, gradient 0% to 40% EtOAc) to afford the title compound (1.88 g) as a colorless foam. UPLC-MS 1: m/z 524.2/526.1 [M−H]$^-$, $t_R$=1.46 min.

Step 4: 2-((2S,3S)-4-Bromo-5-chloro-6-fluoro-3-methyl-2-phenyl-2,3-dihydrobenzofuran-2-yl)pyrrolidine (C-XL-d)

At 0° C., tert-butyl (4-((2S,3S)-4-bromo-5-chloro-6-fluoro-3-methyl-2-phenyl-2,3-dihydrobenzofuran-2-yl)-4-oxobutyl)carbamate (C-XL-c) (1.87 g, 2.63 mmol) was treated with HCl (12 mL, 48.0 mmol, 4 M in dioxane). The reaction mixture was stirred at RT for 1 h. After removal of the solvent, the residue was taken up in MeOH (8 mL) then sodium triacetoxyborohydride (1.67 g, 7.88 mmol) was added at RT and the mixture was stirred for 1 h. A white suspension was obtained. THF (8 mL) was added followed by sodium borohydride (1.49 g, 39.4 mmol). The reaction was quenched with acetone and water. The crude mixture was extracted twice with DCM. The combined organic extracts were washed with water and brine, dried over anhydrous $Na_2SO_4$ and concentrated. The crude product was purified by flash chromatography (silica, DCM/(7 N ammonia in MeOH), gradient 0% to 5% (7 N ammonia in MeOH)) to afford the title compound (873 mg) as a colorless foam. UPLC-MS 1: m/z 410.0/412.0 [M+H]$^+$, $t_R$=0.93 min.

Step 5: Tert-butyl 2-((2S,3S)-4-bromo-5-chloro-6-fluoro-3-methyl-2-phenyl-2,3-dihydrobenzofuran-2-yl)pyrrolidine-1-carboxylate (C-XL-e)

At RT, to a stirred solution of 2-((2S,3S)-4-bromo-5-chloro-6-fluoro-3-methyl-2-phenyl-2,3-dihydrobenzofuran-2-yl)pyrrolidine (C-XL-d) (875 mg, 1.96 mmol) in DCM (15 mL) was added TEA (0.82 mL, 5.87 mmol) followed by Boc-anhydride (0.681 mL, 2.93 mmol). The reaction mixture was stirred at RT for 16 h. Water was added and the mixture was extracted with DCM. The combined organic extracts were washed with water and brine, dried over anhydrous $Na_2SO_4$ and concentrated. The crude product was purified by flash chromatography (silica, EtOAc/Hep, gradient 0% to 20% EtOAc) to afford the title compound (1.05 g) as a colorless foam. $^1$H NMR (600 MHz, DMSO-d$_6$) δ (ppm) 7.39 (d, J=7.5 Hz, 2H), 7.34-7.14 (m, 4H), 4.63 (t, J=5.9 Hz, 1H), 3.77 (s, 1H), 3.43-3.18 (m, 2H), 2.34-1.92 (m, 3H), 1.69-1.51 (m, 4H), 1.41-1.14 (m, 9H). UPLC-MS 1: m/z 510.2/512.2 [M+H]$^+$, $t_R$=1.65 min.

Step 6: Tert-butyl 2-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)pyrrolidine-1-carboxylate (C-XL)

To a stirred mixture of tert-butyl 2-((2S,3S)-4-bromo-5-chloro-6-fluoro-3-methyl-2-phenyl-2,3-dihydrobenzofuran-2-yl)pyrrolidine-1-carboxylate (C-XL-e) (1 g, 1.76 mmol), bis(pinacolato)diboron (0.671 g, 2.64 mmol) and potassium hydroxide (0.247 g, 4.40 mmol) in toluene (12 mL) was added $PdCl_2$(dppf)·$CH_2Cl_2$ adduct (0.144 g, 0.176 mmol) at 60° C. The mixture was stirred at 100° C. for 15 min. The reaction mixture was filtered over Hyflo and concentrated. The crude product was purified by flash chromatography (silica, heptane/EtOAc, gradient 0% to 20% EtOAc) to give the title compound (1.2 g) as a colorless foam. $^1$H NMR (600 MHz, DMSO-d$_6$) δ (ppm) 7.43-7.11 (m, 6H), 4.59 (t, J=5.7 Hz, 1H), 3.90-3.77 (m, 1H), 2.11-1.95 (m, 2H), 1.69-1.57 (m, 4H), 1.50 (d, J=6.9 Hz, 3H), 1.35-1.24 (m, 21H). UPLC-MS 2: m/z 558.2 [M+H]$^+$, $t_R$=8.99 min; absolute configuration at C-2 position of pyrrolidine unassigned.

Synthesis of tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)piperidine-1-carboxylate (C-XLI)

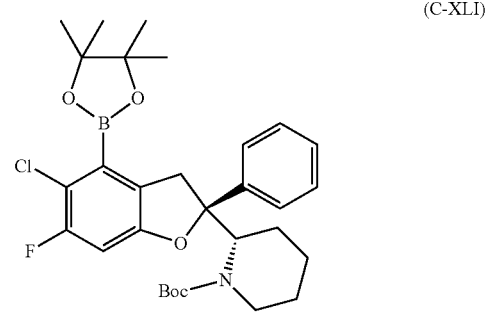 [SMILES: CC(C)(C)OC(=O)N1CCCC[C@H]1[C@@]1(c2ccccc2)Cc2c(cc(F)c(Cl)c2B2OC(C)(C)C(C)(C)O2)O1]

(C-XLI)

Reaction Scheme C-XLI:

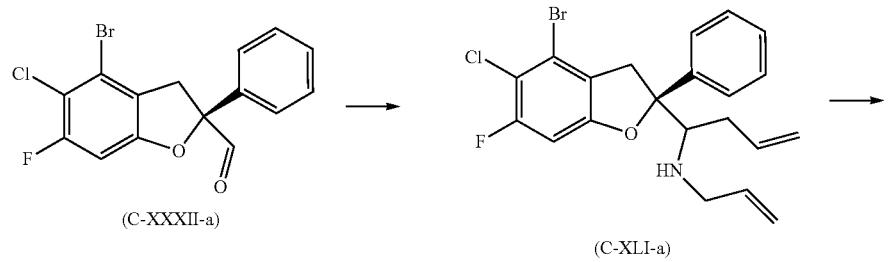

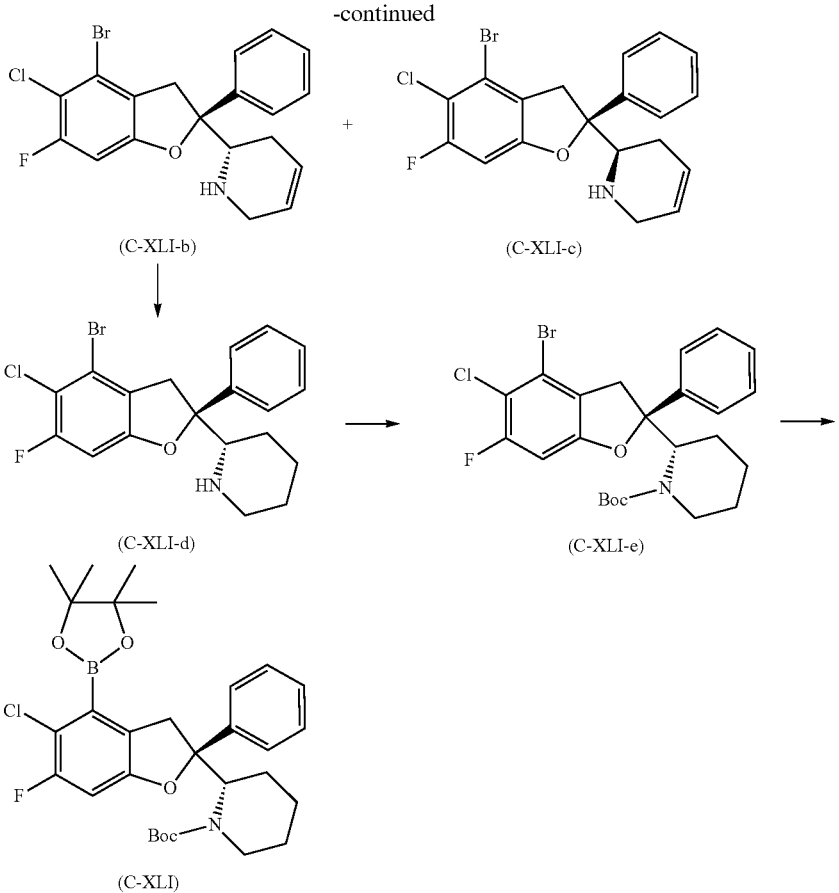

Step 1: N-Allyl-1-((S)-4-bromo-5-chloro-6-fluoro-2-phenyl-2,3-dihydrobenzofuran-2-yl)but-3-en-1-amine (C-XLI-a)

Under Ar, allylamine (9.2 mL, 122 mmol) and AcOH (1.401 mL, 24.47 mmol) were added to a stirred solution of ((S)-4-bromo-5-chloro-6-fluoro-2-phenyl-2,3-dihydrobenzofuran-2-carbaldehyde (C-XXXII-a) (8.7 g, 24.5 mmol) in DCM (75 mL). The reaction mixture was stirred for 3 h, then concentrated and diluted in THF (75 mL). Allyl magnesium bromide in Et$_2$O (36.7 mL, 36.7 mmol) was then added at 0° C. and the RM was stirred for 1 h. The mixture was then quenched by adding a sat solution of NaHCO$_3$ and extracted with DCM. The combined organic layers were washed with a sat solution of NaHCO$_3$, dried over anhydrous Na$_2$SO$_4$ and concentrated. The crude product was purified by flash chromatography (silica, cyclohexane/EtOAc; gradient 0% to 20% EtOAc) to give the title compound (9.1 g) as a diastereomeric mixture. UPLC-MS 1: m/z 436.4/438.4 [M+H]$^+$, $t_R$=1.53/1.56 min.

Step 2: (S)-2-((S)-4-Bromo-5-chloro-6-fluoro-2-phenyl-2,3-dihydrobenzofuran-2-yl)-1,2,3,6-tetrahydropyridine (C-XLI-b) and (R)-2-((S)-4-bromo-5-chloro-6-fluoro-2-phenyl-2,3-dihydrobenzofuran-2-yl)-1,2,3,6-tetrahydropyridine (C-XLI-c)

At RT, under Ar, 2$^{nd}$ generation Grubbs catalyst benzyliden(1,3-bis(2,4,6-trimethylphenyl)-2-imidazolidinyliden)dichloro(tricyclohexylphosphin)ruthenium (0.194 g, 0.229 mmol) was added to a stirred solution of N-allyl-1-((S)-4-bromo-5-chloro-6-fluoro-2-phenyl-2,3-dihydrobenzofuran-2-yl)but-3-en-1-amine (C-XLI-a) (5 g, 11.45 mmol) in toluene (40 mL). The reaction mixture was stirred at 80° C. for 1 h, then was quenched by adding a sat solution of NaHCO$_3$ (100 mL) and extracted twice with EtOAc (2×100 mL). The combined organic layers were washed with a sat solution of NaHCO$_3$ (100 mL), dried over anhydrous Na$_2$SO$_4$ and concentrated. The crude product was purified by flash chromatography (silica, cyclohexane/EtOAc; gradient 0% to 25% EtOAc) to give the title compounds as separate diastereoisomers:

(S)-2-((S)-4-Bromo-5-chloro-6-fluoro-2-phenyl-2,3-dihydrobenzofuran-2-yl)-1,2,3,6-tetrahydropyridine (C-XLI-b) (2.45 g) $^1$H-NMR (400 MHz, DMSO-d$_6$) δ 7.56-7.48 (m, 2H), 7.45-7.27 (m, 3H), 7.12 (d, J=9.5 Hz, 1H), 5.72-5.58 (m, 2H), 3.85 (dd, J=16.4, 1.9 Hz, 1H), 3.42 (dd, J=16.4, 1.5 Hz, 1H), 3.28-3.22 (m, 2H), 3.10 (dd, J=10.5, 3.8 Hz, 1H), 2.03-1.91 (m, 1H), 1.91-1.77 (m, 1H), 1.75-1.61 (m, 1H). UPLC-MS 1: m/z 410.2/412.3 [M+H]$^+$, $t_R$=0.91 min.

(R)-2-((S)-4-Bromo-5-chloro-6-fluoro-2-phenyl-2,3-dihydrobenzofuran-2-yl)-1,2,3,6-tetrahydropyridine (C-XLI-c) (1.15 g) $^1$H-NMR (400 MHz, DMSO-d$_6$) δ 7.49-7.44 (m, 2H), 7.43-7.36 (m, 2H), 7.34-7.27 (m, 1H), 7.17 (d, J=9.6 Hz, 1H), 5.75-5.59 (m, 2H), 4.15 (dd, J=15.9, 2.0 Hz, 1H), 3.31-3.25 (m, 2H), 3.17-3.10 (m, 2H), 1.98-1.83 (m, 1H), 1.63-1.52 (m, 1H), 1.39-1.28 (m, 1H). UPLC-MS 1: m/z 410.3/412.3 [M+H]$^+$, $t_R$=0.95 min.

Step 3: (S)-2-((S)-4-Bromo-5-chloro-6-fluoro-2-phenyl-2,3-dihydrobenzofuran-2-yl)piperidine (C-XLI-d)

At RT, a solution of (S)-2-((S)-4-bromo-5-chloro-6-fluoro-2-phenyl-2,3-dihydrobenzofuran-2-yl)-1,2,3,6-tetrahydropyridine (C-XLI-b) (2.45 g, 5.99 mmol) in THF (50 mL) and MeOH (50 mL) was treated with Raney-Ni (500 mg) and hydrogenated at 0.1 bar overpressure in a shaked flask for 20 h. The reaction mixture was filtered and concentrated. The crude product was purified by flash chromatography (silica, cyclohexane/EtOAc, gradient: 0% to 50% EtOAc) to afford the title compound (2.14 g). UPLC-MS 1: m/z 412.3 [M+H]$^+$, $t_R$=0.95 min.

Step 4: Tert-butyl (S)-2-((S)-4-bromo-5-chloro-6-fluoro-2-phenyl-2,3-dihydrobenzofuran-2-yl)piperidine-1-carboxylate (C-XLI-e)

At RT, Boc-anhydride (1.331 mL, 5.73 mmol) and TEA (1.5 mL, 10.4 mmol) were added to a stirred solution of (S)-2-((S)-4-bromo-5-chloro-6-fluoro-2-phenyl-2,3-dihydrobenzofuran-2-yl)piperidine (C-XLI-d) (2.14 g, 5.21 mmol) in THF (20 mL). The reaction mixture was stirred at RT for 5 d. A sat solution of NaHCO$_3$ (75 mL) was then added and the mixture was extracted twice with EtOAc (2×100 ML). The combined organic extracts were washed with water and brine, dried over anhydrous Na$_2$SO$_4$ and concentrated. The crude product was purified by flash chromatography (silica, cyclohexane/EtOAc, gradient: 0% to 10% EtOAc) to afford the title product (2.14 g). UPLC-MS 1: m/z 454.3/456.3 [M−tertButyl+H]$^+$, $t_R$=1.64 min.

Step 5: Tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)piperidine-1-carboxylate (C-XLI)

A deoxygenated suspension of tert-butyl (S)-2-((S)-4-bromo-5-chloro-6-fluoro-2-phenyl-2,3-dihydrobenzofuran-2-yl)piperidine-1-carboxylate (C-XLI-e) (2.14 g, 4.19 mmol), bis(pinacolato)diboron (1.6 g, 6.3 mmol), KOAc (1.3 g, 12.6 mmol) and PdCl$_2$(dppf)·CH$_2$Cl$_2$ adduct (0.345 g, 0.420 mmol) in toluene (25 mL) was stirred at 100° C. for 16 h under an Ar atmosphere. The reaction mixture was filtered over Celite and concentrated under reduced pressure. The residue was purified by flash chromatography (silica, hexane/EtOAc; gradient: 0 to 10%) to afford the title product (1.94 g) as a colorless solid. UPLC-MS 1: m/z 558.6 [M+H]$^+$, $t_R$=1.65 min.

Synthesis of tert-butyl 3-((S)-5-chloro-6-fluoro-2-phenyl-4-(4,4,5,5-tetramethyl-1,3,2-dioxaborolan-2-yl)-2,3-dihydrobenzfuran-2-yl)morpholine-4-carboxylate (C-XLII)

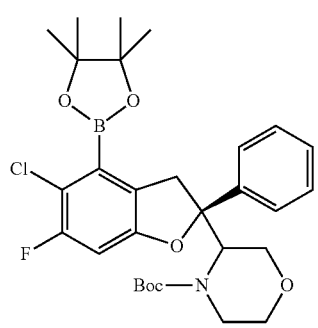

(C-XLII)

Reaction Scheme C-XLII:

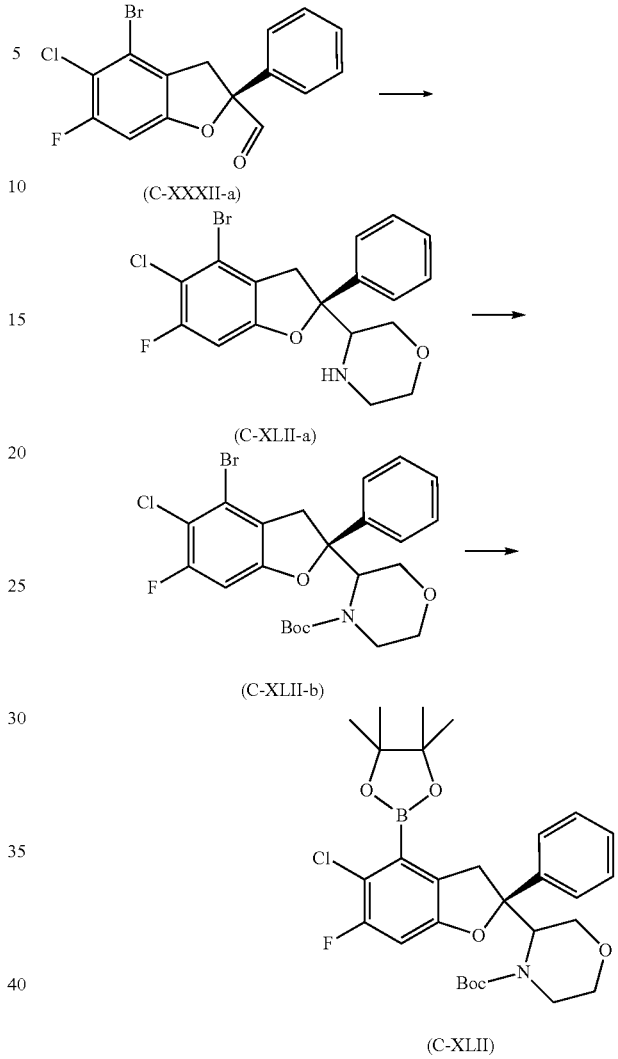

Step 1: 3-((S)-4-Bromo-5-chloro-6-fluoro-2-phenyl-2,3-dihydrobenzofuran-2-yl)morpholine (C-XLII-a)

Under Ar, (S)-4-bromo-5-chloro-6-fluoro-2-phenyl-2,3-dihydrobenzofuran-2-carbaldehyde (C-XXXII-a) (2.5 g, 6.97 mmol) and molecular sieves 4A powder (ca. 100 mg/mmol) were added to a stirred solution the SnAP M Reagent (2.5 g, 6.97 mmol) in DCM (20 mL). The reaction mixture was stirred at RT for 16 h and filtered through Celite to remove the molecular sieves. The filtrate was concentrated under reduced pressure to afford the pure imine. In a separated flask, anhydrous Cu(OTf)$_2$ (2.5 g, 6.97 mmol) was suspended in HFIP (10 mL). 2,6-Lutidine (0.81 mL, 6.97 mmol) was added and the resulting suspension was stirred at RT for 1 h. The solution of the imine dissolved in DCM/HFIP (20 mL, 1:1) was added in one portion and the resulting mixture was stirred at RT for 16 h. A sat solution of NaHCO$_3$ (100 mL) was added and the mixture was extracted twice with DCM (2×75 mL). The combined organic extracts were washed with sat NaHCO$_3$ (50 mL) and brine, dried over anhydrous Na$_2$SO$_4$ and concentrated. The crude product was purified by flash chromatography (silica, cyclohexane/EtOAc, gradient: 0% to 100% EtOAc) to afford the title product (1.34 g) as a diastereomeric mixture. UPLC-MS 1: m/z 412.1/414.1 [M+H]$^+$, $t_R$=0.92 and 0.95 min.

Step 2: Tert-butyl 3-((S)-4-bromo-5-chloro-6-fluoro-2-phenyl-2,3-dihydrobenzofuran-2-yl)morpholine-4-carboxylate (C-XLII-b)

At RT, Boc-anhydride (0.95 mL, 3.96 mmol) and TEA (0.7 mL, 4.95 mmol) were added to a stirred solution of 3-((S)-4-bromo-5-chloro-6-fluoro-2-phenyl-2,3-dihydrobenzofuran-2-yl)morpholine (C-XLII-a) (1.4 g, 3.30 mmol) in DCM (15 mL). The reaction mixture was stirred at RT for 1 h. A sat solution of NaHCO$_3$ (75 mL) was added and the mixture was extracted twice with EtOAc (2×75 mL). The combined organic extracts were washed with sat NaHCO$_3$ (75 mL) and brine, dried over anhydrous Na$_2$SO$_4$ and concentrated. The crude product was purified by flash chromatography (silica, cyclohexane/EtOAc, gradient: 0% to 50% EtOAc) to afford the desired product (1.7 g) as a diastereomeric mixture. UPLC-MS 1: m/z 556.1/558.1 [M+formate]$^-$, $t_R$=1.51 and 1.52 min.

Step 3: Tert-butyl 3-((S)-5-chloro-6-fluoro-2-phenyl-4-(4,4,5,5-tetramethyl-1,3,2-dioxaborolan-2-yl)-2,3-dihydrobenzofuran-2-yl)morpholine-4-carboxylate (C-XLII)

A deoxygenated suspension of tert-butyl 3-((S)-4-bromo-5-chloro-6-fluoro-2-phenyl-2,3-dihydrobenzofuran-2-yl)morpholine-4-carboxylate (C-XLII-b) (995 mg, 1.94 mmol), bis(pinacolato)diboron (739 mg, 2.91 mmol), KOtBu (305 mg, 2.72 mmol) and PdCl$_2$(dppf)·CH$_2$Cl$_2$ adduct (158 mg, 0.194 mmol) in toluene (10 mL) was stirred at 100° C. for 16 h under an Ar atmosphere. The reaction mixture was filtered over Celite and concentrated under reduced pressure. The residue was purified by flash chromatography (silica, hexane/EtOAc; gradient: 0 to 40%) to afford the title product (890 mg) as a diastereomeric mixture. UPLC-MS 1: m/z 560.4/562.4 [M+H]$^+$, $t_R$=1.54 and 1.55 min.

Synthesis of tert-butyl (1-((S)-5-chloro-2-phenyl-4-(4,4,5,5-tetramethyl-1,3,2-dioxaborolan-2-yl)-2,3-dihydrobenzofuran-2-yl)ethyl)carbamate (C-XLIII)

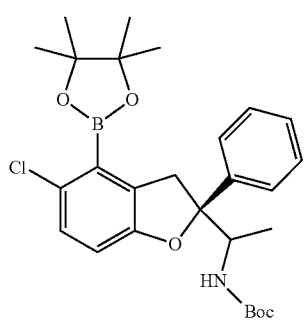

(C-XLIII)

Reaction Scheme C-XLIII:

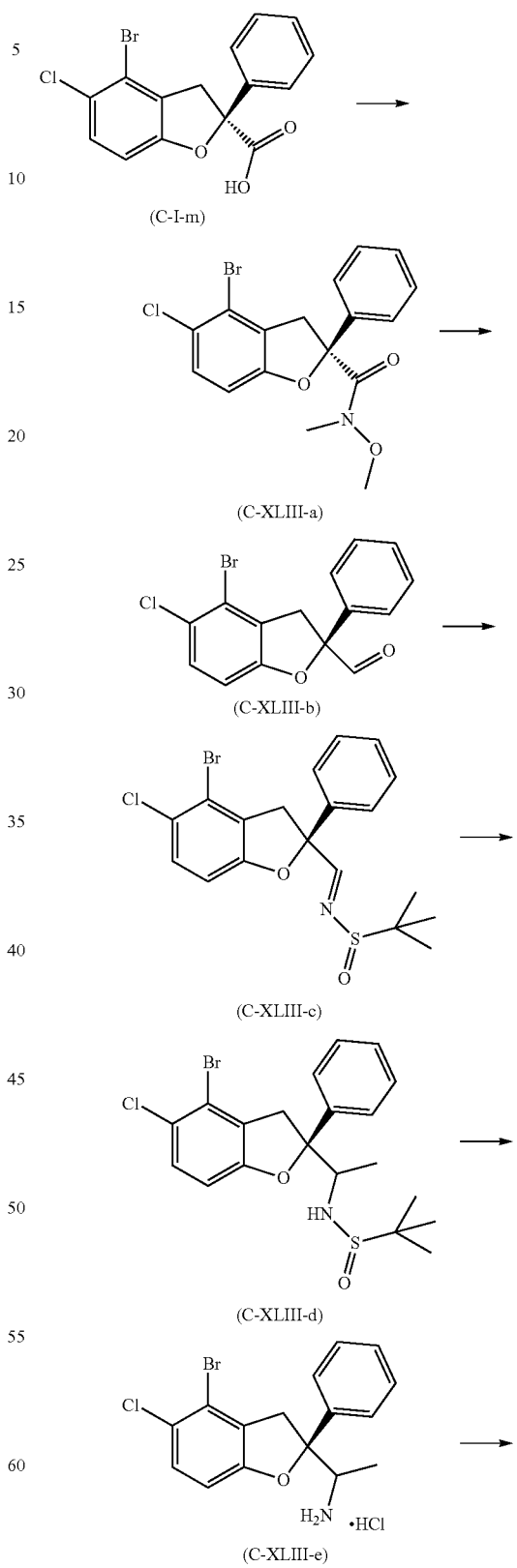

-continued

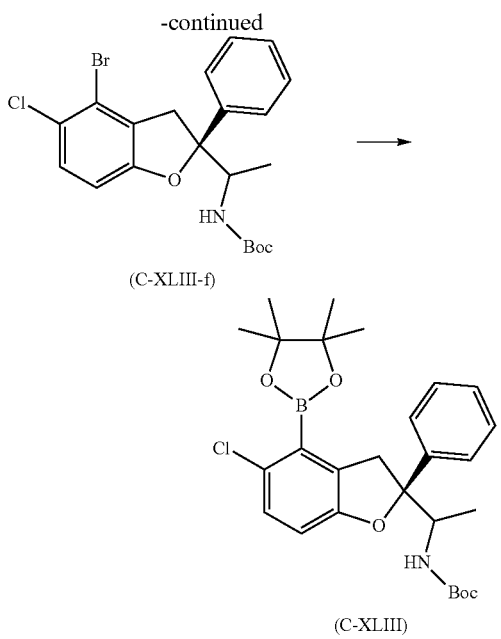

Step 1: (S)-4-Bromo-5-chloro-N-methoxy-N-methyl-2-phenyl-2,3-dihydrobenzofuran-2-carboxamide (C-XLIII-a)

At RT to a solution of (S)-4-bromo-5-chloro-2-phenyl-2,3-dihydrobenzofuran-2-carboxylic acid (C-I-m) (2.0 g, 5.66 mmol) in dioxan (100 mL) were successively added DIPEA (4 mL, 22.7 mmol), HATU (2.58 g, 6.79 mmol) and DMAP (0.035 g, 0.283 mmol). Then N,O-dimethylhydroxylamine (0.662 g, 6.79 mmol) was added and the RM was stirred at RT for 1.5 h. 1 N HCl and water were added. The layers were separated. The organic layer was washed with 1 N NaOH then brine, dried over anhydrous $Na_2SO_4$, filtered and concentrated. The crude material was purified by flash chromatography (silica, cyclohexane 0 EtOAc) to give the title compound (1.7 g) as a light beige solid. UPLC-MS 1: m/z 396.1/398.1 [M+H]$^+$, $t_R$=1.34 min. $^1$H NMR (400 MHz, DMSO-$d_6$) δ (ppm) 7.50-7.25 (m, 6H), 7.02 (d, J=8.5 Hz, 1H), 4.24 (d, J=17.0 Hz, 1H), 3.38 (d, J=16.9 Hz, 1H), 3.27 (d, J=13.6 Hz, 3H), 3.08 (s, 3H), 1.38 (s, 1 H Step 2: (S)-4-Bromo-5-chloro-2-phenyl-2,3-dihydrobenzofuran-2-carbaldehyde (C-XLIII-b)

At −78° C., to a solution of (S)-4-bromo-5-chloro-N-methoxy-N-methyl-2-phenyl-2,3-dihydrobenzofuran-2-carboxamide (C-XLIII-a) (2.5 g, 6.30 mmol) in DCM (300 ml) was added dropwise DIBAL-H (20 mL, 19 mmol, 1 M in THF). The reaction mixture was stirred at −78° C. for 5 h before it was quenched with MeOH. The mixture was acified with 1 N HCl and extracted twice with DCM. The combined organic extracts were washed with water and brine, dried over anhydrous $Na_2SO_4$ and concentrated. The crude product was purified by flash chromatography (silica, cyclohexane/EtOAc, gradient 0% to 10% EtOAc) to afford the title compound (1.4 g). UPLC-MS 1: no ionization, $t_R$=1.22 min.

Step 3: N-((E)-((S)-4-Bromo-5-chloro-2-phenyl-2,3-dihydrobenzofuran-2-yl)methylene)-2-methylpropane-2-sulfinamide (C-XLIII-c)

The title compound (2.16 g) was obtained from (S)-4-bromo-5-chloro-2-phenyl-2,3-dihydrobenzofuran-2-carbaldehyde (C-XLIII-b) (1.4 g, 4.15 mmol) as a crude product which was used directly in the next step without further purification, using similar reaction conditions as described for intermediate C-XXXII step 2. UPLC-MS 1: m/z 440.1/442.1 [M+H]$^+$, $t_R$=1.44/1.45 min.

Step 4: N-(1-((S)-4-Bromo-5-chloro-2-phenyl-2,3-dihydrobenzofuran-2-yl)ethyl)-2-methylpropane-2-sulfinamide (C-XLIII-d)

At 0° C. MeMgBr (3.3 mL, 9.80 mmol, 3 M in $Et_2O$) was added dropwise to a solution of N-((E)-((S)-4-bromo-5-chloro-2-phenyl-2,3-dihydrobenzofuran-2-yl)methylene)-2-methylpropane-2-sulfinamide (C-XLIII-c) (1.08 g, 2.45 mmol) in DCM (12 mL). The reaction mixture was stirred for 1 h at RT, then quenched with sat solution of $NH_4Cl$. 1 N HCl was added to adjust the pH to ca 7. The mixture was extracted twice with DCM. The combined organic extracts were washed with water and brine, dried over anhydrous $Na_2SO_4$ and concentrated. The crude product was purified by flash chromatography (silica, cyclohexane/EtOAc, gradient 0% to 20% EtOAc) to afford the title compound as a diastereomeric mixture (375 mg) as a colorless foam. UPLC-MS 1: m/z 456.1/458.1 [M+H]$^+$, $t_R$=1.36/138 min.

Step 5: 1-((S)-4-Bromo-5-chloro-2-phenyl-2,3-dihydrobenzofuran-2-yl)ethan-1-amine hydrochloride salt (C-XLIII-e)

At RT, a suspension of N-(1-((S)-4-bromo-5-chloro-2-phenyl-2,3-dihydrobenzofuran-2-yl)ethyl)-2-methylpropane-2-sulfinamide (C-XLIII-d) (370 mg, 0.761 mmol) in dioxane (7.7 mL) was treated with HCl (0.4 mL, 1.60 mmol, 4 M in dioxane). The reaction mixture was stirred at RT for 15 min, then filtered. The solid was washed with dioxane, then dried under HV to give the title compound as a diastereomeric mixture (240 mg) as a colorless solid. UPLC-MS 1: m/z 352.0/354.0 [M+H]$^+$, $t_R$=0.87 min.

Step 6: Tert-butyl (1-((S)-4-bromo-5-chloro-2-phenyl-2,3-dihydrobenzofuran-2-yl)ethyl)carbamate (C-XLIII-f)

The title compound (290 mg, colorless oil) was obtained as diastereomeric mixture from 1-((S)-4-bromo-5-chloro-2-phenyl-2,3-dihydrobenzofuran-2-yl)ethan-1-amine hydrochloride salt (C-XLIII-e) (240 mg, 0.617 mmol) using similar reaction conditions as described for intermediate C-XXXIII, step 7. UPLC-MS 1: m/z 352.1/354.1 [M−BOC]$^+$, $t_R$=1.49/1.50 min.

Step 7: Tert-butyl (1-((S)-5-chloro-2-phenyl-4-(4,4,5,5-tetramethyl-1,3,2-dioxaborolan-2-yl)-2,3-dihydrobenzofuran-2-yl)ethyl)carbamate (C-XLIII)

The title compound (190 mg, colorless foam) was obtained as diastereomeric mixture from tert-butyl (1-((S)-4-bromo-5-chloro-2-phenyl-2,3-dihydrobenzofuran-2-yl)ethyl)carbamate (C-XLIII-f) (240 mg, 0.617 mmol) using similar reaction conditions as described for intermediate C-XXXIII, step 8. UPLC-MS 1: m/z 500.4 [M+H]$^+$, $t_R$=1.54 min.

Synthesis of tert-butyl (1-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)ethyl)carbamate (C-XLIV)

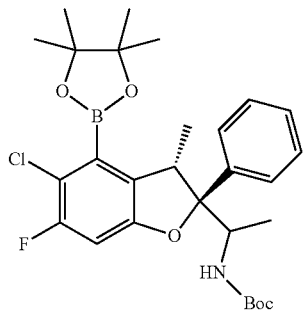

(C-XLIV)

Reaction Scheme C-XLIV:

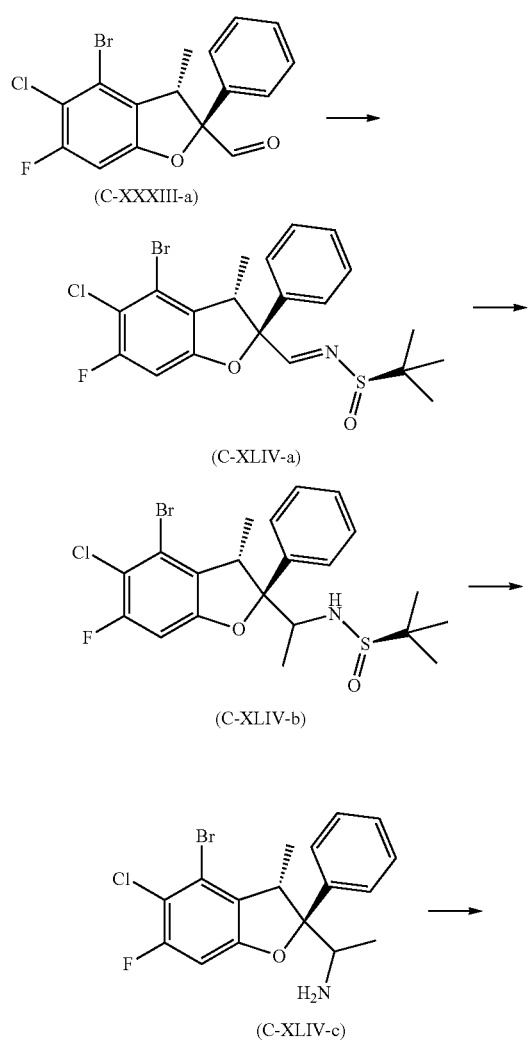

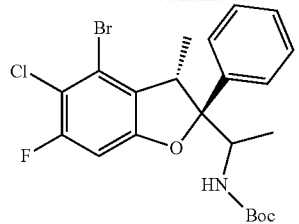

(C-XLIV-d)

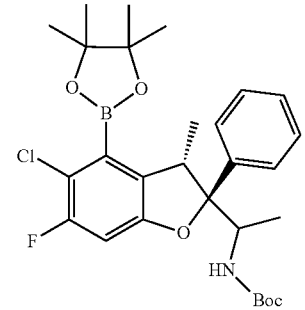

(C-XLIV)

Step 1: (R)—N-((E)-((2S,3S)-4-Bromo-5-chloro-6-fluoro-3-methyl-2-phenyl-2,3-dihydrobenzofuran-2-yl)methylene)-2-methylpropane-2-sulfinamide (C-XLIV-a)

The title compound (1.51 g, white solid) was obtained from (2S,3S)-4-bromo-5-chloro-6-fluoro-3-methyl-2-phenyl-2,3-dihydrobenzofuran-2-carbaldehyde (C-XXXIII-a) (2.49 g, 6.74 mmol) and (R)-2-methyl-2-propanesulfinamide (0.98 g, 8.1 mmol) using similar reaction conditions as described for intermediate C-XXXII, step 2. UPLC-MS 1: m/z 472.1/474.1 [M+H]$^+$, $t_R$=1.47/1.49 min.

Step 2: (R)—N-(1-((2S,3S)-4-Bromo-5-chloro-6-fluoro-3-methyl-2-phenyl-2,3-dihydrobenzofuran-2-yl)ethyl)-2-methylpropane-2-sulfinamide (C-XLIV-b)

At 0° C., MeMgBr (4.26 mL, 12.77 mmol, 3 M in Et$_2$O) was added under Ar to a stirred solution of (R)—N—((E)-((2S,3S)-4-bromo-5-chloro-6-fluoro-3-methyl-2-phenyl-2,3-dihydrobenzofuran-2-yl)methylene)-2-methylpropane-2-sulfinamide (C-XLIV-a) (1.51 g, 3.19 mmol) in DCM (20 mL). The reaction mixture was stirred at RT for 1 h. For workup a sat solution of NH$_4$Cl was added and the mixture was extracted twice with EtOAc. The combined organic extracts were washed with a sat solution of NH$_4$Cl, dried over anhydrous Na$_2$SO$_4$ and concentrated. The crude product was purified by flash chromatography (silica, hexane/EtOAc, gradient: 0% to 75% EtOAc) to afford the desired product as a single diastereomer (1.05 g). UPLC-MS 1: m/z 488.1 [M+H]$^+$, $t_R$=1.44 min.

Step 3: 1-((2S,3S)-4-Bromo-5-chloro-6-fluoro-3-methyl-2-phenyl-2,3-dihydrobenzofuran-2-yl)ethan-1-amine (C-XLIV-c)

At RT, HCl ((2.15 mL, 8.6 mmol), 4 M in dioxane) was added to a solution of (R)—N-(1-((2S,3S)-4-bromo-5-chloro-6-fluoro-3-methyl-2-phenyl-2,3-dihydrobenzofuran-2-yl)ethyl)-2-methylpropane-2-sulfinamide (C-XLIV-b)

(1.05 g, 2.15 mmol) in dioxane (10 mL) and the reaction mixture was stirred for 1 h. For workup a sat solution of NaHCO$_3$ was added and the mixture was extracted with EtOAc. The combined organic extracts were washed with water and brine, dried over anhydrous Na$_2$SO$_4$ and concentrated. The crude product was purified by flash chromatography (silica, hexane/EtOAc, gradient: 0% to 90% EtOAc) to afford the desired product (550 mg). UPLC-MS 1: m/z 384.1/386.1 [M+H]$^+$, $t_R$=0.87 min.

Step 4: Tert-butyl (1-((2S,3S)-4-bromo-5-chloro-6-fluoro-3-methyl-2-phenyl-2,3-dihydrobenzofuran-2-yl)ethyl)carbamate (C-XLIV-d)

Under Ar Boc-anhydride (343 mg, 1.57 mmol) and TEA (0.40 mL, 2.86 mmol) were added to a solution of 1-((2S,3S)-4-Bromo-5-chloro-6-fluoro-3-methyl-2-phenyl-2,3-dihydrobenzofuran-2-yl)ethan-1-amine (C-XLIV-c) (550 mg, 1.43 mmol) in THF (10 mL). After 3 h the reaction mixture was quenched by addition of a sat solution of NaHCO$_3$ (75 mL) and extracted twice with EtOAc. The combined organic layers were washed with a sat solution of NaHCO$_3$, dried over anhydrous Na$_2$SO$_4$ and concentrated. Purification of the crude product by flash chromatography (silica, hexane/EtOAc, gradient: 0% to 10% EtOAc) gave the title product (638 mg) as a colorless solid. UPLC-MS 1: m/z 528.1/530.1 [M+formate]$^-$, $t_R$=1.57 min.

Step 4: Tert-butyl (1-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)ethyl)carbamate (C-XLIV)

The title compound (550 mg, colorless powder) was obtained from tert-butyl (1-((2S,3S)-4-bromo-5-chloro-6-fluoro-3-methyl-2-phenyl-2,3-dihydrobenzofuran-2-yl)ethyl)carbamate (C-XLIV-d) (638 mg, 1.32 mmol), using similar reaction conditions as described for for intermediate C-XXXIII, step 8. UPLC-MS 1: m/z 576.3 [M+formate]$^-$, $t_R$=1.57 min; absolute configuration at C-1 position of ethyl carbamate unassigned.

Synthesis of tert-butyl (S)-2-((S)-1-(tert-butoxycarbonyl)pyrrolidin-2-yl)-5-chloro-6-fluoro-2-phenyl-4-(4,4,5,5-tetramethyl-1,3,2-dioxaborolan-2-yl)indoline-1-carboxylate (C-XLV)

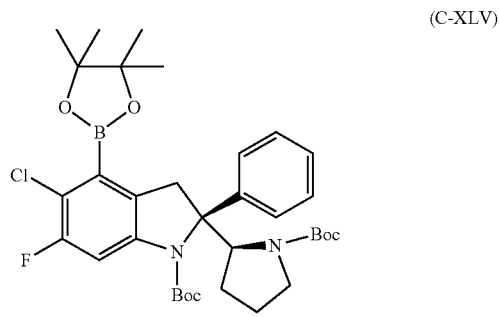 [SMILES: CC(C)(C)OC(=O)N1CCC[C@H]1[C@@]1(c2ccccc2)Cc2c(cc(F)c(Cl)c2B2OC(C)(C)C(C)(C)O2)N1C(=O)OC(C)(C)C]

(C-XLV)

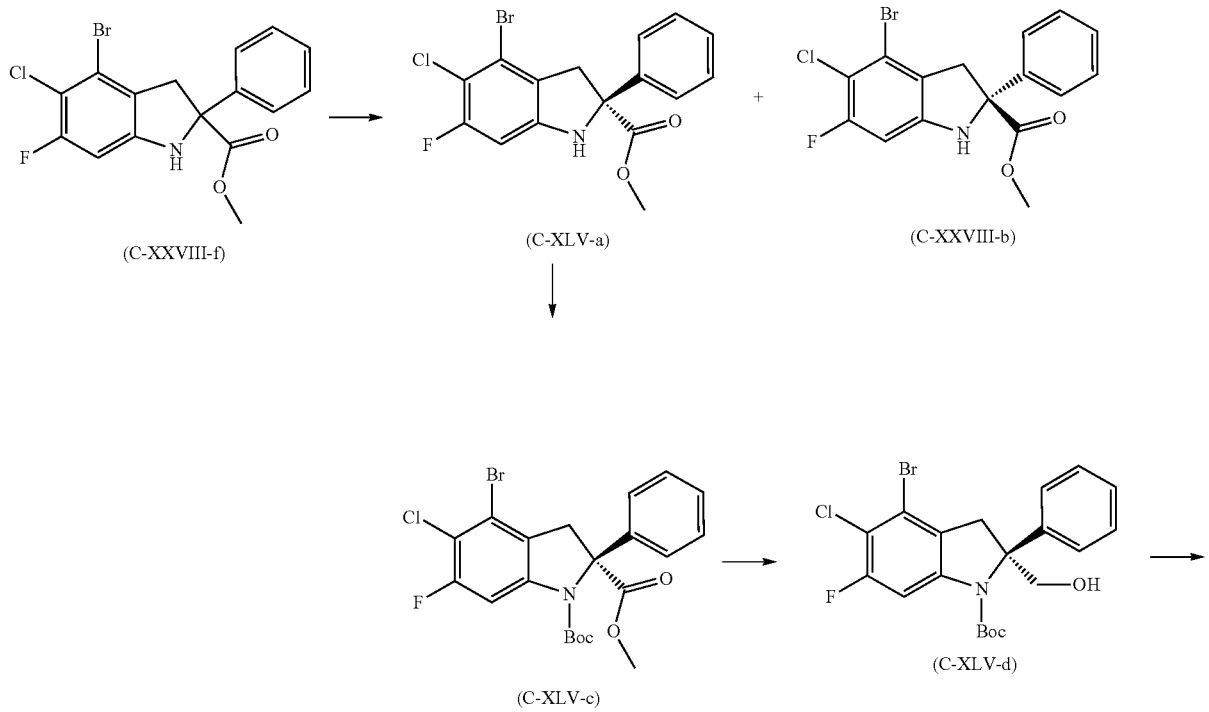

Reaction Scheme XLV:

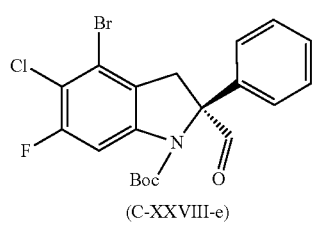
(C-XXVIII-e)

-continued

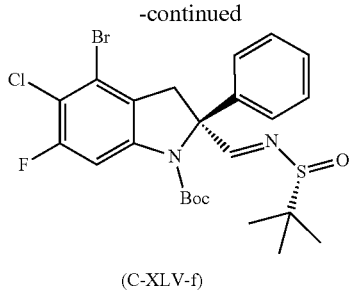
(C-XLV-f)

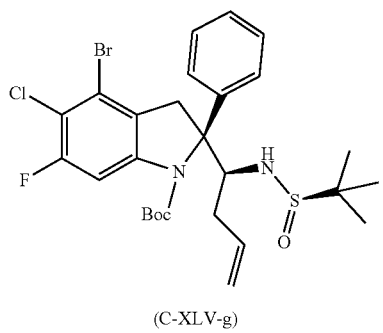
(C-XLV-g)

+

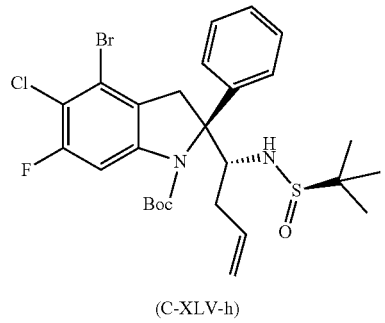
(C-XLV-h)

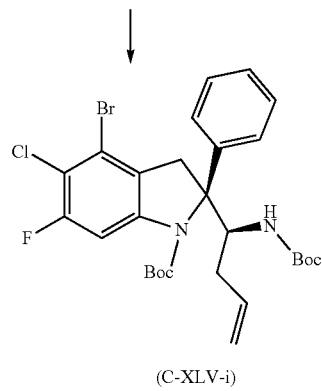
(C-XLV-i)

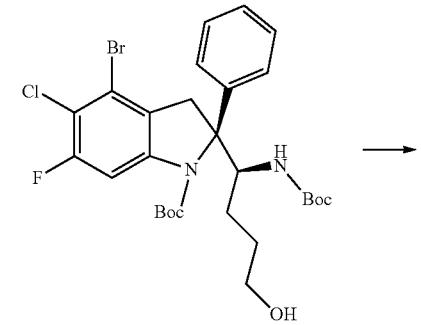
(C-XLV-j)

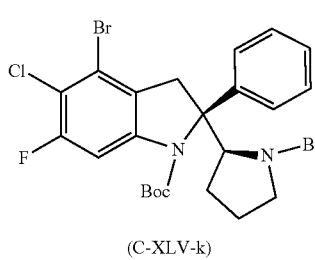
(C-XLV-k)

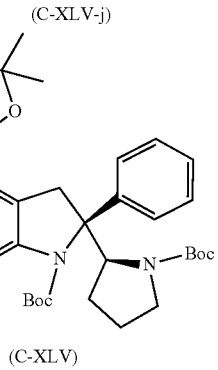
(C-XLV)

Step 1: Methyl (S)-4-bromo-5-chloro-6-fluoro-2-phenylindoline-2-carboxylate (C-XLV-a) and methyl (R)-4-bromo-5-chloro-6-fluoro-2-phenylindoline-2-carboxylate (C-XLV-b)

The racemate methyl-4-bromo-5-chloro-6-fluoro-2-phenylindoline-2-carboxylate (C-XXVIII-f) (37.0 g, 96.2 mmol) was subjected to chiral SFC (Chiralpak AY 300×50 mm I.D., 10 μm, CO$_2$/EtOH (0.1% NH$_3$·H$_2$O) 80:20, flow rate: 200 mL/min, column temperature 38° C.) to afford the two separate enantiomers with >99% e.e., respectively.

Methyl (S)-4-bromo-5-chloro-6-fluoro-2-phenylindoline-2-carboxylate (C-XLV-a) (18.46 g): Chiral HPLC: (Chiralpak AY 150×4.6 mm I.D., 3 μm, heptane/EtOH (0.1% DEA) 90:10, flow rate: 1 mL/min, column temperature 25° C.) t$_R$=3.87 min; UPLC-MS 1: m/z 384.2/386.2 [M+H]$^+$, t$_R$=1.36 min;

Methyl (R)-4-bromo-5-chloro-6-fluoro-2-phenylindoline-2-carboxylate (C-XLV-b) (18.44 g): Chiral HPLC: (Chiralpak AY 150×4.6 mm I.D., 3 μm, heptane/EtOH (0.1%

DEA) 90:10, flow rate: 1 mL/min, column temperature 25° C.) $t_R$=2.73 min; UPLC-MS 1: m/z 384.2/386.2 [M+H]$^+$, $t_R$=1.35 min;

Step 2: 1-(Tert-butyl) 2-methyl (S)-4-bromo-5-chloro-6-fluoro-2-phenylindoline-1,2-dicarboxylate (C-XLV-c)

Under Ar NaH (0.187 g, 7.80 mmol) was added to a stirred solution of methyl (S)-4-bromo-5-chloro-6-fluoro-2-phenylindoline-2-carboxylate (C-XLV-a) (2 g, 5.20 mmol) in DMF (52.0 mL) at 0° C. After 15 min, Boc-anhydride (2.415 mL, 10.40 mmol) was added at 0° C. and stirring at RT was continued for another 18 h. More NaH (0.0935 g, 3.90 mmol) and Boc-anhydride (1.207 mL, 5.20 mmol) were added and stirring was continued at RT for 2 d. For workup water was added followed by extraction with EtOAc. The combined organic extracts were washed with a sat solution of NaHCO$_3$ and dried over anhydrous Na$_2$SO$_4$. Concentration afforded the crude product which was purified by flash chromatography (silica, hexane/EtOAc, gradient: 0% to 8% EtOAc) to give the title compound (2.0 g) as a yellow oil. $^1$H NMR (400 MHz, DMSO-d$_6$) δ (ppm) 7.81 (s, 1H), 7.45-7.28 (m, 5H), 3.92 (d, 1H), 3.78 (s, 3H), 3.33 (d, 1H), 1.37-1.13 (m, 9H). UPLC-MS 3: m/z 384.1 [M−Boc]$^+$, $t_R$=1.45 min.

Step 3: Tert-butyl (S)-4-bromo-5-chloro-6-fluoro-2-(hydroxymethyl)-2-phenylindoline-1-carboxylate (C-XLV-d)

Under Ar LiBH$_4$ (0.189 g, 8.66 mmol) was added portionwise to a stirred solution of 1-(tert-butyl) 2-methyl (S)-4-bromo-5-chloro-6-fluoro-2-phenylindoline-1,2-dicarboxylate (C-XLV-c) (2 g, 2.89 mmol) in THF (28.9 mL) at 0° C. and stirring was continued for 18 h. More LiBH$_4$ (0.189 g, 8.66 mmol) was added portionwise at 0° C. and stirring was continued for 18 h. The reaction mixture was quenched by the addition of MeOH at 0° C. The milky reaction mixture was concentrated. For workup water was added followed by extraction with EtOAc. The combined organic extracts were washed with brine, dried over anhydrous Na$_2$SO$_4$ and concentrated under reduced pressure. The crude product was purified by flash chromatography (silica, hexane/EtOAc; gradient 0% to 16% EtOAc) to give the title product (1.2 g) as a white foam. UPLC-MS 3: no ionization, $t_R$=1.38 min.

Step 4: Tert-butyl (S)-4-bromo-5-chloro-6-fluoro-2-formyl-2-phenylindoline-1-carboxylate (C-XLV-e)

At −78° C. DMSO (0.597 mL, 8.41 mmol) was added to a solution of oxalyl chloride (0.368 mL, 4.20 mmol) in DCM (30.7 mL). After 10 min at −78° C., a solution of tert-butyl (S)-4-bromo-5-chloro-6-fluoro-2-(hydroxymethyl)-2-phenylindoline-1-carboxylate (C-XLV-d) (1.2 g, 2.63 mmol) in DCM (15.36 mL) as well as TEA (1.831 mL, 13.14 mmol) were added and the reaction mixture was stirred at −78° C. for 20 min and at RT for 30 min. The reaction mixture was quenched by the addition of brine, then extracted with DCM. The organic layers were combined and washed with brine, dried over anhydrous Na$_2$SO$_4$ and concentrated to give the title compound (1.1 g) as a yellow foam. $^1$H NMR (400 MHz, DMSO-d$_6$) δ (ppm) 10.02 (s, 1H), 7.86 (s, 1H), 7.50-7.31 (m, 5H), 3.82 (d, J=17.2 Hz, 1H), 3.08 (d, J=17.0 Hz, 1H), 1.21 (s, 9H). UPLC-MS 3: no ionization, $t_R$=1.46 min.

Step 5: Tert-butyl (S)-4-bromo-2-((E)-(((R)-tert-butylsulfinyl)imino)methyl)-5-chloro-6-fluoro-2-phenylindoline-1-carboxylate (C-XLV-f)

At RT Ti(OiEt)$_4$ (1.014 mL, 4.84 mmol) and R(+)-2-methyl-2-propanesulfinamide (0.323 g, 2.66 mmol) were added to a stirred yellow solution of tert-butyl (S)-4-bromo-5-chloro-6-fluoro-2-formyl-2-phenylindoline-1-carboxylate (C-XLV-e) (1.1 g, 2.419 mmol) in THF (24.19 mL). The reaction mixture was stirred at 70° C. for 2 h before it was quenched with a sat solution of NH$_4$Cl and extracted with EtOAc. The reaction mixture was cooled down, brine was added and the mixture was extracted with EtOAc. The combined organic extracts were washed with brine, dried over Na$_2$SO$_4$ and concentrated to give the title compound (1.26 g) as a white foam. $^1$H NMR (400 MHz, DMSO-d$_6$) δ (ppm) 8.59 (s, 1H), 7.52-7.30 (m, 5H), 3.84 (d, J=17.3 Hz, 1H), 1.20-1.06 (br.s, 9H), 1.01 (s, 9H). UPLC-MS 3: $t_R$=1.47 min.

Step 6: Tert-butyl (S)-4-bromo-2-((S)-1-(((R)-tert-butylsulfinyl)amino)but-3-en-1-yl)-5-chloro-6-fluoro-2-phenylindoline-1-carboxylate (C-XLV-g) and tert-butyl (S)-4-bromo-2-((R)-1-(((R)-tert-butylsulfinyl)amino)but-3-en-1-yl)-5-chloro-6-fluoro-2-phenylindoline-1-carboxylate (C-XLV-h)

At 0° C. allylmagnesium bromide (4.52 mL, 4.52 mmol) was added to a stirred solution of tert-butyl (S)-4-bromo-2-((E)-(((R)-tert-butylsulfinyl)imino)methyl)-5-chloro-6-fluoro-2-phenylindoline-1-carboxylate (C-XLV-f) (1.26 g, 2.26 mmol) in DCM (11.3 mL). The reaction mixture was stirred at 0° C. for 1 h. For workup a sat solution of NH$_4$Cl was added and the mixture was extracted with DCM. The combined organic extracts were washed with brine, dried over Na$_2$SO$_4$ and concentrated. The crude product was purified twice by flash chromatography (silica, hexane/EtOAc, gradient: 0% to 30% EtOAc) to afford tert-butyl (S)-4-bromo-2-((S)-1-(((R)-tert-butylsulfinyl)amino)but-3-en-1-yl)-5-chloro-6-fluoro-2-phenylindoline-1-carboxylate (C-XLV-g) (940 mg) and tert-butyl (S)-4-bromo-2-((R)-1-(((R)-tert-butylsulfinyl)amino)but-3-en-1-yl)-5-chloro-6-fluoro-2-phenylindoline-1-carboxylate (C-XLV-h) (300 mg).

Tert-butyl (S)-4-bromo-2-((S)-1-(((R)-tert-butylsulfinyl)amino)but-3-en-1-yl)-5-chloro-6-fluoro-2-phenylindoline-1-carboxylate (C-XLV-g): $^1$H NMR (400 MHz, DMSO-d$_6$) δ (ppm) 7.68 (s, 1H), 7.45-7.28 (m, 3H), 7.21 (d, J=7.7 Hz, 2H), 6.27 (s, 1H), 5.28-5.08 (m, 3H), 4.56 (s, 1H), 3.86 (d, J=17.7 Hz, 1H), 3.26-3.12 (m, 1H), 2.51 (s, 2H), 1.20 (s, 9H), 0.93 (s, 9H). UPLC-MS 3: m/z 599.2/601.2 [M+H]$^+$, $t_R$=1.43 min.

Tert-butyl (S)-4-bromo-2-((R)-1-(((R)-tert-butylsulfinyl)amino)but-3-en-1-yl)-5-chloro-6-fluoro-2-phenylindoline-1-carboxylate (C-XLV-g): UPLC-MS 3: m/z 599.2/601.2 [M+H]$^+$, $t_R$=1.47 min.

Step 7: Tert-butyl (S)-4-bromo-2-((S)-1-((tert-butoxycarbonyl)amino)but-3-en-1-yl)-5-chloro-6-fluoro-2-phenylindoline-1-carboxylate (C-XLV-h)

At 0° C. HCl (1.96 mL, 7.83 mmol, 4 M in dioxane) was added to a solution of tert-butyl (S)-4-bromo-2-((S)-1-(((R)-tert-butylsulfinyl)amino)but-3-en-1-yl)-5-chloro-6-fluoro-2-phenylindoline-1-carboxylate (C-XLV-g) (940 mg, 1.567 mmol) in MeOH (5.2 mL). After 1 h at 0° C. the reaction mixture was concentrated and taken up in THF (10 mL), treated with a sat. aq solution of NaHCO3 (4.48 mL, 31.3 mmol) and Boc-anhydride (437 µl, 1.88 mmol), Stirring at RT was continued for 18 h. For workup water was added followed by extraction with EtOAc. The combined organic extracts were washed with brine, dried over anhydrous Na$_2$SO$_4$ and concentrated under reduced pressure. The crude product was purified by flash chromatography (silica, hexane/EtOAc; gradient 0% to 5% EtOAc) to give the title product (0.81 g) as a white foam. $^1$H NMR (400 MHz, DMSO-d$_6$) b (ppm) 7.73 (s, 1H), 7.41-7.17 (m, 5H), 6.93 (s, 1H), 5.93 (s, 1H), 5.12 (m, 3H), 3.78 (d, J=17.8 Hz, 1H), 3.15 (d, J=17.9 Hz, 1H), 2.39 (m, 2H), 1.30 (s, 9H), 1.21 (br.s, 9H). UPLC-MS 3: m/z 597.2 [M+H]$^+$, $t_R$=1.58 min.

Step 8: Tert-butyl (S)-4-bromo-2-((S)-1-((tert-butoxycarbonyl)amino)-4-hydroxybutyl)-5-chloro-6-fluoro-2-phenylindoline-1-carboxylate (C-XLV-i)

At 0° C. 9-BBN (6.8 mL 3.40 mmol) was added to a solution of tert-butyl (S)-4-bromo-2-((S)-1-((tert-butoxycarbonyl)amino)but-3-en-1-yl)-5-chloro-6-fluoro-2-phenylindoline-1-carboxylate (C-XLV-h) (810 mg, 1.36 mmol) in THF (6.8 mL), the reaction mixture was stirred at RT for 1 h. After cooling down to 0° C. 3N NaOH (4531 µl, 13.59 mmol) was added followed by H$_2$O$_2$ (5553 µl, 54.4 mmol). Stirring at 0° C. for was continued for 15 min. For workup brine was added and the mixture was extracted with EtOAc. The combined organic extracts were washed with brine, dried over anhydrous Na$_2$SO$_4$ and concentrated. The resulting crude product was purified by flash chromatography (silica, cyclohexane/EtOAc, gradient: 0% to 30% EtOAc) to give the desired product (0.81 g) as a colorless oil. $^1$H NMR (400 MHz, DMSO-d$_6$) δ (ppm) 7.73 (s, 1H), 7.40-7.18 (m, 5H), 6.86 (s, 1H), 4.94 (s, 1H), 4.47 (s, 1H), 3.77 (s, 1H), 3.55-3.39 (m, 2H), 3.11 (d, J=17.6 Hz, 1H), 1.81-1.66 (m, 1H), 1.62 (m, 2H), 1.50 (s, 1H), 1.31 (s, 9H), 1.27-1.07 (br.s, 9H). UPLC-MS 3: m/z 613.1 [M+H]$^+$, $t_R$=1.43 min.

Step 9: Tert-butyl (S)-4-bromo-2-((S)-1-(tert-butoxycarbonyl)pyrrolidin-2-yl)-5-chloro-6-fluoro-2-phenylindoline-1-carboxylate (C-XLV-j)

At 0° C. MsCl (123 µl, 1.583 mmol) was added to a stirred solution tert-butyl (S)-4-bromo-2-((S)-1-((tert-butoxycarbonyl)amino)-4-hydroxybutyl)-5-chloro-6-fluoro-2-phenylindoline-1-carboxylate (C-XLV-i) (0.81 g, 1.319 mmol) and DIPEA (346 µl, 1.979 mmol) in DCM (6.6 mL). The reaction mixture was stirred at RT for 30 min and concentrated. For workup brine was added and the mixture was extracted with EtOAc. The combined organic extracts were washed with water and brine, dried over anhydrous Na$_2$SO$_4$ and concentrated to give the mesylate intermediate. NaOtBu (190 mg, 1.979 mmol) was added to a stirred solution of the mesylate intermediate in THF (7 mL), stirring at RT was continued for 3 d, then at 60° C. for 18 h. More NaOtBu (190 mg, 1.98 mmol) was added and the reaction mixture was stirred at 60° C. for another 18 h. For workup water was added and the mixture was extracted with EtOAc. The combined organic extracts were washed with brine, dried over anhydrous Na$_2$SO$_4$ and concentrated. The resulting crude product was purified by flash chromatography (silica, cyclohexane/EtOAc, gradient: 0% to 20% EtOAc) to give the desired product (0.65 g) as a colorless solid. $^1$H NMR (400 MHz, DMSO-d$_6$) δ (ppm) 7.58 (s, 1H), 7.44 (d, J=7.7 Hz, 2H), 7.40-7.21 (m, 3H), 5.32 (m, 1H), 3.57 (m, 1H), 3.36 (d, J=3.4 Hz, 2H), 2.78 (m, 1H), 2.60 (m, 1H), 1.95 (m, 3H), 1.23 (s, 9H), 1.12 (br.s, 9H). UPLC-MS 3: m/z 595.1 [M+H]$^+$, $t_R$=1.58 min. An X-Ray structure confirmed the absolute configuration of the title compound.

Step 10: Tert-butyl (S)-2-((S)-1-(tert-butoxycarbonyl)pyrrolidin-2-yl)-5-chloro-6-fluoro-2-phenyl-4-(4,4,5,5-tetramethyl-1,3,2-dioxaborolan-2-yl)indoline-1-carboxylate (C-XLV)

A deoxygenated suspension of tert-butyl (S)-4-bromo-2-((S)-1-(tert-butoxycarbonyl)pyrrolidin-2-yl)-5-chloro-6-fluoro-2-phenylindoline-1-carboxylate (C-XLV-j) (440 mg, 0.738 mmol), bis(pinacolato)diboron (0.28 g, 1.108 mmol), PdCl$_2$(PPh$_3$)$_2$ (51.8 mg, 0.074 mmol) and KOAc (0.217 g, 2.215 mmol) in toluene (7.5 mL) was stirred at 105° C. for 16 h under an Ar atmosphere. The reaction mixture was filtered over a PL-thiol cartridge and concentrated under reduced pressure. The residue was purified by flash chromatography (silica, hexane/EtOAc; gradient: 0 to 10%) to afford the title product (220 mg) as a colorless oil. UPLC-MS 3: no ionization, $t_R$=1.49 min.

EXAMPLES AND THEIR SYNTHESIS

Example 1, Example 1a and Example 1b: (5-Chloro-2,4-diphenyl-2,3-dihydrobenzofuran-2-yl)methanamine (Example 1), (S)-(5-Chloro-2,4-diphenyl-2,3-dihydrobenzofuran-2-yl)methanamine (Example 1a) and (R)-(5-chloro-2,4-diphenyl-2,3-dihydrobenzofuran-2-yl)methanamine (Example 1b)

Example 1

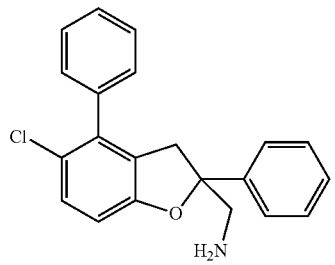

Example 1a

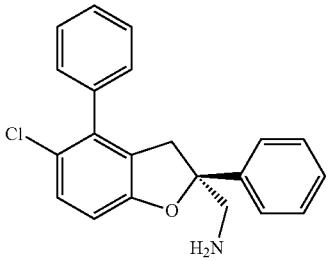

Example 1b

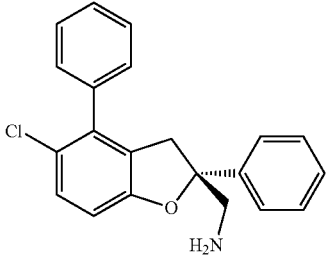

Reaction Scheme Example 1

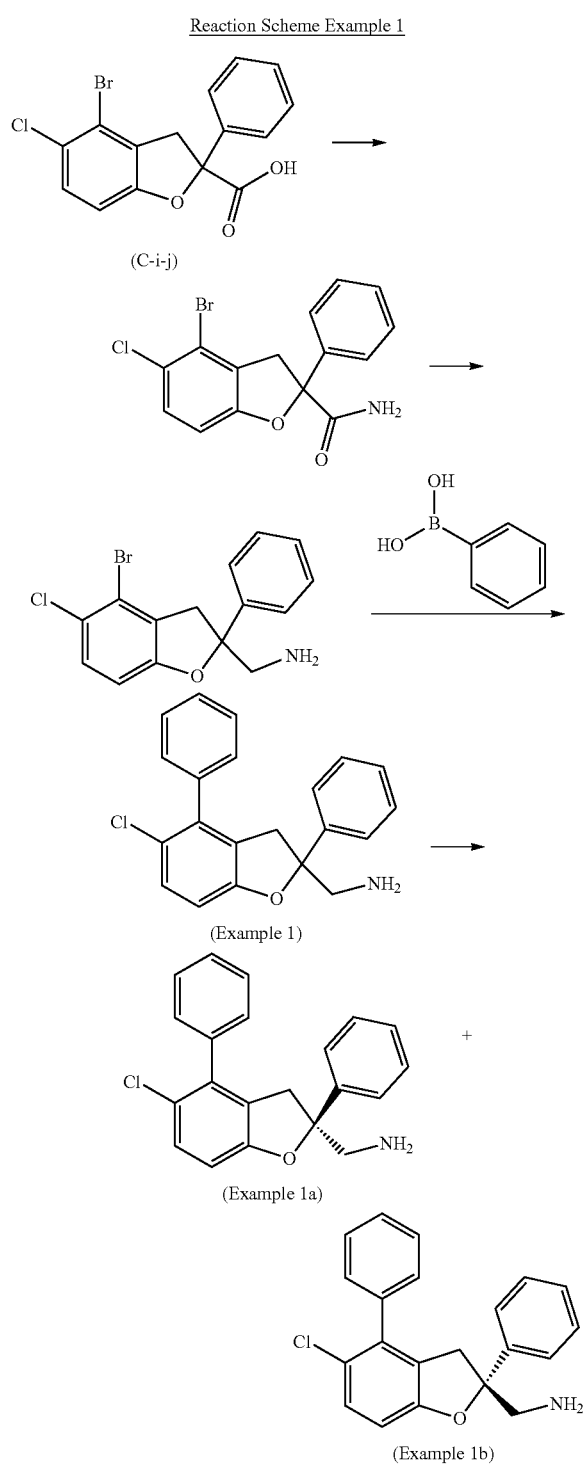

(C-i-j)

(Example 1)

(Example 1a)

(Example 1b)

Step 1: 4-Bromo-5-chloro-2-phenyl-2,3-dihydrobenzofuran-2-carboxamide

4-Bromo-5-chloro-2-phenyl-2,3-dihydrobenzofuran-2-carboxylic acid (200 g, 566 mmol) (C-I-j) was dissolved in DCM (2400 mL) and cooled to 0° C. Oxalyl chloride (94 g, 743 mmol) followed by 3 drops of DMF were added and the reaction mixture was stirred at RT for 1 h. The resulting solution was added within 15 min to a 30% ammonium hydroxide solution (2400 mL, 18.5 mol) at 0° C. The resulting suspension was stirred at 0° C. for 30 min. The solids were filtered off and washed with DCM. The organic phase of the filtrate was separated. The aqueous phase was extracted with DCM and the combined organic extracts were washed with brine, dried over anhydrous $Na_2SO_4$ and concentrated to afford the title compound (198 g). UPLC-MS 1: m/z 353.0 $[M+H]^+$. $t_R$=1.14 min.

Step 2: (4-Bromo-5-chloro-2-phenyl-2,3-dihydrobenzofuran-2-yl)methanamine

4-Bromo-5-chloro-2-phenyl-2,3-dihydrobenzofuran-2-carboxamide was dissolved in THF (3000 mL). Borane-methyl sulfide complex (1106 mL, 2.212 mol, 2 M in THF) was added within 30 min at RT. The solution was stirred at reflux for 7 h. The reaction mixture was cooled to RT and quenched by addition of MeOH (1000 mL) over 30 min. The mixture was stirred at RT for 45 min. The reaction mixture was treated with 1 N HCL (2000 mL) and stirred at RT for 3 h. For workup, DCM was added followed by a sat solution of $NaHCO_3$. The aqueous phase was extracted with DCM and the combined organic extracts were washed with brine, dried over anhydrous $Na_2SO_4$ and concentrated. The crude product was purified by flash chromatography (silica, DCM/(7N $NH_3$ in MeOH) 95:5) to afford the title compound (110 g). UPLC-MS 1: m/z 339.0 $[M+H]^+$. $t_R$=0.85 min.

Step 3: (5-Chloro-2,4-diphenyl-2,3-dihydrobenzofuran-2-yl)methanamine (Example 1)

A mixture of (4-bromo-5-chloro-2-phenyl-2,3-dihydrobenzofuran-2-yl)methanamine (5.1 g, 15.1 mmol), phenylboronic acid (2.20 g, 18.1 mmol), $K_2CO_3$ (6.25 g, 45.2 mmol) and bis(triphenylphosphine)palladium(II) dichloride (0.529 g, 0.75 mmol) in DMF (50 mL) was stirred at 100° C. for 1 h. The reaction mixture was diluted in EtOAc and water. The aqueous phase was extracted with EtOAc and the combined organic extracts were washed with brine, dried over anhydrous $Na_2SO_4$ and concentrated. The crude product was purified by flash chromatography (silica, DCM/(DCM+10% MeOH), gradient: 0% to 30% (DCM+10% MeOH)) to afford the racemic title compound (5.08 g). UPLC-MS 1: m/z 335.0 $[M+H]^+$. $t_R$=0.95 min.

Step 4: (S)-(5-Chloro-2,4-diphenyl-2,3-dihydrobenzofuran-2-yl)methanamine (Example 1a) and (R)-(5-chloro-2,4-diphenyl-2,3-dihydrobenzofuran-2-yl)methanamine (Example 1b)

The racemate (5-chloro-2,4-diphenyl-2,3-dihydrobenzofuran-2-yl)methanamine (1.9 g) was subjected to chiral SFC (ChiralPak IC, 250×30 mm, 5 μm. $CO_2$/(IPA+1% isopropylamine) 7:3, 40° C., flow rate: 100 mL/min, 3 mL/injection, 7 injections, cycle time 20 min) to afford the title compounds as separate enantiomers in an enatiomeric excess of >99%, respectively:

(S)-(5-Chloro-2,4-diphenyl-2,3-dihydrobenzofuran-2-yl)methanamine (Example 1a) (785 mg): Chiral SFC: (Chiralpak IC 250×4.6 mm I.D., 5 μm, $CO_2$/(IPA+1% isopropylamine) 7:3, flow rate: 3 mL/min) $t_R$=2.91 min. $^1$H NMR (400 MHz, DMSO-$d_6$) δ (ppm) 7.49-7.15 (m, 11H), 6.91 (d, J=8.5 Hz, 1H), 3.60 (d, J=16.3 Hz, 1H), 2.98-2.80 (m, 3H), 1.63 (s, 2H). UPLC-MS 1: m/z 336.1 $[M+H]^+$. $t_R$=0.91 min.

(R)-(5-chloro-2,4-diphenyl-2,3-dihydrobenzofuran-2-yl)methanamine (Example 1b) (894 mg): Chiral SFC: (Chiralpak IC 250×4.6 mm I.D., 5 μm, $CO_2$/(IPA+1% isopropylamine) 7:3, flow rate: 3 mL/min) $t_R$=8.52 min. $^1$H NMR (400 MHz, DMSO-$d_6$) δ (ppm) 7.49-7.15 (m, 11H), 6.91 (d, J=8.5 Hz, 1H), 3.60 (d, J=16.3 Hz, 1H), 2.98-2.80 (m, 3H), 1.63 (s, 2H). UPLC-MS 1: m/z 336.1 [M+H]$^+$. $t_R$=0.91 min.

Example 2a, Example 2b, Example 2a-1 and Example 2a-2: N1-(2-((2S*,4S*)-2-(Aminomethyl)-5-chloro-2-phenyl-2,3-dihydrobenzofuran-4-yl)-3-fluorophenyl)ethane-1,2-diamine (Example 2a), N1-(2-((2S*,4R*)-2-(Aminomethyl)-5-chloro-2-phenyl-2,3-dihydrobenzofuran-4-yl)-3-fluorophenyl)ethane-1,2-diamine (Example 2b), N1-(2-((2S,4S)-2-(Aminomethyl)-5-chloro-2-phenyl-2,3-dihydrobenzofuran-4-yl)-3-fluorophenyl)ethane-1,2-diamine (Example 2a-1) and N1-(2-((2R,4R)-2-(aminomethyl)-5-chloro-2-phenyl-2,3-dihydrobenzofuran-4-yl)-3-fluorophenyl)ethane-1,2-diamine (Example 2a-2)

Example 2a

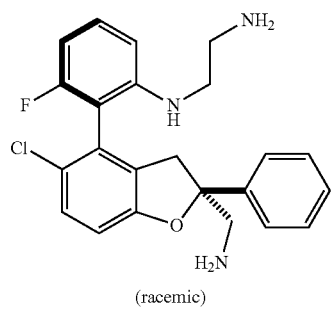

(racemic)

Example 2b

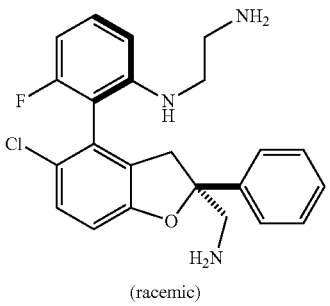

(racemic)

Example 2a-1

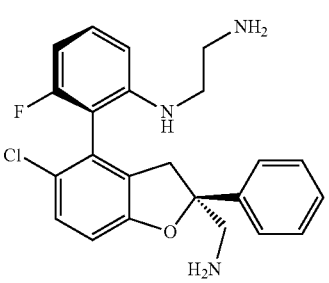

Example 2a-2

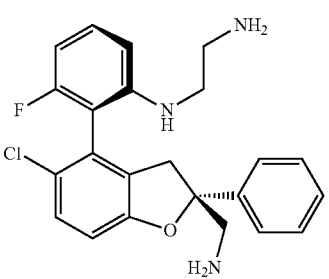

Reaction Scheme Example 2

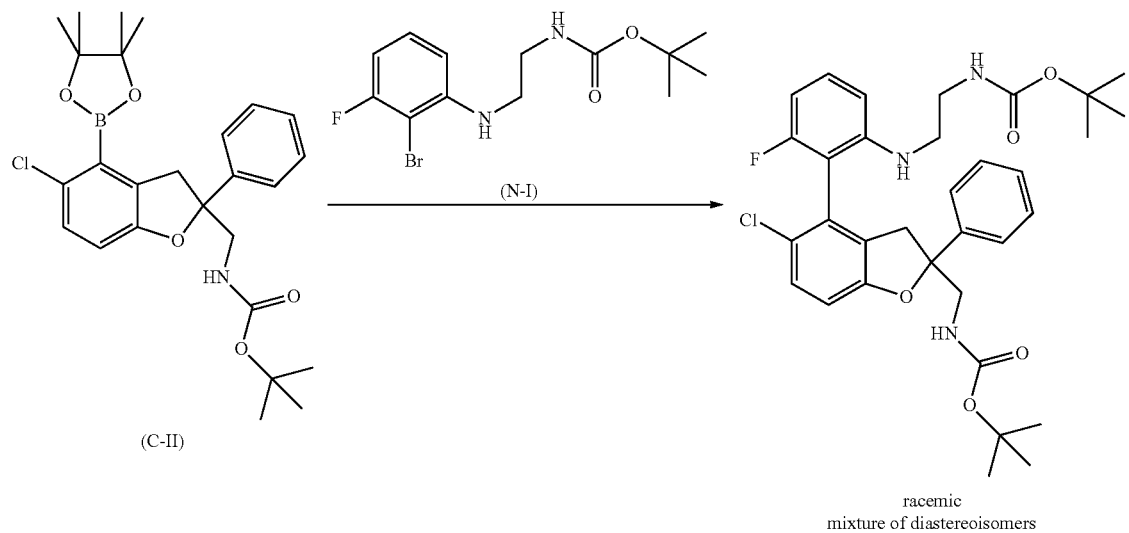

racemic
mixture of diastereoisomers

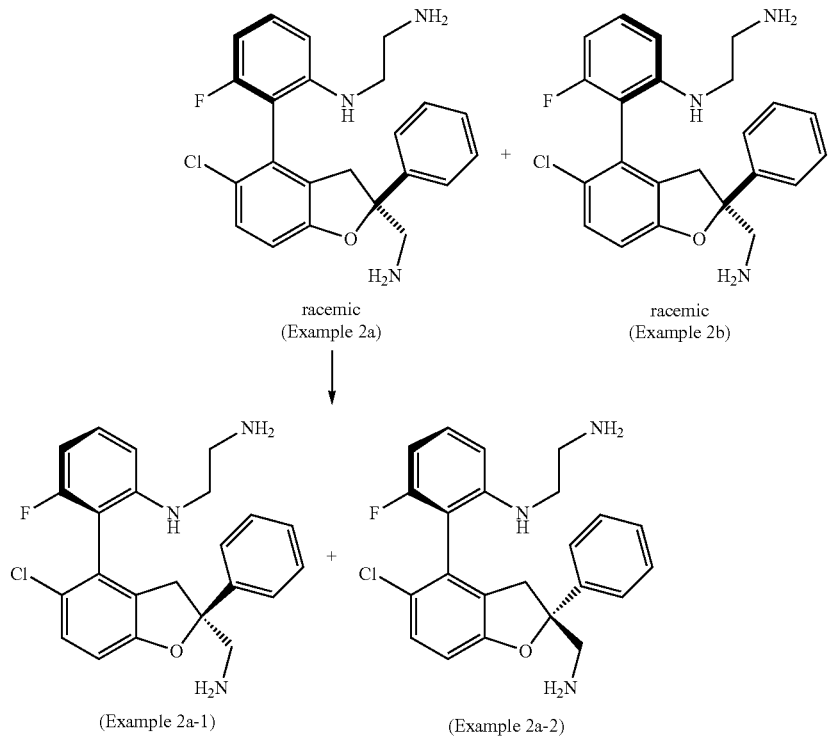

racemic
(Example 2a)

racemic
(Example 2b)

(Example 2a-1)

(Example 2a-2)

Step 1: Tert-butyl ((((2S*,4S*)-4-(2-((2-((tert-butoxycarbonyl)amino)ethyl)amino)-6-fluorophenyl)-5-chloro-2-phenyl-2,3-dihydrobenzofuran-2-yl)methyl)carbamate and tert-butyl ((((2S*,4R*)-4-(2-((2-((tert-butoxycarbonyl)amino)ethyl)amino)-6-fluorophenyl)-5-chloro-2-phenyl-2,3-dihydrobenzofuran-2-yl)methyl)carbamate Pd(dbpf)Cl$_2$ (CAS 95408-45-0) (109 mg, 0.17 mmol) was added to a mixture of tert-butyl ((5-chloro-2-phenyl-4-(4,4,5,5-tetramethyl-1,3,2-dioxaborolan-2-yl)-2,3-dihydrobenzofuran-2-yl)methyl)carbamate (C-II) (500 mg, 0.834 mmol), tert-butyl (2-((2-bromo-3-fluorophenyl)amino)ethyl)carbamate (N-1) (315 mg, 0.92 mmol) and K$_3$PO$_4$ (531 mg, 2.501 mmol) in dioxane (6 mL) and water (2 mL) and the reaction mixture was stirred at 100° C. for 15 min. EtOAc and water were added. The organic phase was separated and the aqueous phase was extracted with EtOAc. The combined organic extracts were washed with brine, dried over anhydrous Na$_2$SO$_4$ and concentrated. The remaining residue was dissolved in MeOH and passed through a PL-thiol MP Resin cartridge (Agilent, StratoSpheres SPE) to remove metal traces. After concentration, the crude product was purified by flash chromatography (silica, hexane/EtOAc, gradient: 0% to 30% EtOAc) to afford a mixture of the racemic title compounds (490 mg). UPLC-MS 1: m/z 612.3 [M+H]$^+$. $t_R$=1.45 min and 1.48 min.

Step 2: N1-(2-((2S*,4S*)-2-(Aminomethyl)-5-chloro-2-phenyl-2,3-dihydrobenzofuran-4-yl)-3-fluorophenyl)ethane-1,2-diamine (Example 2a) and N1-(2-((2S*,4R*)-2-(aminomethyl)-5-chloro-2-phenyl-2,3-dihydrobenzofuran-4-yl)-3-fluorophenyl) ethane-1,2-diamine (Example 2b)

TFA (1 mL, 13.0 mmol) was added to a stirred solution of a mixture of racemic tert-butyl ((((2S*,4S*)-4-(2-((2-((tert-butoxycarbonyl)amino)ethyl)amino)-6-fluorophenyl)-5-chloro-2-phenyl-2,3-dihydrobenzofuran-2-yl)methyl)carbamate and racemic tert-butyl ((((2S*,4R*)-4-(2-((2-((tert-butoxycarbonyl)amino)ethyl)amino)-6-fluorophenyl)-5-chloro-2-phenyl-2,3-dihydrobenzofuran-2-yl)methyl)carbamate (490 mg, 0.41 mmol) in DCM (3 mL) at RT and the reaction mixture was stirred at RT for 45 min. The reaction mixture was diluted with DCM and a sat solution of NaHCO$_3$, the organic phase was separated and the aqueous phase was extracted with DCM. The combined organic extracts were dried over anhydrous Na$_2$SO$_4$ and concentrated. The crude product was purified by preparative HPLC (2 injections, Gilson gx-281. Column: Sunfire C18, 30×100 mm, 5 μm. Flow: 30 mL/min. Gradient: 5% to 40% B in 20 min, A=0.1% TFA in H$_2$O, B=CH$_3$CN. Detection: UV). The collected fractions were basified with a sat solution of NaHCO$_3$, ACN was evaporated under reduced pressure and the resulting aqueous phase was extracted with DCM. The organic extract was washed with brine, dried over anhydrous Na$_2$SO$_4$ and concentrated to afford the racemic title compounds as separate diastereoisomers.

N1-(2-((2S*,4S*)-2-(aminomethyl)-5-chloro-2-phenyl-2,3-dihydrobenzofuran-4-yl)-3-fluorophenyl)ethane-1,2-diamine (Example 2a) (98 mg): $^1$H NMR (400 MHz, DMSO-$d_6$) δ 7.40-7.36 (m, 2H), 7.35-7.29 (m, 3H), 7.28-7.14 (m, 2H), 6.95 (d, J=8.6 Hz, 1H), 6.54 (d, J=8.2 Hz, 1H), 6.39 (t, J=8.8 Hz, 1H), 4.70 (t, J=5.5 Hz, 1H), 3.49 (d, J=16.0 Hz, 1H), 3.11-3.00 (m, 2H), 2.92 (s, 2H), 2.81 (d, J=16.4 Hz, 1H), 2.67 (t, J=6.1 Hz, 2H). UPLC-MS 1: m/z 412.2 [M+H]+. $t_R$=0.68 min.

N1-(2-((2S*,4R*)-2-(aminomethyl)-5-chloro-2-phenyl-2,3-dihydrobenzofuran-4-yl)-3-fluorophenyl)ethane-1,2-diamine (Example 2b) (72 mg): $^1$H NMR (400 MHz, DMSO-$d_6$) δ 7.42-7.36 (m, 2H), 7.36-7.29 (m, 3H), 7.28-7.22 (m, 1H), 7.22-7.15 (m, 1H), 6.94 (d, J=8.6 Hz, 1H), 6.50-6.43 (m, 2H), 4.37 (t, J=5.5 Hz, 1H), 3.38 (d, J=16.1 Hz, 1H), 2.95 (d, J=16.1 Hz, 1H), 2.95-2.79 (m, 4H), 2.46-2.38 (m, 1H), 2.29-2.21 (m, 1H). UPLC-MS 1: m/z 412.2 [M+H]+ $t_R$=0.50 min.

Step 3: N1-(2-((2S,4S)-2-(Aminomethyl)-5-chloro-2-phenyl-2,3-dihydrobenzofuran-4-yl)-3-fluorophenyl)ethane-1,2-diamine (Example 2a-1) and N1-(2-((2R,4R)-2-(aminomethyl)-5-chloro-2-phenyl-2,3-dihydrobenzofuran-4-yl)-3-fluorophenyl)ethane-1,2-diamine (Example 2a-2)

Racemic N1-(2-((2S*,4S*)-2-(aminomethyl)-5-chloro-2-phenyl-2,3-dihydrobenzofuran-4-yl)-3-fluorophenyl)ethane-1,2-diamine (Example 2a) (98 mg) was subjected to chiral preparative HPLC (ChiralPak OZI, 420×50 mm, 20 μm. heptane/DCM/IPA 60:25:15+0.1% TFA: flow rate: 80 mL/min) to afford the title compounds as separate enantiomers in an enatiomeric excess of >99%, respectively.

N1-(2-((2S,4S)-2-(Aminomethyl)-5-chloro-2-phenyl-2,3-dihydrobenzofuran-4-yl)-3-fluorophenyl)ethane-1,2-diamine (39 mg) (Example 2a-1): Chiral HPLC (ChiralPak OZI, 250×4.6 mm, 20 μm. heptane/DCM/IPA 60:25:15+0.1% TFA:, flow rate: 0.7 mL/min) $t_R$=23.09 min. $^1$H NMR (400 MHz, DMSO-$d_6$) δ 7.43-7.13 (m, 7H), 6.95 (d, J=8.5 Hz, 1H), 6.54 (d, J=8.3 Hz, 1H), 6.39 (t, J=8.8 Hz, 1H), 4.70 (t, J=5.6 Hz, 1H), 3.49 (d, J=16.3 Hz, 1H), 3.11-3.00 (m, 2H), 2.93 (s, 2H), 2.81 (d, J=16.2 Hz, 1H), 2.67 (t, J=6.2 Hz, 2H). UPLC-MS 1 m/z 412.1 [M+H]+. $t_R$=0.68 min.

N1-(2-((2R,4R)-2-(aminomethyl)-5-chloro-2-phenyl-2,3-dihydrobenzofuran-4-yl)-3-fluorophenyl)ethane-1,2-diamine (38 mg) (Example 2a-2): Chiral HPLC (ChiralPak OZI, 250×4.6 mm, 20 μm. heptane/DCM/IPA 60:25:15+0.1% TFA:, flow rate: 0.7 mL/min) $t_R$=16.29 min. $^1$H NMR (400 MHz, DMSO-$d_6$) δ 7.43-7.13 (m, 7H), 6.95 (d, J=8.5 Hz, 1H), 6.54 (d, J=8.3 Hz, 1H), 6.39 (t, J=8.8 Hz, 1H), 4.70 (t, J=5.6 Hz, 1H), 3.49 (d, J=16.3 Hz, 1H), 3.11-3.00 (m, 2H), 2.93 (s, 2H), 2.81 (d, J=16.2 Hz, 1H), 2.67 (t, J=6.2 Hz, 2H). UPLC-MS 1: m/z 412.1 [M+H]+. $t_R$=0.68 min.

Example 3a and Example 3b: 2-(2-((2S,4S)-2-(Aminomethyl)-5-chloro-2-phenyl-2,3-dihydrobenzofuran-4-yl)-3-fluorophenoxy)ethanamine (Example 3a) and 2-(2-((2R,4R)-2-(aminomethyl)-5-chloro-2-phenyl-2,3-dihydrobenzofuran-4-yl)-3-fluorophenoxy)ethanamine (Example 3b)

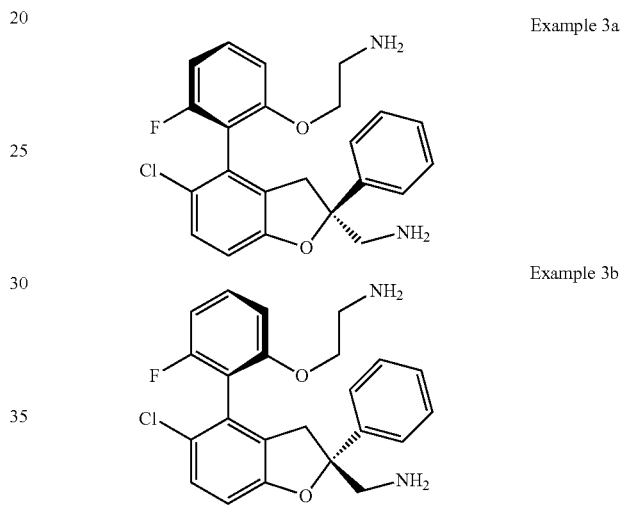

Example 3a

Example 3b

Reaction Scheme Example 3

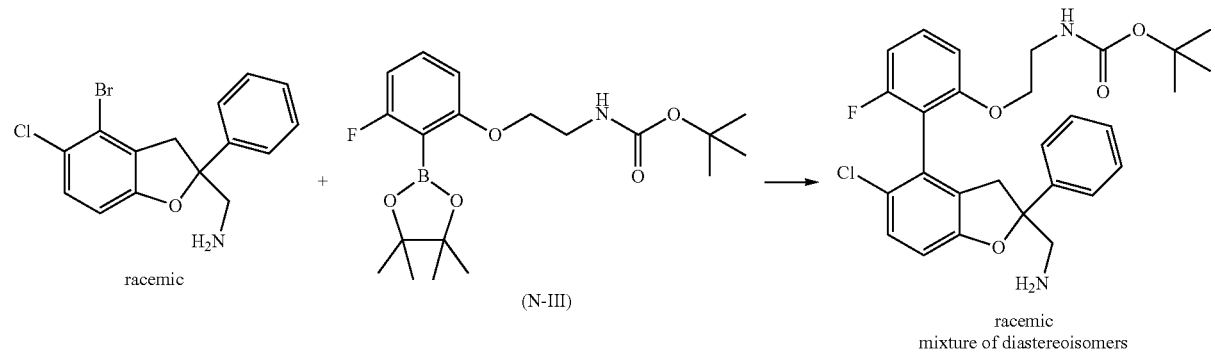

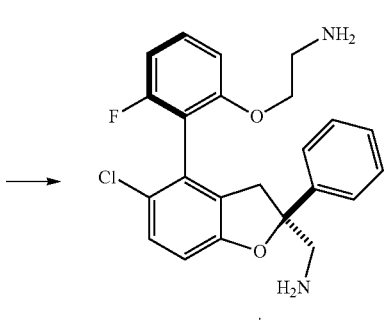 + 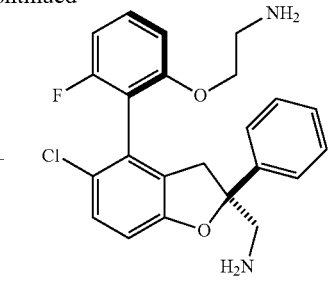

racemic      racemic

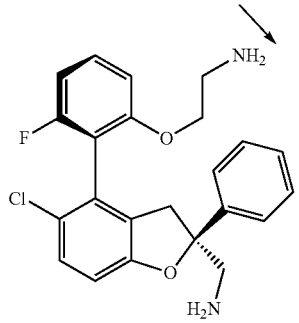 + 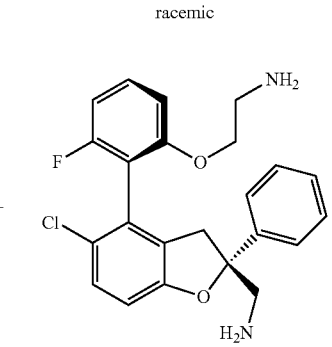

(Example 3a)      (Example 3b)

Step 1: Tert-butyl (2(2-(((2S*,4S*)-2-(aminomethyl)-5-chloro-2-phenyl-2,3-dihydrobenzofuran-4-yl)-3-fluorophenoxy)ethyl)carbamate and tert-butyl (2(2-(((2S*,4R*)-2-(aminoethyl)-5-chloro-2-phenyl-2,3-dihydrobenzofuran-4-yl)-3-fluorophenoxy)ethyl) carbamate A mixture of (4-bromo-5-chloro-2-phenyl-2,3-dihydrobenzofuran-2-yl)methanamine (racemic, prepared in analogy to intermediate C-1-0 in Scheme C-I) (250 mg, 0.74 mmol), tert-butyl (2-(3-fluoro-2-(4,4,5,5-tetramethyl-1,3,2-dioxaborolan-2-yl)phenoxy)ethyl)carbamate (N-Ill) (748 mg, 1.55 mmol), Pd(dbpf)Cl$_2$ (48.1 mg, 0.07 mmol) and K$_3$PO$_4$ (470 mg, 2.22 mmol) in dioxane (3 mL) and H$_2$O (1 mL) was stirred at 100° C. for 15 min. EtOAc and water were added and the organic phase was separated. The aqueous phase was extracted with EtOAc and the combined organic extracts were washed with water and brine, dried over anhydrous Na$_2$SO$_4$ and concentrated. The crude mixture was diluted in MeOH and passed through a PL-thiol MP Resin cartridge (Agilent, StratoSpheres SPE, to remove metal traces). Concentration afforded a yellow oil, which was purified by flash chromatography (silica, DCM/MeOH, gradient: 0% to 5% MeOH) to afford a mixture of the racemic title compounds (410 mg). UPLC MS 1: m/z 513.2 [M+H]$^+$; t$_R$=0.98 min and 1.05 min.

Step 2: 2-(2-(((2S*,4S*)-2-(aminomethyl)-5-chloro-2-phenyl-2,3-dihydrobenzofuran-4-yl)-3-fluorophenoxy)ethan-1-amine and 2-(2-(((2S*,4R*)-2-(aminomethyl)-5-chloro-2-phenyl-2,3-dihydrobenzofuran-4-yl)-3-fluorophenoxy)ethan-1-amine TFA (1 mL, 13.0 mmol) was added to a stirred solution of a mixture of racemic tert-butyl (((2S*,4S*)-4-(2-((2-(((tert-butoxycarbonyl)amino)ethyl)amino)-6-fluorophenyl)-5-chloro-2-phenyl-2,3-dihydrobenzofuran-2-yl)methyl)carbamate and racemic tert-butyl (((2S*,4R*)-4-(2-((2-(((tert-butoxycarbonyl)amino)ethyl)amino)-6-fluorophenyl)-5-chloro-2-phenyl-2,3-dihydrobenzofuran-2-yl)methyl) carbamate (410 mg, 0.57 mmol) in DCM (3 mL) at RT. After 10 min DCM was added followed by a sat solution of NaHCO$_3$. The organic phase was separated and the aqueous phase was extracted with DCM. The combined organic extracts were washed with brine, dried over anhydrous Na$_2$SO$_4$ and concentrated. The crude product was purified by preparative HPLC (Gilson gx-281. Column: Sunfire C18, 30×100 mm, 5 μm. Flow: 30 mL/min. Gradient: 5% to 50% B in 18 min; A=0.1% TFA in H$_2$O, B=CH$_3$CN. Detection: UV). The collected fractions were basified with a sat solution of NaHCO$_3$, the acetonitrile was evaporated under reduced pressure and the resulting aqueous phase was extracted with DCM. The organic extract was dried over anhydrous Na$_2$SO$_4$ and concentrated to afford the racemic title compounds as separate diastereoisomers.

2-(2-(((2S*,4S*)-2-(aminomethyl)-5-chloro-2-phenyl-2,3-dihydrobenzofuran-4-yl)-3-fluorophenoxy)ethan-1-amine (86 mg): $^1$H NMR (400 MHz, DMSO-d$_6$) δ 7.49-7.16 (m, 7H), 6.99-6.82 (m, 3H), 3.84-3.65 (m, 2H), 3.43 (d, J=16.1 Hz, 1H), 3.01-2.81 (m, 3H), 2.37-2.21 (m, 2H), 1.49-1.15 (m, 4H). UPLC MS 1: m/z 413.1 [M+H]$^+$; t$_R$=0.66 min.

2-(2-(((2S*,4R*)-2-(aminomethyl)-5-chloro-2-phenyl-2,3-dihydrobenzofuran-4-yl)-3-fluorophenoxy)ethan-1-amine (16 mg): $^1$H NMR (400 MHz, DMSO-d$_6$) δ 7.49-7.16 (m, 7H), 6.99-6.82 (m, 3H), 3.84-3.65 (m, 2H), 3.43 (d, J=16.1 Hz, 1H), 3.01-2.81 (m, 3H), 2.37-2.21 (m, 2H), 1.49-1.15 (m, 4H). UPLC MS 1: m/z 413.1 [M+H]$^+$; t$_R$=0.48 min.

Step 3: 2-(2-(((2S,4S)-2-(Aminomethyl)-5-chloro-2-phenyl-2,3-dihydrobenzofuran-4-yl)-3-fluorophenoxy)ethanamine (Example 3a) and 2-(2-(((2R,4R)-2-(aminomethyl)-5-chloro-2-phenyl-2,3-dihydrobenzofuran-4-yl)-3-fluorophenoxy) ethanamine (Example 3b)

Racemic 2-(2-(((2S*,4S*)-2-(aminomethyl)-5-chloro-2-phenyl-2,3-dihydrobenzofuran-4-yl)-3-fluorophenoxy)

ethan-1-amine (82 mg) was subjected to chiral preparative HPLC (ChiralPak OZI, 420×50 mm, 20 μm. heptane/DCM/IPA/EtOH 70:10:10:10+0.1% TFA:, flow rate: 80 mL/min) to afford the title compounds as separate enantiomers in an enantiomeric excess of >99%, respectively. After chiral HPLC, both separate enantiomers were purified once again by flash chromatography (silica, DCM/(7N ammonia in MeOH), gradient: 0% to 12% (7N ammonia in MeOH)):

2-(2-((2S,4S)-2-(Aminomethyl)-5-chloro-2-phenyl-2,3-dihydrobenzofuran-4-yl)-3-fluorophenoxy)ethanamine (40 mg, colorless foam) (Example 3a): Chiral HPLC (ChiralPak OZI, 250×4.6 mm, 20 μm. heptane/DCM/IPA/EtOH 70:10:10:10+0.1% TFA:, flow rate: 0.7 mL/min) $t_R$=22.34 min. $^1$H NMR (400 MHz, DMSO-$d_6$) δ 7.44-7.35 (m, 3H), 7.35-7.29 (m, 2H), 7.29-7.20 (m, 2H), 6.98 (d, J=8.5 Hz, 1H), 6.92 (d, J=8.5 Hz, 1H), 6.84 (t, J=8.7 Hz, 1H), 4.07-3.84 (m, 2H), 3.53 (d, J=16.2 Hz, 1H), 2.97-2.69 (m, 5H). UPLC-MS 1 m/z 413.1 [M+H]$^+$. $t_R$=0.68 min.

2-(2-((2R,4R)-2-(Aminomethyl)-5-chloro-2-phenyl-2,3-dihydrobenzofuran-4-yl)-3-fluorophenoxy)ethanamine (36 mg, colorless foam) (Example 3b): Chiral HPLC (ChiralPak OZI, 250×4.6 mm, 20 μm. heptane/DCM/IPA/EtOH 70:10:10:10+0.1% TFA:, flow rate: 0.7 mL/min) $t_R$=15.92 min. $^1$H NMR (400 MHz, DMSO-$d_6$) δ 7.45-7.20 (m, 7H), 6.98 (d, J=8.5 Hz, 1H), 6.92 (d, J=8.5 Hz, 1H), 6.84 (t, J=8.7 Hz, 1H), 4.10-3.84 (m, 2H), 3.53 (d, J=16.2 Hz, 1H), 2.99-2.66 (m, 5H). UPLC-MS 1 m/z 413.1 [M+H]$^+$. $t_R$=0.66 min.

Example 4a and Example 4b: 2-((2S*,4S*)-2-(Aminomethyl)-5-chloro-2-phenyl-2,3-dihydrobenzofuran-4-yl)-3-fluorobenzamide (Example 4a) and 2-((2S*,4R*)-2-(aminomethyl)-5-chloro-2-phenyl-2,3-dihydrobenzofuran-4-yl)-3-fluorobenzamide (Example 4b)

Example 4a

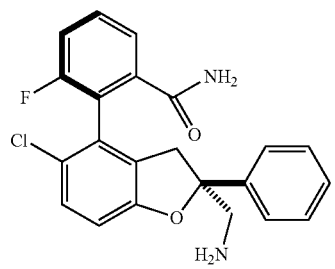

Example 4b

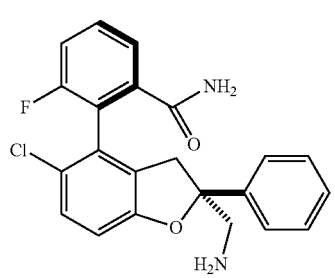

Reaction Scheme Example 4

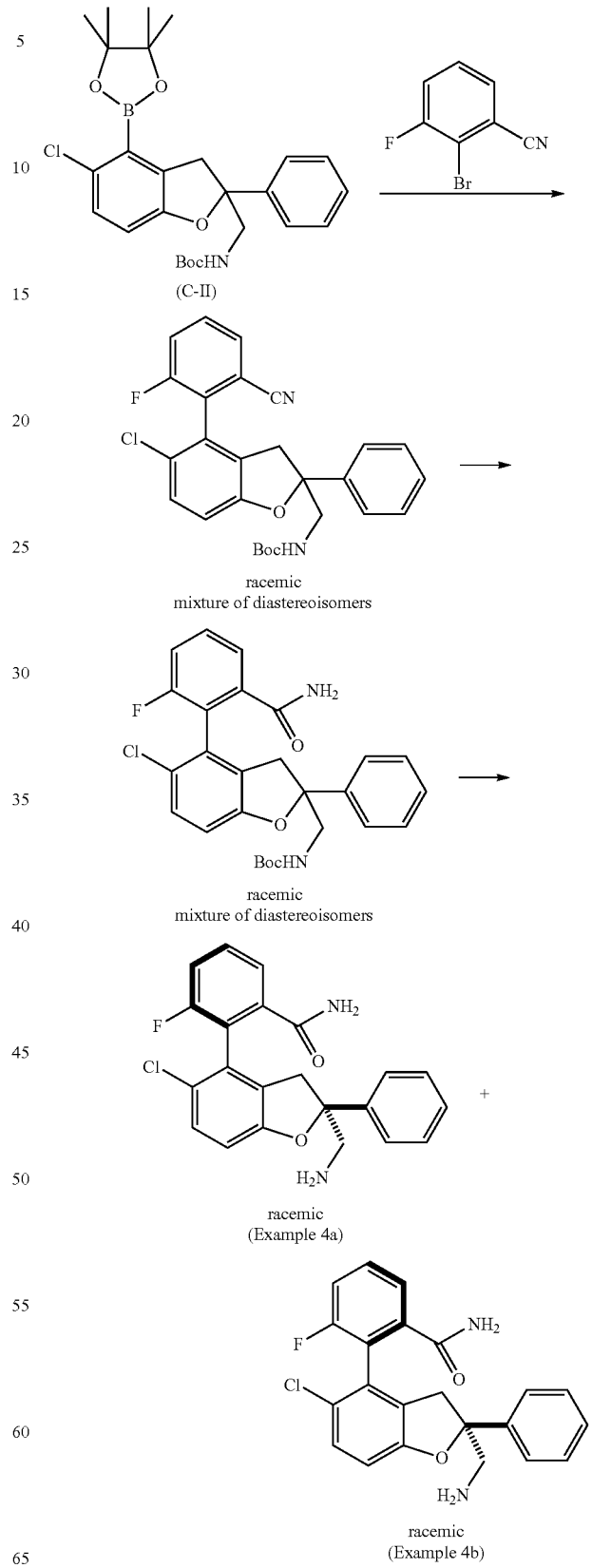

Step 1: Tert-butyl (((2S*,4S*)-5-chloro-4-(2-cyano-6-fluorophenyl)-2-phenyl-2,3-dihydrobenzofuran-2-yl)methyl)carbamate and tert-butyl (((2S*,4R*)-5-chloro-4-(2-cyano-6-fluorophenyl)-2-phenyl-2,3-dihydrobenzofuran-2-yl)methyl)carbamate 2-Bromo-3-fluorobenzonitrile (124 mg, 0.62 mmol), RuPhos Pd G1 (CAS 1028206-60-1) (45 mg, 0.06 mmol) and Na$_2$CO$_3$ (327 mg, 3.1 mmol) were suspended in DMF (2 mL) and H$_2$O (0.6 mL) and the mixture was heated to 100° C. A solution of tert-butyl ((5-chloro-2-phenyl-4-(4,4,5,5-tetramethyl-1,3,2-dioxaborolan-2-yl)-2,3-dihydrobenzofuran-2-yl)methyl)carbamate (C-II) (300 mg, 0.62 mmol) in dioxane (2 mL) was slowly added within 30 min and the reaction mixture was stirred at 100° C. for 15 min. The reaction mixture was diluted in EtOAc/water, extracted with EtOAc and the combined organic extracts were washed with water and brine, dried over anhydrous Na$_2$SO$_4$ and concentrated. The residue was purified by flash chromatography (silica, hexane/EtOAc, gradient: 0% to 40% EtOAc) to afford a mixture of the racemic title compounds (74 mg) as a colorless powder. UPLC-MS 1: products not ionizable, $t_R$=1.33 and 1.36 min.

Step 2: Tert-butyl (((2S*,4S*)-4-(2-carbamoyl-6-fluorophenyl)-5-chloro-2-phenyl-2,3-dihydrobenzofuran-2-yl)methyl)carbamate and tert-butyl (((2S*,4R*)-4-(2-carbamoyl-6-fluorophenyl)-5-chloro-2-phenyl-2,3-dihydrobenzofuran-2-yl)methyl)carbamate A solution of a mixture of tert-butyl (((2S*,4S*)-5-chloro-4-(2-cyano-6-fluorophenyl)-2-phenyl-2,3-dihydrobenzofuran-2-yl)methyl)carbamate and tert-butyl (((2S*,4R*)-5-chloro-4-(2-cyano-6-fluorophenyl)-2-phenyl-2,3-dihydrobenzofuran-2-yl)methyl)carbamate (72 mg, 0.15 mmol) in THF (2 mL), MeOH (2 mL) and NaOH (2 mL, 4.0 mmol, 2 N in water) was stirred at 80° C. for 40 h. The reaction mixture was diluted in DCM/water, extracted with DCM and the combined organic extracts were dried over anhydrous Na$_2$SO$_4$ and concentrated. The crude product was purified by flash chromatography (silica, hexane/EtOAc, gradient: 0% to 75% EtOAc) to yield a mixture of the title compounds (55 mg). UPLC-MS 1: m/z 541.2 [M+formate]$^-$, $t_R$=1.16 and 1.22 min.

Step 3: 2-((2S*,4S*)-2-(Aminomethyl)-5-chloro-2-phenyl-2,3-dihydrobenzofuran-4-yl)-3-fluorobenzamide (Example 4a) and 2-((2S*,4R*)-2-(aminomethyl)-5-chloro-2-phenyl-2,3-dihydrobenzofuran-4-yl)-3-fluorobenzamide (Example 4b)

At RT TFA (1 mL, 13.0 mmol) was added to a stirred solution of a mixture of tert-butyl (((2S*,4S*)-4-(2-carbamoyl-6-fluorophenyl)-5-chloro-2-phenyl-2,3-dihydrobenzofuran-2-yl)methyl)carbamate and tert-butyl (((2S*,4R*)-4-(2-carbamoyl-6-fluorophenyl)-5-chloro-2-phenyl-2,3-dihydrobenzofuran-2-yl)methyl)carbamate (55 mg, 0.11 mmol) in DCM (1 mL) and the reaction mixture was stirred at RT for 10 min. The reaction mixture was diluted in DCM/sat solution of NaHCO$_3$, extracted with DCM, and the combined organic extracts were dried over anhydrous Na$_2$SO$_4$ and concentrated. The residue was purified by flash chromatography (silica, DCM/(7N ammonia in MeOH); gradient: 0% to 7% (7N ammonia in MeOH)) to afford the racemic title compounds as separate diastereoisomers.

2-((2S*,4S*)-2-(Aminomethyl)-5-chloro-2-phenyl-2,3-dihydrobenzofuran-4-yl)-3-fluorobenzamide (18 mg) (Example 4a): $^1$H NMR (400 MHz, DMSO-d$_6$) δ (ppm) 7.68 (s br, 1H), 7.56-7.50 (m, 1H), 7.46-7.43 (m, 1H), 7.40-7.31 (m, 6H), 7.28-7.21 (m, 2H), 6.90 (d, J=8.6 Hz, 1H), 3.50 (d, J=16.4 Hz, 1H), 2.94-2.84 (m, 2H), 2.85 (d, J=16.4 Hz, 1H). UPLC-MS 1: m/z 397.2 [M+H]$^+$, $t_R$=0.76 min.

2-((2S*,4R*)-2-(aminomethyl)-5-chloro-2-phenyl-2,3-dihydrobenzofuran-4-yl)-3-fluorobenzamide (19 mg) (Example 4b): $^1$H NMR (400 MHz, DMSO-d$_6$) δ (ppm) 7.61 (s br, 1H), 7.56-7.49 (m, 1H), 7.45-7.24 (m, 7H), 7.21 (d, J=8.2 Hz, 1H), 7.10 (s br, 1H), 6.86 (d, J=8.6 Hz, 1H), 3.30-3.25 (m, 1H), 3.14 (d, J=16.0 Hz, 1H), 2.95-2.83 (m, 2H). UPLC-MS 1: m/z 397.1 [M+H]$^+$, $t_R$=0.58 min.

Example 5a and Example 5b: 2-((2S,4S)-2-(Aminomethyl)-5-chloro-2-phenyl-2,3-dihydrobenzofuran-4-yl)-3-fluoro-4-methoxybenzamide (Example 5a) and 2-((2S,4R)-2-(aminomethyl)-5-chloro-2-phenyl-2,3-dihydrobenzofuran-4-yl)-3-fluoro-4-methoxybenzamide (Example 5b)

Example 5a

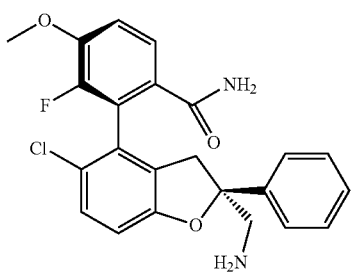

Example 5b

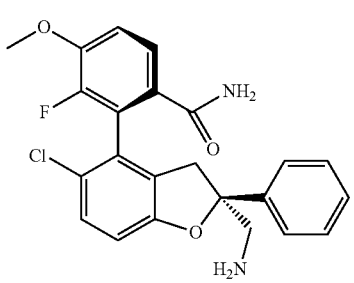

Reaction Scheme Example 5

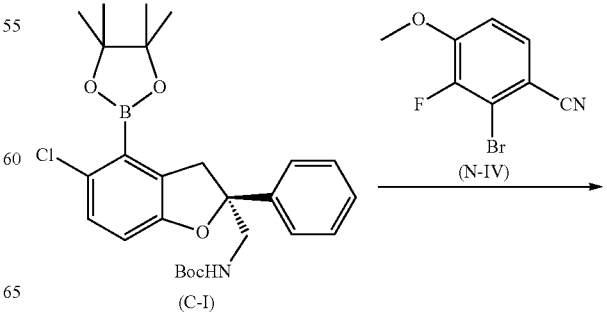

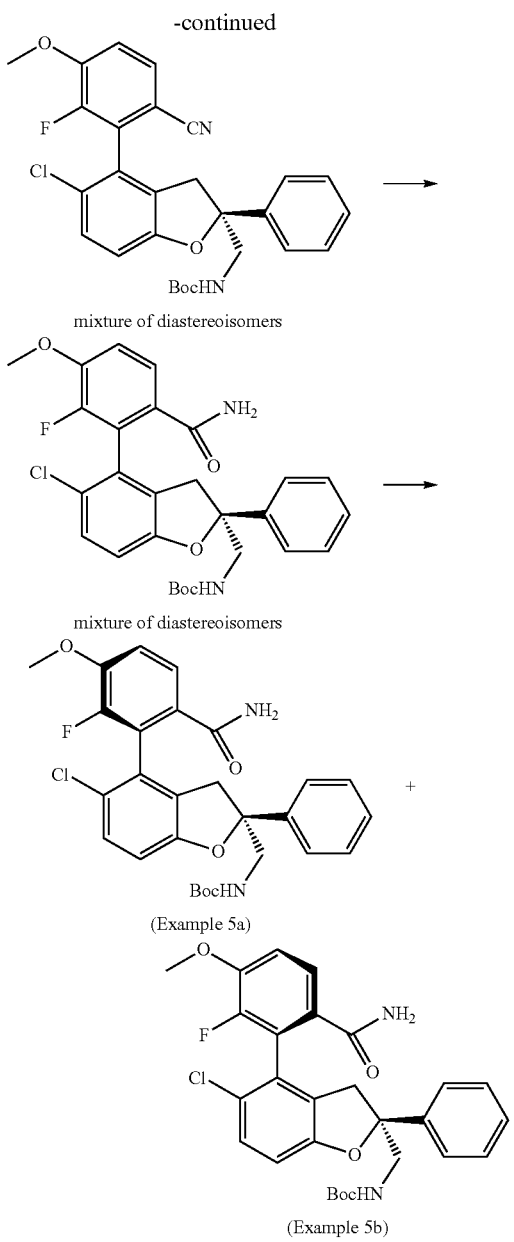

mixture of diastereoisomers mixture of diastereoisomers (Example 5a)

(Example 5b)

Step 1: Tert-butyl (((2S,4S)-5-chloro-4-(6-cyano-2-fluoro-3-methoxyphenyl)-2-phenyl-2,3-dihydrobenzofuran-2-yl)methyl)carbamate and tert-butyl (((2S,4R)-5-chloro-4-(6-cyano-2-fluoro-3-methoxyphenyl)-2-phenyl-2,3-dihydrobenzofuran-2-yl)methyl)carbamate A suspension of (S)-tert-butyl ((5-chloro-2-phenyl-4-(4,4,5,5-tetramethyl-1,3,2-dioxaborolan-2-yl)-2,3-dihydrobenzofuran-2-yl)methyl)carbamate (C-I) (4.5 g, 9.26 mmol), 2-bromo-3-fluoro-4-methoxybenzonitrile (N-IV) (2.56 g, 11.12 mmol), tris(dibenzylideneacetone)dipalladium(0) (0.424 g, 0.463 mmol), 4,6-bis(diphenylphosphino)-10H-phenoxazine (0.511 g, 0.926 mmol) and $K_3PO_4$ (5.90 g, 27.8 mmol) in toluene (50 mL) and water (10 mL) was stirred at 100° C. for 16 h under Ar. The reaction mixture was quenched by the addition of a sat solution of $NaHCO_3$, then extracted with EtOAc. The organic layers were combined and washed with a sat solution of $NaHCO_3$, dried over anhydous $Na_2SO_4$ and concentrated. The residue was purified by flash chromatography (silica, hexane/EtOAc, gradient 0% to 70% EtOAc) to afford a mixture of the title compounds (4.08 g). UPLC-MS 1: m/z 509.3 $[M+H]^+$, $t_R$=1.31 min and 1.34 min.

Step 2: Tert-butyl (((2S,4S)-4-(6-carbamoyl-2-fluoro-3-methoxyphenyl)-5-chloro-2-phenyl-2,3-dihydrobenzofuran-2-yl)methyl)carbamate and tert-butyl (((2S,4R)-4-(6-carbamoyl-2-fluoro-3-methoxyphenyl)-5-chloro-2-phenyl-2,3-dihydrobenzofuran-2-yl)methyl)carbamate At RT hydrido(dimethylphosphinous acid-kP)[hydrogen bis(dimethylphosphinito-kP)]platinum(II) (CAS 173416-05-2) (0.688 g, 1.603 mmol) was added to a solution of a mixture of tert-butyl (((2S,4S)-5-chloro-4-(6-cyano-2-fluoro-3-methoxyphenyl)-2-phenyl-2,3-dihydrobenzofuran-2-yl)methyl)carbamate and tert-butyl (((2S,4R)-5-chloro-4-(6-cyano-2-fluoro-3-methoxyphenyl)-2-phenyl-2,3-dihydrobenzofuran-2-yl)methyl)carbamate (4.08 g, 8.02 mmol) in EtOH (50 mL) and water (10 mL). Then, the reaction mixture was stirred at 80° C. for 1 h. The reaction mixture was quenched by the addition of a sat solution of $NaHCO_3$ and extracted with EtOAc. The organic layers were combined and washed with a sat solution of $NaHCO_3$, dried over anhydrous $Na_2SO_4$ and concentrated. The residue was purified by flash chromatography (silica, hexane/EtOAc, gradient 0% to 100% EtOAc) to afford a mixture of the title compounds (4.02 g). UPLC-MS 1: m/z 527.3 $[M+H]^+$, $t_R$=1.15 min and 1.20 min.

Step 3: 2-((2S,4S)-2-(Aminomethyl)-5-chloro-2-phenyl-2,3-dihydrobenzofuran-4-yl)-3-fluoro-4-methoxybenzamide (Example 5a) and 2-((2S,4R)-2-(aminomethyl)-5-chloro-2-phenyl-2,3-dihydrobenzofuran-4-yl)-3-fluoro-4-methoxybenzamide (Example 5b)

At RT TFA (5.88 mL, 76 mmol) was added to a solution of a mixture of tert-butyl (((2S,4S)-4-(6-carbamoyl-2-fluoro-3-methoxyphenyl)-5-chloro-2-phenyl-2,3-dihydrobenzofuran-2-yl)methyl)carbamate and tert-butyl (((2S,4R)-4-(6-carbamoyl-2-fluoro-3-methoxyphenyl)-5-chloro-2-phenyl-2,3-dihydrobenzofuran-2-yl)methyl)carbamate (4.02 g, 7.63 mmol) in DCM (80 mL) and stirring at RT was continued for 1 h. The reaction mixture was quenched by the addition of a sat solution of $NaHCO_3$ and extracted with DCM. The organic layers were combined and washed with a sat solution of $NaHCO_3$, dried over anhydrous $Na_2SO_4$ and concentrated. The residue was purified by flash chromatography (silica, DCM/(MeOH/$NH_4OH$ (80:20)), gradient 0% to 10% (MeOH/$NH_4OH$ (80:20))) to afford the desired compounds as single diastereoisomers.

2-((2S,4S)-2-(Aminomethyl)-5-chloro-2-phenyl-2,3-dihydrobenzofuran-4-yl)-3-fluoro-4-methoxybenzamide (Example 5a) (1.36 g): $^1$H NMR (400 MHz, DMSO-$d_6$) δ (ppm) 7.53 (s br, 1H), 7.48 (d, J=8.6 Hz, 1H), 7.40-7.31 (m, 4H), 7.28-7.20 (m, 3H), 7.18 (s br, 1H), 6.88 (d, J=8.6 Hz, 1H), 3.88 (s, 3H), 3.45 (d, J=16.4 Hz, 1H), 2.90-2.81 (m, 3H), 1.40 (s br, 2H). UPLC-MS 1: m/z 427.2 $[M+H]^+$, $t_R$=0.76 min.

2-((2S,4R)-2-(Aminomethyl)-5-chloro-2-phenyl-2,3-dihydrobenzofuran-4-yl)-3-fluoro-4-methoxybenzamide (Example 5b) (1.41 g): $^1$H NMR (400 MHz, DMSO-$d_6$) δ (ppm) 7.48-7.42 (m, 2H), 7.40-7.30 (m, 4H), 7.29-7.23 (m, 2H), 7.19 (d, J=8.6 Hz, 1H), 6.94 (s br, 1H), 6.85 (d, J=8.6 Hz, 1H), 3.92 (s, 3H), 3.30 (d, J=16.0 Hz, 1H), 3.07 (d, J=16.0

Hz, 1H), 2.86 (dd, J=19.9, 13.3 Hz, 2H), 1.46 (s br, 2H). UPLC-MS 1: m/z 427.3 [M+H]⁺, $t_R$=0.59 min.

The following compounds were prepared analogously to Example 5a

Example 18: 4-((2S,4S)-2-(Aminomethyl)-5-chloro-2-phenyl-2,3-dihydrobenzofuran-4-yl)-5-fluoro-6-methoxynicotinamide

| Ex. | Structure/Chemical Name | UPLC MS m/z [M + H]⁺ $t_R$ [min] (method) | ¹H NMR |
|---|---|---|---|
| 4a-1 | 2-((2S,4S)-2-(aminomethyl)-5-chloro-2-phenyl-2,3-dihydrobenzofuran-4-yl)-3-fluorobenzamide; 2-bromo-3-fluorobenzonitrile used in Suzuki coupling. The absolute configuration was confirmed by an X-ray cocrystal structure of Example 4a-1 bound to the YAP binding site of TEAD4 | 397.2 0.76 (1) | (400 MHz, DMSO-d₆) δ (ppm) 7.68 (s br, 1H), 7.56-7.50 (m, 1H), 7.47-7.43 (m, 1H), 7.40-7.31 (m, 6H), 7.28-7.22 (m, 2H), 6.90 (d, J = 8.6 Hz, 1H), 3.50 (d, J = 16.0 Hz, 1H), 2.93-2.82 (m, 3H), 1.66 (s br, 2H) |
| 6 | 2-((2S,4R)-2-(aminomethyl)-5-chloro-2-phenyl-2,3-dihydrobenzofuran-4-yl)-3-methylbenzamide; 2-bromo-3-methylbenzonitrile used in Suzuki coupling | 393.2 0.85 (1) | (400 MHz, DMSO-d₆) δ (ppm) 7.51 (s br, 1H), 7.43-7.20 (m, 7H), 7.29-7.20 (m, 2H), 7.18 (s br, 1H), 6.87 (d, J = 8.6 Hz, 1H), 3.43 (d, J = 16.4 Hz, 1H), 2.90 (dd, J = 24.6, 14.1 Hz, 2H), 2.72 (d, J = 16.0 Hz, 1H), 1.75 (s, 3H) |
| 7 | 2-((2S,4S)-2-(aminomethyl)-5-chloro-2-phenyl-2,3-dihydrobenzofuran-4-yl)-3-chlorobenzamide trifluoroacetate salt; 2-bromo-3-chlorobenzonitrile used in Suzuki coupling | 413.1 0.83 (1) | (600 MHz, DMSO-d₆) δ (ppm) 7.98 (s, 1H), 7.91 (s, 2H), 7.65 (d, J = 7.9 Hz, 1H), 7.56 (d, J = 7.6 Hz, 1H), 7.53 (d, J = 7.8 Hz, 1H), 7.50 (d, J = 7.9 Hz, 2H), 7.45-7.40 (m, 3H), 7.38-7.31 (m, 2H), 7.00 (d, J = 8.6 Hz, 1H), 3.48 (d, J = 16.4 Hz, 1H), 3.40 (s, 2H), 2.89 (d, J = 16.3 Hz, 1H) |

-continued

Example 18:
4-((2S,4S)-2-(Aminomethyl)-5-chloro-2-phenyl-2,3-dihydrobenzofuran-4-yl)-5-fluoro-6-methoxynicotinamide

| Ex. | Structure/Chemical Name | UPLC MS m/z [M + H]$^+$ t$_R$ [min] (method) | $^1$H NMR |
|---|---|---|---|
| 8 | 2-((2S,4S)-2-(aminomethyl)-5-chloro-2-phenyl-2,3-dihydrobenzofuran-4-yl)-4-chloro-3-fluorobenzamide; 2-bromo-4-chloro-3-fluorobenzonitrile used in Suzuki coupling | 431.1 0.88 (1) | (600 MHz, DMSO-d$_6$) δ (ppm) 7.82 (s, 1H), 7.75 (t, J = 7.7 Hz, 1H), 7.47 (d, J = 8.4 Hz, 2H), 7.38 (d, J = 7.6 Hz, 2H), 7.34 (t, J = 7.5 Hz, 2H), 7.26 (t, J = 7.7 Hz, 2H), 6.93 (d, J = 8.7 Hz, 1H), 3.50 (d, J = 16.2 Hz, 1H), 2.93-2.80 (m, 3H), 1.35 (s, 2H) |
| 9 | 2-((2S,4S)-2-(aminomethyl)-5-chloro-2-phenyl-2,3-dihydrobenzofuran-4-yl)-3,4-difluorobenzamide; 2-bromo-3,4-difluorobenzonitrile used in Suzuki coupling | 415.1 0.84 (1) | (400 MHz, DMSO-d$_6$) δ (ppm) 7.75 (s br, 1H), 7.64-7.55 (m, 1H), 7.54-7.47 (m, 1H), 7.42-7.31 (m, 5H), 7.30-7.23 (m, 2H), 6.93 (d, J = 8.2 Hz, 1H), 3.50 (d, J = 16.4 Hz, 1H), 2.97-2.82 (m, 3H), 1.43 (s br, 2H) |
| 10 | 2-((2S,4S)-2-(aminomethyl)-5-chloro-2-phenyl-2,3-dihydrobenzofuran-4-yl)-3-fluoro-4-(2-hydroxyethoxy)benzamide; 2-bromo-3-fluoro-4-(2-hydroxyethoxy)benzonitrile (N-VII) used in Suzuki coupling The absolute configuration was confirmed by an X-ray cocrystal structure of Example 10 bound to the YAP binding site of TEAD4 | 457.2 0.64 (1) | (600 MHz, DMSO-d$_6$) δ (ppm) 7.57 (s br, 1H), 7.44 (d, J = 8.6 Hz, 1H), 7.38 (d, J = 7.3 Hz, 2H), 7.33 (t, J = 7.7 Hz, 2H), 7.26 (dt, J = 8.3, 4.9 Hz, 2H), 7.23-7.16 (m, 2H), 6.89 (d, J = 8.5 Hz, 1H), 4.93 (t, J = 5.4 Hz, 1H), 4.11 (t, J = 4.8 Hz, 2H), 3.72 (q, J = 5.0 Hz, 2H), 3.45 (d, J = 16.1 Hz, 1H), 2.92-2.81 (m, 3H), 1.60 (s br, 2H) |

-continued

Example 18:
4-((2S,4S)-2-(Aminomethyl)-5-chloro-2-phenyl-2,3-dihydrobenzofuran-4-yl)-5-fluoro-6-methoxynicotinamide

| Ex. | Structure/Chemical Name | UPLC MS m/z [M + H]+ $t_R$ [min] (method) | $^1$H NMR |
|---|---|---|---|
| 11 | 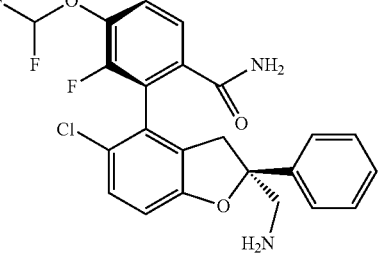<br>2-((2S,4S)-2-(aminomethyl)-5-chloro-2-phenyl-2,3-dihydrobenzofuran-4-yl)-4-(difluoromethoxy)-3-fluorobenzamide; 2-bromo-4-(difluoromethoxy)-3-fluorobenzonitrile (N-V) used in Suzuki coupling | 463.1<br>0.80 (1) | (400 MHz, DMSO-d$_6$) δ (ppm) 7.74 (s br, 1H), 7.53-7.46 (m, 2H), 7.42-7.31 (m, 6H), 7.29-7.23 (m, 2H), 6.92 (d, J = 8.6 Hz, 1H), 3.49 (d, J = 16.4 Hz, 1H), 2.93-2.82 (m, 3H), 1.55 (s br, 2H) |
| 12 | 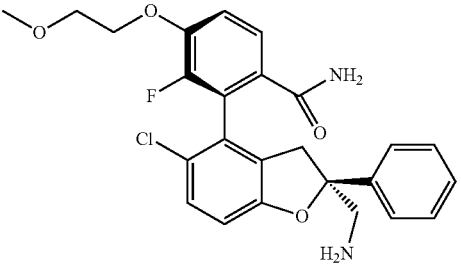<br>2-((2S,4S)-2-(aminomethyl)-5-chloro-2-phenyl-2,3-dihydrobenzofuran-4-yl)-3-fluoro-4-(2-methoxyethoxy)benzamide; 2-bromo-3-fluoro-4-(2-methoxyethoxy)benzonitrile (N-IX) used in Suzuki coupling | 471.2<br>0.78 (1) | (600 MHz, DMSO-d$_6$) δ (ppm) 7.59 (s br, 1H), 7.45 (d, J = 8.6 Hz, 1H), 7.39 (d, J = 7.7 Hz, 2H), 7.34 (t, J = 7.6 Hz, 2H), 7.27 (t, J = 7.5 Hz, 2H), 7.24-7.19 (m, 2H), 6.90 (d, J = 8.5 Hz, 1H), 4.22 (s br, 2H), 3.70-3.63 (m, 2H), 3.45 (d, J = 16.2 Hz, 1H), 3.27 (s, 3H), 2.96-2.82 (m, 3H) |
| 13 | 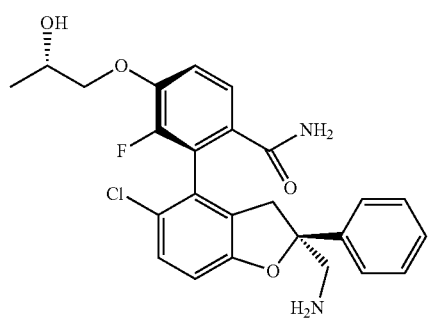<br>2-((2S,4S)-2-(aminomethyl)-5-chloro-2-phenyl-2,3-dihydrobenzofuran-4-yl)-3-fluoro-4-((S)-2-hydroxypropoxy)benzamide; (S)-2-bromo-3-fluoro-4-(2-hydroxypropoxy)benzonitrile (N-XIV) used in Suzuki coupling | 471.3<br>0.70 (1) | (400 MHz, DMSO-d6) δ (ppm) 7.50 (s br, 1H), 7.43 (d, J = 8.6 Hz, 1H), 7.40-7.29 (m, 4H), 7.28-7.18 (m, 3H), 7.15 (s br, 1H), 6.88 (d, J = 8.6 Hz, 1H), 4.90 (d, J = 4.3 Hz, 1H), 3.99-3.86 (m, 3H), 3.44 (d, J = 16.0 Hz, 1H), 2.90-2.81 (m, 3H), 1.34 (s br, 2H), 1.11 (d, J = 5.9 Hz, 3H) |

-continued

Example 18:
4-((2S,4S)-2-(Aminomethyl)-5-chloro-2-phenyl-2,3-dihydrobenzofuran-4-yl)-5-fluoro-6-methoxynicotinamide

| Ex. | Structure/Chemical Name | UPLC MS m/z [M + H]+ $t_R$ [min] (method) | $^1$H NMR |
|---|---|---|---|
| 14 | 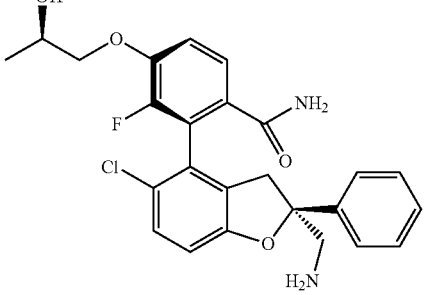<br>2-((2S,4S)-2-(aminomethyl)-5-chloro-2-phenyl-2,3-dihydrobenzofuran-4-yl)-3-fluoro-4-((R)-2-hydroxypropoxy)benzamide; (R)-2-bromo-3-fluoro-4-(2-hydroxypropoxy)benzonitrile (N-XV) used in Suzuki coupling | 471.3<br>0.69 (1) | (400 MHz, DMSO-d$_6$) δ (ppm) 7.51 (s br, 1H), 7.43 (d, J = 8.6 Hz, 1H), 7.38-7.28 (m, 4H), 7.27-7.17 (m, 3H), 7.15 (s br, 1H), 6.88 (d, J = 8.6 Hz, 1H), 4.90 (d, J = 4.7 Hz, 1H), 3.97-3.87 (m, 3H), 3.44 (d, J = 16.0 Hz, 1H), 2.90-2.80 (m, 3H), 1.33 (s br, 2H), 1.11 (d, J = 5.5 Hz, 3H) |
| 15 | 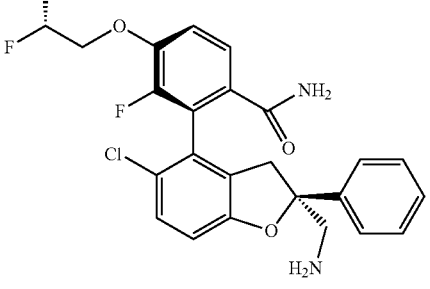<br>2-((2S,4S)-2-(aminomethyl)-5-chloro-2-phenyl-2,3-dihydrobenzofuran-4-yl)-3-fluoro-4-((R)-2-fluoropropoxy)benzamide; (R)-2-bromo-3-fluoro-4-(2-fluoropropoxy)benzonitrile (N-VIII) used in Suzuki coupling | 473.3<br>0.83 (1) | (400 MHz, DMSO-d$_6$) δ (ppm) 7.61 (s br, 1H), 7.49 (d, J = 8.7 Hz, 1H), 7.32-7.23 (m, 8H), 6.93 (d, J = 8.6 Hz, 1H), 5.06 (m, 1H), 4.36-4.18 (m, 2H), 3.49 (d, J = 15.1 Hz, 1H), 2.95-2.86 (m, 3H), 1.38 (dd, J = 23.6, 6.4 Hz, 3H). |
| 16 | 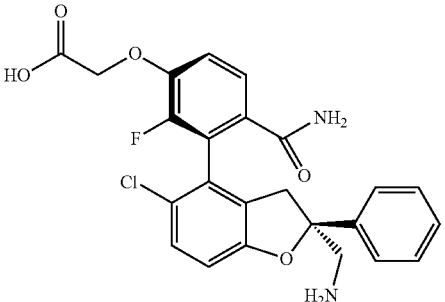<br>2-(3-((2S,4S)-2-(aminomethyl)-5-chloro-2-phenyl-2,3-dihydrobenzofuran-4-yl)-4-carbamoyl-2-fluorophenoxy)acetic acid trifluoroacetate salt; Ethyl 2-(3-bromo-4-cyano-2-fluorophenoxy)acetate (N-XVI) was used in the Suzuki coupling. The ethylester was saponified prior to Boc deprotection | 471.3<br>0.62 (1) | (400 MHz, DMSO-d$_6$) δ (ppm) 7.90 (s br, 3H), 7.75 (s, 1H), 7.50-7.29 (m, 7H), 7.22 (s br, 1H), 7.16 (t, J = 8.6 Hz, 1H), 6.98 (d, J = 8.6 Hz, 1H), 4.81 (s, 2H), 3.48 (d, J = 16.8 Hz, 1H), 3.44-3.31 (m, 2H), 2.94 (d, J = 16.4 Hz, 1H). |

-continued

Example 18:
4-((2S,4S)-2-(Aminomethyl)-5-chloro-2-phenyl-2,3-dihydrobenzofuran-4-yl)-5-fluoro-6-methoxynicotinamide

| Ex. | Structure/Chemical Name | UPLC MS m/z [M + H]$^+$ t$_R$ [min] (method) | $^1$H NMR |
|---|---|---|---|
| 17 | 4-(((R)-4-acetylmorpholin-2-yl)methoxy)-2-((2S,4S)-2-(aminomethyl)-5-chloro-2-phenyl-2,3-dihydrobenzofuran-4-yl)-3-fluorobenzamide; (R)-4-((4-acetylmorpholin-2-yl)methoxy)-2-bromo-3-fluorobenzonitrile (N-XVII) was used in the Suzuki coupling | 554.3 0.67 (1) | (400 MHz, CD$_3$OD) δ (ppm) 7.52-7.48 (m, 1H), 7.42-7.33 (m, 7H), 6.90 (dd, J = 8.6, 2.0 Hz, 1H), 4.49-4.45 (m, 1H), 4.30-4.25 (m, 1H), 4.21-4.16 (m, 3H), 3.96-3.71 (m, 4H), 3.61-3.37 (m, 3H), 3.27-3.20 (m, 1H), 3.07-2.93 (m, 3H), 2.88-2.73 (m, 1H), 2.09 (d, J = 5.9 Hz, 3H). |

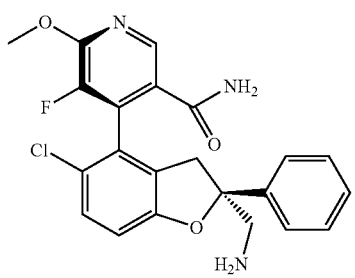

Step 1: Methyl 4-((2S,4S)-2-(((tert-butoxycarbonyl)amino)methyl)-5-chloro-2-phenyl-2,3-dihydrobenzofuran-4-yl)-5-fluoro-6-methoxynicotinate and methyl 4-((2S,4R)-2-(((tert-butoxycarbonyl)amino)methyl)-5-chloro-2-phenyl-2,3-dihydrobenzofuran-4-yl)-5-fluoro-6-methoxynicotinate A 20 mL MW vial was charged with (S)-tert-butyl ((5-chloro-2-phenyl-4-(4,4,5,5-tetramethyl-1,3,2-dioxaborolan-2-yl)-2,3-dihydrobenzofuran-2-yl)methyl)carbamate (C-I) (200 mg, 0.412 mmol), methyl 4-chloro-5-fluoro-6-methoxynicotinate (N-XXIX) (136 mg, 0.618 mmol) and K$_3$PO$_4$ (262 mg, 1.235 mmol). toluene (6 mL) and water (1.5 mL) were added and the mixture was degassed with nitrogen. Then, N-Xantphos (22.71 mg, 0.041 mmol) and Pd$_2$(dba)$_3$ (18.85 mg, 0.021 mmol) were added, the vial was sealed and the reaction mixture was heated at 100° C. for 12 h. After cooling to RT the reaction mixture was partitioned between water and EtOAc. The organic phase was separated and the aqueous phase was extracted again with EtOAc. The combined organic layers were washed with brine, dried over anhydrous Na$_2$SO$_4$ and concentrated. The crude product was purified by flash chromatography (silica, cyclohexane/EtOAc, gradient: 10% to 20% EtOAc) to afford a mixture of the title compounds (122 mg). UPLC-MS 2: m/z 543.1 [M+H]$^+$, t$_R$=7.25 and 7.34 min.

Step 2: 4-((2S,4S)-2-(((Tert-butoxycarbonyl)amino)methyl)-5-chloro-2-phenyl-2,3-dihydrobenzofuran-4-yl)-5-fluoro-6-methoxynicotinic acid and 4-((2S,4R)-2-(((tert-butoxycarbonyl)amino)methyl)-5-chloro-2-phenyl-2,3-dihydrobenzofuran-4-yl)-5-fluoro-6-methoxynicotinic acid A mixture of methyl 4-((2S,4S)-2-(((tert-butoxycarbonyl)amino)methyl)-5-chloro-2-phenyl-2,3-dihydrobenzofuran-4-yl)-5-fluoro-6-methoxynicotinate and 4-((2S,4R)-2-(((tert-butoxycarbonyl)amino)methyl)-5-chloro-2-phenyl-2,3-dihydrobenzofuran-4-yl)-5-fluoro-6-methoxynicotinic acid (122 mg, 0.225 mmol) was dissolved in THF (5 mL) and water (1 mL). LiOH·H$_2$O (94 mg, 2.25 mmol) was added and the reaction mixture was stirred at 55° C. for 4 h. After cooling to RT the reaction mixture was partitioned between EtOAc and a sat solution of NaHSO$_4$. The organic phase was separated, dried over anhydrous Na$_2$SO$_4$ and concentrated to yield a mixture of the title compounds (124 mg). UPLC-MS 1: m/z 529.2 [M+H]$^+$, t$_R$=1.27 and 1.32 min.

Step 3: Tert-butyl (((2S,4S)-4-(5-carbamoyl-3-fluoro-2-methoxypyridin-4-yl)-5-chloro-2-phenyl-2,3-dihydrobenzofuran-2-yl)methyl)carbamate and tert-butyl (((2S,4R)-4-(5-carbamoyl-3-fluoro-2-methoxypyridin-4-yl)-5-chloro-2-phenyl-2,3-dihydrobenzofuran-2-yl)methyl)carbamate A solution of a mixture of 4-((2S,4S)-2-(((tert-butoxycarbonyl)amino)methyl)-5-chloro-2-phenyl-2,3-dihydrobenzofuran-4-yl)-5-fluoro-6-methoxynicotinic acid and 4-((2S,4R)-2-(((tert-butoxycarbonyl)amino)methyl)-5-chloro-2-phenyl-2,3-dihydrobenzofuran-4-yl)-5-fluoro-6-methoxynicotinic acid (120 mg, 0.227 mmol), DIPEA (0.12 mL, 0.68 mmol) and HATU (129 mg, 0.34 mmol) in DMF (2 mL) was stirred for 5 min at RT. $NH_3$ (1.361 mL, 0.681 mmol, 0.5 M in dioxane) was added dropwise and stirring at RT was continued for 2 h. For workup, EtOAc and a 10% citric acid solution were added and the mixture was vigorously stirred for 5 min. The organic layer was separated and washed with a sat solution of $NaHCO_3$ and brine, dried over anhydrous $Na_2SO_4$ and concentrated to afford a mixture of the title compounds. UPLC-MS 1: m/z 528.2 [M+H]$^+$, $t_R$=1.15 and 1.20 min.

Step 4: 4-((2S,4S)-2-(Aminomethyl)-5-chloro-2-phenyl-2,3-dihydrobenzofuran-4-yl)-5-fluoro-6-methoxynicotinamide (Example 18)

TFA (912 µl, 11.8 mmol) was added drowpise to a solution of a mixture of tert-butyl (((2S,4S)-4-(5-carbamoyl-3-fluoro-2-methoxypyridin-4-yl)-5-chloro-2-phenyl-2,3-dihydrobenzofuran-2-yl)methyl)carbamate and tert-butyl (((2S,4R)-4-(5-carbamoyl-3-fluoro-2-methoxypyridin-4-yl)-5-chloro-2-phenyl-2,3-dihydrobenzofuran-2-yl)methyl)carbamate (250 mg, 0.237 mmol) in DCM (4 mL) and stirring was continued at RT for 3 h. The reaction mixture was concentrated and azeotroped with DCM. The residue was purified by preparative HPLC and the diastereoisomers were separated:

4-((2S,4S)-2-(Aminomethyl)-5-chloro-2-phenyl-2,3-dihydrobenzofuran-4-yl)-5-fluoro-6-methoxynicotinamide (25 mg) as a colorless powder (Example 18): $^1$H NMR (400 MHz, $CD_3OD$) δ (ppm) 8.32 (s, 1H), 7.43-7.34 (m, 4H), 7.30-7.24 (m, 2H), 6.94 (d, J=8.6 Hz, 1H), 4.06 (s, 3H), 3.42 (d, J=16.0 Hz, 1H), 3.05 (d, J=16.4 Hz, 1H), 3.04 (d, J=14.1 Hz, 1H), 2.96 (d, J=14.1 Hz, 1H). UPLC-MS 1: m/z 428.2 [M+H]$^+$, $t_R$=0.77 min. The absolute configuration was confirmed by an X-ray cocrystal structure of Example 18 bound to the YAP binding site of TEAD3. Other diastereoisomer 4-((2S,4R)-2-(aminomethyl)-5-chloro-2-phenyl-2,3-dihydrobenzofuran-4-yl)-5-fluoro-6-methoxynicotinamide (16 mg) as a colorless powder: UPLC-MS 1: m/z 428.2 [M+H]$^+$, $t_R$=0.64 min.

Example 19: 4-((2S,4S)-2-(Aminomethyl)-5-chloro-2-phenyl-2,3-dihydrobenzofuran-4-yl)-6-(difluoromethoxy)-5-fluoronicotinamide

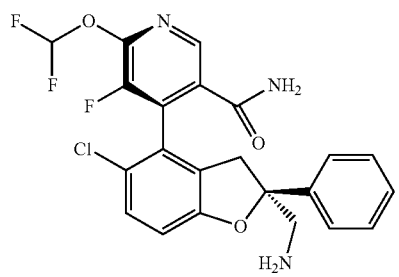

The title compound was prepared analogously to Example 18 from intermediates tert-butyl (S)-((5-chloro-2-phenyl-4-(4,4,5,5-tetramethyl-1,3,2-dioxaborolan-2-yl)-2,3-dihydrobenzofuran-2-yl)methyl)carbamate (C-I) and methyl 4-chloro-6-(difluoromethoxy)-5-fluoronicotinate (N-XXX).

4-((2S,4S)-2-(Aminomethyl)-5-chloro-2-phenyl-2,3-dihydrobenzofuran-4-yl)-6-(difluoromethoxy)-5-fluoronicotinamide (Example 19): $^1$H NMR (400 MHz, DMSO-$d_6$) δ (ppm) 8.36 (s, 1H), 8.01 (s br, 1H), 7.80 (t, J=71.5 Hz, 1H), 7.58 (s br, 1H), 7.40-7.23 (m, 6H), 6.97 (d, J=8.6 Hz, 1H), 3.47 (d, J=16.4 Hz, 1H), 2.99 (d, J=16.0 Hz, 1H), 2.90 (s, 2H). UPLC-MS 1: m/z 464.2 [M+H]$^+$, $t_R$=0.84 min.

Other diastereoisomer 4-((2S,4R)-2-(aminomethyl)-5-chloro-2-phenyl-2,3-dihydrobenzofuran-4-yl)-6-(difluoromethoxy)-5-fluoronicotinamide: UPLC-MS 1: m/z 464.2 [M+H]$^+$, $t_R$=0.68 min.

Example 20: 2-((2S,4S)-2-(Aminomethyl)-5-chloro-2-phenyl-2,3-dihydrobenzofuran-4-yl)-3-fluoro-4-(methylamino)benzamide

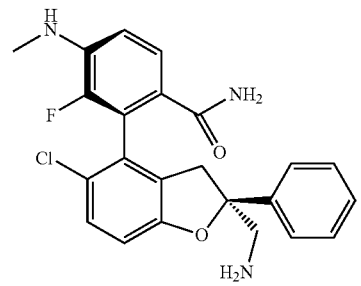

Step 1: Tert-butyl (((2S,4S)-5-chloro-4-(6-cyano-2,3-difluorophenyl)-2-phenyl-2,3-dihydrobenzofuran-2-yl)methyl)carbamate and tert-butyl (((2S,4R)-5-chloro-4-(6-cyano-2,3-difluorophenyl)-2-phenyl-2,3-dihydrobenzofuran-2-yl)methyl)carbamate A mixture of the title compounds (0.89 g, colorless powder) was obtained from (S)-tert-butyl ((5-chloro-2-phenyl-4-(4,4,5,5-tetramethyl-1,3,2-dioxaborolan-2-yl)-2,3-dihydrobenzofuran-2-yl)methyl)carbamate (C-I) (1.5 g, 3.1 mmol), 2-bromo-3,4-difluoro-benzonitrile (0.81 g, 3.7 mmol) using similar reaction conditions as described for Example 5a, step 1. UPLC-MS 1: m/z 397.1 [M+H−Boc]$^+$, $t_R$=1.35 min and 1.38 min.

Step 2: Tert-butyl (((2S,4S)-5-chloro-4-(6-cyano-2-fluoro-3-(methylamino)phenyl)-2-phenyl-2,3-dihydrobenzofuran-2-yl)methyl)carbamate and tert-butyl (((2S,4R)-5-chloro-4-(6-cyano-2-fluoro-3-(methylamino)phenyl)-2-phenyl-2,3-dihydrobenzofuran-2-yl)methyl)carbamate A 5 mL MW vial was charged with a mixture of tert-butyl (((2S,4S)-5-chloro-4-(6-cyano-2,3-difluorophenyl)-2-phenyl-2,3-dihydrobenzofuran-2-yl)methyl)carbamate and tert-butyl (((2S,4R)-5-chloro-4-(6-cyano-2,3-difluorophenyl)-2-phenyl-2,3-dihydrobenzofuran-2-yl)methyl)carbamate (85 mg, 0.171 mmol) and methylamine solution in THF (428 µl, 0.86 mmol, 2 M in THF) and the reaction mixture was heated at 100° C. for 1 h under MW irradiation. The reaction mixture was quenched with 75 mL of sat solution of NaHCO₃, then extracted with EtOAc. The organic layers were combined and washed with a sat solution of NaHCO₃, dried over anhydrous Na₂SO₄ and concentrated. The residue was purified by flash chromatography (silica, hexane/EtOAc; gradient: 0% to 70% EtOAc to afford a mixture of the title compounds (86 mg) as a colorless powder. UPLC-MS 1: m/z 552.2 [M+formate]⁻, $t_R$=1.28 min and 1.30 min.

Step 3: Tert-butyl (((2S,4S)-4-(6-carbamoyl-2-fluoro-3-(methylamino)phenyl)-5-chloro-2-phenyl-2,3-dihydrobenzofuran-2-yl)methyl)carbamate and tert-butyl (((2S,4R)-4-(6-carbamoyl-2-fluoro-3-(methylamino)phenyl)-5-chloro-2-phenyl-2,3-dihydrobenzofuran-2-yl)methyl)carbamate A mixture of the title compounds (80 mg) was obtained from a mixture of tert-butyl (((2S,4S)-5-chloro-4-(6-cyano-2-fluoro-3-(methylamino)phenyl)-2-phenyl-2,3-dihydrobenzofuran-2-yl)methyl)carbamate and tert-butyl (((2S,4R)-5-chloro-4-(6-cyano-2-fluoro-3-(methylamino)phenyl)-2-phenyl-2,3-dihydrobenzofuran-2-yl)methyl)carbamate following the procedure as described for Example 5a, step 2. UPLC-MS 1: m/z 526.2 [M+H]⁺, $t_R$=1.13 min and 1.18 min.

Step 4: 2-((2S,4S)-2-(Aminomethyl)-5-chloro-2-phenyl-2,3-dihydrobenzofuran-4-yl)-3-fluoro-4-(methylamino)benzamide (Example 20)

To a stirred solution of a mixture of tert-butyl (((2S,4S)-4-(6-carbamoyl-2-fluoro-3-(methylamino)phenyl)-5-chloro-2-phenyl-2,3-dihydrobenzofuran-2-yl)methyl)carbamate and tert-butyl (((2S,4R)-4-(6-carbamoyl-2-fluoro-3-(methylamino)phenyl)-5-chloro-2-phenyl-2,3-dihydrobenzofuran-2-yl)methyl)carbamate (80 mg, 0.15 mmol) in DCM (3 mL) was added TFA (0.117 mL, 1.52 mmol) and stirring at RT was continued for 2 h. The reaction mixture was quenched with a sat solution of NaHCO₃, then extracted with DCM. The organic layers were combined and washed with a sat solution of NaHCO₃, dried over anhydrous Na₂SO₄ and concentrated. The residue was purified by flash chromatography (silica:DCM/(MeOH/NH₄OH: 80/20); gradient: 0% to 10% (MeOH/NH₄OH: 80/20)) and the diastereoisomers were separated.

2-((2S,4S)-2-(Aminomethyl)-5-chloro-2-phenyl-2,3-dihydrobenzofuran-4-yl)-3-fluoro-4-(methylamino)benzamide (Example 20): ¹H NMR (400 MHz, DMSO-d₆) δ (ppm) 7-45-7.30 (m, 5H), 7.28-7.21 (m, 2H), 7.19 (d, J=8.6 Hz, 1H), 6.90 (s br, 1H), 6.86 (d, J=8.6 Hz, 1H), 6.66 (t, J=8.6 Hz, 1H), 5.99-5.93 (m, 1H), 3.43-3.24 (m, 2H), 2.88-2.85 (m, 2H), 2.73 (d, J=5.1 Hz, 3H). UPLC-MS 1: m/z 426.2 [M+H]⁺, $t_R$=0.75 min.

Other diastereoisomer 2-((2S,4R)-2-(aminomethyl)-5-chloro-2-phenyl-2,3-dihydrobenzofuran-4-yl)-3-fluoro-4-(methylamino)benzamide: UPLC-MS 1: m/z 426.2 [M+H]⁺, $t_R$=0.62 min.

Example 21: 2-((2S,4S)-5-Chloro-2-((methylamino)methyl)-2-phenyl-2,3-dihydrobenzofuran-4-yl)-3-fluoro-4-methoxybenzamide

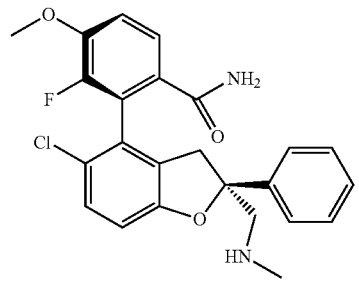

Step 1: (S)-tert-butyl ((5-chloro-2-phenyl-4-(4,4,5,5-tetramethyl-1,3,2-dioxaborolan-2-yl)-2,3-dihydrobenzofuran-2-yl)methyl)(methyl)carbamate At 0° C. sodium hydride (78 mg, 3.09 mmol, 95%) was added to a solution of (S)-tert-butyl ((5-chloro-2-phenyl-4-(4,4,5,5-tetramethyl-1,3,2-dioxaborolan-2-yl)-2,3-dihydrobenzofuran-2-yl)methyl)carbamate (C-I) (500 mg, 1.03 mmol) in DMF (7 mL). After 5 min methyl iodide (644 μl, 10.3 mmol) was added and the reaction mixture was allowed to stir at RT for 3.5 h. Water was added and the reaction mixture was extracted with EtOAc. Drying of the combined organic layers using a phase separator cartridge and concentration gave the crude product which was purified by flash chromatography (silica; cyclohexane/EtOAc; gradient: 0% to 20% EtOAc) to afford the title compound (283 mg) as a colorless foam. UPLC-MS 1: m/z 500.4 [M+H]⁺, $t_R$=1.59 min.

Step 2: Tert-butyl (((2S,4S)-5-chloro-4-(6-cyano-2-fluoro-3-methoxyphenyl)-2-phenyl-2,3-dihydrobenzofuran-2-yl)methyl)(methyl)carbamate and tert-butyl (((2S,4R)-5-chloro-4-(6-cyano-2-fluoro-3-methoxyphenyl)-2-phenyl-2,3-dihydrobenzofuran-2-yl)methyl)(methyl)carbamate A mixture of the title compounds (67 mg, yellow oil) was obtained from (S)-tert-butyl ((5-chloro-2-phenyl-4-(4,4,5,5-tetramethyl-1,3,2-dioxaborolan-2-yl)-2,3-dihydrobenzofuran-2-yl)methyl)(methyl)carbamate (150 mg, 0.300 mmol) and 2-bromo-3-fluoro-4-methoxybenzonitrile (N-IV) (83 mg, 0.36 mmol) using similar reaction conditions as described for Example 5a, step. 1. UPLC-MS 1: m/z 523.4 [M+H]⁺, $t_R$=1.41 min (both diastereoisomers coelute).

Step 3: Tert-butyl (((2S,4S)-4-(6-carbamoyl-2-fluoro-3-methoxyphenyl)-5-chloro-2-phenyl-2,3-dihydrobenzofuran-2-yl)methyl)(methyl)carbamate and tert-butyl (((2S,4R)-4-(6-carbamoyl-2-fluoro-3-methoxyphenyl)-5-chloro-2-phenyl-2,3-dihydrobenzofuran-2-yl)methyl)(methyl)carbamate A mixture of the title compounds was obtained from a mixture of tert-butyl (((2S,4S)-5-chloro-4-(6-cyano-2-fluoro-3-methoxyphenyl)-2-phenyl-2,3-dihydrobenzofuran-2-yl)methyl)(methyl)carbamate and tert-butyl (((2S,4R)-5-chloro-4-(6-cyano-2-fluoro-3-methoxyphenyl)-2-phenyl-2,3-dihydrobenzofuran-2-yl)methyl)(methyl)carbamate following the procedure as described for Example 5a, step 2. UPLC-MS 1: m/z 541.3 [M+H]⁺, $t_R$=1.24 and 1.25 min

Step 4: 2-((2S,4S)-5-chloro-2-((methylamino)methyl)-2-phenyl-2,3-dihydrobenzofuran-4-yl)-3-fluoro-4-methoxybenzamide (Example 21)

The title compound (9 mg, colorless powder) was obtained from a mixture of tert-butyl (((2S,4S)-4-(6-carbamoyl-2-fluoro-3-methoxyphenyl)-5-chloro-2-phenyl-2,3-dihydrobenzofuran-2-yl)methyl)(methyl)carbamate and tert-butyl (((2S,4R)-4-(6-carbamoyl-2-fluoro-3-methoxyphenyl)-5-chloro-2-phenyl-2,3-dihydrobenzofuran-2-yl)methyl)(methyl)carbamate (72 mg, 0.12 mmol) using similar reaction conditions as described for Example 5a, step 3 followed by chromatographic separation of the diastereoisomers.

2-((2S,4S)-5-Chloro-2-((methylamino)methyl)-2-phenyl-2,3-dihydrobenzofuran-4-yl)-3-fluoro-4-methoxybenzamide (Example 21): ¹H NMR (400 MHz, DMSO-d₆) δ (ppm) 7.50 (d, 8.6 Hz, 1H), 7.47 (s br, 1H), 7.43-7.38 (m, 2H), 7.37-7.32 (m, 2H), 7.30-7.21 (m, 3H), 7.18 (s br, 1H), 6.91 (d, J=8.6 Hz, 1H), 3.88 (s, 3H), 3.48 (d, J=16.1 Hz, 1H), 3.00 (s, 2H), 2.86 (d, J=16.1 Hz, 1H), 2.26 (s, 3H). UPLC-MS 1: m/z 441.3 [M+H]⁺, $t_R$=0.79 min.

Other diastereoisomer 2-((2S,4R)-5-chloro-2-((methylamino)methyl)-2-phenyl-2,3-dihydrobenzofuran-4-yl)-3-fluoro-4-methoxybenzamide: UPLC-MS 1: m/z 441.3 [M+H]⁺, $t_R$=0.63 min.

Example 22: 2-((2S,4S)-2-(Aminomethyl)-5-chloro-2-phenyl-2,3-dihydrobenzofuran-4-yl)-3-fluoro-4-methoxy-N-methylbenzamide

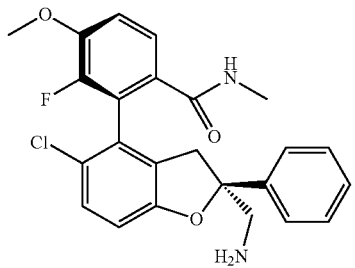

Step 1: Methyl 2-((2S,4S)-2-(((tert-butoxycarbonyl)amino)methyl)-5-chloro-2-phenyl-2,3-dihydrobenzofuran-4-yl)-3,4-difluorobenzoate and methyl 2-((2S,4R)-2-(((tert-butoxycarbonyl)amino)methyl)-5-chloro-2-phenyl-2,3-dihydrobenzofuran-4-yl)-3,4-difluorobenzoate A mixture of the title compounds (365 mg) was obtained from (S)-tert-butyl ((5-chloro-2-phenyl-4-(4,4,5,5-tetramethyl-1,3,2-dioxaborolan-2-yl)-2,3-dihydrobenzofuran-2-yl)methyl)carbamate (C-I) (600 mg, 1.24 mmol) and methyl 2-bromo-3,4-difluorobenzoate (372 mg, 1.482 mmol) using similar reaction conditions as described for Example 5a, step. 1. UPLC-MS 1: m/z 530.3 [M+H]⁺, $t_R$=1.42 min and 1.44 min.

Step 2: 2-((2S,4S)-2-(((Tert-butoxycarbonyl)amino)methyl)-5-chloro-2-phenyl-2,3-dihydrobenzofuran-4-yl)-3,4-difluorobenzoic acid and 2-((2S,4R)-2-(((tert-butoxycarbonyl)amino)methyl)-5-chloro-2-phenyl-2,3-dihydrobenzofuran-4-yl)-3,4-difluorobenzoic acid A mixture of the title compounds (300 mg, colorless powder) was obtained from a mixture of methyl 2-((2S,4S)-2-(((tert-butoxycarbonyl)amino)methyl)-5-chloro-2-phenyl-2,3-dihydrobenzofuran-4-yl)-3,4-difluorobenzoate and methyl 2-((2S,4R)-2-(((tert-butoxycarbonyl)amino)methyl)-5-chloro-2-phenyl-2,3-dihydrobenzofuran-4-yl)-3,4-difluorobenzoate (365 mg, 0.69 mmol) using similar reaction conditions as described for Example 18, step. 2. UPLC-MS 1: m/z 514.4 [M−H]⁻, $t_R$=1.25 min and 1.31 min.

Step 3: Tert-butyl (((2S,4S)-5-chloro-4-(2,3-difluoro-6-(methylcarbamoyl)phenyl)-2-phenyl-2,3-dihydrobenzofuran-2-yl)methyl)carbamate and tert-butyl (((2S,4R)-5-chloro-4-(2,3-difluoro-6-(methylcarbamoyl)phenyl)-2-phenyl-2,3-dihydrobenzofuran-2-yl)methyl)carbamate HBTU (130 mg, 0.342 mmol) was added to a solution of a mixture of 2-((2S,4S)-2-(((tert-butoxycarbonyl)amino)methyl)-5-chloro-2-phenyl-2,3-dihydrobenzofuran-4-yl)-3,4-difluorobenzoic acid and 2-((2S,4R)-2-(((tert-butoxycarbonyl)amino)methyl)-5-chloro-2-phenyl-2,3-dihydrobenzofuran-4-yl)-3,4-difluorobenzoic acid (157 mg, 0.23 mmol), methylamine hydrochloride (23.11 mg, 0.342 mmol) and DIPEA (239 µl, 1.37 mmol) in DMF (2.3 mL). The reaction mixture was stirred at RT for 15 h. EtOAc was added and the organic phase was washed with 1 N HCl, a sat solution of NaHCO₃ and brine. Drying (phase separator cartridge) and evaporation of the solvent afforded the crude product. The title compounds were obtained by preparative HPLC (Waters Sunfire C18 OBD, 5 µm, 30*100 mm, Eluent A: H₂O+0.1% TFA, B: ACN+0.1% TFA, Gradient: 20 to 95% B in 20 min hold 3 min, Flow 40 mL/min) as separate diastereoisomers.

Tert-butyl (((2S,4S)-5-chloro-4-(2,3-difluoro-6-(methylcarbamoyl)phenyl)-2-phenyl-2,3-dihydrobenzofuran-2-yl)methyl)carbamate (39 mg, colorless powder): UPLC-MS 1: m/z 529.3 [M+H]⁺, $t_R$=1.31 min.

Tert-butyl (((2S,4R)-5-chloro-4-(2,3-difluoro-6-(methylcarbamoyl)phenyl)-2-phenyl-2,3-dihydrobenzofuran-2-yl)methyl)carbamate (50 mg, colorless powder): UPLC-MS 1: m/z 529.4 [M+H]⁺, $t_R$=1.24 min.

Step 4: Tert-butyl (((2S,4S)-5-chloro-4-(2-fluoro-3-methoxy-6-(methylcarbamoyl)phenyl)-2-phenyl-2,3-dihydrobenzofuran-2-yl)methyl)carbamate Sodium methoxide in methanol (169 µl, 0.737 mmol, 25%) was added to a solution of tert-butyl (((2S,4S)-5-chloro-4-(2,3-difluoro-6-(methylcarbamoyl)phenyl)-2-phenyl-2,3-dihydrobenzofuran-2-yl)methyl)carbamate (39 mg, 0.074 mmol) in MeOH (1.8 mL) and the reaction mixture was heated under microwave irradiation at 100° C. for 1 h. More sodium methoxide in methanol (169 µl, 0.737 mmol, 25%) was added and heating under microwave irradiation was continued for another 1 h 15 min. A sat solution of NaHCO₃ was added and the mixture was extracted with EtOAc. Drying (phase separator cartridge) of the combined organic layers and concentration gave the title compound (36 mg, 0.057 mmol) as a a colorless powder. UPLC-MS 1: m/z 541.3 [M+H]⁺, $t_R$=1.25 min.

Step 5: 2-((2S,4S)-2-(Aminomethyl)-5-chloro-2-phenyl-2,3-dihydrobenzofuran-4-yl)-3-fluoro-4-methoxy-N-methylbenzamide (Example 22)

A solution of tert-butyl (((2S,4S)-5-chloro-4-(2-fluoro-3-methoxy-6-(methylcarbamoyl)phenyl)-2-phenyl-2,3-dihydrobenzofuran-2-yl)methyl)carbamate (36 mg, 0.057 mmol) in HCl (0.28 mL, 1.13 mmol, 4 M in dioxane) was stirred at RT for 2 h. The solvent was evaporated and the crude product was purified by preparative HPLC.(Waters X-Bridge 018 OBD, 5 μm, 30*100 mm, Eluent A: H₂O+7.3 mM NH₄OH, B: ACN, Gradient: 20% for 4 min, then 20 to 80% B in 20 min hold 3 min, Flow 40 mL/min) to afford the title compound (13 mg) as a colorless powder. ¹H NMR (400 MHz, DMSO-d₆) δ (ppm) 8.11-8.07 (m, 1H), 7.47-7.34 (m, 5H), 7.33-7.27 (m, 2H), 7.25 (d, J=8.6 Hz, 1H), 6.92 (d, J=8.6 Hz, 1H), 3.91 (s, 3H), 3.45 (d, J=16.1 Hz, 1H), 2.91-2.84 (m, 3H), 2.63 (d, J=4.5 Hz, 3H). UPLC-MS 1: m/z 441.4 [M+H]⁺, $t_R$=0.79 min.

The following compounds were prepared analogously to Example 22

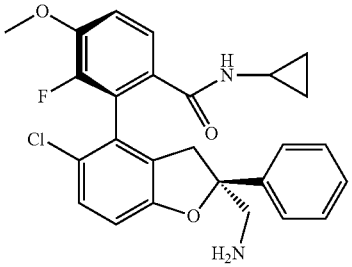

| Ex. | Structure/Chemical Name | UPLC MS m/z [M + H]⁺ $t_R$ [min] (method) | ¹H NMR |
|---|---|---|---|
| 23 | 2-((2S,4S)-2-(aminomethyl)-5-chloro-2-phenyl-2,3-dihydrobenzofuran-4-yl)-N-cyclopropyl-3-fluoro-4-methoxybenzamide | 467.3 0.87 (1) | (400 MHz, DMSO-d₆) δ (ppm) 8.11 (d, J = 3.8 Hz, 1H), 7.45-7.35 (m, 5H), 7.33-7.24 (m, 3H), 6.95 (d, J = 8.6 Hz, 1H), 3.90 (s, 3H), 3.46 (d, J = 16.1 Hz, 1H), 2.98 (s, 2H), 2.88 (d, J = 16.3 Hz, 1H), 2.66-2.59 (m, 1H), 0.65-0.55 (m, 2H), 0.48-0.39 (m, 1H), 0.39-0.30 (m, 1H) |
| 24 | 2-((2S,4S)-2-(aminomethyl)-5-chloro-2-phenyl-2,3-dihydrobenzofuran-4-yl)-3,4-difluoro-N-(1-methyl-1H-pyrazol-5-yl)benzamide | 495.3 0.83 (1) | (400 MHz, DMSO-d₆) δ (ppm) 7.78-7.71 (m, 2H), 7.44-7.28 (m, 7H), 6.98 (d, J = 8.6 Hz, 1H), 6.12 (d, J = 1.8 Hz, 1H), 3.56 (s, 3H), 3.52 (d, J = 16.3 Hz, 1H), 3.00 (d, J = 16.4 Hz, 1H), 2.90 (s, 2H) |
| 25 | 2-((2S,4S)-2-(aminomethyl)-5-chloro-2-phenyl-2,3-dihydrobenzofuran-4-yl)-3-fluoro-4-methoxy-N-(pyridin-3-yl)benzamide | 504.3 0.80 (1) | (400 MHz, DMSO-d₆) δ (ppm) 10.5 (s, 1H), 8.75 (d, J = 2.5 Hz, 1H), 8.27 (dd, J = 4.7, 1.2 Hz, 1H), 8-04-7.99 (m, 1H), 7.68 (d, J = 8.3 Hz, 1H), 7.43-7.28, m, 6H), 7.25 (d, J = 8.6 Hz, 1H), 6.92 (d, J = 8.6 Hz, 1H), 3.96 (s, 3H), 3.50 (d, J = 16.3 Hz, 1H), 2.94 (d, J = 16.3 Hz, 1H), 2.88 (d, J = 2.5 Hz, 2H) |

Example 26: 2-((2S,4S)-5-Chloro-2-((methylamino)methyl)-2-phenyl-2,3-dihydrobenzofuran-4-yl)-3-fluoro-4-methoxy-N-methylbenzamide

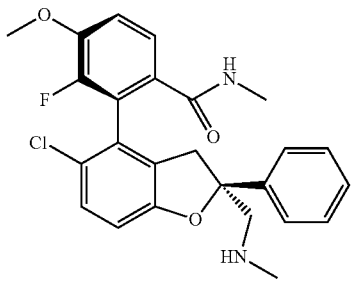

The title compound was prepared analogously to Example 22 starting from (S)-tert-butyl ((5-chloro-2-phenyl-4-(4,4,5,5-tetramethyl-1,3,2-dioxaborolan-2-yl)-2,3-dihydrobenzofuran-2-yl)methyl)(methyl)carbamate (Example. 21, step 1) and methyl 2-bromo-3,4-difluorobenzoate. NMR (400 MHz, DMSO-$d_6$) δ (ppm) 8.06-8.01 (m, 1H), 7.47-7.33 (m, 5H), 7.32-7.26 (m, 2H), 7.24 (d, J=8.6 Hz, 1H), 6.90 (d, J=8.4 Hz, 1H), 3.90 (s, 3H), 3.50 (d, J=16.0 Hz, 1H), 2.88 (s, 2H), 2.83 (d, J=16.0 Hz, 1H), 2.65 (d, J=4.5 Hz, 3H), 2.25 (s, 3H). UPLC-MS 1: m/z 455.3 [M+H]$^+$, $t_R$=0.81 min.

The diastereoisomers were separated after methylamide formation: tert-butyl (((2S,4S)-5-chloro-4-(2,3-difluoro-6-(methylcarbamoyl)phenyl)-2-phenyl-2,3-dihydrobenzofuran-2-yl)methyl)(methyl)carbamate: UPLC-MS 1: m/z 543.4 [M+H]$^+$, $t_R$=1.36 min; tert-butyl (((2S,4R)-5-chloro-4-(2,3-difluoro-6-(methylcarbamoyl)phenyl)-2-phenyl-2,3-dihydrobenzofuran-2-yl)methyl)(methyl)carbamate: UPLC-MS 1: m/z 543.4 [M+H]$^+$, $t_R$=1.34 min.

Example 27a and Example 27b: 2-((2S,4S)-5-Chloro-2-(((trans-4-hydroxycyclohexyl)amino)methyl)-2-phenyl-2,3-dihydrobenzofuran-4-yl)-3-fluoro-4-methoxybenzamide (Example 27a) and 2-((2S,4S)-5-chloro-2-(((cis-4-hydroxycyclohexyl)amino)methyl)-2-phenyl-2,3-dihydrobenzofuran-4-yl)-3-fluoro-4-methoxybenzamide (Example 27b)

Example 27a

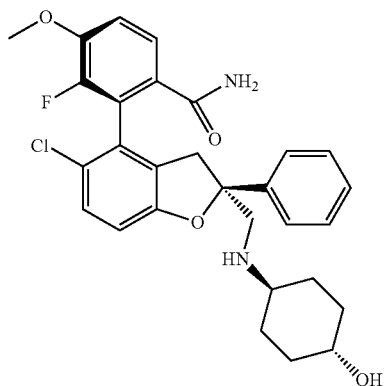

Example 27b

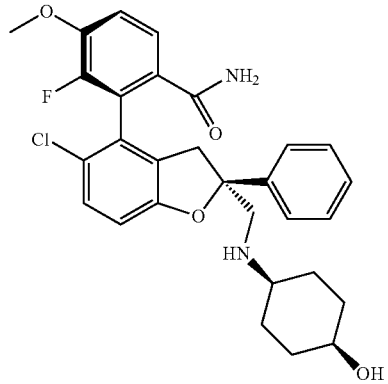

Reaction Scheme Example 27

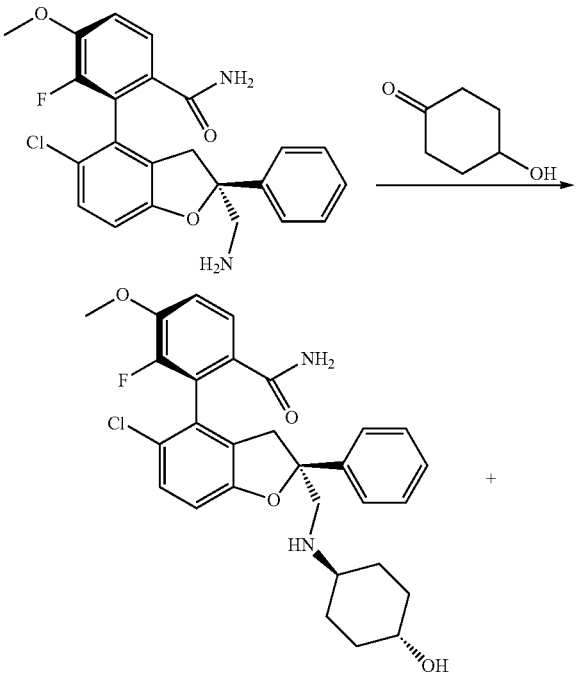

Example 27a

Example 27b

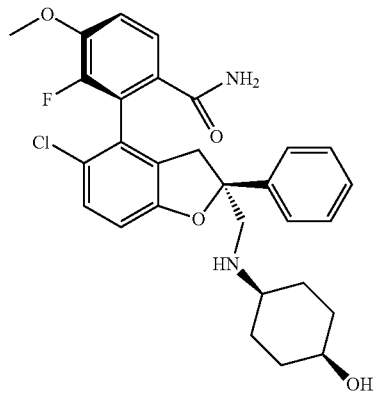

At RT sodium triacetoxyborohydride (894 mg, 4.22 mmol) was added to a solution of 2-((2S,4S)-2-(aminomethyl)-5-chloro-2-phenyl-2,3-dihydrobenzofuran-4-yl)-3-fluoro-4-methoxybenzamide (Example 5a) (600 mg, 1.406 mmol), 4-hydroxycyclohexanone (193 mg, 1.687 mmol) and acetic acid (0.080 mL, 1.406 mmol) in DCM (15 mL). Then, the reaction mixture was stirred at RT for 1 h. The reaction mixture was quenched by the addition of a sat solution of NaHCO$_3$, then extracted with DCM. The organic layers were combined and washed with a sat solution of NaHCO$_3$, dried over anhydrous Na$_2$SO$_4$ and concentrated. The residue was purified by flash chromatography (silica, DCM/MeOH, gradient 0% to 10% MeOH) and the diastereoisomers were separated.

2-((2S,4S)-5-Chloro-2-((((trans)-4-hydroxycyclohexyl)amino)methyl)-2-phenyl-2,3-dihydrobenzofuran-4-yl)-3-fluoro-4-methoxybenzamide (278 mg) (Example 27a): $^1$H NMR (400 MHz, DMSO-d$_6$) δ (ppm) 7.48 (d, J=8.7 Hz, 1H), 7.40-7.34 (m, 3H), 7.30 (t, J=7.4 Hz, 2H), 7.26-7.17 (m, 3H), 7.12 (s, 1H), 6.86 (d, J=8.6 Hz, 1H), 4.35 (d, J=4.4 Hz, 1H), 3.86 (s, 3H), 3.45 (d, J=15.9 Hz, 1H), 3.26-3.20 (m, 1H), 2.99-2.85 (m, 2H), 2.78 (d, J=15.9 Hz, 1H), 2.23-2.11 (m, 1H), 1.75-1.56 (m, 4H), 1.20-1.10 (m, 1H), 1.10-0.94 (m, 2H), 0.93-0.77 (m, 2H). UPLC-MS 2: m/z 525.3 [M+H]$^+$, t$_R$=3.67 min. The absolute configuration was confirmed by an X-ray cocrystal structure of Example 27a bound to the YAP binding site of TEAD4.

2-((2S,4S)-5-Chloro-2-((((cis)-4-hydroxycyclohexyl)amino)methyl)-2-phenyl-2,3-dihydrobenzofuran-4-yl)-3-fluoro-4-methoxybenzamide (350 mg) (Example 27b): $^1$H NMR (400 MHz, DMSO-d$_6$) δ (ppm) 7.49 (d, J=8.6 Hz, 1H), 7.44 (s, 1H), 7.40-7.35 (m, 2H), 7.31 (t, J=7.6 Hz, 2H), 7.27-7.17 (m, 3H), 7.10 (s, 1H), 6.87 (d, J=8.5 Hz, 1H), 4.23 (d, J=3.6 Hz, 1H), 3.86 (s, 3H), 3.50 (d, J=16.0 Hz, 1H), 2.93 (s, 2H), 2.79 (d, J=15.9 Hz, 1H), 2.38-2.29 (m, 1H), 1.56-1.20 (m, 9H). UPLC-MS 2: m/z 525.3 [M+H]$^+$, t$_R$=3.73 min.

Example 28a and Example 28b: (Trans)-4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylic acid (Example 28a) and (cis)-4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylic acid (Example 28b)

Example 28a

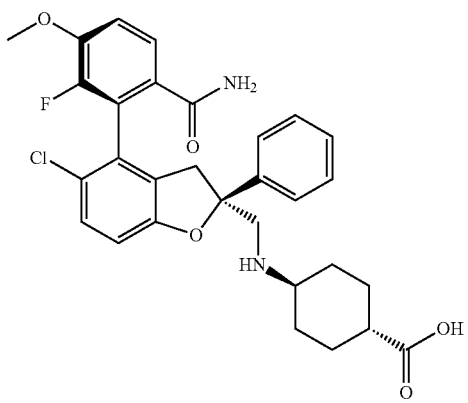

Example 28b

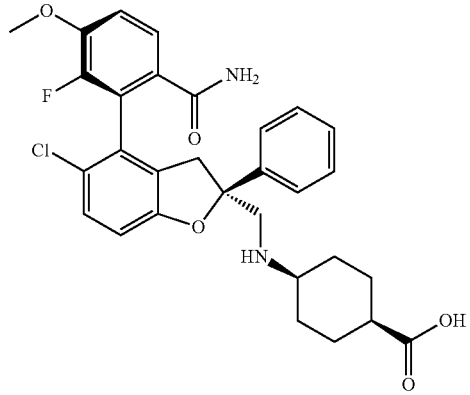

Step 1: (Trans)-methyl 4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylate and (cis)-methyl 4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylate To a stirred solution of 2-((2S,4S)-2-(aminomethyl)-5-chloro-2-phenyl-2,3-dihydrobenzofuran-4-yl)-3-fluoro-4-methoxybenzamide (Example 5a) (100 mg, 0.23 mmol) in DCM (4 mL) was added under Ar 4-oxocyclohexanecarboxylic acid methyl ester (47.6 mg, 0.305 mmol), NaBH(OAc)$_3$ (149 mg, 0.70 mmol) and AcOH (13 µl, 0.23 mmol). Then, the reaction mixture was stirred for 2.5 h at RT. The reaction mixture was quenched with a sat solution of NaHCO$_3$ and extracted with DCM. The organic layers were combined and washed with brine, dried (phase separator cartridge) and concentrated. The residue was purified by preparative HPLC (Waters X-Bridge C18 OBD, 5 µm, 30*100 mm, Eluent A: H$_2$O+7.3 mM NH$_4$OH, B: ACN, Gradient: 10% for 4 min, then 10 to 80% B in 20 min hold 3 min, Flow 40 mL/min). Both diastereoisomers were separated. The fractions from each diastereoisomer were extracted twice with EtOAc/sat solution of NaHCO$_3$. The combined organic layers were washed with brine and dried (phase separator cartridge) to afford:

(Trans)-methyl 4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylate (21 mg): UPLC-MS 1: m/z 567.4 [M+H]$^+$, t$_R$=0.88 min.

(Cis)-methyl 4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylate (47 mg) as colorless powders. UPLC-MS 1: m/z 567.4 [M+H]$^+$, t$_R$=0.89 min.

Step 2a: (Trans)-4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylic acid (Example 28a)

To a stirred solution of (trans)-methyl 4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylate (21 mg, 0.037 mmol) in dioxane (1 mL) and water (0.35 mL) was added LiOH·H$_2$O (2.3 mg, 0.056 mmol).

Then, the reaction mixture was stirred at RT for 16 h. The reaction mixture was concentrated and the residue was purified by preparative HPLC (Waters X-Bridge C18 OBD, 5 μm, 30*100 mm, Eluent A: H$_2$O+7.3 mM NH$_4$OH, B: ACN, Gradient: 10% for 4 min, then 10 to 95% B in 20 min hold 3 min, Flow 40 mL/min). Lyophilisation of the product fractions afforded the title compound (10 mg) as a colorless powder. $^1$H NMR (400 MHz, DMSO-d$_6$) δ (ppm): 11.99 (s br, 1H), 7.53 (d, J=8.6 Hz, 1H), 7.43-7.19 (m, 9H), 6.91 (d, J=8.6 Hz, 1H), 3.90 (s, 3H), 3.51 (d, J=16 Hz, 1H), 3.03-2.94 (m, 2H), 2.83 (d, J=16 Hz, 1H), 2.25-2.21 (m, 1H), 2.11-2.04 (m, 1H) 1.83-1.74 (m, 4H), 1.28-1.18 (m, 2H), 0.96-0.87 (m, 2H). UPLC-MS 1: m/z 553.3 [M+H]$^+$, t$_R$=0.82 min. UPLC-MS 2: m/z 553.3 [M+H]$^+$, t$_R$=3.79 min.

Step 2 b: (Cis)-4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylic acid (Example 28b)

The title compound (18 mg, colorless powder) was obtained from (cis)-methyl 4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylate (47 mg) using similar reaction conditions as described for Example. 28a. $^1$H NMR (400 MHz, DMSO-d$_6$) δ (ppm): 11.93 (s br, 1H), 7.53-7.51 (m, 2H), 7.43-7.23 (m, 7H), 7.11 (s br, 1H), 6.92 (d, J=8.6 Hz, 1H), 3.90 (s, 3H), 3.50 (d, J=16 Hz, 1H), 2.96 (s br, 2H), 2.84 (d, J=16 Hz, 1H), 2.48-2.44 (m, 1H), 2.32-2.25 (m, 1H), 1.78-1.66 (m, 2H), 1.52-1.20 (m, 7H). UPLC-MS 1: m/z 553.3 [M+H]$^+$, t$_R$=0.84 min. UPLC-MS 2: m/z 553.3 [M+H]$^+$, t$_R$=3.90 min.

Example 29: 2-((2R,4S)-2-(Aminomethyl)-5-chloro-2-(thiazol-4-yl)-2,3-dihydrobenzofuran-4-yl)-3-fluoro-4-methoxybenzamide

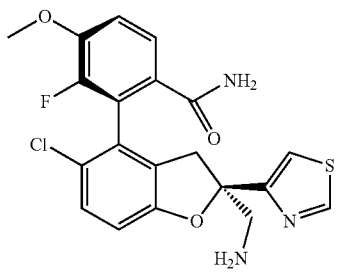

The title compound was prepared analogously to Example 5a from intermediates tert-butyl ((5-chloro-4-(4,4,5,5-tetramethyl-1,3,2-dioxaborolan-2-yl)-2-(thiazol-4-yl)-2,3-dihydrobenzofuran-2-yl)methyl)carbamate (C-III) and 2-bromo-3-fluoro-4-methoxybenzonitrile (N-IV).

After final Boc-deprotection the racemic diastereoisomers were first separated by flash chromatography (silica, DCM/MeOH, gradient: MeOH 0 to 10%): racemic (2R*,4S*) diastereoisomer: UPLC-MS 1: t$_R$=0.68 min, racemic (2R*,4R*) diastereoisomer: UPLC-MS 1: t$_R$=0.56 min. The (2R*,4S*) racemate was subjected to chiral HPLC (Chiralpak AD-H 250×30 mm, 5 μm, EtOH/MeOH 1:1+0.1% DEA, flow rate: 10 mL/min) to afford both enantiomers in an enantiomeric excess of >98%.

2-((2R,4S)-2-(Aminomethyl)-5-chloro-2-(thiazol-4-yl)-2,3-dihydrobenzofuran-4-yl)-3-fluoro-4-methoxybenzamide (Example 29): Chiral HPLC (Chiralpak AD-H 250×4.6 mm, 5 μm, EtOH/MeOH 1:1+0.1% DEA, flow rate: 1 mL/min) t$_R$=3.55 min. $^1$H NMR (400 MHz, DMSO-d$_6$) δ 9.03 (d, J=1.9 Hz, 1H), 7.60 (d, J=1.9 Hz, 1H), 7.50 (s, 1H), 7.44 (d, J=8.6 Hz, 1H), 7.22 (t, J=8.5 Hz, 1H), 7.18 (d, J=8.5 Hz, 1H), 7.12 (s, 1H), 6.80 (d, J=8.5 Hz, 1H), 3.85 (s, 3H), 3.30 (d, J=16.3 Hz, 1H), 3.04 (d, J=16.2 Hz, 1H), 2.98 (s, 2H), 1.60 (br s, 2H). UPLC-MS 1: m/z 434.2 [M+H]$^+$, t$_R$=0.68 min.

Other enantiomer 2-((2S,4R)-2-(aminomethyl)-5-chloro-2-(thiazol-4-yl)-2,3-dihydrobenzofuran-4-yl)-3-fluoro-4-methoxybenzamide: Chiral HPLC (Chiralpak AD-H 250×4.6 mm, 5 μm, EtOH/MeOH 1:1+0.1% DEA, flow rate: 1 mL/min) t$_R$=10.56 min.

Example 30: 2-((2S,4S)-2-(aminomethyl)-5-chloro-2-(2,2-difluorobenzo[d][1,3]dioxol-4-yl)-2,3-dihydrobenzofuran-4-yl)-3-fluorobenzamide

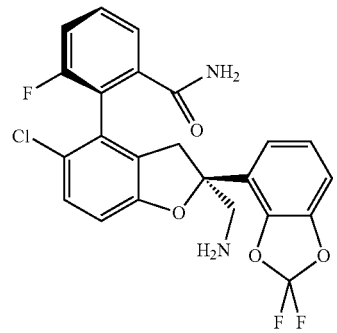

The title compound was prepared analogously to Example 5a from intermediates tert-butyl-((5-chloro-2-(2,2-difluorobenzo[d][1,3]dioxol-4-yl)-4-(4,4,5,5-tetramethyl-1,3,2-dioxaborolan-2-yl)-2,3-dihydrobenzofuran-2-yl)methyl)carbamate (C-IV) and 2-bromo-3-fluorobenzonitrile. After final Boc-deprotection the racemic diastereoisomers were first separated by flash chromatography (silica, DCM/(MeOH+ 2% 7M NH$_3$ in MeOH), gradient: (MeOH+2% 7M NH$_3$ in MeOH) 20 to 100%): racemic (2S*,4S*) diastereoisomer: UPLC-MS 1: t$_R$=0.83 min, racemic (2S*,4R*) diastereoisomer: UPLC-MS 1: t$_R$=0.68 min. The (2S*,4S*) racemate was subjected to chiral HPLC (LuxCellulose 250×21 mm, 2.5 μm, heptane/IPA 7:3+0.05% DEA, flow rate: 10 mL/min) to afford both enantiomers in an enantiomeric excess of >98%, respectively.

2-((2S,4S)-2-(Aminomethyl)-5-chloro-2-(2,2-difluorobenzo[d][1,3]dioxol-4-yl)-2,3-dihydrobenzofuran-4-yl)-3-fluorobenzamide (Example 30): Chiral HPLC (Chiralpak OZ-H 250×4.6 mm, 5 μm, heptane/IPA 6:4+0.05% DEA, flow rate: 1 mL/min) t$_R$=8.73 min. $^1$H NMR (400 MHz, DMSO-d$_6$) δ 7.76 (s, 1H), 7.58-7.51 (m, 1H), 7.45 (dd, J=7.7, 1.2 Hz, 1H), 7.43-7.29 (m, 3H), 7.31-7.13 (m, 3H), 6.93 (d, J=8.5 Hz, 1H), 3.47 (d, J=16.3 Hz, 1H), 3.06-2.90 (m, 3H). UPLC-MS 1: m/z 477.0 [M+H]$^+$, t$_R$=0.86 min.

Other enantiomer 2-((2R,4R)-2-(aminomethyl)-5-chloro-2-(2,2-difluorobenzo[d][1,3]dioxol-4-yl)-2,3-dihydrobenzofuran-4-yl)-3-fluorobenzamide: Chiral HPLC (Chiralpak OZ-H 250×4.6 mm, 5 μm, heptane/IPA 6:4+0.05% DEA, flow rate: 1 mL/min) t$_R$=12.22 min.

Example 31: 2-((2S,4S)-2-(Aminomethyl)-5-chloro-2-(2-fluorophenyl)-2,3-dihydrobenzofuran-4-yl)-3-fluoro-4-methoxybenzamide

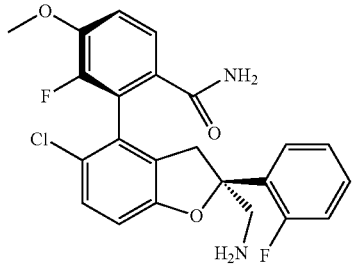

The title compound was prepared analogously to Example 5a from tert-butyl (S)-((5-chloro-2-(2-fluorophenyl)-4-(4,4,5,5-tetramethyl-1,3,2-dioxaborolan-2-yl)-2,3-dihydrobenzofuran-2-yl)methyl)carbamate (C-V) (170 mg, 9.36 mmol) and 2-bromo-3-fluoro-4-methoxybenzonitrile (N-IV). 2-((2S,4S)-2-(Aminomethyl)-5-chloro-2-(2-fluorophenyl)-2,3-dihydrobenzofuran-4-yl)-3-fluoro-4-methoxybenzamide (Example 31): $^1$H NMR (600 MHz, DMSO-$d_6$) δ (ppm) 7.63 (s, 1H), 7.57 (t, J=7.7 Hz, 1H), 7.47 (d, J=8.6 Hz, 1H), 7.38-7.30 (m, 1H), 7.29-7.13 (m, 5H), 6.92 (d, J=8.6 Hz, 1H), 3.87 (s, 3H), 3.44 (d, J=16.0 Hz, 1H), 2.98 (d, J=14.2 Hz, 1H), 2.90 (br. d, J=17.5 Hz, 1H), 2.85 (br. d, J=14.9 Hz, 1H), 1.68 (br. s, 2H). UPLC-MS 1: m/z 445.1/447.2 [M+H]$^+$, $t_R$=0.76 min.

Other diastereoisomer 2-((2S,4R)-2-(aminomethyl)-5-chloro-2-(2-fluorophenyl)-2,3-dihydrobenzofuran-4-yl)-3-fluoro-4-methoxybenzamide: UPLC-MS 1: m/z 445.2/447.1 [M+H]$^+$, $t_R$=0.61 min.

Example 32a and Example 32b: 2-((2S,4S)-2-(Aminomethyl)-5-chloro-6-fluoro-2-phenyl-2,3-dihydrobenzofuran-4-yl)-3-fluorobenzamide (Example 32a) and 2-((2S,4R)-2-(aminomethyl)-5-chloro-6-fluoro-2-phenyl-2,3-dihydrobenzofuran-4-yl)-3-fluorobenzamide (Example 32b)

Example 32a
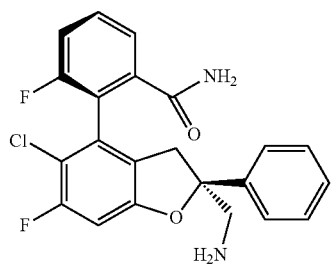

Example 32b
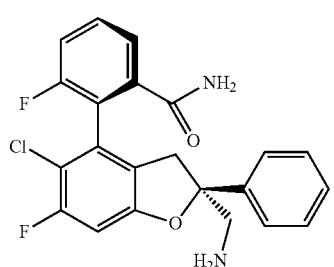

Reaction Scheme Example 32

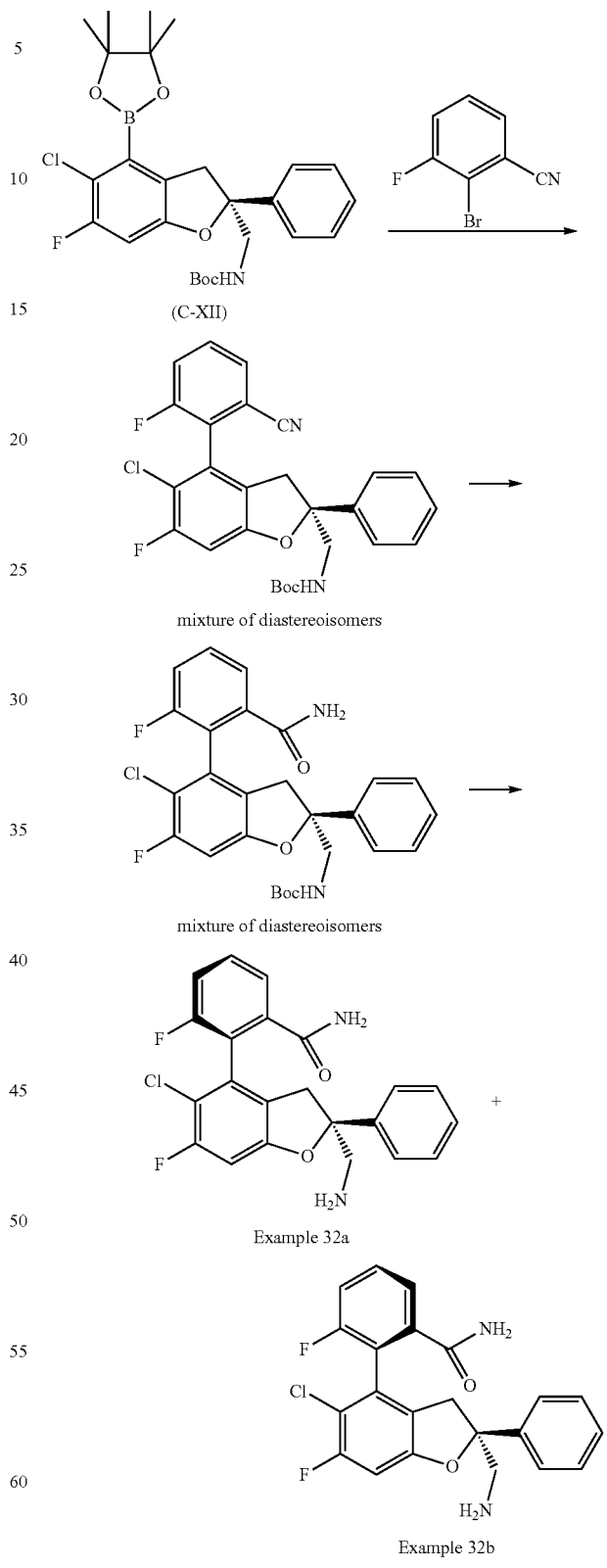

Step 1: Tert-butyl (((2S,4S)-5-chloro-4-(2-cyano-6-fluorophenyl)-6-fluoro-2-phenyl-2,3-dihydrobenzofuran-2-yl)methyl)carbamate and tert-butyl (((2S,4R)-5-chloro-4-(2-cyano-6-fluorophenyl)-6-fluoro-2-phenyl-2,3-dihydrobenzofuran-2-yl)methyl)carbamate A mixture of (S)-tert-butyl ((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII) (220 mg, 0.44 mmol), 2-bromo-3-fluorobenzonitrile (114 mg, 0.57 mmol), tris(dibenzyideneacetone)dipalladium(0) (20 mg, 0.02 mmol), 4,6-bis(diphenylphosphimo)phenoxazine (24 mg, 0.04 mmol) and $K_3PO_4$ (278 mg, 1.31 mmol) was suspended in toluene (2.5 mL) and water (0.5 mL) and purged with Ar. The reaction mixture was stirred at 100° C. for 12 h. EtOAc and a sat solution of $NaHCO_3$ were then added. The aqueous layer was back-extracted with EtOAc. The combined organic layers were washed with brine, dried over anhydrous $Na_2SO_4$ and concentrated. The crude product was purified by flash chromatography (silica, hexane/EtOAc 4:1) to afford a mixture of the title compounds (123 mg). UPLC-MS 1: m/z 497.2 $[M+H]^+$, $t_R$=1.36 and 1.39 min.

Step 2: Tert-butyl (((2S,4S)-4-(2-carbamoyl-6-fluorophenyl)-5-chloro-6-fluoro-2-phenyl-2,3-dihydrobenzofuran-2-yl)methyl)carbamate and tert-butyl (((2S,4R)-4-(2-carbamoyl-6-fluorophenyl)-5-chloro-6-fluoro-2-phenyl-2,3-dihydrobenzofuran-2-yl)methyl)carbamate To a suspension of a mixture of tert-butyl (((2S,4S)-5-chloro-4-(2-cyano-6-fluorophenyl)-6-fluoro-2-phenyl-2,3-dihydrobenzofuran-2-yl)methyl)carbamate and tert-butyl (((2S,4R)-5-chloro-4-(2-cyano-6-fluorophenyl)-6-fluoro-2-phenyl-2,3-dihydrobenzofuran-2-yl)methyl)carbamate (122 mg, 0.246 mmol) in EtOH (3 mL) and water (0.6 mL) was added at RT hydrido (dimethylphosphinousacid-kP)[hydrogen bis(dimethylphosphinito-kP)]platinum (II) (21 mg, 0.05 mmol). The reaction mixture was stirred at 80° C. for 45 min. A sat solution of $NaHCO_3$ (30 mL) was added and the reaction mixture was extracted with EtOAc. The combined organic layers were washed with brine, dried over anhydrous $Na_2SO_4$ and concentrated to afford a mixture of the title compounds (123 mg). UPLC-MS 1: m/z 515.2 $[M+H]^+$, $t_R$=1.18 and 1.26 min.

Step 3: 2-((2S,4S)-2-(Aminomethyl)-5-chloro-6-fluoro-2-phenyl-2,3-dihydrobenzofuran-4-yl)-3-fluorobenzamide (Example 32a) and 2-((2S,4R)-2-(aminomethyl)-5-chloro-6-fluoro-2-phenyl-2,3-dihydrobenzofuran-4-yl)-3-fluorobenzamide (Example 32b)

A solution of a mixture of tert-butyl (((2S,4S)-4-(2-carbamoyl-6-fluorophenyl)-5-chloro-6-fluoro-2-phenyl-2,3-dihydrobenzofuran-2-yl)methyl)carbamate and tert-butyl (((2S,4R)-4-(2-carbamoyl-6-fluorophenyl)-5-chloro-6-fluoro-2-phenyl-2,3-dihydrobenzofuran-2-yl)methyl)carbamate (121 mg, 0.235 mmol) in DCM (1.5 mL) was treated with TFA (0.54 mL, 7.1 mmol). The reaction mixture was stirred at RT for 1 h, then diluted with DCM and concentrated. The crude product was purified by preparative HPLC (reverse phase, gradient: 5% to 100% ACN over 20 min) to afford the title compounds as single diastereoisomers.

2-((2S,4S)-2-(Aminomethyl)-5-chloro-6-fluoro-2-phenyl-2,3-dihydrobenzofuran-4-yl)-3-fluorobenzamide (Example 32a) (28 mg): $^1$H NMR (600 MHz, DMSO-$d_6$) δ (ppm) 7.82 (br. s, 1H), 7.57 (dd, J=7.8 Hz, 1H), 7.48 (d, J=7.7 Hz, 1H), 7.42 (d, J=8.3 Hz, 2H), 7.35 (dt, J=15.0, 7.6 Hz, 4H), 7.27 (t, J=6.9 Hz, 1H), 7.05 (d, J=9.6 Hz, 1H), 3.46 (d, J=15.9 Hz, 1H), 2.94-2.80 (m, 3H), 1.65 (s, 2H). UPLC-MS 1: m/z 415.1 $[M+H]^+$, $t_R$=0.77 min. The absolute configuration was confirmed by an X-ray cocrystal structure of Example 32a bound to the YAP binding site of TEAD3.

2-((2S,4R)-2-(Aminomethyl)-5-chloro-6-fluoro-2-phenyl-2,3-dihydrobenzofuran-4-yl)-3-fluorobenzamide (Example 32b) (20 mg): $^1$H NMR (600 MHz, DMSO-$d_6$) δ (ppm) 7.76 (br. s, 1H), 7.57 (dd, J=7.7 Hz, 1H), 7.49-7.42 (m, 2H), 7.35 (dt, J=15.0, 7.7 Hz, 4H), 7.27 (t, J=7.1 Hz, 1H), 7.18 (s, 1H), 7.00 (d, J=9.7 Hz, 1H), 3.29 (d, J=15.8 Hz, 1H), 3.09 (d, J=15.9 Hz, 1H), 2.91-2.80 (m, 2H), 1.43 (br. s, 2H). UPLC-MS 1: m/z 415.1 $[M+H]^+$, $t_R$=0.61 min.

The following compounds were prepared analogously to Example 32a

| Ex. | Structure/Chemical Name | UPLC MS m/z $[M + H]^+$ $t_R$ [min] (method) | $^1$H NMR |
|---|---|---|---|
| 33 | 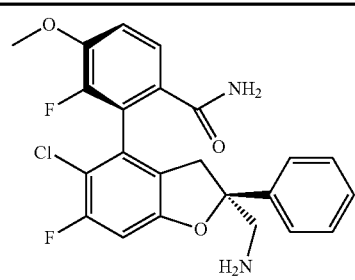<br>2-((2S,4S)-2-(aminomethyl)-5-chloro-6-fluoro-2-phenyl-2,3-dihydrobenzofuran-4-yl)-3-fluoro-4-methoxybenzamide; 2-bromo-3-fluoro-4-methoxybenzonitrile (N-IV) used in Suzuki coupling | 445.3 0.81 (1) | (600 MHz, DMSO-$d_6$) δ (ppm) 7.70 (br. s, 1H), 7.52 (d, J = 8.5 Hz, 1H), 7.40-7.32 (m, 4H), 7.31-7.22 (m, 3H), 7.04 (d, J = 9.7 Hz, 1H), 3.89 (s, 3H), 3.41 (d, J = 15.9 Hz, 1H), 2.95-2.81 (m, 3H), 1.90 (br. s, 2H). |

| Ex. | Structure/Chemical Name | UPLC MS m/z [M + H]+ t_R [min] (method) | ¹H NMR |
|---|---|---|---|
| 34 | 2-((2S,4S)-2-(aminomethyl)-5-chloro-6-fluoro-2-phenyl-2,3-dihydrobenzofuran-4-yl)-4-(cyclopropylmethoxy)-3-fluorobenzamide; 2-bromo-4-(cyclopropylmethoxy)-3-fluorobenzonitrile (N-X) used in Suzuki coupling | 485.1 0.95 (1) | ¹H NMR (600 MHz, DMSO-$d_6$) δ (ppm) 7.69 (s, 1H), 7.48 (dd, J = 8.7, 1.2 Hz, 1H), 7.40-7.32 (m, 4H), 7.30-7.21 (m, 3H), 7.04 (d, J = 9.6 Hz, 1H), 3.95 (d, J = 7.2 Hz, 2H), 3.41 (dd, J = 15.9, 1.4 Hz, 2H), 2.96-2.79 (m, 3H), 1.29-1.17 (m, 1H), 0.62-0.53 (m, 2H), 0.37-0.26 (m, 2H). |
| 35 | 2-((2S,4S)-2-(aminomethyl)-5-chloro-6-fluoro-2-phenyl-2,3-dihydrobenzofuran-4-yl)-4-(difluoromethoxy)-3-fluorobenzamide; 2-bromo-4-(difluoromethoxy)-3-fluorobenzonitrile (N-V) used in Suzuki coupling | 481.2 0.87 (1) | ¹H NMR (600 MHz, DMSO-$d_6$) δ (ppm) 7.89 (s, 1H), 7.57-7.51 (m, 2H), 7.47 (d, J = 3.9 Hz, 1H), 7.39-7.33 (m, 5H), 7.30-7.25 (m, 1H), 7.08 (d, J = 9.6 Hz, 1H), 3.45 (d, J = 16.0 Hz, 1H), 2.96-2.79 (m, 3H), 1.45 (br s, 2H). |
| 36 | 2-((2S,4S)-2-(aminomethyl)-5-chloro-6-fluoro-2-phenyl-2,3-dihydrobenzofuran-4-yl)-4-(1,1-difluoro-2-hydroxyethoxy)-3-fluorobenzamide; 2-bromo-4-(1,1-difluoro-2-hydroxyethoxy)-3-fluorobenzonitrile (N-XXII) used in Suzuki coupling | 511.1 0.72 (1) | 1H NMR (600 MHz, Chloroform-$d_3$) δ (ppm) 7.56-7.43 (m, 2H), 7.39-7.18 (m, 8H), 6.80 (d, J = 9.0 Hz, 1H), 4.04-3.93 (m, 2H), 3.46-3.29 (m, 2H), 3.14-2.99 (m, 2H). |

| Ex. | Structure/Chemical Name | UPLC MS m/z [M + H]+ $t_R$ [min] (method) | ¹H NMR |
|---|---|---|---|
| 37 | 2-((2S,4S)-2-(aminomethyl)-5-chloro-6-fluoro-2-phenyl-2,3-dihydrobenzofuran-4-yl)-3-fluoro-4-(2-methoxyethoxy)benzamide; 2-bromo-3-fluoro-4-(2-methoxyethoxy)benzonitrile (N-IX) used in Suzuki coupling | 489.3 0.66 (1) | (600 MHz, DMSO-d₆) δ (ppm) 7.67 (s, 1H), 7.49 (d, J = 8.6 Hz, 1H), 7.40-7.20 (m, 8H), 7.03 (d, J = 9.7 Hz, 1H), 4.27-4.18 (m, 2H), 3.71-3.62 (m, 2H), 3.41 (d, J = 16.0 Hz, 1H), 2.94-2.81 (m, 3H), 1.46 (br s, 2H) |
| 38 | 2-((2S,4S)-2-(aminomethyl)-5-chloro-6-fluoro-2-phenyl-2,3-dihydrobenzofuran-4-yl)-3-fluoro-4-(2-hydroxyethoxy)benzamide; 2-bromo-3-fluoro-4-(2-((tetrahydro-2H-pyran-2-yl)oxy)ethoxy)benzonitrile (N-VI) used in Suzuki coupling. THP and Boc group cleaved in the last step. | 475.2 0.72 (1) | (600 MHz, DMSO-d₆) δ (ppm) 7.66 (s, 1H), 7.51 (dd, J = 8.7, 1.4 Hz, 1H), 7.42-7.35 (m, 4H), 7.35-7.26 (m, 3H), 7.04 (d, J = 9.6 Hz, 1H), 4.92 (t, J = 5.4 Hz, 1H), 4.14 (t, J = 4.8 Hz, 2H), 3.75 (q, J = 5.1 Hz, 2H), 3.43 (dd, J = 15.9, 1.5 Hz, 1H), 2.94-2.82 (m, 3H), 1.42 (br s, 2H) |
| 39 | 2-((2S,4R)-2-(aminomethyl)-5-chloro-6-fluoro-2-phenyl-2,3-dihydrobenzofuran-4-yl)-4-((1,1-difluoro-2-hydroxyethyl)thio)benzamide; 2-bromo-4-((1,1-difluoro-2-((tetrahydro-2H-pyran-2-yl)oxy)ethyl)thio)benzonitrile (N-XXIII) used in Suzuki coupling | 509.0 0.78 (1) | (600 MHz, DMSO-d₆) δ (ppm) 7.85 (s, 1H), 7.77-7.67 (m, 2H), 7.44 (s, 1H), 7.41-7.31 (m, 5H), 7.32-7.24 (m, 1H), 7.03 (t, J = 9.7 Hz, 1H), 6.04 (s, 1H), 3.77 (t, J = 12.6 Hz, 2H), 3.39 (d, J = 15.9 Hz, 1H), 2.99-2.81 (m, 3H), 1.35 (br s, 2H). |

| Ex. | Structure/Chemical Name | UPLC MS m/z [M + H]+ $t_R$ [min] (method) | $^1$H NMR |
|---|---|---|---|
| 40 | 2-((2S,4S)-2-(aminomethyl)-5-chloro-6-fluoro-2-phenyl-2,3-dihydrobenzofuran-4-yl)-3-fluoro-4-((methylsulfonyl)methoxy)benzamide; 2-bromo-3-fluoro-4-((methylsulfonyl)methoxy)benzonitrile (N-XXIV) used in Suzuki coupling | 523.2 0.68 (1) | (400 MHz, DMSO-d$_6$) δ (ppm) 7.76 (br s, 1H), 7.39 (s, 8 H), 7.06 (d, J = 9.54 Hz, 1H), 5.37-5.58 (m, 2H), 3.44 (d, J = 15.89 Hz, 1H), 3.06 (s, 3H), 2.84-2.95 (m, 3H), 1.88 (br s, 2H). |
| 41 | 2-((2S,4S)-2-(aminomethyl)-5-chloro-6-fluoro-2-phenyl-2,3-dihydrobenzofuran-4-yl)-4-(3,3-difluoropropoxy)-3-fluorobenzamide; 2-bromo-4-(3,3-difluoropropoxy)-3-fluorobenzonitrile (N-XXV) used in Suzuki coupling | 509.1 0.89 (1) | (600 MHz, DMSO-d$_6$) δ (ppm) 7.87 (s, 1H), 7.54 (d, J = 8.6 Hz, 1H), 7.50-7.45 (m, 2H), 7.45-7.40 (m, 2H), 7.39-7.34 (m, 2H), 7.31 (s, 1H), 7.12 (d, J = 9.3 Hz, 1H), 4.34-4.19 (m, 2H), 3.57-3.40 (m, 2H), 1.30-1.17 (m, 5H). |
| 42 | 4-((2S,4S)-2-(aminomethyl)-5-chloro-6-fluoro-2-phenyl-2,3-dihydrobenzofuran-4-yl)-5-fluoro-6-methoxynicotinamide; methyl 4-chloro-5-fluoro-6-methoxynicotinate (N-XXIX) used in Suzuki coupling, synthesis in analogy to Example 18 | 446.2 0.79 (1) | (400 MHz, DMSO-d$_6$) δ 8.40 (br s, 1H), 8.00 (br s, 1H), 7.49 (br s, 1H), 7.47-7.25 (m, 5H), 7.13 (d, J = 9.5 Hz, 1H), 4.04 (s, 3H), 3.45 (d, J = 16.1 Hz, 1H), 3.02-2.88 (m, 3H). |

Example 43: 4-((2S,4S)-2-(Aminomethyl)-5-chloro-6-fluoro-2-phenyl-2,3-dihydrobenzofuran-4-yl)-5-fluoro-6-(2-hydroxyethoxy)nicotinamide

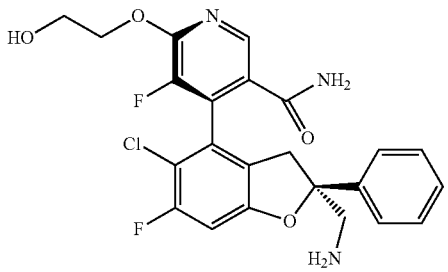

Step 1: Methyl 4-((2S,4S)-2-(((tert-butoxycarbonyl)amino)methyl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate and methyl 4-((2S,4R)-2-(((tert-butoxycarbonyl)amino)methyl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate A mixture of (S)-tert-butyl ((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII) (400 mg, 0.79 mmol), methyl 4-chloro-5-fluoro-6-(2-((tetrahydro-2H-pyran-2-yl)oxy)ethoxy)nicotinate (N-XXXI) (265 mg, 0.79 mmol), N-XantPhos Pd G3 (Aldrich cat. No. 794228) (37 mg, 0.04 mmol) and K$_3$PO$_4$ (506 mg, 2.4 mmol) in toluene (5 mL) and H$_2$O (1 mL) was stirred under Ar for 3 h at 105° C. The reaction mixture was diluted with a sat solution of NaHCO$_3$ and extracted with EtOAc. The combined organic extracts were washed with brine, dried (phase separator cartridge) and concentrated. The reside was purified by flash chromatography (silica; cyclohexane/EtOAc; gradient 0% to 70% EtOAc) to afford a mixture of the title compounds (182 mg). UPLC-MS 1: m/z 675.5 [M+H]$^+$, $t_R$=1.47 min and 1.48 min.

Step 2: 4-((2S,4S)-2-(((Tert-butoxycarbonyl)amino)methyl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinic acid and 4-((2S,4R)-2-(((tert-butoxycarbonyl)amino)methyl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinic acid A solution of a mixture of methyl 4-((2S,4S)-2-(((tert-butoxycarbonyl)amino)methyl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate and methyl 4-((2S,4R)-2-(((tert-butoxycarbonyl)amino)methyl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate (182 mg, 0.27 mmol) in THF (2.3 mL), 2 N NaOH (Volume: 2.3 mL) and MeOH (2.3 mL) was stirred at 50° C. for 45 min. Water was added followed by acidification to pH 1 with 1 N HCl. The mixture was extracted with EtOAc, the combined organic layers were washed with brine, dried (phase separator cartridge) and concentrated to afford a mixture of the title compounds (184 mg). UPLC-MS 1: m/z 661.4 [M+H]$^+$, $t_R$=1.31 min and 1.35 min.

Step 3: Tert-butyl (((2S,4S)-4-(5-carbamoyl-3-fluoro-2-(2-((tetrahydro-2H-pyran-2-yl)oxy)ethoxy)pyridin-4-yl)-5-chloro-6-fluoro-2-phenyl-2,3-dihydrobenzofuran-2-yl)methyl)carbamate and tert-butyl (((2S,4R)-4-(5-carbamoyl-3-fluoro-2-(2-((tetrahydro-2H-pyran-2-yl)oxy)ethoxy)pyridin-4-yl)-5-chloro-6-fluoro-2-phenyl-2,3-dihydrobenzofuran-2-yl)methyl)carbamate A mixture of the title compounds (201 mg) was obtained from a mixture of 4-((2S,4S)-2-(((tert-butoxycarbonyl)amino)methyl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinic acid and 4-((2S,4R)-2-(((tert-butoxycarbonyl)amino)methyl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinic acid (184 mg) using similar reaction conditions as described for Example 18, step. 3. UPLC-MS 1: m/z 660.4 [M+formate]$^−$, $t_R$=1.26 min and 1.32 min.

Step 4: 4-((2S,4S)-2-(Aminomethyl)-5-chloro-6-fluoro-2-phenyl-2,3-dihydrobenzofuran-4-yl)-5-fluoro-6-(2-hydroxyethoxy)nicotinamide (Example 43)

The title compound (56 mg, colorless powder) was obtained from a mixture of tert-butyl (((2S,4S)-4-(5-carbamoyl-3-fluoro-2-(2-((tetrahydro-2H-pyran-2-yl)oxy)ethoxy)pyridin-4-yl)-5-chloro-6-fluoro-2-phenyl-2,3-dihydrobenzofuran-2-yl)methyl)carbamate and tert-butyl (((2S,4R)-4-(5-carbamoyl-3-fluoro-2-(2-((tetrahydro-2H-pyran-2-yl)oxy)ethoxy)pyridin-4-yl)-5-chloro-6-fluoro-2-phenyl-2,3-dihydrobenzofuran-2-yl)methyl)carbamate (201 mg, 0.30 mmol) using similar reaction conditions as described for Example 22, step 5 followed by chromatographic separation of the diastereoisomers.

4-((2S,4S)-2-(Aminomethyl)-5-chloro-6-fluoro-2-phenyl-2,3-dihydrobenzofuran-4-yl)-5-fluoro-6-(2-hydroxyethoxy)nicotinamide (Example 43): $^1$H NMR (400 MHz, DMSO-d$_6$) δ (ppm) 8.37 (s, 1H), 8.00 (s br, 1H), 7.48 (s br, 1H), 7.44-7.35 (m, 4H), 7.34-7.28 (m, 1H), 7.13 (d, J=9.7 Hz, 1H), 4.94 (t, J=5.3 Hz, 1H), 4.50-4.41 (m, 2H), 3.80-3.75 (m, 2H), 3.46 (d, J=15.5 Hz, 1H), 2.99-2.93 (m, 3H). UPLC-MS 1: m/z 476.3 [M+H]$^+$, $t_R$=0.68 min.

Other diastereoisomer 4-((2S,4R)-2-(aminomethyl)-5-chloro-6-fluoro-2-phenyl-2,3-dihydrobenzofuran-4-yl)-5-fluoro-6-(2-hydroxyethoxy)nicotinamide: UPLC-MS 1: m/z 476.3 [M+H]$^+$, $t_R$=0.55 min.

Example 44: 2-((2S,4S)-2-(Aminomethyl)-5-chloro-6-fluoro-2-phenyl-2,3-dihydrobenzofuran-4-yl)-3-fluoro-4-(2-hydroxyethoxy)-N-methylbenzamide

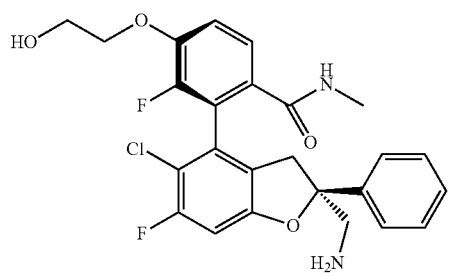

Step 1: Methyl 2-((2S,4S)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate and methyl 2-((2S,4R)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate A mixture of the title compounds (1.04 g) was obtained from (S)-tert-butyl ((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII) (1.2 g, 2.14 mmol) and methyl 2-bromo-3-fluoro-4-(2-((tetrahydro-2H-pyran-2-yl)oxy)ethoxy)benzoate (N-XXVII) (0.89 g, 2.4 mmol) using similar reaction conditions as described for Example 5a, step 1. UPLC-MS 1: m/z 718.4 [M+formate]⁻, $t_R$=1.45 min and 1.47 min.

Step 2: 2-((2S,4S)-2-(((Tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid and 2-((2S,4R)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid 4 N NaOH (5.8 mL, 23.1 mmol) was added to a solution of a mixture of methyl (2S)-2-((S)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate and methyl (2R)-2-((S)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate (1.04 g, 1.54 mmol) in MeOH (15 mL) and THF (5 mL) and stirring at RT was continued overnight: The reaction mixture was diluted with water, cooled to 0° C., acidified to pH 2 with 2 N HCl and extracted with EtOAc. The combined organic layers were washed with brine, dried over anhydrous MgSO₄ and concentrated to afford a mixture of the title compounds (1.10 g, colorless foam). UPLC-MS 1: m/z 658.3 [M−H]⁻, $t_R$=1.30 min and 1.35 min.

Step 3: Tert-butyl (((2S,4S)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)methyl)carbamate and tert-butyl (((2S,4R)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)methyl)carbamate A mixture of the title compounds (1.02 g) was obtained from a mixture of 2-((2S,4S)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid and 2-((2S,4R)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid (1.10 g, 1.5 mmol) using similar reaction conditions as described for Example 22, step 3. UPLC-MS 1: m/z 717.5 [M+formate]⁻, $t_R$=1.28 min and 1.34 min.

Step 4: 2-((2S,4S)-2-(Aminomethyl)-5-chloro-6-fluoro-2-phenyl-2,3-dihydrobenzofuran-4-yl)-3-fluoro-4-(2-hydroxyethoxy)-N-methylbenzamide (Example 44)

The title compound (274 mg, colorless powder) was obtained from a mixture of tert-butyl (((2S,4S)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)methyl)carbamate and tert-butyl (((2S,4R)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)methyl)carbamate (1.03 g, 1.48 mmol) using similar reaction conditions as described for Example 22, step 5 followed by chromatographic separation of the diastereoisomers.

2-((2S,4S)-2-(Aminomethyl)-5-chloro-6-fluoro-2-phenyl-2,3-dihydrobenzofuran-4-yl)-3-fluoro-4-(2-hydroxyethoxy)-N-methylbenzamide (Example 44): ¹H NMR (400 MHz, DMSO-d₆) δ (ppm) 8.18-8.12 (m, 1H), 7.44 (d, J=8.8 Hz, 1H), 7.40-7.25 (m, 6H), 7.03 (d, J=9.7 Hz, 1H), 4.93 (t, J=5.5 Hz, 1H), 4.15-4.11 (m, 2H), 3.76-3.71 (m, 2H), 3.39 (d, J=15.7 Hz, 1H), 2.89 (s, 2H), 2.84 (d, J=15.5 Hz, 1H), 2.62 (d, J=4.5 Hz, 3H), 1.45 (s br, 2H). UPLC-MS 1: m/z 489.3 [M+H]⁺, $t_R$=0.72 min.

Other diastereoisomer 2-((2S,4R)-2-(aminomethyl)-5-chloro-6-fluoro-2-phenyl-2,3-dihydrobenzofuran-4-yl)-3-fluoro-4-(2-hydroxyethoxy)-N-methylbenzamide: UPLC-MS 1: m/z 489.3 [M+H]⁺, $t_R$=0.65 min.

Example 45: 4-((2S,4S)-2-(Aminomethyl)-5-chloro-6-fluoro-2-phenyl-2,3-dihydrobenzofuran-4-yl)-5-fluoro-6-(2-hydroxyethoxy)-N-methylnicotinamide

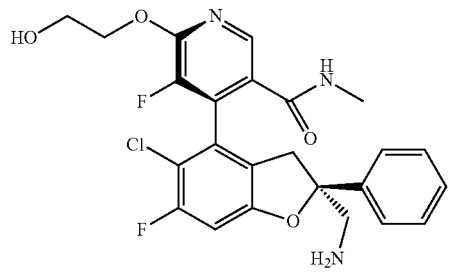

The title compound was prepared analogously to Example 44 from intermediates (S)-tert-butyl ((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII) and methyl 4-chloro-5-fluoro-6-(2-((tetrahydro-2H-pyran-2-yl)oxy)ethoxy)nicotinate N-XXXI followed by chromatographic separation of the diastereoisomers.

4-((2S,4S)-2-(Aminomethyl)-5-chloro-6-fluoro-2-phenyl-2,3-dihydrobenzofuran-4-yl)-5-fluoro-6-(2-hydroxyethoxy)-N-methylnicotinamide (Example 45): ¹H NMR (400 MHz, DMSO-d₆) δ (ppm) 8.48-8.43 (m, 1H), 8.28 (s, 1H), 7.40-7.33 (m, 4H), 7.31-7.26 (m, 1H), 7.10 (d, J=9.7 Hz, 1H), 4.91 (t, J=5.4 Hz, 1H), 4.49-4.39 (m, 2H), 3.78-3.73 (m, 2H), 3.42 (d, J=16.0 Hz, 1H), 2.92 (d, J=16.8 Hz, 1H), 2.89 (s, 2H), 2.66 (d, J=4.5 Hz, 3H), 1.41 (s br, 2H). UPLC-MS 1: m/z 490.1 [M+H]⁺, $t_R$=0.63 min.

Other diastereoisomer 4-((2S,4R)-2-(aminomethyl)-5-chloro-6-fluoro-2-phenyl-2,3-dihydrobenzofuran-4-yl)-5- fluoro-6-(2-hydroxyethoxy)-N-methylnicotinamide: UPLC-MS 1: m/z 490.1 [M+H]⁺, $t_R$=0.57 min.

Example 46: 2-((2S,4S)-5-Chloro-6-fluoro-2-((methylamino)methyl)-2-phenyl-2,3-dihydrobenzofuran-4-yl)-3-fluoro-4-methoxybenzamide

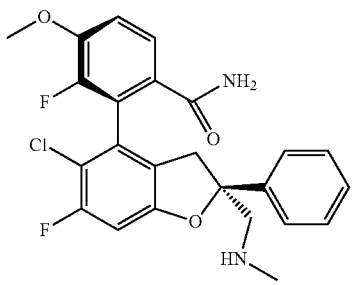

Step 1: Tert-butyl (((2S,4S)-5-chloro-4-(6-cyano-2-fluoro-3-methoxyphenyl)-6-fluoro-2-phenyl-2,3-dihydrobenzofuran-2-yl)methyl)carbamate and tert-butyl (((2S,4R)-5-chloro-4-(6-cyano-2-fluoro-3-methoxyphenyl)-6-fluoro-2-phenyl-2,3-dihydrobenzofuran-2-yl)methyl)carbamate A mixture of the title compounds (200 mg, yellow oil) was obtained from tert-butyl (S)-((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII) (229 mg, 0.455 mmol) and 2-bromo-3-fluoro-4-methoxybenzonitrile (N-IV) (136 mg, 0.59 mmol) using similar reaction conditions as described for Example 5a, step 1. UPLC-MS 1: m/z 571.3 [M+formate]⁻, $t_R$=1.34 min and 1.37 min.

Step 2: Tert-butyl (((2S,4S)-5-chloro-4-(6-cyano-2-fluoro-3-methoxyphenyl)-6-fluoro-2-phenyl-2,3-dihydrobenzofuran-2-yl)methyl)(methyl)carbamate and tert-butyl (((2S,4R)-5-chloro-4-(6-cyano-2-fluoro-3-methoxyphenyl)-6-fluoro-2-phenyl-2,3-dihydrobenzofuran-2-yl)methyl)(methyl)carbamate At 0° C. NaH (31 mg, 0.78 mmol, 60% in mineral oil) was added to a solution of a mixture of tert-butyl (((2S,4S)-5-chloro-4-(6-cyano-2-fluoro-3-methoxyphenyl)-6-fluoro-2-phenyl-2,3-dihydrobenzofuran-2-yl)methyl)carbamate and tert-butyl (((2S,4R)-5-chloro-4-(6-cyano-2-fluoro-3-methoxyphenyl)-6-fluoro-2-phenyl-2,3-dihydrobenzofuran-2-yl)methyl)carbamate (200 mg, 0.38 mmol) in THF (2 mL). After 10 min, methyl iodide (0.05 mL, 2.11 mmol) was added and the reaction mixture was allowed to warm to RT over 1.5 h. The reaction mixture was partitioned between EtOAc and a sat solution of NaHCO₃. The organic layer was separated and the organic layer was extracted with EtOAc. The combined organic phases were dried over anhydrous Na₂SO₄ and concentrated to afford a mixture of the title compounds as a yellow oil. UPLC-MS 1: m/z 541.3 [M+H]⁻, $t_R$=1.43 min and 1.44 min.

Step 3: Tert-butyl (((2S,4S)-4-(6-carbamoyl-2-fluoro-3-methoxyphenyl)-5-chloro-6-fluoro-2-phenyl-2,3-dihydrobenzofuran-2-yl)methyl)(methyl)carbamate and tert-butyl (((2S,4R)-4-(6-carbamoyl-2-fluoro-3-methoxyphenyl)-5-chloro-6-fluoro-2-phenyl-2,3-dihydrobenzofuran-2-yl)methyl)(methyl)carbamate A mixture of the title compounds (142 mg, yellow oil) was obtained from a mixture of tert-butyl (((2S,4S)-5-chloro-4-(6-cyano-2-fluoro-3-methoxyphenyl)-6-fluoro-2-phenyl-2,3-dihydrobenzofuran-2-yl)methyl)(methyl)carbamate and tert-butyl (((2S,4R)-5-chloro-4-(6-cyano-2-fluoro-3-methoxyphenyl)-6-fluoro-2-phenyl-2,3-dihydrobenzofuran-2-yl)methyl)(methyl)carbamate following the procedure as described for Example 5a, step 2. UPLC-MS 1: m/z 559.3 [M+H]⁺, $t_R$=1.27 min and 1.29 min.

Step 4: 2-((2S,4S)-5-Chloro-6-fluoro-2-((methylamino)methyl)-2-phenyl-2,3-dihydrobenzofuran-4-yl)-3-fluoro-4-methoxybenzamide (Example 46)

The title compound (31 mg, light beige powder) was obtained from a mixture of tert-butyl (((2S,4S)-4-(6-carbamoyl-2-fluoro-3-methoxyphenyl)-5-chloro-6-fluoro-2-phenyl-2,3-dihydrobenzofuran-2-yl)methyl)(methyl)carbamate and tert-butyl (((2S,4R)-4-(6-carbamoyl-2-fluoro-3-methoxyphenyl)-5-chloro-6-fluoro-2-phenyl-2,3-dihydrobenzofuran-2-yl)methyl)(methyl)carbamate (140 mg, 0.25 mmol) using similar reaction conditions as described for Example 5a, step 3 followed by chromatographic separation of the diastereoisomers.

2-((2S,4S)-5-Chloro-6-fluoro-2-((methylamino)methyl)-2-phenyl-2,3-dihydrobenzofuran-4-yl)-3-fluoro-4-methoxybenzamide (Example 46): ¹H NMR (600 MHz, DMSO-d₆) δ (ppm) 7.61 (s br, 1H), 7.55 (d, J=8.6 Hz, 1H), 7.42-7.28 (m, 2H), 7.38-7.33 (m, 2H), 7.33-7.27 (m, 2H), 7.25 (s br, 1H), 7.06 (d, J=9.7 Hz, 1H), 3.90 (s, 3H), 3.45 (d, J=15.8 Hz, 1H), 2.91 (s br, 2H), 2.85 (d, J=15.6 Hz, 1H), 2.23 (s, 3H). UPLC-MS 1: m/z 459.3 [M+H]⁺, $t_R$=0.81 min.

Other diastereoisomer 2-((2S,4R)-5-chloro-6-fluoro-2-((methylamino)methyl)-2-phenyl-2,3-dihydrobenzofuran-4-yl)-3-fluoro-4-methoxybenzamide: UPLC-MS 1: m/z 459.3 [M+H]⁺, $t_R$=0.66 min.

Example 47: 4-((2S,4S)-5-Chloro-6-fluoro-2-((methylamino)methyl)-2-phenyl-2,3-dihydrobenzofuran-4-yl)-5-fluoro-6-(2-methoxyethoxy)nicotinamide

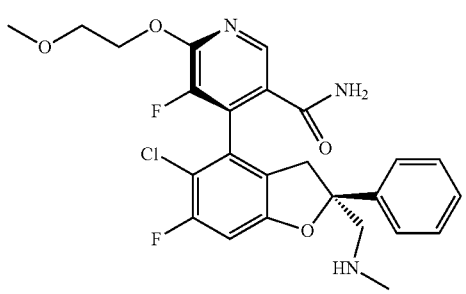

The title compound was prepared analogously to Example 46 from intermediates tert-butyl (S)-((5-chloro-6-fluoro-2- phenyl-4-(4,4,5,5-tetramethyl-1,3,2-dioxaborolan-2-yl)-2,3-dihydrobenzofuran-2-yl)methyl)carbamate (C-XII) and 4-chloro-5-fluoro-6-(2-methoxyethoxy)nicotinonitrile (N-XI) followed by chromatographic separation of the diastereoisomers.

4-((2S,4S)-5-Chloro-6-fluoro-2-((methylamino)methyl)-2-phenyl-2,3-dihydrobenzofuran-4-yl)-5-fluoro-6-(2-methoxyethoxy)nicotinamide (Example 47): $^1$H NMR (400 MHz, DMSO-$d_6$) δ (ppm) 8.36 (s, 1H), 7.88 (s br, 1H), 7.45-7.31 (m, 5H), 7.31-7.25 (m, 1H), 7.11 (d, J=9.8 Hz, 1H), 4.60-4.48 (m, 2H), 3.74-3.68 (m, 2H), 3.47 (d, J=15.9 Hz, 1H), 2.93 (d, J=15.7 Hz, 1H), 2.91 (s, 2H), 2.23 (s, 3H). UPLC-MS 1: m/z 504.2 [M+H]$^+$, $t_R$=0.79 min.

Other diastereoisomer 4-((2S,4R)-5-chloro-6-fluoro-2-((methylamino)methyl)-2-phenyl-2,3-dihydrobenzofuran-4-yl)-5-fluoro-6-(2-methoxyethoxy)nicotinamide: UPLC-MS 1: m/z 504.2 [M+H]$^+$, $t_R$=0.66 min.

Example 48: 2-((2S,4S)-5-Chloro-6-fluoro-2-((methylamino)methyl)-2-phenyl-2,3-dihydrobenzofuran-4-yl)-3-fluoro-4-(2-hydroxyethoxy)benzamide

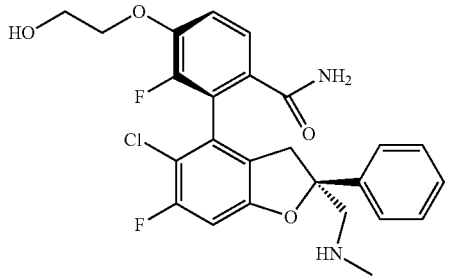

Step 1: Tert-butyl (((2S,4S)-5-chloro-4-(6-cyano-2-fluoro-3-(2-((tetrahydro-2H-pyran-2-yl)oxy)ethoxy)phenyl)-6-fluoro-2-phenyl-2,3-dihydrobenzofuran-2-yl)methyl)carbamate and tert-butyl (((2S,4R)-5-chloro-4-(6-cyano-2-fluoro-3-(2-((tetrahydro-2H-pyran-2-yl)oxy)ethoxy)phenyl)-6-fluoro-2-phenyl-2,3-dihydrobenzofuran-2-yl)methyl)carbamate A mixture of (S)-tert-butyl ((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII) (550 mg, 0.82 mmol), 2-bromo-3-fluoro-4-(2-((tetrahydro-2H-pyran-2-yl)oxy)ethoxy)benzonitrile (N-VI) (282 mg, 0.82 mmol), N-XantPhos Pd G3 (Aldrich cat. No. 794228) (75 mg, 0.082 mmol) and K$_3$PO$_4$ (521 mg, 2.46 mmol) in toluene (3 mL) and H$_2$O (1 mL) was stirred under Ar for 1 h at 105° C. The reaction mixture was diluted with water and extracted with EtOAc. The combined organic extracts were washed with brine, dried (phase separator cartridge) and concentrated. The reside was purified by flash chromatography (silica; cyclohexane/EtOAc; gradient 0 to 50% EtOAc) to afford a mixture of the title compounds (382 mg) as a yellow sticky solid. UPLC-MS 1: m/z 658.6 [M+NH$_4$]$^+$, $t_R$=1.41 min and m/z 641.6 [M+H]$^+$, $t_R$=1.44 min.

Step 2: Tert-butyl (((2S,4S)-5-chloro-4-(6-cyano-2-fluoro-3-(2-((tetrahydro-2H-pyran-2-yl)oxy)ethoxy)phenyl)-6-fluoro-2-phenyl-2,3-dihydrobenzofuran-2-yl)methyl)(methyl)carbamate and tert-butyl (((2S,4R)-5-chloro-4-(6-cyano-2-fluoro-3-(2-((tetrahydro-2H-pyran-2-yl)oxy)ethoxy)phenyl)-6-fluoro-2-phenyl-2,3-dihydrobenzofuran-2-yl)methyl)(methyl)carbamate At 0° C. NaH (23 mg, 0.91 mmol, 95%) was added to a solution of a mixture of tert-butyl (((2S,4S)-5-chloro-4-(6-cyano-2-fluoro-3-(2-((tetrahydro-2H-pyran-2-yl)oxy)ethoxy)phenyl)-6-fluoro-2-phenyl-2,3-dihydrobenzofuran-2-yl)methyl)carbamate and tert-butyl (((2S,4R)-5-chloro-4-(6-cyano-2-fluoro-3-(2-((tetrahydro-2H-pyran-2-yl)oxy)ethoxy)phenyl)-6-fluoro-2-phenyl-2,3-dihydrobenzofuran-2-yl)methyl)carbamate (195 mg, 0.30 mmol) in DMF (3 mL). After 5 min, methyl iodide (190 µl, 3.0 mmol) was added and the reaction mixture was stirred at RT for 30 min. Water was added and the mixture was extracted with EtOAc. The combined organic layers were washed with water and brine, dried (phase separator cartridge) and concentrated to afford a mixture of the title compounds (196 mg) as a yellow oil. UPLC-MS 1: m/z 699.6 [M+formate]$^-$, $t_R$=1.50 min and 1.51 min.

Step 3: Tert-butyl (((2S,4S)-4-(6-carbamoyl-2-fluoro-3-(2-((tetrahydro-2H-pyran-2-yl)oxy)ethoxy)phenyl)-5-chloro-6-fluoro-2-phenyl-2,3-dihydrobenzofuran-2-yl)methyl)(methyl)carbamate and tert-butyl (((2S,4R)-4-(6-carbamoyl-2-fluoro-3-(2-((tetrahydro-2H-pyran-2-yl)oxy)ethoxy)phenyl)-5-chloro-6-fluoro-2-phenyl-2,3-dihydrobenzofuran-2-yl)methyl)(methyl)carbamate A mixture of the title compounds (150 mg, colorless powder) was obtained from a mixture of tert-butyl (((2S,4S)-5-chloro-4-(6-cyano-2-fluoro-3-(2-((tetrahydro-2H-pyran-2-yl)oxy)ethoxy)phenyl)-6-fluoro-2-phenyl-2,3-dihydrobenzofuran-2-yl)methyl)(methyl)carbamate and tert-butyl (((2S,4R)-5-chloro-4-(6-cyano-2-fluoro-3-(2-((tetrahydro-2H-pyran-2-yl)oxy)ethoxy)phenyl)-6-fluoro-2-phenyl-2,3-dihydrobenzofuran-2-yl)methyl)(methyl)carbamate (196 mg) following the procedure as described for Example 5a, step 2. UPLC-MS 1: m/z 673.5 [M+H]$^+$, $t_R$=1.35 min and 1.36 min Step 4: 2-((2S,4S)-5-Chloro-6-fluoro-2-((methylamino)methyl)-2-phenyl-2,3-dihydrobenzofuran-4-yl)-3-fluoro-4-(2-hydroxyethoxy)benzamide (Example 48)

The title compound (21 mg, colorless powder) was obtained from a mixture tert-butyl (((2S,4S)-4-(6-carbamoyl-2-fluoro-3-(2-((tetrahydro-2H-pyran-2-yl)oxy)ethoxy)phenyl)-5-chloro-6-fluoro-2-phenyl-2,3-dihydrobenzofuran-2-yl)methyl)(methyl)carbamate and tert-butyl (((2S,4R)-4-(6-carbamoyl-2-fluoro-3-(2-((tetrahydro-2H-pyran-2-yl)oxy)ethoxy)phenyl)-5-chloro-6-fluoro-2-phenyl-2,3-dihydrobenzofuran-2-yl)methyl)(methyl)carbamate (150 mg, 0.22 mmol) using similar reaction conditions as described for Example 22, step 5 followed by chromatographic separation of the diastereoisomers.

2-((2S,4S)-5-Chloro-6-fluoro-2-((methylamino)methyl)-2-phenyl-2,3-dihydrobenzofuran-4-yl)-3-fluoro-4-(2-hydroxyethoxy)benzamide (Example 48): $^1$H NMR (400 MHz, DMSO-$d_6$) δ (ppm) 7.55 (s br, 1H), 7.50 (d, J=8.1 Hz, 1H), 7.41-7.24 (m, 6H), 7.19 (s br, 1H), 7.03 (d, J=9.7 Hz, 1H), 4.92 (t, J=5.4 Hz, 1H), 4.12 (t, J=4.7 Hz, 2H), 3.72 (dd, J=9.7, 5.0 Hz, 2H), 3.43 (d, J=15.9 Hz, 1H), 2.89 (s, 2H), 2.83 (d, J=15.7 Hz, 1H), 2.21 (s, 3H). UPLC-MS 1: m/z 489.4 [M+H]$^+$, $t_R$=0.69 min.

Other diastereoisomer 2-((2S,4R)-5-chloro-6-fluoro-2-((methylamino)methyl)-2-phenyl-2,3-dihydrobenzofuran-4-yl)-3-fluoro-4-(2-hydroxyethoxy)benzamide: UPLC-MS 1: m/z 489.3 [M+H]$^+$, $t_R$=0.58 min.

Example 49: 4-((2S,4S)-5-Chloro-6-fluoro-2-((methylamino)methyl)-2-phenyl-2,3-dihydrobenzofuran-4-yl)-5-fluoro-6-(2-hydroxyethoxy)nicotinamide

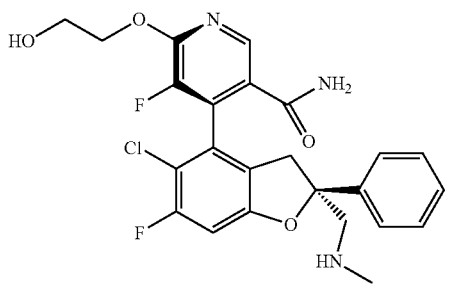

The title compound was prepared analogously to Example 48 from tert-butyl (S)-((5-chloro-6-fluoro-2-phenyl-4-(4,4,5,5-tetramethyl-1,3,2-dioxaborolan-2-yl)-2,3-dihydrobenzofuran-2-yl)methyl)carbamate (C-XII) and 5-fluoro-4-iodo-6-(2-((tetrahydro-2H-pyran-2-yl)oxy)ethoxy)nicotinonitrile (N-XII).

4-((2S,4S)-5-Chloro-6-fluoro-2-((methylamino)methyl)-2-phenyl-2,3-dihydrobenzofuran-4-yl)-5-fluoro-6-(2-hydroxyethoxy)nicotinamide (Example 49): $^1$H NMR (400 MHz, DMSO-d$_6$) δ (ppm) 8.36 (s, 1H), 7.90 (s br, 1H), 7.45-7.33 (m, 5H), 7.33-7.27 (m, 1H), 7.12 (d, J=9.5 Hz, 1H), 4.91 (t, J=5.1 Hz, 1H), 4.49-4.40 (m, 2H), 3.79-3.73 (m, 2H), 3.48 (d, J=15.9 Hz, 1H), 3.01 (s, 2H), 2.94 (d, J=15.9 Hz, 1H), 2.27 (s, 3H). UPLC-MS 1: m/z 490.1 [M+H]$^+$, $t_R$=0.66 min.

Other diastereoisomer 4-((2S,4R)-5-chloro-6-fluoro-2-((methylamino)methyl)-2-phenyl-2,3-dihydrobenzofuran-4-yl)-5-fluoro-6-(2-hydroxyethoxy)nicotinamide: UPLC-MS 1: m/z 490.2 [M+H]$^+$, $t_R$=0.56 min.

Example 50: 2-((2S,4S)-5-Chloro-2-(((cyclopropylmethyl)amino)methyl)-6-fluoro-2-phenyl-2,3-dihydrobenzofuran-4-yl)-4-(difluoromethoxy)-3-fluorobenzamide

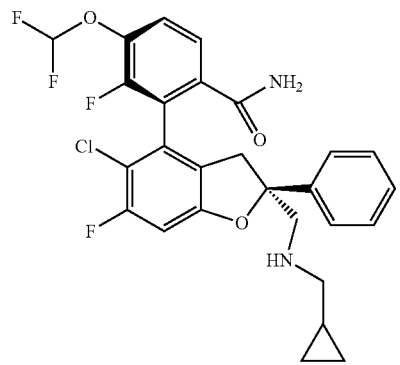

Sodium triacetoxyborohydride (110 mg, 0.52 mmol) was added to a stirred solution of 2-((2S,4S)-2-(aminomethyl)-5-chloro-6-fluoro-2-phenyl-2,3-dihydrobenzofuran-4-yl)-4-(difluoromethoxy)-3-fluorobenzamide (Example 35) (50 mg, 0.10 mmol) and cyclopropanecarbaldehyde (8.0 mg, 0.11 mmol) in THF (1 mL) at RT After 1 h a sat solution of NaHCO$_3$ was added and the mixture was extracted with DCM. The combined organic layers were dried (phase separator cartridge) and concentrated. The residue was purified by preparative HPLC (Waters Sunfire OBD 100×30 mm, 5 μm, Eluent A: H$_2$O+0.1% TFA, Eluent B: ACN, Gradient: 5 to 100% B in 20 min hold 1 min, flow 40 mL/min) to afford the title compound (27 mg) as a colorless powder. $^1$H NMR (600 MHz, DMSO-d$_6$) δ (ppm) 7.82 (s br, 1H), 7.58-7.53 (m, 2H), 7.43-7.35 (m, 5H), 7.36 (t, J=72.8 Hz, 1H), 7.32-7.28 (m, 1H), 7.12 (d, J=9.5 Hz, 1H), 3.51 (d, J=15.8 Hz, 1H), 3.00 (s br, 2H), 2.90 (d, J=15.2 Hz, 1H), 2.36-2.29 (m, 2H), 0.82-0.74 (m, 1H), 0.36-0.29 (m, 2H), 0.03-0.05 (m, 2H). UPLC-MS 1: m/z 535.1 [M+H]$^+$, $t_R$=1.01 min.

Example 51: 2-((2S,4S)-5-Chloro-6-fluoro-2-((methylamino)methyl)-2-phenyl-2,3-dihydrobenzofuran-4-yl)-3-fluoro-4-(2-hydroxyethoxy)-N-methylbenzamide or (2P)-2-{(2S)-5-Chloro-6-fluoro-2-[(methylamino)methyl]-2-phenyl-2,3-dihydro-1-benzofuran-4-yl}-3-fluoro-4-(2-hydroxyethoxy)-N-methylbenzamide

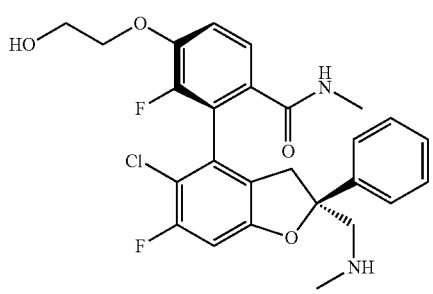

Reaction Scheme Example 51
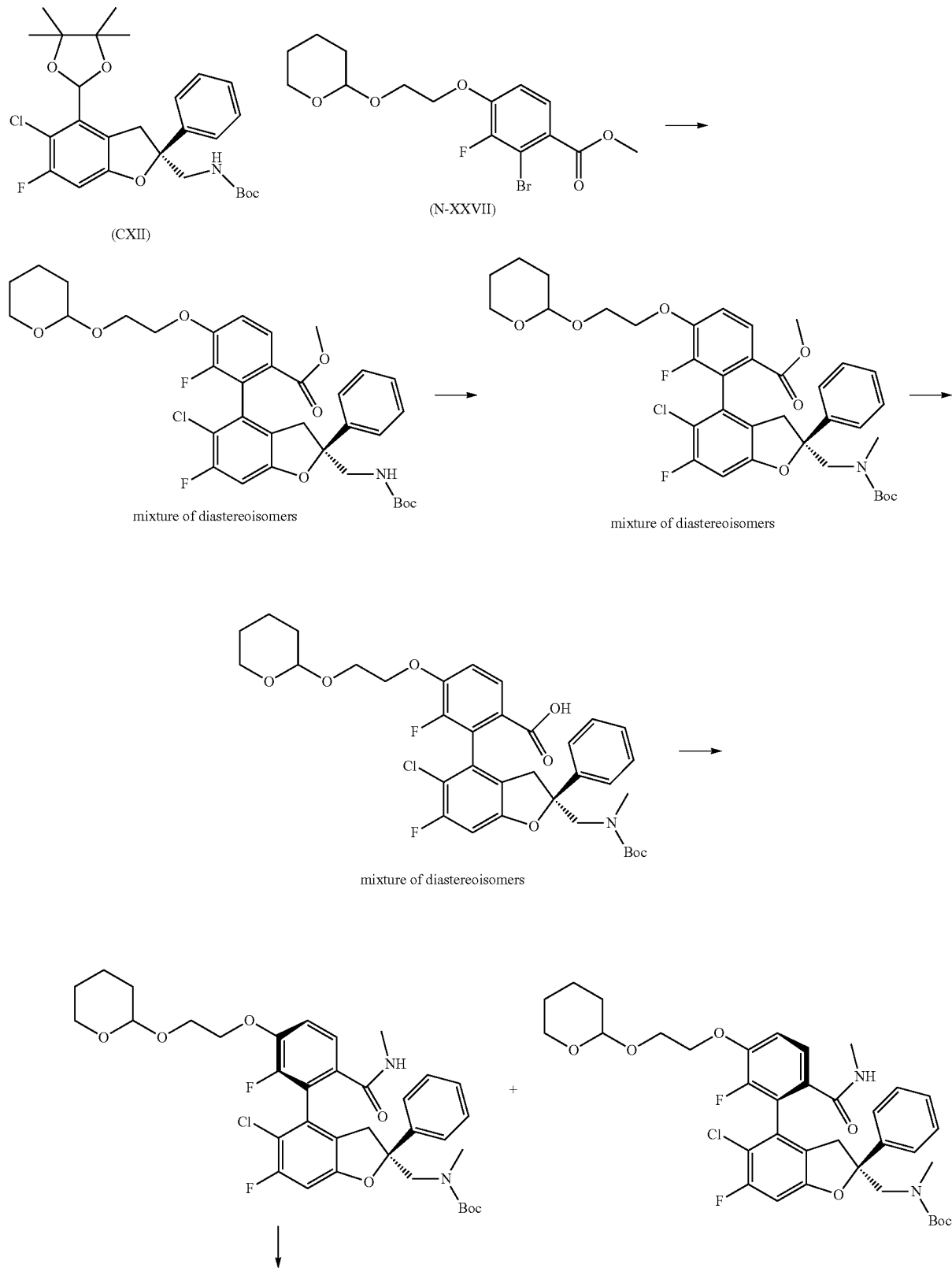

-continued

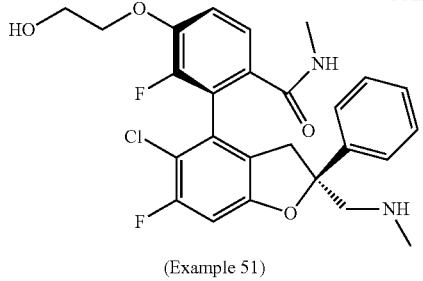

(Example 51)

Step 1: Methyl 2-((2S,4S)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate and methyl 2-((2S,4R)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate Under an Ar atmosphere, a suspension of (S)-tert-butyl ((5-chloro-6-fluoro-2-phenyl-4-(4,4,5,5-tetramethyl-1,3,2-dioxaborolan-2-yl)-2,3-dihydrobenzofuran-4-yl)methyl)carbamate (C-XII) (12 g, 21.44 mmol), methyl 2-bromo-3-fluoro-4-(2-((tetrahydro-2H-pyran-2-yl)oxy)ethoxy)benzoate (N-XXVII) (8.89 g, 23.58 mmol), $K_3PO_4$ (13.65 g, 64.3 mmol), N-Xantphos (1.182 g, 2.144 mmol) and $Pd_2(dba)_3$ (0.982 g, 1.072 mmol) in toluene/water (5:1, 240 mL) was heated at 100° C. for 19 h. The reaction mixture was cooled to RT, poured into a 10% $NaHCO_3$-solution and extracted with EtOAc. The combined organic layers were washed with brine, dried over anhydrous $MgSO_4$ and concentrated. The crude product was purified by flash chromatography (silica, hexane/EtOAc, gradient: 20% to 100% EtOAc) to yield a mixture of the title compounds (11.65 g). UPLC-MS 1: m/z 718.2/719.2 [M+HCOO⁻]⁻, $t_R$=1.44/1.45 min.

Step 2: Methyl 2-((2S,4S)-2-(((tert-butoxycarbonyl)(methyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate and methyl 2-((2S,4R)-2-(((tert-butoxycarbonyl)(methyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate At RT NaH (1.353 g, 33.8 mmol) was added portionwise to a stirred solution of a mixture of methyl 2-((2S,4S)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate and methyl 2-((2S,4R)-2-(((tert-butoxycarbonyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate (11.4 g, 16.91 mmol) in dry DMF (100 mL) and stirring at RT was continued for 15 min. After cooling to 0° C. methyl iodide (2.64 mL, 42.3 mmol) was slowly added and the reaction mixture was stirred at 0° C. for 1.5 h and then at RT for another 30 min. For workup the reaction mixture was poured into a 10% $NH_4Cl$-solution and extracted with EtOAc. The organic layers were combined, dried over anhydrous $MgSO_4$ and concentrated. The crude product was purified by flash chromatography (silica, hexane/EtOAc, gradient: 15% to 60% EtOAc) to yield a mixture of the title compounds (10.0 g). UPLC-MS 1: m/z 705.5/707.4 [M+NH4⁺]⁺, $t_R$=1.53 min.

Step 3: 2-((2S,4S)-2-(((Tert-butoxycarbonyl)(methyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid and 2-((2S,4R)-2-(((tert-butoxycarbonyl)(methyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid A 4 M aqueous solution of NaOH (36.3 mL, 145 mmol) was added to a stirred solution of a mixture of methyl 2-((2S,4S)-2-(((tert-butoxycarbonyl)(methyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate and methyl 2-((2S,4R)-2-(((tert-butoxycarbonyl)(methyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoate (10.0 g, 14.53 mmol) in MeOH (100 mL) and THF (50 mL). After stirring at 40° C. for 7.5 h the reaction mixture was partially concentrated, diluted with water, cooled to 5° C. and acidified with 2 M aqueous HCl. The aqueous phase was extracted with EtOAc. The combined organic layers were washed with brine, dried over $MgSO_4$ and concentrated to afford a mixture of the title compounds (10.8 g). UPLC-MS 1: m/z 672.4 [M–H]⁻, $t_R$=1.39/1.40 min.

Step 4: Tert-butyl (((2S,4S)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)methyl)(methyl)carbamate and tert-butyl (((2S,4R)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)methyl)(methyl)carbamate HATU (8.77 g, 23.07 mmol) was added to a stirred solution of a mixture of 2-((2S,4S)-2-(((tert-butoxycarbonyl)(methyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid and 2-((2S,4R)-2-(((tert-butoxycarbonyl)(methyl)amino)methyl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid (10.8 g, 14.42 mmol), DIPEA (15.11 mL, 87 mmol) and methylamine hydrochloride (1.947 g, 28.8 mmol) in DMF (100 mL) The reaction mixture was stirred at RT for 2 days, then more DIPEA (2.50 mL, 14.5 mmol), methylamine hydrochloride (1.0 g, 14.00 mmol), and HATU (4.35 g, 11.5 mmol) were added and stirring at RT was continued for another 24 h. The reaction mixture was then partially concentrated, poured into a sat solution of NaHCO₃ and extracted with TBME. The combined organic layers were washed with a 10% NaHCO₃-solution and brine, dried over anhydrous MgSO₄, filtered and concentrated. The crude product was purified by flash chromatography (silica, hexane/EtOAc, gradient: 15% to 100% EtOAc) to afford the title compounds as separate diastereoisomers.

Tert-butyl (((2S,4S)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)methyl)(methyl)carbamate (4.53 g): UPLC-MS 1: m/z 687.5 [M+H]⁺, $t_R$=1.41 min.

Tert-butyl (((2S,4R)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)methyl)(methyl)carbamate (3.92 g): UPLC-MS 1: m/z 687.5 [M+H]⁺, $t_R$=1.39 min.

Step 5: 2-((2S,4S)-5-Chloro-6-fluoro-2-((methylamino)methyl)-2-phenyl-2,3-dihydrobenzofuran-4-yl)-3-fluoro-4-(2-hydroxyethoxy)-N-methylbenzamide or (2P)-2-{(2S)-5-Chloro-6-fluoro-2-[(methylamino)methyl]-2-phenyl-2,3-dihydro-1-benzofuran-4-yl}-3-fluoro-4-(2-hydroxyethoxy)-N-methylbenzamide (Example 51)

HCl (33 mL, 131 mmol, 4 M in dioxane) was slowly added to a solution of tert-butyl (((2S,4S)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)methyl)(methyl)carbamate (4.50 g, 6.55 mmol) in 1,4-dioxane (20 mL) and stirring at RT was continued for 5 h. The reaction mixture was poured into a sat solution of NaHCO₃, saturated with solid NaCl and extracted with EtOAc. The combined organic layers were washed with brine, dried over anhydrous MgSO₄, filtered and concentrated. The crude product was purified by flash chromatography (silica, DCM/(DCM/MeOH 4:1+2% 7M NH₃ in MeOH): gradient: 15% to 60% (DCM/MeOH 4:1+ 2% 7M NH₃ in MeOH)) to afford the title compound (2.85 g). ¹H NMR (400 MHz, DMSO-d₆) δ 8.13 (q, J=4.6 Hz, 1H), 7.47-7.41 (m, 1H), 7.41-7.21 (m, 6H), 7.03 (d, J=9.7 Hz, 1H), 4.93 (t, J=5.4 Hz, 1H), 4.12 (t, J=4.9 Hz, 2H), 3.73 (q, J=5.1 Hz, 2H), 3.44 (d, J=15.7 Hz, 1H), 2.88 (s, 2H), 2.79 (d, J=15.7 Hz, 1H), 2.64 (d, J=4.5 Hz, 3H), 2.23 (s, 3H). UPLC-MS 1: m/z 503.6 [M+H]⁺, $t_R$=0.70 min. The absolute configuration was confirmed by an X-ray cocrystal structure of Example 51 bound to the YAP binding site of TEAD4.

The following compounds were prepared analogously to Example 51

| Ex. | Structure/Chemical Name | UPLC MS m/z [M + H]⁺ $t_R$ [min] (method) | ¹H NMR |
|---|---|---|---|
| 52 | 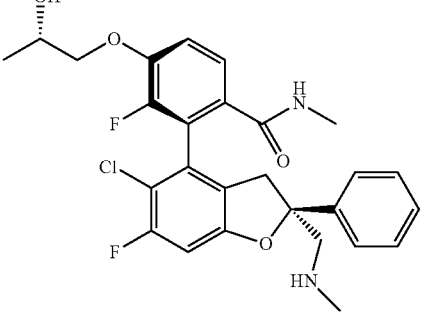<br>2-((2S,4S)-5-chloro-6-fluoro-2-((methylamino)methyl)-2-phenyl-2,3-dihydrobenzofuran-4-yl)-3-fluoro-4-((S)-2-hydroxypropoxy)-N-methylbenzamide; Methyl 2-bromo-3-fluoro-4-((2S)-2-((tetrahydro-2H-pyran-2-yl)oxy)propoxy)benzoate (N-XXVIII) was used in the Suzuki coupling | 517.1 0.75 (1) | (600 MHz, DMSO-d₆) δ (ppm) 8.16 (q, J = 4.7 Hz, 1H), 7.43 (d, J = 8.6 Hz, 1H), 7.41-7.24 (m, 6H), 7.04 (d, J = 9.5 Hz, 1H), 4.95 (d, J = 4.2 Hz, 1H), 4.01-3.89 (m, 3H), 3.44 (d, J = 15.8 Hz, 1H), 2.89 (s, 2H), 2.80 (d, J = 15.8 Hz, 1H), 2.63 (d, J = 4.5 Hz, 3H), 2.24 (s, 3H), 1.13 (d, J = 5.7 Hz, 3H) |
| 53 | 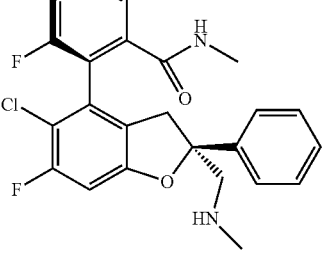 | 504.1 0.67 (1) | (400 MHz, DMSO-d₆) δ (ppm) 8.44 (q, J = 4.5 Hz, 1H), 8.27 (s, 1H), 7.44-7.21 (m, 5H), 7.10 (d, J = 9.6 Hz, 1H), 5.75 (s, 1H), 4.91 (t, J = 5.5 Hz, 1H), 4.49-4.37 (m, 2H), 3.79-3.71 (m, 2H), 3.47 (d, J = 15.8 Hz, 1H), 2.90-2.85 (m, 3H), 2.67 (d, J = 4.5 Hz, 3H), 2.23 (s, 3H). |

| Ex. | Structure/Chemical Name | UPLC MS m/z [M + H]+ t_R [min] (method) | 1H NMR |
|---|---|---|---|
| | 4-((2S,4S)-5-chloro-6-fluoro-2-((methylamino)methyl)-2-phenyl-2,3-dihydrobenzofuran-4-yl)-5-fluoro-6-(2-hydroxyethoxy)-N-methylnicotinamide; Methyl 4-chloro-5-fluoro-6-(2-((tetrahydro-2H-pyran-2-yl)oxy)ethoxy)nicotinate (N-XXXI) used in Suzuki coupling | | |

Example 54a and Example 54b: 2-((2S,4S)-5-Chloro-6-fluoro-2-((((cis)-4-(methylsulfonyl)cyclohexyl)amino)methyl)-2-phenyl-2,3-dihydrobenzofuran-4-yl)-4-(difluoromethoxy)-3-fluorobenzamide (Example 54a) and 2-((2S,4S)-5-chloro-6-fluoro-2-((((trans)-4-(methylsulfonyl)cyclohexyl)amino)methyl)-2-phenyl-2,3-dihydrobenzofuran-4-yl)-4-(difluoromethoxy)-3-fluorobenzamide (Example 54b)

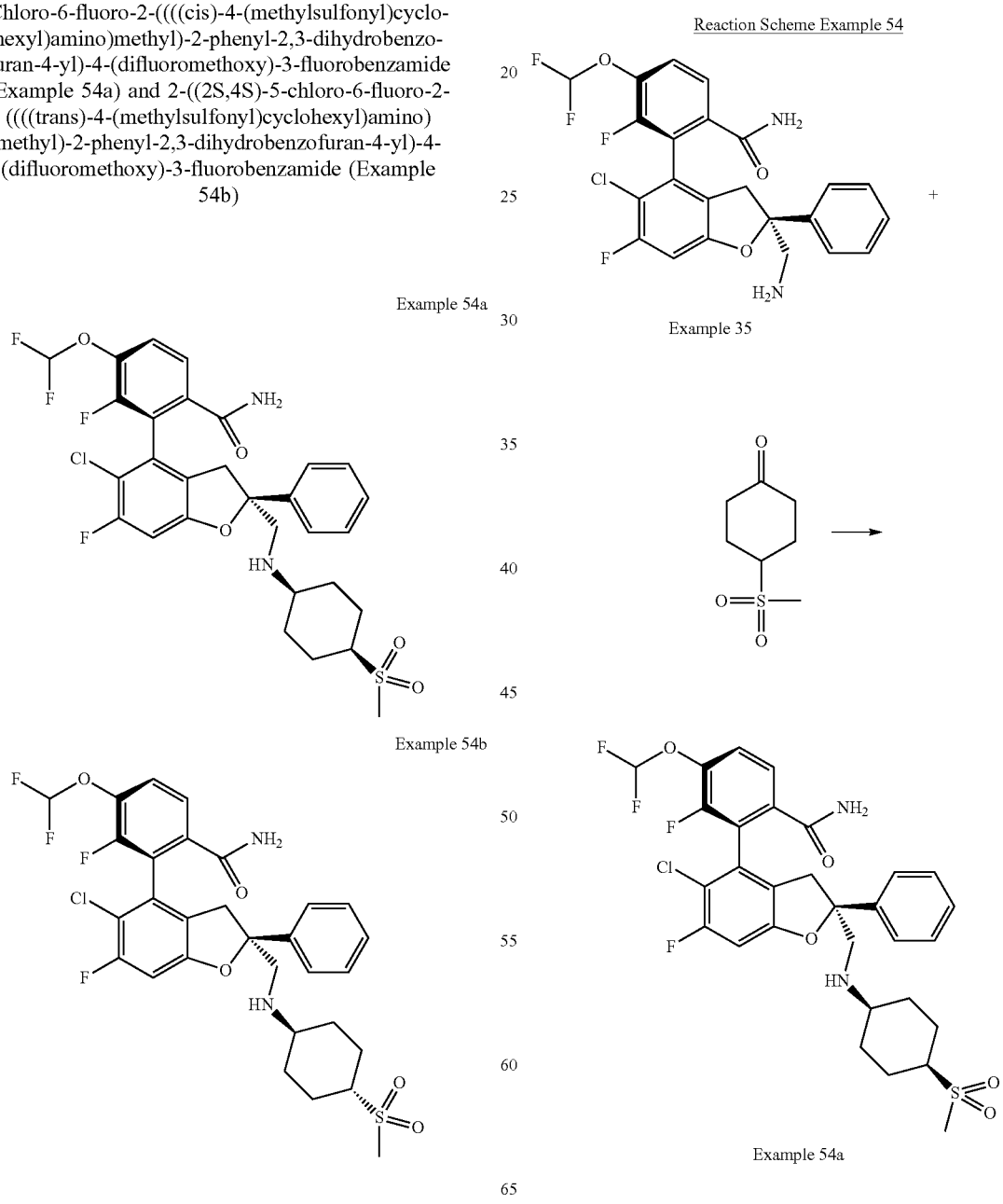

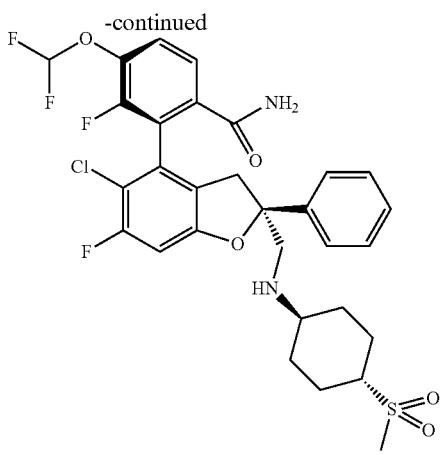

Example 54b

At RT NaBH(OAc)₃ (132 mg, 0.62 mmol) was added to a solution of 2-((2S,4S)-2-(aminomethyl)-5-chloro-6-fluoro-2-phenyl-2,3-dihydrobenzofuran-4-yl)-4-(difluoromethoxy)-3-fluorobenzamide (Example 35) (100 mg, 0.21 mmol), 4-(methylsulfonyl)cyclohexan-1-one (44 mg, 0.25 mmol) and acetic acid (0.012 mL, 0.21 mmol) in DCM (2 mL). Then, the reaction mixture was stirred at RT for 90 min. The reaction mixture was quenched by the addition of a sat solution of NaHCO₃ and extracted with DCM. The organic layers were combined and washed with a sat solution of NaHCO₃, dried over anhydrous Na₂SO₄ and concentrated. The residue was purified by flash chromatography (silica, DCM/MeOH, gradient 0% to 10% MeOH) and the diastereoisomers were separated:

2-((2S,4S)-5-Chloro-6-fluoro-2-((((cis)-4-(methylsulfonyl)cyclohexyl)amino)methyl)-2-phenyl-2,3-dihydrobenzofuran-4-yl)-4-(difluoromethoxy)-3-fluorobenzamide (72 mg) (Example 54a): $^1$H NMR (400 MHz, DMSO-$d_6$) δ (ppm) 7.70 (s, 1H), 7.71-7.50 (m, 2H), 7.44-7.16 (m, 7H), 7.09 (d, J=9.6 Hz, 1H), 3.51 (d, J=15.9 Hz, 1H), 2.99-2.78 (m, 4H), 2.76 (s, 3H), 2.69 (s, 1H), 1.86-1.45 (m, 4H), 1.37-1.35 (m, 2H). UPLC-MS 2: m/z 641.3 [M+H]⁺, $t_R$=4.32 min.

2-((2S,4S)-5-chloro-6-fluoro-2-((((trans)-4-(methylsulfonyl)cyclohexyl)amino)methyl)-2-phenyl-2,3-dihydrobenzofuran-4-yl)-4-(difluoromethoxy)-3-fluorobenzamide (26 mg) (Example 54b): $^1$H NMR (400 MHz, CD₃OD) δ (ppm) 7.83-7.37 (m, 8H), 7.39-6.91 (m, 2H), 3.76-3.53 (m, 2H), 3.48 (s, 1H), 3.17 (d, J=15.8 Hz, 1H), 3.10 (t, J=12.2 Hz, 1H), 3.03 (s, 3H), 2.68-2.48 (m, 1H), 2.41-2.22 (m, 2H), 2.21 (d, J=13.4 Hz, 1H), 2.22-2.03 (m, 1H), 1.68-1.64 (m, 2H), 1.63-1.33 (m, 1H), 1.49-1.16 (m, 3H). UPLC-MS 2: m/z 641.3 [M+H]⁺, $t_R$=4.19 min.

The following compounds were prepared analogously to Example 54a and Example 54b

| Ex. | Structure/Chemical Name | UPLC MS m/z [M + H]⁺ $t_R$ [min] (method) | $^1$H NMR |
|---|---|---|---|
| 55a | 2-((2S,4S)-5-chloro-6-fluoro-2-(((4-(fluoromethyl)-4-hydroxycyclohexyl)amino)methyl)-2-phenyl-2,3-dihydrobenzofuran-4-yl)-4-(difluoromethoxy)-3-fluorobenzamide; 4-(fluoromethyl)-4-hydroxycyclohexan-1-one (S-I) used in reductive amination, absolute stereochemistry on cyclohexyl ring unknown | 611.3 0.91 (1) | (600 MHz, DMSO-d6) δ (ppm) 7.86 (s, 1H), 7.66-7.02 (m, 10H), 4.41 (s, 1H), 4.05 (d, J = 48.1 Hz, 2H), 3.50 (d, J = 15.7 Hz, 1H), 3.00 (s, 2H), 2.87 (d, J = 15.7 Hz, 1H), 2.22 (s, 1H), 1.58-1.47 (m, 2H), 1.45 (s, 2H), 1.24 (s br, 4H). |

| Ex. | Structure/Chemical Name | UPLC MS m/z [M + H]+ $t_R$ [min] (method) | ¹H NMR |
|---|---|---|---|
| 55b | 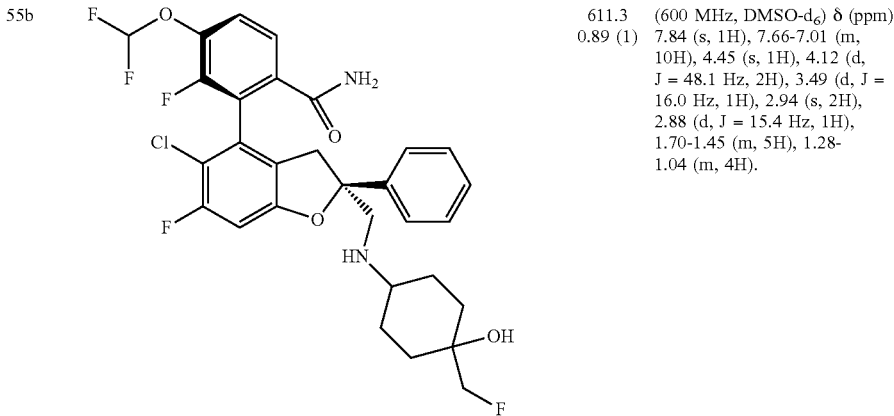<br>2-((2S,4S)-5-chloro-6-fluoro-2-(((4-(fluoromethyl)-4-hydroxycyclohexyl)amino)methyl)-2-phenyl-2,3-dihydrobenzofuran-4-yl)-4-(difluoromethoxy)-3-fluorobenzamide; Absolute stereochemistry on cyclohexyl ring unknown, stereoisomer of Example 55a | 611.3<br>0.89 (1) | (600 MHz, DMSO-$d_6$) δ (ppm) 7.84 (s, 1H), 7.66-7.01 (m, 10H), 4.45 (s, 1H), 4.12 (d, J = 48.1 Hz, 2H), 3.49 (d, J = 16.0 Hz, 1H), 2.94 (s, 2H), 2.88 (d, J = 15.4 Hz, 1H), 1.70-1.45 (m, 5H), 1.28-1.04 (m, 4H). |
| 56a | 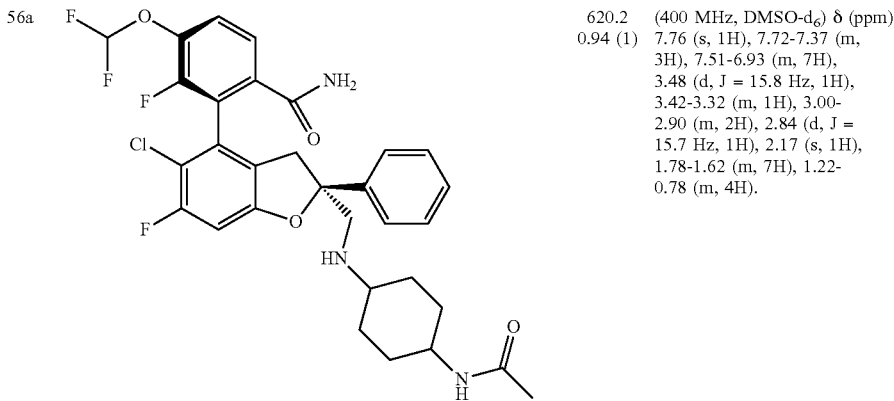<br>2-((2S,4S)-2-(((4-acetamidocyclohexyl)amino)methyl)-5-chloro-6-fluoro-2-phenyl-2,3-dihydrobenzofuran-4-yl)-4-(difluoromethoxy)-3-fluorobenzamide; N-(4-oxocyclohexyl)acetamide used in reductive amination, absolute stereochemistry on cyclohexyl ring unknown | 620.2<br>0.94 (1) | (400 MHz, DMSO-$d_6$) δ (ppm) 7.76 (s, 1H), 7.72-7.37 (m, 3H), 7.51-6.93 (m, 7H), 3.48 (d, J = 15.8 Hz, 1H), 3.42-3.32 (m, 1H), 3.00-2.90 (m, 2H), 2.84 (d, J = 15.7 Hz, 1H), 2.17 (s, 1H), 1.78-1.62 (m, 7H), 1.22-0.78 (m, 4H). |

| Ex. | Structure/Chemical Name | UPLC MS m/z [M + H]+ $t_R$ [min] (method) | $^1$H NMR |
|---|---|---|---|
| 56b | 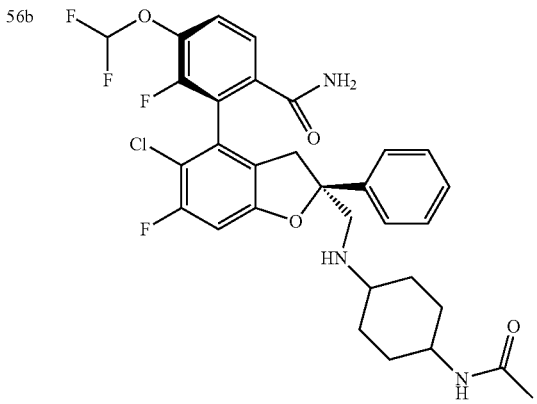<br><br>2-((2S,4S)-2-(((4-acetamidocyclohexyl)amino)methyl)-5-chloro-6-fluoro-2-phenyl-2,3-dihydrobenzofuran-4-yl)-4-(difluoromethoxy)-3-fluorobenzamide; Absolute stereochemistry on cyclohexyl ring unknown, stereoisomer of Example 56a. | 620.2<br>0.93 (1) | (400 MHz, DMSO-$d_6$) δ (ppm) 7.84 (s, 1H), 7.69-7.20 (m, 8H), 7.18-6.95 (m, 1H), 3.59 (s br, 1H), 3.49 (d, J = 15.8 Hz, 1H), 2.96 (s br, 2H), 2.86 (d, J = 15.8 Hz, 1H), 2.43 (s, 1H), 1.75 (s, 3H), 1.53-0.71 (m, 8H). |
| 57a | 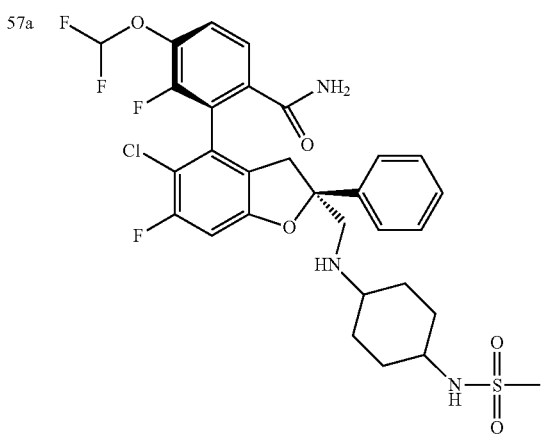<br><br>2-((2S,4S)-5-chloro-6-fluoro-2-(((4-(methylsulfonamido) cyclohexyl)amino) methyl)-2-phenyl-2,3-dihydrobenzofuran-4-yl)-4-(difluoromethoxy)-3-fluorobenzamide; N-(4-oxocyclohexyl)methanesulfonamide used in redcutive amination, absolute stereochemistry on cyclohexyl ring unknown | 656.3<br>0.89 (1) | (400 MHz, DMSO-$d_6$) δ (ppm) 7.76 (s, 1H), 7.68-7.37 (m, 2H), 7.51-6.93 (m, 7H), 6.87 (d, J = 7.2 Hz, 1H), 3.47 (d, J = 16.0 Hz, 1H), 3.05-2.65 (m, 6H), 2.16 (s, 1H), 1.92-1.54 (m, 4H), 1.30-0.94 (m, 4H). |

| Ex. | Structure/Chemical Name | UPLC MS m/z [M + H]+ $t_R$ [min] (method) | ¹H NMR |
|---|---|---|---|
| 57b | 2-((2S,4S)-5-chloro-6-fluoro-2-(((4-(methylsulfonamido) cyclohexyl)amino) methyl)-2-phenyl-2,3-dihydrobenzofuran-4-yl)-4-(difluoromethoxy)-3-fluorobenzamide; Absolute stereochemistry on cyclohexyl ring unknown, stereoisomer of Example 57a | 656.3 0.90 (1) | (400 MHz, DMSO-d₆) δ (ppm) 7.83 (s, 1H), 7.69-7.13 (m, 7H), 7.27-6.95 (m, 1H), 6.77 (d, J = 6.7 Hz, 1H), 3.49 (d, J = 15.9 Hz, 1H), 3.17 (s br, 2H), 3.00-2.85 (m, 5H), 2.41 (s, 1H), 1.63-0.83 (m, 8H). |
| 58a | 2-((2S,4S)-5-chloro-2-(((4-(dimethylcarbamoyl) cyclohexyl)amino) methyl)-6-fluoro-2-phenyl-2,3-dihydrobenzofuran-4-yl)-4-(difluoromethoxy)-3-fluorobenzamide; N,N-dimethyl-4-oxocyclohexanecarboxamide used in reductive amination, absolute stereochemistry on cyclohexyl ring unknown | 634.2 0.97 (1) | (400 MHz, DMSO-d₆) δ (ppm) 7.77 (s, 1H), 7.68-7.52 (m, 2H), 7.51-6.94 (m, 7H), 3.47 (d, J = 15.9 Hz, 1H), 3.04-2.89 (m, 5H), 2.84 (d, J = 15.9 Hz, 1H), 2.75 (s, 3H), 2.42 (t, J = 11.9 Hz, 1H), 2.26-2.15 (m, 1H), 1.92-1.59 (m, 2H), 1.56 (d, J = 13.2 Hz, 2H), 1.44-1.06 (m, 3H), 1.09-0.68 (m, 2H). |

| Ex. | Structure/Chemical Name | UPLC MS m/z [M + H]+ tR [min] (method) | 1H NMR |
|---|---|---|---|
| 58b | 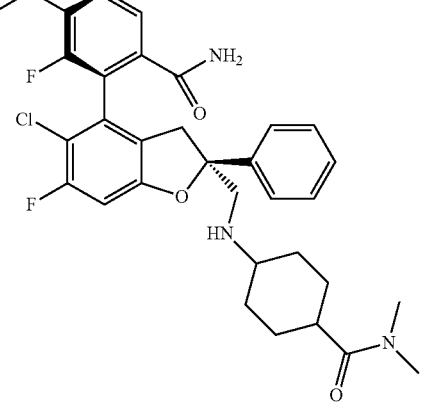<br>2-((2S,4S)-5-chloro-2-(((4-(dimethylcarbamoyl)cyclohexyl)amino)methyl)-6-fluoro-2-phenyl-2,3-dihydrobenzofuran-4-yl)-4-(difluoromethoxy)-3-fluorobenzamide; Absolute stereochemistry on cyclohexyl ring unknown, stereoisomer of Example 58a | 634.2<br>1.02 (1) | (400 MHz, DMSO-6) δ (ppm) 7.84 (s, 1H), 7.69-6.95 (m, 8H), 3.63 (d, J = 15.8 Hz, 1H), 3.18-2.65 (m, 9 H), 2.63 (s, 1H), 2.53 (s, 1H), 1.66-1.50 (m, 4H), 1.46-1.10 (m, 5H). |
| 59a | 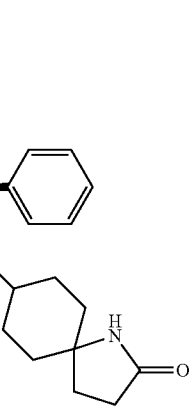<br>2-((2S,4S)-5-chloro-6-fluoro-2-(((2-oxo-1-azaspiro[4.5]decan-8-yl)amino)methyl)-2-phenyl-2,3-dihydrobenzofuran-4-yl)-4-(difluoromethoxy)-3-fluorobenzamide; 1-azaspiro[4.5]decane-2,8-dione used in reductive amination, absolute stereochemistry on spiro[4,5]decanyl ring unknown | 632.3<br>0.87 (1) | (400 MHz, DMSO-d6) δ (ppm) 7.77 (s, 1H), 7.61-7.48 (m, 4H), 7.42-7.14 (m, 7H), 7.06 (d, J = 9.5 Hz, 1H), 3.47 (d, J = 15.8 Hz, 1H), 2.95 (s, 2H), 2.71 (d, J = 15.8 Hz, 1H), 2.22 (s, 1H), 2.09 (t, J = 8.0 Hz, 2H), 1.77-1.55 (m, 4H), 1.46 (d, J = 13.1 Hz, 2H), 1.44-1.10 (m, 4H), 1.05 (s br, 2H). |

| Ex. | Structure/Chemical Name | UPLC MS m/z [M + H]+ $t_R$ [min] (method) | 1H NMR |
|---|---|---|---|
| 59b | 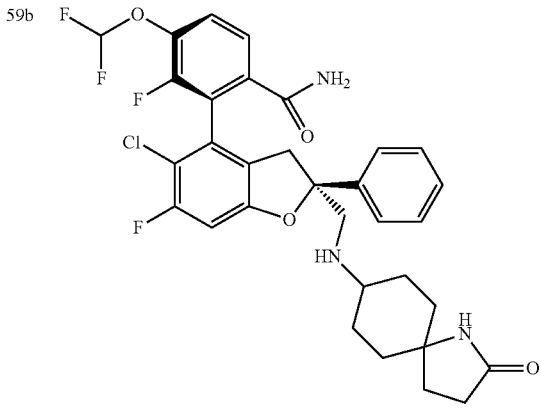<br>2-((2S,4S)-5-chloro-6-fluoro-2-(((2-oxo-1-azaspiro[4.5]decan-8-yl)amino)methyl)-2-phenyl-2,3-dihydrobenzofuran-4-yl)-4-(difluoromethoxy)-3-fluorobenzamide; Absolute stereochemistry on spiro[4,5] decanyl ring unknown, stereoisomer of Example 59a | 632.3<br>0.89 (1) | (400 MHz, DMSO-$d_6$) δ (ppm) 7.91 (s, 1H), 7.79 (s, 1H), 7.60-7.49 (m, 2H), 7.46-7.12 (m, 5H), 7.07 (d, J = 9.5 Hz, 1H), 3.50 (d, J = 15.7 Hz, 1H), 2.97 (s br, 2H), 2.60 (d, J = 15.7 Hz, 1H), 2.30 (s, 1H), 2.12 (t, J = 7.9 Hz, 2H), 1.74-1.65 (m, 2H), 1.52 (s, 4H), 1.34-1.16 (m, 6H). |
| 60 | 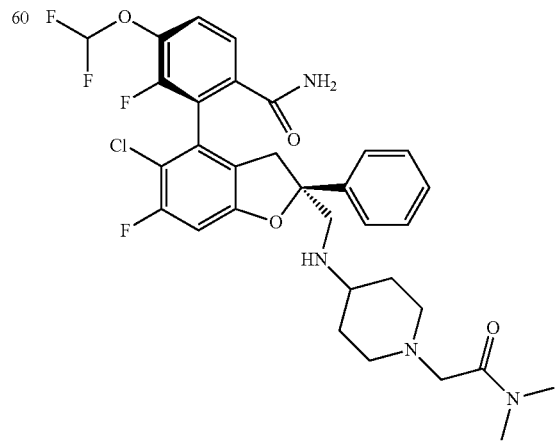<br>2-((2S,4S)-5-chloro-2-(((1-(2-(dimethylamino)-2-oxoethyl)piperidin-4-yl)amino)methyl)-6-fluoro-2-phenyl-2,3-dihydrobenzofuran-4-yl)-4-(difluoromethoxy)-3-fluorobenzamide; N,N-dimethyl-2-(4-oxopiperidin-1-yl)acetamide used in reductive amination | 649.4<br>0.84 (1) | (400 MHz, DMSO-$d_6$) δ (ppm) 7.78 (s, 1H), 7.57-7.47 (m, 2H), 7.40-7.22 (m, 7H), 7.07 (d, J = 9.4 Hz, 1H), 3.48 (d, J = 15.6 Hz, 1H), 3.14-2.59 (m, 11H), 2.25-2.14 (m, 1H), 2.05-1.81 (m, 2H), 1.68-1.55 (m, 2H), 1.22 (s, 1H), 1.12 (s br, 2H). |

| Ex. | Structure/Chemical Name | UPLC MS m/z [M + H]+ t_R [min] (method) | $^1$H NMR |
|---|---|---|---|
| 61a | 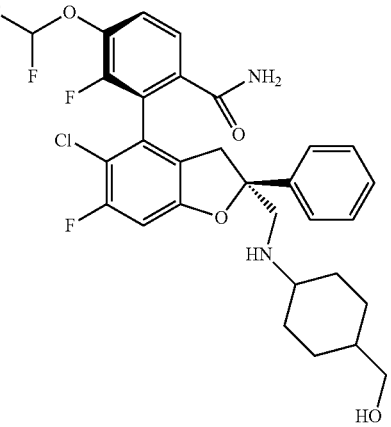<br>2-((2S,4S)-5-chloro-6-fluoro-2-(((4-(hydroxymethyl)cyclohexyl)amino)methyl)-2-phenyl-2,3-dihydrobenzofuran-4-yl)-4-(difluoromethoxy)-3-fluorobenzamide; 4-(hydroxymethyl)cyclohexanone used in reductive amination, absolute stereochemistry on cyclohexyl ring unknown | 593.3<br>0.90 (1) | (400 MHz, DMSO-d$_6$) δ (ppm) 7.81 (s, 1H), 7.57-7.48 (m, 2H), 7.40-7.25 (m, 8H), 7.07 (d, J = 9.7 Hz, 1H), 4.24 (s, 1H), 3.47 (d, J = 15.8 Hz, 1H), 3.18-3.06 (m, 3H), 3.00-2.81 (m, 3H), 2.48 (s, 2H), 1.50-0.90 (m, 8H). |
| 61b | 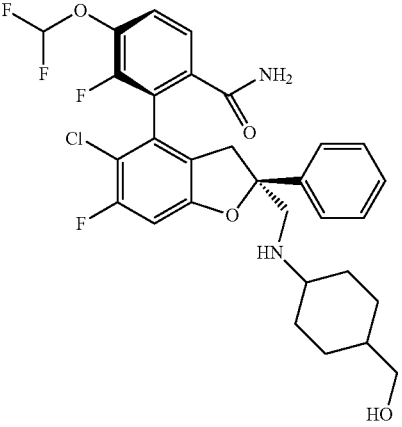<br>2-((2S,4S)-5-chloro-6-fluoro-2-(((4-(hydroxymethyl)cyclohexyl)amino)methyl)-2-phenyl-2,3-dihydrobenzofuran-4-yl)-4-(difluoromethoxy)-3-fluorobenzamide; Absolute stereochemistry on cyclohexyl ring unknown, stereoisomer of Example 61a | 593.3<br>0.89 (1) | (400 MHz, DMSO-d$_6$) δ (ppm) 7.76 (s, 1H), 7.55-7.48 (m, 3H), 7.40-7.14 (m, 7H), 7.07 (d, J = 9.6 Hz, 1H), 4.28 (s, 1H), 3.47 (d, J = 16.0 Hz, 1H), 3.13 (t, J = 6.0 Hz, 2H), 2.97 (s br, 2H), 2.84 (d, J = 16.0 Hz, 1H), 2.16 (s br, 1H), 1.91-1.57 (m, 4H), 1.34-1.02 (m, 2H), 0.93-0.72 (m, 2H). |

| Ex. | Structure/Chemical Name | UPLC MS m/z [M + H]+ t$_R$ [min] (method) | $^1$H NMR |
|---|---|---|---|
| 62a | 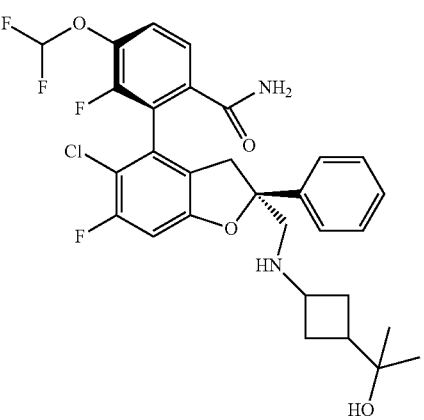<br>2-((2S,4S)-5-chloro-6-fluoro-2-(((3-(2-hydroxypropan-2-yl)cyclobutyl)amino)methyl)-2-phenyl-2,3-dihydrobenzofuran-4-yl)-4-(difluoromethoxy)-3-fluorobenzamide; 3-(2-hydroxypropan-2-yl)cyclobutanone used in reductive amination, absolute stereochemistry on cyclobutyl ring unknown | 593.2<br>1.02 (1) | (400 MHz, DMSO-d$_6$) δ (ppm) 7.80 (s, 1H), 7.68-7.40 (m, 2H), 7.37-7.15 (m, 5H), 7.08 (d, J = 9.7 Hz, 1H), 4.72 (d, J = 5.7 Hz, 1H), 4.07-3.96 (m, 3H), 3.45 (d, J = 15.9 Hz, 1H), 2.90-2.77 (m, 3H), 2.11 (dd, J = 7.1, 5.7 Hz, 1H), 1.88 (dd, J = 17.3, 8.8 Hz, 2H), 1.91-1.53 (m, 2H), 1.60-1.28 (m, 1H), 1.23 (s, 1H), 0.98 (s, 3H), 0.91 (s, 3H). |
| 62b | 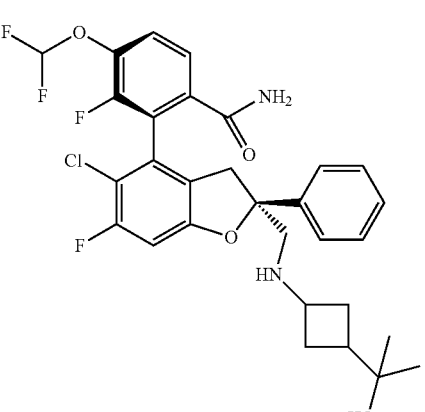<br>2-((2S,4S)-5-chloro-6-fluoro-2-(((3-(2-hydroxypropan-2-yl)cyclobutyl)amino)methyl)-2-phenyl-2,3-dihydrobenzofuran-4-yl)-4-(difluoromethoxy)-3-fluorobenzamide; Absolute stereochemistry on cyclobutyl ring unknown, stereoisomer of Example 62a | 593.2<br>0.98 (1) | (400 MHz, DMSO-d$_6$) δ (ppm) 7.80 (s, 1H), 7.58-7.48 (m, 2H), 7.42-7.14 (m, 5H), 7.08 (d, J = 9.6 Hz, 1H), 3.97 (s, 1H), 3.45 (d, J = 15.1 Hz, 1H), 3.00 (s, 1H), 2.90-2.80 (m, 2H), 2.07 (s, 1H), 1.94 (s br, 2H), 1.51 (s br, 2H), 1.44-1.10 (m, 1H), 0.93 (s, 6H). |

| Ex. | Structure/Chemical Name | UPLC MS m/z [M + H]+ $t_R$ [min] (method) | 1H NMR |
|---|---|---|---|
| 63 | 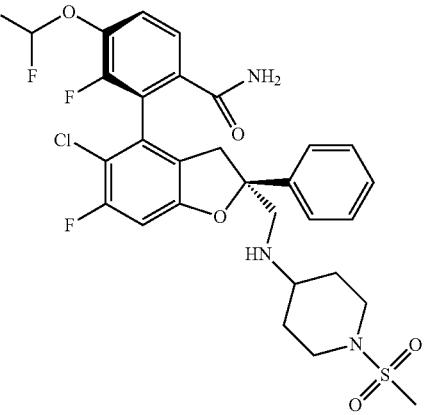<br>2-((2S,4S)-5-chloro-6-fluoro-2-(((1-(methylsulfonyl)piperidin-4-yl)amino)methyl)-2-phenyl-2,3-dihydrobenzofuran-4-yl)-4-(difluoromethoxy)-3-fluorobenzamide; 1-(methylsulfonyl)piperidin-4-one used in reductive amination | 642.3<br>0.92 (1) | (400 MHz, DMSO-d6) δ (ppm) 7.80 (s, 1H), 7.60-7.50 (m, 2H), 7.45-7.15 (m, 6H), 7.09 (d, J = 9.6 Hz, 1H), 3.52 (d, J = 15.7 Hz, 1H), 2.96 (s br, 2H), 2.80 (d, J = 15.7 Hz, 1H), 2.77 (s, 3H), 2.73-2.63 (m, 4H), 1.72-1.55 (m, 2H), 1.38-1.04 (m, 2 H). |
| 64a | 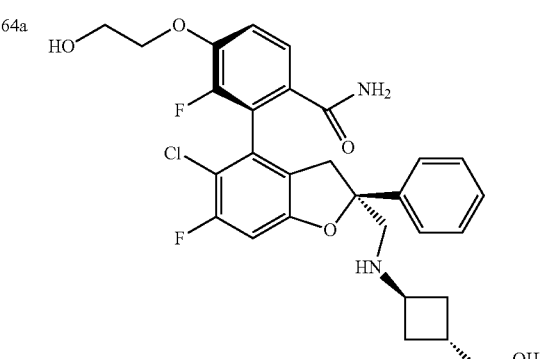<br>2-((2S,4S)-5-chloro-6-fluoro-2-((((trans)-3-(hydroxymethyl)cyclobutyl)amino)methyl)-2-phenyl-2,3-dihydrobenzofuran-4-yl)-3-fluoro-4-(2-hydroxyethoxy)benzamide; Example 38 and 3-(hydroxymethyl)cyclobutanone used in reductive amination | 559.2<br>0.71 (1) | (600 MHz, DMSO-d6) δ (ppm) 7.63 (s, 1H), 7.50 (dd, J = 8.6, 1.3 Hz, 1H), 7.38-7.33 (m, 6H), 7.18 (s, 1H), 7.04 (d, J = 9.6 Hz, 1H), 4.94 (t, J = 5.4 Hz, 1H), 4.42 (s, 1H), 4.11 (t, J = 4.9 Hz, 2H), 3.72 (q, J = 5.2 Hz, 2H), 3.45-3.37 (m, 1H), 3.30 (t, J = 3.6 Hz, 2H), 3.11 (s, 1H), 2.90-2.75 (m, 3H), 2.07 (s, 1H), 1.78 (m, 2H), 1.61 (m, 3H). |
| 64b | 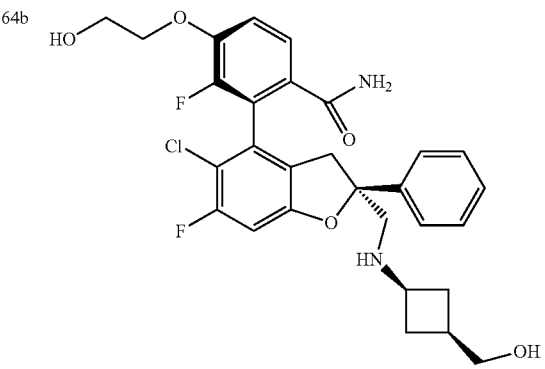 | 559.2<br>0.73 (1) | (600 MHz, DMSO-d6) δ (ppm) 7.64 (s, 1H), 7.55-7.49 (m, 1H), 7.41-7.24 (m, 6H), 7.18 (s, 1H), 7.05 (d, J = 9.6 Hz, 1H), 4.94 (t, J = 5.4 Hz, 1H), 4.11 (t, J = 4.8 Hz, 2H), 3.77-3.71 (m, 2H), 3.41 (d, J = 15.7 Hz, 1H), 3.24 (d, J = 5.8 Hz, 2H), 2.98-2.73 (m, 4H), 2.12-1.94 (m, 2H), 1.88 (s, 1H), 1.25 (s br, 3H). |

| Ex. | Structure/Chemical Name | UPLC MS m/z [M + H]+ t_R [min] (method) | 1H NMR |
|---|---|---|---|
| | 2-((2S,4S)-5-chloro-6-fluoro-2-((((cis)-3-(hydroxymethyl)cyclobutyl)amino)methyl)-2-phenyl-2,3-dihydrobenzofuran-4-yl)-3-fluoro-4-(2-hydroxyethoxy)benzamide; Formed in reductive amination together with Example 64a | | |
| 65a | 2-((2S,4S)-5-chloro-2-((((2R,4r,6S)-2,6-dimethyltetrahydro-2H-pyran-4-yl)amino)methyl)-6-fluoro-2-phenyl-2,3-dihydrobenzofuran-4-yl)-3-fluoro-4-(2-hydroxyethoxy)benzamide; Example 38 and (2R,6S)-2,6-dimethyldihydro-2H-pyran-4(3H)-one used in reductive amination | 587.4 0.77 (1) | (400 MHz, DMSO-d$_6$) δ (ppm) 7.58 (s, 1H), 7.51 (dd, J = 8.6, 1.4 Hz, 1H), 7.39 (d, J = 7.3 Hz, 2H), 7.34 (dd, J = 8.6, 6.6 Hz, 2H), 7.31-7.23 (m, 2H), 7.16 (s, 1H), 7.03 (d, J = 9.6 Hz, 1H), 4.93 (t, J = 5.4 Hz, 1H), 4.13 (t, J = 4.8 Hz, 2H), 3.77-3.72 (m, 3H), 3.46 (d, J = 15.7 Hz, 1H), 3.30-3.22 (m, 2H), 2.96 (t, J = 8.0 Hz, 2H), 2.80 (d, J = 15.7 Hz, 1H), 1.73-1.60 (m, 2H), 1.03 (dd, J = 6.2, 2.5 Hz, 6H), 0.68 (q, J = 11.6 Hz, 2H). |
| 65b | 2-((2S,4S)-5-chloro-2-((((2R,4s,6S)-2,6-dimethyltetrahydro-2H-pyran-4-yl)amino)methyl)-6-fluoro-2-phenyl-2,3-dihydrobenzofuran-4-yl)-3-fluoro-4-(2-hydroxyethoxy)benzamide; Formed in reductive amination together with Example 65a | 587.4 0.81 (1) | (400 MHz, DMSO-d$_6$) δ (ppm) 7.67 (s, 1H), 7.57-7.47 (m, 1H), 7.41 (d, J = 7.3 Hz, 2H), 7.34 (t, J = 7.6 Hz, 2H), 7.31-7.22 (m, 2H), 7.10 (s, 1H), 7.03 (d, J =9.6 Hz, 1H), 4.93 (t, J = 5.4 Hz, 1H), 4.13 (t, J = 4.8 Hz, 2H), 3.74 (q, J = 5.1 Hz, 2H), 3.61-3.47 (m, 1H), 3.48-3.36 (m, 2H), 3.02-2.90 (m, 2H), 2.89-2.76 (m, 2H), 1.50-1.36 (m, 2H), 1.14-0.96 (m, 2H), 0.89 (dd, J = 11.6, 6.2 Hz, 6H). |

| Ex. | Structure/Chemical Name | UPLC MS m/z [M + H]+ tR [min] (method) | 1H NMR |
|---|---|---|---|
| 66a | 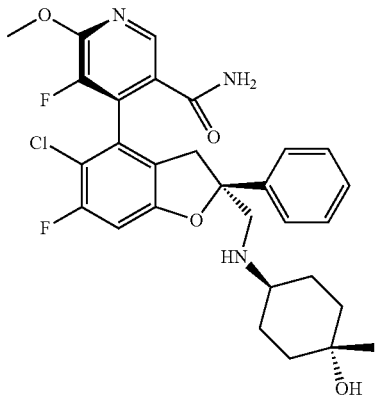<br>4-((2S,4S)-5-chloro-6-fluoro-2-((((trans)-4-hydroxy-4-methylcyclohexyl)amino)methyl)-2-phenyl-2,3-dihydrobenzofuran-4-yl)-5-fluoro-6-methoxynicotinamide; Example 42 and 4-hydroxy-4-methylcyclohexanone used in reductive amination | 558.3<br>0.82 (1) | (400 MHz, DMSO-$d_6$) δ (ppm) 8.40 (s, 1H), 7.94 (s br, 1H), 7.46-7.31 (m, 4H), 7.30 (d, J = 7.1 Hz, 1H), 7.13 (d, J = 9.6 Hz, 1H), 4.07 (s, 1H), 4.03 (s, 3H), 3.48 (d, J = 15.8 Hz, 1H), 3.01-2.89 (m, 3H), 2.35 (s br, 1H), 1.71-1.57 (m, 2H), 1.46-1.36 (m, 2H), 1.28-1.17 (m, 2H), 1.14-1.03 (m, 2H), 1.03 (s, 3H) |
| 66b | 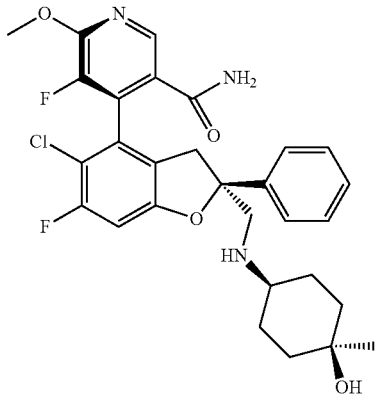<br>4-((2S,4S)-5-chloro-6-fluoro-2-((((cis)-4-hydroxy-4-methylcyclohexyl)amino)methyl)-2-phenyl-2,3-dihydrobenzofuran-4-yl)-5-fluoro-6-methoxynicotinamide; Formed in reductive amination together with Example 66a | 558.3<br>0.87 (1) | (400 MHz, DMSO-$d_6$) δ (ppm) 8.40 (s, 1H), 7.95 (s, 1H), 7.55-7.23 (m, 6H), 7.13 (d, J = 9.7 Hz, 1H), 4.03 (s, 3H), 3.92 (s, 1H), 3.56-3.44 (m, 1H), 3.01-2.84 (m, 3H), 2.27-2.18 (m, 1H), 1.50-1.41 (m, 4H), 1.29-1.14 (m, 4H), 1.05 (s, 3H). |

| Ex. | Structure/Chemical Name | UPLC MS m/z [M + H]+ t_R [min] (method) | ¹H NMR |
|---|---|---|---|
| 67a | 2-((2S,4S)-5-chloro-6-fluoro-2-((((cis)-4-hydroxy-4-methylcyclohexyl)amino)methyl)-2-phenyl-2,3-dihydrobenzofuran-4-yl)-3-fluoro-4-(((R)-tetrahydrofuran-2-yl)methoxy)benzamide; 2-((2S,4S)-2-(Aminomethyl)-5-chloro-6-fluoro-2-phenyl-2,3-dihydrobenzofuran-4-yl)-3-fluoro-4-(((R)-tetrahydrofuran-2-yl)methoxy)benzamide was used for the reductive amination. This compound was prepared analogously to Example 32a using aryl bromide (R)-2-bromo-3-fluoro-4-((tetrahydrofuran-2-yl)methoxy)benzonitrile (N-XVIII). | 627.4 0.91 (1) | (600 MHz, DMSO-d₆) δ (ppm) 7.65 (s, 1H), 7.51 (d, J = 8.7 Hz, 1H), 7.43-7.38 (m, 2H), 7.35 (t, J = 7.7 Hz, 2H), 7.33-7.25 (m, 2H), 7.19 (s, 1H), 7.06 (d, J = 9.6 Hz, 1H), 4.18 (qd, J = 6.8, 3.5 Hz, 1H), 4.13 (dd, J = 10.4, 3.4 Hz, 1H), 4.06 (dd, J = 10.3, 6.5 Hz, 1H), 3.91 (s, 1H), 3.79-3.72 (m, 1H), 3.70-3.63 (m, 1H), 3.46 (d, J = 15.6 Hz, 1H), 2.98 (m, 2H), 2.80 (d, J = 15.6 Hz, 1H), 2.23-2.17 (m, 1H), 2.03-1.95 (m, 1H), 1.92-1.77 (m, 2H), 1.70-1.62 (m, 1H), 1.49-1.40 (m, 4H), 1.29-1.21 (m, 2H), 1.19-1.13 (m, 3H), 1.04 (s, 3H). |
| 67b | 2-((2S,4S)-5-chloro-6-fluoro-2-((((trans)-4-hydroxy-4-methylcyclohexyl)amino)methyl)-2-phenyl-2,3-dihydrobenzofuran-4-yl)-3-fluoro-4-(((R)-tetrahydrofuran-2-yl)methoxy)benzamide; Formed in reductive amination together with Example 67a | 627.4 0.89 (1) | (600 MHz, DMSO-d₆) δ (ppm) 7.64 (s, 1H), 7.51 (d, J = 8.6 Hz, 1H), 7.43-7.38 (m, 2H), 7.37-7.32 (m, 2H), 7.32-7.25 (m, 2H), 7.18 (s, 1H), 7.05 (d, J = 9.6 Hz, 1H), 4.20-4.15 (m, 1H), 4.13 (dd, J = 10.4, 3.5 Hz, 1H), 4.08-4.02 (m, 2H), 3.79-3.73 (m, 1H), 3.70-3.63 (m, 1H), 3.44 (d, J = 15.7 Hz, 1H), 3.01-2.90 (m, 2H), 2.81 (d, J = 15.7 Hz, 1H), 2.36-2.29 (m, 1H), 2.04-1.96 (m, 1H), 1.91-1.77 (m, 2H), 1.71-1.62 (m, 2H), 1.61-1.57 (m, 1H), 1.43-1.34 (m, 2H), 1.26-1.15 (m, 3H), 1.09-1.03 (m, 2H), 1.01 (s, 3H) |

| Ex. | Structure/Chemical Name | UPLC MS m/z [M + H]+ t_R [min] (method) | ¹H NMR |
|---|---|---|---|
| 68a | 2-((2S,4S)-5-chloro-6-fluoro-2-((((trans)-4-hydroxy-4-methylcyclohexyl)amino)methyl)-2-phenyl-2,3-dihydrobenzofuran-4-yl)-4-ethyl-3-fluorobenzamide; 2-((2S,4S)-2-(Aminomethyl)-5-chloro-6-fluoro-2-phenyl-2,3-dihydrobenzofuran-4-yl)-4-ethyl-3-fluorobenzamide was used for the reductive amination. This compound was prepared analogously to Example 32a using aryl bromide 2-bromo-4-ethyl-3-fluorobenzonitrile (N-XIX). | 555.2 1.02 (1) | (600 MHz, DMSO-$d_6$) δ (ppm) 7.69 (s, 1H), 7.48-7.44 (m, 2H), 7.42-7.38 (m, 2H), 7.38-7.32 (m, 2H), 7.31-7.25 (m, 2H), 7.05 (d, J = 9.7 Hz, 1H), 4.06 (s, 1H), 3.46 (d, J = 15.6 Hz, 1H), 3.00-2.89 (m, 2H), 2.81 (d, J = 15.6 Hz, 1H), 2.69-2.60 (m, 2H), 2.37-2.27 (m, 1H), 1.67-1.55 (m, 2H), 1.42-1.35 (m, 2H), 1.27-1.17 (m, 2H), 1.17 (t, J = 7.5Hz, 3H), 1.09-1.02 (m, 2H), 1.01 (s, 3H) |
| 68b | 2-((2S,4S)-5-chloro-6-fluoro-2-((((cis)-4-hydroxy-4-methylcyclohexyl)amino)methyl)-2-phenyl-2,3-dihydrobenzofuran-4-yl)-4-ethyl-3-fluorobenzamide; Formed in reductive amination together with Example 68a | 555.2 1.07 (1) | (600 MHz, DMSO-$d_6$) δ (ppm) 7.71 (s, 1H), 7.49-7.44 (m, 2H), 7.42-7.38 (m, 2H), 7.38-7.33 (m, 2H), 7.32-7.25 (m, 2H), 7.06 (d, J = 9.6 Hz, 1H), 3.91 (s, 1H), 3.47 (d, J = 15.9 Hz, 1H), 3.02-2.93 (m, 2H), 2.80 (d, J = 15.7 Hz, 1H), 2.67-2.59 (m, 2H), 2.25-2.15 (m, 1H), 1.48-1.40 (m, 4H), 1.30-1.20 (m, 2H), 1.20-1.11 (m, 5H), 1.04 (s, 3H). |

| Ex. | Structure/Chemical Name | UPLC MS m/z [M + H]+ t_R [min] (method) | ¹H NMR |
|---|---|---|---|
| 69a | 2-((2S,4S)-5-chloro-6-fluoro-2-((((trans)-4-hydroxy-4-methylcyclohexyl)amino)methyl)-2-phenyl-2,3-dihydrobenzofuran-4-yl)-3-fluoro-4-(1H-imidazol-1-yl)benzamide; 2-((2S,4S)-2-(aminomethyl)-5-chloro-6-fluoro-2-phenyl-2,3-dihydrobenzofuran-4-yl)-3-fluoro-4-(1H-imidazol-1-yl)benzamide was used for the reductive amination. This compound was prepared analogously to Example 32a using aryl bromide 2-bromo-3-fluoro-4-(1H-imidazol-1-yl)benzonitrile (N-XX) | 593.3 0.68 (1) | (600 MHz, DMSO-d₆) δ (ppm) 8.29-8.23 (m, 1H), 8.17-8.10 (m, 2H), 7.90 (t, J = 8.1 Hz, 11H), 7.69 (d, J = 8.1 Hz, 1H), 7.64 (s, 1H), 7.59-7.54 (m, 2H), 7.49-7.45 (m, 2H), 7.43-7.39 (m, 1H), 7.24 (d, J = 9.2 Hz, 1H), 7.15 (s, 1H), 4.47 (s, 1 H), 3.50 (d, J = 15.2 Hz, 1 H), 3.19 (d, J = 15.6 Hz, 1H), 3.00-2.93 (m, 2H), 1.91-1.86 (m, 1 H), 1.58-1.52 (m, 2H), 1.48-1.35 (m, 2H), 1.35-1.20 (m, 4 H), 1.10 (s, 3H) |
| 69b | 2-((2S,4S)-5-chloro-6-fluoro-2-((((cis)-4-hydroxy-4-methylcyclohexyl)amino)methyl)-2-phenyl-2,3-dihydrobenzofuran-4-yl)-3-fluoro-4-(1H-imidazol-1-yl)benzamide; Formed in reductive amination together with Example 69a | 593.3 0.71 (1) | (600 MHz, DMSO-d₆) δ (ppm) 8.11 (s, 1H), 7.93 (s, 1H), 7.86 (t, J = 7.9 Hz, 1H), 7.68-7.62 (m, 2H), 7.48 (s, 1H), 7.44-7.41 (m, 2H), 7.35 (t, J = 7.9 Hz, 2H), 7.30-7.26 (m, 1H), 77.15-7.10 (m, 2H), 3.91 (s, 1H), 3.51 (d, J = 16.0 Hz, 1H), 3.05-2.98 (m, 3H), 2.22-2.19 (m, 1H), 1.49-1.40 (m, 4H), 1.30-1.21 (m, 2H), 1.19-1.12 (m, 2H), 1.05 (s, 3H) |

| Ex. | Structure/Chemical Name | UPLC MS m/z [M + H]+ $t_R$ [min] (method) | 1H NMR |
|---|---|---|---|
| 70 | 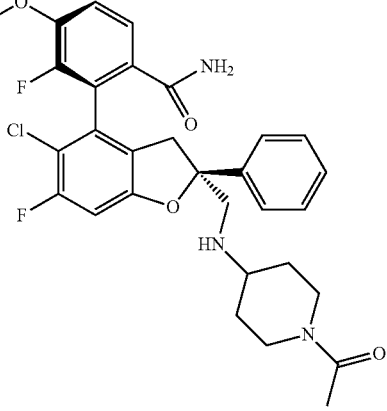<br>2-((2S,4S)-2-(((1-acetylpiperidin-4-yl)amino) methyl)-5-chloro-6-fluoro-2-phenyl-2,3-dihydrobenzofuran-4-yl)-4-(difluoromethoxy)-3-fluorobenzamide; 1-acetylpiperidin-4-one used in reductive amination | 606.3<br>0.88 (1) | (400 MHz, DMSO-$d_6$) δ (ppm) 7.78 (s, 1H), 7.58-7.48 (m, 2H), 7.42-7.24 (m, 7H), 7.15-7.04 (m, 2H), 3.99 (s br, 1H), 3.59 (d, J = 13.5 Hz, 1H), 3.49 (d, J = 15.7 Hz, 1H), 2.97 (s br, 2H), 2.85 (d, J = 15.8 Hz, 1H), 2.60 (d, J = 11.6 Hz, 1H), 1.92 (s, 3H), 1.75-0.80 (m, 9H). |
| 71a | 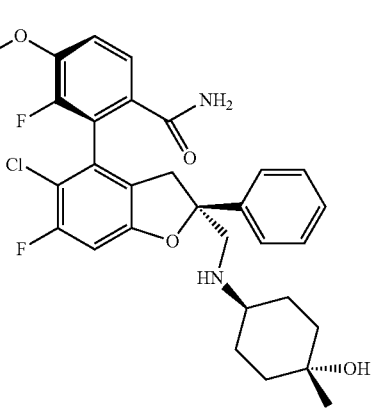<br>2-((2S,4S)-5-chloro-6-fluoro-2-((((trans)-4-hydroxy-4-methylcyclohexyl)amino)methyl)-2-phenyl-2,3-dihydrobenzofuran-4-yl)-3-fluoro-4-(pyrimidin-2-ylmethoxy)benzamide; 2-((2S,4S)-2-(aminomethyl)-5-chloro-6-fluoro-2-phenyl-2,3-dihydrobenzofuran-4-yl)-3-fluoro-4-(pyrimidin-2-ylmethoxy)benzamide was used for the reductive amination. This compound was prepared analogously to Example 32a using aryl bromide 2-bromo-3-fluoro-4-(pyrimidin-2-ylmethoxy)benzonitrile (N-XXI) | 635.4<br>3.62 (2) | (400 MHz, DMSO-$d_6$) δ (ppm) 8.82 (d, J = 4.9 Hz, 2H), 7.59 (s br, 1H), 7.52-7.20 (m, 9H), 7.14 (s br, 1H), 7.03 (d, J = 9.6 Hz, 1H), 5.42 (s, 2H), 4.02 (s, 1H), 3.44 (d, J = 15.8 Hz, 1H), 2.94 (s br, 2H), 2.81 (d, J = 15.7 Hz, 1H), 1.70-1.50 (m, 2H), 1.45-1.30 (m, 2H), 1.25-1.12 (m, 2H), 1.10-0.98 (m, 2H), 0.99 (s, 3H) |

| Ex. | Structure/Chemical Name | UPLC MS m/z [M + H]+ $t_R$ [min] (method) | $^1$H NMR |
|---|---|---|---|
| 71b | 2-((2S,4S)-5-chloro-6-fluoro-2-((((cis)-4-hydroxy-4-methylcyclohexyl)amino)methyl)-2-phenyl-2,3-dihydrobenzofuran-4-yl)-3-fluoro-4-(pyrimidin-2-ylmethoxy)benzamide; Formed in reductive amination together with Example 71a | 635.4 3.78 (2) | (400 MHz, DMSO-$d_6$) δ (ppm) 8.82 (d, J = 5.0 Hz, 2H), 7.60 (s br, 1H), 7.52-7.35 (m, 4H), 7.33 (t, J = 7.5 Hz, 2H), 7.26 (t, J = 8.3 Hz, 2H), 7.15 (s br, 1H), 7.03 (d, J = 9.6 Hz, 1H), 5.42 (s, 2H), 3.87 (s, 1H), 3.45 (d, J = 15.6 Hz, 1H), 2.97 (s br, 2H), 2.80 (d, J = 15.9 Hz, 1H), 2.19 (s br, 1H), 1.50-1.34 (m, 4H), 1.32-1.07 (m, 4H), 1.02 (s, 3H). |

Example 72: 2-((2S,4S)-5-chloro-6-fluoro-2-(((trans-4-hydroxycyclohexyl)amino)methyl)-2-phenyl-2,3-dihydrobenzofuran-4-yl)-4-(difluoromethoxy)-3-fluorobenzamide or (2P)-2-[(2S)-5-Chloro-6-fluoro-2-({[(1 r,4S)-4-hydroxycyclohexyl]amino}methyl)-2-phenyl-2,3-dihydro-1-benzofuran-4-yl]-4-(difluoromethoxy)-3-fluorobenzamide

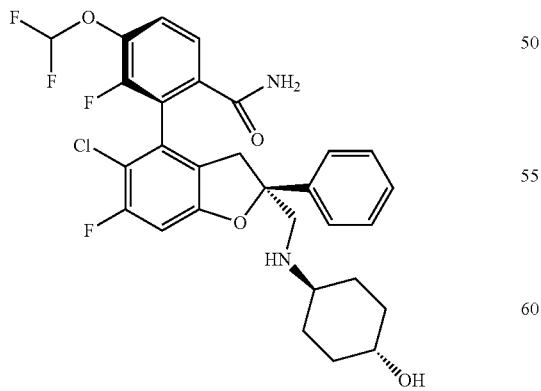

Reaction Scheme Example 72

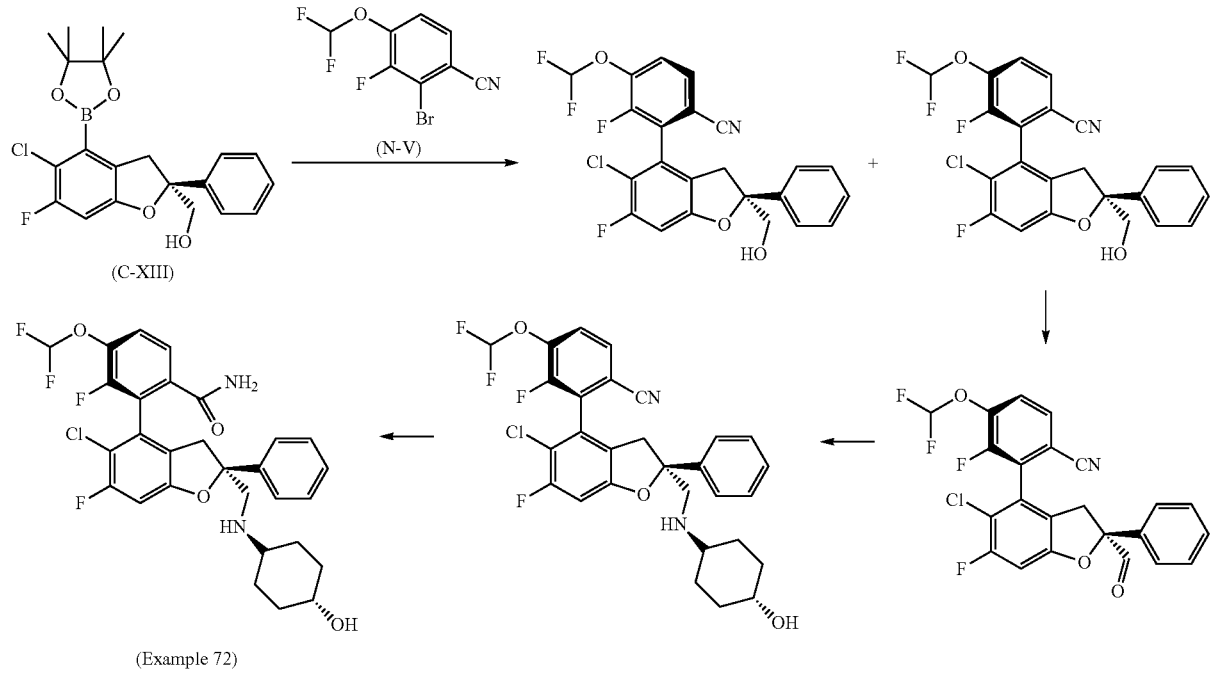

(Example 72)

Step 1: 2-((2S,4R)-5-Chloro-6-fluoro-2-(hydroxymethyl)-2-phenyl-2,3-dihydrobenzofuran-4-yl)-4-(difluoromethoxy)-3-fluorobenzonitrile and 2-((2S,4S)-5-chloro-6-fluoro-2-(hydroxymethyl)-2-phenyl-2,3-dihydrobenzofuran-4-yl)-4-(difluoromethoxy)-3-fluorobenzonitrile A suspension of (S)-(5-chloro-6-fluoro-2-phenyl-4-(4,4,5,5-tetramethyl-1,3,2-dioxaborolan-2-yl)-2,3-dihydrobenzofuran-2-yl)methanol (C-XIII) (10 g, 17.30 mmol), 2-bromo-4-(difluoromethoxy)-3-fluorobenzonitrile (N-V) (5.52 g, 20.76 mmol), tris(dibenzylideneacetone)dipalladium(0) (0.792 g, 0.865 mmol), 4,6-bis(diphenylphosphino)-10H-phenoxazine (0.954 g, 1.730 mmol) and K$_3$PO$_4$ (11.02 g, 51.9 mmol) in toluene (80 mL) and water (20 mL) was stirred at 100° C. for 16 h under Ar. The reaction mixture was quenched by the addition of a sat solution of NaHCO$_3$, then extracted with EtOAc. The organic layers were combined and washed with a sat solution of NaHCO$_3$, dried over anhydrous Na$_2$SO$_4$ and concentrated. The residue was purified by flash chromatography (silica, hexane/EtOAc, gradient 0% to 70% EtOAc) to afford the desired compounds as single diastereoisomers.

2-((2S,4R)-5-Chloro-6-fluoro-2-(hydroxymethyl)-2-phenyl-2,3-dihydrobenzofuran-4-yl)-4-(difluoromethoxy)-3-fluorobenzonitrile (3.21 g): $^1$H NMR (400 MHz, DMSO-d$_6$) δ (ppm) 7.99 (dd, J=8.7, 1.4 Hz, 1H), 7.80-7.68 (m, 1H), 7.57-7.25 (m, 7H), 5.36 (t, J=5.9 Hz, 1H), 3.74-3.56 (m, 2H), 3.56-3.47 (m, 1H), 3.16-3.04 (m, 1H). UPLC-MS 1: m/z 481.3 [M+NH$_4$]$^+$, t$_R$=1.19 min.

2-((2S,4S)-5-Chloro-6-fluoro-2-(hydroxymethyl)-2-phenyl-2,3-dihydrobenzofuran-4-yl)-4-(difluoromethoxy)-3-fluorobenzonitrile (3.14 g): $^1$H NMR (400 MHz, DMSO-d$_6$) δ (ppm) 8.04 (dd, J=8.7, 1.4 Hz, 1H), 7.72 (t, J=8.2 Hz, 1H), 7.68-7.27 (m, 7H), 5.33 (t, J=5.9 Hz, 1H), 3.74-3.60 (m, 2H), 3.54 (d, J=16.2 Hz, 1H), 3.01 (d, J=16.2 Hz, 1H). UPLC-MS 1: m/z 508.2 [M+formate]$^-$, t$_R$=1.20 min.

Step 2: 2-((2S,4S)-5-Chloro-6-fluoro-2-formyl-2-phenyl-2,3-dihydrobenzofuran-4-yl)-4-(difluoromethoxy)-3-fluorobenzonitrile At −78° C. DMSO (0.99 mL, 13.90 mmol) was added to a solution of oxalyl chloride (0.61 mL, 6.95 mmol) in DCM (20 mL). After 30 min at −78° C., a solution of 2-((2S,4S)-5-chloro-6-fluoro-2-(hydroxymethyl)-2-phenyl-2,3-dihydrobenzofuran-4-yl)-4-(difluoromethoxy)-3-fluorobenzonitrile (2.93 g, 6.32 mmol) in DCM (20 mL) as well as TEA (4.40 mL, 31.6 mmol) were added and the reaction mixture was stirred at −78° C. for 2 h. The reaction mixture was quenched by the addition of brine, then extracted with DCM. The organic layers were combined and washed with brine, dried over anhydrous Na$_2$SO$_4$ and concentrated to give the title compound (2.92 g) as a brownish powder. UPLC-MS 1: t$_R$=1.24 min.

Step 3: 2-((2S,4S)-5-Chloro-6-fluoro-2-(((trans-4-hydroxycyclohexyl)amino)methyl)-2-phenyl-2,3-dihydrobenzofuran-4-yl)-4-(difluoromethoxy)-3-fluorobenzonitrile Under Ar trans-4-aminocyclohexanol (1.457 g, 12.65 mmol) and AcOH (0.362 mL, 6.32 mmol) were added to a solution of 2-((2S,4S)-5-chloro-6-fluoro-2-formyl-2-phenyl-2,3-dihydrobenzofuran-4-yl)-4-(difluoromethoxy)-3-fluorobenzonitrile (2.92 g, 6.32 mmol) in 1,2-dichloroethane (25 mL). Then, the reaction mixture was stirred at 85° C. for 30 min. Sodium triacetoxyborohydride (4.02 g, 18.97 mmol) was added and the reaction mixture was stirred at 85° C. for 30 min. The reaction mixture was quenched by the addition of a sat solution of NaHCO$_3$, then extracted with DCM. The organic layers were combined and washed with a sat solution of NaHCO₃, dried over anhydrous Na₂SO₄ and concentrated. The residue was purified by flash chromatography (silica, hexane/EtOAc, gradient 0% to 100% EtOAc) to afford the desired product (2.90 g) as a colorless powder. UPLC-MS 1: m/z 561.2 [M+H]⁺, t$_R$=0.93 min.

Step 4: 2-((2S,4S)-5-Chloro-6-fluoro-2-(((trans-4-hydroxycyclohexyl)amino)methyl)-2-phenyl-2,3-dihydrobenzofuran-4-yl)-4-(difluoromethoxy)-3-fluorobenzamide or (2P)-2-[(2S)-5-Chloro-6-fluoro-2-({[(1r,4S)-4-hydroxycyclohexyl]amino}methyl)-2-phenyl-2,3-dihydro-1-benzofuran-4-yl]-4-(difluoromethoxy)-3-fluorobenzamide (Example 72)

At RT hydrido(dimethylphosphinous acid-kP)[hydrogen bis(dimethylphosphinito-kP)]platinum(II) (0.688 g, 1.603 mmol) was added to a solution of tert-butyl 2-((2S,4S)-5-chloro-6-fluoro-2-(((trans-4-hydroxycyclohexyl)amino)methyl)-2-phenyl-2,3-dihydrobenzofuran-4-yl)-4-(difluoromethoxy)-3-fluorobenzonitrile (2.90 g, 5.17 mmol) in EtOH (20 mL) and water (20 mL). Then, the reaction mixture was stirred at 80° C. for 2 h. The reaction mixture was quenched by the addition of a sat solution of NaHCO₃, then extracted with EtOAc. The organic layers were combined and washed with a sat solution of NaHCO₃, dried over anhydrous Na₂SO₄ and concentrated. The residue was purified by flash chromatography (silica, DCM/MeOH, gradient 0% to 10% MeOH) to afford the title compound (2.33 g) as a colorless powder. ¹H NMR (400 MHz, DMSO-d₆) δ (ppm) 1H NMR (400 MHz, DMSO-d₆) δ 7.79 (s, 1H), 7.60-7.50 (m, 2H), 7.44-7.15 (m, 7H), 7.09 (d, J=9.7 Hz, 1H), 4.40 (d, J=4.4 Hz, 1H), 3.48 (d, J=15.8 Hz, 1H), 3.31-3.22 (m, 1H), 3.03-2.90 (m, 2H), 2.85 (d, J=15.8 Hz, 1H), 2.26-2.15 (m, 1H), 1.83-1.57 (m, 4H), 1.25 (s, 1H), 1.13-0.98 (m, 2H), 0.96-0.79 (in, 2H). UPLC-MS 1: m/z 579.3 [M+H]⁺, t$_R$=0.94 min. The absolute configuration was confirmed by an X-ray cocrystal structure of Example 72 bound to the YAP binding site of TEAD4.

The following compounds were prepared analogously to Example 72 UPLC MS

| Ex. | Structure/Chemical Name | UPLC MS m/z [M + H]⁺ t$_R$ [min] (method) | ¹H NMR |
|---|---|---|---|
| 73 | 2-((2S,4S)-2-((tert-butylamino)methyl)-5-chloro-6-fluoro-2-phenyl-2,3-dihydrobenzofuran-4-yl)-4-(difluoromethoxy)-3-fluorobenzamide; 2-methylpropan-2-amine used in reductive amination | 537.2 0.92 (1) | (600 MHz, DMSO-d₆) δ (ppm) 7.83 (s, 1H), 7.59 – 7.52 (m, 2H), 7.50 – 7.23 (m, 7H), 7.10 (d, J = 9.7 Hz, 1H), 3.52 (d, J = 15.7 Hz, 1H), 2.98 – 2.88 (m, 2H), 2.85 (d, J = 15.7 Hz, 1H), 1.12 (t, J = 7.8 Hz, 1H), 0.92 (s, 9H) |
| 74 | 2-((2S,4S)-5-chloro-6-fluoro-2-((((R)-2-hydroxypropyl)amino)methyl)-2-phenyl-2,3-dihydrobenzofuran-4-yl)-4-(difluoromethoxy)-3-fluorobenzamide; (R)-1-aminopropan-2-ol used in reductive amination | 539.3 0.93 (1) | (400 MHz, DMSO-d₆) δ (ppm) 7.81 (s, 1H), 7.59 – 7.14 (m, 9H), 7.10 (d, J = 9.7 Hz, 1H), 4.32 (d, J = 4.5 Hz, 1H), 3.60 – 3.48 (m, 2H), 3.01 – 2.91 (m, 2H), 2.86 (d, J = 15.7 Hz, 1H), 2.41 – 2.31 (m, 2H), 1.56 (br s, 1H), 0.92 (d, J = 6.2 Hz, 3H) |

-continued

| Ex. | Structure/Chemical Name | UPLC MS m/z [M + H]+ $t_R$ [min] (method) | $^1$H NMR |
|---|---|---|---|
| 75 | 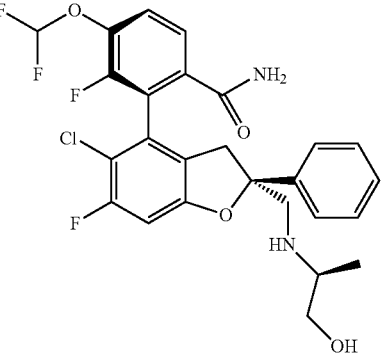<br>2-((2S,4S)-5-chloro-6-fluoro-2-((((S)-1-hydroxypropan-2-yl)amino)methyl)-2-phenyl-2,3-dihydrobenzofuran-4-yl)-4-(difluoromethoxy)-3-fluorobenzamide; (S)-2-amino-1-propanol used in reductive amination | 539.3<br>0.91 (1) | (400 MHz, DMSO-$d_6$) δ (ppm) 7.81 (s, 1H), 7.59 – 7.15 (m, 9H), 7.09 (d, J = 9.7 Hz, 1H), 4.40 (t, J = 5.3 Hz, 1H), 3.47 (d, J = 15.9 Hz, 1H), 3.23 – 3.15 (m, 1H), 3.13 – 2.99 (m, 2H), 2.97 – 2.91 (m, 1H), 2.87 (d, J = 15.8 Hz, 1H), 1.49 (br s, 1H), 1.24 (s, 1H), 0.79 (d, J = 6.3 Hz, 3H) |
| 76 | 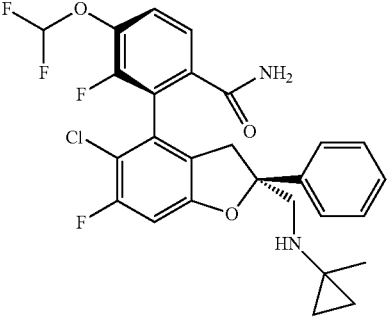<br>2-((2S,4S)-5-chloro-6-fluoro-2-(((1-methylcyclopropyl)amino)methyl)-2-phenyl-2,3-dihydrobenzofuran-4-yl)-4-(difluoromethoxy)-3-fluorobenzamide; 1-methylcyclopropanamine used in reductive amination | 535.3<br>0.95 (1) | (400 MHz, DMSO-$d_6$) δ (ppm) 7.79 (s, 1H), 7.59 – 7.14 (m, 9H), 7.06 (d, J = 9.7 Hz, 1H), 3.44 (d, J = 16.0 Hz, 1H), 3.09 – 2.90 (m, 2H), 2.82 (d, J = 15.3 Hz, 1H), 1.69 (s, 1H), 1.09 (s, 3H), 0.37 (d, J = 9.5 Hz, 1H), 0.28 (d, J = 10.8 Hz, 1H), 0.18 (s, 2H) |
| 77 | 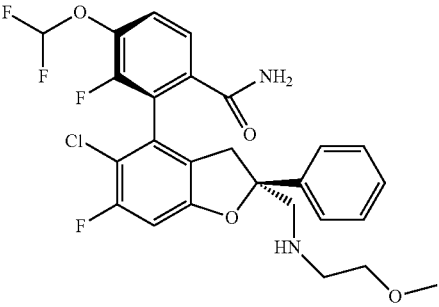<br>2-((2S,4S)-5-chloro-6-fluoro-2-(((2-methoxyethyl)amino)methyl)-2-phenyl-2,3-dihydrobenzofuran-4-yl)-4-(difluoromethoxy)-3-fluorobenzamide; 2-methoxyethanamine used in reductive amination | 540.2/541.1<br>1.03 (1) | (400 MHz, DMSO-$d_6$) δ (ppm) 7.83 (s, 1H), 7.59 – 7.52 (m, 2H), 7.49 – 7.23 (m, 7H), 7.13 (d, J = 9.6 Hz, 1H), 3.49 (d, J = 14.9 Hz, 1H), 3.28 (t, J = 5.5 Hz, 2H), 3.17 (s, 3H), 3.00 (br s, 2H), 2.88 (d, J = 16.0 Hz, 1H), 2.64 – 2.59 (m, 2H), 1.52 (br s, 1H) |

| Ex. | Structure/Chemical Name | UPLC MS m/z [M + H]+ $t_R$ [min] (method) | $^1$H NMR |
|---|---|---|---|
| 78 | 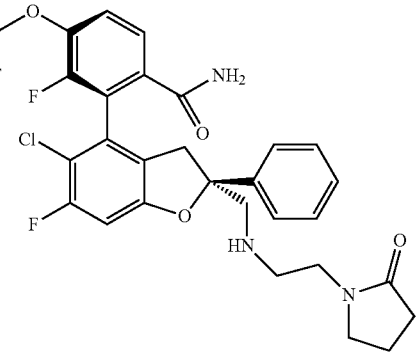<br>2-((2S,4S)-5-chloro-6-fluoro-2-(((2-(2-oxopyrrolidin-1-yl)ethyl)amino)methyl)-2-phenyl-2,3-dihydrobenzofuran-4-yl)-4-(difluoromethoxy)-3-fluorobenzamide; 1-(2-aminoethyl)pyrrolidin-2-one used in reductive amination | 592.2<br>0.90 (1) | (400 MHz, DMSO-d$_6$) δ (ppm) 7.79 (s, 1H), 7.63 – 7.12 (m, 9H), 7.07 (d, J = 9.7 Hz, 1H), 3.45 (d, J = 15.8 Hz, 1H), 3.21 – 3.07 (m, 4H), 3.02 – 2.82 (m, 3H), 2.57 (br s, 2H), 2.12 – 2.03 (m, 2H), 1.83 – 1.71 (m, 2H), 1.61 (br s, 1H) |
| 79 | 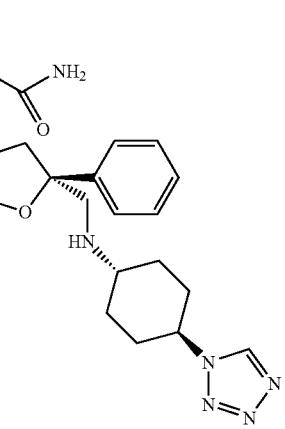<br>2-((2S,4S)-2-((((trans)-4-(1H-tetrazol-1-yl)cyclohexyl)amino)methyl)-5-chloro-6-fluoro-2-phenyl-2,3-dihydrobenzofuran-4-yl)-4-(difluoromethoxy)-3-fluorobenzamide; trans-4-(1H-tetrazol-1-yl)cyclohexanamine (S-II) used in reductive amination | 631.3<br>0.90 (1) | (400 MHz, CDCl3) δ (ppm) 8.54 (s, 1H), 7.62 (d, J = 8.6 Hz, 1H), 7.47 – 7.23 (m, 6H), 6.82 (d, J = 9.0 Hz, 1H), 6.60 (t, J = 72.5 Hz, 1H), 5.52 (d, J = 48.4 Hz, 2H), 4.43 (t, J = 11.9 Hz, 1H), 3.46 (d, J = 15.6 Hz, 1H), 3.20 – 2.97 (m, 3H), 2.51 (t, J = 11.1 Hz, 1H), 2.24 (d, J = 11.0 Hz, 2H), 2.02 (dd, J = 28.7, 14.6 Hz, 2H), 1.82 (q, J = 12.4, 11.2 Hz, 2H), 1.23 (q, J = 13.1, 12.3 Hz, 3H) |
| 80 | 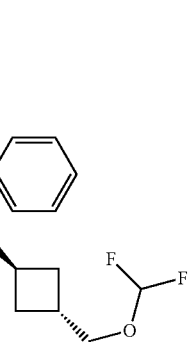<br>2-((2S,4S)-5-chloro-2-(((trans-3-((difluoromethoxy)methyl)cyclobutyl)ami | 615.3<br>0.97 (1) | (400 MHz, DMSO-d$_6$) δ (ppm) 7.80 (s, 1H), 7.61 – 7.14 (m, 9H), 7.08 (d, J = 9.7 Hz, 1H), 6.62 (t, J = 76.4 Hz, 1H), 3.76 (d, J = 7.3 Hz, 2H), 3.46 (d, J = 15.7 Hz, 1H), 3.22 – 3.15 (m, 1H), 2.93 – 2.81 (m, 3H), 2.35 – 2.23 (m, 1H), 1.88 – 1.65 (m, 4H) |

| Ex. | Structure/Chemical Name | UPLC MS m/z [M + H]+ t$_R$ [min] (method) | $^1$H NMR |
|---|---|---|---|
| | no)methyl)-6-fluoro-2-phenyl-2,3-dihydrobenzofuran-4-yl)-4-(difluoromethoxy)-3-fluorobenzamide; trans-3-((difluoromethoxy)methyl)cyclobutanamine (S-III) used in reductive amination | | |
| 81a | 2-((2S,4S)-5-chloro-6-fluoro-2-(((((1S,3R,4R)-3-fluoro-4-hydroxycyclohexyl)amino)methyl)-2-phenyl-2,3-dihydrobenzofuran-4-yl)-4-(difluoromethoxy)-3-fluorobenzamide; (1R,2R,4S)-4-amino-2-fluorocyclohexanol (S-IV) used in reductive amination | 597.2 0.99 (1) | (400 MHz, DMSO-d$_6$) δ (ppm) 7.94 (s, 1H), 7.58 (d, J = 8.8 Hz, 1H), 7.56 – 7.51 (m, 1H), 7.50 – 7.22 (m, 7H), 7.09 (d, J = 9.6 Hz, 1H), 5.08 (d, J = 4.2 Hz, 1H), 4.48 – 4.33 (m, 1H), 3.54 (d, J = 15.1 Hz, 1H), 3.49 – 3.43 (m, 1H), 2.98 – 2.88 (m, 2H), 2.86 (d, J = 15.7 Hz, 1H), 2.72 (br s, 1H), 1.81 – 1.69 (m, 1H), 1.58 – 1.32 (m, 6H) |
| 81b | 2-((2S,4S)-5-chloro-6-fluoro-2-(((((1R,3S,4S)-3-fluoro-4-hydroxycyclohexyl)amino)methyl)-2-phenyl-2,3-dihydrobenzofuran-4-yl)-4-(difluoromethoxy)-3-fluorobenzamide; (1S,2S,4R)-4-amino-2-fluorocyclohexanol (S-V) used in reductive amination | 597.2 0.97 (1) | (400 MHz, DMSO-d$_6$) δ (ppm) 7.91 (s, 1H), 7.58 (d, J = 8.8 Hz, 1H), 7.54 (t, J = 7.9 Hz, 1H), 7.49 – 7.23 (m, 7H), 7.09 (d, J = 9.6 Hz, 1H), 4.98 (d, J = 4.3 Hz, 1H), 4.51 – 4.35 (m, 1H), 3.54 – 3.44 (m, 2H), 2.95 (d, J = 4.9 Hz, 2H), 2.87 (d, J = 15.7 Hz, 1H), 2.70 (br s, 1H), 1.84 – 1.72 (m, 1H), 1.59 – 1.50 (m, 1H), 1.50 – 1.44 (m, 2H), 1.43 – 1.32 (m, 3H) |

| Ex. | Structure/Chemical Name | UPLC MS m/z [M + H]+ t_R [min] (method) | $^1$H NMR |
|---|---|---|---|
| 82 | 2-((2S,4S)-5-chloro-6-fluoro-2-(((trans-3-fluorocyclobutyl)amino)methyl)-2-phenyl-2,3-dihydrobenzofuran-4-yl)-4-(difluoromethoxy)-3-fluorobenzamide; Trans-3-fluoro-cyclobutylamine used in reductive amination | 553.2 1.01 (1) | (400 MHz, DMSO-d$_6$) δ (ppm) 7.85 (s, 1H), 7.58 – 7.52 (m, 2H), 7.49 – 7.23 (m, 7H), 7.10 (d, J = 9.6 Hz, 1H), 5.13 – 4.98 (m, 1H), 3.50 (d, J = 15.2 Hz, 1H), 3.32 (br s, 1H), 2.91 – 2.83 (m, 3H), 2.20 – 2.08 (m, 2H), 2.07 – 1.97 (m, 2H), 1.92 (br s, 1H) |
| 83 | 2-((2S,4S)-5-chloro-6-fluoro-2-((((1R,3S)-3-hydroxycyclohexyl)amino)methyl)-2-phenyl-2,3-dihydrobenzofuran-4-yl)-4-(difluoromethoxy)-3-fluorobenzamide; (1S,3R)-3-aminocyclohexanol used in reductive amination | 579.3 0.92 (1) | (400 MHz, DMSO-d$_6$) δ (ppm) 7.80 (br s, 1H), 7.59 – 7.13 (m, 9H), 7.12 – 7.03 (m, 1H), 3.46 (d, J = 15.5 Hz, 1H), 3.04 – 2.79 (m, 2H), 2.33 – 2.19 (m, 1H), 2.00 – 1.82 (m, 1H), 1.75 – 1.48 (m, 6H), 1.39 – 1.18 (m, 2H), 0.98 – 0.67 (m, 3H) |
| 84 | 2-((2S,4S)-5-chloro-6-fluoro-2-((((trans)-4-hydroxy-1-methylcyclohexyl)amino)methyl)-2-phenyl-2,3-dihydrobenzofuran-4-yl)-4-(difluoromethoxy)-3-fluorobenzamide; | 593.2 0.97 (1) | (400 MHz, MeOH-d$_4$) δ (ppm) 7.85 (s, 1H), 7.60 – 7.13 (m, 9H), 7.07 (d, J = 9.6 Hz, 1H), 4.45 (d, J = 3.5 Hz, 1H), 3.62 (d, J = 15.8 Hz, 1H), 2.93 – 2.75 (m, 3H), 1.61 – 1.02 (m, 9H), 0.94 (s, 1H), 0.86 (s, 3H). |

| Ex. | Structure/Chemical Name | UPLC MS m/z [M + H]+ $t_R$ [min] (method) | ¹H NMR |
|---|---|---|---|
| | Trans-4-amino-4-methylcyclohexanol used in reductive amination | | |

Example 85a and Example 85b: 2-((2S,4S)-5-Chloro-6-fluoro-2-(((6-hydroxyspiro[3.3]heptan-2-yl)amino)methyl)-2-phenyl-2,3-dihydrobenzofuran-4-yl)-4-(difluoromethoxy)-3-fluorobenzamide (Example 85a) and 2-((2S,4S)-5-Chloro-6-fluoro-2-(((6-hydroxyspiro[3.3]heptan-2-yl)amino)methyl)-2-phenyl-2,3-dihydrobenzofuran-4-yl)-4-(difluoromethoxy)-3-fluorobenzamide (Example 85b)

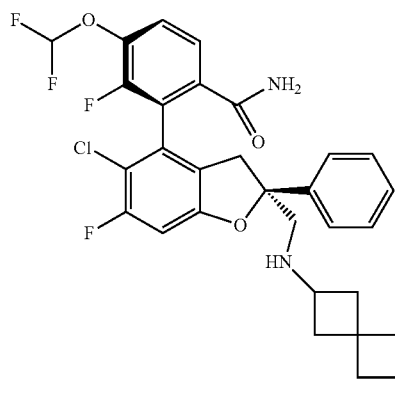

Example 85a

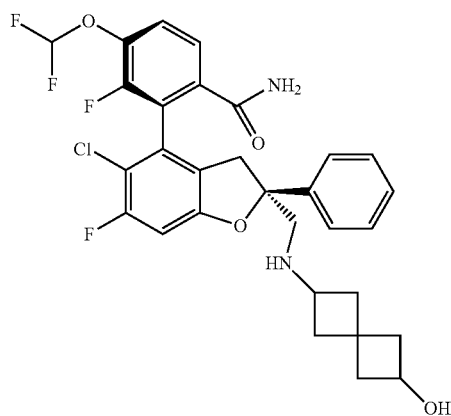

Example 85b

The title compounds were prepared analogously to Example 72. Racemic 6-aminospiro[3.3]heptan-2-ol was used in the reductive amination. Both title compounds were isolated by chiral separation of the diastereomeric mixture after reductive amination using preparative chiral HPLC (Chiralpak IC 250×25 mm I.D., 5 μm, heptane/DCM/EtOH 8:1:1+0.05% DEA, flow rate: 15 mL/min). The absolute configuration of the spiro moiety in the respective title compounds was not determined.

2-((2S,4S)-5-Chloro-6-fluoro-2-(((6-hydroxyspiro[3.3]heptan-2-yl)amino)methyl)-2-phenyl-2,3-dihydrobenzofuran-4-yl)-4-(difluoromethoxy)-3-fluorobenzamide (Example 85a): ¹H NMR (400 MHz, DMSO-d₆) δ (ppm) 7.85 (s, 1H), 7.58 (dd, J=8.5, 1.2 Hz, 1H), 7.51-7.36 (m, 6H), 7.31 (t, J=7.0 Hz, 1H), 7.15-6.73 (m, 2H), 4.05 (p, J=7.3 Hz, 1H), 3.62 (q, J=7.1 Hz, 1H), 3.41 (d, J=15.8 Hz, 1H), 3.13-2.93 (m, 4H), 2.39-2.28 (m, 1H), 2.26-2.01 (m, 3H), 1.91-1.78 (m, 2H), 1.73-1.62 (m, 2H), 1.31 (s, 1H), 1.19 (t, J=7.0 Hz, 1H). UPLC-MS 1: m/z 591.2 [M+H]⁺, $t_R$=0.88 min. Chiral HPLC (Chiralpak IC 250×4.6 mm I.D., 5 μm, heptane/DCM/EtOH 8:1:1+0.05% DEA, flow rate: 1 mL/min): $t_R$=10.63 min 2-((2S,4S)-5-Chloro-6-fluoro-2-(((6-hydroxyspiro[3.3]heptan-2-yl)amino)methyl)-2-phenyl-2,3-dihydrobenzofuran-4-yl)-4-(difluoromethoxy)-3-fluorobenzamide (Example 85b): ¹H NMR (400 MHz, DMSO-d₆) δ (ppm) 7.58 (d, J=8.6 Hz, 1H), 7.51-7.27 (m, 8H), 7.14-6.75 (m, 2H), 4.04 (p, J=7.4 Hz, 1H), 3.41 (d, J=15.8 Hz, 1H), 3.13-2.94 (m, 4H), 2.37-2.27 (m, 1H), 2.21-2.07 (m, 3H), 1.84 (q, J=10.3 Hz, 2H), 1.68 (q, J=8.7 Hz, 2H), 1.30 (br s, 1H), 0.91 (br s, 1H). UPLC-MS 1: m/z 591.2 [M+H]⁺, $t_R$=0.89 min. Chiral HPLC (Chiralpak IC 250×4.6 mm I.D., 5 μm, heptane/DCM/EtOH 8:1:1+0.05% DEA, flow rate: 1 mL/min): $t_R$=11.85 min Example 86: 2-((2S,3S,4S)-2-(Aminomethyl)-5-chloro-3-hydroxy-2-phenyl-2,3-dihydrobenzofuran-4-yl)-3-fluoro-4-methoxybenzamide

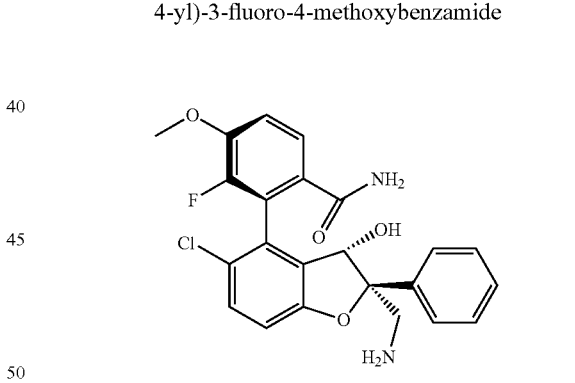

The title compound was prepared analogously to Example 5a from tert-butyl (((2S,3S)-5-chloro-3-hydroxy-2-phenyl-4-(4,4,5,5-tetramethyl-1,3,2-dioxaborolan-2-yl)-2,3-dihydrobenzofuran-2-yl)methyl)carbamate (C-VI) and 2-bromo-3-fluoro-4-methoxybenzonitrile (N-IV). 2-((2S,3S,4S)-2-(Aminomethyl)-5-chloro-3-hydroxy-2-phenyl-2,3-dihydrobenzofuran-4-yl)-3-fluoro-4-methoxybenzamide (Example 86): ¹H NMR (400 MHz, DMSO-d₆) δ (ppm) 7.53 (s br, 1H), 7.50-7.36 (m, 7H), 7.34-7.28 (m, 2H), 7.13 (d, J=8.6 Hz, 1H), 4.96 (s, 1H), 3.90 (s, 3H), 3.28 (d, J=13.9 Hz, 1H), 3.16 (d, J=13.8 Hz, 1H). UPLC-MS 1: m/z 443.3 [M+H]⁺, $t_R$=0.74 min.

Other diastereoisomer 2-((2S,3S,4R)-2-(aminomethyl)-5-chloro-3-hydroxy-2-phenyl-2,3-dihydrobenzofuran-4-yl)-3-fluoro-4-methoxybenzamide: UPLC-MS 1: m/z 443.3 [M+H]⁺, $t_R$=0.58 min.

The following compounds were prepared analogously to Example 86

| Ex. | Structure/Chemical Name | UPLC MS m/z [M + H]+ t_R [min] (method) | ¹H NMR |
|---|---|---|---|
| 87 | 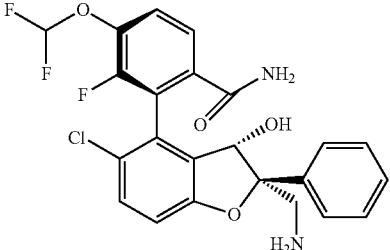<br>2-((2S,3S,4S)-2-(aminomethyl)-5-chloro-3-hydroxy-2-phenyl-2,3-dihydrobenzofuran-4-yl)-4-(difluoromethoxy)-3-fluorobenzamide;<br>2-bromo-4-(difluoromethoxy)-3-fluorobenzonitrile (N-V) used in Suzuki coupling | 479.2<br>0.78 (1) | (400 MHz, DMSO-d₆) δ (ppm) 7.61 – 7.53 (m, 4.3H), 7.50 – 7.43 (m, 3H), 7.41 – 7.36 (m, 3.4H), 7.34 – 7.29 (m, 1H), 7.19 – 7.14 (m, 1.3H), 5.01 (s, 1H), 3.25 (d, J = 13.9 Hz, 1H), 3.14 (d, J = 13.9 Hz, 1H) |
| 88 | 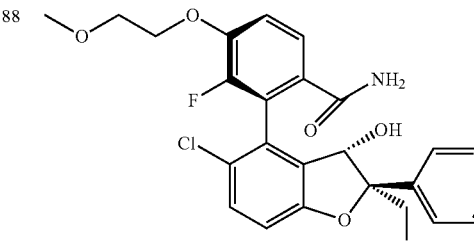<br>2-((2S,3S,4S)-2-(aminomethyl)-5-chloro-3-hydroxy-2-phenyl-2,3-dihydrobenzofuran-4-yl)-3-fluoro-4-(2-methoxyethoxy)benzamide;<br>2-bromo-3-fluoro-4-(2-methoxyethoxy)benzonitrile (N-IX) used in Suzuki coupling | 487.4<br>0.73 (1) | (400 MHz, DMSO-d₆) δ (ppm) 7.52 (s br, 1H), 7.47 – 7.43 (m, 4H), 7.42 – 7.36 (m, 3H), 7.34 – 7.28 (m, 2H), 7.13 (d, J = 8.6 Hz, 1H), 4.98 (s, 1H), 4.26 – 4.23 (m, 2H), 3.70 – 3.67 (m, 2H), 3.30 (s, 3H), 3.24 (d, J = 13.9 Hz, 1H), 3.13 (d, J = 13.9 Hz, 1H) |

Example 89: 2-((2R,3S,4S)-2-(Aminomethyl)-5-chloro-3-hydroxy-2-(pyridin-2-yl)-2,3-dihydrobenzofuran-4-yl)-3-fluoro-4-methoxybenzamide

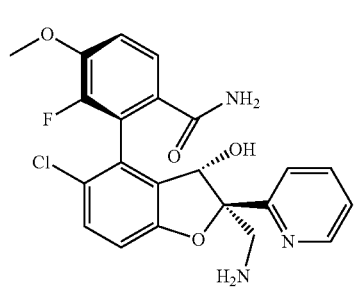

Reaction Scheme Example 89

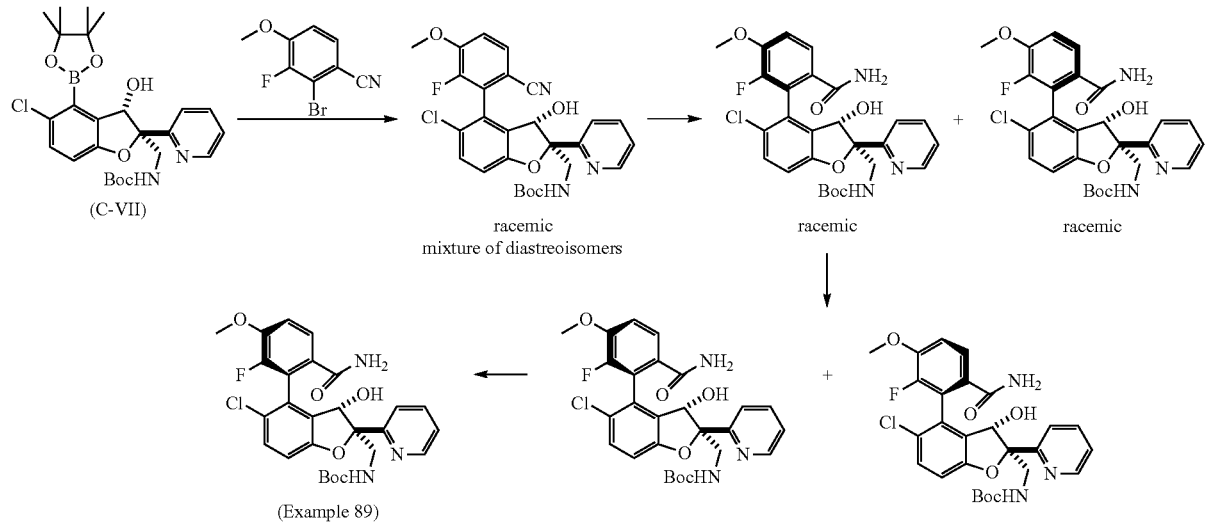

Step 1: Tert-butyl (((2R*,3S*,4S*)-5-chloro-4-(6-cyano-2-fluoro-3-methoxyphenyl)-3-hydroxy-2-(pyridin-2-yl)-2,3-dihydrobenzofuran-2-yl)methyl)carbamate and tert-butyl (((2R*,3S*,4R*)-5-chloro-4-(6-cyano-2-fluoro-3-methoxyphenyl)-3-hydroxy-2-(pyridin-2-yl)-2,3-dihydrobenzofuran-2-yl)methyl) carbamate A mixture of the racemic title compounds (450 mg) was obtained from racemic tert-butyl (((2R*,3S*)-5-chloro-3-hydroxy-2-(pyridin-2-yl)-4-(4,4,5,5-tetramethyl-1,3,2-dioxaborolan-2-yl)-2,3-dihydrobenzofuran-2-yl)methyl)carbamate (C-VII) (847 mg, 1.35 mmol) and 2-bromo-3-fluoro-4-methoxybenzonitrile (N-IV) (403 mg, 1.75 mmol) using similar reaction conditions as described for Example 5a, step. 1. UPLC-MS 1: m/z 526.2 [M+H]+, $t_R$=1.12 min and 1.14 min.

Step 2: Tert-butyl (((2R*,3S*,4S*)-4-(6-carbamoyl-2-fluoro-3-methoxyphenyl)-5-chloro-3-hydroxy-2-(pyridin-2-yl)-2,3-dihydrobenzofuran-2-yl)methyl)carbamate and tert-butyl (((2R*,3S*,4R*)-4-(6-carbamoyl-2-fluoro-3-methoxyphenyl)-5-chloro-3-hydroxy-2-(pyridin-2-yl)-2,3-dihydrobenzofuran-2-yl)methyl)carbamate The racemic title compounds were obtained as separate racemic diastereoisomers from a mixture of racemic tert-butyl (((2R*,3S*,4S*)-5-chloro-4-(6-cyano-2-fluoro-3-methoxyphenyl)-3-hydroxy-2-(pyridin-2-yl)-2,3-dihydrobenzofuran-2-yl)methyl)carbamate and racemic tert-butyl (((2R*,3S*,4R*)-5-chloro-4-(6-cyano-2-fluoro-3-methoxyphenyl)-3-hydroxy-2-(pyridin-2-yl)-2,3-dihydrobenzofuran-2-yl)methyl)carbamate (450 mg) using similar reaction conditions as described for Example 5a, step. 2 followed by flash chromatography (silica, EtOAc/MeOH. Gradient: 0% to 5% MeOH).
Tert-butyl (((2R*,3S*,4S*)-4-(6-carbamoyl-2-fluoro-3-methoxyphenyl)-5-chloro-3-hydroxy-2-(pyridin-2-yl)-2,3-dihydrobenzofuran-2-yl)methyl)carbamate (296 mg): UPLC-MS 1: m/z 544.1 [M+H]+, $t_R$=1.01 min.

Tert-butyl (((2R*,3S*,4R*)-4-(6-carbamoyl-2-fluoro-3-methoxyphenyl)-5-chloro-3-hydroxy-2-(pyridin-2-yl)-2,3-dihydrobenzofuran-2-yl)methyl)carbamate (130 mg): UPLC-MS 1: m/z 544.1 [M+H]+, $t_R$=0.93 min.

Step 3: Tert-butyl (((2R,3S,4S)-4-(6-carbamoyl-2-fluoro-3-methoxyphenyl)-5-chloro-3-hydroxy-2-(pyridin-2-yl)-2,3-dihydrobenzofuran-2-yl)methyl) carbamate and tert-butyl (((2S,3R,4R)-4-(6-carbamoyl-2-fluoro-3-methoxyphenyl)-5-chloro-3-hydroxy-2-(pyridin-2-yl)-2,3-dihydrobenzofuran-2-yl)methyl)carbamate The racemate tert-butyl (((2R*,3S*,4S*)-4-(6-carbamoyl-2-fluoro-3-methoxyphenyl)-5-chloro-3-hydroxy-2-(pyridin-2-yl)-2,3-dihydrobenzofuran-2-yl)methyl)carbamate (288 mg) was subjected to chiral HPLC (ChiralPak OZ-H, 250× 20 mm, 5 µm, heptane/(EtOH+1% DEA) 7:3, flow rate: 10 mL/min, 1.5 mL/injection, 7 injections) to afford the title compounds as separate enantiomers with an enantiomeric excess of >98%, respectively:
Tert-butyl (((2R,3S,4S)-4-(6-carbamoyl-2-fluoro-3-methoxyphenyl)-5-chloro-3-hydroxy-2-(pyridin-2-yl)-2,3-dihydrobenzofuran-2-yl)methyl)carbamate (133 mg): chiral HPLC (ChiralPak OZ-H, 250×4.6 mm, 5 µm, heptane/(EtOH+1% DEA) 6:4, flow rate: 1 mL/min): $t_R$=7.96 min. UPLC-MS 1: m/z 544.1 [M+H]+, $t_R$=1.01 min.
Tert-butyl (((2S,3R,4R)-4-(6-carbamoyl-2-fluoro-3-methoxyphenyl)-5-chloro-3-hydroxy-2-(pyridin-2-yl)-2,3-dihydrobenzofuran-2-yl)methyl)carbamate (121 mg): chiral HPLC (ChiralPak OZ-H, 250×4.6 mm, 5 µm, heptane/(EtOH+1% DEA) 6:4, flow rate: 1 mL/min): $t_R$=11.70 min. UPLC-MS 1: m/z 544.1 [M+H]+, $t_R$=1.01 min.

Step 4: 2-((2R,3S,4S)-2-(Aminomethyl)-5-chloro-3-hydroxy-2-(pyridin-2-yl)-2,3-dihydrobenzofuran-4-yl)-3-fluoro-4-methoxybenzamide (Example 89)

The title compound (100 mg) was obtained from tert-butyl (((2R,3S,4S)-4-(6-carbamoyl-2-fluoro-3-methoxyphenyl)-5-chloro-3-hydroxy-2-(pyridin-2-yl)-2,3-dihydrobenzofuran-2-yl)methyl)carbamate (125 mg) using similar reaction conditions as described for Example 5a, step 3. ¹H NMR (400 MHz, DMSO-d₆) δ (ppm) 8.59-8.56 (m, 1H), 7.76 (td, J=7.8, 2.0 Hz, 1H), 7.49-7.43 (m, 2H), 7.41 (d, J=8.6 Hz, 1H), 7.36 (s br, 1H), 7.33-7.24 (m, 3H), 7.11 (d, J=8.6 Hz, 1H), 6.85 (s br, 1H), 5.20 (s, 1H), 3.86 (s, 3H), 3.28 (d, J=13.7 Hz, 1H), 3.20 (d, J=13.7 Hz, 1H), 1.39 (s br, 2H). UPLC-MS 1: m/z 444.1 [M+H]⁺, t_R=0.66 min.

The absolute configuration of Example 89 was confirmed by an X-ray crystal structure.

Example 90: 2-((2R,3S,4S)-2-(Aminomethyl)-5-chloro-3-hydroxy-2-(6-methoxypyridin-2-yl)-2,3-dihydrobenzofuran-4-yl)-4-(difluoromethoxy)-3-fluorobenzamide

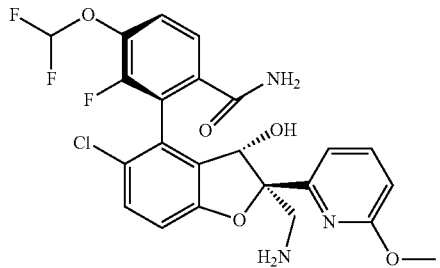

The title compound was prepared analogously as Example 89 from racemic intermediate tert-butyl (((2R*,3S*)-5-chloro-3-hydroxy-2-(6-methoxypyridin-2-yl)-4-(4,4,5,5-tetramethyl-1,3,2-dioxaborolan-2-yl)-2,3-dihydrobenzofuran-2-yl)methyl)carbamate (C-IX) and 2-bromo-4-(difluoromethoxy)-3-fluorobenzonitrile (N-V).

The racemic diastereoisomers were separated after Boc-deprotection by flash chromatography (silica, DCM/(7 N ammonia in MeOH), gradient: 0 to 10% (7N ammonia in MeOH)): racemic (2R*,3S*,4S*) diastereoisomer: UPLC-MS 1: t_R=0.77 min, racemic (2R*,3S*,4R*) diastereoisomer: UPLC-MS 1: t_R=0.63 min. The racemate 2-((2R*,3S*,4S*)-2-(aminomethyl)-5-chloro-3-hydroxy-2-(6-methoxypyridin-2-yl)-2,3-dihydrobenzofuran-4-yl)-4-(difluoromethoxy)-3-fluorobenzamide was subjected to chiral preparative SFC (ChiralPak OZ-H, 250×20 mm, 5 µm, column temperature 40° C., CO₂/(EtOH+1% isopropylamine) 7:3, flow rate: 80 mL/min) to afford the two enantiomers in an enantiomeric excess of >99%, respectively:

2-((2R,3S,4S)-2-(Aminomethyl)-5-chloro-3-hydroxy-2-(6-methoxypyridin-2-yl)-2,3-dihydrobenzofuran-4-yl)-4-(difluoromethoxy)-3-fluorobenzamide (Example 90): chiral SFC (ChiralPak OZ-H, 250×4.6 mm, 5 µm, CO₂/(EtOH+1% isopropylamine) 7:3, flow rate: 3 mL/min): 2.41 min. ¹H NMR (400 MHz, DMSO-d₆) δ (ppm) 7.65 (t, J=7.7 Hz, 1H), 7.54-7.45 (m, 4H), 7.44 (d, J=8.7 Hz, 1H), 7.33 (t, J=72.5 Hz, 1H), 7.11 (d, J=8.7 Hz, 1H), 7.06 (d, J=7.3 Hz, 1H), 6.70 (d, J=8.3 Hz, 1H), 5.29 (s, 1H), 3.80 (s, 3H), 3.28-3.20 (m, 2H), 1.46 (s br, 1H). UPLC-MS 1: m/z 510.2 [M+H]⁺, t_R=0.77 min.

Other enantiomer 2-((2S,3R,4R)-2-(aminomethyl)-5-chloro-3-hydroxy-2-(6-methoxypyridin-2-yl)-2,3-dihydrobenzofuran-4-yl)-4-(difluoromethoxy)-3-fluorobenzamide: chiral SFC (ChiralPak OZ-H, 250×4.6 mm, 5 µm, CO₂/(EtOH+1% isopropylamine) 7:3, flow rate: 3 mL/min): 5.62 min.

Example 91: 2-((2S,3S,4S)-2-(Aminomethyl)-5-chloro-3-hydroxy-2-(2-methoxypyridin-3-yl)-2,3-dihydrobenzofuran-4-yl)-3-fluoro-4-methoxybenzamide

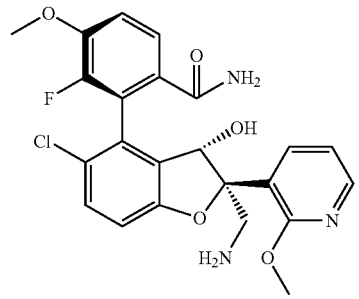

The title compound was prepared analogously to Example 89 from racemic intermediate ((2S*,3S*)-2-(((tert-butoxycarbonyl)amino)methyl)-5-chloro-3-hydroxy-2-(2-methoxypyridin-3-yl)-2,3-dihydrobenzofuran-4-yl)boronic acid (C-X) and 2-bromo-3-fluoro-4-methoxybenzonitrile (N-IV).

After final Boc-deprotection the racemic diastereoisomers were first separated by flash chromatography (silica, DCM/MeOH, gradient: MeOH 0 to 10%): racemic (2S*,3S*,4R*) diastereoisomer: UPLC-MS 1: t_R=0.59 min, racemic (2S*,3S*,4S*) diastereoisomer: UPLC-MS 1: t_R=0.71 min. The racemic (2S*,3S*,4S*) diastereoisomer was subjected to chiral HPLC (Chiralpak AD-H 250×30 mm I.D., 5 µm, EtOH/MeOH 1:1+1% DEA, flow rate: 10 mL/min) to afford both enantiomers in an enantiomeric excess of >98%.

2-((2S,3S,4S)-2-(aminomethyl)-5-chloro-3-hydroxy-2-(2-methoxypyridin-3-yl)-2,3-dihydrobenzofuran-4-yl)-3-fluoro-4-methoxybenzamide (Example 91): Chiral HPLC (Chiralpak AD-H 250×4.6 mm I.D., 5 µm, n-heptane:EtOH 80:20+0.1% DEA, flow rate: 1 mL/min) t_R=10.85 min. ¹H NMR (400 MHz, DMSO-d₆) δ 8.08 (dd, J=5.0, 1.9 Hz, 1H), 7.64 (dd, J=7.4, 1.9 Hz, 1H), 7.44 (dd, J=8.6, 1.4 Hz, 1H), 7.42-7.36 (m, 2H), 7.30 (br s, 1H), 7.26 (t, J=8.5 Hz, 1H), 7.11 (d, J=8.6 Hz, 1H), 6.94 (dd, J=7.5, 4.8 Hz, 1H), 4.92 (s, 1H), 3.85 (s, 3H), 3.84 (s, 3H), 3.31-3.24 (m, 3H), 1.22 (br s, 2H). UPLC-MS 1: m/z 474.1[M+H]⁺, t_R=0.71 min.

Other enantiomer: 2-((2R,3R,4R)-2-(aminomethyl)-5-chloro-3-hydroxy-2-(2-methoxypyridin-3-yl)-2,3-dihydrobenzofuran-4-yl)-3-fluoro-4-methoxybenzamide Chiral HPLC (Chiralpak AD-H 250×4.6 mm I.D., 5 µm, n-heptane:EtOH 80:20+0.1% DEA, flow rate: 1 mL/min) t_R=6.31 min Example 92: 2-((2S,3S,4S)-2-(Aminomethyl)-5-chloro-3-hydroxy-2-(2-oxo-1,2-dihydropyridin-3-yl)-2,3-dihydrobenzofuran-4-yl)-3-fluoro-4-methoxybenzamide

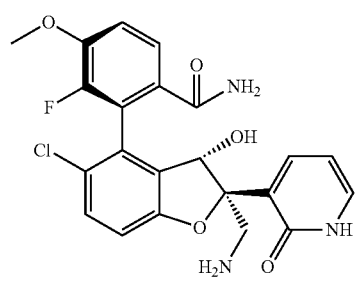

At RT HCl (84 μl, 0.34 mmol, 4 N in dioxane) was added to 2-((2S,3S,4S)-2-(aminomethyl)-5-chloro-3-hydroxy-2-(2-methoxypyridin-3-yl)-2,3-dihydrobenzofuran-4-yl)-3-fluoro-4-methoxybenzamide (Example 91.) (8 mg, 0.017 mmol). After stirring at 50° C. for 3 h, the reaction mixture was concentrated. The residue was purified by preparative HPLC (Waters X-Bridge C18 OBD, 5 μm, 30*100 mm, Eluent A: $H_2O$+7.3 mM $NH_4OH$, Eluent B: ACN, Gradient: 5 to 100% B in 20 min hold 1 min, Flow 40 mL/min) to afford the title compound. $^1$H NMR (600 MHz, DMSO-$d_6$) δ 7.49-7.39 (m, 3H), 7.39-7.34 (m, 2H), 7.33-7.26 (m, 2H), 7.10 (d, J=8.7 Hz, 1H), 6.20 (t, J=6.7 Hz, 1H), 5.07 (s, 1H), 3.89 (s, 3H), 3.43 (d, J=14.0 Hz, 1H), 3.38 (d, J=14.0 Hz, 1H), 1.24 (br s, 2H). UPLC-MS 1: m/z 460.1[M+H]$^+$, $t_R$=0.63 min.

Example 93: 2-((2S,3S,4S)-2-(Aminomethyl)-5-chloro-3-hydroxy-2-(2-(trifluoromethoxy)phenyl)-2,3-dihydrobenzofuran-4-yl)-3-fluoro-4-methoxybenzamide

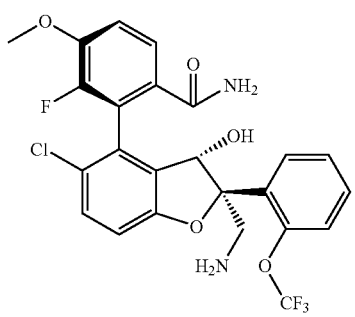

The title compound was prepared analogously to Example 89 from racemic intermediate tert-butyl (((2S*,3S*)-5-chloro-3-hydroxy-4-(4,4,5,5-tetramethyl-1,3,2-dioxaborolan-2-yl)-2-(2-(trifluoromethoxy)phenyl)-2,3-dihydrobenzofuran-2-yl)methyl)carbamate (C-VIII) and 2-bromo-3-fluoro-4-methoxybenzonitrile (N-IV).

After final Boc-deprotection the racemic diastereoisomers were first separated by flash chromatography (silica, DCM/MeOH, gradient: MeOH 0% to 10%): racemic (2S*,3S*,4R*) diastereoisomer: UPLC-MS 1: $t_R$=0.67 min, racemic (2S*,3S*,4S*) diastereoisomer: UPLC-MS 1: $t_R$=0.81 min. The racemic (2S*,3S*,4S*) diastereoisomer was subjected to chiral SFC (ChiralPak OZ-H, 250×25 mm, 5 μm, $CO_2$/(EtOH+1% isopropylamine) 65:35, flow rate: 80 mL/min) to afford both enantiomers in an enantiomeric excess of >99%.

2-((2S,3S,4S)-2-(Aminomethyl)-5-chloro-3-hydroxy-2-(2-(trifluoromethoxy)phenyl)-2,3-dihydrobenzofuran-4-yl)-3-fluoro-4-methoxybenzamide (Example 93): Chiral SFC (ChiralPak OZ-H, 250×4.6 mm, 5 μm, $CO_2$/(EtOH+1% isopropylamine) 65:35, flow rate: 3 mL/min) $t_R$=2.57 min. $^1$H NMR (400 MHz, DMSO-$d_6$) δ 7.59-7.49 (m, 2H), 7.48-7.22 (m, 7H), 7.10 (d, J=8.6 Hz, 1H), 6.93 (s br, 1H), 4.90 (s, 1H), 3.85 (s, 3H), 3.41 (d, J=14.2 Hz, 1H), 3.19 (d, J=14.2 Hz, 1H), 1.42 (s br, 2H). UPLC-MS 1: m/z 527.1 [M+H]$^+$, $t_R$=0.83 min.

2-((2R,3R,4R)-2-(Aminomethyl)-5-chloro-3-hydroxy-2-(2-(trifluoromethoxy)phenyl)-2,3-dihydrobenzofuran-4-yl)-3-fluoro-4-methoxybenzamide Chiral SFC (ChiralPak OZ-H, 250×6 mm, 5 μm, $CO_2$/(EtOH+1% isopropylamine) 65:35, flow rate: 3 mL/min) $t_R$=7.15 min.

Example 94a and Example 94b: 2-((2S,3S,4S)-5-chloro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide (Example 94a) and 2-((2S,3S,4S)-5-chloro-3-hydroxy-2-((((cis)-4-hydroxycyclohexyl)amino)methyl)-2-phenyl-2,3-dihydrobenzofuran-4-yl)-4-(difluoromethoxy)-3-fluorobenzamide (Example 94b)

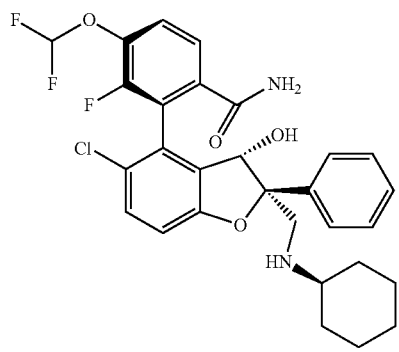

Example 94a

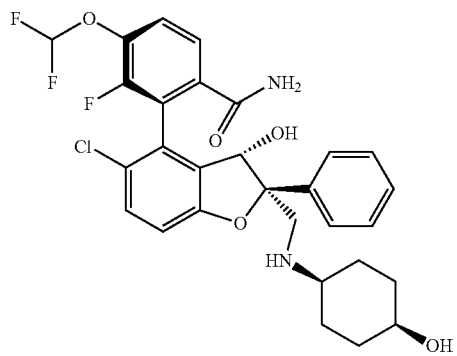

Example 94b

The title compounds were prepared analogously to Examples 27a and 27b from Example 87 and 4-hydroxycyclohexanone.

2-((2S,3S,4S)-5-Chloro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide (Example 94a): $^1$H NMR (400 MHz, DMSO-$d_6$) δ (ppm) 7.55-7.42 (m, 8.3H), 7.38-7.33 (m, 2.4H), 7.32-7.27 (m, 1H), 7.18-7.15 (m, 1.3H), 4.95 (s, 1H), 4.45 (d, J=4.4 Hz, 1H), 3.33-3.26 (m, 1H), 3.24 (s, 2H), 2.29-2.21 (m, 1H), 1.76-1.68 (m, 4H), 1.60-1.50 (s br, 1H), 1.13-1.02 (m, 2H), 0.99-0.85 (m, 2H). UPLC-MS 1: m/z 577.3 [M+H]$^+$, $t_R$=0.78 min.

2-((2S,3S,4S)-5-Chloro-3-hydroxy-2-((((cis)-4-hydroxycyclohexyl)amino)methyl)-2-phenyl-2,3-dihydrobenzofuran-4-yl)-4-(difluoromethoxy)-3-fluorobenzamide (Example 94b): $^1$H NMR (400 MHz, DMSO-$d_6$) δ (ppm) 7.55-7.44 (m, 8.2H), 7.39-7.34 (m, 2.6H), 7.32-7.27 (m, 1H), 7.19-7.16 (m, 1.2H), 4.97 (s, 1H), 4.27 (d, J=3.4 Hz, 1H), 3.60-3.56 (m, 1H), 3.23 (s, 2H), 2.37-2.33 (m, 1H), 1.50-1.30 (m, 8H). UPLC-MS 1: m/z 577.3 [M+H]$^+$, $t_R$=0.80 min.

Example 95a and Example 95b: 2-((2R,3S,4S)-5-Chloro-3-hydroxy-2-((((trans)-4-hydroxycyclohexyl)amino)methyl)-2-(pyridin-2-yl)-2,3-dihydrobenzofuran-4-yl)-3-fluoro-4-methoxybenzamide (Exampl. 95a) and 2-((2R,3S,4S)-5-chloro-3-hydroxy-2-(((((cis)-4-hydroxycyclohexyl)amino)methyl)-2-(pyridin-2-yl)-2,3-dihydrobenzofuran-4-yl)-3-fluoro-4-methoxybenzamide (Example 95b)

Example 95a

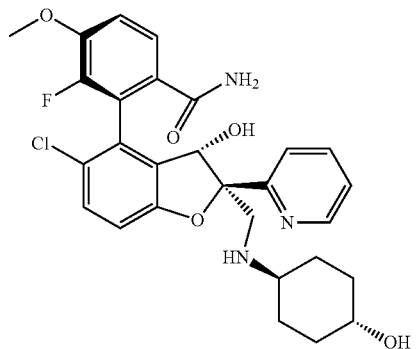

Example 95b

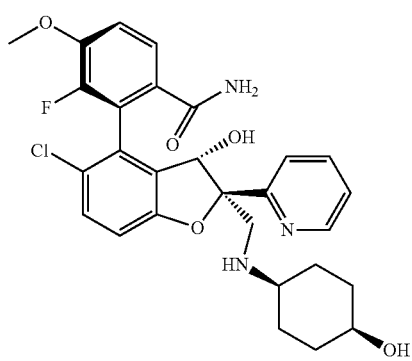

The title compounds were prepared analogously to Example 27a from Example 89 and 4-hydroxycyclohexanone.

2-((2R,3S,4S)-5-Chloro-3-hydroxy-2-((((trans)-4-hydroxycyclohexyl)amino)methyl)-2-(pyridin-2-yl)-2,3-dihydrobenzofuran-4-yl)-3-fluoro-4-methoxybenzamide (Example 95a): $^1$H NMR (400 MHz, DMSO-$d_6$) δ (ppm) 8.56 (d, J=4.9 Hz, 1H), 7.73 (td, J=7.7, 1.3 Hz, 1H), 7.47-7.40 (m, 3H), 7.30-7.24 (m, 4H), 7.12 (d, J=8.7 Hz, 2H), 5.15 (s, 1H), 4.39 (d, J=4.3 Hz, 1H), 3.86 (s, 3H), 3.30-3.20 (m, 2H), 2.21-2.13 (m, 1H), 1.73-1.59 (m, 4H), 1.11-0.95 (m, 2H), 0.95-0.74 (m, 2H). UPLC-MS 1: m/z 542.2 [M+H]$^+$, $t_R$=0.70 min.

2-((2R,3S,4S)-5-Chloro-3-hydroxy-2-(((((cis)-4-hydroxycyclohexyl)amino)methyl)-2-(pyridin-2-yl)-2,3-dihydrobenzofuran-4-yl)-3-fluoro-4-methoxybenzamide (Example 95b): $^1$H NMR (400 MHz, DMSO-$d_6$) δ (ppm) 8.56 (d, J=4.7 Hz, 1H), 7.75 (td, J=7.7, 1.6 Hz, 1H), 7.48-7.40 (m, 3H), 7.30-7.23 (m, 4H), 7.12 (d, J=8.7 Hz, 2H), 5.18 (s, 1H), 4.20 (d, J=3.4 Hz, 1H), 3.55-3.50 (m, 1H), 3.34-3.23 (m, 2H), 2.33-2.27 (m, 1H), 1.46-1.21 (m, 8H). UPLC-MS 1: m/z 542.2 [M+H]$^+$, $t_R$=0.71 min.

Example 96: 2-((2S,3S,4S)-5-Chloro-2-((cyclobutylamino)methyl)-3-hydroxy-2-phenyl-2,3-dihydrobenzofuran-4-yl)-4-(difluoromethoxy)-3-fluorobenzamide

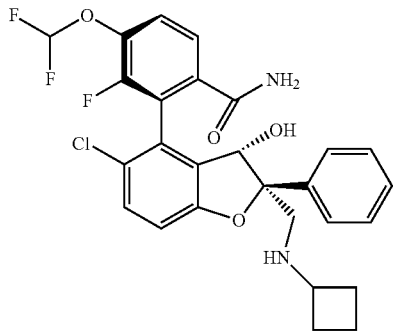

The title compound was prepared analogously to Example 27a from Example 87 and cyclobutanone. $^1$H NMR (400 MHz, DMSO-$d_6$) δ (ppm) 7.56-7.52 (m, 3.3H), 7.48 (d, J=8.6 Hz, 1H), 7.45-7.42 (m, 2H), 7.39-7.34 (m, 2.4H), 7.32-7.27 (m, 1H), 7.19-7.10 (m, 2.3H), 4.94 (s, 1H), 3.18-3.08 (m, 3H), 2.07-1.96 (m, 2H), 1.65-1.46 (m, 4H). UPLC-MS 1: m/z 533.2 [M+H]$^+$, $t_R$=0.85 min. The absolute configuration was confirmed by an X-ray cocrystal structure of Example 96 bound to the YAP binding site of TEAD4.

Example 97: 2-((2S,3S,4S)-2-(Aminomethyl)-5-chloro-6-fluoro-3-hydroxy-2-phenyl-2,3-dihydrobenzofuran-4-yl)-3-fluoro-4-methoxybenzamide

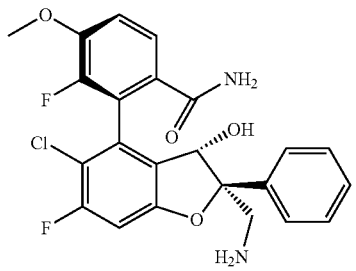

The title compound was prepared analogously to Example 5a from tert-butyl (((2S,3S)-5-chloro-6-fluoro-3-hydroxy-2-phenyl-4-(4,4,5,5-tetramethyl-1,3,2-dioxaborolan-2-yl)-2,3-dihydrobenzofuran-2-yl)methyl)carbamate (C-XIV) and 2-bromo-3-fluoro-4-methoxybenzonitrile (N-IV). The final Boc-deprotection was performed as described in Example 22, step 5.

2-((2S,3S,4S)-2-(Aminomethyl)-5-chloro-6-fluoro-3-hydroxy-2-phenyl-2,3-dihydrobenzofuran-4-yl)-3-fluoro-4-methoxybenzamide (Example 97): $^1$H NMR (400 MHz, DMSO-$d_6$) δ (ppm) 7.55 (s br, 1H), 7.52 (d, J=8.6 Hz, 1H), 7.46-7.36 (m, 5H), 7.36-7.26 (m, 3H), 4.95 (s, 1H), 3.90 (s, 3H), 3.25 (d, J=13.9 Hz, 1H), 3.15 (d, J=13.9 Hz, 1H). UPLC-MS 1: m/z 461.2 [M+H]$^+$, $t_R$=0.78 min.

Other diastereoisomer 2-((2S,3S,4R)-2-(aminomethyl)-5-chloro-6-fluoro-3-hydroxy-2-phenyl-2,3-dihydrobenzofuran-4-yl)-3-fluoro-4-methoxybenzamide: UPLC-MS 1: m/z 461.2 [M+H]$^+$, $t_R$=0.61 min.

Example 98: 2-((2S,3S,4S)-2-(Aminomethyl)-5-chloro-6-fluoro-3-hydroxy-2-phenyl-2,3-dihydrobenzofuran-4-yl)-3-fluoro-4-(2-hydroxyethoxy)benzamide

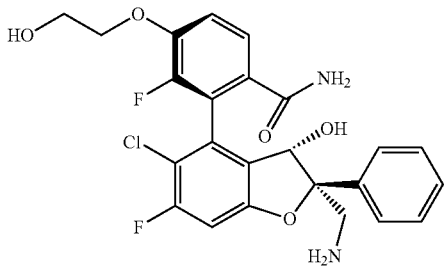

Step 1: Tert-butyl (((2S,3S,4S)-5-chloro-4-(6-cyano-2-fluoro-3-(2-((tetrahydro-2H-pyran-2-yl)oxy)ethoxy)phenyl)-6-fluoro-3-hydroxy-2-phenyl-2,3-dihydrobenzofuran-2-yl)methyl)carbamate and tert-butyl (((2S,3S,4R)-5-chloro-4-(6-cyano-2-fluoro-3-(2-((tetrahydro-2H-pyran-2-yl)oxy)ethoxy)phenyl)-6-fluoro-3-hydroxy-2-phenyl-2,3-dihydrobenzofuran-2-yl)methyl)carbamate The title compounds were obtained from tert-butyl (((2S,3S)-5-chloro-6-fluoro-3-hydroxy-2-phenyl-4-(4,4,5,5-tetramethyl-1,3,2-dioxaborolan-2-yl)-2,3-dihydrobenzofuran-2-yl)methyl)carbamate (C-XIV) (0.50 g, 0.96 mmol) and 2-bromo-3-fluoro-4-(2-((tetrahydro-2H-pyran-2-yl)oxy)ethoxy)benzonitrile (N-VI) (0.33 g, 0.96 mmol) using similar reaction conditions as described for Example 5a, step 1 and isolated as separated diastereoisomers after chromatography:
Tert-butyl (((2S,3S,4S)-5-chloro-6-fluoro-3-hydroxy-2-phenyl-4-(4,4,5,5-tetramethyl-1,3,2-dioxaborolan-2-yl)-2,3-dihydrobenzofuran-2-yl)methyl)carbamate (116 mg, colorless foam): UPLC-MS 1: m/z 657.3 [M+H]⁺, $t_R$=1.36 min.
Tert-butyl (((2S,3S,4R)-5-chloro-6-fluoro-3-hydroxy-2-phenyl-4-(4,4,5,5-tetramethyl-1,3,2-dioxaborolan-2-yl)-2,3-dihydrobenzofuran-2-yl)methyl)carbamate (61 mg, colorless oil): UPLC-MS 1: m/z 657.3 [M+H]⁺, $t_R$=1.34 min.

Step 2: Tert-butyl (((2S,3S,4S)-4-(6-carbamoyl-2-fluoro-3-(2-hydroxyethoxy)phenyl)-5-chloro-6-fluoro-3-hydroxy-2-phenyl-2,3-dihydrobenzofuran-2-yl)methyl)carbamate The title compound (105 mg, slightly yellow foam) was obtained from tert-butyl (((2S,3S,4S)-5-chloro-6-fluoro-3-hydroxy-2-phenyl-4-(4,4,5,5-tetramethyl-1,3,2-dioxaborolan-2-yl)-2,3-dihydrobenzofuran-2-yl)methyl)carbamate (116 mg) using similar reaction conditions as described for Example 5a, step 2. The THP group fell off during this reaction. UPLC-MS 1: m/z 591.3 [M+H]⁺, $t_R$=1.03 min.

Step 3: 2-((2S,3S,4S)-2-(Aminomethyl)-5-chloro-6-fluoro-3-hydroxy-2-phenyl-2,3-dihydrobenzofuran-4-yl)-3-fluoro-4-(2-hydroxyethoxy)benzamide (Example 98)

The title compound (95 mg) was obtained from tert-butyl (((2S,3S,4S)-4-(6-carbamoyl-2-fluoro-3-(2-hydroxyethoxy)phenyl)-5-chloro-6-fluoro-3-hydroxy-2-phenyl-2,3-dihydrobenzofuran-2-yl)methyl)carbamate (105 mg) using similar reaction conditions as described in Example 22, step 5.

¹H NMR (600 MHz, DMSO-d6) δ: 7.57 (s br, 1H), 7.47 (d, J=8.6 Hz, 1H), 7.45-7.42 (m, 3H), 7.41-7.36 (m, 2H), 7.35-7.27 (m, 3H), 6.89 (s br, 1H), 4.97 (t, J=5.5 Hz, 1H), 4.94 (s, 1H), 4.16-4.10 (m, 2H), 3.73 (q, J=5.0 Hz, 2H), 3.24 (d, J=13.8 Hz, 1H), 3.13 (d, J=14.1 Hz, 1H). UPLC-MS 1: m/z 491.3 [M+H]⁺, $t_R$=0.64.

Example 99: 2-((2S,3S,4S)-5-Chloro-2-((cyclobutylamino)methyl)-6-fluoro-3-hydroxy-2-phenyl-2,3-dihydrobenzofuran-4-yl)-3-fluoro-4-(2-hydroxyethoxy)benzamide

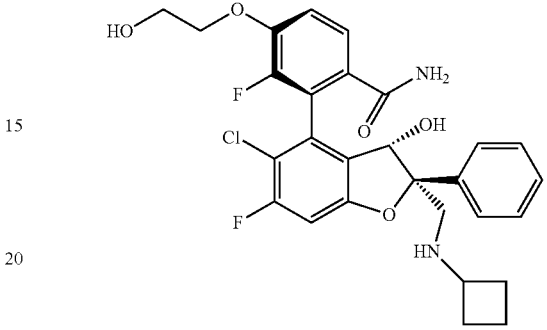

The title compound was prepared analogously to Example 96 from Example 98 and cyclobutanone. ¹H NMR (600 MHz, DMSO-d₆) δ (ppm) 7.50 (s br, 1H), 7.48 (d, J=8.6 Hz, 1H), 7.42-7.39 (m, 3H), 7.38-7.27 (m, 5H), 6.92-6.90 (m, 1H), 4.96 (t, J=5.5 Hz, 1H), 4.85 (s br, 1H), 4.15-4.09 (m, 2H), 3.73 (t, J=5.0 Hz, 2H), 3.15-3.05 (m, 3H), 2.05-1.95 (m, 2H), 1.59-1.45 (m, 4H). UPLC-MS 1: m/z 545.3 [M+H]⁺, $t_R$=0.72 min.

Example 100a and Example 100b: 2-((2S,3S,4S)-5-Chloro-6-fluoro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide or (2P)-2-[(2S,3S)-5-Chloro-6-fluoro-3-hydroxy-2-({[(1r,4S)-4-hydroxycyclohexyl]amino}methyl)-2-phenyl-2,3-dihydro-1-benzofuran-4-yl]-4-(difluoromethoxy)-3-fluorobenzamide (Example 100a) and 2-((2S,3S,4S)-5-chloro-6-fluoro-3-hydroxy-2-((((cis)-4-hydroxycyclohexyl)amino)methyl)-2-phenyl-2,3-dihydrobenzofuran-4-yl)-4-(difluoromethoxy)-3-fluorobenzamide or (2P)-2-[(2S,3S)-5-Chloro-6-fluoro-3-hydroxy-2-({[(1s,4R)-4-hydroxycyclohexyl]amino}methyl)-2-phenyl-2,3-dihydro-1-benzofuran-4-yl]-4-(difluoromethoxy)-3-fluorobenzamide (Example 100b)

Example 100a

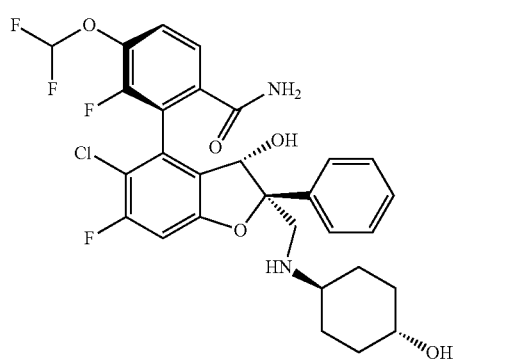

Example 100b

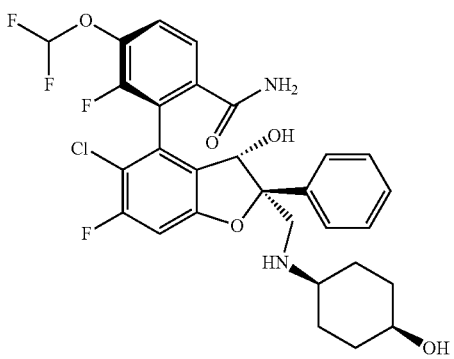

The title compounds were prepared analogously to Examples 94a and 94b. 2-((2S,3S,4S)-5-Chloro-6-fluoro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide or (2P)-2-[(2S,3S)-5-Chloro-6-fluoro-3-hydroxy-2-({[(1r,4S)-4-hydroxycyclohexyl]amino}methyl)-2-phenyl-2,3-dihydro-1-benzofuran-4-yl]-4-(difluoromethoxy)-3-fluorobenzamide (Example 100a): $^1$H NMR (600 MHz, DMSO-d$_6$) δ (ppm) 7.56-7.50 (m, 4H), 7.43-7.40 (m, 2H), 7.36-7.26 (m, 4H), 7.33 (t, J=73 Hz, 1H), 4.90 (s, 1H), 4.45-4.42 (m, 1H), 3.29-3.18 (m, 3H), 2.27-2.20 (m, 1H), 1.72-1.66 (m, 4H), 1.09-1.00 (m, 2H), 0.96-0.86 (m, 2H). UPLC-MS 1: m/z 595.3 [M+H]$^+$, t$_R$=0.87 min.

2-((2S,3S,4S)-5-Chloro-6-fluoro-3-hydroxy-2-((((cis)-4-hydroxycyclohexyl)amino)methyl)-2-phenyl-2,3-dihydrobenzofuran-4-yl)-4-(difluoromethoxy)-3-fluorobenzamide or (2P)-2-[(2S,3S)-5-Chloro-6-fluoro-3-hydroxy-2-({[(1s,4R)-4-hydroxycyclohexyl]amino}methyl)-2-phenyl-2,3-dihydro-1-benzofuran-4-yl]-4-(difluoromethoxy)-3-fluorobenzamide (Example 100b): $^1$H NMR (600 MHz, DMSO-d$_6$) δ (ppm) 7.56-7.52 (m, 4H), 7.44-7.41 (m, 2H), 7.36-7.26 (m, 4H), 7.34 (t, J=72.6 Hz, 1H), 4.92 (s, 1H), 4.25 (d, J=3.3 Hz, 1H), 3.57-3.52 (m, 1H), 3.20 (s, 2H), 2.36-2.31 (m, 1H), 1.45-1.27 (m, 8H). UPLC-MS 1: m/z 594.9 [M+H]$^+$, t$_R$=0.89 min.

Example 101: 2-((2S,3S,4S)-2-(Aminomethyl)-5-chloro-6-fluoro-3-methoxy-2-phenyl-2,3-dihydrobenzofuran-4-yl)-3-fluoro-4-(2-hydroxyethoxy)benzamide

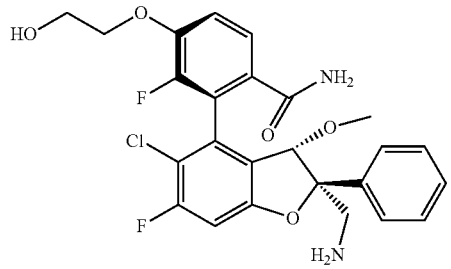

The title compound was prepared analogously to Examples 5a and Example 48 from intermediates tert-butyl (((2S,3S)-5-chloro-6-fluoro-3-methoxy-2-phenyl-4-(4,4,5,5-tetramethyl-1,3,2-dioxaborolan-2-yl)-2,3-dihydrobenzofuran-2-yl)methyl)carbamate (C-XV) and 2-bromo-3-fluoro-4-(2-((tetrahydro-2H-pyran-2-yl)oxy)ethoxy)benzonitrile (N-VI). $^1$H NMR (400 MHz, DMSO-d6) δ: 7.61 (d, J=8.7 Hz, 1H), 7.53-7.48 (m, 2H), 7.48-7.42 (m, 2H), 7.42-7.30 (m, 4H), 7.13 (s br, 1H), 4.95 (t, J=5.1 Hz, 1H), 4.50 (s, 1H), 4.18. 4.09 (m, 2H), 3.76-3.70 (m, 2H), 3.58 (d, J=14.1 Hz, 1H), 3.46 (d, J=14.2 Hz, 1H), 3.05 (s, 3H). UPLC-MS 1: m/z 505.2 [M+H]$^+$, t$_R$=0.64.

The diastereoisomers were separated after Suzuki coupling: tert-butyl (((2S,3S,4S)-5-chloro-4-(6-cyano-2-fluoro-3-(2-((tetrahydro-2H-pyran-2-yl)oxy)ethoxy)phenyl)-6-fluoro-3-methoxy-2-phenyl-2,3-dihydrobenzofuran-2-yl)methyl)carbamate: UPLC-MS 1: m/z 671.3 [M+H]$^+$, t$_R$=1.43; tert-butyl (((2S,3S,4R)-5-chloro-4-(6-cyano-2-fluoro-3-(2-((tetrahydro-2H-pyran-2-yl)oxy)ethoxy)phenyl)-6-fluoro-3-methoxy-2-phenyl-2,3-dihydrobenzofuran-2-yl)methyl)carbamate: UPLC-MS 1: m/z 671.3 [M+H]$^+$, t$_R$=1.42.

Example 102a and Example 102b: 2-((2S,3S,4S)-5-Chloro-6-fluoro-2-((((trans)-4-hydroxycyclohexyl)amino)methyl)-3-methoxy-2-phenyl-2,3-dihydrobenzofuran-4-yl)-4-(difluoromethoxy)-3-fluorobenzamide (Example 102a) and 2-((2S,3S,4S)-5-chloro-6-fluoro-2-((((cis)-4-hydroxycyclohexyl)amino)methyl)-3-methoxy-2-phenyl-2,3-dihydrobenzofuran-4-yl)-4-(difluoromethoxy)-3-fluorobenzamide (Example 102b)

Example 102a

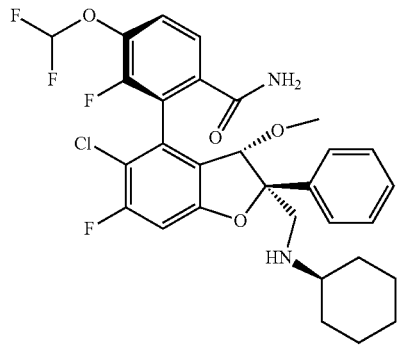

Example 102b

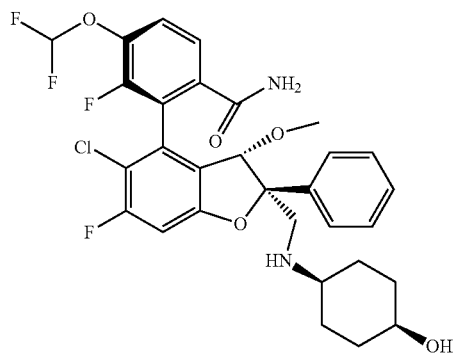

The title compounds were prepared analogously to Examples 94a and 94b. 2-((2S,3S,4S)-5-Chloro-6-fluoro-2-((((trans)-4-hydroxycyclohexyl)amino)methyl)-3-methoxy-2-phenyl-2,3-dihydrobenzofuran-4-yl)-4-(difluoromethoxy)-3-fluorobenzamide (Example 102a): $^1$H NMR (600 MHz, DMSO-d$_6$) δ (ppm) 7.64 (d, J=8.6 Hz, 1H), 7.56 (t, J=8.1 Hz, 1H), 7.48-7.29 (m, 8H), 7.23 (s, 1H), 4.49 (s, 1H), 4.46-4.42 (m, 1H), 3.31-3.19 (m, 3H), 3.03 (s, 3H), 2.23-2.16 (m, 1H), 1.75-1.64 (m, 4H), 1.10-1.01 (m, 2H), 0.94-0.79 (m, 2H). UPLC-MS 1: m/z 609.2 [M+H]$^+$, t$_R$=0.87 min.

2-((2S,3S,4S)-5-Chloro-6-fluoro-2-((((cis)-4-hydroxycyclohexyl)amino)methyl)-3-methoxy-2-phenyl-2,3-dihydrobenzofuran-4-yl)-4-(difluoromethoxy)-3-fluorobenzamide (Example 102b): $^1$H NMR (600 MHz, DMSO-d$_6$) δ (ppm) 7.65 (d, J=9.0 Hz, 1H), 7.56 (t, J=8.1 Hz, 1H), 7.48-7.30 (m, 8H), 7.28-7.23 (m, 1H), 4.51 (s, 1H), 4.28-4.24 (m, 1H), 3.57-3.53 (m, 1H), 3.25-3.18 (m, 2H), 3.05 (s, 3H), 2.36-2.30 (m, 1H), 1.45-1.25 (m, 8H). UPLC-MS 1: m/z 609.2 [M+H]$^+$, t$_R$=0.89 min.

Example 103: 2-((2S,3S,4S)-2-(aminomethyl)-5-chloro-3-methyl-2-phenyl-2,3-dihydrobenzofuran-4-yl)-4-(difluoromethoxy)-3-fluorobenzamide

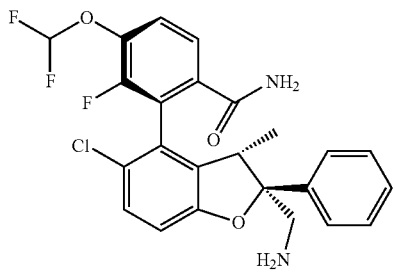

The title compound was prepared analogously to Example 5a from intermediates tert-butyl (((2S,3S)-5-chloro-3-methyl-2-phenyl-4-(4,4,5,5-tetramethyl-1,3,2-dioxaborolan-2-yl)-2,3-dihydrobenzofuran-2-yl)methyl)carbamate (C-XI) and 2-bromo-4-(difluoromethoxy)-3-fluorobenzonitrile (N-V). 2-((2S,3S,4S)-2-(Aminomethyl)-5-chloro-3-methyl-2-phenyl-2,3-dihydrobenzofuran-4-yl)-4-(difluoromethoxy)-3-fluorobenzamide (Example 103): $^1$H NMR (400 MHz, DMSO-d6) δ: 7.80-7.18 (m, 11H), 6.93 (d, J=8.5 Hz, 1H), 3.36-3.33 (m, 1H), 3.10-3.02 (m, 2H), 2.54-2.51 (m, 1H), 1.07 (s br, 1H), 0.92 (d, J=7.2 Hz, 3H). UPLC-MS 1: m/z 477.2 [M+H]$^+$, t$_R$=0.78.

Other diastereoisomer 2-((2S,3S,4R)-2-(aminomethyl)-5-chloro-3-methyl-2-phenyl-2,3-dihydrobenzofuran-4-yl)-4-(difluoromethoxy)-3-fluorobenzamide: UPLC-MS 1: m/z 477.2 [M+H]$^+$, t$_R$ 0.69.

Example 104a and Example 104b: 2-((2S,3S,4S)-5-chloro-2-((((cis)-4-hydroxy-4-methylcyclohexyl)amino)methyl)-3-methyl-2-phenyl-2,3-dihydrobenzofuran-4-yl)-4-(difluoromethoxy)-3-fluorobenzamide (Example 104a) and 2-((2S,3S,4S)-5-chloro-2-((((trans)-4-hydroxy-4-methylcyclohexyl)amino)methyl)-3-methyl-2-phenyl-2,3-dihydrobenzofuran-4-yl)-4-(difluoromethoxy)-3-fluorobenzamide (Example 104b)

Example 104a
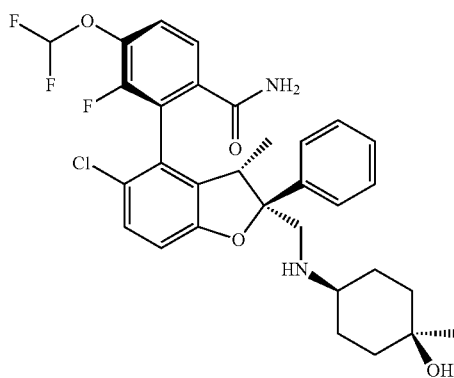

Example 104b
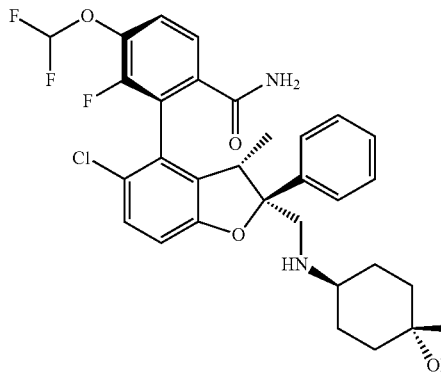

The title compounds were prepared analogously to Examples 27a and 27b from Example 103 and 4-hydroxy-4-methylcyclohexanone. 2-((2S,3S,4S)-5-Chloro-2-((((cis)-4-hydroxy-4-methylcyclohexyl)amino)methyl)-3-methyl-2-phenyl-2,3-dihydrobenzofuran-4-yl)-4-(difluoromethoxy)-3-fluorobenzamide (Example 104a): $^1$H NMR (400 MHz, DMSO-d$_6$) δ: 7.84-7.13 (m, 12H), 6.97 (d, J=8.6 Hz, 1H), 3.89 (s, 1H), 3.23-3.05 (m, 2H), 2.17 (br s, 1H), 1.48-1.39 (m, 4H), 1.33-1.10 (m, 4H), 1.04 (s, 3H), 0.96 (d, J=7.1 Hz, 3H), 0.88-0.70 (m, 1H). UPLC-MS 1: m/z 589.3 [M+H]$^+$, t$_R$=0.84, 2-((2S,3S,4S)-5-Chloro-2-((((trans)-4-hydroxy-4-methylcyclohexyl)amino)methyl)-3-methyl-2-phenyl-2,3-dihydrobenzofuran-4-yl)-4-(difluoromethoxy)-3-fluorobenzamide (Example 104b): $^1$H NMR (400 MHz, DMSO-d$_6$) δ: 7.79-7.11 (m, 12H), 6.96 (d, J=8.4 Hz, 1H), 4.06 (s, 1H), 3.09 (s br, 2H), 2.43-2.27 (m, 1H), 1.68-1.55 (m, 2H), 1.44-1.13 (m, 4H), 1.13-0.93 (m, 8H), 0.91-0.82 (m, 1H). UPLC-MS 1: m/z 589.3 [M+H]$^+$, t$_R$=0.82.

Example 105: 2-((2S,3S,4S)-2-(Aminomethyl)-5-chloro-6-fluoro-3-methyl-2-phenyl-2,3-dihydrobenzofuran-4-yl)-4-(difluoromethoxy)-3-fluorobenzamide

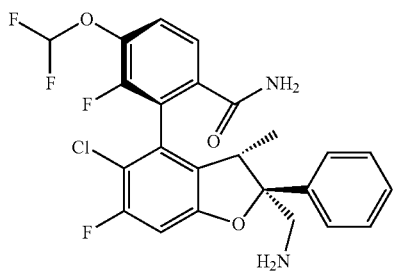

The title compound was prepared analogously to Example 5a from intermediates tert-butyl ((((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)carbamate (C-XVI) and 2-bromo-4-(difluoromethoxy)-3-fluorobenzonitrile (N-V). 2-((2S,3S,4S)-2-(Aminomethyl)-5-chloro-6-fluoro-3-methyl-2-phenyl-2,3-dihydrobenzofuran-4-yl)-4-(difluoromethoxy)-3-fluorobenzamide (Example 105): $^1$H NMR (400 MHz, DMSO-$d_6$) δ (ppm): 7.88 (s, 1H), 7.60 (dd, J=8.6, 1.1 Hz, 1H), 7.52 (t, J=8.1 Hz, 1H), 7.48-7.18 (m, 7H), 7.09 (d, J=9.5 Hz, 1H), 3.32-3.27 (m, 1H), 3.14-3.00 (m, 2H), 1.09 (s br, 2H), 0.91 (d, J=7.2 Hz, 3H). UPLC-MS 1: m/z 495.1 [M+H]$^+$, $t_R$=0.88 min.

Other diastereoisomer 2-((2S,3S,4R)-2-(aminomethyl)-5-chloro-6-fluoro-3-methyl-2-phenyl-2,3-dihydrobenzofuran-4-yl)-4-(difluoromethoxy)-3-fluorobenzamide: UPLC-MS 1: m/z 495.1 [M+H]$^+$, $t_R$=0.79 min.

The following compounds were prepared analogously to Example 105

| Ex. | Structure/Chemical Name | UPLC MS m/z [M + H]$^+$ $t_R$ [min] (method) | $^1$H NMR |
|---|---|---|---|
| 106 | 2-((2S,3S,4S)-2-(aminomethyl)-5-chloro-6-fluoro-3-methyl-2-phenyl-2,3-dihydrobenzofuran-4-yl)-3-fluoro-4-(2-methoxyethoxy)benzamide; 2-bromo-3-fluoro-4-(2-methoxyethoxy)benzonitrile (N-IX) used in Suzuki coupling | 503.2 0.74 (1) | (400 MHz, DMSO-$d_6$) δ (ppm): 7.66 (s br, 1H), 7.57 (d, J = 8.6 Hz, 1H), 7.43 – 7.25 (m, 6H), 7.08 (s br, 1H), 7.04 (d, J = 9.5 Hz, 1H), 4.30 – 4.14 (m, 2H), 3.65 (t, J = 4.5 Hz, 2H), 3.30 (s, 3H), 1 proton under water peak, 3.16 – 2.96 (m, 2H), 1.10 (s br, 2H), 0.90 (d, J = 7.1 Hz, 3H) |
| 107 | 2-((2S,3S,4S)-2-(aminomethyl)-5-chloro-6-fluoro-3-methyl-2-phenyl-2,3-dihydrobenzofuran-4-yl)-3-fluoro-4-(2-hydroxyethoxy)benzamide; Aryl bromide 2-bromo-3-fluoro-4-(2-((tetrahydro-2H-pyran-2-yl)oxy)ethoxy)benzonitrile (N-VI) used in Suzuki coupling. The Boc and THP group were cleaved together in the last step. | 489.3 0.64 (1) | (400 MHz, DMSO-$d_6$) δ (ppm): 7.69 (s br, 1H), 7.58 (d, J = 8.7 Hz, 1H), 7.44 – 7.28 (m, 6H), 7.11 (s br, 1H), 7.07 (d, J = 9.5 Hz, 1H), 4.96 – 4.93 (m, 1H), 4.17 – 4.10 (m, 2H), 3.76 – 3.72 (m, 2H), 3.31 – 3.27 (m, 1H), 3.14 – 3.06 (m, 2H), 1.11 (s br, 2H), 0.94 (d, J = 7.0 Hz, 3H) |

| Ex. | Structure/Chemical Name | UPLC MS m/z [M + H]+ tR [min] (method) | 1H NMR |
|---|---|---|---|
| 108 | 4-((2S,3S,4S)-2-(aminomethyl)-5-chloro-6-fluoro-3-methyl-2-phenyl-2,3-dihydrobenzofuran-4-yl)-5-fluoro-6-(2-methoxyethoxy)nicotinamide; Aryl bromide methyl 4-chloro-5-fluoro-6-(2-methoxyethoxy)nicotinate (N-XXXII) used in Suzuki coupling, synthesis analogously to Example 18 | 504.3 0.78 (1) | (400 MHz, DMSO-$d_6$) δ (ppm): 8.43 (s, 1H), 8.05 (s, 1H), 7.98 – 7.89 (m, 3H), 7.55 – 7.42 (m, 6H), 7.22 (d, J = 9.3 Hz, 1H), 4.58 – 4.49 (m, 2H), 3.77 – 3.69 (m, 2H), 3.55 – 3.40 (m, 1H), 3.30 (s, 3H), 2.70 (s, 2H), 0.98 (d, J = 6.7 Hz, 3H) |
| 109 | 2-((2R,3S,4S)-2-(aminomethyl)-5-chloro-6-fluoro-3-methyl-2-(pyridin-2-yl)-2,3-dihydrobenzofuran-4-yl)-3-fluoro-4-methoxybenzamide; Boronate tert-butyl (((2R,3S)-5-chloro-6-fluoro-3-methyl-2-(pyridin-2-yl)-4-(4,4,5,5-tetramethyl-1,3,2-dioxaborolan-2-yl)-2,3-dihydrobenzofuran-2-yl)methyl) carbamate (C-XVIII) and aryl bromide 2-bromo-3-fluoro-4-methoxybenzonitrile (N-IV) used in Suzuki coupling | 460.4 0.70 (1) | (400 MHz, DMSO-$d_6$) δ (ppm): 8.60 – 8.56 (m, 1H), 7.80 (td, J = 7.8, 1,7 Hz, 1H), 7.68 (s br, 1H), 7.60 (dd, J = 8.6, 1.2 Hz, 1H), 7.52 (d, J = 8.1 Hz, 1H), 7.32 (qd, J = 4.9, 1.0 Hz, 1H), 7.29 (t, J = 8.3 Hz, 1H), 7.11 – 7.05 (m, 2H), 3.89 (s, 3H), 3.50 (q, J = 7.0 Hz, 1H), 3.22 (d, J = 1.7 Hz, 2H), 0.92 (d, J = 7.3 Hz, 3H) |

Example 110: 2-((2S,3S,4S)-5-Chloro-6-fluoro-3-methyl-2-((methylamino)methyl)-2-phenyl-2,3-dihydrobenzofuran-4-yl)-3-fluoro-4-(2-hydroxyethoxy)benzamide

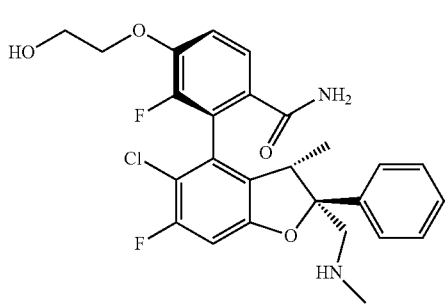

The title compound was prepared analogously to Example 48 from intermediates tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)carbamate (C-XVI) and 2-bromo-3-fluoro-4-(2-((tetrahydro-2H-pyran-2-yl)oxy)ethoxy)benzonitrile (N-VI). During the conversion of the nitrile into the amide group under standard conditions (Example 5a, step 2) the THP group had already been cleaved prior to Boc deprotection.

2-((2S,3S,4S)-5-Chloro-6-fluoro-3-methyl-2-((methylamino)methyl)-2-phenyl-2,3-dihydrobenzofuran-4-yl)-3-fluoro-4-(2-hydroxyethoxy)benzamide (Example 110): 1H NMR (400 MHz, DMSO-$d_6$) δ (ppm): 7.62 (s br, 1H), 7.58 (d, J=8.6 Hz, 1H), 7.45-7.27 (m, 6H), 7.12 (s br, 1H), 7.08 (d=9.4 Hz, 1H), 4.95-4.93 (m, 1H), 4.17-4.10 (m, 2H), 3.75-3.71 (m, 2H), 3.30-3.25 (m, 1H), 3.14-3.06 (m, 2H), 2.23 (s, 3H), 0.94 (d, J=7 Hz, 3H). UPLC-MS 1: m/z 503.4 [M+H]+, $t_R$=0.65 min.

Other diastereoisomer 2-((2S,3S,4R)-5-chloro-6-fluoro-3-methyl-2-((methylamino)methyl)-2-phenyl-2,3-dihydrobenzofuran-4-yl)-3-fluoro-4-(2-hydroxyethoxy)benzamide: UPLC-MS 1: m/z 503.4 [M+H]+, $t_R$=0.59 min.

The following compounds were prepared analogously to Example 110

| Ex. | Structure/Chemical Name | UPLC MS m/z [M + H]+ t_R [min] (method) | ¹H NMR |
|---|---|---|---|
| 111 | 2-((2R,3S,4S)-5-chloro-6-fluoro-3-methyl-2-((methylamino)methyl)-2-(pyridin-2-yl)-2,3-dihydrobenzofuran-4-yl)-3-fluoro-4-(2-methoxyethoxy)benzamide; Boronate tert-butyl (((2R,3S)-5-chloro-6-fluoro-3-methyl-2-(pyridin-2-yl)-4-(4,4,5,5-tetramethyl-1,3,2-dioxaborolan-2-yl)-2,3-dihydrobenzofuran-2-yl)methyl) carbamate (C-XVIII) and aryl bromide 2-bromo-3-fluoro-4-(2-methoxyethoxy)benzonitrile (N-IX) used in Suzuki coupling | 518.4 0.73 (1) | (400 MHz, DMSO-d₆) δ (ppm): 8.59 – 8.53 (m, 1H), 7.77 (td, J = 7.8, 1,7 Hz, 1H), 7.65 (s br, 1H), 7.59 (d, J = 8.6, Hz, 1H), 7.51 (d, J = 8.0 Hz, 1H), 7.34 – 7.27 (m, 2H), 7.12 (s br, 1H), 7.10 (d, J = 9.5 Hz, 1H), 4.30 – 4.20 (m, 2H), 3.69 (t, J = 4.4 Hz, 2H), 3.53 (q, J = 7.1 Hz, 1H), 3.31 (s, 3H), 3.09 (s, 2H), 2.17 (s, 3H), 0.95 (d, J = 7.2 Hz, 3H) |
| 112 | 2-((2R,3S,4S)-5-chloro-6-fluoro-3-methyl-2-((methylamino)methyl)-2-(pyridin-2-yl)-2,3-dihydrobenzofuran-4-yl)-3-fluoro-4-(2-hydroxyethoxy)benzamide; Boronate tert-butyl (((2R,3S)-5-chloro-6-fluoro-3-methyl-2-(pyridin-2-yl)-4-(4,4,5,5-tetramethyl-1,3,2-dioxaborolan-2-yl)-2,3-dihydrobenzofuran-2-yl)methyl)carbamate (C-XVIII) and aryl bromide 2-bromo-3-fluoro-4-(2-((tetrahydro-2H-pyran-2-yl)oxy)ethoxy)benzonitrile (N-VI) used in Suzuki coupling | 504.3 0.59 (1) | (400 MHz, DMSO-d₆) δ (ppm): 8.59 – 8.55 (m, 1H), 7.77 (t, J = 7.7 Hz, 1H), 7.64 (s br, 1H), 7.59 (d, J = 8.7, Hz, 1H), 7.50 (d, J = 8.0 Hz, 1H), 7.34 – 7.28 (m, 2H), 7.14 – 7.07 (m, 2H), 4.95 (t, J = 5.1 Hz, 1H), 4.20 – 4.09 (m, 2H), 3.78 – 3.71 (m, 2H), 3.53 (q, J = 7.5 Hz, 1H), 3.13 – 3.04 (m, 2H), 2.17 (s, 3H), 0.95 (d, J = 7.1 Hz, 3H) |

Example 113: 2-((2S,3S,4S)-5-Chloro-6-fluoro-3-methyl-2-((methylamino)methyl)-2-phenyl-2,3-dihydrobenzofuran-4-yl)-3-fluoro-4-(2-hydroxyethoxy)-N-methylbenzamide

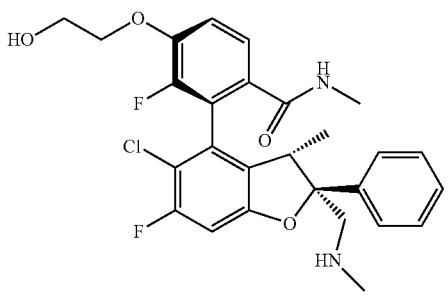

Example 114a and Example 114b: 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide or (2P)-2-[(2S,3S)-5-Chloro-6-fluoro-2-({[(1r,4S)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]benzamide (Example 114a) and 2-((2S,3S,4S)-5-chloro-6-fluoro-2-(((((cis)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide or (2P)-2-[(2S,3S)-5-Chloro-6-fluoro-2-({[(1s,4R)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]benzamide (Example 114b)

The title compound was prepared analogously to Example 51 from intermediates tert-butyl ((((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)carbamate (C-XVI) and methyl 2-bromo-3-fluoro-4-(2-((tetrahydro-2H-pyran-2-yl)oxy)ethoxy)benzoate (N-XXVII). The diastereoisomers were separated after final Boc- and THP deprotection.

2-((2S,3S,4S)-5-Chloro-6-fluoro-3-methyl-2-((methylamino)methyl)-2-phenyl-2,3-dihydrobenzofuran-4-yl)-3-fluoro-4-(2-hydroxyethoxy)-N-methylbenzamide (Example 113): $^1$H NMR (400 MHz, DMSO-$d_6$) δ (ppm): 8.20-8.12 (m, 1H), 7.50-7.28 (m, 7H), 7.06 (d, J=9.5 Hz, 1H), 4.92-4.90 (m, 1H), 4.17-4.05 (m, 2H), 3.74-3.69 (m, 2H), 3.16-2.94 (m, 2H), 2.63-2.61 (m, 1H), 2.45 (s, 3H), 1.24 (s, 3H), 0.94 (d, J=6.9 Hz, 3H), 0.89-0.81 (m, 1H). UPLC-MS 1: m/z 517.2 [M+H]$^+$, $t_R$=0.66 min.

Other diastereoisomer 2-((2S,3S,4R)-5-chloro-6-fluoro-3-methyl-2-((methylamino)methyl)-2-phenyl-2,3-dihydrobenzofuran-4-yl)-3-fluoro-4-(2-hydroxyethoxy)-N-methylbenzamide: UPLC-MS 1: m/z 517.2 [M+H]$^+$, $t_R$=0.63 min.

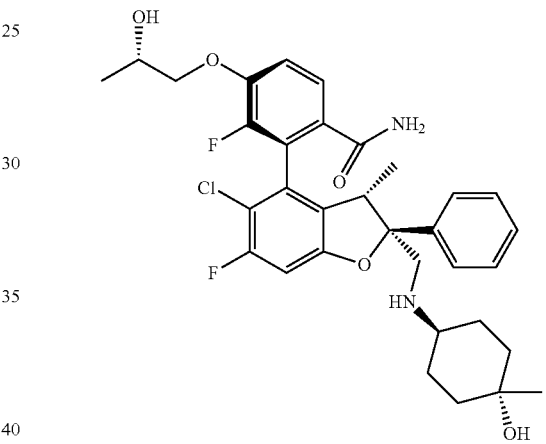

Examplle 114a

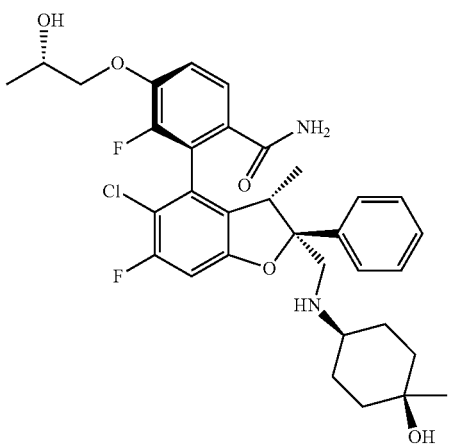

Examplle 114b

Reaction Scheme Example 114
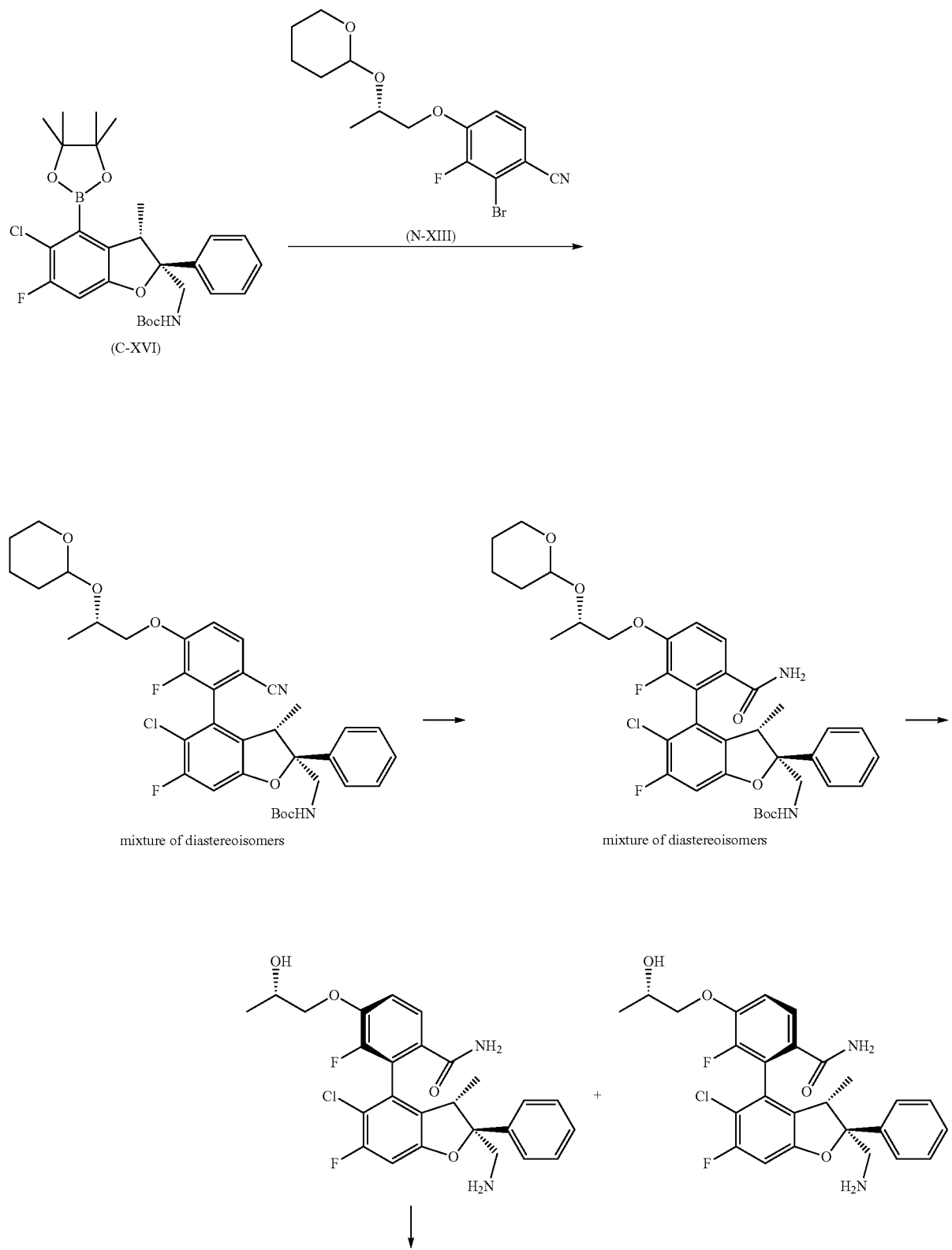

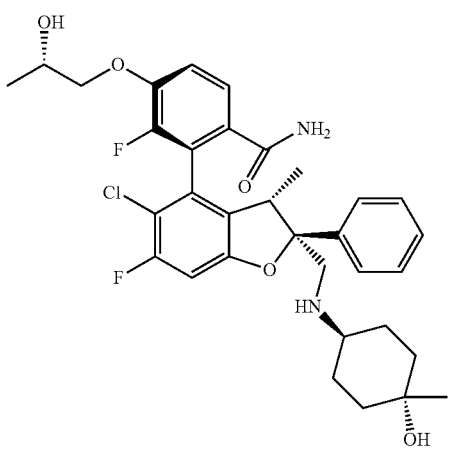

(Example 114a)

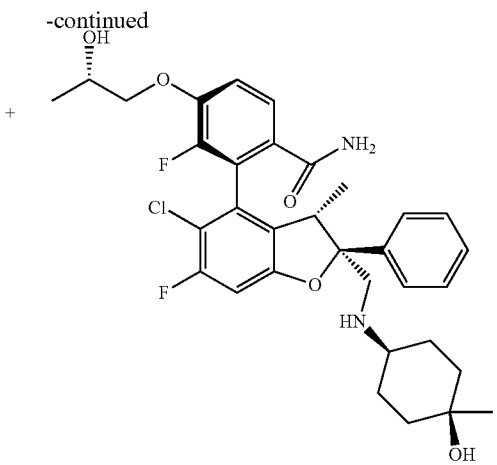

(Example 114b)

Step 1: Tert-butyl (((2S,3S,4S)-5-chloro-4-(6-cyano-2-fluoro-3-((2S)-2-((tetrahydro-2H-pyran-2-yl)oxy)propoxy)phenyl)-6-fluoro-3-methyl-2-phenyl-2,3-dihydrobenzofuran-2-yl)methyl)carbamate and tert-butyl (((2S,3S,4R)-5-chloro-4-(6-cyano-2-fluoro-3-((2S)-2-((tetrahydro-2H-pyran-2-yl)oxy)propoxy)phenyl)-6-fluoro-3-methyl-2-phenyl-2,3-dihydrobenzofuran-2-yl)methyl)carbamate A mixture of tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)carbamate (C-XVI) (550 mg, 1.06 mmol), 2-bromo-3-fluoro-4-((2S)-2-((tetrahydro-2H-pyran-2-yl)oxy)propoxy)benzonitrile (N-XIII) (399 mg, 1.115 mmol), N-XantPhos Pd G3 CAS [1602922-03-1] (98 mg, 0.106 mmol), and K₃PO₄ (376 mg, 3.19 mmol) was suspended in toluene (6 mL) and water (2 mL) and purged with Ar. The reaction mixture was stirred at 100° C. for 21 h. EtOAc and a sat solution of NaHCO₃ were added. The aqueous layer was back-extracted with EtOAc. The combined organic layers were washed with brine, dried over anhydrous Na₂SO₄ and concentrated. The crude product was purified by flash chromatography (silica, hexane/EtOAc, gradient: 5% to 50% EtOAc) to afford a mixture of the title compounds (453 mg). UPLC-MS 1: m/z 669.4 [M+H]$^+$, $t_R$=1.49 and 1.50 min.

Step 2: Tert-butyl (((2S,3S,4S)-4-(6-carbamoyl-2-fluoro-3-((2S)-2-((tetrahydro-2H-pyran-2-yl)oxy)propoxy)phenyl)-5-chloro-6-fluoro-3-methyl-2-phenyl-2,3-dihydrobenzofuran-2-yl)methyl)carbamate and tert-butyl (((2S,3S,4R)-4-(6-carbamoyl-2-fluoro-3-((2S)-2-((tetrahydro-2H-pyran-2-yl)oxy)propoxy)phenyl)-5-chloro-6-fluoro-3-methyl-2-phenyl-2,3-dihydrobenzofuran-2-yl)methyl)carbamate To a suspension of a mixture of tert-butyl (((2S,3S,4S)-5-chloro-4-(6-cyano-2-fluoro-3-((2S)-2-((tetrahydro-2H-pyran-2-yl)oxy)propoxy)phenyl)-6-fluoro-3-methyl-2-phenyl-2,3-dihydrobenzofuran-2-yl)methyl)carbamate and tert-butyl (((2S,3S,4R)-5-chloro-4-(6-cyano-2-fluoro-3-((2S)-2-((tetrahydro-2H-pyran-2-yl)oxy)propoxy)phenyl)-6-fluoro-3-methyl-2-phenyl-2,3-dihydrobenzofuran-2-yl)methyl)carbamate (450 mg, 0.672 mmol) in EtOH (8 mL) and water (2 mL) was added at RT hydrido (dimethylphosphinousacid-kP)[hydrogen bis(dimethylphosphinito-kP)]platinum (II) (58 mg, 0.134 mmol). The reaction mixture was stirred at 80° C. for 1.5 h. A sat solution of NaHCO₃ was added and the reaction mixture was extracted with EtOAc. The combined organic layers were washed with brine, dried over anhydrous Na₂SO₄ and concentrated to afford a mixture of the title compounds (437 mg). UPLC-MS 1: m/z 687.4 [M+H]$^+$, $t_R$=1.34, 1.35, 1.36 and 1.38 min (due to the racemic THP protecting group used 2 peaks are visible in UPLC for this mixture of the title compounds).

Step 3: 2-((2S,3S,4S)-2-(Aminomethyl)-5-chloro-6-fluoro-3-methyl-2-phenyl-2,3-dihydrobenzofuran-4-yl)-3-fluoro-4-((S)-2-hydroxypropoxy)benzamide and 2-((2S,3S,4R)-2-(aminomethyl)-5-chloro-6-fluoro-3-methyl-2-phenyl-2,3-dihydrobenzofuran-4-yl)-3-fluoro-4-((S)-2-hydroxypropoxy)benzamide A mixture of tert-butyl (((2S,3S,4S)-4-(6-carbamoyl-2-fluoro-3-((2S)-2-((tetrahydro-2H-pyran-2-yl)oxy)propoxy)phenyl)-5-chloro-6-fluoro-3-methyl-2-phenyl-2,3-dihydrobenzofuran-2-yl)methyl)carbamate and tert-butyl (((2S,3S,4R)-4-(6-carbamoyl-2-fluoro-3-((2S)-2-((tetrahydro-2H-pyran-2-yl)oxy)propoxy)phenyl)-5-chloro-6-fluoro-3-methyl-2-phenyl-2,3-dihydrobenzofuran-2-yl)methyl)carbamate (434 mg, 0.63 mmol) was dissolved in HCl (4 mL, 4 M in dioxane). The solution was stirred at RT for 1.5 h, then diluted with EtOAc and quenched with a sat solution of NaHCO₃. The aqueous layer was back-extracted with EtOAc. The combined organic layers were washed with brine, dried over anhydrous Na₂SO₄ and concentrated. The crude product was purified by flash chromatography (silica, hexane/EtOAc, gradient: 5% to 50% EtOAc) to afford the desired compounds as separate diastereoisomers.

2-((2S,3S,4S)-2-(Aminomethyl)-5-chloro-6-fluoro-3-methyl-2-phenyl-2,3-dihydrobenzofuran-4-yl)-3-fluoro-4-((S)-2-hydroxypropoxy)benzamide (117 mg): $^1$H NMR (600 MHz, DMSO-d₆) δ (ppm) 7.68 (s, 1H), 7.56 (d, J=8.7 Hz, 1H), 7.44 (d, J=7.3 Hz, 2H), 7.36 (t, J=7.5 Hz, 2H), 7.29 (t, J=7.4 Hz, 2H), 7.13-7.03 (m, 2H), 4.93 (d, J=3.8 Hz, 1H), 3.94 (dd, J=24.3, 5.7 Hz, 3H), 3.30-3.15 (m, 2H), 3.11 (s, 1H), 1.91 (s, 2H), 1.12 (d, J=5.5 Hz, 3H), 0.92 (d, J=7.2 Hz, 3H). UPLC-MS 1: m/z 503.3 [M+H]$^+$, $t_R$=0.69 min.

2-((2S,3S,4R)-2-(Aminomethyl)-5-chloro-6-fluoro-3-methyl-2-phenyl-2,3-dihydrobenzofuran-4-yl)-3-fluoro-4-

((S)-2-hydroxypropoxy)benzamide (169 mg): UPLC-MS 1: m/z 503.3 [M+H]$^+$, $t_R$=0.61 min.

Step 4: 2-((2S,3S,4S)-5-Chloro-6-fluoro-2-(((((trans)-4-hydroxy-4-methylcyclohexyl)amino) methyl)-3-methyl-2-phenyl-2,3-dihydrobenzofuran-4-yl)-3-fluoro-4-((S)-2-hydroxypropoxy)benzamide or (2P)-2-[(2S,3S)-5-Chloro-6-fluoro-2-({[(1r,4S)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]benzamide (Example 114a) and 2-((2S,3S,4S)-5-chloro-6-fluoro-2-(((((cis)-4-hydroxy-4-methylcyclohexyl) amino)methyl)-3-methyl-2-phenyl-2,3-dihydrobenzofuran-4-yl)-3-fluoro-4-((S)-2-hydroxypropoxy) benzamide or (2P)-2-[(2S,3S)-5-Chloro-6-fluoro-2-({[(1s,4R)-4-hydroxy-4-methylcyclohexyl] amino}methyl)-3-methyl-2-phenyl-2,3-dihydro-1-benzofuran-4-yl]-3-fluoro-4-[(2S)-2-hydroxypropoxy]benzamide (Example 114b)

To a solution of 2-((2S,3S,4S)-2-(aminomethyl)-5-chloro-6-fluoro-3-methyl-2-phenyl-2,3-dihydrobenzofuran-4-yl)-3-fluoro-4-((S)-2-hydroxypropoxy)benzamide (115 mg, 0.23 mmol) in DCM (2.8 mL) was added at RT 4-hydroxy-4-methylcyclohexanone (35 mg, 0.27 mmol), followed by sodium triacetoxyborohydride (145 mg, 0.69 mmol) and acetic acid (0.015 mL). The suspension was stirred at RT for 45 min, then quenched with a sat solution of NaHCO$_3$ (20 mL) and extracted with DCM. The combined organic layers were washed with a sat solution of NaHCO$_3$ and brine, dried over anhydrous Na$_2$SO$_4$ and concentrated. The crude material was purified by chiral SFC (Chiralpak AD-H 5 μm 250×30 mm; mobile phase: CO$_2$/[IPA+1% NH$_3$]70/30; flow rate 100 mL/min) to afford the title compounds as single stereoisomers.

2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide or (2P)-2-[(2S,3S)-5-Chloro-6-fluoro-2-({[(1r,4S)-4-hydroxy-4-methylcyclohexyl] amino}methyl)-3-methyl-2-phenyl-2,3-dihydro-1-benzofuran-4-yl]-3-fluoro-4-[(2S)-2-hydroxypropoxy] benzamide (Example 114a) (44 mg): $^1$H NMR (600 MHz, DMSO-d$_6$) δ 7.61 (s br, 1H), 7.57 (d, J=8.8 Hz, 1H), 7.43-7.41 (m, 2H), 7.33 (t, J=7.7 Hz, 2H), 7.30-7.24 (m, 2H), 7.08 (s br, 1H), 7.06 (d, J=9.5 Hz, 1H), 4.93 (s br, 1H), 4.05 (s br, 1H), 3.99-3.94 (m, 2H), 3.93-3.89 (m, 1H), 3.27 (q, J=7.1 Hz, 1H), 3.12-3.06 (m, 2H), 2.33-2.28 (m, 1H), 1.66-1.60 (m, 1H), 1.60-1.55 (m, 1H), 1.39-1.30 (m, 2H), 1.24-1.15 (m, 2H), 1.13 (d, J=6.2 Hz, 3H), 1.07-0.99 (m, 2H), 0.98 (s, 3H), 0.94 (d, J=7.3 Hz, 3H). UPLC-MS 1: m/z 615.3 [M+H]$^+$, $t_R$=0.77 min. Chiral SFC (Chiralpak AD-H 250×4.6 mm; 5 μm; mobile phase: CO$_2$/[IPA+1% isopropylamine] 75:25; flow: 3 mL/min): $t_R$=4.49 min. The absolute configuration was confirmed by an X-ray cocrystal structure of Example 114a bound to the YAP binding site of TEAD4.

2-((2S,3S,4S)-5-Chloro-6-fluoro-2-((((cis)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide or (2P)-2-[(2S,3S)-5-Chloro-6-fluoro-2-({[(1s,4R)-4-hydroxy-4-methylcyclohexyl] amino}methyl)-3-methyl-2-phenyl-2,3-dihydro-1-benzofuran-4-yl]-3-fluoro-4-[(2S)-2-hydroxypropoxy] benzamide (Example 114b) (23 mg): $^1$H NMR (600 MHz, DMSO-d$_6$) δ (ppm) 7.61 (s, 1H), 7.57 (d, J=8.5 Hz, 1H), 7.42 (d, J=7.7 Hz, 2H), 7.33 (t, J=7.6 Hz, 2H), 7.30-7.27 (m, 1H), 7.25 (d, J=7.4 Hz, 1H), 7.07 (d, J=9.5 Hz, 2H), 4.93 (s, 1H), 4.00-3.89 (m, 3H), 3.87 (s, 1H), 3.25 (q, J=7.2 Hz, 1H), 3.15 (d, J=12.5 Hz, 1H), 3.10 (d, J=12.6 Hz, 1H), 2.17 (ddd, J=13.6, 8.2, 3.1 Hz, 1H), 1.45-1.38 (m, 4H), 1.24 (td, J=13.3, 6.6 Hz, 2H), 1.20-1.14 (m, 2H), 1.12 (d, J=5.8 Hz, 3H), 1.03 (s, 3H), 0.93 (d, J=7.1 Hz, 3H). UPLC-MS 1: m/z 615.4 [M+H]$^+$, $t_R$=0.75 min. Chiral SFC (Chiralpak AD-H 250× 4.6 mm; 5 μm; mobile phase: CO$_2$/[IPA+1% isopropylamine] 75:25; flow: 3 mL/min): $t_R$=7.46 min The following compounds were prepared analogously to Example 114a and Example 114b

| Ex. | Structure/Chemical Name | UPLC MS m/z [M + H]$^+$ $t_R$ [min] (method) | $^1$H NMR |
|---|---|---|---|
| 115a | 2-((2S,3S,4S)-5-chloro-6-fluoro-2-(((((trans)-4-hydroxycyclohexyl)amino)methyl)-3-methyl-2-phenyl-2,3-dihydrobenzofuran-4-yl)-4-(difluoromethoxy)-3-fluorobenzamide; Example 105 used in reductive amination | 593.3 0.82 (1) | (400 MHz, DMSO-d6) δ (ppm): 7.80 (s br, 1H), 7.61 (d, J = 8.7 Hz, 1H), 7.53 – 7.49 (m, 1H), 7.42 – 7.23 (m, 7H), 7.14 – 7.08 (m, 1H), 4.38 (d, J = 4.3 Hz, 1H), 3.30 – 3.21 (m, 1H), 3.13 – 3.05 (m, 2H), 2.17 – 2.12 (m, 1H), 1.69 – 1.63 (m, 4H), 1.11 – 0.97 (m, 2H), 0.91 (d, J = 7.0 Hz, 3H), 0.87 – 0.77 (m, 4H) |

-continued

| Ex. | Structure/Chemical Name | UPLC MS m/z [M + H]+ $t_R$ [min] (method) | ¹H NMR |
|---|---|---|---|
| 115b | 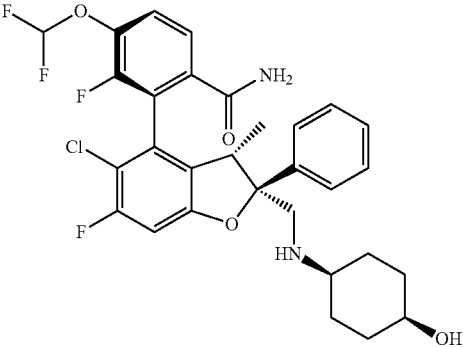<br>2-((2S,3S,4S)-5-chloro-6-fluoro-2-((((cis)-4-hydroxycyclohexyl)amino)methyl)-3-methyl-2-phenyl-2,3-dihydrobenzofuran-4-yl)-4-(difluoromethoxy)-3-fluorobenzamide;<br>Formed in reductive amination step together with Example 115a | 593.3<br>0.84 (1) | (400 MHz, DMSO-d₆) δ (ppm): 7.84 (s, 1H), 7.62 (d, J = 8.6 Hz, 1H), 7.57 –7.24 (m, 7H), 7.12 (d, J = 9.5 Hz, 1H), 4.20 (d, J = 3.5 Hz, 1H), 3.55 – 3.49 (m, 1H), 3.30 – 3.24 (m, 1H), 3.13 – 3.04 (m, 2H), 2.32 – 2.24 (m, 1H), 1.40-1.27 (m, 9H), 0.94 (d, J = 7.1 Hz, 3H), 0.86 – 0.74 (m, 1H) |
| 116a | 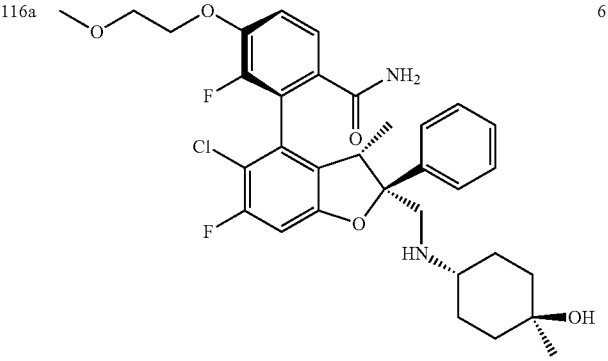<br>2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-methoxyethoxy)benzamide;<br>Example 106 used in reductive amination | 615.5<br>0.81 (1) | (400 MHz, DMSO-d₆) δ (ppm): 7.62 (s br, 1H), 7.58 (d, J = 8.6Hz, 1H), 7.44 – 7.41 (m, 2H), 7.36 – 7.24 (4H), 7.09 – 7.06 (m, 2H), 4.29 – 4.18 (m, 2H), 4.03 (S, 1H), 3.68 – 3.66 (m, 2H), 3.29 (s, 3H), 3.27 – 3.24 (m, 1H), 3.09 (s br, 2H), 2.35 – 2.27 (m, 1H), 1.70 – 1.46 (m, 2H), 1.40-1.15 (m, 4H), 1.10 – 1.00 (m, 2H), 0.98 (s, 3H), 0.94 (d, J = 7.3 Hz, 3H) |
| 116b | 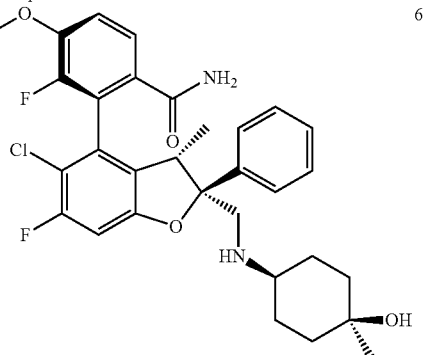<br>2-((2S,3S,4S)-5-chloro-6-fluoro-2-((((cis)-4-hydroxy-4-methylcyclohexyl)amino)methyl)-3-methyl-2-phenyl-2,3-dihydrobenzofuran-4-yl)-3-fluoro-4-(2- | 615.5<br>0.84 (1) | (400 MHz, DMSO-d₆) δ (ppm): 7.62 (s br, 1H), 7.58 (d, J = 8.6 Hz, 1H), 7.43 – 7.28 (m, 6H), 7.08 (s, 1H), 7.07 (d, J = 9.5 Hz, 1H), 4.28 – 4.20 (m, 2H), 3.86 (s, 1H), 3.68 – 3.66 (m, 2H), 3.29 (s, 3H), 3.26 – 3.22 (m, 1H), 3.17 – 3.09 (m, 2H), 2.19 – 2.13 (m, 1H), 1.47 – 1.39 (m, 4H), 1.25-1.15 (m, 5H), 1.03 (s, 3H), 0.93 (d, J = 7.3Hz, 3H) |

| Ex. | Structure/Chemical Name | UPLC MS m/z [M + H]+ $t_R$ [min] (method) | $^1$H NMR |
|---|---|---|---| methoxyethoxy)benzamide;
Formed in reductive amination step together with Example 116a 117a 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-hydroxyethoxy)benzamide or (2P)-2-[(2S,3S)-5-Chloro-6-fluoro-2-({[(1r,4S)-4-hydroxy-4-methylcyclohexyl]amino}methyl)-3-methyl-2-phenyl-2,3-dihydro-1-benzofuran-4-yl]-3-fluoro-4-(2-hydroxyethoxy)benzamide;
Example 107 used in reductive amination
The absolute configuration was confirmed by an X-ray cocrystal structure of Example 117a bound to the YAP binding site of TEAD4.

601.2
0.69 (1)
601.2
2.95 (2)

(600 MHz, DMSO-$d_6$) δ (ppm): 7.64 (s br, 1H), 7.56 (dd, J = 8.6, 1.3 Hz, 1H), 7.43 – 7.40 (m, 2H), 7.35 – 7.31 (m, 2H), 7.30 – 7.24 (m, 2H), 7.09 ( s br, 1H), 7.07 (d, J = 9.5 Hz, 1H), 4.93 (t, J = 5.5 Hz, 1H), 4.16 – 4.08 (m, 2H), 4.05 (s, 1H), 3.72 (q, J = 5.0 Hz, 2H), 3.25 (q, J = 7.2 Hz, 1H), 3.12 – 3.06 (m, 2H), 2.33 – 2.26 (m, 1H), 1.65 – 1.54 (m, 2H), 1.38 – 1.27 (m, 2H), 1.26 – 1.15 (m, 2H), 1.07 – 0.97 (m, 2H), 0.97 (s, 3H), 0.93 (d, J = 7.3 Hz, 3H), 0.87 (s br, 1H).

117b 2-((2S,3S,4S)-5-chloro-6-fluoro-2-((((cis)-4-hydroxy-4-methylcyclohexyl)amino)methyl)-3-methyl-2-phenyl-2,3-dihydrobenzofuran-4-yl)-3-fluoro-4-(2-hydroxyethoxy)benzamide or (2P)-2-[(2S,3S)-5-Chloro-6-fluoro-2-({[(1s,4R)-4-hydroxy-4-methylcyclohexyl]amino}methyl)-3-methyl-2-phenyl-2,3-dihydro-1-benzofuran-4-yl]-3-fluoro-4-(2-hydroxyethoxy)benzamide;
Formed in reductive amination step together with Example 117a 601.5
0.71 (1)
601.3
3.13 (2)

(600 MHz, DMSO-$d_6$) δ (ppm) 7.64 (s br, 1H), 7.57 (dd, J = 8.6 Hz, 0.9 Hz, 1H), 7.43 – 7.40 (m, 2H), 7.35 – 7.32 (m, 2H), 7.30 – 7.24 (m, 2H), 7.08 (s br, 1H), 7.07 (d, J = 9.5 Hz, 1H), 4.93 (t, J = 5.5 Hz, 1H), 4.15 – 4.08 (m, 2H), 3.87 (s, 1H), 3.72 (q, J = 5.0 Hz, 2H), 3.24 (q, J = 7.2 Hz, 1H), 3.18 – 3.13 (m, 1H), 3.12 – 3.08 (m, 1H), 2.19 – 2.13 (m, 1H), 1.45 – 1.39 (m, 4H), 1.27 – 1.11 (m, 4H), 1.02 (s, 3H), 0.93 (d, J = 7.3 Hz, 3H), 0.85 (s br, 1H)

| Ex. | Structure/Chemical Name | UPLC MS m/z [M + H]+ $t_R$ [min] (method) | $^1$H NMR |
|---|---|---|---|
| 118 | 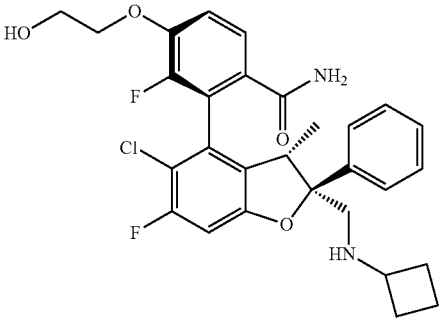<br>2-((2S,3S,4S)-5-chloro-2-((cyclobutylamino)methyl)-6-fluoro-3-methyl-2-phenyl-2,3-dihydrobenzofuran-4-yl)-3-fluoro-4-(2-hydroxyethoxy)benzamide;<br>Prepared in analogy to Example 96 from Example 107 | 543.4<br>0.71 (1) | (400 MHz, MeOD) δ (ppm): 7.61 (d, J = 8.6 Hz, 1H), 7.49-7.22 (m, 6H), 6.92 (d, J = 9.2 Hz, 1H), 4.21 – 4.14 (m, 2H), 3.91 – 3.89 (m, 2H), 3.42 – 3.36 (m, 1H), 3.21 – 3.15 (m, 1H), 3.13 (s, 2H), 2.19 – 2.07 (m, 2H), 1.66 – 1.56 (m, 4H), 1.01 (d, J = 7.2 Hz, 3H) |

Examples such as shown in the table above can also be prepared by an alternative synthesis route as exemplified for Example 114a below:

Alternative synthesis for Example 114a: 2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide or (2P)-2-[(2S,3S)-5-Chloro-6-fluoro-2-({[(1r,4S)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]benzamide

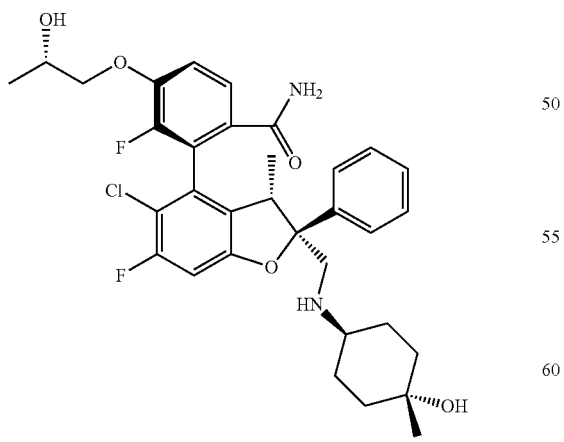

Reaction Scheme Example 114a alternative synthesis
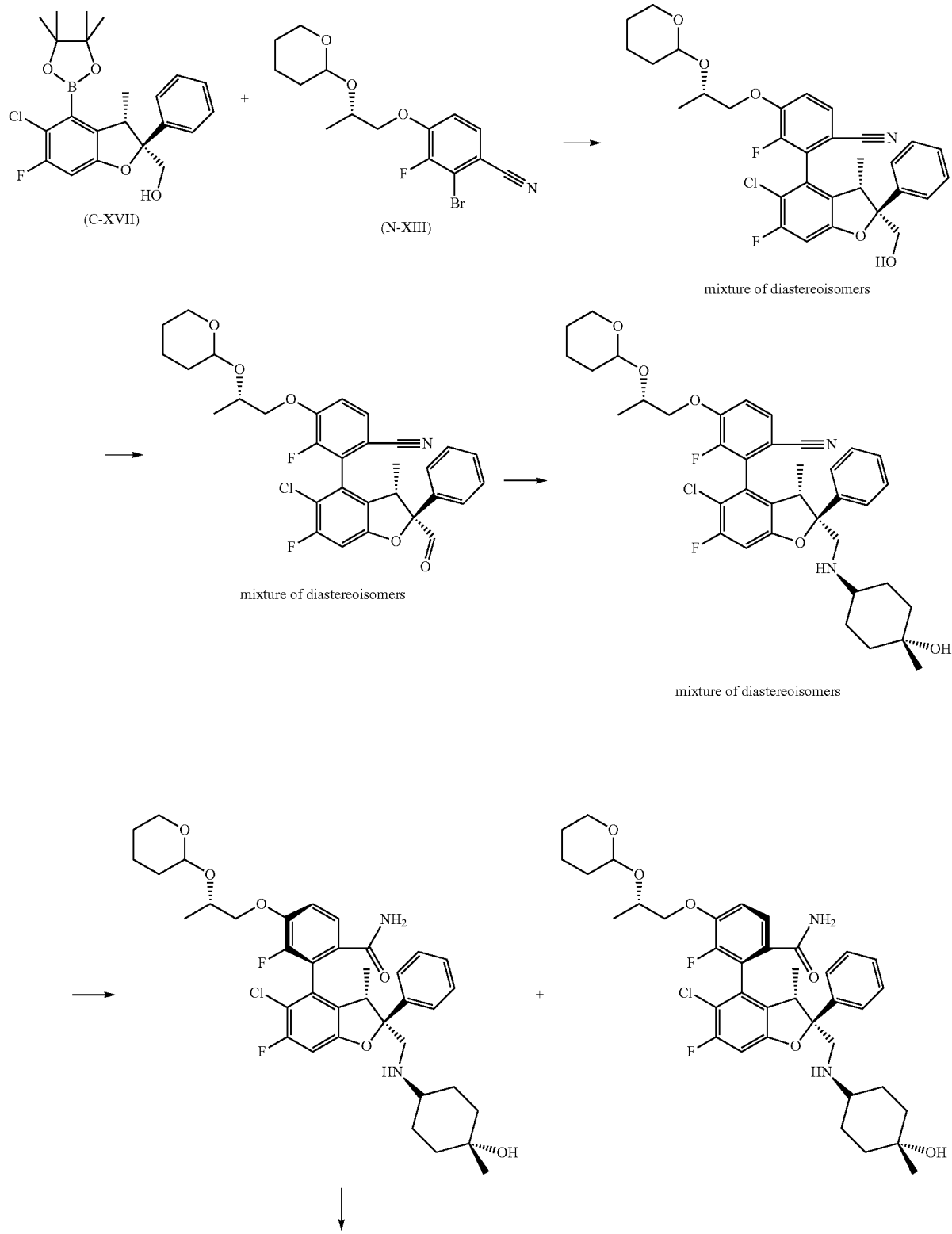

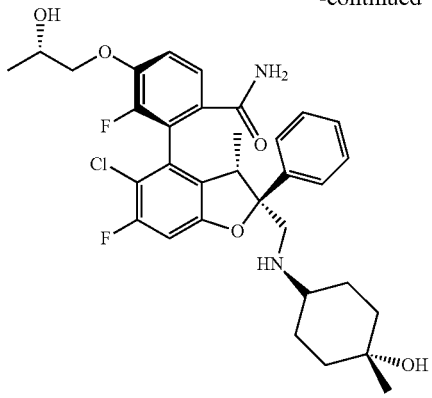

(Example 114a)

Step 1: 2-((2S,3S,4S)-5-Chloro-6-fluoro-2-(hydroxymethyl)-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-5-chloro-6-fluoro-2-(hydroxymethyl)-3-methyl-2-phenyl-2,3-dihydrobenzofuran-4-yl)-3-fluoro-4-((2S)-2-((tetrahydro-2H-pyran-2-yl)oxy)propoxy)benzonitrile A solution of ((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methanol (C-XVII) (15.53 g, 35.2 mmol) in toluene (60 mL) was added drop-wise to a stirred solution of 2-bromo-3-fluoro-4-((2S)-2-((tetrahydro-2H-pyran-2-yl)oxy)propoxy)benzonitrile (N-XIII) (13.88 g, 38.8 mmol), $K_3PO_4$ (22.44 g, 106 mmol) and N-XantPhos Pd G3 (Aldrich cat. No. 794228) (1.623 g, 1.762 mmol) in toluene (80 mL) and water (40 mL) at reflux and stirring at 105° C. was continued for 3 h. EtOAc and water were added and the organic phase was separated. The aqueous phase was extracted with EtOAc, the combined organic extracts were washed with brine, dried over anhydrous $Na_2SO_4$ and concentrated. The crude product was purified by flash chromatography (silica, EtOAc/Hep, gradient: 0% to 80% EtOAc) to afford a mixture of the title compounds (10.41 g). UPLC-MS 1: product not ionizable; $t_R$=1.27 min, 1.28 min and 1.30 min.

Step 2: 2-((2S,3S,4S)-5-Chloro-6-fluoro-2-formyl-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-5-chloro-6-fluoro-2-formyl-3-methyl-2-phenyl-2,3-dihydrobenzofuran-4-yl)-3-fluoro-4-((2S)-2-((tetrahydro-2H-pyran-2-yl)oxy)propoxy)benzonitrile At −78° C. a solution of DMSO (5.80 mL, 82 mmol) in DCM (40 mL) was added to a stirred solution of oxalyl chloride (3.57 mL, 40.8 mmol) in DCM (100 mL) and stirring at −78° C. was continued for 15 min. Then, a solution of a mixture of 2-((2S,3S,4S)-5-chloro-6-fluoro-2-(hydroxymethyl)-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-5-chloro-6-fluoro-2-(hydroxymethyl)-3-methyl-2-phenyl-2,3-dihydrobenzofuran-4-yl)-3-fluoro-4-((2S)-2-((tetrahydro-2H-pyran-2-yl)oxy)propoxy)benzonitrile (14.55 g, 25.5 mmol) in DCM (20 mL) was added. After 15 min. TEA (17.79 mL, 128 mmol) was added and the reaction mixture was allowed to warm to 0° C. over a period of 30 min. DCM and water were added and the organic phase was separated. The organic phase was extracted with DCM and the combined organic extracts were washed with water and brine, dried over anhydrous $Na_2SO_4$ and concentrated to afford a mixture of the title compounds (14.50 g) which was used without further purification in the next step. UPLC-MS 1: m/z 567.3 [M+H]$^+$. $t_R$=1.38 min and 1.39 min.

Step 3: 2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzonitrile At RT acetic acid (2.192 mL, 38.3 mmol) was added to a stirred solution of a mixture of 2-((2S,3S,4S)-5-chloro-6-fluoro-2-formyl-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-5-chloro-6-fluoro-2-formyl-3-methyl-2-phenyl-2,3-dihydrobenzofuran-4-yl)-3-fluoro-4-((2S)-2-((tetrahydro-2H-pyran-2-yl)oxy)propoxy)benzonitrile (14.50 g, 25.5 mmol) and trans-4-amino-1-methylcyclohexanol (3.30 g, 25.5 mmol) in DCE (100 mL) and stirring at 80° C. was continued for 1 h. Sodium triacetoxyborohydride (10.82 g, 51.1 mmol) was added at 60° C. and the reaction mixture was stirred at this temperature for another 15 min. For workup DCM was added followed by a sat solution of $NaHCO_3$. The organic phase was separated and the aqueous phase was extracted with DCM. The combined organic extracts were washed with brine, dried over anhydrous $Na_2SO_4$ and concentrated. The crude product was purified by flash chromatography (silica, DCM/MeOH, gradient: 0% to 6% MeOH) to afford a mixture of the title compounds (10.34 g). UPLC MS 1: m/z 681.3 [M+H]$^+$; $t_R$=1.13 min, 1.15 min and 1.18 min (more than 2 peaks in UPLC due to racemic THP protecting group).

Step 4: 2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzamide and 2-((2S,3S,4R)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzamide Hydrido(dimethylphosphinous acid-kP)[hydrogen bis(dimethylphosphinito-kP)]platinum(II) (0.5 g, 1.165 mmol) was added to a stirred solution of a mixture of 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzonitrile (10.34 g, 15.17 mmol) in EtOH (70 mL) and water (30 mL) and the reaction mixture was stirred at 85° C. for 2 h. EtOAc and water were added and the organic phase was separated. The aqueous phase was extracted with EtOAc, the combined organic extracts were washed with brine, dried over anhydrous $Na_2SO_4$ and concentrated. The remaining residue was dissolved in MeOH and was passed through a PL-thiol MP Resin cartridge (Agilent, StratoSpheres SPE) to remove metal traces. Concentration afforded the crude product which was purified by flash chromatography (silica, DCM/(7N ammonia in MeOH), gradient: 0% to 12% (7N ammonia in MeOH)) to afford the title compounds as separate diastereoisomers For each separated diastereoisomer 2 peaks are visible in UPLC due to the racemic THP protecting group.

2-((2S,3S,4R)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzamide (5.53 g): UPLC-MS 1: m/z 699.3 [M+H]$^+$; $t_R$=0.92 min and 0.95 min 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzamide (4.26 g): UPLC-MS 1: m/z 699.3 [M+H]$^+$; $t_R$=1.02 min and 1.04 min.

Step 5: 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide or (2P)-2-[(2S,3S)-5-Chloro-6-fluoro-2-({[(1r,4S)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]benzamide (Example 114a)

HCl (50 mL, 4 M in dioxane) was added to 2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzamide (4.26 g, 6.09 mmol) at RT and stirring at RT was continued for 2 h. The reaction mixture was quenched by the addition of a sat solution of $NaHCO_3$ and extracted with DCM. The combined organic extracts were dried over anhydrous $Na_2SO_4$ and concentrated. The crude product was purified by flash chromatography (silica, DCM/(7N ammonia in MeOH), gradient: 0% to 13% (7N ammonia in MeOH)) to afford the title compound (3.26 g). $^1$H NMR (600 MHz, DMSO-$d_6$) δ 7.61 (s br, 1H), 7.57 (d, J=8.8 Hz, 1H), 7.43-7.41 (m, 2H), 7.33 (t, J=7.7 Hz, 2H), 7.30-7.24 (m, 2H), 7.08 (s br, 1H), 7.06 (d, J=9.5 Hz, 1H), 4.93 (s br, 1H), 4.05 (s br, 1H), 3.99-3.94 (m, 2H), 3.93-3.89 (m, 1H), 3.27 (q, J=7.1 Hz, 1H), 3.12-3.06 (m, 2H), 2.33-2.28 (m, 1H), 1.66-1.60 (m, 1H), 1.60-1.55 (m, 1H), 1.39-1.30 (m, 2H), 1.24-1.15 (m, 2H), 1.13 (d, J=6.2 Hz, 3H), 1.07-0.99 (m, 2H), 0.98 (s, 3H), 0.94 (d, J=7.3 Hz, 3H). UPLC MS 1: m/z 615.3 [M+H]$^+$; $t_R$=0.77 min. UPLC-MS 2: m/z 615.3 [M+H]$^+$; $t_R$=3.33 min.

Example 119: 4-((2S,3S,4S)-5-Chloro-6-fluoro-2-((((trans-4-hydroxy-4-methylcyclohexyl)amino)methyl)-3-methyl-2-phenyl-2,3-dihydrobenzofuran-4-yl)-5-fluoro-6-(2-hydroxyethoxy)nicotinamide

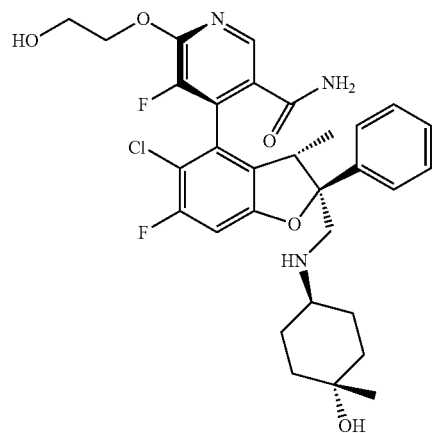

The title compound was prepared analogously to Example 114a (alternative synthesis) from intermediates ((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methanol (C-XVII) and 5-Fluoro-4-iodo-6-(2-((tetrahydro-2H-pyran-2-yl)oxy)ethoxy)nicotinonitrile (N-XII). $^1$H NMR (400 MHz, DMSO-$d_6$) δ (ppm) 8.38 (s, 1H), 7.90 (s, 1H), 7.49-7.40 (m, 2H), 7.38-7.22 (m, 4H), 7.17-7.09 (m, 1H), 4.93-4.85 (m, 1H), 4.51-4.34 (m, 2H), 4.05-3.93 (m, 1H), 3.78-3.68 (m, 2H), 3.09 (s, 2H), 1.60 (s, 3H), 1.29 (d, J=34.8 Hz, 9H), 1.08-0.74 (m, 5H). UPLC-MS 1: m/z 602.2 [M+H]$^+$, $t_R$=0.71 min.

The diastereoisomers were separated prior to final Boc- and THP deprotection: 4-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-5-fluoro-6-(2-((tetrahydro-2H-pyran-2-yl)oxy)ethoxy)nicotinamide: UPLC-MS 1: m/z 686.5 [M+H]$^+$, $t_R$=0.90 min; 4-((2S,3S,4R)-5-chloro-6-fluoro-2-((((trans)-4-hydroxy-4-methylcyclohexyl)amino)methyl)-3-methyl-2-phenyl-2,3-dihydrobenzofuran-4-yl)-5-fluoro-6-(2-((tetrahydro-2H-pyran-2-yl)oxy)ethoxy)nicotinamide: UPLC-MS 1: m/z 686.8 [M+H]$^+$, $t_R$=0.84 min.

Example 120: 2-((2S,3S,4S)-5-Chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzonitrile or (2P)-2-[(2S,3S)-5-Chloro-6-fluoro-2-({[(1r,4S)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]benzonitrile

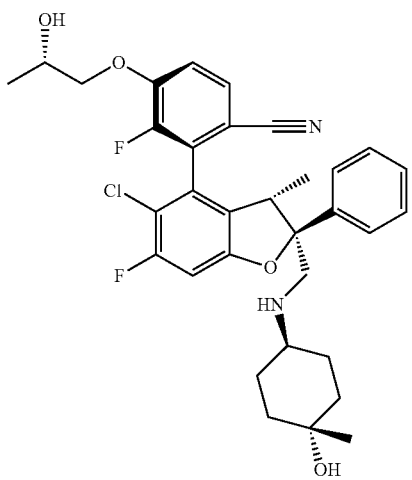

Pyridine p-toluenesulfonate (77 mg, 0.31 mmol) was added to a solution of a mixture of 2-((2S,3S,4S)-5-chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-5-chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-((2S)-2-((tetrahydro-2H-pyran-2-yl)oxy)propoxy)benzonitrile (product of step 3 of alternative synthesis of Example 114a) (105 mg, 0.15 mmol) in EtOH (3 mL) and the reaction mixture was stirred at RT for 16 h and at 60° C. for 2 h. A sat solution of NaHCO₃ was added and the mixture was extracted with EtOAc. The combined organic extracts were washed with a sat solution of NaHCO₃, dried over anhydrous Na₂SO₄ and concentrated. The residue was purified by preparative HPLC and the diastereoisomers were separated.

2-((2S,3S,4S)-5-Chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzonitrile or (2P)-2-[(2S,3S)-5-Chloro-6-fluoro-2-({[(1r,4S)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]benzonitrile (Example 120, 26 mg): $^1$H NMR (400 MHz, DMSO-d₆) δ (ppm) 7.87 (dd, J=8.8, 1.2 Hz, 1H), 7.51-7.42 (m, 3H), 7.38-7.25 (m, 4H), 5.00 (d, J=4.7 Hz, 1H), 4.06-4.02 (m, 3H), 0.4.02-3.95 (m, 1H), 3.39-3.30 (m, 1H), 3.12 (s br, 2H), 2.33-2.26 (m, 1H), 1.67-1.55 (m, 2H), 1.40-1.27 (m, 2H), 1.26-1.25 (m, 2H), 1.13 (d, J=6.1 Hz, 3H), 1.07-1.00 (m, 2H), 1.01-0.97 (m, 6H). UPLC-MS 1: m/z 597.5 [M+H]⁺, t$_R$=0.83 min.

Other diastereoisomer 2-((2S,3S,4R)-5-chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzonitrile: UPLC-MS 1: m/z 597.6 [M+H]⁺, t$_R$=0.80 min.

Example 121: 2-((2S,3S,4S)-5-Chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-hydroxyethoxy)-N-methylbenzamide or (2P)-2-[(2S,3S)-5-Chloro-6-fluoro-2-({[(1r,4S)-4-hydroxy-4-methylcyclohexyl]amino}methyl)-3-methyl-2-phenyl-2,3-dihydro-1-benzofuran-4-yl]-3-fluoro-4-(2-hydroxyethoxy)-N-methylbenzamide

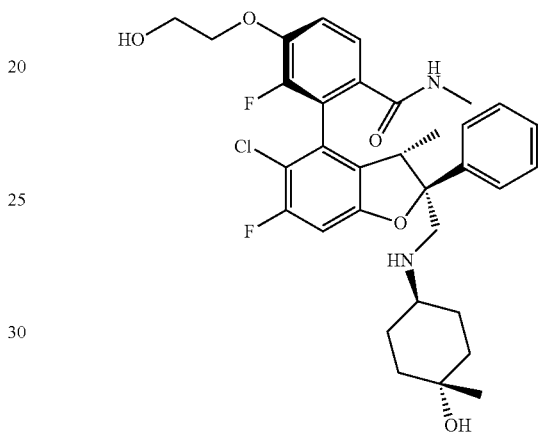

Reaction Scheme Example 121

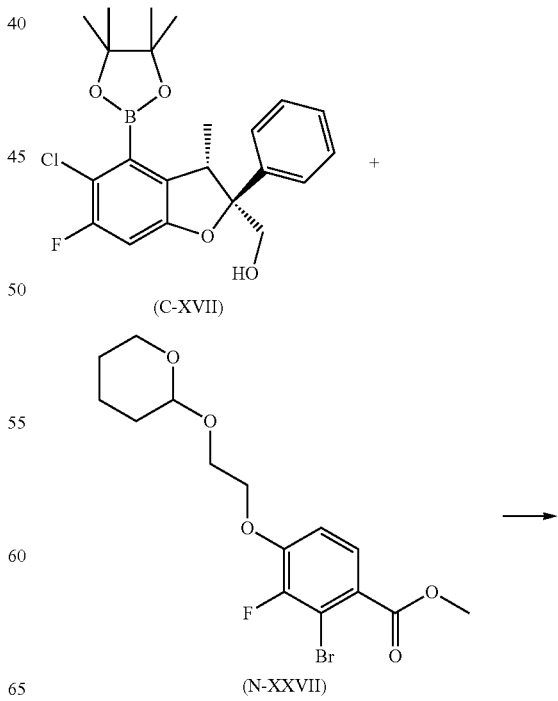

445
-continued

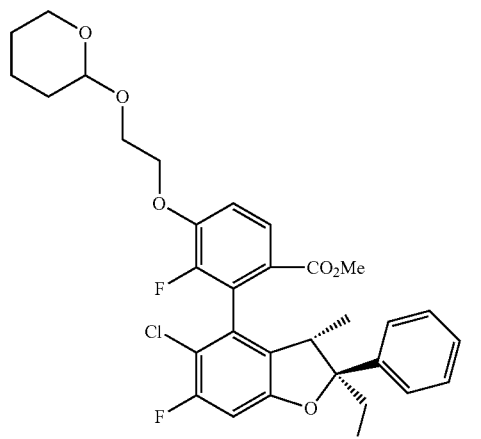

mixture of diastereoisomers

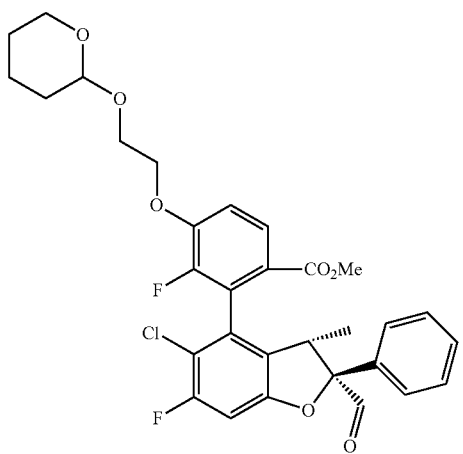

mixture of diastereoisomers

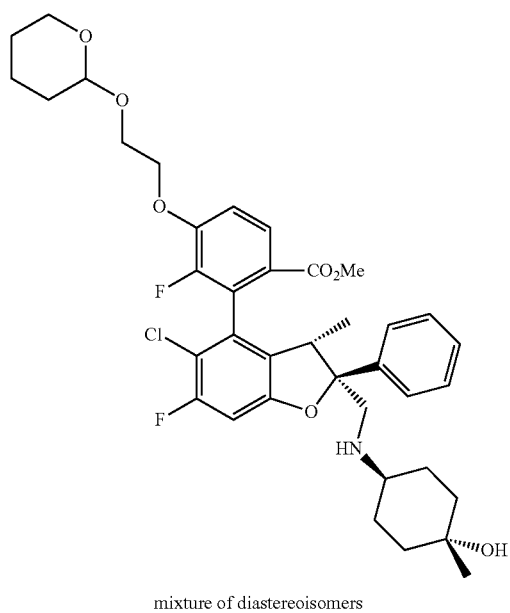

mixture of diastereoisomers

446
-continued

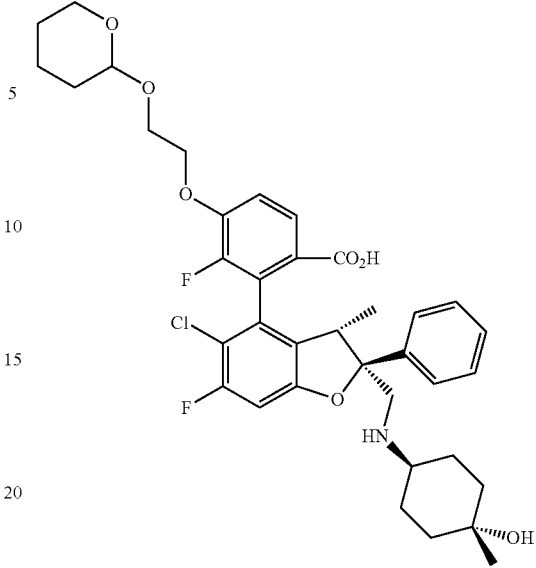

mixture of diastereoisomers

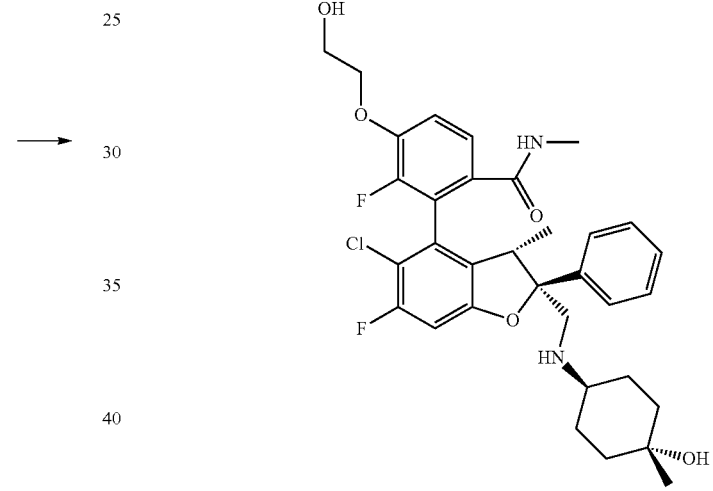

(Example 121)

Step 1: Methyl 2-((2S,3S,4S)-5-chloro-6-fluoro-2-(hydroxymethyl)-3-methyl-2-phenyl-2,3-dihydrobenzofuran-4-yl)-3-fluoro-4-(2-((tetrahydro-2H-pyran-2-yl)oxy)ethoxy)benzoate and methyl 2-((2S,3S,4R)-5-chloro-6-fluoro-2-(hydroxymethyl)-3-methyl-2-phenyl-2,3-dihydrobenzofuran-4-yl)-3-fluoro-4-(2-((tetrahydro-2H-pyran-2-yl)oxy)ethoxy)benzoate A suspension of ((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methanol (C-XVII) (1 g, 2.388 mmol), methyl 2-bromo-3-fluoro-4-(2-((tetrahydro-2H-pyran-2-yl)oxy)ethoxy)benzoate (N-XXVII) (1.081 g, 2.87 mmol), Pd$_2$(dba)$_3$ (0.109 g, 0.119 mmol), 4,6-bis(diphenylphosphino)-10H-phenoxazine (0.132 g, 0.239 mmol) and K$_3$PO$_4$ (1.521 g, 7.17 mmol) in toluene (15 mL) and water (3 mL) was stirred at 100° C. for 16 h under Ar. The reaction mixture was quenched by the addition of a sat solution of NaHCO$_3$, then extracted with EtOAc. The organic layers were combined and washed with a sat solution of NaHCO$_3$, dried over anhydous Na$_2$SO$_4$ and concentrated. The residue was purified by flash chromatography (silica, hexane/

EtOAc, gradient 0% to 100% EtOAc) to afford a mixture of the title compounds (206 mg). UPLC-MS 1: m/z 606.3 [M+17]$^+$, $t_R$=1.26 min.

Step 2: Methyl 2-((2S,3S,4S)-5-chloro-6-fluoro-2-formyl-3-methyl-2-phenyl-2,3-dihydrobenzofuran-4-yl)-3-fluoro-4-(2-((tetrahydro-2H-pyran-2-yl)oxy)ethoxy)benzoate and methyl 2-((2S,3S,4R)-5-chloro-6-fluoro-2-formyl-3-methyl-2-phenyl-2,3-dihydrobenzofuran-4-yl)-3-fluoro-4-(2-((tetrahydro-2H-pyran-2-yl)oxy)ethoxy)benzoate At −78° C. DMSO (0.054 mL, 0.77 mmol) was added to a solution of oxalyl chloride (0.034 mL, 0.383 mmol) in DCM (4 mL). After 30 min at −78° C., a solution of a mixture of methyl 2-((2S,3S,4S)-5-chloro-6-fluoro-2-(hydroxymethyl)-3-methyl-2-phenyl-2,3-dihydrobenzofuran-4-yl)-3-fluoro-4-(2-((tetrahydro-2H-pyran-2-yl)oxy)ethoxy)benzoate and methyl 2-((2S,3S,4R)-5-chloro-6-fluoro-2-(hydroxymethyl)-3-methyl-2-phenyl-2,3-dihydrobenzofuran-4-yl)-3-fluoro-4-(2-((tetrahydro-2H-pyran-2-yl)oxy)ethoxy)benzoate (205 g, 0.35 mmol) in DCM (2 mL) as well as TEA (0.24 mL, 1.740 mmol) were added and the reaction mixture was stirred at −78° C. for 1 h. The reaction mixture was quenched by the addition of brine, then extracted with DCM. The organic layers were combined and washed with brine, dried over anhydrous Na$_2$SO$_4$ and concentrated to give a mixture of the title compounds (200 mg) as a brownish powder. UPLC-MS 1: $t_R$=1.28 min.

Step 3: Methyl 2-((2S,3S,4S)-5-chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-((tetrahydro-2H-pyran-2-yl)oxy)ethoxy)benzoate and methyl 2-((2S,3S,4R)-5-chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-((tetrahydro-2H-pyran-2-yl)oxy)ethoxy)benzoate At RT acetic acid (0.020 mL, 0.344 mmol) was added to a stirred solution of a mixture of methyl 2-((2S,3S,4S)-5-chloro-6-fluoro-2-formyl-3-methyl-2-phenyl-2,3-dihydrobenzofuran-4-yl)-3-fluoro-4-(2-((tetrahydro-2H-pyran-2-yl)oxy)ethoxy)benzoate and methyl 2-((2S,3S,4R)-5-chloro-6-fluoro-2-formyl-3-methyl-2-phenyl-2,3-dihydrobenzofuran-4-yl)-3-fluoro-4-(2-((tetrahydro-2H-pyran-2-yl)oxy)ethoxy)benzoate (202 mg, 0.34 mmol) and trans-4-amino-1-methylcyclohexanol (0.89 g, 0.69 mmol) in DCE (3 mL) and the reaction mixture was stirred at 80° C. for 30 min. Sodium triacetoxyborohydride (219 mg, 1.032 mmol) was added and stirring at 80° C. was continued for 30 min. DCM and a sat solution of NaHCO$_3$ were added and the organic phase was separated. The aqueous phase was extracted with DCM and the combined organic extracts were washed with brine, dried over anhydrous Na$_2$SO$_4$ and concentrated. The crude product was purified by flash chromatography (silica, hexane/EtOAc, gradient 0% to 100% EtOAc) to afford a mixture of the title compounds (135 mg). UPLC-MS 1: m/z 700.4 [M+H]$^+$; $t_R$=1.03 min.

Step 4: 2-((2S,3S,4S)-5-Chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-((tetrahydro-2H-pyran-2-yl)oxy)ethoxy)benzoic acid and 2-((2S,3S,4R)-5-chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-((tetrahydro-2H-pyran-2-yl)oxy)ethoxy)benzoic acid At RT LiOH·H$_2$O (13.34 mg, 0.557 mmol) was added to a solution of a mixture of Methyl 2-((2S,3S,4S)-5-chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-((tetrahydro-2H-pyran-2-yl)oxy)ethoxy)benzoate and methyl 2-((2S,3S,4R)-5-chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-((tetrahydro-2H-pyran-2-yl)oxy)ethoxy)benzoate (130 mg, 0.186 mmol) in dioxane/water (1:1, 4 mL). The clear solution was stirred at RT for 48 h. The reaction mixture was quenched by the addition of 1 N HCl, then extracted with EtOAc. The organic layers were combined, dried over anhydrous Na$_2$SO$_4$ and concentrated to give a mixture of the title compounds (87 mg) in a ratio of 12:1 (during workup the THP group partially fell off). UPLC-MS 1: m/z 686.5 [M+H]$^+$, $t_R$=0.90 and 0.94 min.

Step 5: 2-((2S,3S,4S)-5-Chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-hydroxyethoxy)-N-methylbenzamide or (2P)-2-[(2S,3S)-5-Chloro-6-fluoro-2-({[(1r,4S)-4-hydroxy-4-methylcyclohexyl]amino}methyl)-3-methyl-2,3-dihydro-1-benzofuran-4-yl]-3-fluoro-4-(2-hydroxyethoxy)-N-methylbenzamide (Example 121)

HATU (72 mg, 0.190 mmol) was added to a stirred solution of a mixture of 2-((2S,3S,4S)-5-chloro-6-fluoro-2-(((trans-4-hydroxy-4-methylcyclohexyl)amino)methyl)-3-methyl-2-phenyl-2,3-dihydrobenzofuran-4-yl)-3-fluoro-4-(2-((tetrahydro-2H-pyran-2-yl)oxy)ethoxy)benzoic acid and 2-((2S,3S,4R)-5-chloro-6-fluoro-2-(((trans-4-hydroxy-4-methylcyclohexyl)amino)methyl)-3-methyl-2-phenyl-2,3-dihydrobenzofuran-4-yl)-3-fluoro-4-(2-((tetrahydro-2H-pyran-2-yl)oxy)ethoxy)benzoic acid (87 mg, 0.127 mmol), DIPEA (0.221 mL, 1.27 mmol) and methylamine hydrochloride (42.8 mg, 0.63 mmol) in DMF (4 mL). The reaction mixture was stirred at RT for 1 h. The reaction mixture was quenched by the addition of a sat solution of NaHCO$_3$, then extracted with EtOAc. The organic layers were combined and washed with a sat solution of NaHCO$_3$, dried over anhydous Na$_2$SO$_4$ and concentrated. Then, the residue was dissolved in dioxane (2 mL) and HCl (0.158 mL, 0.634 mmol, 4 M in dioxane) was added and the clear solution was stirred at RT for 1 h. The reaction mixture was quenched by the addition of a sat solution of NaHCO$_3$, then extracted with EtOAc. The organic layers were combined and washed with a sat solution of NaHCO$_3$, dried over anhydous Na$_2$SO$_4$ and concentrated. The residue was purified by flash chromatography (silica, DCM, MeOH, gradient 0% to 10% MeOH) and then by preparative HPLC (Waters Sunfire C18 OBD, 5 µm, 30*100 mm, Eluent A: H$_2$O+0.1% TFA, B:ACN, Gradient: 5% to 100% B in 20 min hold 1 min, Flow 40 mL/min) to afford the title compound (17 mg) as a colorless powder (the other diastereoisomer 2-((2S,3S,4R)-

5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-hydroxyethoxy)-N-methylbenzamide was not isolated). $^1$H NMR (400 MHz, DMSO-$d_6$) δ 8.21 (d, J=4.2 Hz, 1H), 7.48 (d, J=7.5 Hz, 1H), 7.45-7.37 (m, 2H), 7.36-7.23 (m, 4H), 7.07 (d, J=9.6 Hz, 1H), 4.93 (t, J=5.4 Hz, 1H), 4.17-4.06 (m, 2H), 4.04 (s, 1H), 3.72 (q, J=4.9 Hz, 2H), 3.28-3.22 (m, 1H), 3.10-3.06 (m, 2H), 2.62 (d, J=4.6 Hz, 3H), 2.32-2.26 (m, 1H), 1.70-1.50 (m, 2H), 1.42-1.27 (m, 2H), 1.27-1.12 (m, 2H), 1.10-1.00 (m, 2H), 0.98 (s, 3H), 0.94 (d, J=7.1 Hz, 3H). UPLC-MS 1: m/z 615.4 [M+H]$^+$, $t_R$=0.71 min.

Example 122: 2-((2S,3S,4S)-5-Chloro-6-fluoro-3-methyl-2-((methylamino)methyl)-2-phenyl-2,3-dihydrobenzofuran-4-yl)-3-fluoro-4-((S)-2-hydroxypropoxy)-N-methylbenzamide or (2P)-2-{(2S,3S)-5-Chloro-6-fluoro-3-methyl-2-[(methylamino)methyl]-2-phenyl-2,3-dihydro-1-benzofuran-4-yl}-3-fluoro-4-[(2S)-2-hydroxypropoxy]-N-methylbenzamide

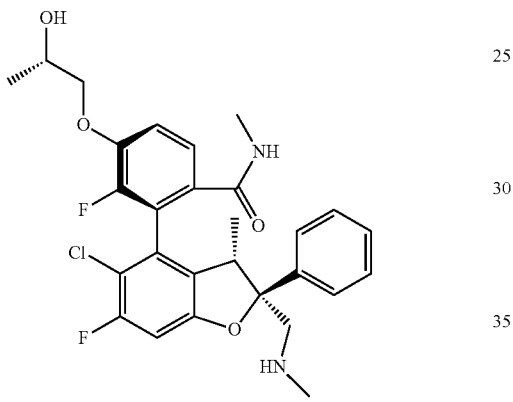

Reaction Scheme Example 122

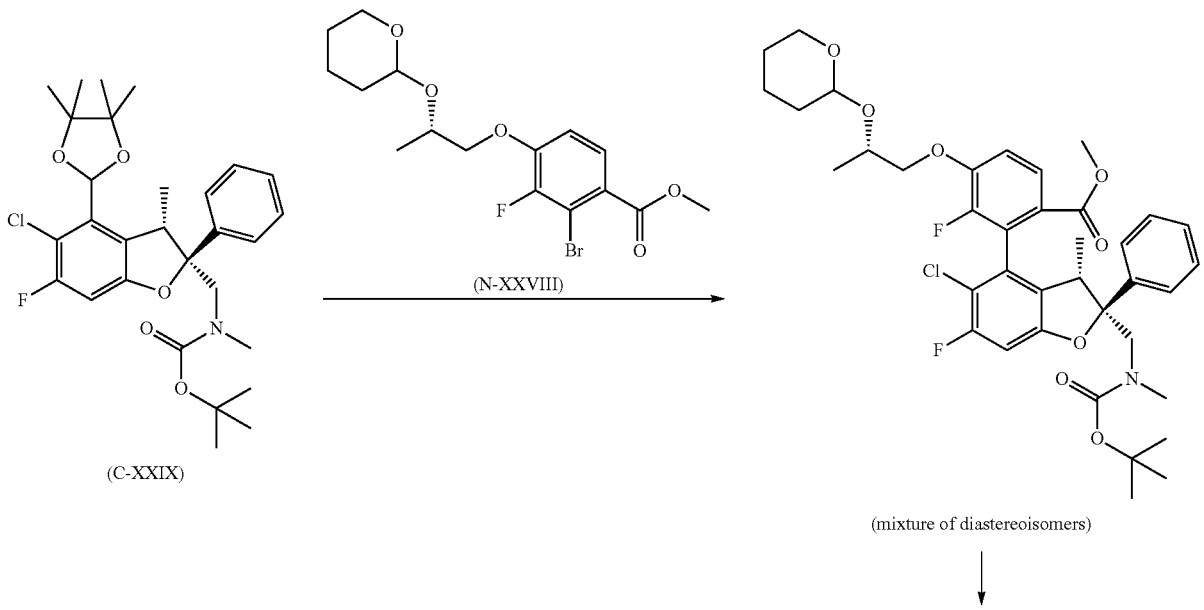

(mixture of diastereoisomers)

451 452

-continued

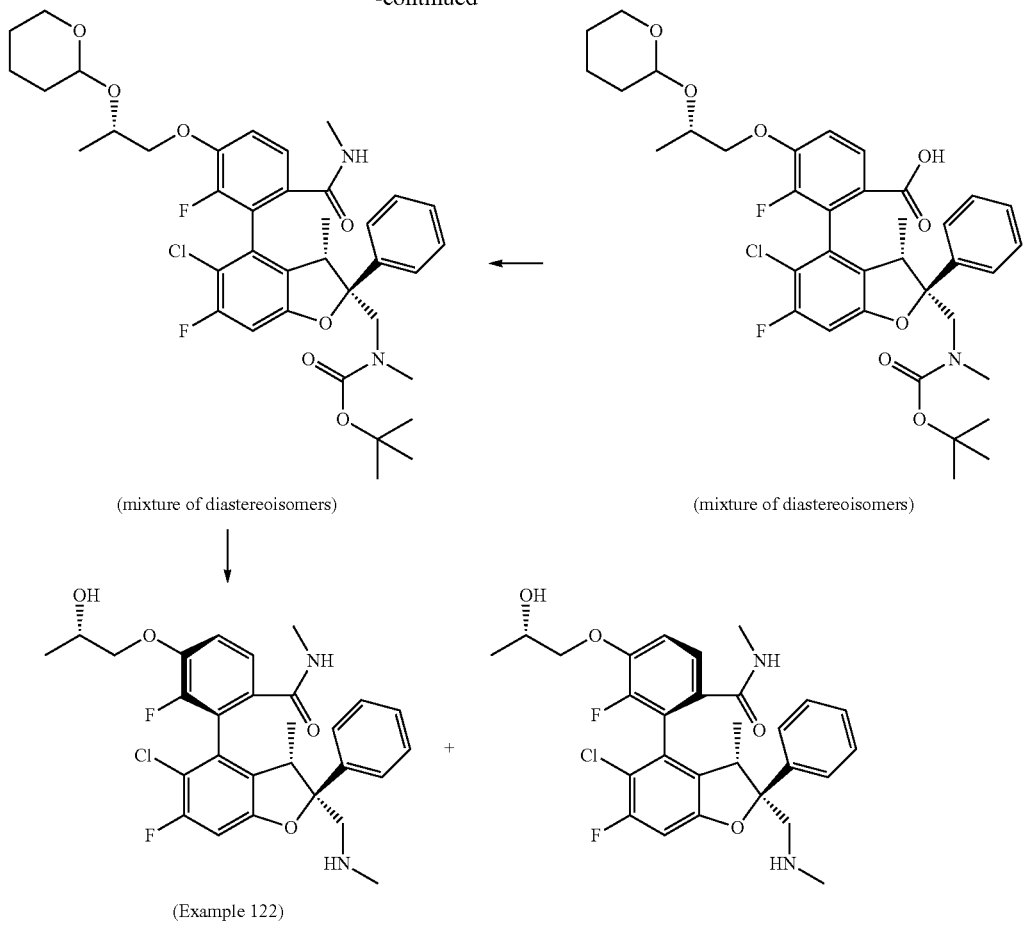

(mixture of diastereoisomers) (mixture of diastereoisomers)

(Example 122)

Step 1: Methyl 2-((2S,3S,4S)-2-(((tert-butoxycarbonyl)(methyl)amino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzoate and methyl 2-((2S,3S,4R)-2-(((tert-butoxycarbonyl)(methyl)amino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzoate A solution of tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)(methyl)carbamate (C-XXIX) (5.55 g, 10.4 mmol) in toluene (20 mL) was added to a stirred solution of methyl 2-bromo-3-fluoro-4-((2S)-2-((tetrahydro-2H-pyran-2-yl)oxy)propoxy)benzoate (N-XXVIII) (4.90 g, 12.5 mmol), N-XantPhos (0.576 g, 1.04 mmol), Pd$_2$dba$_3$ (0.478 g, 0.52 mmol) and K$_3$PO$_4$ (6.65 g, 31.3 mmol) in toluene (30 mL) and water (10 mL) at 100° C. and stirring at 100° C. was continued for 16 h. The reaction mixture was diluted in EtOAc and water, the organic phase was separated and the aqueous phase was extracted with EtOAc. The combined organic extracts were washed with brine, dried over anhydrous Na$_2$SO$_4$ and concentrated. The crude product was purified by flash chromatography (silica, EtOAc/heptane, gradient 0% to 100% EtOAc) to afford a mixture of the title compounds (1.7 g) as a yellow foam. UPLC-MS 1: m/z 616.6 [M+H−BOC]$^+$, t$_R$=1.59 min.

Step 2: 2-((2S,3S,4S)-2-(((tert-butoxycarbonyl)(methyl)amino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzoic acid and 2-((2S,3S,4R)-2-(((tert-butoxycarbonyl)(methyl)amino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzoic acid At RT sodium hydroxide (10.6 mL, 21.2 mmol, 2N in water) was added to a stirred solution of a mixture of methyl 2-((2S,3S,4S)-2-(((tert-butoxycarbonyl)(methyl)amino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzoate and methyl 2-((2S,3S,4R)-2-(((tert-butoxycarbonyl)(methyl)amino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzoate (1.7 g, 2.11 mmol) in THF (12 mL) and MeOH (12 mL). The reaction mixture was stirred at RT for 1 h, then at 45° C. for 16 h. THF and MeOH were evaporated. The resulting aqueous phase was acidified with 2N HCl to pH 3 and extracted with DCM. The combined organic extracts were dried over anhydrous Na$_2$SO$_4$ and concentrated to afford a mixture of the title products (1.67 g). UPLC-MS 1: m/z 602.6 [M+H−BOC]$^+$, t$_R$=1.44 min, 1.45 min, 1.46 min and 1.47 min.

Step 3: Tert-butyl (((2S,3S,4S)-5-chloro-6-fluoro-4-(2-fluoro-6-(methylcarbamoyl)-3-((2S)-2-((tetrahydro-2H-pyran-2-yl)oxy)propoxy)phenyl)-3-methyl-2-phenyl-2,3-dihydrobenzofuran-2-yl)methyl)(methyl)carbamate and tert-butyl (((2S,3S,4R)-5-chloro-6-fluoro-4-(2-fluoro-6-(methylcarbamoyl)-3-((2S)-2-((tetrahydro-2H-pyran-2-yl)oxy)propoxy)phenyl)-3-methyl-2-phenyl-2,3-dihydrobenzofuran-2-yl)methyl)(methyl)carbamate At RT DIPEA (1.592 mL, 9.11 mmol) was added to a stirred suspension of a mixture of 2-((2S,3S,4S)-2-(((tert-butoxycarbonyl)(methyl)amino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzoic acid and 2-((2S,3S,4R)-2-(((tert-butoxycarbonyl)(methyl)amino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzoic acid (1.6 g, 2.28 mmol), methylamine hydrochloride (0.769 g, 11.4 mmol) and TBTU (1.097 g, 3.42 mmol) in DMF (25 mL) and the reaction mixture was stirred at RT for 1.5 h. The reaction mixture was diluted in EtOAc and water, the organic phase was separated and aqueous phase was extracted with EtOAc. The combined organic extracts were washed with brine, dried over anhydrous $Na_2SO_4$ and concentrated. The crude product was purified by flash chromatography (silica, EtOAc/heptane, gradient 0% to 100% EtOAc) to afford a mixture of the title compounds (1.62 g) as a colorless foam. UPLC-MS 1: m/z 715.7 $[M+H]^+$, $t_R$=1.45 min, 1.46 min and 1.48 min.

Step 4: 2-((2S,3S,4S)-5-chloro-6-fluoro-3-methyl-2-((methylamino)methyl)-2-phenyl-2,3-dihydrobenzofuran-4-yl)-3-fluoro-4-((S)-2-hydroxypropoxy)-N-methylbenzamide or (2P)-2-{(2S,3S)-5-Chloro-6-fluoro-3-methyl-2-[(methylamino)methyl]-2-phenyl-2,3-dihydro-1-benzofuran-4-yl}-3-fluoro-4-[(2S)-2-hydroxypropoxy]-N-methylbenzamide (Example 122)

HCl (30 mL, 120 mmol, 4N in dioxane) was added to a mixture of tert-butyl (((2S,3S,4S)-5-chloro-6-fluoro-4-(2-fluoro-6-(methylcarbamoyl)-3-((2S)-2-((tetrahydro-2H-pyran-2-yl)oxy)propoxy)phenyl)-3-methyl-2-phenyl-2,3-dihydrobenzofuran-2-yl)methyl)(methyl)carbamate and tert-butyl (((2S,3S,4R)-5-chloro-6-fluoro-4-(2-fluoro-6-(methylcarbamoyl)-3-((2S)-2-((tetrahydro-2H-pyran-2-yl)oxy)propoxy)phenyl)-3-methyl-2-phenyl-2,3-dihydrobenzofuran-2-yl)methyl)(methyl)carbamate (1.62 g, 1.42 mmol) at 0° C. and the reaction mixture was stirred at RT for 30 min. The reaction mixture was diluted in DCM and added to a sat solution of $NaHCO_3$ The mixture was extracted with DCM and the combined organic extracts were washed with brine, dried over anhydrous $Na_2SO_4$ and concentrated. The crude product was purified by flash chromatography (silica, (7N ammonia in MeOH)/DCM, gradient 0% to 12% (7N ammonia in MeOH)) to afford a colorless foam which was further purified by preparative HPLC (Waters X-Bridge C18 OBD, 5 μm, 30*100 mm, eluent A: $H_2O$+7.3 mM $NH_4OH$, eluent B: ACN, gradient: 15% B for 4 min, then 15 to 45% B in 40 min hold 3 min, flow 40 mL/min). Lyophilisation of the product fractions afforded the separated diastereoisomers as colorless powders.

2-((2S,3S,4S)-5-Chloro-6-fluoro-3-methyl-2-((methylamino)methyl)-2-phenyl-2,3-dihydrobenzofuran-4-yl)-3-fluoro-4-((S)-2-hydroxypropoxy)-N-methylbenzamide or (2P)-2-{(2S,3S)-5-Chloro-6-fluoro-3-methyl-2-[(methylamino)methyl]-2-phenyl-2,3-dihydro-1-benzofuran-4-yl}-3-fluoro-4-[(2S)-2-hydroxypropoxy]-N-methylbenzamide (Example 122) (604 mg): $^1$H NMR (400 MHz, DMSO-$d_6$) δ 8.16 (d, J=4.9 Hz, 1H), 7.48 (d, J=8.6 Hz, 1H), 7.45-7.38 (m, 2H), 7.38-7.23 (m, 4H), 7.06 (d, J=9.5 Hz, 1H), 4.93 (d, J=4.1 Hz, 1H), 4.00-3.88 (m, 3H), 3.29-3.21 (m, 1H), 3.14-2.95 (m, 2H), 2.63 (d, J=4.5 Hz, 3H), 2.20 (s, 3H), 1.12 (d, J=5.4 Hz, 3H), 0.93 (d, J=7.2 Hz, 3H). UPLC-MS 1: m/z 531.4 $[M+H]^+$, $t_R$=0.72 min.

Other diastereoisomer 2-((2S,3S,4R)-5-chloro-6-fluoro-3-methyl-2-((methylamino)methyl)-2-phenyl-2,3-dihydrobenzofuran-4-yl)-3-fluoro-4-((S)-2-hydroxypropoxy)-N-methylbenzamide (60 mg): UPLC-MS 1: m/z 531.5 $[M+H]^+$, $t_R$=0.67 min.

Example 123: 2-((2S,3S,4S)-2-(Aminomethyl)-5-chloro-6-fluoro-3-methyl-2-phenyl-2,3-dihydrobenzofuran-4-yl)-3-fluoro-4-((S)-2-hydroxypropoxy)benzamide

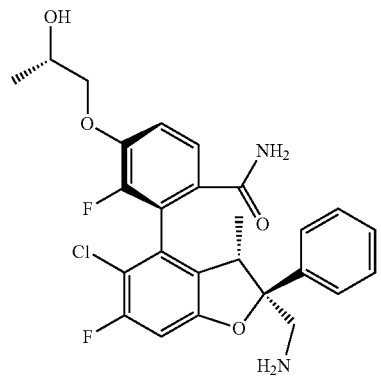

Reaction Scheme Example 123

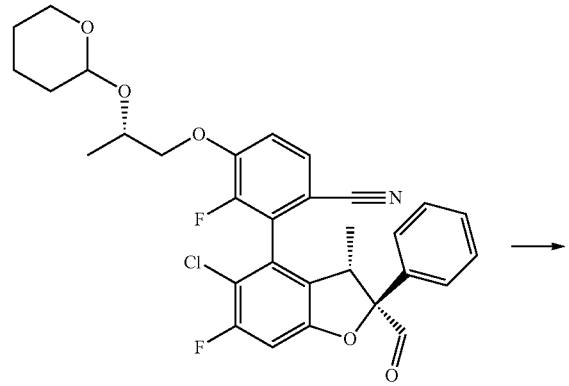

mixture of diastereoisomers

455
-continued

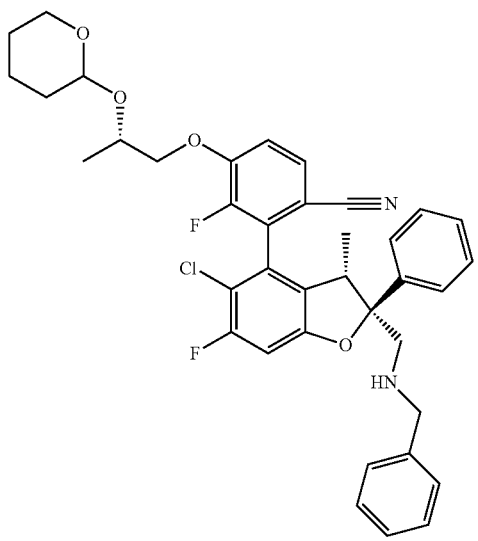

mixture of diastereoisomers

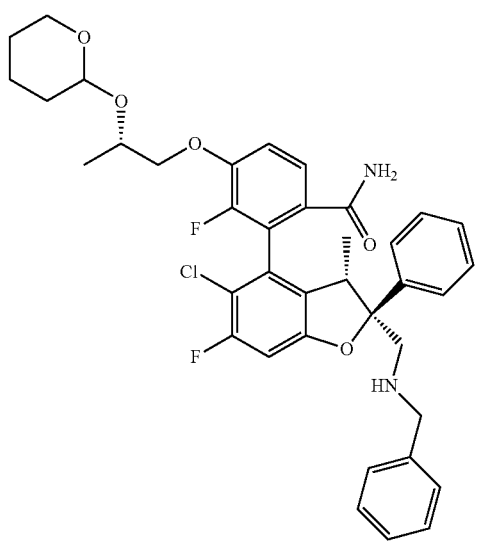

mixture of diastereoisomers

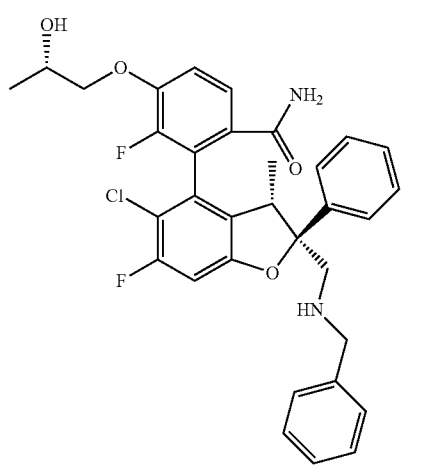

mixture of diastereoisomers

456
-continued

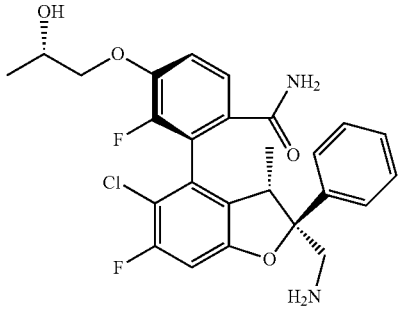

Example 123

+

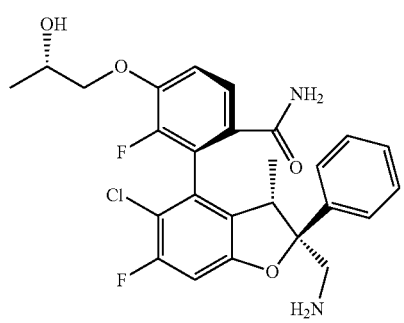

Step 1: 2-((2S,3S,4S)-2-((Benzylamino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-2-((Benzylamino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzonitrile To a stirred solution of a mixture of 2-((2S,3S,4S)-5-chloro-6-fluoro-2-formyl-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-5-chloro-6-fluoro-2-formyl-3-methyl-2-phenyl-2,3-dihydrobenzofuran-4-yl)-3-fluoro-4-((2S)-2-((tetrahydro-2H-pyran-2-yl)oxy)propoxy)benzonitrile (product of step 1 in alternative synthesis of Example 114a) (200 mg, 0.35 mmol) and benzylamine (113 mg, 1.06 mmol) in DCE (5 mL) was added acetic acid (0.030 mL, 0.53 mmol) and the reaction mixture was stirred at 80° C. for 30 min. After cooling to RT, sodium triacetoxyborohydride (149 mg, 0.70 mmol) was added and stirring at 80° C. was continued for 2 h. DCM was added followed by a sat solution of NaHCO$_3$. The organic phase was separated and the aqueous phase was extracted with DCM. The combined organic extracts were washed with brine, dried over anhydrous Na$_2$SO$_4$ and concentrated. The crude product was purified by flash chromatography (silica, heptane/EtOAc, gradient: 0% to 50% EtOAc) to afford a mixture of the title compounds (178 mg). UPLC MS 1: m/z 659.3 [M+H]$^+$; t$_R$=1.21 min and 1.23 min.

Step 2: 2-((2S,3S,4S)-2-((Benzylamino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzamide and 2-((2S,3S,4R)-2-((benzylamino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzamide To a stirred solution of a mixture of 2-((2S,3S,4S)-2-((benzylamino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzonitrile and 2-((2S,3S,4R)-2-((benzylamino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzonitrile (178 mg, 0.21 mmol) in EtOH (3 mL) and water (1 mL) was added hydrido(dimethylphosphinous acid-kP)[hydrogen bis(dimethylphosphinito-kP)]platinum(II) (17.62 mg, 0.041 mmol) and reactants were stirred at 80° C. for 1 h. EtOAc and water were added. The organic phase was separated and the aqueous phase was extracted with EtOAc. The combined organic extracts were washed with brine, dried over anhydrous $Na_2SO_4$ and concentrated. The crude product was purified by flash chromatography (silica, EtOAc/Hep, gradient: 0% to 100% EtOAc) to afford a mixture of the title compounds (130 mg). UPLC MS 1: m/z 677.3 $[M+H]^+$; $t_R$=1.00 min, 1.02 min, 1.03 min and 1.05 min (each diastereoisomer splits up into 2 peaks in UPLC due to racemic THP group).

Step 3: 2-((2S,3S,4S)-2-((Benzylamino)methyl)-5-chloro-6-fluoro-3-methyl-2-phenyl-2,3-dihydrobenzofuran-4-yl)-3-fluoro-4-((S)-2-hydroxypropoxy)benzamide and 2-((2S,3S,4R)-2-((benzylamino)methyl)-5-chloro-6-fluoro-3-methyl-2-phenyl-2,3-dihydrobenzofuran-4-yl)-3-fluoro-4-((S)-2-hydroxypropoxy)benzamide At 0° C. HCl (4 mL, 16.0 mmol, 4 M in dioxane) was added to a mixture of 2-((2S,3S,4S)-2-((benzylamino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzamide and 2-((2S,3S,4R)-2-((benzylamino)methyl)-5-chloro-6-fluoro-3-methyl-2-phenyl-2,3-dihydrobenzofuran-4-yl)-3-fluoro-4-((2S)-2-((tetrahydro-2H-pyran-2-yl)oxy)propoxy)benzamide (130 mg, 0.15 mmol) and stirring at 0° C. was continued for 15 min. DCM was added followed by a sat solution of $NaHCO_3$. The organic phase was separated and the aqueous phase was extracted with DCM. The combined organic extracts were washed with brine, dried over anhydrous $Na_2SO_4$ and concentrated. The crude product was purified by flash chromatography (silica, DCM/(7N ammonia in MeOH), gradient: 0% to 8% (7N ammonia in MeOH)) to afford a mixture of the title compounds (90 mg). UPLC MS 1: m/z 593.2 $[M+H]^+$; $t_R$=0.76 min and 0.80 min.

Step 4: 2-((2S,3S,4S)-2-(Aminomethyl)-5-chloro-6-fluoro-3-methyl-2-phenyl-2,3-dihydrobenzofuran-4-yl)-3-fluoro-4-((S)-2-hydroxypropoxy)benzamide (Example 123)

At RT Pd/C (10 mg, 0.094 mmol, 10 wt-%) was added to a stirred solution of a mixture of 2-((2S,3S,4S)-2-((benzylamino)methyl)-5-chloro-6-fluoro-3-methyl-2-phenyl-2,3-dihydrobenzofuran-4-yl)-3-fluoro-4-((S)-2-hydroxypropoxy)benzamide and 2-((2S,3S,4R)-2-((benzylamino)methyl)-5-chloro-6-fluoro-3-methyl-2-phenyl-2,3-dihydrobenzofuran-4-yl)-3-fluoro-4-((S)-2-hydroxypropoxy)benzamide (90 mg, 0.14 mmol) in MeOH (5 mL) and the reaction mixture was stirred under a $H_2$ atmosphere for 2.5 h at RT. The reaction mixture was filtered through Celite and concentrated. The crude product was purified by flash chromatography (silica, DCM/(7N ammonia in MeOH), gradient: 0% to 12% (7N ammonia in MeOH)) followed by preparative HPLC (Waters X-Bridge C18 OBD, 5 μm, 30*100 mm, Eluent A: $H_2O$+7.3 mM $NH_4OH$, B:ACN, Gradient: 10% to 50% B in 20 min hold 1 min, Flow 40 mL/min). Acetonitrile from product fractions was evaporated and the resulting aqueous phase was extracted with DCM; the combined organic extracts were washed with brine, dried over anhydrous $Na_2SO_4$ and concentrated to afford the separated diastereoisomers.

2-((2S,3S,4S)-2-(Aminomethyl)-5-chloro-6-fluoro-3-methyl-2-phenyl-2,3-dihydrobenzofuran-4-yl)-3-fluoro-4-((S)-2-hydroxypropoxy)benzamide (Example 123) (10 mg). $^1$H NMR (600 MHz, DMSO-d6) δ 7.69 (s, 1H), 7.55 (d, J=8.5 Hz, 1H), 7.46-7.40 (m, 2H), 7.39-7.32 (m, 2H), 7.32-7.22 (m, 2H), 7.10 (s, 1H), 7.05 (d, J=9.6 Hz, 1H), 4.95 (d, J=4.2 Hz, 1H), 4.04-3.82 (m, 3H), 3.28 (q, J=7.3 Hz, 1H), 3.15-3.02 (m, 2H), 1.38-1.01 (m, 5H), 0.91 (d, J=7.2 Hz, 3H). UPLC MS 1: m/z 503.1 $[M+H]^+$; $t_R$=0.68 min.

Other diastereoisomer 2-((2S,3S,4R)-2-(aminomethyl)-5-chloro-6-fluoro-3-methyl-2-phenyl-2,3-dihydrobenzofuran-4-yl)-3-fluoro-4-((S)-2-hydroxypropoxy)benzamide: UPLC MS 1: m/z 503.1 $[M+H]^+$; $t_R$=0.59 min.

Example 124: 2-(2-((2S,3S,4S)-2-(Aminomethyl)-5-chloro-6-fluoro-3-methyl-2-phenyl-2,3-dihydrobenzofuran-4-yl)-3,4-difluorophenoxy)ethan-1-ol

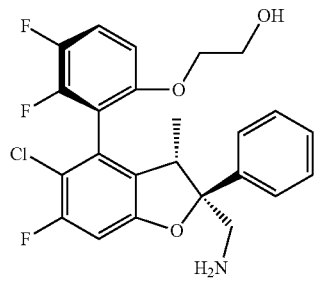

Step 1: Tert-butyl (((2S,3S,4S)-5-chloro-4-(2,3-difluoro-6-(2-hydroxyethoxy)phenyl)-6-fluoro-3-methyl-2-phenyl-2,3-dihydrobenzofuran-2-yl)methyl)carbamate and tert-butyl (((2S,3S,4R)-5-chloro-4-(2,3-difluoro-6-(2-hydroxyethoxy)phenyl)-6-fluoro-3-methyl-2-phenyl-2,3-dihydrobenzofuran-2-yl)methyl)carbamate A mixture of tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)carbamate (C-XVI) (300 mg, 0.58 mmol), 2-(2-bromo-3,4-difluorophenoxy)ethanol (N-II) (161 mg, 0.64 mmol), Pd(dbpf)Cl$_2$ (76 mg, 0.12 mmol) and $K_3PO_4$ (369 mg, 1.74 mmol) in dioxane (4.3 mL) and $H_2O$ (1.4 mL) was stirred under Ar at 100° C. for 30 min. After cooling to RT the reaction mixture was diluted with EtOAc and water, the organic phase was separated and the aqeuous phase was extracted with EtOAc. The combined organic extracts were washed with a sat solution of NaHCO$_3$, dried (phase separator cartridge) and concentrated. The residue was purified by flash chromatography (silica, cyclohexane/EtOAc, gradient: 0% to 70% EtOAc) to afford a mixture of the title compounds (112 mg).

Step 2: 2-(2-((2S,3S,4S)-2-(Aminomethyl)-5-chloro-6-fluoro-3-methyl-2-phenyl-2,3-dihydrobenzofuran-4-yl)-3,4-difluorophenoxy)ethan-1-ol The title compound (6.5 mg) was obtained using similar reaction conditions as described for Example 22, step. 5 and the diastereoisomers were separated by preparative HPLC (Waters X-Bridge C18 OBD, 5 µm, 30*100 mm, Eluent A: H$_2$O+7.3 mM NH$_4$OH, B: ACN, Gradient: 10% for 4 min, then 10 to 60% B in 20 min hold 3 min, Flow 40 mL/min).

2-(2-((2S,3S,4S)-2-(Aminomethyl)-5-chloro-6-fluoro-3-methyl-2-phenyl-2,3-dihydrobenzofuran-4-yl)-3,4-difluorophenoxy)ethan-1-ol (Example 124) (112 mg): $^1$H NMR (400 MHz, DMSO-d6) δ 7.50-7.30 (m, 6H), 7.21 (d, J=9.4 Hz, 1H), 7.03 (td, J=8.6, 3.6 Hz, 1H), 4.69-4.63 (m, 1H), 4.10-4.00 (m, 2H), 3.53-3.45 (m, 3H), 2 protons hidden under H$_2$O peak, 0.98 (d, J=7.2 Hz, 3H). UPLC MS 1: m/z 464.3 [M+H]$^+$; t$_R$=0.89 min.

Other diastereoisomer 2-(2-((2S,3S,4R)-2-(aminomethyl)-5-chloro-6-fluoro-3-methyl-2-phenyl-2,3-dihydrobenzofuran-4-yl)-3,4-difluorophenoxy)ethan-1-ol: UPLC MS 1: m/z 464.3 [M+H]$^+$; t$_R$=0.80 min.

Example 125: 2-((2R,3S,4S)-5-Chloro-6-fluoro-2-(6-hydroxypyridin-2-yl)-3-methyl-2-((methylamino)methyl)-2,3-dihydrobenzofuran-4-yl)-3-fluoro-4-methoxybenzamide

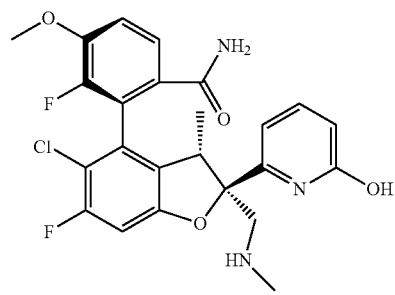

The title compound was prepared analogously to Example 114a alternative synthesis from intermediates ((2S,3S)-2-(6-(benzyloxy)pyridin-2-yl)-5-chloro-6-fluoro-3-methyl-4-(4,4,5,5-tetramethyl-1,3,2-dioxaborolan-2-yl)-2,3-dihydrobenzofuran-2-yl)methanol (C-XIX) and 2-bromo-3-fluoro-4-methoxybenzonitrile (N-IV). The reductive amination of the intermediate aldehyde with methylamine hydrochloride was performed as described for Example 122 and the methylamine was kept unprotected. The benzyl protecting group was cleaved in the last step. $^1$H NMR (600 MHz, DMSO-d$_6$) δ (ppm) 7.72 (s br, 1H), 7.60 (d, J=8.8 Hz, 1H), 7.36 (s br, 1H), 7.29 (t, J=8.5 Hz, 1H), 7.11 (s, 1H), 7.08 (d, J=9.4 Hz, 1H), 6.35-6.00 (br, 2H), 3.90 (s, 3H), 3.30-3.15 (m, 2H), 2.99 (d, J=12.8 Hz, 1H), 2.22 (s, 3H), 0.87 (d, J=6.7 Hz, 3H). UPLC-MS 1: m/z 490.1 [M+H]$^+$, t$_R$=0.63 min.

The diastereoisomers were separated prior to benzyl deprotection: 2-((2R,3S,4S)-2-(6-(benzyloxy)pyridin-2-yl)-5-chloro-6-fluoro-3-methyl-2-((methylamino)methyl)-2,3-dihydrobenzofuran-4-yl)-3-fluoro-4-methoxybenzamide: UPLC-MS 1: m/z 580.4 [M+H]$^+$, t$_R$=0.94 min; 2-((2R,3S,4R)-2-(6-(benzyloxy)pyridin-2-yl)-5-chloro-6-fluoro-3-methyl-2-((methylamino)methyl)-2,3-dihydrobenzofuran-4-yl)-3-fluoro-4-methoxybenzamide: UPLC-MS 1: m/z 580.2 [M+H]$^+$, t$_R$=0.83 min.

Example 126: 2-((2R,3S,4S)-5-Chloro-6-fluoro-2-(((((trans)-4-hydroxy-4-methylcyclohexyl)amino)methyl)-3-methyl-2-(pyridin-2-yl)-2,3-dihydrobenzofuran-4-yl)-3-fluoro-4-(2-methoxyethoxy)benzamide

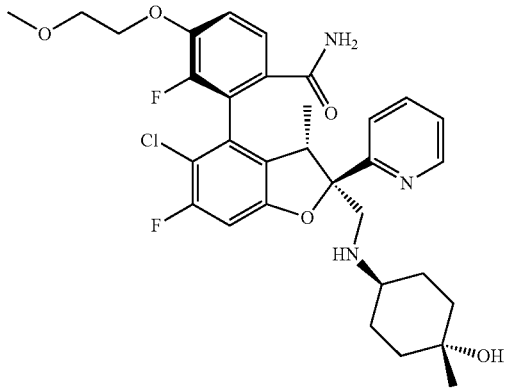

The title compound was prepared analogously to Example 5a, from (trans)-4-(((((2R,3S)-5-chloro-6-fluoro-3-methyl-2-(pyridin-2-yl)-4-(4,4,5,5-tetramethyl-1,3,2-dioxaborolan-2-yl)-2,3-dihydrobenzofuran-2-yl)methyl)amino)-1-methylcyclohexan-1-ol (C-XX) and 2-bromo-3-fluoro-4-(2-methoxyethoxy)benzonitrile (N-IX) by Suzuki coupling followed by nitrile hydrolysis to the corresponding amide and separation of the diastereoisomers.

2-((2R,3S,4S)-5-Chloro-6-fluoro-2-(((((trans)-4-hydroxy-4-methylcyclohexyl)amino)methyl)-3-methyl-2-(pyridin-2-yl)-2,3-dihydrobenzofuran-4-yl)-3-fluoro-4-(2-methoxyethoxy)benzamide (Example 126): $^1$H NMR (400 MHz, DMSO-d$_6$) δ (ppm) 8.55-8.53 (m, 1H), 7.75 (td, J=7.7, 1.8 Hz, 1H), 7.67 (s, 1H), 7.58-7.56 (m, 1H), 7.50-7.48 (m, 1H), 7.37-7.23 (m, 2H), 7.19-6.99 (m, 2H), 4.31-4.16 (m, 2H), 4.00 (s, 1H), 3.68-3.66 (m, 2H), 3.53 (q, J=7.0 Hz, 1H), 3.29 (s, 3H), 3.13-3.11 (m, 2H), 2.30-2.23 (m, 1H), 1.69-0.82 (m, 15H). UPLC-MS 1: m/z 616.3 [M+H]$^+$, t$_R$=0.72 min.

Other diastereoisomer 2-((2R,3S,4R)-5-Chloro-6-fluoro-2-(((((trans)-4-hydroxy-4-methylcyclohexyl)amino)methyl)-3-methyl-2-(pyridin-2-yl)-2,3-dihydrobenzofuran-4-yl)-3-fluoro-4-(2-methoxyethoxy)benzamide: UPLC-MS 1: m/z 616.3 [M+H]$^+$, t$_R$=0.68 min.

Example 127: 2-((2S,3S,4S)-5-Chloro-6-fluoro-2-((((trans)-4-hydroxy-4-methylcyclohexyl)amino)methyl)-3-methyl-2-(pyridin-3-yl)-2,3-dihydrobenzofuran-4-yl)-3-fluoro-4-methoxybenzamide

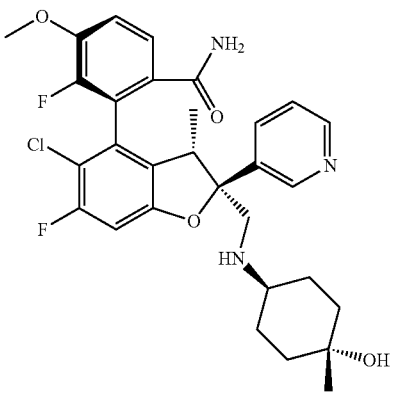

The title compound was prepared analogously to Example 5a from (trans)-4-((((2S,3S)-5-chloro-6-fluoro-3-methyl-2-(pyridin-3-yl)-4-(4,4,5,5-tetramethyl-1,3,2-dioxaborolan-2-yl)-2,3-dihydrobenzofuran-2-yl)methyl)amino)-1-methyl-cyclohexan-1-ol (C-XXI) and 2-bromo-3-fluoro-4-methoxybenzonitrile (N-IV) by Suzuki coupling followed by nitrile hydrolysis to the corresponding amide and separation of the diastereoisomers.

2-((2S,3S,4S)-5-Chloro-6-fluoro-2-((((trans)-4-hydroxy-4-methylcyclohexyl)amino)methyl)-3-methyl-2-(pyridin-3-yl)-2,3-dihydrobenzofuran-4-yl)-3-fluoro-4-methoxybenzamide (Example 127): $^1$H NMR (600 MHz, DMSO-$d_6$) δ (ppm) 8.62 (d, J=1.8 Hz, 1H), 8.45 (dd, J=4.7, 1.3 Hz, 1H), 7.82-7.79 (m, 1H), 7.72 (s br, 1H), 7.60 (d, J=8.7 Hz, 1H), 7.34 (dd, J=7.8, 4.9 Hz, 1H), 7.28 (t, J=8.5 Hz, 1H), 7.11 (d, J=9.5 Hz, 1H), 7.10 (s br, 1H), 4.04 (s, 1H), 3.88 (s, 3H), 3.23 (q, J=7.0 Hz, 1H), 3.15-3.08 (m, 2H), 2.31-2.25 (m, 1H), 1.64-1.59 (m, 1H), 1.59-1.54 (m, 1H), 1.36-1.31 (m, 1H), 1.28-1.22 (m, 1H), 1.20-1.11 (m, 2H), 1.09-0.97 (m, 2H), 0.96 (s, 3H), 0.94 (d, J=7.1 Hz, 3H). UPLC-MS 1: m/z 572.2 [M+H]$^+$, $t_R$=0.68 min.

Other diastereoisomer 2-((2S,3S,4R)-5-chloro-6-fluoro-2-((((trans)-4-hydroxy-4-methylcyclohexyl)amino)methyl)-3-methyl-2-(pyridin-3-yl)-2,3-dihydrobenzofuran-4-yl)-3-fluoro-4-methoxybenzamide: UPLC-MS 1: m/z 572.2 [M+H]$^+$, $t_R$=0.67 min.

Example 128: 2-((2S,4R)-2-(Aminomethyl)-2-phenyl-5-(trifluoromethyl)-2,3-dihydrobenzofuran-4-yl)-4-methoxybenzamide

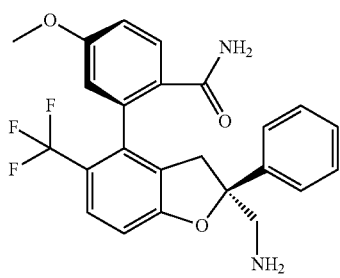

The title compound was prepared analogously to Example 5a starting from tert-butyl (S)-((2-phenyl-4-(4,4,5,5-tetramethyl-1,3,2-dioxaborolan-2-yl)-5-(trifluoromethyl)-2,3-dihydrobenzofuran-2-yl)methyl)carbamate (C-XXII) and 2-bromo-4-methoxybenzonitrile. 2-((2S,4R)-2-(Aminomethyl)-2-phenyl-5-(trifluoromethyl)-2,3-dihydrobenzofuran-4-yl)-4-methoxybenzamide (Example 128): $^1$H NMR (400 MHz, DMSO-$d_6$) δ (ppm) 7.64 (d, J=8.6 Hz, 1H), 7.48 (d, J=8.2 Hz, 1H), 7.43 (s br, 1H), 7.39-7.29 (m, 4H), 7.27-7.22 (m, 1H), 7.02-6.95 (m, 3H), 6.58 (d, J=2.7 Hz, 1H), 3.71 (s, 3H), 3.31 (d, J=16.4 Hz, 1H), 2.91-2.79 (m, 3H), 1.36 (s br, 2H). UPLC-MS 1: m/z 443.2 [M+H]$^+$, $t_R$=0.89 min.

Other diastereoisomer 2-((2S,4S)-2-(aminomethyl)-2-phenyl-5-(trifluoromethyl)-2,3-dihydrobenzofuran-4-yl)-4-methoxybenzamide: UPLC-MS 1: m/z 443.2 [M+H]$^+$, $t_R$=0.69.

Example 129: 2-((2S,4R)-5-Cyano-2-((((trans)-4-hydroxy-4-methylcyclohexyl)amino)methyl)-2-phenyl-2,3-dihydrobenzofuran-4-yl)-3-fluoro-4-methoxy-N-methylbenzamide

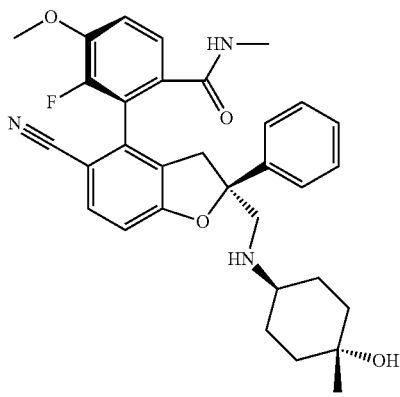

The title compound was prepared analogously to Example 121 from (S)-2-(hydroxymethyl)-2-phenyl-4-(4,4,5,5-tetramethyl-1,3,2-dioxaborolan-2-yl)-2,3-dihydrobenzofuran-5-carbonitrile (C-XXIII) and methyl 2-bromo-3-fluoro-4-methoxybenzoate (N-XXVI). UPLC-MS 1: m/z 544.4 [M+H]$^+$, $t_R$=0.77 min. According to UPLC-MS the other diastereoisomer was not formed.

Example 130: (S)-2-((((trans)-4-Hydroxycyclohexyl)amino)methyl)-2,4-diphenyl-2,3-dihydrobenzofuran-5-carbonitrile

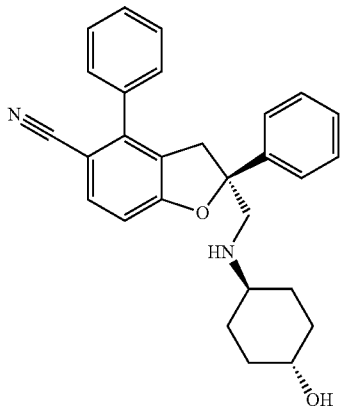 [SMILES: N#Cc1ccc2c(c1-c1ccccc1)C[C@@](CN[C@H]1CC[C@H](O)CC1)(c1ccccc1)O2]

PdCl$_2$(dppf)·CH$_2$Cl$_2$ adduct (22.9 mg, 0.028 mmol) was added to a stirred solution of (S)-4-bromo-2-((((trans)-4-hydroxycyclohexyl)amino)methyl)-2-phenyl-2,3-dihydrobenzofuran-5-carbonitrile (C-XXIV) (120 mg, 0.281 mmol), phenylboronic acid (51.4 mg, 0.421 mmol) and K$_3$PO$_4$ (238 mg, 1.123 mmol) in dioxane (4 mL) and H$_2$O (1.3 mL). The reaction mixture was stirred at 100° C. for 1 h. The reaction mixture was quenched by the addition of a sat solution of NaHCO$_3$ and extracted with EtOAc. The combined organic layers were washed with a sat solution of NaHCO$_3$, dried over anhydrous Na$_2$SO$_4$ and concentrated. The crude product was purified by flash chromatography (silica, hexane/EtOAc; gradient 0% to 100% EtOAc) to give the title compound (103 mg) as a colorless foam. $^1$H NMR (400 MHz, DMSO-d$_6$) δ 7.75 (d, J=8.3 Hz, 1H), 7.57-7.39 (m, 7H), 7.38-7.23 (m, 3H), 7.09 (d, J=8.3 Hz, 1H), 4.40 (d, J=4.4 Hz, 1H), 3.73 (d, J=16.1 Hz, 1H), 3.17-2.87 (m, 3H), 2.65-2.43 (m, 1H), 2.29-2.14 (m, 1H), 1.83-1.58 (m, 4H), 1.12-0.84 (m, 4H). UPLC-MS 1: m/z 425.3 [M+H]$^+$, t$_R$=0.79 min.

Example 131: 2-((2S,4S)-2-(Aminomethyl)-5-chloro-2-phenyl-2,3-dihydrofuro[2,3-b]pyridin-4-yl)-3-fluorobenzamide

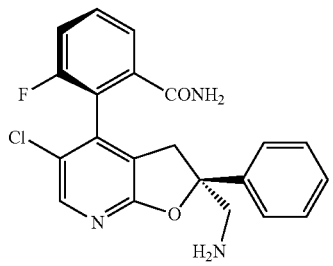

The title compound was prepared analogously to Example 5a from intermediates tert-butyl (S)-((4-bromo-5-chloro-2-phenyl-2,3-dihydrofuro[2,3-b]pyridin-2-yl)methyl)carbamate (C-XXV) and 3-fluoro-2-(4,4,5,5-tetramethyl-1,3,2-dioxaborolan-2-yl)benzonitrile (N-IV). In the Suzuki coupling SPhos-Pd-G2 was used. The racemic diastereoisomers were separated after the hydrolysis of the nitrile to the amide by SFC (Reprospher PEI 250×30 mm, 5 μm, CO$_2$/MeOH 15% to 25% in 10 min, flow rate: 30 mL/min): tert-butyl (((2S,4S)-4-(2-carbamoyl-6-fluorophenyl)-5-chloro-2-phenyl-2,3-dihydrofuro[2,3-b]pyridin-2-yl)methyl)carbamate: UPLC-MS 1 m/z 498.4 [M+H]$^+$, t$_R$=1.09 min and tert-butyl (((2S,4R)-4-(2-carbamoyl-6-fluorophenyl)-5-chloro-2-phenyl-2,3-dihydrofuro[2,3-b]pyridin-2-yl)methyl)carbamate: UPLC-MS 1 m/z 498.4 [M+H]$^+$, t$_R$=1.03 min.

Tert-butyl (((2S,4S)-4-(2-carbamoyl-6-fluorophenyl)-5-chloro-2-phenyl-2,3-dihydrofuro[2,3-b]pyridin-2-yl)methyl)carbamate was Boc-deprotected to afford the title compound. 2-((2S,4S)-2-(Aminomethyl)-5-chloro-2-phenyl-2,3-dihydrofuro[2,3-b]pyridin-4-yl)-3-fluorobenzamide (Example 131): $^1$H NMR (600 MHz, DMSO-d$_6$) δ ppm 8.07 (s, 1H), 7.97 (s, 1H), 7.67-7.26 (m, 9H), 3.58 (d, J=16.8 Hz, 1H), 2.98 (d, J=16.8 Hz, 1H), 2.93 (s, 2H). UPLC-MS 1 m/z 398.3 [M+H]$^+$, t$_R$=0.68 min.

Example 132: 2-(2-(Aminomethyl)-6-chloro-2-phenyl-2,3-dihydrobenzofuran-7-yl)-3-fluoro-4-methoxybenzamide

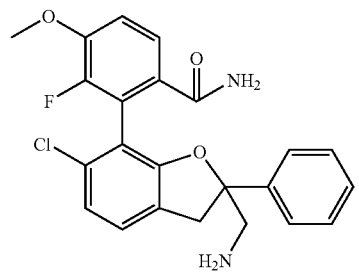 [SMILES: COc1ccc(C(N)=O)c(-c2c(Cl)ccc3c2OC(CN)(c2ccccc2)C3)c1F]

The title compound was prepared analogously to Example 5a from intermediates tert-butyl ((6-chloro-2-phenyl-7-(4,4,5,5-tetramethyl-1,3,2-dioxaborolan-2-yl)-2,3-dihydrobenzofuran-2-yl)methyl)carbamate (C-XXVI) and 2-bromo-3-fluoro-4-methoxybenzonitrile (N-IV).

After final Boc-deprotection the racemic diastereoisomers were first separated by preparative HPLC (SunFire RP18 30×100 mm, solvent: ACN/water): racemic diastereoisomer 1: UPLC-MS 1: t$_R$=0.81 min, racemic diastereoisomer 2: UPLC-MS 1: t$_R$=0.63 min. The racemic diastereoisomer 1 was subjected to chiral HPLC (Chiralpak AS-H 250×20 mm 5 μm, heptane/EtOH 6:4+0.1% DEA, flow rate: 10 mL/min) to afford both enantiomers in an enantiomeric excess of >97%. 2-(2-(Aminomethyl)-6-chloro-2-phenyl-2,3-dihydrobenzofuran-7-yl)-3-fluoro-4-methoxybenzamide with unknown absolute configuration (Example 132): Chiral HPLC (Chiralpak AS-H 250×4.6 mm 5 μm, heptane/EtOH 6:4+0.1% DEA, flow rate: 1 mL/min) t$_R$=8.11 min. $^1$H NMR (400 MHz, DMSO-d$_6$) δ 7.63 (s br, 1H), 7.47 (dd, J=8.6, 1.5 Hz, 1H), 7.36-7.17 (m, 7H), 7.17-7.07 (m, 2H), 6.92 (d, J=7.8 Hz, 1H), 3.93 (s, 3H), 3.79 (d, J=16.0 Hz, 1H), 3.19 (d, J=16.0 Hz, 1H), 2.96-2.78 (m, 2H). UPLC-MS 1: m/z 434.2 [M+H]$^+$, t$_R$=0.68 min.

Other enantiomer 2-(2-(aminomethyl)-6-chloro-2-phenyl-2,3-dihydrobenzofuran-7-yl)-3-fluoro-4-methoxybenzamide with unknown absolute configuration: Chiral HPLC (Chiralpak AS-H 250×4.6 mm 5 μm, heptane/EtOH 6:4+ 0.1% DEA, flow rate: 1 mL/min) t$_R$=14.17 min.

Example 133: 2-(2-(Aminomethyl)-5-chloro-2-phenylbenzo[d][1,3]dioxol-4-yl)-3-fluorobenzamide

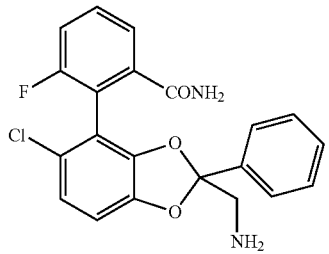 [SMILES: NCC1(c2ccccc2)Oc2ccc(Cl)c(-c3c(F)cccc3C(N)=O)c2O1]

The title compound was prepared analogously to Example 5a from intermediates tert-butyl ((4-bromo-5-chloro-2-phenylbenzo[d][1,3]dioxol-2-yl)methyl)carbamate (C-XXVII) and 3-fluoro-2-(4,4,5,5-tetramethyl-1,3,2-dioxaborolan-2-yl)benzonitrile. In the Suzuki coupling SPhos-Pd-G2 was used. The racemic diastereoisomers tert-butyl ((5-chloro-4-(2-cyano-6-fluorophenyl)-2-phenylbenzo[d][1,3]dioxol-2-yl)methyl)carbamate were separated after the Suzuki coupling by flash chromatography (silica, heptane/EtOAc; gradient 0% to 30% EtOAc). Racemic diastereoisomer 1: $^1$H NMR (600 MHz, DMSO-$d_6$) δ ppm 7.97-7.72 (m, 3H), 7.59-7.34 (m, 4H), 7.23-7.03 (m, 3H), 3.65 (s, 2H), 1.25 (s, 9H). UPLC-MS 1: m/z 481.3 [M+H]$^+$, $t_R$=1.29 min. Racemic diastereoisomer 2: $^1$H NMR (600 MHz, DMSO-$d_6$) δ ppm 7.96-7.71 (m, 3H), 7.57-7.37 (m, 4H), 7.13 (td, J=17.4, 7.4 Hz, 3H), 3.65 (qd, J=15.1, 6.5 Hz, 2H), 1.27 (s, 9H). UPLC-MS 1: m/z 481.3 [M+H]$^+$, $t_R$=1.34 min. Racemic diastereoisomer 2 was converted into the corresponding amide and the enantiomers of tert-butyl ((4-(2-carbamoyl-6-fluorophenyl)-5-chloro-2-phenylbenzo[d][1,3]dioxol-2-yl)methyl)carbamate were separated by chiral HPLC (Chiralcel OD-H 250×20 mm 5 μm, heptane/EtOH/MeOH 90:5:5, flow rate: 10 mL/min);

Enantiomer 1: Chiral HPLC (Chiralcel OD-3 100×2 mm 3 μm, heptane/EtOH/MeOH 85:7.5:7.5, flow rate: 0.42 mL/min) $t_R$=2.37 min Enantiomer 2: Chiral HPLC (Chiralcel OD-3 100×2 mm 3 μm, heptane/EtOH/MeOH 85:7.5:7.5, flow rate: 0.42 mL/min) $t_R$=4.67 min Enantiomer 1 was Boc-deprotected to afford the title compound with unknown absolute configuration. $^1$H NMR (600 MHz, DMSO-$d_6$) δ ppm 7.87 (s, 1H), 7.65-7.36 (m, 9H), 6.94 (qd, J=8.4, 1.8 Hz, 2H), 3.17-3.00 (m, 2H). UPLC-MS m/z 399.3 [M+H]$^+$, $t_R$=0.76 min. Chiral HPLC: (CHIRALPAK IA; heptane/DCM/EtOH 65:30:5, flow: 1 mL/minute) $t_R$=11.2 min, >99% ee.

Example 134: 2-((2S,4S)-2-(aminomethyl)-5-chloro-6-fluoro-2-phenylindolin-4-yl)-3-fluorobenzamide

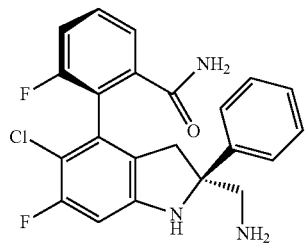

Reaction Scheme Example 134

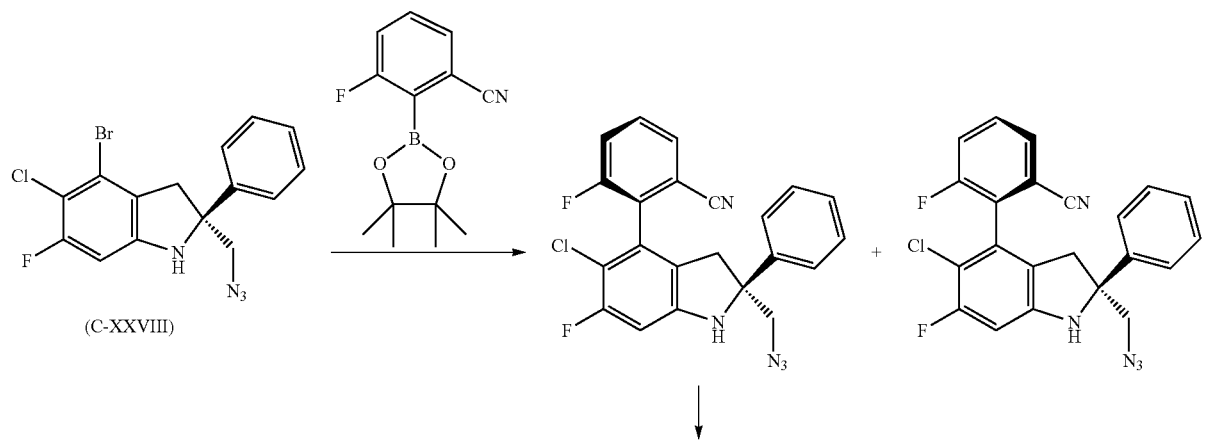

Reaction Scheme Example 134

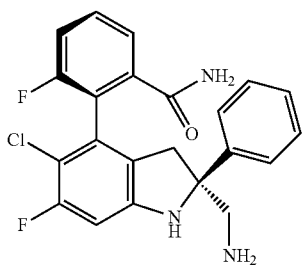
(Example 134)

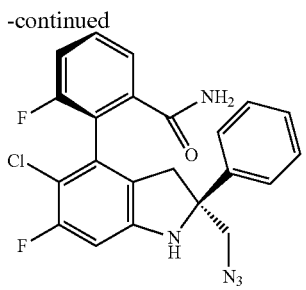
-continued

Step 1: 2-((2S,4S)-2-(Azidomethyl)-5-chloro-6-fluoro-2-phenylindolin-4-yl)-3-fluorobenzonitrile, and 2-((2S,4R)-2-(azidomethyl)-5-chloro-6-fluoro-2-phenylindolin-4-yl)-3-fluorobenzonitrile A mixture of (S)-2-(azidomethyl)-4-bromo-5-chloro-6-fluoro-2-phenylindoline (C-XXVIII) (645 mg, 1.69 mmol), 3-fluoro-2-(4,4,5,5-tetramethyl-1,3,2-dioxaborolan-2-yl) benzonitrile (CAS 62741-47-5) (590 mg, 2.388 mmol), $K_3PO_4$ (3.4 mL, 5.10 mmol, 1.5 M in water) and SPhos Pd G2 catalyst (140 mg, 0.194 mmol), suspended in THF (10 mL), was purged with Ar, then stirred for 6 h at 90° C. Water was added and the mixture was extracted with EtOAc. The aqueous layer was back-extracted with EtOAc. The organic layers were washed with water and brine, combined, dried over anhydrous $Na_2SO_4$ and concentrated. The crude product was purified by flash chromatography (silica, heptane/EtOAC 5% to 22% EtOAc) to afford the separated diastereoisomers: 2-((2S,4S)-2-(azidomethyl)-5-chloro-6-fluoro-2-phenylindolin-4-yl)-3-fluorobenzonitrile (156 mg): UPLC-MS 1: m/z 422.1/424.2 [M+H]+, $t_R$=1.27 min. 2-((2S,4R)-2-(azidomethyl)-5-chloro-6-fluoro-2-phenylindolin-4-yl)-3-fluorobenzonitrile (217 mg) UPLC-MS 1: m/z 422.2/424.1 [M+H]+, $t_R$=1.25 min.

Step 2: 2-((2S,4S)-2-(Azidomethyl)-5-chloro-6-fluoro-2-phenylindolin-4-yl)-3-fluorobenzamide The title compound (105 mg) was obtained from 2-((2S,4S)-2-(azidomethyl)-5-chloro-6-fluoro-2-phenylindolin-4-yl)-3-fluorobenzonitrile (150 mg, 0.36 mmol) using similar reaction conditions as described for Example 5a, step 2. UPLC-MS 1: m/z 440.1/442.1 [M+H]+, $t_R$=1.11 min.

Step 3: 2-((2S,4S)-2-(Aminomethyl)-5-chloro-6-fluoro-2-phenylindolin-4-yl)-3-fluorobenzamide Example 134

To a stirred solution of 2-((2S,4S)-2-(azidomethyl)-5-chloro-6-fluoro-2-phenylindolin-4-yl)-3-fluorobenzamide (100 mg, 0.227 mmol) in THF (5 mL), cooled at 0° C., was added trimethylphosphine (0.4 mL, 0.364 mmol, 1 M in THF) followed by water (0.1 mL). The reaction mixture was stirred at RT for 1.5 h. A solution of 5% $NaHCO_3$ was added, and the mixture was extracted with EtOAc. The organic phase was washed twice with brine. The aqueous layers were back-extracted with EtOAc. The combined organic phases were dried over anhydrous $Na_2SO_4$ and concentrated. The crude product was purified by flash chromatography (silica, DCM/MeOH, gradient: 0% to 20% MeOH) to afford the title compound (80 mg). UPLC-MS 1: m/z 414.2/416.2 [M+H]+, $t_R$=0.77 min. $^1$H NMR (600 MHz, $CDCl_3$) δ (ppm) 7.51-7.45 (m, 2H), 7.35-7.30 (m, 4H), 7.25-7.20 (m, 2H), 6.59 (d, J=9.4 Hz, 1H), 6.25 (br s, 1H), 5.84 (br s, 1H), 5.61 (br s, 1H), 3.12 (d, J=12.9 Hz, 1H), 3.10-3.00 (m, 2H), 2.90 (dd, J=16.2, 1.9 Hz, 1H). The absolute configuration was confirmed by an X-ray cocrystal structure of Example 134 bound to the YAP binding site of TEAD4.

The following examples were prepared in analogy to previous examples:

Example 135: 2-((2S,4S)-5-Chloro-2-((cyclohexylamino)methyl)-2-phenyl-2,3-dihydrobenzofuran-4-yl)-4-(difluoromethoxy)-3-fluorobenzamide

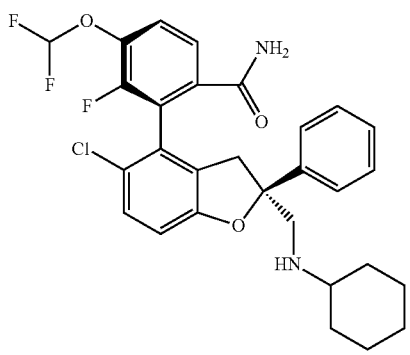

UPLC-MS 1: m/z 545.2 [M+H]+, $t_R$=1.03 min.

469

Example 136a and Example 136b: 2-((2S,3S,4S)-5-Chloro-6-fluoro-3-hydroxy-2-((((cis)-4-methoxycyclohexyl)amino)methyl)-2-phenyl-2,3-dihydrobenzofuran-4-yl)-4-(difluoromethoxy)-3-fluorobenzamide and 2-((2S,3S,4S)-5-chloro-6-fluoro-3-hydroxy-2-((((trans)-4-methoxycyclohexyl)amino)methyl)-2-phenyl-2,3-dihydrobenzofuran-4-yl)-4-(difluoromethoxy)-3-fluorobenzamide (Exampel 136a)

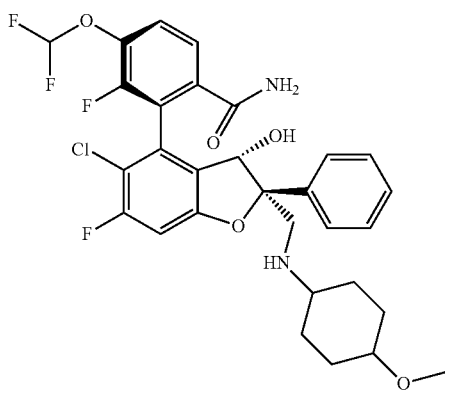

(Exampel 136b)

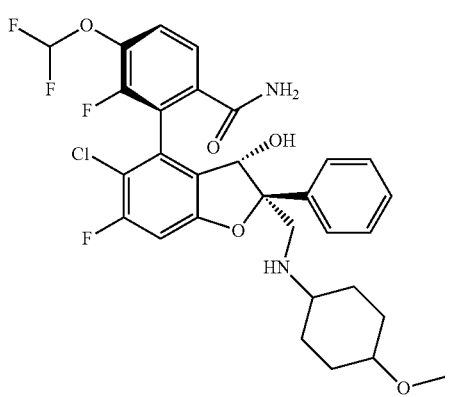

470

Example 137a and Example 137b: Methyl (cis)-4-(((((2S,4S)-4-(6-carbamoyl-2,3-difluorophenyl)-5-chloro-2-phenyl-2,3-dihydrobenzofuran-2-yl)methyl)amino)cyclohexane-1-carboxylate (Example 137a) and methyl (trans)-4-(((((2S,4S)-4-(6-carbamoyl-2,3-difluorophenyl)-5-chloro-2-phenyl-2,3-dihydrobenzofuran-2-yl)methyl)amino)cyclohexane-1-carboxylate (Example 137b)

(Exampel 137a)

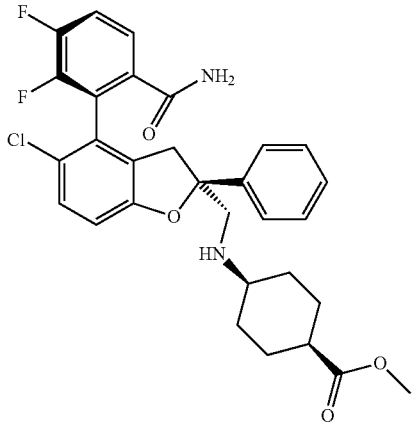

(Exampel 137b)

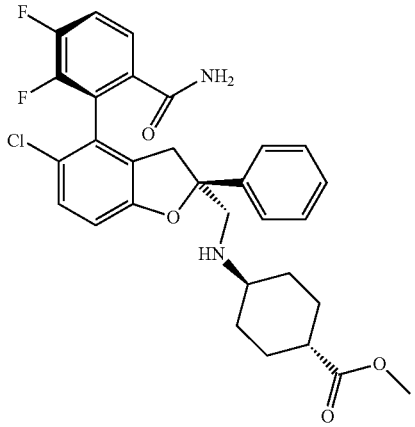

Example 136a and 136b have cis- and trans-configuration at the cyclohexyl ring, respectively. The absolute stereochemistry at the cyclohexyl ring for the respective examples was not determined.

Example 136a: UPLC-MS 1: m/z 609.2 [M+H]$^+$, $t_R$=0.94 min.

Example 136b: UPLC-MS 1: m/z 609.2 [M+H]$^+$, $t_R$=0.96 min.

Example 137a: UPLC-MS 1: m/z 555.2 [M+H]$^+$, $t_R$=0.99 min.

Example 137b: UPLC-MS 1: m/z 555.2 [M+H]$^+$, $t_R$=0.96 min.

Example 138a and Example 138b: 2-((2S,4S)-2-((((Trans)-4-carbamoylcyclohexyl)amino)methyl)-5-chloro-2-phenyl-2,3-dihydrobenzofuran-4-yl)-3-fluorobenzamide (Example 138a) and 2-((2S,4S)-2-((((cis)-4-carbamoylcyclohexyl)amino)methyl)-5-chloro-2-phenyl-2,3-dihydrobenzofuran-4-yl)-3-fluorobenzamide (Example 138b)

Example 139a and Example 139b: 2-((2S,4S)-5-Chloro-2-((((trans)-4-(methylcarbamoyl)cyclohexyl)amino)methyl)-2-phenyl-2,3-dihydrobenzofuran-4-yl)-3-fluorobenzamide (Example 139a) and 2-((2S,4S)-5-chloro-2-((((cis)-4-(methylcarbamoyl)cyclohexyl)amino)methyl)-2-phenyl-2,3-dihydrobenzofuran-4-yl)-3-fluorobenzamide (Example 139b)

(Exampel 138a)

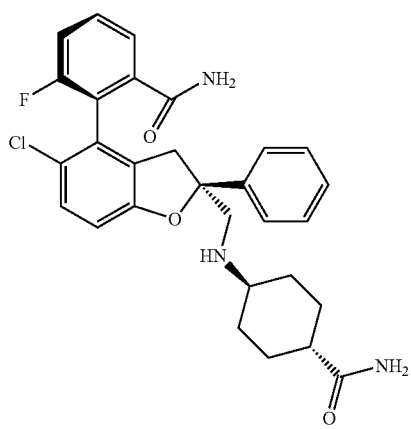

(Exampel 139a)

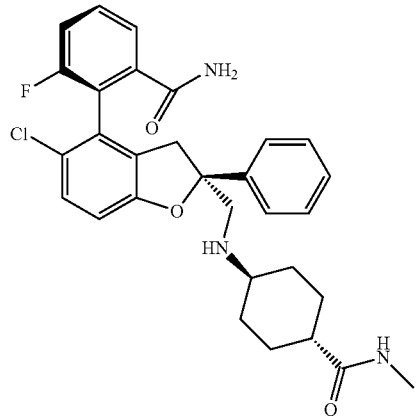

(Exampel 138b)

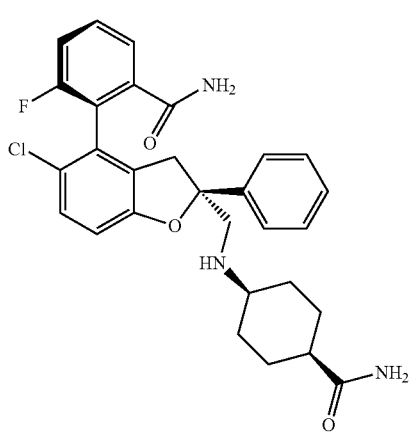

(Exampel 139b)

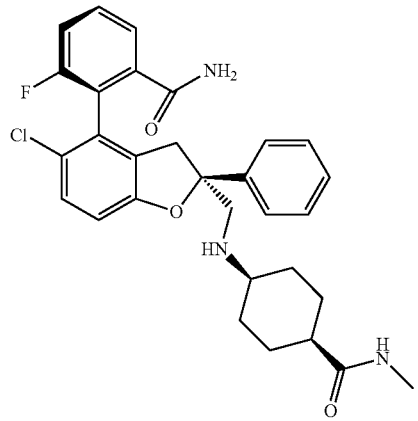

Example 138a: UPLC-MS 1: m/z 522.3 [M+H]$^+$, $t_R$=0.82 min.

Example 138b: UPLC-MS 1: m/z 522.3 [M+H]$^+$, $t_R$=0.80 min.

Example 139a: UPLC-MS 1: m/z 536.3 [M+H]$^+$, $t_R$=0.81 min.

Example 139b: UPLC-MS 1: m/z 536.3 [M+H]$^+$, $t_R$=0.85 min.

Example 140a and Example 140b: 2-((2S,4S)-5-Chloro-2-((((cis)-3-(difluoromethyl)cyclobutyl)amino)methyl)-6-fluoro-2-phenyl-2,3-dihydrobenzofuran-4-yl)-3-fluoro-4-(2-hydroxyethoxy)benzamide and 2-((2S,4S)-5-chloro-2-((((trans)-3-(difluoromethyl)cyclobutyl)amino)methyl)-6-fluoro-2-phenyl-2,3-dihydrobenzofuran-4-yl)-3-fluoro-4-(2-hydroxyethoxy)benzamide (Exampel 140a)

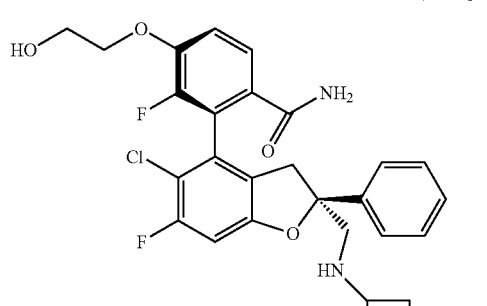

(Exampel 140b)

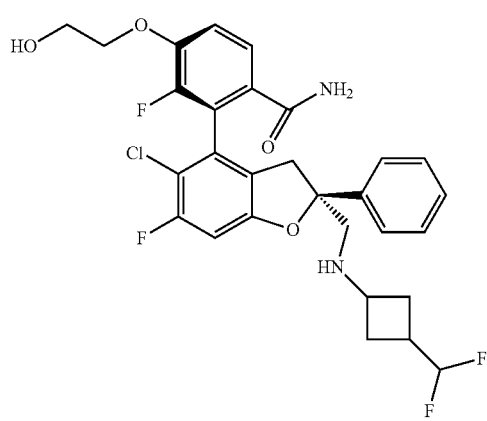

Example 140a and 140b have cis- and trans-configuration at the cyclobutyl ring, respectively. The absolute stereochemistry at the cyclobutyl ring for the respective examples was not determined.

Example 140a: UPLC-MS 1: m/z 579.2 [M+H]$^+$, $t_R$=0.76 min.

Example 140b: UPLC-MS 1: m/z 579.2 [M+H]$^+$, $t_R$=0.79 min.

Example 141: 2-((2S,4S)-2-(Aminomethyl)-5-chloro-6-fluoro-2-phenyl-2,3-dihydrobenzofuran-4-yl)-3-fluoro-4-(2-hydroxyethoxy-1,1,2,2-d4)-N-methylbenzamide

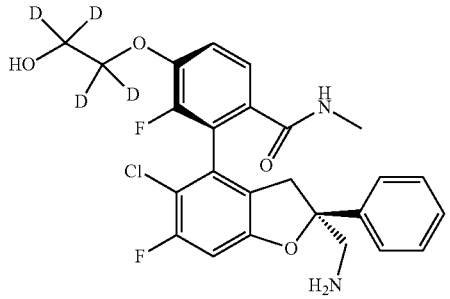

UPLC-MS 1: m/z 493.3 [M+H]$^+$, $t_R$=0.72 min.

Example 142: 2-((2S,4S)-5-Chloro-6-fluoro-2-(((methyl-d3)amino)methyl)-2-phenyl-2,3-dihydrobenzofuran-4-yl)-4-(difluoromethoxy)-3-fluorobenzamide

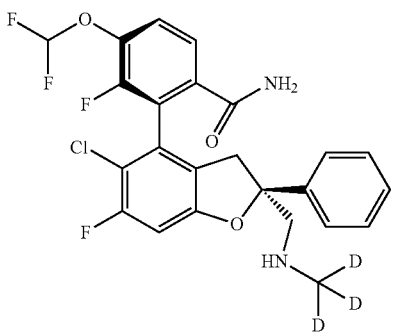

UPLC-MS 1: m/z 498.3 [M+H]$^+$, $t_R$=0.84 min.

Example 143: 2-((2S,4S)-5-Chloro-6-fluoro-2-(((methyl-d3)amino)methyl)-2-phenyl-2,3-dihydrobenzofuran-4-yl)-3-fluoro-4-(2-hydroxyethoxy-1,1,2,2-d4)benzamide

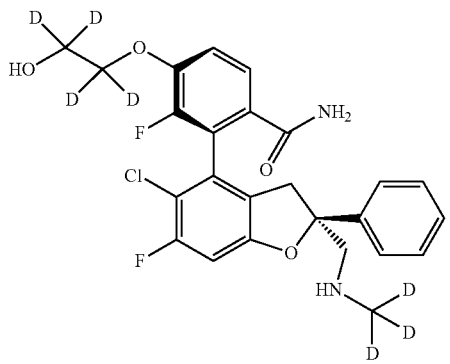

UPLC-MS 1: m/z 496.4 [M+H]$^+$, $t_R$=0.67 min

Example 144: 2-((2S,3S,4S)-5-Chloro-6-fluoro-3-methyl-2-((methylamino)methyl)-2-phenyl-2,3-dihydrobenzofuran-4-yl)-3-fluoro-4-methoxybenzamide or (2P)-2-{(2S,3S)-5-Chloro-6-fluoro-3-methyl-2-[(methylamino)methyl]-2-phenyl-2,3-dihydro-1-benzofuran-4-yl}-3-fluoro-4-methoxybenzamide

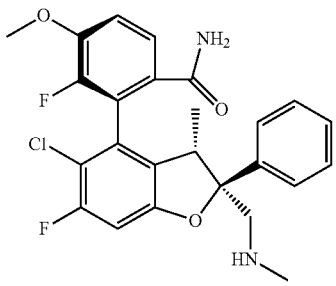

bamate (C-XXIX) (30 g, 46.3 mmol) in toluene (40 mL) was added to a stirred solution of 2-bromo-3-fluoro-4-methoxybenzonitrile (N-IV) (12.77 g, 55.5 mmol), N-XantPhos (2.55 g, 4.63 mmol), $Pd_2dba_3$ (2.12 g, 2.31 mmol) and $K_3PO_4$ (29.5 g, 139 mmol) in toluene (100 mL) and water (40 mL) at 10000. Having stirred at 100° C. for 3 d the crude mixture was diluted in water and extracted with EtOAc. The combined organic extracts were washed with brine, dried over anhydrous $Na_2SO_4$ and concentrated. The crude product was purified by flash chromatography (silica, EtOAc/heptane, gradient 0% to 60% EtOAc) to afford a mixture of the title compounds (12.86 g) as a yellow foam. UPLC-MS 1: m/z 499.2 [M+2H−tBu]$^+$, $t_R$=1.42 min and 1.44 min.

Reaction Scheme Example 144

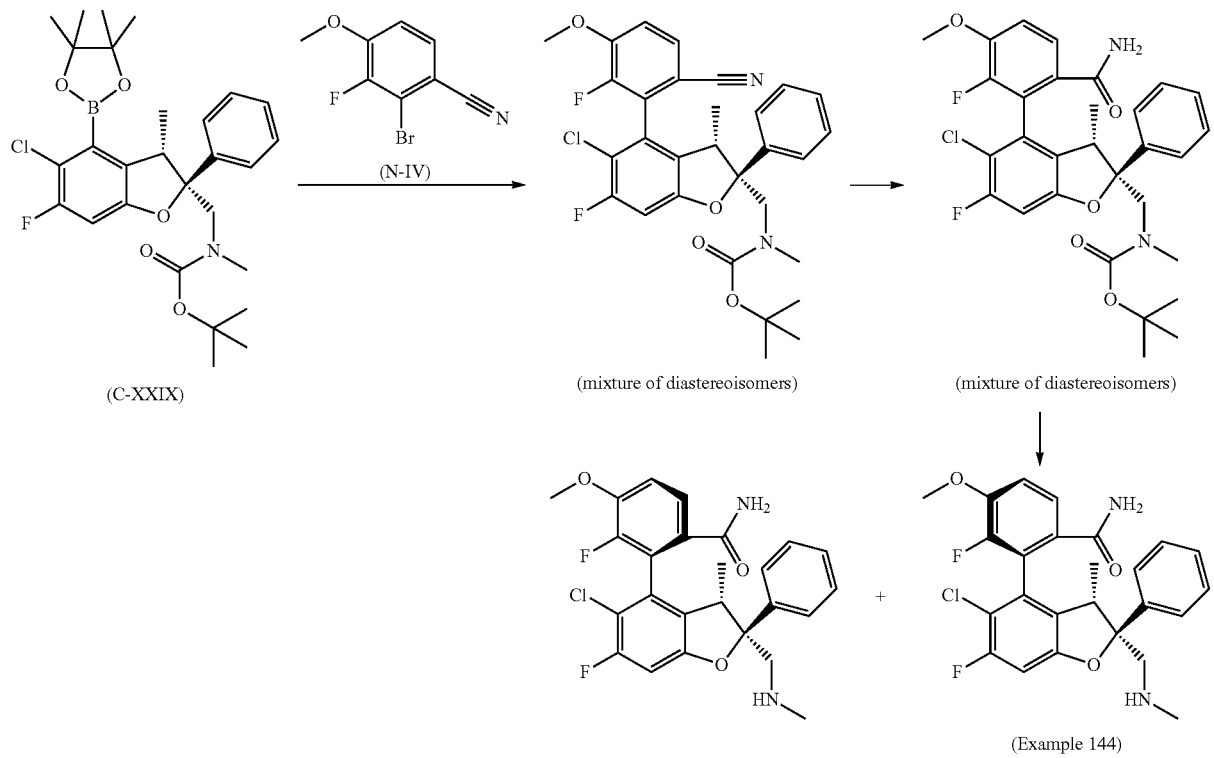

(Example 144)

Step 1: Tert-butyl (((2S,3S,4S)-5-chloro-4-(6-cyano-2-fluoro-3-methoxyphenyl)-6-fluoro-3-methyl-2-phenyl-2,3-dihydrobenzofuran-2-yl)methyl)(methyl)carbamate and tert-butyl (((2S,3S,4R)-5-chloro-4-(6-cyano-2-fluoro-3-methoxyphenyl)-6-fluoro-3-methyl-2-phenyl-2,3-dihydrobenzofuran-2-yl)methyl)(methyl)carbamate A solution of tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)(methyl)car- Step 2: Tert-butyl (((2S,3S,4S)-4-(6-carbamoyl-2-fluoro-3-methoxyphenyl)-5-chloro-6-fluoro-3-methyl-2-phenyl-2,3-dihydrobenzofuran-2-yl)methyl)(methyl)carbamate and tert-butyl (((2S,3S,4R)-4-(6-carbamoyl-2-fluoro-3-methoxyphenyl)-5-chloro-6-fluoro-3-methyl-2-phenyl-2,3-dihydrobenzofuran-2-yl)methyl)(methyl)carbamate To a stirred solution of a mixture of tert-butyl (((2S,3S,4S)-5-chloro-4-(6-cyano-2-fluoro-3-methoxyphenyl)-6- fluoro-3-methyl-2-phenyl-2,3-dihydrobenzofuran-2-yl)methyl)(methyl)carbamate and tert-butyl (((2S,3S,4R)-5-chloro-4-(6-cyano-2-fluoro-3-methoxyphenyl)-6-fluoro-3-methyl-2-phenyl-2,3-dihydrobenzofuran-2-yl)methyl)(methyl)carbamate (12.86 g, 22.94 mmol) in EtOH (150 mL) and water (50 mL) was added hydrido(dimethylphosphinous acid-kP)[hydrogen bis(dimethylphosphinito-kP)]platinum(II) (CAS 173416-05-2) (0.985 g, 2.29 mmol) and the reaction mixture was stirred at 80° C. for 2 h. The crude mixture was concentrated, then diluted in EtOAc and water and extracted with EtOAc. The organic extracts were washed with brine, dried over anhydrous $Na_2SO_4$ and concentrated. The crude products were purified by flash chromatography (silica, EtOAc/heptane, gradient 0% to 100% EtOAc) to afford a mixture of the title compounds (12.5 g) as a colorless foam. UPLC-MS 1: m/z 473.2 [M+H−BOC]$^+$, $t_R$=1.25 min and 1.27 min.

Step 3: 2-((2S,3S,4S)-5-Chloro-6-fluoro-3-methyl-2-((methylamino)methyl)-2-phenyl-2,3-dihydrobenzofuran-4-yl)-3-fluoro-4-methoxybenzamide or (2P)-2-{(2S,3S)-5-Chloro-6-fluoro-3-methyl-2-[(methylamino)methyl]-2-phenyl-2,3-dihydro-1-benzofuran-4-yl}-3-fluoro-4-methoxybenzamide (Example 144)

To a stirred solution of a mixture of tert-butyl (((2S,3S,4S)-4-(6-carbamoyl-2-fluoro-3-methoxyphenyl)-5-chloro-6-fluoro-3-methyl-2-phenyl-2,3-dihydrobenzofuran-2-yl)methyl)(methyl)carbamate and tert-butyl (((2S,3S,4R)-4-(6-carbamoyl-2-fluoro-3-methoxyphenyl)-5-chloro-6-fluoro-3-methyl-2-phenyl-2,3-dihydrobenzofuran-2-yl)methyl)(methyl)carbamate (12.5 g, 21.81 mmol) in DCM (120 mL) was added TFA (60 mL, 779 mmol) at RT. After 30 min, the reaction was complete and the reaction mixture was slowly added to a sat solution of $NaHCO_3$. The mixture was extracted with DCM and the combined organic extracts were washed with brine, dried over anhydrous $Na_2SO_4$ and concentrated. The crude product was purified by flash chromatography (silica, (7N ammonia in MeOH)/DCM, gradient 0% to 8% (7N ammonia in MeOH)) to afford the separated diastereoisomers as colorless foams.

2-((2S,3S,4S)-5-Chloro-6-fluoro-3-methyl-2-((methylamino)methyl)-2-phenyl-2,3-dihydrobenzofuran-4-yl)-3-fluoro-4-methoxybenzamide or (2P)-2-{(2S,3S)-5-Chloro-6-fluoro-3-methyl-2-[(methylamino)methyl]-2-phenyl-2,3-dihydro-1-benzofuran-4-yl}-3-fluoro-4-methoxybenzamide (Example 144) (4.82 g) $^1$H NMR (600 MHz, DMSO-$d_6$) δ 7.68-7.55 (m, 2H), 7.48-7.39 (m, 2H), 7.39-7.22 (m, 4H), 7.13 (s, 1H), 7.06 (d, J=9.5 Hz, 1H), 3.89 (s, 3H), 3.25 (q, J=7.1 Hz, 1H), 3.12-2.96 (m, 2H), 2.18 (s, 3H), 1.10 (s br, 1H), 0.92 (d, J=7.1 Hz, 3H). UPLC-MS 1: m/z 473.2 [M+H]$^+$, $t_R$=0.77 min. The absolute configuration was confirmed by an X-ray cocrystal structure of Example 144 bound to the YAP binding site of TEAD4.

Other diastereoisomer 2-((2S,3S,4R)-5-chloro-6-fluoro-3-methyl-2-((methylamino)methyl)-2-phenyl-2,3-dihydrobenzofuran-4-yl)-3-fluoro-4-methoxybenzamide (4.37 g): UPLC-MS 1: m/z 473.2 [M+H]$^+$, $t_R$=0.69 min.

Example 145: 4-((2S,3S,4S)-5-Chloro-6-fluoro-3-methyl-2-((methylamino)methyl)-2-phenyl-2,3-dihydrobenzofuran-4-yl)-5-fluoro-6-(2-hydroxyethoxy)-N-methylnicotinamide or (4P)-4-{(2S,3S)-5-Chloro-6-fluoro-3-methyl-2-[(methylamino)methyl]-2-phenyl-2,3-dihydro-1-benzofuran-4-yl}-5-fluoro-6-(2-hydroxyethoxy)-N-methylpyridine-3-carboxamide

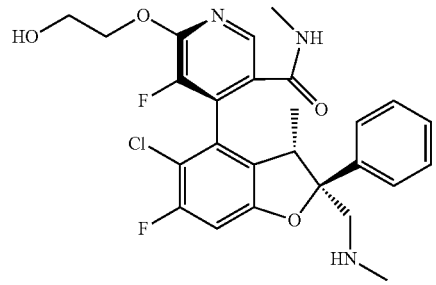

Reaction Scheme Example 145

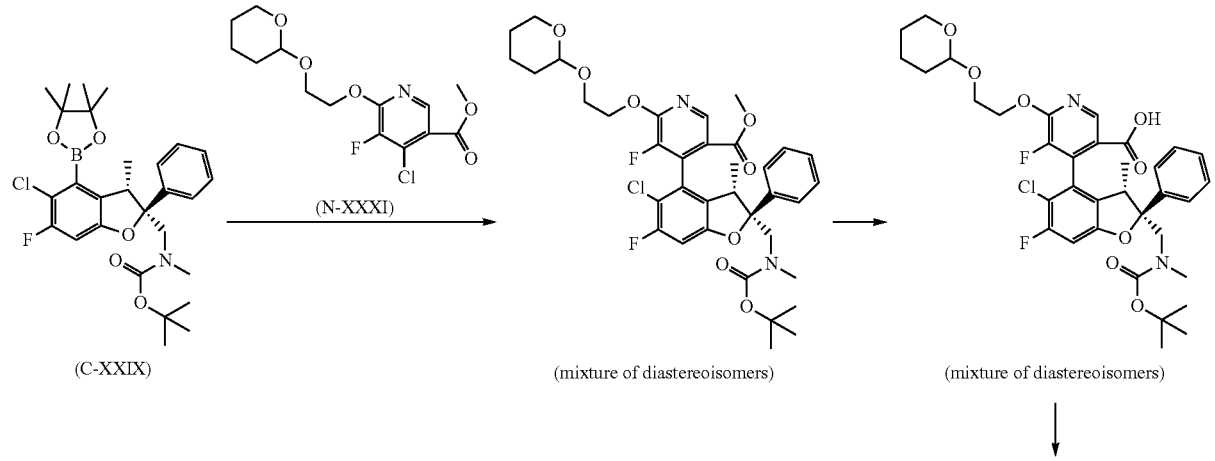

(C-XXIX)      (N-XXXI)      (mixture of diastereoisomers)      (mixture of diastereoisomers)

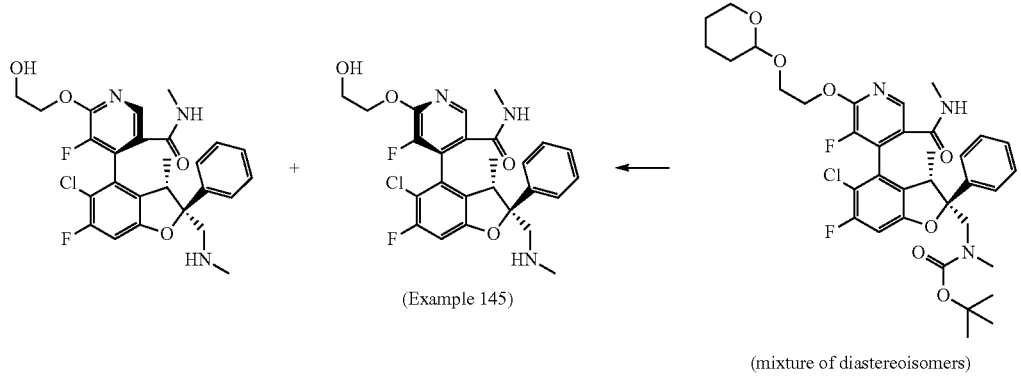

(Example 145)

(mixture of diastereoisomers)

Step 1: Methyl 4-((2S,3S,4S)-2-(((tert-butoxycarbonyl)(methyl)amino)methyl)-5-chloro-6-fluoro-3-methyl-2-phenyl-2,3-dihydrobenzofuran-4-yl)-5-fluoro-6-(2-((tetrahydro-2H-pyran-2-yl)oxy)ethoxy) nicotinate and methyl 4-((2S,3S,4R)-2-(((tert-butoxycarbonyl) (methyl)amino)methyl)-5-chloro-6-fluoro-3-methyl-2-phenyl-2,3-dihydrobenzofuran-4-yl)-5-fluoro-6-(2-((tetrahydro-2H-pyran-2-yl)oxy) ethoxy)nicotinate A solution of tert-butyl (((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)methyl)(methyl)carbamate (C-XXIX) (3.667 g, 5.86 mmol) in toluene (10 mL) was added to a stirred solution of methyl 4-chloro-5-fluoro-6-(2-((tetrahydro-2H-pyran-2-yl)oxyethoxy) nicotinate (N-XXXI) (2.347 g, 7.03 mmol), N-XantPhos (0.323 g, 0.586 mmol), Pd$_2$dba$_3$ (0.268 g, 0.29 mmol) and K$_3$PO$_4$ (3.73 g, 17.58 mmol) in toluene (15 mL) and water (5 mL) at 100° C. and the reaction mixture was stirred at 100° C. for 16 h. The reaction mixture was diluted in water and extracted with EtOAc. The combined organic extracts were washed with brine, dried over anhydrous Na$_2$SO$_4$ and concentrated. The crude product was purified by flash chromatography (silica, EtOAc/heptane, gradient 0% to 50% EtOAc) to afford a mixture of the title compounds (1.7 g) as a yellow foam. UPLC-MS 1: m/z 703.3 [M+H]$^+$, t$_R$=1.52 min.

Step 2: 4-((2S,3S,4S)-2-(((Tert-butoxycarbonyl) (methyl)amino)methyl)-5-chloro-6-fluoro-3-methyl-2-phenyl-2,3-dihydrobenzofuran-4-yl)-5-fluoro-6-(2-((tetrahydro-2H-pyran-2-yl)oxy)ethoxy)nicotinic acid and 4-((2S,3S,4R)-2-(((tert-butoxycarbonyl) (methyl)amino)methyl)-5-chloro-6-fluoro-3-methyl-2-phenyl-2,3-dihydrobenzofuran-4-yl)-5-fluoro-6-(2-((tetrahydro-2H-pyran-2-yl)oxy)ethoxy)nicotinic acid To a stirred solution of a mixture of methyl 4-((2S,3S,4S)-2-(((tert-butoxycarbonyl)(methyl)amino)methyl)-5-chloro-6-fluoro-3-methyl-2-phenyl-2,3-dihydrobenzofuran-4-yl)-5-fluoro-6-(2-((tetrahydro-2H-pyran-2-yl)oxy)ethoxy) nicotinate and methyl 4-((2S,3S,4R)-2-(((tert-butoxycarbonyl)(methyl)amino)methyl)-5-chloro-6-fluoro-3-methyl-2-phenyl-2,3-dihydrobenzofuran-4-yl)-5-fluoro-6-(2-((tetrahydro-2H-pyran-2-yl)oxy)ethoxy)nicotinate (1.7 g, 2.03 mmol) in THF (10 mL) and MeOH (10 mL) was added sodium hydroxide (10 mL, 20.0 mmol, 2N in water) at RT and the reaction mixture was stirred at RT for 15 min, then at 50° C. for 1 h. THF and MeOH were evaporated and the resulting aqueous phase was acidified to pH 3-4 with 2 N HCl. The aqueous phase was extracted with EtOAc and the combined organic extracts were washed with brine, dried over anhydrous Na$_2$SO$_4$ and concentrated. The crude product was purified by flash chromatography (silica, EtOAc/heptane, gradient 0% to 100% EtOAc) to afford a mixture of the title compounds (1.49 g) as a yellow foam. UPLC-MS 1: m/z 689.3 [M+H]$^+$, t$_R$=1.37 min and 1.39 min.

Step 3: Tert-butyl (((2S,3S,4S)-5-chloro-6-fluoro-4-(3-fluoro-5-(methylcarbamoyl)-2-(2-((tetrahydro-2H-pyran-2-yl)oxy)ethoxy)pyridin-4-yl)-3-methyl-2-phenyl-2,3-dihydrobenzofuran-2-yl)methyl)(methyl) carbamate and Tert-butyl (((2S,3S,4R)-5-chloro-6-fluoro-4-(3-fluoro-5-(methylcarbamoyl)-2-(2-((tetrahydro-2H-pyran-2-yl)oxy)ethoxy)pyridin-4-yl)-3-methyl-2-phenyl-2,3-dihydrobenzofuran-2-yl) methyl)(methyl)carbamate To a stirred suspension of a mixture of 4-((2S,3S,4S)-2-(((tert-butoxycarbonyl)(methyl)amino)methyl)-5-chloro-6-fluoro-3-methyl-2-phenyl-2,3-dihydrobenzofuran-4-yl)-5-fluoro-6-(2-((tetrahydro-2H-pyran-2-yl)oxy)ethoxy) nicotinic acid and 4-((2S,3S,4R)-2-(((tert-butoxycarbonyl) (methyl)amino)methyl)-5-chloro-6-fluoro-3-methyl-2-phenyl-2,3-dihydrobenzofuran-4-yl)-5-fluoro-6-(2-((tetrahydro-2H-pyran-2-yl)oxy)ethoxy)nicotinic acid (1.489 g, 1.75 mmol), methylamine hydrochloride (0.591 g, 8.75 mmol) and TBTU (0.843 g, 2.63 mmol) in DMF (12 mL) was added DIPEA (1.22 mL, 7.0 mmol) at RT and the reaction mixture were stirred at RT for 16 h. The reaction mixture was diluted in water and extracted with EtOAc. The combined organic extracts were washed with brine, dried over anhydrous Na$_2$SO$_4$ and concentrated. The crude product was purified by flash chromatography (silica, EtOAc/heptane, gradient 0% to 100% EtOAc) to afford a mixture of the title compounds (1.5 g) as a colorless foam. UPLC-MS 1: m/z 702.8 [M+H]$^+$, t$_R$=1.43 min and 1.44 min.

Step 4: 4-((2S,3S,4S)-5-chloro-6-fluoro-3-methyl-2-((methylamino)methyl)-2-phenyl-2,3-dihydrobenzofuran-4-yl)-5-fluoro-6-(2-hydroxyethoxy)-N-methyl-nicotinamide or (4P)-4-{(2S,3S)-5-Chloro-6-fluoro-3-methyl-2-[(methylamino)methyl]-2-phenyl-2,3-dihydro-1-benzofuran-4-yl}-5-fluoro-6-(2-hydroxyethoxy)-N-methylpyridine-3-carboxamide (Example 145)

To a stirred solution of a mixture of tert-butyl (((2S,3S,4S)-5-chloro-6-fluoro-4-(3-fluoro-5-(methylcarbamoyl)-2-

(2-((tetrahydro-2H-pyran-2-yl)oxy)ethoxy)pyridin-4-yl)-3-methyl-2-phenyl-2,3-dihydrobenzofuran-2-yl)methyl)(methyl)carbamate and tert-butyl (((2S,3S,4R)-5-chloro-6-fluoro-4-(3-fluoro-5-(methylcarbamoyl)-2-(2-((tetrahydro-2H-pyran-2-yl)oxy)ethoxy)pyridin-4-yl)-3-methyl-2-phenyl-2,3-dihydrobenzofuran-2-yl)methyl)(methyl) carbamate (1.5 g, 1.47 mmol) in DCM (15 mL) was added TFA (10 mL, 130 mmol) at 0° C. and the reaction mixture was stirred at 0° C. for 30 min. The reaction mixture was added to a sat solution of NaHCO$_3$ and extracted with DCM. The combined organic extracts were washed with brine, dried over anhydrous Na$_2$SO$_4$ and concentrated. The crude products were purified by flash chromatography (silica, (7N ammonia in MeOH)/DCM, gradient 0% to 10% (7N ammonia in MeOH)) to afford a colorless foam which was further purified by preparative HPLC (XBridge-C18 5 µm, 50×250 mm), eluent A: H$_2$O+0.1% TFA, eluent B: CH$_3$CN, gradient: 11% to 31% B in 21 min, flow: 100 mL/min). The collected fractions were basified with a sat solution of NaHCO$_3$, the acetonitrile was evaporated and the resulting aqueous phases were extracted with DCM, the combined organic extracts were washed with brine, dried over anhydrous Na$_2$SO$_4$ and concentrated to afford the separated diastereoisomers as colorless solids.

4-((2S,3S,4S)-5-chloro-6-fluoro-3-methyl-2-((methylamino)methyl)-2-phenyl-2,3-dihydrobenzofuran-4-yl)-5-fluoro-6-(2-hydroxyethoxy)-N-methylnicotinamide (4P)-4-{(2S,3S)-5-Chloro-6-fluoro-3-methyl-2-[(methylamino)methyl]-2-phenyl-2,3-dihydro-1-benzofuran-4-yl}-5-fluoro-6-(2-hydroxyethoxy)-N-methylpyridine-3-carboxamide (Example 145) (394 mg): $^1$H NMR (400 MHz, DMSO-d$_6$) δ 8.44 (d, J=4.6 Hz, 1H), 8.31 (s, 1H), 7.47-7.39 (m, 2H), 7.38-7.32 (m, 2H), 7.30-7.24 (m, 1H), 7.13 (d, J=9.6 Hz, 1H), 4.90 (t, J=5.4 Hz, 1H), 4.55-4.29 (m, 2H), 3.74 (q, J=5.1 Hz, 2H), 3.39-3.26 (m, 1H), 3.14-2.97 (m, 2H), 2.66 (d, J=4.4 Hz, 3H), 2.20 (s, 3H), 0.98 (d, J=7.1 Hz, 3H). UPLC-MS 1: m/z 518.5 [M+H]$^+$, t$_R$=0.66 min.

Other diastereoisomer 4-((2S,3R,4R)-5-chloro-6-fluoro-3-methyl-2-((methylamino)methyl)-2-phenyl-2,3-dihydrobenzofuran-4-yl)-5-fluoro-6-(2-hydroxyethoxy)-N-methylnicotinamide (30 mg): UPLC-MS 1: m/z 518.5 [M+H]$^+$, t$_R$=0.63 min.

Example 146: 2-((2S,3R,4S)-5-Chloro-6-fluoro-3-(methoxymethyl)-2-((methylamino)methyl)-2-phenyl-2,3-dihydrobenzofuran-4-yl)-3-fluoro-4-methoxybenzamide

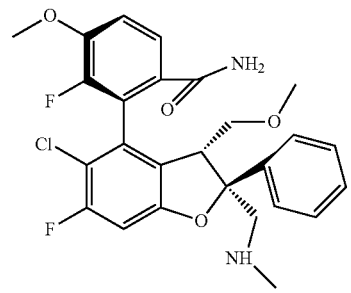

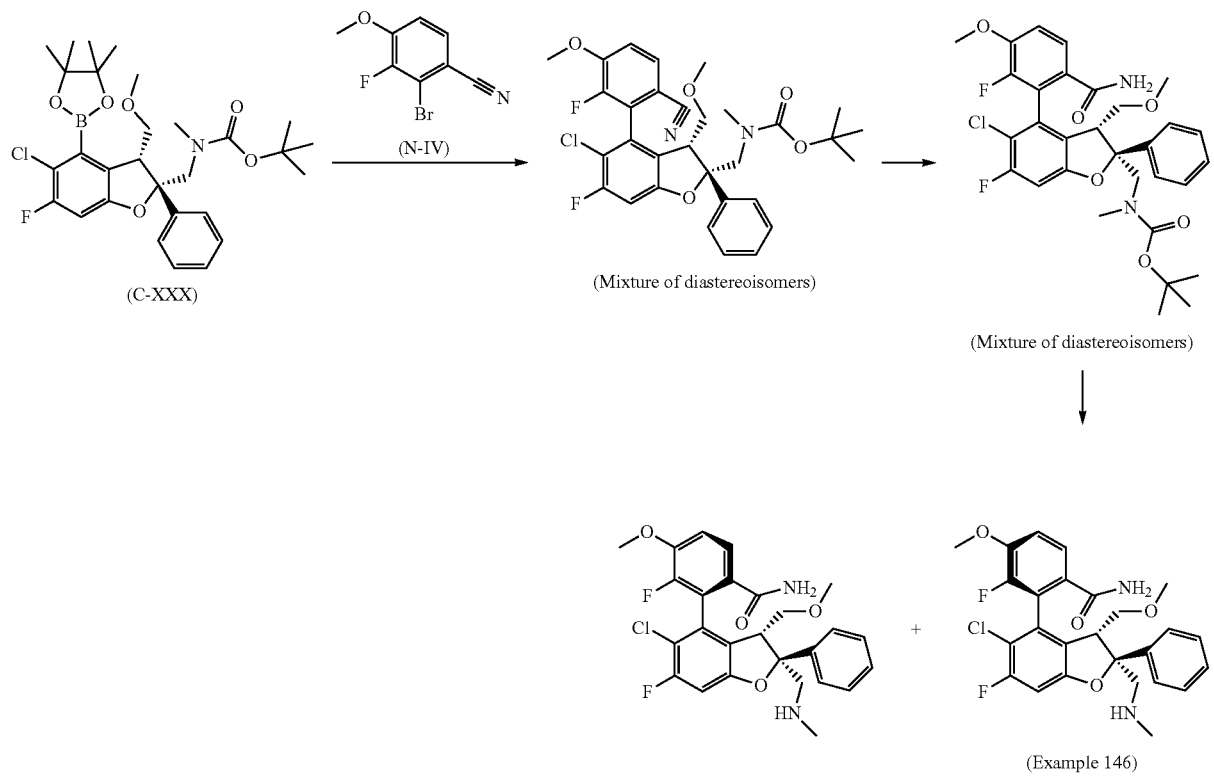

Reaction Scheme Example 146

(C-XXX)

(N-IV)

(Mixture of diastereoisomers)

(Mixture of diastereoisomers)

(Example 146)

Step 1: Tert-butyl (((2S,3R,4S)-5-chloro-4-(6-cyano-2-fluoro-3-methoxyphenyl)-6-fluoro-3-(methoxymethyl)-2-phenyl-2,3-dihydrobenzofuran-2-yl)methyl)(methyl)carbamate and tert-butyl (((2S,3R,4R)-5-chloro-4-(6-cyano-2-fluoro-3-methoxyphenyl)-6-fluoro-3-(methoxymethyl)-2-phenyl-2,3-dihydrobenzofuran-2-yl)methyl)(methyl)carbamate A solution of tert-butyl (((2S,3R)-5-chloro-6-fluoro-3-(methoxymethyl)-2-phenyl-4-(4,4,5,5-tetramethyl-1,3,2-dioxaborolan-2-yl)-2,3-dihydrobenzofuran-2-yl)methyl)(methyl)carbamate (C-XXX) (1.074 g, 1.53 mmol) in toluene (6 mL) was added to a stirred solution of 2-bromo-3-fluoro-4-methoxybenzonitrile (N-IV) (0.422 g, 1.84 mmol), N-XantPhos (0.084 g, 0.153 mmol), Pd$_2$dbas (0.070 g, 0.076 mmol) and K$_3$PO$_4$ (0.974 g, 4.59 mmol) in toluene (9 mL) and water (3 mL) at 105° C. and the reaction mixture was stirred at 105° C. for 6.5 h. The crude mixture was diluted in EtOAc and water and extracted with EtOAc. The combined organic extracts were washed with water and brine, dried over anhydrous Na$_2$SO$_4$ and concentrated. The crude product was purified by flash chromatography (silica, heptane/EtOAc, gradient 0% to 50% EtOAc) to afford a mixture of the title compounds (620 mg) as a colorless foam. UPLC-MS 1: m/z 585.5 [M+H]$^+$, $t_R$=1.41 min.

Step 2: Tert-butyl (((2S,3R,4S)-4-(6-carbamoyl-2-fluoro-3-methoxyphenyl)-5-chloro-6-fluoro-3-(methoxymethyl)-2-phenyl-2,3-dihydrobenzofuran-2-yl)methyl)(methyl)carbamate and tert-butyl (((2S,3R,4R)-4-(6-carbamoyl-2-fluoro-3-methoxyphenyl)-5-chloro-6-fluoro-3-(methoxymethyl)-2-phenyl-2,3-dihydrobenzofuran-2-yl)methyl)(methyl)carbamate To a stirred solution of a mixture of tert-butyl (((2S,3R,4S)-5-chloro-4-(6-cyano-2-fluoro-3-methoxyphenyl)-6-fluoro-3-(methoxymethyl)-2-phenyl-2,3-dihydrobenzofuran-2-yl)methyl)(methyl)carbamate and tert-butyl (((2S,3R,4R)-5-chloro-4-(6-cyano-2-fluoro-3-methoxyphenyl)-6-fluoro-3-(methoxymethyl)-2-phenyl-2,3-dihydrobenzofuran-2-yl)methyl)(methyl)carbamate (620 mg, 1.04 mmol) in EtOH (6 mL) and water (2 mL) was added hydrido(dimethylphosphinous acid-kP)[hydrogen bis(dimethylphosphinito-kP)]platinum(II) (CAS 173416-05-2) (89 mg, 0.21 mmol) and the reaction mixture wqw stirred at 85° C. for 1.5 h. The crude mixture was diluted in EtOAc and water and extracted with EtOAc. The organic extract was washed with brine, dried over anhydrous Na$_2$SO$_4$ and concentrated. The residue was diluted in MeOH and passed through a PL-thiol MP Resin cartridge (Agilent, StratoSpheres SPE) to remove metal traces. Concentration afforded a yellow oil. The crude product was purified by flash chromatography (silica, heptane/EtOAc, gradient 0% to 100% EtOAc) to afford a mixture of the title compounds (600 mg) as a colorless foam. UPLC-MS 1: m/z 603.5 [M+H]$^+$, $t_R$=1.25 min.

Step 3: 2-((2S,3R,4S)-5-chloro-6-fluoro-3-(methoxymethyl)-2-((methylamino)methyl)-2-phenyl-2,3-dihydrobenzofuran-4-yl)-3-fluoro-4-methoxybenzamide (Example 146)

To a stirred solution of a mixture of tert-butyl (((2S,3R,4S)-4-(6-carbamoyl-2-fluoro-3-methoxyphenyl)-5-chloro-6-fluoro-3-(methoxymethyl)-2-phenyl-2,3-dihydrobenzofuran-2-yl)methyl)(methyl)carbamate and tert-butyl (((2S,3R,4R)-4-(6-carbamoyl-2-fluoro-3-methoxyphenyl)-5-chloro-6-fluoro-3-(methoxymethyl)-2-phenyl-2,3-dihydrobenzofuran-2-yl)methyl)(methyl)carbamate (600 mg, 0.995 mmol) in DCM (3 mL) was added TFA (3 mL, 38.9 mmol) at RT and the reaction mixture was stirred at RT for 15 min. The reaction mixture was added to a sat solution of NaHCO$_3$.and extracted with DCM, the combined organic extracts were washed with brine, dried over anhydrous Na$_2$SO$_4$ and concentrated. The crude product was purified by flash chromatography (silica, (7N DCM/ammonia in MeOH), gradient 0% to 10% (7N ammonia in MeOH)) to afford a colorless foam which was further purified by preparative HPLC (Waters X-Bridge C18 OBD, 5 μm, 30*100 mm, Eluent A: H$_2$O+7.3 mM NH$_4$OH, B:ACN, Gradient: 15% to 60% B in 25 min hold 1 min, Flow 40 mL/min). The collected fractions were basified with a sat solution of NaHCO$_3$, acetonitrile was evaporated and the resulting aqueous phases were extracted with DCM. The organic extracts were washed with brine, dried over anhydrous Na$_2$SO$_4$ and concentrated to afford the separated diastereoisomers as colorless powders.

2-((2S,3R,4S)-5-Chloro-6-fluoro-3-(methoxymethyl)-2-((methylamino)methyl)-2-phenyl-2,3-dihydrobenzofuran-4-yl)-3-fluoro-4-methoxybenzamide (Example 146) (211 mg): $^1$H NMR (400 MHz, DMSO-d$_6$) δ 7.61 (dd, J=8.6, 1.4 Hz, 1H), 7.41 (s, 1H), 7.38-7.22 (m, 6H), 7.16 (s, 1H), 7.12 (d, J=9.6 Hz, 1H), 3.88 (s, 3H), 3.53 (dd, J=10.6, 8.3 Hz, 1H), 3.39 (dd, J=8.2, 2.9 Hz, 1H), 3.23 (dd, J=10.6, 3.0 Hz, 1H), 3.18 (s, 2H), 2.98 (s, 3H), 2.19 (s, 3H), 1.43-0.89 (m, 1H). UPLC-MS 1: m/z 503.5 [M+H]$^+$, $t_R$=0.77 min.

Other diastereoisomer 2-((2S,3R,4R)-5-chloro-6-fluoro-3-(methoxymethyl)-2-((methylamino)methyl)-2-phenyl-2,3-dihydrobenzofuran-4-yl)-3-fluoro-4-methoxybenzamide (140 mg): UPLC-MS 1: m/z 503.5 [M+H]$^+$, $t_R$=0.70 min.

Example 147: 2-((2S,3R,4S)-5-Chloro-6-fluoro-3-(hydroxymethyl)-2-((methylamino)methyl)-2-phenyl-2,3-dihydrobenzofuran-4-yl)-3-fluoro-4-methoxybenzamide

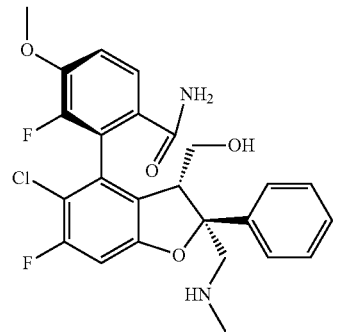

Reaction Scheme Example 147

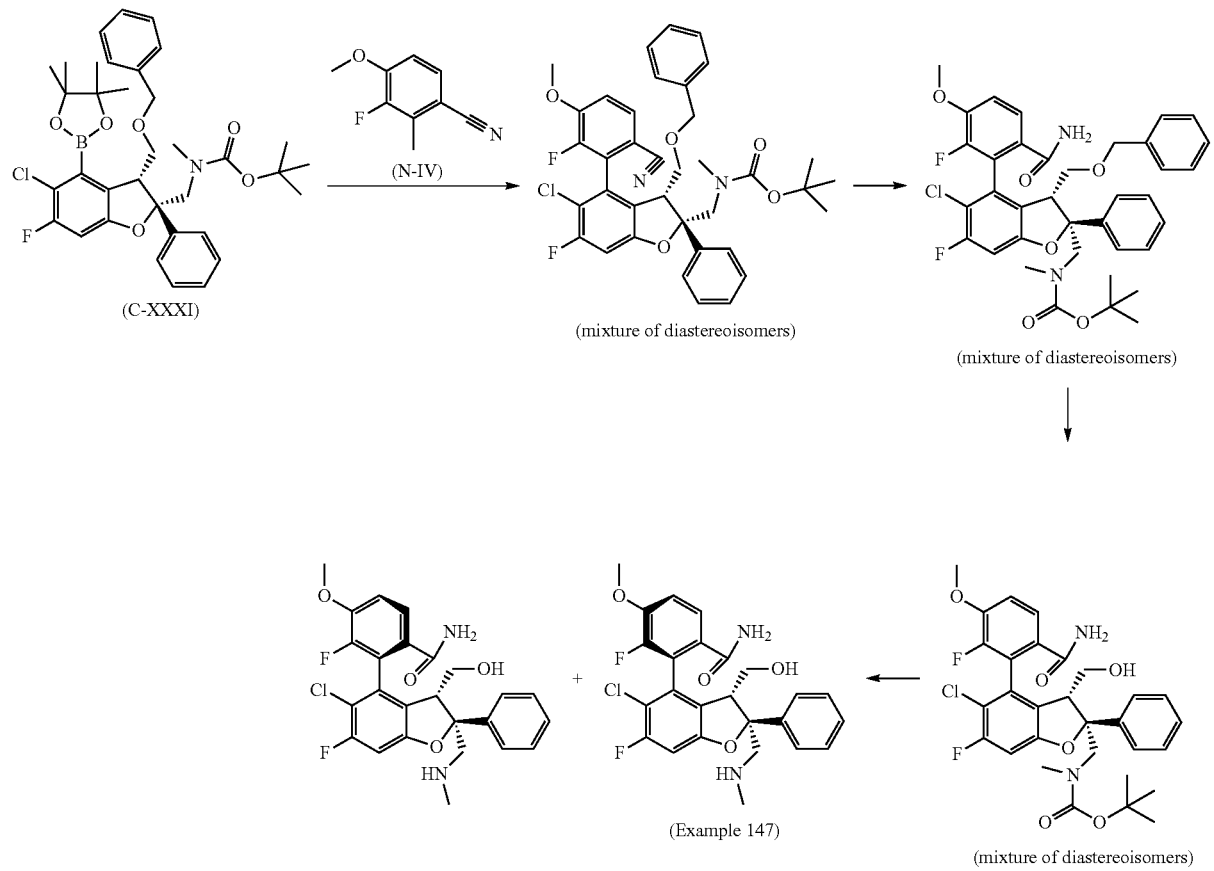

(Example 147)

Step 1: Tert-butyl (((2S,3R,4S)-3-((benzyloxy)methyl)-5-chloro-4-(6-cyano-2-fluoro-3-methoxyphenyl)-6-fluoro-2-phenyl-2,3-dihydrobenzofuran-2-yl)methyl)(methyl)carbamate and Tert-butyl (((2S,3R,4R)-3-((benzyloxy)methyl)-5-chloro-4-(6-cyano-2-fluoro-3-methoxyphenyl)-6-fluoro-2-phenyl-2,3-dihydrobenzofuran-2-yl)methyl)(methyl)carbamate A solution of tert-butyl (((2S,3R)-3-((benzyloxy)methyl)-5-chloro-6-fluoro-2-phenyl-4-(4,4,5,5-tetramethyl-1,3,2-dioxaborolan-2-yl)-2,3-dihydrobenzofuran-2-yl)methyl)(methyl)carbamate (C-XXXI) (745 mg, 0.841 mmol) in toluene (6 mL) was added to a stirred solution of 2-bromo-3-fluoro-4-methoxybenzonitrile (N-IV) (387 mg, 1.682 mmol), N-XantPhos (CAS 261733-18-0) (46.4 mg, 0.084 mmol), Pd$_2$dba$_3$ (38.5 mg, 0.042 mmol) and K$_3$PO$_4$ (714 mg, 3.36 mmol) in toluene (9 mL) and water (3 mL) at 105° C. and the reaction mixture was stirred at 105° C. for 6 h. The reaction mixture was diluted in water and extracted with EtOAc. The combined organic extracts were washed with brine, dried over anhydrous Na$_2$SO$_4$ and concentrated. The crude product was purified by flash chromatography (silica, heptane/EtOAc, gradient 0% to 50% EtOAc) to afford a mixture of the title compounds (380 mg) as a colorless foam. UPLC-MS 1: m/z 661.7 [M+H]$^+$, t$_R$=1.51 min and 1.52 min.

Step 2: Tert-butyl (((2S,3R,4S)-3-((benzyloxy)methyl)-4-(6-carbamoyl-2-fluoro-3-methoxyphenyl)-5-chloro-6-fluoro-2-phenyl-2,3-dihydrobenzofuran-2-yl)methyl)(methyl)carbamate and tert-butyl (((2S,3R,4R)-3-((benzyloxy)methyl)-4-(6-carbamoyl-2-fluoro-3-methoxyphenyl)-5-chloro-6-fluoro-2-phenyl-2,3-dihydrobenzofuran-2-yl)methyl)(methyl)carbamate To a stirred solution of a mixture of tert-butyl (((2S,3R,4S)-3-((benzyloxy)methyl)-5-chloro-4-(6-cyano-2-fluoro-3-methoxyphenyl)-6-fluoro-2-phenyl-2,3-dihydrobenzofuran-2-yl)methyl)(methyl)carbamate and tert-butyl (((2S,3R,4R)-3-((benzyloxy)methyl)-5-chloro-4-(6-cyano-2-fluoro-3-methoxyphenyl)-6-fluoro-2-phenyl-2,3-dihydrobenzofuran-2-yl)methyl)(methyl)carbamate (380 mg, 0.55 mmol) in EtOH (6 mL) and water (2 mL) was added hydrido(dimethylphosphinous acid-kP)[hydrogen bis(dimethylphosphinito-kP)]platinum(II) (CAS 173416-05-2) (47.4 mg, 0.11 mmol) and the reaction mixture was stirred at 85° C. for 1.5 h. The reaction mixture was diluted in water and extracted with EtOAc. The combined organic extracts were washed with brine, dried over anhydrous Na$_2$SO$_4$ and concentrated. The residue was diluted in MeOH and passed through a PL-thiol MP Resin cartridge (Agilent, Strato-Spheres SPE) to remove metal traces. Concentration afforded a yellow oil. The crude product was purified by flash chromatography (silica, heptane/EtOAc, gradient 50% to 100% EtOAc) to afford a mixture of the title compounds (370 mg) as a colorless foam. UPLC-MS 1: m/z 679.6 [M+H]$^+$, t$_R$=1.33 min and 1.36 min.

Step 3: Tert-butyl (((2S,3R,4S)-4-(6-carbamoyl-2-fluoro-3-methoxyphenyl)-5-chloro-6-fluoro-3-(hydroxymethyl)-2-phenyl-2,3-dihydrobenzofuran-2-yl)methyl)(methyl)carbamate and Tert-butyl (((2S,3R,4R)-4-(6-carbamoyl-2-fluoro-3-methoxyphenyl)-5-chloro-6-fluoro-3-(hydroxymethyl)-2-phenyl-2,3-dihydrobenzofuran-2-yl)methyl)(methyl)carbamate To a stirred solution of a mixture of tert-butyl (((2S,3R,4S)-3-((benzyloxy)methyl)-4-(6-carbamoyl-2-fluoro-3-methoxyphenyl)-5-chloro-6-fluoro-2-phenyl-2,3-dihydrobenzofuran-2-yl)methyl)(methyl)carbamate and tert-butyl (((2S,3R,4R)-3-((benzyloxy)methyl)-4-(6-carbamoyl-2-fluoro-3-methoxyphenyl)-5-chloro-6-fluoro-2-phenyl-2,3-dihydrobenzofuran-2-yl)methyl)(methyl)carbamate (370 mg, 0.54 mmol) in MeOH (10 mL) was added Pd—C(50 mg, 0.470 mmol, 10 wt-%) at RT and the reaction mixture was stirred under atmospheric pressure of $H_2$ for 2 h at RT. More Pd—C(50 mg, 0.470 mmol, 10 wt-%) was added and stirring under atmospheric pressure of $H_2$ at RT was continued for 2 h. The reaction mixture was filtered over Hyflo and concentrated. The crude product was purified by flash chromatography (silica, heptane/EtOAc, gradient 50% to 100% EtOAc) to give a mixture of the title compounds (298 mg) as a colorless foam. UPLC-MS 1: m/z 589.5 [M+H]$^+$, $t_R$=1.14 min and 1.22 min.

Step 4: 2-((2S,3R,4S)-5-chloro-6-fluoro-3-(hydroxymethyl)-2-((methylamino)methyl)-2-phenyl-2,3-dihydrobenzofuran-4-yl)-3-fluoro-4-methoxybenzamide (Example 147)

To a stirred solution of a mixture of tert-butyl (((2S,3R,4S)-4-(6-carbamoyl-2-fluoro-3-methoxyphenyl)-5-chloro-6-fluoro-3-(hydroxymethyl)-2-phenyl-2,3-dihydrobenzofuran-2-yl)methyl)(methyl)carbamate and tert-butyl (((2S,3R,4R)-4-(6-carbamoyl-2-fluoro-3-methoxyphenyl)-5-chloro-6-fluoro-3-(hydroxymethyl)-2-phenyl-2,3-dihydrobenzofuran-2-yl)methyl)(methyl)carbamate (298 mg, 0.506 mmol) in DCM (3 mL) was added TFA (2 mL, 26.0 mmol) at RT and the reaction mixture was stirred at RT for 15 min. The reaction mixture was added to a sat solution of $NaHCO_3$ And extracted with DCM. The combined organic extracts were washed with brine, dried over anhydrous $Na_2SO_4$ and concentrated. The crude product was purified by preparative HPLC (Waters X-Bridge C18 OBD, 5 µm, 30*100 mm, Eluent A: $H_2O$+7.3 mM $NH_4OH$, B:ACN, Gradient: 15% to 60% B in 25 min hold 1 min, Flow 40 mL/min). The acetonitrile from the collected fractions was evaporated and the resulting aqueous phases were extracted with DCM. The organic extracts were washed with brine, dried over anhydrous $Na_2SO_4$ and concentrated to afford the separated diastereoisomers.

2-((2S,3R,4S)-5-Chloro-6-fluoro-3-(hydroxymethyl)-2-((methylamino)methyl)-2-phenyl-2,3-dihydrobenzofuran-4-yl)-3-fluoro-4-methoxybenzamide (Example 147) (131 mg): $^1$H NMR (600 MHz, DMSO-$d_6$) δ 7.64 (s, 1H), 7.55 (d, J=8.6 Hz, 1H), 7.41 (d, J=7.7 Hz, 2H), 7.38-7.24 (m, 5H), 7.16 (d, J=9.4 Hz, 1H), 6.38 (br s, 1H), 3.88 (s, 3H), 3.74 (d, J=12.7 Hz, 1H), 3.35-3.30 (m, 2H), 3.12 (d, J=13.0 Hz, 1H), 3.07 (dd, J=12.7, 5.0 Hz, 1H), 2.23 (s, 3H). UPLC-MS 1: m/z 489.5 [M+H]$^+$, $t_R$=0.77 min Other diastereoisomer 2-((2S,3R,4R)-5-chloro-6-fluoro-3-(hydroxymethyl)-2-((methylamino)methyl)-2-phenyl-2,3-dihydrobenzofuran-4-yl)-3-fluoro-4-methoxybenzamide (63 mg): UPLC-MS 1: m/z 489.5 [M+H]$^+$, $t_R$=0.64 min.

Example 148: 2-((2S,3S,4S)-5-Chloro-6-fluoro-2-(((((trans)-4-hydroxy-4-methylcyclohexyl)amino)methyl)-3-methyl-2-phenyl-2,3-dihydrobenzofuran-4-yl)-3-fluoro-4-(2-hydroxy-2-methylpropoxy)benzamide

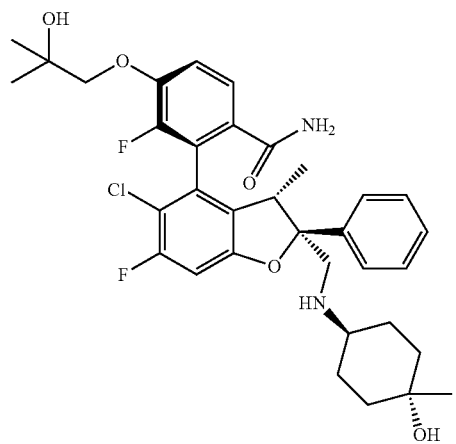

Reaction Scheme Example 148

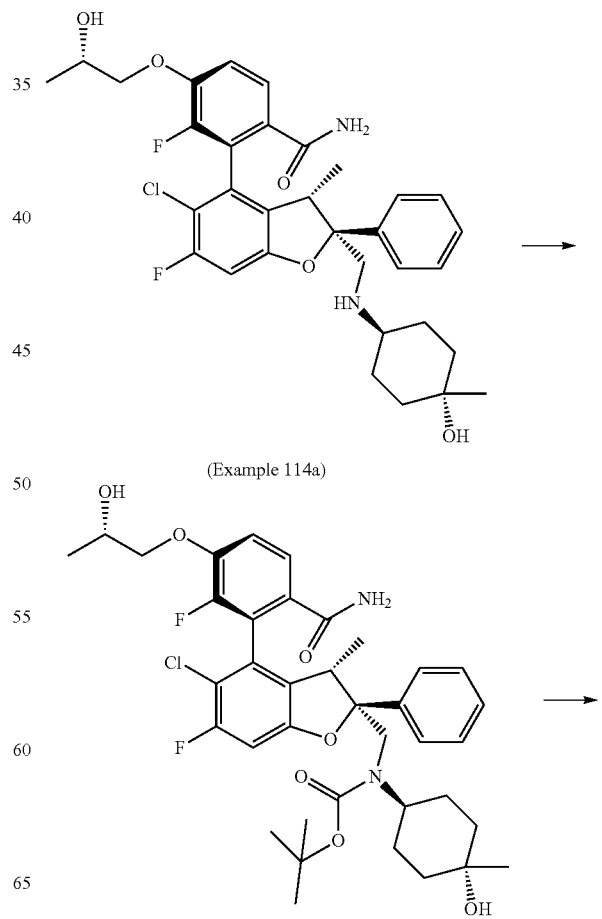

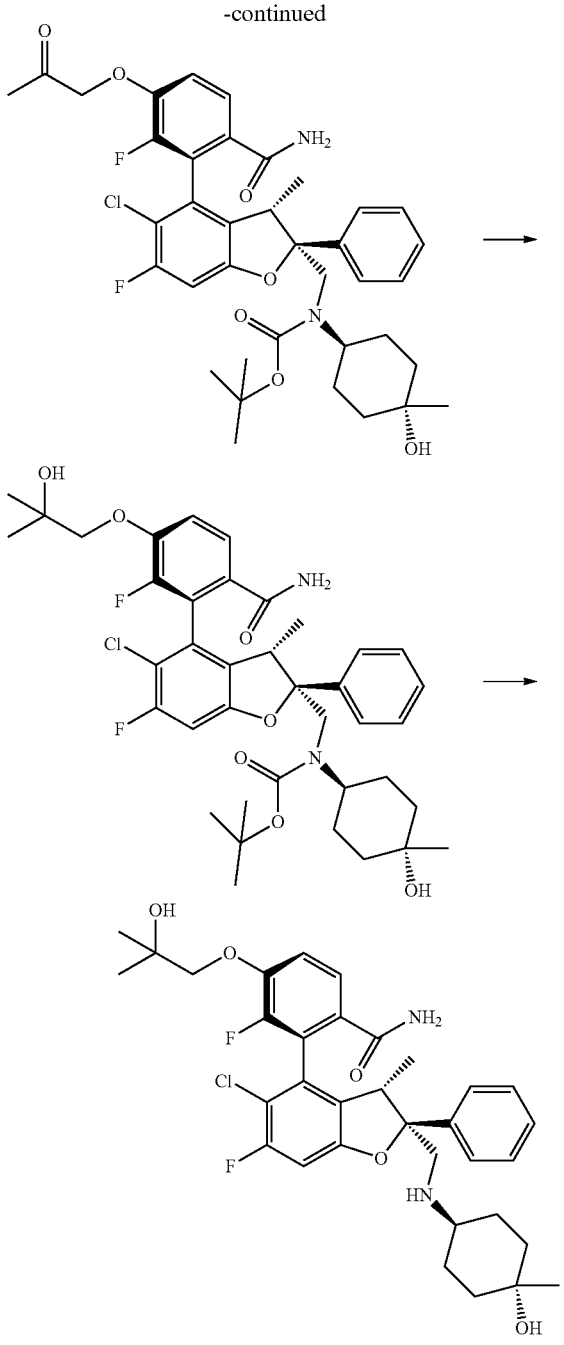

(Example 148)

Step 1: Tert-butyl (((2S,3S,4S)-4-(6-carbamoyl-2-fluoro-3-((S)-2-hydroxypropoxy)phenyl)-5-chloro-6-fluoro-3-methyl-2-phenyl-2,3-dihydrobenzofuran-2-yl)methyl)((1 r,4S)-4-hydroxy-4-methylcyclohexyl)carbamate 2-((2S,3S,4S)-5-Chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide or (2P)-2-[(2S,3S)-5-Chloro-6-fluoro-2-({[(1 r,4S)-4-hydroxy-4-methylcyclohexyl]amino}methyl)-3-methyl-2-phenyl-2,3-dihydro-1-benzofuran-4-yl]-3-fluoro-4-[(2S)-2-hydroxypropoxy]

benzamide (Example 114a) (2000 mg, 3.25 mmol) was dissolved in THF (50 mL) and water (10 mL). BOC$_2$O (1.06 g, 4.99 mmol) and 4 M NaOH solution (2.5 mL) were added and the reaction mixture was stirret at RT for 5 d. The reaction mixture was diluted with TBME and washed with water and brine. The aqueous phases were washed with TBME. The organic layers were combined, dried over MgSO$_4$ and concentrated. The crude product was dissolved in MeOH (30 mL) and stirred with K$_2$CO$_3$ (2 g) at RT overnight. The reaction mixture was filtered and concentrated and redissolved in EtOAc. The organic layer was washed with water and brine, dried over MgSO$_4$ and concentrated. The crude product was purified by flash chromatography (silica, DCM/MeOH, gradient 2% to 10% MeOH) to afford the title compound (2000 mg) as a colorless powder. UPLC-MS 3: m/z 715.2 [M+H]$^+$; $t_R$=1.10 min.

Step 2: Tert-butyl (((2S,3S,4S)-4-(6-Carbamoyl-2-fluoro-3-(2-oxopropoxy)phenyl)-5-chloro-6-fluoro-3-methyl-2-phenyl-2,3-dihydrobenzofuran-2-yl)methyl)((trans)-4-hydroxy-4-methylcyclohexyl)carbamate To a solution of tert-butyl (((2S,3S,4S)-4-(6-carbamoyl-2-fluoro-3-((S)-2-hydroxypropoxy)phenyl)-5-chloro-6-fluoro-3-methyl-2-phenyl-2,3-dihydrobenzofuran-2-yl)methyl)((trans)-4-hydroxy-4-methylcyclohexyl)carbamate (1750 mg, 2.447 mmol) in DCM (50 mL) was added at 0° C. Dess-Martin periodinane (1090 mg, 2.57 mmol) in portions. The reaction mixture was stirred at 0° C. for 3 h. The reaction mixture was diluted with DCM and washed with a 10% solution of Na$_2$S$_2$O$_3$ followed by a sat solution of NaHCO$_3$. The organic layer was dried over anhydrous MgSO$_4$ and concentrated. The crude product was purified by flash chromatography (silica, DCM/MeOH, gradient 2% to 10% MeOH) to afford the title compound (1350 mg) as a beige powder. UPLC-MS 3: m/z 713.3 [M+H]$^+$; $t_R$=1.10 min.

Step 3: Tert-butyl (((2S,3S,4S)-4-(6-carbamoyl-2-fluoro-3-(2-hydroxy-2-methylpropoxy)phenyl)-5-chloro-6-fluoro-3-methyl-2-phenyl-2,3-dihydrobenzofuran-2-yl)methyl)((trans)-4-hydroxy-4-methylcyclohexyl)carbamate Tert-butyl (((2S,3S,4S)-4-(6-carbamoyl-2-fluoro-3-(2-oxopropoxy)phenyl)-5-chloro-6-fluoro-3-methyl-2-phenyl-2,3-dihydrobenzofuran-2-yl)methyl)((trans)-4-hydroxy-4-methylcyclohexyl)carbamate (100 mg, 0.140 mmol) was dissolved in THF (3 mL) and cooled to −20° C. under a N$_2$ atmosphere. MeMgBr (0.280 mL, 0.840 mmol, 3 M in Et$_2$O) was added dropwise. The solution was stirred at −20° C. for 60 min, then quenched with 10% NH$_4$Cl-solution. The aqueous layer was extracted with EtOAc. The combined organic layers were combined, dried over anhydrous MgSO$_4$ and concentrated. The crude product was purified by flash chromatography (silica, DCM/MeOH, gradient: 1% to 6% MeOH) to afford the title compound (25 mg) as colorless solid. UPLC-MS 3: m/z 729.2 [M+H]$^+$; $t_R$=1.13 min.

Step 4: 2-((2S,3S,4S)-5-Chloro-6-fluoro-2-(((trans)-4-hydroxy-4-methylcyclohexyl)amino)methyl)-3-methyl-2-phenyl-2,3-dihydrobenzofuran-4-yl)-3-fluoro-4-(2-hydroxy-2-methylpropoxy)benzamide (Example 148)

Tert-butyl (((2S,3S,4S)-4-(6-carbamoyl-2-fluoro-3-(2-hydroxy-2-methylpropoxy)phenyl)-5-chloro-6-fluoro-3- methyl-2-phenyl-2,3-dihydrobenzofuran-2-yl)methyl)((trans)-4-hydroxy-4-methylcyclohexyl)carbamate (25 mg, 0.034 mmol) was dissolved in HCl (0.4 mL, 4 M in dioxane). The solution was stirred at RT for 2.5 h and then quenched with a sat solution of NaHCO₃. The aqueous layer was extracted with DCM. The combined organic layers were concentrated. The crude product was recrystallized from diisopropylether to obtain the title compound (19.5 mg) as a colorless solid. ¹H NMR (600 MHz, DMSO-d₆) δ 7.62 (s br, 1H), 7.56 (d, J=8.8 Hz, 1H), 7.46-7.38 (m, 2H), 7.37-7.21 (m, 4H), 7.06 (d, J=9.6 Hz, 1H), 4.66 (s, 1H), 4.03 (s, 1H), 3.90-3.79 (m, 2H), 3.26 (q, J=7.2 Hz, 1H), 3.08 (s br, 2H), 2.33-2.25 (m, 1H), 1.66-1.60 (m, 2H), 1.37-1.27 (m, 2H), 1.26-1.11 (m, 8H), 1.07-0.99 (m, 2H), 0.98 (s, 3H), 0.93 (d, J=7.2 Hz, 3H). UPLC-MS 3: m/z 630.4 [M+H]⁺, t$_R$=0.79 min.

Example 149: 2-((2S,4S)-2-(Azetidin-2-yl)-5-chloro-6-fluoro-2-phenyl-2,3-dihydrobenzofuran-4-yl)-3-fluoro-4-(2-hydroxyethoxy)-N-methylbenzamide

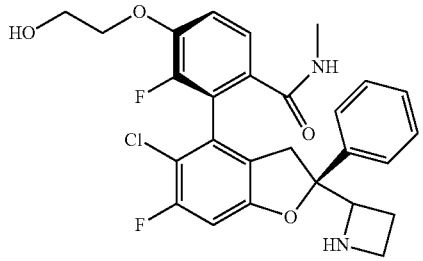

Reaction Scheme Example 149

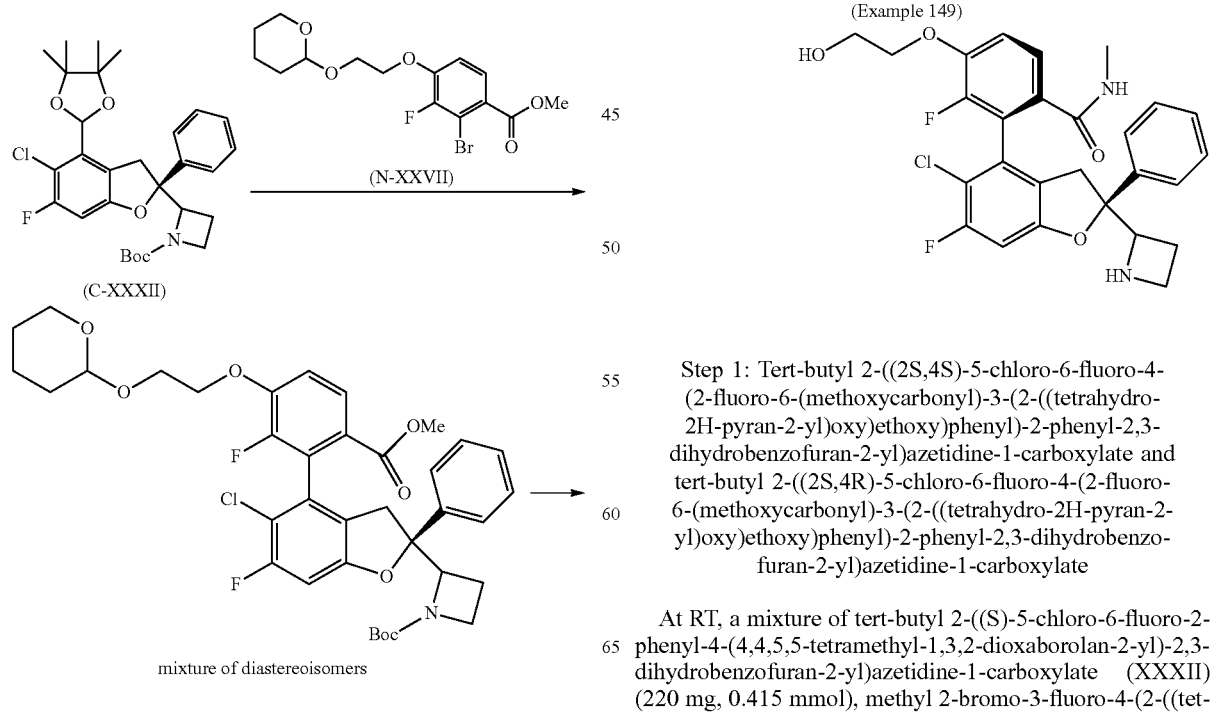

mixture of diastereoisomers

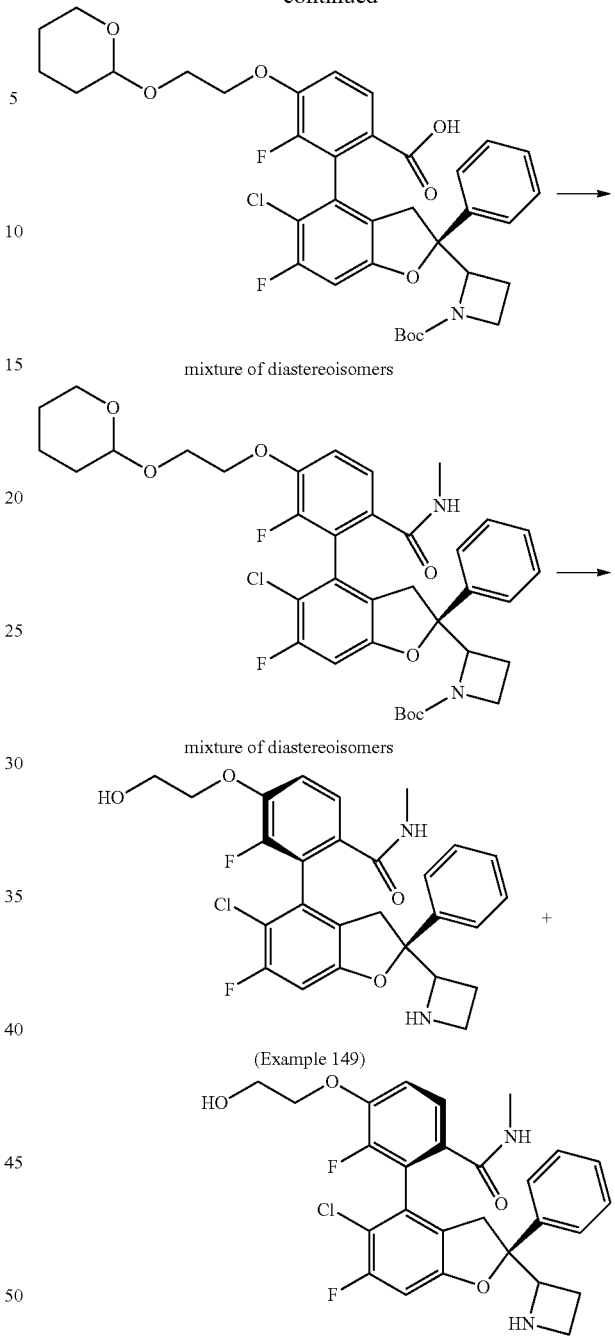

Step 1: Tert-butyl 2-((2S,4S)-5-chloro-6-fluoro-4-(2-fluoro-6-(methoxycarbonyl)-3-(2-((tetrahydro-2H-pyran-2-yl)oxy)ethoxy)phenyl)-2-phenyl-2,3-dihydrobenzofuran-2-yl)azetidine-1-carboxylate and tert-butyl 2-((2S,4R)-5-chloro-6-fluoro-4-(2-fluoro-6-(methoxycarbonyl)-3-(2-((tetrahydro-2H-pyran-2-yl)oxy)ethoxy)phenyl)-2-phenyl-2,3-dihydrobenzofuran-2-yl)azetidine-1-carboxylate At RT, a mixture of tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)azetidine-1-carboxylate (XXXII) (220 mg, 0.415 mmol), methyl 2-bromo-3-fluoro-4-(2-((tetrahydro-2H-pyran-2-yl)oxy)ethoxy)benzoate (N-XXVII) (235 mg, 0.623 mmol) and potassium triphosphate (264 mg, 1.25 mmol) suspended in toluene (4 mL) and water (0.8 mL) was degassed with Ar. N-Xantphos (22.9 mg, 0.042 mmol) and Pd$_2$(dba)$_3$ (19 mg, 0.021 mmol) were added. The reaction mixture was heated at 100° C. for 12 h. After cooling to RT the reaction mixture was partitioned between water and EtOAc. The organic phase was separated and the aqueous phase was extracted again with EtOAc. The combined organic layers were washed with brine, dried over anhydrous Na$_2$SO$_4$, filtered and concentrated. The crude product was purified by flash chromatography (silica, cyclohexane/EtOAc, gradient: 0% to 30% EtOAc) to afford a mixture of the title compounds (165 mg). UPLC-MS 1: m/z 700.3 [M+H]$^+$, $t_R$=1.50 min.

Step 2: 2-((2S,4S)-2-(1-(Tert-butoxycarbonyl)azetidin-2-yl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid and 2-((2S,4R)-2-(1-(tert-butoxycarbonyl)azetidin-2-yl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid At RT, to a stirred solution of a mixture of tert-butyl 2-((2S,4S)-5-chloro-6-fluoro-4-(2-fluoro-6-(methoxycarbonyl)-3-(2-((tetrahydro-2H-pyran-2-yl)oxy)ethoxy)phenyl)-2-phenyl-2,3-dihydrobenzofuran-2-yl)azetidine-1-carboxylate and tert-butyl 2-((2S,4R)-5-chloro-6-fluoro-4-(2-fluoro-6-(methoxycarbonyl)-3-(2-((tetrahydro-2H-pyran-2-yl)oxy)ethoxy)phenyl)-2-phenyl-2,3-dihydrobenzofuran-2-yl)azetidine-1-carboxylate (160 mg, 0.229 mmol) in MeOH (1.9 mL) and THF (0.95 mL) was added 4 M NaOH aq. (0.57 mL, 2.29 mmol). The reaction mixture was stirred at 40° C. for 5 h. After cooling to RT, water was added and the pH was adjusted to ~2 with 2 N HCl. The mixture was extracted twice with EtOAc. The combined organic layers were washed with brine, dried over anhydrous Na$_2$SO$_4$, filtered and concentrated to give a mixture of the title compounds which was used in the next step without further purification. UPLC-MS 1: m/z 684.1/686.0 [M−H]$^-$, $t_R$=1.37 and 1.39 min.

Step 3: Tert-butyl 2-((2S,4S)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)azetidine-1-carboxylate and tert-butyl 2-((2S,4R)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)azetidine-1-carboxylate At RT, to a stirred solution of a mixture of 2-((2S,4S)-2-(1-(Tert-butoxycarbonyl)azetidin-2-yl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid and 2-((2S,4R)-2-(1-(tert-butoxycarbonyl)azetidin-2-yl)-5-chloro-6-fluoro-2-phenyl-2,3-dihydrobenzofuran-4-yl)-3-fluoro-4-(2-((tetrahydro-2H-pyran-2-yl)oxy)ethoxy)benzoic acid (120 mg, 0.175 mmol) in DMF (1.4 mL) were successively added DIPEA (0.183 mL, 1.05 mmol), methylamine hydrochloride (24 mg, 0.35 mmol) and HATU (106 mg, 0.28 mmol). The reaction mixture was stirred at RT for 3 h. A sat. solution of NaHCO$_3$ was added. The mixture was extracted twice with TBME. The combined organic layers were washed with brine, dried over anhydrous Na$_2$SO$_4$ filtered and concentrated to give a mixture of the title compounds (125 mg) which was used in the next step without further purification. UPLC-MS 1: m/z 743.1/745.1 [M+formate]$^-$, $t_R$=1.38 and 1.41 min.

Step 4: 2-((2S,4S)-2-(Azetidin-2-yl)-5-chloro-6-fluoro-2-phenyl-2,3-dihydrobenzofuran-4-yl)-3-fluoro-4-(2-hydroxyethoxy)-N-methylbenzamide (Example 149) and 2-((2S,4R)-2-(azetidin-2-yl)-5-chloro-6-fluoro-2-phenyl-2,3-dihydrobenzofuran-4-yl)-3-fluoro-4-(2-hydroxyethoxy)-N-methylbenzamide To a stirred solution of a mixture of tert-butyl 2-((2S,4S)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)azetidine-1-carboxylate and tert-butyl 2-((2S,4R)-5-chloro-6-fluoro-4-(2-fluoro-6-(methylcarbamoyl)-3-(2-((tetrahydro-2H-pyran-2-yl)oxy)ethoxy)phenyl)-2-phenyl-2,3-dihydrobenzofuran-2-yl)azetidine-1-carboxylate in DCM (5 mL) was slowly added TFA (0.18 mL, 2.37 mmol). The reaction mixture was stirred at RT for 45 min, then quenched with a sat solution of NaHCO$_3$. The mixture was extracted twice with EtOAc. The combined organic layers were washed with brine, dried over anhydrous Na$_2$SO$_4$ filtered and concentrated. The crude material was purified by preparative HPLC and the diastereoisomers were separated:

2-((2S,4S)-2-(Azetidin-2-yl)-5-chloro-6-fluoro-2-phenyl-2,3-dihydrobenzofuran-4-yl)-3-fluoro-4-(2-hydroxyethoxy)-N-methylbenzamide (Example 149) (6.8 mg): UPLC-MS 1: m/z 515.1/517.0 [M+H]$^+$, $t_R$=0.68 min.

Other diastereomer 2-((2S,4R)-2-(azetidin-2-yl)-5-chloro-6-fluoro-2-phenyl-2,3-dihydrobenzofuran-4-yl)-3-fluoro-4-(2-hydroxyethoxy)-N-methylbenzamide (Example) (7 mg): UPLC-MS 1: m/z 515.1/517.0 [M+H]$^+$, $t_R$=0.64 min.

Example 150: 2-((2S,3S,4S)-2-(Azetidin-2-yl)-5-chloro-6-fluoro-3-methyl-2-phenyl-2,3-dihydrobenzofuran-4-yl)-3-fluoro-4-((S)-2-hydroxypropoxy)-N-methylbenzamide

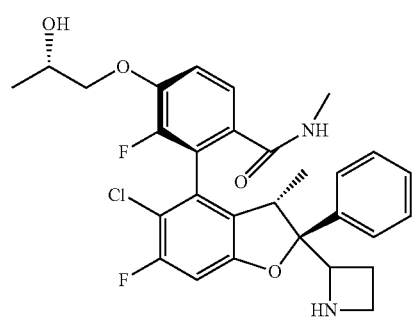

The title compound was prepared analogously to Example 149 from tert-butyl 2-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)azetidine-1-carboxylate (C-XXXIII) and methyl (S)-2-bromo-3-fluoro-4-(2-hydroxypropoxy)benzoate (N-XXXIII). The diastereoisomers were separated after final Boc- and THP deprotection. $^1$H NMR (600 MHz, DMSO-d$_6$) δ (ppm) 8.22 (d, J=4.8 Hz, 1H), 7.46 (t, J=7.5 Hz, 3H), 7.35-7.19 (m, 5H), 7.17 (d, J=9.5 Hz, 1H), 4.95 (d, J=4.0 Hz, 1H), 4.46 (t, J=7.6 Hz, 1H), 3.95 (q, J=6.5 Hz, 2H), 3.89 (t, J=6.5 Hz, 1H), 3.23 (q, J=7.3 Hz, 1H), 2.94 (td, J=7.9, 4.1 Hz, 1H), 2.60 (d, J=4.6 Hz, 3H), 2.26-2.10 (m, 2H), 1.11 (d, J=5.3 Hz, 3H), 0.85 (d, J=7.2 Hz, 3H). UPLC-MS 1: m/z 543.2/545.3 [M+H]$^+$, $t_R$=0.72 min.

Example 151: (2-((2S,4S)-5-Chloro-6-fluoro-2-phenyl-2-((S)-pyrrolidin-2-yl)-2,3-dihydrobenzofuran-4-yl)-3-fluoro-4-(2-hydroxyethoxy)benzamide

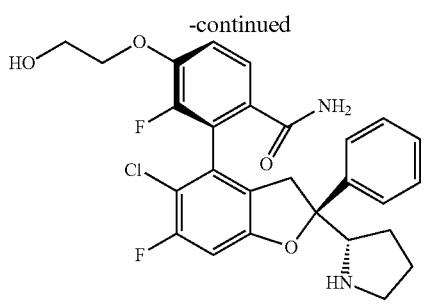

(Example 151)

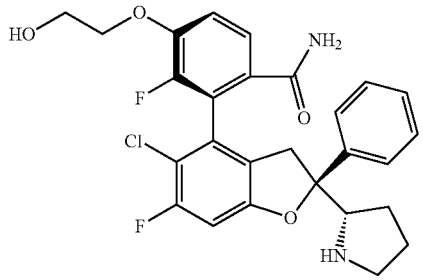

Reaction Scheme Example.151

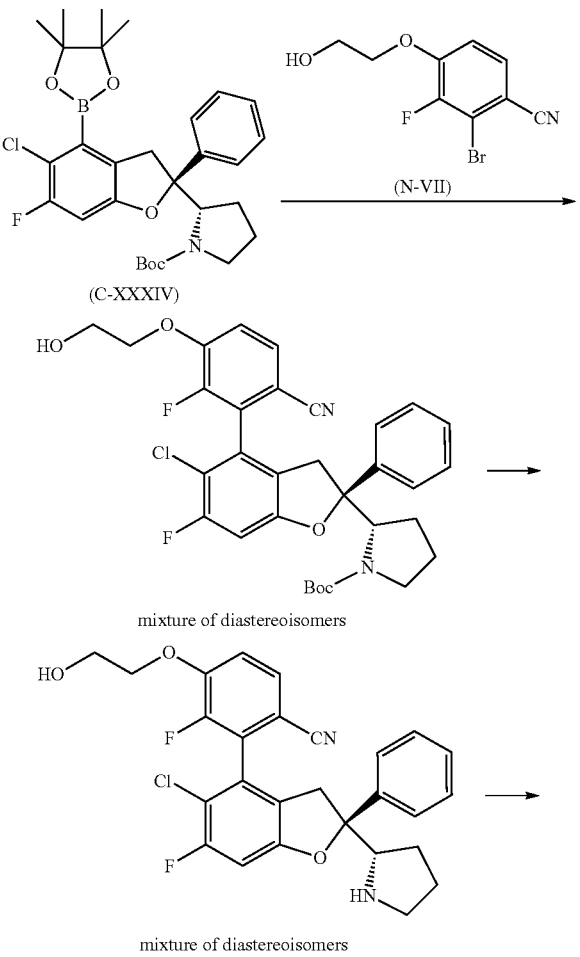

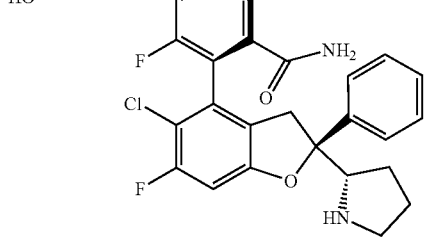

Step 1: Tert-butyl (S)-2-((2S,4S)-5-chloro-4-(6-cyano-2-fluoro-3-(2-hydroxyethoxy)phenyl)-6-fluoro-2-phenyl-2,3-dihydrobenzofuran-2-yl)pyrrolidine-1-carboxylate and tert-butyl (S)-2-((2S,4R)-5-chloro-4-(6-cyano-2-fluoro-3-(2-hydroxyethoxy)phenyl)-6-fluoro-2-phenyl-2,3-dihydrobenzofuran-2-yl)pyrrolidine-1-carboxylate A mixture pf the title compounds (961 mg) was obtained from tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate (C-XXXIV) (1.4 g, 2.57 mmol) and 2-bromo-3-fluoro-4-(2-hydroxyethoxy)benzonitrile (N-VII) (0.736 g, 2.83 mmol) using similar reaction conditions as described for Example 149, step 1. UPLC-MS 1: m/z 597.4/599.4 [M+H]$^+$, $t_R$=1.34 min.

Step 2: 2-((2S,4S)-5-Chloro-6-fluoro-2-phenyl-2-((S)-pyrrolidin-2-yl)-2,3-dihydrobenzofuran-4-yl)-3-fluoro-4-(2-hydroxyethoxy)benzonitrile and 2-((2S,4R)-5-chloro-6-fluoro-2-phenyl-2-((S)-pyrrolidin-2-yl)-2,3-dihydrobenzofuran-4-yl)-3-fluoro-4-(2-hydroxyethoxy)benzonitrile At RT, a mixture of tert-butyl (S)-2-((2S,4S)-5-chloro-4-(6-cyano-2-fluoro-3-(2-hydroxyethoxy)phenyl)-6-fluoro-2-phenyl-2,3-dihydrobenzofuran-2-yl)pyrrolidine-1-carboxylate and tert-butyl (S)-2-((2S,4R)-5-chloro-4-(6-cyano-2-fluoro-3-(2-hydroxyethoxy)phenyl)-6-fluoro-2-phenyl-2,3-dihydrobenzofuran-2-yl)pyrrolidine-1-carboxylate (961 mg, 1.60 mmol) was treated with HCl (4 mL, 16.1 mmol, 4 M in dioxane) for 16 h. The reaction mixture was quenched with a sat solution of NaHCO$_3$. The combined organic layers were washed with sat. NaHCO$_3$ and brine, dried over anhydrous Na$_2$SO$_4$ and concentrated. The residue was purified by flash chromatography (silica, DCM/MeOH, gradient: 0% to 10% MeOH) to give a mixture of the title compounds (288 g), as a colorless solid. UPLC-MS 1: m/z 497.3/499.3 [M+H]$^+$, $t_R$=0.76 and 0.77 min.

Step 3: 2-((2S,4S)-5-Chloro-6-fluoro-2-phenyl-2-((S)-pyrrolidin-2-yl)-2,3-dihydrobenzofuran-4-yl)-3-fluoro-4-(2-hydroxyethoxy)benzamide (Example 151) and 2-((2S,4R)-5-chloro-6-fluoro-2-phenyl-2-((S)-pyrrolidin-2-yl)-2,3-dihydrobenzofuran-4-yl)-3-fluoro-4-(2-hydroxyethoxy)benzamide A mixture of the title compounds was obtained from a mixture of 2-((2S,4S)-5-chloro-6-fluoro-2-phenyl-2-((S)-pyrrolidin-2-yl)-2,3-dihydrobenzofuran-4-yl)-3-fluoro-4-(2-hydroxyethoxy)benzonitrile and 2-((2S,4R)-5-chloro-6-fluoro-2-phenyl-2-((S)-pyrrolidin-2-yl)-2,3-dihydrobenzofuran-4-yl)-3-fluoro-4-(2-hydroxyethoxy)benzonitrile (245 mg, 0.493 mmol) using similar reaction conditions as described for Example 5a, step 2 followed by flash chromatography (silica, DCM/MeOH, gradient 4 to 14% MeOH) to separate the diastereomers.

2-((2S,4S)-5-chloro-6-fluoro-2-phenyl-2-((S)-pyrrolidin-2-yl)-2,3-dihydrobenzofuran-4-yl)-3-fluoro-4-(2-hydroxyethoxy)benzamide (Example 151) (107 mg): $^1$H NMR (400 MHz, DMSO-d$_6$) δ (ppm) 7.61 (s br, 1H), 7.51 (dd, J=8.7, 1.3 Hz, 1H), 7.48-7.41 (m, 2H), 7.37-7.18 (m, 5H), 7.02 (d, J=9.6 Hz, 1H), 4.96 (t, J=5.4 Hz, 1H), 4.14 (t, J=4.8 Hz, 2H), 3.75 (q, J=5.2 Hz, 2H), 3.52 (t, J=7.8 Hz, 1H), 3.47 (d, J=16.0 Hz, 1H), 2.87 (d, J=16.0 Hz, 1H), 2.74-2.66 (m, 1H), 2.62-2.55 (m, 1H), 1.62-1.52 (m, 1H), 1.51-1.37 (m, 2H), 1.38-1.27 (m, 1H). UPLC-MS 1: m/z 515.4/517.4 [M+H]$^+$, t$_R$=0.66 min.

Other diastereomer 2-((2S,4R)-5-chloro-6-fluoro-2-phenyl-2-((S)-pyrrolidin-2-yl)-2,3-dihydrobenzofuran-4-yl)-3-fluoro-4-(2-hydroxyethoxy)benzamide (112 mg) UPLC-MS 1: m/z 515.4/517.4 [M+H]$^+$, t$_R$=0.59 min.

Example 152: 2-((2S,4S)-5-Chloro-6-fluoro-2-phenyl-2-((S)-pyrrolidin-2-yl)-2,3-dihydrobenzofuran-4-yl)-3-fluoro-4-((S)-2-hydroxypropoxy)benzamide

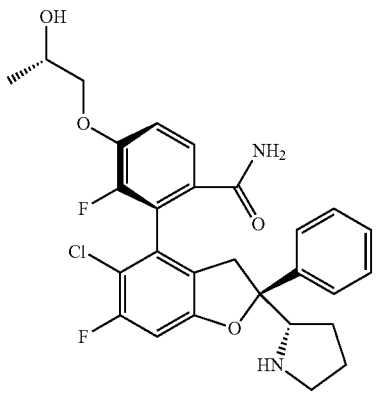

The title compound (92 mg, white powder) was prepared analogously to Example 151, starting from tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate (C-XXXIV) (600 mg, 1.103 mmol) and (S)-2-bromo-3-fluoro-4-(2-hydroxypropoxy)benzonitrile (N-XIV) (648 mg, 1.655 mmol). The diastereomers were separated at the last step. 2-((2S,4S)-5-Chloro-6-fluoro-2-phenyl-2-((S)-pyrrolidin-2-yl)-2,3-dihydrobenzofuran-4-yl)-3-fluoro-4-((S)-2-hydroxypropoxy)benzamide (Example. 152): $^1$H NMR (600 MHz, DMSO-d$_6$) δ (ppm) 7.62 (s, 1H), 7.50 (d, J=8.8 Hz, 1H), 7.47-7.40 (m, 2H), 7.36-7.18 (m, 5H), 7.02 (d, J=9.6 Hz, 1H), 4.96 (d, J=4.1 Hz, 1H), 4.08-3.87 (m, 3H), 3.61-3.50 (m, 1H), 3.46 (d, J=15.9 Hz, 1H), 2.87 (d, J=15.9 Hz, 1H), 2.77-2.66 (m, 1H), 2.66-2.56 (m, 1H), 1.69-1.52 (m, 1H), 1.52-1.38 (m, 2H), 1.38-1.26 (m, 1H), 1.14 (d, J=5.5 Hz, 3H). UPLC-MS 1: m/z 529.3/531.3 [M+H]$^+$, t$_R$=0.70 min.

Other diastereomer 2-((2S,4R)-5-chloro-6-fluoro-2-phenyl-2-((S)-pyrrolidin-2-yl)-2,3-dihydrobenzofuran-4-yl)-3-fluoro-4-((S)-2-hydroxypropoxy)benzamide UPLC-MS 1: m/z 529.4/531.4 [M+H]$^+$, t$_R$=0.65 min.

Example 153: 2-((2S,4S)-5-Chloro-6-fluoro-2-phenyl-2-((S)-pyrrolidin-2-yl)-2,3-dihydrobenzofuran-4-yl)-3-fluoro-4-(2-hydroxyethoxy)-N-methylbenzamide

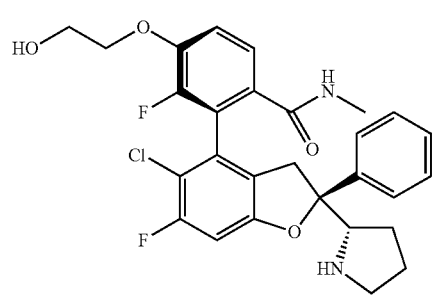

Reaction Scheme Example.153

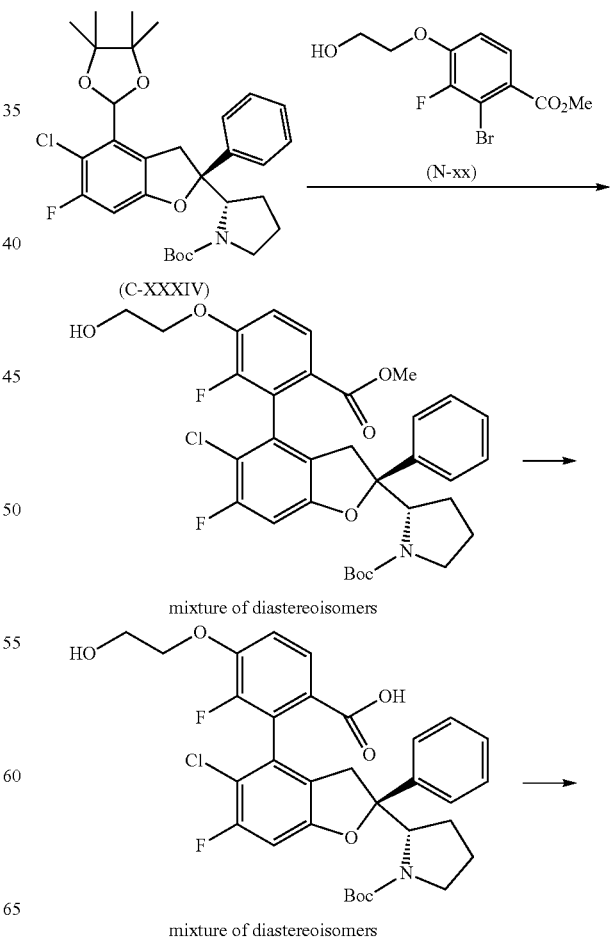

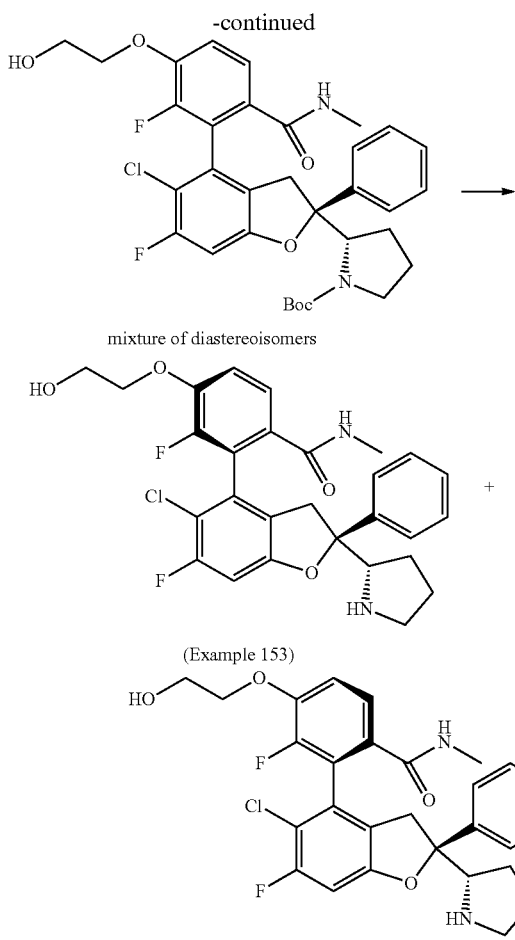

(Example 153)

Step 1: Tert-butyl (S)-2-((2S,4S)-5-chloro-6-fluoro-4-(2-fluoro-3-(2-hydroxyethoxy)-6-(methoxycarbonyl)phenyl)-2-phenyl-2,3-dihydrobenzofuran-2-yl)pyrrolidine-1-carboxylate and tert-butyl (S)-2-((2S, 4R)-5-chloro-6-fluoro-4-(2-fluoro-3-(2-hydroxyethoxy)-6-(methoxycarbonyl)phenyl)-2-phenyl-2,3-dihydrobenzofuran-2-yl)pyrrolidine-1-carboxylate A suspension of tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate (C-XXXIV) (3.73 g, 6.86 mmol), methyl 2-bromo-3-fluoro-4-(2-hydroxyethoxy)benzoate (N-XXXIV) (3.02 g, 10.29 mmol), K₃PO₄ (4.37 g, 20.6 mmol), N-Xantphos (0.378 g, 0.686 mmol) and Pd₂(dba)₃ (0.314 g, 0.343 mmol) in toluene/water (5:1, 240 mL) was degassed with Ar and heated at 100° C. for 19 h. At RT, a sat solution of NaHCO₃ was added and the mixture was extracted twice with EtOAc. The combined organic layers were washed with brine, dried over anhydrous Na₂SO₄ and concentrated. The crude products were purified by flash chromatography (silica, cyclohexane/EtOAc, gradient: 0% to 80% EtOAc) to yield a mixture of the title compounds (3.95 g) as a yellow oil. UPLC-MS 1: m/z 630.6/632.6 [M+H]⁺, $t_R$=1.37 and 1.38 min.

Step 2: 2-((2S,4S)-2-((S)-1-(Tert-butoxycarbonyl)pyrrolidin-2-yl)-5-chloro-6-fluoro-2-phenyl-2,3-dihydrobenzofuran-4-yl)-3-fluoro-4-(2-hydroxyethoxy)benzoic acid and 2-((2S,4R)-2-((S)-1-(tert-butoxycarbonyl)pyrrolidin-2-yl)-5-chloro-6-fluoro-2-phenyl-2,3-dihydrobenzofuran-4-yl)-3-fluoro-4-(2-hydroxyethoxy)benzoic acid At RT, to a stirred solution of a mixture of tert-butyl (S)-2-((2S,4S)-5-chloro-6-fluoro-4-(2-fluoro-3-(2-hydroxyethoxy)-6-(methoxycarbonyl)phenyl)-2-phenyl-2,3-dihydrobenzofuran-2-yl)pyrrolidine-1-carboxylate and tert-butyl (S)-2-((2S,4R)-5-chloro-6-fluoro-4-(2-fluoro-3-(2-hydroxyethoxy)-6-(methoxycarbonyl)phenyl)-2-phenyl-2,3-dihydrobenzofuran-2-yl)pyrrolidine-1-carboxylate in dioxane (15 mL) and water (15 mL) was added LiOH·H₂O (0.721 g, 30.1 mmol). The reaction mixture was stirred for 6 h at 60° C. before it was quenched with water and acidified with 1 N HCl. The mixture was extracted twice with DCM. The combined organic layers were washed with brine, dried over anhydrous Na₂SO₄ and concentrated to give a mixture of the title compounds (3.34 g) as a brown oil, which was used directly in the next step. UPLC-MS 1: m/z 614.5/616.5 [M+H]⁺, $t_R$=1.19 and 1.20 min.

Step 3: Tert-butyl (S)-2-((2S,4S)-5-chloro-6-fluoro-4-(2-fluoro-3-(2-hydroxyethoxy)-6-(methylcarbamoyl)phenyl)-2-phenyl-2,3-dihydrobenzofuran-2-yl)pyrrolidine-1-carboxylate and tert-butyl (S)-2-((2S, 4R)-5-chloro-6-fluoro-4-(2-fluoro-3-(2-hydroxyethoxy)-6-(methylcarbamoyl)phenyl)-2-phenyl-2,3-dihydrobenzofuran-2-yl)pyrrolidine-1-carboxylate A mixture of the title compounds (2.64 g, brown oil) was obtained from a mixture of 2-((2S,4S)-2-((S)-1-(tert-butoxycarbonyl)pyrrolidin-2-yl)-5-chloro-6-fluoro-2-phenyl-2,3-dihydrobenzofuran-4-yl)-3-fluoro-4-(2-hydroxyethoxy)benzoic acid and 2-((2S,4R)-2-((S)-1-(tert-butoxycarbonyl)pyrrolidin-2-yl)-5-chloro-6-fluoro-2-phenyl-2,3-dihydrobenzofuran-4-yl)-3-fluoro-4-(2-hydroxyethoxy)benzoic acid (3.34 g, 5.42 mmol) using similar reaction conditions as described for Example 149, step 3. UPLC-MS 1: m/z 629.5/631.5 [M+H]⁺, $t_R$=1.23 and 1.26 min.

Step 4: 2-((2S,4S)-5-Chloro-6-fluoro-2-phenyl-2-((S)-pyrrolidin-2-yl)-2,3-dihydrobenzofuran-4-yl)-3-fluoro-4-(2-hydroxyethoxy)-N-methylbenzamide (Example 153) and 2-((2S,4R)-5-chloro-6-fluoro-2-phenyl-2-((S)-pyrrolidin-2-yl)-2,3-dihydrobenzofuran-4-yl)-3-fluoro-4-(2-hydroxyethoxy)-N-methylbenzamide A mixture of the title compounds was obtained from a mixture of tert-butyl (S)-2-((2S,4S)-5-chloro-6-fluoro-4-(2-fluoro-3-(2-hydroxyethoxy)-6-(methylcarbamoyl)phenyl)-2-phenyl-2,3-dihydrobenzofuran-2-yl)pyrrolidine-1-carboxylate and tert-butyl (S)-2-((2S,4R)-5-chloro-6-fluoro-4-(2-fluoro-3-(2-hydroxyethoxy)-6-(methylcarbamoyl)phenyl)-2-phenyl-2,3-dihydrobenzofuran-2-yl)pyrrolidine-1-carboxylate (3.34 g, 5.42 mmol) using similar reaction conditions as described for Example 22, step 5. The diastereoisomers were separated by flash chromatography (silica, DCM/MeOH, gradient 1 to 14% MeOH).

2-((2S,4S)-5-Chloro-6-fluoro-2-phenyl-2-((S)-pyrrolidin-2-yl)-2,3-dihydrobenzofuran-4-yl)-3-fluoro-4-(2-hydroxyethoxy)-N-methylbenzamide (Example 153) (303 mg): $^1$H NMR (400 MHz, DMSO-$d_6$) δ (ppm) 8.10 (q, J=4.5 Hz, 1H), 7.46-7.41 (m, 3H), 7.38-7.22 (m, 4H), 7.01 (d, J=9.7 Hz, 1H), 4.96 (t, J=5.4 Hz, 1H), 4.14 (t, J=4.9 Hz, 2H), 3.75 (q, J=5.1 Hz, 2H), 3.58-3.52 (m, 1H), 3.42 (dd, J=16.0, 1.8 Hz, 1H), 2.87 (dd, J=15.8, 1.6 Hz, 1H), 2.79-2.71 (m, 1H), 2.70-2.65 (m, 1H), 2.63 (d, J=4.6 Hz, 3H), 1.60-1.36 (m, 4H). UPLC-MS 1: m/z 529.4/531.4 [M+H]$^+$, $t_R$=0.67 min.

Other diastereomer 2-((2S,4R)-5-chloro-6-fluoro-2-phenyl-2-((S)-pyrrolidin-2-yl)-2,3-dihydrobenzofuran-4-yl)-3-fluoro-4-(2-hydroxyethoxy)-N-methylbenzamide (Example) (375 mg) UPLC-MS 1: m/z 529.5/531.5 [M+H]$^+$, $t_R$=0.58 min.

Example 154: 2-((2S,4S)-5-Chloro-6-fluoro-2-phenyl-2-((S)-pyrrolidin-2-yl)-2,3-dihydrobenzofuran-4-yl)-3-fluoro-4-((S)-2-hydroxypropoxy)-N-methylbenzamide

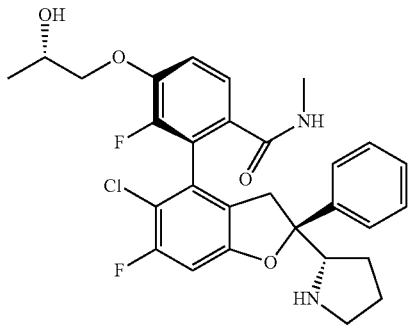

The title compound was prepared analogously to Example 153, starting from tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate (C-XXXIV) and methyl (S)-2-bromo-3-fluoro-4-(2-hydroxypropoxy)benzoate (N-XXXIII).

2-((2S,4S)-5-Chloro-6-fluoro-2-phenyl-2-((S)-pyrrolidin-2-yl)-2,3-dihydrobenzofuran-4-yl)-3-fluoro-4-((S)-2-hydroxypropoxy)-N-methylbenzamide (Example. 154): $^1$H NMR (400 MHz, DMSO-$d_6$) δ (ppm) 8.10 (q, J=4.5 Hz, 1H), 7.46-7.41 (m, 3H), 7.38-7.20 (m, 4H), 7.01 (d, J=9.6 Hz, 1H), 4.96 (d, J=4.3 Hz, 1H), 4.06-3.86 (m, 3H), 3.55 (t, J=6.7 Hz, 1H), 3.42 (dd, J=15.9 Hz, 1.7 Hz, 1H), 2.87 (dd, J=15.9 1.5 Hz, 1H), 2.78-2.71 (m, 1H), 2.69-2.65 (m, 1H), 2.63 (d, J=4.8 Hz, 3H), 1.67-1.34 (m, 4H), 1.15 (d, J=5.8 Hz, 3H). UPLC-MS 1: m/z 543.4 [M+H]$^+$, $t_R$=0.74 min.

Other diastereomer 2-((2S,4R)-5-chloro-6-fluoro-2-phenyl-2-((S)-pyrrolidin-2-yl)-2,3-dihydrobenzofuran-4-yl)-3-fluoro-4-((S)-2-hydroxypropoxy)-N-methylbenzamide: UPLC-MS 1: m/z 543.4 [M+H]$^+$, $t_R$=0.67 min.

Example 155: 4-((2S,4S)-5-Chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide or (4P)-4-{(2S)-5-Chloro-6-fluoro-2-phenyl-2-[(2S)-pyrrolidin-2-yl]-2,3-dihydro-1-benzofuran-4-yl}-5-fluoro-6-(2-hydroxyethoxy)-N-methylpyridine-3-carboxamide

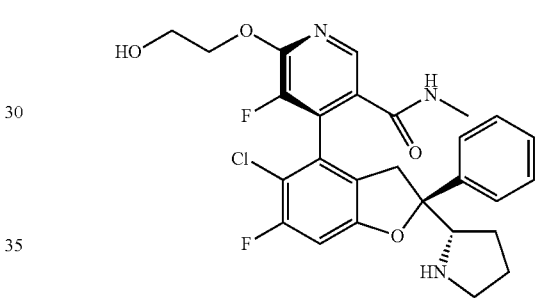

The title compound could be synthesized via the following routes.

Reaction Scheme 1 Example 155

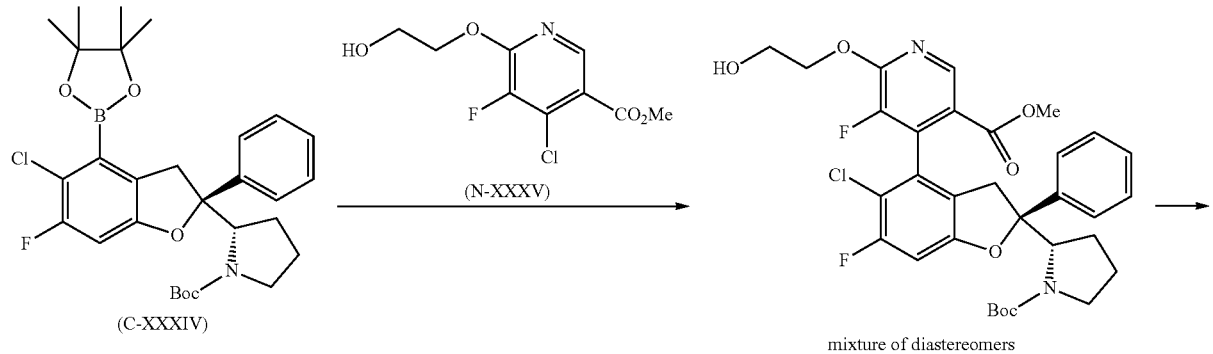

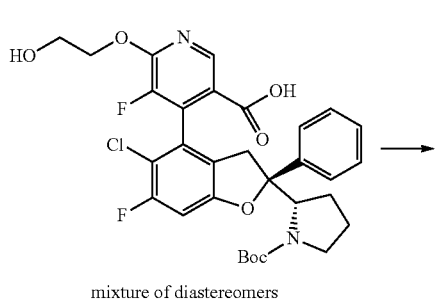

mixture of diastereomers

-continued

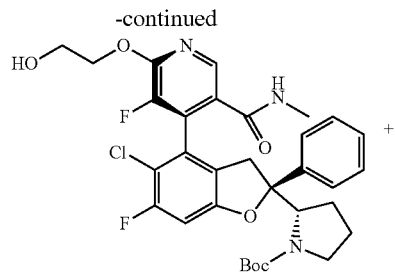

+

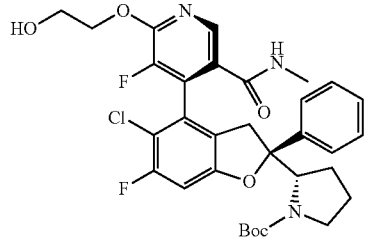

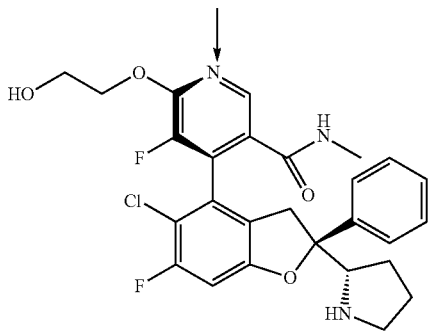

(Example 155)

Step 1: Methyl 4-(2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-hydroxyethoxy)nicotinate A suspension of tert-butyl (S)-2-((S)-5-chloro-6-fluoro-2-phenyl-4-(4,4,5,5-tetramethyl-1,3,2-dioxaborolan-2-yl)-2,3-dihydrobenzofuram-2-yl)pyrrolidine-1-carboxylate (C-XXXIV) (4.16 g, 7.65 mmol), methyl 4-chloro-5-fluoro-6-(2-hydroxyethoxy)nicotinate (N-XXXV) (2.86 g, 11.47 mmol), $K_3PO_4$ (4.87 g, 22.95 mmol), N-Xantphos (0.421 g, 0.765 mmol) and $Pd_2(dba)_3$ (0.350 g, 0.382 mmol) in toluene/water (ratio 5:1, 48 mL) was degassed with Ar and heated at 100° C. for 20 h. At RT, a sat solution of $NaHCO_3$ was added and the mixture was extracted twice with EtOAc. The combined organic layers were washed with brine, dried over anhydrous $Na_2SO_4$ and concentrate. The crude products were purified by flash chromatography (silica, cyclohexane/EtrOAc, gradient: 0% to 80% EtOAc) to yield a mixture of the title compounds (1.1 g) as a yellow oil. UPLC-MS 1: m/z 631.3/633.3 [M+H]$^+$, $t_R$=1.39 min.

Step 2: 4-((2S,4S)-2-((S)-1-(Tert-butoxycarbonyl)pyrrolidin-2-yl)-5-chloro-6-fluoro-2-phenyl-2,3-dihydrobenzofuran-4-yl)-5-fluoro-6-(2-hydroxyethoxy)nicotinic acid and 4-((2S,4R)-2-((S)-1-(tert-butoxycarbonyl)pyrrolidin-2-yl)-5-chloro-6-fluoro-2-phenyl-2,3-hydrobenzofuran-4-yl)-5-fluor-6-(2-hydroxyethoxy)nicotinic acid LiOH·$H_2O$ (0.55 g, 22.98 mmol) was added to a solution of a mixture of methyl 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-hydroxyethoxy)nicotinate and methyl 4-((2S,4R)-2-(S)-1-(tert-butoxycarbonyl)pyrrolidin-2-yl)-5-chloro-6-fluoro-2-phenyl-2,3-dihydrobenzofuran-4-yl)-5-fluoro-6-(2-hydroxyethoxy)nicotinate (1.4 g, 2.30 mmol) in dioxane (5 mL) and water (5 mL) and the reaction mixture was stirred at 70° C. for 8 h. The reaction mixture was dilated with water (100 mL) acidified with 1 N HCl and extracted twice with DCM. The organic layers were combined, dried over anhydrous $Na_2SO_4$ and concentrated to afford a mixture of the title compounds (1.52 g) as a colorless powder which was used without further purification in the next step. UPLC-MS 1: m/z 617.3/619.3 [M+H]$^+$, $t_R$=1.19 and 1.20 min.

Step 3: Tert-butyl (S)-2-((2S,4S)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)pyrrolidine-1-carboxylate and tert-butyl (S)-2-((2S,4R)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)pyrrolidine-1-carboxylate HATU (1.5 g, 3.94 mmol) was added to a stirred solution of a mixture of 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-hydroxyethoxy)nicotinic acid and 4-((2S,4R)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-hydroxyethoxy)nicotinic acid (1.52 g, 2.46 mmol), DIPEA (2.6 mL, 14.8 mmol) and methylamine hydrochloride (0.35 g, 4.95 mmol) in DMF (15 mL). The reaction mixture was stirred at RT for 1 h. A sat solution of $NaHCO_3$ was added and the mixture was extracted twice with EtOAc. The combined organic layers were washed with a sat solution of $NaHCO_3$ and water, dried over anhydrous $Na_2SO_4$, filtered and concentrated. The crude product was purified by flash chromatography (silica, cyclohexane/EtOAc, gradient: 0% to 80% EtOAc) to afford the title compounds as separate diastereoisomers.

Tert-butyl (S)-2-((2S,4S)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)pyrrolidine-1-carboxylate (483 mg): UPLC-MS 1: m/z 630.3/632.3 [M+H]$^+$, $t_R$=1.26 min.

Other diastereomer tert-butyl (S)-2-((2S,4R)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)

pyrrolidine-1-carboxylate (634 mg): UPLC-MS 1: m/z 630.3/632.3 [M+H]$^+$, $t_R$=1.23 min.

Step 4: 4-((2S,4S)-5-Chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide or (4P)-4-{(2S)-5-Chloro-6-fluoro-2-phenyl-2-[(2S)-pyrrolidin-2-yl]-2,3-dihydro-1-benzofuran-4-yl}-5-fluoro-6-(2-hydroxyethoxy)-N-methylpyridine-3-carboxamide (Example 155)

At RT, HCl (1.9 mL, 7.67 mmol, 4 M in dioxane) was added to a stirred solution of ert-butyl (S)-2-((2S,4S)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)pyrrolidine-1-carboxylate (483 mg, 0.767 mmol) in dioxane (10 mL). The reaction mixture was stirred at RT for 40 h, then was quenched with a sat solution of NaHCO$_3$ and extracted twice with EtOAc. The combined organic layers were washed with a sat solution of NaHCO$_3$, dried over anhydrous Na$_2$SO$_4$, filtered and concentrated. The crude product was purified by flash chromatography (silica, DCM/MeOH, gradient: 0% to 15% EtOAc) to afford the title compound (303 mg) as a colorless powder. $^1$H NMR (600 MHz, DMSO-d$_6$) δ (ppm) 8.42 (q, J=4.6 Hz, 1H), 8.27 (s, 1H), 7.46-7.42 (m, 2H), 7.33 (t, J=7.6 Hz, 2H), 7.26 (dd, J=8.3, 6.2 Hz, 1H), 7.07 (d, J=9.6 Hz, 1H), 4.95 (t, J=5.5 Hz, 1H), 4.44 (ddt, J=21.1, 10.9, 5.5 Hz, 2H), 3.76 (q, J=5.1 Hz, 2H), 3.51 (t, J=6.8 Hz, 1H), 3.43 (d, J=16.0 Hz, 1H), 2.96 (d, J=16.0 Hz, 1H), 2.74 (dt, J=12.6, 6.4 Hz, 1H), 2.66 (d, J=4.6 Hz, 3H), 2.65-2.60 (m, 1H), 2.29 (s br, 1H), 1.55-1.43 (m, 2H), 1.42-1.33 (m, 2H). UPLC-MS 1: m/z 530.5/532.5 [M+H]$^+$, $t_R$=0.69 min. UPLC-MS 2: m/z 530.5/532.5 [M+H]$^+$, $t_R$=3.02 min. The absolute configuration was confirmed by an X-ray cocrystal structure of Example 155 bound to the YAP binding site of TEAD3.

Reaction Scheme 2 Example 155

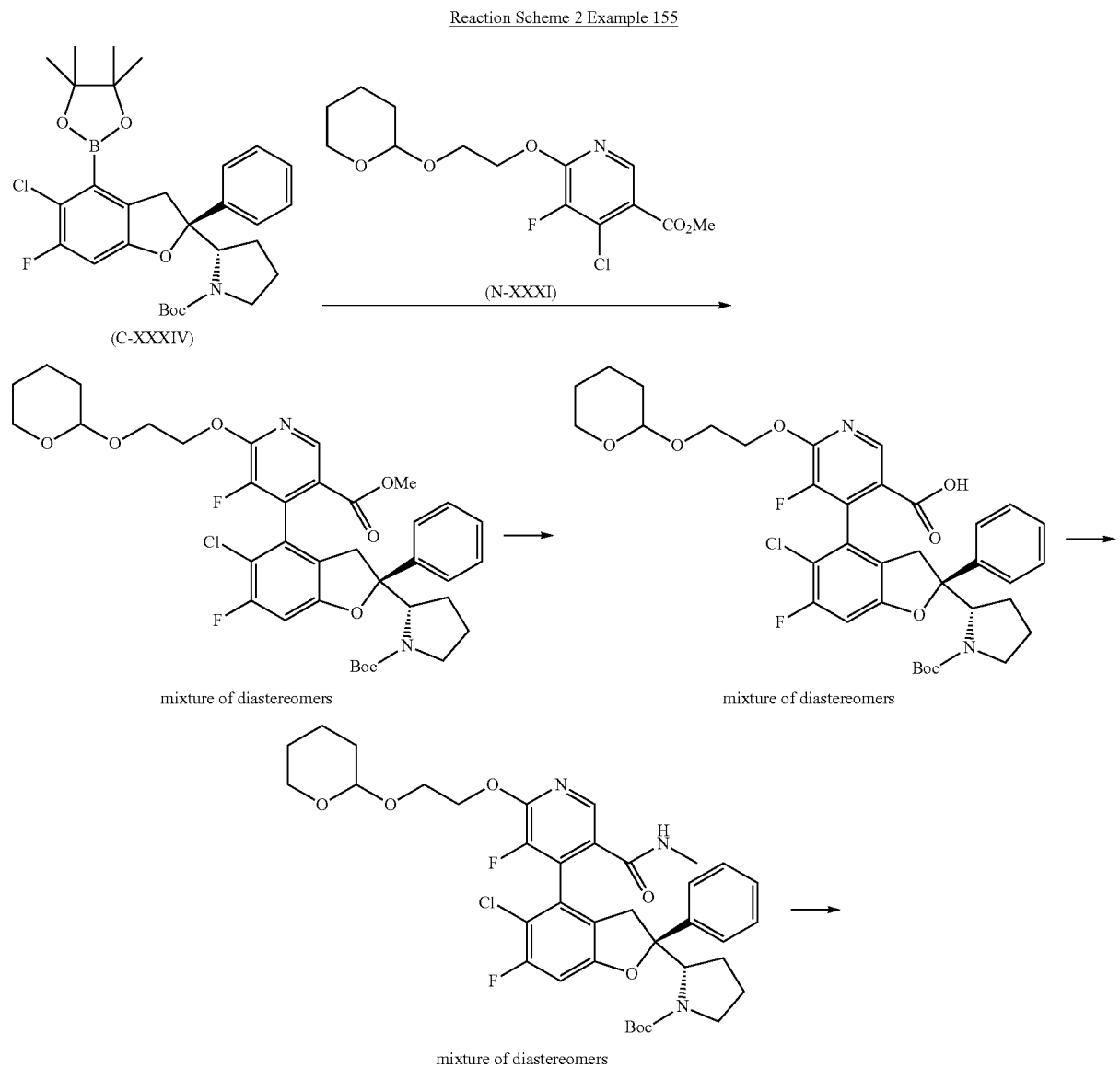

Reaction Scheme 2 Example 155

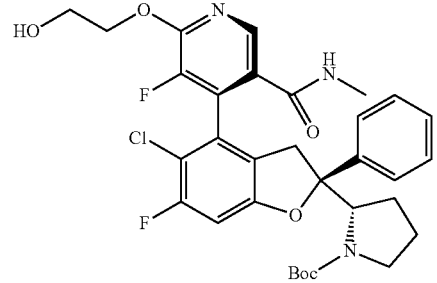

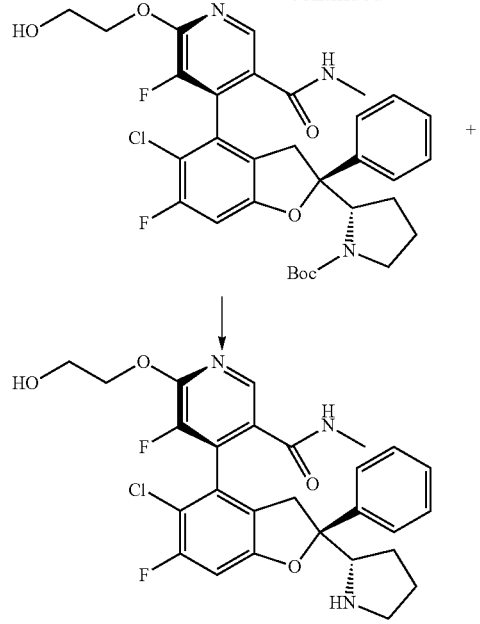

(Example 155)

Step 1: Methyl 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate and methyl 4-((2S,4R)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate A suspension of tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate (C-XXXIV) (8.83 g, 16.2 mmol), methyl 4-chloro-5-fluoro-6-(2-((tetrahydro-2H-pyran-2-yl)oxy)ethoxy)nicotinate (N-XXXI) (6.50 g, 19.5 mmol), $K_3PO_4$ (10.34 g, 48.7 mmol), N-Xantphos (0.896 g, 1.62 mmol) and $Pd_2(dba)_3$ (0.743 g, 0.81 mmol) in toluene (175 mL) and water (35 mL) was stirred at 100° C. for 20 h. At RT, a sat solution of $NaHCO_3$ was added and the mixture extracted twice with EtOAc. The combined organic layers were washed with a sat solution of $NaHCO_3$, dried over anhydrous $Na_2SO_4$ and concentrated. The crude product was purified by flash chromatography (silica, heptane/EtOAc, gradient: 10% to 33% EtOAc) to yield a mixture of the title compounds (6.25 g). UPLC-MS 1: m/z 715.7 [M+H]$^+$, $t_R$=1.61 min.

Step 2: 4-((2S,4S)-2-((S)-1-(Tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinic acid and 4-((2S,4R)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinic acid NaOH (21.9 mL, 87 mmol, 4 M in water) was added to a solution of a mixture of methyl 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate and methyl 4-((2S,4R)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate (6.25 g, 8.7 mmol) in MeOH (50 mL) and THF (25 mL). The reaction mixture was stirred at RT for 2.5 h before it was cooled to 5° C. and quenched by the addition of a 10% aqueous solution of $NaH_2PO_4$ (500 mL). The resulting suspension was extraced twice with TBME, the combined organic layers were washed with water, dried over anhydrous $Na_2SO_4$ and concentrated to afford a mixture of the title products (5.84 g) which was used in the following step without further purification. UPLC-MS 1: m/z 701.7 [M+H]$^+$, $t_R$=1.45 and 1.46 min.

Step 3: Tert-butyl (2S)-2-((2S,4S)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate and tert-butyl (2S)-2-((2S,4R)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate HATU (4.76 g, 12.5 mmol), DIPEA (8.20 mL, 47.0 mmol) and methylamine hydrochloride (1.32 g, 19.6 mmol) were added to a stirred solution of a mixture of 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinic acid and 4-((2S,4R)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinic acid (5.84 g, 7.83 mmol) in DMF (40 mL). The reaction mixture was stirred at RT for 3 h. A sat solution of $NaHCO_3$ was added and the mixture was extracted twice with EtOAc.

The combined organic layers were dried over anhydrous Na₂SO₄, filtered and concentrated. The crude product was purified by flash chromatography (silica, TBME/EtOAc, gradient: 5% to 100% EtOAc) to afford:

Tert-butyl (2S)-2-((2S,4S)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate (535 mg): UPLC-MS 1: m/z 714.7 [M+H]$^+$, $t_R$=1.50 min.

Tert-butyl (2S)-2-((2S,4R)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate (700 mg): UPLC-MS 1: m/z 714.7 [M+H]$^+$, $t_R$=1.47 min.

Mixture of tert-butyl (2S)-2-((2S,4S)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate and tert-butyl (2S)-2-((2S,4R)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate (2.548 g): UPLC-MS 1: m/z 714.7 [M+H]$^+$, $t_R$=1.47 and 1.50 min.

Step 4: Tert-butyl (S)-2-((2S,4S)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)pyrrolidine-1-carboxylate and tert-butyl (S)-2-((2S,4R)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)pyrrolidine-1-carboxylate Pyridinium p-toluenesulfonate (1.414 g, 5.63 mmol) was added to a solution of a mixture of tert-butyl (2S)-2-((2S,4S)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate and tert-butyl (2S)-2-((2S,4R)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate (2.01 g, 2.81 mmol) in EtOH (10 mL) and the reaction mixture was stirred at RT for 23 h. A sat solution of NaHCO₃ was added and the mixture was extracted with EtOAc. The combined organic layers were washed with a sat solution of NaHCO₃, dried over anhydrous Na₂SO₄ and concentrated. The crude product was subjected to flash chromatography (silica, EtOAc) to afford the title compounds as separate diastereoisomers:

Tert-butyl (S)-2-((2S,4S)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)pyrrolidine-1-carboxylate (917 mg): UPLC-MS 1: m/z 630.6 [M+H]$^+$, $t_R$=1.27 min.

Tert-butyl (S)-2-((2S,4R)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)pyrrolidine-1-carboxylate (557 mg): UPLC-MS 1: m/z 630.6 [M+H]$^+$, $t_R$=1.24 min.

Step 5: 4-((2S,4S)-5-Chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide or (4P)-4-{(2S)-5-Chloro-6-fluoro-2-phenyl-2-[(2S)-pyrrolidin-2-yl]-2,3-dihydro-1-benzofuran-4-yl}-5-fluoro-6-(2-hydroxyethoxy)-N-methylpyridine-3-carboxamide (Example. 155)

At 0° C. HCl (6.05 mL, 199 mmol, 4 M in dioxane) was added over 5 min to a solution of tert-butyl (S)-2-((2S,4S)-5-chloro-6-fluoro-4-(3-fluoro-2-(2-hydroxyethoxy)-5-(methylcarbamoyl)pyridin-4-yl)-2-phenyl-2,3-dihydrobenzofuran-2-yl)pyrrolidine-1-carboxylate (1.254 g, 1.99 mmol) in dioxane (15 mL). The reaction mixture was stirred at 0° C. for 2 h, 4 h at RT and another 12 h at 4° C. A sat solution of NaHCO₃ was added and the mixture was extracted twice with EtOAc. The combined organic layers were washed with a sat solution of NaHCO₃, dried over anhydrous Na₂SO₄ and concentrated. The crude product was purified by flash chromatography (DCM/MeOH/(7N ammonia in MeOH), gradient 95:5:05 to 90:10:0.5) to afford the title compound (743 mg) as a colorless foam. ¹H NMR (600 MHz, DMSO-d₆) δ (ppm) 8.42 (q, J=4.6 Hz, 1H), 8.27 (s, 1H), 7.46-7.42 (m, 2H), 7.33 (t, J=7.6 Hz, 2H), 7.26 (dd, J=8.3, 6.2 Hz, 1H), 7.07 (d, J=9.6 Hz, 1H), 4.95 (t, J=5.5 Hz, 1H), 4.44 (ddt, J=21.1, 10.9, 5.5 Hz, 2H), 3.76 (q, J=5.1 Hz, 2H), 3.51 (t, J=6.8 Hz, 1H), 3.43 (d, J=16.0 Hz, 1H), 2.96 (d, J=16.0 Hz, 1H), 2.74 (dt, J=12.6, 6.4 Hz, 1H), 2.66 (d, J=4.6 Hz, 3H), 2.65-2.60 (m, 1H), 2.29 (s br, 1H), 1.55-1.43 (m, 2H), 1.42-1.33 (m, 2H). UPLC-MS 1: m/z 530.5/532.5 [M+H]$^+$, $t_R$=0.69 min. UPLC-MS 2: m/z 530.5/532.5 [M+H]$^+$, $t_R$=3.02 min.

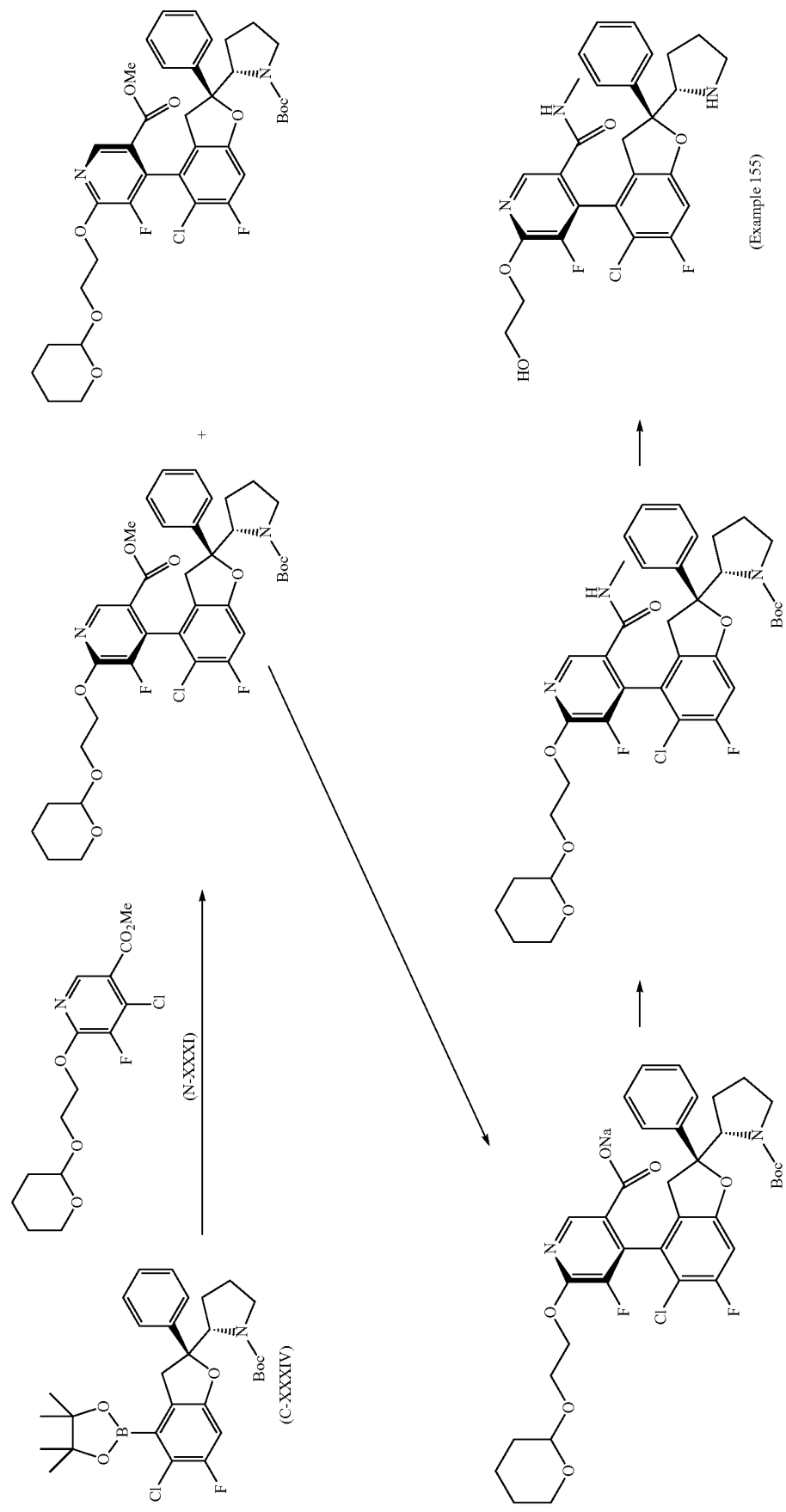

Step 1: Methyl 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate and methyl 4-((2S,4R)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate A 1 L three-necked round bottomed flask was charged with (S)-2-((S)-5-chloro-6-fluoro-2-phenyl-4-(4,4,5,5-tetramethyl-1,3,2-dioxaborolan-2-yl)-2,3-dihydrobenzofuran-2-yl)pyrrolidine-1-carboxylate (C-XXXIV) (22.1 g, 40.65 mmol), methyl 4-chloro-5-fluoro-6-(2-((tetrahydro-2H-pyran-2-yl)oxy)ethoxy)nicotinate (N-XXXI) (14.9 g, 44.72 mmol), $K_3PO_4$ (25.9 g, 121.96 mmol), water (100 mL) and toluene (300 mL). The mixture was degassed with nitrogen for 20 min. $Pd_2(dba)_3$ (1.86 g, 2.03 mmol) and N-Xantphos (2.24 g, 4.06 mmol) were added under nitrogen in one portion. The mixture was heated at 100° C. for 20 h. The mixture was cooled to RT and the organic phase was separated. The aqueous phase was extracted with toluene (100 mL). The combined organic phases were filtered through Celite and concentrated to dryness. The residue was purified by slurrying in a mixture of toluene, MTBE and n-heptane. The resulting suspension was filtered. The filter cake was recrystallized from toluene and n-heptane to give methyl 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate (7.5 g) as an off-white solid. $^1H$ NMR (400 MHz, $CDCl_3$) δ 8.72 (s, 1H), 7.39-7.34 (m, 2H), 7.34-7.27 (m, 3H), 6.75 (d, J=9.1 Hz, 1H), 4.76-4.61 (m, 3H), 4.41-4.28 (m, 1H), 4.19-4.08 (m, 1H), 3.92-3.81 (m, 2H), 3.76 (s, 3H), 3.72-2.84 (m, 5H), 2.01-1.44 (m, 10H), 1.27 (s, 9H). UPLC-MS 5: HRMS m/z calcd for $C_{37}H_{42}ClF_2N_2O_8$ $[M+H]^+$ 715.2592, found 715.2544.

Step 2: Sodium 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate A 1 L three-necked round bottomed flask was charged with methyl 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate (50.0 g, 69.91 mmol) and 1,4-dioxane (300 mL). A solution of NaOH (5.6 g, 139.83 mmol) in water (150 mL) was added dropwise at RT. The mixture was heated to 40° C. and stirred for 16 h. The mixture was concentrated to remove most of the 1,4-dioxane and extracted with MTBE (500 mL). The organic layer was washed with brine (500 mL), separated and concentrated to dryness to afford the title compound (53.0 g) as an off-white solid. $^1H$ NMR (400 MHz, $CDCl_3$) δ 8.18 (s, 1H), 7.47 (d, J=7.5 Hz, 2H), 7.32 (dt, J=12.8, 7.1 Hz, 3H), 6.70 (d, J=8.9 Hz, 1H), 4.67 (s, 1H), 4.63-4.43 (m, 2H), 4.37-4.22 (m, 2H), 4.11-3.94 (m, 1H), 3.91-3.75 (m, 2H), 3.56-3.34 (m, 2H), 3.33-3.23 (m, 1H), 2.72-2.54 (m, 1H), 1.98-1.35 (m, 10H), 1.24 (s, 9H). UPLC-MS 5: HRMS m/z calcd for $C_{36}H_{38}ClF_2N_2O_8$ [M-Na]-699.2290, found 699.2238.

Step 3: Tert-butyl (2S)-2-((2S,4S)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate A 1 L three-necked round bottomed flask was charged with sodium 4-((2S,4S)-2-((S)-1-(tert-butoxycarbonyl)pyrrolidin-2-yl)-5-chloro-6-fluoro-2-phenyl-2,3-dihydrobenzofuran-4-yl)-5-fluoro-6-(2-((tetrahydro-2H-pyran-2-yl)oxy)ethoxy)nicotinate (20.0 g, 27.66 mmol) and DMA (100 mL). The solution was cooled to 5-10° C. DIPEA (16.1 g, 124.46 mmol) and $MeNH_2 \cdot HCl$ (3.7 g, 55.32 mmol) were then added in one portion. The mixture was stirred for 20 min. HATU (15.8 g, 41.49 mmol) was added portionwise at 5-10° C. The reaction mixture was then stirred at RT for 2 h before it was diluted with MTBE (300 mL). A solution of NaOH (4.4 g, 110.6 mmol) in water (300 mL) was added dropwise at RT. The mixture was stirred for 10 min and the phases were separated. The aqueous phase was extracted with MTBE (200 mL). The combined organic phases were washed with water (200 mL), 15 wt % aq. citric acid (200 mL), brine (200 mL), and then concentrated to dryness to give the title compound (18.2 g) as a foam. $^1H$ NMR (400 MHz, $CDCl_3$) δ 8.37 (s, 1H), 7.45-7.32 (m, 5H), 7.07 (s, 1H), 6.81 (d, J=9.0 Hz, 1H), 4.77-4.53 (m, 3H), 4.20 (d, J=8.3 Hz, 1H), 4.15-4.05 (m, 1H), 3.94-3.78 (m, 2H), 3.74-3.61 (m, 1H), 3.55-3.45 (m, 1H), 3.30-3.09 (m, 2H), 2.90 (s, 1H), 2.72 (s, 3H), 2.05-1.45 (m, 10H), 1.28 (s, 9H). UPLC-MS 5: HRMS m/z calcd for $C_{37}H_{43}ClF_2N_3O_7$ $[M+H]^+$714.2752, found 714.2723.

Step 4: 4-((2S,4S)-5-Chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide or (4P)-4-{(2S)-5-Chloro-6-fluoro-2-phenyl-2-[(2S)-pyrrolidin-2-yl]-2,3-dihydro-1-benzofuran-4-yl}-5-fluoro-6-(2-hydroxyethoxy)-N-methylpyridine-3-carboxamide (Example 155)

A 250 mL three-necked round bottomed flask was charged with tert-butyl (2S)-2-((2S,4S)-5-chloro-6-fluoro-4-(3-fluoro-5-(methylcarbamoyl)-2-(2-((tetrahydro-2H-pyran-2-yl)oxy)ethoxy)pyridin-4-yl)-2-phenyl-2,3-dihydrobenzofuran-2-yl)pyrrolidine-1-carboxylate (20.0 g, 28.00 mmol), IPA (100 mL) and ethane-1,2-diol (20 mL). HCl (28 mL, 5-6 N in IPA) was then added in one portion. The reaction mixture was stirred at RT for 16 h. The reaction was cooled to 10° C. IPAc (200 mL) and a solution of NaOH (7.8 g, 195.0 mmol) in water (200 mL) were added. The mixture was stirred at RT for 10 min and the phases were separated. The aqueous phase was extracted with IPAc (200 mL). The combined organic phases were washed with brine (200 mL) and concentrated to dryness. The residue was dissolved in THF (100 mL) to give a clear yellow solution. A solution of succinic acid (3.64 g, 30.8 mmol) in THF (75 mL) was added dropwise. The resulting white suspension was stirred for 13 h and filtered. The filter cake was dissolved in water (340 mL) and cooled to 10° C. A solution of NaOH (2.3 g, 57.5 mmol) in water (85 mL) was added dropwise. The resulting suspension was stirred for 1 h and filtered. The filter cake was washed with water (85 mL×2) and dried under vacuum to give the title compound (10.3 g) as an off-white solid. $^1H$ NMR (600 MHz, DMSO-$d_6$) δ (ppm) 8.42 (q, J=4.6 Hz, 1H), 8.27 (s, 1H), 7.46-7.42 (m, 2H), 7.33 (t, J=7.6 Hz, 2H), 7.26 (dd, J=8.3, 6.2 Hz, 1H), 7.07 (d, J=9.6 Hz, 1H), 4.95 (t, J=5.5 Hz, 1H), 4.44 (ddt, J=21.1, 10.9, 5.5 Hz, 2H), 3.76 (q, J=5.1 Hz, 2H), 3.51 (t, J=6.8 Hz, 1H), 3.43 (d, J=16.0 Hz, 1H), 2.96 (d, J=16.0 Hz, 1H), 2.74 (dt, J=12.6, 6.4 Hz, 1H), 2.66 (d, J=4.6 Hz, 3H), 2.65-2.60 (m, 1H), 2.29 (s br, 1H), 1.55-1.43 (m, 2H), 1.42-1.33 (m, 2H). UPLC-MS 1: m/z 530.5/532.5 $[M+H]^+$, $t_R$=0.69 min. UPLC-MS 2: m/z 530.5/532.5 $[M+H]^+$, $t_R$=3.02 min.

Example 156 and Example 157: 2-((4-((2S,4S)-5-Chloro-6-fluoro-2-phenyl-2-((S)-pyrrolidin-2-yl)-2,3-dihydrobenzofuran-4-yl)-3-fluoro-5-(methylcarbamoyl)pyridin-2-yl)oxy)acetic acid (Example 156) and 4-((2S,4S)-5-chloro-6-fluoro-2-phenyl-2-((S)-pyrrolidin-2-yl)-2,3-dihydrobenzofuran-4-yl)-5-fluoro-6-hydroxy-N-methylnicotinamide (Example 157)

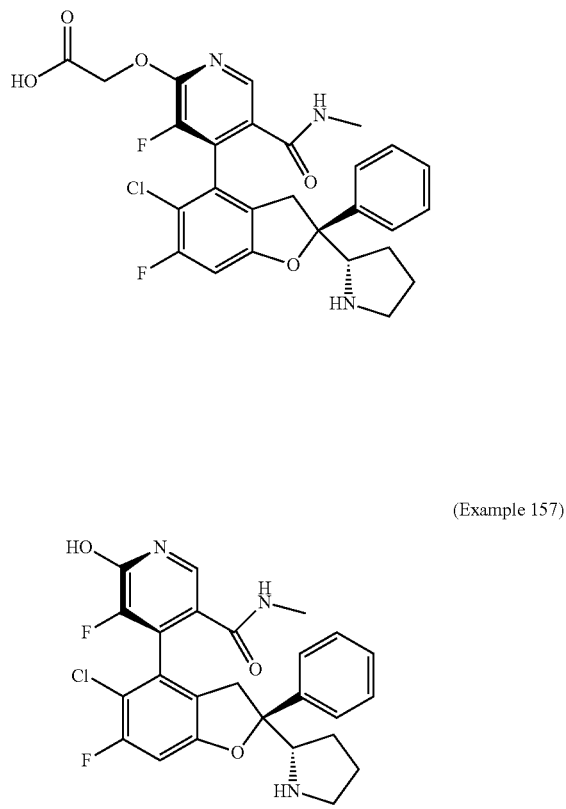

(Example 156)

(Example 157)

Reaction Scheme Example 156 and Example. 157

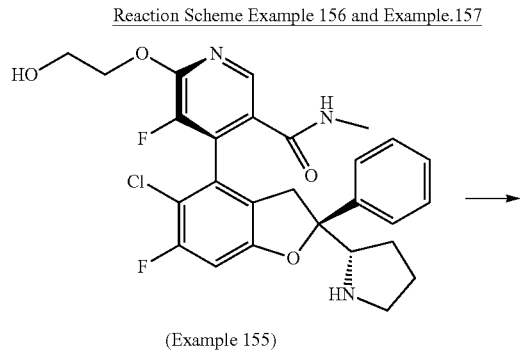

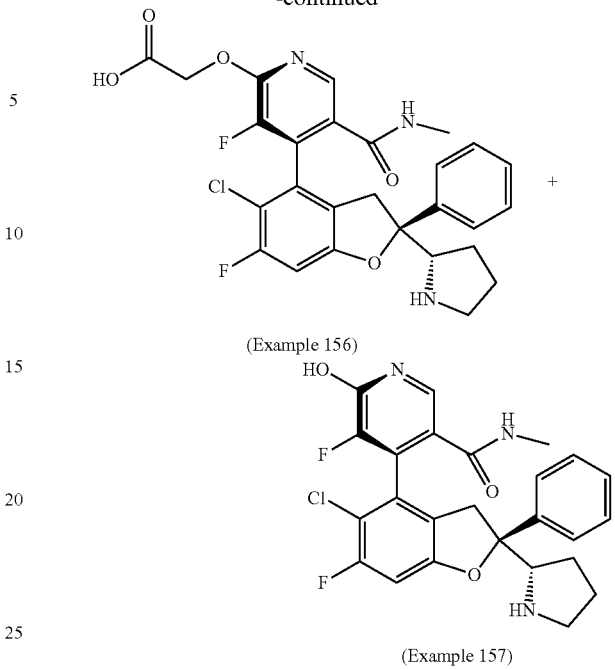

(Example 156)

(Example 157)

At 0° C., Jones reagent (0.57 mL, 1.132 mmol) was added to a stirred solution of –((2S,4S)-5-chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide or (4P)-4-{(2S)-5-Chloro-6-fluoro-2-phenyl-2-[(2S)-pyrrolidin-2-yl]-2,3-dihydro-1-benzofuran-4-yl}-5-fluoro-6-(2-hydroxyethoxy)-N-methylpyridine-3-carboxamide (Example 155) (200 mg, 0.377 mmol) in acetone (5 mL). The reaction mixture was stirred at 0° C. for 2 h, then at RT for 2 h. The mixture was then poured into a 10% NaHCO$_3$ aq. solution and was extracted twice with EtOAc. The aqueous phase was acidified to pH ~3 with 2 N HCl and was extracted with EtOAc (3 times) then with DCM (3 times). The combined organic layers were dried over anhydrous Na$_2$SO$_4$ and concentrated. The crude material was purified by preparative SFC to give the title products: (17.5 mg) as beige solid. UPLC-MS 1: m/z 544.1/546.1 [M+H]$^+$, t$_R$=0.74 min.

2-((4-((2S,4S)-5-Chloro-6-fluoro-2-phenyl-2-((S)-pyrrolidin-2-yl)-2,3-dihydrobenzofuran-4-yl)-3-fluoro-5-(methylcarbamoyl)pyridin-2-yl)oxy)acetic acid (17.5 mg) (Example 156): $^1$H NMR (400 MHz, DMSO-d$_6$) δ (ppm) 8.48 (q, J=4.5 Hz, 1H), 8.26 (s, 1H), 7.50-7.44 (m, 2H), 7.40-7.34 (m, 2H), 7.33-7.25 (m, 1H), 7.11 (d, J=9.6 Hz, 1H), 4.90 (d, J=3.3 Hz, 2H), 3.72-3.65 (m, 1H), 3.48 (d, J=J=16.0 Hz, 1H), 2.97 (d, J=16.1 Hz, 1H), 2.88-2.71 (m, 2H), 2.67 (d, J=4.5 Hz, 2H), 1.72-1.40 (m, 4H). UPLC-MS 3: m/z 544.1 [M+H]$^+$, t$_R$=0.74 min.

4-((2S,4S)-5-Chloro-6-fluoro-2-phenyl-2-((S)-pyrrolidin-2-yl)-2,3-dihydrobenzofuran-4-yl)-5-fluoro-6-hydroxy-N-methylnicotinamide (19 mg) (Example 157): H NMR (400 MHz, DMSO-d$_6$) δ (ppm) 8.22 (q, J=4.4 Hz, 1H), 7.70 (s, 1H), 7.52-7.46 (m, 2H), 7.45-7.24 (m, 4H), 7.06 (d, J=9.6 Hz, 1H), 3.78-3.68 (m, 1H), 3.47 (d, J=16.2 Hz, 1H), 3.08 (d, J=16.1 Hz, 1H), 2.86-2.74 (m, 2H), 2.61 (d, J=4.5 Hz, 3H), 1.73-1.43 (m, 4H). UPLC-MS 3: m/z 486.1 [M+H]$^+$, t$_R$=0.70 min.

Example 158: 2-((2S,4S)-5-Chloro-6-fluoro-2-(4-hydroxypyrrolidin-2-yl)-2-phenyl-2,3-dihydrobenzofuran-4-yl)-4-(difluoromethoxy)-3-fluorobenzamide

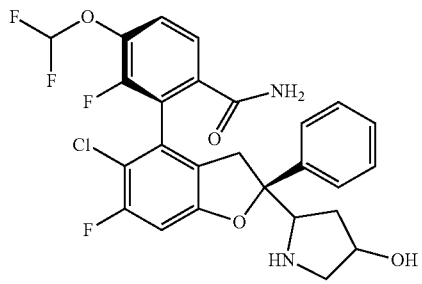

The title compound was prepared analogously to Example 5a, starting from tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)-4-hydroxypyrrolidine-1-carboxylate (C-XXXV) and 2-bromo-4-(difluoromethoxy)-3-fluorobenzonitrile (N-V). The product, with a diastereomeric excess of >98%, was isolated by flash chromatography (silica, cyclohexane/EtOAc, gradient: 0-20% EtOAc) after the Suzuki cross-coupling followed by preparative chiral SFC separation (Chiralpak IC 250×25 mm I.D., 5 µm, CO$_2$/MeOH (0.1% NH$_3$) 85:15, flow rate: 80 mL/min) at the last step. Chiral SFC: (Chiralpak IC 250×4.6 mm I.D., 5 µm, CO$_2$/MeOH (0.1% NH$_3$) 85:15) $t_R$=10.11 min; $^1$H NMR (600 MHz, DMSO-d$_6$) δ (ppm) 7.85-7.36 (m, 7H), 7.34-6.92 (m, 2H), 4.41 (s, 1H), 4.07 (t, J=8.4 Hz, 1H), 3.65 (d, J=15.4 Hz, 1H), 3.21 (d, J=15.3 Hz, 1H), 3.16-3.10 (m, 1H), 2.88 (d, J=11.3 Hz, 1H), 2.04-1.85 (m, 2H), 1.47 (s br, 2H). UPLC-MS 1: m/z 537.2 [M+H]$^+$, $t_R$=0.88 min.

Example 159: 2-((2S,4S)-5-Chloro-6-fluoro-2-(4-hydroxy-4-methylpyrrolidin-2-yl)-2-phenyl-2,3-dihydrobenzofuran-4-yl)-3-fluoro-4-((S)-2-hydroxypropoxy)benzamide

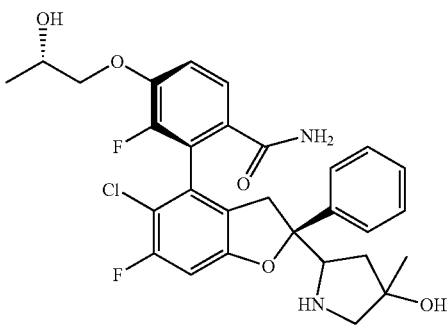

Reaction Scheme Example.159

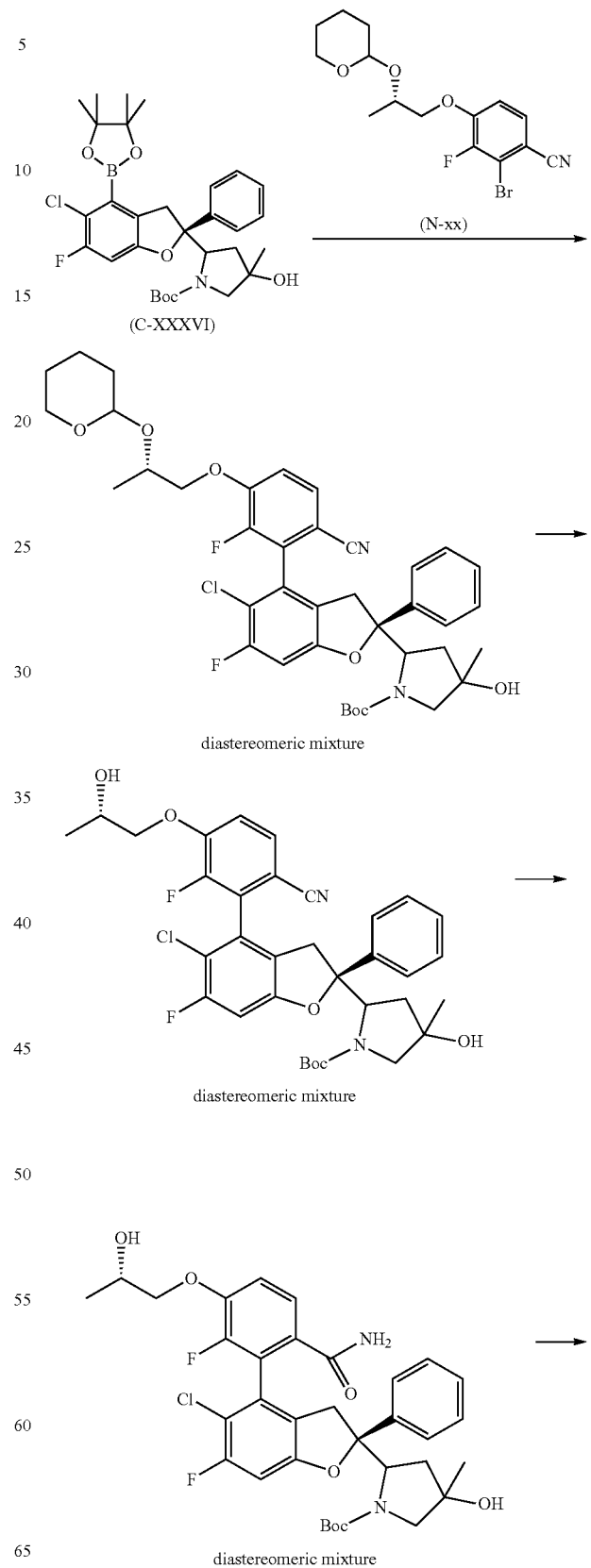

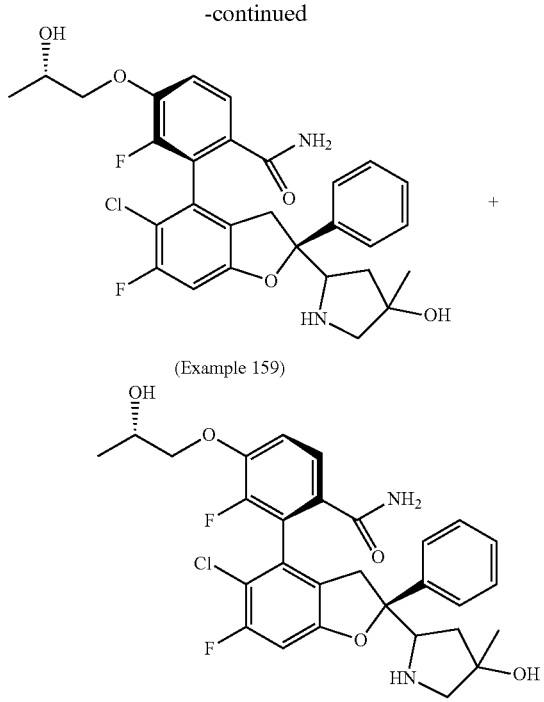

(Example 159)

Step 1 Tert-butyl 2-((2S,4S)-5-chloro-4-(6-cyano-2-fluoro-3-((2S)-2-((tetrahydro-2H-pyran-2-yl)oxy)propoxy)phenyl)-6-fluoro-2-phenyl-2,3-dihydrobenzofuran-2-yl)-4-hydroxy-4-methylpyrrolidine-1-carboxylate and tert-butyl 2-((2S,4R)-5-chloro-4-(6-cyano-2-fluoro-3-((2S)-2-((tetrahydro-2H-pyran-2-yl)oxy)propoxy)phenyl)-6-fluoro-2-phenyl-2,3-dihydrobenzofuran-2-yl)-4-hydroxy-4-methylpyrrolidine-1-carboxylate A mixture of the title compounds (70 mg) was obtained from tert-butyl 2-((S)-5-chloro-6-fluoro-2-phenyl-4-(4,4,5,5-tetramethyl-1,3,2-dioxaborolan-2-yl)-2,3-dihydrobenzofuran-2-yl)-4-hydroxy-4-methylpyrrolidine-1-carboxylate (C-XXXVI) (145 mg, 0.169 mmol) and 2-bromo-3-fluoro-4-((2S)-2-((tetrahydro-2H-pyran-2-yl)oxy)propoxy)benzonitrile (N-XIII) (80 mg, 0.22 mmol) using similar reaction conditions as described for Example 149, step 1. UPLC-MS 1: m/z 725.5 [M+H]$^+$, $t_R$=1.41/1.42/1.43/1.47 min.

Step 2: Tert-butyl 2-((2S,4S)-5-chloro-4-(6-cyano-2-fluoro-3-((S)-2-hydroxypropoxy)phenyl)-6-fluoro-2-phenyl-2,3-dihydrobenzofuran-2-yl)-4-hydroxy-4-methylpyrrolidine-1-carboxylate and tert-butyl 2-((2S,4R)-5-chloro-4-(6-cyano-2-fluoro-3-((S)-2-hydroxypropoxy)phenyl)-6-fluoro-2-phenyl-2,3-dihydrobenzofuran-2-yl)-4-hydroxy-4-methylpyrrolidine-1-carboxylate To a solution of a mixture of tert-butyl 2-((2S,4S)-5-chloro-4-(6-cyano-2-fluoro-3-((2S)-2-((tetrahydro-2H-pyran-2-yl)oxy)propoxy)phenyl)-6-fluoro-2-phenyl-2,3-dihydrobenzofuran-2-yl)-4-hydroxy-4-methylpyrrolidine-1-carboxylate and tert-butyl 2-((2S,4R)-5-chloro-4-(6-cyano-2-fluoro-3-((2S)-2-((tetrahydro-2H-pyran-2-yl)oxy)propoxy)phenyl)-6-fluoro-2-phenyl-2,3-dihydrobenzofuran-2-yl)-4-hydroxy-4-methylpyrrolidine-1-carboxylate (70 mg, 0.097 mmol) in EtOH (0.5 mL) was added pyridinium p-toluenesulfonate (49 mg, 0.19 mmol) and the reaction mixture was stirred at RT for 16 h. A sat solution of NaHCO$_3$ was added. The mixture was extracted twice with EtOAc. The combined organic layers were dried over anhydrous Na$_2$SO$_4$ and concentrated to afford a mixture of the title compounds (60 mg). UPLC-MS 1, m/z 641.4 [M+H]$^+$, $t_R$=1.19/1.21 min.

Step 3: Tert-butyl 2-((2S,4S)-4-(6-carbamoyl-2-fluoro-3-((S)-2-hydroxypropoxy)phenyl)-5-chloro-6-fluoro-2-phenyl-2,3-dihydrobenzofuran-2-yl)-4-hydroxy-4-methylpyrrolidine-1-carboxylate and tert-butyl 2-((2S,4R)-4-(6-carbamoyl-2-fluoro-3-((S)-2-hydroxypropoxy)phenyl)-5-chloro-6-fluoro-2-phenyl-2,3-dihydrobenzofuran-2-yl)-4-hydroxy-4-methylpyrrolidine-1-carboxylate A mixture of the title compounds was obtained from a mixture of tert-butyl 2-((2S,4S)-5-chloro-4-(6-cyano-2-fluoro-3-((S)-2-hydroxypropoxy)phenyl)-6-fluoro-2-phenyl-2,3-dihydrobenzofuran-2-yl)-4-hydroxy-4-methylpyrrolidine-1-carboxylate and tert-butyl 2-((2S,4R)-5-chloro-4-(6-cyano-2-fluoro-3-((S)-2-hydroxypropoxy)phenyl)-6-fluoro-2-phenyl-2,3-dihydrobenzofuran-2-yl)-4-hydroxy-4-methylpyrrolidine-1-carboxylate (60 mg, 0.085 mmol) using similar reaction conditions as described for Example 5a, step 2. The resulting crude material was used directly in the next step without further purification. UPLC-MS 1: m/z 659.4/661.4 [M+H]$^+$, $t_R$=1.04 and 1.09 min.

Step 4: 2-((2S,4S)-5-Chloro-6-fluoro-2-(4-hydroxy-4-methylpyrrolidin-2-yl)-2-phenyl-2,3-dihydrobenzofuran-4-yl)-3-fluoro-4-((S)-2-hydroxypropoxy)benzamide (Example 159) and 2-((2S,4R)-5-chloro-6-fluoro-2-(4-hydroxy-4-methylpyrrolidin-2-yl)-2-phenyl-2,3-dihydrobenzofuran-4-yl)-3-fluoro-4-((S)-2-hydroxypropoxy)benzamide The title compounds were obtained from the diastereomeric mixture of tert-butyl 2-((2S,4S)-4-(6-carbamoyl-2-fluoro-3-((S)-2-hydroxypropoxy)phenyl)-5-chloro-6-fluoro-2-phenyl-2,3-dihydrobenzofuran-2-yl)-4-hydroxy-4-methylpyrrolidine-1-carboxylate and tert-butyl 2-((2S,4R)-4-(6-carbamoyl-2-fluoro-3-((S)-2-hydroxypropoxy)phenyl)-5-chloro-6-fluoro-2-phenyl-2,3-dihydrobenzofuran-2-yl)-4-hydroxy-4-methylpyrrolidine-1-carboxylate using similar reaction conditions as described for Example 149, step 4, followed by preparative HPLC to separate the diastereomers.

2-((2S,4S)-5-Chloro-6-fluoro-2-(4-hydroxy-4-methylpyrrolidin-2-yl)-2-phenyl-2,3-dihydrobenzofuran-4-yl)-3-fluoro-4-((S)-2-hydroxypropoxy)benzamide (Example 159) (11 mg) $^1$H NMR (600 MHz, DMSO-d$_6$) δ (ppm) 7.51 (d, J=8.6 Hz, 1H), 7.48 (s, 1H), 7.43 (d, J=7.6 Hz, 2H), 7.36-7.25 (m, 4H), 7.22 (s, 1H), 7.00 (d, J=9.7 Hz, 1H), 4.98 (d, J=4.2 Hz, 1H), 4.41 (d, J=2.3 Hz, 1H), 4.02-3.90 (m, 3H), 3.57-3.47 (m, 2H), 2.90 (d, J=15.9 Hz, 1H), 1.52-1.38 (m, 2H), 1.17-1.11 (m, 6H). UPLC-MS 1: m/z 559.3 [M+H]$^+$, $t_R$=0.74 min.

Other diastereomer 2-((2S,4R)-5-chloro-6-fluoro-2-(4-hydroxy-4-methylpyrrolidin-2-yl)-2-phenyl-2,3-dihydrobenzofuran-4-yl)-3-fluoro-4-((S)-2-hydroxypropoxy)benzamide (6 mg): UPLC-MS 1: m/z 559.3/561.3 [M+H]$^+$, $t_R$=0.63 min.

521

Example 160: (2S,4R)-2-((S)-5-chloro-6-fluoro-2,4-diphenyl-2,3-dihydrobenzofuran-2-yl)-4-fluoropyrrolidine

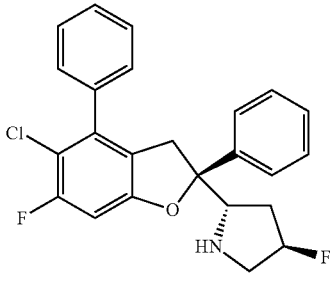 [SMILES: Fc1cc2c(c(-c3ccccc3)c1Cl)C[C@](c1ccccc1)([C@@H]1C[C@@H](F)CN1)O2]

Reaction Scheme Example 160

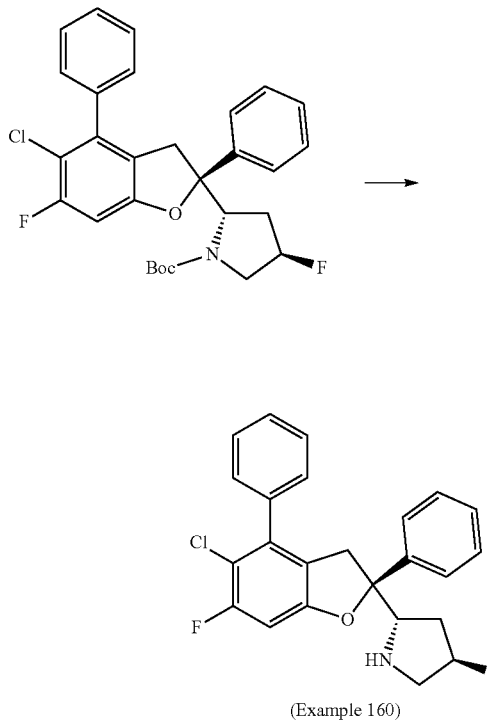

(C-XXXVII)

(Example 160)

522

Step 1: Tert-butyl (2S,4R)-2-((S)-5-chloro-6-fluoro-2,4-diphenyl-2,3-dihydrobenzofuran-2-yl)-4-fluoropyrrolidine-1-carboxylate A mixture of tert-butyl (2S,4R)-2-((S)-4-bromo-5-chloro-6-fluoro-2-phenyl-2,3-dihydrobenzofuran-2-yl)-4-fluoropyrrolidine-1-carboxylate (C-XXXVII) (109 mg, 0.212 mmol), phenylboronic acid (38.7 mg, 0.318 mmol), $K_3PO_4$ (180 mg, 0.847 mmol) and $PdCl_2(dppf) \cdot CH_2Cl_2$ adduct (18 mg, 0.022 mmol) in dioxane (5 mL) and water (1 mL) was stirred at 100° C. for 1 h. The reaction mixture was partitioned between EtOAc and water. The aqueous phase was extracted with EtOAc and the combined organic extracts were washed with brine, dried over anhydrous $Na_2SO_4$ and concentrated. The residue was purified by flash chromatography (silica, hexane/EtOAc; gradient: 0 to 100%) to afford the title compound. UPLC-MS 1: m/z 512.1 $[M+H]^+$, $t_R$=1.44 min.

Step 2: (2S,4R)-2-((S)-5-Chloro-6-fluoro-2,4-diphenyl-2,3-dihydrobenzofuran-2-yl)-4-fluoropyrrolidine (Example 160)

The title compound was obtained from tert-butyl (2S,4R)-2-((S)-5-chloro-6-fluoro-2,4-diphenyl-2,3-dihydrobenzofuran-2-yl)-4-fluoropyrrolidine-1-carboxylate (105 mg, 0.205 mmol) using similar reaction conditions as described for Example 149, step 4. $^1$H-NMR (400 MHz, DMSO-$d_6$) δ (ppm) 7.57-7.40 (m, 5H), 7.38-7.20 (m, 5H), 7.06 (d, J=9.6 Hz, 1H), 5.04 (dt, J=54.9, 3.5 Hz, 1H), 3.81 (dd, J=9.7, 6.8 Hz, 1H), 3.53 (dd, J=16.0, 1.8 Hz, 1H), 3.09 (dd, J=15.9, 1.5 Hz, 1H), 3.05-2.76 (m, 2H), 2.77-2.54 (m, 1H), 1.90-1.72 (m, 1H), 1.70-1.47 (m, 1H). UPLC-MS 1: m/z 412.1 $[M+HI]^+$, $t_R$=0.99 min.

Example 161: 2-((2S,4S)-5-Chloro-6-fluoro-2-phenyl-2-((S)-piperidin-2-yl)-2,3-dihydrobenzofuran-4-yl)-3-fluoro-4-(2-hydroxyethoxy)-N-methylbenzamide

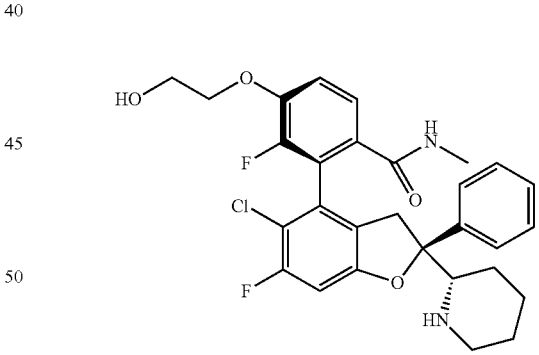

The title compound was prepared analogously to Example 155. from tert-butyl (S)-2-((S)-5-chloro-6-fluoro-2-phenyl-4-(4,4,5,5-tetramethyl-1,3,2-dioxaborolan-2-yl)-2,3-dihydrobenzofuran-2-yl)piperidine-1-carboxylate (C-XLI) and methyl 2-bromo-3-fluoro-4-(2-hydroxyethoxy)benzoate (N-XXXIV) followed by chromatographic separation of the diastereoisomers at the last step of N-Boc deprotection.

2-((2S,4S)-5-Chloro-6-fluoro-2-phenyl-2-((S)-piperidin-2-yl)-2,3-dihydrobenzofuran-4-yl)-3-fluoro-4-(2-hydroxyethoxy)-N-methylbenzamide (Example. 161): $^1$H NMR (400 MHz, DMSO-$d_6$) δ (ppm) 8.25 (q, J=4.5 Hz, 1H), 7.47-7.26 (m, 7H), 7.00 (d, J=9.6 Hz, 1H), 4.96 (t, J=5.4 Hz, 1H), 4.15 (t, J=4.8 Hz, 2H), 3.76 (q, J=5.1 Hz, 2H), 3.59 (dd, J=16.1, 1.9 Hz, 1H), 3.00-2.73 (m, 3H), 2.65 (d, J=4.5 Hz, 3H), 1.76-1.59 (m, 1H), 1.53-1.37 (m, 2H), 1.30-1.08 (m, 4H), 1.03-0.89 (m, 1H). UPLC-MS 1: m/z 543.5/545.5 [M+H]$^+$, t$_R$=0.71 min.

Other diastereoisomer 2-((2S,4R)-5-chloro-6-fluoro-2-phenyl-2-((S)-piperidin-2-yl)-2,3-dihydrobenzofuran-4-yl)-3-fluoro-4-(2-hydroxyethoxy)-N-methylbenzamide (161 mg): UPLC-MS 1: m/z 543.5 [M+H]$^+$, t$_R$=0.66 min.

Example 162: (3-((S)-5-Chloro-6-fluoro-2,4-diphenyl-2,3-dihydrobenzofuran-2-yl)morpholine

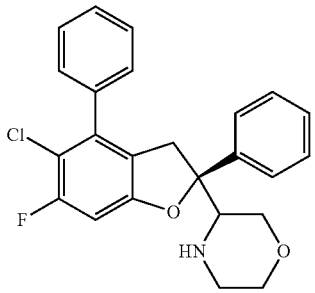 [SMILES: Fc1cc2c(c(-c3ccccc3)c1Cl)C[C@](c1ccccc1)(C1COCCN1)O2]

The diastereomeric mixture of 3-((S)-4-bromo-5-chloro-6-fluoro-2-phenyl-2,3-dihydrobenzofuran-2-yl)morpholine (C-XLII-b) (36 mg, 0.087 mmol) was subjected to chiral separation (ChiralPak IB-N, 530×250 mm I.D., 5 μm. CO2/MeOH+0.1% NH3, 90:10), 25° C., flow rate: 80 mL/min) to afford the two diastereoisomers with an diastereoisomeric excess of >99%, respectively.

Diastereoisomer 1 (15 mg): Chiral SFC: (Chiralpak AY-H 100×3 mm I.D., 3 μm, Hexane/EtOH 96:4, flow rate: 0.420 mL/min) t$_R$=2.25 min.

Diastereoisomer 2 (15 mg): Chiral SFC: (Chiralpak AY-H 100×3 mm I.D., 3 μm, Hexane/EtOH 96:4, flow rate: 0.420 mL/min) t$_R$=3.22 min.

The title compound (15 mg, white solid) was obtained from 3-((S)-4-bromo-5-chloro-6-fluoro-2-phenyl-2,3-dihydrobenzofuran-2-yl)morpholine (diastereoisomer 2) (15 mg, 0.036 mmol) and phenylboronic acid (6.65 mg, 0.055 mmol) using similar reaction conditions as described for Example 160, step 1. $^1$H NMR (400 MHz, DMSO-d$_6$) δ (ppm)$^1$H NMR (400 MHz, DMSO-d$_6$) δ 7.53-7.23 (m, 10H), 7.14 (d, J=9.7 Hz, 1H), 3.57 (d, J=10.5 Hz, 1H), 3.25-3.03 (m, 3H), 2.95-2.61 (m, 6H). UPLC-MS 1: m/z 410.1 [M+H]$^+$, t$_R$=1.04 min.

Example 163: 2-((2S,4S)-5-Chloro-6-fluoro-2-(morpholin-3-yl)-2-phenyl-2,3-dihydrobenzofuran-4-yl)-3-fluoro-4-methoxybenzamide

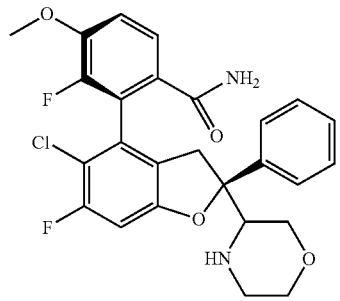

The title compound (39 mg) was prepared analogously to Example 5a from intermediates tert-butyl 3-((S)-5-chloro-6-fluoro-2-phenyl-4-(4,4,5,5-tetramethyl-1,3,2-dioxaborolan-2-yl)-2,3-dihydrobenzofuran-2-yl)morpholine-4-carboxylate (C-XLII) (890 mg, 1.59 mmol) and 2-bromo-3-fluoro-4-methoxybenzonitrile (N-IV) (439 mg, 1.91 mmol). After Suzuki coupling two mixtures of 2 diastereoisomers, respectively were isolated by flash chromatography (silica, hexane(EtOAc, gradient: 0 to 100% EtOAc). After final Boc deprotection the two mixtures of two diastereoisomers, respectively, were subjected to chiral SFC (method 1: ChiralCel OD, 250×30 mm I.D., 5 μm. (CO$_2$/IPA+0.1% NH$_3$·H$_2$O) 60:40, flow rate: 50 mL/min; method 2: Chiralpak AD, 250×30 mm I.D., 5 μm CO$_2$/(EtOH+0.1% NH$_3$·H$_2$O) 86:14, flow rate: 80 mL/min) to afford all four diastereoisomers with a diastereoisomeric excess of >99%, respectively.

2-((2S,4S)-5-Chloro-6-fluoro-2-(morpholin-3-yl)-2-phenyl-2,3-dihydrobenzofuran-4-yl)-3-fluoro-4-methoxybenzamide (Example. 163)—diastereoisomer 1: Chiral SFC (ChiralCel OD, 150×4.6 mm I.D., 3 μm. CO2/IPA (+0.05% DEA) 95:5 to 60:40; flow rate: 2.5 mL/min) t$_R$=6.35 min $^1$H NMR (400 MHz, DMSO-d$_6$) δ (ppm) 7.69 (s, 1H), 7.55 (d, J=8.6 Hz, 1H), 7.46-7.26 (m, 6H), 7.20 (s, 1H), 7.03 (d, J=9.5 Hz, 1H), 3.91 (s, 3H), 3.71-3.48 (m, 3H), 3.23-3.13 (m, 1H), 3.12-3.05 (m, 1H), 3.00 (t, J=10.3 Hz, 1H), 2.91 (d, J=16.0 Hz, 1H), 2.71 (t, J=15.8 Hz, 2H), 1.94 (s, 1H). UPLC-MS 1: m/z 501.1/503.1 [M+H]$^+$, t$_R$=0.80 mi.

Diastereoisomer 2 (61 mg): Chiral SFC (ChiralCel OD, 150×4.6 mm I.D., 3 μm. CO2/IPA(+0.05% DEA), 5-40%), flow rate: 2.5 mL/min) t$_R$=5.81 m UPLC-MS 1: m/z 501.1/503.1 [M+H]$^+$, t$_R$=0.87 min.

Diastereoisomer 3 (24 mg): Chiral SFC (ChiralPak AD, 100×4.6 mm I.D., 5 μm. CO2/MeOH (+20 mM NH$_4$OAc), 13%)) t$_R$=2.17 min UPLC-MS 1: m/z 501.3/503.3 [M+H]$^+$, t$_R$=0.68 min.

Diastereoisomer 4 (59 mg): Chiral SFC (ChiralPak AD, 100×4.6 mm I.D., 5 μm. CO2/MeOH (+20 mM NH$_4$OAc), 13%)) t$_R$=3.53 m UPLC-MS 1: m/z 5011.3/503.3 [M+H]$^+$, t$_R$=0.69 min.

The following compounds were prepared similarly to Example 5a:

| Ex. | Structure/Chemical Name | UPLC MS m/z [M + H]+ t_R [min] (method) | ¹H NMR |
|---|---|---|---|
| 164 | 2-((2S,3S,4S)-5-chloro-6-fluoro-3-hydroxy-2-phenyl-2-(pyrrolidin-2-yl)-2,3-dihydrobenzofuran-4-yl)-3-fluoro-4-methoxybenzamide; Compound (C-XXXVIII) and aryl bromide 2-bromo-3-fluoro-4-methoxybenzonitrile (N-IV) were used in the Suzuki coupling | 501.3 0.80 (1) | (400 MHz, DMSO-d₆) δ (ppm) δ 7.67 – 7.53 (m, 3H), 7.53 – 7.40 (m, 2H), 7.40 – 7.19 (m, 5H), 7.08 – 6.86 (m, 1H), 4.97 (s, 1H), 3.99 – 3.69 (m, 4H), 2.80 – 2.64 (m, 1H), 1.84 – 1.63 (m, 1H), 1.58 – 1.30 (m, 2H), 1.22 – 1.01 (m, 1H). |
| 165 | 2-((2S,3S,4S)-5-chloro-6-fluoro-3-methoxy-2-phenyl-2-(pyrrolidin-2-yl)-2,3-dihydrobenzofuran-4-yl)-3-fluoro-4-methoxybenzamide; Compound (C-XXXIX) and aryl bromide 2-bromo-3-fluoro-4-methoxybenzonitrile (N-IV) were used in the Suzuki coupling. | 515.3 0.75 (1) | (400 MHz, DMSO-d₆) δ (ppm) δ 7.63 – 7.56 (m, 3H), 7.37 – 7.22 (m, 5H), 7.14 (s, 1H), 7.00 (s, 1H), 4.53 (s, 1H), 4.00 – 3.88 (m, 4H), 3.04 (s, 3H), 2.77 – 2.62 (m, 1H), 2.39 – 2.21 (m, 2H), 1.88 – 1.74 (m, 1H), 1.54 – 1.29 (m, 2H), 1.14 – 1.06 (m, 1H). |
| 166 | 2-((2S,3S,4S)-5-chloro-6-fluoro-3-methoxy-2-phenyl-2-(pyrrolidin-2-yl)-2,3-dihydrobenzofuran-4-yl)-3-fluoro-4-(2-hydroxyethoxy)benzamide; Compound (C-XXXIX) and aryl bromide 2-bromo-3-fluoro-4-(2-((tetrahydro-2H-pyran-2-yl)oxy)ethoxy)benzonitrile (N-VI) were used in the Suzuki coupling. | 545.5 0.72 (1) | (400 MHz, DMSO-d₆) δ (ppm) 7.63 – 7.52 (m, 3H), 7.40 – 7.19 (m, 5H), 7.13 (s, 1H), 6.99 (s, 1H), 4.92 (t, J = 5.4 Hz, 1H), 4.53 (s, 1H), 4.23 – 4.05 (m, 2H), 4.01 – 3.85 (m, 1H), 3.85 – 3.64 (m, 2H), 3.06 (s, 3H), 2.78 – 2.61 (m, 1H), 2.38 – 2.23 (m, 2H), 1.89 – 1.76 (m, 1H), 1.56 – 1.29 (m, 2H), 1.19 – 1.01 (m, 1H). |

| Ex. | Structure/Chemical Name | UPLC MS m/z [M + H]+ $t_R$ [min] (method) | $^1$H NMR |
|---|---|---|---|
| 167 | 2-((2S,3S,4S)-5-chloro-6-fluoro-3-methyl-2-phenyl-2-(pyrrolidin-2-yl)-2,3-dihydrobenzofuran-4-yl)-3-fluoro-4-((S)-2-hydroxypropoxy)benzamide; Compound (C-XL) and aryl 2-bromo-3-fluoro-4-((2S)-2-((tetrahydro-2H-pyran-2-yl)oxy)propoxy)benzonitrile (N-XIII) were used in the Suzuki coupling. | 543.2 0.70 (1) | (600 MHz, DMSO-d$_6$) δ 7.69 (s, 1H), 7.55 (d, J = 8.7 Hz, 1H), 7.51 (d, J = 7.7 Hz, 2H), 7.28 (q, J = 7.5, 7.1 Hz, 3H), 7.23 (d, J = 7.2 Hz, 1H), 7.07 (s, 1H), 7.05 (s, 1H), 4.95 (d, J = 4.3 Hz, 1H), 4.02 – 3.93 (m, 2H), 3.91 (dd, J = 8.9, 3.5 Hz, 1H), 3.80 (t, J = 7.1 Hz, 1H), 3.28 (q, J = 7.8 Hz, 1H), 2.66 – 2.61 (m, 1H), 2.26 (q, J = 7.5 Hz, 1H), 1.83 – 1.76 (m, 1H), 1.43 (dq, J = 13.7, 7.2 Hz, 1H), 1.33 (q, J = 7.0 Hz, 1H), 1.13 (d, J = 5.7 Hz, 3H), 1.02 (d, J = 7.0 Hz, 3H), 0.95 (d, J = 9.8 Hz, 1H) |

Example 168: 2-((2S,4S)-2-(1-Aminoethyl)-5-chloro-2-phenyl-2,3-dihydrobenzofuran-4-yl)-3-fluoro-4-methoxybenzamide

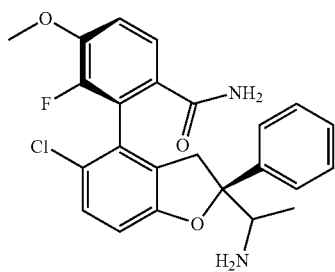

The title compound (39 mg) was prepared analogously to Example 5a from intermediates tert-butyl (1-((S)-5-chloro-2-phenyl-4-(4,4,5,5-tetramethyl-1,3,2-dioxaborolan-2-yl)-2,3-dihydrobenzofuran-2-yl)ethyl)carbamate (C-XLIII) and 2-bromo-3-fluoro-4-methoxybenzonitrile (N-IV).

2-((2S,4S)-2-(1-Aminoethyl)-5-chloro-2-phenyl-2,3-dihydrobenzofuran-4-yl)-3-fluoro-4-methoxybenzamide (Example. 168): $^1$H NMR (600 MHz, DMSO-d$_6$) δ (ppm) 7.61 (br s, 1H), 7.49 (d, J=8.6 Hz, 1H), 7.43 (d, J=7.6 Hz, 2H), 7.35 (t, J=7.6 Hz, 2H), 7.28 (t, J=8.0 Hz, 2H), 7.20 (d, J=8.6 Hz, 2H), 6.87 (d, J=8.6 Hz, 1H), 3.90 (s, 3H), 3.52 (d, J=16.3 Hz, 1H), 3.16 (q, J=6.2 Hz, 1H), 2.93 (d, J=16.5 Hz, 1H), 0.85 (d, J=6.6 Hz, 3H). UPLC-MS 1: m/z 441.3 [M+H]$^+$, $t_R$=0.77 min.

Other diastereoisomer 2-((2S,4R)-2-(1-aminoethyl)-5-chloro-2-phenyl-2,3-dihydrobenzofuran-4-yl)-3-fluoro-4-methoxybenzamide: UPLC-MS 1: m/z 441.3 [M+H]$^+$, $t_R$=0.64 min.

Example 169: 2-((2S,3S,4S)-2-(1-Aminoethyl)-5-chloro-6-fluoro-3-methyl-2-phenyl-2,3-dihydrobenzofuran-4-yl)-3-fluoro-4-(2-methoxyethoxy)benzamide

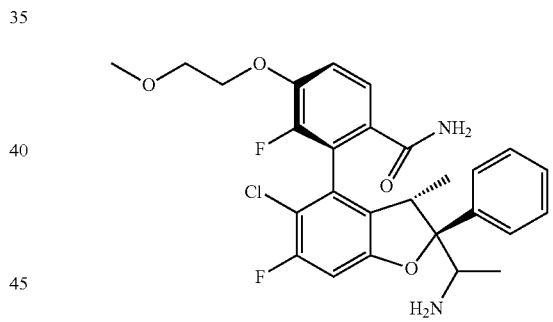

The title compound (39 mg) was prepared analogously to Example 151 from intermediates tert-butyl (1-((2S,3S)-5-chloro-6-fluoro-3-methyl-2-phenyl-4-(4,4,5,5-tetramethyl-1,3,2-dioxaborolan-2-yl)-2,3-dihydrobenzofuran-2-yl)ethyl)carbamate (C-XLIV) and 2-bromo-3-fluoro-4-(2-methoxyethoxy)benzonitrile (N-IX).

2-((2S,3S,4S)-2-(1-Aminoethyl)-5-chloro-6-fluoro-3-methyl-2-phenyl-2,3-dihydrobenzofuran-4-yl)-3-fluoro-4-(2-methoxyethoxy)benzamide (Example. 169): $^1$H NMR (400 MHz, DMSO-d$_6$) b (ppm) 7.69 (s br, 1H), 7.56 (dd, J=8.8, 1.4 Hz, 1H), 7.53-7.46 (m, 2H), 7.36-7.19 (m, 4H), 7.07 (s br, 1H), 7.04 (d, J=9.6 Hz, 1H), 4.33-4.18 (m, 2H), 3.70 (t, J=4.5 Hz, 2H), 3.45-3.37 (m, 2H), 3.30 (s, 3H), 1.24 (s br, 2H), 1.03 (d, J=6.9 Hz, 3H), 0.83 (d, J=6.4 Hz, 3H). UPLC-MS 1: m/z 517.3 [M+H]$^+$, $t_R$=0.79 min.

Other diastereoisomer 2-((2S,3S,4R)-2-(1-aminoethyl)-5-chloro-6-fluoro-3-methyl-2-phenyl-2,3-dihydrobenzofuran-4-yl)-3-fluoro-4-(2-methoxyethoxy)benzamide: UPLC-MS 1: m/z 517.3 [M+H]$^+$, $t_R$=0.73 min.

Example 170: 2-((2S,4S)-5-Chloro-6-fluoro-2-phenyl-2-((S)-pyrrolidin-2-yl)indolin-4-yl)-3-fluoro-4-(2-hydroxyethoxy)benzamide or (2P)-2-{(2S)-5-Chloro-6-fluoro-2-phenyl-2-[(2S)-pyrrolidin-2-yl]-2,3-dihydro-1H-indol-4-yl}-3-fluoro-4-(2-hydroxyethoxy)benzamide

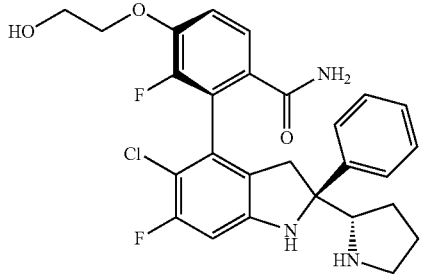

The title compound was prepared analogously to Example 5a from intermediates tert-butyl (S)-2-((S)-1-(tert-butoxycarbonyl)pyrrolidin-2-yl)-5-chloro-6-fluoro-2-phenyl-4-(4,4,5,5-tetramethyl-1,3,2-dioxaborolan-2-yl)indoline-1-carboxylate (C-XLV) and 2-bromo-3-fluoro-4-(2-((tetrahydro-2H-pyran-2-yl)oxy)ethoxy)benzonitrile (N-VI). After Suzuki coupling and transformation of the nitrile into the amide first the THP group was cleaved using pyridinium p-toluenesulfonate before the two Boc groups were cleaved using 4 M HCl in dioxane. The diastereoisomers were separated after THP and BOC deprotection.

2-((2S,4S)-5-Chloro-6-fluoro-2-phenyl-2-((S)-pyrrolidin-2-yl)indolin-4-yl)-3-fluoro-4-(2-hydroxyethoxy)benzamide (Example. 170): $^1$H NMR (400 MHz, DMSO-$d_6$) δ (ppm) 7.45 (d, J=8.5 Hz, 2H), 7.37 (d, J=7.5 Hz, 2H), 7.34-7.14 (m, 5H), 6.70 (s, 1H), 6.51 (d, J=10.4 Hz, 1H), 4.92 (t, J=5.4 Hz, 1H), 4.11 (t, J=4.9 Hz, 2H), 3.73 (q, J=5.1 Hz, 2H), 3.19 (d, J=16.4 Hz, 1H), 2.52 (dd, 1H), 2.50-2.44 (m, 3H), 2.07-1.93 (m, 1H), 1.67 (s, 1H), 1.43 (d, J=23.0 Hz, 3H). UPLC-MS 3: m/z 514.2 [M+H]$^+$, $t_R$=0.71 min.

Other diastereoisomer 2-((2S,4R)-5-chloro-6-fluoro-2-phenyl-2-((S)-pyrrolidin-2-yl)indolin-4-yl)-3-fluoro-4-(2-hydroxyethoxy)benzamide: UPLC-MS 3: m/z 514.2 [M+H]$^+$, $t_R$=0.65 min.

The following examples were prepared in analogy to previous examples:

Example 171: 2-((2S,4S)-5-Chloro-6-fluoro-2-phenyl-2-((S)-pyrrolidin-2-yl)indolin-4-yl)-3-fluoro-4-methoxybenzamide

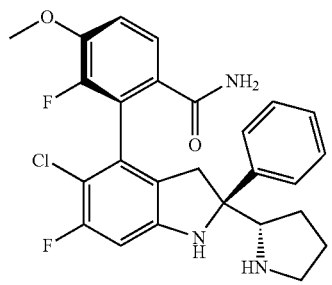

UPLC-MS 3: m/z 484.2 [M+H]$^+$, $t_R$=0.79 min.

Example 172: 2-((2S,4S)-5-Chloro-6-fluoro-2-phenyl-2-((S)-pyrrolidin-2-yl)indolin-4-yl)-3-fluoro-4-((S)-2-hydroxypropoxy)-N-methylbenzamide

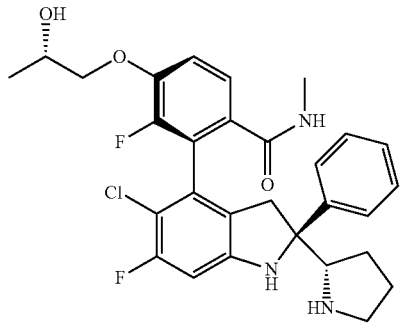

UPLC-MS 4: m/z 542.3 [M+H]$^+$, $t_R$=0.65 min.

Example 173: 4-((2S,4S)-5-Chloro-6-fluoro-2-phenyl-2-((S)-pyrrolidin-2-yl)indolin-4-yl)-5-fluoro-6-(2-hydroxyethoxy)-N-methylnicotinamide

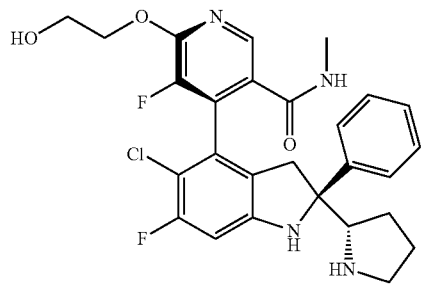

UPLC-MS 4: m/z 529.1 [M+H]$^+$, $t_R$=0.61 min.

Example 174: 2-((2S,4S)-5-Chloro-6-fluoro-2-phenyl-2-((S)-pyrrolidin-2-yl)-2,3-dihydrobenzofuran-4-yl)-3-fluoro-4-methoxybenzamide

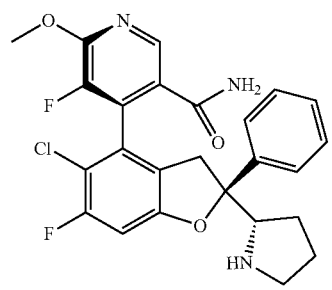

$^1$H NMR (400 MHz, DMSO-$d_6$) δ (ppm) 7.59 (s, 1H), 7.54 (dd, J=8.6, 1.4 Hz, 1H), 7.46-7.40 (m, 2H), 7.37-7.20 (m, 5H), 7.01 (d, J=9.7 Hz, 1H), 3.90 (s, 3H), 3.54-3.42 (m, 2H), 2.87 (d, J=15.7 Hz, 1H), 2.70 (dt, J=9.8, 6.5 Hz, 1H), 2.58 (dt, J=9.7, 6.2 Hz, 1H), 2.30 (s br, 1H), 1.62-1.51 (m, 1H), 1.50-1.37 (m, 2H), 1.35-1.22 (m, 1H). UPLC-MS 4: m/z 485.3 [M+H]⁺, $t_R$=0.71 min.

Example 175: 2-((2S,4S)-5-Chloro-6-fluoro-2-phenyl-2-((S)-pyrrolidin-2-yl)-2,3-dihydrobenzofuran-4-yl)-3-fluoro-4-methoxy-N-methylbenzamide

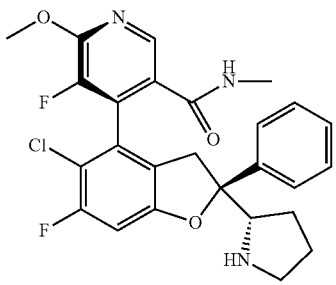

¹H NMR (400 MHz, DMSO-d₆) δ (ppm) 8.08 (d, J=4.8 Hz, 1H), 7.47 (dd, J=8.6, 1.4 Hz, 1H), 7.45-7.40 (m, 2H), 7.35-7.22 (m, 4H), 7.00 (d, J=9.7 Hz, 1H), 3.90 (s, 3H), 3.50 (t, J=6.8 Hz, 1H), 3.40 (dd, J=15.9, 1.7 Hz, 1H), 2.86 (d, J=15.6 Hz, 1H), 2.76-2.68 (m, 1H), 2.65-2.58 (m, 1H), 2.62 (d, J=4.5 Hz, 3H), 2.32 (s br, 1H), 1.58-1.42 (m, 2H), 1.41-1.31 (m, 2H). UPLC-MS 4: m/z 499.3 [M+H]⁺, $t_R$=0.70 min.

Example 176: 2-((2S,3S,4S)-2-(Aminomethyl)-5-chloro-6-fluoro-3-methyl-2-phenyl-2,3-dihydrobenzofuran-4-yl)-3-fluoro-4-methoxybenzamide

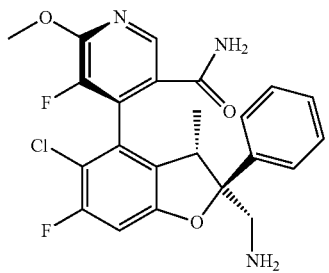

¹H NMR (600 MHz, DMSO-d₆) δ (ppm) 7.71 (s, 1H), 7.60 (dd, J=8.7, 1.2 Hz, 1H), 7.46-7.40 (m, 2H), 7.40-7.33 (m, 2H), 7.33-7.25 (m, 2H), 7.12 (s, 1H), 7.06 (d, J=9.5 Hz, 1H), 3.89 (s, 3H), 3.28 (q, J=7.1 Hz, 1H), 3.16-3-01 (m, 2H), 1.14 (s br, 2H), 0.92 (d, J=7.2 Hz, 3H). UPLC-MS 3: m/z 459.2 [M+H]⁺, $t_R$=0.76 min.

In-Vitro Biochemical Assays

Avi-humanTEAD4²¹⁷⁻⁴³⁴ (1 nM, produced as described in Hau et al. ChemBioChem 14, 1218, 2013) and LANCE Eu-W1024 Streptavidin (0.5 nM, PerkinElmer) were first pre-incubated for 1 h at room temperature in HEPES (pH 7.4, 50 mM), KCl (100 mM), Tween-20 (0.05%), TCEP (0.25 mM), EDTA (1 mM), and BSA (0.05%)]. N-terminus Cy5 labeled humanYAP⁶⁰⁻¹⁰⁰ (20 nM) was then added to this preparation. Compounds were dissolved at 10 mM in 100% DMSO and serial dilutions were made in 100% DMSO. The diluted compound solutions were incubated in white 384-well plates (Greiner Bio-One) for 1 h at room temperature with the above described mix. The final DMSO concentration present in the assay was 1%. The fluorescence was measured (50 μs delay between excitation and fluorescence, 75 μs integration time) with a Genios Pro reader (Tecan) and use of an excitation wavelength of 340 nm and emission wavelengths of 620 nm and 665 nm. Data analyses were carried out by using the TR-FRET ratio emission 655 nm/620 nm. The IC₅₀ values were estimated by fitting the data by nonlinear fit regression (GraphPad Prism). In the "alternative" format, the assay was conducted in the presence of 5 nM His-humanTEAD4²¹⁷⁻⁴³⁴, 10 nM N-biotinylated YAP⁶⁰⁻¹⁰⁰, 0.2 nM anti-His Europium labelled antibody and 10 nM SA-XL665. Results generated in this alternative format are marked with a star *) in the table below.

| Example | IC₅₀ [μM] |
|---|---|
| 1 | 6.8*⁾ |
| 1a | 1.22 |
| 1b | >100 |
| 2a | 0.036*⁾ |
| 2b | 247.8*⁾ |
| 2a-1 | 0.026 |
| 2a-2 | 1.31 |
| 3a | 0.016 |
| 3b | 18 |
| 4a | 0.034 |
| 4b | >100 |
| 5a | 0.005 |
| 5b | 23.3 |
| 4a-1 | 0.02 |
| 6 | 0.376 |
| 7 | 0.065 |
| 8 | 0.004 |
| 9 | 0.004 |
| 10 | 0.003 |
| 11 | 0.021 |
| 12 | 0.0015 |
| 13 | 0.006 |
| 14 | 0.015 |
| 15 | 0.01 |
| 16 | 0.006 |
| 17 | 0.013 |
| 18 | 0.004 |
| 19 | 0.003 |
| 20 | 0.124 |
| 21 | 0.004 |
| 22 | 0.009 |
| 23 | 0.009 |
| 24 | 0.006 |
| 25 | 0.005 |
| 26 | 0.021 |
| 27a | 0.001 |
| 27b | 0.001 |
| 28a | 0.003 |
| 28b | 0.003 |
| 29 | 0.01 |
| 30 | 0.143 |
| 31 | 0.003 |
| 32a | 0.033*⁾ |
| 32b | >100 |
| 33 | 0.003 |
| 34 | 0.009 |
| 35 | 0.009 |
| 36 | 0.01 |
| 37 | 0.002 |
| 38 | 0.002 |
| 39 | 0.102 |
| 40 | 0.042 |
| 41 | 0.089 |
| 42 | 0.006 |
| 43 | 0.005 |
| 44 | 0.006 |
| 45 | 0.01 |
| 46 | 0.003 |
| 47 | 0.004 |
| 48 | 0.002 |

| Example | IC$_{50}$ [μM] |
|---|---|
| 49 | 0.005 |
| 50 | 0.03 |
| 51 | 0.003 |
| 52 | 0.011 |
| 53 | 0.006 |
| 54a | 0.075 |
| 54b | 0.022 |
| 55a | <0.001 |
| 55b | 0.002 |
| 56a | 0.002 |
| 56b | 0.011 |
| 57a | 0.003 |
| 57b | 0.006 |
| 58a | 0.004 |
| 58b | 0.006 |
| 59a | 0.006 |
| 59b | 0.005 |
| 60 | 0.02 |
| 61a | 0.008 |
| 61b | 0.01 |
| 62a | 0.016 |
| 62b | 0.006 |
| 63 | 0.069 |
| 64a | 0.002 |
| 64b | 0.003 |
| 65a | 0.004 |
| 65b | 0.455 |
| 66a | 0.002 |
| 66b | 0.002 |
| 67a | 0.002 |
| 67b | 0.003 |
| 68a | 0.01 |
| 68b | 0.012 |
| 69a | 0.005 |
| 69b | 0.004 |
| 70 | 0.02 |
| 71a | 0.002 |
| 71b | 0.001 |
| 72 | 0.002 |
| 73 | 0.014 |
| 74 | 0.033 |
| 75 | 0.038 |
| 76 | 0.05 |
| 77 | 0.071 |
| 78 | 0.16 |
| 79 | 0.011 |
| 80 | 0.014 |
| 81a | 0.033 |
| 81b | 0.032 |
| 82 | 0.119 |
| 83 | 0.024 |
| 84 | 0.041 |
| 85a | 0.004 |
| 85b | 0.007 |
| 86 | 0.003 |
| 87 | 0.03 |
| 88 | 0.007 |
| 89 | 0.019 |
| 90 | 0.022 |
| 91 | 0.022 |
| 92 | 0.022 |
| 93 | 0.009 |
| 94a | 0.002 |
| 94b | 0.003 |
| 95a | 0.008 |
| 95b | 0.007 |
| 96 | 0.005 |
| 97 | 0.004 |
| 98 | 0.005 |
| 99 | 0.002 |
| 100a | 0.002 |
| 100b | 0.005 |
| 10 | 0.003 |
| 102a | 0.003 |
| 102b | 0.004 |
| 103 | 0.005 |
| 104a | 0.003 |
| 104b | 0.002 |
| 105 | 0.002 |
| 106 | <0.001 |
| 107 | 0.002 |
| 108 | 0.002 |
| 109 | 0.003 |
| 110 | 0.001 |
| 111 | 0.004 |
| 112 | 0.001 |
| 113 | 0.002 |
| 114a | 0.002 |
| 114b | 0.002 |
| 115a | 0.002 |
| 115b | 0.002 |
| 116a | <0.001 |
| 116b | 0.001 |
| 117a | <0.001 |
| 117b | 0.001 |
| 118 | 0.001 |
| 119 | 0.002 |
| 120 | 0.003 |
| 121 | 0.002 |
| 122 | 0.006 |
| 123 | 0.002 |
| 124 | 0.011 |
| 125 | 0.011 |
| 126 | 0.002 |
| 127 | 0.006 |
| 128 | 0.176 |
| 129 | 0.025 |
| 130 | 0.797 |
| 131 | 1.29 |
| 132 | 2.08 |
| 133 | 0.695 |
| 134 | 0.074 |
| 135 | 0.007 |
| 136a | 0.007 |
| 136b | 0.007 |
| 137a | 0.005 |
| 137b | 0.006 |
| 138a | 0.018*) |
| 138b | 0.018*) |
| 139a | 0.021 |
| 139b | 0.011 |
| 140a | 0.004 |
| 140b | 0.006 |
| 141 | 0.005 |
| 142 | 0.007 |
| 143 | 0.003 |
| 144 | 0.002 |
| 145 | 0.005 |
| 146 | 0.003 |
| 147 | 0.001 |
| 148 | 0.004 |
| 149 | 0.005 |
| 150 | 0.004 |
| 151 | 0.002 |
| 152 | 0.002 |
| 153 | <0.001 |
| 154 | 0.008 |
| 155 | 0.009 |
| 156 | 0.011 |
| 157 | 0.075 |
| 158 | 0.005 |
| 159 | 0.122 |
| 160 | 4.4 |
| 161 | 0.029 |
| 162 | 1.52 |
| 163 | 0.13 |
| 164 | 0.004 |
| 165 | 0.005 |
| 166 | 0.008 |
| 167 | 0.01 |
| 168 | 0.012 |
| 169 | 0.007 |
| 170 | 0.001 |
| 171 | 0.002 |

-continued

| Example | IC$_{50}$ [μM] |
|---------|----------------|
| 172 | 0.015 |
| 173 | 0.014 |
| 174 | 0.003 |
| 175 | 0.004 |
| 176 | 0.003 |

In-Vitro Cellular Assays

NCI-H2052 mesothelioma cells (RRID:CVCL_1518) bearing pathway activating mutations upstream of YAP (homozygous deletion of LATS2 and mutation of NF2) were obtained from ATCC, while MKN-45 gastric adenocarcinoma cells (RRID:CVCL 0434) genomically deleted for YAP were obtained from JCRB.

To enable monitoring of YAP-dependent pathway activity, NCl-H2052 cells were stably transduced with a lentivirus expressing firefly-luciferase under the control of a promoter consisting of 10× the sequence ATTCCTC (based on the muscle-specific cytidine-adenosine-thymidine (MCAT) promoter (5'-CATTCCT-3')-element) that had been cloned into the pGL4.27 vector (Promega, WI, USA), followed by subcloning into pLENTI6TR (Invitrogen, CA, USA). This cell line was also transduced with a Tet-pLKO-puro-based construct mediating tetracycline-inducible expression of a short-hairpin directed against the 3'UTR of the YAP1 mRNA (5'-CATGAGACAATTTCCATATA-3'). The resulting cell line, NCI-H2052 Tet-On shYAP_2371 pLenti6 MCAT_Luc, was selected and maintained in growth medium (RPMI 1640 (Amimed Cat #1-41F01-I), 2 mM L-Glutamine (Amimed Cat #5-10K50-H), 1% MEM Non-essential amino acids (Amimed Cat #5-13K00-H), 10% fetal calf serum (Gibco Cat #A31608-01 Lot 42F0863K), 1 mM sodium pyruvate (Amimed Cat #5-60F00-H), 1× Penicillin/Streptomycin (Amimed Cat #4-01F00-H)) containing 0.5 μg/mL puromycin (Gibco Cat #A11138-03) and 1 μg/mL blasticidin (Gibco Cat #A11139-03) at 37° C. in a humidified 5% $CO_2$ incubator.

As a specificity control, MKN-45 cells were stably transduced with a Ubc-Luc reporter construct, in which constitutive expression of firefly luciferase is driven by the promoter of the ubiquitin C housekeeping gene. The resulting cell line, MKN-45/Ubc-luc, was selected and maintained in growth medium (RPMI 1640 (Amimed #1-41F01-1), 2 mM L-Glutamine (Amimed Cat #5-10K50-H), 10% fetal calf serum (Amimed #2-01F30-1 Lot K08815P), 1% MEM Non-essential amino acids (Amimed Cat #5-13K00-H), 1× Penicillin/Streptomycin (Amimed Cat #4-01F00-H)) containing 1 μg/mL blasticidin (Gibco Cat #A11139-03) at 37° C. in a humidified 5% $CO_2$ incubator.

Compound Solutions

Stock solutions of compounds were prepared at a concentration of 10 mM in DMSO and stored at 4° C. Where necessary to afford a full dose-response curve, the stock solutions were pre-diluted in DMSO to 1'000-fold the desired reduced start concentration. On the day after cell seeding, eleven 2-fold serial dilutions of each compound were dispensed directly into the cell assay plates using a HP 300D non-contact Digital Dispenser (TECAN, Mannedorf, Switzerland). The final concentration of DMSO was normalized to 0.1% in all wells.

YAP Reporter Gene Activity Assay

The ability of compounds to inhibit YAP-dependent transcription was assessed in NCI-H2052 Tet-On shYAP_2371 pLenti6 MCAT_Luc cells, while specificity (lack of unspecific inhibition of luciferase expression of activity) was assessed in MKN-45/Ubc-luc cells. Individual cell lines were seeded at 2'500 cells/20 μl/well into white-wall, clear-bottom 384-well plates (Greiner, Cat #781098) and incubated over night at 37° C. prior to addition of serial compound dilutions as described above. Following incubation for 24 hours at 37° C., compound-mediated modulation of reporter-gene activity was quantified 5 min after addition of 20 μl BrightGlo (Promega, Cat #E2620), by measuring luminescence intensity on a multi-mode plate-reader (TECAN, Männedorf, Switzerland, Integration time 100 ms). For data analysis, the assay background value determined in wells containing medium, but no cells, was subtracted from all data points. Dose-dependent compound effects were expressed as % of vehicle-treated control (luminescence signal produced by cells receiving DMSO only) and IC50s calculated using a four-parametric fit model.

Proliferation Assay

The functional effect of compounds on cell proliferation was assessed using NCI-H2052 Tet-On shYAP_2371 pLenti6 MCAT_Luc and MKN-45/Ubc-luc cells by quantifying the reducing capacity of live cells using the redox indicator dye resazurin. Briefly, individual cell lines were seeded at 750 cells/20 μl/well (NCI-H2052) or 500 cells/20 μL/well (MKN-45) into black-wall, clear-bottom 384-well plates (Corning, Cat #3712) and incubated over night at 37° C. prior to addition of serial compound dilutions as described above. Following incubation for 72 hours at 37° C., compound-mediated modulation of cell viability was quantified 4 hours after addition of 5 μl resazurin sodium salt (SIGMA Cat #R7017, 0.85 μg/mL in phosphate-buffered saline) by measuring the fluorescence intensity of resorufin (the reduced form on resazurin) on a multi-mode plate-reader (TECAN, Männedorf, Switzerland, Ex/Em 544/590 nm). For data analysis, the assay background value determined in wells containing medium, but no cells, was subtracted from all data points. To enable differentiation of cytotoxic from cytostatic compounds, the number of viable cells was assessed relative to that observed at the time of compound addition using a separate cell plate (day 0). The effect of a particular test compound concentration on cell proliferation/viability was expressed as percentage of day 0-corrected fluorescence reading obtained for cells treated with vehicle only (DMSO, final concentration 0.1%), which was set as 100%, whereas the fluorescence reading for wells containing medium only, but no cells, was set as −100%. Compound concentrations leading to half-maximal growth inhibition (GI50) were determined using standard four parameter curve fitting.

| | Reporter gene assay | | Proliferation assay | |
|---|---|---|---|---|
| Example | NCI-H2052 IC$_{50}$ [μM] | MKN-45 IC$_{50}$ [μM] | NCI-H2052 GI$_{50}$ [μM] | MKN-45 GI$_{50}$ [μM] |
| 5a | 0.13 | >20 | 0.28 | >10 |
| 5b | >10 | >10 | >10 | >10 |
| 4a-1 | 0.6 | >10 | 0.59 | >10 |
| 10 | 0.064 | >10 | 0.099 | >10 |
| 11 | 0.173 | >20 | 0.284 | >10 |
| 12 | 0.037 | >20 | 0.086 | >10 |
| 13 | 0.102 | >10 | 0.166 | >10 |
| 14 | 0.176 | >10 | 0.19 | >10 |
| 15 | 0.27 | >10 | 0.276 | >10 |
| 18 | 0.379 | 19.5 | 0.553 | >12.5 |
| 20 | 2.92 | >10 | 6.88 | >10 |
| 21 | 0.154 | >10 | 0.247 | >10 |
| 22 | 0.157 | >20 | 0.256 | >10 |

|  | Reporter gene assay | | Proliferation assay | |
| --- | --- | --- | --- | --- |
| Example | NCI-H2052 IC$_{50}$ [μM] | MKN-45 IC$_{50}$ [μM] | NCI-H2052 GI$_{50}$ [μM] | MKN-45 GI$_{50}$ [μM] |
| 25 | 0.106 | >10 | 0.145 | >10 |
| 26 | 0.144 | >20 | 0.31 | >10 |
| 27a | 0.026 | >10 | 0.081 | >10 |
| 27b | 0.078 | >10 | 0.182 | >10 |
| 28a | 0.086 | >10 | 0.224 | >10 |
| 28b | 0.055 | >10 | 0.148 | >10 |
| 29 | 2.005 | >10 | 1.85 | >10 |
| 30 | 4.77 | >10 | 6.84 | >10 |
| 31 | 0.343 | >10 | 0.346 | >10 |
| 32a | 0.498 | >10 | 0.833 | 6.12 |
| 33 | 0.161 | >10 | 0.161 | >10 |
| 35 | 0.276 | >10 | 0.31 | >10 |
| 37 | 0.033 | >10 | 0.052 | >10 |
| 38 | 0.024 | >10 | 0.029 | >10 |
| 39 | 2.15 | >10 | 2.83 | >10 |
| 42 | 0.391 | >10 | 0.493 | 9.4 |
| 43 | 0.047 | >10 | 0.094 | >10 |
| 44 | 0.069 | >10 | 0.109 | >10 |
| 47 | 0.05 | >10 | 0.035 | >10 |
| 51 | 0.062 | >10 | 0.071 | >10 |
| 52 | 0.109 | >10 | 0.174 | >10 |
| 54a | 0.147 | >10 | 0.67 | >10 |
| 54b | 0.118 | >10 | 0.258 | >10 |
| 56a | 0.07 | >10 | 0.195 | >10 |
| 56b | 0.194 | 7.6 | 0.372 | >10 |
| 58a | 0.067 | >10 | 0.125 | >10 |
| 58b | 0.104 | >10 | 0.167 | >10 |
| 62a | 0.203 | >10 | 0.24 | >10 |
| 62b | 0.054 | >10 | 0.089 | >10 |
| 64a | 0.015 | >10 | 0.036 | >10 |
| 64b | 0.022 | >10 | 0.041 | >10 |
| 69a | 0.08 | >10 | 0.111 | >10 |
| 69b | 0.114 | 7.8 | 0.171 | 6.7 |
| 72 | 0.039 | 9.8 | 0.072 | >10 |
| 74 | 0.419 | >10 | 0.674 | >10 |
| 81a | 0.231 | >10 | 0.467 | >10 |
| 81b | 0.316 | >10 | 0.571 | >10 |
| 83 | 0.394 | >10 | 0.503 | >10 |
| 86 | 0.119 | >10 | 0.129 | >10 |
| 88 | 0.091 | >10 | 0.242 | >10 |
| 89 | 0.596 | >10 | 1.6 | >10 |
| 90 | 1.43 | >10 | 1.7 | >10 |
| 91 | 0.96 | >10 | 1.93 | >10 |
| 94a | 0.045 | >10 | 0.068 | >10 |
| 94b | 0.083 | >10 | 0.101 | >10 |
| 96 | 0.084 | >10 | 0.188 | >10 |
| 97 | 0.065 | >10 | 0.117 | >10 |
| 99 | 0.023 | >10 | 0.026 | >10 |
| 101 | 0.067 | >10 | 0.106 | >10 |
| 103 | 0.108 | >10 | 0.172 | >10 |
| 104a | 0.035 | >10 | 0.144 | 6.2 |
| 104b | 0.022 | >10 | 0.055 | >10 |
| 106 | 0.014 | >10 | 0.013 | >10 |
| 109 | 0.075 | >10 | 0.086 | >10 |
| 110 | 0.014 | >4 | 0.027 | >4 |
| 113 | 0.021 | >10 | 0.029 | >10 |
| 114a | 0.018 | >10 | 0.023 | >10 |
| 114b | 0.023 | >10 | 0.034 | >10 |
| 117a | 0.015 | >10 | 0.014 | >10 |
| 117b | 0.016 | >10 | 0.03 | >10 |
| 118 | 0.01 | >5.5 | 0.015 | >5.5 |
| 119 | 0.022 | >10 | 0.028 | >10 |
| 120 | 0.02 | >10 | 0.022 | >10 |
| 121 | 0.02 | >10 | 0.036 | >10 |
| 122 | 0.085 | >10 | 0.059 | >10 |
| 123 | 0.025 | >10 | 0.044 | >10 |
| 124 | 1.23 | >10 | 1.07 | >10 |
| 125 | 0.671 | >10 | 1.18 | >7.5 |
| 126 | 0.045 | >10 | 0.076 | >10 |
| 127 | 0.065 | >10 | 0.141 | >10 |
| 128 | 5.72 | >10 | 7.05 | >10 |
| 129 | 0.615 | >10 | 0.892 | >10 |
| 134 | 2.31 | >10 | 1.57 | >10 |
| 135 | 0.247 | >10 | 0.627 | 8.64 |
| 138a | 0.239 | >20 | 0.366 | >13.3 |
| 138b | 0.221 | 7.63 | 0.435 | >10 |
| 140a | 0.023 | >10 | 0.028 | >10 |
| 140b | 0.028 | >10 | 0.029 | >10 |
| 144 | 0.01 | >8 | 0.01 | >8 |
| 145 | 0.046 | >20 | 0.058 | >20 |
| 146 | 0.025 | >10 | 0.023 | >10 |
| 147 | 0.011 | >3.3 | 0.005 | >3.3 |
| 148 | 0.054 | >20 | 0.053 | >20 |
| 149 | 0.096 | >10 | 0.1 | >10 |
| 150 | 0.074 | >10 | 0.085 | >10 |
| 151 | 0.015 | >10 | 0.022 | >10 |
| 152 | 0.036 | >10 | 0.025 | >10 |
| 153 | 0.024 | >10 | 0.104 | >10 |
| 154 | 0.077 | >10 | 0.059 | >10 |
| 155 | 0.048 | >20 | 0.041 | >20 |
| 158 | 0.093 | >10 | 0.181 | >10 |
| 159 | 1.06 | >15 | 0.856 | >15 |
| 161 | 0.174 | >10 | 0.167 | >10 |
| 162 | 1.00 | >10 | 1.76 | >10 |
| 164 | 0.107 | >10 | 0.107 | >10 |
| 165 | 0.082 | >10 | 0.131 | >10 |
| 166 | 0.136 | >10 | 0.256 | >10 |
| 167 | 0.058 | >10 | 0.082 | >10 |
| 168 | 0.253 | >10 | 0.267 | >10 |
| 169 | 0.153 | >10 | 0.246 | 7.83 |
| 170 | 0.012 | >8 | 0.023 | >8 |
| 171 | 0.116 | 15.5 | 0.073 | 13 |
| 172 | 0.144 | >20 | 0.104 | >20 |
| 173 | 0.187 | >20 | 0.158 | >20 |
| 174 | 0.037 | 12 | 0.021 | 11 |
| 175 | 0.062 | 13 | 0.05 | 7 |
| 176 | 0.018 | 11 | 0.021 | 16 |

As shown in the data presented above, the compounds of the invention are potent YAP/TAZ-TEAD PPI inhibitors. The results indicate that the compounds may therefore be useful in the treatment of diseases or conditions mediated by YAP overexpression and/or YAP amplification and/or YAP/TAZ-TEAD interaction, such as cancers.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

Those skilled in the art will recognize, or be able to ascertain, using no more than routine experimentation, numerous equivalents to the specific embodiments described specifically herein.

Such equivalents are intended to be encompassed in the scope of the following claims.

The invention claimed is:

1. A compound of formula (Ia), or a pharmaceutically acceptable salt thereof,

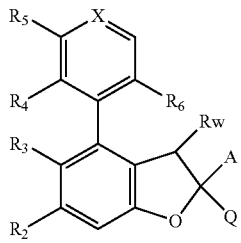
(Ia)

wherein
X is selected from CH and N;
A is selected from
(i) phenyl, wherein the phenyl is optionally substituted with halo; or haloC$_1$-C$_3$alkoxy;
(ii) a 5- or 6-membered aromatic heterocyclic ring comprising at least one heteroatom selected from N, O, and S, wherein the aromatic heterocyclic ring is optionally substituted with hydroxy; C$_1$-C$_3$alkoxy; or oxo; and
(iii) a halobenzodioxole moiety of formula

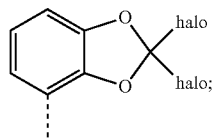

R$_w$ is selected from (i) hydrogen; (ii) hydroxy; (iii) C$_1$-C$_3$alkoxy; (iv) hydroxy-C$_1$-C$_3$alkyl; (v) C$_1$-C$_3$alkyl; and (vi) C$_1$-C$_3$alkoxy-C$_1$-C$_3$alkyl;
Q is selected from (i) —C(R$^7$)$_2$-N(R$^8$)—R$_1$; (ii) 9- or 10-membered partially saturated heteroaryl comprising at least one N heteroatom; and (iii) 4-, 5- or 6-membered saturated heterocyclic ring comprising at least one heteroatom or heteroatom group selected from N, O, S, —S(=O) and —S(=O)$_2$, with the proviso that at least one N heteroatom is present, wherein the heterocyclic ring is unsubstituted or substituted with one or more substituents independently selected from hydroxy, C$_1$-C$_3$alkyl, C$_1$-C$_3$alkoxy, halo and C$_1$-C$_3$alkylene forming a bridge between two ring atoms of the saturated heterocyclic ring, thus forming a bridged bicyclic structure;
R$_1$ is selected from (i) hydrogen; (ii) C$_1$-C$_6$alkyl which is optionally deuterated; and (iii) (CH$_2$)$_{0-2}$R$_{1a}$;
R$_{1a}$ is selected from (i) hydroxyC$_1$-C$_4$alkyl; (ii) C$_1$-C$_3$alkoxy; (iii) a 5- or 6-membered saturated heterocyclic ring comprising at least one heteroatom selected from N and O, wherein the saturated heterocyclic ring is optionally substituted with one or more substituents independently selected from C$_1$-C$_3$alkyl; (CH$_2$)$_{0-1}$C(O)di(C$_1$-C$_3$alkyl)amino; SO$_2$C$_1$-C$_3$alkyl; C(O)C$_1$-C$_3$alkyl; or oxo; and (iv) C$_3$-C$_6$cycloalkyl optionally substituted with one or more substituents independently selected from hydroxy; hydroxyC$_1$-C$_4$alkyl; C$_1$-C$_6$alkoxy; C(O)OC$_1$-C$_3$alkyl; CO$_2$H; SO$_2$C$_1$-C$_3$alkyl; haloC$_1$-C$_3$alkyl; NHR$^{1b}$; (CH$_2$)$_{0-1}$C(O)NR$^{1c}$R$^{1d}$; C$_1$-C$_6$alkyl; haloC$_1$-C$_3$alkoxy-C$_1$-C$_3$alkyl; halo; a 5- or 6-membered aromatic heterocyclic ring comprising at least one heteroatom selected from N, O, and S; and two R$^{1c}$ groups,
wherein the two R$^{1c}$ attached at the same carbon atom form together with the carbon atom to which they are attached a 5-membered saturated heterocyclic ring comprising at least one heteroatom selected from N and O, or a C$_3$-C$_6$cycloalkyl, wherein the saturated heterocyclic ring or cycloalkyl are optionally substituted with hydroxy or oxo;
R$^{1b}$ is selected from (i) C(O)C$_1$-C$_3$alkyl; and (ii) SO$_2$C$_1$-C$_3$alkyl;
R$^{1c}$ and R$^{1d}$ are each independently selected from (i) hydrogen; (ii) C$_1$-C$_3$alkyl; and (iii) hydroxyC$_1$-C$_4$alkyl;
R$_2$ is selected from (i) hydrogen; and (ii) halo;
R$_3$ is selected from (i) halo; (ii) haloC$_1$-C$_3$alkyl; and (iii) cyano;
R$_4$ is selected from (i) hydrogen; (ii) halo; and (iii) C$_1$-C$_3$alkyl;
R$_5$ is selected from (i) hydrogen; (ii) C$_1$-C$_6$alkoxy optionally substituted with C$_3$-C$_6$cycloalkyl; CO$_2$H; SO$_2$C$_1$-C$_3$alkyl; a 5- or 6-membered aromatic heterocyclic ring comprising at least one heteroatom selected from N, O, and S; or a 5- or 6-membered saturated heterocyclic ring comprising at least one heteroatom selected from N and O, wherein the ring is optionally substituted with C(O)C$_1$-C$_3$alkyl; (iii) halo; (iv) hydroxyC$_1$-C$_6$alkoxy, wherein the alkoxy is optionally deuterated; (v) haloC$_1$-C$_6$alkoxy optionally substituted with hydroxy; (vi) S-haloC$_1$-C$_3$alkyl optionally substituted with hydroxy; (vii) C$_1$-C$_3$alkoxyC$_1$-C$_3$alkoxy; (viii) NR$^{5a}$R$^{5b}$; (ix) C$_1$-C$_3$alkyl; (x) a 5- or 6-membered aromatic heterocyclic ring comprising at least one heteroatom selected from N, O, and S; and (xi) hydroxy;
R$^{5a}$ and R$^{5b}$ are each independently selected from (i) hydrogen; and (ii) C$_1$-C$_3$alkyl; or
R$^{5a}$ and R$^{5b}$ together with the nitrogen atom to which they are attached form a 5- or 6-membered saturated heterocyclic ring, wherein the saturated heterocyclic ring optionally in addition carries a hydroxy group;
R$_6$ is selected from (i) hydrogen; (ii) cyano; (iii) C(O)NR$^{6a}$; (iv) NHR$^{6b}$; and (v) C$_1$-C$_3$alkoxy substituted with NH$_2$ or hydroxy;
R$^{6a}$ is selected from (i) hydrogen; (ii) C$_1$-C$_3$alkyl; (iii) C$_3$-C$_6$cycloalkyl; and (iv) a 5- or 6-membered aromatic heterocyclic ring comprising at least one heteroatom selected from N, O, and S, wherein the aromatic heterocyclic ring is optionally substituted with C$_1$-C$_3$alkyl;
R$^{6b}$ is C$_1$-C$_3$alkyl substituted with NH$_2$ or hydroxy;
R$^7$ is each independently selected from hydrogen and C$_1$-C$_3$alkyl; and
R$^8$ is hydrogen or C$_1$-C$_3$-alkyl.

2. A compound of formula (Ia) according to claim 1, or a pharmaceutically acceptable salt thereof, which is a compound of formula (Ic)

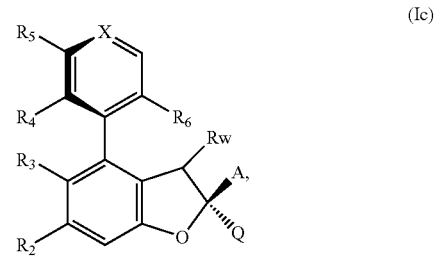
(Ic)

or a pharmaceutically acceptable salt thereof.

3. A compound of formula (Ia) according to claim 1, or a pharmaceutically acceptable salt thereof, which is a compound of formula (Id)

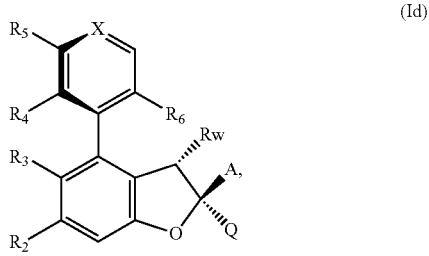

(Id)

or a pharmaceutically acceptable salt thereof.

4. A compound of formula (Ia) according to claim 1, or a pharmaceutically acceptable salt thereof, wherein
X is selected from CH and N;
A is selected from
(i) phenyl, wherein the phenyl is optionally substituted with halo; or haloC$_1$-C$_3$alkoxy;
(ii) a 5- or 6-membered aromatic heterocyclic ring comprising at least one heteroatom selected from N, O, and S, wherein the aromatic heterocyclic ring is optionally substituted with hydroxy; C$_1$-C$_3$alkoxy; or oxo; and
(iii) a halobenzodioxole moiety of formula

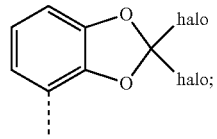

R$_w$ is selected from (i) hydrogen; (ii) hydroxy; (iii) C$_1$-C$_3$alkoxy; (iv) hydroxy-C$_1$-C$_3$alkyl; (v) C$_1$-C$_3$alkyl; and (vi) C$_1$-C$_3$alkoxy-C$_1$-C$_3$alkyl;
Q is selected from (i) —C(R$^7$)$_2$—N(R$^8$)—R$^1$; (ii) 9- or 10-membered partially saturated heteroaryl comprising at least one N heteroatom; and (iii) 4-, 5- or 6-membered saturated heterocyclic ring comprising at least one heteroatom selected from N, O and S, with the proviso that at least one N heteroatom is present, and wherein the N is optionally present in the α-position to the atom binding Q to the rest of the molecule, and wherein the heterocyclic ring is unsubstituted or substituted with one or more substituents independently selected from hydroxy, C$_1$-C$_3$alkyl, C$_1$-C$_3$alkoxy, halo and a methylene group, wherein the methylene group forms a bridge between two ring atoms of the saturated heterocyclic ring, thus forming a bridged bicyclic structure;
R$_1$ is selected from hydrogen; C$_1$-C$_6$alkyl; and (CH$_2$)$_{0-2}$R$_{1a}$ wherein
R$_{1a}$ is selected from (i) C$_1$-C$_3$alkoxy; (ii) C$_3$-C$_6$cycloalkyl optionally substituted with one or more substituents independently selected from hydroxy;
hydroxyC$_1$-C$_4$alkyl; C$_1$-C$_4$alkoxy; C(O)OC$_1$-C$_3$alkyl; CO$_2$H; C(O)NR$^{1c}$R$^{1d}$; C$_1$-C$_6$alkyl; halo; haloC$_1$-C$_3$alkoxy-C$_1$-C$_3$alkyl; SO$_2$C$_1$-C$_3$alkyl; haloC$_1$-C$_3$alkyl; NHR$^{1b}$; C(O)NR$^{1c}$R$^{1d}$; a 5- or 6-membered aromatic heterocyclic ring comprising at least one heteroatom selected from N, O, and S; and two R$^{1c}$ groups, wherein the two R$^{1c}$ groups are attached at the same carbon atom and form together with the carbon atom to which they are attached a 5-membered saturated heterocyclic ring comprising at least one heteroatom selected from N and O, or a C$_3$-C$_6$cycloalkyl, wherein the saturated heterocyclic ring or cycloalkyl are optionally substituted with hydroxy or oxo; and (iii) a 5- or 6-membered saturated heterocyclic ring comprising at least one heteroatom selected from N and O, wherein the saturated heterocyclic ring is optionally substituted one or more substituents independently selected from C$_1$-C$_3$alkyl; (CH$_2$)$_{0-1}$C(O)di(C$_1$-C$_3$alkyl) amino; SO$_2$C$_1$-C$_3$alkyl; C(O)C$_1$-C$_3$alkyl; and oxo;
R$^{1b}$ is selected from C(O)C$_1$-C$_3$alkyl; and SO$_2$C$_1$-C$_3$alkyl;
R$^{1c}$ and R$^{1d}$ are each independently selected from (i) hydrogen; (ii) C$_1$-C$_3$alkyl; and (iii) hydroxyC$_1$-C$_4$alkyl,
R$_2$ is hydrogen or halo,
R$_3$ is halo; haloC$_1$-C$_3$alkyl; or cyano,
R$_4$ is selected from hydrogen; halo; and C$_1$-C$_3$alkyl,
R$_5$ is selected from (i) hydrogen; (ii) halo-C$_1$-C$_6$alkoxy optionally substituted with hydroxy; (iii) S-haloC$_1$-C$_3$alkyl optionally substituted with hydroxy; (iv) C$_1$-C$_3$alkoxyC$_1$-C$_3$alkoxy; (v) C$_1$-C$_6$alkoxy optionally substituted with SO$_2$C$_1$-C$_3$alkyl, C$_3$-C$_6$cycloalkyl, CO$_2$H or a 5- or 6-membered saturated heterocyclic ring comprising at least one heteroatom selected from N and O, wherein the ring is optionally substituted with C(O)C$_1$-C$_3$alkyl; (vi) C$_1$-C$_3$alkyl; (vii) hydroxyC$_1$-C$_6$alkoxy; (viii) a 5- or 6-membered aromatic heterocyclic ring comprising at least one heteroatom selected from N, O, and S; and (ix) hydroxy,
R$_6$ is cyano; C(O)NHR$^{6a}$; NHR$^{6b}$; or C$_1$-C$_3$alkoxy substituted with NH$_2$ or hydroxy,
R$^{6a}$ is selected from (i) hydrogen; (ii) C$_1$-C$_3$alkyl; (iii) C$_3$-C$_6$cycloalkyl; and (iv) a 5- or 6-membered aromatic heterocyclic ring comprising at least one heteroatom selected from N, O, and S, wherein the aromatic heterocyclic ring is optionally substituted with C$_1$-C$_3$alkyl;
R$^{6b}$ is C$_1$-C$_3$alkyl substituted with NH$_2$ or hydroxy;
R$^7$ is each independently selected from hydrogen and C$_1$-C$_3$alkyl, and
R$^8$ is hydrogen or C$_1$-C$_3$alkyl.

5. A compound of formula (Ia) according to claim 1, or a pharmaceutically acceptable salt thereof, wherein
X is selected from CH; and N;
A is phenyl, wherein the phenyl is optionally substituted with halo; or haloC$_1$-C$_3$alkoxy;
R$_w$ is selected from (i) hydrogen; (ii) C$_1$-C$_3$alkoxy; (iii) hydroxy-C$_1$-C$_3$alkyl; (iv) C$_1$-C$_3$alkyl; and (v) C$_1$-C$_3$alkoxy-C$_1$-C$_3$alkyl;
Q is selected from (i) —C(R$^7$)$_2$—NH—R$_1$; and (ii) 4-, 5- or 6-membered saturated heterocyclic ring comprising one or two heteroatoms independently selected from N, O and S, with the proviso that at least one N heteroatom is present, wherein the N is present in the α-position to the atom binding Q to the rest of the molecule, and wherein the heterocyclic ring is unsubstituted or substituted with one or more substituents independently selected from hydroxy, C$_1$-C$_3$alkyl and halo;
R$_1$ is selected from (i) C$_1$-C$_6$alkyl; and (ii) R$_{1a}$; wherein R$_{1a}$ is selected from C$_3$-C$_6$cycloalkyl optionally substituted with one or more substituents independently selected from hydroxy; C$_1$-C$_6$alkyl; and halo;
R$_2$ is hydrogen or halo;
R$_3$ is halo;

R₄ is selected from (i) hydrogen; and (ii) halo;
R₅ is selected from halo-$C_1$-$C_6$alkoxy, hydroxy, $C_1$-$C_6$alkoxy; and hydroxy$C_1$-$C_6$alkoxy;
R₆ is C(O)NHR$^{6a}$;
R$^{6a}$ is selected from (i) hydrogen; and (ii) $C_1$-$C_3$alkyl; and
R⁷ is each independently selected from hydrogen and $C_1$-$C_3$alkyl.

6. A compound of formula (Ia) according to claim 1, or a pharmaceutically acceptable salt thereof, wherein
X is selected from CH; and N;
A is phenyl, wherein the phenyl is optionally substituted with halo; or halo$C_1$-$C_3$alkoxy;
R$_w$ is selected from (i) hydrogen; and (ii) $C_1$-$C_3$alkyl,
Q is selected from (i) —C(R⁷)₂—NH—R₁; and (ii) 4-, 5- or 6-membered saturated heterocyclic ring comprising one or two heteroatoms independently selected from N and O, with the proviso that at least one N heteroatom is present and is in the α-position to the carbon atom binding Q to the rest of the molecule, wherein the heterocyclic ring is unsubstituted or substituted with one or more substituents independently selected from hydroxy, $C_1$-$C_3$alkyl and halo;
R₁ is selected from (i) $C_1$-$C_6$alkyl; and (ii) R$_{1a}$; wherein R$_{1a}$ is $C_3$-$C_6$cycloalkyl optionally substituted with one or more substituents independently selected from hydroxy; $C_1$-$C_6$alkyl; and halo;
R₂ is halo;
R₃ is halo;
R₄ is halo;
R₅ is selected from $C_1$-$C_6$alkoxy; and hydroxy$C_1$-$C_6$alkoxy;
R₆ is C(O)NHR$^{6a}$;
R$^{6a}$ is selected from (i) hydrogen; and (ii) $C_1$-$C_3$alkyl; and each R⁷ is hydrogen.

7. A compound of formula (Ia) according to claim 1, or a pharmaceutically acceptable salt thereof, where the compound is selected from the group consisting of
(S)-(5-chloro-2,4-diphenyl-2,3-dihydrobenzofuran-2-yl) methanamine N1-(2-((2S,4S)-2-(aminomethyl)-5-chloro-2-phenyl-2,3-dihydrobenzofuran-4-yl)-3-fluoro-phenyl)ethane-1,2-diamine;
2-(2-((2S,4S)-2-(aminomethyl)-5-chloro-2-phenyl-2,3-dihydrobenzofuran-4-yl)-3-fluoro-phenoxy) ethanamine;
2-((2S,4S)-2-(aminomethyl)-5-chloro-2-phenyl-2,3-dihydrobenzofuran-4-yl)-3-fluorobenzamide;
2-((2S,4S)-2-(aminomethyl)-5-chloro-2-phenyl-2,3-dihydrobenzofuran-4-yl)-3-fluoro-4-methoxybenzamide;
2-((2S,4R)-2-(aminomethyl)-5-chloro-2-phenyl-2,3-dihydrobenzofuran-4-yl)-3-methylbenzamide;
2-((2S,4S)-2-(aminomethyl)-5-chloro-2-phenyl-2,3-dihydrobenzofuran-4-yl)-4-chloro-3-fluorobenzamide;
2-((2S,4S)-2-(aminomethyl)-5-chloro-2-phenyl-2,3-dihydrobenzofuran-4-yl)-3,4-difluorobenzamide;
2-((2S,4S)-2-(aminomethyl)-5-chloro-2-phenyl-2,3-dihydrobenzofuran-4-yl)-3-fluoro-4-(2-hydroxyethoxy) benzamide;
2-((2S,4S)-2-(aminomethyl)-5-chloro-2-phenyl-2,3-dihydrobenzofuran-4-yl)-4-(difluoro-methoxy)-3-fluorobenzamide;
2-((2S,4S)-2-(aminomethyl)-5-chloro-2-phenyl-2,3-dihydrobenzofuran-4-yl)-3-fluoro-4-(2-methoxyethoxy) benzamide;
2-((2S,4S)-2-(aminomethyl)-5-chloro-2-phenyl-2,3-dihydrobenzofuran-4-yl)-3-fluoro-4-((S)-2-hydroxypropoxy)benzamide;
2-((2S,4S)-2-(aminomethyl)-5-chloro-2-phenyl-2,3-dihydrobenzofuran-4-yl)-3-fluoro-4-((R)-2-hydroxypropoxy)benzamide;
2-((2S,4S)-2-(aminomethyl)-5-chloro-2-phenyl-2,3-dihydrobenzofuran-4-yl)-3-fluoro-4-((R)-2-fluoropropoxy) benzamide;
4-(((R)-4-acetylmorpholin-2-yl)methoxy)-2-((2S,4S)-2-(aminomethyl)-5-chloro-2-phenyl-2,3-dihydrobenzofuran-4-yl)-3-fluorobenzamide;
4-((2S,4S)-2-(aminomethyl)-5-chloro-2-phenyl-2,3-dihydrobenzofuran-4-yl)-5-fluoro-6-methoxynicotinamide;
4-((2S,4S)-2-(aminomethyl)-5-chloro-2-phenyl-2,3-dihydrobenzofuran-4-yl)-6-(difluoromethoxy)-5-fluoronicotinamide;
2-((2S,4S)-2-(aminomethyl)-5-chloro-2-phenyl-2,3-dihydrobenzofuran-4-yl)-3-fluoro-4-(methylamino)benzamide;
2-((2S,4S)-5-chloro-2-((methylamino)methyl)-2-phenyl-2,3-dihydrobenzofuran-4-yl)-3-fluoro-4-methoxybenzamide,
2-((2S,4S)-2-(aminomethyl)-5-chloro-2-phenyl-2,3-dihydrobenzofuran-4-yl)-3-fluoro-4-methoxy-N-methylbenzamide;
2-((2S,4S)-2-(aminomethyl)-5-chloro-2-phenyl-2,3-dihydrobenzofuran-4-yl)-N-cyclopropyl-3-fluoro-4-methoxybenzamide;
2-((2S,4S)-2-(aminomethyl)-5-chloro-2-phenyl-2,3-dihydrobenzofuran-4-yl)-3,4-difluoro-N-(1-methyl-1H-pyrazol-5-yl)benzamide;
2-((2S,4S)-2-(aminomethyl)-5-chloro-2-phenyl-2,3-dihydrobenzofuran-4-yl)-3-fluoro-4-methoxy-N-(pyridin-3-yl)benzamide;
2-((2S,4S)-5-chloro-2-((methylamino)methyl)-2-phenyl-2,3-dihydrobenzofuran-4-yl)-3-fluoro-4-methoxy-N-methylbenzamide,
2-((2S,4S)-5-chloro-2-(((trans-4-hydroxycyclohexyl)amino)methyl)-2-phenyl-2,3-dihydrobenzofuran-4-yl)-3-fluoro-4-methoxybenzamide;
2-((2S,4S)-5-chloro-2-(((cis-4-hydroxycyclohexyl)amino)methyl)-2-phenyl-2,3-dihydrobenzofuran-4-yl)-3-fluoro-4-methoxybenzamide;
(trans)-4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylic acid;
(cis)-4-((((2S,4S)-4-(6-carbamoyl-2-fluoro-3-methoxyphenyl)-5-chloro-2-phenyl-2,3-dihydrobenzofuran-2-yl)methyl)amino)cyclohexanecarboxylic acid;
2-((2R,4S)-2-(aminomethyl)-5-chloro-2-(thiazol-4-yl)-2,3-dihydrobenzofuran-4-yl)-3-fluoro-4-methoxybenzamide;
2-((2S,4S)-2-(aminomethyl)-5-chloro-2-(2,2-difluorobenzo[d][1,3]dioxol-4-yl)-2,3-dihydrobenzofuran-4-yl)-3-fluorobenzamide;
2-((2S,4S)-2-(aminomethyl)-5-chloro-2-(2-fluorophenyl)-2,3-dihydrobenzofuran-4-yl)-3-fluoro-4-methoxybenzamide;
2-((2S,4S)-2-(aminomethyl)-5-chloro-6-fluoro-2-phenyl-2,3-dihydrobenzofuran-4-yl)-3-fluorobenzamide;
2-((2S,4S)-2-(aminomethyl)-5-chloro-6-fluoro-2-phenyl-2,3-dihydrobenzofuran-4-yl)-3-fluoro-4-methoxybenzamide;
2-((2S,4S)-2-(aminomethyl)-5-chloro-6-fluoro-2-phenyl-2,3-dihydrobenzofuran-4-yl)-4-(cyclopropylmethoxy)-3-fluorobenzamide;
2-((2S,4S)-2-(aminomethyl)-5-chloro-6-fluoro-2-phenyl-2,3-dihydrobenzofuran-4-yl)-4-(difluoromethoxy)-3-fluorobenzamide;

2-((2S,4S)-2-(aminomethyl)-5-chloro-6-fluoro-2-phenyl-2,3-dihydrobenzofuran-4-yl)-4-(1,1-difluoro-2-hydroxyethoxy)-3-fluorobenzamide;

2-((2S,4S)-2-(aminomethyl)-5-chloro-6-fluoro-2-phenyl-2,3-dihydrobenzofuran-4-yl)-3-fluoro-4-(2-methoxyethoxy)benzamide;

2-((2S,4S)-2-(aminomethyl)-5-chloro-6-fluoro-2-phenyl-2,3-dihydrobenzofuran-4-yl)-3-fluoro-4-(2-hydroxyethoxy)benzamide;

2-((2S,4R)-2-(aminomethyl)-5-chloro-6-fluoro-2-phenyl-2,3-dihydrobenzofuran-4-yl)-4-((1,1-difluoro-2-hydroxyethyl)thio)benzamide;

2-((2S,4S)-2-(aminomethyl)-5-chloro-6-fluoro-2-phenyl-2,3-dihydrobenzofuran-4-yl)-3-fluoro-4-((methylsulfonyl)methoxy)benzamide;

2-((2S,4S)-2-(aminomethyl)-5-chloro-6-fluoro-2-phenyl-2,3-dihydrobenzofuran-4-yl)-4-(3,3-difluoropropoxy)-3-fluorobenzamide;

4-((2S,4S)-2-(aminomethyl)-5-chloro-6-fluoro-2-phenyl-2,3-dihydrobenzofuran-4-yl)-5-fluoro-6-methoxynicotinamide;

4-((2S,4S)-2-(aminomethyl)-5-chloro-6-fluoro-2-phenyl-2,3-dihydrobenzofuran-4-yl)-5-fluoro-6-(2-hydroxyethoxy)nicotinamide;

2-((2S,4S)-2-(aminomethyl)-5-chloro-6-fluoro-2-phenyl-2,3-dihydrobenzofuran-4-yl)-3-fluoro-4-(2-hydroxyethoxy)-N-methylbenzamide;

4-((2S,4S)-2-(aminomethyl)-5-chloro-6-fluoro-2-phenyl-2,3-dihydrobenzofuran-4-yl)-5-fluoro-6-(2-hydroxyethoxy)-N-methylnicotinamide;

2-((2S,4S)-5-chloro-6-fluoro-2-((methylamino)methyl)-2-phenyl-2,3-dihydrobenzofuran-4-yl)-3-fluoro-4-methoxybenzamide;

4-((2S,4S)-5-chloro-6-fluoro-2-((methylamino)methyl)-2-phenyl-2,3-dihydrobenzofuran-4-yl)-5-fluoro-6-(2-methoxyethoxy)nicotinamide;

2-((2S,4S)-5-chloro-6-fluoro-2-((methylamino)methyl)-2-phenyl-2,3-dihydrobenzofuran-4-yl)-3-fluoro-4-(2-hydroxyethoxy)benzamide;

4-((2S,4S)-5-chloro-6-fluoro-2-((methylamino)methyl)-2-phenyl-2,3-dihydrobenzofuran-4-yl)-5-fluoro-6-(2-hydroxyethoxy)nicotinamide, 2-((2S,4S)-5-chloro-6-fluoro-2-(((cyclopropylmethyl)amino)methyl)-6-fluoro-2-phenyl-2,3-dihydrobenzofuran-4-yl)-4-(difluoromethoxy)-3-fluorobenzamide;

2-((2S,4S)-5-chloro-6-fluoro-2-((methylamino)methyl)-2-phenyl-2,3-dihydrobenzofuran-4-yl)-3-fluoro-4-(2-hydroxyethoxy)-N-methylbenzamide;

2-((2S,4S)-5-chloro-6-fluoro-2-((methylamino)methyl)-2-phenyl-2,3-dihydrobenzofuran-4-yl)-3-fluoro-4-((S)-2-hydroxypropoxy)-N-methylbenzamide;

4-((2S,4S)-5-chloro-6-fluoro-2-((methylamino)methyl)-2-phenyl-2,3-dihydrobenzofuran-4-yl)-5-fluoro-6-(2-hydroxyethoxy)-N-methylnicotinamide;

2-((2S,4S)-5-chloro-6-fluoro-2-((((cis)-4-(methylsulfonyl)cyclohexyl)amino)methyl)-2-phenyl-2,3-dihydrobenzofuran-4-yl)-4-(difluoromethoxy)-3-fluorobenzamide;

2-((2S,4S)-5-chloro-6-fluoro-2-((((trans)-4-(methylsulfonyl)cyclohexyl)amino)methyl)-2-phenyl-2,3-dihydrobenzofuran-4-yl)-4-(difluoromethoxy)-3-fluorobenzamide;

2-((2S,4S)-5-chloro-6-fluoro-2-(((4-(fluoromethyl)-4-hydroxycyclohexyl)amino)methyl)-2-phenyl-2,3-dihydrobenzofuran-4-yl)-4-(difluoromethoxy)-3-fluorobenzamide;

2-((2S,4S)-2-(((4-acetamidocyclohexyl)amino)methyl)-5-chloro-6-fluoro-2-phenyl-2,3-dihydrobenzofuran-4-yl)-4-(difluoromethoxy)-3-fluorobenzamide;

2-((2S,4S)-5-chloro-6-fluoro-2-(((4-(methylsulfonamido)cyclohexyl)amino)methyl)-2-phenyl-2,3-dihydrobenzofuran-4-yl)-4-(difluoromethoxy)-3-fluorobenzamide;

2-((2S,4S)-5-chloro-2-(((4-(dimethylcarbamoyl)cyclohexyl)amino)methyl)-6-fluoro-2-phenyl-2,3-dihydrobenzofuran-4-yl)-4-(difluoromethoxy)-3-fluorobenzamide;

2-((2S,4S)-5-chloro-6-fluoro-2-(((2-oxo-1-azaspiro[4.5]decan-8-yl)amino)methyl)-2-phenyl-2,3-dihydrobenzofuran-4-yl)-4-(difluoromethoxy)-3-fluorobenzamide;

2-((2S,4S)-5-chloro-2-(((1-(2-(dimethylamino)-2-oxoethyl)piperidin-4-yl)amino)methyl)-6-fluoro-2-phenyl-2,3-dihydrobenzofuran-4-yl)-4-(difluoromethoxy)-3-fluorobenzamide;

2-((2S,4S)-5-chloro-6-fluoro-2-(((4-(hydroxymethyl)cyclohexyl)amino)methyl)-2-phenyl-2,3-dihydrobenzofuran-4-yl)-4-(difluoromethoxy)-3-fluorobenzamide;

2-((2S,4S)-5-chloro-6-fluoro-2-(((3-(2-hydroxypropan-2-yl)cyclobutyl)amino)methyl)-2-phenyl-2,3-dihydrobenzofuran-4-yl)-4-(difluoromethoxy)-3-fluorobenzamide;

2-((2S,4S)-5-chloro-6-fluoro-2-(((1-(methylsulfonyl)piperidin-4-yl)amino)methyl)-2-phenyl-2,3-dihydrobenzofuran-4-yl)-4-(difluoromethoxy)-3-fluorobenzamide;

2-((2S,4S)-5-chloro-6-fluoro-2-((((trans)-3-(hydroxymethyl)cyclobutyl)amino)methyl)-2-phenyl-2,3-dihydrobenzofuran-4-yl)-3-fluoro-4-(2-hydroxyethoxy)benzamide;

2-((2S,4S)-5-chloro-6-fluoro-2-((((cis)-3-(hydroxymethyl)cyclobutyl)amino)methyl)-2-phenyl-2,3-dihydrobenzofuran-4-yl)-3-fluoro-4-(2-hydroxyethoxy)benzamide;

2-((2S,4S)-5-chloro-2-(((((2R,4r,6S)-2,6-dimethyltetrahydro-2H-pyran-4-yl)amino)methyl)-6-fluoro-2-phenyl-2,3-dihydrobenzofuran-4-yl)-3-fluoro-4-(2-hydroxyethoxy)benzamide;

2-((2S,4S)-5-chloro-2-(((((2R,4s,6S)-2,6-dimethyltetrahydro-2H-pyran-4-yl)amino)methyl)-6-fluoro-2-phenyl-2,3-dihydrobenzofuran-4-yl)-3-fluoro-4-(2-hydroxyethoxy)benzamide;

4-((2S,4S)-5-chloro-6-fluoro-2-((((trans)-4-hydroxy-4-methylcyclohexyl)amino)methyl)-2-phenyl-2,3-dihydrobenzofuran-4-yl)-5-fluoro-6-methoxynicotinamide;

4-((2S,4S)-5-chloro-6-fluoro-2-((((cis)-4-hydroxy-4-methylcyclohexyl)amino)methyl)-2-phenyl-2,3-dihydrobenzofuran-4-yl)-5-fluoro-6-methoxynicotinamide;

2-((2S,4S)-5-chloro-6-fluoro-2-((((cis)-4-hydroxy-4-methylcyclohexyl)amino)methyl)-2-phenyl-2,3-dihydrobenzofuran-4-yl)-3-fluoro-4-(((R)-tetrahydrofuran-2-yl)methoxy)benzamide;

2-((2S,4S)-5-chloro-6-fluoro-2-((((trans)-4-hydroxy-4-methylcyclohexyl)amino)methyl)-2-phenyl-2,3-dihydrobenzofuran-4-yl)-3-fluoro-4-(((R)-tetrahydrofuran-2-yl)methoxy)benzamide;

2-((2S,4S)-5-chloro-6-fluoro-2-((((trans)-4-hydroxy-4-methylcyclohexyl)amino)methyl)-2-phenyl-2,3-dihydrobenzofuran-4-yl)-4-ethyl-3-fluorobenzamide;

2-((2S,4S)-5-chloro-6-fluoro-2-((((cis)-4-hydroxy-4-methylcyclohexyl)amino)methyl)-2-phenyl-2,3-dihydrobenzofuran-4-yl)-4-ethyl-3-fluorobenzamide;

2-((2S,4S)-5-chloro-6-fluoro-2-((((trans)-4-hydroxy-4-methylcyclohexyl)amino)methyl)-2-phenyl-2,3-dihydrobenzofuran-4-yl)-3-fluoro-4-(1H-imidazol-1-yl)benzamide;

2-((2S,4S)-5-chloro-6-fluoro-2-((((cis)-4-hydroxy-4-methylcyclohexyl)amino)methyl)-2-phenyl-2,3-dihydrobenzofuran-4-yl)-3-fluoro-4-(1H-imidazol-1-yl)benzamide;

2-((2S,4S)-2-(((1-acetylpiperidin-4-yl)amino)methyl)-5-chloro-6-fluoro-2-phenyl-2,3-dihydrobenzofuran-4-yl)-4-(difluoromethoxy)-3-fluorobenzamide;

2-((2S,4S)-5-chloro-6-fluoro-2-((((trans)-4-hydroxy-4-methylcyclohexyl)amino)methyl)-2-phenyl-2,3-dihydrobenzofuran-4-yl)-3-fluoro-4-(pyrimidin-2-ylmethoxy)benzamide;

2-((2S,4S)-5-chloro-6-fluoro-2-((((cis)-4-hydroxy-4-methylcyclohexyl)amino)methyl)-2-phenyl-2,3-dihydrobenzofuran-4-yl)-3-fluoro-4-(pyrimidin-2-ylmethoxy)benzamide;

2-((2S,4S)-5-chloro-6-fluoro-2-((((trans)-4-hydroxycyclohexyl)amino)methyl)-2-phenyl-2,3-dihydrobenzofuran-4-yl)-4-(difluoromethoxy)-3-fluorobenzamide;

2-((2S,4S)-2-((tert-butylamino)methyl)-5-chloro-6-fluoro-2-phenyl-2,3-dihydrobenzofuran-4-yl)-4-(difluoromethoxy)-3-fluorobenzamide;

2-((2S,4S)-5-chloro-6-fluoro-2-((((R)-2-hydroxypropyl)amino)methyl)-2-phenyl-2,3-dihydrobenzofuran-4-yl)-4-(difluoromethoxy)-3-fluorobenzamide;

2-((2S,4S)-5-chloro-6-fluoro-2-((((S)-1-hydroxypropan-2-yl)amino)methyl)-2-phenyl-2,3-dihydrobenzofuran-4-yl)-4-(difluoromethoxy)-3-fluorobenzamide;

2-((2S,4S)-5-chloro-6-fluoro-2-(((1-methylcyclopropyl)amino)methyl)-2-phenyl-2,3-di-hydrobenzofuran-4-yl)-4-(difluoromethoxy)-3-fluorobenzamide;

2-((2S,4S)-5-chloro-6-fluoro-2-(((2-methoxyethyl)amino)methyl)-2-phenyl-2,3-dihydro-benzofuran-4-yl)-4-(difluoromethoxy)-3-fluorobenzamide;

2-((2S,4S)-5-chloro-6-fluoro-2-(((2-(2-oxopyrrolidin-1-yl)ethyl)amino)methyl)-2-phenyl-2,3-dihydrobenzofuran-4-yl)-4-(difluoromethoxy)-3-fluorobenzamide;

2-((2S,4S)-2-((((trans)-4-(1H-tetrazol-1-yl)cyclohexyl)amino)methyl)-5-chloro-6-fluoro-2-phenyl-2,3-dihydrobenzofuran-4-yl)-4-(difluoromethoxy)-3-fluorobenzamide;

2-((2S,4S)-5-chloro-2-(((trans-3-((difluoromethoxy)methyl)cyclobutyl)amino)methyl)-6-fluoro-2-phenyl-2,3-dihydrobenzofuran-4-yl)-4-(difluoromethoxy)-3-fluorobenzamide;

2-((2S,4S)-5-chloro-6-fluoro-2-((((1S,3R,4R)-3-fluoro-4-hydroxycyclohexyl)amino)methyl)-2-phenyl-2,3-dihydrobenzofuran-4-yl)-4-(difluoromethoxy)-3-fluorobenzamide;

2-((2S,4S)-5-chloro-6-fluoro-2-((((1R,3S,4S)-3-fluoro-4-hydroxycyclohexyl)amino)methyl)-2-phenyl-2,3-dihydrobenzofuran-4-yl)-4-(difluoromethoxy)-3-fluorobenzamide;

2-((2S,4S)-5-chloro-6-fluoro-2-(((trans-3-fluorocyclobutyl)amino)methyl)-2-phenyl-2,3-dihydrobenzofuran-4-yl)-4-(difluoromethoxy)-3-fluorobenzamide;

2-((2S,4S)-5-chloro-6-fluoro-2-((((1R,3S)-3-hydroxycyclohexyl)amino)methyl)-2-phenyl-2,3-dihydrobenzofuran-4-yl)-4-(difluoromethoxy)-3-fluorobenzamide;

2-((2S,4S)-5-chloro-6-fluoro-2-((((trans)-4-hydroxy-1-methylcyclohexyl)amino)methyl)-2-phenyl-2,3-dihydrobenzofuran-4-yl)-4-(difluoromethoxy)-3-fluorobenzamide;

2-((2S,4S)-5-chloro-6-fluoro-2-(((6-hydroxyspiro[3.3]heptan-2-yl)amino)methyl)-2-phenyl-2,3-dihydrobenzofuran-4-yl)-4-(difluoromethoxy)-3-fluorobenzamide;

2-((2S,3S,4S)-2-(aminomethyl)-5-chloro-3-hydroxy-2-phenyl-2,3-dihydrobenzofuran-4-yl)-3-fluoro-4-methoxybenzamide;

2-((2S,3S,4S)-2-(aminomethyl)-5-chloro-3-hydroxy-2-phenyl-2,3-dihydrobenzofuran-4-yl)-4-(difluoromethoxy)-3-fluorobenzamide;

2-((2S,3S,4S)-2-(aminomethyl)-5-chloro-3-hydroxy-2-phenyl-2,3-dihydrobenzofuran-4-yl)-3-fluoro-4-(2-methoxyethoxy)benzamide;

2-((2R,3S,4S)-2-(aminomethyl)-5-chloro-3-hydroxy-2-(pyridin-2-yl)-2,3-dihydrobenzofuran-4-yl)-3-fluoro-4-methoxybenzamide;

2-((2R,3 S,4S)-2-(aminomethyl)-5-chloro-3-hydroxy-2-(6-methoxypyridin-2-yl)-2,3-dihydrobenzofuran-4-yl)-4-(difluoromethoxy)-3-fluorobenzamide;

2-((2S,3 S,4S)-2-(aminomethyl)-5-chloro-3-hydroxy-2-(2-methoxypyridin-3-yl)-2,3-dihydrobenzofuran-4-yl)-3-fluoro-4-methoxybenzamide;

2-((2S,3 S,4S)-2-(aminomethyl)-5-chloro-3-hydroxy-2-(2-oxo-1,2-dihydropyridin-3-yl)-2,3-dihydrobenzofuran-4-yl)-3-fluoro-4-methoxybenzamide;

2-((2S,3 S,4S)-2-(aminomethyl)-5-chloro-3-hydroxy-2-(2-(trifluoromethoxy)phenyl)-2,3-dihydrobenzofuran-4-yl)-3-fluoro-4-methoxybenzamide;

2-((2S,3 S,4S)-5-chloro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide;

2-((2S,3 S,4S)-5-chloro-3-hydroxy-2-((((cis)-4-hydroxycyclohexyl)amino)methyl)-2-phenyl-2,3-dihydrobenzofuran-4-yl)-4-(difluoromethoxy)-3-fluorobenzamide;

2-((2R,3 S,4S)-5-chloro-3-hydroxy-2-((((trans)-4-hydroxycyclohexyl)amino)methyl)-2-(pyridin-2-yl)-2,3-dihydrobenzofuran-4-yl)-3-fluoro-4-methoxybenzamide;

2-((2R,3 S,4S)-5-chloro-3-hydroxy-2-((((cis)-4-hydroxycyclohexyl)amino)methyl)-2-(pyridin-2-yl)-2,3-dihydrobenzofuran-4-yl)-3-fluoro-4-methoxybenzamide;

2-((2S,3 S,4S)-5-chloro-2-((cyclobutylamino)methyl)-3-hydroxy-2-phenyl-2,3-dihydrobenzofuran-4-yl)-4-(difluoromethoxy)-3-fluorobenzamide;

2-((2S,3 S,4S)-2-(aminomethyl)-5-chloro-6-fluoro-3-hydroxy-2-phenyl-2,3-dihydrobenzofuran-4-yl)-3-fluoro-4-methoxybenzamide;

2-((2S,3 S,4S)-2-(aminomethyl)-5-chloro-6-fluoro-3-hydroxy-2-phenyl-2,3-dihydrobenzofuran-4-yl)-3-fluoro-4-(2-hydroxyethoxy)benzamide;

2-((2S,3 S,4S)-5-chloro-2-((cyclobutylamino)methyl)-6-fluoro-3-hydroxy-2-phenyl-2,3-dihydrobenzofuran-4-yl)-3-fluoro-4-(2-hydroxyethoxy)benzamide;

2-((2S,3 S,4S)-5-chloro-6-fluoro-3-hydroxy-2-((((trans)-4-hydroxycyclohexyl)amino)methyl)-2-phenyl-2,3-dihydrobenzofuran-4-yl)-4-(difluoromethoxy)-3-fluorobenzamide;

2-((2S,3 S,4S)-5-chloro-6-fluoro-3-hydroxy-2-((((cis)-4-hydroxycyclohexyl)amino)methyl)-2-phenyl-2,3-dihydrobenzofuran-4-yl)-4-(difluoromethoxy)-3-fluorobenzamide;

2-((2S,3 S,4S)-2-(aminomethyl)-5-chloro-6-fluoro-3-methoxy-2-phenyl-2,3-dihydrobenzofuran-4-yl)-3-fluoro-4-(2-hydroxyethoxy)benzamide;

2-((2S,3 S,4S)-5-chloro-6-fluoro-2-((((trans)-4-hydroxycyclohexyl)amino)methyl)-3-methoxy-2-phenyl-2,3-dihydrobenzofuran-4-yl)-4-(difluoromethoxy)-3-fluorobenzamide;

2-((2S,3S,4S)-5-chloro-6-fluoro-2-((((cis)-4-hydroxycyclohexyl)amino)methyl)-3-methoxy-2-phenyl-2,3-dihydrobenzofuran-4-yl)-4-(difluoromethoxy)-3-fluorobenzamide;

2-((2S,3S,4S)-2-(aminomethyl)-5-chloro-3-methyl-2-phenyl-2,3-dihydrobenzofuran-4-yl)-4-(difluoromethoxy)-3-fluorobenzamide;

2-((2S,3S,4S)-5-chloro-2-((((cis)-4-hydroxy-4-methylcyclohexyl)amino)methyl)-3-methyl-2-phenyl-2,3-dihydrobenzofuran-4-yl)-4-(difluoromethoxy)-3-fluorobenzamide;

2-((2S,3S,4S)-5-chloro-2-((((trans)-4-hydroxy-4-methylcyclohexyl)amino)methyl)-3-methyl-2-phenyl-2,3-dihydrobenzofuran-4-yl)-4-(difluoromethoxy)-3-fluorobenzamide;

2-((2S,3S,4S)-2-(aminomethyl)-5-chloro-6-fluoro-3-methyl-2-phenyl-2,3-dihydrobenzofuran-4-yl)-4-(difluoromethoxy)-3-fluorobenzamide;

2-((2S,3S,4S)-2-(aminomethyl)-5-chloro-6-fluoro-3-methyl-2-phenyl-2,3-dihydrobenzofuran-4-yl)-3-fluoro-4-(2-methoxyethoxy)benzamide;

2-((2S,3S,4S)-2-(aminomethyl)-5-chloro-6-fluoro-3-methyl-2-phenyl-2,3-dihydrobenzofuran-4-yl)-3-fluoro-4-(2-hydroxyethoxy)benzamide;

4-((2S,3S,4S)-2-(aminomethyl)-5-chloro-6-fluoro-3-methyl-2-phenyl-2,3-dihydrobenzofuran-4-yl)-5-fluoro-6-(2-methoxyethoxy)nicotinamide;

2-((2R,3S,4S)-2-(aminomethyl)-5-chloro-6-fluoro-3-methyl-2-(pyridin-2-yl)-2,3-dihydrobenzofuran-4-yl)-3-fluoro-4-methoxybenzamide;

2-((2S,3S,4S)-5-chloro-6-fluoro-3-methyl-2-((methylamino)methyl)-2-phenyl-2,3-dihy-drobenzofuran-4-yl)-3-fluoro-4-(2-hydroxyethoxy)benzamide;

2-((2R,3S,4S)-5-chloro-6-fluoro-3-methyl-2-((methylamino)methyl)-2-(pyridin-2-yl)-2,3-dihydrobenzofuran-4-yl)-3-fluoro-4-(2-methoxyethoxy)benzamide;

2-((2R,3S,4S)-5-chloro-6-fluoro-3-methyl-2-((methylamino)methyl)-2-(pyridin-2-yl)-2,3-dihydrobenzofuran-4-yl)-3-fluoro-4-(2-hydroxyethoxy)benzamide;

2-((2S,3S,4S)-5-chloro-6-fluoro-3-methyl-2-((methylamino)methyl)-2-phenyl-2,3-dihydrobenzofuran-4-yl)-3-fluoro-4-(2-hydroxyethoxy)-N-methylbenzamide;

2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide;

2-((2S,3S,4S)-5-chloro-6-fluoro-2-((((cis)-4-hydroxy-4-methylcyclohexyl)amino)methyl)-3-methyl-2-phenyl-2,3-dihydrobenzofuran-4-yl)-3-fluoro-4-((S)-2-hydroxypropoxy)benzamide;

2-((2S,3S,4S)-5-chloro-6-fluoro-2-(((trans-4-hydroxycyclohexyl)amino)methyl)-3-methyl-2-phenyl-2,3-dihydrobenzofuran-4-yl)-4-(difluoromethoxy)-3-fluorobenzamide;

2-((2S,3S,4S)-5-chloro-6-fluoro-2-((((cis)-4-hydroxycyclohexyl)amino)methyl)-3-methyl-2-phenyl-2,3-dihydrobenzofuran-4-yl)-4-(difluoromethoxy)-3-fluorobenzamide;

2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-methoxyethoxy)benzamide;

2-((2S,3S,4S)-5-chloro-6-fluoro-2-((((cis)-4-hydroxy-4-methylcyclohexyl)amino)methyl)-3-methyl-2-phenyl-2,3-dihydrobenzofuran-4-yl)-3-fluoro-4-(2-methoxyethoxy)benzamide;

2-((2S,3S,4S)-5-chloro-6-fluoro-2-(((trans-4-hydroxy-4-methylcyclohexyl)amino)methyl)-3-methyl-2-phenyl-2,3-dihydrobenzofuran-4-yl)-3-fluoro-4-(2-hydroxyethoxy)benzamide;

2-((2S,3S,4S)-5-chloro-6-fluoro-2-(((cis-4-hydroxy-4-methylcyclohexyl)amino)methyl)-3-methyl-2-phenyl-2,3-dihydrobenzofuran-4-yl)-3-fluoro-4-(2-hydroxyethoxy)benzamide;

2-((2S,3S,4S)-5-chloro-2-((cyclobutylamino)methyl)-6-fluoro-3-methyl-2-phenyl-2,3-dihydrobenzofuran-4-yl)-3-fluoro-4-(2-hydroxyethoxy)benzamide;

4-((2S,3S,4S)-5-chloro-6-fluoro-2-((((trans-4-hydroxy-4-methylcyclohexyl)amino)methyl)-3-methyl-2-phenyl-2,3-dihydrobenzofuran-4-yl)-5-fluoro-6-(2-hydroxyethoxy)nicotinamide;

2-((2S,3 S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-hydroxypropoxy)-N-methylbenzonitrile;

2-((2S,3 S,4S)-5-chloro-6-fluoro-3-methyl-2-((methylamino)methyl)-2-phenyl-2,3-dihydrobenzofuran-4-yl)-3-fluoro-4-((S)-2-hydroxypropoxy)-N-methylbenzamide, 2-((2S,3 S,4S)-2-(aminomethyl)-5-chloro-6-fluoro-3-methyl-2-phenyl-2,3-dihydrobenzofuran-4-yl)-3-fluoro-4-((S)-2-hydroxypropoxy)benzamide;

2-(2-((2S,3 S,4S)-2-(aminomethyl)-5-chloro-6-fluoro-3-methyl-2-phenyl-2,3-dihydrobenzofuran-4-yl)-3,4-difluorophenoxy)ethan-1-ol, 2-((2R,3 S,4S)-5-chloro-6-fluoro-2-(6-hydroxypyridin-2-yl)-3-methyl-2-((methylamino)-methyl)-2,3-dihydrobenzofuran-4-yl)-3-fluoro-4-methoxybenzamide;

2-((2R,3 S,4S)-5-chloro-6-fluoro-2-((((trans)-4-hydroxy-4-methylcyclohexyl)amino)methyl)-3-methyl-2-(pyridin-2-yl)-2,3-dihydrobenzofuran-4-yl)-3-fluoro-4-(2-methoxyethoxy)benzamide;

2-((2S,3 S,4S)-5-chloro-6-fluoro-2-((((trans)-4-hydroxy-4-methylcyclohexyl)amino)methyl)-3-methyl-2-(pyridin-3-yl)-2,3-dihydrobenzofuran-4-yl)-3-fluoro-4-methoxybenzamide;

2-((2S,4R)-2-(aminomethyl)-2-phenyl-5-(trifluoromethyl)-2,3-dihydrobenzofuran-4-yl)-4-methoxybenzamide;

2-((2S,4R)-5-cyano-2-((((trans)-4-hydroxy-4-methylcyclohexyl)amino)methyl)-2-phenyl-2,3-dihydrobenzofuran-4-yl)-3-fluoro-4-methoxy-N-methylbenzamide;

(S)-2-((((trans)-4-hydroxycyclohexyl)amino)methyl)-2,4-diphenyl-2,3-dihydrobenzofuran-5-carbonitrile;

2-((2S,4S)-2-(aminomethyl)-5-chloro-2-phenyl-2,3-dihydrofuro[2,3-b]pyridin-4-yl)-3-fluorobenzamide;

2-((2S,4S)-5-chloro-2-((cyclohexylamino)methyl)-2-phenyl-2,3-dihydrobenzofuran-4-yl)-4-(difluoromethoxy)-3-fluorobenzamide;

2-((2S,3 S,4S)-5-chloro-6-fluoro-3-hydroxy-2-((((cis)-4-methoxycyclohexyl)amino)methyl)-2-phenyl-2,3-dihydrobenzofuran-4-yl)-4-(difluoromethoxy)-3-fluorobenzamide;

2-((2S,3 S,4S)-5-chloro-6-fluoro-3-hydroxy-2-((((trans)-4-methoxycyclohexyl)amino)methyl)-2-phenyl-2,3-dihydrobenzofuran-4-yl)-4-(difluoromethoxy)-3-fluorobenzamide;

methyl (cis)-4-(((((2S,4S)-4-(6-carbamoyl-2,3-difluorophenyl)-5-chloro-2-phenyl-2,3-dihydrobenzofuran-2-yl)methyl)amino)cyclohexane-1-carboxylate;

methyl (trans)-4-(((((2S,4S)-4-(6-carbamoyl-2,3-difluorophenyl)-5-chloro-2-phenyl-2,3-dihydrobenzofuran-2-yl)methyl)amino)cyclohexane-1-carboxylate;

2-((2S,4S)-2-((((trans)-4-carbamoylcyclohexyl)amino)methyl)-5-chloro-2-phenyl-2,3-dihydrobenzofuran-4-yl)-3-fluorobenzamide;
2-((2S,4S)-2-((((cis)-4-carbamoylcyclohexyl)amino)methyl)-5-chloro-2-phenyl-2,3-dihydrobenzofuran-4-yl)-3-fluorobenzamide;
2-((2S,4S)-5-chloro-2-((((trans)-4-(methylcarbamoyl)cyclohexyl)amino)methyl)-2-phenyl-2,3-dihydrobenzofuran-4-yl)-3-fluorobenzamide;
2-((2S,4S)-5-chloro-2-((((cis)-4-(methylcarbamoyl)cyclohexyl)amino)methyl)-2-phenyl-2,3-dihydrobenzofuran-4-yl)-3-fluorobenzamide;
2-((2S,4S)-5-chloro-2-((((cis)-3-(difluoromethyl)cyclobutyl)amino)methyl)-6-fluoro-2-phenyl-2,3-dihydrobenzofuran-4-yl)-3-fluoro-4-(2-hydroxyethoxy)benzamide;
2-((2S,4S)-5-chloro-2-((((trans)-3-(difluoromethyl)cyclobutyl)amino)methyl)-6-fluoro-2-phenyl-2,3-dihydrobenzofuran-4-yl)-3-fluoro-4-(2-hydroxyethoxy)benzamide;
2-((2S,4S)-2-(aminomethyl)-5-chloro-6-fluoro-2-phenyl-2,3-dihydrobenzofuran-4-yl)-3-fluoro-4-(2-hydroxyethoxy-1,1,2,2-d4)-N-methylbenzamide;
2-((2S,4S)-5-chloro-6-fluoro-2-(((methyl-d3)amino)methyl)-2-phenyl-2,3-dihydrobenzofuran-4-yl)-4-(difluoromethoxy)-3-fluorobenzamide;
2-((2S,3 S,4S)-5-chloro-6-fluoro-3-methyl-2-((methylamino)methyl)-2-phenyl-2,3-dihydrobenzofuran-4-yl)-3-fluoro-4-methoxybenzamide,
4-((2S,3S,4S)-5-chloro-6-fluoro-3-methyl-2-((methylamino)methyl)-2-phenyl-2,3-dihydrobenzofuran-4-yl)-5-fluoro-6-(2-hydroxyethoxy)-N-methylnicotinamide;
2-((2S,3R,4S)-5-chloro-6-fluoro-3-(methorymethyl)-2-((methylamino)methyl)-2-phenyl-2,3-dihydrobenzofuran-4-yl)-3-fluoro-4-methoxybenzamide,
2-((2S,3R,4S)-5-chloro-6-fluoro-3-(hydroxymethyl)-2-((methylamino)methyl)-2-phenyl-2,3-dihydrobenzofuran-4-yl)-3-fluoro-4-methoxybenzamide,
2-((2S,3S,4S)-5-chloro-6-fluoro-2-((((trans)-4-hydroxy-4-methylcyclohexyl)amino)methyl)-3-methyl-2-phenyl-2,3-dihydrobenzofuran-4-yl)-3-fluoro-4-(2-hydroxy-2-methylpropoxy)benzamide;
2-((2 S,4 S)-2-(azetidin-2-yl)-5-chloro-6-fluoro-2-phenyl-2,3-dihydrobenzofuran-4-yl)-3-fluoro-4-(2-hydroxyethoxy)-N-methylbenzamide;
2-((2S,3S,4S)-2-(azetidin-2-yl)-5-chloro-6-fluoro-3-methyl-2-phenyl-2,3-dihydrobenzofuran-4-yl)-3-fluoro-4-((S)-2-hydroxypropoxy)-N-methylbenzamide;
(2-((2S,4S)-5-chloro-6-fluoro-2-phenyl-2-((S)-pyrrolidin-2-yl)-2,3-dihydrobenzofuran-4-yl)-3-fluoro-4-(2-hydroxyethoxy)benzamide;
2-((2S,4S)-5-chloro-6-fluoro-2-phenyl-2-((S)-pyrrolidin-2-yl)-2,3-dihydrobenzofuran-4-yl)-3-fluoro-4-((S)-2-hydroxypropoxy)benzamide;
2-((2S,4S)-5-chloro-6-fluoro-2-phenyl-2-((S)-pyrrolidin-2-yl)-2,3-dihydrobenzofuran-4-yl)-3-fluoro-4-(2-hydroxyethoxy)-N-methylbenzamide;
2-((2S,4S)-5-chloro-6-fluoro-2-phenyl-2-((S)-pyrrolidin-2-yl)-2,3-dihydrobenzofuran-4-yl)-3-fluoro-4-((S)-2-hydroxpropoxy)-N-methylbenzamide;
4-((2S,4S)-5-chloro-6-fluoro-2-phenyl-2-((S)-pyrrolidin-2-yl)-2,3-dihydrobenzofuran-4-yl)-5-fluoro-6-(2-hydroxyethoxy)-N-methylnicotinamide;
2-((4-((2S,4S)-5-chloro-6-fluoro-2-phenyl-2-((S)-pyrrolidin-2-yl)-2,3-dihydrobenzofuran-4-yl)-3-fluoro-5-(methylcarbamoyl)pyridin-2-yl)oxy)acetic acid,
4-((2S,4S)-5-chloro-6-fluoro-2-phenyl-2-((S)-pyrrolidin-2-yl)-2,3-dihydrobenzofuran-4-yl)-5-fluoro-6-hydroxy-N-methylnicotinamide;
2-((2S,4S)-5-chloro-6-fluoro-2-(4-hydroxypyrrolidin-2-yl)-2-phenyl-2,3-dihydrobenzofuran-4-yl)-4-(difluoromethoxy)-3-fluorobenzamide;
2-((2S,4S)-5-chloro-6-fluoro-2-(4-hydroxy-4-methylpyrrolidin-2-yl)-2-phenyl-2,3-dihydrobenzofuran-4-yl)-3-fluoro-4-((S)-2-hydroxypropoxy)benzamide;
(2S,4R)-2-((S)-5-chloro-6-fluoro-2,4-diphenyl-2,3-dihydrobenzofuran-2-yl)-4-fluoropyrrolidine;
2-((2S,4S)-5-chloro-6-fluoro-2-phenyl-2-((S)-piperidin-2-yl)-2,3-dihydrobenzofuran-4-yl)-3-fluoro-4-(2-hydroxyethoxy)-N-methylbenzamide;
(3-((S)-5-chloro-6-fluoro-2,4-diphenyl-2,3-dihydrobenzofuran-2-yl)morpholine;
2-((2S,4S)-5-chloro-6-fluoro-2-(morpholin-3-yl)-2-phenyl-2,3-dihydrobenzofuran-4-yl)-3-fluoro-4-methoxybenzamide;
2-((2S,3S,4S)-5-chloro-6-fluoro-3-hydroxy-2-phenyl-2-(pyrrolidin-2-yl)-2,3-dihydrobenzofuran-4-yl)-3-fluoro-4-methoxybenzamide;
2-((2S,3S,4S)-5-chloro-6-fluoro-3-methoxy-2-phenyl-2-(pyrrolidin-2-yl)-2,3-dihydrobenzofuran-4-yl)-3-fluoro-4-methoxybenzamide;
2-((2S,3S,4S)-5-chloro-6-fluoro-3-methoxy-2-phenyl-2-(pyrrolidin-2-yl)-2,3-dihydrobenzofuran-4-yl)-3-fluoro-4-(2-hydroxy)benzamide;
2-((2S,3S,4S)-5-chloro-6-fluoro-3-methyl-2-phenyl-2-(pyrrolidin-2-yl)-2,3-dihydrobenzofuran-4-yl)-3-fluoro-4-((S)-2-hydroxy)benzamide;
2-((2S,4S)-2-(1-aminoethyl)-5-chloro-2-phenvl-2,3-dihydrobenzofuran-4-yl)-3-fluoro-4-methoxybenzamide;
2-((2S,3S,4S)-2-(1-aminoethyl)-5-chloro-6-fluoro-3-methyl-2-phenyl-2,3-dihydrobenzofuran-4-yl)-3-fluoro-4-(2-methoxyethoxy)benzamide;
2-((2S,4S)-5-chloro-6-fluoro-2-phenyl-2-((S)-pyrrolidin-2-yl)-2,3-dihydrobenzofuran-4-yl)-3-fluoro-4-methoxybenzamide;
2-((2S,4S)-5-chloro-6-fluoro-2-phenyl-2-((S)-pyrrolidin-2-yl)-2,3-dihydrobenzofuran-4-yl)-3-fluoro-4-methoxy-N-methylbenzamide; and
2-((2S,3 S,4S)-2-(aminomethyl)-5-chloro-6-fluoro-3-methyl-2-phenyl-2,3-dihydrobenzofuran-4-yl)-3-fluoro-4-methoxybenzamide;

or a pharmaceutically acceptable salt thereof.

8. A compound of formula (Ia) according to claim 1, or a pharmaceutically acceptable salt thereof, wherein the compound is selected from the group consisting of

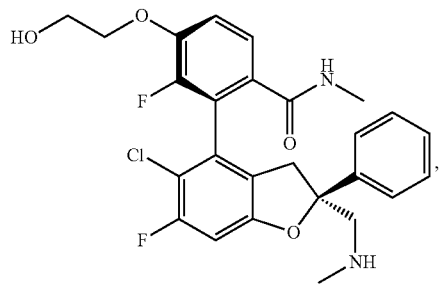

553
-continued
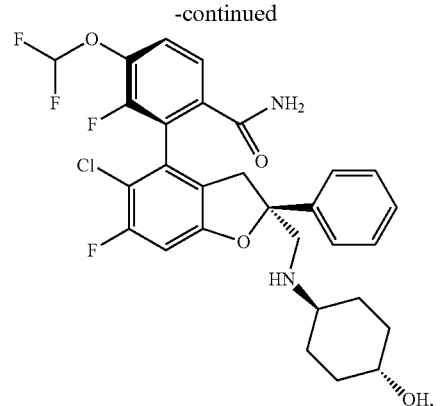
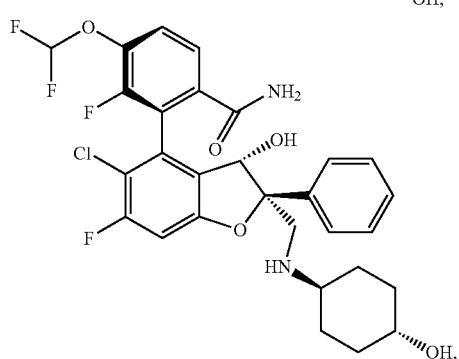
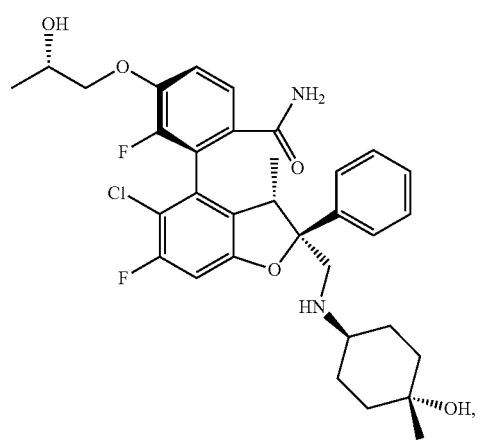
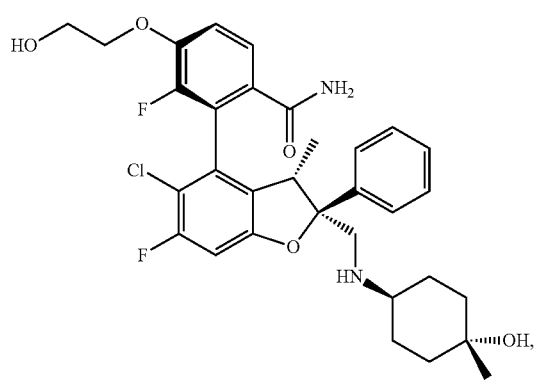
554
-continued
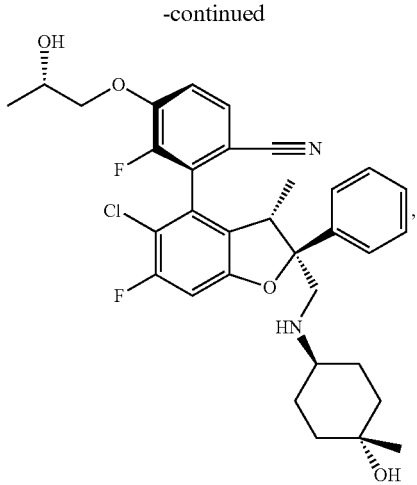
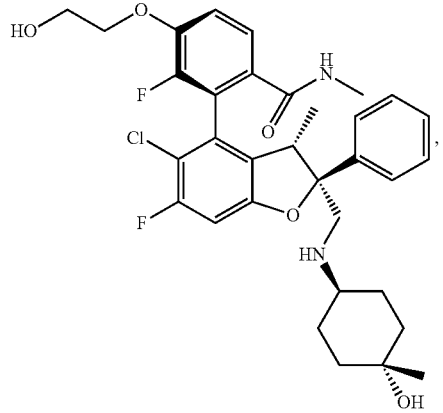
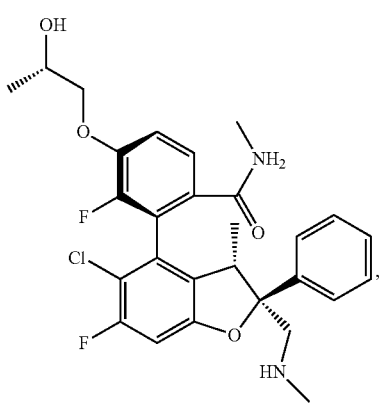
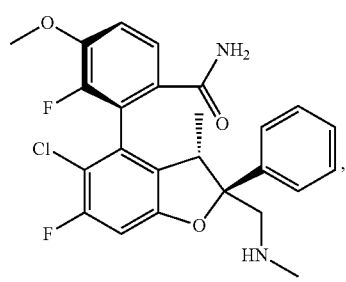

-continued

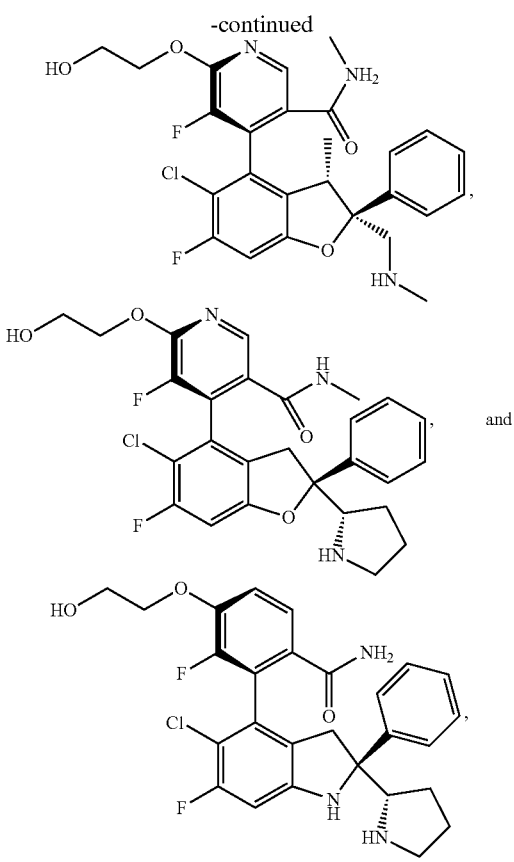

or a pharmaceutically acceptable salt thereof.

9. A compound of formula (Ia) according to claim 1, or a pharmaceutically acceptable salt thereof, wherein A is phenyl.

10. A compound of formula (Ia) according to claim 1, or a pharmaceutically acceptable salt thereof, wherein Q is $-C(R^7)_2-N(R_8)-R_1$, or is selected from the group consisting of:

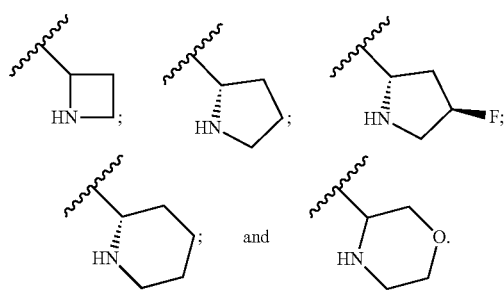

11. A compound of formula (Ia) according to claim 1, or a pharmaceutically acceptable salt thereof, wherein X is N.

12. A compound of formula (Ia) according to claim 1, or a pharmaceutically acceptable salt thereof, wherein $R_w$ is selected from (i) hydrogen; (ii) $C_1$-$C_3$alkyl; and (iii) hydroxy-$C_1$-$C_3$alkyl.

13. A compound of formula (Ia) according to claim 1, or a pharmaceutically acceptable salt thereof, wherein $R_2$ is fluoro.

14. A compound of formula (Ia) according to claim 1, or a pharmaceutically acceptable salt thereof, wherein $R_3$ is chloro.

15. A compound of formula (Ia) according to claim 1, or a pharmaceutically acceptable salt thereof, wherein $R_4$ is fluoro.

16. A compound of formula (Ia) according to claim 1, or a pharmaceutically acceptable salt thereof, wherein $R_5$ is selected from $C_1$-$C_6$alkoxy; and hydroxy$C_1$-$C_6$alkoxy.

17. A compound of formula (Ia) according to claim 1, or a pharmaceutically acceptable salt thereof, wherein $R_6$ is selected from (i) cyano; and (ii) $C(O)NR^{6a}$.

18. A pharmaceutical composition comprising a compound according to claim 1, or a pharmaceutically acceptable salt thereof, and at least one pharmaceutically acceptable carrier.

19. A combination comprising a compound of formula (Ia) according to claim 1, or a pharmaceutically acceptable salt thereof, and one or more therapeutically active agents.

20. A method of treating a cancer in a subject having the cancer, wherein the method comprises administering to the subject a therapeutically effective amount of a compound of formula (Ia) according to claim 1, or a pharmaceutically acceptable salt thereof.

21. The method of claim 20, wherein the cancer harbors (i) one or more YAP or TAZ fusions; or (ii) one or more NF2, LATS1, or LATS2 truncating mutations or deletions.

22. The method of claim 20, wherein the cancer is selected from mesothelioma, carcinoma, poroma, porocarcinoma, supratentorial ependymoma, epithelioid hemangioendothelioma, ependymal tumor, breast cancer, lung cancer, ovarian cancer, colorectal cancer, melanoma, pancreatic cancer, prostate cancer, gastric cancer, esophageal cancer, liver cancer, neuroblastoma, schwannoma, kidney cancer, sarcoma, bone cancer, brain cancer, medulloblastoma, glioma, meningioma, and head and neck cancer.

23. The method of claim 20, wherein the cancer is a solid tumor.

24. The method of claim 20, wherein the cancer is mesothelioma.

25. A compound which is:

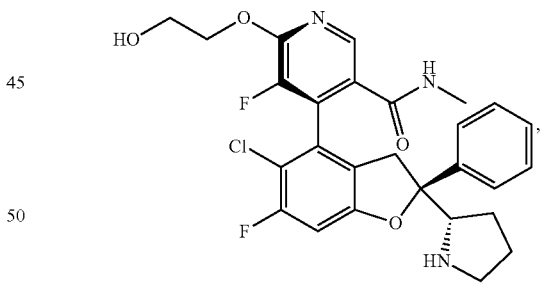

or a pharmaceutically acceptable salt thereof.

26. A pharmaceutical composition comprising a compound, or a pharmaceutically acceptable salt thereof, according to claim 25, and at least one pharmaceutically acceptable carrier.

27. A combination comprising the compound, or a pharmaceutically acceptable salt thereof, according to claim 25, and one or more therapeutically active agents.

28. A method of treating a cancer in a subject having the cancer, wherein the method comprises administering to the subject a therapeutically effective amount of a compound, or a pharmaceutically acceptable salt thereof, according to claim 25.

29. The method of claim 28, wherein the cancer wherein the cancer harbors (i) one or more YAP or TAZ fusions; or (ii) one or more NF2, LATS1, or LATS2 truncating mutations or deletions.

30. The method of claim 28, wherein the cancer is selected from mesothelioma, carcinoma, poroma, porocarcinoma, supratentorial ependymoma, epithelioid hemangioendothelioma, ependymal tumor, breast cancer, lung cancer, ovarian cancer, colorectal cancer, melanoma, pancreatic cancer, prostate cancer, gastric cancer, esophageal cancer, liver cancer, neuroblastoma, schwannoma, kidney cancer, sarcoma, bone cancer, brain cancer, medulloblastoma, glioma, meningioma, and head and neck cancer.

31. The method of claim 28, wherein the cancer is mesothelioma.

32. The method of claim 28, wherein the cancer is a solid tumor.

33. A compound which is:

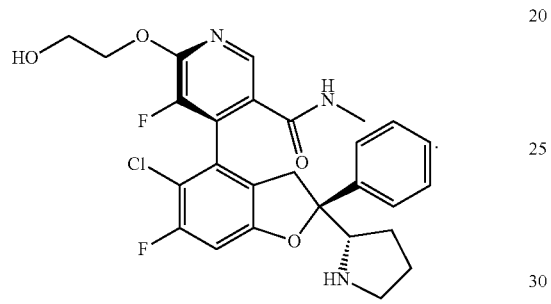

* * * * *